United States Patent
Chuang et al.

(10) Patent No.: US 11,414,424 B2
(45) Date of Patent: Aug. 16, 2022

(54) CARDIAC SARCOMERE INHIBITORS

(71) Applicant: Cytokinetics, Inc., South San Francisco, CA (US)

(72) Inventors: Chihyuan Chuang, Millbrae, CA (US); Bradley P. Morgan, Oakland, CA (US); Mark Vanderwal, Oakland, CA (US); Luke W. Ashcraft, San Francisco, CA (US); Kevin Lau, San Mateo, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

(21) Appl. No.: 16/557,281

(22) Filed: Aug. 30, 2019

(65) Prior Publication Data

US 2020/0109148 A1 Apr. 9, 2020

Related U.S. Application Data

(60) Provisional application No. 62/726,162, filed on Aug. 31, 2018.

(51) Int. Cl.
| | |
|---|---|
| *C07D 487/10* | (2006.01) |
| *A61P 9/04* | (2006.01) |
| *C07D 241/08* | (2006.01) |
| *C07D 241/38* | (2006.01) |
| *C07D 401/04* | (2006.01) |
| *C07D 401/06* | (2006.01) |
| *C07D 401/08* | (2006.01) |
| *C07D 403/08* | (2006.01) |
| *C07D 405/04* | (2006.01) |
| *C07D 405/12* | (2006.01) |
| *C07D 405/14* | (2006.01) |
| *C07D 409/14* | (2006.01) |
| *C07D 413/08* | (2006.01) |
| *C07D 413/14* | (2006.01) |
| *C07D 417/08* | (2006.01) |
| *C07D 491/107* | (2006.01) |

(52) U.S. Cl.
CPC .............. *C07D 487/10* (2013.01); *A61P 9/04* (2018.01); *C07D 241/08* (2013.01); *C07D 241/38* (2013.01); *C07D 401/04* (2013.01); *C07D 401/06* (2013.01); *C07D 401/08* (2013.01); *C07D 403/08* (2013.01); *C07D 405/04* (2013.01); *C07D 405/12* (2013.01); *C07D 405/14* (2013.01); *C07D 409/14* (2013.01); *C07D 413/08* (2013.01); *C07D 413/14* (2013.01); *C07D 417/08* (2013.01); *C07D 491/107* (2013.01)

(58) Field of Classification Search
CPC .. C07D 487/10; C07D 241/08; C07D 241/38; C07D 401/04; C07D 401/06; C07D 401/08; C07D 403/08; C07D 405/04; C07D 405/12; C07D 405/14; C07D 409/14; C07D 413/08; C07D 413/14; C07D 417/08; C07D 491/107; A61P 9/04
See application file for complete search history.

(56) References Cited

U.S. PATENT DOCUMENTS

| | | |
|---|---|---|
| 5,846,514 A | 12/1998 | Foster |
| 5,919,785 A | 7/1999 | Dinsmore |
| 6,334,997 B1 | 1/2002 | Foster |
| 9,181,200 B2 | 11/2015 | Oslob |
| 9,199,945 B2 | 12/2015 | Oslob |
| 9,663,516 B2 | 5/2017 | Oslob |
| 9,925,177 B2 | 3/2018 | Oslob |
| 2006/0173183 A1 | 8/2006 | Powers |
| 2006/0241110 A1 | 10/2006 | Morgan |
| 2013/0018055 A1 | 1/2013 | Aebi et al. |
| 2016/0176868 A1 | 6/2016 | Oslob et al. |

(Continued)

FOREIGN PATENT DOCUMENTS

| | | |
|---|---|---|
| CL | 201503689 A | 12/2015 |
| CL | 202002399 A1 | 9/2020 |

(Continued)

OTHER PUBLICATIONS

Ito et al. In Cancer Science 94(1), 3-8 (2003).*

(Continued)

*Primary Examiner* — Alicia L Otton

(74) *Attorney, Agent, or Firm* — Morrison & Foerster LLP

(57) ABSTRACT

Provided are compounds of Formula (I):

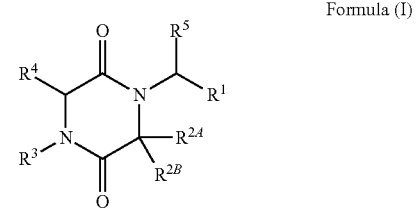

Formula (I)

or a pharmaceutically acceptable salt thereof, wherein $R^1$, $R^{2A}$, $R^{2B}$, $R^3$, $R^4$, and $R^5$ are as defined herein. Also provided is a pharmaceutically acceptable composition comprising a compound of Formula (I), or a pharmaceutically acceptable salt thereof. Also provided are methods of using a compound of Formula (I), or a pharmaceutically acceptable salt thereof.

57 Claims, No Drawings

(56) References Cited

U.S. PATENT DOCUMENTS

| | | |
|---|---|---|
| 2016/0289211 A1 | 10/2016 | Ashcraft |
| 2019/0256504 A1 | 8/2019 | Chuang |
| 2021/0147399 A1 | 5/2021 | Chuang et al. |
| 2021/0253563 A1 | 8/2021 | Morgan et al. |
| 2021/0276991 A1 | 9/2021 | Morgan et al. |

FOREIGN PATENT DOCUMENTS

| | | |
|---|---|---|
| CL | 202100443 A1 | 2/2021 |
| WO | WO03059265 A2 | 7/2003 |
| WO | WO03059265 A3 | 6/2004 |
| WO | WO2004064730 A2 | 8/2004 |
| WO | WO2007078815 A2 | 7/2007 |
| WO | WO2007117180 A1 | 10/2007 |
| WO | WO2012101011 A2 | 8/2012 |
| WO | 2014205234 A1 | 12/2014 |
| WO | WO2014205223 A1 | 12/2014 |
| WO | WO2017103219 A1 | 6/2017 |
| WO | WO2017103223 A1 | 6/2017 |
| WO | WO2017222951 A1 | 12/2017 |
| WO | WO2018089433 A1 | 5/2018 |
| WO | WO2019144041 A1 | 7/2019 |

OTHER PUBLICATIONS

Santra et al., J. Org. Chem., 2011, 76, pp. 2261-2264.*
STN Registry database entry for CAS RN 1348860-91-2, Entry Date Dec. 5, 2011, Accessed Feb. 13, 2021.*
Williams et al., J. Am. Chem. Soc., 1982, 104, pp. 6092-6099.*
STN Registry database entry for CAS RN 953060-71-4, entry date of Nov. 12, 2007, Accessed Jul. 15, 2021.*
Berge et al. (1977). "Pharmaceutical Salts," J. Pharm. Sci. 66(1):1-19.
Caputo, S. et al. (Nov. 28, 2017). "Diversity-Oriented Synthesis of Various Enantiopure Heterocycles by Coupling Organocatalysis with Multicomponent Reactions : Diversity-Oriented Synthesis of Various Enantiopure Heterocycles by Coupling Organocatalysis with Multicomponent Reactions," European J. of Chem. 2017 (45):6619-6628.
Dahl, L.K. et al. (Jun. 1, 1962). "Effects of Chronic Excess Salt Ingestion Evidence That Genetic Factors Play an Important Role in Susceptibility to Experimental Hypertension," J Exp Med. 115(6):1173-1190.
Database Registry (Jun. 18, 2008). RN-1028938-65-9 Emory MLSC database: "2, 5-Piperazinediones, 4-[(4-chlorophenyl)methyl]-3-(4-methoxyphenyl)-1-(2-phenylethyl)-," Chemical Abstracts Service, 1 page.
Database Registry (Jun. 24, 2008). RN-1030378-92-7 Emory MLSC database: "1-Piperazineacetamide, 3-(2-fluorophenyl)-N-(2-methylcyclohexyl)-4-[(4-methylphenyl)methyl]-2,5-dioxo," Chemical Abstracts Service, 1 page.
Database Registry (Nov. 4, 2011). RN-1340679-26-6 ChemDiv, Inc.: "2, 5-Piperazinedione, 1-(-3_methylbutyl)-4-(phenylmethyl)-3-(3-pyridinyl)," Chemical Abstracts Service, 3 pages.
Dean, D. C. (2000). "Recent Advances in the Synthesis and Applications of Radiolabeled Compounds for the Drug Discovery and Development," Curr. Pharm. Des. 6(10): Preface Only, 1 page.
Evans, A.E. (Mar. 1981, e-pub. Jan. 9, 2007). "Synthesis of Radiolabeled Compounds," J Radio Anal. Chem. 64 (1-2):9-32.
Fillmore, N. et al. (2018). "Uncoupling of Glycolysis from Glucose Oxidation Accompanies the Development of Heart Failure with Preserved Ejection Fraction," Mol. Med. 24(3):1-12.
Geisterfer-Lowrance, A.A.T. et al. (May 3, 1996). "A Mouse Model of Familial Hypertrophic Cardiomyopathy," Science 272(5262):731-734.
Green, E. M. et al. (Feb. 5, 2016). "A Small-Molecule Inhibitor of Sarcomere Contractility Suppresses Hypertrophic Cardiomyopathy in Mice," Science 351(6273):617-621.
Guazzi, M. et al. (Sep. 26, 2017). "Cardiopulmonary Exercise Testing: What Is its Value?," J. Am. Coll. Cardiol. 70(13):1618-1636.
Hargrave, J.D. et al. (Nov. 21, 2010, e-pub. Sep. 8, 2010). "Rhodium-Catalysed Conjugate Addition of Arylboronic Acids to Enantiopure Dehydroamino Acid Derivatives," Org. Biomol. Chem. 8(22):5120-5125.
Hartung, A. et al. (Dec. 11, 2012). "One-Pot Ugi/Aza-Michael Synthesis of Highly Substituted 2,5-Diketopiperazines with Anti-Proliferative Properties," Molecules Online 17(12):14685-14699.
International Search Report and Written Opinion of the International Searching Authority dated Aug. 28, 2019, for PCT Patent Application No. PCT/US2019/038907, filed Jun. 25, 2019, 12 pages.
International Search Report and Written Opinion of the International Searching Authority dated Aug. 28, 2019, for PCT Patent Application No. PCT/US2019/038908, filed Jun. 25, 2019, 14 pages.
International Search Report and Written Opinion of the International Searching Authority dated May 20, 2019, for PCT Patent Application No. PCT/US2019/014344, filed Jan. 18, 2019, 19 pages.
Invitation to Pay Additional Fees dated Mar. 28, 2019, for PCT Patent Application No. PCT/US2019/014344, filed Jan. 18, 2019, 14 pages.
Jackson, P. et al. (Aug. 22, 2018). "Appendage and Scaffold Diverse Fully Functionalized Small-Molecule Probes via a Minimalist Terminal Alkyne-Aliphatic Diazirine Isocyanide," J. Org. Chem. 83(18):11245-11253.
Jiang, J. et al. (Oct. 4, 2013, e-pub. Jul. 14, 2014). "Allele-specific Silencing of Mutant Myh6 Allele in Mice Suppresses Hypertrophic Cardiomyopathy," Science 342(6154):111-114, 11 pages.
Kabalka, G.W. et al. (1989). "The Synthesis of Radiolabeled Compounds via Organometallic Intermediates," Tetrahedron 45(21):6601-6621.
Kaim, L.E. et al. (2007, e-pub. Jan. 24, 2007). "New Indolizine Template from the Ugi Reaction," Synlett 2 (1):227-230.
Kim-Mitsuyama, S. et al. (Oct. 2004). "Additive Beneficial Effects of the Combination of a Calcium Channel Blocker and an Angiotensin Blocker on a Hypertensive Rat-Heart Failure Model," Hypertens Res. 27(10):771-779.
Lee, M. et al. (May 25, 2016). "Convenient asymmetric synthesis of 1,3,4,6-tetrasubstituted 2,5-diketopiperazines," Arkivoc 2016(4):100-113.
Lee, M. et al. (May 19, 2016). "Stereoselective Nucleophile Substitution of [alpha]-Bromo Tertiary Amides for Asymmetric Synthesis of Highly Substituted 2,5-Diketopiperazines," Bull. Korean Chem. Soc. 37(6):981-984.
Lesma, G. et al. (Jun. 18, 2014). "Asymmetric Ugi 3CR on isatin -derived ketimine: synthesis of chiral 3,3-disubstituted 3-aminooxindole derivatives," Beilstein Journal of Organic Chemistry 10:1383-1389.
Malhotra, R. et al. (Aug. 2016, e-pub. Jun. 8, 2016). "Cardiopulmonary Exercise Testing in Heart Failure," JACC Heart Fail 4(8):607-616.
Mamoun, O. et al. (1995, e-pub. Sep. 23, 2006). "Synthesis of Methyl 3-Amino-3-pyrrolidinecarboxylates: A Convenient Access to Cucurbitine and Analogues," Synthetic Communications 25(9):1295-1302.
Parker, M.F.L. et al. (Feb. 27, 2014). "Acceleration of an Aromatic Claisen Rearrangement via a Designed Spiroligozyme Catalyst that Mimics the Ketosteroid Isomerase Catalytic Dyad," J. American Chem. Soc. 136 (10):3817-3827.
Pettersson, M. et al. (Oct. 1, 2015). "Design, Synthesis and Evaluation of 2,5-Diketopiperazines as Inhibitors of the MDM2-p53 Interaction," PLOS One 10(10):e0137867, 19 pages.
Pyne, S.G. et al. (1993). "Asymmetric Synthesis of Chiral Cyclic Amino Acids by Diels-Alder Reactions of (2S)- and (2R)-4-Methyleneoxazolidin-5-ones," Aust. J Chem. 46(1):73-93.
Rowin, E.J. et al. (Nov. 2017). "Role of Exercise Testing in Hypertrophic Cardiomyopathy," JACC: Cariovasc Imaging. 10(11):1374-1386.
Sakata, Y. et al. (Jan. 2001). "Renin Angiotensin System-Dependent Hypertrophy as a Contributor to Heart Failure in Hypertensive Rats:

(56) References Cited

OTHER PUBLICATIONS

Different Characteristics From Renin Angiotensin System-Independent Hypertrophy," J. Am. Coll. Cardiol. 37(1):293-299.
Santra, S. et al. (Apr. 1, 2011, e-pub. Feb. 25, 2011). "A Rapid, One-Pot, Microwave-Influenced Synthesis of Spiro-2,5-diketopiperazines via a Cascade Ugi/6-Exo-Trig Aza-Michael Reaction," Journal of Organic Chemistry 76 (7):2261-2264.
Taub, P.R. et al. (Oct. 1, 2013). "Perturbations in Skeletal Muscle Sarcomere Structure in Patients with Heart Failure and Type 2 Diabetes: Restorative Effects of (-)-epicatechinrich Cocoa," Clinical Science 125(8):383-389.
U.S. Appl. No. 16/557,281, filed Aug. 30, 2019. (not submitted herewith pursuant to the waiver of 37 C.F.R. §1.98(a)(2)(iii) issued by the Office on Sep. 21, 2004).
Walvoord, R.R. et al. (Nov. 4, 2014). "Quantification of Electrophilic Activation by Hydrogen-Bonding Organocatalysts", J. American Chem. Soc. 136(45):16055-16065.
Williams, R. et al. (Nov. 3, 1992). "Asymmetric synthesis of S-(-)-Cucurbitine," Tetrahedron Letters 33 (45):6755-6758.
Williams, R.M. et al. (Nov. 1982). "A New and Efficient Cyclization Reaction to Construct the Bicyclomycin Ring System: Synthesis of N,N'-dimethyl-4-desmethylenebicyclomycin",Journal of the American Chemical Society 104(22):6092-6099.
Yates, P. et al. (Jan. 1, 1983). "Synthesis of piperazine-2,5-diones related to bicyclomycin. 1.3-acetoxy-1,4-dibenzyl-3-[1-(2-methoxyethyl)-andl-(2-hydroxyethyl )ethenyl] pi perazi ne-2,5-dione. 1. Route via acyclic intermediates", Canadian Journal of Chemistry 61(3):519-528.
Yoshifuji, S. et al. (Aug. 1995). "Stereospecific Synthesis of (R)- and (S)-Baclofen and (R)- and (S)-PCPGABA [4-Amino-2-(4-chlorophenyl)butyric Acid]via (R)- and (S)-3-(4-Chlorophenyl)pyrrolidines," Chem Pharm Bull 42(8) 1302-1306.
International Preliminary Report on Patentability dated Jan. 7, 2021, for Patent Application No. PCT/US2019/038907, filed Jun. 25, 2019, 7 pages.
International Preliminary Report on Patentability dated Jan. 7, 2021, for Patent Application No. PCT/US2019/038908, filed Jun. 25, 2019, 8 pages.
International Preliminary Report on Patentability dated Jul. 30, 2020, for Patent Application No. PCT/US2019/014344, filed Jan. 18, 2019, 11 pages.
International Search Report and Written Opinion of the International Searching Authority dated Nov. 10, 2020, for PCT Patent Application No. PCT/US2020/042387, filed Jul. 16, 2020, 13 pages.
International Search Report and Written Opinion of the International Searching Authority dated Nov. 5, 2020, for PCT Patent Application No. PCT/US2020/042389, filed Jul. 16, 2020, 13 pages.
International Search Report and Written Opinion of the International Searching Authority dated Nov. 6, 2020, for PCT Patent Application No. PCT/US2020/042390, filed Jul. 16, 2020, 14 pages.
Philipson, D. J. et al. (2017, e-pub. Aug. 31, 2017). "Emerging Pharmacologic and Structural Therapies for Hypertrophic Cardiomyopathy," Heart Fail Rev. 22(6):879-888.
U.S. Appl. No. 17/013,472, filed Sep. 4, 2020, by Chuang Chihyuan et al. (not submitted herewith pursuant to the waiver of 37 C.F.R. §1.98(a)(2)(iii) issued by the Office on Sep. 21, 2004).
U.S. Appl. No. 17/255,336, filed Jun. 25, 2019, by Bradley Morgan et al. (not submitted herewith pursuant to the waiver of 37 C.F.R. §1.98(a)(2)(iii) issued by the Office on Sep. 21, 2004).
U.S. Appl. No. 17/255,379, filed Jun. 25, 2019, by Bradley Morgan et al. (not submitted herewith pursuant to the waiver of 37 C.F.R. §1.98(a)(2)(iii) issued by the Office on Sep. 21, 2004).

* cited by examiner

CARDIAC SARCOMERE INHIBITORS

CROSS-REFERENCE TO RELATED APPLICATIONS

This application claims priority to U.S. Provisional Application No. 62/726,162, filed Aug. 31, 2018, entitled "CARDIAC SARCOMERE INHIBITORS," the contents of which are hereby incorporated by reference in their entirety for all purposes.

FIELD

Provided herein are heterocyclic compounds, pharmaceutical compositions comprising such compounds, and methods of treating various cardiac diseases and conditions with such compounds.

BACKGROUND

The disclosure relates to certain chemical entities that selectively modulate the cardiac sarcomere, and specifically to certain chemical entities, pharmaceutical compositions and methods for treating various cardiac diseases and conditions.

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either 'hyper' or 'hypo' contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic $Ca^{2+}$ and cyclic AMP concentrations in the inotropically stimulated myocardium. Given the limitations of current agents, new approaches are needed to improve cardiac function in HCM and HFpEF.

There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac myosin) has been identified as an important means to achieve this improved therapeutic index. The present disclosure provides such agents (particularly cardiac sarcomere inhibitors) and methods for their use. These agents are allosteric inhibitors of cardiac myosin. Benefits of these compounds include a wider therapeutic index, less impact on cardiac relaxation, better pharmacokinetics, and better safety.

The present disclosure provides chemical entities, pharmaceutical compositions and methods for the treatment of heart failure including HCM and HFpEF. The compositions are inhibitors of the cardiac sarcomere, for example, inhibitors of cardiac myosin.

BRIEF SUMMARY

In one aspect, provided is a compound of Formula (I), or a pharmaceutically acceptable salt thereof:

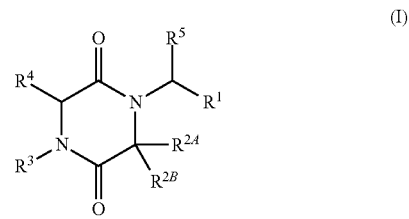

wherein:
R$^1$ is selected from the group consisting of substituted or unsubstituted phenyl and substituted or unsubstituted pyridyl;
R$^{2A}$, R$^{2B}$, and R$^3$ are defined by any one of (i)-(iii):
(i) R$^{2A}$ is H or substituted or unsubstituted alkyl;
R$^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and
R$^3$ is substituted or unsubstituted phenyl or substituted or unsubstituted pyridyl;
or
(ii) R$^{2A}$ is H or substituted or unsubstituted alkyl;
R$^{2B}$ is substituted or unsubstituted phenyl or substituted or unsubstituted pyridyl; and
R$^3$ is substituted or unsubstituted alkyl;
or
(iii) R$^{2A}$ and R$^{2B}$ are taken together with the carbon atom to which they are attached to form G$^1$, wherein G$^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; and
R$^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;

R$^4$ is H or substituted or unsubstituted alkyl; and

R$^5$ is H or substituted or unsubstituted alkyl;

wherein, when one or more of provisions (a)-(c) apply, then R$^1$ is substituted or unsubstituted pyridyl or phenyl substituted with at least one substituent other than methyl or methoxy:

(a) R$^{2A}$ and R$^{2B}$ are as defined by (i) and R$^3$ is substituted or unsubstituted phenyl;

(b) R$^{2A}$ and R$^3$ are as defined by (ii) and R$^{2B}$ is 4-methoxyphenyl;

(c) R$^{2A}$, and R$^{2B}$— are as defined by (iii) and R$^3$ is 4-methoxyphenylmethyl.

In another aspect, provided is a compound of Formula (Ia), or a pharmaceutically acceptable salt thereof:

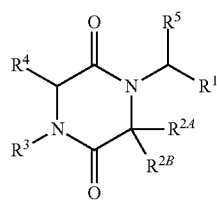

(Ia)

wherein:

R$^1$ is selected from the group consisting of substituted or unsubstituted phenyl and substituted or unsubstituted pyridyl;

R$^{2A}$ is H or substituted or unsubstituted alkyl;

R$^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;

R$^3$ is substituted or unsubstituted phenyl or substituted or unsubstituted pyridyl;

R$^4$ is H or substituted or unsubstituted alkyl; and

R$^5$ is H or substituted or unsubstituted alkyl;

wherein, when R$^3$ is substituted or unsubstituted phenyl, R$^1$ is substituted or unsubstituted pyridyl or phenyl substituted with at least one substituent other than methyl or methoxy.

In another aspect, provided is a compound of Formula (Ib), or a pharmaceutically acceptable salt thereof:

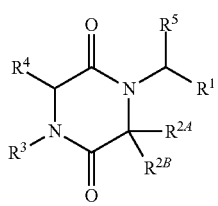

(Ib)

wherein:

R$^1$ is selected from the group consisting of substituted or unsubstituted phenyl and substituted or unsubstituted pyridyl;

R$^{2A}$ is H or substituted or unsubstituted alkyl;

R$^{2B}$ is substituted or unsubstituted phenyl or substituted or unsubstituted pyridyl;

R$^3$ is substituted or unsubstituted alkyl;

R$^4$ is H or substituted or unsubstituted alkyl; and

R$^5$ is H or substituted or unsubstituted alkyl;

wherein, when R$^{2B}$ is 4-methoxyphenyl, R$^1$ is substituted or unsubstituted pyridyl or phenyl substituted with at least one substituent other than methyl or methoxy.

In another aspect, provided is a compound of Formula (Ic), or a pharmaceutically acceptable salt thereof:

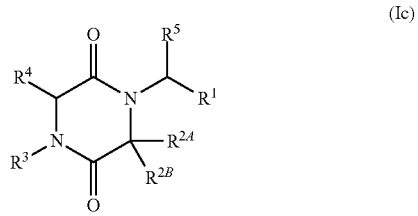

(Ic)

wherein:

R$^1$ is selected from the group consisting of substituted or unsubstituted pyridyl and substituted or unsubstituted pyridyl;

R$^{2A}$ and R$^{2B}$ are taken together with the carbon atom to which they are attached to form G$^1$, wherein G$^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring;

R$^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;

R$^4$ is H or substituted or unsubstituted alkyl; and

R$^5$ is H or substituted or unsubstituted alkyl;

wherein, when R$^3$ is 4-methoxyphenylmethyl, R$^1$ is substituted or unsubstituted pyridyl or phenyl substituted with at least one substituent other than methyl or methoxy.

In another aspect, provided is a compound of Formula (Id), or a pharmaceutically acceptable salt thereof:

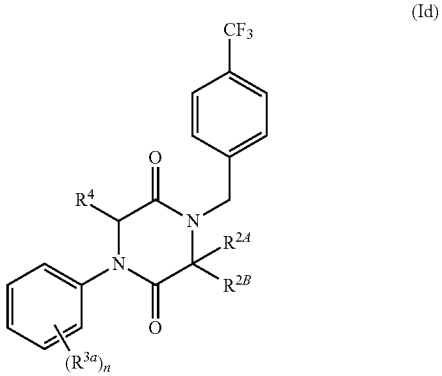

(Id)

wherein:

R$^{2A}$ is H or substituted or unsubstituted alkyl;

R$^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;

n is 0, 1, or 2;

$R^{3a}$ is selected from the group consisting of halo and cyano; and $R^4$ is H.

In another aspect, provided is a compound of Formula (Ie), or a pharmaceutically acceptable salt thereof:

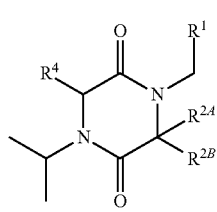

(Ie)

wherein:

$R^1$ is selected from the group consisting of substituted or unsubstituted phenyl and substituted or unsubstituted pyridyl;

$R^{2A}$ is H or substituted or unsubstituted alkyl;

$R^{2B}$ is substituted or unsubstituted phenyl or substituted or unsubstituted pyridyl; and $R^4$ is H;

wherein, when $R^{2B}$ is 4-methoxyphenyl, $R^1$ is substituted or unsubstituted pyridyl or phenyl substituted with at least one substituent other than methyl or methoxy.

In another aspect, provided is a compound of Formula (If), or a pharmaceutically acceptable salt thereof:

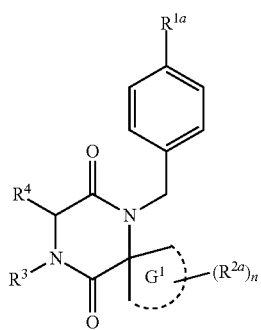

(If)

wherein:

$G^1$ is selected from the group consisting of substituted or unsubstituted cycloalkyl, substituted or unsubstituted cycloalkenyl, substituted or unsubstituted cycloalkynyl, and substituted or unsubstituted heterocyclyl ring, each of which is optionally fused to a phenyl ring;

$R^{1a}$ is selected from the group consisting of cyano, halo, substituted or unsubstituted alkoxy, substituted or unsubstituted alkyl, and substituted or unsubstituted heterocyclyl;

$R^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl;

n is 0, 1, 2, or 3;

$R^3$ is selected from the group consisting of substituted or unsubstituted alkyl, substituted or unsubstituted cycloalkyl, substituted or unsubstituted heterocyclyl, and substituted or unsubstituted aryl; and $R^4$ is H;

wherein, when $R^3$ is 4-methoxyphenylmethyl, $R^{1a}$ is not methyl or methoxy.

In another aspect, provided is a compound of Formula (Ig), or a pharmaceutically acceptable salt thereof:

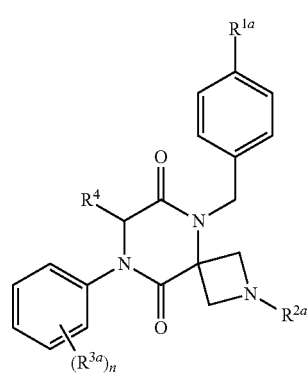

(Ig)

wherein:

$R^{1a}$ is selected from the group consisting of cyano, halo, substituted or unsubstituted alkoxy, substituted or unsubstituted alkyl, and substituted or unsubstituted heterocyclyl;

$R^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl;

n is 0, 1, 2, or 3;

$R^{1a}$ is selected from the group consisting of halo and cyano; and $R^4$ is H.

In another aspect, provided is a compound of Formula (Ih), or a pharmaceutically acceptable salt thereof:

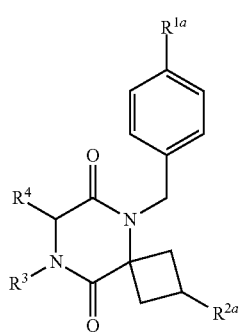

(Ih)

wherein:

$R^{1a}$ is selected from the group consisting of cyano, halo, substituted or unsubstituted alkoxy, substituted or unsubstituted alkyl, and substituted or unsubstituted heterocyclyl;

$R^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl;

$R^3$ is selected from the group consisting of substituted or unsubstituted alkyl, substituted or unsubstituted cycloalkyl, substituted or unsubstituted heterocyclyl, and substituted or unsubstituted aryl; and $R^4$ is H;

wherein, when $R^3$ is 4-methoxyphenylmethyl, $R^{1a}$ is not methyl or methoxy.

In another aspect, provided is a compound of Formula (Ii), or a pharmaceutically acceptable salt thereof:

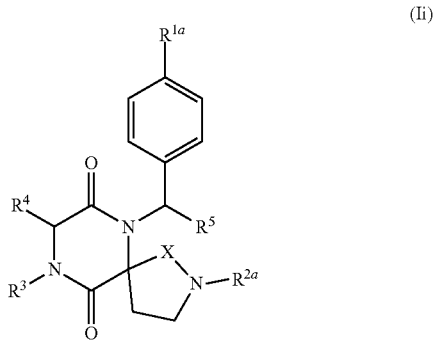

(Ii)

wherein:

$R^{1a}$ is selected from the group consisting of cyano, halo, substituted or unsubstituted alkoxy, substituted or unsubstituted alkyl, and substituted or unsubstituted heterocyclyl;

$R^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl;

$R^3$ is selected from the group consisting of substituted or unsubstituted alkyl, substituted or unsubstituted cycloalkyl, substituted or unsubstituted heterocyclyl, and substituted or unsubstituted aryl;

$R^4$ is H;

$R^5$ is H or substituted or unsubstituted alkyl; and

X is —CH$_2$— or —C(O)—;

wherein, when $R^3$ is 4-methoxyphenylmethyl, $R^{1a}$ is not methyl or methoxy.

In another aspect, provided is a compound of Formula (Ij), or a pharmaceutically acceptable salt thereof:

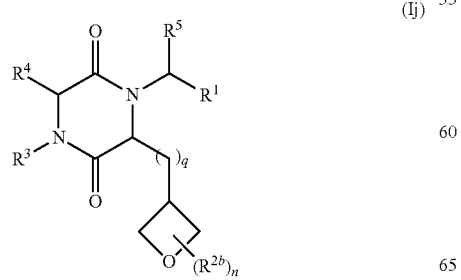

(Ij)

wherein:

$R^1$ is substituted or unsubstituted phenyl;

each $R^{2b}$ is independently substituted or unsubstituted alkyl;

$R^3$ is substituted or unsubstituted phenyl or substituted or unsubstituted pyridyl;

$R^4$ is H;

$R^5$ is H or substituted or unsubstituted alkyl;

n is 0, 1, or 2; and q is 0 or 1, wherein, when $R^3$ is substituted or unsubstituted phenyl, then R' is phenyl substituted with at least one substituent other than methyl or methoxy.

In another aspect, provided is a compound of Formula (Ik-1), or a pharmaceutically acceptable salt thereof:

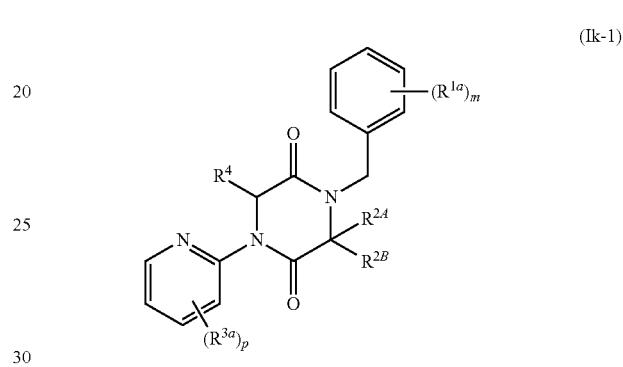

(Ik-1)

wherein:

$R^{2A}$ is H or substituted or unsubstituted alkyl;

$R^{2B}$ is selected from the group consisting of substituted or unsubstituted alkyl, substituted or unsubstituted cycloalkyl, and substituted or unsubstituted heterocyclyl;

m is 0, 1, or 2;

p is 0, 1, or 2;

each $R^{1a}$ is independently selected from the group consisting of halo and substituted or unsubstituted alkyl;

each $R^{1a}$ is independently selected from the group consisting of halo, cyano, substituted or unsubstituted alkyl, substituted or unsubstituted alkenyl, and substituted or unsubstituted alkoxy; and $R^4$ is H.

In another aspect, provided is a compound of Formula (Ik-2), or a pharmaceutically acceptable salt thereof:

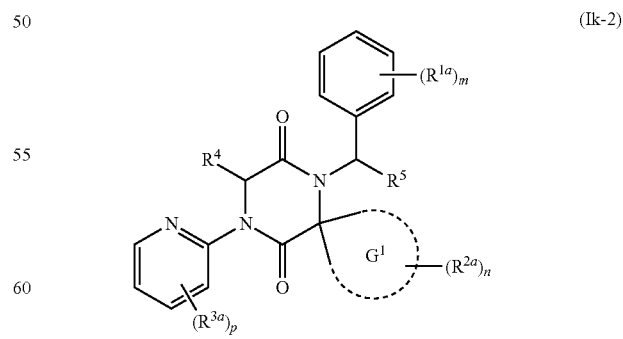

(Ik-2)

wherein:

$G^1$ is selected from the group consisting of substituted or unsubstituted cycloalkyl and substituted or unsubstituted heterocyclyl;

each $R^{1a}$ is independently selected from the group consisting of halo and substituted or unsubstituted alkyl;

each $R^{2a}$ is independently selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminothionyl, substituted or unsubstituted aminocarbonylamino, and substituted or unsubstituted alkyl;

each $R^{3a}$ is independently selected from the group consisting of halo, cyano, and substituted or unsubstituted alkyl, $R^4$ is H;

$R^5$ is H or substituted or unsubstituted alkyl;

m is 0, 1, or 2;

n is 0, 1, or 2; and p is 0, 1, or 2.

In another aspect, provided is a compound of Formula (II), or a pharmaceutically acceptable salt thereof:

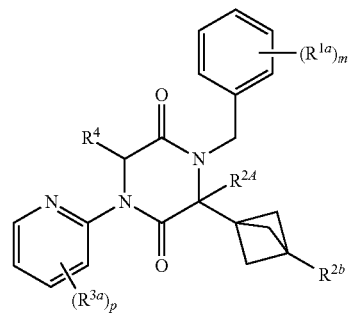

(II)

wherein:

$R^{2A}$ is H or substituted or unsubstituted alkyl;

$R^{2b}$ is selected from the group consisting of H, substituted or unsubstituted alkyl, substituted or unsubstituted alkoxycarbonyl, substituted or unsubstituted aminoacyl, and hydroxy;

m is 0, 1, or 2;

p is 0, 1, or 2;

each $R^{1a}$ is independently selected from the group consisting of halo and substituted or unsubstituted alkyl;

each $R^{1a}$ is independently halo; and $R^4$ is H.

In another aspect, provided is a compound of Formula (Im), or a pharmaceutically acceptable salt thereof:

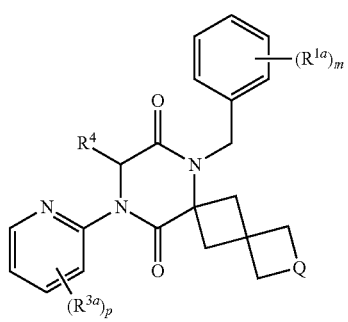

(Im)

wherein:

Q is —O— or —N($R^{2b}$)—;

$R^{2b}$ is selected from the group consisting of H and substituted or unsubstituted acyl;

m is 0, 1, or 2;

p is 0, 1, or 2;

each $R^{1a}$ is independently selected from the group consisting of halo and substituted or unsubstituted alkyl;

each $R^{1a}$ is independently halo; and $R^4$ is H.

In another aspect, provided is a compound of Formula (In-1), or a pharmaceutically acceptable salt thereof:

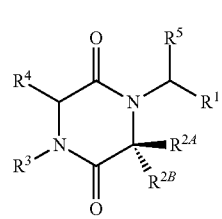

(In-1)

wherein:

$R^1$ is selected from the group consisting of substituted or unsubstituted phenyl and substituted or unsubstituted pyridyl;

$R^{2A}$, $R^{2B}$, and $R^3$ are defined by any one of (i)-(iii):

(i) $R^{2A}$ is H or substituted or unsubstituted alkyl;

$R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and $R^3$ is substituted or unsubstituted phenyl or substituted or unsubstituted pyridyl;

or (ii) $R^{2A}$ is H or substituted or unsubstituted alkyl;

$R^{2B}$ is substituted or unsubstituted phenyl or substituted or unsubstituted pyridyl; and $R^3$ is substituted or unsubstituted alkyl;

or (iii) $R^{2A}$ and $R^{2B}$ are taken together with the carbon atom to which they are attached to form $G^1$, wherein $G^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; and $R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;

$R^4$ is H or substituted or unsubstituted alkyl; and $R^5$ is H or substituted or unsubstituted alkyl;

wherein, when one or more of provisions (a)-(c) apply, then $R^1$ is substituted or unsubstituted pyridyl or phenyl substituted with at least one substituent other than methyl or methoxy:

(a) $R^{2A}$ and $R^{2B}$ are as defined by (i) and $R^3$ is substituted or unsubstituted phenyl;

(b) $R^{2A}$ and $R^3$ are as defined by (ii) and $R^{2B}$ is 4-methoxyphenyl;
(c) $R^{2A}$, and $R^{2B}$— are as defined by (iii) and $R^3$ is 4-methoxyphenylmethyl.

In another aspect, provided is a compound of Formula (In-2), or a pharmaceutically acceptable salt thereof:

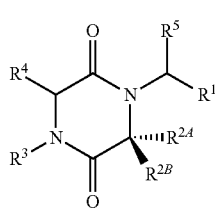

(In-2)

wherein:
$R^1$ is selected from the group consisting of substituted or unsubstituted phenyl and substituted or unsubstituted pyridyl;
$R^{2A}$, $R^{2B}$, and $R^3$ are defined by any one of (i)-(iii):
(i) $R^{2A}$ is H or substituted or unsubstituted alkyl;
$R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and
$R^3$ is substituted or unsubstituted phenyl or substituted or unsubstituted pyridyl;
or
(ii) $R^{2A}$ is H or substituted or unsubstituted alkyl;
$R^{2B}$ is substituted or unsubstituted phenyl or substituted or unsubstituted pyridyl; and
$R^3$ is substituted or unsubstituted alkyl;
or
(iii) $R^{2A}$ and $R^{2B}$ are taken together with the carbon atom to which they are attached to form $G^1$, wherein $G^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; and
$R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;
$R^4$ is H or substituted or unsubstituted alkyl; and
$R^5$ is H or substituted or unsubstituted alkyl;
wherein, when one or more of provisions (a)-(c) apply, then $R^1$ is substituted or unsubstituted pyridyl or phenyl substituted with at least one substituent other than methyl or methoxy:
(a) $R^{2A}$ and $R^{2B}$ are as defined by (i) and $R^3$ is substituted or unsubstituted phenyl;
(b) $R^{2A}$ and $R^3$ are as defined by (ii) and $R^{2B}$ is 4-methoxyphenyl;
(c) $R^{2A}$, and $R^{2B}$— are as defined by (iii) and $R^3$ is 4-methoxyphenylmethyl.

Provided in some embodiments are compounds selected from the group consisting of compounds of Table 1, or a pharmaceutically acceptable salt thereof.

Provided in some aspects is a pharmaceutical composition containing a compound of Formula (I) or any variation thereof, or a pharmaceutically acceptable salt thereof, and a pharmaceutically acceptable excipient.

Provided in some aspects are methods of treating heart disease in a subject in need thereof, the method comprising administering to the subject a compound of Formula (I) or any variation thereof, or a pharmaceutically acceptable salt thereof, or a pharmaceutical composition containing a compound of Formula (I) or any variation thereof or a pharmaceutically acceptable salt thereof. In some embodiments, the heart disease is hypertrophic cardiomyopathy (HCM). In some embodiments, the HCM is obstructive or nonobstructive or is caused by sarcomeric and/or non-sarcomeric mutations. In some embodiments, the heart disease is heart failure with preserved ejection fraction (HFpEF). In some embodiments, the heart disease is selected from the group consisting of diastolic dysfunction, primary or secondary restrictive cardiomyopathy, myocardial infarction, angina pectoris, and left ventricular outflow tract obstruction. In some embodiments, the heart disease is hypertensive heart disease, congenital heart disease, cardiac ischemia, coronary heart disease, diabetic heart disease, congestive heart failure, right heart failure, cardiorenal syndrome, or infiltrative cardiomyopathy. In some embodiments, the heart disease is a condition that is or is related to cardiac senescence and/or diastolic dysfunction due to aging. In some embodiments, the heart disease is a condition that is or is related to left ventricular hypertrophy and/or concentric left ventricular remodeling.

Provided in other aspects are methods of treating a disease or condition associated with HCM in a subject in need thereof, wherein the method comprises administering to the subject a compound of Formula (I) or any variation thereof, or a pharmaceutically acceptable salt thereof, or a pharmaceutical composition containing a compound of Formula (I) or any variation thereof or a pharmaceutically acceptable salt thereof. In some embodiments, the disease or condition is selected from the group consisting of Fabry's Disease, Danon Disease, mitochondrial cardiomyopathies, and Noonan Syndrome.

Provided in some aspects are methods of treating a disease or condition that is associated with secondary left ventricular wall thickening in a subject in need thereof, wherein the method comprises administering to the subject a compound of Formula (I) or any variation thereof, or a pharmaceutically acceptable salt thereof, or a pharmaceutical composition containing a compound of Formula (I) or any variation thereof or a pharmaceutically acceptable salt thereof. In some embodiments, the disease or condition is selected from the group consisting of hypertension, valvular heart diseases (such as aortic stenosis and Mitral valve regurgitation), metabolic syndromes (such as diabetes and obesity), end stage renal disease, scleroderma, sleep apnea, amyloidosis, Fabry's disease, Friedreich Ataxia, Danon disease, Noonan syndrome, and Pompe disease.

Provided in other aspects are methods of treating a disease or condition that is associated with small left ventricular cavity and cavity obliteration, hyperdynamic left ventricular contraction, myocardial ischemia, or cardiac fibrosis. Also provided are methods of treating muscular dystrophies (e.g., Duchenne muscular dystrophy) or glycogen storage diseases.

Also provided are methods of inhibiting the cardiac sarcomere, wherein the method involves contacting the cardiac sarcomere with a compound of Formula (I) or any variation thereof, or a pharmaceutically acceptable salt thereof, or a pharmaceutical composition containing a compound of Formula (I) or any variation thereof or a pharmaceutically acceptable salt thereof.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (Ia), (Ib), (Ic), (Id), (Ie), (If), (Ig), (Ih), (Ii), (Ij), (Ik-1), (Ik-2), (Il), (Im), (In-1), and (In-2), including all substructures, subgenera, preferences, embodiments, examples and particular compounds defined and/or described herein. References to a compound of Formula (I) and subgroups thereof, such as Formula (Ia), (Ib), (Ic), (Id), (Ie), (If), (Ig), (Ih), (Ii), (Ij), (Ik-1), (Ik-2), (Il), (Im), (In-1), and (In-2), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (Ia), (Ib), (Ic), (Id), (Ie), (If), (Ig), (Ih), (Ii), (Ij), (Ik-1), (Ik-2), (Il), (Im), (In-1), and (In-2), include polymorphs, solvates, co-crystals, isomers, tautomers and/or oxides thereof. In some embodiments, references to a compound of Formula (I) and subgroups thereof, such as Formula (Ia), (Ib), (Ic), (Id), (Ie), (If), (Ig), (Ih), (Ii), (Ij), (Ik-1), (Ik-2), (Il), (Im), (In-1), and (In-2), include polymorphs, solvates, and/or co-crystals thereof. In some embodiments, references to a compound of Formula (I) and subgroups thereof, such as Formula (Ia), (Ib), (Ic), (Id), (Ie), (If), (Ig), (Ih), (Ii), (Ij), (Ik-1), (Ik-2), (Il), (Im), (In-1), and (In-2), include isomers, tautomers and/or oxides thereof. In some embodiments, references to a compound of Formula (I) and subgroups thereof, such as Formula (Ia), (Ib), (Ic), (Id), (Ie), (If), (Ig), (Ih), (Ii), (Ij), (Ik-1), (Ik-2), (Il), (Im), (In-1), and (In-2), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Cycloalkynyl" refers to an unsaturated hydrocarbon group within a cycloalkyl having at least one site of acetylenic unsaturation (i.e., having at least one moiety of the formula CC). Cycloalkynyl can consist of one ring, such as cyclooctyne, or multiple rings. One cycloalkynyl moiety is an unsaturated cyclic hydrocarbon having from 5 to 10 annular carbon atoms (a "$C_5$-$C_{10}$ cycloalkynyl"). Examples include cyclopentyne, cyclohexyne, cycloheptyne, cyclooctyne, cyclononyne, and the like.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

The term "heterocycle," "heterocyclyl," or "heterocyclic" refers to a saturated, partially unsaturated, or unsaturated 4-12 membered ring containing at least one heteroatom independently selected from nitrogen, oxygen, and sulfur. Unless otherwise specified, the heteroatom may be carbon or nitrogen linked, a —CH$_2$— group can optionally be replaced by a —C(O)—, and a ring sulfur atom may be optionally oxidized to form a sulfinyl or sulfonyl group. Heterocycles can be aromatic (heteroaryls) or non-aromatic. In addition, not all rings of a polycyclic heterocyclyl group may be aromatic (e.g., aryl or heteroaryl). For example, a 1,2,3,4-tetrahydroquinolin-1-yl group and a 1,2,3,4-tetrahydroquinolin-8-yl group are both considered a heterocyclyl group.

"Heterocycle," "heterocyclyl," or "heterocyclic" also includes bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

"Halogen" or "halo" refers to fluoro, chloro, bromo or iodo.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxyl group protected with a hydroxyl protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocyclyl, aralkyl, aminosulfonyl, sulfonylamino, sulfonyl, oxo, and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^{2}$H, $^{3}$H, $^{11}$C, $^{13}$C and/or $^{14}$C. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to modulate the cardiac sarcomere. As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of the cardiac sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I), or pharmaceutically acceptable salts thereof:

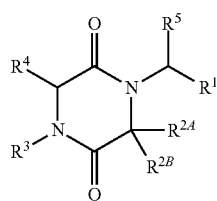

(I)

wherein:
$R^1$ is selected from the group consisting of substituted or unsubstituted phenyl and substituted or unsubstituted pyridyl;
$R^{2A}$, $R^{2B}$, and $R^3$ are defined by any one of (i)-(iii):
  (i) $R^{2A}$ is H or substituted or unsubstituted alkyl;
    $R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and
    $R^3$ is substituted or unsubstituted phenyl or substituted or unsubstituted pyridyl;
  or
  (ii) $R^{2A}$ is H or substituted or unsubstituted alkyl;
    $R^{2B}$ is substituted or unsubstituted phenyl or substituted or unsubstituted pyridyl; and
    $R^3$ is substituted or unsubstituted alkyl;
  or
  (iii) $R^{2A}$ and $R^{2B}$ are taken together with the carbon atom to which they are attached to form $G^1$, wherein $G^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; and
    $R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;
$R^4$ is H or substituted or unsubstituted alkyl; and
$R^5$ is H or substituted or unsubstituted alkyl;
wherein, when one or more of provisions (a)-(c) apply, then $R^1$ is substituted or unsubstituted pyridyl or phenyl substituted with at least one substituent other than methyl or methoxy:
  (a) $R^{2A}$ and $R^{2B}$ are as defined by (i) and $R^3$ is substituted or unsubstituted phenyl;
  (b) $R^{2A}$ and $R^3$ are as defined by (ii) and $R^{2B}$ is 4-methoxyphenyl;
  (c) $R^{2A}$ and $R^{2B}$ are as defined by (iii) and $R^3$ is 4-methoxyphenylmethyl.

In some embodiments of Formula (I), $R^4$ and $R^5$ are each independently H. In some embodiments of Formula (I), at least one of $R^4$ and $R^5$ is other than H. In some embodiments of Formula (I), $R^4$ is substituted or unsubstituted alkyl. In some embodiments of Formula (I), $R^4$ is methyl. In some embodiments of Formula (I), $R^4$ is alkyl substituted with alkoxy. In some embodiments of Formula (I), $R^4$ is methoxymethyl. In some embodiments of Formula (I), $R^5$ is substituted or unsubstituted alkyl. In some embodiments of Formula (I), $R^5$ is methyl. In some embodiments of Formula (I), $R^5$ is substituted alkyl. In some embodiments of Formula (I), $R^5$ is hydroxymethyl.

In some embodiments of Formula (I), $R^1$ is unsubstituted pyridyl or unsubstituted phenyl. In some embodiments of Formula (I), $R^1$ is 2-pyridyl. In some embodiments of Formula (I), $R^1$ is phenyl or pyridinyl, each of which is substituted with one or more (e.g., 1 or 2 or 3 or 1-4 or 1-3 or 2-4) substituents independently selected from the group consisting of cyano, halo, substituted or unsubstituted alkoxy, substituted or unsubstituted alkyl, and substituted or unsubstituted diazirinyl. In some embodiments of Formula (I), $R^1$ is pyridyl substituted with one or two halo selected from the group consisting of F and Cl. In some embodiments of Formula (I), $R^1$ is pyridyl substituted with —$CF_3$. In some embodiments of Formula (I), $R^1$ is phenyl substituted with one or more (e.g., 1 or 2 or 3 or 1-4 or 1-3 or 2-4) halo selected from the group consisting of F and Cl. In some embodiments of Formula (I), $R^1$ is phenyl substituted with one or more (e.g., 1 or 2 or 3 or 1-4 or 1-3 or 2-4) methyl. In some embodiments of Formula (I), $R^1$ is phenyl substituted with one or more (e.g., 1 or 2 or 3 or 1-4 or 1-3 or 2-4) cyano. In some embodiments of Formula (I), $R^1$ is phenyl substituted with one or more (e.g., 1 or 2 or 3 or 1-4 or 1-3 or 2-4) —$CF_3$. In some embodiments of Formula (I), $R^1$ is phenyl substituted with one halo and one cyano. In some embodiments of Formula (I), $R^1$ is phenyl substituted with one $C_1$ and one F. In some embodiments of Formula (I), $R^1$ is phenyl substituted with one halo and one —$CF_3$. In some embodiments of Formula (I), $R^1$ is phenyl substituted with diazirinyl. In some embodiments of Formula (I), $R^1$ is phenyl substituted with diazirinyl substituted with trifluoromethyl.

In some embodiments of Formula (I), the carbon bearing the $R^{2A}$ and $R^{2B}$ moieties is in the "S" stereochemical configuration. In some embodiments of Formula (I), the carbon bearing the $R^{2A}$ and $R^{2B}$ moieties is in the "R" stereochemical configuration. It is understood that for any of the embodiments of formula (I) and subformulae thereof provided herein, the disclosure includes embodiments wherein the carbon bearing the $R^{2A}$ and $R^{2B}$ moieties is in the "S" stereochemical configuration and embodiments wherein the carbon bearing the $R^{2A}$ and $R^{2B}$ moieties is in the "R" stereochemical configuration.

It is understood that each of variables described herein may be combined with the other variables the same as if each and every combination were specifically and individually listed. For example, each $R^1$ of Formula (I) may be combined with each of $R^{2A}$, $R^{2B}$, $R^3$, $R^4$, and $R^5$ either individually or collectively. It is also understood that this applies to Formula (I) and each of the subgroups: Formula (Ia), (Ib), (Ic), (Id), (Ie), (If), (Ig), (Ih), (Ii), (Ij), (Ik-1), (Ik-2), (Il), (Im), (In-1), and (In-2) described herein.

In another aspect, the compound of Formula (I) is a compound of Formula (Ia), or a pharmaceutically acceptable salt thereof:

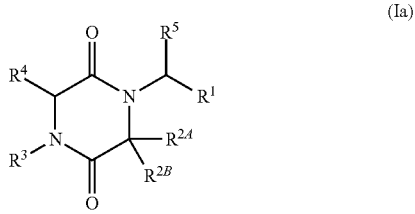

(Ia)

wherein $R^1$ is selected from the group consisting of substituted or unsubstituted phenyl and substituted or unsubstituted pyridyl; $R^{2A}$ is H or substituted or unsubstituted alkyl; $R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; $R^3$ is substituted or unsubstituted phenyl or substituted or unsubstituted pyridyl; $R^4$ is H or substituted or unsubstituted alkyl; and $R^5$ is H or substituted or unsubstituted alkyl; wherein, when $R^3$ is substituted or unsubstituted phenyl, $R^1$ is substituted or unsubstituted pyridyl or phenyl substituted with at least one substituent other than methyl or methoxy.

In some embodiments of Formula (Ia), $R^4$ and $R^5$ are each independently H. In some embodiments of Formula (Ia), at least one of $R^4$ and $R^5$ is other than H.

In some embodiments of Formula (Ia), $R^3$ is substituted or unsubstituted pyridyl. In some embodiments of Formula (Ia), $R^3$ is 2-pyridyl. In some embodiments of Formula (Ia), $R^3$ is unsubstituted phenyl. In some embodiments of Formula (Ia), $R^3$ is phenyl or pyridyl, each of which is substituted with one or more (e.g., 1 or 2 or 3 or 1-4 or 1-3 or 2-4) halo substituents selected from the group consisting of F and Cl. In some embodiments of Formula (Ia), $R^3$ is phenyl or pyridyl, each of which is substituted with two halo substituents selected from the group consisting of F and Cl. In some embodiments of Formula (Ia), $R^3$ is phenyl or pyridyl, each of which is substituted with two F. In some embodiments of Formula (Ia), $R^3$ is phenyl or pyridyl, each of which is substituted with two Cl. In some embodiments of Formula (Ia), $R^3$ is phenyl or pyridyl, each of which is substituted with one F and one Cl. In some embodiments of Formula (Ia), $R^3$ is phenyl or pyridyl, each of which is substituted with one or more (e.g., 1 or 2 or 3 or 1-4 or 1-3 or 2-4) CN substituents. In some embodiments of Formula (Ia), $R^3$ is phenyl or pyridyl, each of which is substituted with two CN substituents. In some embodiments of Formula (Ia), $R^3$ is phenyl or pyridyl, each of which is substituted with one halo and one CN substituents. In some embodiments of Formula (Ia), $R^3$ is phenyl or pyridyl, each of which is substituted with one Cl and one CN. In some embodiments of Formula (Ia), $R^3$ is phenyl or pyridyl, each of which is substituted with one F and one CN.

In some embodiments of Formula (Ia), $R^{2A}$ is H. In some embodiments of Formula (Ia), $R^{2A}$ is substituted or unsubstituted alkyl. In some embodiments of Formula (Ia), $R^{2A}$ is substituted or unsubstituted methyl. In some embodiments of Formula (Ia), $R^{2A}$ is methyl.

In some embodiments of Formula (Ia), $R^{2B}$ is H. In some embodiments of Formula (Ia), $R^{2B}$ is substituted or unsubstituted alkyl. In some embodiments of Formula (Ia), $R^{2B}$ is selected from the group consisting of methyl, isopropyl, and propyl. In some embodiments of Formula (Ia), $R^{2B}$ is alkyl substituted with hydroxyl or substituted or unsubstituted alkoxy. In some embodiments of Formula (Ia), $R^{2B}$ is hydroxymethyl. In some embodiments of Formula (Ia), $R^{2B}$ is substituted alkoxyalkyl. In some embodiments of Formula (Ia), $R^{2B}$ is trifluoromethoxymethyl. In some embodiments of Formula (Ia), $R^{2B}$ is substituted or unsubstituted cycloalkyl. In some embodiments of Formula (Ia), $R^{2B}$ is substituted or unsubstituted $C_3$-$C_7$ cycloalkyl. In some embodiments of Formula (Ia), $R^{2B}$ is cyclobutanyl. In some embodiments of Formula (Ia), $R^{2B}$ is substituted or unsubstituted heterocyclyl. In some embodiments of Formula (Ia), $R^{2B}$ is substituted or unsubstituted $C_3$-$C_7$ heterocyclyl. In some embodiments of Formula (Ia), $R^{2B}$ is substituted or unsubstituted $C_3$-$C_7$ heterocyclyl, which contains one or more (e.g., 1 or 2 or 3 or 1-4 or 1-3 or 2-4) of N or O annular atoms. In some embodiments of Formula (Ia), $R^{2B}$ is oxetanyl. In some embodiments of Formula (Ia), $R^{2B}$ is 3-oxetanyl.

In some embodiments of Formula (Ia), $R^1$ is substituted or unsubstituted pyridyl. In some embodiments of Formula (Ia), $R^1$ is 2-pyridyl. In some embodiments of Formula (Ia), $R^1$ is unsubstituted phenyl. In some embodiments of Formula (Ia), $R^1$ is phenyl or pyridyl, each of which is substituted with one or more (e.g., 1 or 2 or 3 or 1-4 or 1-3 or 2-4) substituents independently selected from the group consisting of cyano, halo, alkoxy, —$CF_3$, alkyl, and diazirinyl. In some embodiments of Formula (Ia), $R^1$ is phenyl or pyridyl each of which is substituted with substituted alkyl. In some embodiments of Formula (Ia), $R^1$ is phenyl or pyridyl each of which is substituted with —$CF_3$. In some embodiments of Formula (Ia), $R^1$ is phenyl substituted with 4-$CF_3$.

In some embodiments of Formula (Ia), $R^1$ is phenyl substituted with —$CF_3$ and $R^3$ is phenyl substituted with two halo substituents. In some embodiments of Formula (Ia), $R^1$ is phenyl substituted with —$CF_3$ and $R^3$ is phenyl substituted with one halo and one CN. In some embodiments of Formula (Ia), $R^1$ is substituted or unsubstituted pyridyl and $R^3$ is phenyl substituted with two halo. In some embodiments of Formula (Ia), $R^1$ is substituted or unsubstituted pyridyl and $R^3$ is phenyl substituted with one halo and one CN. In some embodiments of Formula (Ia), $R^1$ is 2-pyridyl and $R^3$ is phenyl substituted with two halo. In some embodiments of Formula (Ia), $R^1$ is 2-pyridyl and $R^3$ is phenyl substituted with one halo and one CN. In some embodiments of Formula (Ia), $R^1$ is phenyl substituted with —$CF_3$ and $R^3$ is phenyl.

In some embodiments of Formula (Ia), $R^1$ is phenyl substituted with —$CF_3$, $R^{2A}$ is H, $R^{2B}$ is 3-oxetanyl, $R^3$ is phenyl substituted with one or more substituents selected from the group consisting of F and Cl, $R^4$ is H, and $R^5$ is H. In some embodiments of Formula (Ia), $R^1$ is phenyl substituted with —$CF_3$, $R^{2A}$ is H, $R^{2B}$ is 3-oxetanyl, $R^3$ is pyridyl substituted with one or more substituents selected from the group consisting of F and Cl, $R^4$ is H, and $R^5$ is H. In some embodiments of Formula (Ia), $R^1$ is phenyl substituted with —$CF_3$, $R^{2A}$ is H, $R^{2B}$ is isopropyl, $R^3$ is phenyl substituted with one or more substituents selected from the group consisting of F and Cl, $R^4$ is H, and $R^5$ is H. In some embodiments of Formula (Ia), $R^1$ is phenyl substituted with —$CF_3$, $R^{2A}$ is H, $R^{2B}$ is isopropyl, $R^3$ is pyridyl substituted with one or more substituents selected from the group consisting of F and Cl, $R^4$ is H, and $R^5$ is H.

In some embodiments of Formula (Ia): $R^4$ and $R^5$ are each independently H; $R^3$ is phenyl or pyridyl, each of which is substituted with two halo substituents selected from the group consisting of F and Cl; $R^{2A}$ is H or methyl; $R^{2B}$ is selected from the group consisting of methyl, isopropyl, propyl, hydroxymethyl, trifluoromethoxymethyl, cyclobutanyl, and 3-oxetanyl; and $R^1$ is phenyl or pyridyl, each of which is substituted with —$CF_3$.

In another aspect, the compound of Formula (I) is a compound of Formula (Ib), or a pharmaceutically acceptable salt thereof:

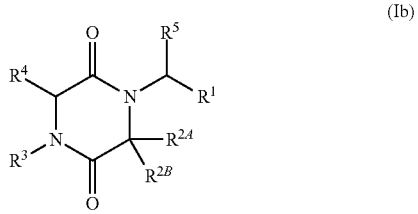

(Ib)

wherein $R^1$ is selected from the group consisting of substituted or unsubstituted phenyl and substituted or unsubstituted pyridyl; $R^{2A}$ is H or substituted or unsubstituted alkyl; $R^{2B}$ is substituted or unsubstituted phenyl or substituted or unsubstituted pyridyl; $R^3$ is substituted or unsubstituted alkyl; $R^4$ is H or substituted or unsubstituted alkyl; and $R^5$ is H or substituted or unsubstituted alkyl; wherein, when $R^{2B}$ is 4-methoxyphenyl, $R^1$ is substituted or unsubstituted pyridyl or phenyl substituted with at least one substituent other than methyl or methoxy.

In some embodiments of Formula (Ib), $R^4$ and $R^5$ are each independently H. In some embodiments of Formula (Ib), at least one of $R^4$ and $R^5$ is other than H.

In some embodiments of Formula (Ib), $R^{2A}$ is H. In some embodiments of Formula (Ib), $R^{2A}$ is substituted or unsubstituted alkyl. In some embodiments of Formula (Ib), $R^{2A}$ is substituted or unsubstituted methyl. In some embodiments of Formula (Ia), $R^{2A}$ is methyl.

In some embodiments of Formula (Ib), $R^{2B}$ is substituted or unsubstituted pyridyl. In some embodiments of Formula (Ib), $R^{2B}$ is 2-pyridyl. In some embodiments, $R^{2B}$ is substituted or unsubstituted phenyl. In some embodiments of Formula (Ib), $R^{2B}$ is phenyl or pyridyl, each of which is substituted with one or more (e.g., 1 or 2 or 3 or 1-4 or 1-3 or 2-4) substituents independently selected from the group consisting of halo, substituted or unsubstituted alkoxy, and substituted or unsubstituted alkyl. In some embodiments of Formula (Ib), $R^{2B}$ is pyridyl substituted with one or more substituents (e.g., 1 or 2 or 3 or 1-4 or 1-3 or 2-4) selected from the group consisting of halo and substituted or unsubstituted alkyl. In some embodiments of Formula (Ib), $R^{2B}$ is pyridyl substituted with one or more (e.g., 1 or 2 or 3 or 1-4 or 1-3 or 2-4) halo. In some embodiments of Formula (Ib), $R^{2B}$ is phenyl substituted with one or more (e.g., 1 or 2 or 3 or 1-4 or 1-3 or 2-4) halo. In some embodiments of Formula (Ib), $R^{2B}$ is phenyl substituted with one or more (e.g., 1 or 2 or 3 or 1-4 or 1-3 or 2-4) —$CF_3$. In some embodiments of Formula (Ib), $R^{2B}$ is phenyl substituted with one or more (e.g., 1 or 2 or 3 or 1-4 or 1-3 or 2-4) alkoxy. In some embodiments of Formula (Ib), $R^{2B}$ is phenyl substituted with one or more (e.g., 1 or 2 or 3 or 1-4 or 1-3 or 2-4) methoxy.

In some embodiments of Formula (Ib), $R^3$ is substituted or unsubstituted $C_1$-$C_{10}$ alkyl. In some embodiments of Formula (Ib), $R^3$ is unsubstituted $C_1$-$C_{10}$ alkyl. In some embodiments of Formula (Ib), $R^3$ is unsubstituted $C_2$-$C_6$ alkyl. In some embodiments of Formula (Ib), $R^3$ is unsubstituted $C_3$-$C_5$ alkyl. In some embodiments of Formula (Ib), $R^3$ is unsubstituted $C_3$ alkyl. In some embodiments of Formula (Ib), $R^3$ is unsubstituted isopropyl.

In some embodiments of Formula (Ib), $R^1$ is substituted or unsubstituted pyridyl. In some embodiments of Formula (Ib), $R^1$ is 2-pyridyl. In some embodiments of Formula (Ib), $R^1$ is substituted or unsubstituted phenyl. In some embodiments of Formula (Ib), $R^1$ is phenyl or pyridinyl, each of which is substituted with one or more substituents (e.g., 1 or 2 or 3 or 1-4 or 1-3 or 2-4) independently selected from the group consisting of cyano, halo, substituted or unsubstituted alkoxy, substituted or unsubstituted alkyl, and substituted or unsubstituted diazirinyl. In some embodiments of Formula (Ib), $R^1$ is pyridyl substituted with one or more (e.g., 1 or 2 or 3 or 1-4 or 1-3 or 2-4) halo. In some embodiments of Formula (Ib), $R^1$ is pyridyl substituted with one or more (e.g., 1 or 2 or 3 or 1-4 or 1-3 or 2-4) —$CF_3$. In some embodiments of Formula (Ib), $R^1$ is phenyl substituted with one or more (e.g., 1 or 2 or 3 or 1-4 or 1-3 or 2-4) halo. In some embodiments of Formula (Ib), $R^1$ is phenyl substituted with one or more (e.g., 1 or 2 or 3 or 1-4 or 1-3 or 2-4) —$CF_3$. In some embodiments of Formula (Ib), $R^1$ is phenyl substituted with one or more (e.g., 1 or 2 or 3 or 1-4 or 1-3 or 2-4) —CN. In some embodiments of Formula (Ib), $R^1$ is phenyl substituted with one or more (e.g., 1 or 2 or 3 or 1-4 or 1-3 or 2-4) methyl.

In some embodiments of Formula (Ib), $R^{2B}$ is 4-methoxyphenyl and $R^1$ is substituted or unsubstituted pyridyl. In some embodiments of Formula (Ib), $R^{2B}$ is 4-methoxyphenyl and $R^1$ is 2-pyridyl. In some embodiments of Formula (Ib), $R^{2B}$ is 4-methoxyphenyl and $R^1$ is 2-pyridyl substituted with one or more (e.g., 1 or 2 or 3 or 1-4 or 1-3 or 2-4) halo. In some embodiments of Formula (Ib), $R^{2B}$ is 4-methoxyphenyl and $R^1$ is phenyl substituted with one or more (e.g., 1 or 2 or 3 or 1-4 or 1-3 or 2-4) halo. In some embodiments of Formula (Ib), $R^{2B}$ is 4-methoxyphenyl and $R^1$ is phenyl substituted with 4-$C_1$.

In some embodiments of Formula (Ib), $R^1$ is pyridyl substituted with one or more substituents independently selected from the group consisting of halo and —$CF_3$, $R^{2A}$ is H, $R^{2B}$ is pyridyl substituted with one or more substituents selected from the group consisting of F and $C_1$, $R^3$ is isopropyl, $R^4$ is H, and $R^5$ is H. In some embodiments of Formula (Ib), $R^1$ is phenyl substituted with one or more substituents independently selected from the group consisting of halo, —$CF_3$, —CN, and methyl, $R^{2A}$ is H, $R^{2B}$ is pyridyl substituted with one or more substituents selected from the group consisting of F and Cl, $R^3$ is isopropyl, $R^4$ is H, and $R^5$ is H. In some embodiments of Formula (Ib), $R^1$ is pyridyl substituted with one or more substituents independently selected from the group consisting of halo and —$CF_3$, $R^{2A}$ is methyl, $R^{2B}$ is pyridyl substituted with one or more substituents selected from the group consisting of F and Cl, $R^3$ is isopropyl, $R^4$ is H, and $R^5$ is H. In some embodiments of Formula (Ib), $R^1$ is phenyl substituted with one or more substituents independently selected from the group consisting of halo, —$CF_3$, —CN, and methyl, $R^{2A}$ is methyl, $R^{2B}$ is pyridyl substituted with one or more substituents selected from the group consisting of F and Cl, $R^3$ is isopropyl, $R^4$ is H, and $R^5$ is H.

In another aspect, the compound of Formula (I) is a compound of Formula (Ic), or a pharmaceutically acceptable salt thereof:

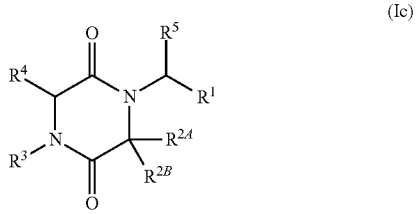

(Ic)

wherein $R^1$ is selected from the group consisting of substituted or unsubstituted pyridyl and substituted or unsubstituted phenyl; $R^{2A}$ and $R^{2B}$ are taken together with the carbon atom to which they are attached to form $G^1$, wherein $G^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; $R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; $R^4$ is H or substituted or unsubstituted alkyl; and $R^5$ is H or substituted or unsubstituted alkyl; wherein, when $R^3$ is 4-methoxyphenylmethyl, $R^1$ is substituted or unsubstituted pyridyl or phenyl substituted with at least one substituent other than methyl or methoxy.

In some embodiments of Formula (Ic), $R^4$ and $R^5$ are each independently H. In some embodiments of Formula (Ic), at least one of $R^4$ and $R^5$ is other than H. In some embodiments of Formula (Ic), $R^4$ is substituted or unsubstituted alkyl. In some embodiments of Formula (Ic), $R^4$ is methyl. In some embodiments of Formula (Ic), $R^4$ is alkyl substituted with alkoxy. In some embodiments of Formula (Ic), $R^4$ is methoxymethyl. In some embodiments of Formula (Ic), $R^5$ is substituted or unsubstituted alkyl. In some embodiments of Formula (Ic), $R^5$ is methyl. In some embodiments of Formula (Ic), $R^5$ is substituted alkyl. In some embodiments of Formula (Ic), $R^5$ is hydroxymethyl.

In some embodiments of Formula (Ic), $G^1$ is selected from the group consisting of substituted or unsubstituted cycloalkyl, substituted or unsubstituted heterocyclyl, and substituted or unsubstituted 2,3-dihydro-1H-indene. In some embodiments of Formula (Ic), $G^1$ is substituted or unsubstituted $C_3$-$C_6$ cycloalkyl. In some embodiments of Formula (Ic), $G^1$ is substituted or unsubstituted $C_3$-$C_6$ heterocyclyl. In some embodiments of Formula (Ic), $G^1$ is substituted or unsubstituted cyclopropyl. In some embodiments of Formula (Ic), $G^1$ is substituted or unsubstituted cyclobutanyl. In some embodiments of Formula (Ic), $G^1$ is substituted or unsubstituted azetidinyl. In some embodiments of Formula (Ic), $G^1$ is substituted or unsubstituted tetrahydrofuranyl. In some embodiments of Formula (Ic), $G^1$ is substituted or unsubstituted pyrrolidinyl. In some embodiments of Formula (Ic), $G^1$ is substituted or unsubstituted pyrrolidin-2-one-yl.

In some embodiments of Formula (Ic), $G^1$ is heterocyclyl or cycloalkyl, each of which is substituted with one or more (e.g., 1 or 2 or 3 or 1-4 or 1-3 or 2-4) substituents selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminothionyl, substituted or unsubstituted aminocarbonylamino, and substituted or unsubstituted alkyl. In some embodiments of Formula (Ic), $G^1$ is heterocyclyl substituted with substituted or unsubstituted phenyl. In some embodiments of Formula (Ic), $G^1$ is heterocyclyl substituted with phenyl which is substituted with halo. In some embodiments of Formula (Ic), $G^1$ is heterocyclyl substituted with substituted or unsubstituted heteroaryl. In some embodiments of Formula (Ic), $G^1$ is heterocyclyl substituted with substituted or unsubstituted pyridyl. In some embodiments of Formula (Ic), $G^1$ is heterocyclyl substituted with pyridyl which is substituted one or more (e.g., 1 or 2 or 3 or 1-4 or 1-3 or 2-4) substituents selected from the group consisting of alkyl, CN, hydroxyl, alkoxycarbonyl, methoxycarbonyl, alkoxy, carboxyl, cycloalkyl, halo, and aminoacyl. In some embodiments of Formula (Ic), $G^1$ is heterocyclyl substituted with substituted or unsubstituted pyrimidyl. In some embodiments of Formula (Ic), $G^1$ is heterocyclyl substituted with substituted or unsubstituted pyrazolyl. In some embodiments of Formula (Ic), $G^1$ is heterocyclyl substituted with pyrazolyl which is substituted with alkyl. In some embodiments of Formula (Ic), $G^1$ is heterocyclyl substituted with substituted or unsubstituted thiazolyl. In some embodiments of Formula (Ic), $G^1$ is heterocyclyl substituted thiazolyl which is substituted with aminoacyl. In some embodiments of Formula (Ic), $G^1$ is heterocyclyl substituted with substituted or unsubstituted alkoxycarbonyl. In some embodiments of Formula (Ic), $G^1$ is heterocyclyl substituted with methoxycarbonyl. In some embodiments of Formula (Ic), $G^1$ is heterocyclyl substituted with substituted or unsubstituted aminoacyl. In some embodiments of Formula (Ic), $G^1$ is heterocyclyl substituted with methylaminoacyl. In some embodiments of Formula (Ic), $G^1$ is heterocyclyl substituted with aminoacyl which is substituted with one or more (e.g., 1 or 2 or 3 or 1-4 or 1-3 or 2-4) substituents selected from the group consisting of aryl, cycloalkyl, pyridyl, pyrazolyl, and alkoxyalkyl. In some embodiments of Formula (Ic), $G^1$ is heterocyclyl substituted with substituted or unsubstituted pyridin-on-yl. In some embodiments of Formula (Ic), $G^1$ is heterocyclyl substituted with pyridin-on-yl which is substituted with alkyl. In some embodiments of Formula (Ic), $G^1$ is heterocyclyl substituted with substituted or unsubstituted oxadiazolyl. In some embodiments of Formula (Ic), $G^1$ is heterocyclyl substituted with oxadiazolyl which is substituted with one or more (e.g., 1 or 2 or 3 or 1-4 or 1-3 or 2-4) substituents selected from the group consisting of alkyl and phenyl. In some embodiments of Formula (Ic), $G^1$ is heterocyclyl substituted with substituted or unsubstituted 9-membered bicyclic heterocyclyl. In some embodiments of Formula (Ic), $G^1$ is heterocyclyl substituted with —C(O)H. In some embodiments of Formula (Ic), $G^1$ is heterocyclyl substituted with substituted or unsubstituted pyridazinyl. In some embodiments of Formula (Ic), $G^1$ is heterocyclyl substituted with pyridazinyl which is substituted with one or more (e.g., 1 or 2 or 3 or 1-4 or 1-3 or 2-4) substituents selected from the group consisting of halo, alkoxy, alkyl, and aminoacyl. In some embodiments of Formula (Ic), $G^1$ is heterocyclyl substituted with substituted or unsubstituted aminothionyl. In some embodiments of Formula (Ic), $G^1$ is heterocyclyl substituted with aminothionyl which is substituted with alkyl. In some embodiments of Formula (Ic), $G^1$ is heterocyclyl substituted with substituted or unsubstituted acyl. In some embodiments of Formula (Ic), $G^1$ is heterocyclyl substituted with acyl which is substituted with one or more (e.g., 1 or 2 or 3 or 1-4 or 1-3 or 2-4) substituents selected from the group consisting of cycloalkyl, alkyl, and heterocyclyl. In some embodiments of Formula (Ic), $G^1$ is heterocyclyl substituted with acyl which is substituted with morpholinyl. In some embodiments of Formula (Ic), $G^1$ is heterocyclyl substituted with substituted or unsubstituted aminocarbonylamino. In some embodiments of Formula (Ic), $G^1$ is heterocyclyl substituted with aminocarbonylamino which is substituted with one or more (e.g., 1 or 2 or 3 or 1-4 or 1-3 or 2-4) substituents selected from the group consisting of cycloalkyl and heterocyclyl.

In some embodiments of Formula (Ic), $G^1$ is cycloalkyl substituted with substituted or unsubstituted phenyl. In some embodiments of Formula (Ic), $G^1$ is cycloalkyl substituted with substituted or unsubstituted thiazolyl. In some embodiments of Formula (Ic), $G^1$ is cycloalkyl substituted with thiazolyl which is substituted with alkyl. In some embodiments of Formula (Ic), $G^1$ is cycloalkyl substituted with substituted or unsubstituted oxazolyl. In some embodiments of Formula (Ic), $G^1$ is cycloalkyl substituted with oxazolyl which is substituted with alkyl. In some embodiments of Formula (Ic), $G^1$ is cycloalkyl substituted with substituted or unsubstituted aminoacyl. In some embodiments of Formula (Ic), $G^1$ is cycloalkyl substituted with aminoacyl which is substituted with one or more (e.g., 1 or 2 or 3 or 1-4 or 1-3 or 2-4) substituents selected from the group consisting of alkyl, heterocyclyl, and cycloalkyl. In some embodiments of Formula (Ic), $G^1$ is cycloalkyl substituted with substituted or unsubstituted oxadizaolyl. In some embodiments of Formula (Ic), $G^1$ is cycloalkyl substituted with oxadizaolyl which is substituted with one or more substituents (e.g., 1 or 2 or 3 or 1-4 or 1-3 or 2-4) selected from the group consisting of cycloalkyl and alkyl. In some embodiments of Formula (Ic), $G^1$ is cycloalkyl substituted with substituted or unsubstituted acyl. In some embodiments of Formula (Ic), $G^1$ is cycloalkyl substituted with acyl which is substituted with heterocyclyl. In some embodiments of Formula (Ic), $G^1$ is cycloalkyl substituted with substituted or unsubstituted aminocarbonylamino. In some embodiments of Formula (Ic), $G^1$ is cycloalkyl substituted with aminocarbonylamino which is substituted with one or more (e.g., 1 or 2 or 3 or 1-4 or 1-3 or 2-4) substituents selected from the group consisting of alkyl, cycloalkyl, and heterocyclyl. In some embodiments of Formula (Ic), $G^1$ is cycloalkyl substituted with substituted or unsubstituted alkoxycarbonyl. In some embodiments of Formula (Ic), $G^1$ is cycloalkyl substituted with alkoxycarbonyl which is substituted with alkyl. In some embodiments of Formula (Ic), $G^1$ is cycloalkyl substituted with substituted or unsubstituted alkyl. In some embodiments of Formula (Ic), $G^1$ is cycloalkyl substituted with alkyl which is substituted with hydroxyl. In some embodiments of Formula (Ic), $G^1$ is cycloalkyl substituted with hydroxyl.

In some embodiments of Formula (Ic), $R^3$ is selected from the group consisting of substituted or unsubstituted alkyl, substituted or unsubstituted cycloalkyl, substituted or unsubstituted heterocyclyl, and substituted or unsubstituted aryl. In some embodiments of Formula (Ic), $R^3$ is phenyl substituted with one or more (e.g., 1 or 2 or 3 or 1-4 or 1-3 or 2-4) substituents selected from the group consisting of nitro, alkoxy, halo, cycloalkyl, cyano, alkenyl, alkoxycarbonyl, phenylcarbonyl, and alkyl. In some embodiments of Formula (Ic), $R^3$ is cycloalkyl substituted with one or more (e.g., 1 or 2 or 3 or 1-4 or 1-3 or 2-4) substituents selected from the group consisting of alkyl, cyano, and halo. In some embodiments of Formula (Ic), $R^3$ is alkyl substituted with one or more (e.g., 1 or 2 or 3 or 1-4 or 1-3 or 2-4) substituents selected from the group consisting of alkoxy, cyano, and halo.

In some embodiments of Formula (Ic), $R^1$ is substituted or unsubstituted pyridyl. In some embodiments of Formula (Ic), $R^1$ is 2-pyridyl. In some embodiments of Formula (Ic), $R^1$ is substituted or unsubstituted phenyl. In some embodiments of Formula (Ic), $R^1$ is phenyl or pyridinyl, each of which is substituted with one or more (e.g., 1 or 2 or 3 or 1-4 or 1-3 or 2-4) substituents independently selected from the group consisting of cyano, halo, substituted or unsubstituted alkoxy, substituted or unsubstituted alkyl, and substituted or unsubstituted diazirinyl. In some embodiments of Formula (Ic), $R^1$ is phenyl substituted with one or more (e.g., 1 or 2 or 3 or 1-4 or 1-3 or 2-4) halo. In some embodiments of Formula (Ic), $R^1$ is phenyl substituted with one or more (e.g., 1 or 2 or 3 or 1-4 or 1-3 or 2-4) —$CF_3$. In some embodiments of Formula (Ic), $R^1$ is phenyl substituted with one or more (e.g., 1 or 2 or 3 or 1-4 or 1-3 or 2-4) methyl. In some embodiments of Formula (Ic), $R^1$ is phenyl substituted with one or more (e.g., 1 or 2 or 3 or 1-4 or 1-3 or 2-4) diazirinyl. In some embodiments of Formula (Ic), $R^1$ is phenyl substituted with trifluoromethyldiazirinyl.

In some embodiments of Formula (Ic), $R^1$ is phenyl substituted with Cl and $R^3$ is substituted with 4-methoxyphenylmethyl. In some embodiments of Formula (Ic), $R^1$ is phenyl substituted with F and $R^3$ is substituted with 4-methoxyphenylmethyl. In some embodiments of Formula (Ic), $R^1$ is phenyl substituted with —$CF_3$ and $R^3$ is substituted with 4-methoxyphenylmethyl. In some embodiments of Formula (Ic), $R^1$ is phenyl substituted with trifluoromethyldiazirinyl and $R^3$ is substituted with 4-methoxyphenylmethyl.

In another aspect, the compound of Formula (I) is a compound of Formula (Id), or a pharmaceutically acceptable salt thereof:

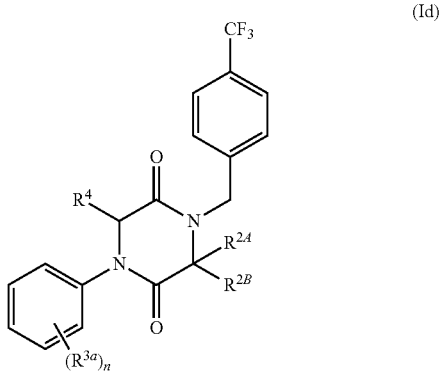

(Id)

wherein $R^{2A}$ is H or substituted or unsubstituted alkyl; $R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; n is 0, 1, or 2; each $R^{1a}$ is independently selected from the group consisting of halo and cyano; and $R^4$ is H.

In some embodiments of Formula (Id), $R^{2A}$ is H. In some embodiments of Formula (Id), $R^{2A}$ is substituted or unsubstituted alkyl. In some embodiments of Formula (Id), $R^{2A}$ is substituted or unsubstituted methyl. In some embodiments of Formula (Id), $R^{2A}$ is methyl.

In some embodiments of Formula (Id), $R^{2B}$ is H. In some embodiments of Formula (Id), $R^{2B}$ is substituted or unsubstituted alkyl. In some embodiments of Formula (Id), $R^{2B}$ is selected from the group consisting of methyl, isopropyl, and propyl. In some embodiments of Formula (Id), $R^{2B}$ is alkyl substituted with hydroxyl or substituted or unsubstituted alkoxy. In some embodiments of Formula (Id), $R^{2B}$ is hydroxymethyl. In some embodiments of Formula (Id), $R^{2B}$ is substituted alkoxyalkyl. In some embodiments of Formula (Id), $R^{2B}$ is trifluoromethoxymethyl. In some embodiments of Formula (Id), $R^{2B}$ is substituted or unsubstituted cycloalkyl. In some embodiments of Formula (Id), $R^{2B}$ is substituted or unsubstituted $C_3$-$C_7$ cycloalkyl. In some embodiments of Formula (Id), $R^{2B}$ is cyclobutanyl. In some embodiments of Formula (Id), $R^{2B}$ is substituted or unsubstituted heterocyclyl. In some embodiments of Formula (Id), $R^{2B}$ is substituted or unsubstituted $C_3$-$C_7$ heterocyclyl. In some embodiments of Formula (Id), $R^{2B}$ is substituted or unsubstituted $C_3$-$C_7$ heterocyclyl, which contains one or more (e.g., 1 or 2 or 3 or 1-4 or 1-3 or 2-4) of S, N, or O atom. In some embodiments of Formula (Id), $R^{2B}$ is oxetanyl. In some embodiments of Formula (Id), $R^{2B}$ is 3-oxetanyl.

In some embodiments of Formula (Id), n is 0. In some embodiments of Formula (Id), n is 1. In some embodiments of Formula (Id), n is 2. In some embodiments of Formula (Id), each $R^{3a}$ is halo, such as $C_1$ or F. In some embodiments of Formula (Id), each $R^{3a}$ is cyano. In some embodiments of Formula (Id), n is 2, one $R^{3a}$ is halo and one $R^{3a}$ is cyano. In some embodiments of Formula (Id), n is 2 and both $R^{3a}$ are halo. In some embodiments of Formula (Id), n is 2 and both $R^{3a}$ are cyano. In some embodiments of Formula (Id), n is 2 and $R^{3a}$ are 2-F and 4-F. In some embodiments of Formula (Id), n is 2 and $R^{3a}$ are 2-Cl and 4-Cl. In some embodiments of Formula (Id), n is 2 and $R^{3a}$ are 2-F and 4-Cl. In some embodiments of Formula (Id), n is 2 and $R^{3a}$ are 2-F and 4-CN. In some embodiments of Formula (Id), n is 2 and $R^{3a}$ are 2-Cl and 4-CN. In some embodiments of Formula (Id), n is 2 and $R^{3a}$ are 2-CN and 4-Cl. In some embodiments of Formula (Id), n is 2 and $R^{3a}$ are 2-CN and 4-F. In some embodiments of Formula (Id), n is 2 and $R^{3a}$ are 2-CN and 4-CN.

In some embodiments of Formula (Id), $R^{2A}$ is H, $R^{2B}$ is trifluoromethoxymethyl, n is 1, and $R^{3a}$ is cyano or halo. In some embodiments of Formula (Id), $R^{2A}$ is H, $R^{2B}$ is 3-oxetanyl, n is 1, and $R^{3a}$ is cyano or halo. In some embodiments of Formula (Id), $R^{2A}$ is H, $R^{2B}$ is cyclobutanyl, n is 1, and $R^{3a}$ is cyano or halo. In some embodiments of Formula (Id), $R^{2A}$ is H, $R^{2B}$ is trifluoromethoxymethyl, n is 2, and each $R^{3a}$ is independently cyano or halo. In some embodiments of Formula (Id), $R^{2A}$ is H, $R^{2B}$ is 3-oxetanyl, n is 2, and each $R^{3a}$ is independently cyano or halo. In some embodiments of Formula (Id), $R^{2A}$ is H, $R^{2B}$ is cyclobutanyl, n is 2, and each $R^{3a}$ is independently cyano or halo.

In another aspect, the compound of Formula (I) is a compound of Formula (Ie), or a pharmaceutically acceptable salt thereof:

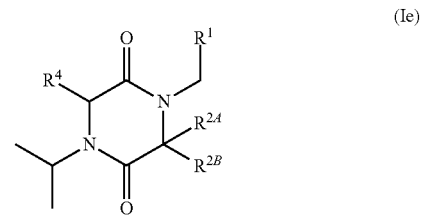

(Ie)

wherein $R^1$ is selected from the group consisting of substituted or unsubstituted phenyl and substituted or unsubstituted pyridyl; $R^{2A}$ is H or substituted or unsubstituted alkyl; $R^{2B}$ is substituted or unsubstituted phenyl or substituted or unsubstituted pyridyl; and $R^4$ is H; wherein, when $R^{2B}$ is 4-methoxyphenyl, $R^1$ is substituted or unsubstituted pyridyl or phenyl substituted with at least one substituent other than methyl or methoxy.

In some embodiments of Formula (Ie), $R^{2A}$ is H. In some embodiments of Formula (Ie), $R^{2A}$ is substituted or unsubstituted alkyl. In some embodiments of Formula (Ie), $R^{2A}$ is substituted or unsubstituted methyl. In some embodiments of Formula (Ie), $R^{2A}$ is methyl.

In some embodiments of Formula (Ie), $R^{2B}$ is substituted or unsubstituted pyridyl. In some embodiments of Formula (Ie), $R^{2B}$ is 2-pyridyl. In some embodiments, $R^{2B}$ is substituted or unsubstituted phenyl. In some embodiments of Formula (Ie), $R^{2B}$ is phenyl or pyridyl, each of which is substituted with one or more (e.g., 1 or 2 or 3 or 1-4 or 1-3 or 2-4) substituents independently selected from the group consisting of halo, substituted or unsubstituted alkoxy, and substituted or unsubstituted alkyl. In some embodiments of Formula (Ie), $R^{2B}$ is pyridyl substituted with one or more (e.g., 1 or 2 or 3 or 1-4 or 1-3 or 2-4) substituents selected from the group consisting of halo and substituted or unsubstituted alkyl. In some embodiments of Formula (Ie), $R^{2B}$ is pyridyl substituted with one or more (e.g., 1 or 2 or 3 or 1-4 or 1-3 or 2-4) halo. In some embodiments of Formula (Ie), R$^{2B}$ is phenyl substituted with one or more (e.g., 1 or 2 or 3 or 1-4 or 1-3 or 2-4) halo. In some embodiments of Formula (Ie), R$^{2B}$ is phenyl substituted with one or more (e.g., 1 or 2 or 3 or 1-4 or 1-3 or 2-4) —CF$_3$. In some embodiments of Formula (Ie), R$^{2B}$ is phenyl substituted with one or more (e.g., 1 or 2 or 3 or 1-4 or 1-3 or 2-4) alkoxy. In some embodiments of Formula (Ie), R$^2$Bis phenyl substituted with one or more (e.g., 1 or 2 or 3 or 1-4 or 1-3 or 2-4) methoxy.

In some embodiments of Formula (Ie), R$^1$ is substituted or unsubstituted pyridyl. In some embodiments of Formula (Ie), R$^1$ is 2-pyridyl. In some embodiments of Formula (Ie), R$^1$ is unsubstituted phenyl. In some embodiments of Formula (Ie), R$^1$ is phenyl or pyridinyl, each of which is substituted with one or more substituents independently selected from the group consisting of cyano, halo, and substituted or unsubstituted alkyl. In some embodiments of Formula (Ie), R$^1$ is pyridyl substituted with one or more (e.g., 1 or 2 or 3 or 1-4 or 1-3 or 2-4) halo. In some embodiments of Formula (Ie), R$^1$ is pyridyl substituted with one or more (e.g., 1 or 2 or 3 or 1-4 or 1-3 or 2-4) —CF$_3$. In some embodiments of Formula (Ie), R$^1$ is phenyl substituted with one or more (e.g., 1 or 2 or 3 or 1-4 or 1-3 or 2-4) halo. In some embodiments of Formula (Ie), R$^1$ is phenyl substituted with one or more (e.g., 1 or 2 or 3 or 1-4 or 1-3 or 2-4) —CF$_3$. In some embodiments of Formula (Ie), R$^1$ is phenyl substituted with one or more (e.g., 1 or 2 or 3 or 1-4 or 1-3 or 2-4) CN. In some embodiments of Formula (Ie), R$^1$ is phenyl substituted with one or more (e.g., 1 or 2 or 3 or 1-4 or 1-3 or 2-4) methyl.

In some embodiments of Formula (Ie), R$^{2B}$ is 4-methoxyphenyl and R$^1$ is substituted or unsubstituted pyridyl. In some embodiments of Formula (Ie), R$^{2B}$ is 4-methoxyphenyl and R$^1$ is 2-pyridyl. In some embodiments of Formula (Ie), R$^{2B}$ is 4-methoxyphenyl and R$^1$ is 2-pyridyl substituted with one or more (e.g., 1 or 2 or 3 or 1-4 or 1-3 or 2-4) halo. In some embodiments of Formula (Ie), R$^{2B}$ is 4-methoxyphenyl and R$^1$ is phenyl substituted with one or more (e.g., 1 or 2 or 3 or 1-4 or 1-3 or 2-4) halo. In some embodiments of Formula (Ie), R$^{2B}$ is 4-methoxyphenyl and R$^1$ is phenyl substituted with 4-C$_1$.

In another aspect, the compound of Formula (I) is a compound of Formula (If), or a pharmaceutically acceptable salt thereof:

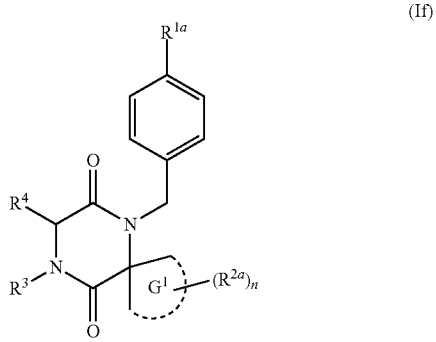

(If)

wherein G$^1$ is selected from the group consisting of substituted or unsubstituted cycloalkyl, substituted or unsubstituted cycloalkenyl, substituted or unsubstituted cycloalkynyl, and substituted or unsubstituted heterocyclyl ring, each of which is optionally fused to a phenyl ring; R$^{1a}$ is selected from the group consisting of cyano, halo, substituted or unsubstituted alkoxy, substituted or unsubstituted alkyl, and substituted or unsubstituted heterocyclyl; each R$^{2a}$ is independently selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl; n is 0, 1, 2, or 3; R$^3$ is selected from the group consisting of substituted or unsubstituted alkyl, substituted or unsubstituted cycloalkyl, substituted or unsubstituted heterocyclyl, and substituted or unsubstituted aryl; and R$^4$ is H; wherein, when R$^3$ is 4-methoxyphenylmethyl, R$^{1a}$ is not methyl or methoxy.

It is understood that the G$^1$ group is the ring including the carbon atom that it shares with the piperazinedione ring.

In some embodiments of Formula (If), G$^1$ is selected from the group consisting of substituted or unsubstituted cycloalkyl, substituted or unsubstituted heterocyclyl, and substituted or unsubstituted 2,3-dihydro-1H-indene. In some embodiments of Formula (Ic), G$^1$ is substituted or unsubstituted C$_3$-C$_6$ cycloalkyl. In some embodiments of Formula (Ic), G$^1$ is substituted or unsubstituted C$_3$-C$_6$ heterocyclyl. In some embodiments of Formula (Ic), G$^1$ is substituted or unsubstituted cyclopropyl. In some embodiments of Formula (Ic), G$^1$ is substituted or unsubstituted cyclobutanyl. In some embodiments of Formula (Ic), G$^1$ is substituted or unsubstituted azetidinyl. In some embodiments of Formula (Ic), G$^1$ is substituted or unsubstituted tetrahydrofuranyl. In some embodiments of Formula (Ic), G$^1$ is substituted or unsubstituted pyrrolidinyl. In some embodiments of Formula (Ic), G$^1$ is substituted or unsubstituted pyrrolidin-2-one-yl.

In some embodiments of Formula (If), G$^1$ is heterocyclyl substituted with one or more (e.g., 1 or 2 or 3 or 1-4 or 1-3 or 2-4) R$^{2a}$. Each R$^{2a}$ selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminothionyl, substituted or unsubstituted aminocarbonylamino, and substituted or unsubstituted alkyl. In some embodiments of Formula (If), R$^{2a}$ is substituted or unsubstituted phenyl. In some embodiments of Formula (If), R$^{2a}$ is phenyl substituted with halo. In some embodiments of Formula (If), R$^{2a}$ is substituted or unsubstituted heteroaryl. In some embodiments of Formula (If), R$^{2a}$ is substituted or unsubstituted pyridyl. In some embodiments of Formula (If), R$^{2a}$ is pyridyl substituted with one or more (e.g., 1 or 2 or 3 or 1-4 or 1-3 or 2-4) substituents selected from the group consisting of alkyl, CN, hydroxyl, alkoxycarbonyl, methoxycarbonyl, alkoxy, carboxyl, cycloalkyl, halo, and aminoacyl. In some embodiments of Formula (If), R$^{2a}$ is substituted or unsubstituted pyrimidyl. In some embodiments of Formula (If), R$^{2a}$ is substituted or unsubstituted pyrazolyl. In some embodiments of Formula (If), R$^{2a}$ is pyrazolyl substituted with alkyl. In some embodiments of Formula (If), R$^{2a}$ is substituted or unsubstituted thiazolyl. In some embodiments of Formula (If), R$^{2a}$ is thiazolyl substituted with aminoacyl. In some embodiments of Formula (If), R$^{2a}$ is substituted or unsubstituted alkoxycarbonyl. In some embodiments of Formula (If), R$^{2a}$ is methoxycarbonyl. In some embodiments of Formula (If), R$^{2a}$ is substituted or unsubstituted aminoacyl. In some embodiments of Formula (If), R$^{2a}$ is methylaminoacyl. In some embodiments of Formula (If), R$^{2a}$ is aminoacyl substituted with one or more (e.g., 1 or 2 or 3 or 1-4 or 1-3 or 2-4) substituents selected from the group consisting of aryl, cycloalkyl, pyridyl, pyrazolyl, and alkoxyalkyl. In some embodiments of Formula (If), $R^{2a}$ is substituted or unsubstituted pyridin-one-yl. In some embodiments of Formula (If), $R^{2a}$ is pyridin-on-yl substituted with alkyl. In some embodiments of Formula (If), $R^{2a}$ is substituted or unsubstituted oxadiazolyl. In some embodiments of Formula (If), $R^{2a}$ is oxadiazolyl substituted with one or more (e.g., 1 or 2 or 3 or 1-4 or 1-3 or 2-4) substituents selected from the group consisting of alkyl and phenyl. In some embodiments of Formula (If), $R^{2a}$ is substituted or unsubstituted 9-membered bicyclic heterocyclyl. In some embodiments of Formula (If), $R^{2a}$ is —C(O)H. In some embodiments of Formula (If), $R^{2a}$ is substituted or unsubstituted pyridazinyl. In some embodiments of Formula (If), $R^{2a}$ is pyridazinyl substituted with one or more (e.g., 1 or 2 or 3 or 1-4 or 1-3 or 2-4) substituents selected from the group consisting of halo, alkoxy, alkyl, and aminoacyl. In some embodiments of Formula (If), $R^{2a}$ is substituted or unsubstituted aminothionyl. In some embodiments of Formula (If), $R^{2a}$ is aminothionyl substituted with alkyl. In some embodiments of Formula (If), $R^{2a}$ is substituted or unsubstituted acyl. In some embodiments of Formula (If), $R^{2a}$ is acyl substituted with one or more (e.g., 1 or 2 or 3 or 1-4 or 1-3 or 2-4) substituents selected from the group consisting of cycloalkyl, alkyl, and heterocyclyl. In some embodiments of Formula (If), $R^{2a}$ is acyl substituted with morpholinyl. In some embodiments of Formula (If), $R^{2a}$ is substituted or unsubstituted aminocarbonylamino. In some embodiments of Formula (If), $R^{2a}$ is aminocarbonylamino substituted with one or more (e.g., 1 or 2 or 3 or 1-4 or 1-3 or 2-4) substituents selected from the group consisting of cycloalkyl and heterocyclyl.

In some embodiments of Formula (If), $G^1$ is cycloalkyl substituted with one or more (e.g., 1 or 2 or 3 or 1-4 or 1-3 or 2-4) $R^{2a}$. In some embodiments of Formula (If), $R^{2a}$ is substituted or unsubstituted phenyl. In some embodiments of Formula (If), $R^{2a}$ is substituted or unsubstituted thiazolyl. In some embodiments of Formula (If), $R^{2a}$ is thiazolyl substituted with alkyl. In some embodiments of Formula (If), $R^{2a}$ is substituted or unsubstituted oxazolyl. In some embodiments of Formula (If), $R^{2a}$ is oxazolyl substituted with alkyl. In some embodiments of Formula (If), $R^{2a}$ is substituted or unsubstituted aminoacyl. In some embodiments of Formula (If), $R^{2a}$ is aminoacyl substituted with one or more (e.g., 1 or 2 or 3 or 1-4 or 1-3 or 2-4) substituents selected from the group consisting of alkyl, heterocyclyl, and cycloalkyl. In some embodiments of Formula (If), $R^{2a}$ is substituted or unsubstituted oxadiazolyl. In some embodiments of Formula (If), $R^{2a}$ is oxadiazolyl substituted with one or more (e.g., 1 or 2 or 3 or 1-4 or 1-3 or 2-4) substituents selected from the group consisting of cycloalkyl and alkyl. In some embodiments of Formula (If), $R^{2a}$ is substituted or unsubstituted acyl. In some embodiments of Formula (If), $R^{2a}$ is acyl substituted with heterocyclyl. In some embodiments of Formula (If), $R^{2a}$ is substituted or unsubstituted aminocarbonylamino. In some embodiments of Formula (If), $R^{2a}$ is aminocarbonylamino substituted with one or more (e.g., 1 or 2 or 3 or 1-4 or 1-3 or 2-4) substituents selected from the group consisting of alkyl, cycloalkyl, and heterocyclyl. In some embodiments of Formula (If), $R^{2a}$ is substituted or unsubstituted alkoxycarbonyl. In some embodiments of Formula (If), $R^{2a}$ is alkoxycarbonyl substituted with alkyl. In some embodiments of Formula (If), $R^{2a}$ is substituted or unsubstituted alkyl. In some embodiments of Formula (If), $R^{2a}$ is alkyl substituted with hydroxyl. In some embodiments of Formula (If), $R^{2a}$ is hydroxyl.

In some embodiments of Formula (If), $R^3$ is selected from the group consisting of substituted or unsubstituted alkyl, substituted or unsubstituted cycloalkyl, substituted or unsubstituted heterocyclyl, and substituted or unsubstituted aryl. In some embodiments of Formula (If), $R^3$ is phenyl substituted with one or more (e.g., 1 or 2 or 3 or 1-4 or 1-3 or 2-4) substituents selected from the group consisting of nitro, alkoxy, halo, cycloalkyl, cyano, alkenyl, alkoxycarbonyl, phenylcarbonyl, and alkyl. In some embodiments of Formula (If), $R^3$ is cycloalkyl substituted with one or more (e.g., 1 or 2 or 3 or 1-4 or 1-3 or 2-4) substituents selected from the group consisting of alkyl, cyano, and halo. In some embodiments of Formula (If), $R^3$ is alkyl substituted with one or more (e.g., 1 or 2 or 3 or 1-4 or 1-3 or 2-4) substituents selected from the group consisting of alkoxy, cyano, and halo.

In some embodiments of Formula (If), $R^{1a}$ is selected from the group consisting of cyano, halo, substituted or unsubstituted alkoxy, substituted or unsubstituted alkyl, and substituted or unsubstituted diazirinyl. In some embodiments of Formula (If), $R^{1a}$ is halo. In some embodiments of Formula (If), $R^{1a}$ is —CF$_3$. In some embodiments of Formula (If), $R^{1a}$ is methyl. In some embodiments of Formula (If), $R^{1a}$ is diazirinyl. In some embodiments of Formula (If), $R^{1a}$ is trifluoromethyldiazirinyl.

In some embodiments of Formula (If), $R^{1a}$ is Cl and $R^3$ is substituted with 4-methoxyphenylmethyl. In some embodiments of Formula (If), $R^{1a}$ is F and $R^3$ is substituted with 4-methoxyphenylmethyl. In some embodiments of Formula (If), $R^{1a}$ is —CF$_3$ and $R^3$ is substituted with 4-methoxyphenylmethyl. In some embodiments of Formula (If), $R^{1a}$ is trifluoromethyldiazirinyl and $R^3$ is substituted with 4-methoxyphenylmethyl.

In some embodiments of Formula (I), Formula (Ic), and Formula (If), $G^1$ is selected from the group consisting of:

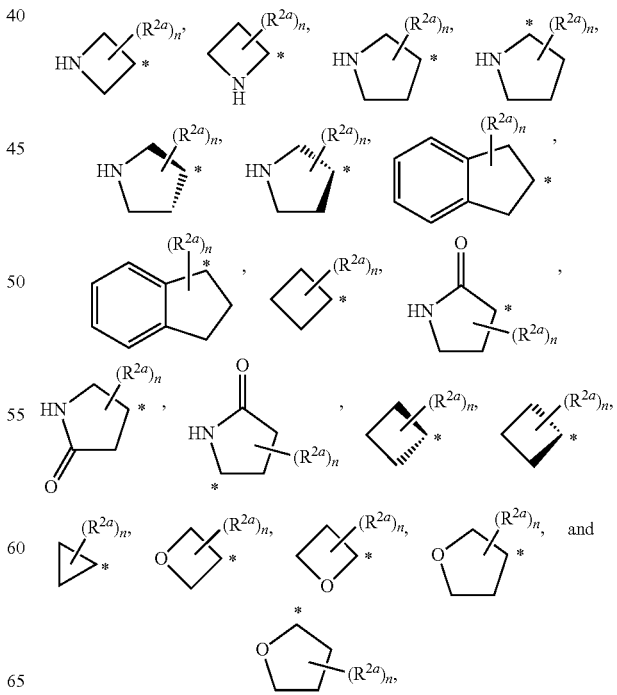

wherein * indicates the point of attachment to the parent structure,

R$^{2a}$. is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl; and n is 0, 1, 2, or 3.

In some embodiments of Formula (I), Formula (Ic), and Formula (If), G$^1$ is substituted with one or more (e.g., 1 or 2 or 3 or 1-4 or 1-3 or 2-4) R$^{2a}$ independently selected from the group consisting of:

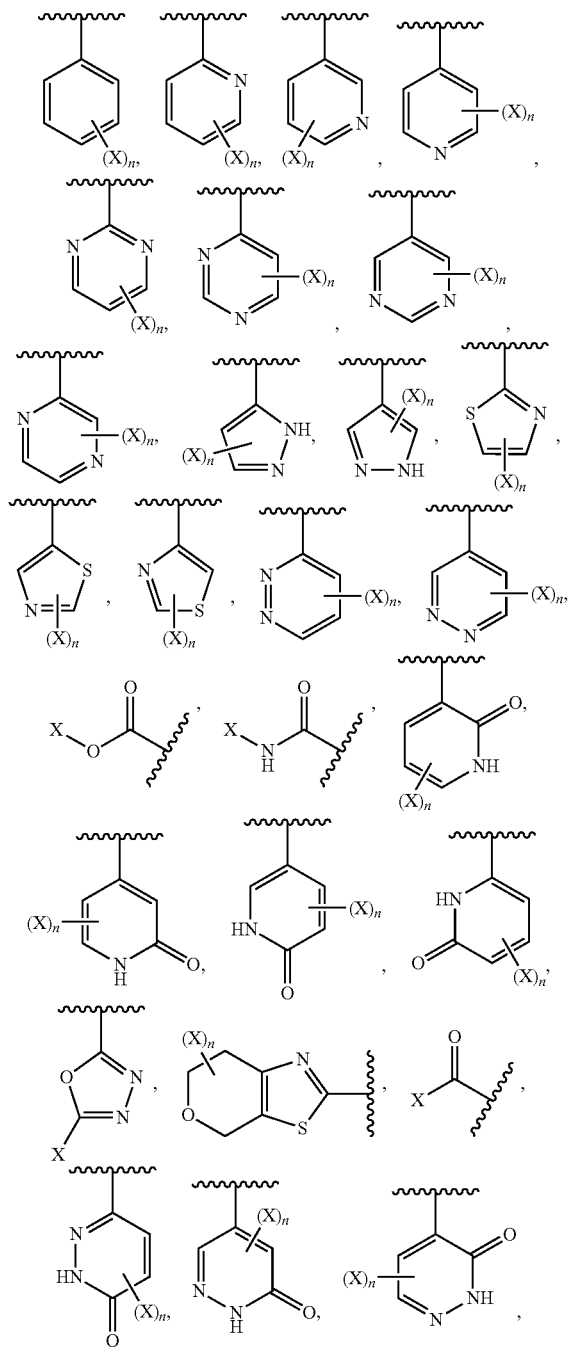

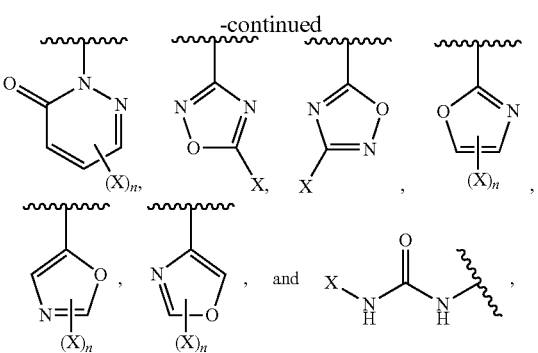

wherein n is 0-3 and each X is independently selected from the group consisting of H, halo, alkyl, cyano, hydroxyl, cycloalkyl, alkoxycarbonyl, carboxyl, aminoacyl, aryl, heteroaryl, alkoxy, alkoxyalkyl, aminothionyl, and heterocyclyl.

In another aspect, provided is a compound of Formula (Ig), or a pharmaceutically acceptable salt thereof:

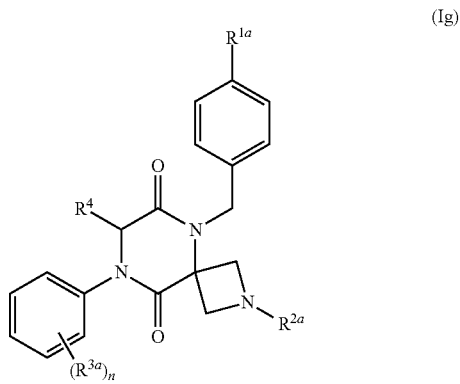

(Ig)

wherein R$^{1a}$ is selected from the group consisting of cyano, halo, substituted or unsubstituted alkoxy, substituted or unsubstituted alkyl, and substituted or unsubstituted heterocyclyl; R$^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl; n is 0, 1, 2, or 3; each R$^{3a}$ is independently selected from the group consisting of substituted or unsubstituted alkoxy, substituted or unsubstituted alkyl, substituted or unsubstituted alkenyl, halo, nitro, and cyano; and R$^4$ is H.

In some embodiments of Formula (Ig), R$^{1a}$ is selected from the group consisting of cyano, halo, substituted or unsubstituted alkoxy, substituted or unsubstituted alkyl, and substituted or unsubstituted diazirinyl. In some embodiments of Formula (Ig), R$^{1a}$ is halo. In some embodiments of Formula (Ig), R$^{1a}$ is —CF$_3$. In some embodiments of Formula (Ig), R$^{1a}$ is methyl. In some embodiments of Formula (Ig), R$^{1a}$ is diazirinyl. In some embodiments of Formula (Ig), R$^{1a}$ is trifluoromethyldiazirinyl.

In some embodiments of Formula (Ig), n is 0. In some embodiments of Formula (Ig), n is 1. In some embodiments of Formula (Ig), n is 2. In some embodiments of Formula (Ig), each R$^{3a}$ is halo, such as C$_1$ or F. In some embodiments of Formula (Ig), each $R^{3a}$ is cyano. In some embodiments of Formula (Ig), n is 2, one $R^{3a}$ is halo and one $R^{3a}$ is cyano. In some embodiments of Formula (If), n is 2 and both $R^{3a}$ are halo. In some embodiments of Formula (If), n is 2 and both $R^{3a}$ are cyano. In some embodiments of Formula (If), n is 2 and $R^{3a}$ are 2-F and 4-F. In some embodiments of Formula (Ig), n is 2 and $R^{3a}$ are 2-Cl and 4-Cl. In some embodiments of Formula (Ig), n is 2 and $R^{3a}$ are 2-F and 4-Cl. In some embodiments of Formula (Ig), n is 2 and $R^{3a}$ are 3-F and 4-Cl. In some embodiments of Formula (Ig), n is 2 and $R^{3a}$ are 3-F and 4-CN. In some embodiments of Formula (Ig), n is 2 and $R^{3a}$ are 4-F and 3-Cl. In some embodiments of Formula (Ig), n is 2 and $R^{3a}$ are 2-F and 4-CN. In some embodiments of Formula (Ig), n is 2 and $R^{3a}$ are 2-Cl and 4-CN. In some embodiments of Formula (Ig), n is 2 and $R^{3a}$ are 2-CN and 4-Cl. In some embodiments of Formula (Ig), n is 2 and $R^{3a}$ are 2-CN and 4-F. In some embodiments of Formula (Ig), n is 2 and $R^{3a}$ are 2-CN and 4-CN. In some embodiments of Formula (Ig), $R^{3a}$ is nitro. In some embodiments of Formula (Ig), n is 1 and $R^{3a}$ is 4-nitro. In some embodiments of Formula (Ig), n is 1 and $R^{3a}$ is 4-Cl or 3-Cl. In some embodiments of Formula (Ig), n is 1 and $R^{3a}$ is 4-F or 3-F. In some embodiments of Formula (Ig), n is 1 and $R^{1a}$ is 4-CN or 3-CN. In some embodiments of Formula (Ig), $R^{1a}$ is difluoromethoxy. In some embodiments of Formula (Ig), $R^{1a}$ is propenyl. In some embodiments of Formula (Ig), $R^{3a}$ is methyl. In some embodiments of Formula (Ig), n is 2 and $R^{3a}$ are 3-methyl and 4-Cl. In some embodiments of Formula (Ig), n is 2 and $R^{3a}$ are 3-methyl and 4-CN. In some embodiments of Formula (Ig), n is 2 and $R^{3a}$ are 3-F and 4-difluoromethoxy.

In some embodiments of Formula (Ig), $R^{2a}$ is substituted or unsubstituted phenyl. In some embodiments of Formula (Ig), $R^{2a}$ is substituted or unsubstituted aminoacyl. In some embodiments of Formula (Ig), $R^{2a}$ is aminoacyl substituted with one or more (e.g., 1 or 2 or 3 or 1-4 or 1-3 or 2-4) substituents selected from the group consisting of alkyl, heterocyclyl, and cycloalkyl. In some embodiments of Formula (Ig), $R^{2a}$ is substituted or unsubstituted oxadiazolyl. In some embodiments of Formula (Ig), $R^{2a}$ is oxadiazolyl substituted with one or more (e.g., 1 or 2 or 3 or 1-4 or 1-3 or 2-4) substituents selected from the group consisting of cycloalkyl and alkyl. In some embodiments of Formula (Ig), $R^{2a}$ is substituted or unsubstituted acyl. In some embodiments of Formula (Ig), $R^{2a}$ is acyl substituted with heterocyclyl. In some embodiments of Formula (Ig), $R^{2a}$ is acyl substituted with aryl. In some embodiments of Formula (Ig), $R^{2a}$ is acyl substituted with phenyl. In some embodiments of Formula (Ig), $R^{2a}$ is acyl substituted with alkyl. In some embodiments of Formula (Ig), $R^{2a}$ is substituted or unsubstituted pyridyl. In some embodiments of Formula (Ig), $R^{2a}$ is pyridyl substituted with CN or halo. In some embodiments of Formula (Ig), $R^{2a}$ is substituted or unsubstituted aminocarbonylamino. In some embodiments of Formula (Ig), $R^{2a}$ is aminocarbonylamino substituted with one or more (e.g., 1 or 2 or 3 or 1-4 or 1-3 or 2-4) substituents selected from the group consisting of alkyl, cycloalkyl, and heterocyclyl. In some embodiments of Formula (Ig), $R^{2a}$ is substituted or unsubstituted alkoxycarbonyl. In some embodiments of Formula (Ig), $R^{2a}$ is alkoxycarbonyl substituted with alkyl. In some embodiments of Formula (Ig), $R^{2a}$ is substituted or unsubstituted alkyl. In some embodiments of Formula (Ig), $R^{2a}$ is alkyl substituted with hydroxyl. In some embodiments of Formula (Ig), $R^{2a}$ is alkyl substituted with halo. In some embodiments of Formula (Ig), $R^{2a}$ is hydroxyl. In some embodiments of Formula (Ig), $R^{2a}$ is substituted or unsubstituted aminosulfonyl. In some embodiments of Formula (Ig), $R^{2a}$ is aminosulfonyl substituted with alkyl.

In another aspect, provided is a compound of Formula (Ih), or a pharmaceutically acceptable salt thereof:

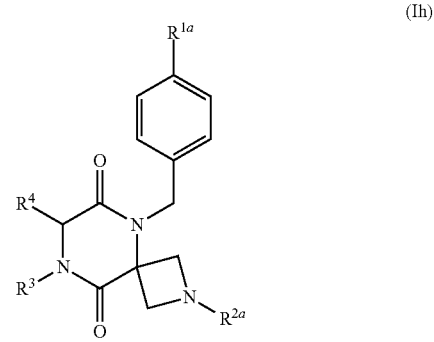

(Ih)

wherein $R^{1a}$ is selected from the group consisting of cyano, halo, substituted or unsubstituted alkoxy, substituted or unsubstituted alkyl, and substituted or unsubstituted heterocyclyl; $R^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl; $R^3$ is selected from the group consisting of substituted or unsubstituted alkyl, substituted or unsubstituted cycloalkyl, substituted or unsubstituted heterocyclyl, and substituted or unsubstituted aryl; and $R^4$ is H; wherein, when $R^3$ is 4-methoxyphenylmethyl, $R^{1a}$ is not methyl or methoxy.

In some embodiments of Formula (Ih), $R^{1a}$ is selected from the group consisting of cyano, halo, substituted or unsubstituted alkoxy, substituted or unsubstituted alkyl, and substituted or unsubstituted diazirinyl. In some embodiments of Formula (Ih), $R^{1a}$ is halo. In some embodiments of Formula (Ih), $R^{1a}$ is —$CF_3$. In some embodiments of Formula (Ih), $R^{1a}$ is methyl. In some embodiments of Formula (Ih), $R^{1a}$ is diazirinyl. In some embodiments of Formula (Ih), $R^{1a}$ is trifluoromethyldiazirinyl.

In some embodiments of Formula (Ih), $R^{2a}$ is substituted or unsubstituted phenyl. In some embodiments of Formula (Ih), $R^{2a}$ is substituted or unsubstituted aminoacyl. In some embodiments of Formula (Ih), $R^{2a}$ is aminoacyl substituted with one or more (e.g., 1 or 2 or 3 or 1-4 or 1-3 or 2-4) substituents selected from the group consisting of alkyl, heterocyclyl, and cycloalkyl. In some embodiments of Formula (Ih), $R^{2a}$ is substituted or unsubstituted oxadiazolyl. In some embodiments of Formula (Ih), $R^{2a}$ is oxadiazolyl substituted with one or more (e.g., 1 or 2 or 3 or 1-4 or 1-3 or 2-4) substituents selected from the group consisting of cycloalkyl and alkyl. In some embodiments of Formula (Ih), $R^{2a}$ is substituted or unsubstituted acyl. In some embodiments of Formula (Ih), $R^{2a}$ is acyl substituted with heterocyclyl. In some embodiments of Formula (Ih), $R^{2a}$ is acyl substituted with aryl. In some embodiments of Formula (Ih), $R^{2a}$ is acyl substituted with phenyl. In some embodiments of Formula (Ih), $R^{2a}$ is acyl substituted with alkyl. In some embodiments of Formula (Ih), $R^{2a}$ is substituted or unsubstituted pyridyl. In some embodiments of Formula (Ih), $R^{2a}$ is pyridyl substituted with CN or halo. In some embodiments of Formula (Ih), $R^{2a}$ is substituted or unsubstituted aminocarbonylamino. In some embodiments of Formula (Ih), $R^{2a}$ is aminocarbonylamino substituted with one or more (e.g., 1 or 2 or 3 or 1-4 or 1-3 or 2-4) substituents selected from the group consisting of alkyl, cycloalkyl, and heterocyclyl. In some embodiments of Formula (Ih), $R^{2a}$ is substituted or unsubstituted alkoxycarbonyl. In some embodiments of Formula (Ih), $R^{2a}$ is alkoxycarbonyl substituted with alkyl. In some embodiments of Formula (Ih), $R^{2a}$ is substituted or unsubstituted alkyl. In some embodiments of Formula (Ih), $R^{2a}$ is alkyl substituted with hydroxyl. In some embodiments of Formula (Ih), $R^{2a}$ is alkyl substituted with halo. In some embodiments of Formula (Ih), $R^{2a}$ is hydroxyl. In some embodiments of Formula (Ih), $R^{2a}$ is substituted or unsubstituted aminosulfonyl. In some embodiments of Formula (Ih), $R^{2a}$ is aminosulfonyl substituted with alkyl. In some embodiments of Formula (Ih), $R^{2a}$ is substituted or unsubstituted thiazolyl. In some embodiments of Formula (Ih), $R^{2a}$ is thiazolyl substituted with alkyl. In some embodiments of Formula (Ih), $R^{2a}$ is substituted or unsubstituted oxazolyl. In some embodiments of Formula (Ih), $R^{2a}$ is oxazolyl substituted with alkyl.

In some embodiments of Formula (Ih), $R^3$ is selected from the group consisting of substituted or unsubstituted alkyl, substituted or unsubstituted cycloalkyl, substituted or unsubstituted heterocyclyl, and substituted or unsubstituted aryl. In some embodiments of Formula (Ih), $R^3$ is phenyl substituted with one or more (e.g., 1 or 2 or 3 or 1-4 or 1-3 or 2-4) substituents selected from the group consisting of nitro, alkoxy, halo, cycloalkyl, cyano, alkenyl, alkoxycarbonyl, phenylcarbonyl, and alkyl. In some embodiments, $R^3$ is phenyl substituted with CN and F. In some embodiments of Formula (Ih), $R^3$ is alkyl substituted with one or more (e.g., 1 or 2 or 3 or 1-4 or 1-3 or 2-4) substituents selected from the group consisting of alkoxy, cyano, and halo. In some embodiments, $R^3$ is isopropyl.

In another aspect, provided is a compound of Formula (Ii), or a pharmaceutically acceptable salt thereof:

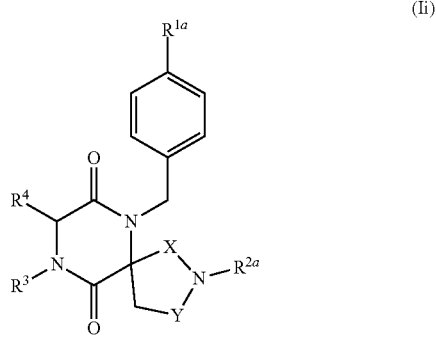

(Ii)

wherein $R^{1a}$ is selected from the group consisting of cyano, halo, substituted or unsubstituted alkoxy, substituted or unsubstituted alkyl, and substituted or unsubstituted heterocyclyl; $R^{2a}$ is selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl; $R^3$ is selected from the group consisting of substituted or unsubstituted alkyl, substituted or unsubstituted cycloalkyl, substituted or unsubstituted heterocyclyl, and substituted or unsubstituted aryl; $R^4$ is H; $R^5$ is H or substituted or unsubstituted alkyl; and X and Y are independently —CH$_2$— or —C(O)—; wherein, when $R^3$ is 4-methoxyphenylmethyl, $R^{1a}$ is not methyl or methoxy.

In some embodiments of Formula (Ii), $R^{1a}$ is selected from the group consisting of cyano, halo, substituted or unsubstituted alkoxy, substituted or unsubstituted alkyl, and substituted or unsubstituted diazirinyl. In some embodiments of Formula (Ii), $R^{1a}$ is halo. In some embodiments of Formula (Ii), $R^{1a}$ is —CF$_3$. In some embodiments of Formula (Ii), $R^{1a}$ is methyl. In some embodiments of Formula (Ii), $R^{1a}$ is Cl. In some embodiments of Formula (Ih), $R^{1a}$ is trifluoromethyldiazirinyl.

In some embodiments of Formula (Ii), $R^{2a}$ is substituted or unsubstituted phenyl. In some embodiments of Formula (Ii), $R^{2a}$ is substituted or unsubstituted pyridyl. In some embodiments of Formula (Ii), $R^{2a}$ is pyridyl substituted with alkyl, CN or halo. In some embodiments of Formula (Ii), $R^{2a}$ is substituted or unsubstituted pyrimidyl. In some embodiments of Formula (Ii), $R^{2a}$ is substituted or unsubstituted pyridazinyl. In some embodiments of Formula (Ii), $R^{2a}$ is pyridazinyl substituted with one or more (e.g., 1 or 2 or 3 or 1-4 or 1-3 or 2-4) substituents selected from the group consisting of halo, alkoxy, alkyl, and aminoacyl. In some embodiments of Formula (Ii), $R^{2a}$ is substituted or unsubstituted aminoacyl. In some embodiments of Formula (Ii), $R^{2a}$ is aminoacyl substituted with one or more (e.g., 1 or 2 or 3 or 1-4 or 1-3 or 2-4) substituents selected from the group consisting of alkyl, heterocyclyl, aryl, heteroaryl, and cycloalkyl. In some embodiments of Formula (Ii), $R^{2a}$ is substituted or unsubstituted pyrazolyl. In some embodiments of Formula (Ii), $R^{2a}$ is pyrazolyl substituted with alkyl. In some embodiments of Formula (Ii), $R^{2a}$ is substituted or unsubstituted oxadiazolyl. In some embodiments of Formula (Ii), $R^{2a}$ is oxadiazolyl substituted with one or more (e.g., 1 or 2 or 3 or 1-4 or 1-3 or 2-4) substituents selected from the group consisting of cycloalkyl and alkyl. In some embodiments of Formula (Ii), $R^{2a}$ is substituted or unsubstituted acyl. In some embodiments of Formula (Ii), $R^{2a}$ is acyl substituted with heterocyclyl. In some embodiments of Formula (Ii), $R^{2a}$ is acyl substituted with aryl. In some embodiments of Formula (Ii), $R^{2a}$ is acyl substituted with phenyl. In some embodiments of Formula (Ii), $R^{2a}$ is acyl substituted with alkyl. In some embodiments of Formula (Ii), $R^{2a}$ is substituted or unsubstituted aminocarbonylamino. In some embodiments of Formula (Ii), $R^{2a}$ is aminocarbonylamino substituted with one or more (e.g., 1 or 2 or 3 or 1-4 or 1-3 or 2-4) substituents selected from the group consisting of alkyl, cycloalkyl, and heterocyclyl. In some embodiments of Formula (Ii), $R^{2a}$ is substituted or unsubstituted alkoxycarbonyl. In some embodiments of Formula (Ii), $R^{2a}$ is alkoxycarbonyl substituted with alkyl. In some embodiments of Formula (Ii), $R^{2a}$ is substituted or unsubstituted alkyl. In some embodiments of Formula (Ii), $R^{2a}$ is alkyl substituted with hydroxyl. In some embodiments of Formula (Ii), $R^{2a}$ is alkyl substituted with halo. In some embodiments of Formula (Ii), $R^{2a}$ is hydroxyl. In some embodiments of Formula (Ii), $R^{2a}$ is substituted or unsubstituted aminosulfonyl. In some embodiments of Formula (Ii), $R^{2a}$ is aminosulfonyl substituted with alkyl. In some embodiments of Formula (Ii), $R^{2a}$ is substituted or unsubstituted thiazolyl. In some embodiments of Formula (Ii), $R^{2a}$ is thiazolyl substituted with alkyl. In some embodiments of Formula (Ii), $R^{2a}$ is substituted or unsubstituted oxazolyl. In some embodiments of Formula (Ii), $R^{2a}$ is oxazolyl substituted with alkyl.

In some embodiments of Formula (Ii), $R^3$ is selected from the group consisting of substituted or unsubstituted alkyl, substituted or unsubstituted cycloalkyl, substituted or unsubstituted heterocyclyl, and substituted or unsubstituted aryl. In some embodiments of Formula (Ii), $R^3$ is phenyl substituted with one or more (e.g., 1 or 2 or 3 or 1-4 or 1-3 or 2-4) substituents selected from the group consisting of nitro, alkoxy, halo, cycloalkyl, cyano, alkenyl, alkoxycarbonyl, phenylcarbonyl, and alkyl. In some embodiments of Formula (Ii), $R^3$ is phenyl substituted with CN and F. In some embodiments of Formula (Ii), $R^3$ is phenyl substituted with CN or Cl. In some embodiments of Formula (Ii), $R^3$ is cycloalkyl substituted with one or more (e.g., 1 or 2 or 3 or 1-4 or 1-3 or 2-4) substituents selected from the group consisting of alkyl, cyano, and halo. In some embodiments of Formula (Ii), $R^3$ is cyclopropyl substituted with alkyl. In some embodiments of Formula (Ii), $R^3$ is alkyl substituted with one or more (e.g., 1 or 2 or 3 or 1-4 or 1-3 or 2-4) substituents selected from the group consisting of alkoxy, cyano, and halo. In some embodiments of Formula (Ii), $R^3$ is isopropyl, methyl, or ethyl. In some embodiments of Formula (Ii), $R^3$ is substituted or unsubstituted heterocyclyl. In some embodiments of Formula (Ii), $R^3$ is furanyl.

In some embodiments of Formula (Ii), $R^5$ is substituted or unsubstituted alkyl. In some embodiments of Formula (Ii), $R^5$ is methyl. In some embodiments of Formula (Ii), $R^5$ is substituted alkyl. In some embodiments of Formula (Ii), $R^5$ is hydroxymethyl. In some embodiments of Formula (Ii), $R^5$ is H.

In some embodiments of Formula (Ii), X and Y are independently —$CH_2$— or —C(O)—. In some embodiments of Formula (Ii), X and Y are both —$CH_2$—. In some embodiments of Formula (Ii), X is —$CH_2$— and Y is —C(O)—. In some embodiments of Formula (Ii), Y is —$CH_2$— and X is —C(O)—.

In another aspect, the compound of Formula (I) is a compound of Formula (Ij), or a pharmaceutically acceptable salt thereof:

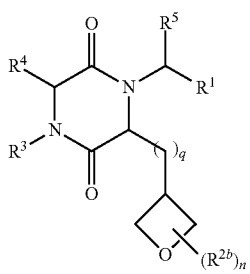

(Ij)

wherein $R^1$ is substituted or unsubstituted phenyl; each $R^{2b}$ is independently substituted or unsubstituted alkyl; $R^3$ is substituted or unsubstituted phenyl or substituted or unsubstituted pyridyl; $R^4$ is H; $R^5$ is H or substituted or unsubstituted alkyl; n is 0, 1, or 2; and q is 0 or 1; wherein, when $R^3$ is substituted or unsubstituted phenyl, then $R^1$ is substituted or unsubstituted pyridyl or phenyl substituted with at least one substituent other than methyl or methoxy.

In some embodiments of Formula (Ij), $R^1$ is substituted or unsubstituted phenyl. In some embodiments of Formula (Ij), $R^1$ is phenyl substituted with one or more (e.g., 1 or 2 or 3 or 1-4 or 1-3 or 2-4) substituents selected from the group consisting of halo, unsubstituted alkyl, and alkyl substituted with one or more halo groups. In some embodiments of Formula (Ij), $R^1$ is phenyl substituted with halo. In some embodiments of Formula (Ij), $R^1$ is phenyl substituted with F or $C_1$. In some embodiments of Formula (Ij), $R^1$ is phenyl substituted with unsubstituted alkyl. In some embodiments of Formula (Ij), $R^1$ is phenyl substituted with methyl or ethyl. In some embodiments of Formula (Ij), $R^1$ is phenyl substituted with alkyl substituted with one or more halo groups. In some embodiments of Formula (Ij), $R^1$ is phenyl substituted with —$CHF_2$ or —$CF_3$. In some embodiments of Formula (Ij), $R^1$ is phenyl substituted with 4-Cl. In some embodiments of Formula (Ij), $R^1$ is phenyl substituted with 4-$CF_3$. In some embodiments of Formula (Ij), $R^1$ is phenyl substituted with two or more groups selected from the group consisting of F, Cl, methyl and —$CF_3$. In some embodiments of Formula (Ij), $R^1$ is phenyl substituted with two F groups. In some embodiments of Formula (Ij), $R^1$ is phenyl substituted with F and Cl. In some embodiments of Formula (Ij), $R^1$ is phenyl substituted with F and methyl. In some embodiments of Formula (Ij), $R^1$ is phenyl substituted with F and —$CF_3$.

In some embodiments of Formula (Ij), n is 0, 1, or 2. In some embodiments of Formula (Ij), n is 0. In some embodiments of Formula (Ij), n is 1. In some embodiments of Formula (Ij), n is 1, and $R^{2b}$ is substituted or unsubstituted alkyl. In some embodiments of Formula (Ij), n is 1, and $R^{2b}$ is unsubstituted alkyl. In some embodiments of Formula (Ij), n is 1, and $R^{2b}$ is methyl.

In some embodiments of Formula (Ij), $R^3$ is substituted or unsubstituted phenyl. In some embodiments of Formula (Ij), $R^3$ is phenyl substituted with one or more (e.g., 1 or 2 or 3 or 1-4 or 1-3 or 2-4) substituents selected from the group consisting of halo and cyano. In some embodiments of Formula (Ij), $R^3$ is phenyl substituted with halo. In some embodiments of Formula (Ij), $R^3$ is phenyl substituted with F, Cl, or Br. In some embodiments of Formula (Ij), $R^3$ is phenyl substituted with cyano. In some embodiments of Formula (Ij), $R^3$ is phenyl substituted with two or more groups selected from the group consisting of F, Cl, Br, and cyano. In some embodiments of Formula (Ij), $R^3$ is phenyl substituted with F and Cl. In some embodiments of Formula (Ij), $R^3$ is phenyl substituted with F and Br. In some embodiments of embodiments of Formula (Ij), $R^3$ is phenyl substituted with F and cyano.

In some embodiments of Formula (Ij), $R^3$ is substituted or unsubstituted pyridinyl. In some embodiments of Formula (Ij), $R^3$ is pyridinyl substituted with one or more (e.g., 1 or 2 or 3 or 1-4 or 1-3 or 2-4) substituents selected from the group consisting of halo, substituted or unsubstituted alkyl, substituted or unsubstituted alkenyl, and substituted or unsubstituted alkoxy. In some embodiments of Formula (Ij), $R^3$ is pyridinyl substituted with halo. In some embodiments of Formula (Ij), $R^3$ is pyridinyl substituted with F or Cl. In some embodiments of Formula (Ij), $R^3$ is pyridinyl substituted with unsubstituted alkyl. In some embodiments of Formula (Ij), $R^3$ is pyridinyl substituted with methyl. In some embodiments of Formula (Ij), $R^3$ is pyridinyl substituted with unsubstituted alkenyl. In some embodiments of Formula (Ij), $R^3$ is pyridinyl substituted with —$CH=CH_2$. In some embodiments of Formula (Ij), $R^3$ is pyridinyl substituted with alkoxy optionally substituted with halo. In some embodiments of Formula (Ij), $R^3$ is pyridinyl substituted with methoxy or —$OCHF_2$. In some embodiments of Formula (Ij), $R^3$ is pyridinyl substituted with two or more groups selected from the group consisting of halo, substituted or unsubstituted alkyl, substituted or unsubstituted alkenyl, and substituted or unsubstituted alkoxy. In some embodiments of Formula (Ij), $R^3$ is pyridinyl substituted with F and Cl. In some embodiments of Formula (Ij), $R^3$ is pyridinyl substituted with Cl and methyl. In some embodiments of Formula (Ij), $R^3$ is pyridinyl substituted with F and methoxy. In some embodiments of Formula (Ij), $R^3$ is pyridinyl substituted with F and —OCHF$_2$. In some embodiments of Formula (Ij), $R^3$ is pyridinyl substituted with F and —CH═CH$_2$. In some embodiments of Formula (Ij), $R^3$ is substituted or unsubstituted pyridin-2-yl.

In some embodiments of Formula (Ij), $R^5$ is H. In some embodiments of Formula (Ij), $R^5$ is substituted or unsubstituted alkyl. In some embodiments of Formula (Ij), $R^5$ is methyl.

In some embodiments of Formula (Ij), q is 0. In some embodiments of Formula (Ij), q is 1.

In some embodiments of Formula (Ij), $R^1$ is phenyl substituted with one or more substituents selected from the group consisting of F, Cl, methyl, —CHF$_2$, and —CF$_3$, n is 0, $R^3$ is pyridinyl substituted with one or more substituents selected from the group consisting of F, Cl, methyl, —CH═CH$_2$, methoxy, and —OCHF$_2$, $R^5$ is H, and q is 0. In some embodiments of Formula (Ij), $R^1$ is phenyl substituted with one or more substituents selected from the group consisting of F, Cl, methyl, —CHF$_2$, and —CF$_3$, n is 0, $R^3$ is phenyl substituted with one or more substituents selected from the group consisting of F, Cl, Br, and cyano, $R^5$ is H, and q is 0. In some embodiments of Formula (Ij), $R^1$ is phenyl substituted with one or more substituents selected from the group consisting of F, Cl, methyl, —CHF$_2$, and —CF$_3$, n is 1, $R^{2b}$ is methyl, $R^3$ is pyridinyl substituted with one or more substituents selected from the group consisting of F, Cl, methyl, —CH═CH$_2$, methoxy, and —OCHF$_2$, $R^5$ is H, and q is 0. In some embodiments of Formula (Ij), $R^1$ is phenyl substituted with one or more substituents selected from the group consisting of F, Cl, methyl, —CHF$_2$, and —CF$_3$, n is 1, $R^{2b}$ is methyl, $R^3$ is phenyl substituted with one or more substituents selected from the group consisting of F, Cl, Br, and cyano, $R^5$ is H, and q is 0. In some embodiments of Formula (Ij), $R^1$ is phenyl substituted with one or more substituents selected from the group consisting of F, Cl, methyl, —CHF$_2$, and —CF$_3$, n is 0, $R^3$ is pyridinyl substituted with one or more substituents selected from the group consisting of F, Cl, methyl, —CH═CH$_2$, methoxy, and —OCHF$_2$, $R^5$ is H, and q is 1. In some embodiments of Formula (Ij), $R^1$ is phenyl substituted with one or more substituents selected from the group consisting of F, Cl, methyl, —CHF$_2$, and —CF$_3$, n is 0, $R^3$ is phenyl substituted with one or more substituents selected from the group consisting of F, Cl, Br, and cyano, $R^5$ is H, and q is 1. In some embodiments of Formula (Ij), $R^1$ is phenyl substituted with one or more substituents selected from the group consisting of F, Cl, methyl, —CHF$_2$, and —CF$_3$, n is 1, $R^{2b}$ is methyl, $R^3$ is pyridinyl substituted with one or more substituents selected from the group consisting of F, Cl, methyl, —CH═CH$_2$, methoxy, and —OCHF$_2$, $R^5$ is H, and q is 1. In some embodiments of Formula (Ij), $R^1$ is phenyl substituted with one or more substituents selected from the group consisting of F, Cl, methyl, —CHF$_2$, and —CF$_3$, n is 1, $R^{2b}$ is methyl, $R^3$ is phenyl substituted with one or more substituents selected from the group consisting of F, C$_1$, Br, and cyano, $R^5$ is H, and q is 1.

In some embodiments of Formula (Ij): $R^1$ is phenyl substituted with one substituent selected from the group consisting of F, Cl, methyl, ethyl, —CHF$_2$ or —CF$_3$; n is 0 or n is 1, and $R^{2b}$ is methyl; $R^3$ is pyridinyl substituted with two substituents selected from the group consisting of F, Cl, methyl, —CH═CH$_2$, methoxy, and —OCHF$_2$; $R^5$ is H; and q is 0 or 1.

In another aspect, the compound of Formula (I) is a compound of Formula (Ik-1), or a pharmaceutically acceptable salt thereof:

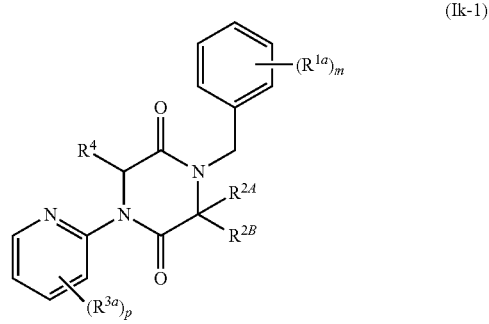

(Ik-1)

wherein $R^{2A}$ is H or substituted or unsubstituted alkyl; $R^{2B}$ is selected from the group consisting of substituted or unsubstituted alkyl, substituted or unsubstituted cycloalkyl, and substituted or unsubstituted heterocyclyl; m is 0, 1, or 2; p is 0, 1, or 2; each $R^{1a}$ is independently selected from the group consisting of halo and substituted or unsubstituted alkyl; each $R^{1a}$ is independently selected from the group consisting of halo, cyano, substituted or unsubstituted alkyl, substituted or unsubstituted alkenyl, and substituted or unsubstituted alkoxy; and $R^4$ is H.

In some embodiments of Formula (Ik-1), $R^{2A}$ is H. In some embodiments of Formula (Ik-1), $R^{2A}$ is substituted or unsubstituted alkyl. In some embodiments of Formula (Ik-1), $R^{2A}$ is substituted or unsubstituted methyl. In some embodiments of Formula (Ik-1), $R^{2A}$ is methyl.

In some embodiments of Formula (Ik-1), $R^{2B}$ is substituted or unsubstituted alkyl. In some embodiments of Formula (Ik-1), $R^{2B}$ is isopropyl. In some embodiments of Formula (Ik-1), $R^{2B}$ is substituted alkyl. In some embodiments of Formula (Ik-1), $R^{2B}$ is alkyl substituted with halo. In some embodiments of Formula (Ik-1), $R^{2B}$ is —CHF$_2$. In some embodiments of Formula (Ik-1), $R^{2B}$ is alkyl substituted with —OH. In some embodiments of Formula (Ik-1), $R^{2B}$ is —CH(OH)CH$_3$. In some embodiments of Formula (Ik-1), $R^{2B}$ is —CH$_2$OH. In some embodiments of Formula (Ik-1), $R^{2B}$ is —CH$_2$CH$_2$SCH$_3$. In some embodiments of Formula (Ik-1), $R^{2B}$ is —CH$_2$CH$_2$S(O)$_2$CH$_3$. In some embodiments of Formula (Ik-1), $R^{2B}$ is —CH$_2$N(H)C(O)CH$_3$. In some embodiments of Formula (Ik-1), $R^{2B}$ is —CH$_2$CH$_2$C(O)NH$_2$. In some embodiments of Formula (Ik-1), $R^{2B}$ is alkyl substituted with heterocyclyl. In some embodiments of Formula (Ik-1), $R^{2B}$ is C$_1$-C$_2$ alkyl substituted with heterocyclyl. In some embodiments of Formula (Ik-1), $R^{2B}$ is methyl substituted with oxetanyl. In some embodiments of Formula (Ik-1), $R^{2B}$ is methyl substituted with azetidinyl.

In some embodiments of Formula (Ik-1), $R^{2B}$ is substituted or unsubstituted cycloalkyl. In some embodiments of Formula (Ik-1), $R^{2B}$ is substituted or unsubstituted C$_3$-C$_5$ cycloalkyl. In some embodiments of Formula (Ik-1), $R^{2B}$ is unsubstituted cyclopropyl. In some embodiments of Formula (Ik-1), $R^{2B}$ is unsubstituted cyclobutyl. In some embodiments of Formula (Ik-1), $R^{2B}$ is cyclobutyl substituted with hydroxyl. In some embodiments of Formula (Ik-1), $R^{2B}$ is cyclobutyl substituted with methoxy. In some embodiments of Formula (Ik-1), $R^{2B}$ is polycyclic cycloalkyl. In some embodiments of Formula (Ik-1), $R^{2B}$ is substituted or unsubstituted bicyclo[1.1.1]pentanyl. In some embodiments of Formula (Ik-1), $R^{2B}$ is bicyclo[1.1.1]pentanyl substituted by a group selected from the group consisting of hydroxy, alkoxycarbonyl, carbamoyl, and hydroxymethyl.

In some embodiments of Formula (Ik-1), $R^{2B}$ is substituted or unsubstituted heterocyclyl. In some embodiments of Formula (Ik-1), $R^{2B}$ is substituted or unsubstituted 4-membered to 7-membered heterocyclyl. In some embodiments of Formula (Ik-1), $R^{2B}$ is substituted or unsubstituted 4-membered to 7-membered heterocyclyl, which contains one or more (e.g., 1 or 2 or 3 or 1-4 or 1-3 or 2-4) of N, O, or S atom. In some embodiments of Formula (Ik-1), $R^{2B}$ is substituted or unsubstituted 4- to 6-membered heterocyclyl containing one N atom. In some embodiments of Formula (Ik-1), $R^{2B}$ is substituted or unsubstituted azetidinyl. In some embodiments of Formula (Ik-1), $R^{2B}$ is 3-azetidinyl substituted with aminoacyl or acyl. In some embodiments of Formula (Ik-1), $R^{2B}$ is substituted or unsubstituted 4- to 6-membered heterocyclyl containing one O atom. In some embodiments of Formula (Ik-1), $R^{2B}$ is substituted or unsubstituted oxetanyl. In some embodiments of Formula (Ik-1), $R^{2B}$ is unsubstituted 3-oxetanyl. In some embodiments of Formula (Ik-1), $R^{2B}$ is 3-oxetanyl substituted with methyl. In some embodiments of Formula (Ik-1), $R^{2B}$ is substituted or unsubstituted tetrahydro-2H-pyranyl. In some embodiments of Formula (Ik-1), $R^{2B}$ is unsubstituted tetrahydro-2H-pyranyl. In some embodiments of Formula (Ik-1), $R^{2B}$ is substituted or unsubstituted 4- to 6-membered heterocyclyl containing one S atom. In some embodiments of Formula (Ik-1), $R^{2B}$ is substituted or unsubstituted 4-tetrahydro-2H-thiopyranyl.

In some embodiments of Formula (Ik-1), both $R^{2A}$ and $R^{2B}$ are methyl. In some embodiments of Formula (Ik-1), $R^{2A}$ is methyl and $R^{2B}$ is substituted methyl. In some embodiments of Formula (Ik-1), $R^{2A}$ is methyl and $R^{2B}$ is —$CH_2OH$. In some embodiments of Formula (Ik-1), $R^{2A}$ is methyl and $R^{2B}$ is —$CH_2N(H)C(O)CH_3$. In some embodiments of Formula (Ik-1), $R^{2A}$ is methyl and $R^{2B}$ is —$CHF_2$.

In some embodiments of Formula (Ik-1), m is 0. In some embodiments of Formula (Ik-1), m is 1. In some embodiments of Formula (Ik-1), m is 2. In some embodiments of Formula (Ik-1), each $R^{1a}$ is independently selected from the group consisting of halo and substituted or unsubstituted alkyl. In some embodiments of Formula (Ik-1), m is 1, and $R^{1a}$ is on the 4-position of the phenyl moiety. In some embodiments of Formula (Ik-1), m is 1, and $R^{1a}$ is halo. In some embodiments of Formula (Ik-1), m is 1, and $R^{1a}$ is 4-F. In some embodiments of Formula (Ik-1), m is 1, and $R^{1a}$ is 4-Cl. In some embodiments of Formula (Ik-1), m is 1, and $R^{1a}$ is substituted or unsubstituted $C_1$-$C_3$ alkyl. In some embodiments of Formula (Ik-1), m is 1, and $R^{1a}$ is 4-methyl. In some embodiments of Formula (Ik-1), m is 1, and $R^{1a}$ is 4-ethyl. In some embodiments of Formula (Ik-1), m is 1, and $R^{1a}$ is 4-$CHF_2$. In some embodiments of Formula (Ik-1), m is 1, and $R^{1a}$ is 4-$CF_3$. In some embodiments of Formula (Ik-1), m is 2, and the two $R^{1a}$ groups are on the 3-position and 4-position of the phenyl moiety. In some embodiments of Formula (Ik-1), m is 2, and $R^{1a}$ are 3-F and 4-F. In some embodiments of Formula (Ik-1), m is 2, and $R^{1a}$ are 3-F and 4-Cl. In some embodiments of Formula (Ik-1), m is 2, and $R^{1a}$ are 3-F and 4-methyl. In some embodiments of Formula (Ik-1), m is 2, and $R^{1a}$ are 3-F and 4-$CF_3$. In some embodiments of Formula (Ik-1), m is 2, and $R^{1a}$ are 3-Cl and 4-F. In some embodiments of Formula (Ik-1), m is 2, and $R^{1a}$ are 3-methyl and 4-F.

In some embodiments of Formula (Ik-1), p is 0. In some embodiments of Formula (Ik-1), p is 1. In some embodiments of Formula (Ik-1), p is 2. In some embodiments of Formula (Ik-1), p is 2, and each $R^{3a}$ is independently selected from the group consisting of halo, cyano, substituted or unsubstituted $C_1$-$C_3$ alkyl, substituted or unsubstituted $C_2$-$C_3$ alkenyl, and substituted or unsubstituted $C_1$-$C_3$ alkoxy. In some embodiments of Formula (Ik-1), p is 2, and each $R^{3a}$ is independently F, Cl, Br, cyano, methyl, —$CH=CH_2$, —$OCH_3$, or —$OCHF_2$. In some embodiments of Formula (Ik-1), p is 2, and at least one $R^{3a}$ is F. In some embodiments of Formula (Ik-1), p is 2, and at least one $R^{3a}$ is 3-F. In some embodiments of Formula (Ik-1), p is 2, and one $R^{3a}$ is 3-F and one $R^{3a}$ is on the 5-position of the pyridinyl moiety and is selected from the group consisting of halo, cyano, unsubstituted $C_1$-$C_3$ alkyl, unsubstituted $C_2$-$C_3$ alkenyl, and substituted or unsubstituted $C_1$-$C_3$ alkoxy. In some embodiments of Formula (Ik-1), p is 2, and $R^{3a}$ are 3-F and 5-Cl. In some embodiments of Formula (Ik-1), p is 2, and $R^{3a}$ are 3-F and 5-Br. In some embodiments of Formula (Ik-1), p is 2, and $R^{3a}$ are 3-F and 5-cyano. In some embodiments of Formula (Ik-1), p is 2, and $R^{3a}$ are 3-F and 5-methyl. In some embodiments of Formula (Ik-1), p is 2, and $R^{3a}$ are 3-F and 5-ethenyl. In some embodiments of Formula (Ik-1), p is 2, and $R^{3a}$ are 3-F and 5-methoxy. In some embodiments of Formula (Ik-1), p is 2, and $R^{3a}$ are 3-F and 5-$OCH_3$. In some embodiments of Formula (Ik-1), p is 2, and $R^{3a}$ are 3-F and 5-$OCHF_2$. In some embodiments of Formula (Ik-1), p is 2, and $R^{3a}$ are 3-methyl and 5-$C_1$.

In some embodiments of Formula (Ik-1), $R^{2A}$ is H, $R^{2B}$ is isopropyl, m is 1, $R^{1a}$ is selected from the group consisting of F, Cl, and —$CF_3$, p is 1, and $R^{3a}$ is selected from the group consisting of F, Cl, and cyano. In some embodiments of Formula (Ik-1), $R^{2A}$ is H, $R^{2B}$ is 3-oxetanyl, m is 1, $R^{1a}$ is selected from the group consisting of F, Cl, and —$CF_3$, p is 1, and $R^{3a}$ is selected from the group consisting of F, Cl, and cyano. In some embodiments of Formula (Ik-1), $R^{2A}$ is methyl, $R^{2B}$ is methyl, m is 1, $R^{1a}$ is selected from the group consisting of F, Cl, and —$CF_3$, p is 1, and $R^{3a}$ is selected from the group consisting of F, Cl, and cyano.

In some embodiments of Formula (Ik-1), $R^{2A}$ is H, $R^{2B}$ is isopropyl, m is 1, $R^{1a}$ is selected from the group consisting of F, Cl, and —$CF_3$, p is 2, and each $R^{3a}$ is independently selected from the group consisting of F, Cl, and cyano. In some embodiments of Formula (Ik-1), $R^{2A}$ is H, $R^{2B}$ is 3-oxetanyl, m is 1, $R^{1a}$ is selected from the group consisting of F, Cl, and —$CF_3$, p is 2, and each $R^{3a}$ is independently selected from the group consisting of F, Cl, and cyano. In some embodiments of Formula (Ik-1), $R^{2A}$ is methyl, $R^{2B}$ is methyl, m is 1, $R^{1a}$ is selected from the group consisting of F, Cl, and —$CF_3$, p is 2, and each $R^{3a}$ is independently selected from the group consisting of F, Cl, and cyano.

In some embodiments of Formula (Ik-1), $R^{2A}$ is H, $R^{2B}$ is isopropyl, m is 2, each $R^{1a}$ is independently selected from the group consisting of F, Cl, and —$CF_3$, p is 1, and $R^{3a}$ is selected from the group consisting of F, Cl, and cyano. In some embodiments of Formula (Ik-1), $R^{2A}$ is H, $R^{2B}$ is 3-oxetanyl, m is 2, each $R^{1a}$ is independently selected from the group consisting of F, Cl, and —$CF_3$, p is 1, and $R^{3a}$ is selected from the group consisting of F, Cl, and cyano. In some embodiments of Formula (Ik-1), $R^{2A}$ is methyl, $R^{2B}$ is methyl, m is 2, each $R^{1a}$ is independently selected from the group consisting of F, Cl, and —$CF_3$, p is 1, and $R^{3a}$ is selected from the group consisting of F, Cl, and cyano.

In some embodiments of Formula (Ik-1), $R^{2A}$ is H, $R^{2B}$ is isopropyl, m is 2, each $R^{1a}$ is independently selected from the group consisting of F, Cl, and —$CF_3$, p is 2, and each $R^{3a}$ is independently selected from the group consisting of F, Cl, and cyano. In some embodiments of Formula (Ik-1), $R^{2A}$ is H, $R^{2B}$ is 3-oxetanyl, m is 2, each $R^{1a}$ is independently selected from the group consisting of F, Cl, and —$CF_3$, p is 2, and each $R^{3a}$ is independently selected from the group consisting of F, Cl, and cyano. In some embodiments of Formula (Ik-1), $R^{2A}$ is methyl, $R^{2B}$ is methyl, m is 2, each $R^{1a}$ is independently selected from the group consisting of F, Cl, and —$CF_3$, p is 2, and each $R^{3a}$ is independently selected from the group consisting of F, Cl, and cyano.

In some embodiments of Formula (Ik-1): $R^{2A}$ is H or methyl; $R^{2B}$ is selected from the group consisting of isopropyl, —$CHF_2$, —$CH(OH)CH_3$, —$CH_2OH$, —$CH_2CH_2SCH_3$, —$CH_2CH_2S(O)_2CH_3$, —$CH_2N(H)C(O)CH_3$, —$CH_2CH_2C(O)NH_2$, methyl substituted with oxetanyl or azetidinyl, cyclopropyl, cyclobutyl, 3-azetidinyl substituted with aminoacyl or acyl, 3-oxetanyl, 3-oxetanyl substituted with methyl, tetrahydro-2H-pyranyl, and 4-tetrahydro-2H-thiopyranyl; m is 1; $R^{1a}$ is 4-F, 4-Cl, 4-methyl, 4-$CHF_2$, and 4-$CF_3$; p is 2; and the two $R^{3a}$ groups are selected from the group consisting of 3-F and 5-Cl, 3-F and 5-Br, 3-F and 5-cyano, 3-F and 5-methyl, 3-F and 5-ethenyl, 3-F and 5-methoxy, 3-F and 5-$OCH_3$, 3-F and 5-$OCHF_2$, and 3-methyl and 5-Cl.

In another aspect, the compound of Formula (I) is a compound of Formula (Ik-2), or a pharmaceutically acceptable salt thereof:

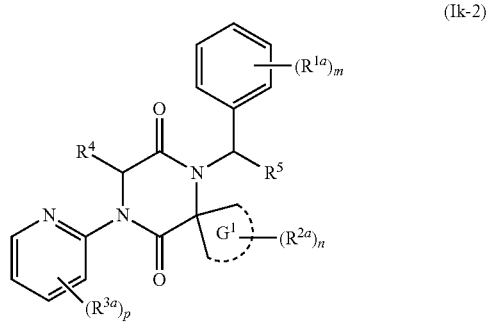

(Ik-2)

wherein $G^1$ is selected from the group consisting of substituted or unsubstituted cycloalkyl and substituted or unsubstituted heterocyclyl; each $R^{1a}$ is independently selected from the group consisting of halo and substituted or unsubstituted alkyl; each $R^{2a}$ is independently selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminothionyl, substituted or unsubstituted aminocarbonylamino, and substituted or unsubstituted alkyl; each $R^{3a}$ is independently selected from the group consisting of halo, cyano, and substituted or unsubstituted alkyl; $R^4$ is H; $R^5$ is H or substituted or unsubstituted alkyl; m is 0, 1, or 2; n is 0, 1, or 2; and p is 0, 1, or 2.

In some embodiments of Formula (Ik-2), $G^1$ is substituted or unsubstituted cycloalkyl. In some embodiments of Formula (Ik-2), $G^1$ is substituted or unsubstituted cyclopropyl. In some embodiments of Formula (Ik-2), $G^1$ is substituted or unsubstituted cyclobutanyl. In some embodiments of Formula (Ik-2), $G^1$ is substituted or unsubstituted 4-membered to 6-membered heterocyclyl, which contains one or more (e.g., 1 or 2 or 3 or 1-4 or 1-3 or 2-4) of N or O atom. In some embodiments of Formula (Ik-2), $G^1$ is substituted or unsubstituted 4-membered to 6-membered heterocyclyl, which contains one N atom. In some embodiments of Formula (Ik-2), $G^1$ is substituted or unsubstituted azetidinyl. In some embodiments of Formula (Ik-2), $G^1$ is substituted or unsubstituted piperidinyl. In some embodiments of Formula (Ik-2), $G^1$ is substituted or unsubstituted 4-membered heterocyclyl, which contains one O atom. In some embodiments of Formula (Ik-2), $G^1$ is substituted or unsubstituted oxetanyl. In some embodiments of Formula (Ik-2), $G^1$ is substituted or unsubstituted tetrahydrofuranyl.

In some embodiments of Formula (Ik-2), m is 0. In some embodiments of Formula (Ik-2), m is 1, and $R^{1a}$ is selected from the group consisting of halo and substituted or unsubstituted alkyl. In some embodiments of Formula (Ik-2), m is 1, and $R^{1a}$ is on the 4-position of the phenyl moiety. In some embodiments of Formula (Ik-2), m is 1, and $R^{1a}$ is 4-F. In some embodiments of Formula (Ik-2), m is 1, and $R^{1a}$ is 4-Cl. In some embodiments of Formula (Ik-2), m is 1, and $R^{1a}$ is $C_1$-$C_3$ alkyl optionally substituted with halo. In some embodiments of Formula (Ik-2), m is 1, and $R^{1a}$ is 4-methyl. In some embodiments of Formula (Ik-2), m is 1, and $R^{1a}$ is 4-$CHF_2$. In some embodiments of Formula (Ik-2), m is 1, and $R^{1a}$ is 4-$CF_3$.

In some embodiments of Formula (Ik-2), n is 0. In some embodiments of Formula (Ik-2), n is 1. In some embodiments of Formula (Ik-2), n is 2.

In some embodiments of Formula (Ik-2), each $R^{2a}$ is independently selected from the group consisting of halo, substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted alkyl, and hydroxy. In some embodiments of Formula (Ik-2), $R^{2a}$ is halo, such as fluoro. In some embodiments of Formula (Ik-2), $R^{2a}$ is substituted or unsubstituted aryl. In some embodiments of Formula (Ik-2), $R^{2a}$ is substituted or unsubstituted phenyl. In some embodiments of Formula (Ik-2), $R^{2a}$ is phenyl substituted with one or more (e.g., 1 or 2 or 3 or 1-4 or 1-3 or 2-4) substituents selected from the group consisting of halo, alkoxycarbonyl, substituted or unsubstituted amino, and substituted or unsubstituted aminoacyl. In some embodiments of Formula (Ik-2), $R^{2a}$ is phenyl substituted with halo. In some embodiments of Formula (Ik-2), $R^{2a}$ is phenyl substituted with alkoxycarbonyl. In some embodiments of Formula (Ik-2), $R^{2a}$ is phenyl substituted with methoxycarbonyl. In some embodiments of Formula (Ik-2), $R^{2a}$ is phenyl substituted with substituted or unsubstituted amino. In some embodiments of Formula (Ik-2), $R^{2a}$ is phenyl substituted with methylamino. In some embodiments of Formula (Ik-2), $R^{2a}$ is phenyl substituted with substituted or unsubstituted aminoacyl. In some embodiments of Formula (Ik-2), $R^{2a}$ is phenyl substituted with methylaminoacyl. In some embodiments of Formula (Ik-2), $R^{2a}$ is phenyl substituted with two substituents selected from the group consisting of methoxycarbonyl, methylamino, and methylaminoacyl. In some embodiments of Formula (Ik-2), $R^{2a}$ is substituted or unsubstituted heteroaryl. In some embodiments of Formula (Ik-2), $R^{2a}$ is substituted or unsubstituted oxadiazolyl. In some embodiments of Formula (Ik-2), $R^{2a}$ is unsubstituted oxadiazolyl. In some embodiments of Formula (Ik-2), $R^{2a}$ is oxadiazolyl substituted with cycloalkyl. In some embodiments of Formula (Ik-2), $R^{2a}$ is oxadiazolyl substituted with cyclopropyl. In some embodiments of Formula (Ik-2), $R^{2a}$ is substituted or unsubstituted pyridinyl. In some embodiments of Formula (Ik-2), $R^{2a}$ is unsubstituted pyridinyl. In some embodiments of Formula (Ik-2), $R^{2a}$ is pyridinyl substituted with halo, such as F. In some embodiments of Formula (Ik-2), $R^{2a}$ is pyridinyl substituted with cyano. In some embodiments of Formula (Ik-2), $R^{2a}$ is substituted or unsubstituted pyridin-2-yl. In some embodiments of Formula (Ik-2), $R^{2a}$ is substituted or unsubstituted alkoxycarbonyl. In some embodiments of Formula (Ik-2), $R^{2a}$ is methoxycarbonyl. In some embodiments of Formula (Ik-2), $R^{2a}$ is ethoxycarbonyl. In some embodiments of Formula (Ik-2), $R^{2a}$ is substituted or unsubstituted aminoacyl. In some embodiments of Formula (Ik-2), $R^{2a}$ is unsubstituted aminoacyl. In some embodiments of Formula (Ik-2), $R^{2a}$ is aminoacyl substituted with one or more (e.g., 1 or 2 or 3 or 1-4 or 1-3 or 2-4) substituents selected from the group consisting of $C_1$-$C_3$ alkyl, $C_3$-$C_6$ cycloalkyl, and 4-membered to 7-membered heterocyclyl. In some embodiments of Formula (Ik-2), $R^{2a}$ is aminoacyl substituted with $C_1$-$C_3$ alkyl. In some embodiments of Formula (Ik-2), $R^{2a}$ is methylaminoacyl, ethylaminoacyl, or isopropylaminoacyl. In some embodiments of Formula (Ik-2), $R^{2a}$ is dimethylaminoacyl. In some embodiments of Formula (Ik-2), $R^{2a}$ is cyclopropylaminoacyl. In some embodiments of Formula (Ik-2), $R^{2a}$ is tetrahydropyranylaminoacyl. In some embodiments of Formula (Ik-2), $R^{2a}$ is substituted or unsubstituted acyl. In some embodiments of Formula (Ik-2), $R^{2a}$ is unsubstituted acyl. In some embodiments of Formula (Ik-2), $R^{2a}$ is acyl substituted with one or more (e.g., 1 or 2 or 3 or 1-4 or 1-3 or 2-4) substituents selected from the group consisting of substituted or unsubstituted alkyl and substituted or unsubstituted aryl. In some embodiments of Formula (Ik-2), $R^{2a}$ is acyl substituted with methyl. In some embodiments of Formula (Ik-2), $R^{2a}$ is acyl substituted with phenyl, wherein the phenyl is optionally substituted with amino. In some embodiments of Formula (Ik-2), $R^{2a}$ is substituted or unsubstituted alkyl. In some embodiments of Formula (Ik-2), $R^{2a}$ is $C_1$-$C_3$ alkyl substituted with halo. In some embodiments of Formula (Ik-2), $R^{2a}$ is ethyl substituted with two fluoro groups, such as —$CH_2CHF_2$. In some embodiments of Formula (Ik-2), $R^{2a}$ is hydroxy.

In some embodiments of Formula (Ik-2), p is 0. In some embodiments of Formula (Ik-2), p is 1. In some embodiments of Formula (Ik-2), p is 1, and $R^{3a}$ is halo. In some embodiments of Formula (Ik-2), p is 1, and $R^{3a}$ is 5-Cl. In some embodiments of Formula (Ik-2), p is 2. In some embodiments of Formula (Ik-2), p is 2, and each $R^{3a}$ is independently halo, cyano, or substituted or unsubstituted $C_1$-$C_3$ alkyl. In some embodiments of Formula (Ik-2), p is 2, and each $R^{3a}$ is independently F, Cl, Br, cyano, or methyl. In some embodiments of Formula (Ik-2), p is 2, and at least one $R^{3a}$ is F or methyl. In some embodiments of Formula (Ik-2), p is 2, and at least one $R^{3a}$ is 3-F or 3-methyl. In some embodiments of Formula (Ik-2), p is 2, and one $R^{3a}$ is on the 3-position of the pyridinyl moiety and is selected from the group consisting of F and methyl, and one $R^{3a}$ is on the 5-position of the pyridinyl moiety and is selected from the group consisting of halo, cyano, and unsubstituted $C_1$-$C_3$ alkyl. In some embodiments of Formula (Ik-2), p is 2, and $R^{3a}$ are 3-F and 5-Cl. In some embodiments of Formula (Ik-2), p is 2, and $R^{3a}$ are 3-F and 5-Br. In some embodiments of Formula (Ik-1), p is 2, and $R^{3a}$ are 3-F and 5-cyano. In some embodiments of Formula (Ik-2), p is 2, and $R^{3a}$ are 3-methyl and 5-Cl. In some embodiments of Formula (Ik-2), p is 2, and $R^{3a}$ are 3-methyl and 5-cyano.

In some embodiments of Formula (Ik-2), $R^5$ is H. In some embodiments of Formula (Ik-2), $R^5$ is substituted or unsubstituted alkyl. In some embodiments of Formula (Ik-2), $R^5$ is methyl.

In some embodiments of Formula (Ik-2), $G^1$ is cyclobutanyl, m is 1, $R^{1a}$ is selected the group consisting of F, Cl, and —$CF_3$, n is 0, p is 1, $R^{3a}$ is selected from the group consisting of F, Cl, and cyano, and $R^5$ is H. In some embodiments of Formula (Ik-2), $G^1$ is azetidinyl, m is 1, $R^{1a}$ is selected from the group consisting of F, Cl, and —$CF_3$, n is 0, p is 1, $R^{3a}$ is selected from the group consisting of F, Cl, and cyano, and $R^5$ is H. In some embodiments of Formula (Ik-2), $G^1$ is oxetanyl, m is 1, $R^{1a}$ is selected from the group consisting of F, Cl, and —$CF_3$, n is 0, p is 1, $R^{3a}$ is selected from the group consisting of F, Cl, and cyano, and $R^5$ is H. In some embodiments of Formula (Ik-2), $G^1$ is cyclobutanyl, m is 1, $R^{1a}$ is selected from the group consisting of F, Cl, and —$CF_3$, n is 0, p is 1, $R^{3a}$ is selected from the group consisting of F, Cl, and cyano, and $R^5$ is methyl. In some embodiments of Formula (Ik-2), $G^1$ is azetidinyl, m is 1, $R^{1a}$ is selected from the group consisting of F, Cl, and —$CF_3$, n is 0, p is 1, $R^{3a}$ is selected from the group consisting of F, Cl, and cyano, and $R^5$ is methyl. In some embodiments of Formula (Ik-2), $G^1$ is oxetanyl, m is 1, $R^{1a}$ is selected from the group consisting of F, Cl, and —$CF_3$, n is 0, p is 1, $R^{3a}$ is selected from the group consisting of F, Cl, and cyano, and $R^5$ is methyl.

In some embodiments of Formula (Ik-2), $G^1$ is cyclobutanyl, m is 1, $R^{1a}$ is selected from the group consisting of F, Cl, and —$CF_3$, n is 0, p is 2, each $R^{3a}$ is independently selected from the group consisting of F, Cl, and cyano, and $R^5$ is H. In some embodiments of Formula (Ik-2), $G^1$ is azetidinyl, m is 1, $R^{1a}$ is selected from the group consisting of F, Cl, and —$CF_3$, n is 0, p is 2, each $R^{3a}$ is independently selected from the group consisting of F, Cl, and cyano, and $R^5$ is H. In some embodiments of Formula (Ik-2), $G^1$ is oxetanyl, m is 1, $R^{1a}$ is selected from the group consisting of F, Cl, and —$CF_3$, n is 0, p is 2, each $R^{3a}$ is independently selected from the group consisting of F, Cl, and cyano, and $R^5$ is H. In some embodiments of Formula (Ik-2), $G^1$ is cyclobutanyl, m is 1, $R^{1a}$ is selected from the group consisting of F, Cl, and —$CF_3$, n is 0, p is 2, each $R^{3a}$ is independently selected from the group consisting of F, Cl, and cyano, and $R^5$ is methyl. In some embodiments of Formula (Ik-2), $G^1$ is azetidinyl, m is 1, $R^{1a}$ is selected from the group consisting of F, Cl, and —$CF_3$, n is 0, p is 2, each $R^{3a}$ is independently selected from the group consisting of F, Cl, and cyano, and $R^5$ is methyl. In some embodiments of Formula (Ik-2), $G^1$ is oxetanyl, m is 1, $R^{1a}$ is selected from the group consisting of F, Cl, and —$CF_3$, n is 0, p is 2, each $R^{3a}$ is independently selected from the group consisting of F, Cl, and cyano, and $R^5$ is methyl.

In some embodiments of Formula (Ik-2), $G^1$ is cyclobutanyl, m is 2, each $R^{1a}$ is independently selected from the group consisting of F, Cl, and —$CF_3$, n is 0, p is 1, $R^{3a}$ is selected from the group consisting of F, Cl, and cyano, and $R^5$ is H. In some embodiments of Formula (Ik-2), $G^1$ is azetidinyl, m is 2, each $R^{1a}$ is independently selected from the group consisting of F, Cl, and —$CF_3$, n is 0, p is 1, $R^{3a}$ is selected from the group consisting of F, Cl, and cyano, and $R^5$ is H. In some embodiments of Formula (Ik-2), $G^1$ is oxetanyl, m is 2, each $R^{1a}$ is independently selected from the group consisting of F, Cl, and —$CF_3$, n is 0, p is 1, $R^{3a}$ is selected from the group consisting of F, Cl, and cyano, and $R^5$ is H. In some embodiments of Formula (Ik-2), $G^1$ is cyclobutanyl, m is 2, each $R^{1a}$ is independently selected from the group consisting of F, Cl, and —$CF_3$, n is 0, p is 1, $R^{3a}$ is selected from the group consisting of F, Cl, and cyano, and $R^5$ is methyl. In some embodiments of Formula (Ik-2), $G^1$ is azetidinyl, m is 2, each $R^{1a}$ is independently selected from the group consisting of F, Cl, and —$CF_3$, n is 0, p is 1, $R^{3a}$ is selected from the group consisting of F, Cl, and cyano, and $R^5$ is methyl. In some embodiments of Formula (Ik-2), $G^1$ is oxetanyl, m is 2, each $R^{1a}$ is independently selected from the group consisting of F, Cl, and —CF$_3$, n is 0, p is 1, R$^{3a}$ is selected from the group consisting of F, Cl, and cyano, and R$^5$ is methyl.

In some embodiments of Formula (Ik-2), G$^1$ is cyclobutanyl, m is 2, each R$^{1a}$ is independently selected from the group consisting of F, Cl, and —CF$_3$, n is 0, p is 2, each R$^{3a}$ is independently selected from the group consisting of F, Cl, and cyano, and R$^5$ is H. In some embodiments of Formula (Ik-2), G$^1$ is azetidinyl, m is 2, each R$^{1a}$ is independently selected from the group consisting of F, Cl, and —CF$_3$, n is 0, p is 2, each R$^{3a}$ is independently selected from the group consisting of F, Cl, and cyano, and R$^5$ is H. In some embodiments of Formula (Ik-2), G$^1$ is oxetanyl, m is 2, each R$^{1a}$ is independently selected from the group consisting of F, Cl, and —CF$_3$, n is 0, p is 2, each R$^{3a}$ is independently selected from the group consisting of F, Cl, and cyano, and R$^5$ is H. In some embodiments of Formula (Ik-2), G$^1$ is cyclobutanyl, m is 2, each R$^{1a}$ is independently selected from the group consisting of F, Cl, and —CF$_3$, n is 0, p is 2, each R$^{3a}$ is independently selected from the group consisting of F, Cl, and cyano, and R$^5$ is methyl. In some embodiments of Formula (Ik-2), G$^1$ is azetidinyl, m is 2, each R$^{1a}$ is independently selected from the group consisting of F, Cl, and —CF$_3$, n is 0, p is 2, each R$^{3a}$ is independently selected from the group consisting of F, Cl, and cyano, and R$^5$ is methyl. In some embodiments of Formula (Ik-2), G$^1$ is oxetanyl, m is 2, each R$^{1a}$ is independently selected from the group consisting of F, Cl, and —CF$_3$, n is 0, p is 2, each R$^{3a}$ is independently selected from the group consisting of F, Cl, and cyano, and R$^5$ is methyl.

In another aspect, the compound of Formula (I) is a compound of Formula (Il), or a pharmaceutically acceptable salt thereof:

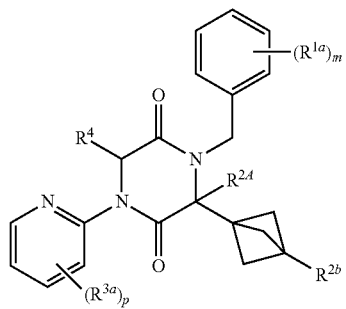

(Il)

wherein R$^{2A}$ is H or substituted or unsubstituted alkyl; R$^{2b}$ is selected from the group consisting of H, substituted or unsubstituted alkyl, substituted or unsubstituted alkoxycarbonyl, substituted or unsubstituted aminoacyl, and hydroxy; m is 0, 1, or 2; p is 0, 1, or 2; each R$^{1a}$ is independently selected from the group consisting of halo and substituted or unsubstituted alkyl; each R$^{3a}$ is independently halo; and R$^4$ is H.

In some embodiments of Formula (Il), R$^{2A}$ is H.

In some embodiments of Formula (Il), R$^{2b}$ is selected from the group consisting of substituted or unsubstituted alkyl, substituted or unsubstituted alkoxycarbonyl, substituted or unsubstituted aminoacyl, and hydroxy. In some embodiments of Formula (Il), R$^{2b}$ is selected from the group consisting of substituted or unsubstituted alkyl, substituted or unsubstituted alkoxycarbonyl, substituted or unsubstituted aminoacyl, and hydroxy. In some embodiments of Formula (Il), R$^{2b}$ is selected from the group consisting of substituted C$_1$-C$_3$ alkyl, unsubstituted C$_1$-C$_3$ alkoxycarbonyl, unsubstituted aminoacyl, and hydroxy. In some embodiments of Formula (Il), R$^{2b}$ is C$_1$-C$_3$ alkyl substituted with hydroxy. In some embodiments of Formula (Il), R$^{2b}$ is —CH$_2$OH. In some embodiments of Formula (Il), R$^{2b}$ is methoxycarbonyl. In some embodiments of Formula (Il), R$^{2b}$ is ethoxycarbonyl. In some embodiments of Formula (Il), R$^{2b}$ is unsubstituted aminoacyl. In some embodiments of Formula (Il), R$^{2b}$ is hydroxy.

In some embodiments of Formula (Il), m is 1, and R$^{1a}$ is selected from the group consisting of halo and substituted or unsubstituted alkyl. In some embodiments of Formula (Il), m is 1, and R$^{1a}$ is on the 4-position of the phenyl moiety. In some embodiments of Formula (Il), m is 1, and R$^{1a}$ is 4-F. In some embodiments of Formula (Il), m is 1, and R$^{1a}$ is 4-Cl. In some embodiments of Formula (Il), m is 1, and R$^{1a}$ is C$_1$-C$_3$ alkyl optionally substituted with halo. In some embodiments of Formula (Il), m is 1, and R$^{1a}$ is 4-methyl. In some embodiments of Formula (Il), m is 1, and R$^{1a}$ is 4-CHF$_2$. In some embodiments of Formula (Il), m is 1, and R$^{1a}$ is 4-CF$_3$.

In some embodiments of Formula (Il), p is 2, and each R$^{3a}$ is independently halo. In some embodiments of Formula (Il), p is 2, and each R$^{3a}$ is independently F or Cl. In some embodiments of Formula (Il), p is 2, and one R$^{3a}$ is 3-halo and one R$^{3a}$ is 5-halo. In some embodiments of Formula (Il), p is 2, and R$^{3a}$ are 3-F and 5-Cl.

In another aspect, the compound of Formula (I) is a compound of Formula (Im), or a pharmaceutically acceptable salt thereof:

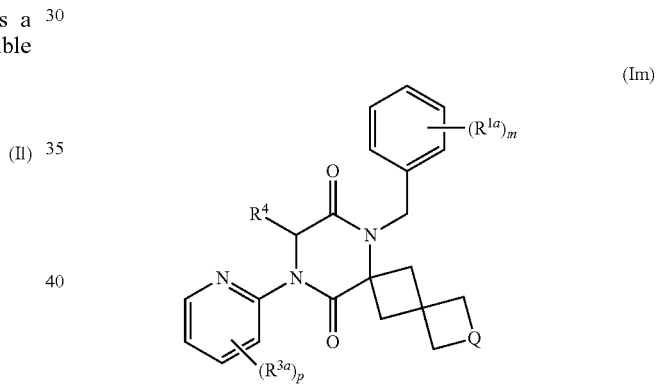

(Im)

wherein Q is —O— or —N(R$^{2b}$)—; R$^{2b}$ is selected from the group consisting of H and substituted or unsubstituted acyl; m is 0, 1, or 2; p is 0, 1, or 2; each R$^{1a}$ is independently selected from the group consisting of halo and substituted or unsubstituted alkyl; each R$^{3a}$ is independently halo; and R$^4$ is H.

In some embodiments of Formula (Im), Q is —O—. In some embodiments of Formula (Im), Q is —N(R$^{2b}$)—.

In some embodiments of Formula (Im), R$^{2b}$ is substituted or unsubstituted acyl. In some embodiments of Formula (Im), R$^{2b}$ is unsubstituted acyl. In some embodiments of Formula (Im), R$^{2b}$ is acyl substituted with alkyl. In some embodiments of Formula (Im), R$^{2b}$ is acyl substituted with methyl.

In some embodiments of Formula (Im), m is 1, and R$^{1a}$ is selected from the group consisting of halo and substituted or unsubstituted alkyl. In some embodiments of Formula (Im), m is 1, and R$^{1a}$ is on the 4-position of the phenyl moiety. In some embodiments of Formula (Im), m is 1, and R$^{1a}$ is 4-F. In some embodiments of Formula (Im), m is 1, and R$^{1a}$ is 4-Cl. In some embodiments of Formula (Im), m is 1, and R$^{1a}$ is C$_1$-C$_3$ alkyl optionally substituted with halo. In some embodiments of Formula (Im), m is 1, and $R^{1a}$ is 4-methyl. In some embodiments of Formula (Im), m is 1, and $R^{1a}$ is 4-CHF$_2$. In some embodiments of Formula (Im), m is 1, and $R^{1a}$ is 4-CF$_3$.

In some embodiments of Formula (Im), p is 2, and each $R^{3a}$ is independently halo. In some embodiments of Formula (Im), p is 2, and each $R^{3a}$ is independently F or C$_1$. In some embodiments of Formula (Im), p is 2, and one $R^{3a}$ is 3-halo and one $R^{3a}$ is 5-halo. In some embodiments of Formula (Im), p is 2, and $R^{3a}$ are 3-F and 5-C$_1$.

In another aspect, the compound of Formula (I) is a compound of Formula (In-1) or Formula (In-2), or a pharmaceutically acceptable salt thereof:

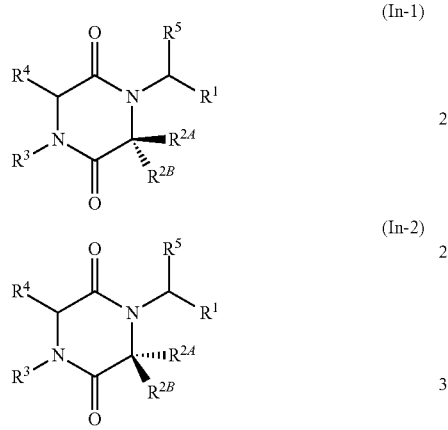

wherein:

$R^1$ is selected from the group consisting of substituted or unsubstituted phenyl and substituted or unsubstituted pyridyl;

$R^{2A}$, $R^{2B}$, and $R^3$ are defined by any one of (i)-(iii):
(i) $R^{2A}$ is H or substituted or unsubstituted alkyl;
$R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and
$R^3$ is substituted or unsubstituted phenyl or substituted or unsubstituted pyridyl;
or
(ii) $R^{2A}$ is H or substituted or unsubstituted alkyl;
$R^{2B}$ is substituted or unsubstituted phenyl or substituted or unsubstituted pyridyl; and
$R^3$ is substituted or unsubstituted alkyl;
or
(iii) $R^{2A}$ and $R^{2B}$ are taken together with the carbon atom to which they are attached to form $G^1$, wherein $G^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; and
$R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;

$R^4$ is H or substituted or unsubstituted alkyl; and
$R^5$ is H or substituted or unsubstituted alkyl;

wherein, when one or more of provisions (a)-(c) apply, then $R^1$ is substituted or unsubstituted pyridyl or phenyl substituted with at least one substituent other than methyl or methoxy:
(a) $R^{2A}$ and $R^{2B}$ are as defined by (i) and $R^3$ is substituted or unsubstituted phenyl;
(b) $R^{2A}$ and $R^3$ are as defined by (ii) and $R^{2B}$ is 4-methoxyphenyl;
(c) $R^{2A}$, and $R^{2B}$— are as defined by (iii) and $R^3$ is 4-methoxyphenylmethyl.

In some embodiments, provided herein are compounds and salts thereof described in Table 1.

TABLE 1

| No. | Structure | Name |
|---|---|---|
| 1 | 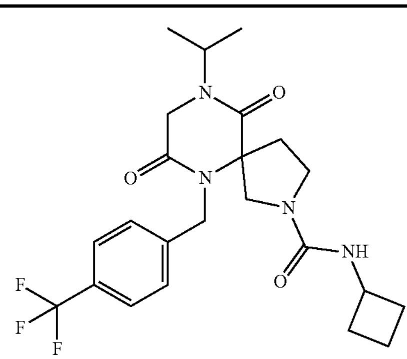 | N-cyclobutyl-9-isopropyl-7,10-dioxo-6-(4-(trifluoromethyl)benzyl)-2,6,9-triazaspiro[4.5]-decane-2-carboxamide |

TABLE 1-continued

| No. | Structure | Name |
| --- | --- | --- |
| 2 | 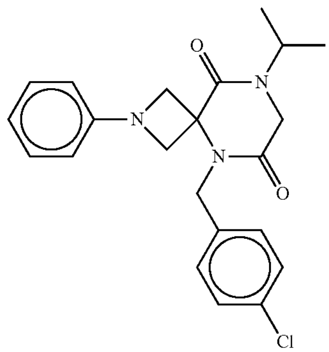 | 5-(4-chlorobenzyl)-8-isopropyl-2-phenyl-2,5,8-triazaspiro[3.5]nonane-6,9-dione |
| 3 | 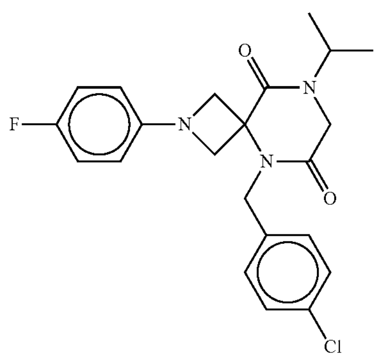 | 5-(4-chlorobenzyl)-2-(4-fluorophenyl)-8-isopropyl-2,5,8-triazaspiro[3.5]-nonane-6,9-dione |
| 4 | 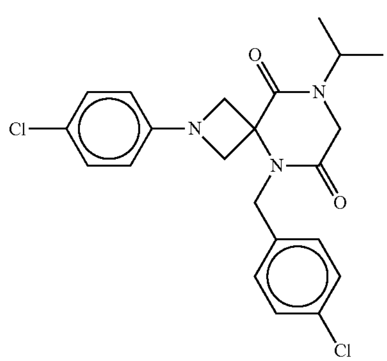 | 5-(4-chlorobenzyl)-2-(4-chlorophenyl)-8-isopropyl-2,5,8-triazaspiro[3.5]-nonane-6,9-dione |
| 5 | 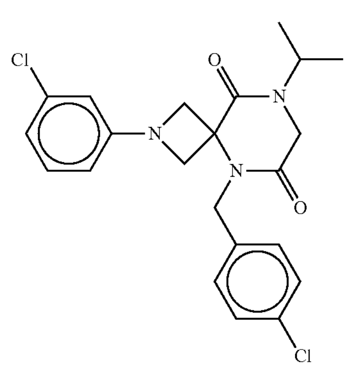 | 5-(4-chlorobenzyl)-2-(3-chlorophenyl)-8-isopropyl-2,5,8-triazaspiro[3.5]-nonane-6,9-dione |

TABLE 1-continued

| No. | Structure | Name |
|---|---|---|
| 6 | 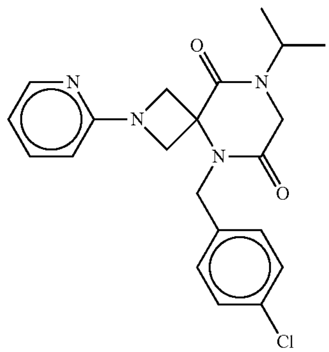 | 5-(4-chlorobenzyl)-8-isopropyl-2-(pyridin-2-yl)-2,5,8-triazaspiro[3.5]-nonane-6,9-dione |
| 7 | 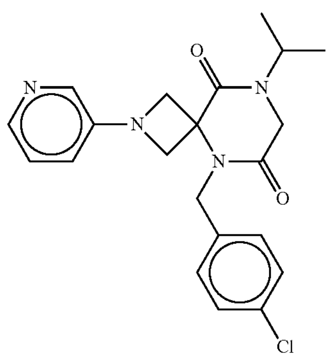 | 5-(4-chlorobenzyl)-8-isopropyl-2-(pyridin-3-yl)-2,5,8-triazaspiro[3.5]-nonane-6,9-dione |
| 8 | 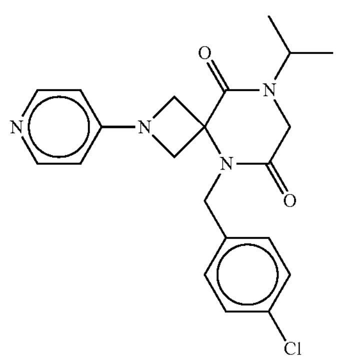 | 5-(4-chlorobenzyl)-8-isopropyl-2-(pyridin-4-yl)-2,5,8-triazaspiro[3.5]-nonane-6,9-dione |
| 9 | 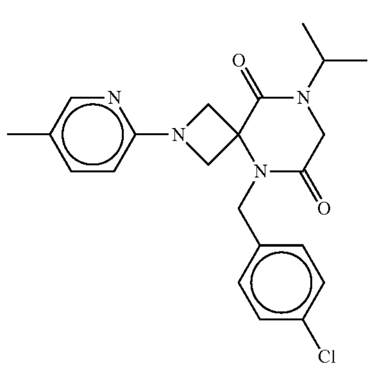 | 5-(4-chlorobenzyl)-8-isopropyl-2-(5-methyl-pyridin-2-yl)-2,5,8-triazaspiro[3.5]nonane-6,9-dione |

TABLE 1-continued

| No. | Structure | Name |
|---|---|---|
| 10 | 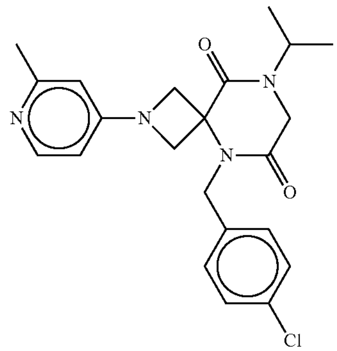 | 5-(4-chlorobenzyl)-8-isopropyl-2-(2-methyl-pyridin-4-yl)-2,5,8-triazaspiro[3.5]nonane-6,9-dione |
| 11 | 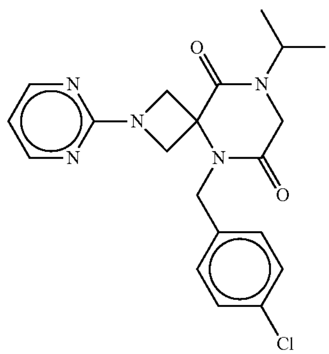 | 5-(4-chlorobenzyl)-8-isopropyl-2-(pyrimidin-2-yl)-2,5,8-triazaspiro-[3.5]nonane-6,9-dione |
| 12 | 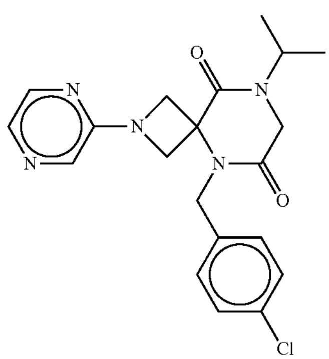 | 5-(4-chlorobenzyl)-8-isopropyl-2-(pyrazin-2-yl)-2,5,8-triazaspiro-[3.5]nonane-6,9-dione |
| 13 | 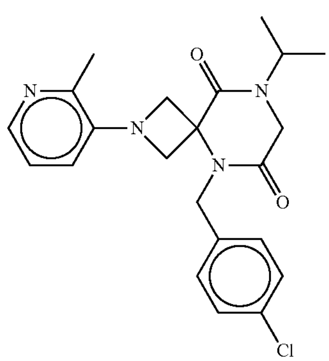 | 5-(4-chlorobenzyl)-8-isopropyl-2-(2-methyl-pyridin-3-yl)-2,5,8-triazaspiro[3.5]nonane-6,9-dione |

TABLE 1-continued

| No. | Structure | Name |
|---|---|---|
| 14 | 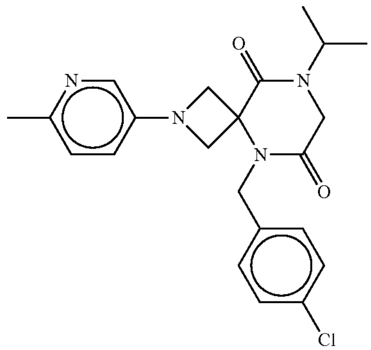 | 5-(4-chlorobenzyl)-8-isopropyl-2-(6-methyl-pyridin-3-yl)-2,5,8-triazaspiro[3.5]nonane-6,9-dione |
| 15 | 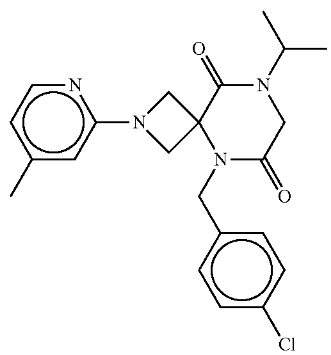 | 5-(4-chlorobenzyl)-8-isopropyl-2-(4-methyl-pyridin-2-yl)-2,5,8-triazaspiro[3.5]nonane-6,9-dione |
| 16 | 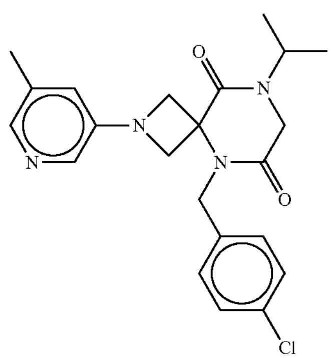 | 5-(4-chlorobenzyl)-8-isopropyl-2-(5-methyl-pyridin-3-yl)-2,5,8-triazaspiro[3.5]nonane-6,9-dione |
| 17 | 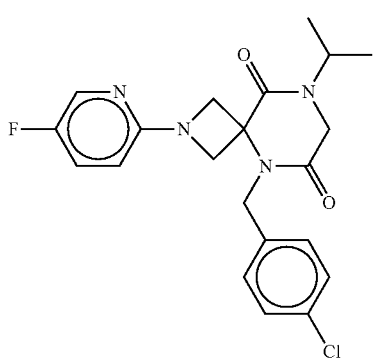 | 5-(4-chlorobenzyl)-2-(5-fluoropyridin-2-yl)-8-isopropyl-2,5,8-triazaspiro[3.5]nonane-6,9-dione |

TABLE 1-continued

| No. | Structure | Name |
|-----|-----------|------|
| 18 | 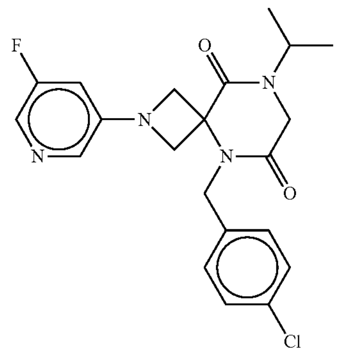 | 5-(4-chlorobenzyl)-2-(5-fluoropyridin-3-yl)-8-isopropyl-2,5,8-triazaspiro[3.5]nonane-6,9-dione |
| 19 | 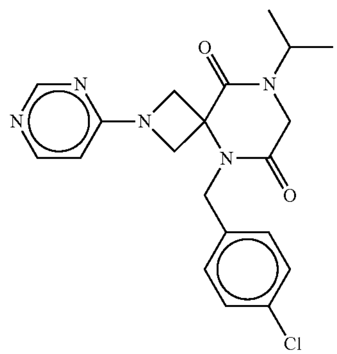 | 5-(4-chlorobenzyl)-8-isopropyl-2-(pyrimidin-4-yl)-2,5,8-triazaspiro-[3.5]nonane-6,9-dione |
| 20 | 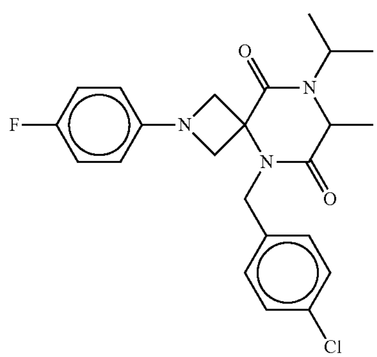 | 5-(4-chlorobenzyl)-2-(4-fluorophenyl)-8-isopropyl-7-methyl-2,5,8-triazaspiro[3.5]-nonane-6,9-dione |
| 21 | 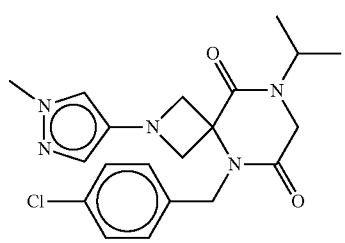 | 5-(4-chlorobenzyl)-8-isopropyl-2-(1-methyl-1H-pyrazol-4-yl)-2,5,8-triazaspiro[3.5]nonane-6,9-dione |
| 22 | 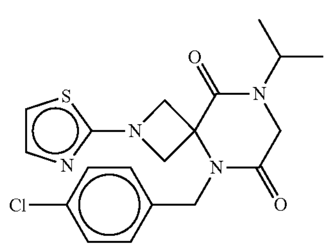 | 5-(4-chlorobenzyl)-8-isopropyl-2-(thiazol-2-yl)-2,5,8-triazaspiro[3.5]-nonane-6,9-dione |

TABLE 1-continued
| No. | Structure | Name |
|---|---|---|
| 23 | 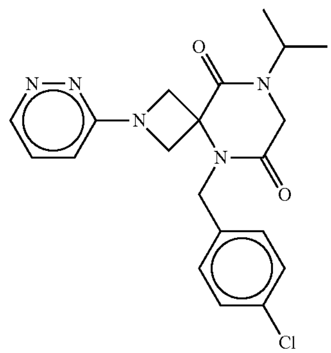 | 5-(4-chlorobenzyl)-8-isopropyl-2-(pyridazin-3-yl)-2,5,8-triazaspiro[3.5]-nonane-6,9-dione |
| 24 | 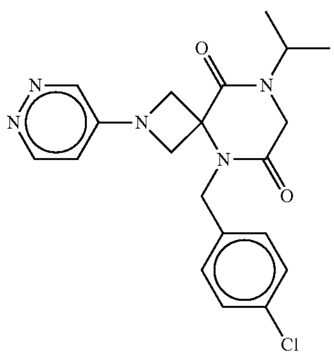 | 5-(4-chlorobenzyl)-8-isopropyl-2-(pyridazin-4-yl)-2,5,8-triazaspiro[3.5]-nonane-6,9-dione |
| 25 | 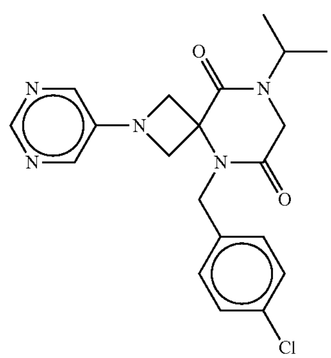 | 5-(4-chlorobenzyl)-8-isopropyl-2-(pyrimidin-5-yl)-2,5,8-triazaspiro-[3.5]nonane-6,9-dione |
| 26 | 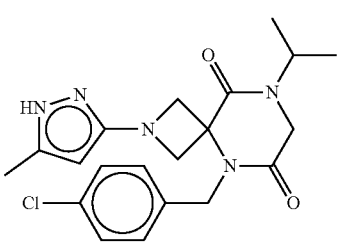 | 5-(4-chlorobenzyl)-8-isopropyl-2-(5-methyl-1H-pyrazol-3-yl)-2,5,8-triazaspiro[3.5]nonane-6,9-dione |

TABLE 1-continued

| No. | Structure | Name |
|---|---|---|
| 27 | 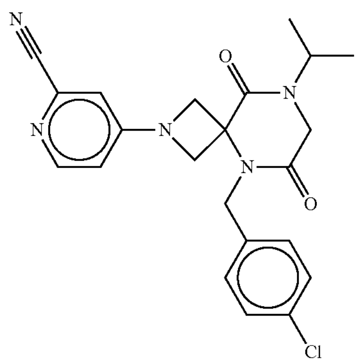 | 4-(5-(4-chlorobenzyl)-8-isopropyl-6,9-dioxo-2,5,8-triazaspiro[3.5]nonan-2-yl)picolinonitrile |
| 28 | 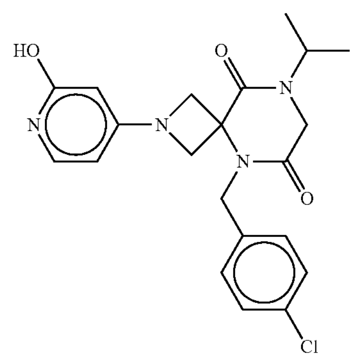 | 5-(4-chlorobenzyl)-2-(2-hydroxypyridin-4-yl)-8-isopropyl-2,5,8-triazaspiro[3.5]nonane-6,9-dione |
| 29 | 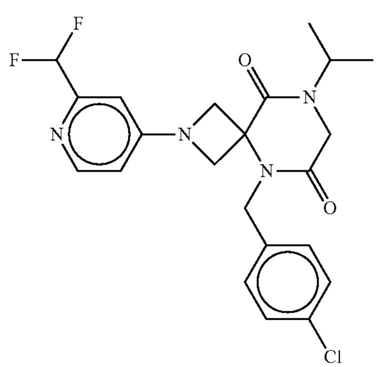 | 5-(4-chlorobenzyl)-2-(2-(difluoromethyl)pyridin-4-yl)-8-isopropyl-2,5,8-triazaspiro[3.5]nonane-6,9-dione |
| 30 | 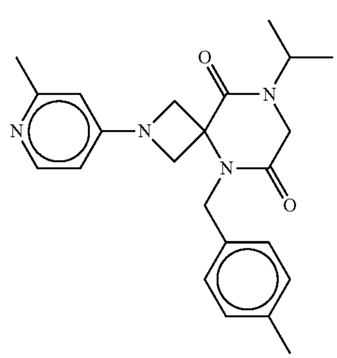 | 8-isopropyl-5-(4-methylbenzyl)-2-(2-methylpyridin-4-yl)-2,5,8-triazaspiro[3.5]-nonane-6,9-dione |

TABLE 1-continued

| No. | Structure | Name |
| --- | --- | --- |
| 31 | 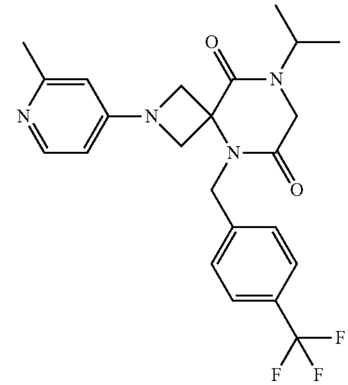 [SMILES: Cc1cc(N2CC3(C2)C(=O)N(C(C)C)CC(=O)N3Cc2ccc(C(F)(F)F)cc2)ccn1] | 8-isopropyl-2-(2-methylpyridin-4-yl)-5-(4-(trifluoromethyl)benzyl)-2,5,8-triazaspiro[3.5]-nonane-6,9-dione |
| 32 | 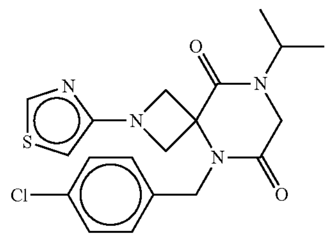 | 5-(4-chlorobenzyl)-8-isopropyl-2-(thiazol-4-yl)-2,5,8-triazaspiro[3.5]-nonane-6,9-dione |
| 33 | 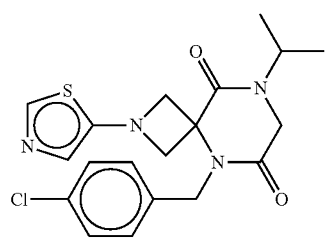 | 5-(4-chlorobenzyl)-8-isopropyl-2-(thiazol-5-yl)-2,5,8-triazaspiro[3.5]-nonane-6,9-dione |
| 34 | 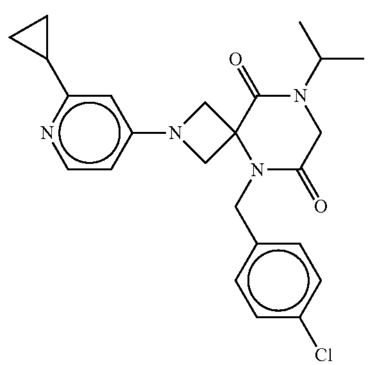 | 5-(4-chlorobenzyl)-2-(2-cyclopropylpyridin-4-yl)-8-isopropyl-2,5,8-triazaspiro[3.5]nonane-6,9-dione |
| 35 | 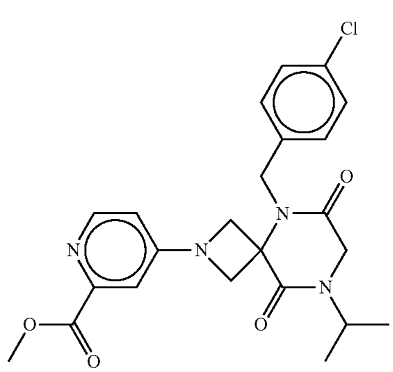 | methyl 4-(5-(4-chlorobenzyl)-8-isopropyl-6,9-dioxo-2,5,8-triazaspiro[3.5]nonan-2-yl)picolinate |

TABLE 1-continued

| No. | Structure | Name |
|---|---|---|
| 36 | 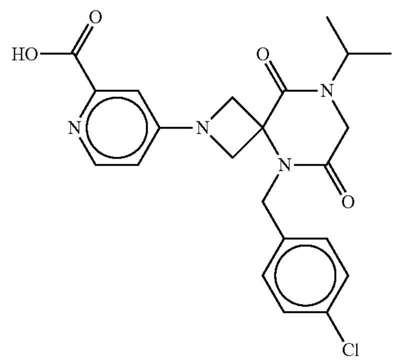 | 4-(5-(4-chlorobenzyl)-8-isopropyl-6,9-dioxo-2,5,8-triazaspiro[3.5]nonan-2-yl)picolinic acid |
| 37 | 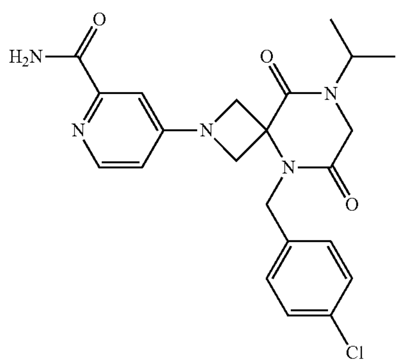 [SMILES: CC(C)N1CC(=O)N(Cc2ccc(Cl)cc2)C2(CN(c3ccnc(C(N)=O)c3)C2)C1=O] | 4-(5-(4-chlorobenzyl)-8-isopropyl-6,9-dioxo-2,5,8-triazaspiro[3.5]nonan-2-yl)picolinamide |
| 38 | 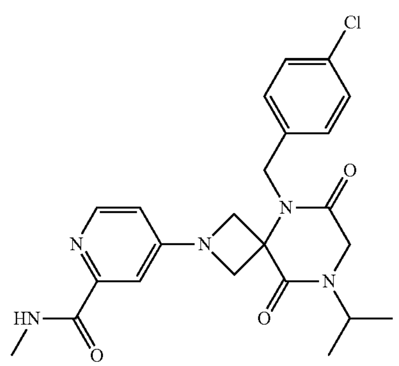 [SMILES: CNC(=O)c1cc(N2CC3(C2)C(=O)N(C(C)C)CC(=O)N3Cc2ccc(Cl)cc2)ccn1] | 4-(5-(4-chlorobenzyl)-8-isopropyl-6,9-dioxo-2,5,8-triazaspiro-[3.5]nonan-2-yl)-N-methylpicolinamide |
| 39 | 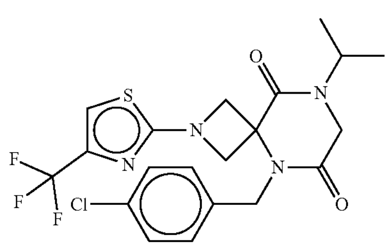 | 5-(4-chlorobenzyl)-8-isopropyl-2-(4-(trifluoromethyl)thiazol-2-yl)-2,5,8-triazaspiro-[3.5]nonane-6,9-dione |
| 40 | 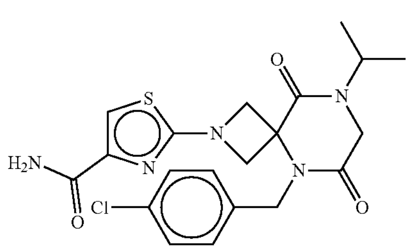 | 2-(5-(4-chlorobenzyl)-8-isopropyl-6,9-dioxo-2,5,8-triazaspiro[3.5]nonan-2-yl)thiazole-4-carboxamide |

TABLE 1-continued

| No. | Structure | Name |
|---|---|---|
| 41 | 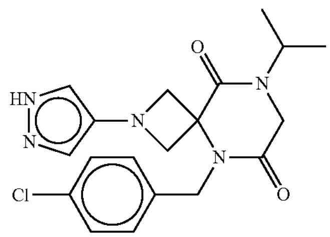 | 5-(4-chlorobenzyl)-8-isopropyl-2-(1H-pyrazol-4-yl)-2,5,8-triazaspiro-[3.5]nonane-6,9-dione |
| 42 | 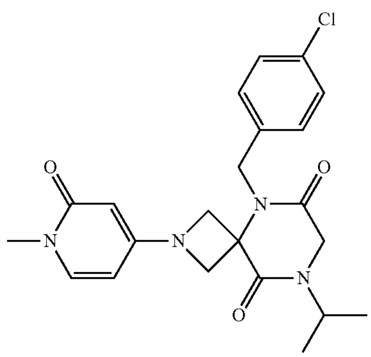 [SMILES: CC(C)N1CC(=O)N(Cc2ccc(Cl)cc2)C2(CN(c3ccn(C)c(=O)c3)C2)C1=O] | 5-(4-chlorobenzyl)-8-isopropyl-2-(1-methyl-2-oxo-1,2-dihydropyridin-4-yl)-2,5,8-triazaspiro-[3.5]nonane-6,9-dione |
| 43 | 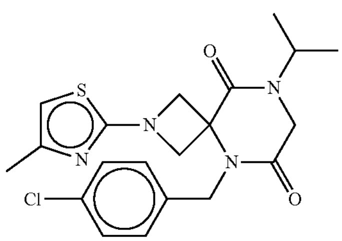 | 5-(4-chlorobenzyl)-8-isopropyl-2-(4-methyl-thiazol-2-yl)-2,5,8-triazaspiro[3.5]nonane-6,9-dione |
| 44 | 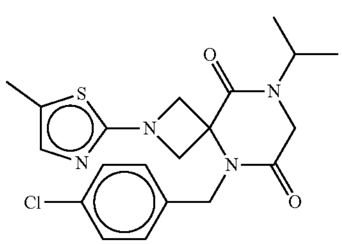 | 5-(4-chlorobenzyl)-8-isopropyl-2-(5-methyl-thiazol-2-yl)-2,5,8-triazaspiro[3.5]nonane-6,9-dione |
| 45 | 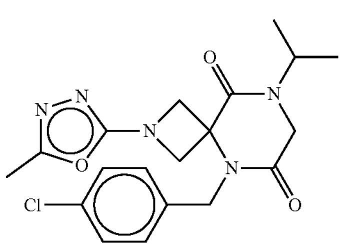 | 5-(4-chlorobenzyl)-8-isopropyl-2-(5-methyl-1,3,4-oxadiazol-2-yl)-2,5,8-triazaspiro[3.5]-nonane-6,9-dione |

TABLE 1-continued

| No. | Structure | Name |
|---|---|---|
| 46 | 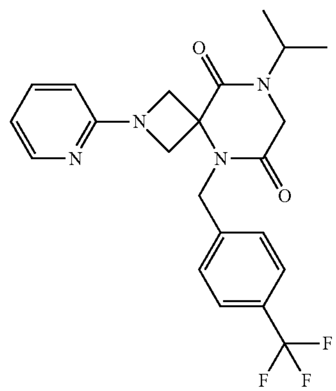 [SMILES: CC(C)N1CC(=O)N(Cc2ccc(C(F)(F)F)cc2)C2(CN(c3ccccn3)C2)C1=O] | 8-isopropyl-2-(pyridin-2-yl)-5-(4-(trifluoromethyl)benzyl)-2,5,8-triazaspiro[3.5]nonane-6,9-dione |
| 47 | 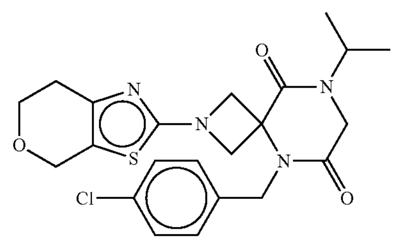 | 5-(4-chlorobenzyl)-2-(6,7-dihydro-4H-pyrano[4,3-d]thiazol-2-yl)-8-isopropyl-2,5,8-triazaspiro[3.5]nonane-6,9-dione |
| 48 | 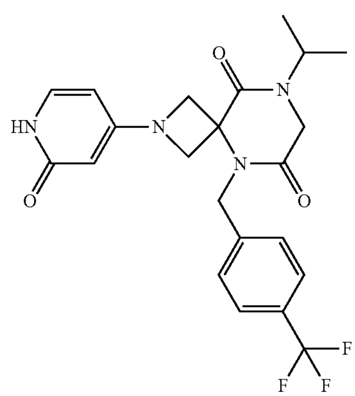 [SMILES: CC(C)N1CC(=O)N(Cc2ccc(C(F)(F)F)cc2)C2(CN(c3cc[nH]c(=O)c3)C2)C1=O] | 8-isopropyl-2-(2-oxo-1,2-dihydropyridin-4-yl)-5-(4-(trifluoromethyl)benzyl)-2,5,8-triazaspiro[3.5]nonane-6,9-dione |
| 49 | 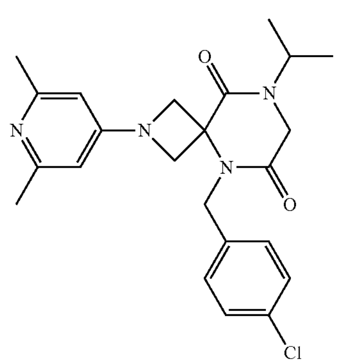 [SMILES: Cc1cc(N2CC3(C2)C(=O)N(C(C)C)CC(=O)N3Cc2ccc(Cl)cc2)cc(C)n1] | 5-(4-chlorobenzyl)-2-(2,6-dimethylpyridin-4-yl)-8-isopropyl-2,5,8-triazaspiro[3.5]nonane-6,9-dione |

TABLE 1-continued

| No. | Structure | Name |
|---|---|---|
| 50 | 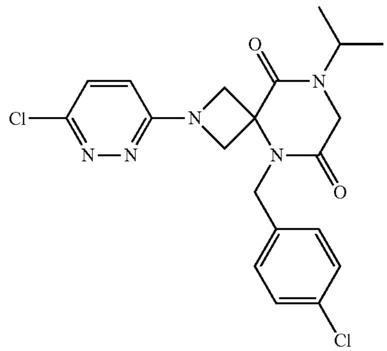 [SMILES: CC(C)N1CC(=O)N(Cc2ccc(Cl)cc2)C2(CN(c3ccc(Cl)nn3)C2)C1=O] | 5-(4-chlorobenzyl)-2-(6-chloropyridazin-3-yl)-8-isopropyl-2,5,8-triazaspiro[3.5]nonane-6,9-dione |
| 51 | 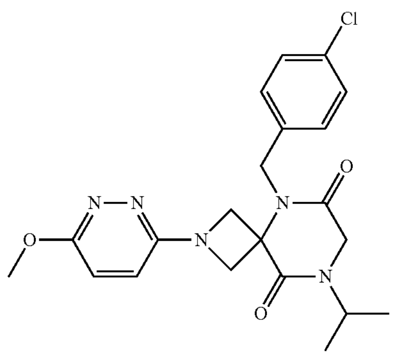 [SMILES: COc1ccc(N2CC3(C2)C(=O)N(C(C)C)CC(=O)N3Cc2ccc(Cl)cc2)nn1] | 5-(4-chlorobenzyl)-8-isopropyl-2-(6-methoxypyridazin-3-yl)-2,5,8-triazaspiro-[3.5]nonane-6,9-dione |
| 52 | 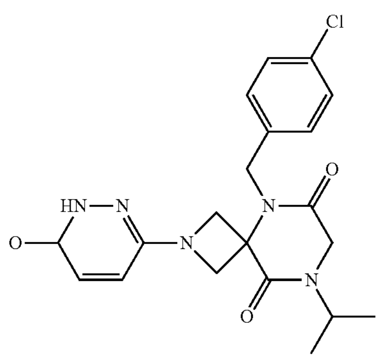 [SMILES: CC(C)N1CC(=O)N(Cc2ccc(Cl)cc2)C2(CN(C3=NNC(O)C=C3)C2)C1=O] | 5-(4-chlorobenzyl)-8-isopropyl-2-(6-oxo-1,6-dihydropyridazin-3-yl)-2,5,8-triazaspiro[3.5]-nonane-6,9-dione |
| 53 | 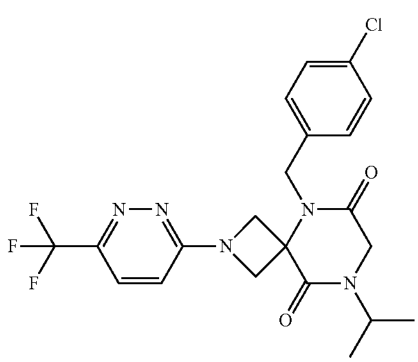 [SMILES: CC(C)N1CC(=O)N(Cc2ccc(Cl)cc2)C2(CN(c3ccc(C(F)(F)F)nn3)C2)C1=O] | 5-(4-chlorobenzyl)-8-isopropyl-2-(6-(trifluoromethyl)pyridazin-3-yl)-2,5,8-triazaspiro-[3.5]nonane-6,9-dione |

TABLE 1-continued

| No. | Structure | Name |
|---|---|---|
| 54 | 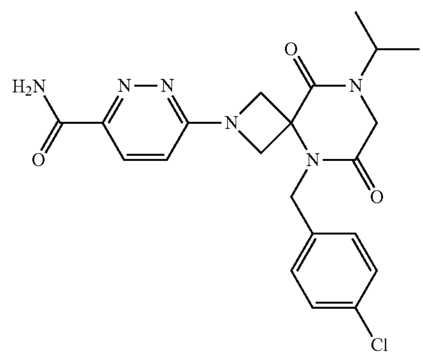 [SMILES: CC(C)N1CC(=O)N(Cc2ccc(Cl)cc2)C2(CN(c3ccc(C(N)=O)nn3)C2)C1=O] | 6-(5-(4-chlorobenzyl)-8-isopropyl-6,9-dioxo-2,5,8-triazaspiro[3.5]-nonan-2-yl)pyridazine-3-carboxamide |
| 55 | 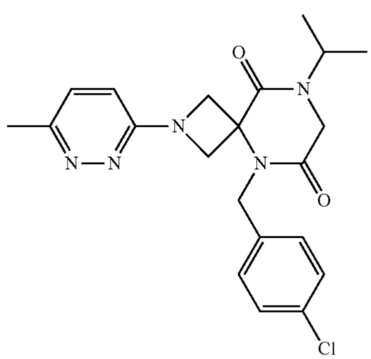 [SMILES: Cc1ccc(N2CC3(C2)C(=O)N(C(C)C)CC(=O)N3Cc2ccc(Cl)cc2)nn1] | 5-(4-chlorobenzyl)-8-isopropyl-2-(6-methylpyridazin-3-yl)-2,5,8-triazaspiro[3.5]-nonane-6,9-dione |
| 56 | 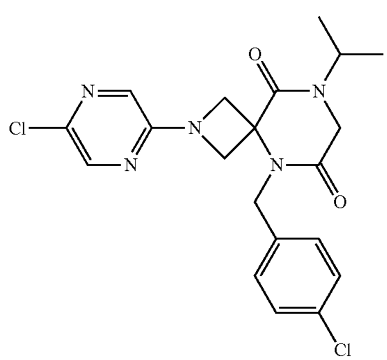 [SMILES: CC(C)N1CC(=O)N(Cc2ccc(Cl)cc2)C2(CN(c3cnc(Cl)cn3)C2)C1=O] | 5-(4-chlorobenzyl)-2-(5-chloropyrazin-2-yl)-8-isopropyl-2,5,8-triazaspiro[3.5]nonane-6,9-dione |
| 57 | 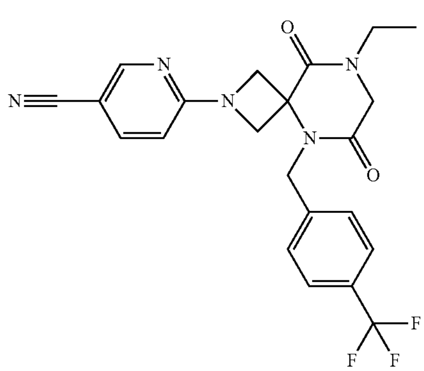 [SMILES: CCN1CC(=O)N(Cc2ccc(C(F)(F)F)cc2)C2(CN(c3ccc(C#N)cn3)C2)C1=O] | 6-(8-ethyl-6,9-dioxo-5-(4-(trifluoromethyl)benzyl)-2,5,8-triazaspiro[3.5]-nonan-2-yl)nicotinonitrile |

TABLE 1-continued

| No. | Structure | Name |
|---|---|---|
| 58 | 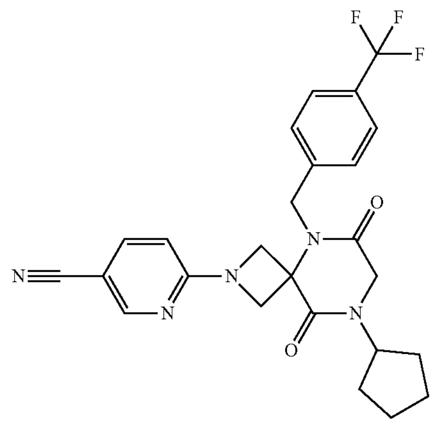 [SMILES: N#Cc1ccc(N2CC3(C2)C(=O)N(C2CCCC2)CC(=O)N3Cc2ccc(C(F)(F)F)cc2)nc1] | 6-(8-cyclopentyl-6,9-dioxo-5-(4-(trifluoromethyl)benzyl)-2,5,8-triazaspiro[3.5]-nonan-2-yl)nicotinonitrile |
| 59 | 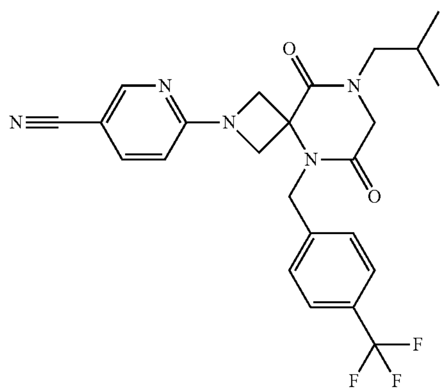 [SMILES: CC(C)CN1CC(=O)N(Cc2ccc(C(F)(F)F)cc2)C2(CN(c3ccc(C#N)cn3)C2)C1=O] | 6-(8-isobutyl-6,9-dioxo-5-(4-(trifluoromethyl)benzyl)-2,5,8-triazaspiro[3.5]-nonan-2-yl)nicotinonitrile |
| 60 | 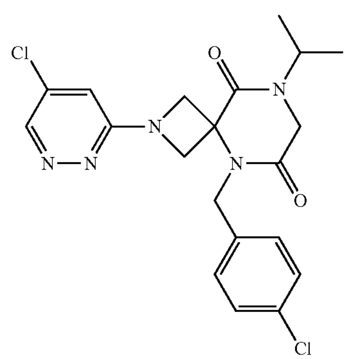 [SMILES: CC(C)N1CC(=O)N(Cc2ccc(Cl)cc2)C2(CN(c3cc(Cl)cnn3)C2)C1=O] | 5-(4-chlorobenzyl)-2-(5-chloropyridazin-3-yl)-8-isopropyl-2,5,8-triazaspiro[3.5]nonane-6,9-dione |
| 61 | 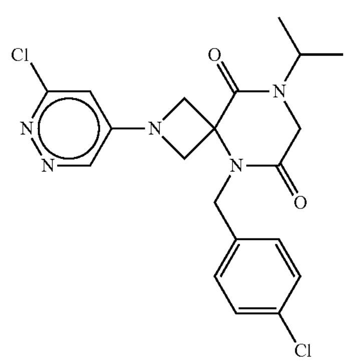 | 5-(4-chlorobenzyl)-2-(6-chloropyridazin-4-yl)-8-isopropyl-2,5,8-triazaspiro[3.5]nonane-6,9-dione |

TABLE 1-continued

| No. | Structure | Name |
| --- | --- | --- |
| 62 | 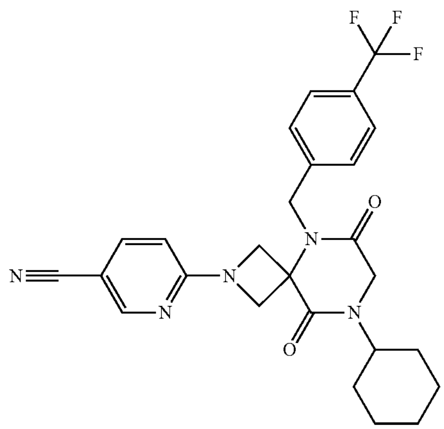 [SMILES: N#Cc1ccc(N2CC3(C2)C(=O)N(C2CCCCC2)CC(=O)N3Cc2ccc(C(F)(F)F)cc2)nc1] | 6-(8-cyclohexyl-6,9-dioxo-5-(4-(trifluoromethyl)-benzyl)-2,5,8-triazaspiro[3.5]nonan-2-yl)nicotinonitrile |
| 63 | 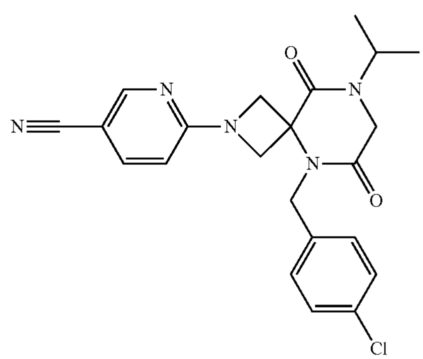 [SMILES: CC(C)N1CC(=O)N(Cc2ccc(Cl)cc2)C2(CN(c3ccc(C#N)cn3)C2)C1=O] | 6-(5-(4-chlorobenzyl)-8-isopropyl-6,9-dioxo-2,5,8-triazaspiro[3.5]nonan-2-yl)nicotinonitrile |
| 64 | 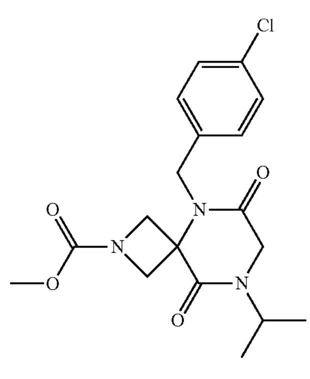 [SMILES: COC(=O)N1CC2(C1)C(=O)N(C(C)C)CC(=O)N2Cc1ccc(Cl)cc1] | methyl 5-(4-chlorobenzyl)-8-isopropyl-6,9-dioxo-2,5,8-triazaspiro[3.5]-nonane-2-carboxylate |
| 65 | 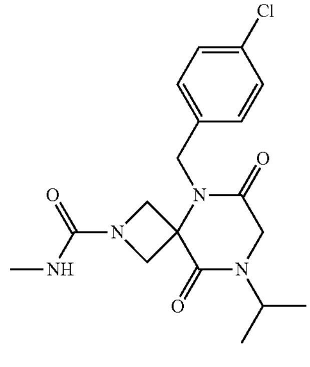 [SMILES: CNC(=O)N1CC2(C1)C(=O)N(C(C)C)CC(=O)N2Cc1ccc(Cl)cc1] | 5-(4-chlorobenzyl)-8-isopropyl-N-methyl-6,9-dioxo-2,5,8-triazaspiro-[3.5]nonane-2-carboxamide |

TABLE 1-continued

| No. | Structure | Name |
|---|---|---|
| 66 | 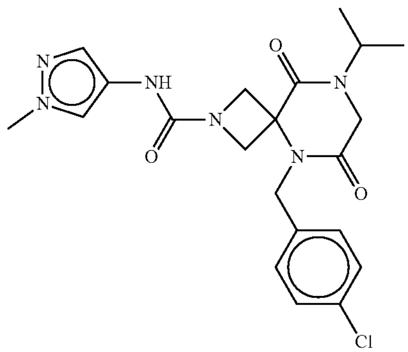 | 5-(4-chlorobenzyl)-8-isopropyl-N-(1-methyl-1H-pyrazol-4-yl)-6,9-dioxo-2,5,8-triazaspiro[3.5]-nonane-2-carboxamide |
| 67 | 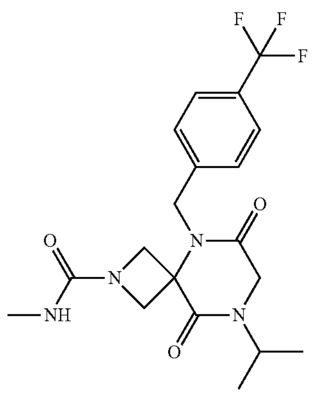 [SMILES: CNC(=O)N1CC2(C1)C(=O)N(C(C)C)CC(=O)N2Cc1ccc(C(F)(F)F)cc1] | 8-isopropyl-N-methyl-6,9-dioxo-5-(4-(trifluoromethyl)benzyl)-2,5,8-triazaspiro[3.5]-nonane-2-carboxamide |
| 68 | 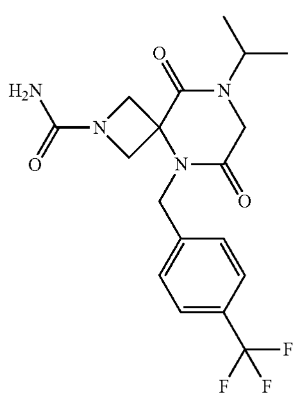 [SMILES: CC(C)N1CC(=O)N(Cc2ccc(C(F)(F)F)cc2)C2(CN(C(N)=O)C2)C1=O] | 8-isopropyl-6,9-dioxo-5-(4-(trifluoromethyl)benzyl)-2,5,8-triazaspiro[3.5]-nonane-2-carboxamide |
| 69 | 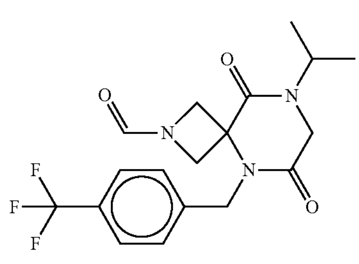 | 8-isopropyl-6,9-dioxo-5-(4-(trifluoromethyl)benzyl)-2,5,8-triazaspiro[3.5]-nonane-2-carbaldehyde |

TABLE 1-continued

| No. | Structure | Name |
| --- | --- | --- |
| 70 | 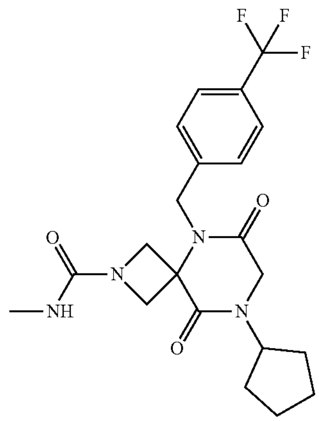 [SMILES: CNC(=O)N1CC2(C1)C(=O)N(C1CCCC1)CC(=O)N2Cc1ccc(C(F)(F)F)cc1] | 8-cyclopentyl-N-methyl-6,9-dioxo-5-(4-(trifluoromethyl)benzyl)-2,5,8-triazaspiro[3.5]-nonane-2-carboxamide |
| 71 | 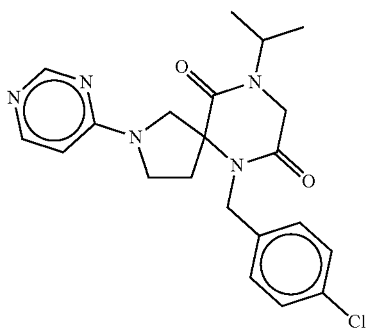 | 6-(4-chlorobenzyl)-9-isopropyl-2-(pyrimidin-4-yl)-2,6,9-triazaspiro-[4.5]decane-7,10-dione |
| 72 | 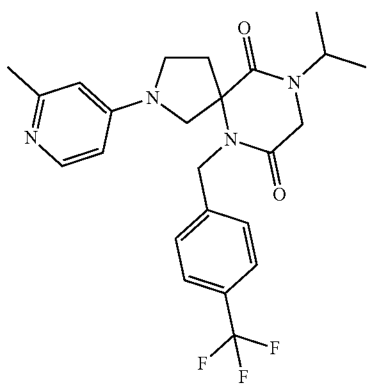 [SMILES: Cc1cc(N2CCC3(C2)C(=O)N(C(C)C)CC(=O)N3Cc2ccc(C(F)(F)F)cc2)ccn1] | 9-isopropyl-2-(2-methylpyridin-4-yl)-6-(4-(trifluoromethyl)benzyl)-2,6,9-triazaspiro[4.5]-decane-7,10-dione |
| 73 | 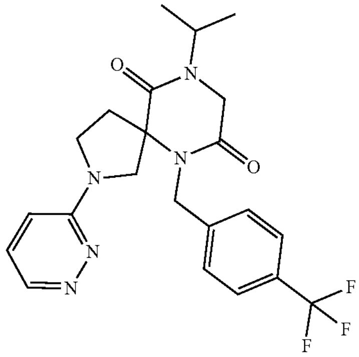 [SMILES: CC(C)N1CC(=O)N(Cc2ccc(C(F)(F)F)cc2)C2(CCN(c3cccnn3)C2)C1=O] | 9-isopropyl-2-(pyridazin-3-yl)-6-(4-(trifluoromethyl)benzyl)-2,6,9-triazaspiro[4.5]-decane-7,10-dione |

TABLE 1-continued

| No. | Structure | Name |
|-----|-----------|------|
| 74 | 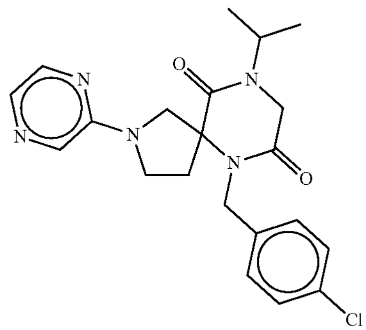 | 6-(4-chlorobenzyl)-9-isopropyl-2-(pyrazin-2-yl)-2,6,9-triazaspiro[4.5]decane-7,10-dione |
| 75 | 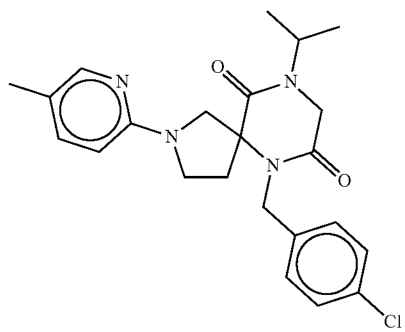 | 6-(4-chlorobenzyl)-9-isopropyl-2-(5-methylpyridin-2-yl)-2,6,9-triazaspiro[4.5]decane-7,10-dione |
| 76 | 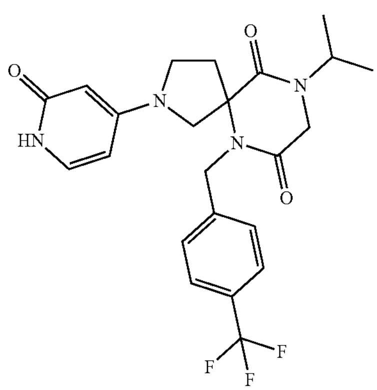 [SMILES: CC(C)N1CC(=O)N(Cc2ccc(C(F)(F)F)cc2)C2(CCN(c3cc[nH]c(=O)c3)C2)C1=O] | 9-isopropyl-2-(2-oxo-1,2-dihydropyridin-4-yl)-6-(4-(trifluoromethyl)benzyl)-2,6,9-triazaspiro[4.5]decane-7,10-dione |
| 77 | 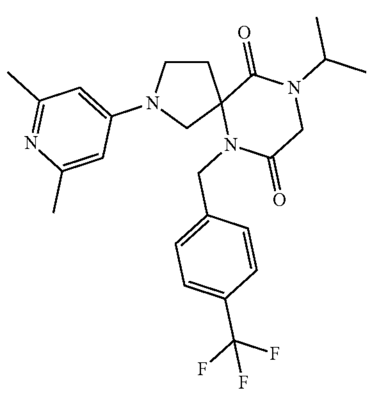 [SMILES: Cc1cc(N2CCC3(C2)C(=O)N(C(C)C)CC(=O)N3Cc2ccc(C(F)(F)F)cc2)cc(C)n1] | 2-(2,6-dimethylpyridin-4-yl)-9-isopropyl-6-(4-(trifluoromethyl)benzyl)-2,6,9-triazaspiro[4.5]decane-7,10-dione |

TABLE 1-continued

| No. | Structure | Name |
|---|---|---|
| 78 | 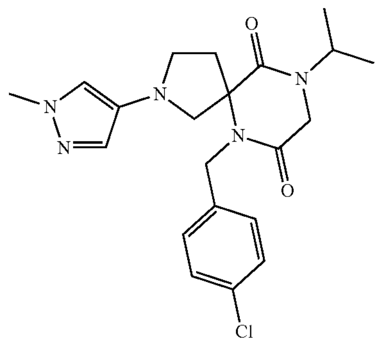 [SMILES: CC(C)N1CC(=O)N(Cc2ccc(Cl)cc2)C2(CCN(c3cnn(C)c3)C2)C1=O] | 6-(4-chlorobenzyl)-9-isopropyl-2-(1-methyl-1H-pyrazol-4-yl)-2,6,9-triazaspiro[4.5]decane-7,10-dione |
| 79 | 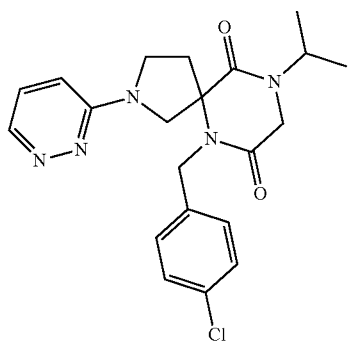 [SMILES: CC(C)N1CC(=O)N(Cc2ccc(Cl)cc2)C2(CCN(c3cccnn3)C2)C1=O] | 6-(4-chlorobenzyl)-9-isopropyl-2-(pyridazin-3-yl)-2,6,9-triazaspiro[4.5]-decane-7,10-dione |
| 80 | 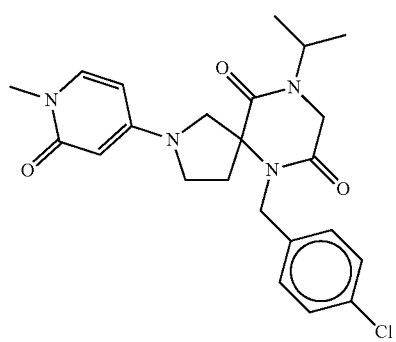 | 6-(4-chlorobenzyl)-9-isopropyl-2-(1-methyl-2-oxo-1,2-dihydropyridin-4-yl)-2,6,9-triazaspiro-[4.5]decane-7,10-dione |
| 81 | 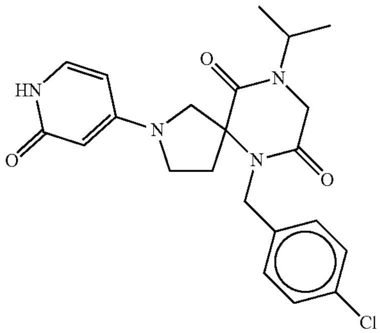 | 6-(4-chlorobenzyl)-9-isopropyl-2-(2-oxo-1,2-dihydropyridin-4-yl)-2,6,9-triazaspiro[4.5]decane-7,10-dione |

TABLE 1-continued

| No. | Structure | Name |
| --- | --- | --- |
| 82 | 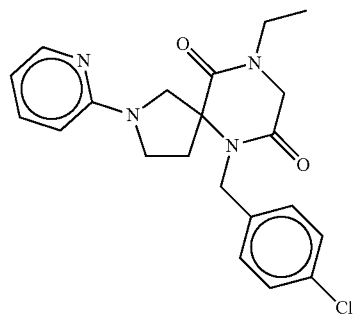 | 6-(4-chlorobenzyl)-9-ethyl-2-(pyridin-2-yl)-2,6,9-triazaspiro[4.5]decane-7,10-dione |
| 83 | 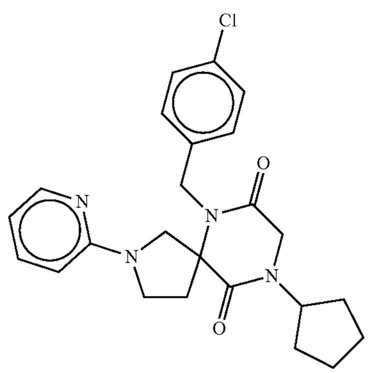 | 6-(4-chlorobenzyl)-9-cyclopentyl-2-(pyridin-2-yl)-2,6,9-triazaspiro[4.5]decane-7,10-dione |
| 84 | 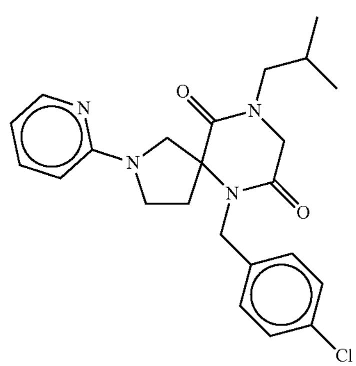 | 6-(4-chlorobenzyl)-9-isobutyl-2-(pyridin-2-yl)-2,6,9-triazaspiro[4.5]decane-7,10-dione |
| 85 | 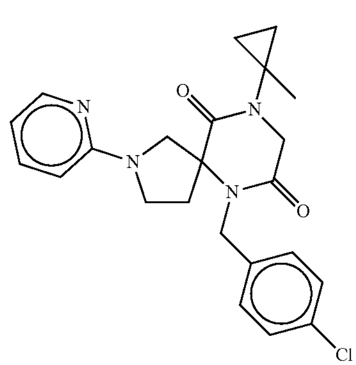 | 6-(4-chlorobenzyl)-9-(1-methylcyclopropyl)-2-(pyridin-2-yl)-2,6,9-triazaspiro[4.5]decane-7,10-dione |

TABLE 1-continued
| No. | Structure | Name |
|---|---|---|
| 86 | 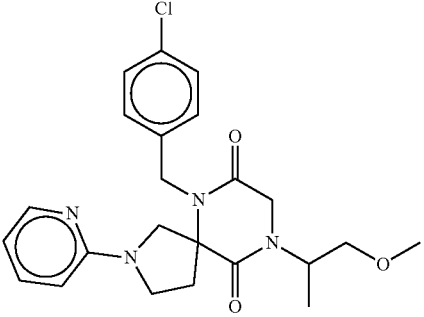 | 6-(4-chlorobenzyl)-9-(1-methoxypropan-2-yl)-2-(pyridin-2-yl)-2,6,9-triazaspiro[4.5]decane-7,10-dione |
| 87 | 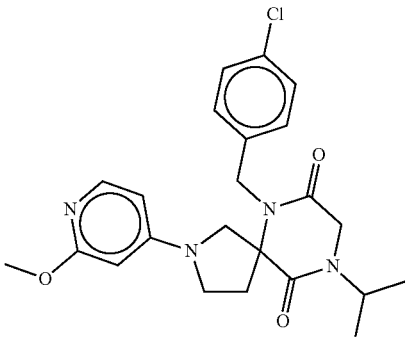 | 6-(4-chlorobenzyl)-9-isopropyl-2-(2-methoxypyridin-4-yl)-2,6,9-triazaspiro[4.5]-decane-7,10-dione |
| 88 | 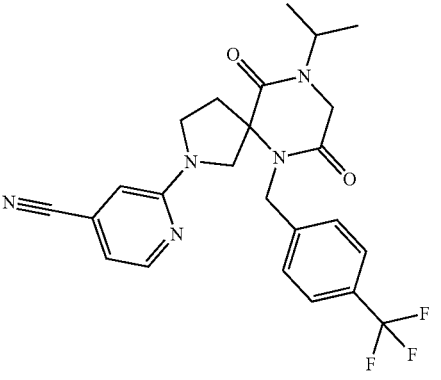 [SMILES: CC(C)N1CC(=O)N(Cc2ccc(C(F)(F)F)cc2)C2(CCN(c3cc(C#N)ccn3)C2)C1=O] | 2-(9-isopropyl-7,10-dioxo-6-(4-(trifluoromethyl)-benzyl)-2,6,9-triazaspiro[4.5]decan-2-yl)isonicotinonitrile |
| 89 | 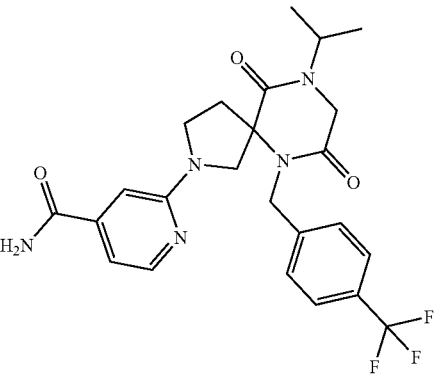 [SMILES: CC(C)N1CC(=O)N(Cc2ccc(C(F)(F)F)cc2)C2(CCN(c3cc(C(N)=O)ccn3)C2)C1=O] | 2-(9-isopropyl-7,10-dioxo-6-(4-(trifluoromethyl)-benzyl)-2,6,9-triazaspiro[4.5]decan-2-yl)isonicotinamide |

TABLE 1-continued

| No. | Structure | Name |
|---|---|---|
| 90 | 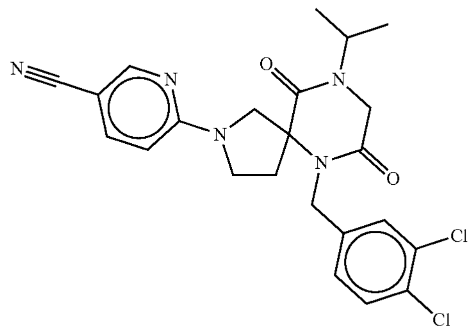 | 6-(6-(3,4-dichlorobenzyl)-9-isopropyl-7,10-dioxo-2,6,9-triazaspiro[4.5]-decan-2-yl)nicotinonitrile |
| 91 | 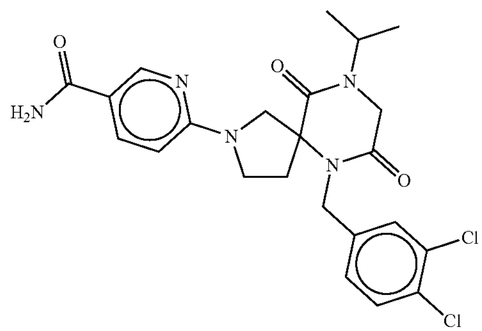 | 6-(6-(3,4-dichlorobenzyl)-9-isopropyl-7,10-dioxo-2,6,9-triazaspiro[4.5]decan-2-yl)nicotinamide |
| 92 | 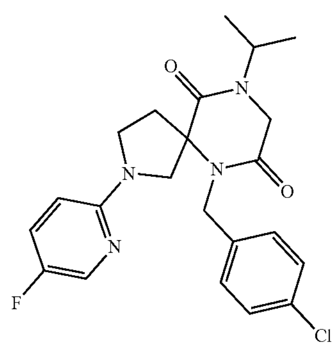 [SMILES: CC(C)N1CC(=O)N(Cc2ccc(Cl)cc2)C2(CCN(c3ccc(F)cn3)C2)C1=O] | 6-(4-chlorobenzyl)-2-(5-fluoropyridin-2-yl)-9-isopropyl-2,6,9-triazaspiro[4.5]decane-7,10-dione |
| 93 | 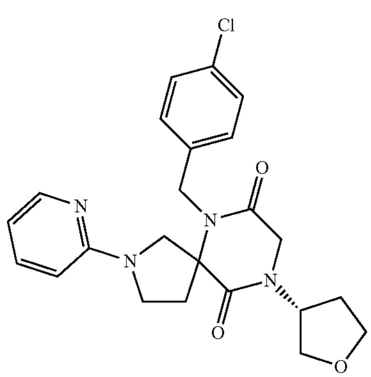 [SMILES: O=C1CN([C@@H]2CCOC2)C(=O)C2(CCN(c3ccccn3)C2)N1Cc1ccc(Cl)cc1] | 6-(4-chlorobenzyl)-2-(pyridin-2-yl)-9-((R)-tetrahydrofuran-3-yl)-2,6,9-triazaspiro-[4.5]decane-7,10-dione |

| No. | Structure | Name |
|---|---|---|
| 94 | 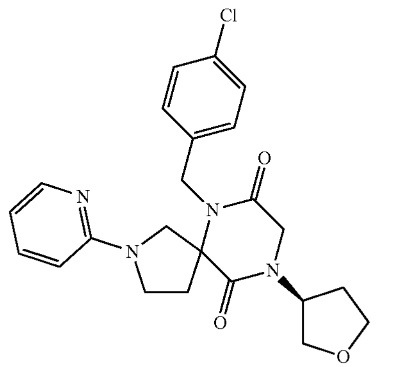 [SMILES: O=C1CN([C@H]2CCOC2)C(=O)C2(CCN(c3ccccn3)C2)N1Cc1ccc(Cl)cc1] | 6-(4-chlorobenzyl)-2-(pyridin-2-yl)-9-((S)-tetrahydrofuran-3-yl)-2,6,9-triazaspiro[4.5]decane-7,10-dione |
| 95 | 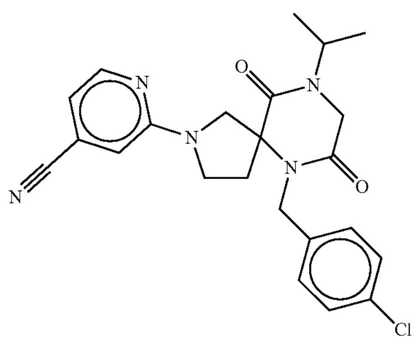 | 2-(6-(4-chlorobenzyl)-9-isopropyl-7,10-dioxo-2,6,9-triazaspiro[4.5]decan-2-yl)isonicotinonitrile |
| 96 | 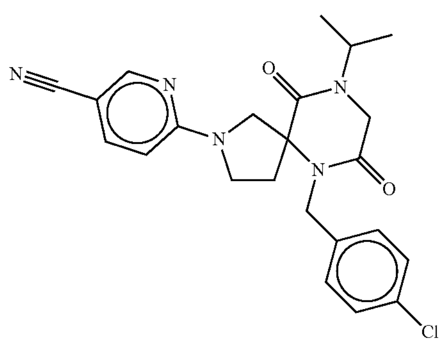 | 6-(6-(4-chlorobenzyl)-9-isopropyl-7,10-dioxo-2,6,9-triazaspiro[4.5]decan-2-yl)nicotinonitrile |
| 97 | 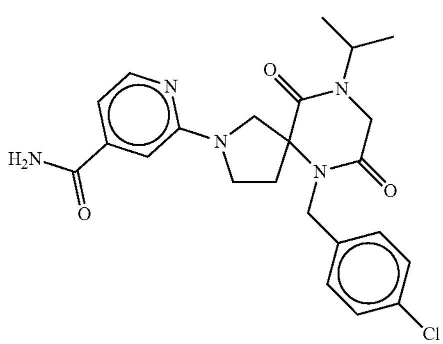 | 2-(6-(4-chlorobenzyl)-9-isopropyl-7,10-dioxo-2,6,9-triazaspiro[4.5]decan-2-yl)isonicotinamide |

TABLE 1-continued

| No. | Structure | Name |
|---|---|---|
| 98 | 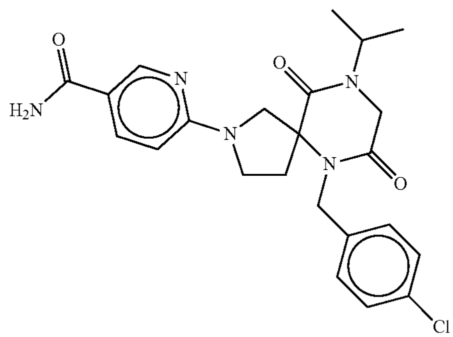 | 6-(6-(4-chlorobenzyl)-9-isopropyl-7,10-dioxo-2,6,9-triazaspiro[4.5]decan-2-yl)nicotinamide |
| 99 | 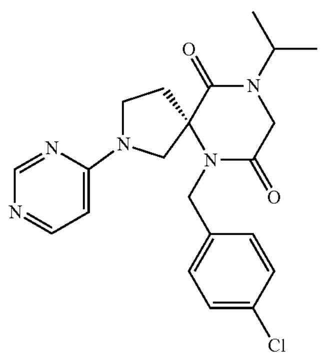 [SMILES: CC(C)N1CC(=O)N(Cc2ccc(Cl)cc2)[C@]2(CCN(c3ccncn3)C2)C1=O] | (S)-6-(4-chlorobenzyl)-9-isopropyl-2-(pyrimidin-4-yl)-2,6,9-triazaspiro-[4.5]decane-7,10-dione |
| 100 | 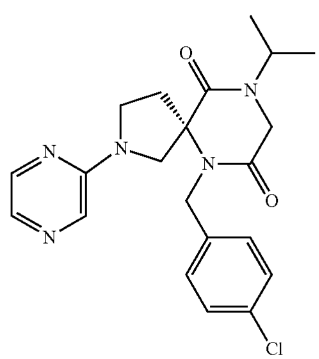 [SMILES: CC(C)N1CC(=O)N(Cc2ccc(Cl)cc2)[C@]2(CCN(c3cnccn3)C2)C1=O] | (S)-6-(4-chlorobenzyl)-9-isopropyl-2-(pyrazin-2-yl)-2,6,9-triazaspiro[4.5]decane-7,10-dione |
| 101 | 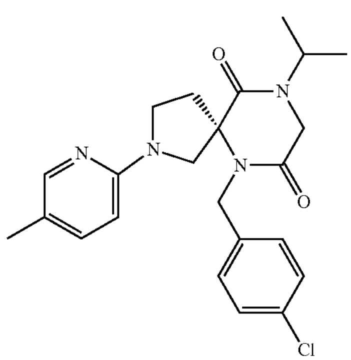 [SMILES: Cc1ccc(N2CC[C@]3(C2)C(=O)N(C(C)C)CC(=O)N3Cc2ccc(Cl)cc2)nc1] | (S)-6-(4-chlorobenzyl)-9-isopropyl-2-(5-methylpyridin-2-yl)-2,6,9-triazaspiro-[4.5]decane-7,10-dione |

TABLE 1-continued

| No. | Structure | Name |
|---|---|---|
| 102 | 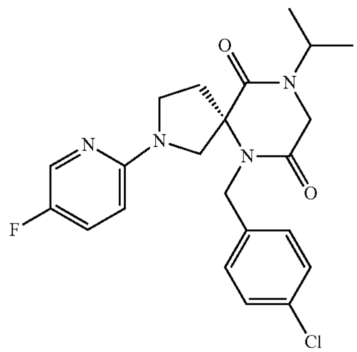 [SMILES: CC(C)N1CC(=O)N(Cc2ccc(Cl)cc2)[C@]2(CCN(c3ccc(F)cn3)C2)C1=O] | (S)-6-(4-chlorobenzyl)-2-(5-fluoropyridin-2-yl)-9-isopropyl-2,6,9-triazaspiro-[4.5]decane-7,10-dione |
| 103 | 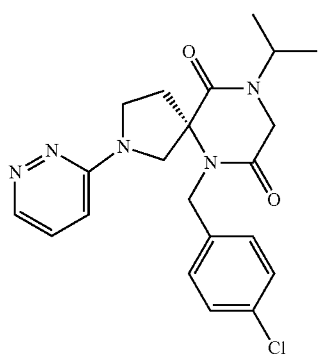 [SMILES: CC(C)N1CC(=O)N(Cc2ccc(Cl)cc2)[C@]2(CCN(c3cccnn3)C2)C1=O] | (S)-6-(4-chlorobenzyl)-9-isopropyl-2-(pyridazin-3-yl)-2,6,9-triazaspiro[4.5]decane-7,10-dione |
| 104 | 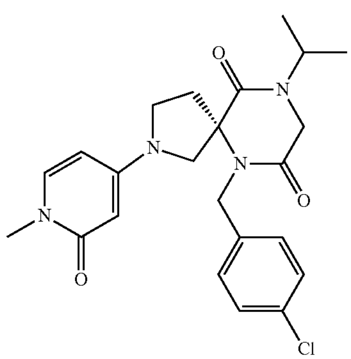 [SMILES: CC(C)N1CC(=O)N(Cc2ccc(Cl)cc2)[C@]2(CCN(c3ccn(C)c(=O)c3)C2)C1=O] | (S)-6-(4-chlorobenzyl)-9-isopropyl-2-(1-methyl-2-oxo-1,2-dihydropyridin-4-yl)-2,6,9-triazaspiro[4.5]-decane-7,10-dione |
| 105 | 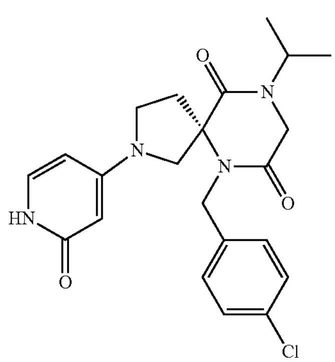 [SMILES: CC(C)N1CC(=O)N(Cc2ccc(Cl)cc2)[C@]2(CCN(c3cc[nH]c(=O)c3)C2)C1=O] | (S)-6-(4-chlorobenzyl)-9-isopropyl-2-(2-oxo-1,2-dihydropyridin-4-yl)-2,6,9-triazaspiro[4.5]decane-7,10-dione |

TABLE 1-continued

| No. | Structure | Name |
|---|---|---|
| 106 | 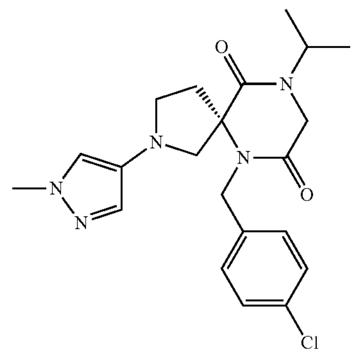 [SMILES: CC(C)N1CC(=O)N(Cc2ccc(Cl)cc2)[C@]2(CCN(c3cnn(C)c3)C2)C1=O] | (S)-6-(4-chlorobenzyl)-9-isopropyl-2-(1-methyl-1H-pyrazol-4-yl)-2,6,9-triazaspiro[4.5]decane-7,10-dione |
| 107 | 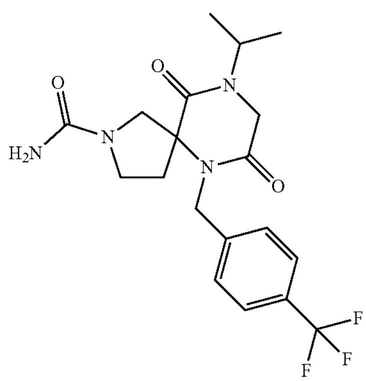 [SMILES: CC(C)N1CC(=O)N(Cc2ccc(C(F)(F)F)cc2)C2(CCN(C(N)=O)C2)C1=O] | 9-isopropyl-7,10-dioxo-6-(4-(trifluoromethyl)benzyl)-2,6,9-triazaspiro[4.5]decane-2-carboxamide |
| 108 | 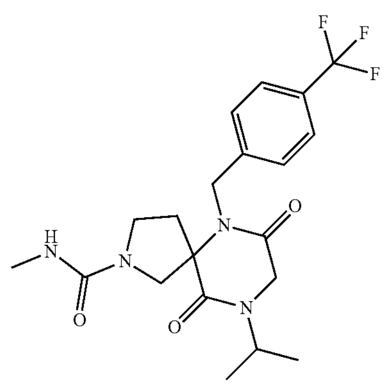 [SMILES: CNC(=O)N1CCC2(C1)C(=O)N(C(C)C)CC(=O)N2Cc1ccc(C(F)(F)F)cc1] | 9-isopropyl-N-methyl-7,10-dioxo-6-(4-(trifluoromethyl)-benzyl)-2,6,9-triazaspiro[4.5]-decane-2-carboxamide |
| 109 | 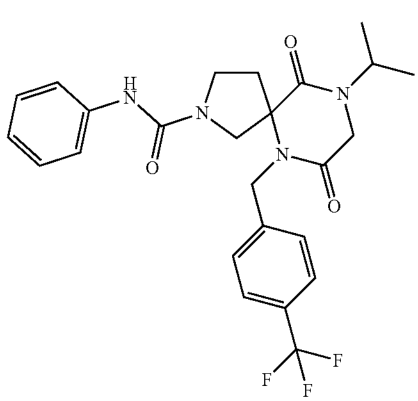 [SMILES: CC(C)N1CC(=O)N(Cc2ccc(C(F)(F)F)cc2)C2(CCN(C(=O)Nc3ccccc3)C2)C1=O] | 9-isopropyl-7,10-dioxo-N-phenyl-6-(4-(trifluoromethyl)benzyl)-2,6,9-triazaspiro[4.5]decane-2-carboxamide |

TABLE 1-continued

| No. | Structure | Name |
|---|---|---|
| 110 | 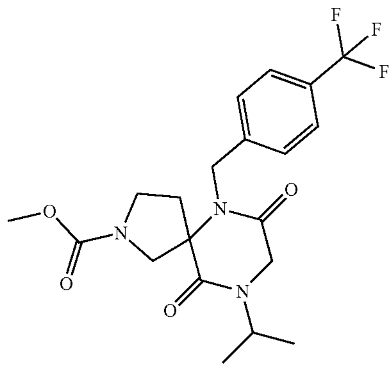 [SMILES: COC(=O)N1CCC2(C1)C(=O)N(C(C)C)CC(=O)N2Cc1ccc(C(F)(F)F)cc1] | methyl 9-isopropyl-7,10-dioxo-6-(4-(trifluoromethyl)benzyl)-2,6,9-triazaspiro[4.5]decane-2-carboxylate |
| 111 | 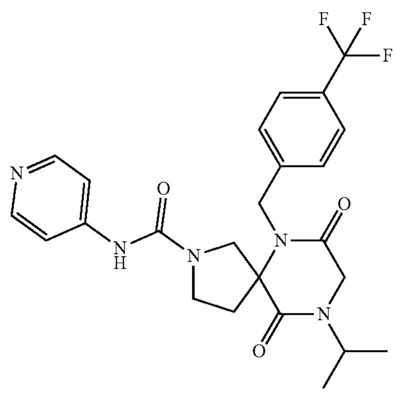 [SMILES: CC(C)N1CC(=O)N(Cc2ccc(C(F)(F)F)cc2)C2(CCN(C(=O)Nc3ccncc3)C2)C1=O] | 9-isopropyl-7,10-dioxo-N-(pyridin-4-yl)-6-(4-(trifluoromethyl)benzyl)-2,6,9-triazaspiro[4.5]-decane-2-carboxamide |
| 112 | 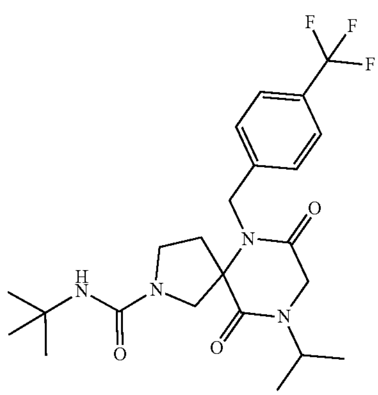 [SMILES: CC(C)N1CC(=O)N(Cc2ccc(C(F)(F)F)cc2)C2(CCN(C(=O)NC(C)(C)C)C2)C1=O] | N-(tert-butyl)-9-isopropyl-7,10-dioxo-6-(4-(trifluoromethyl)benzyl)-2,6,9-triazaspiro[4.5]-decane-2-carboxamide |
| 113 | 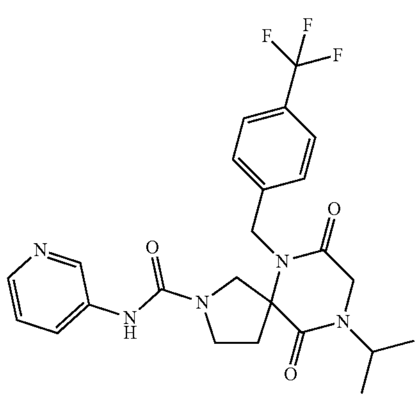 [SMILES: CC(C)N1CC(=O)N(Cc2ccc(C(F)(F)F)cc2)C2(CCN(C(=O)Nc3cccnc3)C2)C1=O] | 9-isopropyl-7,10-dioxo-N-(pyridin-3-yl)-6-(4-(trifluoromethyl)benzyl)-2,6,9-triazaspiro[4.5]-decane-2-carboxamide |

TABLE 1-continued

| No. | Structure | Name |
|---|---|---|
| 114 | 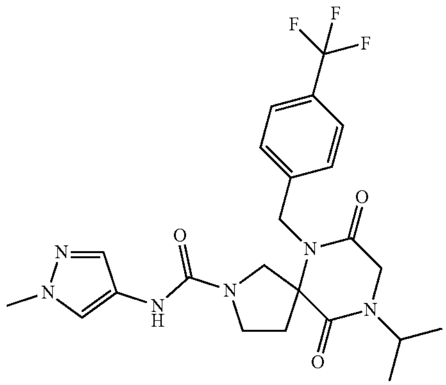 [SMILES: CC(C)N1CC(=O)N(Cc2ccc(C(F)(F)F)cc2)C2(CCN(C(=O)Nc3cnn(C)c3)C2)C1=O] | 9-isopropyl-N-(1-methyl-1H-pyrazol-4-yl)-7,10-dioxo-6-(4-(trifluoromethyl)benzyl)-2,6,9-triazaspiro[4.5]decane-2-carboxamide |
| 115 | 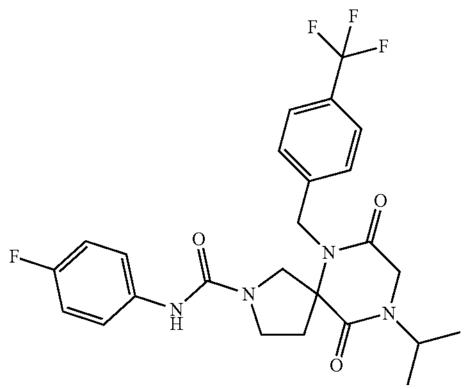 [SMILES: CC(C)N1CC(=O)N(Cc2ccc(C(F)(F)F)cc2)C2(CCN(C(=O)Nc3ccc(F)cc3)C2)C1=O] | N-(4-fluorophenyl)-9-isopropyl-7,10-dioxo-6-(4-(trifluoromethyl)benzyl)-2,6,9-triazaspiro[4.5]decane-2-carboxamide |
| 116 | 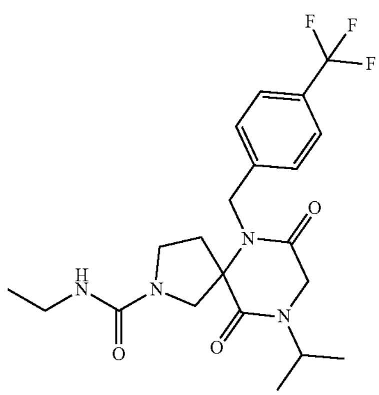 [SMILES: CCNC(=O)N1CCC2(C1)C(=O)N(C(C)C)CC(=O)N2Cc1ccc(C(F)(F)F)cc1] | N-ethyl-9-isopropyl-7,10-dioxo-6-(4-(trifluoromethyl)benzyl)-2,6,9-triazaspiro[4.5]decane-2-carboxamide |
| 117 | 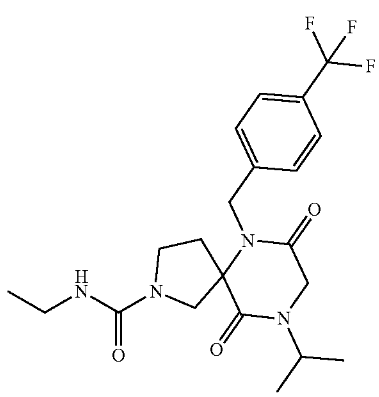 [SMILES: CCNC(=O)N1CCC2(C1)C(=O)N(C(C)C)CC(=O)N2Cc1ccc(C(F)(F)F)cc1] | N,9-diisopropyl-7,10-dioxo-6-(4-(trifluoromethyl)benzyl)-2,6,9-triazaspiro[4.5]decane-2-carboxamide |

TABLE 1-continued

| No. | Structure | Name |
|---|---|---|
| 118 | 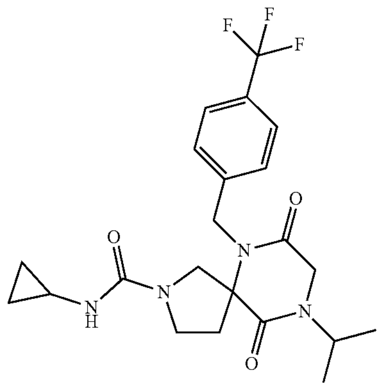 [SMILES: CC(C)N1CC(=O)N(Cc2ccc(C(F)(F)F)cc2)C2(CCN(C(=O)NC3CC3)C2)C1=O] | N-cyclopropyl-9-isopropyl-7,10-dioxo-6-(4-(trifluoromethyl)benzyl)-2,6,9-triazaspiro[4.5]decane-2-carboxamide |
| 119 | 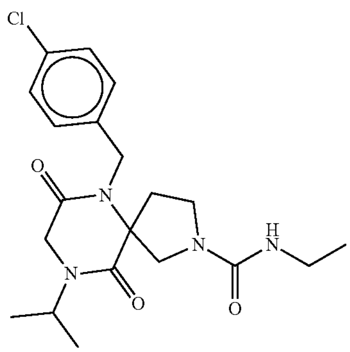 | 6-(4-chlorobenzyl)-N-ethyl-9-isopropyl-7,10-dioxo-2,6,9-triazaspiro[4.5]-decane-2-carboxamide |
| 120 | 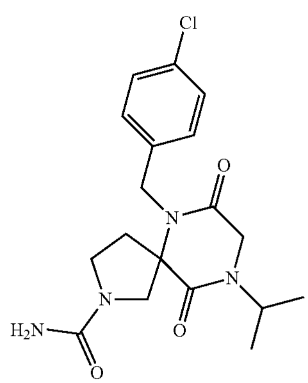 [SMILES: CC(C)N1CC(=O)N(Cc2ccc(Cl)cc2)C2(CCN(C(N)=O)C2)C1=O] | 6-(4-chlorobenzyl)-9-isopropyl-7,10-dioxo-2,6,9-triazaspiro[4.5]decane-2-carboxamide |
| 121 | 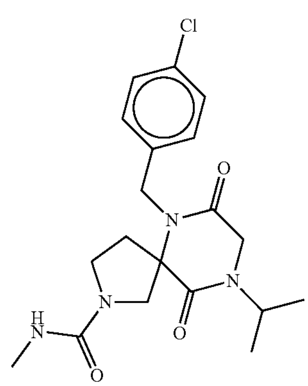 | 6-(4-chlorobenzyl)-9-isopropyl-N-methyl-7,10-dioxo-2,6,9-triazaspiro[4.5]-decane-2-carboxamide |

TABLE 1-continued

| No. | Structure | Name |
|-----|-----------|------|
| 122 | 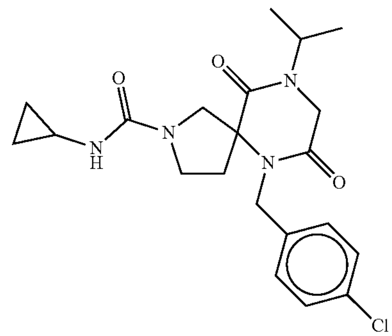 | 6-(4-chlorobenzyl)-N-cyclopropyl-9-isopropyl-7,10-dioxo-2,6,9-triazaspiro[4.5]decane-2-carboxamide |
| 123 | 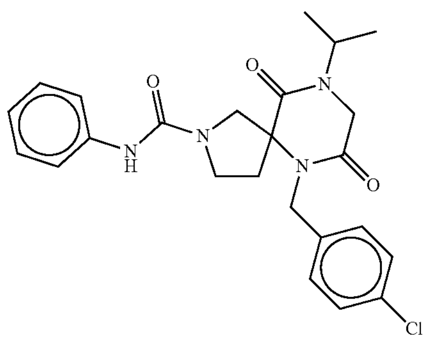 | 6-(4-chlorobenzyl)-9-isopropyl-7,10-dioxo-N-phenyl-2,6,9-triazaspiro-[4.5]decane-2-carboxamide |
| 124 | 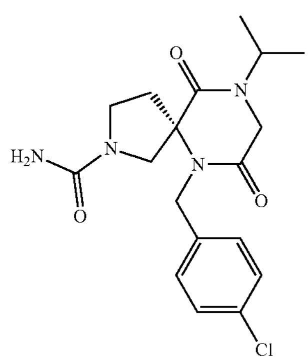 [SMILES: CC(C)N1CC(=O)N(Cc2ccc(Cl)cc2)[C@]2(CCN(C(N)=O)C2)C1=O] | (S)-6-(4-chlorobenzyl)-9-isopropyl-7,10-dioxo-2,6,9-triazaspiro[4.5]decane-2-carboxamide |
| 125 | 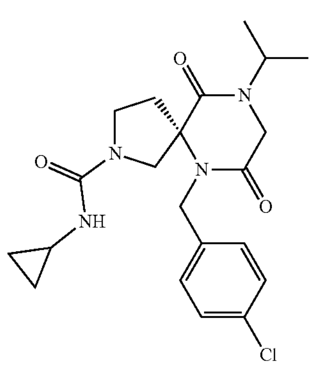 [SMILES: CC(C)N1CC(=O)N(Cc2ccc(Cl)cc2)[C@]2(CCN(C(=O)NC3CC3)C2)C1=O] | (S)-6-(4-chlorobenzyl)-N-cydopropyl-9-isopropyl-7,10-dioxo-2,6,9-triazaspiro-[4.5]decane-2-carboxamide |

TABLE 1-continued

| No. | Structure | Name |
|---|---|---|
| 126 | 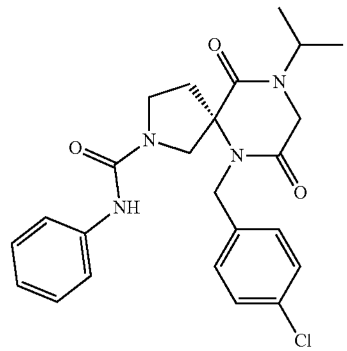 [SMILES: CC(C)N1CC(=O)N(Cc2ccc(Cl)cc2)[C@]2(CCN(C(=O)Nc3ccccc3)C2)C1=O] | (S)-6-(4-chlorobenzyl)-9-isopropyl-7,10-dioxo-N-phenyl-2,6,9-triazaspiro-[4.5]decane-2-carboxamide |
| 127 | 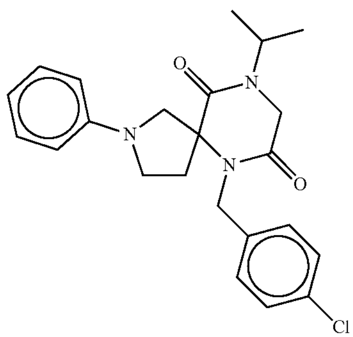 | 6-(4-chlorobenzyl)-9-isopropyl-2-phenyl-2,6,9-triazaspiro[4.5]decane-7,10-dione |
| 128 | 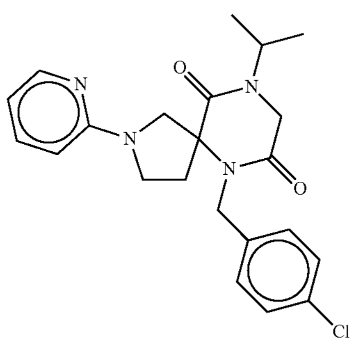 | 6-(4-chlorobenzyl)-9-isopropyl-2-(pyridin-2-yl)-2,6,9-triazaspiro[4.5]decane-7,10-dione |
| 129 | 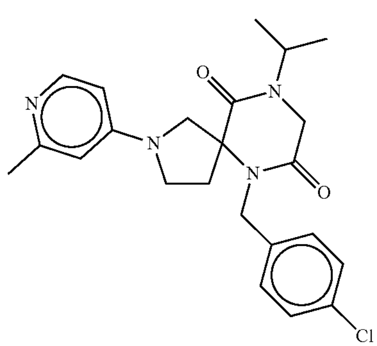 | 6-(4-chlorobenzyl)-9-isopropyl-2-(2-methyl-pyridin-4-yl)-2,6,9-triazaspiro-[4.5]decane-7,10-dione |

TABLE 1-continued

| No. | Structure | Name |
| --- | --- | --- |
| 130 | 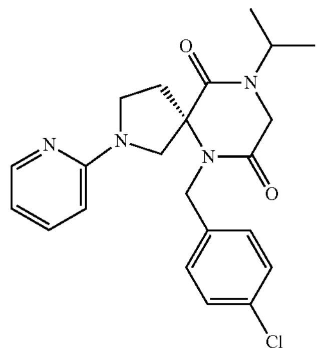 [SMILES: CC(C)N1CC(=O)N(Cc2ccc(Cl)cc2)[C@]2(CCN(c3ccccn3)C2)C1=O] | (S)-6-(4-chlorobenzyl)-9-isopropyl-2-(pyridin-2-yl)-2,6,9-triazaspiro[4.5]-decane-7,10-dione |
| 131 | 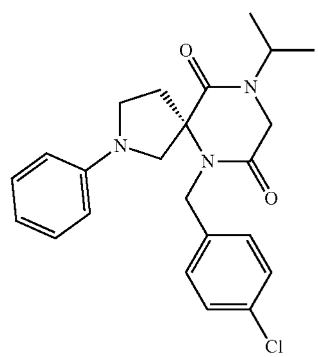 [SMILES: CC(C)N1CC(=O)N(Cc2ccc(Cl)cc2)[C@]2(CCN(c3ccccc3)C2)C1=O] | (S)-6-(4-chlorobenzyl)-9-isopropyl-2-phenyl-2,6,9-triazaspiro[4.5]decane-7,10-dione |
| 132 | 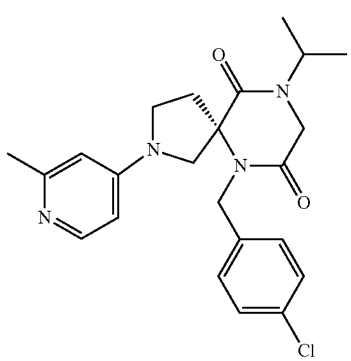 [SMILES: Cc1cc(N2CC[C@]3(C2)C(=O)N(C(C)C)CC(=O)N3Cc2ccc(Cl)cc2)ccn1] | (S)-6-(4-chlorobenzyl)-9-isopropyl-2-(2-methyl-pyridin-4-yl)-2,6,9-triazaspiro[4.5]decane-7,10-dione |
| 133 | 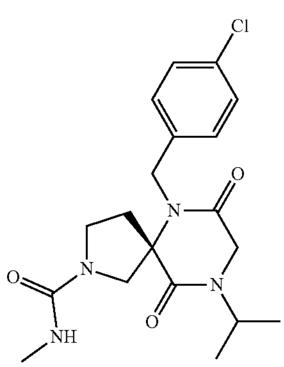 [SMILES: CNC(=O)N1CC[C@]2(C1)C(=O)N(C(C)C)CC(=O)N2Cc1ccc(Cl)cc1] | (S)-6-(4-chlorobenzyl)-9-isopropyl-N-methyl-7,10-dioxo-2,6,9-triazaspiro-[4.5]decane-2-carboxamide |

TABLE 1-continued
| No. | Structure | Name |
|---|---|---|
| 134 | 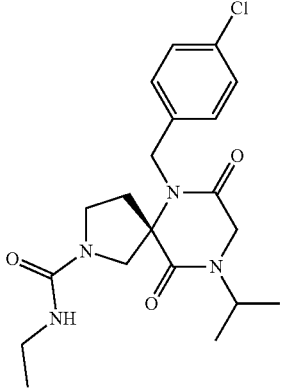 [SMILES: CCNC(=O)N1CC[C@]2(C1)C(=O)N(C(C)C)CC(=O)N2Cc1ccc(Cl)cc1] | (S)-6-(4-chlorobenzyl)-N-ethyl-9-isopropyl-7,10-dioxo-2,6,9-triazaspiro-[4.5]decane-2-carboxamide |
| 135 | 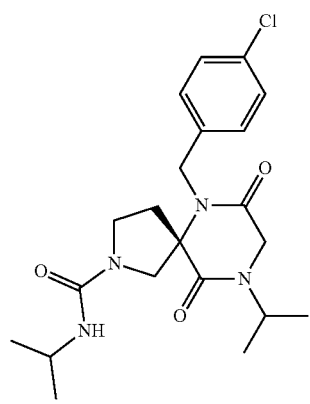 [SMILES: CC(C)NC(=O)N1CC[C@]2(C1)C(=O)N(C(C)C)CC(=O)N2Cc1ccc(Cl)cc1] | (S)-6-(4-chlorobenzyl)-N,9-diisopropyl-7,10-dioxo-2,6,9-triazaspiro-[4.5]decane-2-carboxamide |
| 136 | 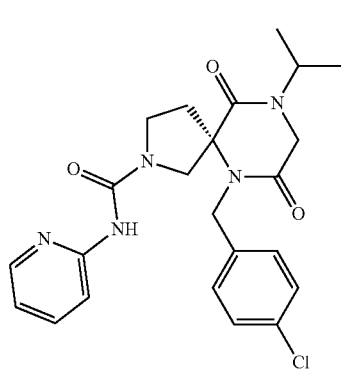 [SMILES: CC(C)N1CC(=O)N(Cc2ccc(Cl)cc2)[C@]2(CCN(C(=O)Nc3ccccn3)C2)C1=O] | (S)-6-(4-chlorobenzyl)-9-isopropyl-7,10-dioxo-N-(pyridin-2-yl)-2,6,9-triazaspiro[4.5]decane-2-carboxamide |
| 137 | 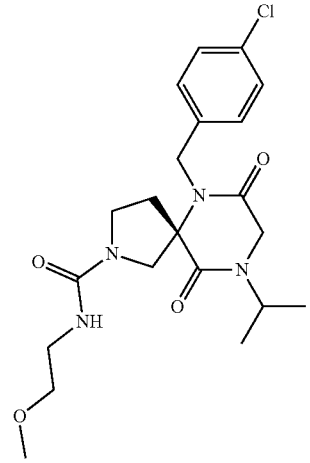 [SMILES: COCCNC(=O)N1CC[C@]2(C1)C(=O)N(C(C)C)CC(=O)N2Cc1ccc(Cl)cc1] | (S)-6-(4-chlorobenzyl)-9-isopropyl-N-(2-methoxyethyl)-7,10-dioxo-2,6,9-triazaspiro-[4.5]decane-2-carboxamide |

TABLE 1-continued

| No. | Structure | Name |
| --- | --- | --- |
| 138 | 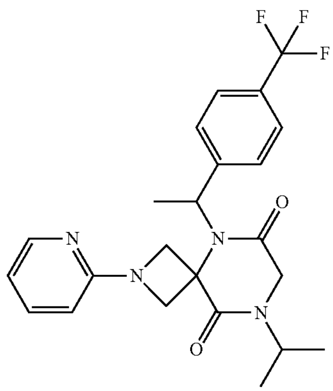 [SMILES: CC(C)N1CC(=O)N(C(C)c2ccc(C(F)(F)F)cc2)C2(CN(c3ccccn3)C2)C1=O] | 8-isopropyl-2-(pyridin-2-yl)-5-(1-(4-(trifluoromethyl)phenyl)ethyl)-2,5,8-triazaspiro[3.5]nonane-6,9-dione |
| 139 | 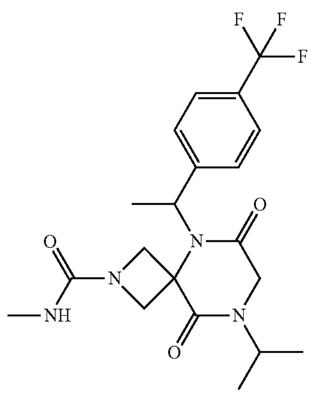 [SMILES: CNC(=O)N1CC2(C1)C(=O)N(C(C)C)CC(=O)N2C(C)c1ccc(C(F)(F)F)cc1] | 8-isopropyl-N-methyl-6,9-dioxo-5-(1-(4-(trifluoromethyl)phenyl)ethyl)-2,5,8-triazaspiro[3.5]nonane-2-carboxamide |
| 140 | 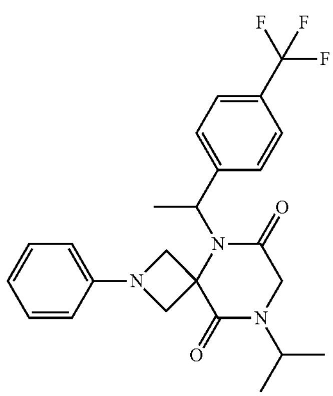 [SMILES: CC(C)N1CC(=O)N(C(C)c2ccc(C(F)(F)F)cc2)C2(CN(c3ccccc3)C2)C1=O] | 8-isopropyl-2-phenyl-5-(1-(4-(trifluoromethyl)phenyl)ethyl)-2,5,8-triazaspiro[3.5]nonane-6,9-dione |
| 141 | 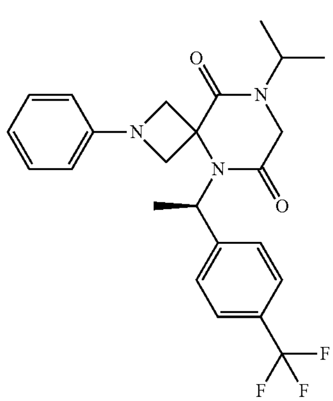 [SMILES: CC(C)N1CC(=O)N([C@H](C)c2ccc(C(F)(F)F)cc2)C2(CN(c3ccccc3)C2)C1=O] | (R)-8-isopropyl-2-phenyl-5-(1-(4-(trifluoromethyl)phenyl)ethyl)-2,5,8-triazaspiro[3.5]nonane-6,9-dione |

TABLE 1-continued

| No. | Structure | Name |
|---|---|---|
| 142 | 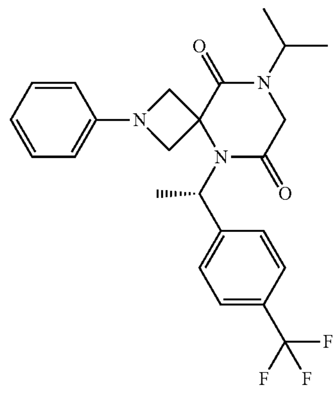 [SMILES: CC(C)N1CC(=O)N([C@@H](C)c2ccc(C(F)(F)F)cc2)C2(CN(c3ccccc3)C2)C1=O] | (S)-8-isopropyl-2-phenyl-5-(1-(4-(trifluoromethyl)-phenyl)ethyl)-2,5,8-triazaspiro[3.5]nonane-6,9-dione |
| 143 | 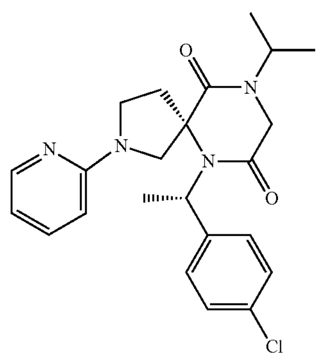 [SMILES: CC(C)N1CC(=O)N([C@@H](C)c2ccc(Cl)cc2)[C@]2(CCN(c3ccccn3)C2)C1=O] | (S)-6-((S)-1-(4-chlorophenyl)ethyl)-9-isopropyl-2-(pyridin-2-yl)-2,6,9-triazaspiro[4.5]-decane-7,10-dione |
| 144 | 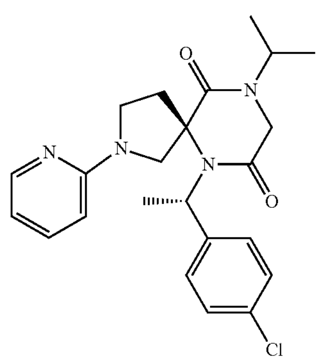 [SMILES: CC(C)N1CC(=O)N([C@@H](C)c2ccc(Cl)cc2)[C@@]2(CCN(c3ccccn3)C2)C1=O] | (R)-6-((S)-1-(4-chlorophenyl)ethyl)-9-isopropyl-2-(pyridin-2-yl)-2,6,9-triazaspiro[4.5]-decane-7,10-dione |
| 145 | 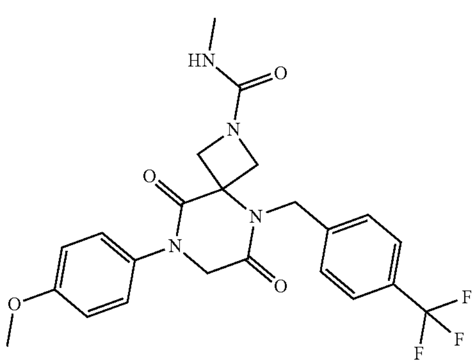 [SMILES: CNC(=O)N1CC2(C1)C(=O)N(c1ccc(OC)cc1)CC(=O)N2Cc1ccc(C(F)(F)F)cc1] | 8-(4-methoxyphenyl)-N-methyl-6,9-dioxo-5-(4-(trifluoromethyl)benzyl)-2,5,8-triazaspiro[3.5]-nonane-2-carboxamide |

TABLE 1-continued

| No. | Structure | Name |
|---|---|---|
| 146 | 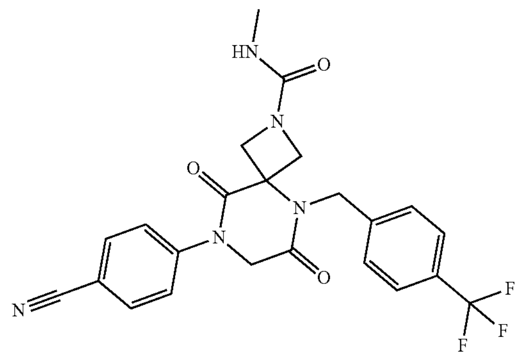 [SMILES: CNC(=O)N1CC2(C1)C(=O)N(c1ccc(C#N)cc1)CC(=O)N2Cc1ccc(C(F)(F)F)cc1] | 8-(4-cyanophenyl)-N-methyl-6,9-dioxo-5-(4-(trifluoromethyl)benzyl)-2,5,8-triazaspiro[3.5]-nonane-2-carboxamide |
| 147 | 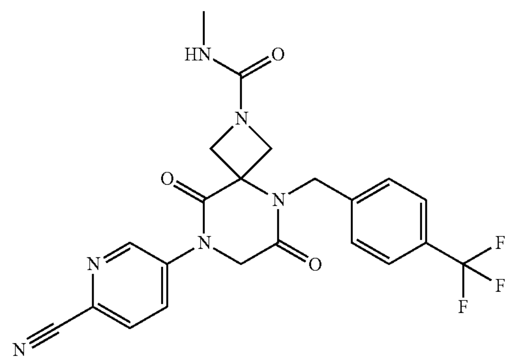 [SMILES: CNC(=O)N1CC2(C1)C(=O)N(c1ccc(C#N)nc1)CC(=O)N2Cc1ccc(C(F)(F)F)cc1] | 8-(6-cyanopyridin-3-yl)-N-methyl-6,9-dioxo-5-(4-(trifluoromethyl)benzyl)-2,5,8-triazaspiro[3.5]-nonane-2-carboxamide |
| 148 | 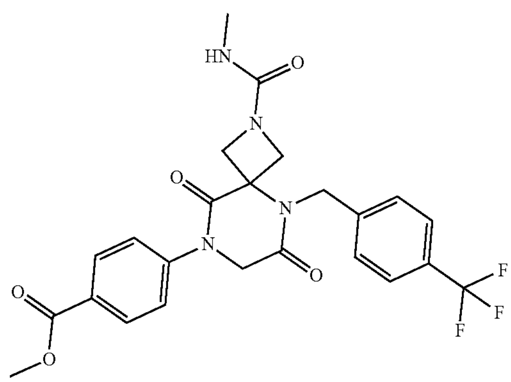 [SMILES: CNC(=O)N1CC2(C1)C(=O)N(c1ccc(C(=O)OC)cc1)CC(=O)N2Cc1ccc(C(F)(F)F)cc1] | methyl 4-(2-(methylcarbamoyl)-6,9-dioxo-5-(4-(trifluoromethyl)benzyl)-2,5,8-triazaspiro[3.5]nonan-8-yl)benzoate |
| 149 | 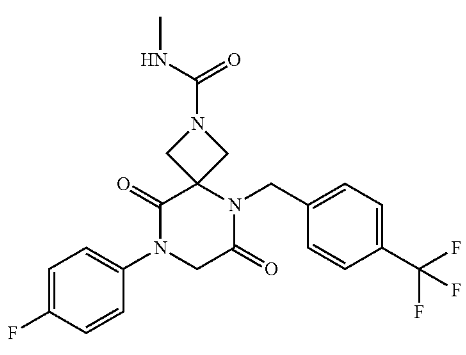 [SMILES: CNC(=O)N1CC2(C1)C(=O)N(c1ccc(F)cc1)CC(=O)N2Cc1ccc(C(F)(F)F)cc1] | 8-(4-fluorophenyl)-N-methyl-6,9-dioxo-5-(4-(trifluoromethyl)benzyl)-2,5,8-triazaspiro[3.5]-nonane-2-carboxamide |

TABLE 1-continued

| No. | Structure | Name |
|---|---|---|
| 150 | 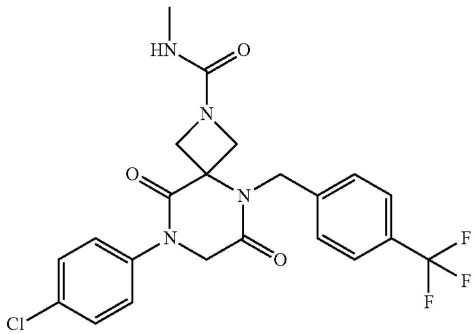 [SMILES: CNC(=O)N1CC2(C1)C(=O)N(c1ccc(Cl)cc1)CC(=O)N2Cc1ccc(C(F)(F)F)cc1] | 8-(4-chlorophenyl)-N-methyl-6,9-dioxo-5-(4-(trifluoromethyl)benzyl)-2,5,8-triazaspiro[3.5]-nonane-2-carboxamide |
| 151 | 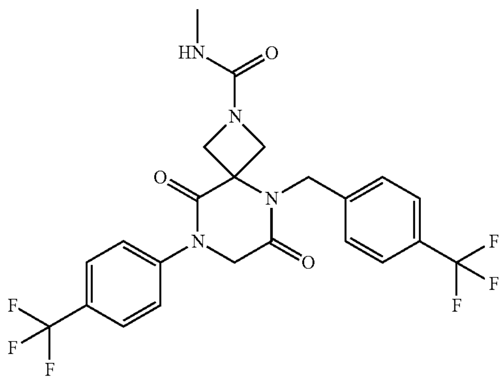 [SMILES: CNC(=O)N1CC2(C1)C(=O)N(c1ccc(C(F)(F)F)cc1)CC(=O)N2Cc1ccc(C(F)(F)F)cc1] | N-methyl-6,9-dioxo-5-(4-(trifluoromethyl)benzyl)-8-(4-(trifluoromethyl)phenyl)-2,5,8-triazaspiro[3.5]nonane-2-carboxamide |
| 152 | 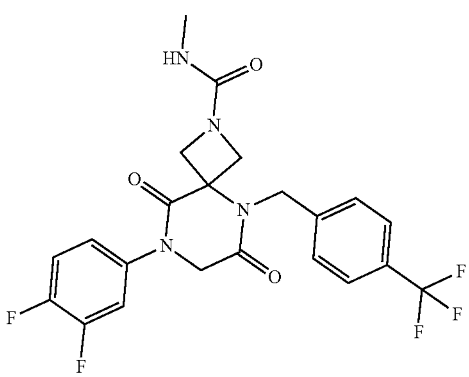 [SMILES: CNC(=O)N1CC2(C1)C(=O)N(c1ccc(F)c(F)c1)CC(=O)N2Cc1ccc(C(F)(F)F)cc1] | 8-(3,4-difluorophenyl)-N-methyl-6,9-dioxo-5-(4-(trifluoromethyl)benzyl)-2,5,8-triazaspiro[3.5]nonane-2-carboxamide |
| 153 | 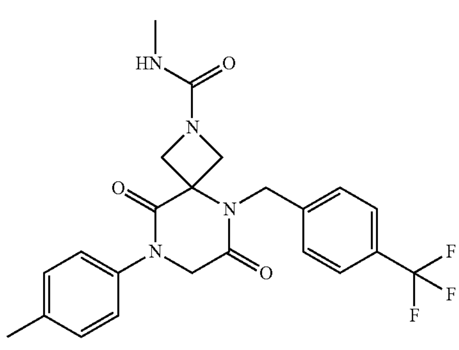 [SMILES: CNC(=O)N1CC2(C1)C(=O)N(c1ccc(C)cc1)CC(=O)N2Cc1ccc(C(F)(F)F)cc1] | N-methyl-6,9-dioxo-8-(p-tolyl)-5-(4-(trifluoromethyl)benzyl)-2,5,8-triazaspiro[3.5]-nonane-2-carboxamide |

TABLE 1-continued

| No. | Structure | Name |
|---|---|---|
| 154 | 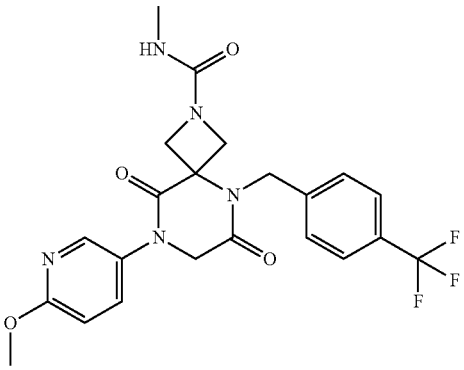 [SMILES: CNC(=O)N1CC2(C1)C(=O)N(c1ccc(OC)nc1)CC(=O)N2Cc1ccc(C(F)(F)F)cc1] | 8-(6-methoxypyridin-3-yl)-N-methyl-6,9-dioxo-5-(4-(trifluoromethyl)benzyl)-2,5,8-triazaspiro[3.5]-nonane-2-carboxamide |
| 155 | 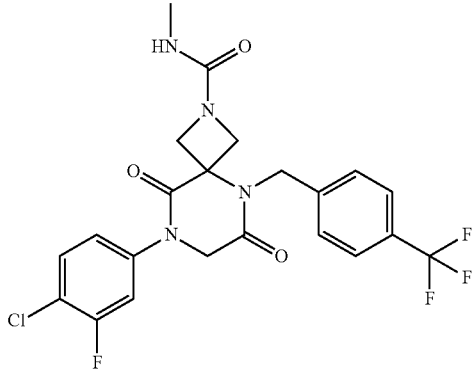 [SMILES: CNC(=O)N1CC2(C1)C(=O)N(c1ccc(Cl)c(F)c1)CC(=O)N2Cc1ccc(C(F)(F)F)cc1] | 8-(4-chloro-3-fluorophenyl)-N-methyl-6,9-dioxo-5-(4-(trifluoromethyl)benzyl)-2,5,8-triazaspiro[3.5]-nonane-2-carboxamide |
| 156 | 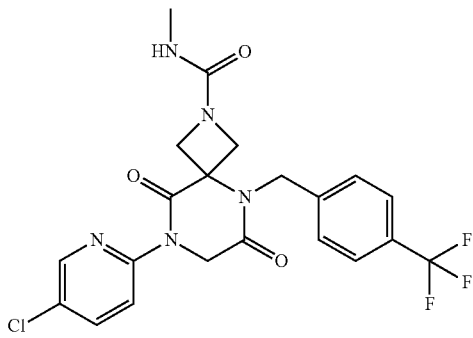 [SMILES: CNC(=O)N1CC2(C1)C(=O)N(c1ccc(Cl)cn1)CC(=O)N2Cc1ccc(C(F)(F)F)cc1] | 8-(5-chloropyridin-2-yl)-N-methyl-6,9-dioxo-5-(4-(trifluoromethyl)benzyl)-2,5,8-triazaspiro[3.5]-nonane-2-carboxamide |
| 157 | 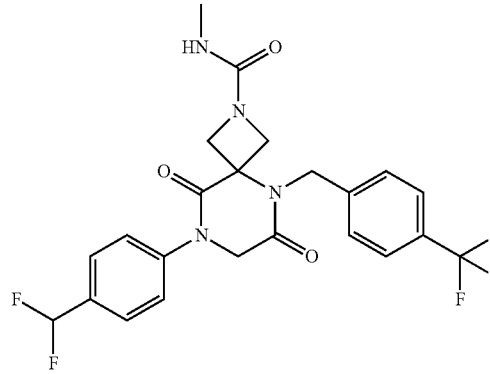 | 8-(4-(difluoromethyl)-phenyl)-N-methyl-6,9-dioxo-5(4-(trifluoromethyl)-benzyl)-2,5,8-triazaspiro-[3.5]nonane-2-carboxamide |

TABLE 1-continued

| No. | Structure | Name |
|---|---|---|
| 158 | 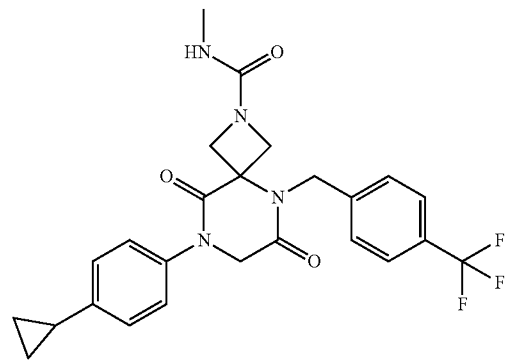 [SMILES: CNC(=O)N1CC2(C1)C(=O)N(c1ccc(C3CC3)cc1)CC(=O)N2Cc1ccc(C(F)(F)F)cc1] | 8-(4-cyclopropylphenyl)-N-methyl-6,9-dioxo-5-(4-(trifluoromethyl)benzyl)-2,5,8-triazaspiro[3.5]nonane-2-carboxamide |
| 159 | 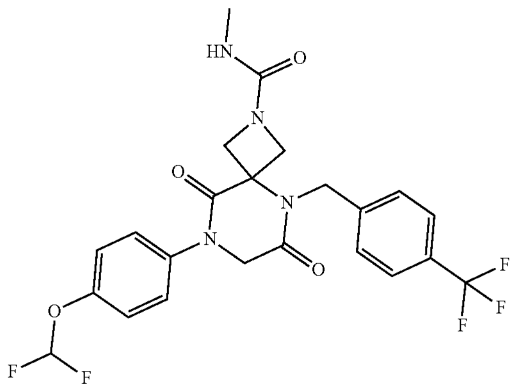 [SMILES: CNC(=O)N1CC2(C1)C(=O)N(c1ccc(OC(F)F)cc1)CC(=O)N2Cc1ccc(C(F)(F)F)cc1] | 8-(4-(difluoromethoxy)phenyl)-N-methyl-6,9-dioxo-5-(4-(trifluoromethyl)benzyl)-2,5,8-triazaspiro[3.5]nonane-2-carboxamide |
| 160 | 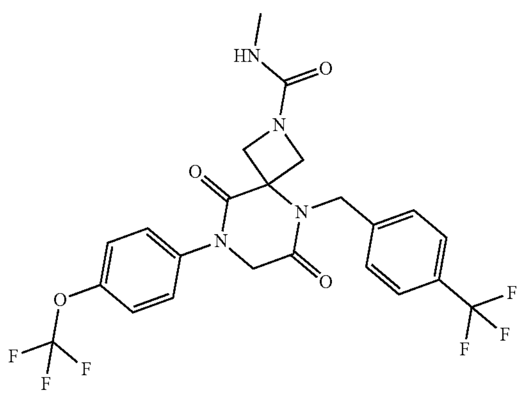 [SMILES: CNC(=O)N1CC2(C1)C(=O)N(c1ccc(OC(F)(F)F)cc1)CC(=O)N2Cc1ccc(C(F)(F)F)cc1] | N-methyl-6,9-dioxo-8-(4-(trifluoromethoxy)phenyl)-5-(4-(trifluoromethyl)benzyl)-2,5,8-triazaspiro[3.5]nonane-2-carboxamide |
| 161 | 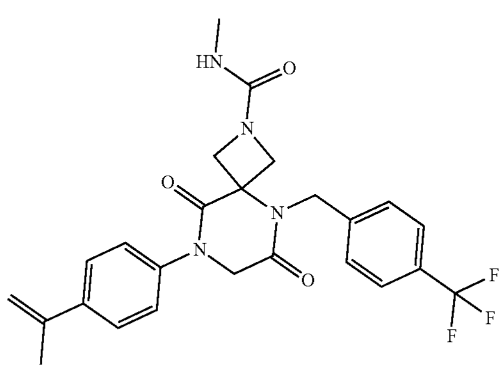 [SMILES: C=C(C)c1ccc(N2CC(=O)N(Cc3ccc(C(F)(F)F)cc3)C3(CN(C(=O)NC)C3)C2=O)cc1] | N-methyl-6,9-dioxo-8-(4-(prop-1-en-2-yl)phenyl)-5-(4-(trifluoromethyl)benzyl)-2,5,8-triazaspiro[3.5]nonane-2-carboxamide |

TABLE 1-continued

| No. | Structure | Name |
|---|---|---|
| 162 | 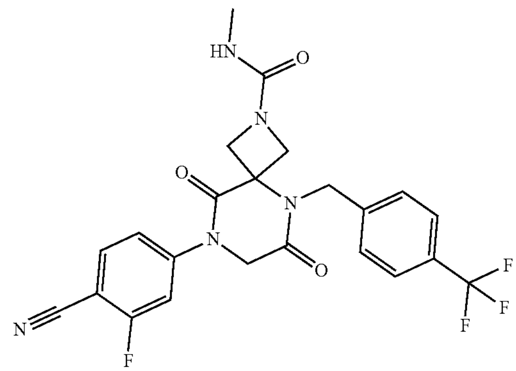 [SMILES: CNC(=O)N1CC2(C1)C(=O)N(c1ccc(C#N)c(F)c1)CC(=O)N2Cc1ccc(C(F)(F)F)cc1] | 8-(4-cyano-3-fluorophenyl)-N-methyl-6,9-dioxo-5-(4-(trifluoromethyl)benzyl)-2,5,8-triazaspiro[3.5]-nonane-2-carboxamide |
| 163 | 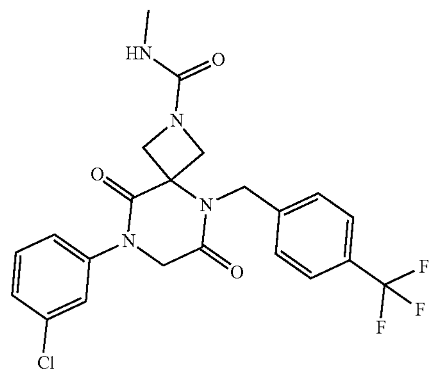 [SMILES: CNC(=O)N1CC2(C1)C(=O)N(c1cccc(Cl)c1)CC(=O)N2Cc1ccc(C(F)(F)F)cc1] | 8-(3-chlorophenyl)-N-methyl-6,9-dioxo-5-(4-(trifluoromethyl)benzyl)-2,5,8-triazaspiro[3.5]-nonane-2-carboxamide |
| 164 | 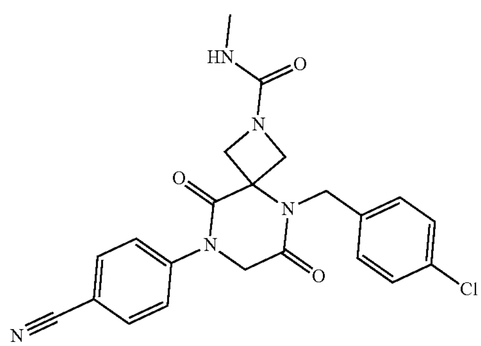 [SMILES: CNC(=O)N1CC2(C1)C(=O)N(c1ccc(C#N)cc1)CC(=O)N2Cc1ccc(Cl)cc1] | 5-(4-chlorobenzyl)-8-(4-cyanophenyl)-N-methyl-6,9-dioxo-2,5,8-triazaspiro-[3.5]nonane-2-carboxamide |
| 165 | 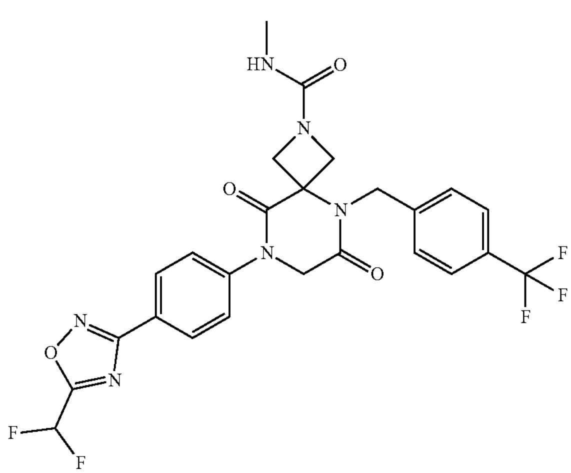 [SMILES: CNC(=O)N1CC2(C1)C(=O)N(c1ccc(-c3noc(C(F)F)n3)cc1)CC(=O)N2Cc1ccc(C(F)(F)F)cc1] | 8-(4-(5-(difluoromethyl)-1,2,4-oxadiazol-3-yl)-phenyl)-N-methyl-6,9-dioxo-5-(4-(trifluoromethyl)-benzyl)-2,5,8-triazaspiro-[3.5]nonane-2-carboxamide |

TABLE 1-continued

| No. | Structure | Name |
|---|---|---|
| 166 | 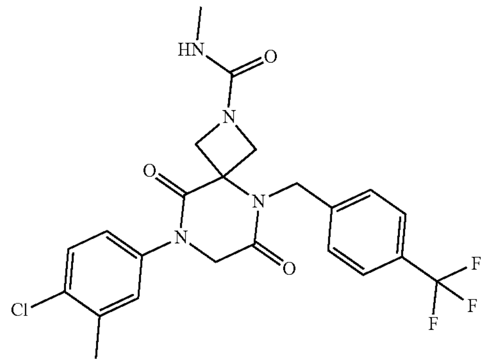 [SMILES: CNC(=O)N1CC2(C1)C(=O)N(c1ccc(Cl)c(C)c1)CC(=O)N2Cc1ccc(C(F)(F)F)cc1] | 8-(4-chloro-3-methyl-phenyl)-N-methyl-6,9-dioxo-5-(4-(trifluoromethyl)-benzyl)-2,5,8-triazaspiro-[3.5]nonane-2-carboxamide |
| 167 | 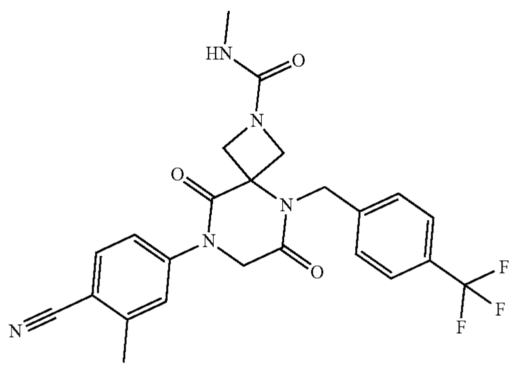 [SMILES: CNC(=O)N1CC2(C1)C(=O)N(c1ccc(C#N)c(C)c1)CC(=O)N2Cc1ccc(C(F)(F)F)cc1] | 8-(4-cyano-3-methyl-phenyl)-N-methyl-6,9-dioxo-5-(4-(trifluoromethyl)-benzyl)-2,5,8-triazaspiro-[3.5]nonane-2-carboxamide |
| 168 | 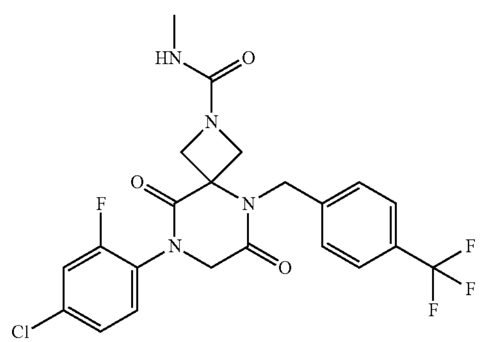 [SMILES: CNC(=O)N1CC2(C1)C(=O)N(c1ccc(Cl)cc1F)CC(=O)N2Cc1ccc(C(F)(F)F)cc1] | 8-(4-chloro-2-fluoro-phenyl)-N-methyl-6,9-dioxo-5-(4-(trifluoromethyl)benzyl)-2,5,8-triazaspiro[3.5]nonane-2-carboxamide |
| 169 | 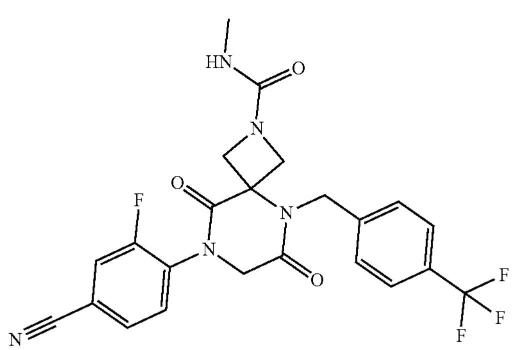 [SMILES: CNC(=O)N1CC2(C1)C(=O)N(c1ccc(C#N)cc1F)CC(=O)N2Cc1ccc(C(F)(F)F)cc1] | 8-(4-cyano-2-fluoro-phenyl)-N-methyl-6,9-dioxo-5-(4-(trifluoromethyl)-benzyl)-2,5,8-triazaspiro-[3.5]nonane-2-carboxamide |

TABLE 1-continued

| No. | Structure | Name |
|---|---|---|
| 170 | 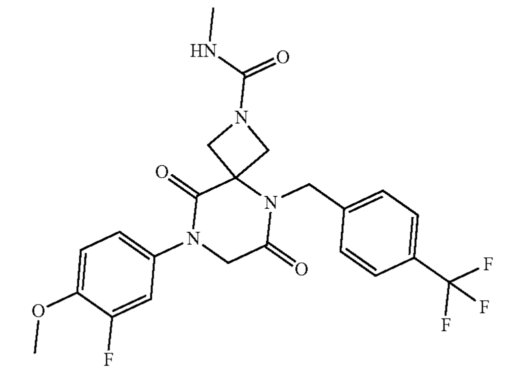 [SMILES: CNC(=O)N1CC2(C1)C(=O)N(c1ccc(OC)c(F)c1)CC(=O)N2Cc1ccc(C(F)(F)F)cc1] | 8-(3-fluoro-4-methoxy-phenyl)-N-methyl-6,9-dioxo-5-(4-(trifluoromethyl)-benzyl)-2,5,8-triazaspiro-[3.5]nonane-2-carboxamide |
| 171 | 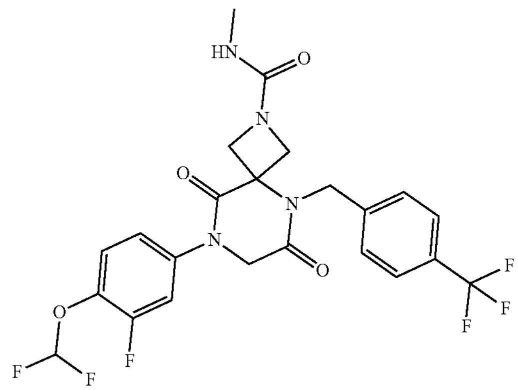 [SMILES: CNC(=O)N1CC2(C1)C(=O)N(c1ccc(OC(F)F)c(F)c1)CC(=O)N2Cc1ccc(C(F)(F)F)cc1] | 8-(4-(difluoromethoxy)-3-fluorophenyl)-N-methyl-6,9-dioxo-5-(4-(trifluoromethyl)benzyl)-2,5/8-triazaspiro[3.5]-nonane-2-carboxamide |
| 172 | 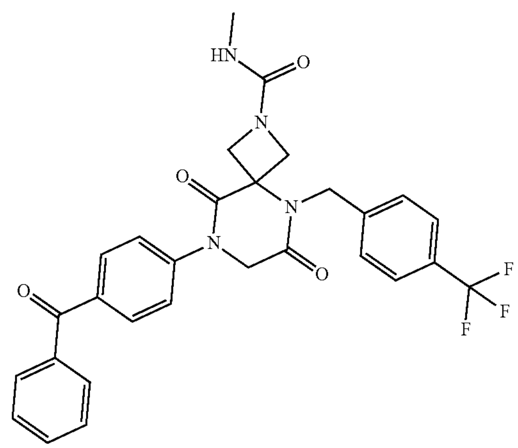 [SMILES: CNC(=O)N1CC2(C1)C(=O)N(c1ccc(C(=O)c3ccccc3)cc1)CC(=O)N2Cc1ccc(C(F)(F)F)cc1] | 8-(4-benzoylphenyl)-N-methyl-6,9-dioxo-5-(4-(trifluoromethyl)benzyl)-2,5,8-triazaspiro[3.5]-nonane-2-carboxamide |
| 173 | 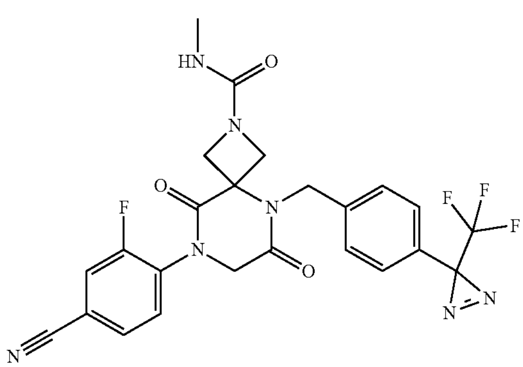 [SMILES: CNC(=O)N1CC2(C1)C(=O)N(c1ccc(C#N)cc1F)CC(=O)N2Cc1ccc(C2(C(F)(F)F)N=N2)cc1] | 8-(4-cyano-2-fluorophenyl)-N-methyl-6,9-dioxo-5-(4-(3-(trifluoromethyl)-3H-diazirin-3-yl)benzyl)-2,5,8-triazaspiro[3.5]nonane-2-carboxamide |

TABLE 1-continued

| No. | Structure | Name |
| --- | --- | --- |
| 174 | 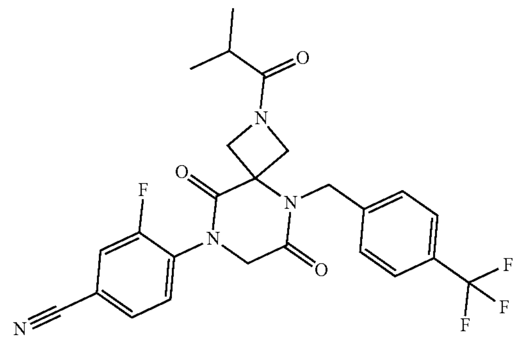 [SMILES: CC(C)C(=O)N1CC2(C1)C(=O)N(c1ccc(C#N)cc1F)CC(=O)N2Cc1ccc(C(F)(F)F)cc1] | 3-fluoro-4-(2-isobutyryl-6,9-dioxo-5-(4-(trifluoromethyl)benzyl)-2,5,8-triazaspiro[3.5]nonan-8-yl)benzonitrile |
| 175 | 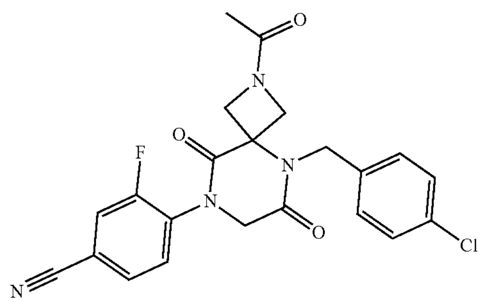 [SMILES: CC(=O)N1CC2(C1)C(=O)N(c1ccc(C#N)cc1F)CC(=O)N2Cc1ccc(Cl)cc1] | 4-(2-acetyl-5-(4-chlorobenzyl)-6,9-dioxo-2,5,8-triazaspiro[3.5]nonan-8-yl)-3-fluorobenzonitrile |
| 176 | 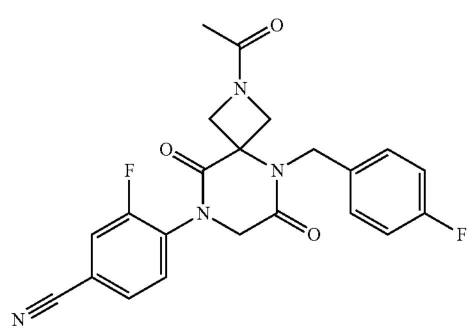 [SMILES: CC(=O)N1CC2(C1)C(=O)N(c1ccc(C#N)cc1F)CC(=O)N2Cc1ccc(F)cc1] | 4-(2-acetyl-5-(4-fluoro-benzyl)-6,9-dioxo-2,5,8-triazaspiro[3.5]nonan-8-yl)-3-fluorobenzonitrile |
| 177 | 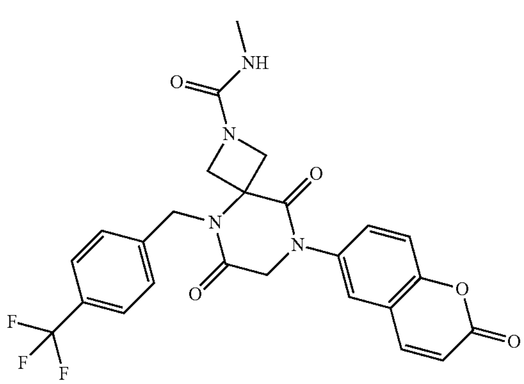 [SMILES: CNC(=O)N1CC2(C1)C(=O)N(c1ccc3oc(=O)ccc3c1)CC(=O)N2Cc1ccc(C(F)(F)F)cc1] | N-methyl-6,9-dioxo-8-(2-oxo-2H-chromen-6-yl)-5-(4-(trifluoromethyl)benzyl)-2,5,8-triazaspiro[3.5]-nonane-2-carboxamide |

TABLE 1-continued

| No. | Structure | Name |
|---|---|---|
| 178 | 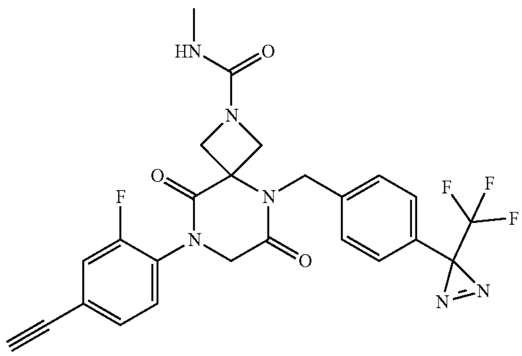 [SMILES: C#Cc1ccc(N2CC(=O)N(Cc3ccc(C4(C(F)(F)F)N=N4)cc3)C3(CN(C(=O)NC)C3)C2=O)c(F)c1] | 8-(4-ethynyl-2-fluoro-phenyl)-N-methyl-6,9-dioxo-5-(4-(3-(trifluoromethyl)-3H-diazirin-3-yl)benzyl)-2,5,8-triazaspiro[3.5]nonane-2-carboxamide |
| 179 | 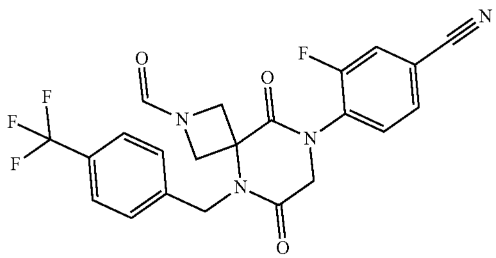 [SMILES: N#Cc1ccc(N2CC(=O)N(Cc3ccc(C(F)(F)F)cc3)C3(CN(C=O)C3)C2=O)c(F)c1] | 3-fluoro-4-(2-formyl-6,9-dioxo-5-(4-(trifluoro-methyl)benzyl)-2,5,8-triazaspiro[3.5]nonan-8-yl)benzonitrile |
| 180 | 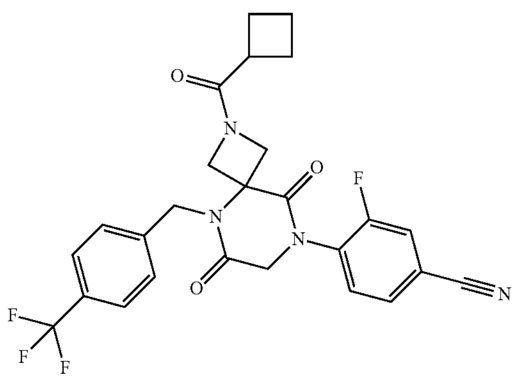 [SMILES: N#Cc1ccc(N2CC(=O)N(Cc3ccc(C(F)(F)F)cc3)C3(CN(C(=O)C4CCC4)C3)C2=O)c(F)c1] | 4-(2-(cyclobutanecarbonyl)-6,9-dioxo-5-(4-(trifluoromethyl)benzyl)-2,5,8-triazaspiro[3.5]nonan-8-yl)-3-fluorobenzonitrile |
| 181 | 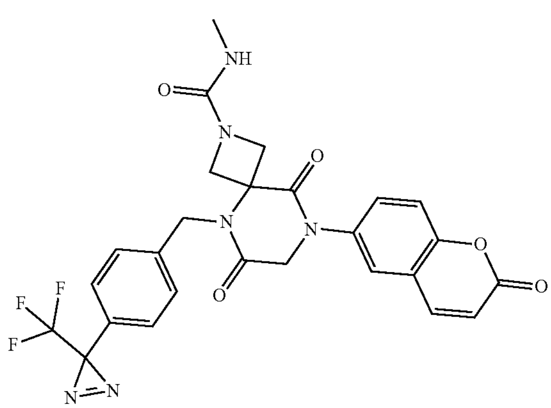 [SMILES: CNC(=O)N1CC2(C1)C(=O)N(c1ccc3oc(=O)ccc3c1)CC(=O)N2Cc1ccc(C2(C(F)(F)F)N=N2)cc1] | N-methyl-6,9-dioxo-8-(2-oxo-2H-chromen-6-yl)-5-(4-(3-(trifluoromethyl)-3H-diazirin-3-yl)benzyl)-2,5,8-triazaspiro[3.5]-nonane-2-carboxamide |

TABLE 1-continued

| No. | Structure | Name |
|---|---|---|
| 182 | 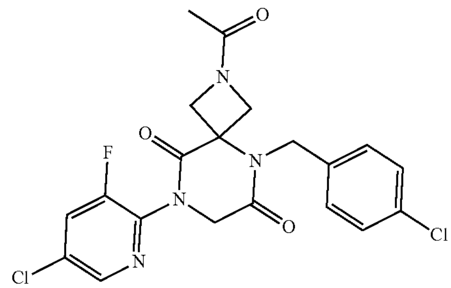 [SMILES: CC(=O)N1CC2(C1)C(=O)N(c1ncc(Cl)cc1F)CC(=O)N2Cc1ccc(Cl)cc1] | 2-acetyl-8-(5-chloro-3-fluoropyridin-2-yl)-5-(4-chlorobenzyl)-2,5,8-triazaspiro[3.5]nonane-6,9-dione |
| 183 | 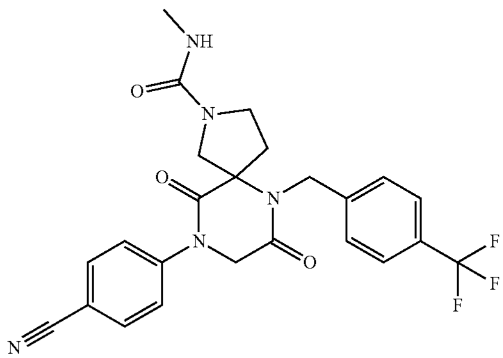 [SMILES: CNC(=O)N1CCC2(C1)C(=O)N(c1ccc(C#N)cc1)CC(=O)N2Cc1ccc(C(F)(F)F)cc1] | 9-(4-cyanophenyl)-N-methyl-7,10-dioxo-6-(4-(trifluoromethyl)benzyl)-2,6,9-triazaspiro[4.5]-decane-2-carboxamide |
| 184 | 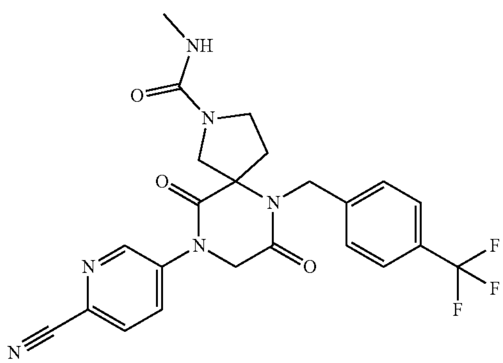 [SMILES: CNC(=O)N1CCC2(C1)C(=O)N(c1ccc(C#N)nc1)CC(=O)N2Cc1ccc(C(F)(F)F)cc1] | 9-(6-cyanopyridin-3-yl)-N-methyl-7,10-dioxo-6-(4-(trifluoromethyl)benzyl)-2,6,9-triazaspiro[4.5]-decane-2-carboxamide |
| 185 | 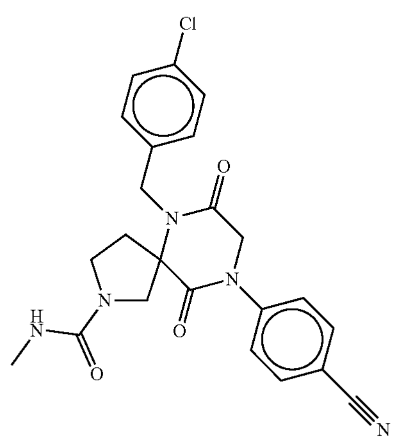 | 6-(4-chlorobenzyl)-9-(4-cyanophenyl)-N-methyl-7,10-dioxo-2,6,9-triazaspiro[4.5]decane-2-carboxamide |

TABLE 1-continued

| No. | Structure | Name |
|---|---|---|
| 186 | 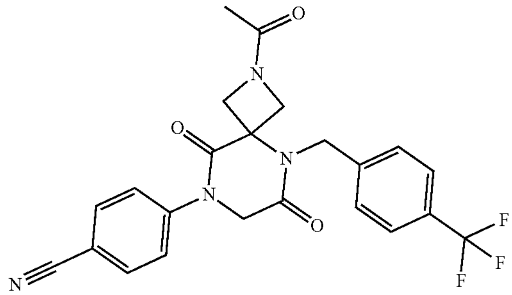 [SMILES: CC(=O)N1CC2(C1)C(=O)N(c1ccc(C#N)cc1)CC(=O)N2Cc1ccc(C(F)(F)F)cc1] | 4-(2-acetyl-6,9-dioxo-5-(4-(trifluoromethyl)benzyl)-2,5,8-triazaspiro[3.5]nonan-8-yl)benzonitrile |
| 187 | 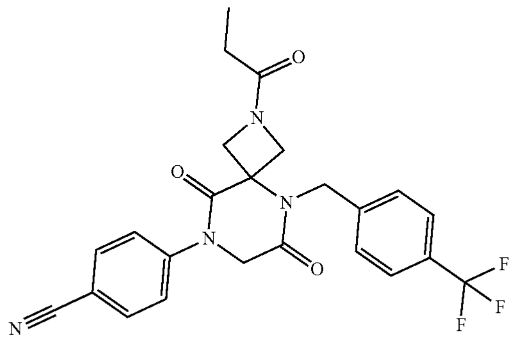 [SMILES: CCC(=O)N1CC2(C1)C(=O)N(c1ccc(C#N)cc1)CC(=O)N2Cc1ccc(C(F)(F)F)cc1] | 4-(6,9-dioxo-2-propionyl-5-(4-(trifluoromethyl)benzyl)-2,5,8-triazaspiro[3.5]nonan-8-yl)benzonitrile |
| 188 | 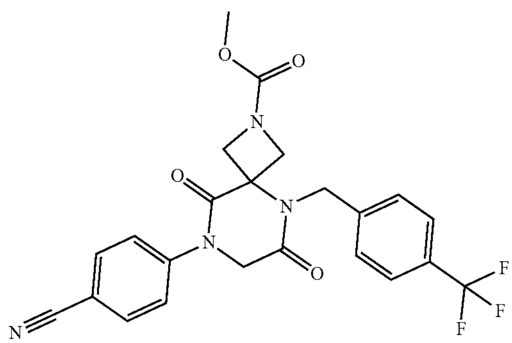 [SMILES: COC(=O)N1CC2(C1)C(=O)N(c1ccc(C#N)cc1)CC(=O)N2Cc1ccc(C(F)(F)F)cc1] | methyl 8-(4-cyanophenyl)-6,9-dioxo-5-(4-(trifluoromethyl)benzyl)-2,5,8-triazaspiro[3.5]-nonane-2-carboxylate |
| 189 | 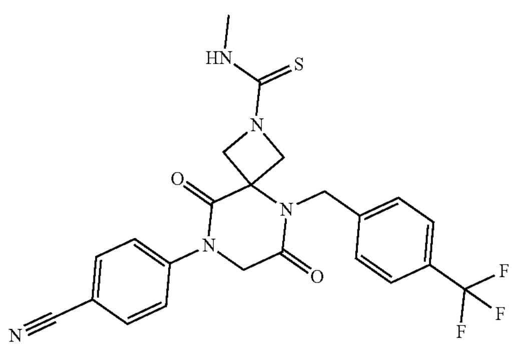 [SMILES: CNC(=S)N1CC2(C1)C(=O)N(c1ccc(C#N)cc1)CC(=O)N2Cc1ccc(C(F)(F)F)cc1] | 8-(4-cyanophenyl)-N-methyl-6,9-dioxo-5-(4-(trifluoromethyl)benzyl)-2,5,8-triazaspiro[3.5]-nonane-2-carbothioamide |
| 190 | 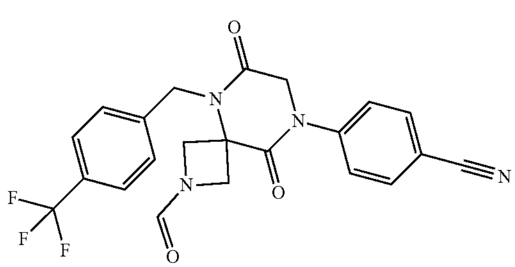 [SMILES: N#Cc1ccc(N2CC(=O)N(Cc3ccc(C(F)(F)F)cc3)C3(CN(C=O)C3)C2=O)cc1] | 4-(2-formyl-6,9-dioxo-5-(4-(trifluoromethyl)benzyl)-2,5,8-triazaspiro[3.5]nonan-8-yl)benzonitrile |

TABLE 1-continued

| No. | Structure | Name |
|---|---|---|
| 191 | 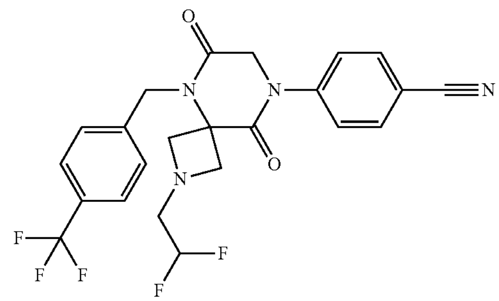 [SMILES: N#Cc1ccc(N2CC(=O)N(Cc3ccc(C(F)(F)F)cc3)C3(CN(CC(F)F)C3)C2=O)cc1] | 4-(2-(2,2-difluoroethyl)-6,9-dioxo-5-(4-(trifluoromethyl)benzyl)-2,5,8-triazaspiro[3.5]nonan-8-yl)benzonitrile |
| 192 | 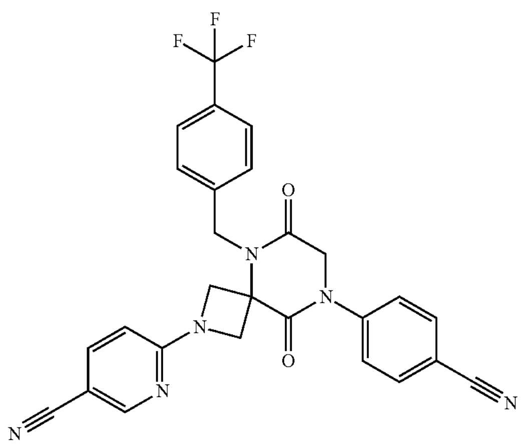 [SMILES: N#Cc1ccc(N2CC(=O)N(Cc3ccc(C(F)(F)F)cc3)C3(CN(c4ccc(C#N)cn4)C3)C2=O)cc1] | 6-(8-(4-cyanophenyl)-6,9-dioxo-5-(4-(trifluoromethyl)benzyl)-2,5,8-triazaspiro[3.5]nonan-2-yl)nicotinonitrile |
| 193 | 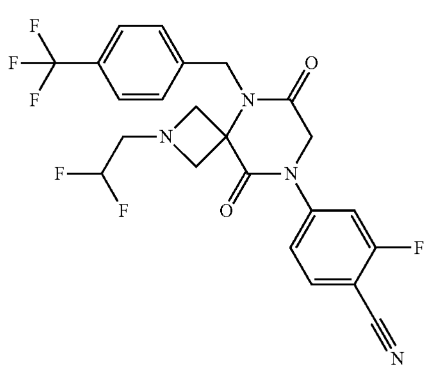 [SMILES: N#Cc1ccc(N2CC(=O)N(Cc3ccc(C(F)(F)F)cc3)C3(CN(CC(F)F)C3)C2=O)cc1F] | 4-(2-(2,2-difluoroethyl)-6,9-dioxo-5-(4-(trifluoromethyl)benzyl)-2,5,8-triazaspiro[3.5]nonan-8-yl)-2-fluorobenzonitrile |
| 194 | 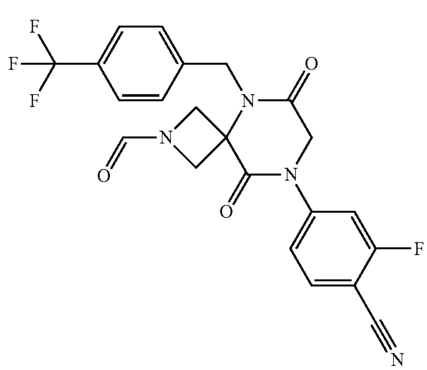 [SMILES: N#Cc1ccc(N2CC(=O)N(Cc3ccc(C(F)(F)F)cc3)C3(CN(C=O)C3)C2=O)cc1F] | 2-fluoro-4-(2-formyl-6,9-dioxo-5-(4-(trifluoromethyl)benzyl)-2,5,8-triazaspiro[3.5]nonan-8-yl)benzonitrile |

TABLE 1-continued

| No. | Structure | Name |
|---|---|---|
| 195 | 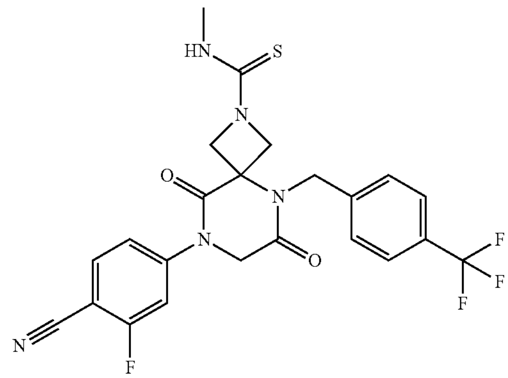 [SMILES: CNC(=S)N1CC2(C1)C(=O)N(c1ccc(C#N)c(F)c1)CC(=O)N2Cc1ccc(C(F)(F)F)cc1] | 8-(4-cyano-3-fluorophenyl)-N-methyl-6,9-dioxo-5-(4-(trifluoromethyl)benzyl)-2,5,8-triazaspiro[3.5]nonane-2-carbothioamide |
| 196 | 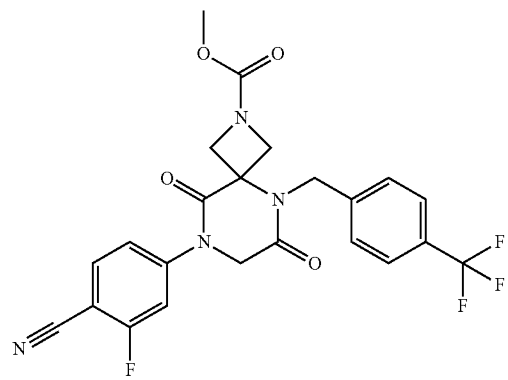 [SMILES: COC(=O)N1CC2(C1)C(=O)N(c1ccc(C#N)c(F)c1)CC(=O)N2Cc1ccc(C(F)(F)F)cc1] | methyl 8-(4-cyano-3-fluorophenyl)-6,9-dioxo-5-(4-(trifluoromethyl)benzyl)-2,5,8-triazaspiro[3.5]nonane-2-carboxylate |
| 197 | 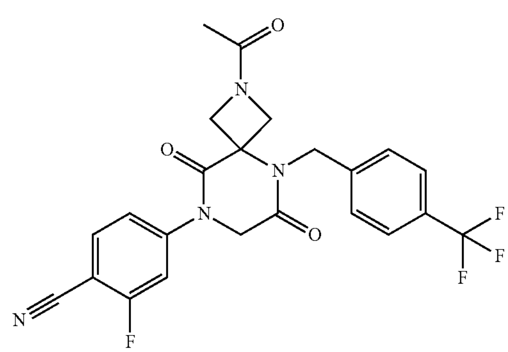 [SMILES: CC(=O)N1CC2(C1)C(=O)N(c1ccc(C#N)c(F)c1)CC(=O)N2Cc1ccc(C(F)(F)F)cc1] | 4-(2-acetyl-6,9-dioxo-5-(4-(trifluoromethyl)benzyl)-2,5,8-triazaspiro[3.5]nonan-8-yl)-2-fluorobenzonitrile |
| 198 | 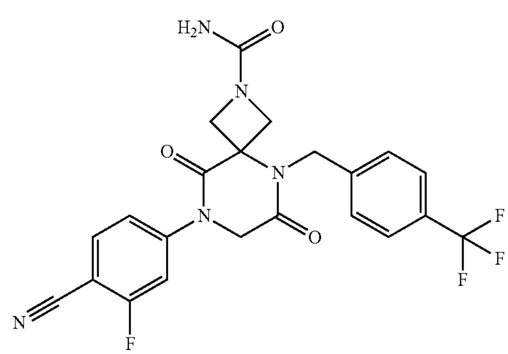 [SMILES: N#Cc1ccc(N2CC(=O)N(Cc3ccc(C(F)(F)F)cc3)C3(CN(C(N)=O)C3)C2=O)cc1F] | 8-(4-cyano-3-fluorophenyl)-6,9-dioxo-5-(4-(trifluoromethyl)benzyl)-2,5,8-triazaspiro[3.5]nonane-2-carboxamide |

TABLE 1-continued

| No. | Structure | Name |
|---|---|---|
| 199 | 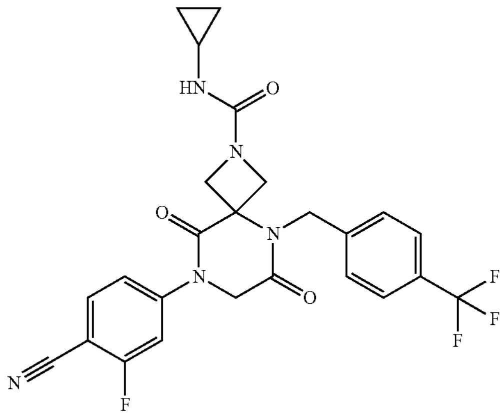 [SMILES: N#Cc1ccc(N2CC(=O)N(Cc3ccc(C(F)(F)F)cc3)C3(CN(C(=O)NC4CC4)C3)C2=O)cc1F] | 8-(4-cyano-3-fluorophenyl)-N-cyclopropyl-6,9-dioxo-5-(4-(trifluoromethyl)benzyl)-2,5,8-triazaspiro[3.5]nonane-2-carboxamide |
| 200 | 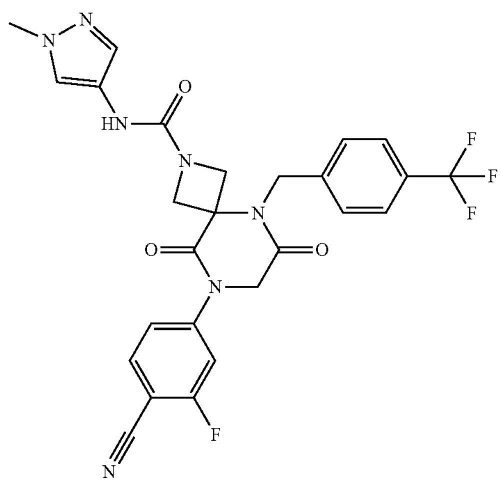 [SMILES: Cn1cc(NC(=O)N2CC3(C2)C(=O)N(c2ccc(C#N)c(F)c2)CC(=O)N3Cc2ccc(C(F)(F)F)cc2)cn1] | 8-(4-cyano-3-fluorophenyl)-N-(1-methyl-1H-pyrazol-4-yl)-6,9-dioxo-5-(4-(trifluoromethyl)benzyl)-2,5,8-triazaspiro[3.5]nonane-2-carboxamide |
| 201 | 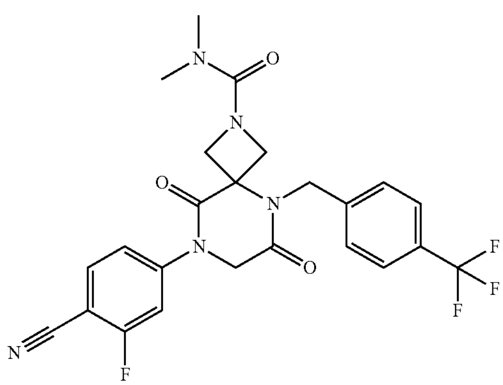 [SMILES: CN(C)C(=O)N1CC2(C1)C(=O)N(c1ccc(C#N)c(F)c1)CC(=O)N2Cc1ccc(C(F)(F)F)cc1] | 8-(4-cyano-3-fluorophenyl)-N,N-dimethyl-6,9-dioxo-5-(4-(trifluoromethyl)benzyl)-2,5,8-triazaspiro[3.5]nonane-2-carboxamide |
| 202 | 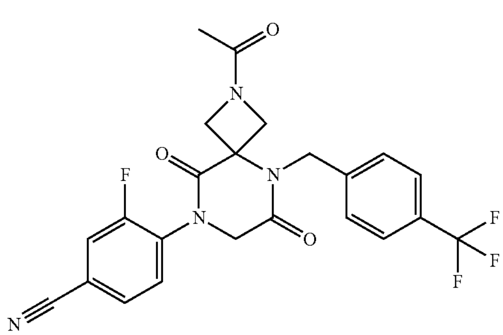 [SMILES: CC(=O)N1CC2(C1)C(=O)N(c1ccc(C#N)cc1F)CC(=O)N2Cc1ccc(C(F)(F)F)cc1] | 4-(2-acetyl-6,9-dioxo-5-(4-(trifluoromethyl)benzyl)-2,5,8-triazaspiro[3.5]nonan-8-yl)-3-fluorobenzonitrile |

TABLE 1-continued

| No. | Structure | Name |
|---|---|---|
| 203 | 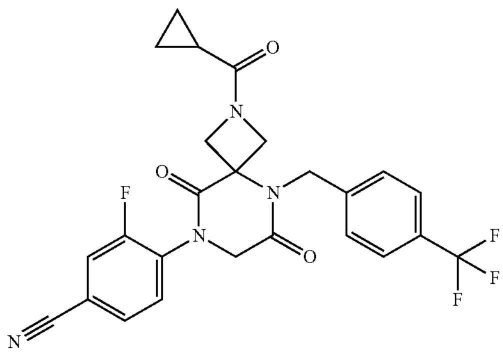 [SMILES: N#Cc1ccc(N2CC(=O)N(Cc3ccc(C(F)(F)F)cc3)C3(CN(C(=O)C4CC4)C3)C2=O)c(F)c1] | 4-(2-(cyclopropanecarbonyl)-6,9-dioxo-5-(4-(trifluoromethyl)benzyl)-2,5,8-triazaspiro[3.5]nonan-8-yl)-3-fluorobenzonitrile |
| 204 | 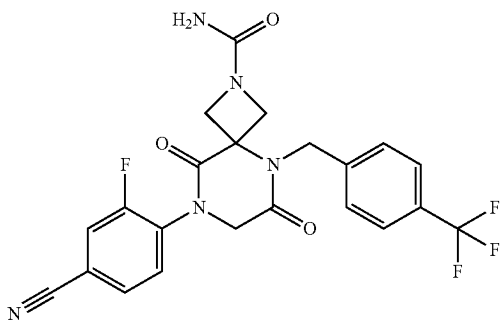 [SMILES: N#Cc1ccc(N2CC(=O)N(Cc3ccc(C(F)(F)F)cc3)C3(CN(C(N)=O)C3)C2=O)c(F)c1] | 8-(4-cyano-2-fluorophenyl)-6,9-dioxo-5-(4-(trifluoromethyl)benzyl)-2,5,8-triazaspiro[3.5]nonane-2-carboxamide |
| 205 | 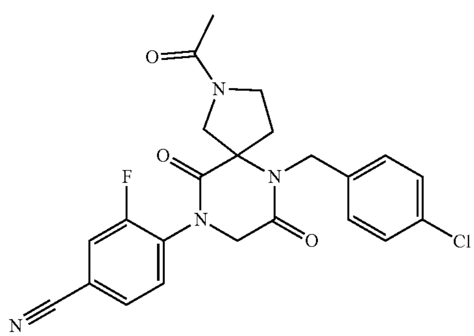 [SMILES: CC(=O)N1CCC2(C1)C(=O)N(c1ccc(C#N)cc1F)CC(=O)N2Cc1ccc(Cl)cc1] | 4-(2-acetyl-6-(4-chlorobenzyl)-7,10-dioxo-2,6,9-triazaspiro[4.5]decan-9-yl)-3-fluorobenzonitrile |
| 206 | 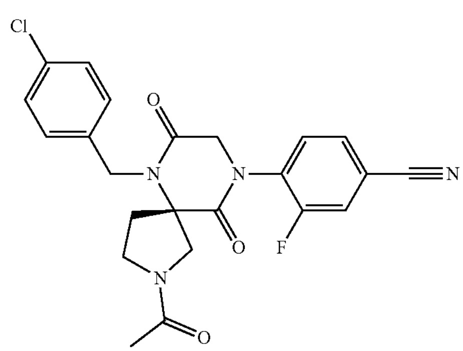 [SMILES: CC(=O)N1CC[C@]2(C1)C(=O)N(c1ccc(C#N)cc1F)CC(=O)N2Cc1ccc(Cl)cc1] | (S)-4-(2-acetyl-6-(4-chlorobenzyl)-7,10-dioxo-2,6,9-triazaspiro[4.5]decan-9-yl)-3-fluorobenzonitrile |

TABLE 1-continued

| No. | Structure | Name |
|---|---|---|
| 207 | 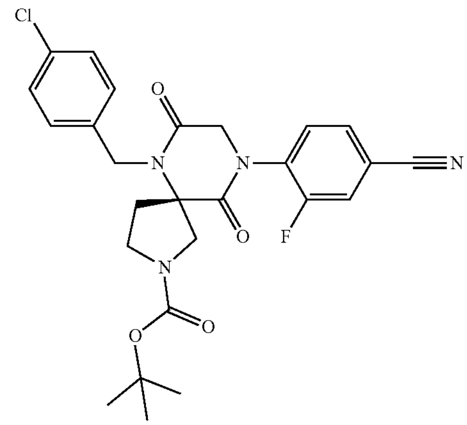 [SMILES: CC(C)(C)OC(=O)N1CC[C@]2(C1)C(=O)N(c1ccc(C#N)cc1F)CC(=O)N2Cc1ccc(Cl)cc1] | tert-butyl (S)-6-(4-chlorobenzyl)-9-(4-cyano-2-fluorophenyl)-7,10-dioxo-2,6,9-triazaspiro[4.5]decane-2-carboxylate |
| 208 | 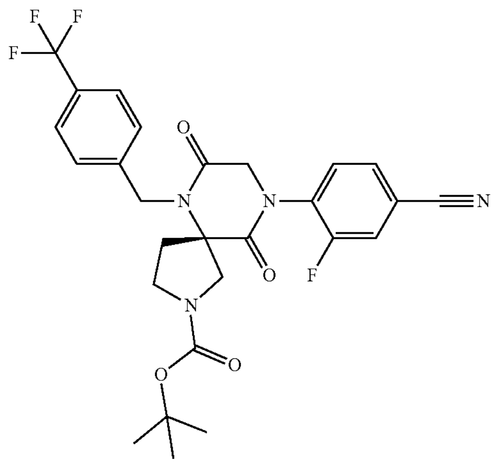 [SMILES: CC(C)(C)OC(=O)N1CC[C@]2(C1)C(=O)N(c1ccc(C#N)cc1F)CC(=O)N2Cc1ccc(C(F)(F)F)cc1] | tert-butyl (S)-9-(4-cyano-2-fluorophenyl)-7,10-dioxo-6-(4-(trifluoromethyl)benzyl)-2,6,9-triazaspiro[4.5]decane-2-carboxylate |
| 209 | 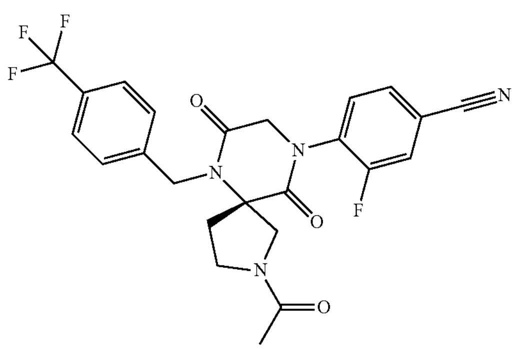 [SMILES: CC(=O)N1CC[C@]2(C1)C(=O)N(c1ccc(C#N)cc1F)CC(=O)N2Cc1ccc(C(F)(F)F)cc1] | (S)-4-(2-acetyl-7,10-dioxo-6-(4-(trifluoromethyl)benzyl)-2,6,9-triazaspiro-[4.5]decan-9-yl)-3-fluorobenzonitrile |
| 210 | 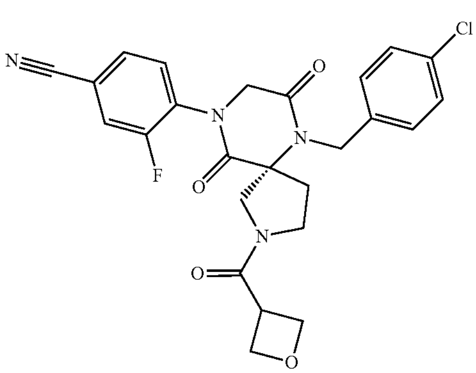 [SMILES: N#Cc1ccc(N2CC(=O)N(Cc3ccc(Cl)cc3)[C@@]3(CCN(C(=O)C4COC4)C3)C2=O)c(F)c1] | (S)-4-(6-(4-chlorobenzyl)-2-(oxetane-3-carbonyl)-7,10-dioxo-2,6,9-triazaspiro[4.5]decan-9-yl)-3-fluorobenzonitrile |

TABLE 1-continued

| No. | Structure | Name |
|---|---|---|
| 211 | 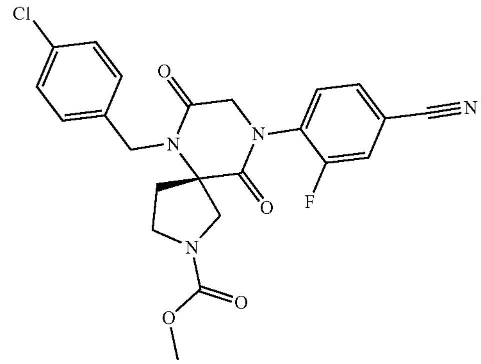 [SMILES: COC(=O)N1CC[C@]2(C1)C(=O)N(c1ccc(C#N)cc1F)CC(=O)N2Cc1ccc(Cl)cc1] | methyl (S)-6-(4-chlorobenzyl)-9-(4-cyano-2-fluorophenyl)-7,10-dioxo-2,6,9-triazaspiro-[4.5]decane-2-carboxylate |
| 212 | 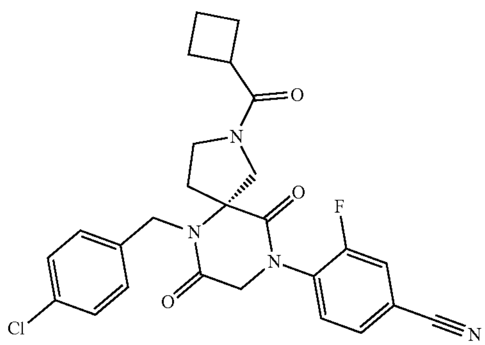 [SMILES: N#Cc1ccc(N2CC(=O)N(Cc3ccc(Cl)cc3)[C@@]3(CCN(C(=O)C4CCC4)C3)C2=O)c(F)c1] | (S)-4-(6-(4-chlorobenzyl)-2-(cyclobutanecarbonyl)-7,10-dioxo-2,6,9-triazaspiro[4.5]decan-9-yl)-3-fluorobenzonitrile |
| 213 | 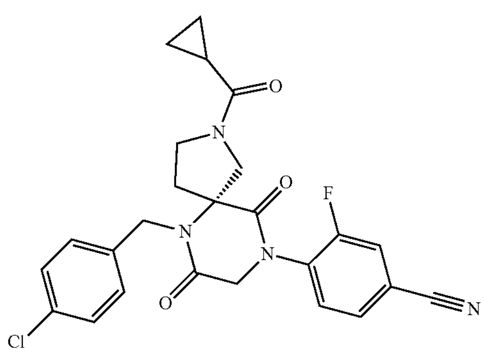 [SMILES: N#Cc1ccc(N2CC(=O)N(Cc3ccc(Cl)cc3)[C@@]3(CCN(C(=O)C4CC4)C3)C2=O)c(F)c1] | (S)-4-(6-(4-chlorobenzyl)-2-(cyclopropanecarbonyl)-7,10-dioxo-2,6,9-triazaspiro[4.5]decan-9-yl)-3-fluorobenzonitrile |
| 214 | 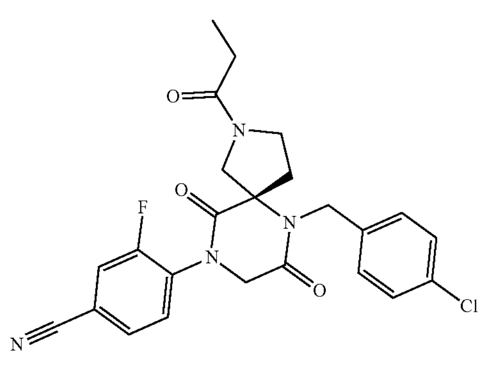 [SMILES: CCC(=O)N1CC[C@]2(C1)C(=O)N(c1ccc(C#N)cc1F)CC(=O)N2Cc1ccc(Cl)cc1] | (S)-4-(6-(4-chlorobenzyl)-7,10-dioxo-2-propionyl-2,6,9-triazaspiro[4.5]decan-9-yl)-3-fluorobenzonitrile |

TABLE 1-continued

| No. | Structure | Name |
|-----|-----------|------|
| 215 | 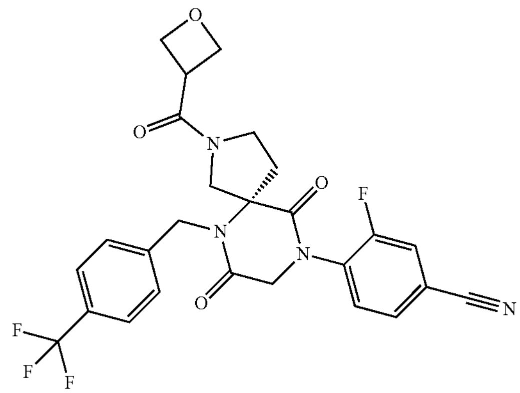 [SMILES: N#Cc1ccc(N2CC(=O)N(Cc3ccc(C(F)(F)F)cc3)[C@]3(CCN(C(=O)C4COC4)C3)C2=O)c(F)c1] | (S)-3-fluoro-4-(2-(oxetane-3-carbonyl)-7,10-dioxo-6-(4-(trifluoromethyl)benzyl)-2,6,9-triazaspiro[4.5]decan-9-yl)benzonitrile |
| 216 | 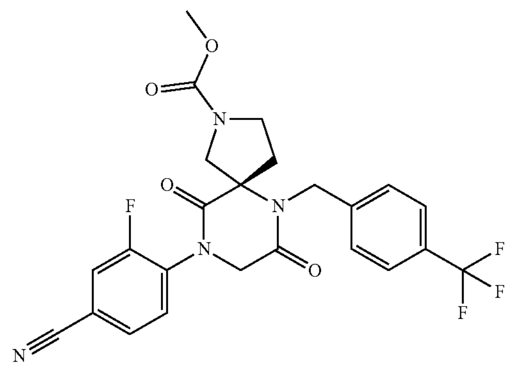 [SMILES: COC(=O)N1CC[C@]2(C1)C(=O)N(c1ccc(C#N)cc1F)CC(=O)N2Cc1ccc(C(F)(F)F)cc1] | methyl (S)-9-(4-cyano-2-fluorophenyl)-7,10-dioxo-6-(4-(trifluoromethyl)benzyl)-2,6,9-triazaspiro[4.5]decane-2-carboxylate |
| 217 | 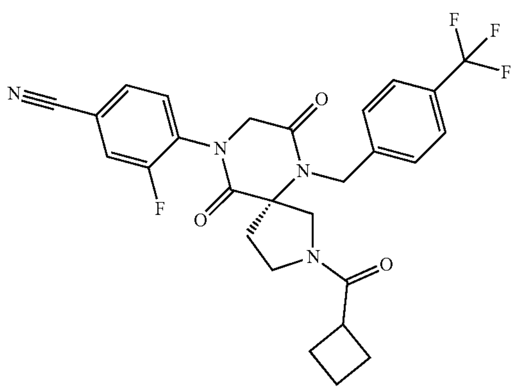 [SMILES: N#Cc1ccc(N2CC(=O)N(Cc3ccc(C(F)(F)F)cc3)[C@]3(CCN(C(=O)C4CCC4)C3)C2=O)c(F)c1] | (S)-4-(2-(cyclobutane-carbonyl)-7,10-dioxo-6-(4-(trifluoromethyl)benzyl)-2,6,9-triazaspiro[4.5]decan-9-yl)-3-fluorobenzonitrile |
| 218 | 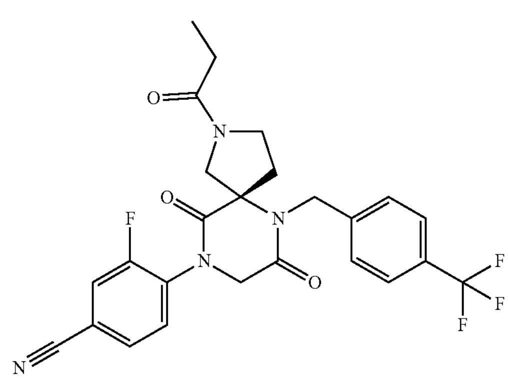 [SMILES: CCC(=O)N1CC[C@]2(C1)C(=O)N(c1ccc(C#N)cc1F)CC(=O)N2Cc1ccc(C(F)(F)F)cc1] | (S)-4-(7,10-dioxo-2-propionyl-6-(4-(trifluoromethyl)benzyl)-2,6,9-triazaspiro[4.5]decan-9-yl)-3-fluorobenzonitrile |

TABLE 1-continued

| No. | Structure | Name |
|---|---|---|
| 219 | 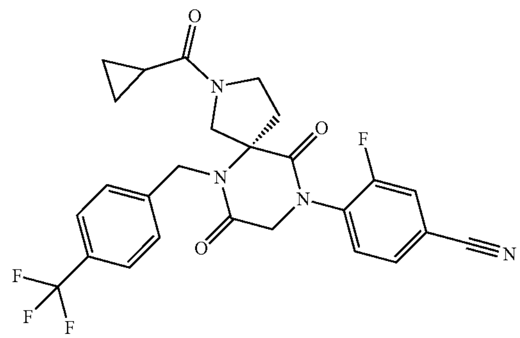 [SMILES: N#Cc1ccc(N2CC(=O)N(Cc3ccc(C(F)(F)F)cc3)[C@]3(CCN(C(=O)C4CC4)C3)C2=O)c(F)c1] | (S)-4-(2-(cyclopropane-carbonyl)-7,10-dioxo-6-(4-(trifluoromethyl)benzyl)-2,6,9-triazaspiro[4.5]decan-9-yl)-3-fluorobenzonitrile |
| 220 | 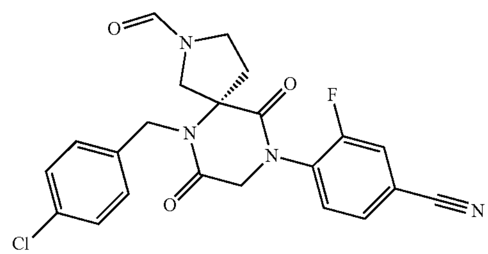 [SMILES: N#Cc1ccc(N2CC(=O)N(Cc3ccc(Cl)cc3)[C@]3(CCN(C=O)C3)C2=O)c(F)c1] | (S)-4-(6-(4-chlorobenzyl)-2-formyl-7,10-dioxo-2,6,9-triazaspiro[4.5]decan-9-yl)-3-fluorobenzonitrile |
| 221 | 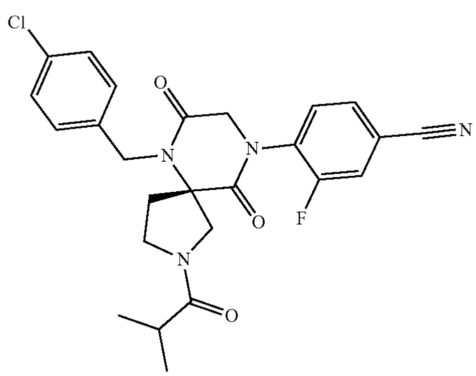 [SMILES: CC(C)C(=O)N1CC[C@]2(C1)C(=O)N(c1ccc(C#N)cc1F)CC(=O)N2Cc1ccc(Cl)cc1] | (S)-4-(6-(4-chlorobenzyl)-2-isobutyryl-7,10-dioxo-2,6,9-triazaspiro[4.5]decan-9-yl)-3-fluorobenzonitrile |
| 222 | 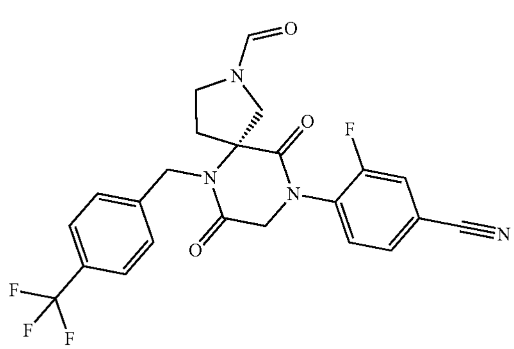 [SMILES: N#Cc1ccc(N2CC(=O)N(Cc3ccc(C(F)(F)F)cc3)[C@@]3(CCN(C=O)C3)C2=O)c(F)c1] | (S)-3-fluoro-4-(2-formyl-7,10-dioxo-6-(4-(trifluoromethyl)benzyl)-2,6,9-triazaspiro[4.5]decan-9-yl)benzonitrile |

TABLE 1-continued

| No. | Structure | Name |
|---|---|---|
| 223 | 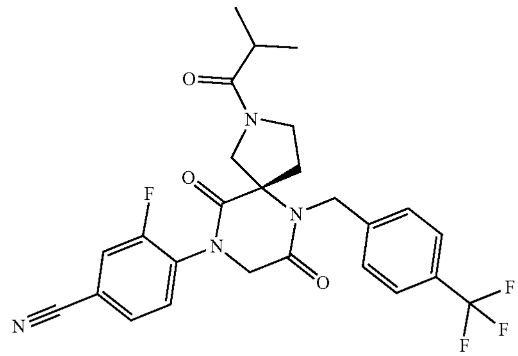 [SMILES: CC(C)C(=O)N1CC[C@]2(C1)C(=O)N(c1ccc(C#N)cc1F)CC(=O)N2Cc1ccc(C(F)(F)F)cc1] | (S)-3-fluoro-4-(2-isobutyryl-7,10-dioxo-6-(4-(trifluoromethyl)benzyl)-2,6,9-triazaspiro[4.5]decan-9-yl)benzonitrile |
| 224 | 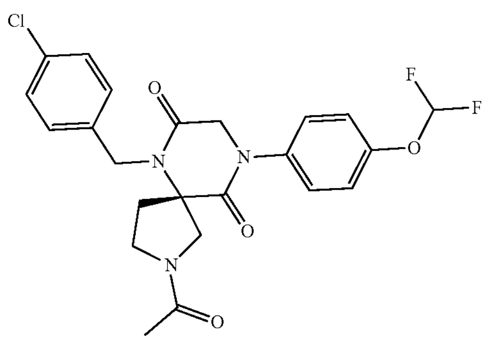 [SMILES: CC(=O)N1CC[C@]2(C1)C(=O)N(c1ccc(OC(F)F)cc1)CC(=O)N2Cc1ccc(Cl)cc1] | (S)-2-acetyl-6-(4-chlorobenzyl)-9-(4-(difluoromethoxy)phenyl)-2,6,9-triazaspiro[4.5]decane-7,10-dione |
| 225 | 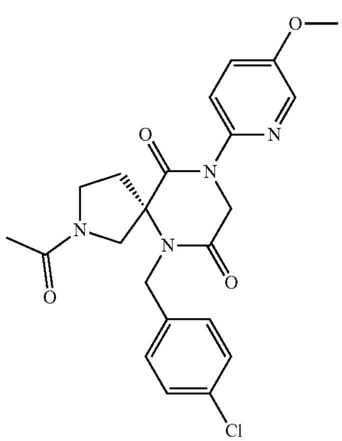 [SMILES: COc1ccc(N2CC(=O)N(Cc3ccc(Cl)cc3)[C@]3(CCN(C(C)=O)C3)C2=O)nc1] | (S)-2-acetyl-6-(4-chlorobenzyl)-9-(5-methoxypyridin-2-yl)-2,6,9-triazaspiro[4.5]decane-7,10-dione |
| 226 | 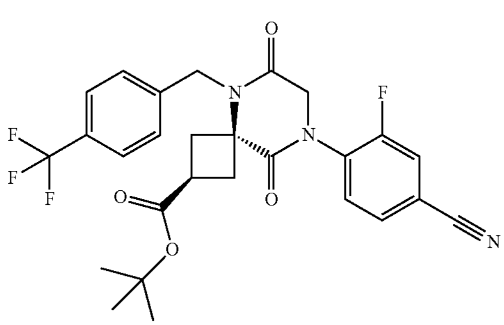 [SMILES: CC(C)(C)OC(=O)[C@H]1C[C@@]2(C1)C(=O)N(c1ccc(C#N)cc1F)CC(=O)N2Cc1ccc(C(F)(F)F)cc1] | tert-butyl (2s,4s)-8-(4-cyano-2-fluorophenyl)-6,9-dioxo-5-(4-(trifluoromethyl)benzyl)-5,8-diazaspiro[3.5]nonane-2-carboxylate |

TABLE 1-continued

| No. | Structure | Name |
|---|---|---|
| 227 | 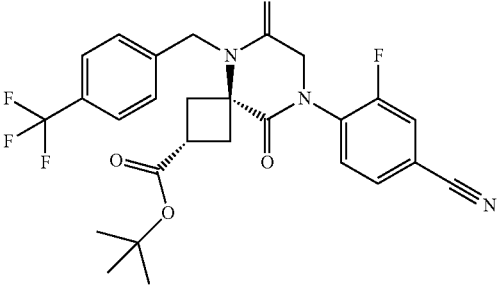 | tert-butyl (2r,4r)-8-(4-cyano-2-fluorophenyl)-6,9-dioxo-5-(4-(trifluoromethyl)benzyl)-5,8-diazaspiro[3.5]nonane-2-carboxylate |
| 228 | 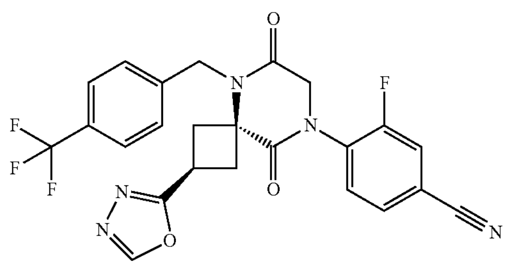 [SMILES: N#Cc1ccc(N2CC(=O)N(Cc3ccc(C(F)(F)F)cc3)[C@]3(C[C@@H](c4nnco4)C3)C2=O)c(F)c1] | 4-((2s,4s)-2-(1,3,4-oxadiazol-2-yl)-6,9-dioxo-5-(4-(trifluoromethyl)benzyl)-5,8-diazaspiro[3.5]nonan-8-yl)-3-fluorobenzonitrile |
| 229 | 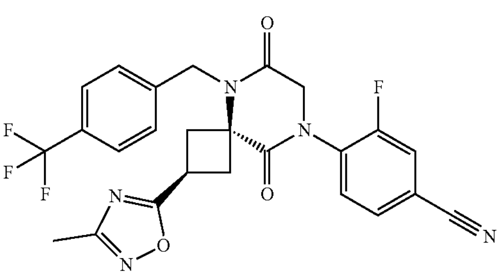 [SMILES: Cc1noc([C@H]2C[C@@]3(C2)C(=O)N(c2ccc(C#N)cc2F)CC(=O)N3Cc2ccc(C(F)(F)F)cc2)n1] | 3-fluoro-4-((2s,4s)-2-(3-methyl-1,2,4-oxadiazol-5-yl)-6,9-dioxo-5-(4-(trifluoromethyl)benzyl)-5,8-diazaspiro[3.5]nonan-8-yl)benzonitrile |
| 230 | 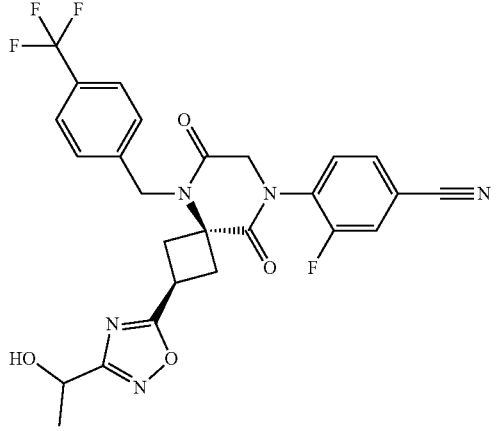 [SMILES: CC(O)c1noc([C@H]2C[C@@]3(C2)C(=O)N(c2ccc(C#N)cc2F)CC(=O)N3Cc2ccc(C(F)(F)F)cc2)n1] | 3-fluoro-4-((2s,4s)-2-(3-(1-hydroxyethyl)-1,2,4-oxadiazol-5-yl)-6,9-dioxo-5-(4-(trifluoromethyl)benzyl)-5,8-diazaspiro[3.5]nonan-8-yl)benzonitrile |

TABLE 1-continued

| No. | Structure | Name |
|---|---|---|
| 231 | 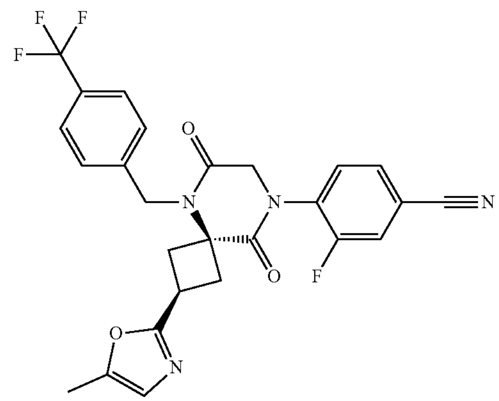 [SMILES: Cc1cnc([C@H]2C[C@@]3(C2)C(=O)N(c2ccc(C#N)cc2F)CC(=O)N3Cc2ccc(C(F)(F)F)cc2)o1] | 3-fluoro-4-((2s,4s)-2-(5-methyloxazol-2-yl)-6,9-dioxo-5-(4-trifluoromethyl)-benzyl)-5,8-diazaspiro-[3.5]nonan-8-yl]benzonitrile |
| 232 | 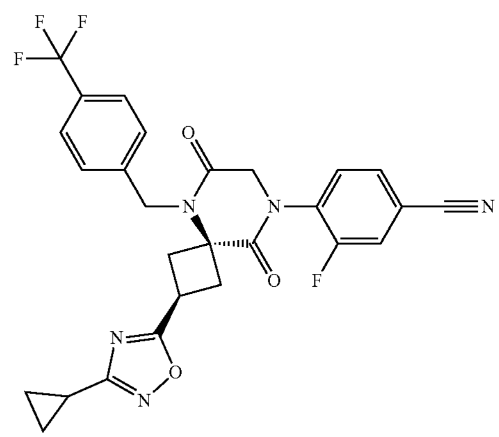 [SMILES: N#Cc1ccc(N2CC(=O)N(Cc3ccc(C(F)(F)F)cc3)[C@]3(C[C@@H](c4nc(C5CC5)no4)C3)C2=O)c(F)c1] | 4-((2s,4s)-2-(3-cyclopropyl-1,2,4-oxadiazol-5-yl)-6,9-dioxo-5-(4-(trifluoromethyl)benzyl)-5,8-diazaspiro[3.5]nonan-8-yl)-3-fluorobenzonitrile |
| 233 | 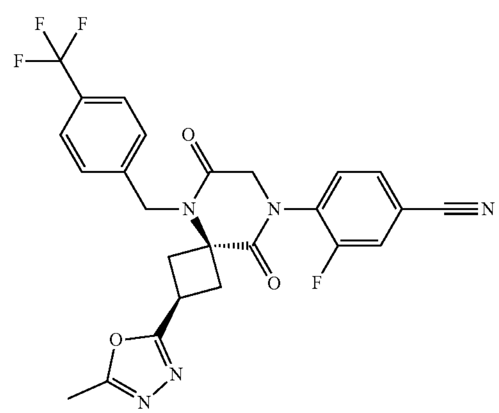 [SMILES: Cc1nnc([C@H]2C[C@@]3(C2)C(=O)N(c2ccc(C#N)cc2F)CC(=O)N3Cc2ccc(C(F)(F)F)cc2)o1] | 3-fluoro-4-((2s,4s)-2-(5-methyl-1,3,4-oxadiazol-2-yl)-6,9-dioxo-5-(4-(trifluoromethyl)benzyl)-5,8-diazaspiro[3.5]nonan-8-yl)benzonitrile |
| 234 | 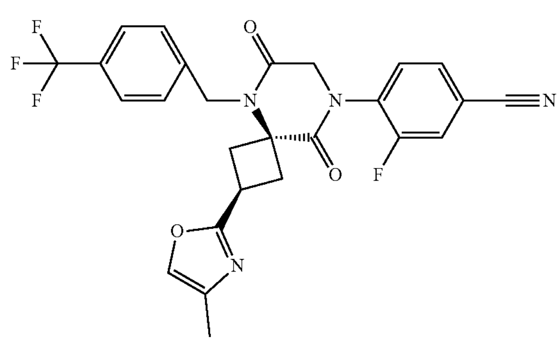 [SMILES: Cc1coc([C@H]2C[C@@]3(C2)C(=O)N(c2ccc(C#N)cc2F)CC(=O)N3Cc2ccc(C(F)(F)F)cc2)n1] | 3-fluoro-4-((2s,4s)-2-(4-methyloxazol-2-yl)-6,9-dioxo-5-(4-(trifluoromethyl)benzyl)-5,8-diazaspiro[3.5]nonan-8-yl)benzonitrile |

TABLE 1-continued

| No. | Structure | Name |
|---|---|---|
| 235 | 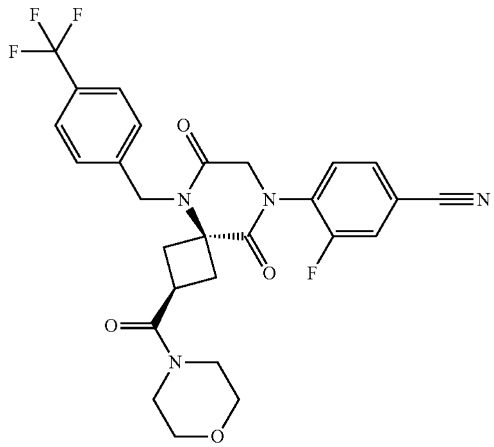 [SMILES: N#Cc1ccc(N2CC(=O)N(Cc3ccc(C(F)(F)F)cc3)[C@]3(C[C@@H](C(=O)N4CCOCC4)C3)C2=O)c(F)c1] | 3-fluoro-4-((2s,4s)-2-(morpholine-4-carbonyl)-6,9-dioxo-5-(4-(trifluoromethyl)benzyl)-5,8-diazaspiro[3.5]nonan-8-yl)benzonitrile |
| 236 | 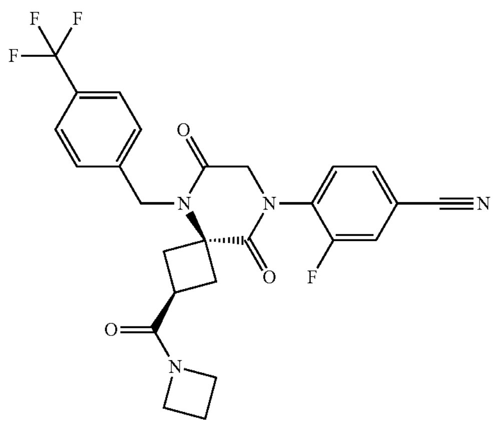 [SMILES: N#Cc1ccc(N2CC(=O)N(Cc3ccc(C(F)(F)F)cc3)[C@]3(C[C@@H](C(=O)N4CCC4)C3)C2=O)c(F)c1] | 4-((2s,4s)-2-(azetidine-1-carbonyl)-6,9-dioxo-5-(4-(trifluoromethyl)benzyl)-5,8-diazaspiro[3.5]nonan-8-yl)-3-fluorobenzonitrile |
| 237 | 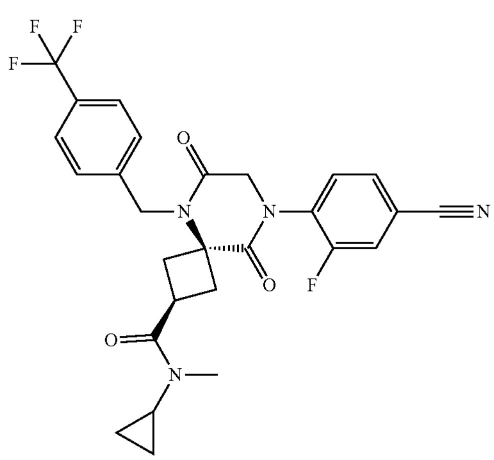 [SMILES: CN(C(=O)[C@H]1C[C@@]2(C1)C(=O)N(c1ccc(C#N)cc1F)CC(=O)N2Cc1ccc(C(F)(F)F)cc1)C1CC1] | (2s,4s)-8-(4-cyano-2-fluorophenyl)-N-cyclopropyl-N-methyl-6,9-dioxo-5-(4-(trifluoromethyl)benzyl)-5,8-diazaspiro[3.5]nonane-2-carboxamide |

TABLE 1-continued

| No. | Name |
|---|---|
| 238 | 3-fluoro-4-((2s,4s)-2-(4-hydroxypiperidine-1-carbonyl)-6,9-dioxo-5-(4-(trifluoromethyl)benzyl)-5,8-diazaspiro[3.5]nonan-8-yl)benzonitrile |
| 239 | 4-((2s,4s)-2-(5-(difluoromethyl)-1,3,4-oxadiazol-2-yl)-6,9-dioxo-5-(4-(trifluoromethyl)-benzyl)-5,8-diazaspiro-[3.5]nonan-8-yl)-3-fluorobenzonitrile |
| 240 | 4-((2s,4s)-2-(5-(difluoromethyl)-1,3,4-oxadiazol-2-yl)-6,9-dioxo-5-(4-(trifluoromethyl)-benzyl)-5,8-diazaspiro-[3.5]nonan-8-yl)-3-fluorobenzonitrile |

TABLE 1-continued
| No. | Structure | Name |
|---|---|---|
| 241 | 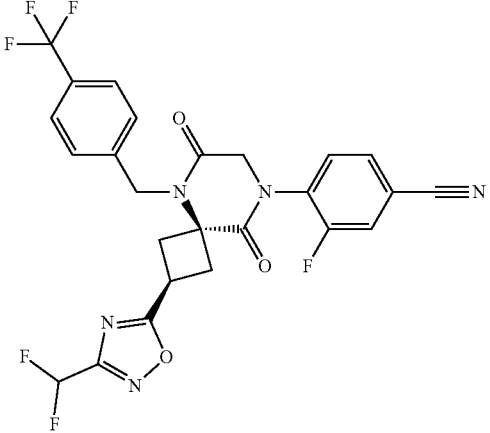 [SMILES: N#Cc1ccc(N2CC(=O)N(Cc3ccc(C(F)(F)F)cc3)[C@]3(C[C@@H](c4nc(C(F)F)no4)C3)C2=O)c(F)c1] | 4-((2s,4s)-2-(3-(difluoromethyl)-1,2,4-oxadiazol-5-yl)-6,9-dioxo-5-(4-(trifluoromethyl)-benzyl)-5,8-diazaspiro-[3.5]nonan-8-yl)-3-fluorobenzonitrile |
| 242 | 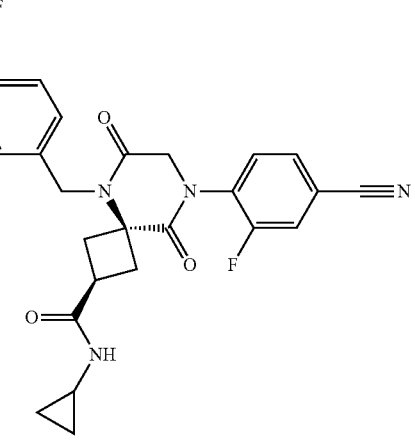 | (2s,4s)-8-(4-cyano-2-fluorophenyl)-N-cydopropyl-6,9-dioxo-5-(4-(trifluoromethyl)benzyl)-5,8-diazaspiro[3.5]nonane-2-carboxamide |
| 243 | 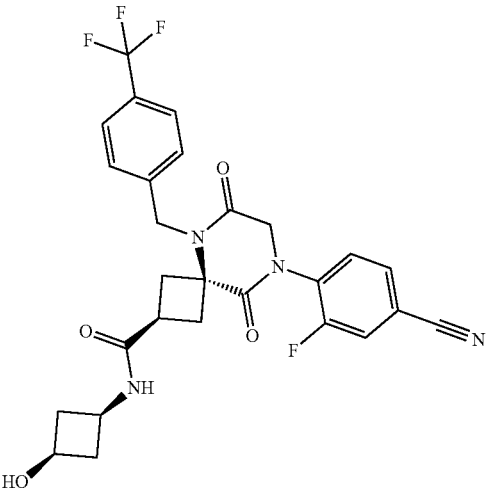 [SMILES: N#Cc1ccc(N2CC(=O)N(Cc3ccc(C(F)(F)F)cc3)[C@]3(C[C@@H](C(=O)N[C@H]4C[C@@H](O)C4)C3)C2=O)c(F)c1] | (2s,4S)-8-(4-cyano-2-fluorophenyl)-N-((1s,3S)-3-hydroxycyclobutyl)-6,9-dioxo-5-(4-(trifluoromethyl)benzyl)-5,8-diazaspiro[3.5]nonane-2-carboxamide |

TABLE 1-continued
| No. | Structure | Name |
|---|---|---|
| 244 | 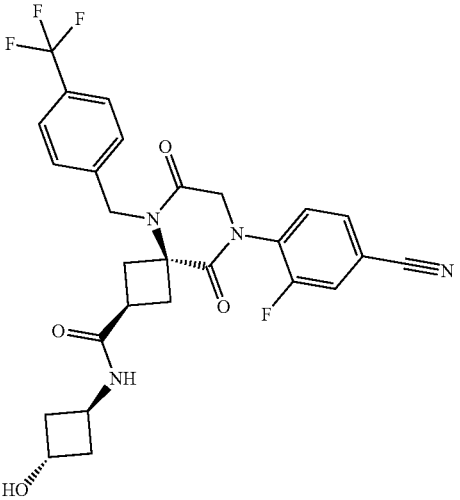 [SMILES: N#Cc1ccc(N2CC(=O)N(Cc3ccc(C(F)(F)F)cc3)[C@]3(C[C@@H](C(=O)N[C@H]4C[C@H](O)C4)C3)C2=O)c(F)c1] | (2s,4S)-8-(4-cyano-2-fluorophenyl)-N-((1r,3R)-3-hydroxycyclobutyl)-6,9-dioxo-5-(4-(trifluoromethyl)benzyl)-5,8-diazaspiro[3.5]nonane-2-carboxamide |
| 245 | 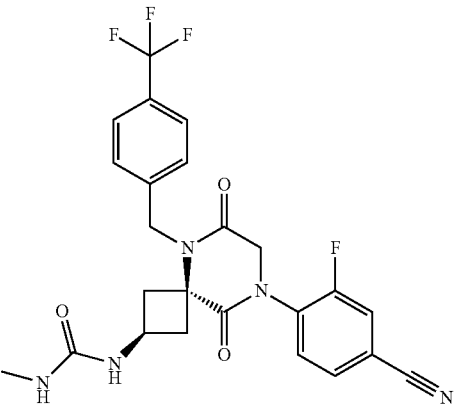 [SMILES: CNC(=O)N[C@H]1C[C@@]2(C1)C(=O)N(c1ccc(C#N)cc1F)CC(=O)N2Cc1ccc(C(F)(F)F)cc1] | 1-((2s,4s)-8-(4-cyano-2-fluorophenyl)-6,9-dioxo-5-(4-(trifluoromethyl)benzyl)-5,8-diazaspiro[3.5]nonan-2-yl)-3-methylurea |
| 246 | 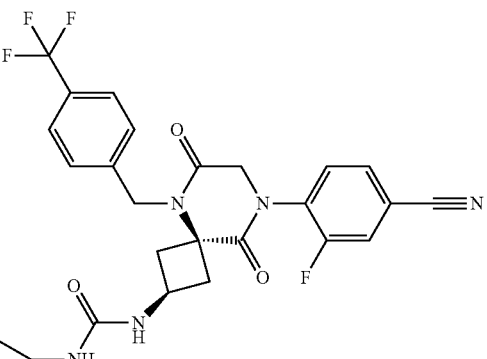 | 1-((2s,4s)-8-(4-cyano-2-fluorophenyl)-6,9-dioxo-5-(4-(trifluoromethyl)benzyl)-5,8-diazaspiro[3.5]nonan-2-yl)-3-cyclopropylurea |

TABLE 1-continued
| No. | Structure | Name |
|---|---|---|
| 247 | 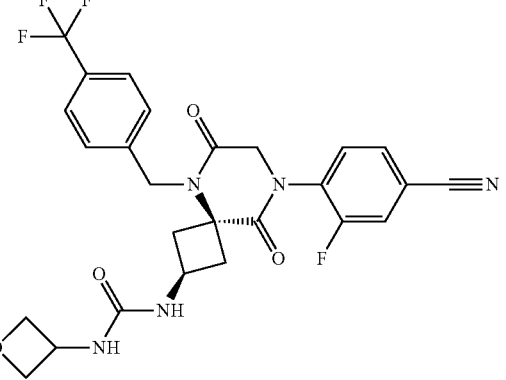 | 1-((2s,4s)-8-(4-cyano-2-fluorophenyl)-6,9-dioxo-5-(4-(trifluoromethyl)benzyl)-5,8-diazaspiro[3.5]nonan-2-yl)-3-(oxetan-3-yl)urea |
| 248 | 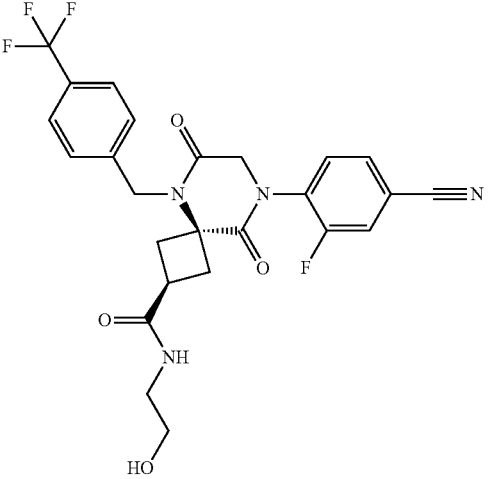 [SMILES: N#Cc1ccc(N2CC(=O)N(Cc3ccc(C(F)(F)F)cc3)[C@]3(C[C@@H](C(=O)NCCO)C3)C2=O)c(F)c1] | (2s,4s)-8-(4-cyano-2-fluorophenyl)-N-(2-hydroxyethyl)-6,9-dioxo-5-(4-(trifluoromethyl)benzyl)-5,8-diazaspiro[3.5]nonane-2-carboxamide |
| 249 | 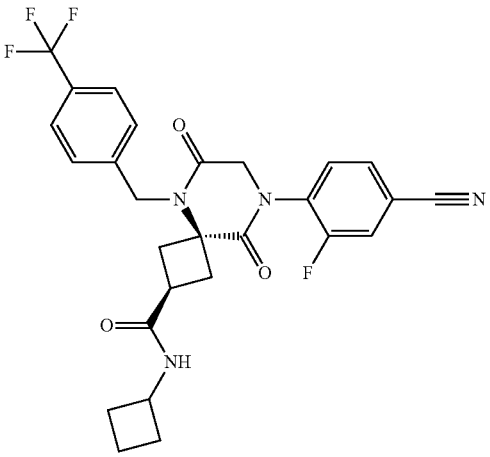 [SMILES: N#Cc1ccc(N2CC(=O)N(Cc3ccc(C(F)(F)F)cc3)[C@]3(C[C@@H](C(=O)NC4CCC4)C3)C2=O)c(F)c1] | (2s,4s)-8-(4-cyano-2-fluorophenyl)-N-cyclobutyl-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 250 | 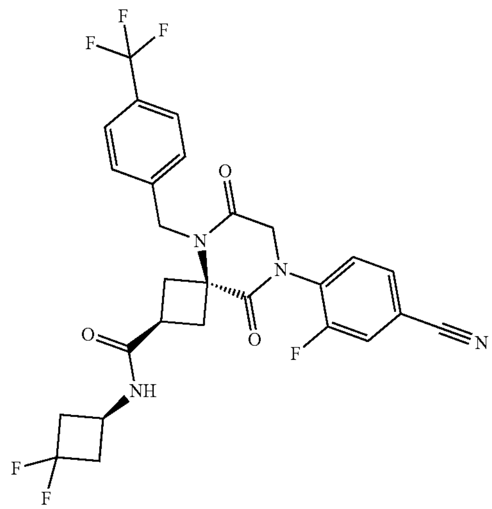 | (2s,4s)-8-(4-cyano-2-fluorophenyl)-N-(3,3-difluorocyclobutyl)-6,9-dioxo-5-(4-(trifluoromethyl)benzyl)-5,8-diazaspiro[3.5]nonane-2-carboxamide |
| 251 | 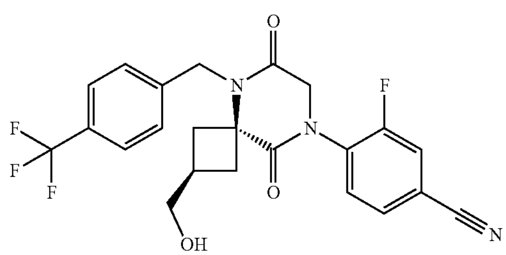 [SMILES: N#Cc1ccc(N2CC(=O)N(Cc3ccc(C(F)(F)F)cc3)[C@]3(C[C@@H](CO)C3)C2=O)c(F)c1] | 3-fluoro-4-((2s,4s)-2-(hydroxymethyl)-6,9-dioxo-5-(4-(trifluoromethyl)benzyl)-5,8-diazaspiro[3.5]nonan-8-yl)benzonitrile |
| 252 | 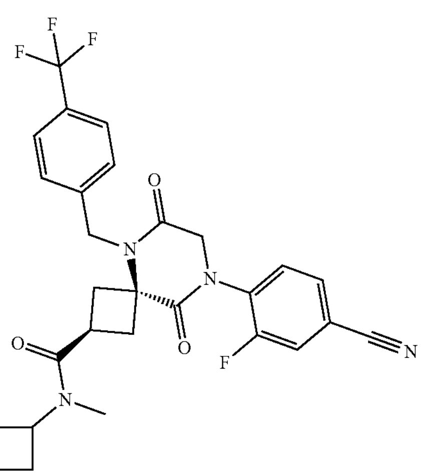 | (2s,4s)-8-(4-cyano-2-fluorophenyl)-N-methyl-N-(oxetan-3-yl)-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 253 | 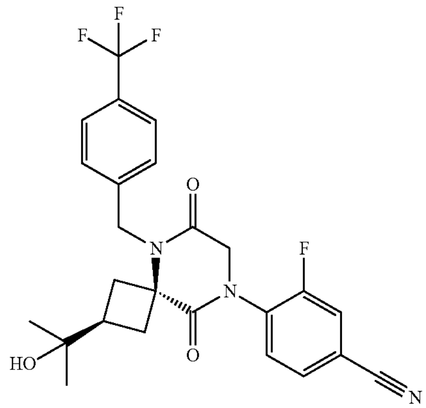 [SMILES: CC(C)(O)[C@H]1C[C@@]2(C1)C(=O)N(c1ccc(C#N)cc1F)CC(=O)N2Cc1ccc(C(F)(F)F)cc1] | 3-fluoro-4-((2s,4s)-2-(2-hydroxypropan-2-yl)-6,9-dioxo-5-(4-(trifluoromethyl)benzyl)-5,8-diazaspiro[3.5]nonan-8-yl)benzonitrile |
| 254 | 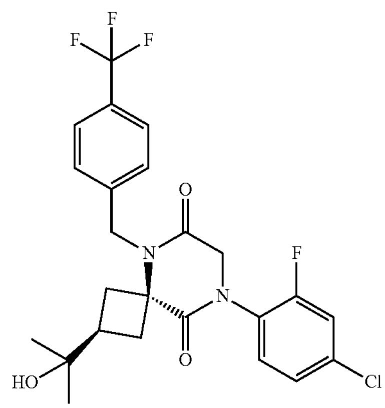 [SMILES: CC(C)(O)[C@H]1C[C@@]2(C1)C(=O)N(c1ccc(Cl)cc1F)CC(=O)N2Cc1ccc(C(F)(F)F)cc1] | (2s,4s)-8-(4-chloro-2-fluorophenyl)-2-(2-hydroxypropan-2-yl)-5-(4-(trifluoromethyl)benzyl)-5,8-diazaspiro[3.5]nonane-6,9-dione |
| 255 | 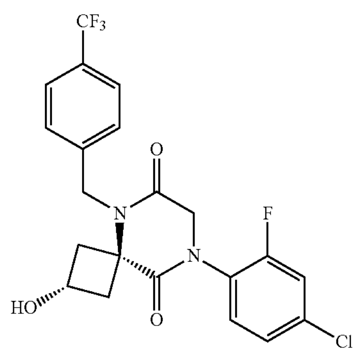 [SMILES: O=C1CN(c2ccc(Cl)cc2F)C(=O)[C@]2(C[C@@H](O)C2)N1Cc1ccc(C(F)(F)F)cc1] | (2s,4s)-8-(4-chloro-2-fluorophenyl)-2-hydroxy-5-(4-(trifluoromethyl)benzyl)-5,8-diazaspiro[3.5]nonane-6,9-dione |
| 256 | 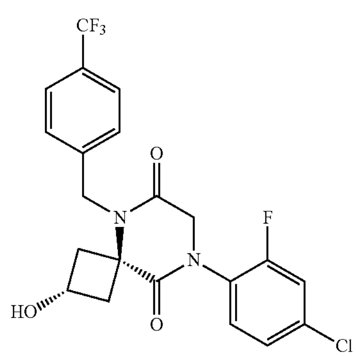 [SMILES: O=C1CN(c2ccc(Cl)cc2F)C(=O)[C@]2(C[C@@H](O)C2)N1Cc1ccc(C(F)(F)F)cc1] | 3-fluoro-4-((2s,4s)-2-hydroxy-6,9-dioxo-5-(4-(trifluoromethyl)benzyl)-5,8-diazaspiro[3.5]nonan-8-yl)benzonitrile |

TABLE 1-continued

| No. | Structure | Name |
|---|---|---|
| 257 | 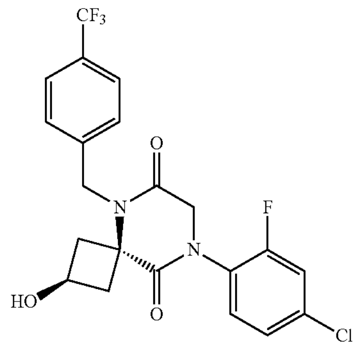 [SMILES: O=C1CN(c2ccc(Cl)cc2F)C(=O)[C@]2(C[C@H](O)C2)N1Cc1ccc(C(F)(F)F)cc1] | (2r,4r)-8-(4-chloro-2-fluorophenyl)-2-hydroxy-5-(4-(trifluoromethyl)benzyl)-5,8-diazaspiro[3.5]nonane-6,9-dione |
| 258 | 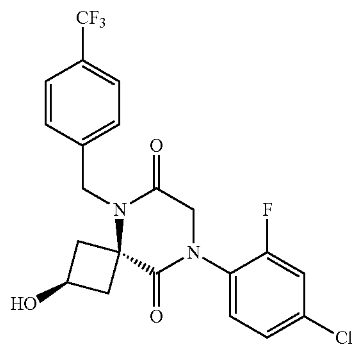 [SMILES: O=C1CN(c2ccc(Cl)cc2F)C(=O)[C@]2(C[C@H](O)C2)N1Cc1ccc(C(F)(F)F)cc1] | 3-fluoro-4-((2r,4r)-2-hydroxy-6,9-dioxo-5-(4-(trifluoromethyl)benzyl)-5,8-diazaspiro[3.5]nonan-8-yl)benzonitrile |
| 259 | 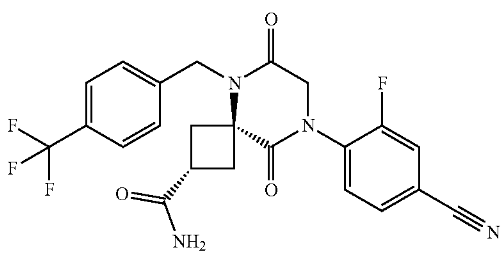 [SMILES: N#Cc1ccc(N2CC(=O)N(Cc3ccc(C(F)(F)F)cc3)[C@]3(C[C@H](C(N)=O)C3)C2=O)c(F)c1] | (2r,4r)-8-(4-cyano-2-fluorophenyl)-6,9-dioxo-5-(4-(trifluoromethyl)benzyl)-5,8-diazaspiro[3.5]nonane-2-carboxamide |
| 260 | 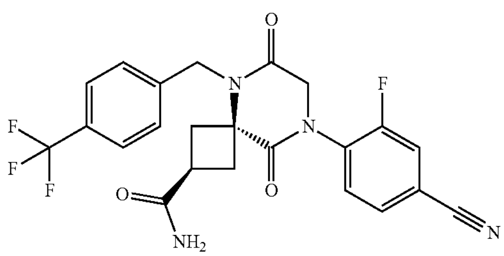 [SMILES: N#Cc1ccc(N2CC(=O)N(Cc3ccc(C(F)(F)F)cc3)[C@]3(C[C@@H](C(N)=O)C3)C2=O)c(F)c1] | (2s,4s)-8-(4-cyano-2-fluorophenyl)-6,9-dioxo-5-(4-(trifluoromethyl)benzyl)-5,8-diazaspiro[3.5]nonane-2-carboxamide |
| 261 | 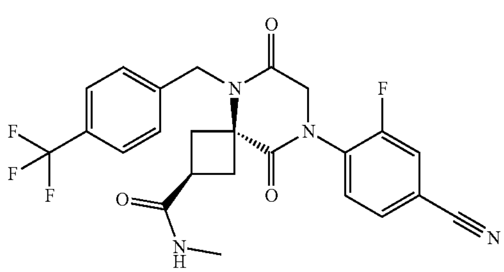 [SMILES: CNC(=O)[C@H]1C[C@@]2(C1)C(=O)N(c1ccc(C#N)cc1F)CC(=O)N2Cc1ccc(C(F)(F)F)cc1] | (2s,4s)-8-(4-cyano-2-fluorophenyl)-N-methyl-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 262 | 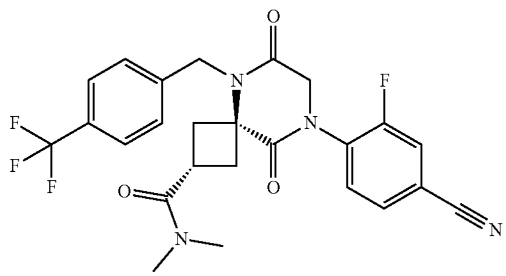 [SMILES: CN(C)C(=O)[C@H]1C[C@]2(C1)C(=O)N(c1ccc(C#N)cc1F)CC(=O)N2Cc1ccc(C(F)(F)F)cc1] | (2r,4r)-8-(4-cyano-2-fluorophenyl)-N,N-dimethyl-6,9-dioxo-5-(4-(trifluoromethyl)benzyl)-5,8-diazaspiro[3.5]nonane-2-carboxamide |
| 263 | 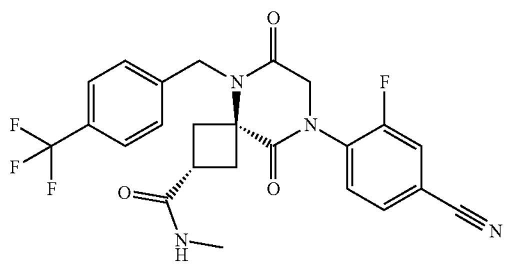 [SMILES: CNC(=O)[C@H]1C[C@]2(C1)C(=O)N(c1ccc(C#N)cc1F)CC(=O)N2Cc1ccc(C(F)(F)F)cc1] | (2r,4r)-8-(4-cyano-2-fluorophenyl)-N-methyl-6,9-dioxo-5-(4-(trifluoromethyl)benzyl)-5,8-diazaspiro[3.5]nonane-2-carboxamide |
| 264 | 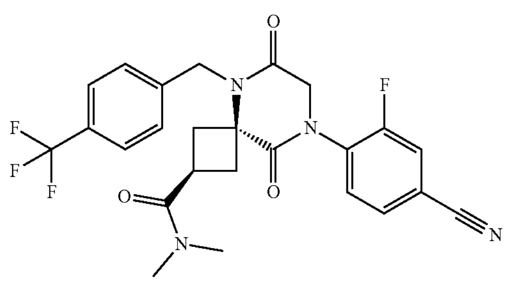 [SMILES: CN(C)C(=O)[C@H]1C[C@@]2(C1)C(=O)N(c1ccc(C#N)cc1F)CC(=O)N2Cc1ccc(C(F)(F)F)cc1] | (2s,4s)-8-(4-cyano-2-fluorophenyl)-N,N-dimethyl-6,9-dioxo-5-(4-(trifluoromethyl)benzyl)-5,8-diazaspiro[3.5]nonane-2-carboxamide |
| 265 | 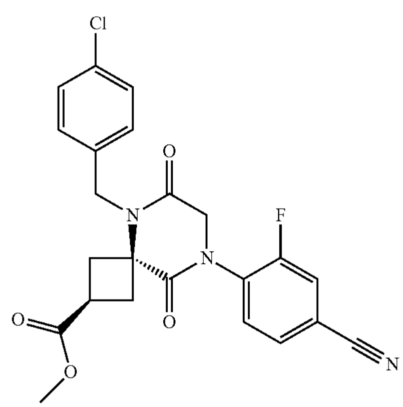 [SMILES: COC(=O)[C@H]1C[C@@]2(C1)C(=O)N(c1ccc(C#N)cc1F)CC(=O)N2Cc1ccc(Cl)cc1] | methyl (2s,4s)-5-(4-chlorobenzyl)-8-(4-cyano-2-fluorophenyl)-6,9-dioxo-5,8-diazaspiro[3.5]nonane-2-carboxylate |
| 266 | 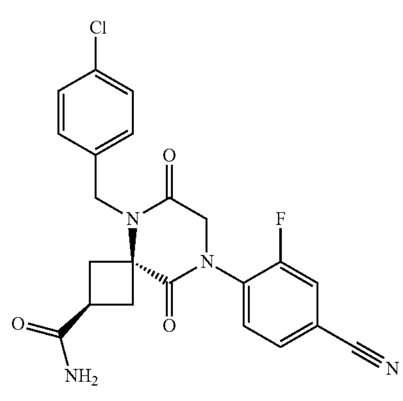 [SMILES: N#Cc1ccc(N2CC(=O)N(Cc3ccc(Cl)cc3)[C@]3(C[C@@H](C(N)=O)C3)C2=O)c(F)c1] | (2s,4s)-5-(4-chlorobenzyl)-8-(4-cyano-2-fluorophenyl)-6,9-dioxo-5,8-diazaspiro-[3.5]nonane-2-carboxamide |

TABLE 1-continued

| No. | Structure | Name |
|---|---|---|
| 267 | 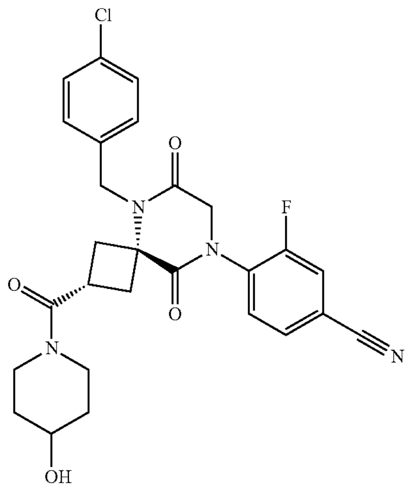 [SMILES: N#Cc1ccc(N2CC(=O)N(Cc3ccc(Cl)cc3)[C@]3(C[C@@H](C(=O)N4CCC(O)CC4)C3)C2=O)c(F)c1] | 4-((2s,4s)-5-(4-chloro-benzyl)-2-(4-hydroxy-piperidine-1-carbonyl)-6,9-dioxo-5,8-diazaspiro-[3.5]nonan-8-yl)-3 fluorobenzonitrile |
| 268 | 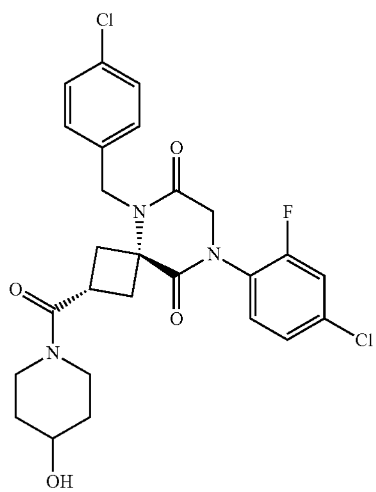 [SMILES: O=C1CN(c2ccc(Cl)cc2F)C(=O)[C@]2(C[C@H](C(=O)N3CCC(O)CC3)C2)N1Cc1ccc(Cl)cc1] | (2s,4s)-8-(4-chloro-2-fluorophenyl)-5-(4-chlorobenzyl)-2-(4-hydroxypiperidine-1-carbonyl)-5,8-diazaspiro-[3.5]nonane-6,9-dione |
| 269 | 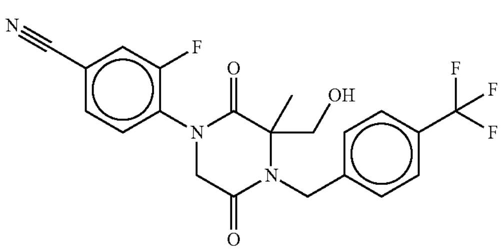 | 3-fluoro-4-(3-(hydroxy-methyl)-3-methyl-2,5-dioxo-4-(4-(trifluoro-methyl)benzyl)piperazin-1-yl)benzonitrile |
| 270 | 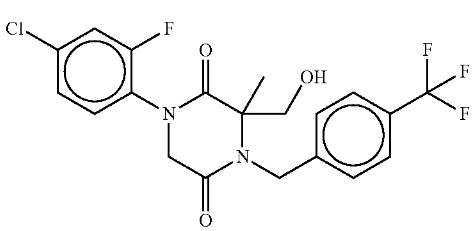 | 1-(4-chloro-2-fluorophenyl)-3-(hydroxymethyl)-3-methyl-4-(4-(trifluoro-methyl)benzyl)piperazine-2,5-dione |

TABLE 1-continued

| No. | Structure | Name |
|---|---|---|
| 271 | 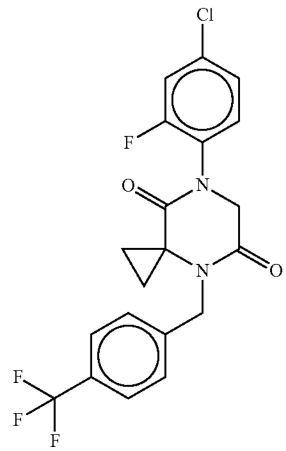 | 7-(4-chloro-2-fluorophenyl)-4-(4-(trifluoromethyl)-benzyl)-4,7-diazaspiro-[2.5]octane-5,8-dione |
| 272 | 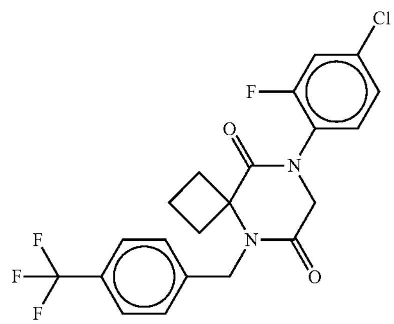 | 8-(4-chloro-2-fluorophenyl)-5-(4-(trifluoromethyl)-benzyl)-5,8-diazaspiro-[3.5]nonane-6,9-dione |
| 273 | 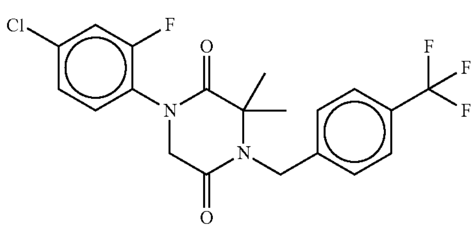 | 1-(4-chloro-2-fluorophenyl)-3,3-dimethyl-4-(4-(trifluoromethyl)benzyl)-piperazine-2,5-dione |
| 274 | 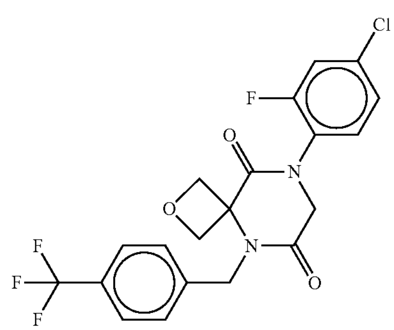 | 8-(4-chloro-2-fluorophenyl)-5-(4-(trifluoromethyl)-benzyl)-2-oxa-5,8-diazaspiro[3.5]nonane-6,9-dione |
| 275 | 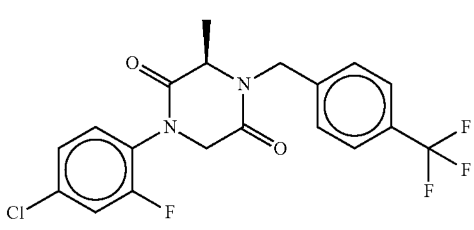 | (R)-1-(4-chloro-2-fluoro-phenyl)-3-methyl-4-(4-(trifluoromethyl)benzyl)-piperazine-2,5-dione |

TABLE 1-continued

| No. | Structure | Name |
|---|---|---|
| 276 | 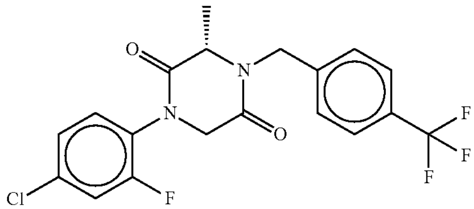 | (S)-1-(4-chloro-2-fluoro-phenyl)-3-methyl-4-(4-(trifluoromethyl)benzyl)-piperazine-2,5-dione |
| 277 | 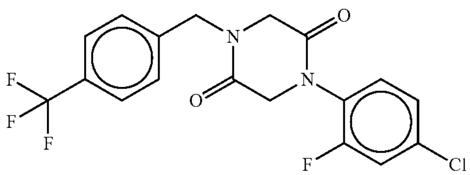 | 1-(4-chloro-2-fluorophenyl)-4-(4-(trifluoromethyl)-benzyl)piperazine-2,5-dione |
| 278 | 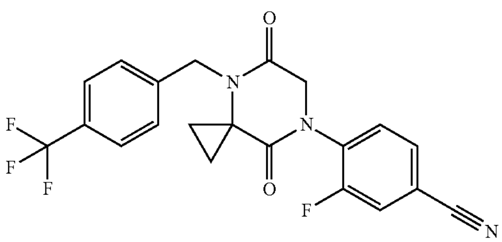 [SMILES: N#Cc1ccc(N2CC(=O)N(Cc3ccc(C(F)(F)F)cc3)C3(CC3)C2=O)c(F)c1] | 4-(5,8-dioxo-4-(4-(trifluoromethyl)benzyl)-4,7-diazaspiro[2.5]octan-7-yl)-3-fluorobenzonitrile |
| 279 | 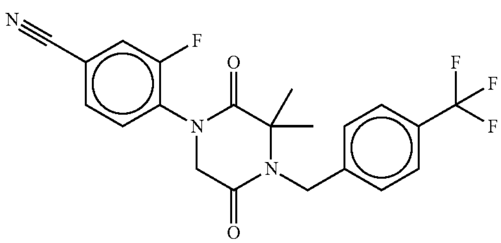 | 4-(3,3-dimethyl-2,5-dioxo-4-(4-(trifluoromethyl)-benzyl)piperazin-1-yl)-3-fluorobenzonitrile |
| 280 | 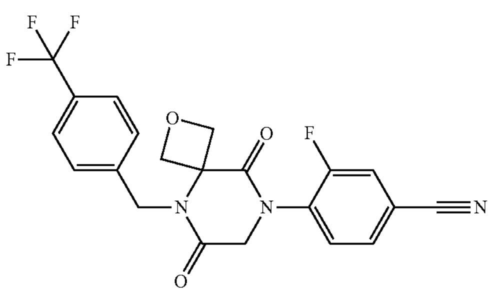 [SMILES: N#Cc1ccc(N2CC(=O)N(Cc3ccc(C(F)(F)F)cc3)C3(COC3)C2=O)c(F)c1] | 4-(6,9-dioxo-5-(4-(trifluoromethyl)benzyl)-2-oxa-5,8-diazaspiro[3.5]-nonan-8-yl)-3-fluorobenzonitrile |
| 281 | 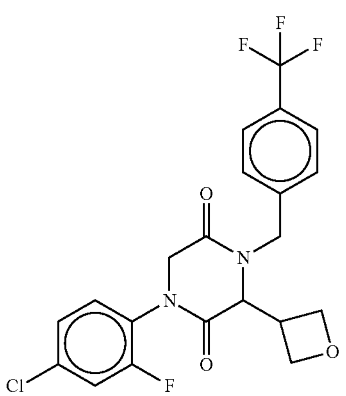 | 1-(4-chloro-2-fluorophenyl)-3-(oxetan-3-yl)-4-(4-(trifluoromethyl)benzyl)-piperazine-2,5-dione |

TABLE 1-continued

| No. | Structure | Name |
|---|---|---|
| 282 | 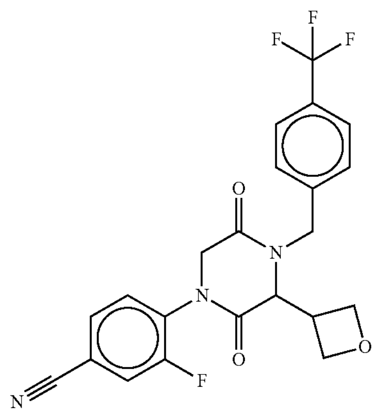 | 3-fluoro-4-(3-(oxetan-3-yl)-2,5-dioxo-4-(4-(trifluoromethyl)benzyl)-piperazin-1-yl)benzonitrile |
| 283 | 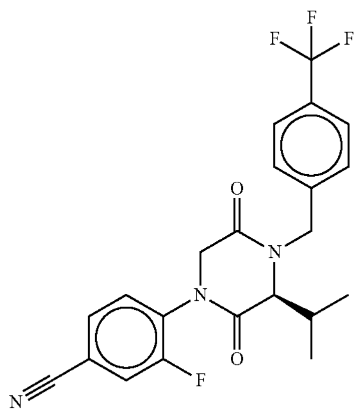 | (S)-3-fluoro-4-(3-isopropyl-2,5-dioxo-4-(4-(trifluoromethyl)benzyl)-piperazin-1-yl)benzonitrile |
| 284 | 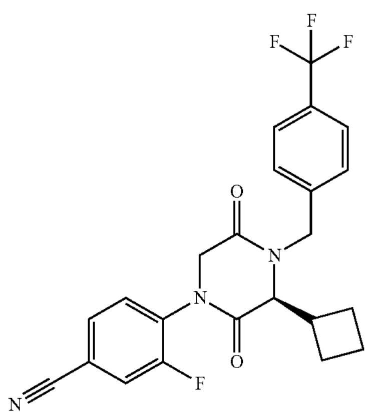 [SMILES: N#Cc1ccc(N2CC(=O)N(Cc3ccc(C(F)(F)F)cc3)[C@@H](C3CCC3)C2=O)c(F)c1] | (S)-4-(3-cyclobutyl-2,5-dioxo-4-(4-(trifluoromethyl)-benzyl)piperazin-1-yl)-3-fluorobenzonitrile |
| 285 | 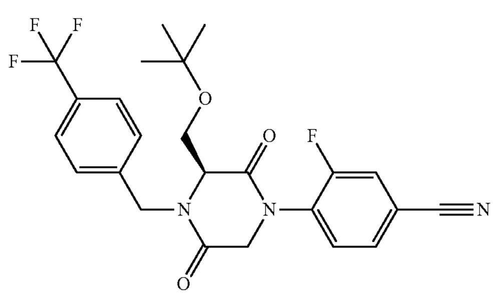 [SMILES: CC(C)(C)OC[C@H]1C(=O)N(c2ccc(C#N)cc2F)CC(=O)N1Cc1ccc(C(F)(F)F)cc1] | (S)-4-(3-(tert-butoxymethyl)-2,5-dioxo-4-(4-(trifluoromethyl)benzyl)piperazin-1-yl)-3-fluorobenzonitrile |

TABLE 1-continued

| No. | Structure | Name |
|---|---|---|
| 286 | 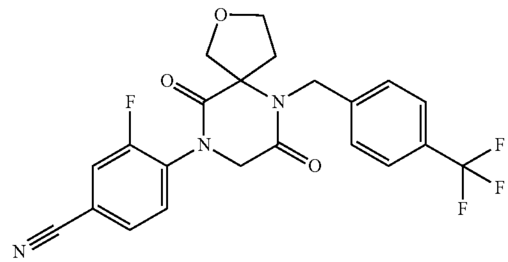 [SMILES: N#Cc1ccc(N2CC(=O)N(Cc3ccc(C(F)(F)F)cc3)C3(CCOC3)C2=O)c(F)c1] | 4-(7,10-dioxo-6-(4-(trifluoromethyl)benzyl)-2-oxa-6,9-diazaspiro[4.5]decan-9-yl)-3-fluorobenzonitrile |
| 287 | 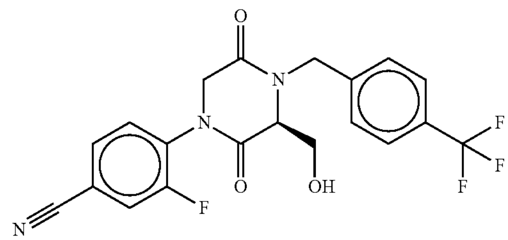 | (S)-3-fluoro-4-(3-(hydroxymethyl)-2,5-dioxo-4-(4-(trifluoromethyl)-benzyl)piperazin-1-yl)-benzonitrile |
| 288 | 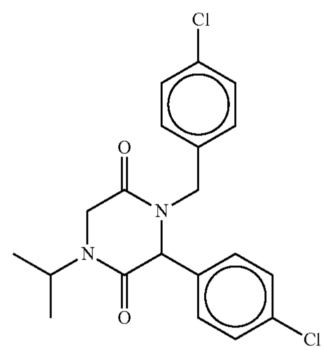 | 4-(4-chlorobenzyl)-3-(4-chlorophenyl)-1-isopropyl-piperazine-2,5-dione |
| 289 | 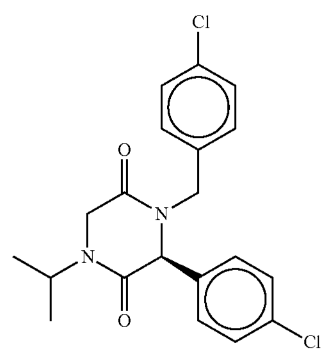 | (S)-4-(4-chlorobenzyl)-3-(4-chlorophenyl)-1-isopropylpiperazine-2,5-dione |
| 290 | 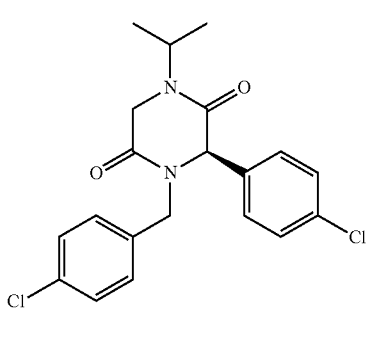 [SMILES: CC(C)N1CC(=O)N(Cc2ccc(Cl)cc2)[C@H](c2ccc(Cl)cc2)C1=O] | (R)-4-(4-chlorobenzyl)-3-(4-chlorophenyl)-1-isopropylpiperazine-2,5-dione |

TABLE 1-continued
| No. | Structure | Name |
|---|---|---|
| 291 | 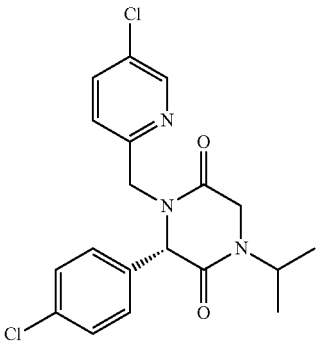 [SMILES: CC(C)N1CC(=O)N(Cc2ccc(Cl)cn2)[C@@H](c2ccc(Cl)cc2)C1=O] | (S)-3-(4-chlorophenyl)-4-((5-chloropyridin-2-yl)-methyl)-1-isopropyl-piperazine-2,5-dione |
| 292 | 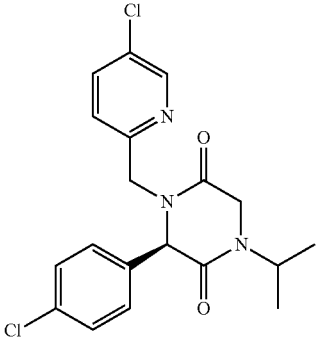 [SMILES: CC(C)N1CC(=O)N(Cc2ccc(Cl)cn2)[C@H](c2ccc(Cl)cc2)C1=O] | (R)-3-(4-chlorophenyl)-4-((5-chloropyridin-2-yl)methyl)-1-isopropyl-piperazine-2,5-dione |
| 293 | 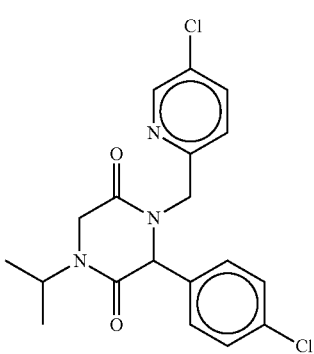 | 3-(4-chlorophenyl)-4-((5-chloropyridin-2-yl)methyl)-1-isopropylpiperazine-2,5-dione |
| 294 | 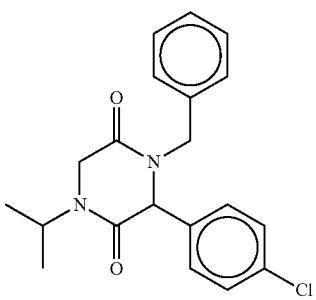 | 4-benzyl-3-(4-chlorophenyl)-1-isopropylpiperazine-2,5-dione |

TABLE 1-continued

| No. | Structure | Name |
|---|---|---|
| 295 | 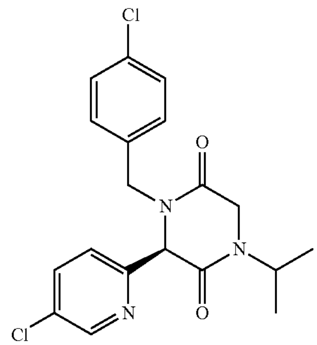 [SMILES: CC(C)N1CC(=O)N(Cc2ccc(Cl)cc2)[C@H](c2ccc(Cl)cn2)C1=O] | (R)-4-(4-chlorobenzyl)-3-(5-chloropyridin-2-yl)-1-isopropylpiperazine-2,5-dione |
| 296 | 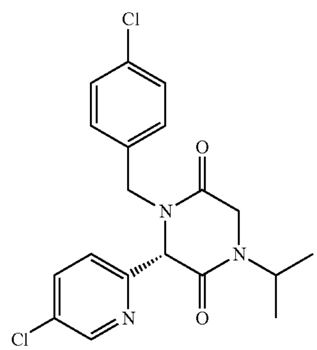 [SMILES: CC(C)N1CC(=O)N(Cc2ccc(Cl)cc2)[C@@H](c2ccc(Cl)cn2)C1=O] | (S)-4-(4-chlorobenzyl)-3-(5-chloropyridin-2-yl)-1-isopropylpiperazine-2,5-dione |
| 297 | 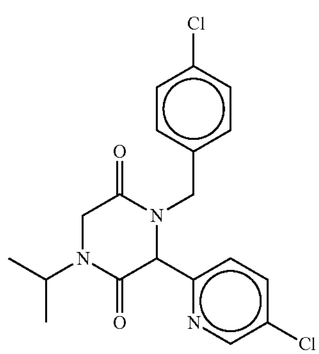 | 4-(4-chlorobenzyl)-3-(5-chloropyridin-2-yl)-1-isopropylpiperazine-2,5-dione |
| 298 | 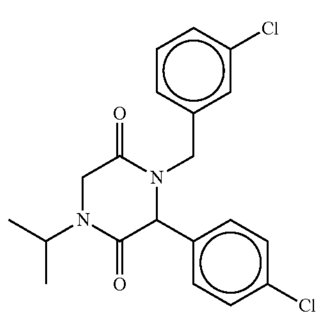 | 4-(3-chlorobenzyl)-3-(4-chlorophenyl)-1-isopropylpiperazine-2,5-dione |

TABLE 1-continued

| No. | Structure | Name |
|---|---|---|
| 299 | 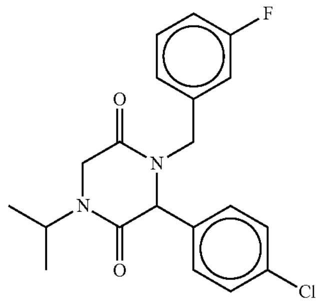 | 3-(4-chlorophenyl)-4-(3-fluorobenzyl)-1-isopropylpiperazine-2,5-dione |
| 300 | 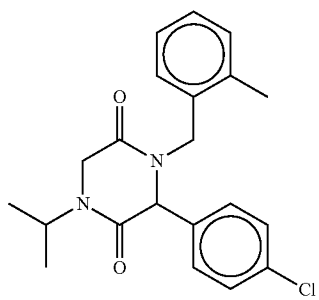 | 3-(4-chlorophenyl)-1-isopropyl-4-(2-methylbenzyl)piperazine-2,5-dione |
| 301 | 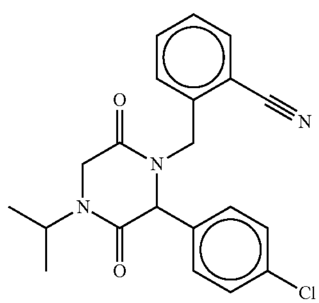 | 2-((2-(4-chlorophenyl)-4-isopropyl-3,6-dioxo-piperazin-1-yl)methyl)-benzonitrile |
| 302 | 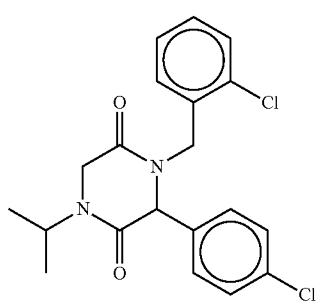 | 4-(2-chlorobenzyl)-3-(4-chlorophenyl)-1-isopropylpiperazine-2,5-dione |
| 303 | 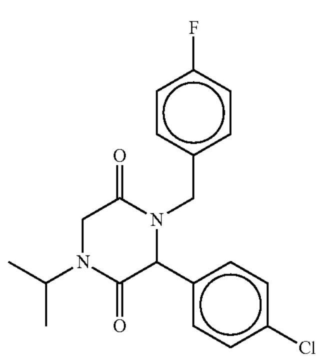 | 3-(4-chlorophenyl)-4-(4-fluorobenzyl)-1-isopropylpiperazine-2,5-dione |

TABLE 1-continued
| No. | Structure | Name |
|---|---|---|
| 304 | 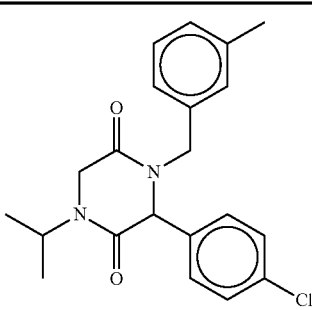 | 3-(4-chlorophenyl)-1-isopropyl-4-(3-methyl-benzyl)piperazine-2,5-dione |
| 305 | 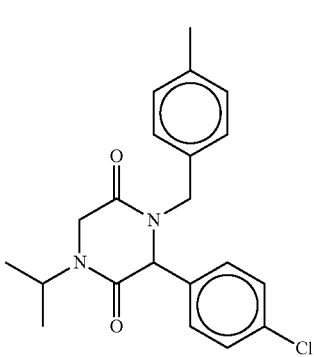 | 3-(4-chlorophenyl)-1-isopropyl-4-(4-methylbenzyl)piperazine-2,5-dione |
| 306 | 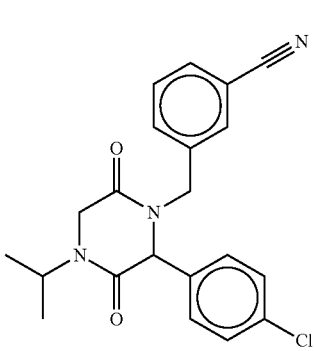 | 3-((2-(4-chlorophenyl)-4-isopropyl-3,6-dioxo-piperazin-1-yl)methyl)-benzonitrile |
| 307 | 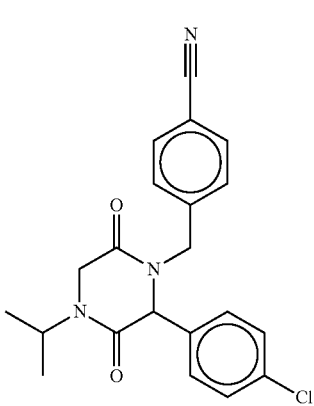 | 4-((2-(4-chlorophenyl)-4-isopropyl-3,6-dioxo-piperazin-1-yl)methyl)-benzonitrile |

TABLE 1-continued

| No. | Structure | Name |
|---|---|---|
| 308 | 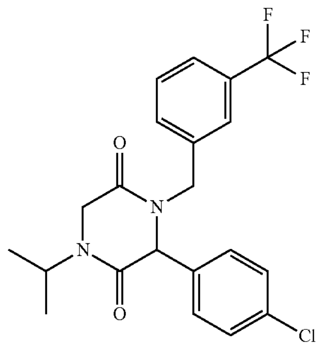 [SMILES: CC(C)N1CC(=O)N(Cc2cccc(C(F)(F)F)c2)C(c2ccc(Cl)cc2)C1=O] | 3-(4-chlorophenyl)-1-isopropyl-4-(3-(trifluoromethyl)benzyl)piperazine-2,5-dione |
| 309 | 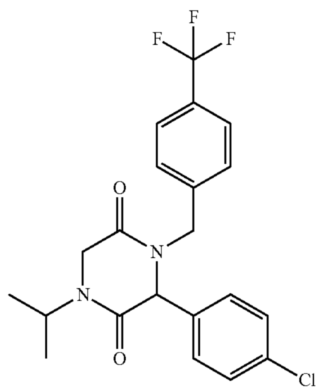 [SMILES: CC(C)N1CC(=O)N(Cc2ccc(C(F)(F)F)cc2)C(c2ccc(Cl)cc2)C1=O] | 3-(4-chlorophenyl)-1-isopropyl-4-(4-(trifluoromethyl)benzyl)piperazine-2,5-dione |
| 310 | 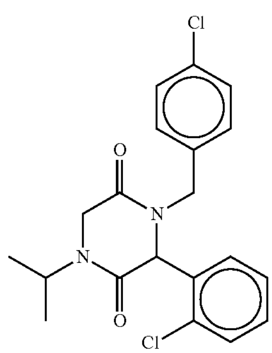 | 4-(4-chlorobenzyl)-3-(2-chlorophenyl)-1-isopropylpiperazine-2,5-dione |
| 311 | 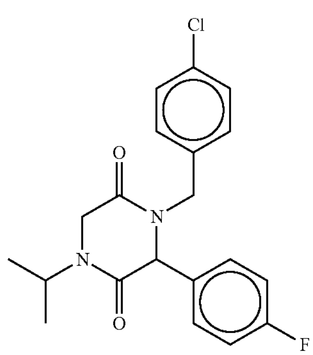 | 4-(4-chlorobenzyl)-3-(4-fluorophenyl)-1-isopropylpiperazine-2,5-dione |

TABLE 1-continued

| No. | Structure | Name |
|---|---|---|
| 312 | 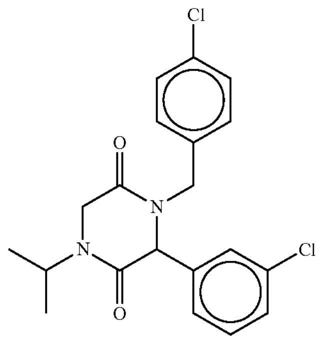 | 4-(4-chlorobenzyl)-3-(3-chlorophenyl)-1-isopropylpiperazine-2,5-dione |
| 313 | 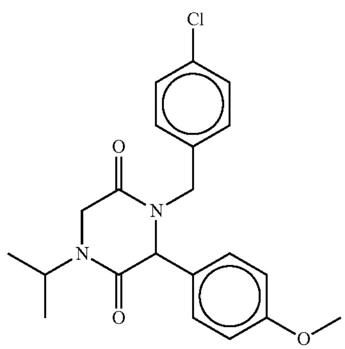 | 4-(4-chlorobenzyl)-1-isopropyl-3-(4-methoxyphenyl)piperazine-2,5-dione |
| 314 | 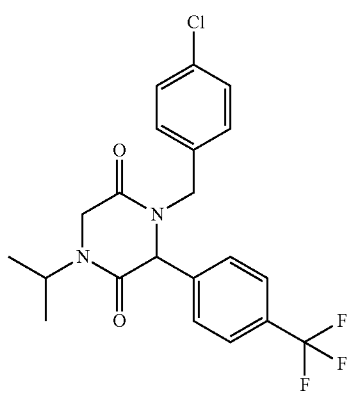 [SMILES: CC(C)N1CC(=O)N(Cc2ccc(Cl)cc2)C(c2ccc(C(F)(F)F)cc2)C1=O] | 4-(4-chlorobenzyl)-1-isopropyl-3-(4-(trifluoromethyl)phenyl)piperazine-2,5-dione |
| 315 | 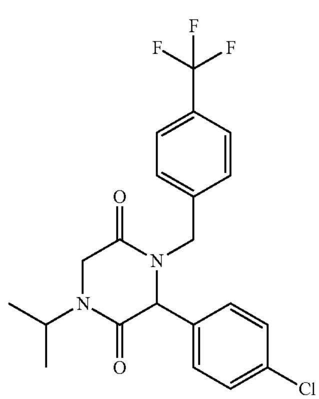 [SMILES: CC(C)N1CC(=O)N(Cc2ccc(C(F)(F)F)cc2)C(c2ccc(Cl)cc2)C1=O] | 3-(4-chlorophenyl)-1-isopropyl-4-((5-(trifluoromethyl)pyridin-2-yl)methyl)piperazine-2,5-dione |

TABLE 1-continued

| No. | Structure | Name |
|---|---|---|
| 316 | 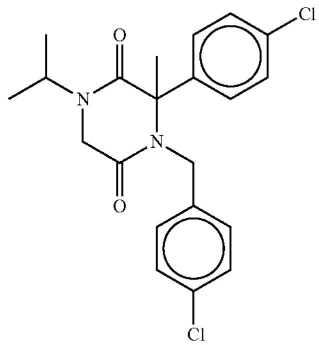 | 4-(4-chlorobenzyl)-3-(4-chlorophenyl)-1-isopropyl-3-methylpiperazine-2,5-dione |
| 317 | 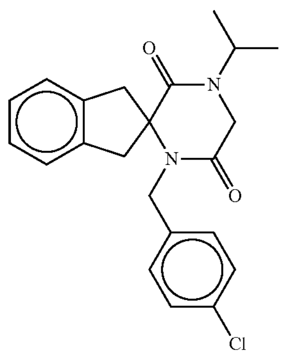 | 1'-(4-chlorobenzyl)-4'-isopropyl-1,3-dihydrospiro[indene-2,2'-piperazine]-3',6'-dione |
| 318 | 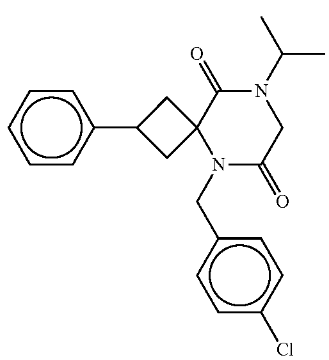 | 5-(4-chlorobenzyl)-8-isopropyl-2-phenyl-5,8-diazaspiro[3.5]nonane-6,9-dione |
| 319 | 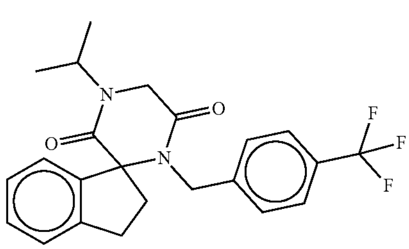 | 4'-isopropyl-1'-(4-(trifluoromethyl)benzyl)-2,3-dihydrospiro[indene-1,2'-piperazine]-3',6'-dione |

TABLE 1-continued

| No. | Structure | Name |
|---|---|---|
| 320 | 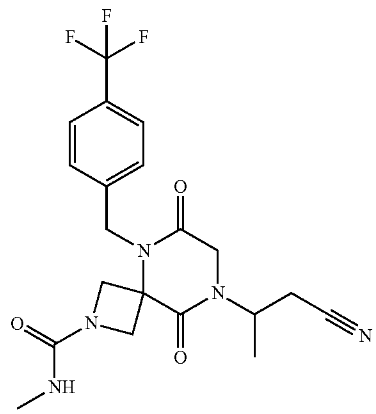 [SMILES: CNC(=O)N1CC2(C1)C(=O)N(C(C)CC#N)CC(=O)N2Cc1ccc(C(F)(F)F)cc1] | 8-(1-cyanopropan-2-yl)-N-methyl-6,9-dioxo-5-(4-(trifluoromethyl)benzyl)-2,5,8-triazaspiro[3.5]-nonane-2-carboxamide |
| 321 | 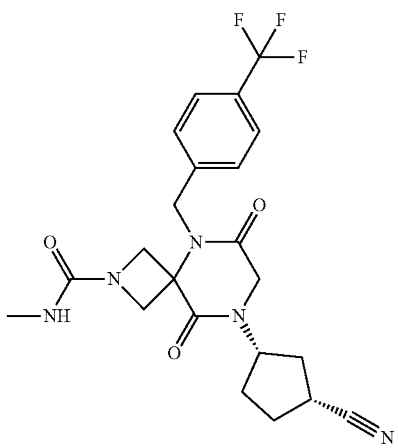 [SMILES: CNC(=O)N1CC2(C1)C(=O)N([C@H]1CC[C@@H](C#N)C1)CC(=O)N2Cc1ccc(C(F)(F)F)cc1] | 8-((1S,3R)-3-cyano-cyclopentyl)-N-methyl-6,9-dioxo-5-(4-(trifluoromethyl)benzyl)-2,5,8-triazaspiro[3.5]-nonane-2-carboxamide |
| 322 | 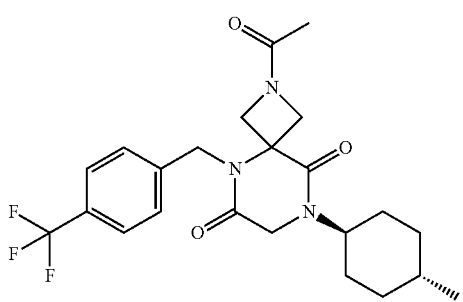 [SMILES: CC(=O)N1CC2(C1)C(=O)N([C@H]1CC[C@H](C)CC1)CC(=O)N2Cc1ccc(C(F)(F)F)cc1] | 2-acetyl-8-((1r,4r)-4-methylcyclohexyl)-5-(4-(trifluoromethyl)benzyl)-2,5,8-triazaspiro[3.5]-nonane-6,9-dione |
| 323 | 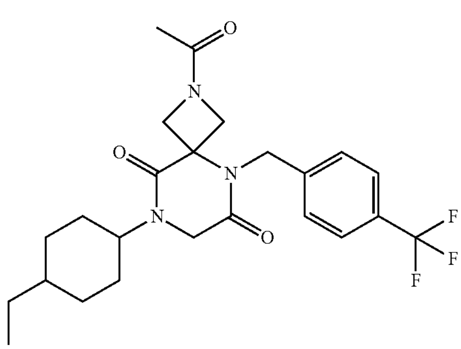 [SMILES: CCC1CCC(N2CC(=O)N(Cc3ccc(C(F)(F)F)cc3)C3(CN(C(C)=O)C3)C2=O)CC1] | 2-acetyl-8-(4-ethylcyclohexyl)-5-(4-(trifluoromethyl)benzyl)-2,5,8-triazaspiro[3.5]nonane-6,9-dione |

TABLE 1-continued

| No. | Structure | Name |
|---|---|---|
| 324 | 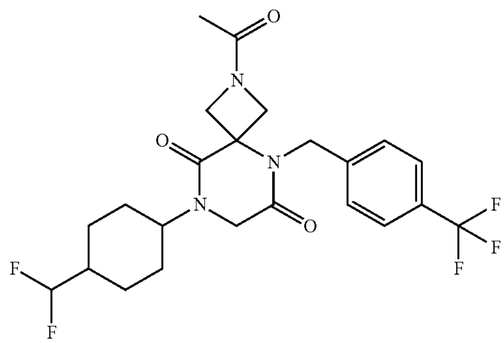 [SMILES: CC(=O)N1CC2(C1)C(=O)N(C1CCC(C(F)F)CC1)CC(=O)N2Cc1ccc(C(F)(F)F)cc1] | 2-acetyl-8-(4-(difluoromethyl)cyclohexyl)-5-(4-(trifluoromethyl)benzyl)-2,5,8-triazaspiro[3.5]-nonane-6,9-dione |
| 325 | 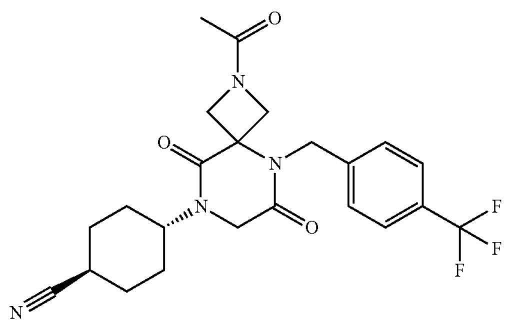 [SMILES: CC(=O)N1CC2(C1)C(=O)N([C@H]1CC[C@H](C#N)CC1)CC(=O)N2Cc1ccc(C(F)(F)F)cc1] | (1r,4r)-4-(2-acetyl-6,9-dioxo-5-(4-(trifluoromethyl)benzyl)-2,5,8-triazaspiro[3.5]nonan-8-yl)cyclohexane-1-carbonitrile |
| 326 | 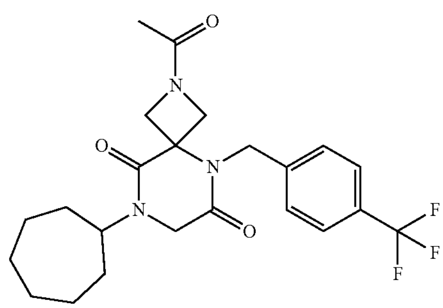 [SMILES: CC(=O)N1CC2(C1)C(=O)N(C1CCCCCC1)CC(=O)N2Cc1ccc(C(F)(F)F)cc1] | 2-acetyl-8-cycloheptyl-5-(4-(trifluoromethyl)benzyl)-2,5,8-triazaspiro[3.5]-nonane-6,9-dione |
| 327 | 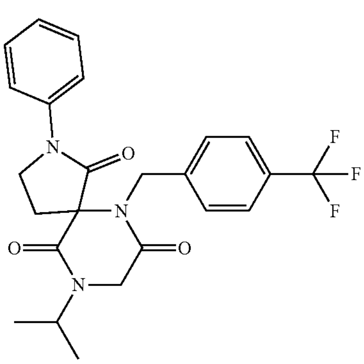 [SMILES: CC(C)N1CC(=O)N(Cc2ccc(C(F)(F)F)cc2)C2(CCN(c3ccccc3)C2=O)C1=O] | 9-isopropyl-2-phenyl-6-(4-(trifluoromethyl)benzyl)-2,6,9-triazaspiro[4.5]-decane-1,7,10-trione |

TABLE 1-continued

| No. | Structure | Name |
|---|---|---|
| 328 | 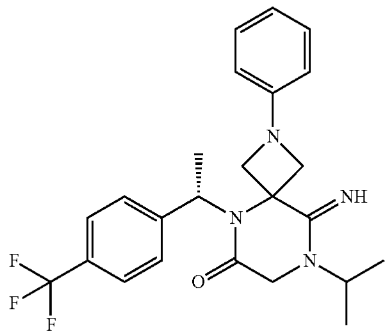 [SMILES: CC(C)N1CC(=O)N([C@@H](C)c2ccc(C(F)(F)F)cc2)C2(CN(c3ccccc3)C2)C1=N] | (S)-9-imino-8-isopropyl-2-phenyl-5-(1-(4-(trifluoromethyl)phenyl)ethyl)-2,5,8-triazaspiro[3.5]nonan-6-one |
| 329 | 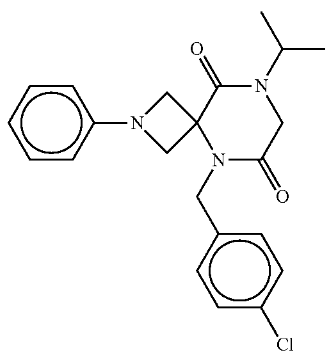 | 5-(4-chlorobenzyl)-8-isopropyl-7-methyl-2-phenyl-2,5,8-triazaspiro[3.5]nonane-6,9-dione |
| 330 | 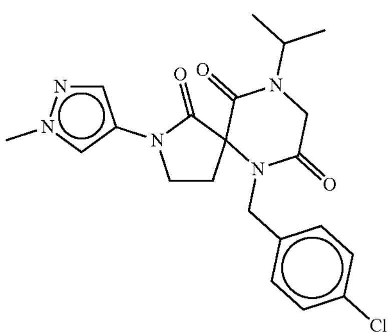 | 6-(4-chlorobenzyl)-9-isopropyl-2-(1-methyl-1H-pyrazol-4-yl)-2,6,9-triazaspiro[4.5]decane-1,7,10-trione |
| 331 | 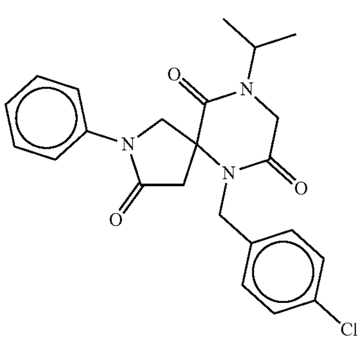 | 6-(4-chlorobenzyl)-9-isopropyl-2-phenyl-2,6,9-triazaspiro[4.5]decane-3,7,10-trione |

TABLE 1-continued

| No. | Structure | Name |
|---|---|---|
| 332 | 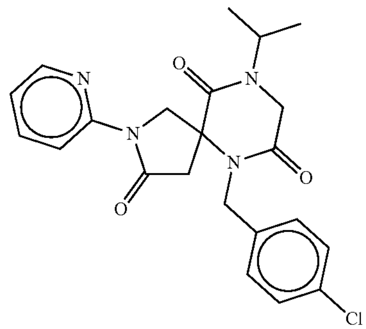 | 6-(4-chlorobenzyl)-9-isopropyl-2-(pyridin-2-yl)-2,6,9-triazaspiro[4.5]decane-3,7,10-trione |
| 333 | 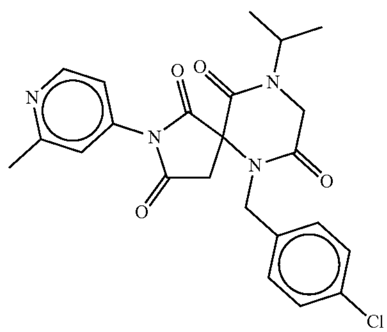 | 6-(4-chlorobenzyl)-9-isopropyl-2-(2-methyl-pyridin-4-yl)-2,6,9-triazaspiro[4.5]decane-1,7,10-trione |
| 334 | 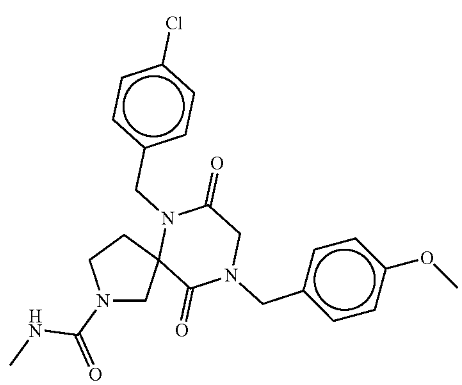 | 6-(4-chlorobenzyl)-9-(4-methoxybenzyl)-N-methyl-7,10-dioxo-2,6,9-triazaspiro[4.5]decane-2-carboxamide |
| 335 | 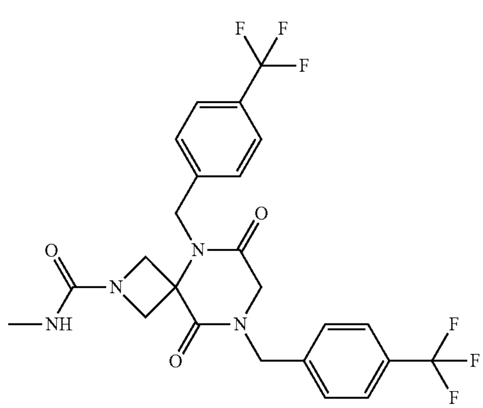 [SMILES: CNC(=O)N1CC2(C1)C(=O)N(Cc1ccc(C(F)(F)F)cc1)CC(=O)N2Cc1ccc(C(F)(F)F)cc1] | N-methyl-6,9-dioxo-5,8-bis(4-(trifluoromethyl)-benzyl)-2,5,8-triazaspiro[3.5]nonane-2-carboxamide |

TABLE 1-continued

| No. | Structure | Name |
|---|---|---|
| 336 | 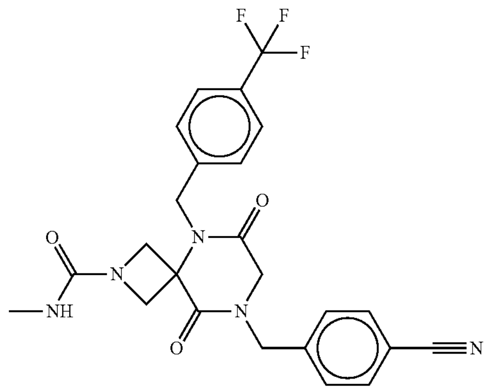 | 8-(4-cyanobenzyl)-N-methyl-6,9-dioxo-5-(4-(trifluoromethyl)benzyl)-2,5,8-triazaspiro[3.5]-nonane-2-carboxamide |
| 337 | 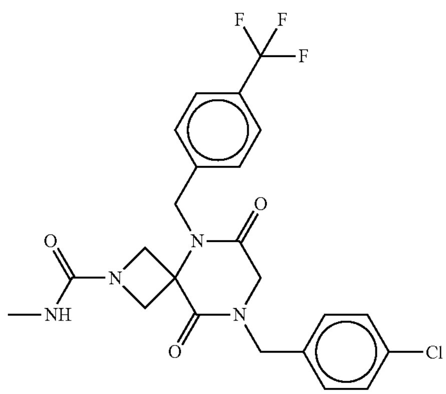 | 8-(4-chlorobenzyl)-N-methyl-6,9-dioxo-5-(4-(trifluoromethyl)benzyl)-2,5,8-triazaspiro[3.5]-nonane-2-carboxamide |
| 338 | 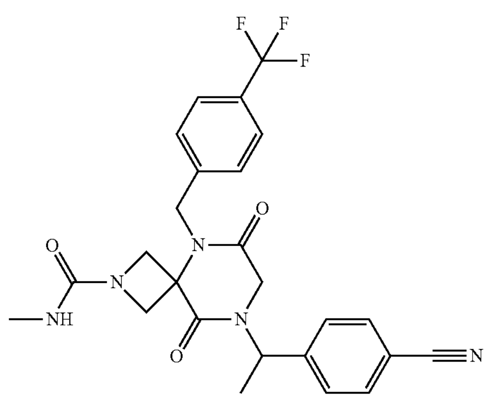 [SMILES: CNC(=O)N1CC2(C1)C(=O)N(C(C)c1ccc(C#N)cc1)CC(=O)N2Cc1ccc(C(F)(F)F)cc1] | 8-(1-(4-cyanophenyl)ethyl)-N-methyl-6,9-dioxo-5-(4-(trifluoromethyl)benzyl)-2,5,8-triazaspiro[3.5]-nonane-2-carboxamide |
| 339 | 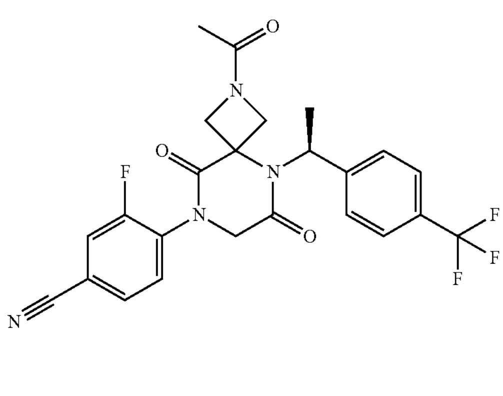 [SMILES: CC(=O)N1CC2(C1)C(=O)N(c1ccc(C#N)cc1F)CC(=O)N2[C@@H](C)c1ccc(C(F)(F)F)cc1] | (S)-4-(2-acetyl-6,9-dioxo-5-(1-(4-(trifluoromethyl)-phenyl)ethyl)-2,5,8-triazaspiro[3.5]nonan-8-yl)-3-fluorobenzonitrile |

TABLE 1-continued

| No. | Structure | Name |
|---|---|---|
| 340 | 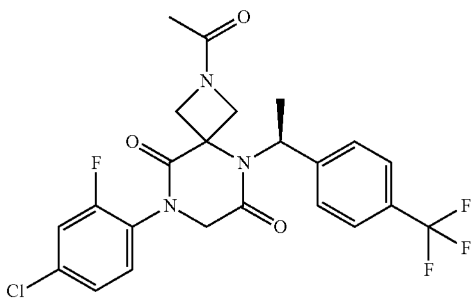 [SMILES: CC(=O)N1CC2(C1)C(=O)N(c1ccc(Cl)cc1F)CC(=O)N2[C@@H](C)c1ccc(C(F)(F)F)cc1] | (S)-2-acetyl-8-(4-chloro-2-fluorophenyl)-5-(1-(4-(trifluoromethyl)phenyl)-ethyl)-2,5,8-triazaspiro[3.5]nonane-6,9-dione |
| 341 | 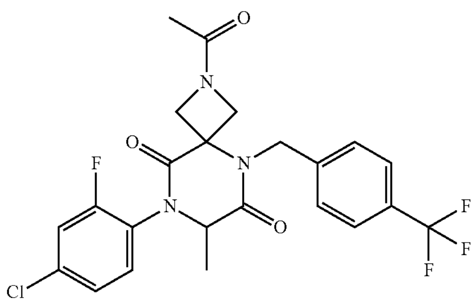 [SMILES: CC(=O)N1CC2(C1)C(=O)N(c1ccc(Cl)cc1F)C(C)C(=O)N2Cc1ccc(C(F)(F)F)cc1] | 2-acetyl-8-(4-chloro-2-fluorophenyl)-7-methyl-5-(4-(trifluoromethyl)benzyl)-2,5,8-triazaspiro[3.5]-nonane-6,9-dione |
| 342 | 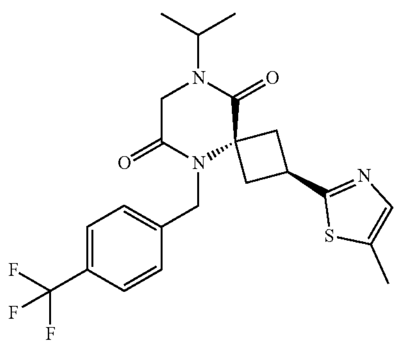 [SMILES: Cc1cnc([C@H]2C[C@]3(C2)C(=O)N(C(C)C)CC(=O)N3Cc2ccc(C(F)(F)F)cc2)s1] | (2r,4r)-8-isopropyl-2-(5-methylthiazol-2-yl)-5-(4-(trifluoromethyl)benzyl)-5,8-diazaspiro[3.5]nonane-6,9-dione |
| 343 | 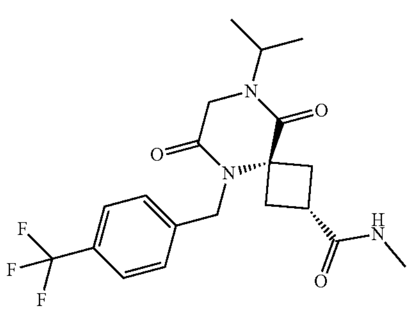 [SMILES: CNC(=O)[C@H]1C[C@@]2(C1)C(=O)N(C(C)C)CC(=O)N2Cc1ccc(C(F)(F)F)cc1] | (2s,4s)-8-isopropyl-N-methyl-6,9-dioxo-5-(4-(trifluoromethyl)benzyl)-5,8-diazaspiro[3.5]nonane-2-carboxamide |
| 344 | 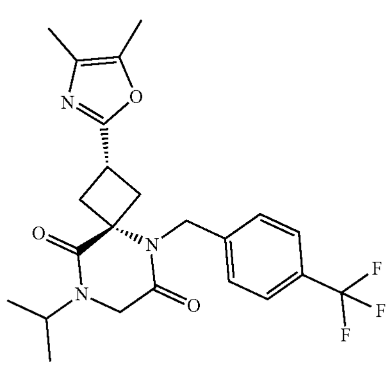 [SMILES: Cc1nc([C@H]2C[C@@]3(C2)C(=O)N(C(C)C)CC(=O)N3Cc2ccc(C(F)(F)F)cc2)oc1C] | (2s,4s)-2-(4,5-dimethyl-oxazol-2-yl)-8-isopropyl-5-(4-(trifluoromethyl)benzyl)-5,8-diazaspiro[3.5]nonane-6,9-dione |

TABLE 1-continued

| No. | Structure | Name |
|---|---|---|
| 345 | 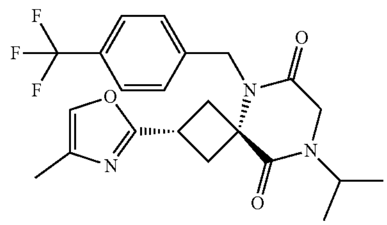 [SMILES: Cc1coc([C@H]2C[C@@]3(C2)C(=O)N(C(C)C)CC(=O)N3Cc2ccc(C(F)(F)F)cc2)n1] | (2s,4s)-8-isopropyl-2-(4-methyloxazol-2-yl)-5-(4-(trifluoromethyl)benzyl)-5,8-diazaspiro[3.5]nonane-6,9-dione |
| 346 | 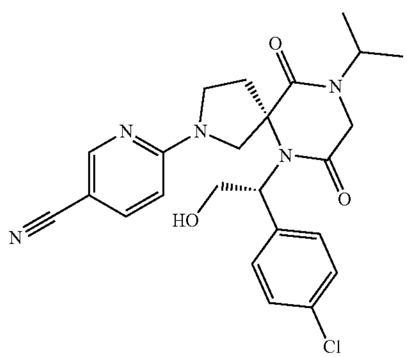 [SMILES: CC(C)N1CC(=O)N([C@@H](CO)c2ccc(Cl)cc2)[C@]2(CCN(c3ccc(C#N)cn3)C2)C1=O] | 6-((S)-6-((R)-1-(4-chlorophenyl)-2-hydroxyethyl)-9-isopropyl-7,10-dioxo-2,6,9-triazaspiro[4.5]decan-2-yl)-nicotinonitrile |
| 347 | 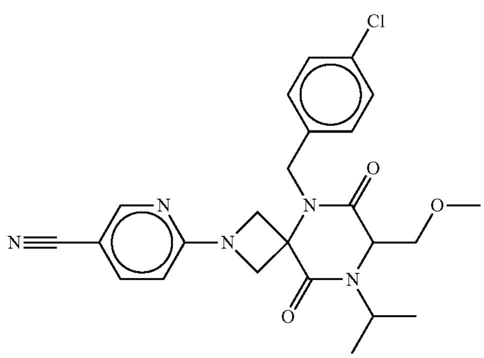 | 6-(5-(4-chlorobenzyl)-8-isopropyl-7-(methoxymethyl)-6,9-dioxo-2,5,8-triazaspiro[3.5]nonan-2-yl)nicotinonitrile |
| 348 | 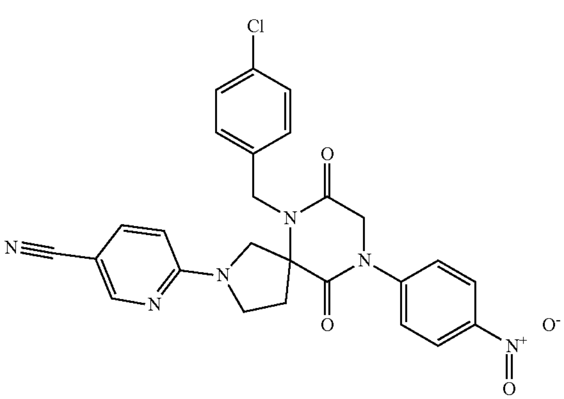 | 6-(6-(4-chlorobenzyl)-9-(4-nitrophenyl)-7,10-dioxo-2,6,9-triazaspiro[4.5]decan-2-yl)nicotinonitrile |

TABLE 1-continued

| No. | Structure | Name |
|---|---|---|
| 349 | 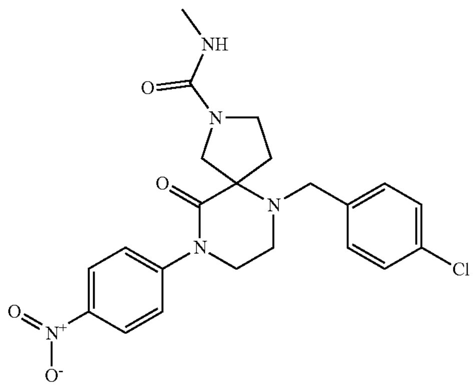 [SMILES: CNC(=O)N1CCC2(C1)C(=O)N(c1ccc([N+](=O)[O-])cc1)CCN2Cc1ccc(Cl)cc1] | 6-(4-chlorobenzyl)-N-methyl-9-(4-nitrophenyl)-7,10-dioxo-2,6,9-triazaspiro[4.5]decane-2-carboxamide |
| 350 | 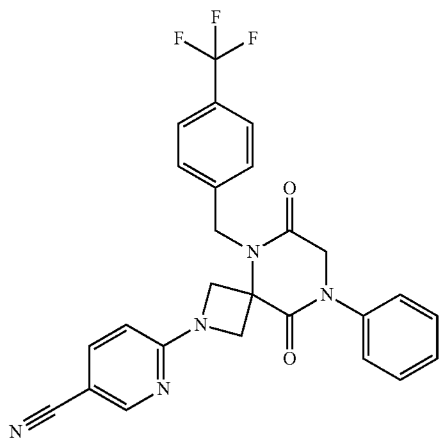 [SMILES: N#Cc1ccc(N2CC3(C2)C(=O)N(c2ccccc2)CC(=O)N3Cc2ccc(C(F)(F)F)cc2)nc1] | 6-(6,9-dioxo-8-phenyl-5-(4-(trifluoromethyl)benzyl)-2,5,8-triazaspiro[3.5]nonan-2-yl)nicotinonitrile |
| 351 | 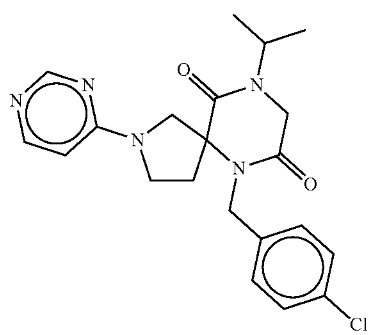 | 6-(4-chlorobenzyl)-9-isopropyl-2-(pyrimidin-4-yl)-2,6,9-triazaspiro-[4.5]decane-7,10-dione |
| 352 | 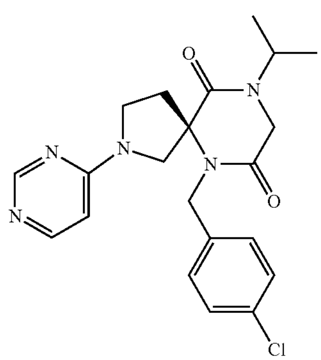 [SMILES: CC(C)N1CC(=O)N(Cc2ccc(Cl)cc2)[C@@]2(CCN(c3ccncn3)C2)C1=O] | (R)-6-(4-chlorobenzyl)-9-isopropyl-2-(pyrimidin-4-yl)-2,6,9-triazaspiro-[4.5]decane-7,10-dione |

TABLE 1-continued

| No. | Structure | Name |
|---|---|---|
| 353 | 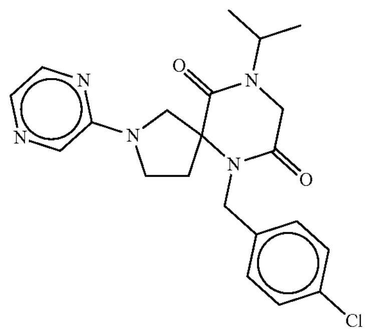 | 6-(4-chlorobenzyl)-9-isopropyl-2-(pyrazin-2-yl)-2,6,9-triazaspiro[4.5]-decane-7,10-dione |
| 354 | 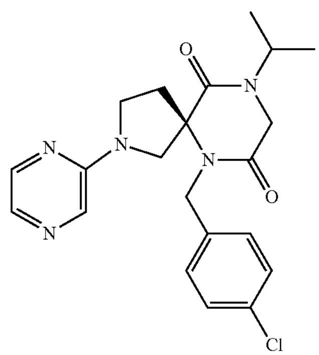 | (R)-6-(4-chlorobenzyl)-9-isopropyl-2-(pyrazin-2-yl)-2,6,9-triazaspiro[4.5]-decane-7,10-dione |
| 355 | 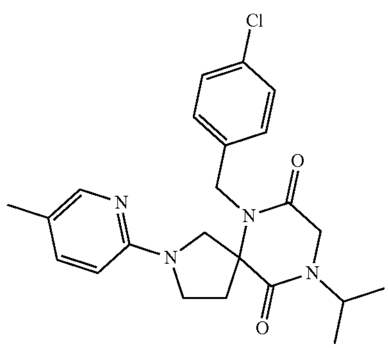 [SMILES: Cc1ccc(N2CCC3(C2)C(=O)N(C(C)C)CC(=O)N3Cc2ccc(Cl)cc2)nc1] | 6-(4-chlorobenzyl)-9-isopropyl-2-(5-methyl-pyridin-2-yl)-2,6,9-triazaspiro[4.5]decane-7,10-dione |
| 356 | 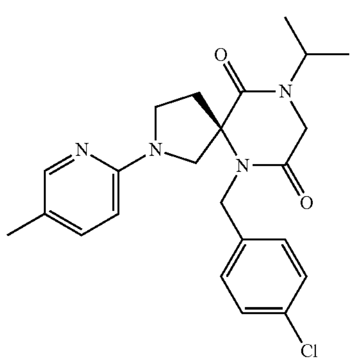 [SMILES: Cc1ccc(N2CC[C@@]3(C2)C(=O)N(C(C)C)CC(=O)N3Cc2ccc(Cl)cc2)nc1] | (R)-6-(4-chlorobenzyl)-9-isopropyl-2-(5-methyl-pyridin-2-yl)-2,6,9-triazaspiro[4.5]decane-7,10-dione |

TABLE 1-continued

| No. | Structure | Name |
|---|---|---|
| 357 | 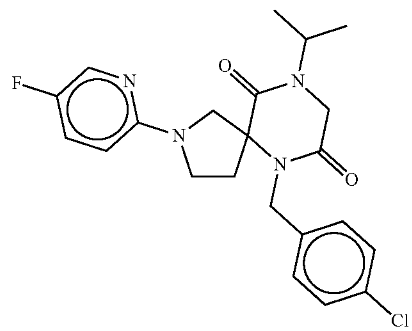 | 6-(4-chlorobenzyl)-2-(5-fluoropyridin-2-yl)-9-isopropyl-2,6,9-triazaspiro[4.5]decane-7,10-dione |
| 358 | 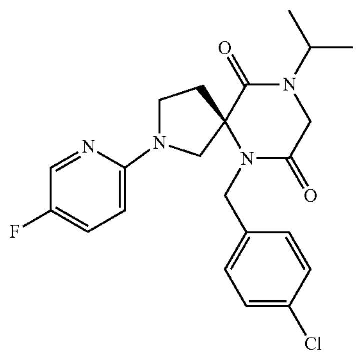 [SMILES: CC(C)N1CC(=O)N(Cc2ccc(Cl)cc2)[C@@]2(CCN(c3ccc(F)cn3)C2)C1=O] | (R)-6-(4-chlorobenzyl)-2-(5-fluoropyridin-2-yl)-9-isopropyl-2,6,9-triazaspiro[4.5]decane-7,10-dione |
| 359 | 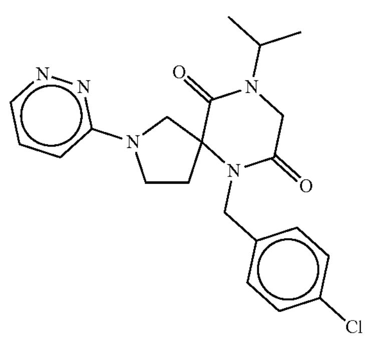 | 6-(4-chlorobenzyl)-9-isopropyl-2-(pyridazin-3-yl)-2,6,9-triazaspiro-[4.5]decane-7,10-dione |
| 360 | 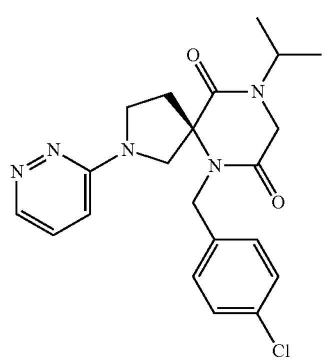 [SMILES: CC(C)N1CC(=O)N(Cc2ccc(Cl)cc2)[C@@]2(CCN(c3cccnn3)C2)C1=O] | (R)-6-(4-chlorobenzyl)-9-isopropyl-2-(pyridazin-3-yl)-2,6,9-triazaspiro-[4.5]decane-7,10-dione |

TABLE 1-continued

| No. | Structure | Name |
|---|---|---|
| 361 | 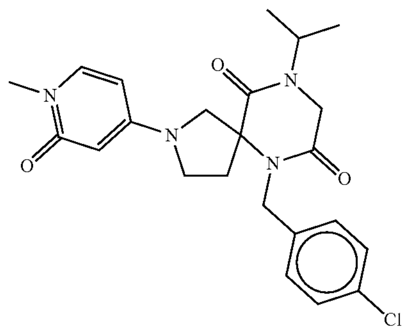 | 6-(4-chlorobenzyl)-9-isopropyl-2-(1-methyl-2-oxo-1,2-dihydropyridin-4-yl)-2,6,9-triazaspiro[4.5]-decane-7,10-dione |
| 362 | 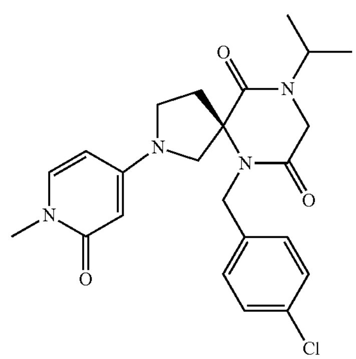 [SMILES: CC(C)N1CC(=O)N(Cc2ccc(Cl)cc2)[C@@]2(CCN(c3ccn(C)c(=O)c3)C2)C1=O] | (R)-6-(4-chlorobenzyl)-9-isopropyl-2-(1-methyl-2-oxo-1,2-dihydropyridin-4-yl)-2,6,9-triazaspiro-[4.5]decane-7,10-dione |
| 363 | 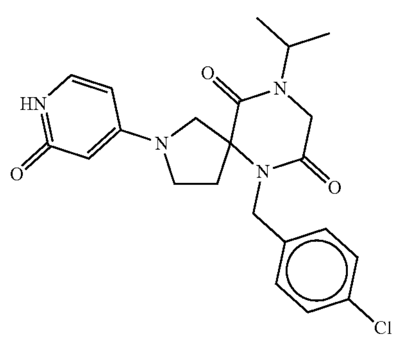 | 6-(4-chlorobenzyl)-9-isopropyl-2-(2-oxo-1,2-dihydropyridin-4-yl)-2,6,9-triazaspiro[4.5]decane-7,10-dione |
| 364 | 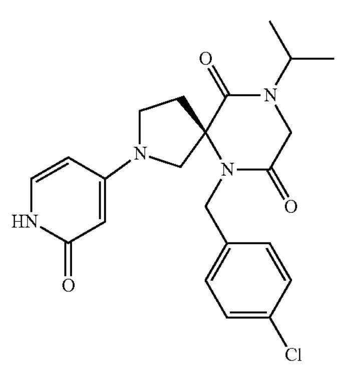 [SMILES: CC(C)N1CC(=O)N(Cc2ccc(Cl)cc2)[C@@]2(CCN(c3cc[nH]c(=O)c3)C2)C1=O] | (R)-6-(4-chlorobenzyl)-9-isopropyl-2-(2-oxo-1,2-dihydropyridin-4-yl)-2,6,9-triazaspiro[4.5]decane-7,10-dione |

TABLE 1-continued

| No. | Structure | Name |
|---|---|---|
| 365 | 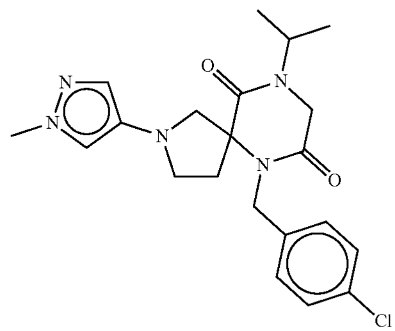 | 6-(4-chlorobenzyl)-9-isopropyl-2-(1-methyl-1H-pyrazol-4-yl)-2,6,9-triazaspiro[4.5]decane-7,10-dione |
| 366 | 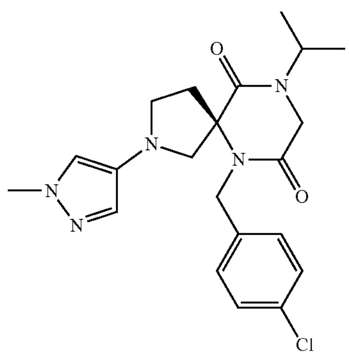 [SMILES: CC(C)N1CC(=O)N(Cc2ccc(Cl)cc2)[C@@]2(CCN(c3cnn(C)c3)C2)C1=O] | (R)-6-(4-chlorobenzyl)-9-isopropyl-2-(1-methyl-1H-pyrazol-4-yl)-2,6,9-triazaspiro[4.5]decane-7,10-dione |
| 367 | 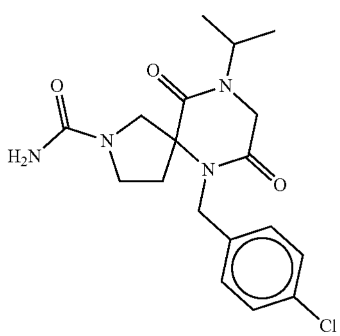 | 6-(4-chlorobenzyl)-9-isopropyl-7,10-dioxo-2,6,9-triazaspiro[4.5]decane-2-carboxamide |
| 368 | 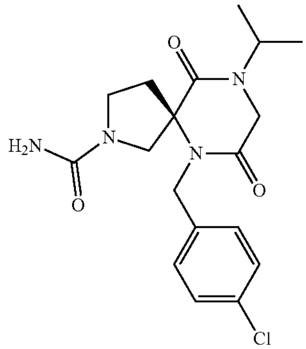 [SMILES: CC(C)N1CC(=O)N(Cc2ccc(Cl)cc2)[C@@]2(CCN(C(N)=O)C2)C1=O] | (R)-6-(4-chlorobenzyl)-9-isopropyl-7,10-dioxo-2,6,9-triazaspiro[4.5]decane-2-carboxamide |

TABLE 1-continued

| No. | Structure | Name |
|---|---|---|
| 369 | 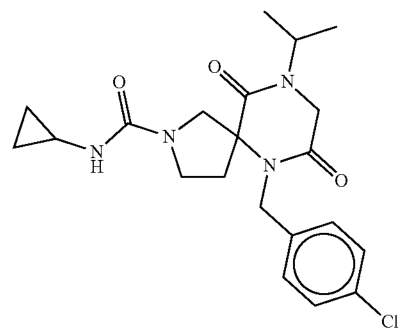 | 6-(4-chlorobenzyl)-N-cyclopropyl-9-isopropyl-7,10-dioxo-2,6,9-triazaspiro[4.5]decane-2-carboxamide |
| 370 | 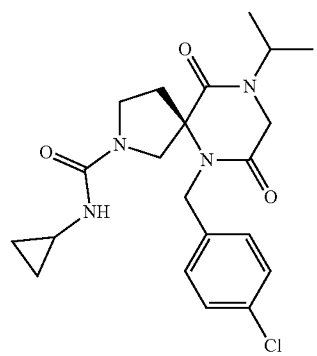 [SMILES: CC(C)N1CC(=O)N(Cc2ccc(Cl)cc2)[C@@]2(CCN(C(=O)NC3CC3)C2)C1=O] | (R)-6-(4-chlorobenzyl)-N-cyclopropyl-9-isopropyl-7,10-dioxo-2,6,9-triazaspiro[4.5]decane-2-carboxamide |
| 371 | 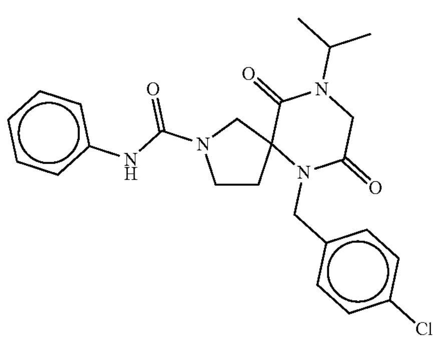 | 6-(4-chlorobenzyl)-9-isopropyl-7,10-dioxo-N-phenyl-2,6,9-triazaspiro-[4.5]decane-2-carboxamide |
| 372 | 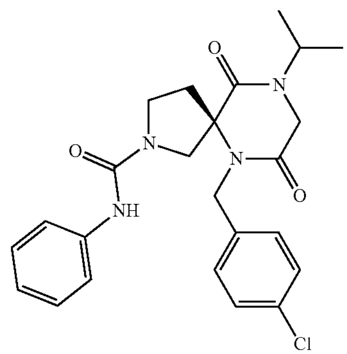 [SMILES: CC(C)N1CC(=O)N(Cc2ccc(Cl)cc2)[C@@]2(CCN(C(=O)Nc3ccccc3)C2)C1=O] | (R)-6-(4-chlorobenzyl)-9-isopropyl-7,10-dioxo-N-phenyl-2,6,9-triazaspiro-[4.5]decane-2-carboxamide |

TABLE 1-continued

| No. | Structure | Name |
|---|---|---|
| 373 | 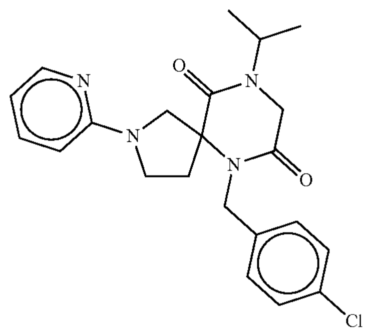 | 6-(4-chlorobenzyl)-9-isopropyl-2-(pyridin-2-yl)-2,6,9-triazaspiro[4.5]-decane-7,10-dione |
| 374 | 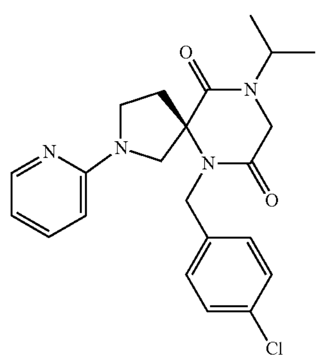 [SMILES: CC(C)N1CC(=O)N(Cc2ccc(Cl)cc2)[C@@]2(CCN(c3ccccn3)C2)C1=O] | (R)-6-(4-chlorobenzyl)-9-isopropyl-2-(pyridin-2-yl)-2,6,9-triazaspiro[4.5]-decane-7,10-dione |
| 375 | 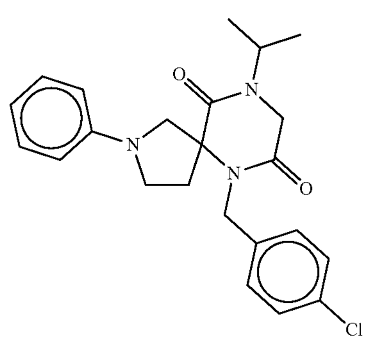 | 6-(4-chlorobenzyl)-9-isopropyl-2-phenyl-2,6,9-triazaspiro[4.5]decane-7,10-dione |
| 376 | 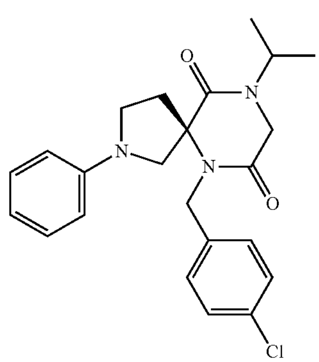 [SMILES: CC(C)N1CC(=O)N(Cc2ccc(Cl)cc2)[C@@]2(CCN(c3ccccc3)C2)C1=O] | (R)-6-(4-chlorobenzyl)-9-isopropyl-2-phenyl-2,6,9-triazaspiro[4.5]decane-7,10-dione |

TABLE 1-continued

| No. | Structure | Name |
|---|---|---|
| 377 | 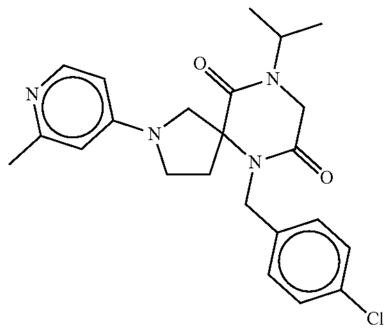 | 6-(4-chlorobenzyl)-9-isopropyl-2-(2-methyl-pyridin-4-yl)-2,6,9-triazaspiro[4.5]decane-7,10-dione |
| 378 | 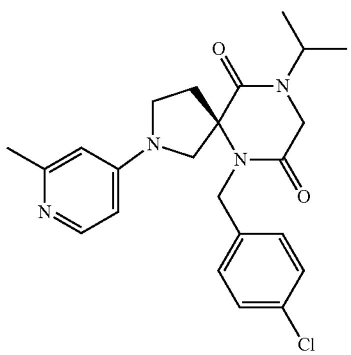 [SMILES: Cc1cc(N2CC[C@@]3(C2)C(=O)N(C(C)C)CC(=O)N3Cc2ccc(Cl)cc2)ccn1] | (R)-6-(4-chlorobenzyl)-9-isopropyl-2-(2-methyl-pyridin-4-yl)-2,6,9-triazaspiro[4.5]decane-7,10-dione |
| 379 | 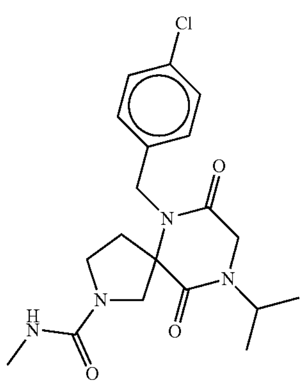 | 6-(4-chlorobenzyl)-9-isopropyl-N-methyl-7,10-dioxo-2,6,9-triazaspiro-[4.5]decane-2-carboxamide |
| 380 | 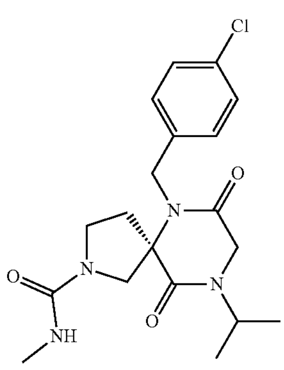 [SMILES: CNC(=O)N1CC[C@@]2(C1)C(=O)N(C(C)C)CC(=O)N2Cc1ccc(Cl)cc1] | (R)-6-(4-chlorobenzyl)-9-isopropyl-N-methyl-7,10-dioxo-2,6,9-triazaspiro-[4.5]decane-2-carboxamide |

TABLE 1-continued

| No. | Structure | Name |
|---|---|---|
| 381 | 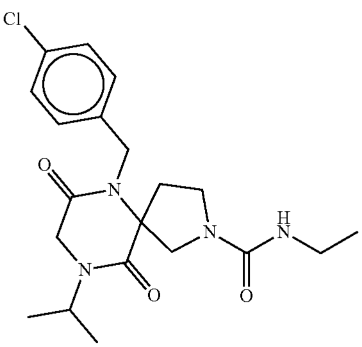 | 6-(4-chlorobenzyl)-N-ethyl-9-isopropyl-7,10-dioxo-2,6,9-triazaspiro[4.5]-decane-2-carboxamide |
| 382 | 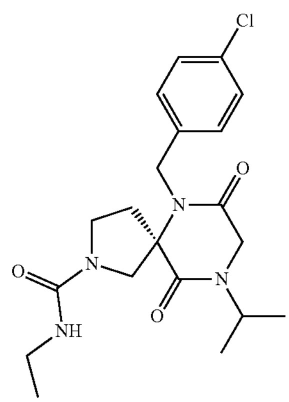 [SMILES: CCNC(=O)N1CC[C@@]2(C1)C(=O)N(C(C)C)CC(=O)N2Cc1ccc(Cl)cc1] | (R)-6-(4-chlorobenzyl)-N-ethyl-9-isopropyl-7,10-dioxo-2,6,9-triazaspiro-[4.5]decane-2-carboxamide |
| 383 | 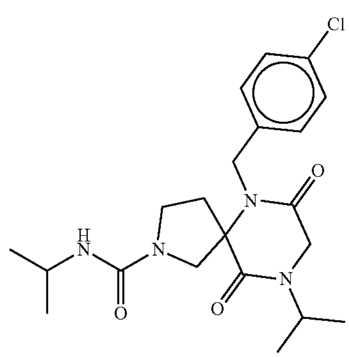 | 6-(4-chlorobenzyl)-N,9-diisopropyl-7,10-dioxo-2,6,9-triazaspiro[4.5]-decane-2-carboxamide |
| 384 | 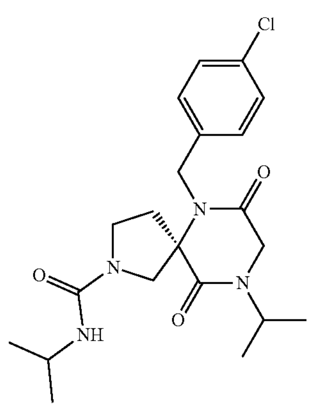 [SMILES: CC(C)NC(=O)N1CC[C@@]2(C1)C(=O)N(C(C)C)CC(=O)N2Cc1ccc(Cl)cc1] | (R)-6-(4-chlorobenzyl)-N,9-diisopropyl-7,10-dioxo-2,6,9-triazaspiro-[4.5]decane-2-carboxamide |

TABLE 1-continued

| No. | Structure | Name |
| --- | --- | --- |
| 385 | 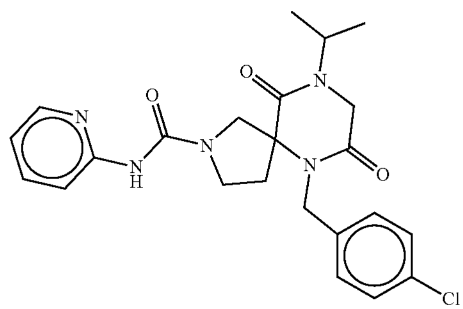 | 6-(4-chlorobenzyl)-9-isopropyl-7,10-dioxo-N-(pyridin-2-yl)-2,6,9-triazaspiro[4.5]decane-2-carboxamide |
| 386 | 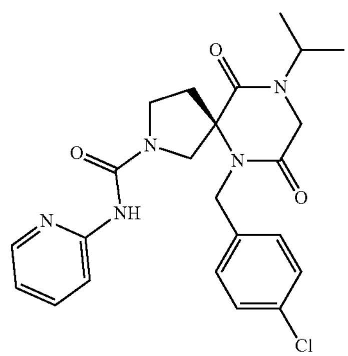 [SMILES: CC(C)N1CC(=O)N(Cc2ccc(Cl)cc2)[C@@]2(CCN(C(=O)Nc3ccccn3)C2)C1=O] | (R)-6-(4-chlorobenzyl)-9-isopropyl-7,10-dioxo-N-(pyridin-2-yl)-2,6,9-triazaspiro[4.5]decane-2-carboxamide |
| 387 | 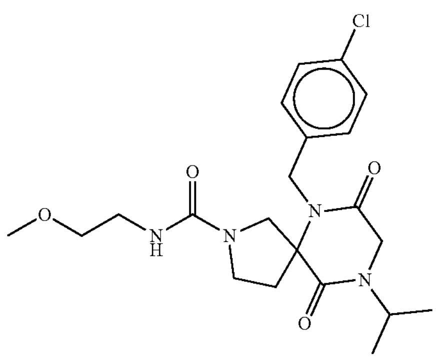 | 6-(4-chlorobenzyl)-9-isopropyl-N-(2-methoxy-ethyl)-7,10-dioxo-2,6,9-triazaspiro[4.5]decane-2-carboxamide |
| 388 | 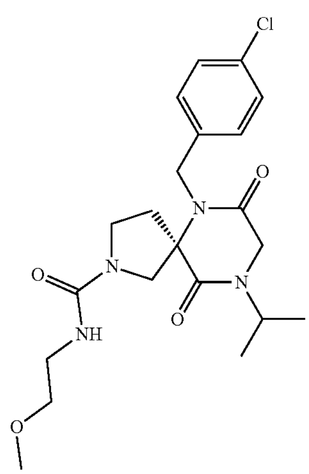 [SMILES: COCCNC(=O)N1CC[C@@]2(C1)C(=O)N(C(C)C)CC(=O)N2Cc1ccc(Cl)cc1] | (R)-6-(4-chlorobenzyl)-9-isopropyl-N-(2-methoxy-ethyl)-7,10-dioxo-2,6,9-triazaspiro[4.5]decane-2-carboxamide |

TABLE 1-continued

| No. | Structure | Name |
|---|---|---|
| 389 | 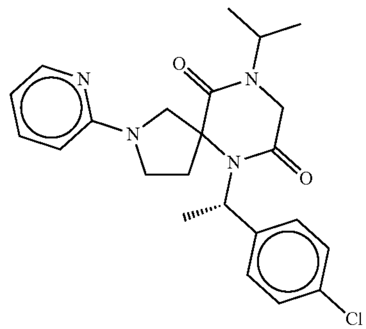 | 6-((S)-1-(4-chlorophenyl)-ethyl)-9-isopropyl-2-(pyridin-2-yl)-2,6,9-triazaspiro[4.5]decane-7,10-dione |
| 390 | 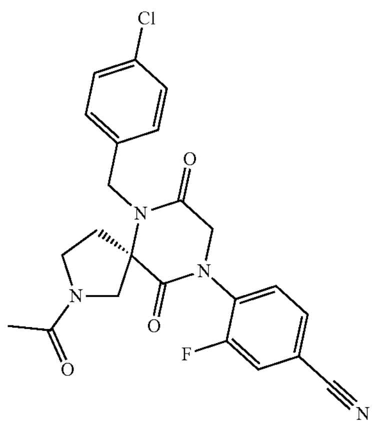 [SMILES: CC(=O)N1CC[C@@]2(C1)C(=O)N(c1ccc(C#N)cc1F)CC(=O)N2Cc1ccc(Cl)cc1] | (R)-4-(2-acetyl-6-(4-chlorobenzyl)-7,10-dioxo-2,6,9-triazaspiro[4.5]decan-9-yl)-3-fluorobenzonitrile |
| 391 | 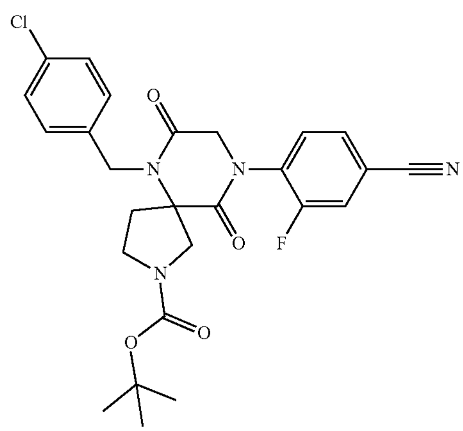 [SMILES: CC(C)(C)OC(=O)N1CCC2(C1)C(=O)N(c1ccc(C#N)cc1F)CC(=O)N2Cc1ccc(Cl)cc1] | tert-butyl 6-(4-chlorobenzyl)-9-(4-cyano-2-fluorophenyl)-7,10-dioxo-2,6,9-triazaspiro[4.5]decane-2-carboxylate |
| 392 | 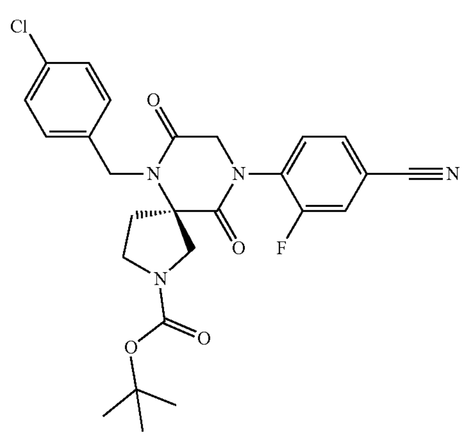 [SMILES: CC(C)(C)OC(=O)N1CC[C@@]2(C1)C(=O)N(c1ccc(C#N)cc1F)CC(=O)N2Cc1ccc(Cl)cc1] | tert-butyl (R)-6-(4-chlorobenzyl)-9-(4-cyano-2-fluorophenyl)-7,10-dioxo-2,6,9-triazaspiro[4.5]decane-2-carboxylate |

TABLE 1-continued

| No. | Structure | Name |
|---|---|---|
| 393 | 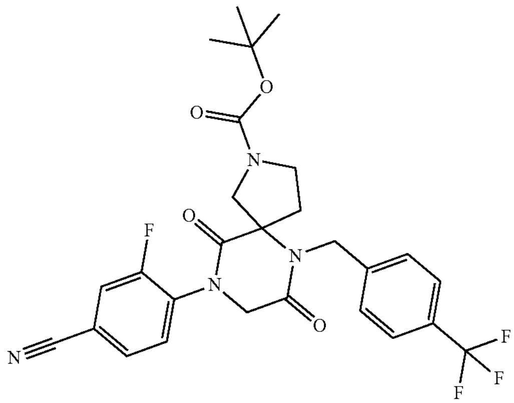 [SMILES: CC(C)(C)OC(=O)N1CCC2(C1)C(=O)N(c1ccc(C#N)cc1F)CC(=O)N2Cc1ccc(C(F)(F)F)cc1] | tert-butyl 9-(4-cyano-2-fluorophenyl)-7,10-dioxo-6-(4-(trifluoromethyl)-benzyl)-2,6,9-triazaspiro-[4.5]decane-2-carboxylate |
| 394 | 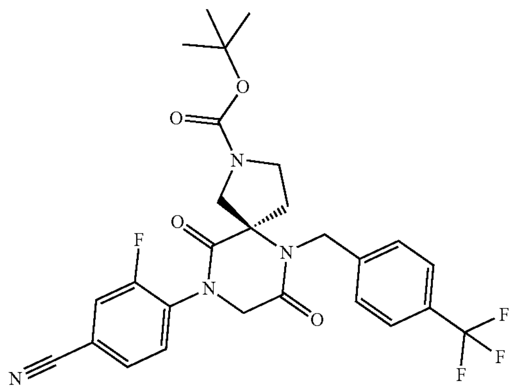 [SMILES: CC(C)(C)OC(=O)N1CC[C@@]2(C1)C(=O)N(c1ccc(C#N)cc1F)CC(=O)N2Cc1ccc(C(F)(F)F)cc1] | tert-butyl (R)-9-(4-cyano-2-fluorophenyl)-7,10-dioxo-6-(4-(trifluoromethyl)benzyl)-2,6,9-triazaspiro[4.5]decane-2-carboxylate |
| 395 | 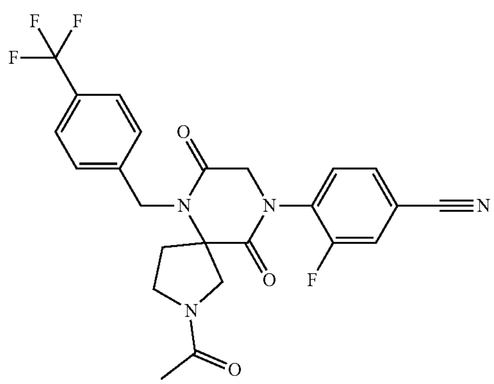 | 4-(2-acetyl-7,10-dioxo-6-(4-(trifluoromethyl)benzyl)-2,6,9-triazaspiro[4.5]decan-9-yl)-3-fluorobenzonitrile |
| 396 | 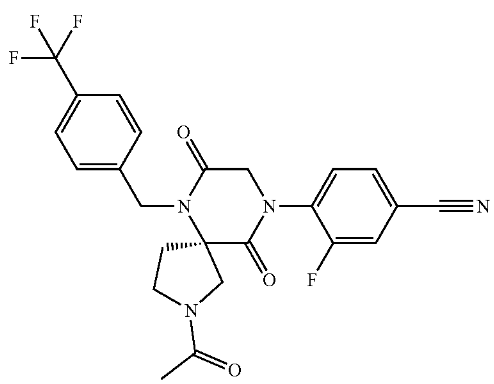 [SMILES: CC(=O)N1CC[C@@]2(C1)C(=O)N(c1ccc(C#N)cc1F)CC(=O)N2Cc1ccc(C(F)(F)F)cc1] | (R)-4-(2-acetyl-7,10-dioxo-6-(4-(trifluoromethyl)benzyl)-2,6,9-triazaspiro[4.5]decan-9-yl)-3-fluorobenzonitrile |

TABLE 1-continued

| No. | Structure | Name |
|---|---|---|
| 397 | 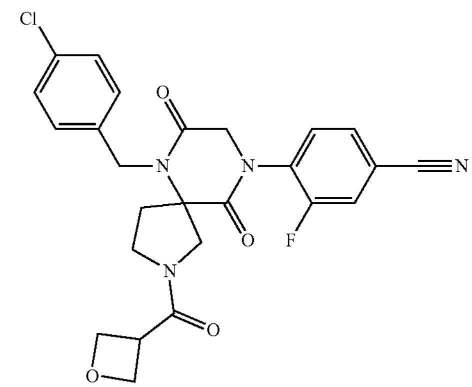 | 4-(6-(4-chlorobenzyl)-2-(oxetane-3-carbonyl)-7,10-dioxo-2,6,9-triazaspiro[4.5]decan-9-yl)-3-fluorobenzonitrile |
| 398 | 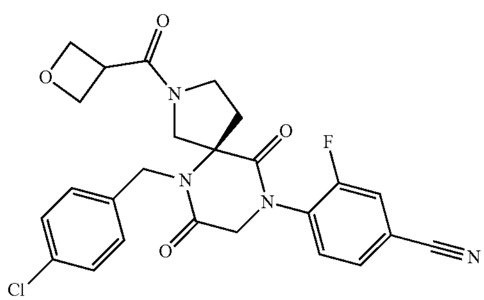 [SMILES: N#Cc1ccc(N2CC(=O)N(Cc3ccc(Cl)cc3)[C@@]3(CCN(C(=O)C4COC4)C3)C2=O)c(F)c1] | (R)-4-(6-(4-chlorobenzyl)-2-(oxetane-3-carbonyl)-7,10-dioxo-2,6,9-triazaspiro[4.5]decan-9-yl)-3-fluorobenzonitrile |
| 399 | 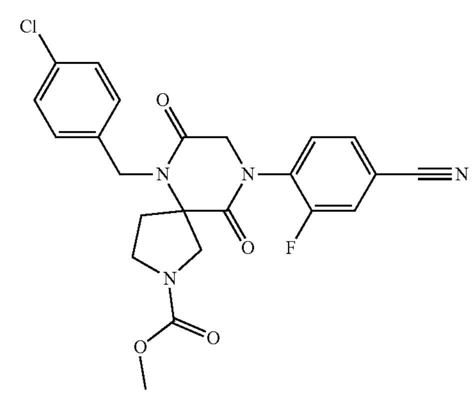 [SMILES: COC(=O)N1CCC2(C1)C(=O)N(c1ccc(C#N)cc1F)CC(=O)N2Cc1ccc(Cl)cc1] | methyl 6-(4-chlorobenzyl)-9-(4-cyano-2-fluorophenyl)-7,10-dioxo-2,6,9-triazaspiro[4.5]decane-2-carboxylate |
| 400 | 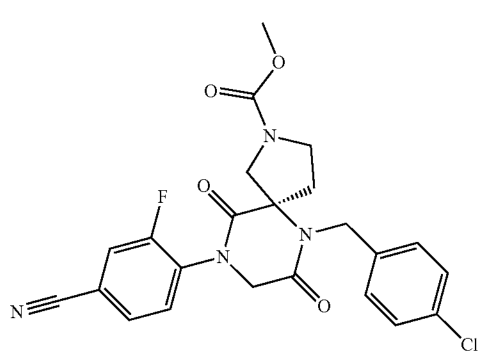 [SMILES: COC(=O)N1CC[C@@]2(C1)C(=O)N(c1ccc(C#N)cc1F)CC(=O)N2Cc1ccc(Cl)cc1] | methyl (R)-6-(4-chlorobenzyl)-9-(4-cyano-2-fluorophenyl)-7,10-dioxo-2,6,9-triazaspiro[4.5]-decane-2-carboxylate |

TABLE 1-continued

| No. | Structure | Name |
|---|---|---|
| 401 | 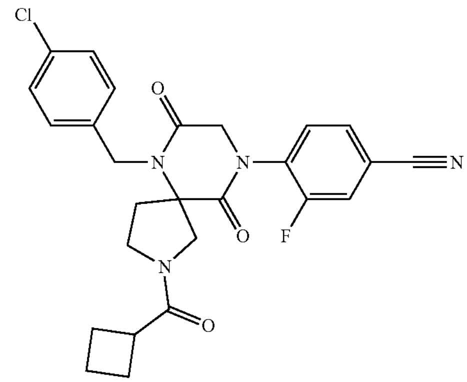 [SMILES: N#Cc1ccc(N2CC(=O)N(Cc3ccc(Cl)cc3)C3(CCN(C(=O)C4CCC4)C3)C2=O)c(F)c1] | 4-(6-(4-chlorobenzyl)-2-(cyclobutanecarbonyl)-7,10-dioxo-2,6,9-triazaspiro[4.5]decan-9-yl)-3-fluorobenzonitrile |
| 402 | 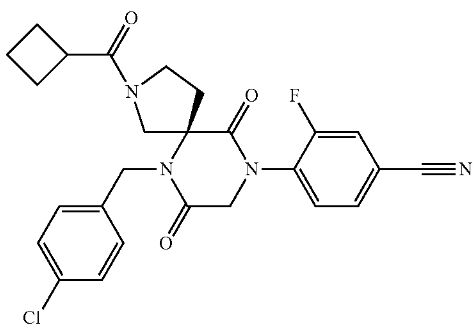 [SMILES: N#Cc1ccc(N2CC(=O)N(Cc3ccc(Cl)cc3)[C@@]3(CCN(C(=O)C4CCC4)C3)C2=O)c(F)c1] | (R)-4-(6-(4-chlorobenzyl)-2-(cyclobutanecarbonyl)-7,10-dioxo-2,6,9-triazaspiro[4.5]decan-9-yl)-3-fluorobenzonitrile |
| 403 | 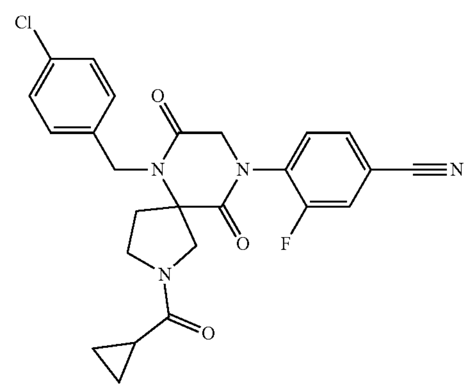 [SMILES: N#Cc1ccc(N2CC(=O)N(Cc3ccc(Cl)cc3)C3(CCN(C(=O)C4CC4)C3)C2=O)c(F)c1] | 4-(6-(4-chlorobenzyl)-2-(cyclopropanecarbonyl)-7,10-dioxo-2,6,9-triazaspiro[4.5]decan-9-yl)-3-fluorobenzonitrile |
| 404 | 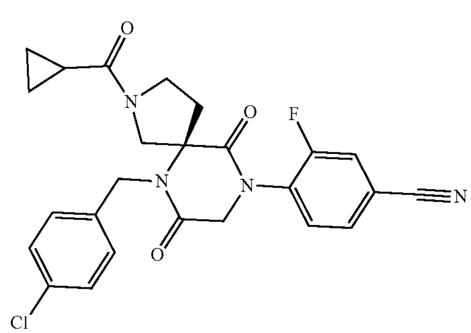 [SMILES: N#Cc1ccc(N2CC(=O)N(Cc3ccc(Cl)cc3)[C@@]3(CCN(C(=O)C4CC4)C3)C2=O)c(F)c1] | (R)-4-(6-(4-chlorobenzyl)-2-(cyclopropanecarbonyl)-7,10-dioxo-2,6,9-triazaspiro[4.5]decan-9-yl)-3-fluorobenzonitrile |

TABLE 1-continued

| No. | Structure | Name |
|---|---|---|
| 405 | 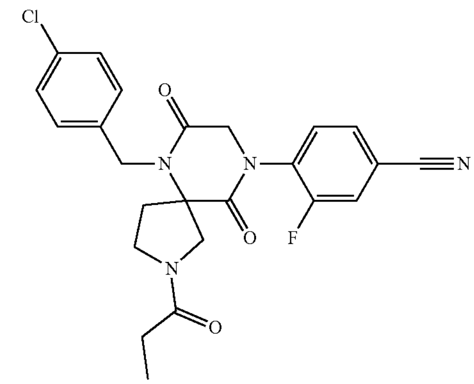 [SMILES: CCC(=O)N1CCC2(C1)C(=O)N(c1ccc(C#N)cc1F)CC(=O)N2Cc1ccc(Cl)cc1] | 4-(6-(4-chlorobenzyl)-7,10-dioxo-2-propionyl-2,6,9-triazaspiro[4.5]decan-9-yl)-3-fluorobenzonitrile |
| 406 | 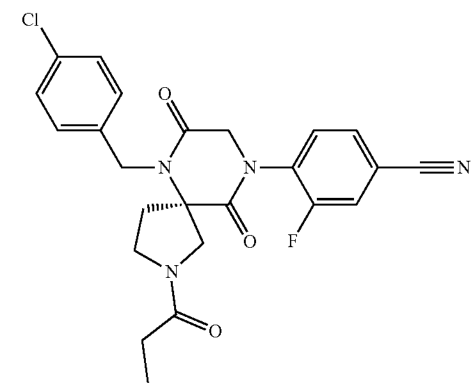 [SMILES: CCC(=O)N1CC[C@@]2(C1)C(=O)N(c1ccc(C#N)cc1F)CC(=O)N2Cc1ccc(Cl)cc1] | (R)-4-(6-(4-chlorobenzyl)-7,10-dioxo-2-propionyl-2,6,9-triazaspiro[4.5]decan-9-yl)-3-fluorobenzonitrile |
| 407 | 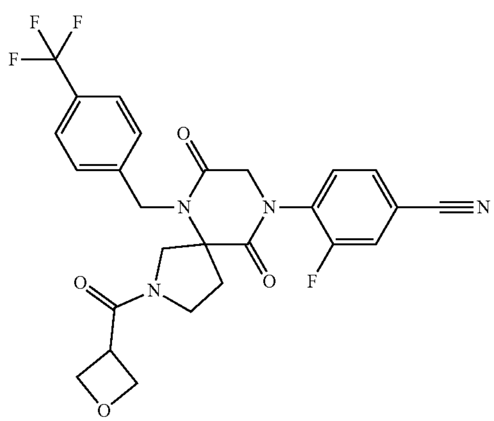 [SMILES: N#Cc1ccc(N2CC(=O)N(Cc3ccc(C(F)(F)F)cc3)C3(CCN(C(=O)C4COC4)C3)C2=O)c(F)c1] | 3-fluoro-4-(2-(oxetane-3-carbonyl)-7,10-dioxo-6-(4-(trifluoromethyl)benzyl)-2,6,9-triazaspiro[4.5]decan-9-yl)benzonitrile |
| 408 | 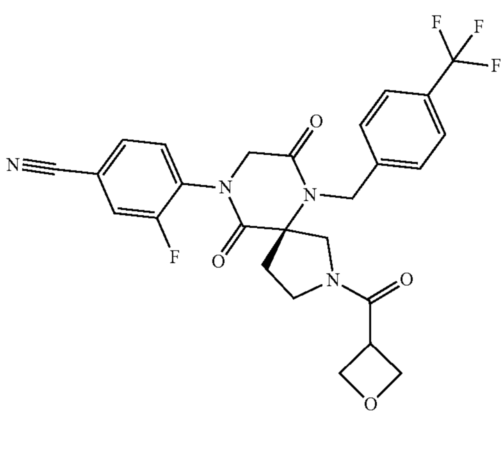 [SMILES: N#Cc1ccc(N2CC(=O)N(Cc3ccc(C(F)(F)F)cc3)[C@@]3(CCN(C(=O)C4COC4)C3)C2=O)c(F)c1] | (R)-3-fluoro-4-(2-(oxetane-3-carbonyl)-7,10-dioxo-6-(4-(trifluoromethyl)benzyl)-2,6,9-triazaspiro[4.5]decan-9-yl)benzonitrile |

TABLE 1-continued
| No. | Structure | Name |
|---|---|---|
| 409 | 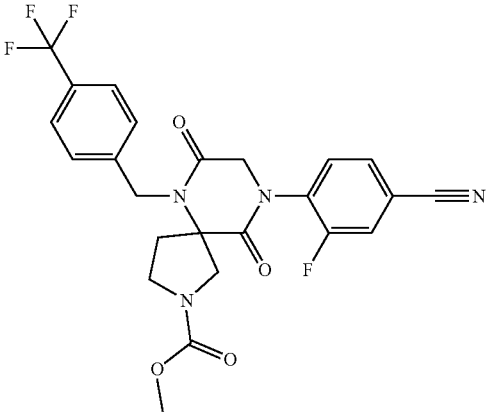 [SMILES: COC(=O)N1CCC2(C1)C(=O)N(c1ccc(C#N)cc1F)CC(=O)N2Cc1ccc(C(F)(F)F)cc1] | methyl 9-(4-cyano-2-fluoro-phenyl)-7,10-dioxo-6-(4-(trifluoromethyl)benzyl)-2,6,9-triazaspiro[4.5]-decane-2-carboxylate |
| 410 | 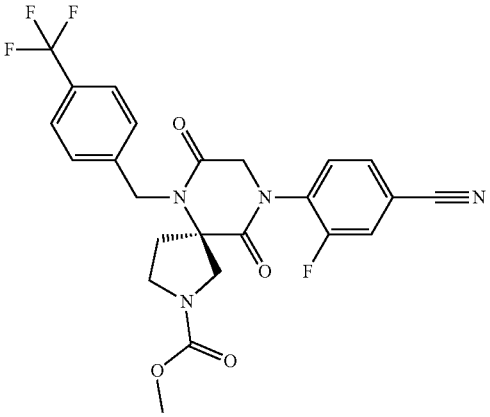 | methyl (R)-9-(4-cyano-2-fluorophenyl)-7,10-dioxo-6-(4-(trifluororriethyl)benzyl)-2,6,9-triazaspiro[4.5]decane-2-carboxylate |
| 411 | 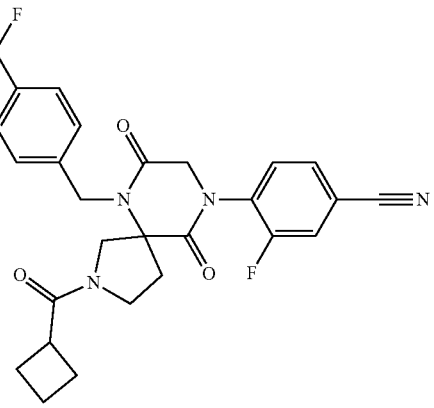 | 4-(2-(cyclobutanecarbonyl)-7,10-dioxo-6-(4-(trifluoromethyl)benzyl)-2,6,9-triazaspiro[4.5]decan-9-yl)-3-fluorobenzonitrile |

TABLE 1-continued

| No. | Structure | Name |
|---|---|---|
| 412 | 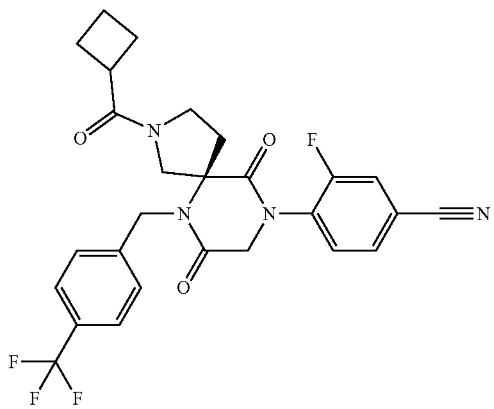 | (R)-4-(2-(cyclobutane-carbonyl)-7,10-dioxo-6-(4-(trifluoromethyl)benzyl)-2,6,9-triazaspiro[4.5]decan-9-yl)-3-fluorobenzonitrile |
| 413 | 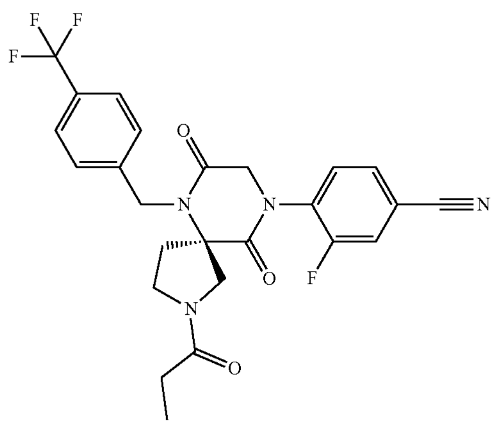 [SMILES: COC(=O)N1CC[C@@]2(C1)C(=O)N(c1ccc(C#N)cc1F)CC(=O)N2Cc1ccc(C(F)(F)F)cc1] | 4-(7,10-dioxo-2-propionyl-6-(4-(trifluoromethyl)-benzyl)-2,6,9-triazaspiro-[4.5]decan-9-yl)-3-fluorobenzonitrile |
| 414 | 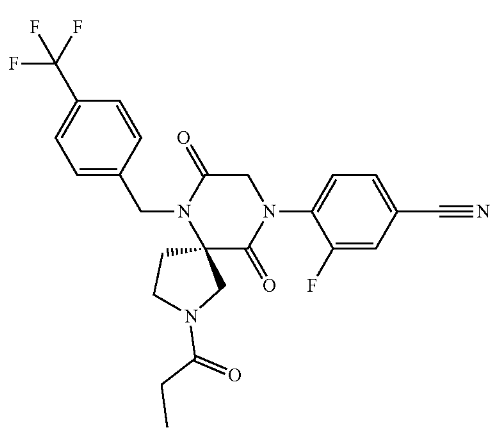 [SMILES: CCC(=O)N1CC[C@@]2(C1)C(=O)N(c1ccc(C#N)cc1F)CC(=O)N2Cc1ccc(C(F)(F)F)cc1] | (R)-4-(7,10-dioxo-2-propionyl-6-(4-(trifluoromethyl)benzyl)-2,6,9-triazaspiro[4.5]decan-9-yl)-3-fluorobenzonitrile |

TABLE 1-continued

| No. | Structure | Name |
| --- | --- | --- |
| 415 | 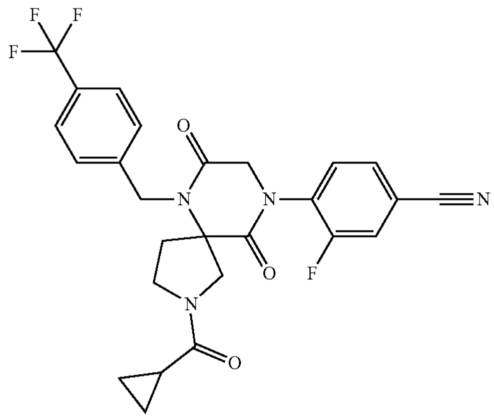 [SMILES: N#Cc1ccc(N2CC(=O)N(Cc3ccc(C(F)(F)F)cc3)C3(CCN(C(=O)C4CC4)C3)C2=O)c(F)c1] | 4-(2-(cyclopropanecarbonyl)-7,10-dioxo-6-(4-(trifluoromethyl)benzyl)-2,6,9-triazaspiro[4.5]decan-9-yl)-3-fluorobenzonitrile |
| 416 | 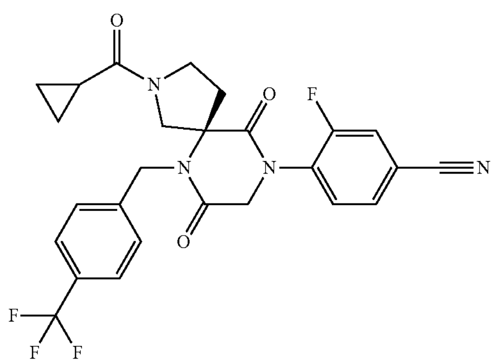 [SMILES: N#Cc1ccc(N2CC(=O)N(Cc3ccc(C(F)(F)F)cc3)[C@@]3(CCN(C(=O)C4CC4)C3)C2=O)c(F)c1] | (R)-4-(2-(cyclopropanecarbonyl)-7,10-dioxo-6-(4-(trifluoromethyl)benzyl)-2,6,9-triazaspiro[4.5]decan-9-yl)-3-fluorobenzonitrile |
| 417 | 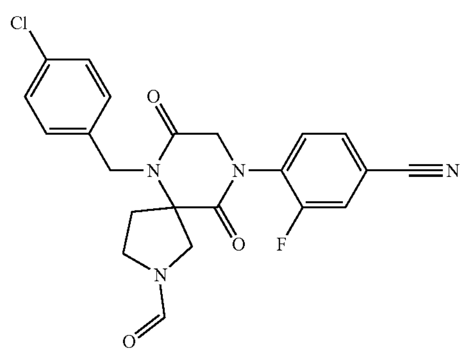 [SMILES: N#Cc1ccc(N2CC(=O)N(Cc3ccc(Cl)cc3)C3(CCN(C=O)C3)C2=O)c(F)c1] | 4-(6-(4-chlorobenzyl)-2-formyl-7,10-dioxo-2,6,9-triazaspiro[4.5]decan-9-yl)-3-fluorobenzonitrile |
| 418 | 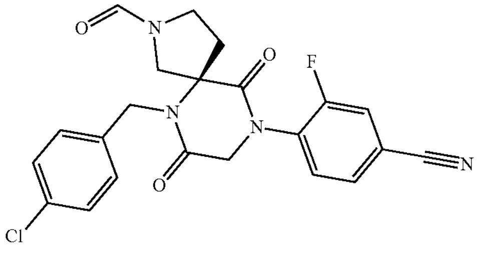 [SMILES: N#Cc1ccc(N2CC(=O)N(Cc3ccc(Cl)cc3)[C@@]3(CCN(C=O)C3)C2=O)c(F)c1] | (R)-4-(6-(4-chlorobenzyl)-2-formyl-7,10-dioxo-2,6,9-triazaspiro[4.5]decan-9-yl)-3-fluorobenzonitrile |

TABLE 1-continued

| No. | Structure | Name |
|---|---|---|
| 419 | 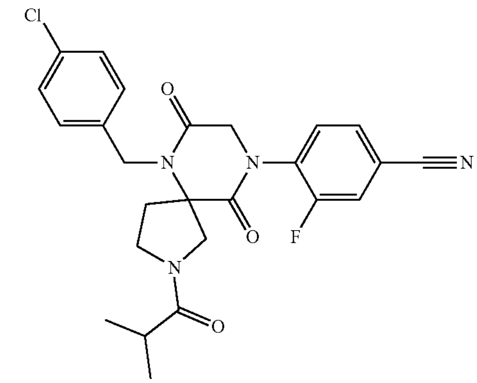 [SMILES: CC(C)C(=O)N1CCC2(C1)C(=O)N(c1ccc(C#N)cc1F)CC(=O)N2Cc1ccc(Cl)cc1] | 4-(6-(4-chlorobenzyl)-2-isobutyryl-7,10-dioxo-2,6,9-triazaspiro[4.5]decan-9-yl)-3-fluorobenzonitrile |
| 420 | 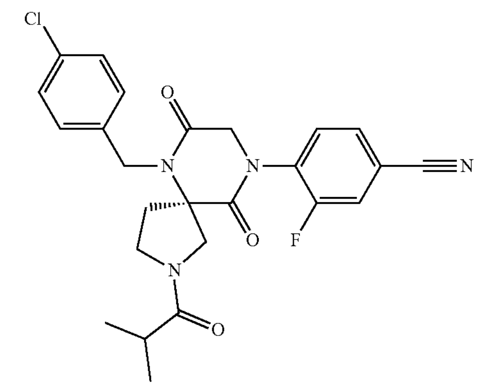 [SMILES: CC(C)C(=O)N1CC[C@@]2(C1)C(=O)N(c1ccc(C#N)cc1F)CC(=O)N2Cc1ccc(Cl)cc1] | (R)-4-(6-(4-chlorobenzyl)-2-isobutyryl-7,10-dioxo-2,6,9-triazaspiro[4.5]decan-9-yl)-3-fluorobenzonitrile |
| 421 | 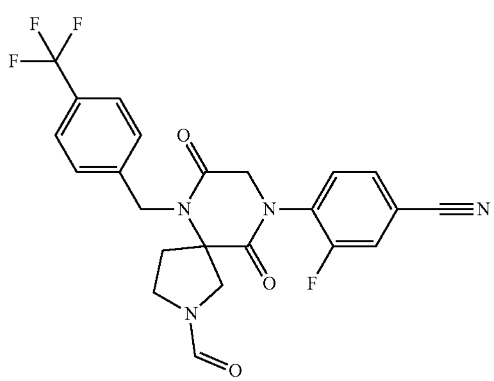 [SMILES: N#Cc1ccc(N2CC(=O)N(Cc3ccc(C(F)(F)F)cc3)C3(CCN(C=O)C3)C2=O)c(F)c1] | 3-fluoro-4-(2-formyl-7,10-dioxo-6-(4-(trifluoromethyl)benzyl)-2,6,9-triazaspiro[4.5]decan-9-yl)benzonitrile |
| 422 | 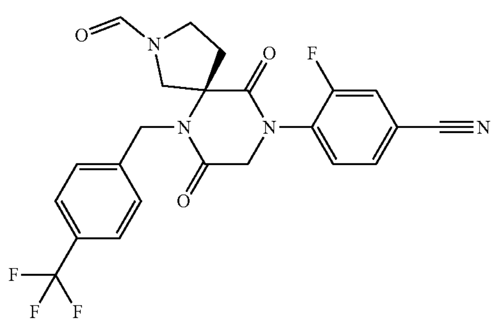 [SMILES: N#Cc1ccc(N2CC(=O)N(Cc3ccc(C(F)(F)F)cc3)[C@@]3(CCN(C=O)C3)C2=O)c(F)c1] | (R)-3-fluoro-4-(2-formyl-7,10-dioxo-6-(4-(trifluoromethyl)benzyl)-2,6,9-triazaspiro[4.5]decan-9-yl)benzonitrile |

TABLE 1-continued

| No. | Structure | Name |
|---|---|---|
| 423 | 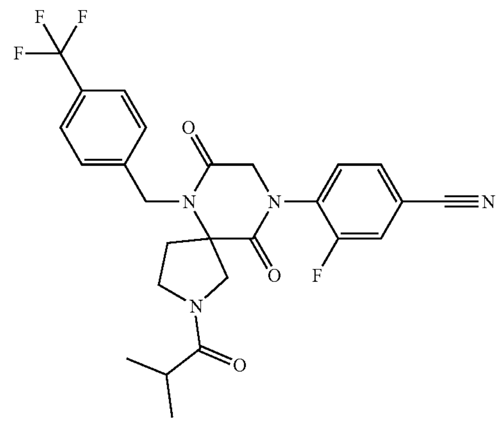 | 3-fluoro-4-(2-isobutyryl-7,10-dioxo-6-(4-(trifluoromethyl)benzyl)-2,6,9-triazaspiro[4.5]decan-9-yl)benzonitrile |
| 424 | 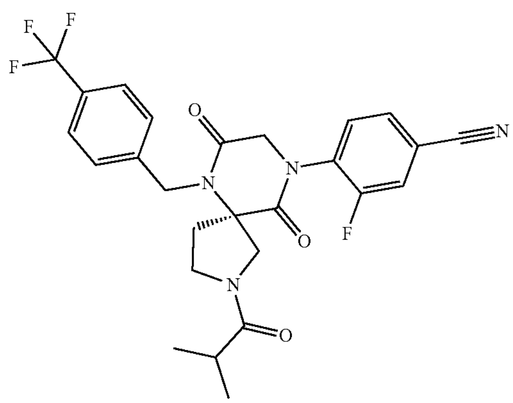 [SMILES: CC(C)C(=O)N1CC[C@@]2(C1)C(=O)N(c1ccc(C#N)cc1F)CC(=O)N2Cc1ccc(C(F)(F)F)cc1] | (R)-3-fluoro-4-(2-isobutyryl-7,10-dioxo-6-(4-(trifluoromethyl)benzyl)-2,6,9-triazaspiro[4.5]decan-9-yl)benzonitrile |
| 425 | 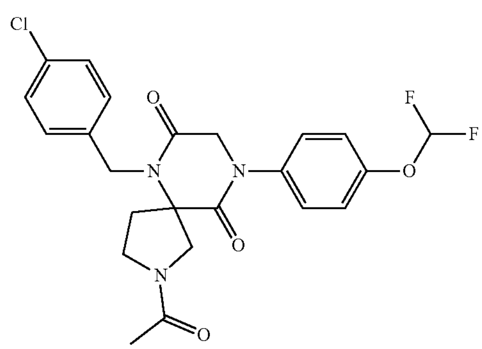 [SMILES: CC(=O)N1CCC2(C1)C(=O)N(c1ccc(OC(F)F)cc1)CC(=O)N2Cc1ccc(Cl)cc1] | 2-acetyl-6-(4-chlorobenzyl)-9-(4-(difluoromethoxy)-phenyl)-2,6,9-triazaspiro-[4.5]decane-7,10-dione |
| 426 | 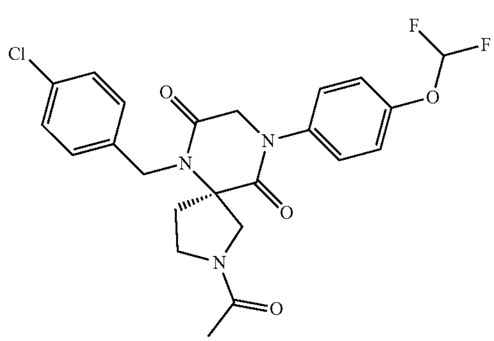 [SMILES: CC(=O)N1CC[C@@]2(C1)C(=O)N(c1ccc(OC(F)F)cc1)CC(=O)N2Cc1ccc(Cl)cc1] | (R)-2-acetyl-6-(4-chloro-benzyl)-9-(4-(difluoro-methoxy)phenyl)-2,6,9-triazaspiro[4.5]decane-7,10-dione |

TABLE 1-continued

| No. | Structure | Name |
|---|---|---|
| 427 | 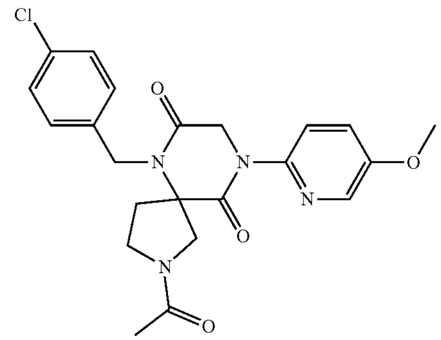 [SMILES: COc1ccc(N2CC(=O)N(Cc3ccc(Cl)cc3)C3(CCN(C(C)=O)C3)C2=O)nc1] | 2-acetyl-6-(4-chlorobenzyl)-9-(5-methoxypyridin-2-yl)-2,6,9-triazaspiro[4.5]-decane-7,10-dione |
| 428 | 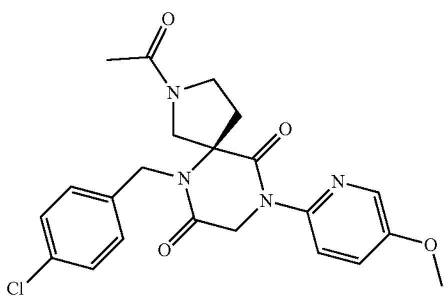 [SMILES: COc1ccc(N2CC(=O)N(Cc3ccc(Cl)cc3)[C@@]3(CCN(C(C)=O)C3)C2=O)nc1] | (R)-2-acetyl-6-(4-chlorobenzyl)-9-(5-methoxypyridin-2-yl)-2,6,9-triazaspiro[4.5]decane-7,10-dione |
| 429 | 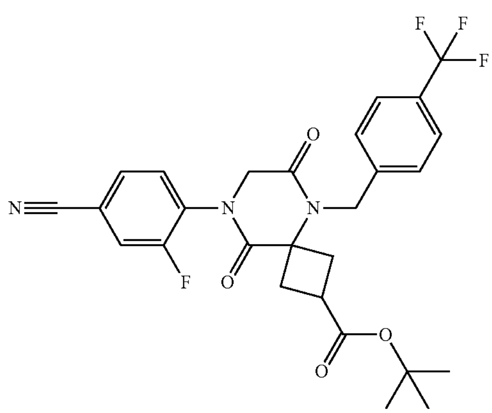 [SMILES: CC(C)(C)OC(=O)C1CC2(C1)C(=O)N(c1ccc(C#N)cc1F)CC(=O)N2Cc1ccc(C(F)(F)F)cc1] | tert-butyl 8-(4-cyano-2-fluorophenyl)-6,9-dioxo-5-(4-(trifluoromethyl)benzyl)-5,8-diazaspiro[3.5]nonane-2-carboxylate |
| 430 | 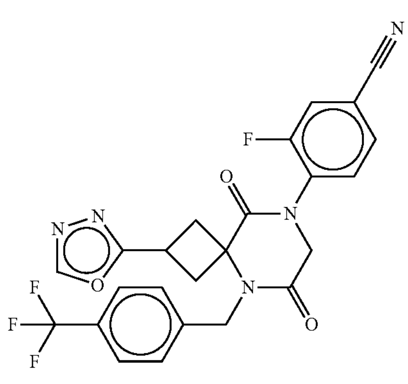 | 4-(2-(1,3,4-oxadiazol-2-yl)-6,9-dioxo-5-(4-(trifluoromethyl)benzyl)-5,8-diazaspiro[3.5]nonan-8-yl)-3-fluorobenzonitrile |

TABLE 1-continued

| No. | Structure | Name |
|---|---|---|
| 431 | 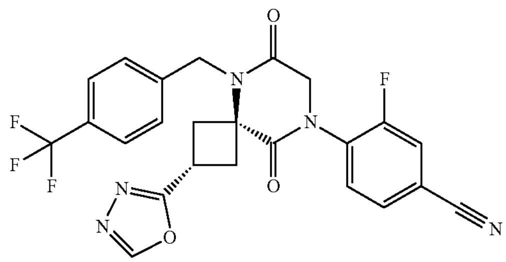 [SMILES: N#Cc1ccc(N2CC(=O)N(Cc3ccc(C(F)(F)F)cc3)[C@]3(C[C@H](c4nnco4)C3)C2=O)c(F)c1] | 4-((2r,4r)-2-(1,3,4-oxadiazol-2-yl)-6,9-dioxo-5-(4-(trifluoromethyl)-benzyl)-5,8-diazaspiro-[3.5]nonan-8-yl)-3-fluorobenzonitrile |
| 432 | 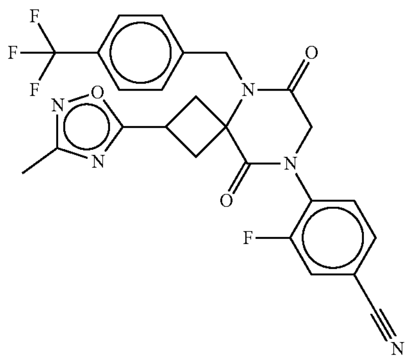 | 3-fluoro-4-(2-(3-methyl-1,2,4-oxadiazol-5-yl)-6,9-dioxo-5-(4-(trifluoromethyl)-benzyl)-5,8-diazaspiro[3.5]-nonan-8-yl)benzonitrile |
| 433 | 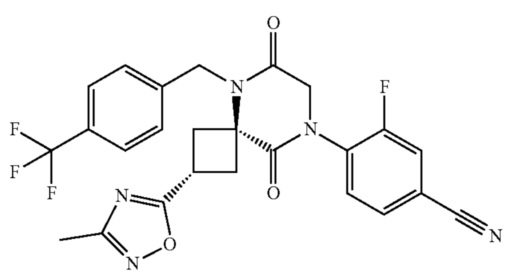 [SMILES: Cc1noc([C@H]2C[C@]3(C2)C(=O)N(c2ccc(C#N)cc2F)CC(=O)N3Cc2ccc(C(F)(F)F)cc2)n1] | 3-fluoro-4-((2r,4r)-2-(3-methyl-1,2,4-oxadiazol-5-yl)-6,9-dioxo-5-(4-(trifluoromethyl)benzyl)-5,8-diazaspiro[3.5]nonan-8-yl)benzonitrile |
| 434 | 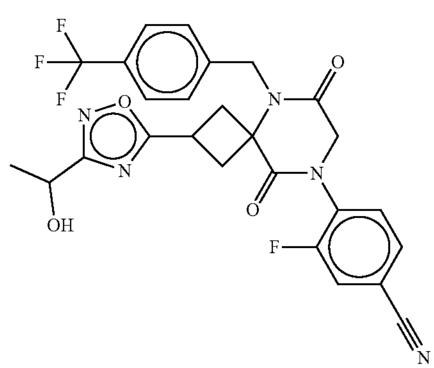 | 3-fluoro-4-(2-(3-(1-hydroxyethyl)-1,2,4-oxadiazol-5-yl)-6,9-dioxo-5-(4-(trifluoromethyl)-benzyl)-5,8-diazaspiro[3.5]-nonan-8-yl)benzonitrile |

TABLE 1-continued

| No. | Structure | Name |
|---|---|---|
| 435 | 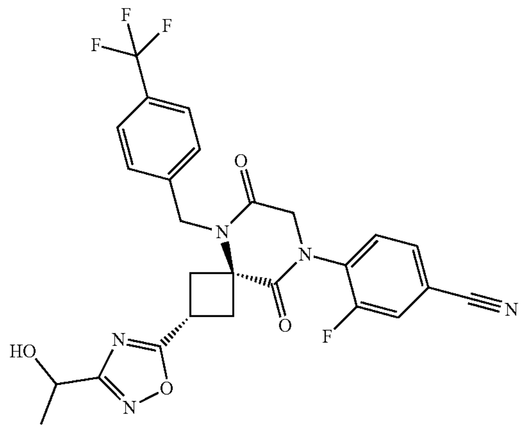 [SMILES: CC(O)c1noc([C@H]2C[C@]3(C2)C(=O)N(c2ccc(C#N)cc2F)CC(=O)N3Cc2ccc(C(F)(F)F)cc2)n1] | 3-fluoro-4-((2r,4r)-2-(3-(1-hydroxyethyl)-1,2,4-oxadiazol-5-yl)-6,9-dioxo-5-(4-(trifluoromethyl)benzyl)-5,8-diazaspiro[3.5]-nonan-8-yl)benzonitrile |
| 436 | 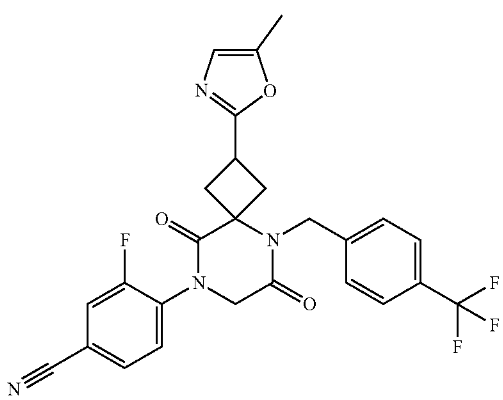 [SMILES: Cc1cnc(C2CC3(C2)C(=O)N(c2ccc(C#N)cc2F)CC(=O)N3Cc2ccc(C(F)(F)F)cc2)o1] | 3-fluoro-4-(2-(5-methyl-oxazol-2-yl)-6,9-dioxo-5-(4-trifluoromethyl)benzyl)-5,8-diazaspiro[3.5]nonan-8-yl)benzonitrile |
| 437 | 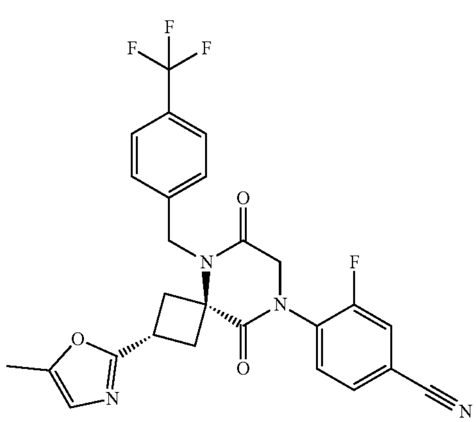 [SMILES: Cc1cnc([C@H]2C[C@]3(C2)C(=O)N(c2ccc(C#N)cc2F)CC(=O)N3Cc2ccc(C(F)(F)F)cc2)o1] | 3-fluoro-4-((2r,4r)-2-(5-methyloxazol-2-yl)-6,9-dioxo-5-(4-(trifluoromethyl)-benzyl)-5,8-diazaspiro[3.5]-nonan-8-yl)benzonitrile |

TABLE 1-continued

| No. | Structure | Name |
|---|---|---|
| 438 | 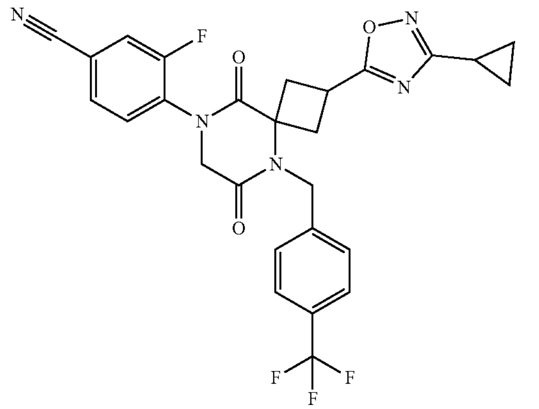 [SMILES: N#Cc1ccc(N2CC(=O)N(Cc3ccc(C(F)(F)F)cc3)C3(CC(c4nc(C5CC5)no4)C3)C2=O)c(F)c1] | 4-(2-(3-cyclopropyl-1,2,4-oxadiazol-5-yl)-6,9-dioxo-5-(4-(trifluoromethyl)benzyl)-5,8-diazaspiro[3.5]nonan-8-yl)-3-fluorobenzonitrile |
| 439 | 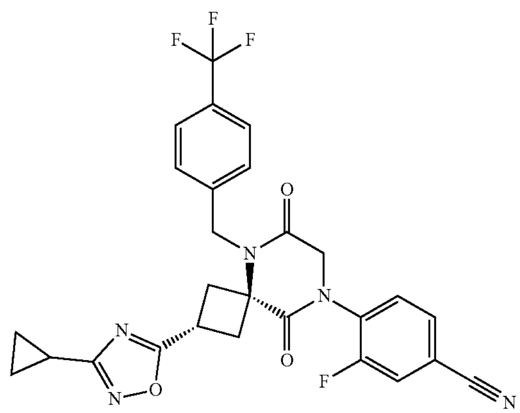 [SMILES: N#Cc1ccc(N2CC(=O)N(Cc3ccc(C(F)(F)F)cc3)[C@]3(C[C@H](c4nc(C5CC5)no4)C3)C2=O)c(F)c1] | 4-((2r,4r)-2-(3-cyclopropyl-1,2,4-oxadiazol-5-yl)-6,9-dioxo-5-(4-(trifluoromethyl)-benzyl)-5,8-diazaspiro[3.5]-nonan-8-yl)-3-fluoro-benzonitrile |
| 440 | 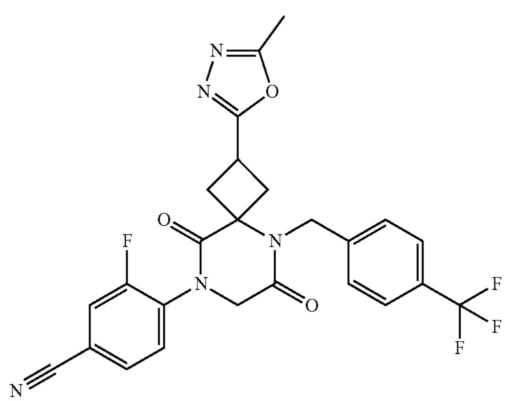 [SMILES: Cc1nnc(C2CC3(C2)C(=O)N(c2ccc(C#N)cc2F)CC(=O)N3Cc2ccc(C(F)(F)F)cc2)o1] | 3-fluoro-4-(2-(5-methyl-1,3,4-oxadiazol-2-yl)-6,9-dioxo-5-(4-(trifluoromethyl)-benzyl)-5,8-diazaspiro[3.5]nonan-8-yl)benzonitrile |
| 441 | 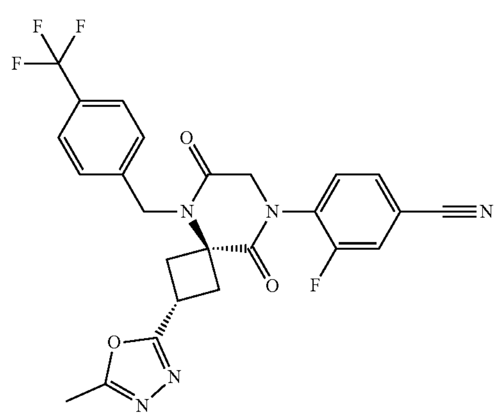 [SMILES: Cc1nnc([C@H]2C[C@]3(C2)C(=O)N(c2ccc(C#N)cc2F)CC(=O)N3Cc2ccc(C(F)(F)F)cc2)o1] | 3-fluoro-4-((2r,4r)-2-(5-methyl-1,3,4-oxadiazol-2-yl)-6,9-dioxo-5-(4-(trifluoromethyl)benzyl)-5,8-diazaspiro[3.5]nonan-8-yl)benzonitrile |

TABLE 1-continued

| No. | Structure | Name |
|---|---|---|
| 442 | 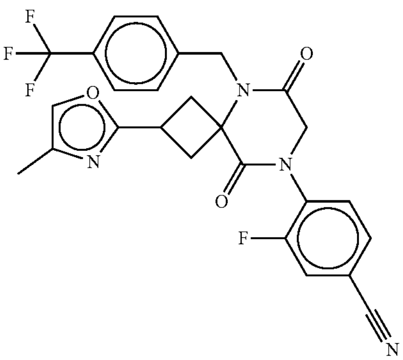 | 3-fluoro-4-(2-(4-methyloxazol-2-yl)-6,9-dioxo-5-(4-(trifluoromethyl)benzyl)-5,8-diazaspiro[3.5]nonan-8-yl)benzonitrile |
| 443 | 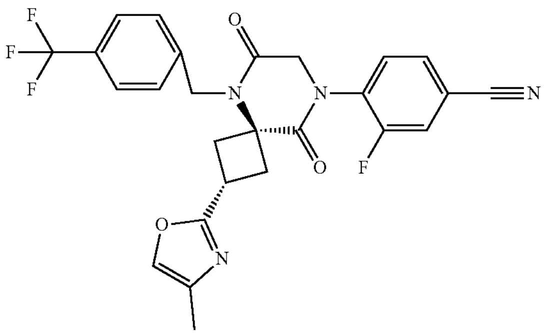 [SMILES: Cc1coc([C@H]2C[C@]3(C2)C(=O)N(c2ccc(C#N)cc2F)CC(=O)N3Cc2ccc(C(F)(F)F)cc2)n1] | 3-fluoro-4-((2r,4r)-2-(4-methyloxazol-2-yl)-6,9-dioxo-5-(4-(trifluoromethyl)-benzyl)-5,8-diazaspiro-[3.5]nonan-8-yl)benzonitrile |
| 444 | 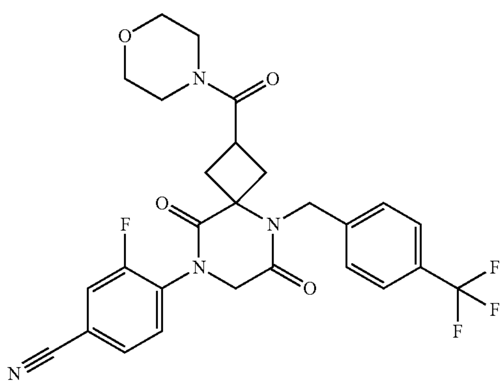 [SMILES: N#Cc1ccc(N2CC(=O)N(Cc3ccc(C(F)(F)F)cc3)C3(CC(C(=O)N4CCOCC4)C3)C2=O)c(F)c1] | 3-fluoro-4-(2-(morpholine-4-carbonyl)-6,9-dioxo-5-(4-(trifluoromethyl)benzyl)-5,8-diazaspiro[3.5]nonan-8-yl)benzonitrile |
| 445 | 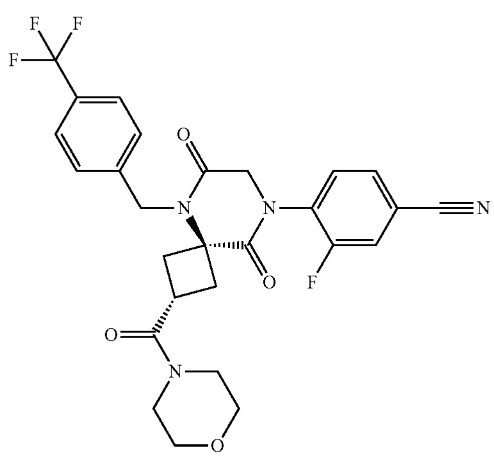 [SMILES: N#Cc1ccc(N2CC(=O)N(Cc3ccc(C(F)(F)F)cc3)[C@]3(C[C@H](C(=O)N4CCOCC4)C3)C2=O)c(F)c1] | 3-fluoro-4-((2r,4r)-2-(morpholine-4-carbonyl)-6,9-dioxo-5-(4-(trifluoromethyl)benzyl)-5,8-diazaspiro[3.5]nonan-8-yl)benzonitrile |

TABLE 1-continued

| No. | Structure | Name |
|---|---|---|
| 446 | 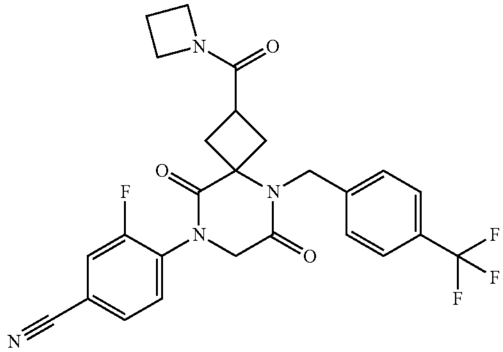 [SMILES: N#Cc1ccc(N2CC(=O)N(Cc3ccc(C(F)(F)F)cc3)C3(CC(C(=O)N4CCC4)C3)C2=O)c(F)c1] | 4-(2-(azetidine-1-carbonyl)-6,9-dioxo-5-(4-(trifluoromethyl)benzyl)-5,8-diazaspiro[3.5]nonan-8-yl)-3-fluorobenzonitrile |
| 447 | 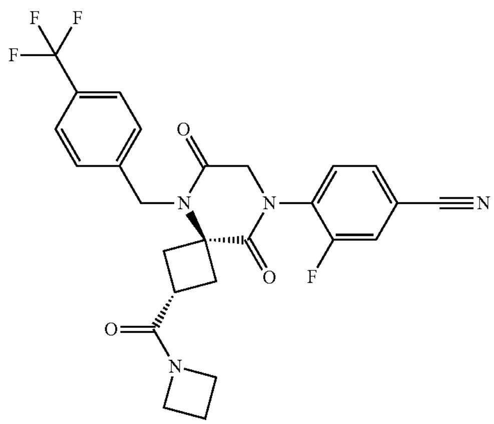 [SMILES: N#Cc1ccc(N2CC(=O)N(Cc3ccc(C(F)(F)F)cc3)[C@]3(C[C@H](C(=O)N4CCC4)C3)C2=O)c(F)c1] | 4-((2r,4r)-2-(azetidine-1-carbonyl)-6,9-dioxo-5-(4-(trifluoromethyl)benzyl)-5,8-diazaspiro[3.5]nonan-8-yl)-3-fluorobenzonitrile |
| 448 | 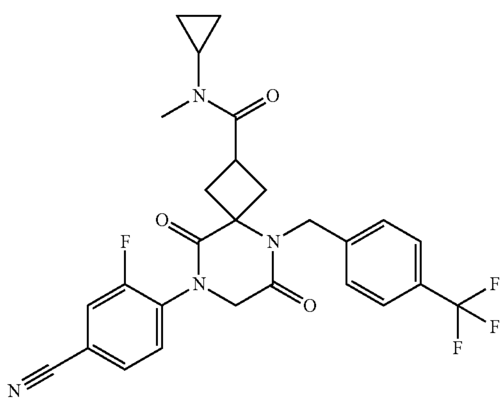 [SMILES: CN(C(=O)C1CC2(C1)C(=O)N(c1ccc(C#N)cc1F)CC(=O)N2Cc1ccc(C(F)(F)F)cc1)C1CC1] | 8-(4-cyano-2-fluorophenyl)-N-cyclopropyl-N-methyl-6,9-dioxo-5-(4-(trifluoromethyl)benzyl)-5,8-diazaspiro[3.5]nonane-2-carboxamide |
| 449 | 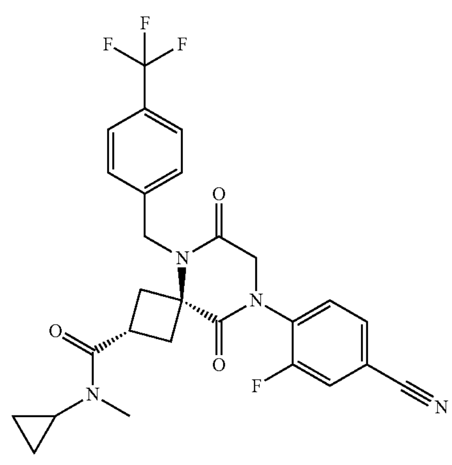 [SMILES: CN(C(=O)[C@H]1C[C@]2(C1)C(=O)N(c1ccc(C#N)cc1F)CC(=O)N2Cc1ccc(C(F)(F)F)cc1)C1CC1] | (2r,4r)-8-(4-cyano-2-fluorophenyl)-N-cyclopropyl-N-methyl-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 450 | 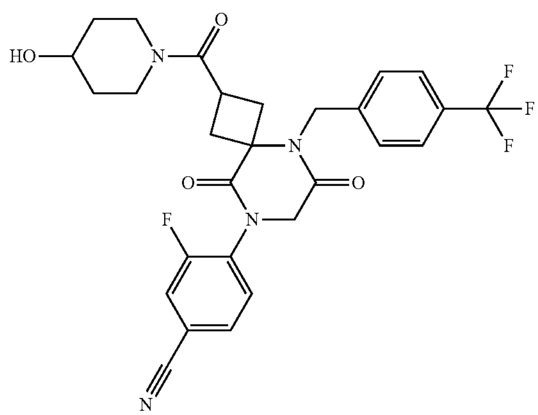 [SMILES: N#Cc1ccc(N2CC(=O)N(Cc3ccc(C(F)(F)F)cc3)C3(CC(C(=O)N4CCC(O)CC4)C3)C2=O)c(F)c1] | 3-fluoro-4-(2-(4-hydroxy-piperidine-1-carbonyl)-6,9-dioxo-5-(4-(trifluoromethyl)benzyl)-5,8-diazaspiro[3.5]nonan-8-yl)benzonitrile |
| 451 | 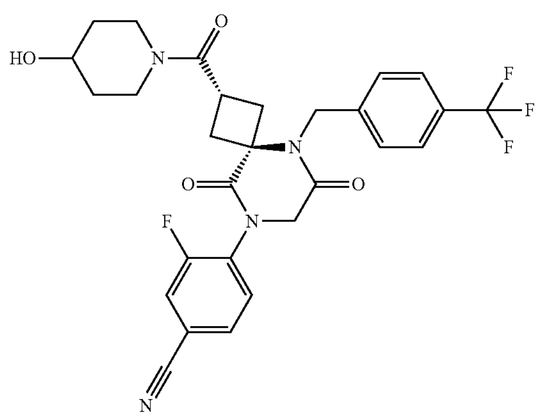 [SMILES: N#Cc1ccc(N2CC(=O)N(Cc3ccc(C(F)(F)F)cc3)[C@]3(C[C@H](C(=O)N4CCC(O)CC4)C3)C2=O)c(F)c1] | 3-fluoro-4-((2r,4r)-2-(4-hydroxypiperidine-1-carbonyl)-6,9-dioxo-5-(4-(trifluoromethyl)benzyl)-5,8-diazaspiro[3.5]nonan-8-yl)benzonitrile |
| 452 | 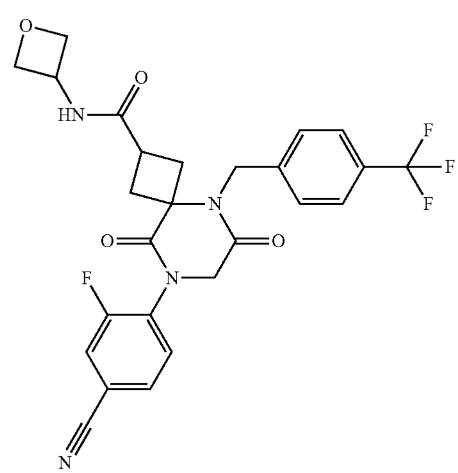 [SMILES: N#Cc1ccc(N2CC(=O)N(Cc3ccc(C(F)(F)F)cc3)C3(CC(C(=O)NC4COC4)C3)C2=O)c(F)c1] | 8-(4-cyano-2-fluorophenyl)-N-(oxetan-3-yl)-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 453 | 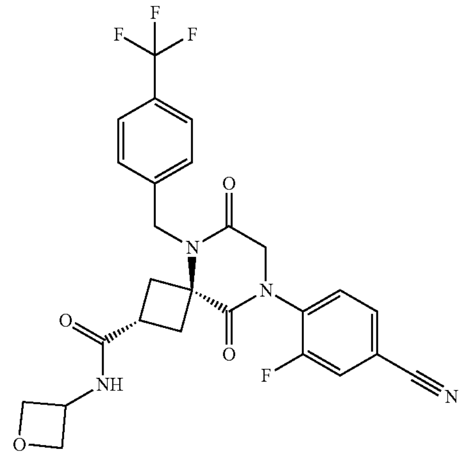 [SMILES: N#Cc1ccc(N2CC(=O)N(Cc3ccc(C(F)(F)F)cc3)[C@]3(C[C@H](C(=O)NC4COC4)C3)C2=O)c(F)c1] | (2r,4r)-8-(4-cyano-2-fluorophenyl)-N-(oxetan-3-yl)-6,9-dioxo-5-(4-(trifluoromethyl)benzyl)-5,8-diazaspiro[3.5]nonane-2-carboxamide |
| 454 | 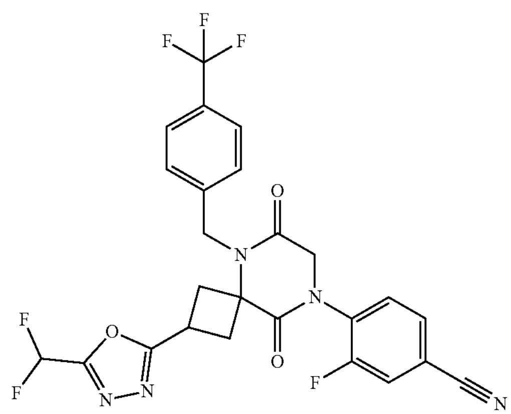 [SMILES: N#Cc1ccc(N2CC(=O)N(Cc3ccc(C(F)(F)F)cc3)C3(CC(c4nnc(C(F)F)o4)C3)C2=O)c(F)c1] | 4-(2-(5-(difluoromethyl)-1,3,4-oxadiazol-2-yl)-6,9-dioxo-5-(4-(trifluoromethyl)benzyl)-5,8-diazaspiro[3.5]-nonan-8-yl)-3-fluorobenzonitrile |
| 455 | 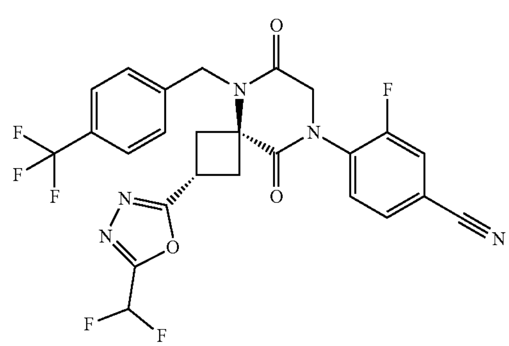 [SMILES: N#Cc1ccc(N2CC(=O)N(Cc3ccc(C(F)(F)F)cc3)[C@]3(C[C@H](c4nnc(C(F)F)o4)C3)C2=O)c(F)c1] | 4-((2r,4r)-2-(5-(difluoromethyl)-1,3,4-oxadiazol-2-yl)-6,9-dioxo-5-(4-(trifluoromethyl)benzyl)-5,8-diazaspiro[3.5]nonan-8-yl)-3-fluorobenzonitrile |

TABLE 1-continued

| No. | Structure | Name |
|---|---|---|
| 456 | 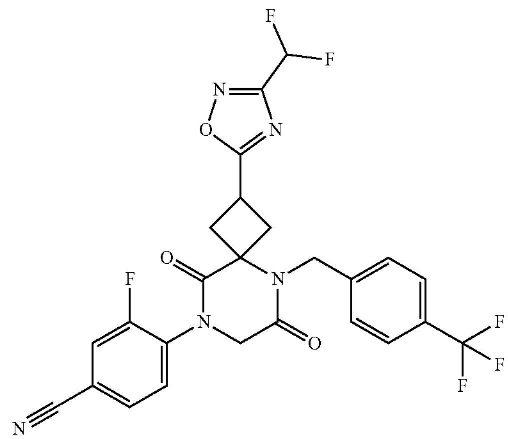 [SMILES: N#Cc1ccc(N2CC(=O)N(Cc3ccc(C(F)(F)F)cc3)C3(CC(c4nc(C(F)F)no4)C3)C2=O)c(F)c1] | 4-(2-(3-(difluoromethyl)-1,2,4-oxadiazol-5-yl)-6,9-dioxo-5-(4-(trifluoromethyl)-benzyl)-5,8-diazaspiro-[3.5]nonan-8-yl)-3-fluorobenzonitrile |
| 457 | 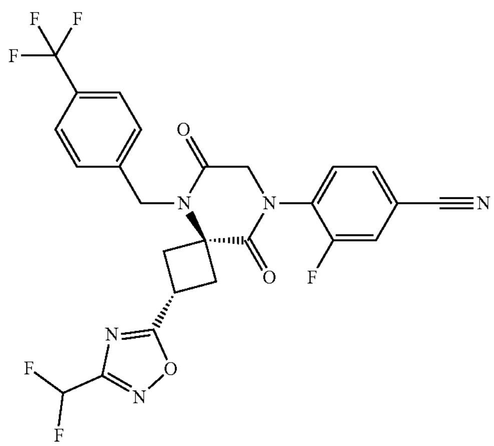 [SMILES: N#Cc1ccc(N2CC(=O)N(Cc3ccc(C(F)(F)F)cc3)[C@]3(C[C@H](c4nc(C(F)F)no4)C3)C2=O)c(F)c1] | 4-((2r,4r)-2-(3-(difluoromethyl)-1,2,4-oxadiazol-5-yl)-6,9-dioxo-5-(4-(trifluoromethyl)-benzyl)-5,8-diazaspiro-[3.5]nonan-8-yl)-3-fluorobenzonitrile |
| 458 | 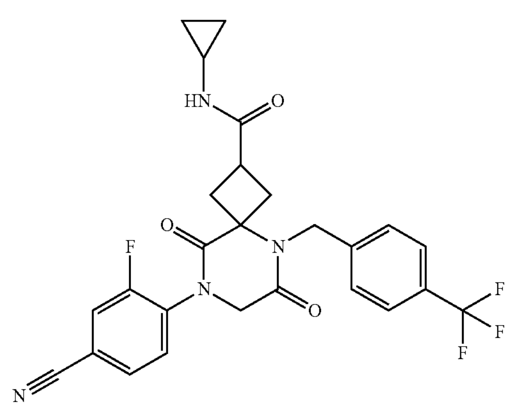 [SMILES: N#Cc1ccc(N2CC(=O)N(Cc3ccc(C(F)(F)F)cc3)C3(CC(C(=O)NC4CC4)C3)C2=O)c(F)c1] | 8-(4-cyano-2-fluorophenyl)-N-cyclopropyl-6,9-dioxo-5-(4-(trifluoromethyl)-benzyl)-5,8-diazaspiro[3.5]-nonane-2-carboxamide |

TABLE 1-continued
| No. | Structure | Name |
|---|---|---|
| 459 | 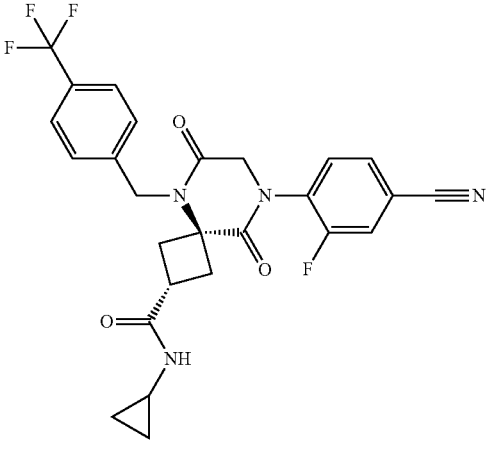 [SMILES: N#Cc1ccc(N2CC(=O)N(Cc3ccc(C(F)(F)F)cc3)[C@]3(C[C@H](C(=O)NC4CC4)C3)C2=O)c(F)c1] | (2r,4r)-8-(4-cyano-2-fluoro-phenyl)-N-cyclopropyl-6,9-dioxo-5-(4-(trifluoromethyl)benzyl)-5,8-diazaspiro[3.5]nonane-2-carboxamide |
| 460 | 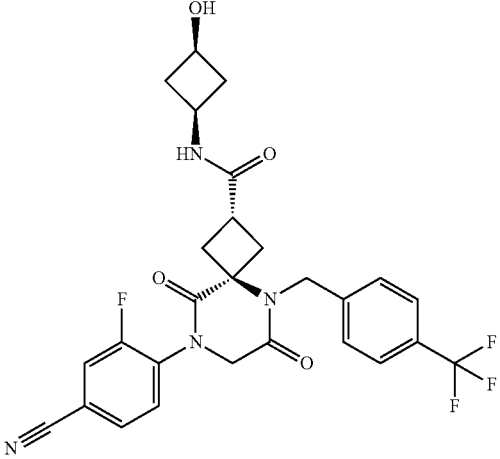 [SMILES: N#Cc1ccc(N2CC(=O)N(Cc3ccc(C(F)(F)F)cc3)[C@]3(C[C@H](C(=O)N[C@H]4C[C@@H](O)C4)C3)C2=O)c(F)c1] | (2r,4R)-8-(4-cyano-2-fluorophenyl)-N-((1s,3S)-3-hydroxycyclobutyl)-6,9-dioxo-5-(4-(trifluoromethyl)benzyl)-5,8-diazaspiro[3.5]nonane-2-carboxamide |
| 461 | 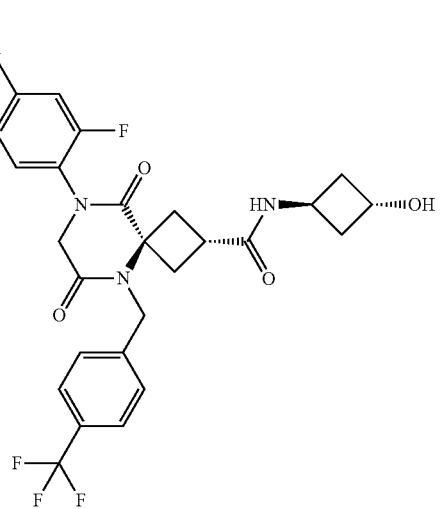 | (2r,4R)-8-(4-cyano-2-fluorophenyl)-N-((1r,3R)-3-hydroxycyclobutyl)-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 462 | 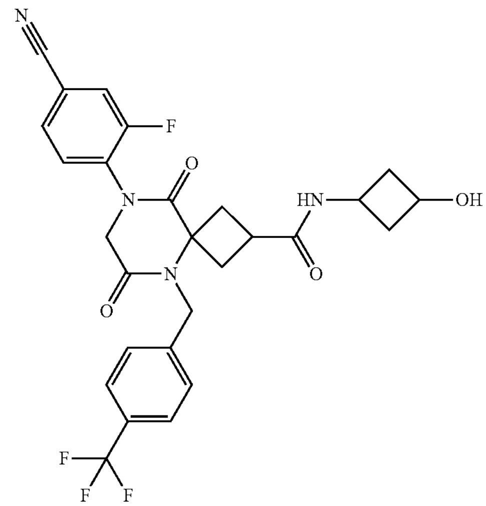 [SMILES: N#Cc1ccc(N2CC(=O)N(Cc3ccc(C(F)(F)F)cc3)C3(CC(C(=O)NC4CC(O)C4)C3)C2=O)c(F)c1] | 8-(4-cyano-2-fluorophenyl)-N-(3-hydroxycyclobutyl)-6,9-dioxo-5-(4-(trifluoromethyl)benzyl)-5,8-diazaspiro[3.5]nonane-2-carboxamide |
| 463 | 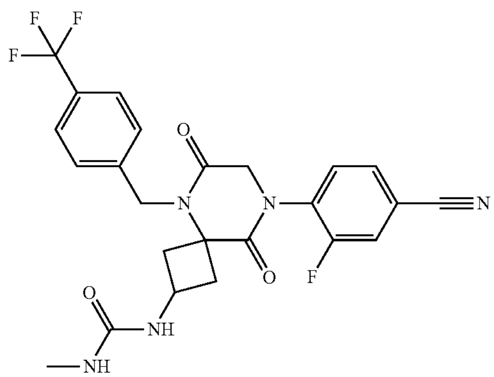 [SMILES: CNC(=O)NC1CC2(C1)C(=O)N(c1ccc(C#N)cc1F)CC(=O)N2Cc1ccc(C(F)(F)F)cc1] | 1-(8-(4-cyano-2-fluorophenyl)-6,9-dioxo-5-(4-(trifluoromethyl)benzyl)-5,8-diazaspiro[3.5]nonan-2-yl)-3-methylurea |
| 464 | 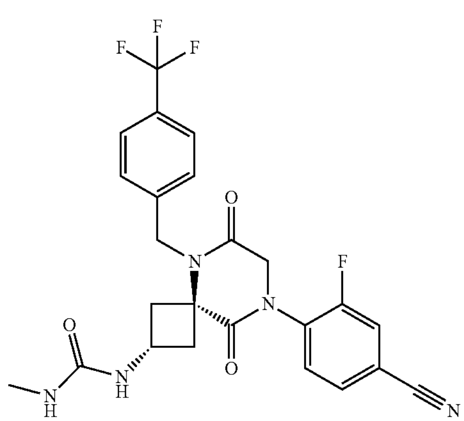 [SMILES: CNC(=O)N[C@H]1C[C@]2(C1)C(=O)N(c1ccc(C#N)cc1F)CC(=O)N2Cc1ccc(C(F)(F)F)cc1] | 1-((2r,4r)-8-(4-cyano-2-fluorophenyl)-6,9-dioxo-5-(4-(trifluoromethyl)benzyl)-5,8-diazaspiro[3.5]nonan-2-yl)-3-methylurea |

TABLE 1-continued

| No. | Structure | Name |
|---|---|---|
| 465 | 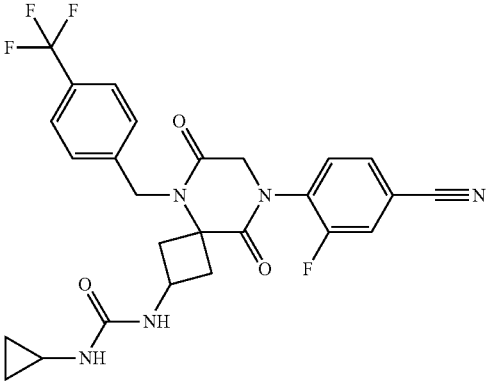 [SMILES: N#Cc1ccc(N2CC(=O)N(Cc3ccc(C(F)(F)F)cc3)C3(CC(NC(=O)NC4CC4)C3)C2=O)c(F)c1] | 1-(8-(4-cyano-2-fluorophenyl)-6,9-dioxo-5-(4-(trifluoromethyl)benzyl)-5,8-diazaspiro[3.5]nonan-2-yl)-3-cyclopropylurea |
| 466 | 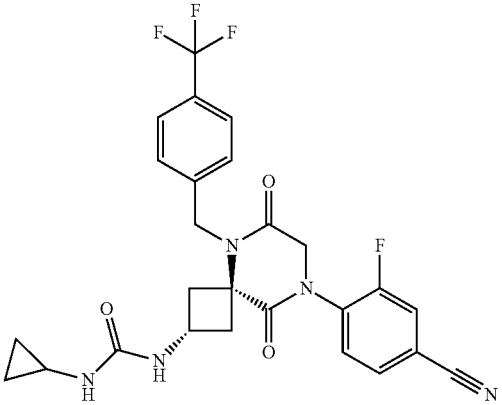 [SMILES: N#Cc1ccc(N2CC(=O)N(Cc3ccc(C(F)(F)F)cc3)[C@]3(C[C@H](NC(=O)NC4CC4)C3)C2=O)c(F)c1] | 1-((2r,4r)-8-(4-cyano-2-fluorophenyl)-6,9-dioxo-5-(4-(trifluoromethyl)benzyl)-5,8-diazaspiro[3.5]nonan-2-yl)-3-cyclopropylurea |
| 467 | 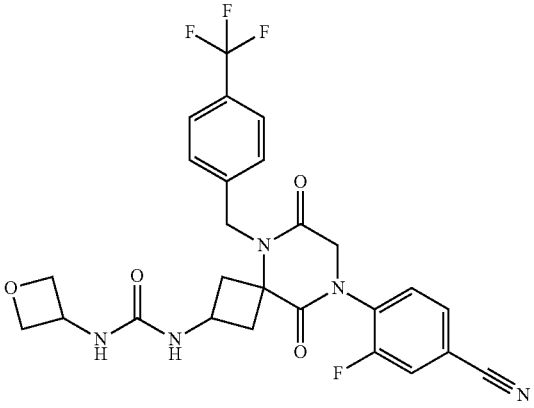 [SMILES: N#Cc1ccc(N2CC(=O)N(Cc3ccc(C(F)(F)F)cc3)C3(CC(NC(=O)NC4COC4)C3)C2=O)c(F)c1] | 1-(8-(4-cyano-2-fluorophenyl)-6,9-dioxo-5-(4-(trifluoromethyl)benzyl)-5,8-diazaspiro[3.5]nonan-2-yl)-3-(oxetan-3-yl)urea |
| 468 | 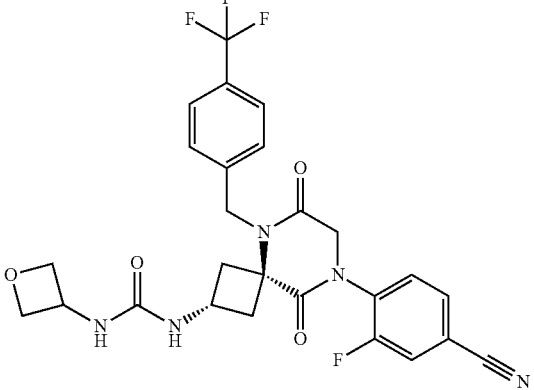 | 1-((2r,4r)-8-(4-cyano-2-fluorophenyl)-6,9-dioxo-5-(4-(trifluoromethyl)benzyl)-5,8-diazaspiro[3.5]nonan-2-yl)-3-(oxetan-3-yl)urea |

TABLE 1-continued
| No. | Structure | Name |
|---|---|---|
| 469 | 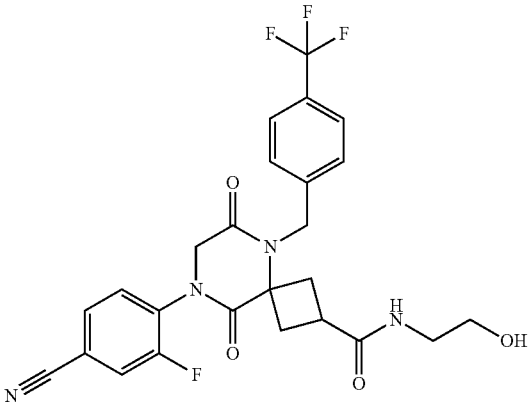 [SMILES: N#Cc1ccc(N2CC(=O)N(Cc3ccc(C(F)(F)F)cc3)C3(CC(C(=O)NCCO)C3)C2=O)c(F)c1] | 8-(4-cyano-2-fluorophenyl)-N-(2-hydroxyethyl)-6,9-dioxo-5-(4-(trifluoromethyl)benzyl)-5,8-diazaspiro[3.5]nonane-2-carboxamide |
| 470 | 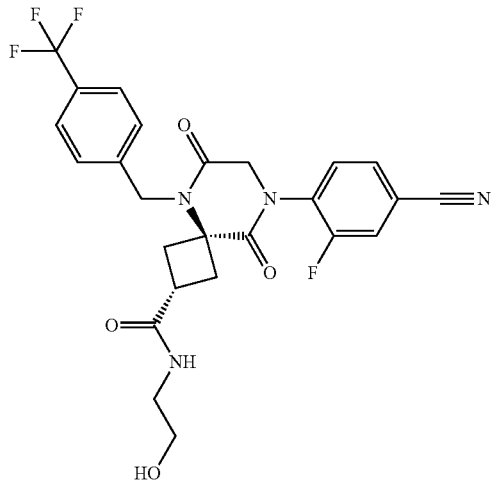 [SMILES: N#Cc1ccc(N2CC(=O)N(Cc3ccc(C(F)(F)F)cc3)[C@]3(C[C@H](C(=O)NCCO)C3)C2=O)c(F)c1] | (2r,4r)-8-(4-cyano-2-fluorophenyl)-N-(2-hydroxyethyl)-6,9-dioxo-5-(4-(trifluoromethyl)benzyl)-5,8-diazaspiro[3.5]nonane-2-carboxamide |
| 471 | 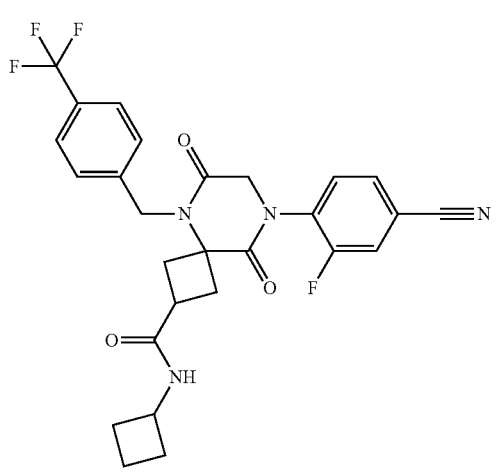 [SMILES: N#Cc1ccc(N2CC(=O)N(Cc3ccc(C(F)(F)F)cc3)C3(CC(C(=O)NC4CCC4)C3)C2=O)c(F)c1] | 8-(4-cyano-2-fluorophenyl)-N-cyclobutyl-6,9-dioxo-5-(4-(trifluoromethyl)benzyl)-5,8-diazaspiro[3.5]nonane-2-carboxamide |

TABLE 1-continued
| No. | Structure | Name |
|---|---|---|
| 472 | 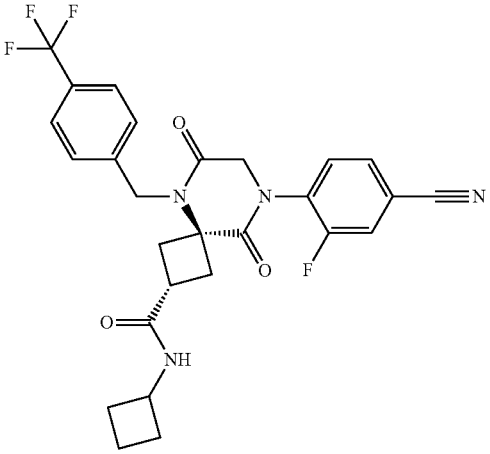 [SMILES: N#Cc1ccc(N2CC(=O)N(Cc3ccc(C(F)(F)F)cc3)[C@]3(C[C@H](C(=O)NC4CCC4)C3)C2=O)c(F)c1] | (2r,4r)-8-(4-cyano-2-fluorophenyl)-N-cyclobutyl-6,9-dioxo-5-(4-(trifluoromethyl)benzyl)-5,8-diazaspiro[3.5]nonane-2-carboxamide |
| 473 | 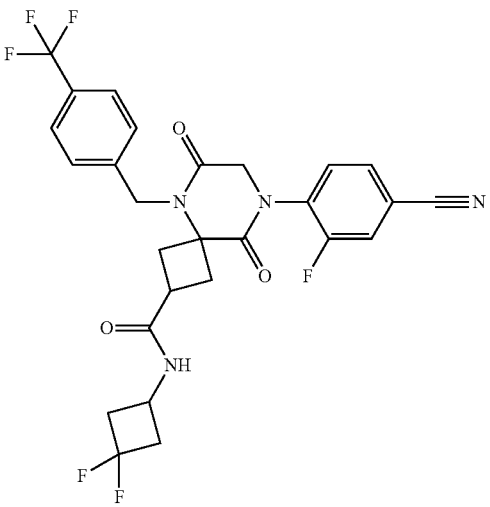 [SMILES: N#Cc1ccc(N2CC(=O)N(Cc3ccc(C(F)(F)F)cc3)C3(CC(C(=O)NC4CC(F)(F)C4)C3)C2=O)c(F)c1] | 8-(4-cyano-2-fluorophenyl)-N-(3,3-difluorocyclobutyl)-6,9-dioxo-5-(4-(trifluoromethyl)benzyl)-5,8-diazaspiro[3.5]nonane-2-carboxamide |
| 474 | 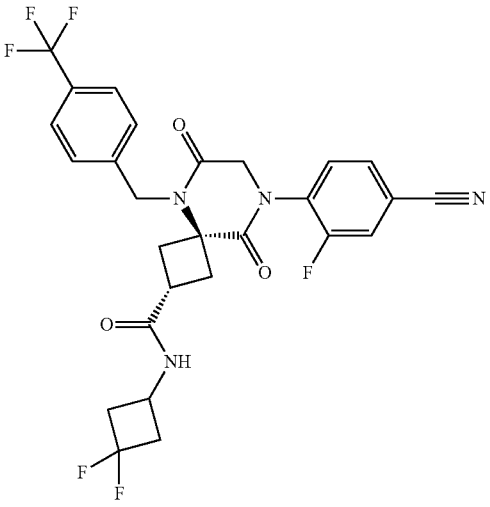 [SMILES: N#Cc1ccc(N2CC(=O)N(Cc3ccc(C(F)(F)F)cc3)[C@]3(C[C@H](C(=O)NC4CC(F)(F)C4)C3)C2=O)c(F)c1] | (2r,4r)-8-(4-cyano-2-fluorophenyl)-N-(3,3-difluorocyclobutyl)-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 475 | 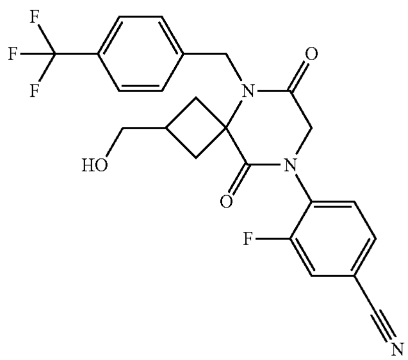 [SMILES: N#Cc1ccc(N2CC(=O)N(Cc3ccc(C(F)(F)F)cc3)C3(CC(CO)C3)C2=O)c(F)c1] | 3-fluoro-4-(2-(hydroxymethyl)-6,9-dioxo-5-(4-(trifluoromethyl)benzyl)-5,8-diazaspiro[3.5]nonan-8-yl)benzonitrile |
| 476 | 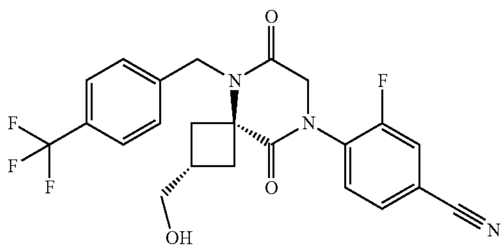 [SMILES: N#Cc1ccc(N2CC(=O)N(Cc3ccc(C(F)(F)F)cc3)[C@]3(C[C@H](CO)C3)C2=O)c(F)c1] | 3-fluoro-4-((2r,4r)-2-(hydroxymethyl)-6,9-dioxo-5-(4-(trifluoromethyl)benzyl)-5,8-diazaspiro[3.5]nonan-8-yl)benzonitrile |
| 477 | 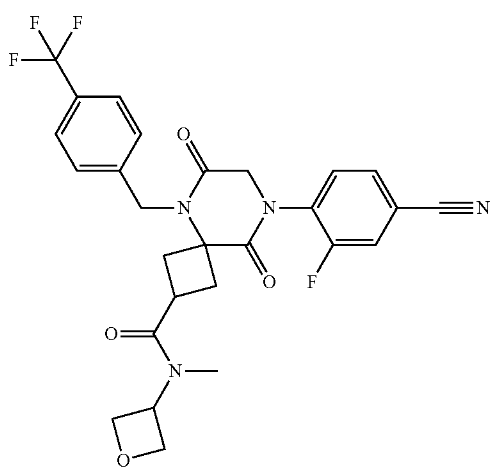 [SMILES: CN(C(=O)C1CC2(C1)C(=O)N(c1ccc(C#N)cc1F)CC(=O)N2Cc1ccc(C(F)(F)F)cc1)C1COC1] | 8-(4-cyano-2-fluorophenyl)-N-methyl-N-(oxetan-3-yl)-6,9-dioxo-5-(4-(trifluoromethyl)benzyl)-5,8-diazaspiro[3.5]nonane-2-carboxamide |
| 478 | 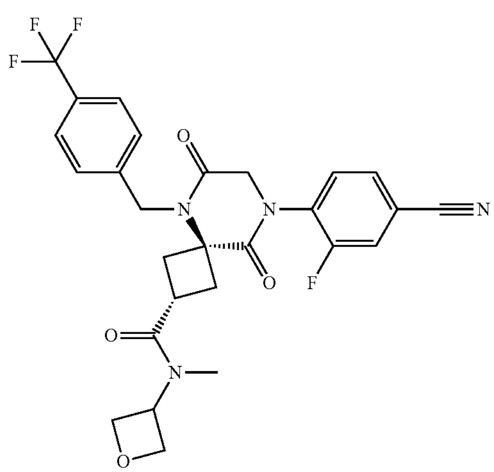 [SMILES: CN(C(=O)[C@H]1C[C@]2(C1)C(=O)N(c1ccc(C#N)cc1F)CC(=O)N2Cc1ccc(C(F)(F)F)cc1)C1COC1] | (2r,4r)-8-(4-cyano-2-fluorophenyl)-N-methyl-N-(oxetan-3-yl)-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 479 | 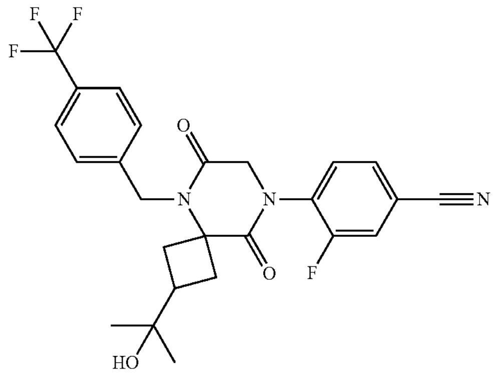 [SMILES: CC(C)(O)C1CC2(C1)C(=O)N(c1ccc(C#N)cc1F)CC(=O)N2Cc1ccc(C(F)(F)F)cc1] | 3-fluoro-4-(2-(2-hydroxypropan-2-yl)-6,9-dioxo-5-(4-(trifluoromethyl)benzyl)-5,8-diazaspiro[3.5]nonan-8-yl)benzonitrile |
| 480 | 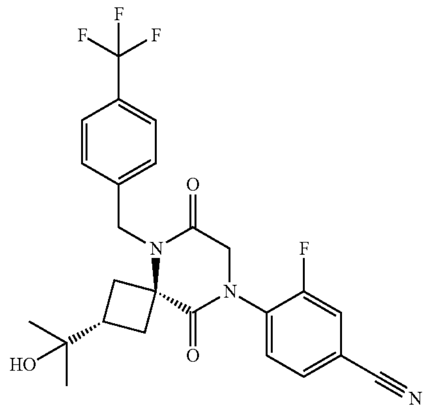 [SMILES: CC(C)(O)[C@H]1C[C@]2(C1)C(=O)N(c1ccc(C#N)cc1F)CC(=O)N2Cc1ccc(C(F)(F)F)cc1] | 3-fluoro-4-((2r,4r)-2-(2-hydroxypropan-2-yl)-6,9-dioxo-5-(4-(trifluoromethyl)benzyl)-5,8-diazaspiro[3.5]nonan-8-yl)benzonitrile |
| 481 | 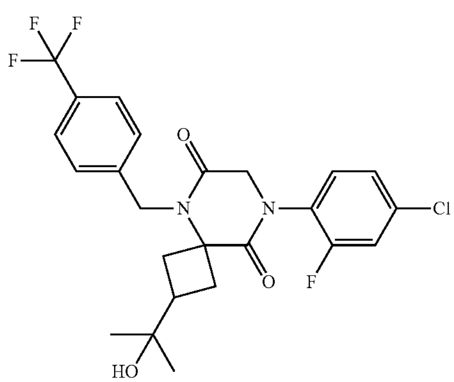 [SMILES: CC(C)(O)C1CC2(C1)C(=O)N(c1ccc(Cl)cc1F)CC(=O)N2Cc1ccc(C(F)(F)F)cc1] | 8-(4-chloro-2-fluorophenyl)-2-(2-hydroxypropan-2-yl)-5-(4-(trifluoromethyl)benzyl)-5,8-diazaspiro[3.5]nonane-6,9-dione |
| 482 | 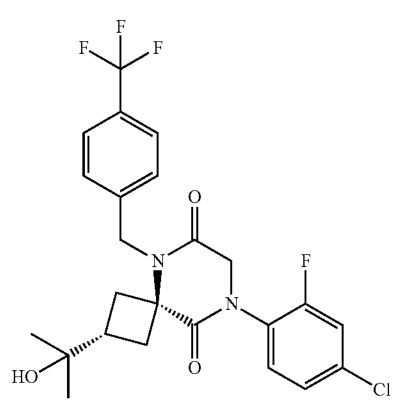 [SMILES: CC(C)(O)[C@H]1C[C@]2(C1)C(=O)N(c1ccc(Cl)cc1F)CC(=O)N2Cc1ccc(C(F)(F)F)cc1] | (2r,4r)-8-(4-chloro-2-fluorophenyl)-2-(2-hydroxypropan-2-yl)-5-(4-(trifluoromethyl)benzyl)-5,8-diazaspiro[3.5]nonane-6,9-dione |

TABLE 1-continued

| No. | Structure | Name |
|---|---|---|
| 483 | 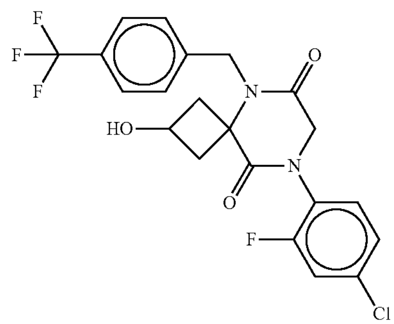 | 8-(4-chloro-2-fluorophenyl)-2-hydroxy-5-(4-(trifluoromethyl)benzyl)-5,8-diazaspiro[3.5]nonane-6,9-dione |
| 484 | 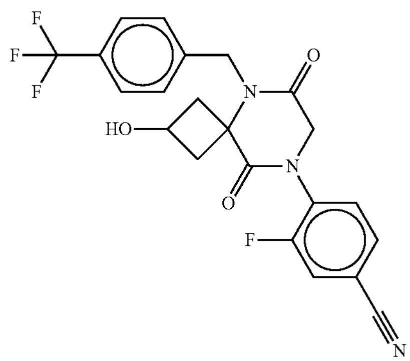 | 3-fluoro-4-(2-hydroxy-6,9-dioxo-5-(4-(trifluoromethyl)benzyl)-5,8-diazaspiro[3.5]nonan-8-yl)benzonitrile |
| 485 | 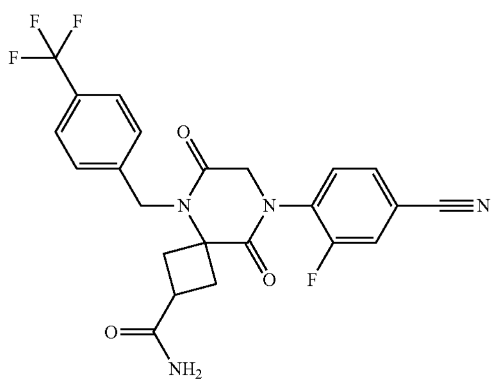 [SMILES: N#Cc1ccc(N2CC(=O)N(Cc3ccc(C(F)(F)F)cc3)C3(CC(C(N)=O)C3)C2=O)c(F)c1] | 8-(4-cyano-2-fluorophenyl)-6,9-dioxo-5-(4-(trifluoromethyl)benzyl)-5,8-diazaspiro[3.5]nonane-2-carboxamide |
| 486 | 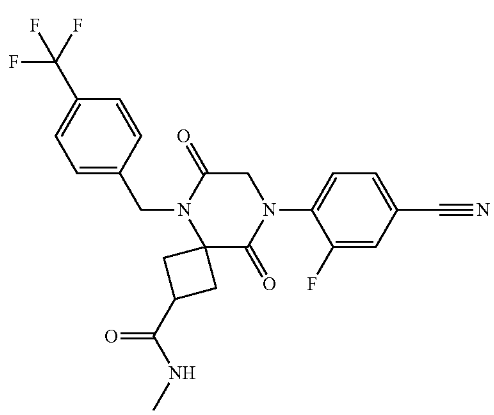 [SMILES: CNC(=O)C1CC2(C1)C(=O)N(c1ccc(C#N)cc1F)CC(=O)N2Cc1ccc(C(F)(F)F)cc1] | 8-(4-cyano-2-fluorophenyl)-N-methyl-6,9-dioxo-5-(4-(trifluoromethyl)benzyl)-5,8-diazaspiro[3.5]nonane-2-carboxamide |

TABLE 1-continued

| No. | Structure | Name |
|---|---|---|
| 487 | 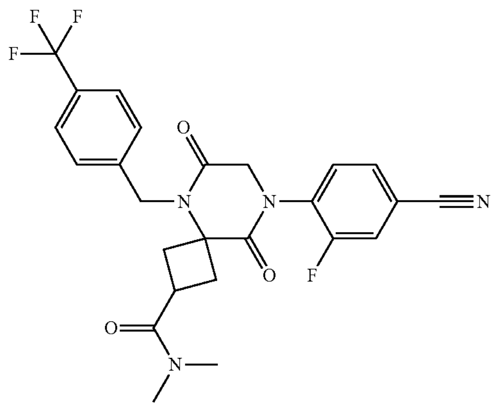 | 8-(4-cyano-2-fluorophenyl)-N,N-dimethyl-6,9-dioxo-5-(4-(trifluoromethyl)benzyl)-5,8-diazaspiro[3.5]nonane-2-carboxamide |
| 488 | 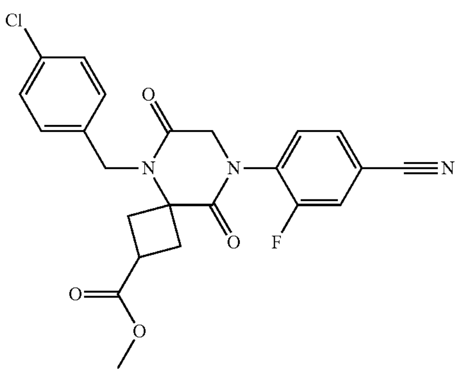 [SMILES: COC(=O)C1CC2(C1)C(=O)N(c1ccc(C#N)cc1F)CC(=O)N2Cc1ccc(Cl)cc1] | methyl 5-(4-chlorobenzyl)-8-(4-cyano-2-fluorophenyl)-6,9-dioxo-5,8-diazaspiro-[3.5]nonane-2-carboxylate |
| 489 | 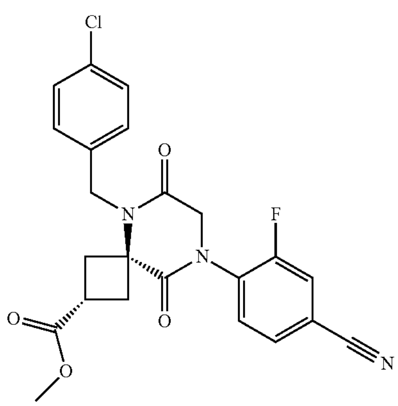 [SMILES: COC(=O)[C@H]1C[C@]2(C1)C(=O)N(c1ccc(C#N)cc1F)CC(=O)N2Cc1ccc(Cl)cc1] | methyl (2r,4r)-5-(4-chlorobenzyl)-8-(4-cyano-2-fluorophenyl)-6,9-dioxo-5,8-diazaspiro[3.5]nonane-2-carboxylate |
| 490 | 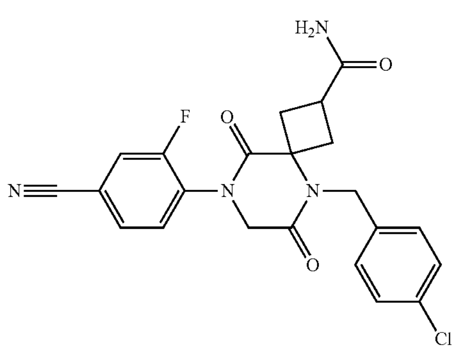 [SMILES: N#Cc1ccc(N2CC(=O)N(Cc3ccc(Cl)cc3)C3(CC(C(N)=O)C3)C2=O)c(F)c1] | 5-(4-chlorobenzyl)-8-(4-cyano-2-fluorophenyl)-6,9-dioxo-5,8-diazaspiro-[3.5]nonane-2-carboxamide |

TABLE 1-continued

| No. | Structure | Name |
|---|---|---|
| 491 | 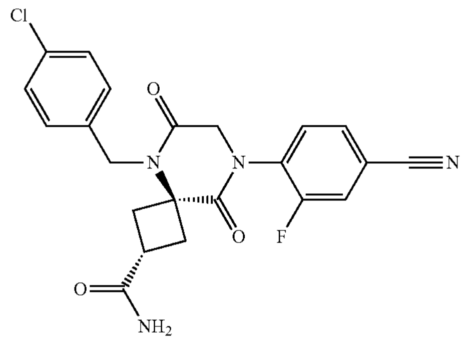 [SMILES: N#Cc1ccc(N2CC(=O)N(Cc3ccc(Cl)cc3)[C@]3(C[C@H](C(N)=O)C3)C2=O)c(F)c1] | (2r,4r)-5-(4-chlorobenzyl)-8-(4-cyano-2-fluorophenyl)-6,9-dioxo-5,8-diazaspiro[3.5]nonane-2-carboxamide |
| 492 | 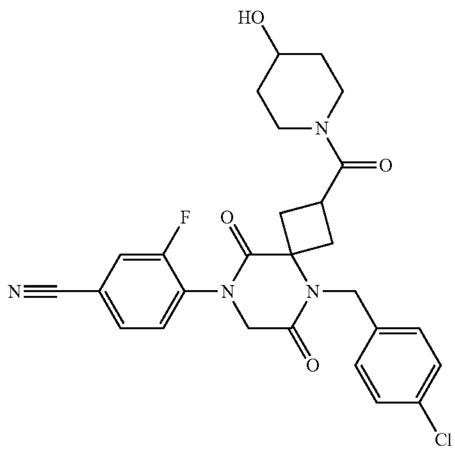 [SMILES: N#Cc1ccc(N2CC(=O)N(Cc3ccc(Cl)cc3)C3(CC(C(=O)N4CCC(O)CC4)C3)C2=O)c(F)c1] | 4-(5-(4-chlorobenzyl)-2-(4-hydroxypiperidine-1-carbonyl)-6,9-dioxo-5,8-diazaspiro[3.5]nonan-8-yl)-3-fluorobenzonitrile |
| 493 | 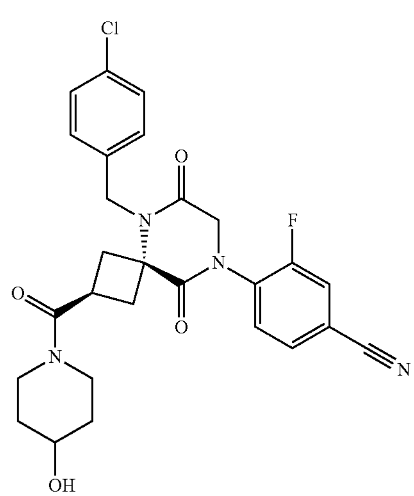 [SMILES: N#Cc1ccc(N2CC(=O)N(Cc3ccc(Cl)cc3)[C@]3(C[C@H](C(=O)N4CCC(O)CC4)C3)C2=O)c(F)c1] | 4-((2r,4r)-5-(4-chlorobenzyl)-2-(4-hydroxypiperidine-1-carbonyl)-6,9-dioxo-5,8-diazaspiro[3.5]nonan-8-yl)-3-fluorobenzonitrile |

TABLE 1-continued

| No. | Structure | Name |
|-----|-----------|------|
| 494 | 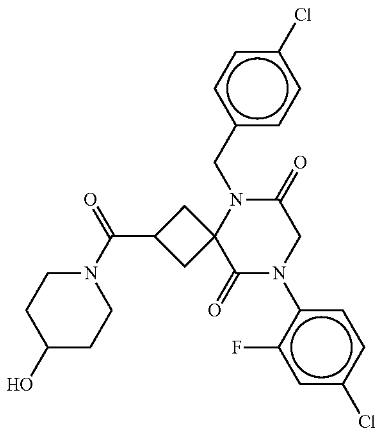 | 8-(4-chloro-2-fluoro-phenyl)-5-(4-chlorobenzyl)-2-(4-hydroxypiperidine-1-carbonyl)-5,8-diazaspiro[3.5]nonane-6,9-dione |
| 495 | 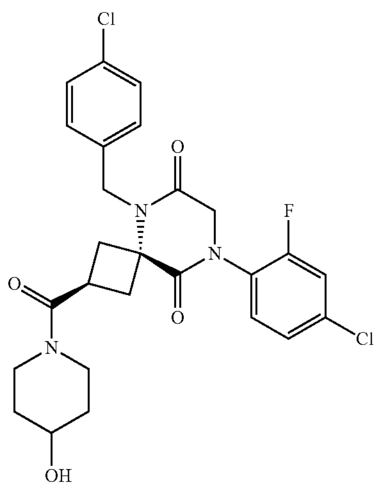 [SMILES: O=C1CN(c2ccc(Cl)cc2F)C(=O)[C@]2(C[C@@H](C(=O)N3CCC(O)CC3)C2)N1Cc1ccc(Cl)cc1] | (2r,4r)-8-(4-chloro-2-fluorophenyl)-5-(4-chlorobenzyl)-2-(4-hydroxypiperidine-1-carbonyl)-5,8-diazaspiro[3.5]nonane-6,9-dione |
| 496 | 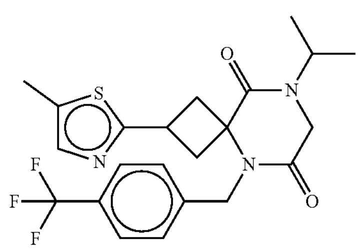 | 8-isopropyl-2-(5-methylthiazol-2-yl)-5-(4-(trifluoromethyl)benzyl)-5,8-diazaspiro[3.5]nonane-6,9-dione |
| 497 | 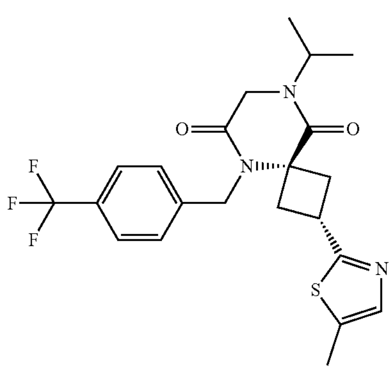 [SMILES: Cc1cnc([C@H]2C[C@@]3(C2)C(=O)N(C(C)C)CC(=O)N3Cc2ccc(C(F)(F)F)cc2)s1] | (2s,4s)-8-isopropyl-2-(5-methylthiazol-2-yl)-5-(4-(trifluoromethyl)benzyl)-5,8-diazaspiro[3.5]nonane-6,9-dione |

TABLE 1-continued

| No. | Structure | Name |
|---|---|---|
| 498 | 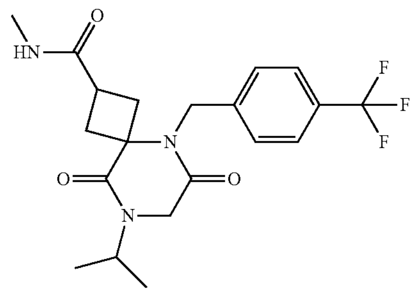 [SMILES: CNC(=O)C1CC2(C1)C(=O)N(C(C)C)CC(=O)N2Cc1ccc(C(F)(F)F)cc1] | 8-isopropyl-N-methyl-6,9-dioxo-5-(4-(trifluoromethyl)benzyl)-5,8-diazaspiro[3.5]nonane-2-carboxamide |
| 499 | 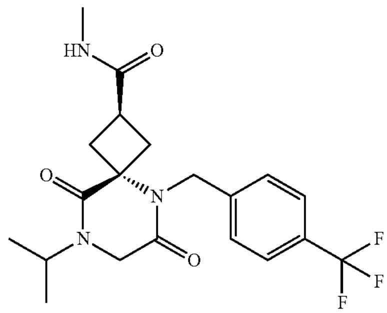 [SMILES: CNC(=O)[C@H]1C[C@]2(C1)C(=O)N(C(C)C)CC(=O)N2Cc1ccc(C(F)(F)F)cc1] | (2r,4r)-8-isopropyl-N-methyl-6,9-dioxo-5-(4-(trifluoromethyl)benzyl)-5,8-diazaspiro[3.5]nonane-2-carboxamide |
| 500 | 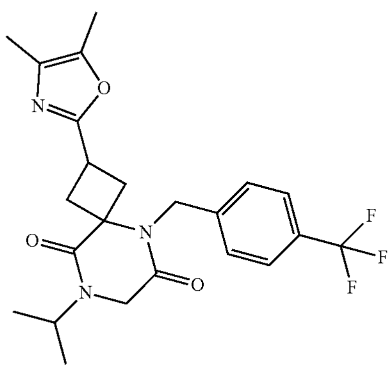 [SMILES: Cc1nc(C2CC3(C2)C(=O)N(C(C)C)CC(=O)N3Cc2ccc(C(F)(F)F)cc2)oc1C] | 2-(4,5-dimethyloxazol-2-yl)-8-isopropyl-5-(4-(trifluoromethyl)benzyl)-5,8-diazaspiro[3.5]nonane-6,9-dione |
| 501 | 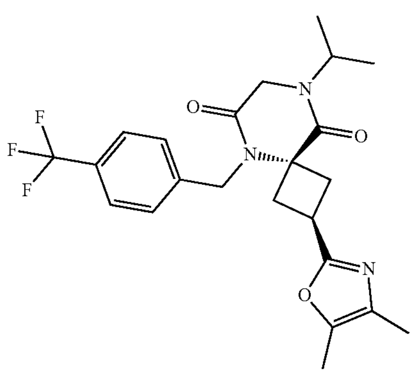 [SMILES: Cc1nc([C@H]2C[C@]3(C2)C(=O)N(C(C)C)CC(=O)N3Cc2ccc(C(F)(F)F)cc2)oc1C] | (2r,4r)-2-(4,5-dimethyl-oxazol-2-yl)-8-isopropyl-5-(4-(trifluoromethyl)benzyl)-5,8-diazaspiro[3.5]nonane-6,9-dione |
| 502 | 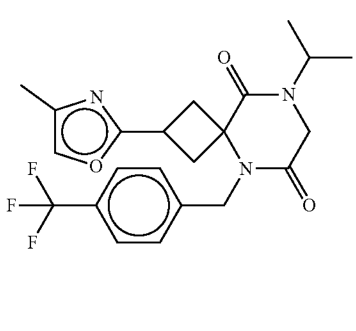 | 8-isopropyl-2-(4-methyloxazol-2-yl)-5-(4-(trifluoromethyl)benzyl)-5,8-diazaspiro[3.5]nonane-6,9-dione |

TABLE 1-continued

| No. | Structure | Name |
|---|---|---|
| 503 | 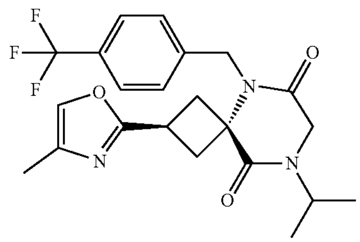 [SMILES: Cc1coc([C@H]2C[C@]3(C2)C(=O)N(C(C)C)CC(=O)N3Cc2ccc(C(F)(F)F)cc2)n1] | (2r,4r)-8-isopropyl-2-(4-methyloxazol-2-yl)-5-(4-(trifluoromethyl)benzyl)-5,8-diazaspiro[3.5]nonane-6,9-dione |
| 504 | 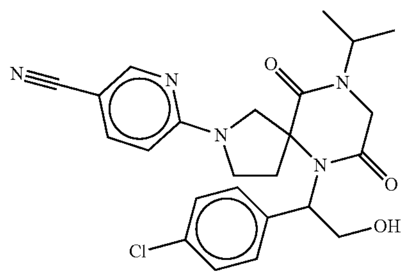 | 6-(6-(1-(4-chlorophenyl)-2-hydroxyethyl)-9-isopropyl-7,10-dioxo-2,6,9-triazaspiro[4.5]decan-2-yl)nicotinonitrile |
| 505 | 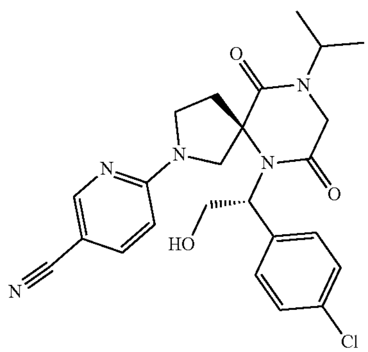 [SMILES: CC(C)N1CC(=O)N([C@@H](CO)c2ccc(Cl)cc2)[C@@]2(CCN(c3ccc(C#N)cn3)C2)C1=O] | 6-((R)-6-((R)-1-(4-chlorophenyl)-2-hydroxyethyl)-9-isopropyl-7,10-dioxo-2,6,9-triazaspiro[4.5]decan-2-yl)nicotinonitrile |
| 506 | 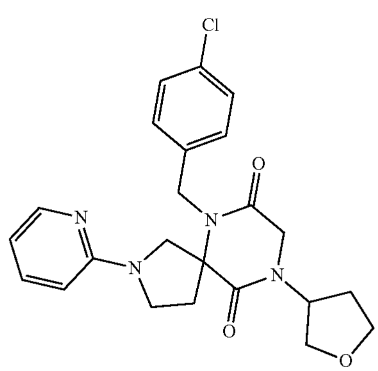 [SMILES: O=C1CN(C2CCOC2)C(=O)C2(CCN(c3ccccn3)C2)N1Cc1ccc(Cl)cc1] | 6-(4-chlorobenzyl)-2-(pyridin-2-yl)-9-(tetrahydrofuran-3-yl)-2,6,9-triazaspiro[4.5]decane-7,10-dione |
| 507 | 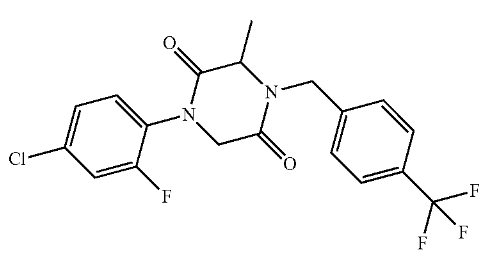 [SMILES: CC1C(=O)N(c2ccc(Cl)cc2F)CC(=O)N1Cc1ccc(C(F)(F)F)cc1] | 1-(4-chloro-2-fluorophenyl)-3-methyl-4-(4-(trifluoromethyl)benzyl)-piperazine-2,5-dione |

TABLE 1-continued

| No. | Structure | Name |
|---|---|---|
| 508 | 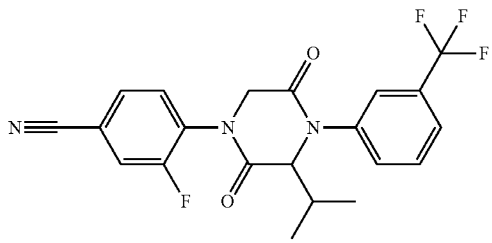 [SMILES: CC(C)C1C(=O)N(c2ccc(C#N)cc2F)CC(=O)N1c1cccc(C(F)(F)F)c1] | 3-fluoro-4-(3-isopropyl-2,5-dioxo-4-(4-(trifluoromethyl)benzyl)-piperazin-1-yl)benzonitrile |
| 509 | 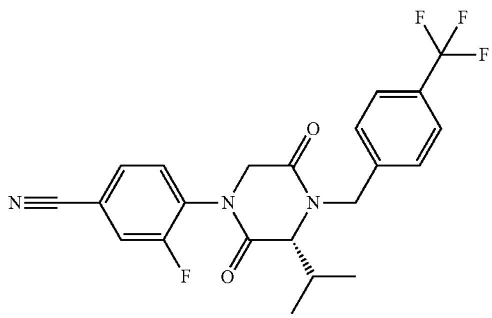 [SMILES: CC(C)[C@@H]1C(=O)N(c2ccc(C#N)cc2F)CC(=O)N1Cc1ccc(C(F)(F)F)cc1] | (R)-3-fluoro-4-(3-isopropyl-2,5-dioxo-4-(4-(trifluoromethyl)benzyl)-piperazin-1-yl)benzonitrile |
| 510 | 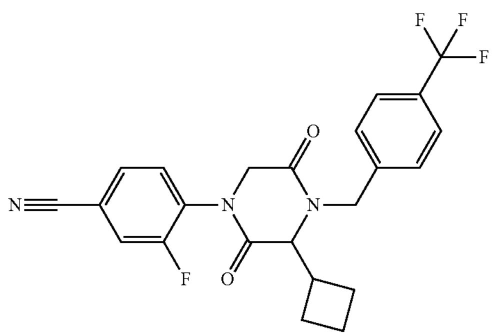 | 4-(3-cyclobutyl-2,5-dioxo-4-(4-(trifluoromethyl)-benzyl)piperazin-1-yl)-3-fluorobenzonitrile |
| 511 | 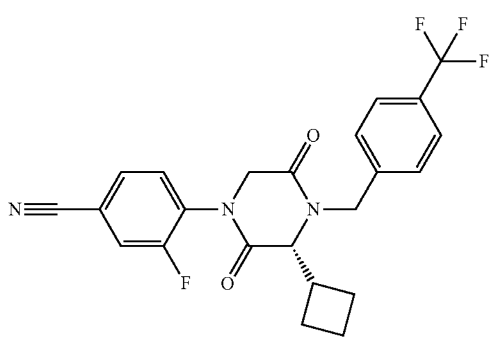 [SMILES: N#Cc1ccc(N2CC(=O)N(Cc3ccc(C(F)(F)F)cc3)[C@H](C3CCC3)C2=O)c(F)c1] | (R)-4-(3-cyclobutyl-2,5-dioxo-4-(4-(trifluoromethyl)benzyl)piperazin-1-yl)-3-fluorobenzonitrile |
| 512 | 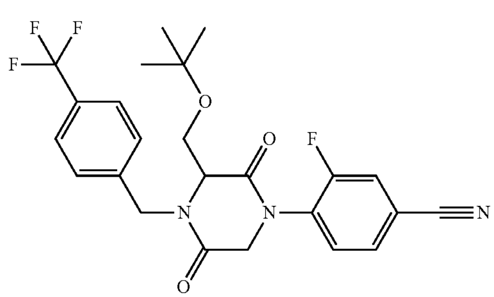 | 4-(3-(tert-butoxymethyl)-2,5-dioxo-4-(4-(trifluoromethyl)benzyl)piperazin-1-yl)-3-fluorobenzonitrile |

TABLE 1-continued

| No. | Structure | Name |
|---|---|---|
| 513 | 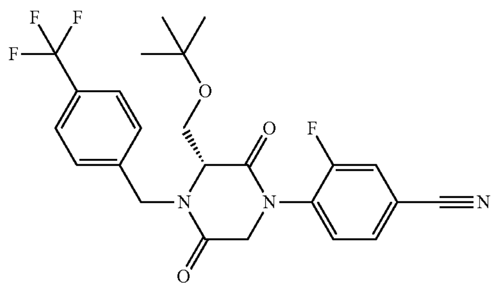 [SMILES: CC(C)(C)OC[C@@H]1C(=O)N(c2ccc(C#N)cc2F)CC(=O)N1Cc1ccc(C(F)(F)F)cc1] | (R)-4-(3-(tert-butoxymethyl)-2,5-dioxo-4-(4-(trifluoromethyl)benzyl)-piperazin-1-yl)-3-fluorobenzonitrile |
| 514 | 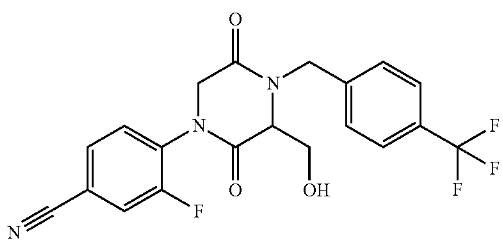 [SMILES: N#Cc1ccc(N2CC(=O)N(Cc3ccc(C(F)(F)F)cc3)C(CO)C2=O)c(F)c1] | 3-fluoro-4-(3-(hydroxymethyl)-2,5-dioxo-4-(4-(trifluoromethyl)benzyl)piperazin-1-yl)-benzonitrile |
| 515 | 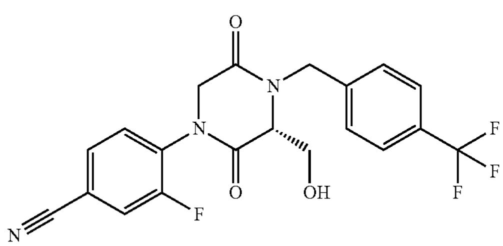 [SMILES: N#Cc1ccc(N2CC(=O)N(Cc3ccc(C(F)(F)F)cc3)[C@H](CO)C2=O)c(F)c1] | (R)-3-fluoro-4-(3-(hydroxymethyl)-2,5-dioxo-4-(4-(trifluoromethyl)benzyl)piperazin-1-yl)-benzonitrile |
| 516 | 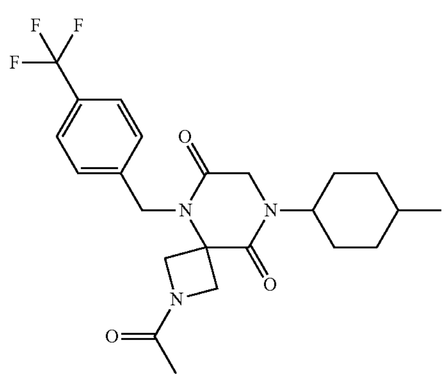 [SMILES: CC(=O)N1CC2(C1)C(=O)N(C1CCC(C)CC1)CC(=O)N2Cc1ccc(C(F)(F)F)cc1] | 2-acetyl-8-(4-methylcyclohexyl)-5-(4-(trifluoromethyl)benzyl)-2,5,8-triazaspiro[3.5]-nonane-6,9-dione |
| 517 | 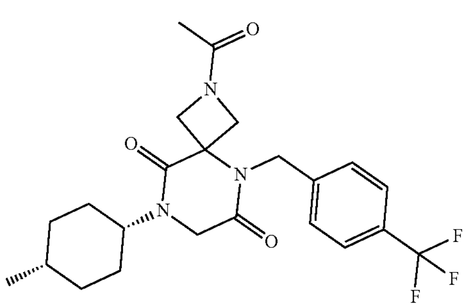 [SMILES: CC(=O)N1CC2(C1)C(=O)N([C@H]1CC[C@@H](C)CC1)CC(=O)N2Cc1ccc(C(F)(F)F)cc1] | 2-acetyl-8-((1s,4s)-4-methylcyclohexyl)-5-(4-(trifluoromethyl)benzyl)-2,5,8-triazaspiro[3.5]-nonane-6,9-dione |

TABLE 1-continued

| No. | Structure | Name |
|---|---|---|
| 518 | 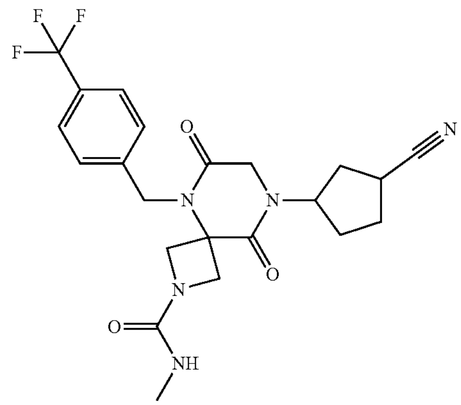 [SMILES: CNC(=O)N1CC2(C1)C(=O)N(C1CCC(C#N)C1)CC(=O)N2Cc1ccc(C(F)(F)F)cc1] | 8-(3-cyanocydopentyl)-N-methyl-6,9-dioxo-5-(4-(trifluoromethyl)benzyl)-2,5,8-triazaspiro[3.5]-nonane-2-carboxamide |
| 519 | 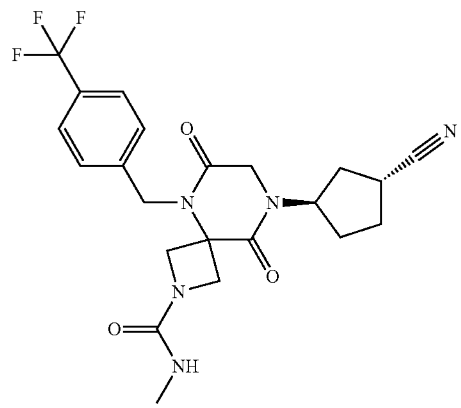 [SMILES: CNC(=O)N1CC2(C1)C(=O)N([C@@H]1CC[C@@H](C#N)C1)CC(=O)N2Cc1ccc(C(F)(F)F)cc1] | 8-((1R,3R)-3-cyano-cyclopentyl)-N-methyl-6,9-dioxo-5-(4-(trifluoromethyl)benzyl)-2,5,8-triazaspiro[3.5]-nonane-2-carboxamide |
| 520 | 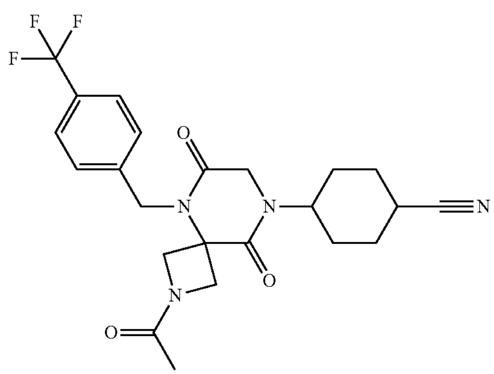 [SMILES: CC(=O)N1CC2(C1)C(=O)N(C1CCC(C#N)CC1)CC(=O)N2Cc1ccc(C(F)(F)F)cc1] | 4-(2-acetyl-6,9-dioxo-5-(4-(trifluoromethyl)benzyl)-2,5,8-triazaspiro[3.5]-nonan-8-yl)cyclohexane-1-carbonitrile |
| 521 | 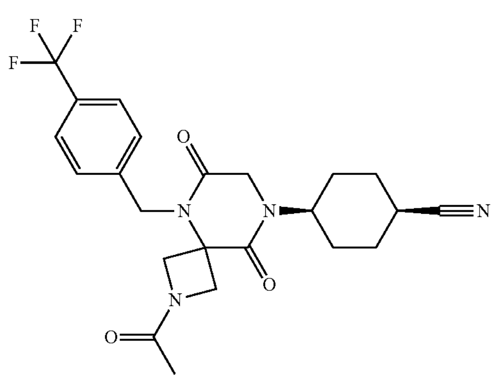 [SMILES: CC(=O)N1CC2(C1)C(=O)N([C@H]1CC[C@@H](C#N)CC1)CC(=O)N2Cc1ccc(C(F)(F)F)cc1] | (1s,4s)-4-(2-acetyl-6,9-dioxo-5-(4-(trifluoromethyl)-benzyl)-2,5,8-triazaspiro-[3.5]nonan-8-yl)cyclo-hexane-1-carbonitrile |

TABLE 1-continued

| No. | Structure | Name |
|---|---|---|
| 522 | 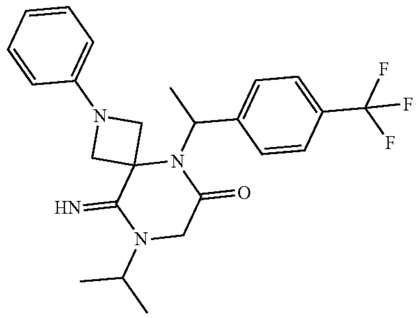 [SMILES: CC(C)N1CC(=O)N(C(C)c2ccc(C(F)(F)F)cc2)C2(CN(c3ccccc3)C2)C1=N] | 9-imino-8-isopropyl-2-phenyl-5-(1-(4-(trifluoromethyl)phenyl)-ethyl)-2,5,8-triazaspiro-[3.5]nonan-6-one |
| 523 | 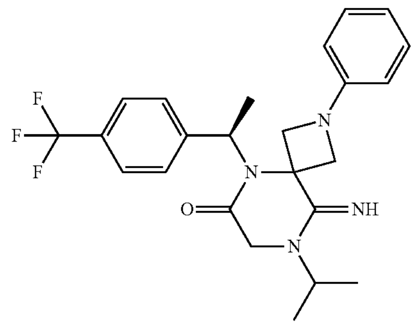 [SMILES: CC(C)N1CC(=O)N([C@H](C)c2ccc(C(F)(F)F)cc2)C2(CN(c3ccccc3)C2)C1=N] | (R)-9-imino-8-isopropyl-2-phenyl-5-(1-(4-(trifluoromethyl)phenyl)-ethyl)-2,5,8-triazaspiro-[3.5]nonan-6-one |
| 524 | 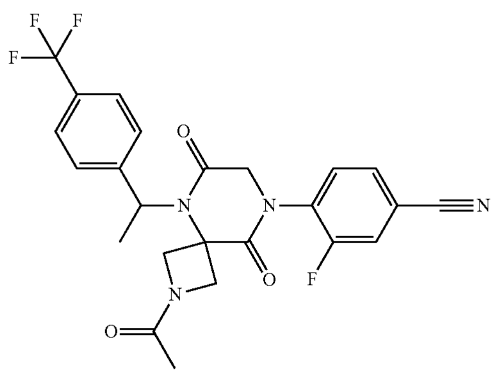 [SMILES: CC(=O)N1CC2(C1)C(=O)N(c1ccc(C#N)cc1F)CC(=O)N2C(C)c1ccc(C(F)(F)F)cc1] | 4-(2-acetyl-6,9-dioxo-5-(1-(4-(trifluoromethyl)phenyl)-ethyl)-2,5,8-triazaspiro[3.5]-nonan-8-yl)-3-fluoro-benzonitrile |
| 525 | 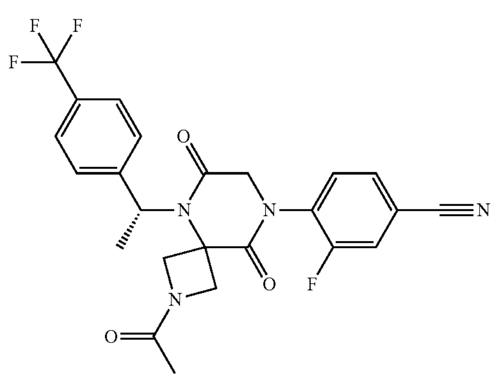 | (R)-4-(2-acetyl-6,9-dioxo-5-(1-(4-(trifluoromethyl)-phenyl)ethyl)-2,5,8-triazaspiro[3.5]nonan-8-yl)-3-fluorobenzonitrile |

TABLE 1-continued

| No. | Structure | Name |
|---|---|---|
| 526 | 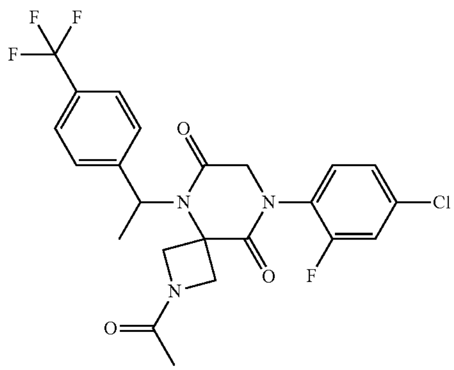 [SMILES: CC(=O)N1CC2(C1)C(=O)N(c1ccc(Cl)cc1F)CC(=O)N2C(C)c1ccc(C(F)(F)F)cc1] | 2-acetyl-8-(4-chloro-2-fluorophenyl)-5-(1-(4-(trifluoromethyl)phenyl)-ethyl)-2,5,8-triazaspiro-[3.5]nonane-6,9-dione |
| 527 | 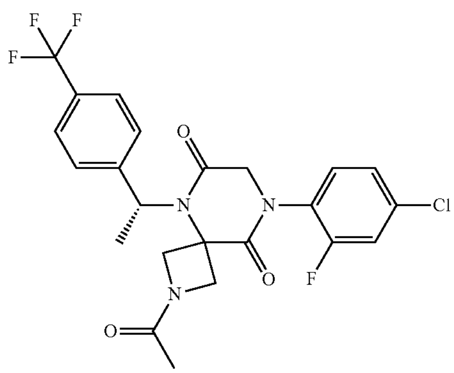 [SMILES: CC(=O)N1CC2(C1)C(=O)N(c1ccc(Cl)cc1F)CC(=O)N2[C@H](C)c1ccc(C(F)(F)F)cc1] | (R)-2-acetyl-8-(4-chloro-2-fluorophenyl)-5-(1-(4-(trifluoromethyl)phenyl)-ethyl)-2,5,8-triazaspiro-[3.5]nonane-6,9-dione |
| 528 | 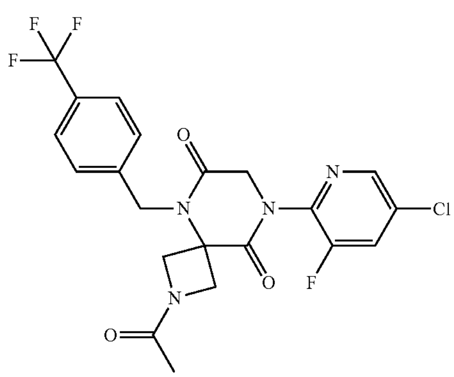 [SMILES: CC(=O)N1CC2(C1)C(=O)N(c1ncc(Cl)cc1F)CC(=O)N2Cc1ccc(C(F)(F)F)cc1] | 2-acetyl-8-(5-chloro-3-fluoropyridin-2-yl)-5-(4-(trifluoromethyl)benzyl)-2,5,8-triazaspiro[3.5]-nonane-6,9-dione |
| 529 | 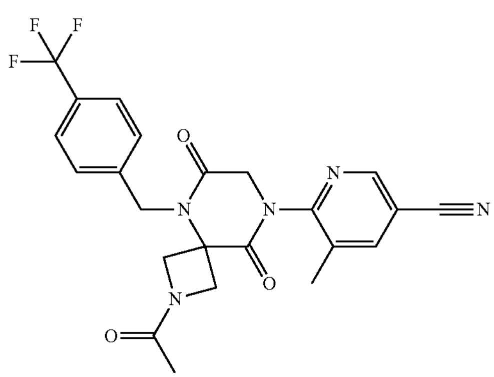 [SMILES: CC(=O)N1CC2(C1)C(=O)N(c1ncc(C#N)cc1C)CC(=O)N2Cc1ccc(C(F)(F)F)cc1] | 6-(2-acetyl-6,9-dioxo-5-(4-(trifluoromethyl)benzyl)-2,5,8-triazaspiro[3.5]nonan-8-yl)-5-methylnicotinonitrile |

TABLE 1-continued
| No. | Structure | Name |
|---|---|---|
| 530 | 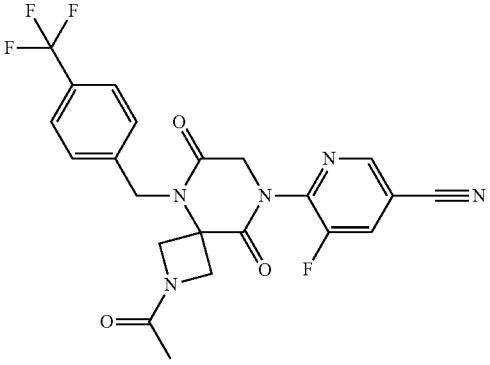 | 6-(2-acetyl-6,9-dioxo-5-(4-(trifluoromethyl)benzyl)-2,5,8-triazaspiro[3.5]nonan-8-yl)-5-fluoronicotinonitrile |
| 531 | 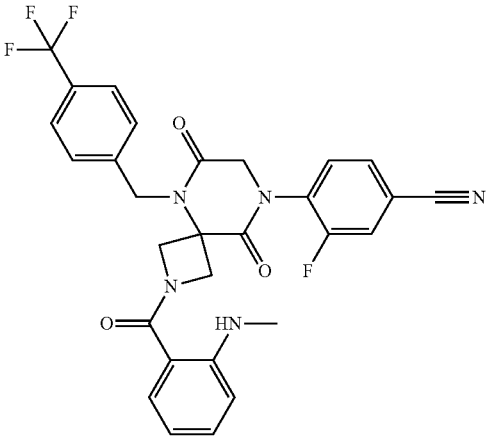 [SMILES: CNc1ccccc1C(=O)N1CC2(C1)C(=O)N(c1ccc(C#N)cc1F)CC(=O)N2Cc1ccc(C(F)(F)F)cc1] | 3-fluoro-4-(2-(2-(methylamino)benzoyl)-6,9-dioxo-5-(4-(trifluoromethyl)benzyl)-2,5,8-triazaspiro[3.5]nonan-8-yl)benzonitrile |
| 532 | 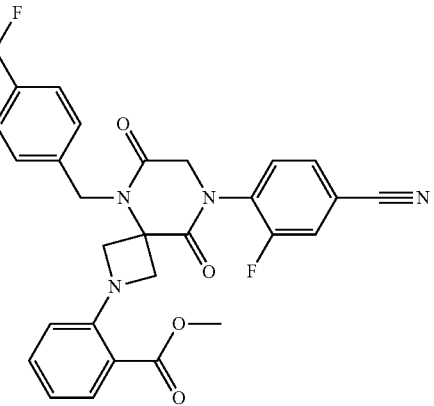 | methyl 2-(8-(4-cyano-2-fluorophenyl)-6,9-dioxo-5-(4-(trifluoromethyl)benzyl)-2,5,8-triazaspiro[3.5]nonan-2-yl)benzoate |

TABLE 1-continued
| No. | Structure | Name |
|---|---|---|
| 533 | 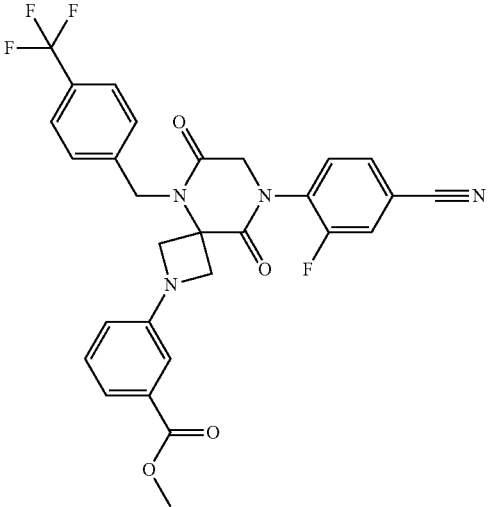 [SMILES: COC(=O)c1cccc(N2CC3(C2)C(=O)N(c2ccc(C#N)cc2F)CC(=O)N3Cc2ccc(C(F)(F)F)cc2)c1] | methyl 3-(8-(4-cyano-2-fluorophenyl)-6,9-dioxo-5-(4-(trifluoromethyl)benzyl)-2,5,8-triazaspiro[3.5]nonan-2-yl)benzoate |
| 534 | 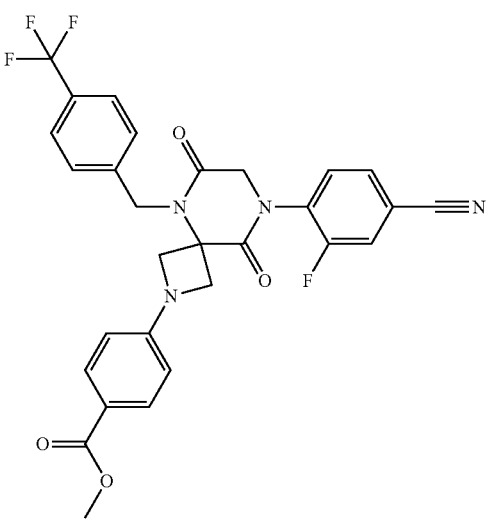 [SMILES: COC(=O)c1ccc(N2CC3(C2)C(=O)N(c2ccc(C#N)cc2F)CC(=O)N3Cc2ccc(C(F)(F)F)cc2)cc1] | methyl 4-(8-(4-cyano-2-fluorophenyl)-6,9-dioxo-5-(4-(trifluoromethyl)benzyl)-2,5,8-triazaspiro[3.5]nonan-2-yl)benzoate |
| 535 | 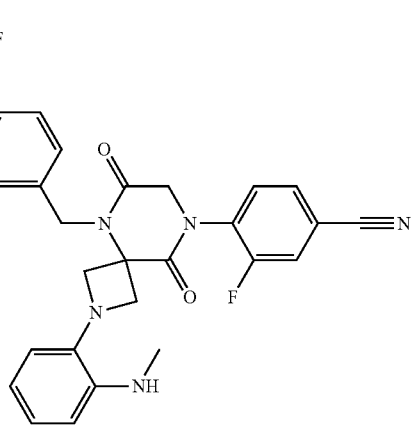 | 3-fluoro-4-(2-(2-(methylamino)phenyl)-6,9-dioxo-5-(4-(trifluoromethyl)-benzyl)-2,5,8-triazaspiro-[3.5]nonan-8-yl)benzonitrile |

TABLE 1-continued
| No. | Structure | Name |
|---|---|---|
| 536 | 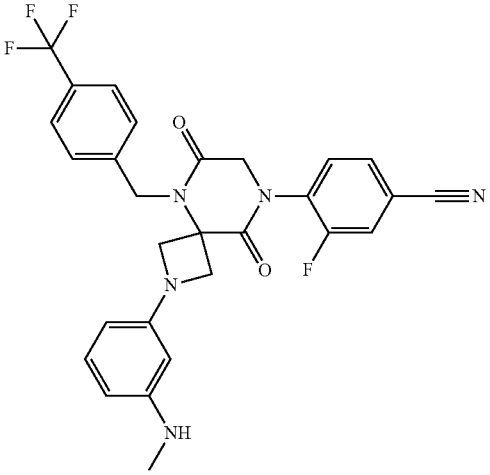 [SMILES: CNc1cccc(N2CC3(C2)C(=O)N(c2ccc(C#N)cc2F)CC(=O)N3Cc2ccc(C(F)(F)F)cc2)c1] | 3-fluoro-4-(2-(3-(methyl-amino)phenyl)-6,9-dioxo-5-(4-(trifluoromethyl)-benzyl)-2,5,8-triazaspiro-[3.5]nonan-8-yl)benzonitrile |
| 537 | 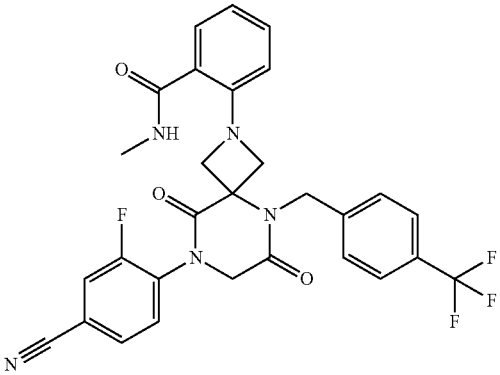 [SMILES: CNC(=O)c1ccccc1N1CC2(C1)C(=O)N(c1ccc(C#N)cc1F)CC(=O)N2Cc1ccc(C(F)(F)F)cc1] | 2-(8-(4-cyano-2-fluorophenyl)-6,9-dioxo-5-(4-(trifluoromethyl)benzyl)-2,5,8-triazaspiro[3.5]nonan-2-yl)-N-methylbenzamide |
| 538 | 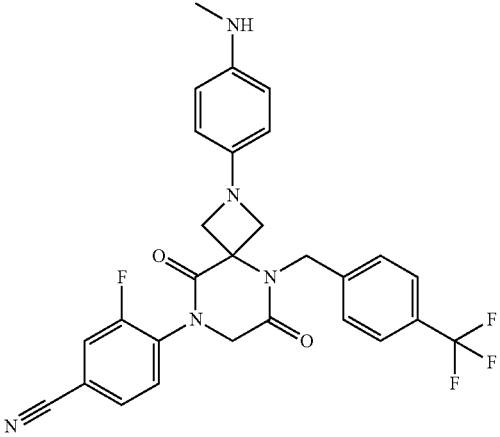 [SMILES: CNc1ccc(N2CC3(C2)C(=O)N(c2ccc(C#N)cc2F)CC(=O)N3Cc2ccc(C(F)(F)F)cc2)cc1] | 3-fluoro-4-(2-(4-(methylamino)phenyl)-6,9-dioxo-5-(4-(trifluoromethyl)benzyl)-2,5,8-triazaspiro[3.5]nonan-8-yl)benzonitrile |

TABLE 1-continued

| No. | Structure | Name |
| --- | --- | --- |
| 539 | 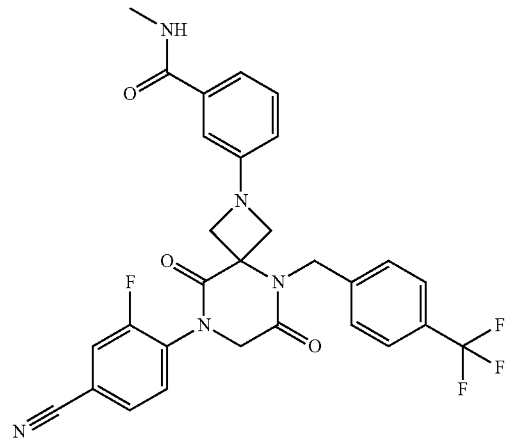 [SMILES: CNC(=O)c1cccc(N2CC3(C2)C(=O)N(c2ccc(C#N)cc2F)CC(=O)N3Cc2ccc(C(F)(F)F)cc2)c1] | 3-(8-(4-cyano-2-fluorophenyl)-6,9-dioxo-5-(4-(trifluoromethyl)benzyl)-2,5,8-triazaspiro[3.5]nonan-2-yl)-N-methylbenzamide |
| 540 | 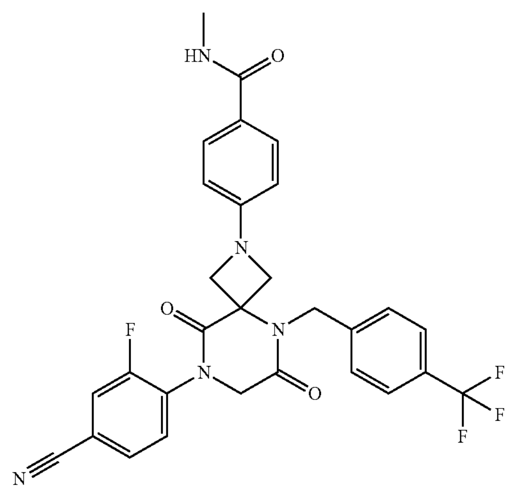 [SMILES: CNC(=O)c1ccc(N2CC3(C2)C(=O)N(c2ccc(C#N)cc2F)CC(=O)N3Cc2ccc(C(F)(F)F)cc2)cc1] | 4-(8-(4-cyano-2-fluorophenyl)-6,9-dioxo-5-(4-(trifluoromethyl)benzyl)-2,5,8-triazaspiro[3.5]nonan-2-yl)-N-methylbenzamide |
| 541 | 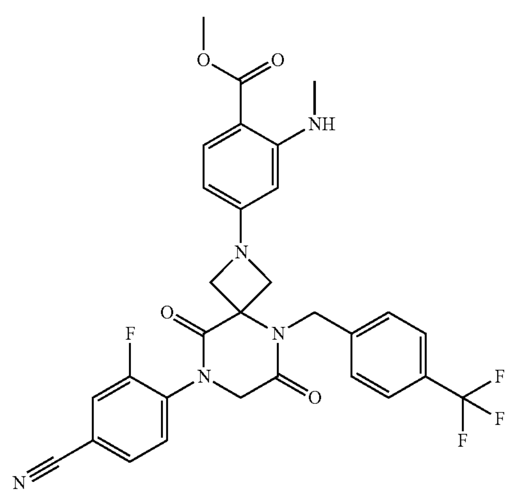 [SMILES: CNc1cc(N2CC3(C2)C(=O)N(c2ccc(C#N)cc2F)CC(=O)N3Cc2ccc(C(F)(F)F)cc2)ccc1C(=O)OC] | methyl 4-(8-(4-cyano-2-fluorophenyl)-6,9-dioxo-5-(4-(trifluoromethyl)benzyl)-2,5,8-triazaspiro[3.5]nonan-2-yl)-2-(methylamino)-benzoate |

| No. | Structure | Name |
| --- | --- | --- |
| 542 | 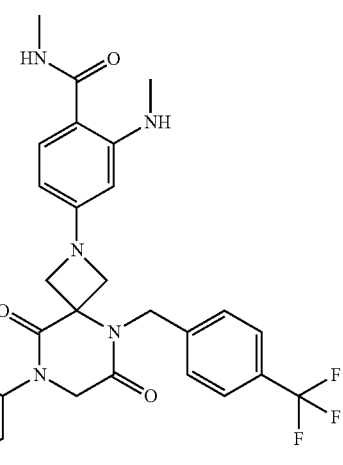 | 4-(8-(4-cyano-2-fluoro-phenyl)-6,9-dioxo-5-(4-(trifluoromethyl)benzyl)-2,5,8-triazaspiro[3.5]nonan-2-yl)-N-methyl-2-(methylamino)benzamide |
| 543 | 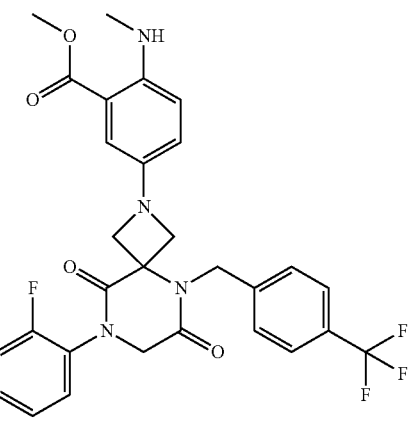 | methyl 5-(8-(4-cyano-2-fluorophenyl)-6,9-dioxo-5-(4-(trifluoromethyl)benzyl)-2,5,8-triazaspiro[3.5]nonan-2-yl)-2-(methylamino)-benzoate |
| 544 | 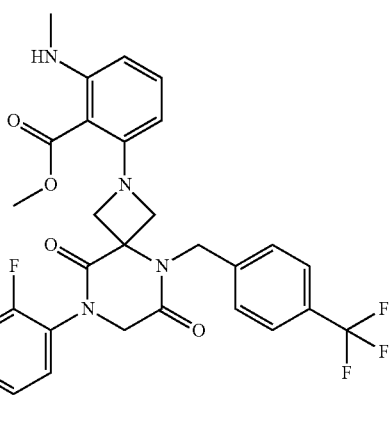 | methyl 2-(8-(4-cyano-2-fluorophenyl)-6,9-dioxo-5-(4-(trifluoromethyl)benzyl)-2,5,8-triazaspiro[3.5]nonan-2-yl)-6-(methylamino)-benzoate |

TABLE 1-continued

| No. | Structure | Name |
|---|---|---|
| 545 | 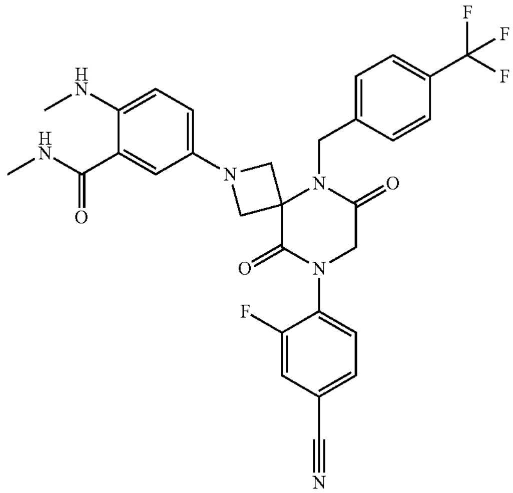 [SMILES: CNC(=O)c1cc(N2CC3(C2)C(=O)N(c2ccc(C#N)cc2F)CC(=O)N3Cc2ccc(C(F)(F)F)cc2)ccc1NC] | 5-(8-(4-cyano-2-fluorophenyl)-6,9-dioxo-5-(4-(trifluoromethyl)benzyl)-2,5,8-triazaspiro[3.5]nonan-2-yl)-N-methyl-2-(methylamino)benzamide |
| 546 | 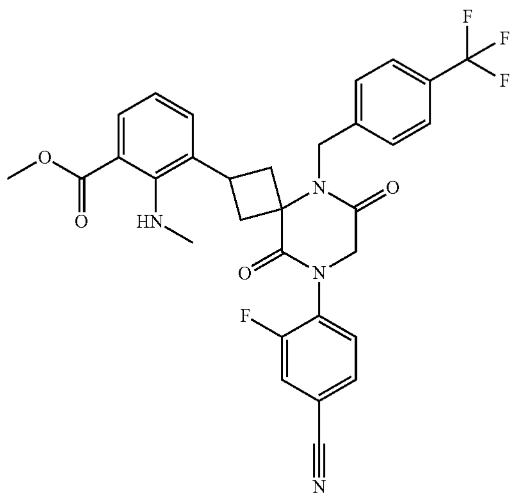 [SMILES: CNc1c(C(=O)OC)cccc1C1CC2(C1)C(=O)N(c1ccc(C#N)cc1F)CC(=O)N2Cc1ccc(C(F)(F)F)cc1] | methyl 3-(8-(4-cyano-2-fluorophenyl)-6,9-dioxo-5-(4-(trifluoromethyl)benzyl)-2,5,8-triazaspiro[3.5]nonan-2-yl)-2-(methylamino)-benzoate |
| 547 | 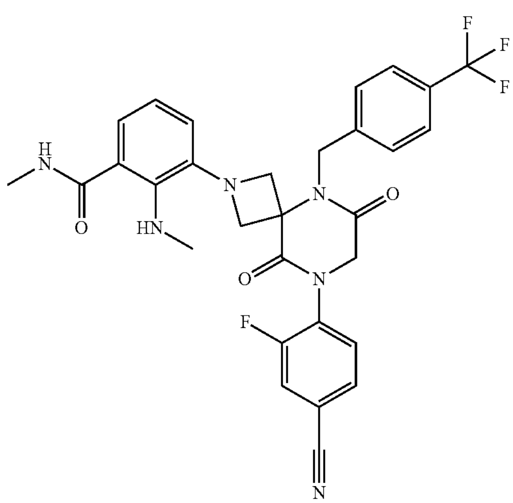 [SMILES: CNC(=O)c1cccc(N2CC3(C2)C(=O)N(c2ccc(C#N)cc2F)CC(=O)N3Cc2ccc(C(F)(F)F)cc2)c1NC] | 3-(8-(4-cyano-2-fluorophenyl)-6,9-dioxo-5-(4-(trifluoromethyl)benzyl)-2,5,8-triazaspiro[3.5]nonan-2-yl)-N-methyl-2-(methylamino)benzamide |

TABLE 1-continued

| No. | Structure | Name |
|---|---|---|
| 548 | 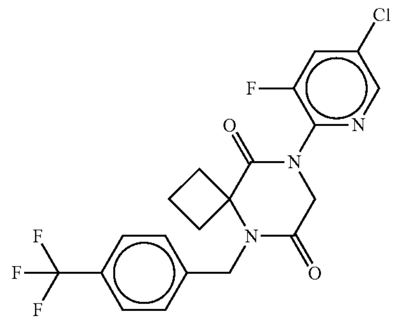 | 8-(5-chloro-3-fluoropyridin-2-yl)-5-(4-(trifluoromethyl)-benzyl)-5,8-diazaspiro-[3.5]nonane-6,9-dione |
| 549 | 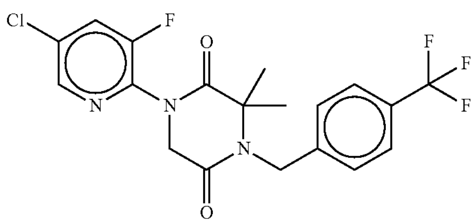 | 1-(5-chloro-3-fluoropyridin-2-yl)-3,3-dimethyl-4-(4-(trifluoromethyl)benzyl)-piperazine-2,5-dione |
| 550 | 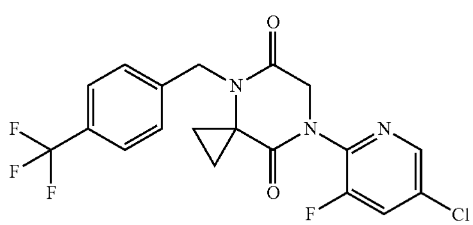 [SMILES: O=C1CN(c2ncc(Cl)cc2F)C(=O)C2(CC2)N1Cc1ccc(C(F)(F)F)cc1] | 7-(5-chloro-3-fluoropyridin-2-yl)-4-(4-(trifluoromethyl)-benzyl)-4,7-diazaspiro-[2.5]octane-5,8-dione |
| 551 | 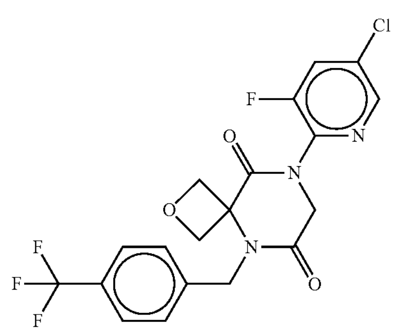 | 8-(5-chloro-3-fluoropyridin-2-yl)-5-(4-(trifluoromethyl)-benzyl)-2-oxa-5,8-diazaspiro[3.5]nonane-6,9-dione |
| 552 | 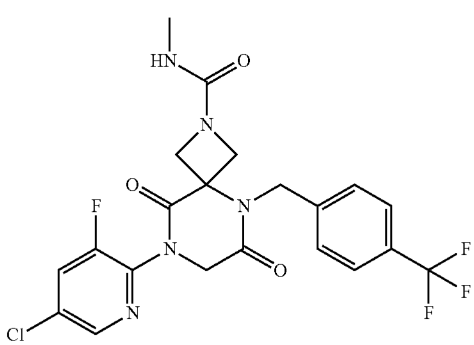 [SMILES: CNC(=O)N1CC2(C1)C(=O)N(c1ncc(Cl)cc1F)CC(=O)N2Cc1ccc(C(F)(F)F)cc1] | 8-(5-chloro-3-fluoropyridin-2-yl)-N-methyl-6,9-dioxo-5-(4-(trifluoromethyl)-benzyl)-2,5,8-triazaspiro-[3.5]nonane-2-carboxamide |

TABLE 1-continued
| No. | Structure | Name |
|---|---|---|
| 553 | 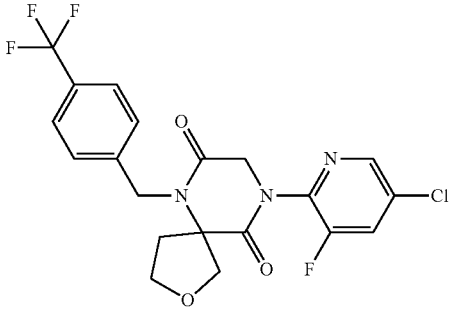 [SMILES: O=C1CN(c2ncc(Cl)cc2F)C(=O)C2(CCOC2)N1Cc1ccc(C(F)(F)F)cc1] | 9-(5-chloro-3-fluoropyridin-2-yl)-6-(4-(trifluoromethyl)-benzyl)-2-oxa-6,9-diazaspiro[4.5]decane-7,10-dione |
| 554 | 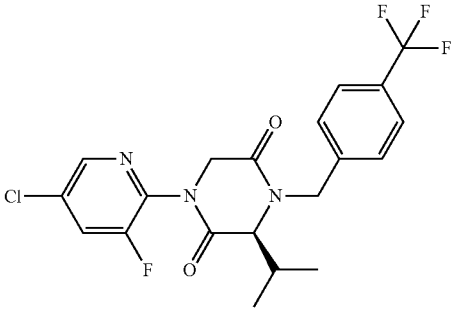 [SMILES: CC(C)[C@H]1C(=O)N(c2ncc(Cl)cc2F)CC(=O)N1Cc1ccc(C(F)(F)F)cc1] | (S)-1-(5-chloro-3-fluoro-pyridin-2-yl)-3-isopropyl-4-(4-(trifluoromethyl)-benzyl)piperazine-2,5-dione |
| 555 | 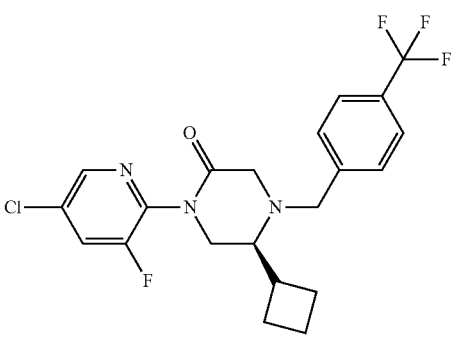 [SMILES: O=C1CN(Cc2ccc(C(F)(F)F)cc2)[C@@H](C2CCC2)CN1c1ncc(Cl)cc1F] | (S)-1-(5-chloro-3-fluoro-pyridin-2-yl)-3-cyclobutyl-4-(4-(trifluoromethyl)-benzyl)piperazine-2,5-dione |
| 556 | 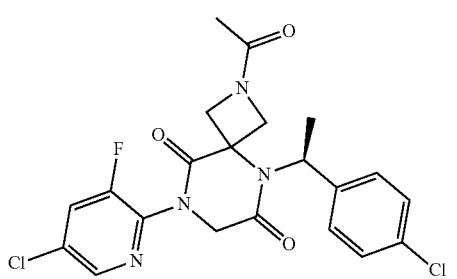 [SMILES: CC(=O)N1CC2(C1)C(=O)N(c1ncc(Cl)cc1F)CC(=O)N2[C@@H](C)c1ccc(Cl)cc1] | (S)-2-acetyl-8-(5-chloro-3-fluoropyridin-2-yl)-5-(1-(4-chlorophenyl)ethyl)-2,5,8-triazaspiro[3.5]nonane-6,9-dione |

TABLE 1-continued

| No. | Structure | Name |
|---|---|---|
| 557 | 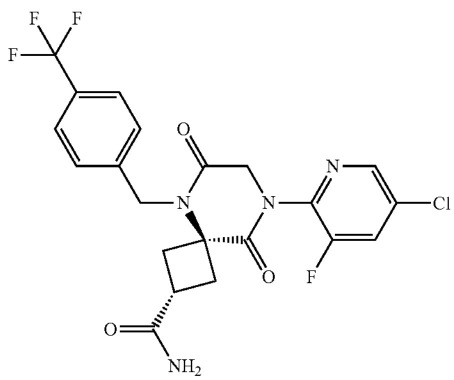 | (2r,4r)-8-(5-chloro-3-fluoro-pyridin-2-yl)-6,9-dioxo-5-(4-(trifluoromethyl)benzyl)-5,8-diazaspiro[3.5]nonane-2-carboxamide |
| 558 | 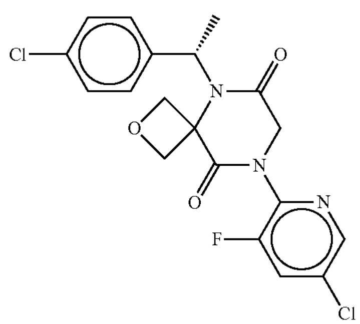 | (S)-8-(5-chloro-3-fluoro-pyridin-2-yl)-5-(2-(4-chlorophenyl)ethyl)-2-oxa-5,8-diazaspiro[3.5]nonane-6,9-dione |
| 559 | 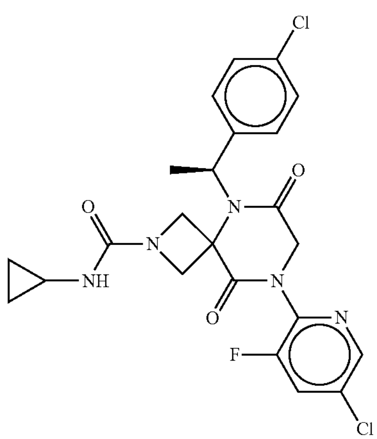 | (S)-8-(5-chloro-3-fluoro-pyridin-2-yl)-5-(1-(4-chlorophenyl)ethyl)-N-cyclopropyl-6,9-dioxo-2,5,8-triazaspiro[3.5]-nonane-2-carboxamide |
| 560 | 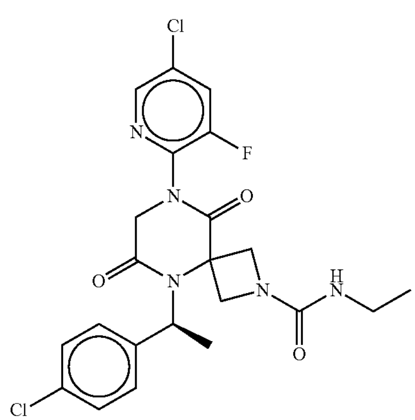 | (S)-8-(5-chloro-3-fluoro-pyridin-2-yl)-5-(1-(4-chlorophenyl)ethyl)-N-ethyl-6,9-dioxo-2,5,8-triazaspiro[3.5]nonane-2-carboxamide |

TABLE 1-continued

| No. | Structure | Name |
|---|---|---|
| 561 | 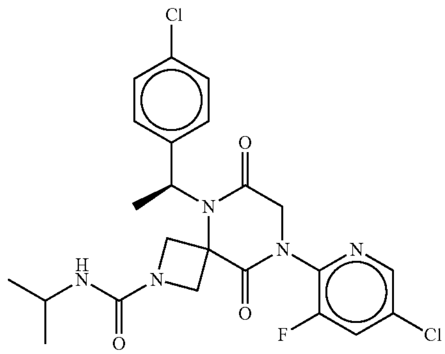 | (S)-8-(5-chloro-3-fluoro-pyridin-2-yl)-5-(1-(4-chlorophenyl)ethyl)-N-isopropyl-6,9-dioxo-2,5,8-triazaspiro[3.5]nonane-2-carboxamide |
| 562 | 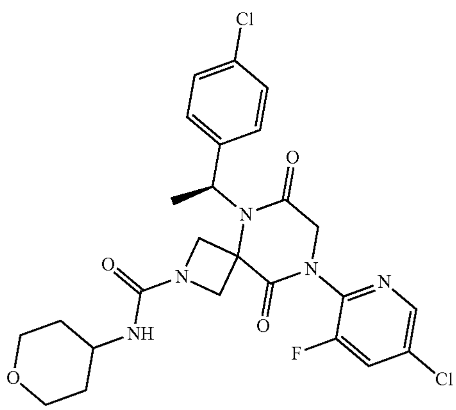 [SMILES: C[C@@H](c1ccc(Cl)cc1)N1C(=O)CN(c2ncc(Cl)cc2F)C(=O)C12CN(C(=O)NC1CCOCC1)C2] | (S)-8-(5-chloro-3-fluoro-pyridin-2-yl)-5-(1-(4-chlorophenyl)ethyl)-6,9-dioxo-N-(tetrahydro-2H-pyran-4-yl)-2,5,8-triazaspiro[3.5]nonane-2-carboxamide |
| 563 | 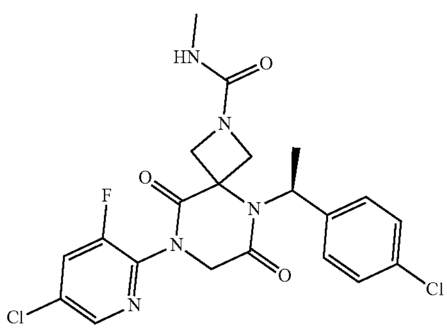 [SMILES: CNC(=O)N1CC2(C1)C(=O)N(c1ncc(Cl)cc1F)CC(=O)N2[C@@H](C)c1ccc(Cl)cc1] | (S)-8-(5-chloro-3-fluoro-pyridin-2-yl)-5-(1-(4-chlorophenyl)ethyl)-N-methyl-6,9-dioxo-2,5,8-triazaspiro[3.5]nonane-2-carboxamide |
| 564 | 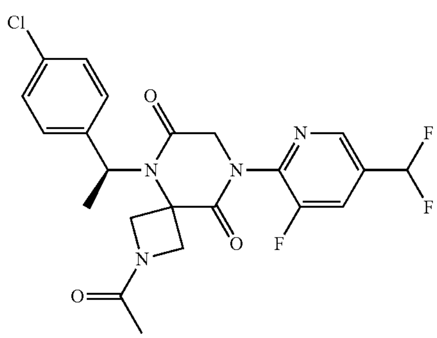 [SMILES: CC(=O)N1CC2(C1)C(=O)N(c1ncc(C(F)F)cc1F)CC(=O)N2[C@@H](C)c1ccc(Cl)cc1] | (S)-2-acetyl-5-(1-(4-chlorophenyl)ethyl)-8-(5-(difluoromethyl)-3-fluoropyridin-2-yl)-2,5,8-triazaspiro[3.5]nonane-6,9-dione |

TABLE 1-continued

| No. | Structure | Name |
|---|---|---|
| 565 | 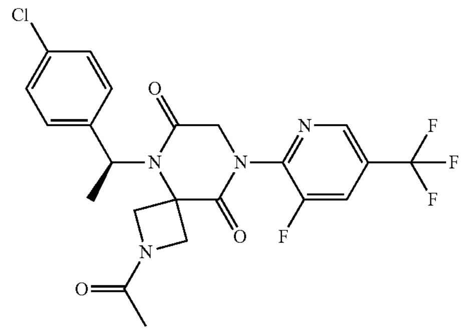 [SMILES: CC(=O)N1CC2(C1)C(=O)N(c1ncc(C(F)(F)F)cc1F)CC(=O)N2[C@@H](C)c1ccc(Cl)cc1] | (S)-2-acetyl-5-(1-(4-chlorophenyl)ethyl)-8-(3-fluoro-5-(trifluoromethyl)-pyridin-2-yl)-2,5,8-triazaspiro[3.5]nonane-6,9-dione |
| 566 | 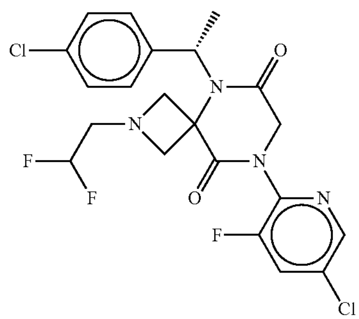 | (S)-8-(5-chloro-3-fluoro-pyridin-2-yl)-5-(1-(4-chlorophenyl)ethyl)-2-(2,2-difluoroethyl)-2,5,8-triazaspiro[3.5]nonane-6,9-dione |
| 567 | 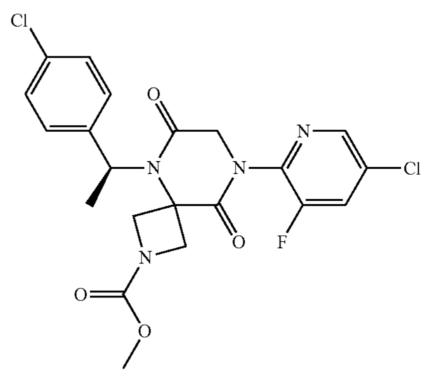 [SMILES: COC(=O)N1CC2(C1)C(=O)N(c1ncc(Cl)cc1F)CC(=O)N2[C@@H](C)c1ccc(Cl)cc1] | methyl (S)-8-(5-chloro-3-fluoropyridin-2-yl)-5-(1-(4-chlorophenyl)ethyl)-6,9-dioxo-2,5,8-triazaspiro-[3.5]nonane-2-carboxylate |
| 568 | 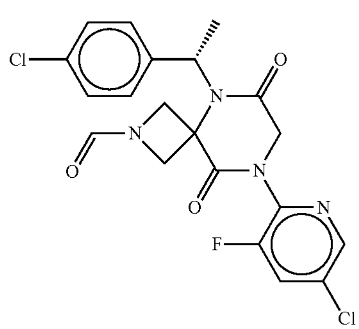 | (S)-8-(5-chloro-3-fluoro-pyridin-2-yl)-5-(1-(4-chlorophenyl)ethyl)-6,9-dioxo-2,5,8-triazaspiro-[3.5]nonane-2-carbaldehyde |

TABLE 1-continued

| No. | Structure | Name |
|---|---|---|
| 569 | 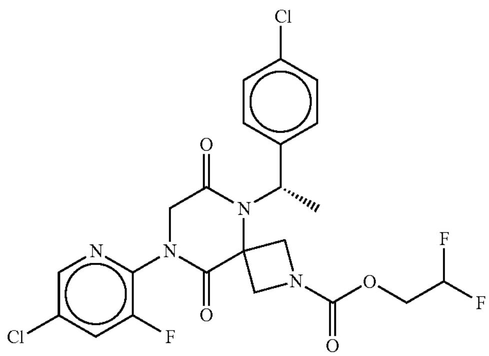 | 2,2-difluoroethyl (S)-8-(5-chloro-3-fluoropyridin-2-yl)-5-(1-(4-chlorophenyl)-ethyl)-6,9-dioxo-2,5,8-triazaspiro[3.5]nonane-2-carboxylate |
| 570 | 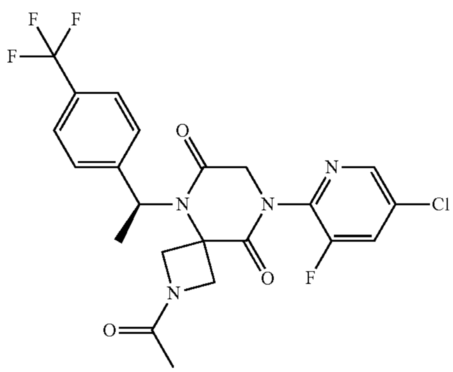 | (S)-2-acetyl-8-(5-chloro-3-fluoropyridin-2-yl)-5-(1-(4-(trifluoromethyl)phenyl)-ethyl)-2,5,8-triazaspiro-[3.5]nonane-6,9-dione |
| 571 | 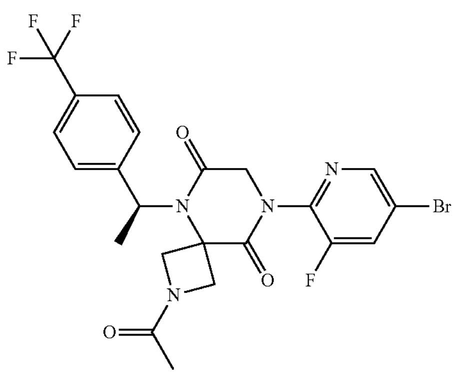 | (S)-2-acetyl-8-(5-bromo-3-fluoropyridin-2-yl)-5-(1-(4-(trifluoromethyl)phenyl)-ethyl)-2,5,8-triazaspiro-[3.5]nonane-6,9-dione |
| 572 | 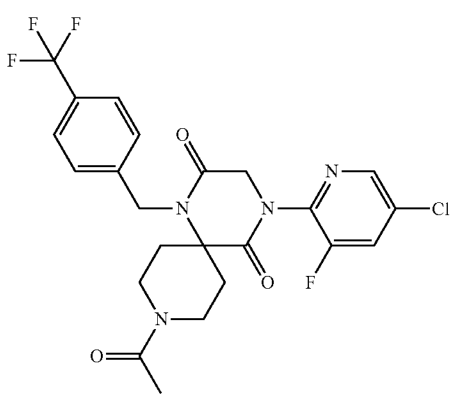 [SMILES: CC(=O)N1CCC2(CC1)C(=O)N(c1ncc(Cl)cc1F)CC(=O)N2Cc1ccc(C(F)(F)F)cc1] | 9-acetyl-4-(5-chloro-3-fluoropyridin-2-yl)-1-(4-(trifluoromethyl)benzyl)-1,4,9-triazaspiro[5.5]-undecane-2,5-dione |

TABLE 1-continued

| No. | Structure | Name |
|-----|-----------|------|
| 573 | 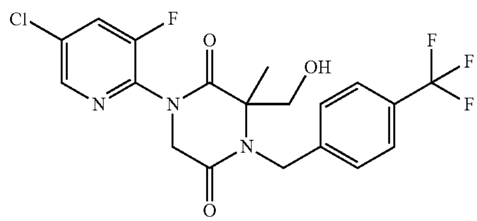 [SMILES: CC1(CO)C(=O)N(c2ncc(Cl)cc2F)CC(=O)N1Cc1ccc(C(F)(F)F)cc1] | 1-(5-chloro-3-fluoropyridin-2-yl)-3-(hydroxymethyl)-3-methyl-4-(4-(trifluoromethyl)benzyl)piperazine-2,5-dione |
| 574 | 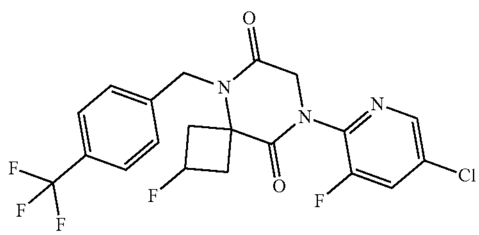 [SMILES: O=C1CN(c2ncc(Cl)cc2F)C(=O)C2(CC(F)C2)N1Cc1ccc(C(F)(F)F)cc1] | 8-(5-chloro-3-fluoropyridin-2-yl)-2-fluoro-5-(4-(trifluoromethyl)benzyl)-5,8-diazaspiro[3.5]nonane-6,9-dione |
| 575 | 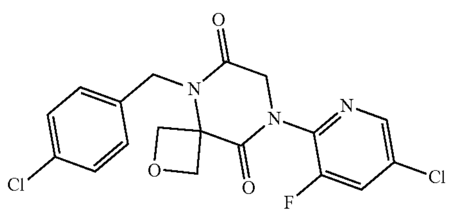 [SMILES: O=C1CN(c2ncc(Cl)cc2F)C(=O)C2(COC2)N1Cc1ccc(Cl)cc1] | 8-(5-chloro-3-fluoropyridin-2-yl)-5-(4-chlorobenzyl)-2-oxa-5,8-diazaspiro[3.5]-nonane-6,9-dione |
| 576 | 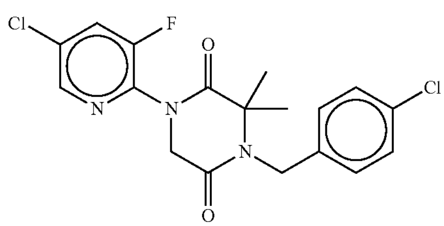 | 1-(5-chloro-3-fluoropyridin-2-yl)-4-(4-chlorobenzyl)-3,3-dimethylpiperazine-2,5-dione |
| 577 | 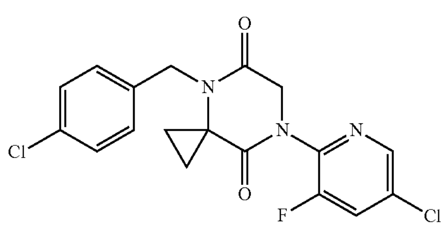 [SMILES: O=C1CN(c2ncc(Cl)cc2F)C(=O)C2(CC2)N1Cc1ccc(Cl)cc1] | 7-(5-chloro-3-fluoropyridin-2-yl)-4-(4-chlorobenzyl)-4,7-diazaspiro[2.5]octane-5,8-dione |
| 578 | 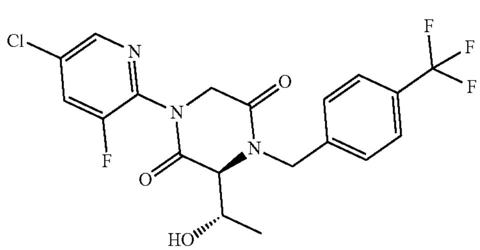 [SMILES: C[C@H](O)[C@H]1C(=O)N(c2ncc(Cl)cc2F)CC(=O)N1Cc1ccc(C(F)(F)F)cc1] | (S)-1-(5-chloro-3-fluoropyridin-2-yl)-3-((S)-1-hydroxyethyl)-4-(4-(trifluoromethyl)benzyl)-piperazine-2,5-dione |

TABLE 1-continued

| No. | Structure | Name |
|---|---|---|
| 579 | 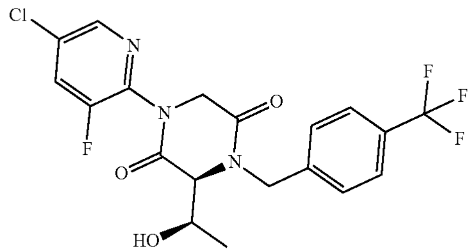 [SMILES: C[C@@H](O)[C@H]1C(=O)N(c2ncc(Cl)cc2F)CC(=O)N1Cc1ccc(C(F)(F)F)cc1] | (S)-1-(5-chloro-3-fluoro-pyridin-2-yl)-3-((R)-1-hydroxyethyl)-4-(4-(trifluoromethyl)benzyl)-piperazine-2,5-dione |
| 580 | 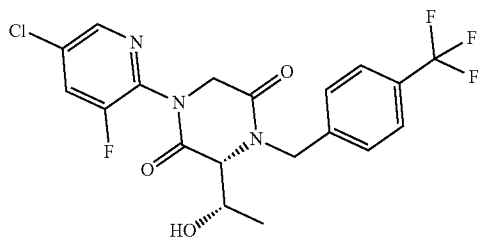 [SMILES: C[C@H](O)[C@@H]1C(=O)N(c2ncc(Cl)cc2F)CC(=O)N1Cc1ccc(C(F)(F)F)cc1] | (R)-1-(5-chloro-3-fluoro-pyridin-2-yl)-3-((S)-1-hydroxyethyl)-4-(4-(trifluoromethyl)benzyl)-piperazine-2,5-dione |
| 581 | 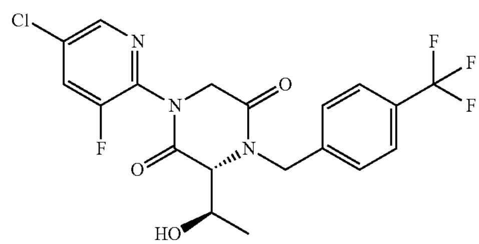 [SMILES: C[C@@H](O)[C@@H]1C(=O)N(c2ncc(Cl)cc2F)CC(=O)N1Cc1ccc(C(F)(F)F)cc1] | (R)-1-(5-chloro-3-fluoro-pyridin-2-yl)-3-((R)-1-hydroxyethyl)-4-(4-(trifluoromethyl)benzyl)-piperazine-2,5-dione |
| 582 | 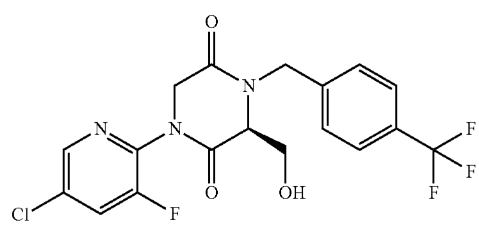 [SMILES: O=C1[C@H](CO)N(Cc2ccc(C(F)(F)F)cc2)C(=O)CN1c1ncc(Cl)cc1F] | (S)-1-(5-chloro-3-fluoro-pyridin-2-yl)-3-(hydroxymethyl)-4-(4-(trifluoromethyl)benzyl)-piperazine-2,5-dione |
| 583 | 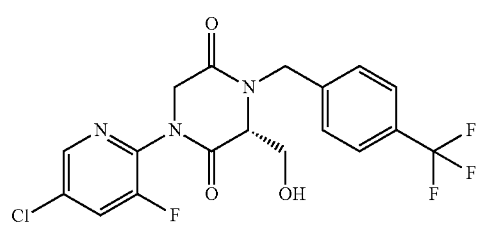 [SMILES: O=C1[C@@H](CO)N(Cc2ccc(C(F)(F)F)cc2)C(=O)CN1c1ncc(Cl)cc1F] | (R)-1-(5-chloro-3-fluoro-pyridin-2-yl)-3-(hydroxymethyl)-4-(4-(trifluoromethyl)benzyl)-piperazine-2,5-dione |
| 584 | 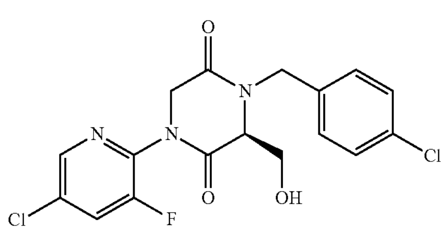 [SMILES: O=C1[C@H](CO)N(Cc2ccc(Cl)cc2)C(=O)CN1c1ncc(Cl)cc1F] | (S)-1-(5-chloro-3-fluoro-pyridin-2-yl)-4-(4-chlorobenzyl)-3-(hydroxymethyl)piperazine-2,5-dione |

TABLE 1-continued

| No. | Structure | Name |
|---|---|---|
| 585 | 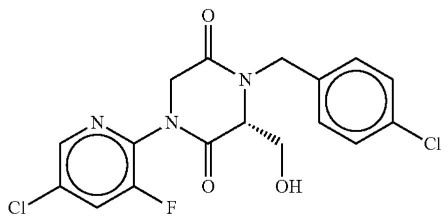 | (R)-1-(5-chloro-3-fluoro-pyridin-2-yl)-4-(4-chloro-benzyl)-3-(hydroxy-methyl)piperazine-2,5-dione |
| 586 | 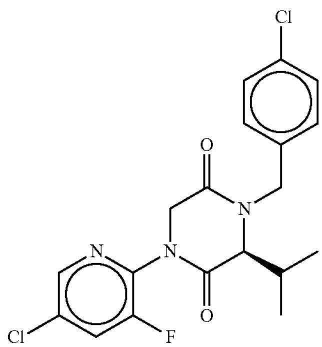 | (S)-1-(5-chloro-3-fluoropyridin-2-yl)-4-(4-chlorobenzyl)-3-isopropylpiperazine-2,5-dione |
| 587 | 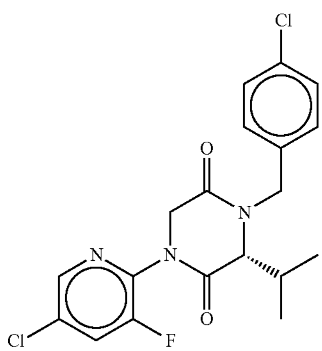 | (R)-1-(5-chloro-3-fluoro-pyridin-2-yl)-4-(4-chlorobenzyl)-3-isopropylpiperazine-2,5-dione |
| 588 | 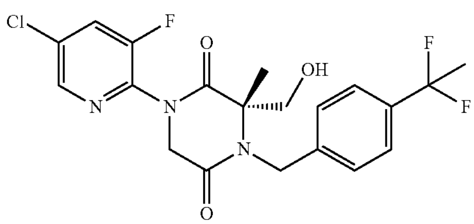 [SMILES: CC(F)(F)c1ccc(CN2C(=O)CN(c3ncc(Cl)cc3F)C(=O)[C@]2(C)CO)cc1] | (S)-1-(5-chloro-3-fluoro-pyridin-2-yl)-3-(hydroxy-methyl)-3-methyl-4-(4-(trifluoromethyl)-benzyl)piperazine-2,5-dione |
| 589 | 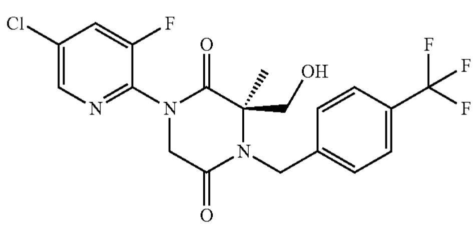 [SMILES: C[C@@]1(CO)C(=O)N(c2ncc(Cl)cc2F)CC(=O)N1Cc1ccc(C(F)(F)F)cc1] | (R)-1-(5-chloro-3-fluoro-pyridin-2-yl)-3-(hydroxy-methyl)-3-methyl-4-(4-(trifluoromethyl)-benzyl)piperazine-2,5-dione |
| 590 | 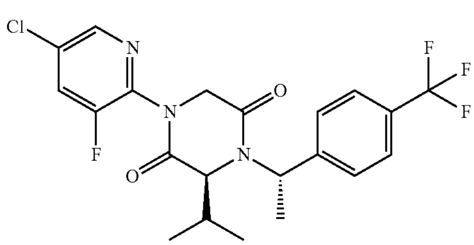 [SMILES: CC(C)[C@H]1C(=O)N(c2ncc(Cl)cc2F)CC(=O)N1[C@@H](C)c1ccc(C(F)(F)F)cc1] | (S)-1-(5-chloro-3-fluoro-pyridin-2-yl)-3-isopropyl-4-((S)-1-(4-(trifluoro-methyl)phenyl)ethyl)piperazine-2,5-dione |

TABLE 1-continued

| No. | Structure | Name |
|---|---|---|
| 591 | 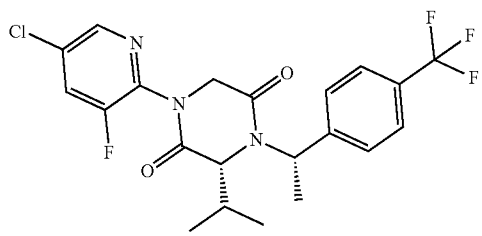 [SMILES: CC(C)[C@@H]1C(=O)N(c2ncc(Cl)cc2F)CC(=O)N1[C@@H](C)c1ccc(C(F)(F)F)cc1] | (R)-1-(5-chloro-3-fluoro-pyridin-2-yl)-3-isopropyl-4-((S)-1-(4-(trifluoro-methyl)phenyl)ethyl)piperazine-2,5-dione |
| 592 | 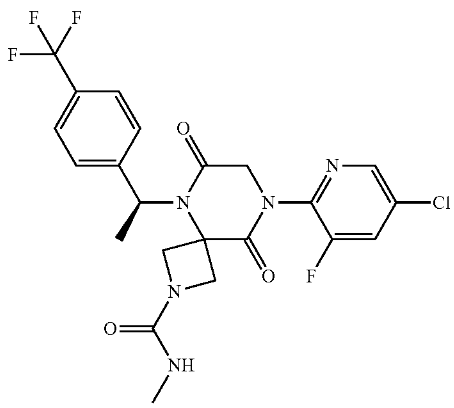 [SMILES: CNC(=O)N1CC2(C1)C(=O)N(c1ncc(Cl)cc1F)CC(=O)N2[C@@H](C)c1ccc(C(F)(F)F)cc1] | (S)-8-(5-chloro-3-fluoro-pyridin-2-yl)-N-methyl-6,9-dioxo-5-(1-(4-(trifluoromethyl)phenyl)-ethyl)-2,5,8-triazaspiro-[3.5]nonane-2-carboxamide |
| 593 | 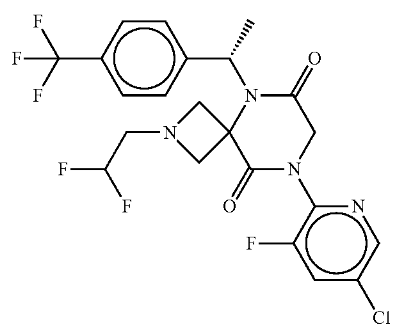 | (S)-8-(5-chloro-3-fluoro-pyridin-2-yl)-2-(2,2-difluoroethyl)-5-(1-(4-(trifluoromethyl)phenyl)-ethyl)-2,5,8-triazaspiro-[3.5]nonane-6,9-dione |
| 594 | 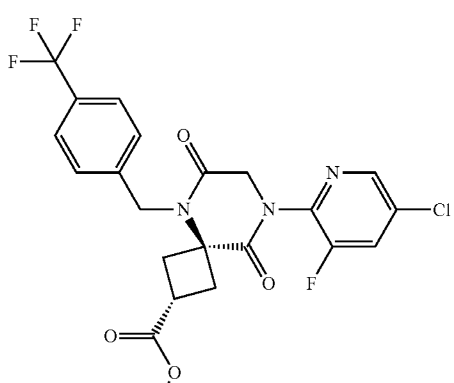 | ethyl (2r,4r)-8-(5-chloro-3-fluoropyridin-2-yl)-6,9-dioxo-5-(4-(trifluoro-methyl)benzyl)-5,8-diazaspiro[3.5]nonane-2-carboxylate |

TABLE 1-continued

| No. | Structure | Name |
|---|---|---|
| 595 | 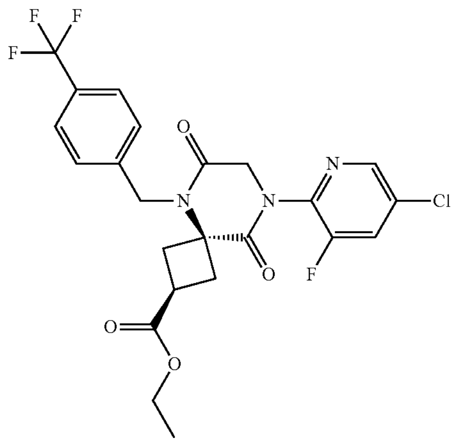 [SMILES: CCOC(=O)[C@H]1C[C@@]2(C1)C(=O)N(c1ncc(Cl)cc1F)CC(=O)N2Cc1ccc(C(F)(F)F)cc1] | ethyl (2s,4s)-8-(5-chloro-3-fluoropyridin-2-yl)-6,9-dioxo-5-(4-(trifluoromethyl)benzyl)-5,8-diazaspiro[3.5]nonane-2-carboxylate |
| 596 | 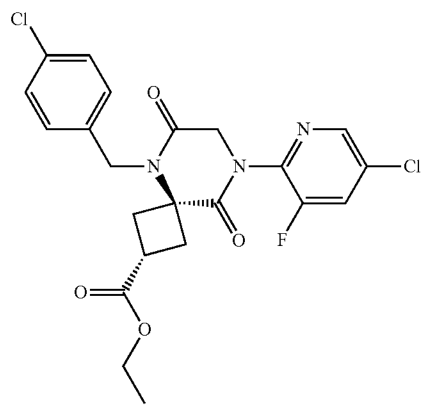 [SMILES: CCOC(=O)[C@H]1C[C@]2(C1)C(=O)N(c1ncc(Cl)cc1F)CC(=O)N2Cc1ccc(Cl)cc1] | ethyl (2r,4r)-8-(5-chloro-3-fluoropyridin-2-yl)-5-(4-chlorobenzyl)-6,9-dioxo-5,8-diazaspiro[3.5]nonane-2-carboxylate |
| 597 | 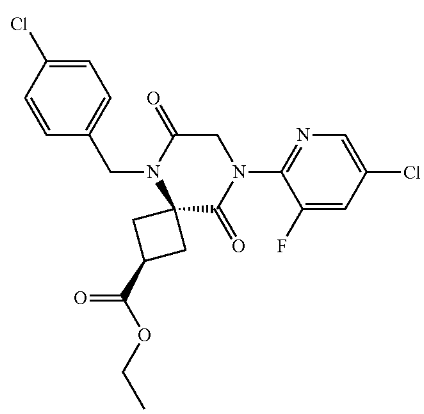 [SMILES: CCOC(=O)[C@H]1C[C@@]2(C1)C(=O)N(c1ncc(Cl)cc1F)CC(=O)N2Cc1ccc(Cl)cc1] | ethyl (2s,4s)-8-(5-chloro-3-fluoropyridin-2-yl)-5-(4-chlorobenzyl)-6,9-dioxo-5,8-diazaspiro[3.5]nonane-2-carboxylate |
| 598 | 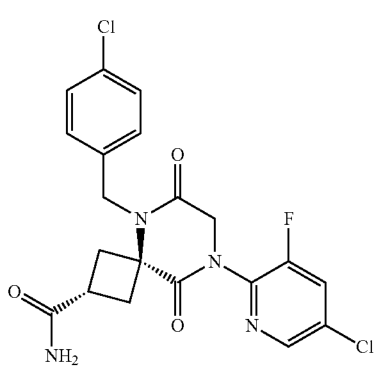 [SMILES: NC(=O)[C@H]1C[C@]2(C1)C(=O)N(c1ncc(Cl)cc1F)CC(=O)N2Cc1ccc(Cl)cc1] | (2r,4r)-8-(5-chloro-3-fluoropyridin-2-yl)-5-(4-chlorobenzyl)-6,9-dioxo-5,8-diazaspiro[3.5]nonane-2-carboxamide |

TABLE 1-continued

| No. | Structure | Name |
|---|---|---|
| 599 | 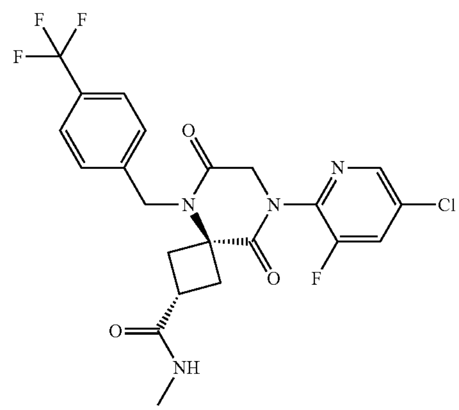 [SMILES: CNC(=O)[C@H]1C[C@]2(C1)C(=O)N(c1ncc(Cl)cc1F)CC(=O)N2Cc1ccc(C(F)(F)F)cc1] | (2r,4r)-8-(5-chloro-3-fluoropyridin-2-yl)-N-methyl-6,9-dioxo-5-(4-(trifluoromethyl)benzyl)-5,8-diazaspiro[3.5]nonane-2-carboxamide |
| 600 | 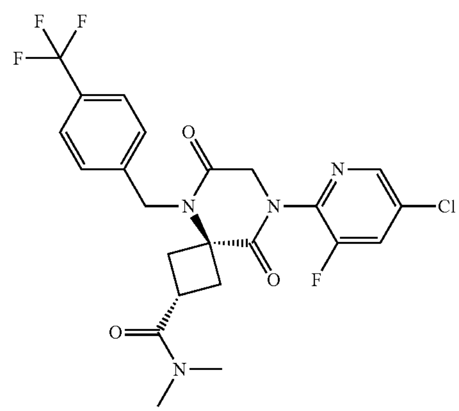 [SMILES: CN(C)C(=O)[C@H]1C[C@]2(C1)C(=O)N(c1ncc(Cl)cc1F)CC(=O)N2Cc1ccc(C(F)(F)F)cc1] | (2r,4r)-8-(5-chloro-3-fluoropyridin-2-yl)-N,N-dimethyl-6,9-dioxo-5-(4-(trifluoromethyl)benzyl)-5,8-diazaspiro[3.5]nonane-2-carboxamide |
| 601 | 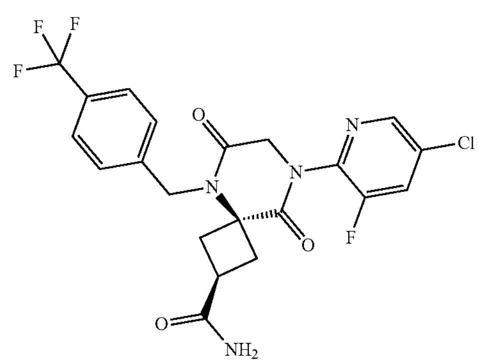 [SMILES: NC(=O)[C@H]1C[C@@]2(C1)C(=O)N(c1ncc(Cl)cc1F)CC(=O)N2Cc1ccc(C(F)(F)F)cc1] | (2s,4s)-8-(5-chloro-3-fluoropyridin-2-yl)-6,9-dioxo-5-(4-(trifluoromethyl)benzyl)-5,8-diazaspiro[3.5]nonane-2-carboxamide |
| 602 | 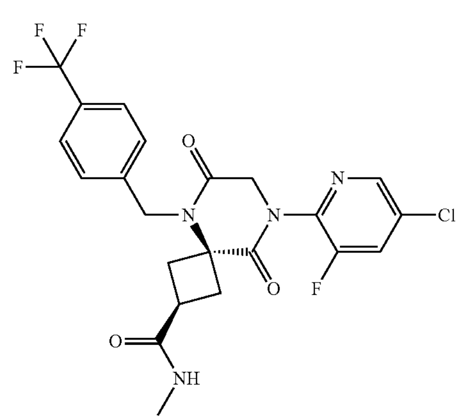 [SMILES: CNC(=O)[C@H]1C[C@@]2(C1)C(=O)N(c1ncc(Cl)cc1F)CC(=O)N2Cc1ccc(C(F)(F)F)cc1] | (2s,4s)-8-(5-chloro-3-fluoropyridin-2-yl)-N-methyl-6,9-dioxo-5-(4-(trifluoromethyl)benzyl)-5,8-diazaspiro[3.5]-nonane-2-carboxamide |

TABLE 1-continued

| No. | Structure | Name |
|---|---|---|
| 603 | 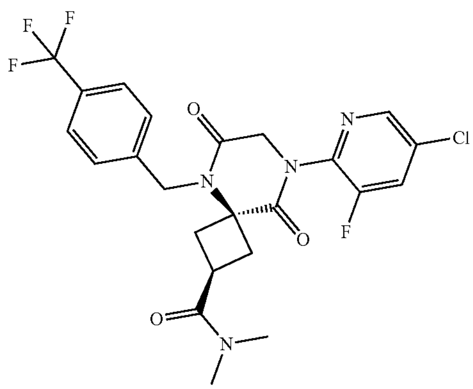 [SMILES: CN(C)C(=O)[C@H]1C[C@@]2(C1)C(=O)N(c1ncc(Cl)cc1F)CC(=O)N2Cc1ccc(C(F)(F)F)cc1] | (2s,4s)-8-(5-chloro-3-fluoropyridin-2-yl)-N,N-dimethyl-6,9-dioxo-5-(4-(trifluoromethyl)benzyl)-5,8-diazaspiro[3.5]nonane-2-carboxamide |
| 604 | 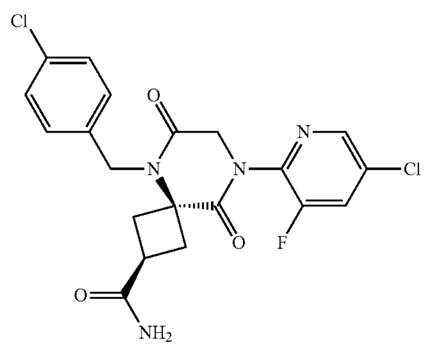 [SMILES: NC(=O)[C@H]1C[C@@]2(C1)C(=O)N(c1ncc(Cl)cc1F)CC(=O)N2Cc1ccc(Cl)cc1] | (2s,4s)-8-(5-chloro-3-fluoropyridin-2-yl)-5-(4-chlorobenzyl)-6,9-dioxo-5,8-diazaspiro[3.5]nonane-2-carboxamide |
| 605 | 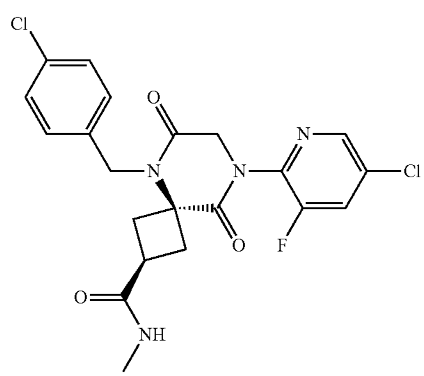 [SMILES: CNC(=O)[C@H]1C[C@@]2(C1)C(=O)N(c1ncc(Cl)cc1F)CC(=O)N2Cc1ccc(Cl)cc1] | (2s,4s)-8-(5-chloro-3-fluoropyridin-2-yl)-5-(4-chlorobenzyl)-N-methyl-6,9-dioxo-5,8-diazaspiro[3.5]nonane-2-carboxamide |
| 606 | 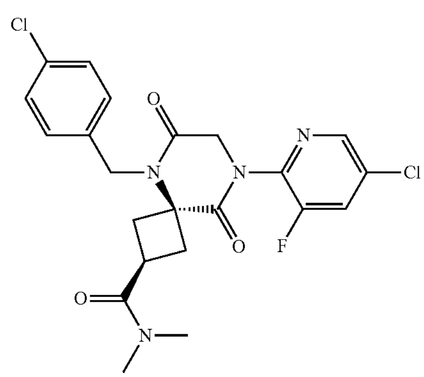 [SMILES: CN(C)C(=O)[C@H]1C[C@@]2(C1)C(=O)N(c1ncc(Cl)cc1F)CC(=O)N2Cc1ccc(Cl)cc1] | (2s,4s)-8-(5-chloro-3-fluoropyridin-2-yl)-5-(4-chlorobenzyl)-N,N-dimethyl-6,9-dioxo-5,8-diazaspiro[3.5]nonane-2-carboxamide |

TABLE 1-continued

| No. | Structure | Name |
|---|---|---|
| 607 | 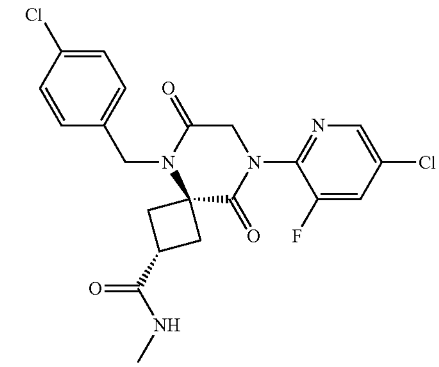 [SMILES: CNC(=O)[C@H]1C[C@]2(C1)C(=O)N(c1ncc(Cl)cc1F)CC(=O)N2Cc1ccc(Cl)cc1] | (2r,4r)-8-(5-chloro-3-fluoropyridin-2-yl)-5-(4-chlorobenzyl)-N-methyl-6,9-dioxo-5,8-diazaspiro[3.5]nonane-2-carboxamide |
| 608 | 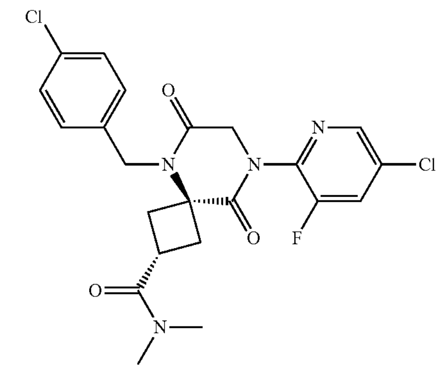 [SMILES: CN(C)C(=O)[C@H]1C[C@]2(C1)C(=O)N(c1ncc(Cl)cc1F)CC(=O)N2Cc1ccc(Cl)cc1] | (2r,4r)-8-(5-chloro-3-fluoro-pyridin-2-yl)-5-(4-chloro-benzyl)-N,N-dimethyl-6,9-dioxo-5,8-diazaspiro[3.5]-nonane-2-carboxamide |
| 609 | 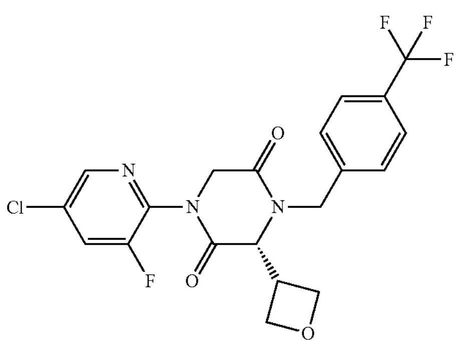 | (R)-1-(5-chloro-3-fluoro-pyridin-2-yl)-3-(oxetan-3-yl)-4-(4-(trifluoro-methyl)benzyl)piperazine-2,5-dione |
| 610 | 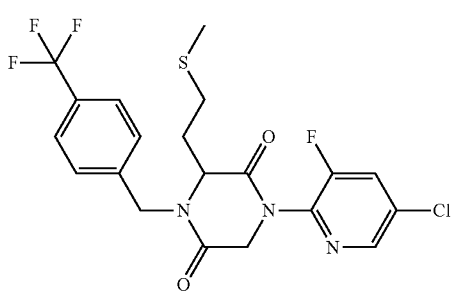 [SMILES: CSCCC1C(=O)N(c2ncc(Cl)cc2F)CC(=O)N1Cc1ccc(C(F)(F)F)cc1] | 1-(5-chloro-3-fluoropyridin-2-yl)-3-(2-(methylthio)-ethyl)-4-(4-(trifluoro-methyl)-benzyl)piperazine-2,5-dione |

TABLE 1-continued

| No. | Structure | Name |
| --- | --- | --- |
| 611 | 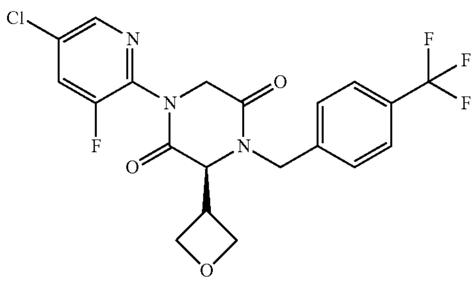 [SMILES: O=C1[C@H](C2COC2)N(Cc2ccc(C(F)(F)F)cc2)C(=O)CN1c1ncc(Cl)cc1F] | (S)-1-(5-chloro-3-fluoro-pyridin-2-yl)-3-(oxetan-3-yl)-4-(4-(trifluoromethyl)benzyl)piperazine-2,5-dione |
| 612 | 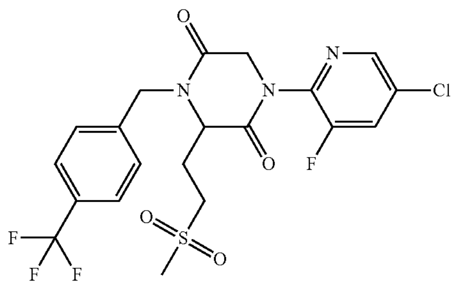 [SMILES: CS(=O)(=O)CCC1C(=O)N(c2ncc(Cl)cc2F)CC(=O)N1Cc1ccc(C(F)(F)F)cc1] | 1-(5-chloro-3-fluoropyridin-2-yl)-3-(2-(methylsulfonyl)ethyl)-4-(4-(trifluoromethyl)benzyl)piperazine-2,5-dione |
| 613 | 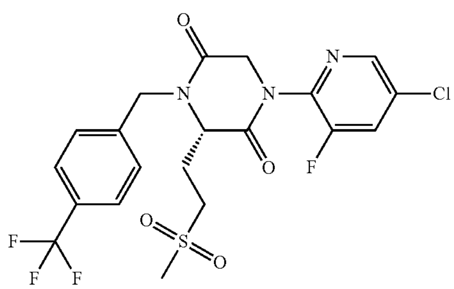 [SMILES: CS(=O)(=O)CC[C@H]1C(=O)N(c2ncc(Cl)cc2F)CC(=O)N1Cc1ccc(C(F)(F)F)cc1] | (S)-1-(5-chloro-3-fluoropyridin-2-yl)-3-(2-(methylsulfonyl)ethyl)-4-(4-(trifluoromethyl)benzyl)piperazine-2,5-dione |
| 614 | 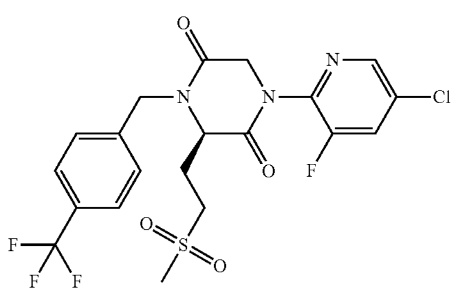 [SMILES: CS(=O)(=O)CC[C@@H]1C(=O)N(c2ncc(Cl)cc2F)CC(=O)N1Cc1ccc(C(F)(F)F)cc1] | (R)-1-(5-chloro-3-fluoropyridin-2-yl)-3-(2-(methylsulfonyl)ethyl)-4-(4-(trifluoromethyl)benzyl)piperazine-2,5-dione |
| 615 | 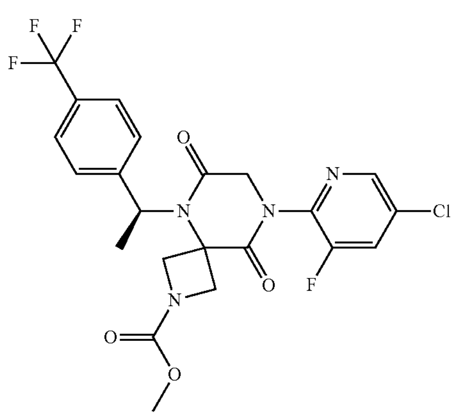 [SMILES: COC(=O)N1CC2(C1)C(=O)N(c1ncc(Cl)cc1F)CC(=O)N2[C@@H](C)c1ccc(C(F)(F)F)cc1] | methyl (S)-8-(5-chloro-3-fluoropyridin-2-yl)-6,9-dioxo-5-(1-(4-(trifluoromethyl)phenyl)ethyl)-2,5,8-triazaspiro[3.5]nonane-2-carboxylate |

TABLE 1-continued

| No. | Structure | Name |
|---|---|---|
| 616 | 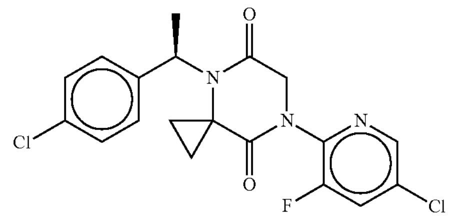 | (R)-7-(5-chloro-3-fluoro-pyridin-2-yl)-4-(1-(4-chlorophenyl)ethyl)-4,7-diazaspiro[2.5]octane-5,8-dione |
| 617 | 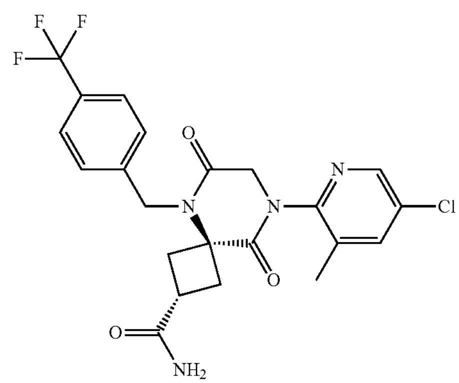 [SMILES: Cc1cc(Cl)cnc1N1CC(=O)N(Cc2ccc(C(F)(F)F)cc2)[C@]2(C[C@H](C(N)=O)C2)C1=O] | (2r,4r)-8-(5-chloro-3-methyl-pyridin-2-yl)-6,9-dioxo-5-(4-(trifluoromethyl)benzyl)-5,8-diazaspiro[3.5]nonane-2-carboxamide |
| 618 | 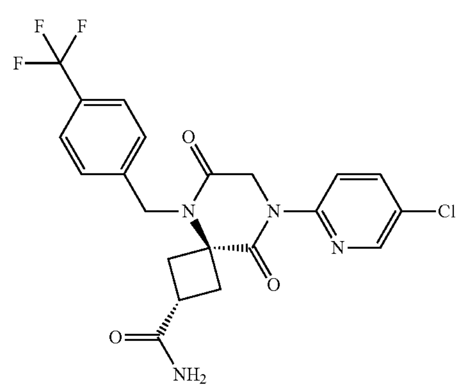 [SMILES: NC(=O)[C@H]1C[C@]2(C1)C(=O)N(c1ccc(Cl)cn1)CC(=O)N2Cc1ccc(C(F)(F)F)cc1] | (2r,4r)-8-(5-chloropyridin-2-yl)-6,9-dioxo-5-(4-(trifluoromethyl)benzyl)-5,8-diazaspiro[3.5]nonane-2-carboxamide |
| 619 | 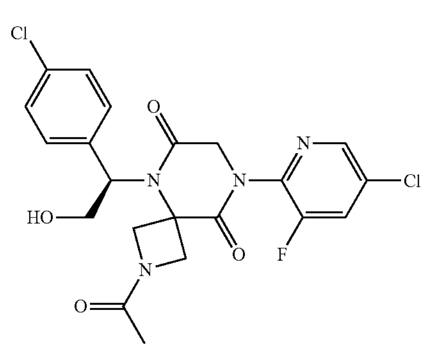 [SMILES: CC(=O)N1CC2(C1)C(=O)N(c1ncc(Cl)cc1F)CC(=O)N2[C@@H](CO)c1ccc(Cl)cc1] | (R)-2-acetyl-8-(5-chloro-3-fluoropyridin-2-yl)-5-(1-(4-chlorophenyl)-2-hydroxy-ethyl)-2,5,8-triazaspiro-[3.5]nonane-6,9-dione |

TABLE 1-continued

| No. | Structure | Name |
|---|---|---|
| 620 | 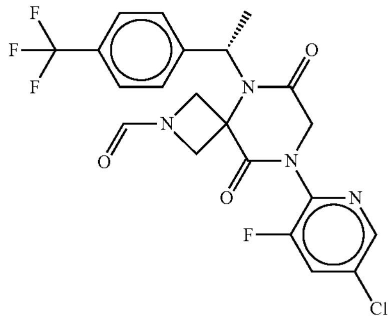 | (S)-8-(5-chloro-3-fluoro-pyridin-2-yl)-6,9-dioxo-5-(1-(4-(trifluoromethyl)-phenyl)ethyl)-2,5,8-triazaspiro[3.5]nonane-2-carbaldehyde |
| 621 | 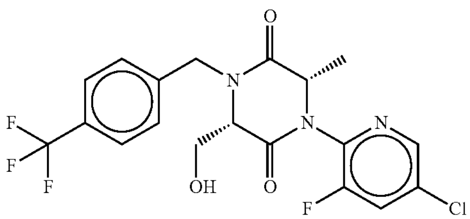 | (3S,6S)-1-(5-chloro-3-fluoropyridin-2-yl)-3-(hydroxymethyl)-6-methyl-4-(4-(trifluoromethyl)-benzyl)piperazine-2,5-dione |
| 622 | 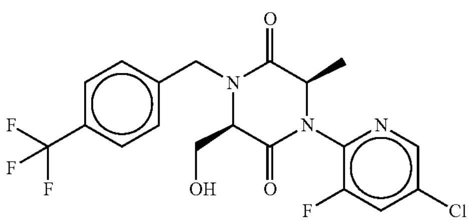 | (3R,6R)-1-(5-chloro-3-fluoropyridin-2-yl)-3-(hydroxymethyl)-6-methyl-4-(4-(trifluoromethyl)-benzyl)piperazine-2,5-dione |
| 623 | 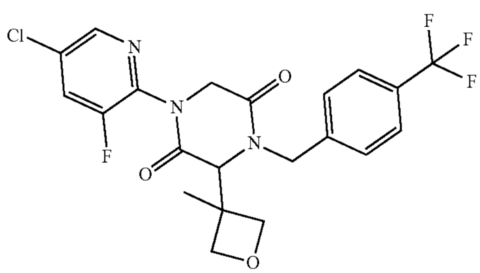 [SMILES: CC1(C2C(=O)N(c3ncc(Cl)cc3F)CC(=O)N2Cc2ccc(C(F)(F)F)cc2)COC1] | 1-(5-chloro-3-fluoropyridin-2-yl)-3-(3-methyloxetan-3-yl)-4-(4-(trifluoromethyl)-benzyl)piperazine-2,5-dione |
| 624 | 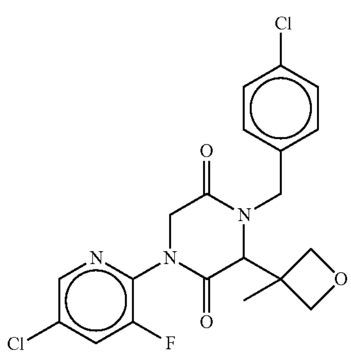 | 1-(5-chloro-3-fluoropyridin-2-yl)-4-(4-chlorobenzyl)-3-(3-methyloxetan-3-yl)-piperazine-2,5-dione |

TABLE 1-continued

| No. | Structure | Name |
|---|---|---|
| 625 | 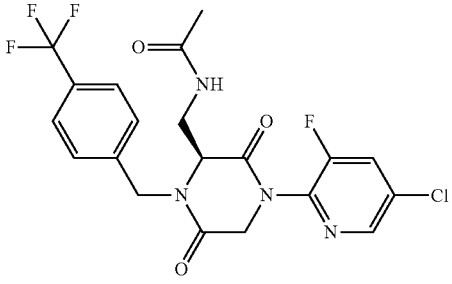 [SMILES: CC(=O)NC[C@H]1C(=O)N(c2ncc(Cl)cc2F)CC(=O)N1Cc1ccc(C(F)(F)F)cc1] | (S)-N-((4-(5-chloro-3-fluoropyridin-2-yl)-3,6-dioxo-1-(4-(trifluoromethyl)benzyl)piperazin-2-yl)methyl)acetamide |
| 626 | 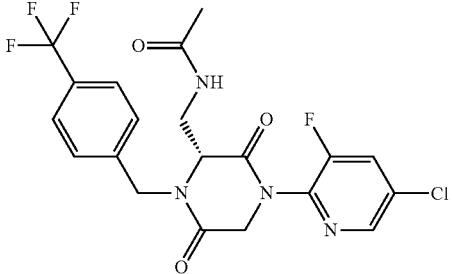 | (R)-N-((4-(5-chloro-3-fluoropyridin-2-yl)-3,6-dioxo-1-(4-(trifluoromethyl)benzyl)piperazin-2-yl)methyl)acetamide |
| 627 | 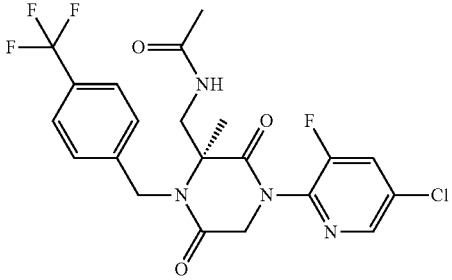 [SMILES: CC(=O)NC[C@@]1(C)C(=O)N(c2ncc(Cl)cc2F)CC(=O)N1Cc1ccc(C(F)(F)F)cc1] | (S)-N-((4-(5-chloro-3-fluoropyridin-2-yl)-2-methyl-3,6-dioxo-1-(4-(trifluoromethyl)benzyl)-piperazin-2-yl)methyl)-acetamide |
| 628 | 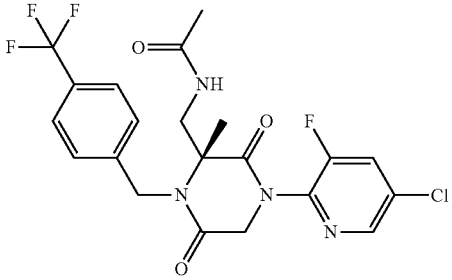 [SMILES: CC(=O)NC[C@]1(C)C(=O)N(c2ncc(Cl)cc2F)CC(=O)N1Cc1ccc(C(F)(F)F)cc1] | (R)-N-((4-(5-chloro-3-fluoropyridin-2-yl)-2-methyl-3,6-dioxo-1-(4-(trifluoromethyl)benzyl)-piperazin-2-yl)methyl)-acetamide |
| 629 | 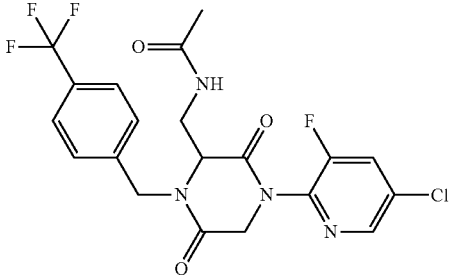 [SMILES: CC(=O)NCC1C(=O)N(c2ncc(Cl)cc2F)CC(=O)N1Cc1ccc(C(F)(F)F)cc1] | N-((4-(5-chloro-3-fluoropyridin-2-yl)-3,6-dioxo-1-(4-(trifluoromethyl)-benzyl)piperazin-2-yl)-methyl)acetamide |

TABLE 1-continued

| No. | Structure | Name |
|---|---|---|
| 630 | 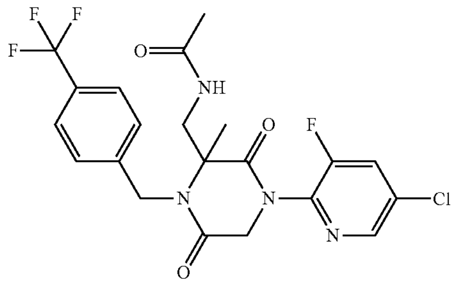 | N-((4-(5-chloro-3-fluoro-pyridin-2-yl)-2-methyl-3,6-dioxo-1-(4-(trifluoromethyl)benzyl)-piperazin-2-yl)-methyl)acetamide |
| 631 | 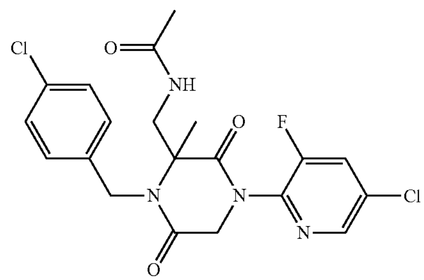 | N-((4-(5-chloro-3-fluoro-pyridin-2-yl)-1-(4-chloro-benzyl)-2-methyl-3,6-dioxopiperazin-2-yl)-methyl)acetamide |
| 632 | 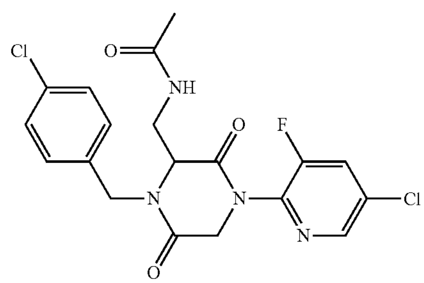 [SMILES: CC(=O)NCC1C(=O)N(c2ncc(Cl)cc2F)CC(=O)N1Cc1ccc(Cl)cc1] | N-((4-(5-chloro-3-fluoro-pyridin-2-yl)-1-(4-chloro-benzyl)-3,6-dioxopiperazin-2-yl)methyl)acetamide |
| 633 | 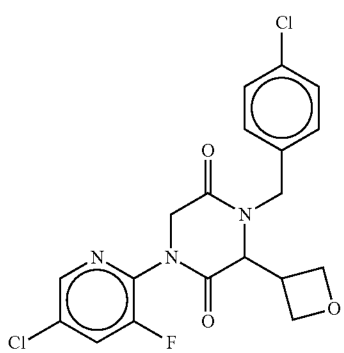 | 1-(5-chloro-3-fluoropyridin-2-yl)-4-(4-chlorobenzyl)-3-(oxetan-3-yl)piperazine-2,5-dione |
| 634 | 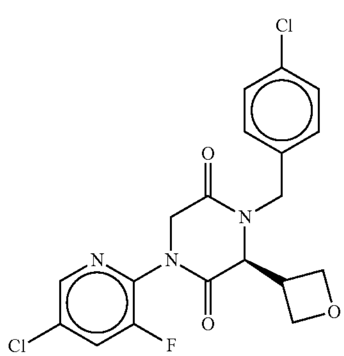 | (S)-1-(5-chloro-3-fluoro-pyridin-2-yl)-4-(4-chloro-benzyl)-3-(oxetan-3-yl)-piperazine-2,5-dione |

TABLE 1-continued

| No. | Structure | Name |
|---|---|---|
| 635 | 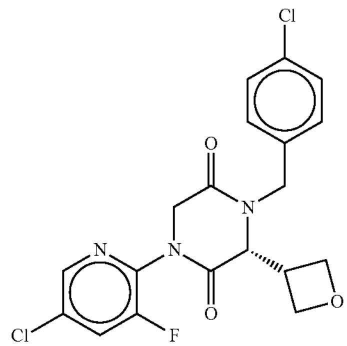 | (R)-1-(5-chloro-3-fluoro-pyridin-2-yl)-4-(4-chloro-benzyl)-3-(oxetan-3-yl)-piperazine-2,5-dione |
| 636 | 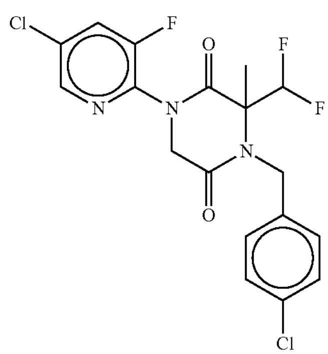 | 1-(5-chloro-3-fluoropyridin-2-yl)-4-(4-chlorobenzyl)-3-(difluoromethyl)-3-methylpiperazine-2,5-dione |
| 637 | 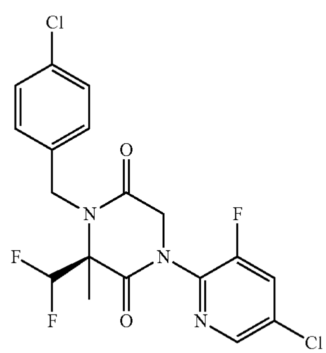 [SMILES: C[C@@]1(C(F)F)C(=O)N(c2ncc(Cl)cc2F)CC(=O)N1Cc1ccc(Cl)cc1] | (S)-1-(5-chloro-3-fluoro-pyridin-2-yl)-4-(4-chloro-benzyl)-3-(difluoromethyl)-3-methylpiperazine-2,5-dione |
| 638 | 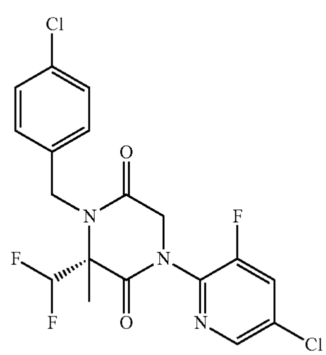 [SMILES: C[C@]1(C(F)F)C(=O)N(c2ncc(Cl)cc2F)CC(=O)N1Cc1ccc(Cl)cc1] | (R)-1-(5-chloro-3-fluoropyridin-2-yl)-4-(4-chlorobenzyl)-3-(difluoromethyl)-3-methylpiperazine-2,5-dione |

TABLE 1-continued

| No. | Structure | Name |
|---|---|---|
| 639 | 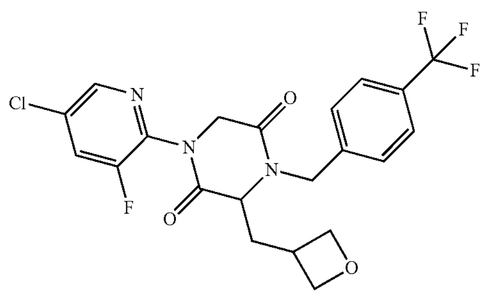 [SMILES: O=C1C(CC2COC2)N(Cc2ccc(C(F)(F)F)cc2)C(=O)CN1c1ncc(Cl)cc1F] | 1-(5-chloro-3-fluoropyridin-2-yl)-3-(oxetan-3-ylmethyl)-4-(4-(trifluoromethyl)benzyl)piperazine-2,5-dione |
| 640 | 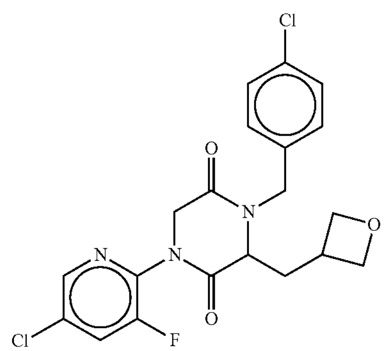 | 1-(5-chloro-3-fluoropyridin-2-yl)-4-(4-chlorobenzyl)-3-(oxetan-3-ylmethyl)-piperazine-2,5-dione |
| 641 | 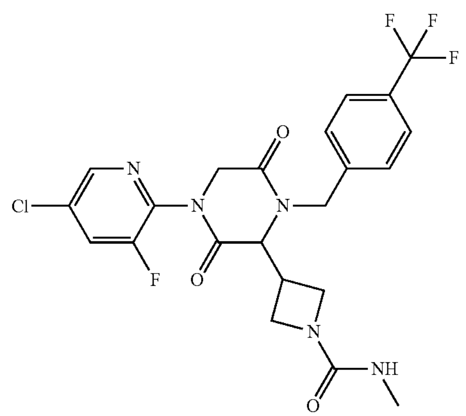 [SMILES: CNC(=O)N1CC(C2C(=O)N(c3ncc(Cl)cc3F)CC(=O)N2Cc2ccc(C(F)(F)F)cc2)C1] | 3-(4-(5-chloro-3-fluoro-pyridin-2-yl)-3,6-dioxo-1-(4-(trifluoromethyl)benzyl)piperazin-2-yl)-N-methylazetidine-1-carboxamide |
| 642 | 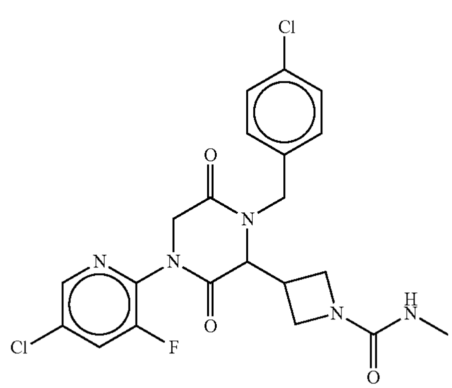 | 3-(4-(5-chloro-3-fluoro-pyridin-2-yl)-1-(4-chloro-benzyl)-3,6-dioxopiperin-2-yl)-N-methylazetidine-1-carboxamide |

TABLE 1-continued

| No. | Structure | Name |
|---|---|---|
| 643 | 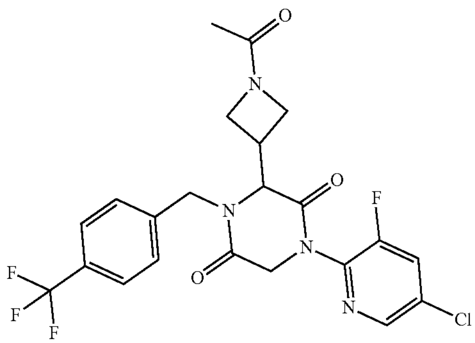 [SMILES: CC(=O)N1CC(C2C(=O)N(c3ncc(Cl)cc3F)CC(=O)N2Cc2ccc(C(F)(F)F)cc2)C1] | 3-(1-acetylazetidin-3-yl)-1-(5-chloro-3-fluoropyridin-2-yl)-4-(4-(trifluoromethyl)benzyl)piperazine-2,5-dione |
| 644 | 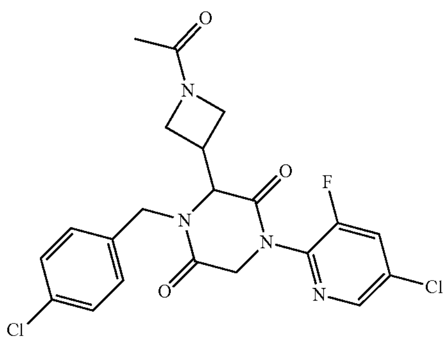 [SMILES: CC(=O)N1CC(C2C(=O)N(c3ncc(Cl)cc3F)CC(=O)N2Cc2ccc(Cl)cc2)C1] | 3-(1-acetylazetidin-3-yl)-1-(5-chloro-3-fluoropyridin-2-yl)-4-(4-chlorobenzyl)-piperazine-2,5-dione |
| 645 | 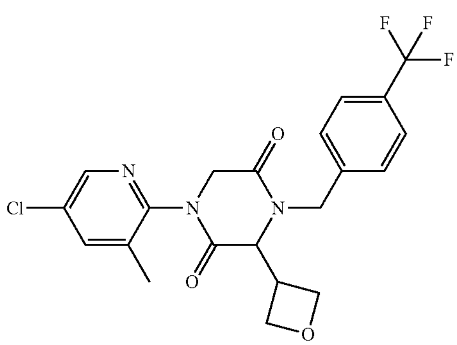 [SMILES: Cc1cc(Cl)cnc1N1CC(=O)N(Cc2ccc(C(F)(F)F)cc2)C(C2COC2)C1=O] | 1-(5-chloro-3-methylpyridin-2-yl)-3-(oxetan-3-yl)-4-(4-(trifluoromethyl)benzyl)-piperazine-2,5-dione |
| 646 | 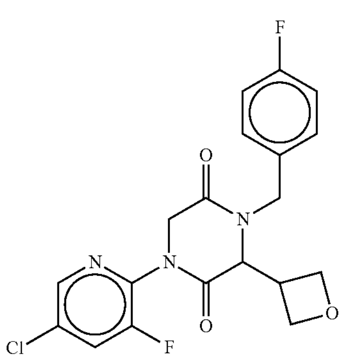 | 1-(5-chloro-3-fluoropyridin-2-yl)-4-(4-fluorobenzyl)-3-(oxetan-3-yl)piperazine-2,5-dione |

TABLE 1-continued

| No. | Structure | Name |
|---|---|---|
| 647 | 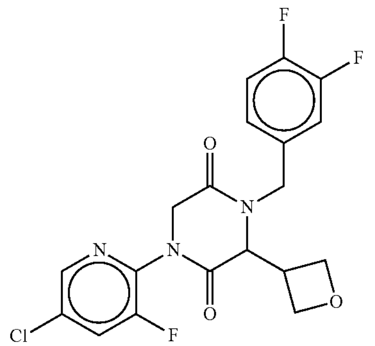 | 1-(5-chloro-3-fluoropyridin-2-yl)-4-(3,4-difluorobenzyl)-3-(oxetan-3-yl)piperazine-2,5-dione |
| 648 | 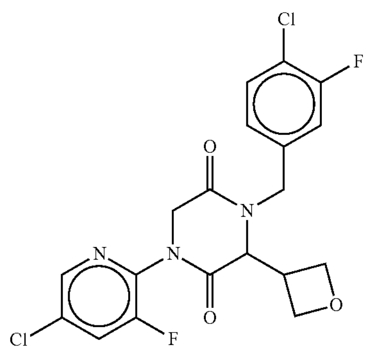 | 4-(4-chloro-3-fluorobenzyl)-1-(5-chloro-3-fluoropyridin-2-yl)-3-(oxetan-3-yl)-piperazine-2,5-dione |
| 649 | 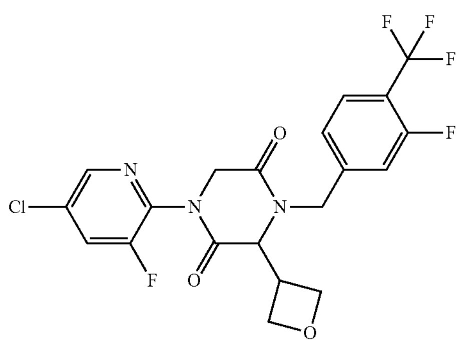 [SMILES: O=C1C(C2COC2)N(Cc2ccc(C(F)(F)F)c(F)c2)C(=O)CN1c1ncc(Cl)cc1F] | 1-(5-chloro-3-fluoropyridin-2-yl)-4-(3-fluoro-4-(trifluoromethyl)benzyl)-3-(oxetan-3-yl)piperazine-2,5-dione |
| 650 | 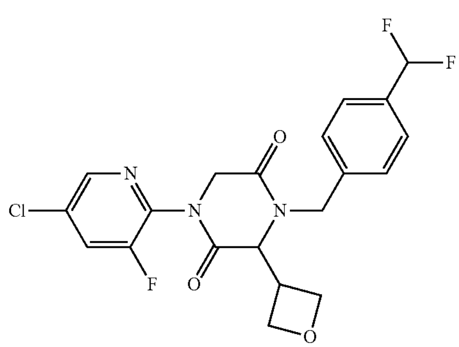 [SMILES: O=C1C(C2COC2)N(Cc2ccc(C(F)F)cc2)C(=O)CN1c1ncc(Cl)cc1F] | 1-(5-chloro-3-fluoropyridin-2-yl)-4-(4-(difluoromethyl)benzyl)-3-(oxetan-3-yl)piperazine-2,5-dione |

TABLE 1-continued

| No. | Structure | Name |
|---|---|---|
| 651 | 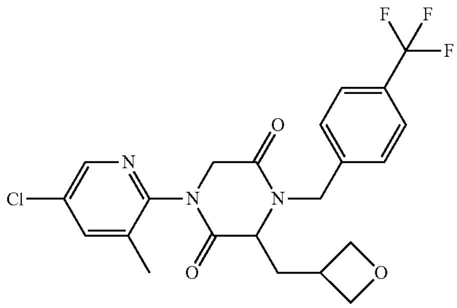 [SMILES: Cc1cc(Cl)cnc1N1CC(=O)N(Cc2ccc(C(F)(F)F)cc2)C(CC2COC2)C1=O] | 1-(5-chloro-3-methylpyridin-2-yl)-3-(oxetan-3-ylmethyl)-4-(4-(trifluoromethyl)benzyl)piperazine-2,5-dione |
| 652 | 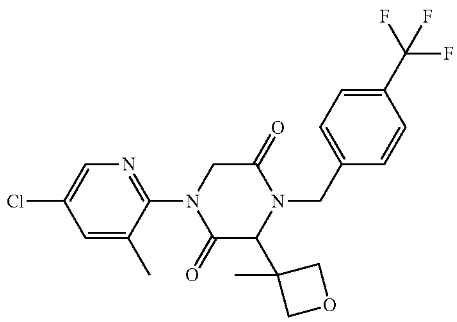 [SMILES: Cc1cc(Cl)cnc1N1CC(=O)N(Cc2ccc(C(F)(F)F)cc2)C(C2(C)COC2)C1=O] | 1-(5-chloro-3-methylpyridin-2-yl)-3-(3-methyloxetan-3-yl)-4-(4-(trifluoromethyl)benzyl)piperazine-2,5-dione |
| 653 | 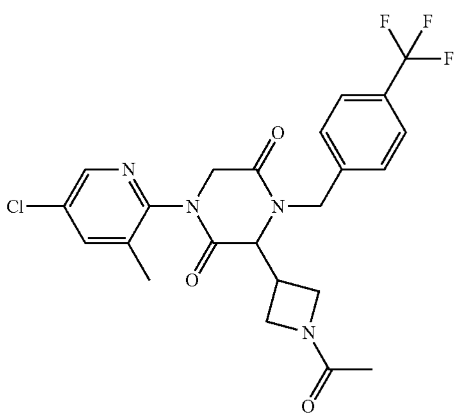 [SMILES: CC(=O)N1CC(C2C(=O)N(c3ncc(Cl)cc3C)CC(=O)N2Cc2ccc(C(F)(F)F)cc2)C1] | 3-(1-acetylazetidin-3-yl)-1-(5-chloro-3-methylpyridin-2-yl)-4-(4-(trifluoromethyl)benzyl)piperazine-2,5-dione |
| 654 | 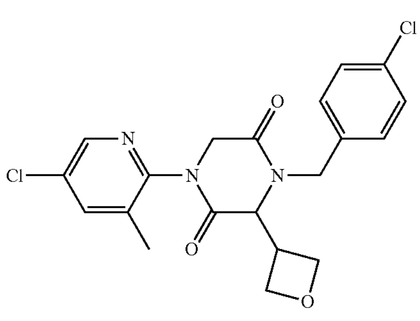 [SMILES: Cc1cc(Cl)cnc1N1CC(=O)N(Cc2ccc(Cl)cc2)C(C2COC2)C1=O] | 1-(5-chloro-3-methylpyridin-2-yl)-4-(4-chlorobenzyl)-3-(oxetan-3-yl)piperazine-2,5-dione |

TABLE 1-continued

| No. | Structure | Name |
|---|---|---|
| 655 | 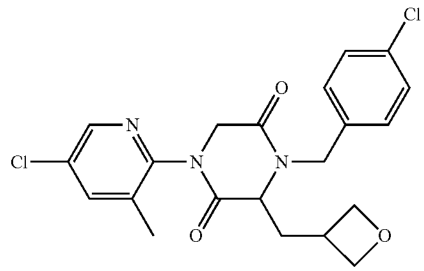 [SMILES: Cc1cc(Cl)cnc1N1CC(=O)N(Cc2ccc(Cl)cc2)C(CC2COC2)C1=O] | 1-(5-chloro-3-methylpyridin-2-yl)-4-(4-chlorobenzyl)-3-(oxetan-3-ylmethyl)-piperazine-2,5-dione |
| 656 | 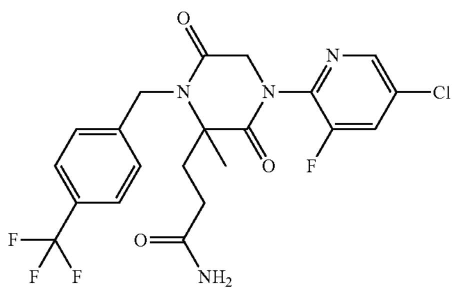 [SMILES: CC1(CCC(N)=O)C(=O)N(c2ncc(Cl)cc2F)CC(=O)N1Cc1ccc(C(F)(F)F)cc1] | 3-(4-(5-chloro-3-fluoro-pyridin-2-yl)-2-methyl-3,6-dioxo-1-(4-(trifluoro-methyl)benzyl)piperazin-2-yl)propanamide |
| 657 | 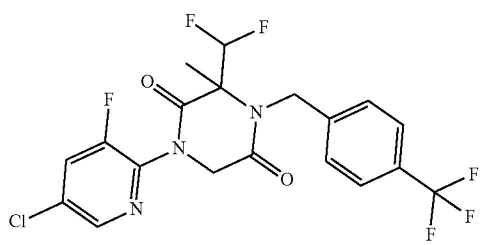 | 1-(5-chloro-3-fluoropyridin-2-yl)-3-(difluoromethyl)-3-methyl-4-(4-(trifluoro-methyl)-benzyl)piperazine-2,5-dione |
| 658 | 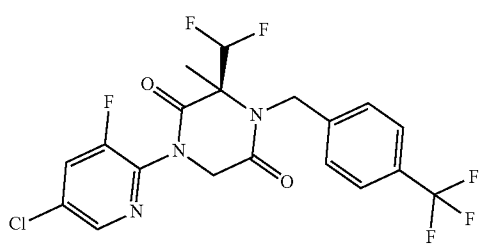 [SMILES: C[C@@]1(C(F)F)C(=O)N(c2ncc(Cl)cc2F)CC(=O)N1Cc1ccc(C(F)(F)F)cc1] | (S)-1-(5-chloro-3-fluoro-pyridin-2-yl)-3-(difluoro-methyl)-3-methyl-4-(4-(trifluoromethyl)benzyl)-piperazine-2,5-dione |
| 659 | 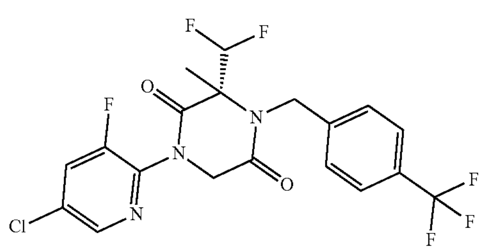 [SMILES: C[C@]1(C(F)F)C(=O)N(c2ncc(Cl)cc2F)CC(=O)N1Cc1ccc(C(F)(F)F)cc1] | (R)-1-(5-chloro-3-fluoro-pyridin-2-yl)-3-(difluoro-methyl)-3-methyl-4-(4-(trifluoromethyl)benzyl)-piperazine-2,5-dione |

TABLE 1-continued

| No. | Structure | Name |
|---|---|---|
| 660 | 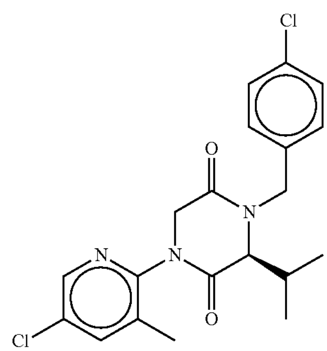 | (S)-1-(5-chloro-3-methylpyridin-2-yl)-4-(4-chlorobenzyl)-3-isopropyl-piperazine-2,5-dione |
| 661 | 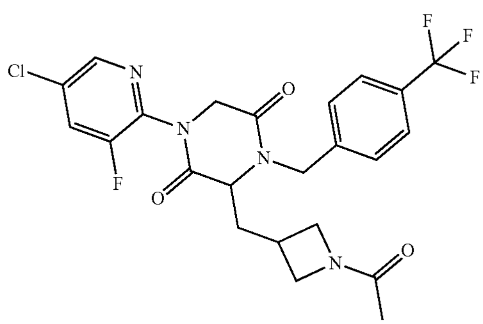 [SMILES: CC(=O)N1CC(CC2C(=O)N(c3ncc(Cl)cc3F)CC(=O)N2Cc2ccc(C(F)(F)F)cc2)C1] | 3-((1-acetylazetidin-3-yl)methyl)-1-(5-chloro-3-fluoropyridin-2-yl)-4-(4-(trifluoromethyl)benzyl)-piperazine-2,5-dione |
| 662 | 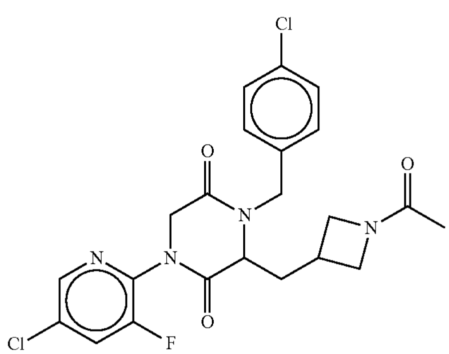 | 3-((1-acetylazetidin-3-yl)methyl)-1-(5-chloro-3-fluoropyridin-2-yl)-4-(4-chlorobenzyl)piperazine-2,5-dione |
| 663 | 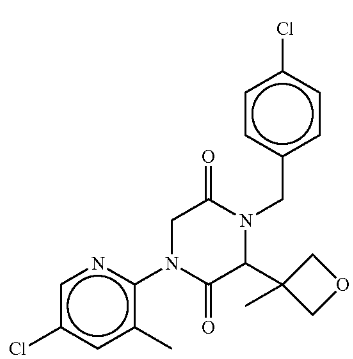 | 1-(5-chloro-3-methylpyridin-2-yl)-4-(4-chlorobenzyl)-3-(3-methyloxetan-3-yl)-piperazine-2,5-dione |

TABLE 1-continued

| No. | Structure | Name |
|-----|-----------|------|
| 664 | 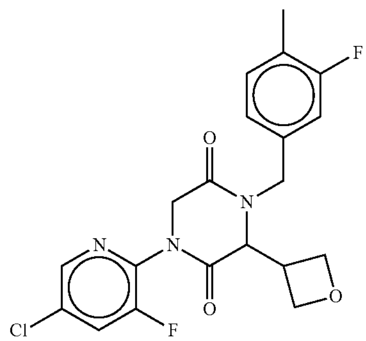 | 1-(5-chloro-3-fluoropyridin-2-yl)-4-(3-fluoro-4-methylbenzyl)-3-(oxetan-3-yl)piperazine-2,5-dione |
| 665 | 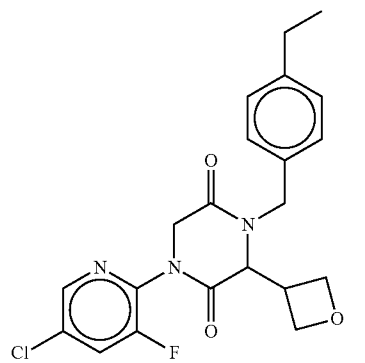 | 1-(5-chloro-3-fluoropyridin-2-yl)-4-(4-ethylbenzyl)-3-(oxetan-3-yl)piperazine-2,5-dione |
| 666 | 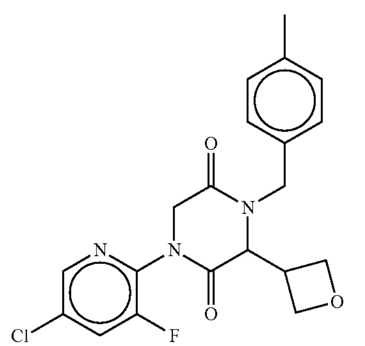 | 1-(5-chloro-3-fluoropyridin-2-yl)-4-(4-methylbenzyl)-3-(oxetan-3-yl)piperazine-2,5-dione |
| 667 | 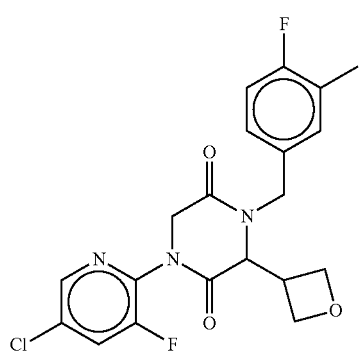 | 1-(5-chloro-3-fluoropyridin-2-yl)-4-(4-fluoro-3-methylbenzyl)-3-(oxetan-3-yl)-piperazine-2,5-dione |

TABLE 1-continued

| No. | Structure | Name |
|-----|-----------|------|
| 668 | 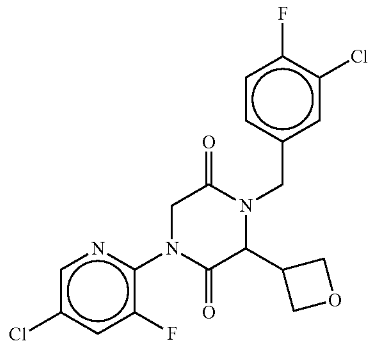 | 1-(5-chloro-3-fluoropyridin-2-yl)-4-(3-chloro-4-fluorobenzyl)-3-(oxetan-3-yl)piperazine-2,5-dione |
| 669 | 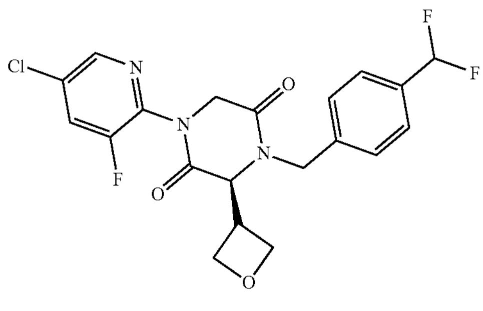 [SMILES: O=C1[C@H](C2COC2)N(Cc2ccc(C(F)F)cc2)C(=O)CN1c1ncc(Cl)cc1F] | (S)-1-(5-chloro-3-fluoro-pyridin-2-yl)-4-(4-(difluoromethyl)benzyl)-3-(oxetan-3-yl)piperazine-2,5-dione |
| 670 | 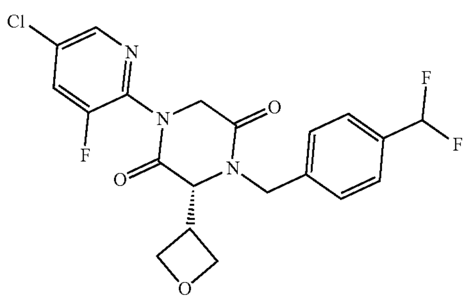 [SMILES: O=C1[C@@H](C2COC2)N(Cc2ccc(C(F)F)cc2)C(=O)CN1c1ncc(Cl)cc1F] | (R)-1-(5-chloro-3-fluoro-pyridin-2-yl)-4-(4-(difluoromethyl)benzyl)-3-(oxetan-3-yl)piperazine-2,5-dione |
| 671 | 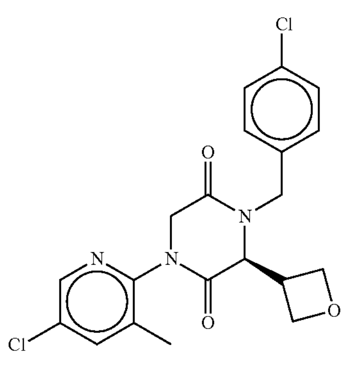 | (S)-1-(5-chloro-3-methylpyridin-2-yl)-4-(4-chlorobenzyl)-3-(oxetan-3-yl)piperazine-2,5-dione |

TABLE 1-continued

| No. | Structure | Name |
|---|---|---|
| 672 | 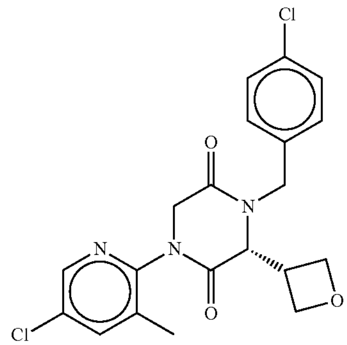 | (R)-1-(5-chloro-3-methylpyridin-2-yl)-4-(4-chlorobenzyl)-3-(oxetan-3-yl)piperazine-2,5-dione |
| 673 | 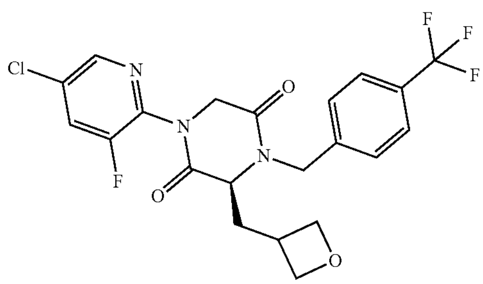 [SMILES: O=C1[C@H](CC2COC2)N(Cc2ccc(C(F)(F)F)cc2)C(=O)CN1c1ncc(Cl)cc1F] | (S)-1-(5-chloro-3-fluoropyridin-2-yl)-3-(oxetan-3-ylmethyl)-4-(4-(trifluoromethyl)benzyl)-piperazine-2,5-dione |
| 674 | 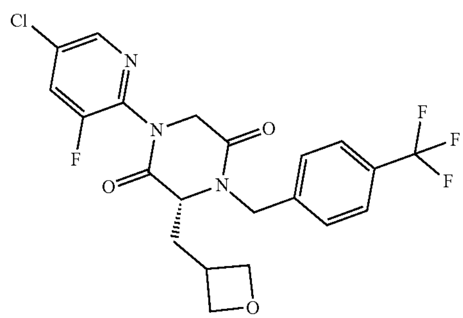 [SMILES: O=C1[C@@H](CC2COC2)N(Cc2ccc(C(F)(F)F)cc2)C(=O)CN1c1ncc(Cl)cc1F] | (R)-1-(5-chloro-3-fluoropyridin-2-yl)-3-(oxetan-3-ylmethyl)-4-(4-(trifluoromethyl)benzyl)-piperazine-2,5-dione |
| 675 | 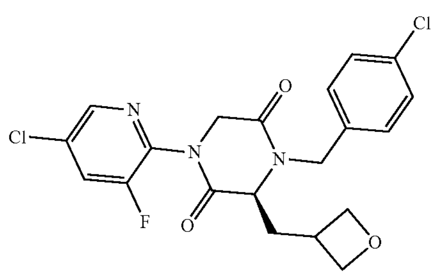 [SMILES: O=C1[C@H](CC2COC2)N(Cc2ccc(Cl)cc2)C(=O)CN1c1ncc(Cl)cc1F] | (S)-1-(5-chloro-3-fluoropyridin-2-yl)-4-(4-chlorobenzyl)-3-(oxetan-3-ylmethyl)piperazine-2,5-dione |
| 676 | 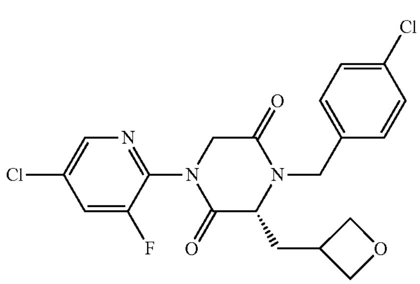 [SMILES: O=C1[C@@H](CC2COC2)N(Cc2ccc(Cl)cc2)C(=O)CN1c1ncc(Cl)cc1F] | (R)-1-(5-chloro-3-fluoropyridin-2-yl)-4-(4-chlorobenzyl)-3-(oxetan-3-yl)methyl)piperazine-2,5-dione |

TABLE 1-continued

| No. | Structure | Name |
|---|---|---|
| 677 | 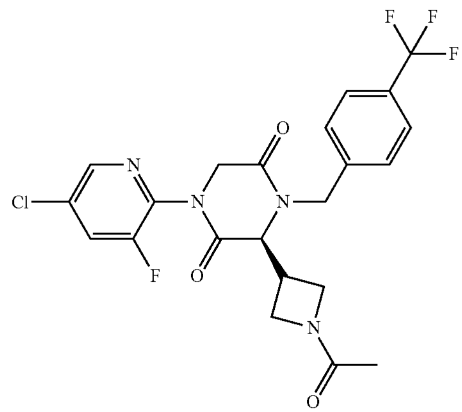 [SMILES: CC(=O)N1CC([C@H]2C(=O)N(c3ncc(Cl)cc3F)CC(=O)N2Cc2ccc(C(F)(F)F)cc2)C1] | (S)-3-(1-acetylazetidin-3-yl)-1-(5-chloro-3-fluoropyridin-2-yl)-4-(4-(trifluoromethyl)benzyl)-piperazine-2,5-dione |
| 678 | 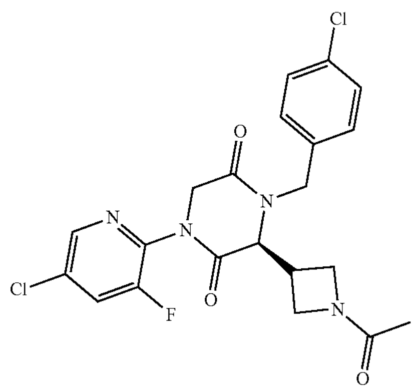 [SMILES: CC(=O)N1CC([C@H]2C(=O)N(c3ncc(Cl)cc3F)CC(=O)N2Cc2ccc(Cl)cc2)C1] | (S)-3-(1-acetylazetidin-3-yl)-1-(5-chloro-3-fluoropyridin-2-yl)-4-(4-chlorobenzyl)piperazine-2,5-dione |
| 679 | 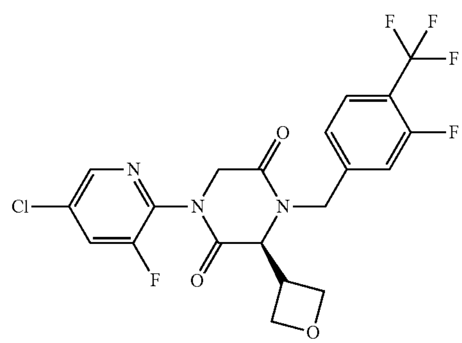 [SMILES: O=C1[C@H](C2COC2)N(Cc2ccc(C(F)(F)F)c(F)c2)C(=O)CN1c1ncc(Cl)cc1F] | (S)-1-(5-chloro-3-fluoro-pyridin-2-yl)-4-(3-fluoro-4-(trifluoromethyl)benzyl)-3-(oxetan-3-yl)piperazine-2,5-dione |
| 680 | 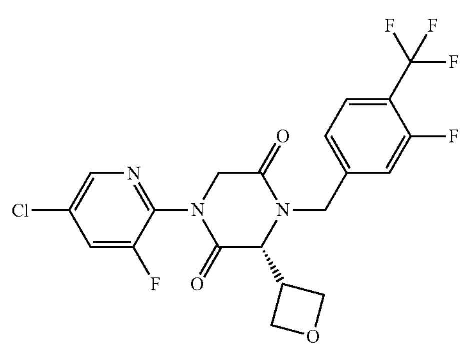 | (R)-1-(5-chloro-3-fluoro-pyridin-2-yl)-4-(3-fluoro-4-(trifluoromethyl)benzyl)-3-(oxetan-3-yl)piperazine-2,5-dione |

TABLE 1-continued

| No. | Structure | Name |
|---|---|---|
| 681 | 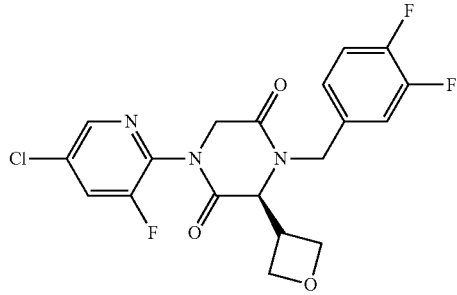 | (S)-1-(5-chloro-3-fluoro-pyridin-2-yl)-4-(3,4-difluorobenzyl)-3-(oxetan-3-yl)piperazine-2,5-dione |
| 682 | 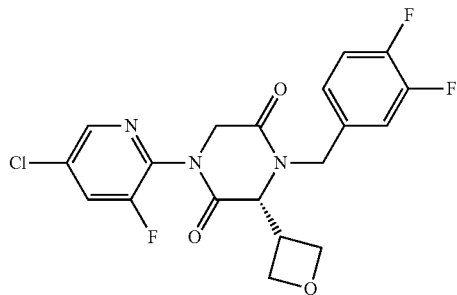 | (R)-1-(5-chloro-3-fluoro-pyridin-2-yl)-4-(3,4-difluorobenzyl)-3-(oxetan-3-yl)piperazine-2,5-dione |
| 683 | 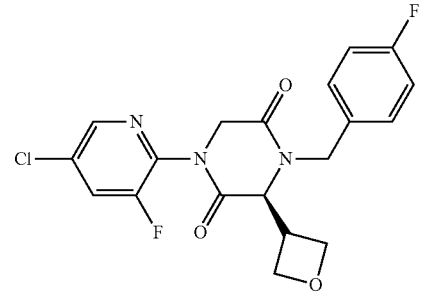 | (S)-1-(5-chloro-3-fluoropyridin-2-yl)-4-(4-fluorobenzyl)-3-(oxetan-3-yl)piperazine-2,5-dione |
| 684 | 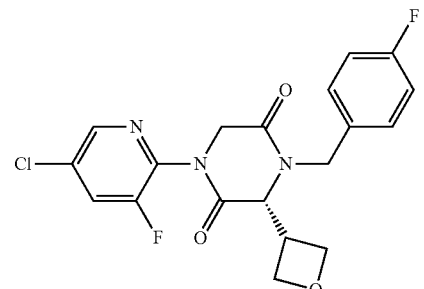 | (R)-1-(5-chloro-3-fluoro-pyridin-2-yl)-4-(4-fluorobenzyl)-3-(oxetan-3-yl)piperazine-2,5-dione |
| 685 | 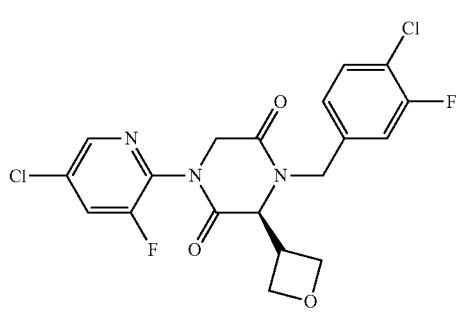 [SMILES: O=C1[C@H](C2COC2)N(Cc2ccc(F)c(F)c2)C(=O)CN1c1ncc(Cl)cc1F] | (S)-4-(4-chloro-3-fluoro-benzyl)-1-(5-chloro-3-fluoropyridin-2-yl)-3-(oxetan-3-yl)piperazine-2,5-dione |

TABLE 1-continued

| No. | Structure | Name |
|---|---|---|
| 686 | 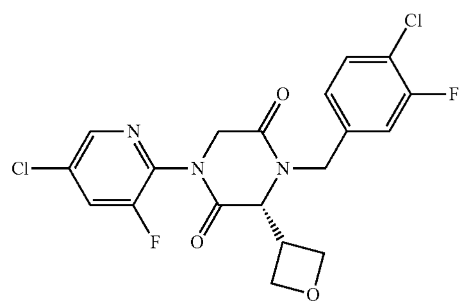 [SMILES: O=C1[C@@H](C2COC2)N(Cc2ccc(F)c(F)c2)C(=O)CN1c1ncc(Cl)cc1F] | (R)-4-(4-chloro-3-fluoro-benzyl)-1-(5-chloro-3-fluoropyridin-2-yl)-3-(oxetan-3-yl)piperazine-2,5-dione |
| 687 | 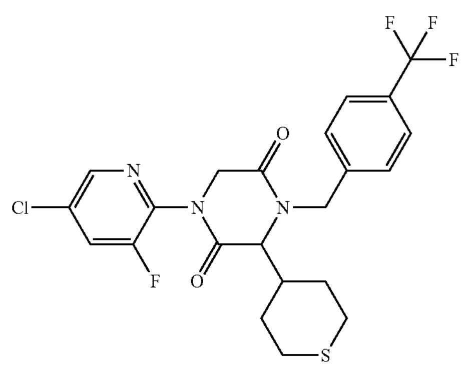 | 1-(5-chloro-3-fluoropyridin-2-yl)-3-(tetrahydro-2H-thiopyran-4-yl)-4-(4-(trifluoromethyl)benzyl)-piperazine-2,5-dione |
| 688 | 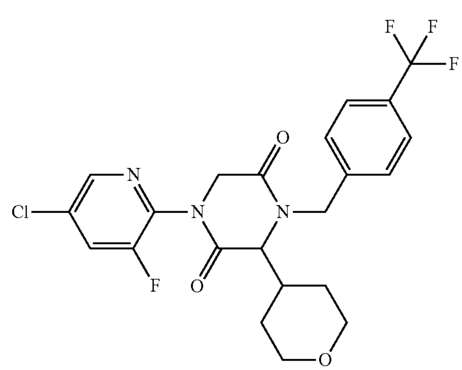 [SMILES: O=C1C(C2CCSCC2)N(Cc2ccc(C(F)(F)F)cc2)C(=O)CN1c1ncc(Cl)cc1F] | 1-(5-chloro-3-fluoropyridin-2-yl)-3-(tetrahydro-2H-pyran-4-yl)-4-(4-(trifluoromethyl)benzyl)piperazine-2,5-dione |
| 689 | 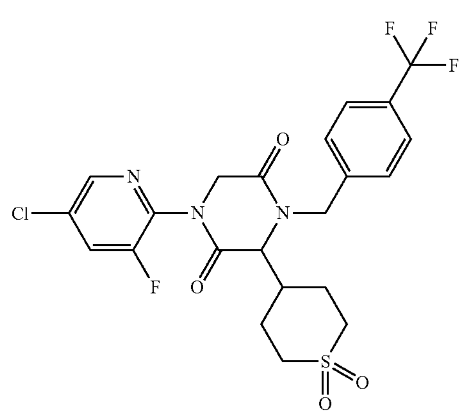 [SMILES: O=C1C(C2CCS(=O)(=O)CC2)N(Cc2ccc(C(F)(F)F)cc2)C(=O)CN1c1ncc(Cl)cc1F] | 1-(5-chloro-3-fluoropyridin-2-yl)-3-(1,1-dioxidotetrahydro-2H-thiopyran-4-yl)-4-(4-(trifluoromethyl)benzyl)piperazine-2,5-dione |

TABLE 1-continued

| No. | Structure | Name |
|---|---|---|
| 690 | 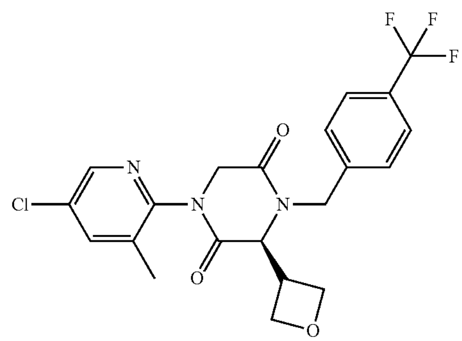 [SMILES: Cc1cc(Cl)cnc1N1CC(=O)N(Cc2ccc(C(F)(F)F)cc2)[C@@H](C2COC2)C1=O] | (S)-1-(5-chloro-3-methyl-pyridin-2-yl)-3-(oxetan-3-yl)-4-(4-(trifluoromethyl)-benzyl)piperazine-2,5-dione |
| 691 | 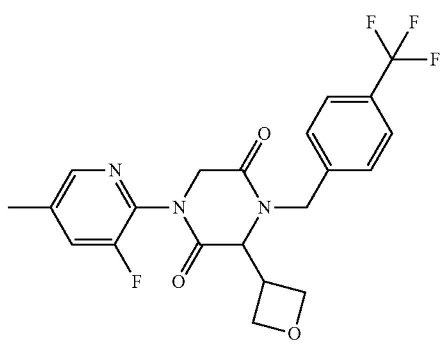 | 1-(3-fluoro-5-methylpyridin-2-yl)-3-(oxetan-3-yl)-4-(4-(trifluoromethyl)benzyl)-piperazine-2,5-dione |
| 692 | 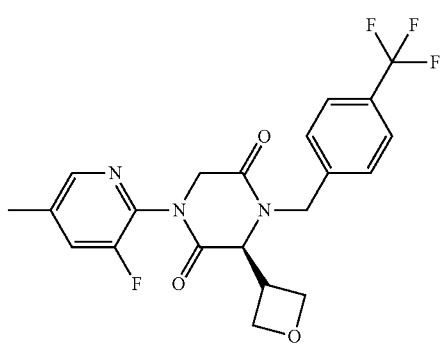 [SMILES: Cc1cnc(N2CC(=O)N(Cc3ccc(C(F)(F)F)cc3)[C@@H](C3COC3)C2=O)c(F)c1] | (S)-1-(3-fluoro-5-methyl-pyridin-2-yl)-3-(oxetan-3-yl)-4-(4-(trifluoromethyl)-benzyl)piperazine-2,5-dione |
| 693 | 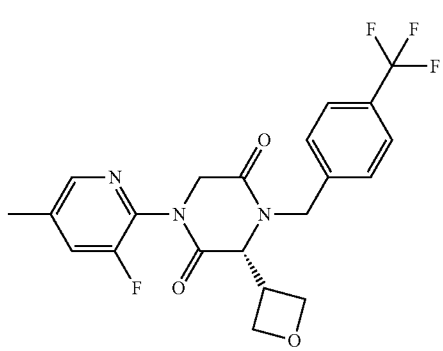 [SMILES: Cc1cnc(N2CC(=O)N(Cc3ccc(C(F)(F)F)cc3)[C@H](C3COC3)C2=O)c(F)c1] | (R)-1-(3-fluoro-5-methyl-pyridin-2-yl)-3-(oxetan-3-yl)-4-(4-(trifluoromethyl)-benzyl)piperazine-2,5-dione |

TABLE 1-continued

| No. | Structure | Name |
|---|---|---|
| 694 | 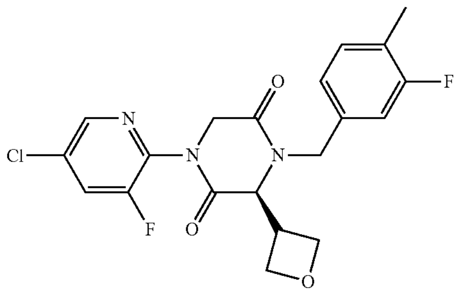 [SMILES: Cc1ccc(CN2C(=O)CN(c3ncc(Cl)cc3F)C(=O)[C@@H]2C2COC2)cc1F] | (S)-1-(5-chloro-3-fluoro-pyridin-2-yl)-4-(3-fluoro-4-methylbenzyl-3-(oxetan-3-yl)piperazine-2,5-dione |
| 695 | 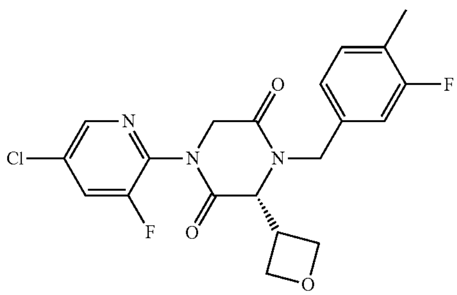 [SMILES: Cc1ccc(CN2C(=O)CN(c3ncc(Cl)cc3F)C(=O)[C@H]2C2COC2)cc1F] | (R)-1-(5-chloro-3-fluoro-pyridin-2-yl)-4-(3-fluoro-4-methylbenzyl)-3-(oxetan-3-yl)piperazine-2,5-dione |
| 696 | 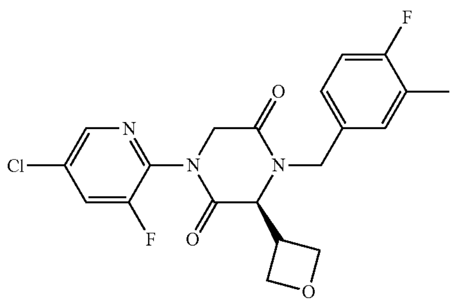 [SMILES: Cc1cc(CN2C(=O)CN(c3ncc(Cl)cc3F)C(=O)[C@@H]2C2COC2)ccc1F] | (S)-1-(5-chloro-3-fluoro-pyridin-2-yl)-4-(4-fluoro-3-methylbenzyl)-3-(oxetan-3-yl)piperazine-2,5-dione |
| 697 | 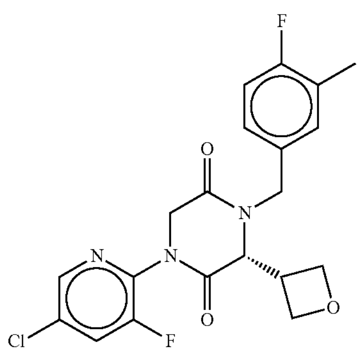 | (R)-1-(5-chloro-3-fluoro-pyridin-2-yl)-4-(4-fluoro-3-methylbenzyl)-3-(oxetan-3-yl)piperazine-2,5-dione |
| 698 | 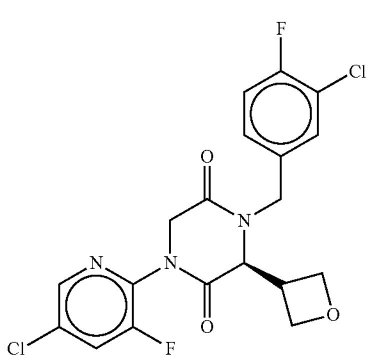 | (S)-1-(5-chloro-3-fluoro-pyridin-2-yl)-4-(3-chloro-4-fluorobenzyl)-3-(oxetan-3-yl)piperazine-2,5-dione |

TABLE 1-continued

| No. | Structure | Name |
|---|---|---|
| 699 | 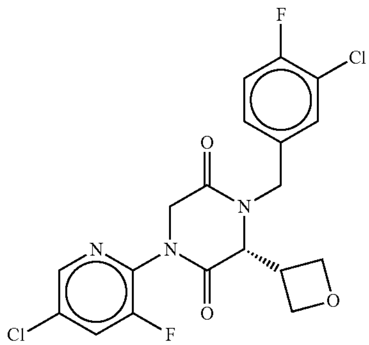 | (R)-1-(5-chloro-3-fluoro-pyridin-2-yl)-4-(3-chloro-4-fluorobenzyl)-3-(oxetan-3-yl)piperazine-2,5-dione |
| 700 | 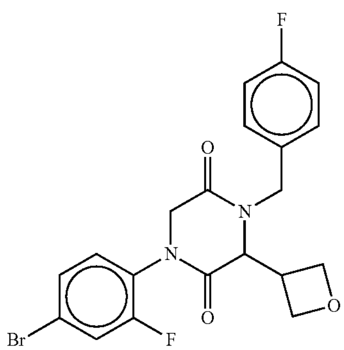 | 1-(4-bromo-2-fluoro-phenyl)-4-(4-fluorobenzyl)-3-(oxetan-3-yl)piperazine-2,5-dione |
| 701 | 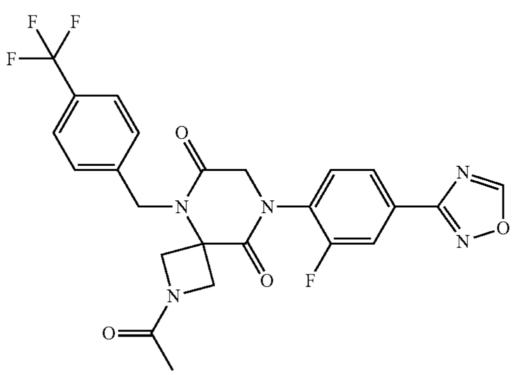 [SMILES: CC(=O)N1CC2(C1)C(=O)N(c1ccc(-c3ncon3)cc1F)CC(=O)N2Cc1ccc(C(F)(F)F)cc1] | 2-acetyl-8-(2-fluoro-4-(1,2,4-oxadiazol-3-yl)-phenyl)-5-(4-(trifluoro-methyl)benzyl)-2,5,8-triazaspiro[3.5)nonane-6,9-dione |
| 702 | 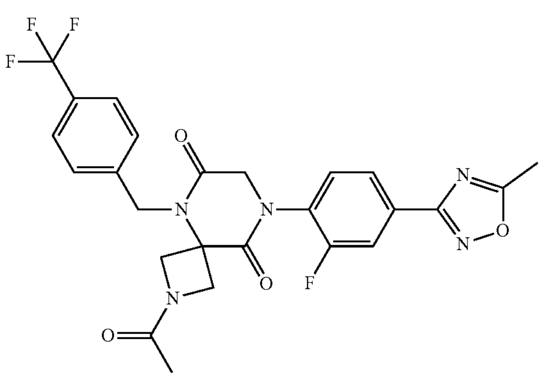 [SMILES: CC(=O)N1CC2(C1)C(=O)N(c1ccc(-c3noc(C)n3)cc1F)CC(=O)N2Cc1ccc(C(F)(F)F)cc1] | 2-acetyl-8-(2-fluoro-4-(5-methyl-1,2,4-oxadiazol-3-yl)phenyl)-5-(4-(trifluoro-methyl)benzyl)-2,5,8-triazaspiro[3.5]nonane-6,9-dione |

TABLE 1-continued

| No. | Structure | Name |
|---|---|---|
| 703 | 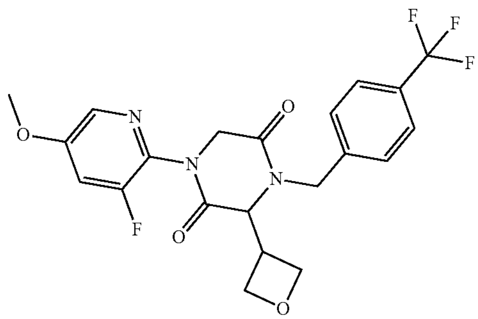 [SMILES: COc1cnc(N2CC(=O)N(Cc3ccc(C(F)(F)F)cc3)C(C3COC3)C2=O)c(F)c1] | 1-(3-fluoro-5-methoxy-pyridin-2-yl)-3-(oxetan-3-yl)-4-(4-(trifluoromethyl)-benzyl)piperazine-2,5-dione |
| 704 | 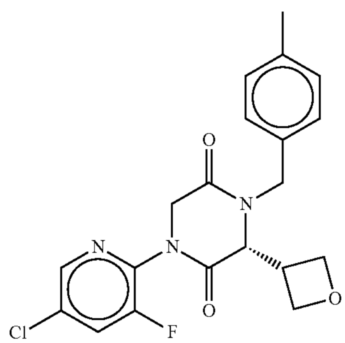 | (R)-1-(5-chloro-3-fluoro-pyridin-2-yl)-4-(4-methyl-benzyl)-3-(oxetan-3-yl)-piperazine-2,5-dione |
| 705 | 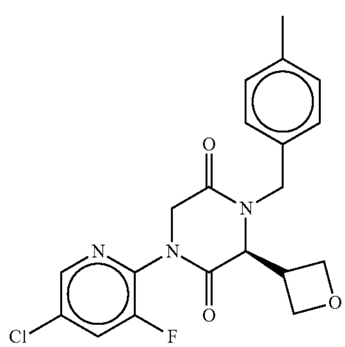 | (S)-1-(5-chloro-3-fluoro-pyridin-2-yl)-4-(4-methyl-benzyl)-3-(oxetan-3-yl)piperazine-2,5-dione |
| 706 | 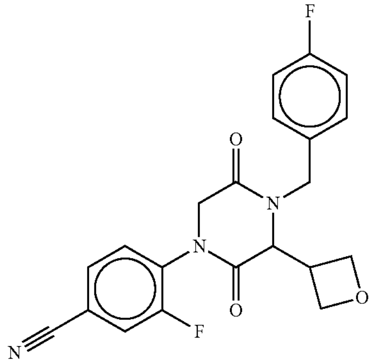 | 3-fluoro-4-(4-(4-fluoro-benzyl)-3-(oxetan-3-yl)-2,5-dioxopiperazin-1-yl)benzonitrile |

TABLE 1-continued

| No. | Structure | Name |
| --- | --- | --- |
| 707 | 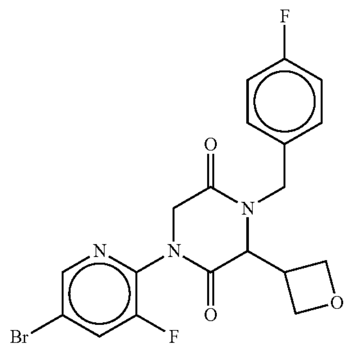 | 1-(5-bromo-3-fluoropyridin-2-yl)-4-(4-fluorobenzyl)-3-(oxetan-3-yl)piperazine-2,5-dione |
| 708 | 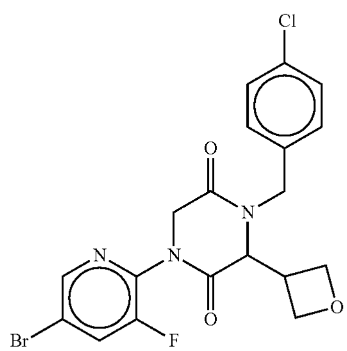 | 1-(5-bromo-3-fluoropyridin-2-yl)-4-(4-chlorobenzyl)-3-(oxetan-3-yl)piperazine-2,5-dione |
| 709 | 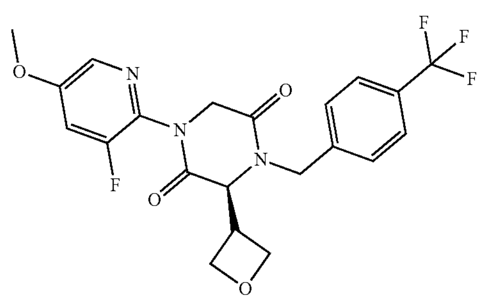 [SMILES: COc1cnc(N2CC(=O)N(Cc3ccc(C(F)(F)F)cc3)[C@@H](C3COC3)C2=O)c(F)c1] | (S)-1-(3-fluoro-5-methoxy-pyridin-2-yl)-3-(oxetan-3-yl)-4-(4-(trifluoromethyl)-benzyl)piperazine-2,5-dione |
| 710 | 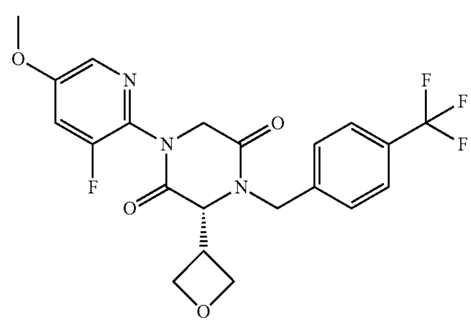 [SMILES: COc1cnc(N2CC(=O)N(Cc3ccc(C(F)(F)F)cc3)[C@H](C3COC3)C2=O)c(F)c1] | (R)-1-(3-fluoro-5-methoxy-pyridin-2-yl)-3-(oxeldn-3-yl)-4-(4-(trifluoromethyl)-benzyl)piperazine-2,5-dione |

TABLE 1-continued

| No. | Structure | Name |
| --- | --- | --- |
| 711 | 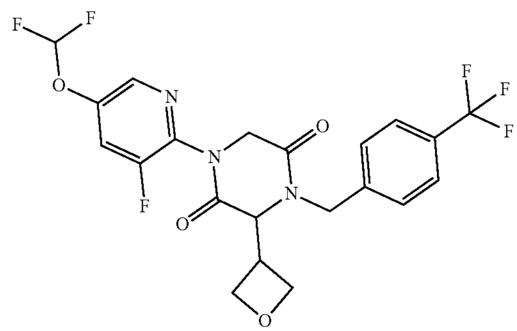 [SMILES: O=C1C(C2COC2)N(Cc2ccc(C(F)(F)F)cc2)C(=O)CN1c1ncc(OC(F)F)cc1F] | 1-(5-(difluoromethoxy)-3-fluoropyridin-2-yl)-3-(oxetan-3-yl)-4-(4-(trifluoromethyl)benzyl)-piperazine-2,5-dione |
| 712 | 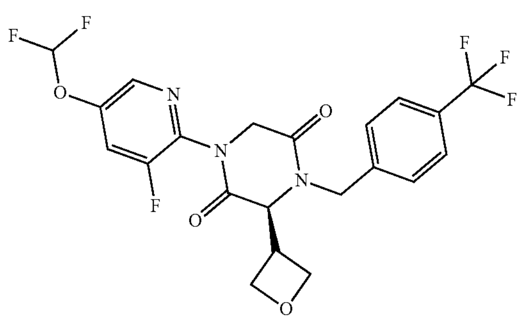 [SMILES: O=C1[C@H](C2COC2)N(Cc2ccc(C(F)(F)F)cc2)C(=O)CN1c1ncc(OC(F)F)cc1F] | (S)-1-(5-(difluoromethoxy)-3-fluoropyridin-2-yl)-3-(oxetan-3-yl)-4-(4-(trifluoromethyl)benzyl)-piperazine-2,5-dione |
| 713 | 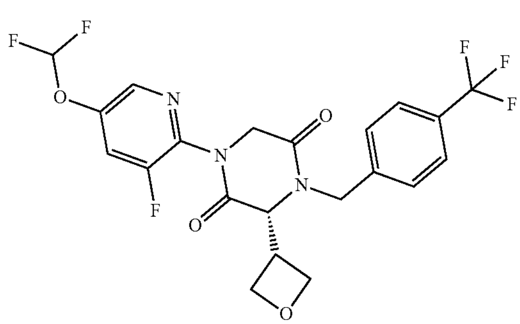 [SMILES: O=C1[C@@H](C2COC2)N(Cc2ccc(C(F)(F)F)cc2)C(=O)CN1c1ncc(OC(F)F)cc1F] | (R)-1-(5-(difluoromethoxy)-3-fluoropyridin-2-yl)-3-(oxetan-3-yl)-4-(4-(trifluoromethyl)benzyl)-piperazine-2,5-dione |
| 714 | 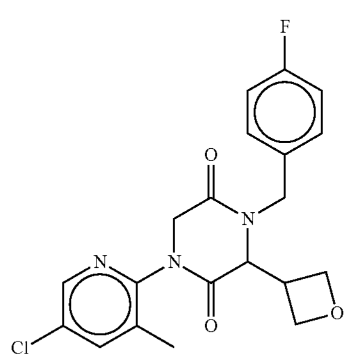 | 1-(5-chloro-3-methylpyridin-2-yl)-4-(4-fluorobenzyl)-3-(oxetan-3-yl)piperazine-2,5-dione |

TABLE 1-continued

| No. | Structure | Name |
|---|---|---|
| 715 | 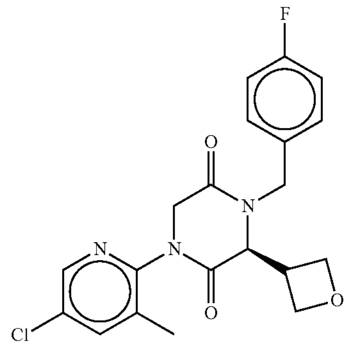 | (S)-1-(5-chloro-3-methyl-pyridin-2-yl)-4-(4-fluoro-benzyl)-3-(oxetan-3-yl)-piperazine-2,5-dione |
| 716 | 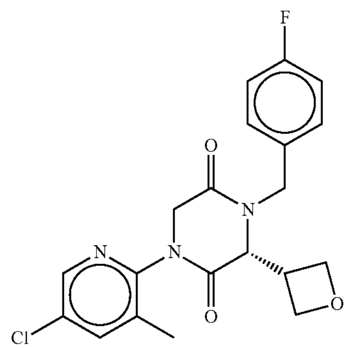 | (R)-1-(5-chloro-3-methyl-pyridin-2-yl)-4-(4-fluoro-benzyl)-3-(oxetan-3-yl)-piperazine-2,5-dione |
| 717 | 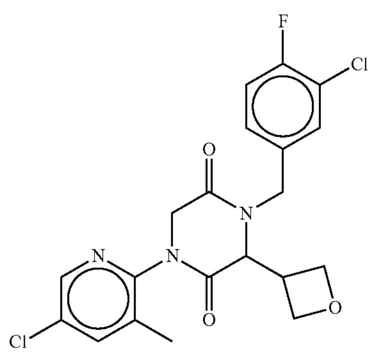 | 1-(5-chloro-3-methyl-pyridin-2-yl)-4-(3-chloro-4-fluorobenzyl)-3-(oxetan-3-yl)piperazine-2,5-dione |
| 718 | 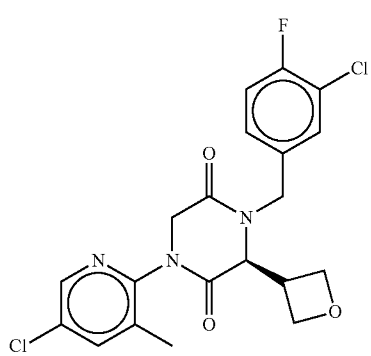 | (S)-1-(5-chloro-3-methyl-pyridin-2-yl)-4-(3-chloro-4-fluorobenzyl)-3-(oxetan-3-yl)piperazine-2,5-dione |

TABLE 1-continued

| No. | Structure | Name |
|---|---|---|
| 719 | 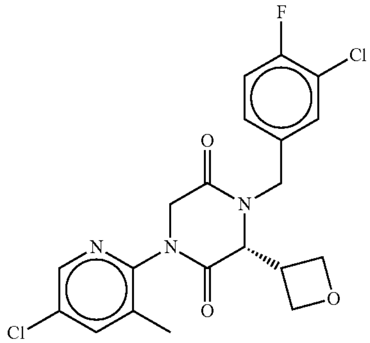 | (R)-1-(5-chloro-3-methyl-pyridin-2-yl)-4-(3-chloro-4-fluorobenzyl)-3-(oxetan-3-yl)piperazine-2,5-dione |
| 720 | 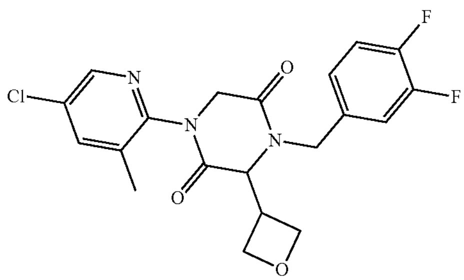 [SMILES: Cc1cc(Cl)cnc1N1CC(=O)N(Cc2ccc(F)c(F)c2)C(C2COC2)C1=O] | 1-(5-chloro-3-methyl-pyridin-2-yl)-4-(3,4-difluorobenzyl)-3-(oxetan-3-yl)piperazine-2,5-dione |
| 721 | 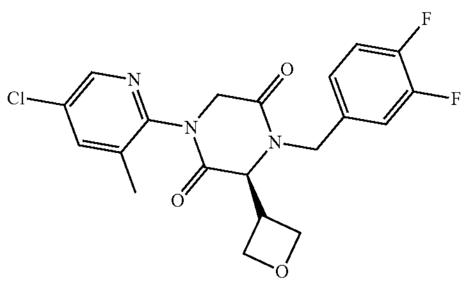 [SMILES: Cc1cc(Cl)cnc1N1CC(=O)N(Cc2ccc(F)c(F)c2)[C@@H](C2COC2)C1=O] | (S)-1-(5-chloro-3-methyl-pyridin-2-yl)-4-(3,4-difluorobenzyl)-3-(oxetan-3-yl)piperazine-2,5-dione |
| 722 | 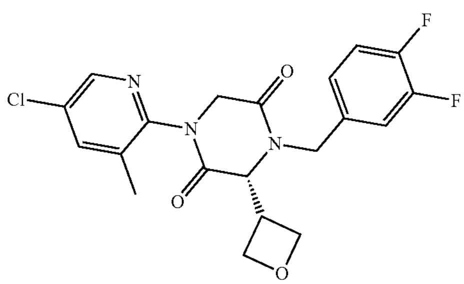 [SMILES: Cc1cc(Cl)cnc1N1CC(=O)N(Cc2ccc(F)c(F)c2)[C@H](C2COC2)C1=O] | (R)-1-(5-chloro-3-methyl-pyridin-2-yl)-4-(3,4-difluorobenzyl)-3-(oxetan-3-yl)piperazine-2,5-dione |
| 723 | 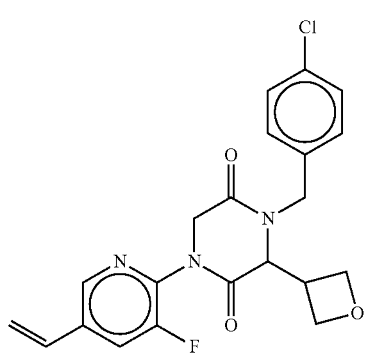 | 4-(4-chlorobenzyl)-1-(3-fluoro-5-vinylpyridin-2-yl)-3-(oxetan-3-yl)piperazine-2,5-dione |

TABLE 1-continued

| No. | Structure | Name |
|---|---|---|
| 724 | 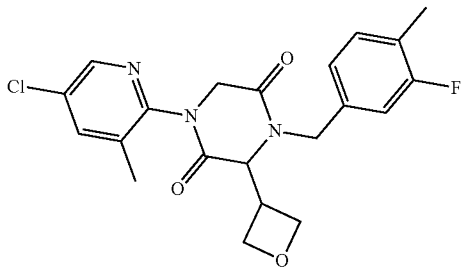 [SMILES: Cc1ccc(CN2C(=O)CN(c3ncc(Cl)cc3C)C(=O)C2C2COC2)cc1F] | 1-(5-chloro-3-methyl-pyridin-2-yl)-4-(3-fluoro-4-methylbenzyl)-3-(oxetan-3-yl)piperazine-2,5-dione |
| 725 | 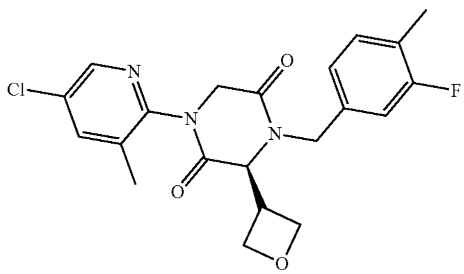 [SMILES: Cc1ccc(CN2C(=O)CN(c3ncc(Cl)cc3C)C(=O)[C@@H]2C2COC2)cc1F] | (S)-1-(5-chloro-3-methyl-pyridin-2-yl)-4-(3-fluoro-4-methylbenzyl)-3-(oxetan-3-yl)piperazine-2,5-dione |
| 726 | 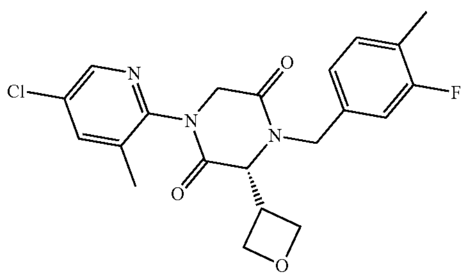 [SMILES: Cc1ccc(CN2C(=O)CN(c3ncc(Cl)cc3C)C(=O)[C@H]2C2COC2)cc1F] | (R)-1-(5-chloro-3-methyl-pyridin-2-yl)-4-(3-fluoro-4-methylberuyl)-3-(oxetan-3-yl)piperazine-2,5-dione |
| 727 | 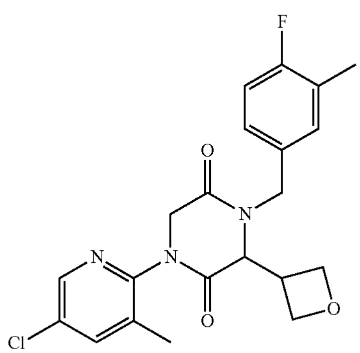 [SMILES: Cc1cc(CN2C(=O)CN(c3ncc(Cl)cc3C)C(=O)C2C2COC2)ccc1F] | 1-(5-chloro-3-methyl-pyridin-2-yl)-4-(4-fluoro-3-methylbenzyl)-3-(oxetan-3-yl)piperazine-2,5-dione |
| 728 | 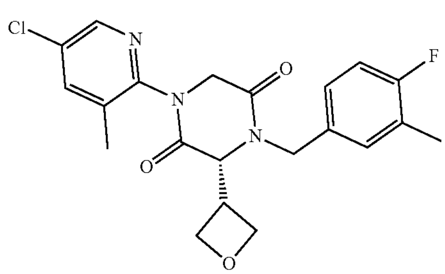 [SMILES: Cc1cc(CN2C(=O)CN(c3ncc(Cl)cc3C)C(=O)[C@H]2C2COC2)ccc1F] | (R)-l-(5-chloro-3-methyl-pyridin-2-yl)-4-(4-fluoro-3-methylbenzyl)-3-(oxetan-3-yl)piperazine-2,5-dione |

TABLE 1-continued

| No. | Structure | Name |
|---|---|---|
| 729 | 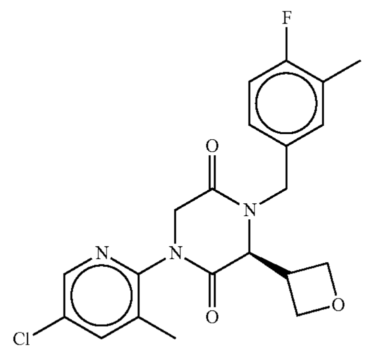 | (S)-1-(5-chloro-3-methyl-pyridin-2-yl)-4-(4-fluoro-3-methylbenzyl)-3-(oxetan-3-yl)piperazine-2,5-dione |
| 730 | 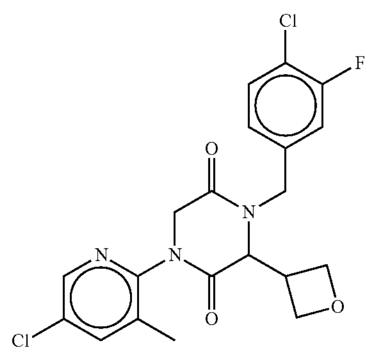 | 4-(4-chloro-3-fluoro-benzyl)-1-(5-chloro-3-methylpyridin-2-yl)-3-(oxetan-3-yl)-piperazine-2,5-dione |
| 731 | 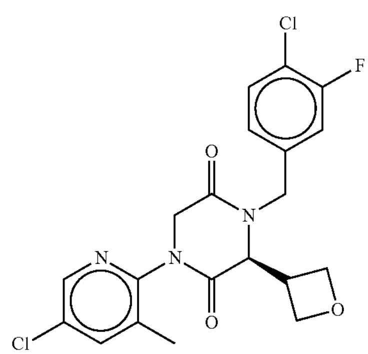 | (S)-4-(4-chloro-3-fluoro-benzyl)-1-(5-chloro-3-methylpyridin-2-yl)-3-(oxetan-3-yl)piperazine-2,5-dione |
| 732 | 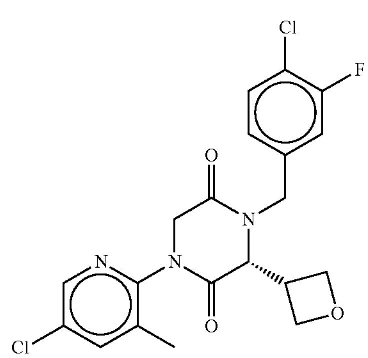 | (R)-4-(4-chloro-3-fluoro-benzyl)-1-(5-chloro-3-methylpyridin-2-yl)-3-(oxetan-3-yl)piperazine-2,5-dione |

TABLE 1-continued

| No. | Structure | Name |
|---|---|---|
| 733 | 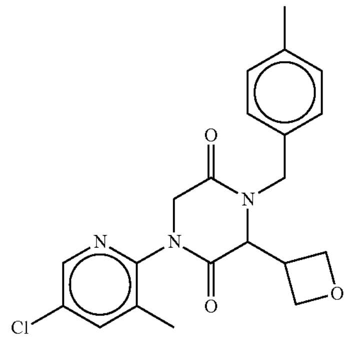 | 1-(5-chloro-3-methyl-pyridin-2-yl)-4-(4-methyl-benzyl)-3-(oxetan-3-yl)-piperazine-2,5-dione |
| 734 | 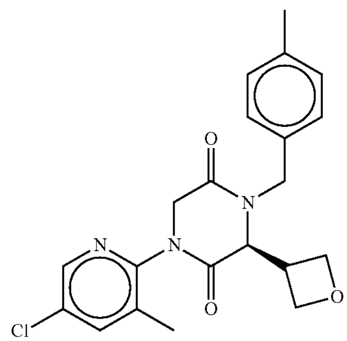 | (S)-1-(5-chloro-3-methyl-pyridin-2-yl)-4-(4-methyl-benzyl)-3-(oxetan-3-yl)piperazine-2,5-dione |
| 735 | 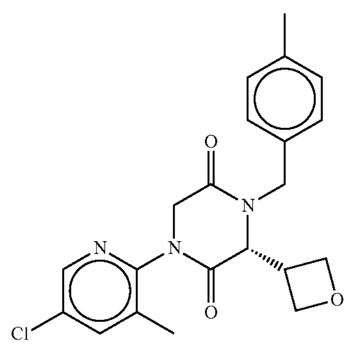 | (R)-1-(5-chloro-3-methyl-pyridin-2-yl)-4-(4-methyl-benzyl)-3-(oxetan-3-yl)-piperazine-2,5-dione |
| 736 | 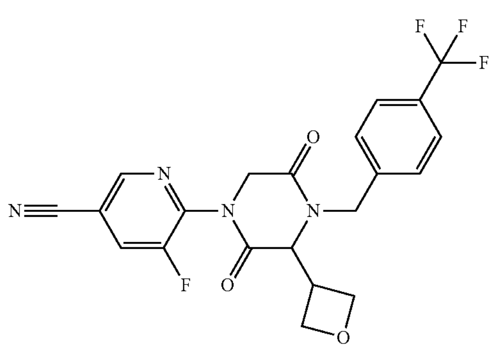 [SMILES: N#Cc1cnc(N2CC(=O)N(Cc3ccc(C(F)(F)F)cc3)C(C3COC3)C2=O)c(F)c1] | 5-fluoro-6-(3-(oxetan-3-yl)-2,5-dioxo-4-(4-(trifluoromethyl)benzyl)-piperazin-1-yl)nicotinonitrile |

TABLE 1-continued

| No. | Structure | Name |
|---|---|---|
| 737 | 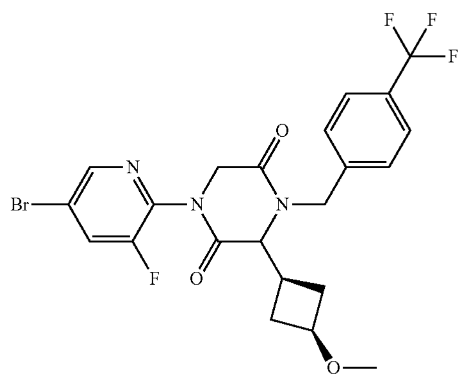 [SMILES: CO[C@H]1C[C@@H](C2C(=O)N(c3ncc(Br)cc3F)CC(=O)N2Cc2ccc(C(F)(F)F)cc2)C1] | 1-(5-bromo-3-fluoropyridin-2-yl)-3-((1s,3s)-3-methoxycyclobutyl)-4-(4-(trifluoromethyl)benzyl)piperazine-2,5-dione |
| 738 | 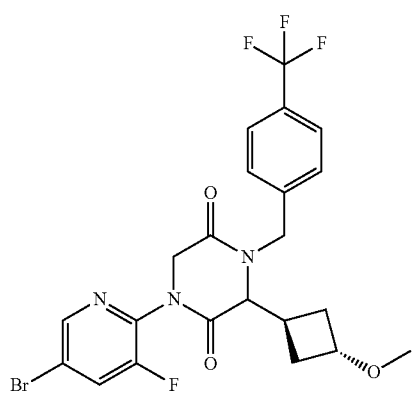 [SMILES: CO[C@H]1C[C@H](C2C(=O)N(c3ncc(Br)cc3F)CC(=O)N2Cc2ccc(C(F)(F)F)cc2)C1] | 1-(5-bromo-3-fluoropyridin-2-yl)-3-((1r,3r)-3-methoxycyclobutyl)-4-(4-(trifluoromethyl)benzyl)piperazine-2,5-dione |
| 739 | 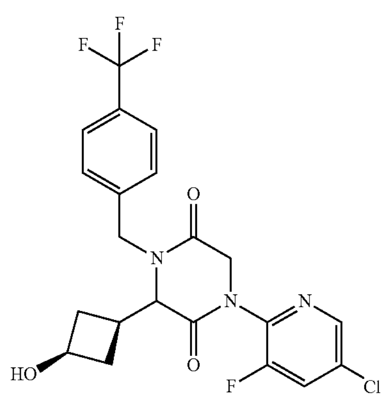 [SMILES: O=C1C([C@H]2C[C@@H](O)C2)N(Cc2ccc(C(F)(F)F)cc2)C(=O)CN1c1ncc(Cl)cc1F] | 1-(5-chloro-3-fluoropyridin-2-yl)-3-((1s,3s)-3-hydroxycyclobutyl)-4-(4-(trifluoromethyl)benzyl)piperazine-2,5-dione |
| 740 | 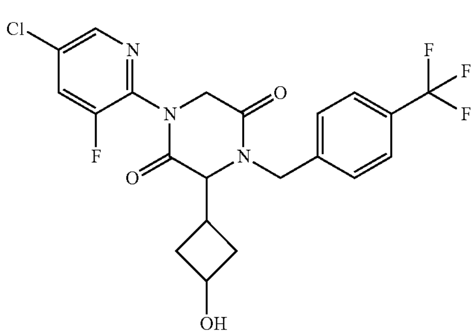 [SMILES: O=C1C(C2CC(O)C2)N(Cc2ccc(C(F)(F)F)cc2)C(=O)CN1c1ncc(Cl)cc1F] | 1-(5-chloro-3-fluoropyridin-2-yl)-3-(3-hydroxycyclobutyl)-4-(4-(trifluoromethyl)benzyl)piperazine-2,5-dione |

TABLE 1-continued

| No. | Structure | Name |
|---|---|---|
| 741 | 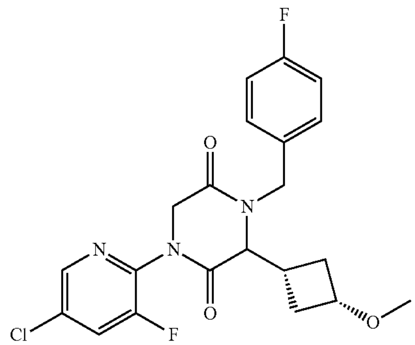 [SMILES: CO[C@H]1C[C@@H](C2C(=O)N(c3ncc(Cl)cc3F)CC(=O)N2Cc2ccc(F)cc2)C1] | 1-(5-chloro-3-fluoropyridin-2-yl)-4-(4-fluorobenzyl)-3-((1s,3s)-3-methoxycyclobutyl)piperazine-2,5-dione |
| 742 | 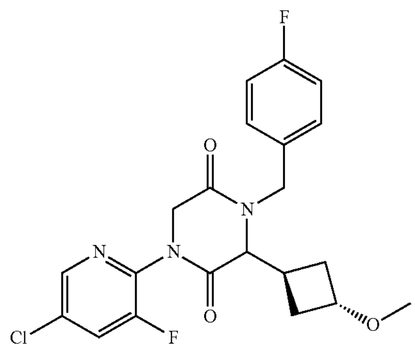 [SMILES: CO[C@H]1C[C@H](C2C(=O)N(c3ncc(Cl)cc3F)CC(=O)N2Cc2ccc(F)cc2)C1] | 1-(5-chloro-3-fluoropyridin-2-yl)-4-(4-fluorobenzyl)-3-((1r,3r)-3-methoxycyclobutyl)piperazine-2,5-dione |
| 743 | 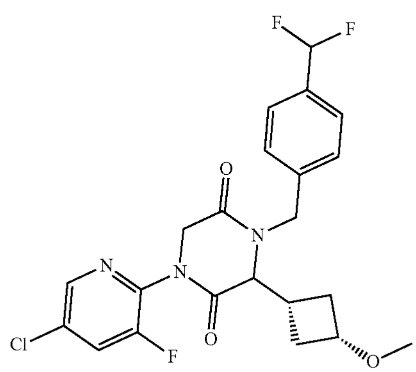 [SMILES: CO[C@H]1C[C@@H](C2C(=O)N(c3ncc(Cl)cc3F)CC(=O)N2Cc2ccc(C(F)F)cc2)C1] | 1-(5-chloro-3-fluoropyridin-2-yl)-4-(4-(difluoromethyl)benzyl)-3-((1s,3s)-3-methoxycyclobutyl)-piperazine-2,5-dione |
| 744 | 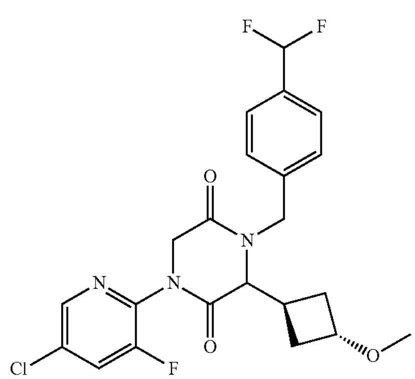 [SMILES: CO[C@H]1C[C@H](C2C(=O)N(c3ncc(Cl)cc3F)CC(=O)N2Cc2ccc(C(F)F)cc2)C1] | 1-(5-chloro-3-fluoropyridin-2-yl)-4-(4-(difluoromethyl)benzyl)-3-((1r,3r)-3-methoxycyclobutyl)-piperazine-2,5-dione |

TABLE 1-continued

| No. | Structure | Name |
|---|---|---|
| 745 | 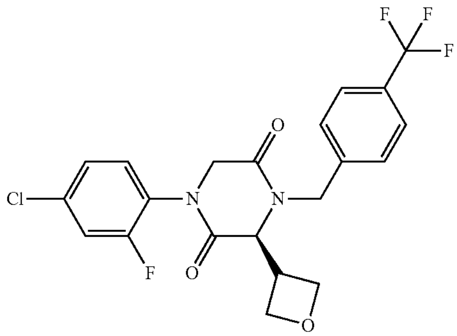 [SMILES: O=C1[C@H](C2COC2)N(Cc2ccc(C(F)(F)F)cc2)C(=O)CN1c1ccc(Cl)cc1F] | (S)-1-(4-chloro-2-fluoro-phenyl)-3-(oxetan-3-yl)-4-(4-(trifluoromethyl)-benzyl)piperazine-2,5-dione |
| 746 | 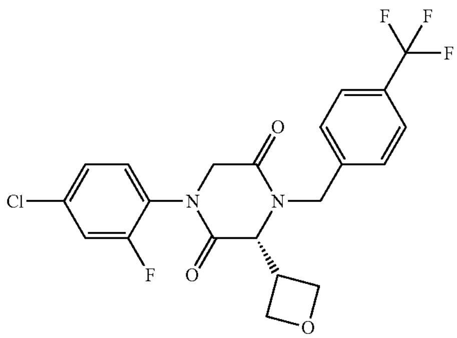 [SMILES: O=C1[C@@H](C2COC2)N(Cc2ccc(C(F)(F)F)cc2)C(=O)CN1c1ccc(Cl)cc1F] | (R)-1-(4-chloro-2-fluoro-phenyl)-3-(oxetan-3-yl)-4-(4-(trifluoromethyl)-benzyl)piperazine-2,5-dione |
| 747 | 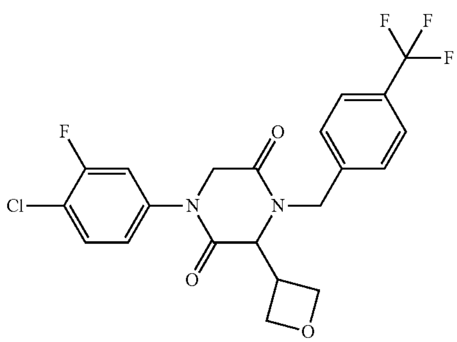 [SMILES: O=C1C(C2COC2)N(Cc2ccc(C(F)(F)F)cc2)C(=O)CN1c1ccc(Cl)c(F)c1] | 1-(4-chloro-3-fluorophenyl)-3-(oxetan-3-yl)-4-(4-(trifluoromethyl)benzyl)-piperazine-2,5-dione |
| 748 | 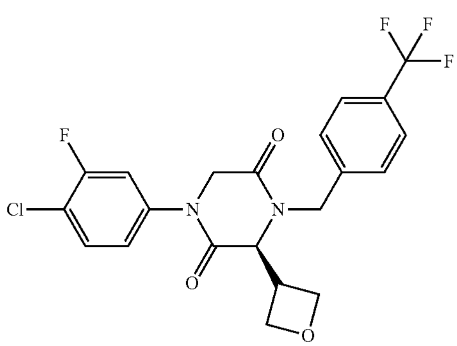 [SMILES: O=C1[C@H](C2COC2)N(Cc2ccc(C(F)(F)F)cc2)C(=O)CN1c1ccc(Cl)c(F)c1] | (S)-1-(4-chloro-3-fluoro-phenyl)-3-(oxetan-3-yl)-4-(4-(trifluoromethyl)-benzyl)piperazine-2,5-dione |

TABLE 1-continued

| No. | Structure | Name |
|---|---|---|
| 749 | 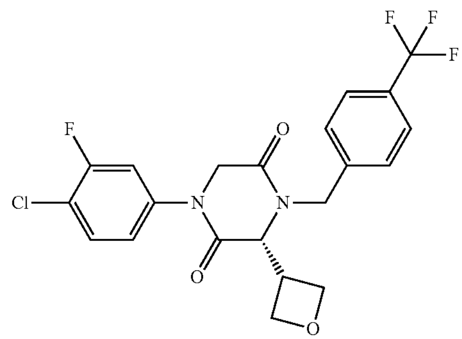 [SMILES: O=C1[C@@H](C2COC2)N(Cc2ccc(C(F)(F)F)cc2)C(=O)CN1c1ccc(Cl)c(F)c1] | (R)-1-(4-chloro-3-fluorophenyl)-3-(oxetan-3-yl)-4-(4-(trifluoromethyl)benzyl)piperazine-2,5-dione |
| 750 | 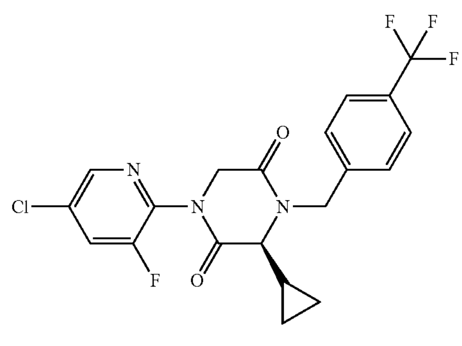 [SMILES: O=C1[C@H](C2CC2)N(Cc2ccc(C(F)(F)F)cc2)C(=O)CN1c1ncc(Cl)cc1F] | (S)-1-(5-chloro-3-fluoropyridin-2-yl)-3-cyclopropyl-4-(4-(trifluoromethyl)benzyl)piperazine-2,5-dione |
| 751 | 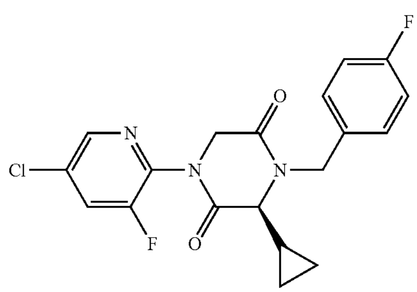 [SMILES: O=C1[C@H](C2CC2)N(Cc2ccc(F)cc2)C(=O)CN1c1ncc(Cl)cc1F] | (S)-1-(5-chloro-3-fluoropyridin-2-yl)-3-cyclopropyl-4-(4-fluorobenzyl)piperazine-2,5-dione |
| 752 | 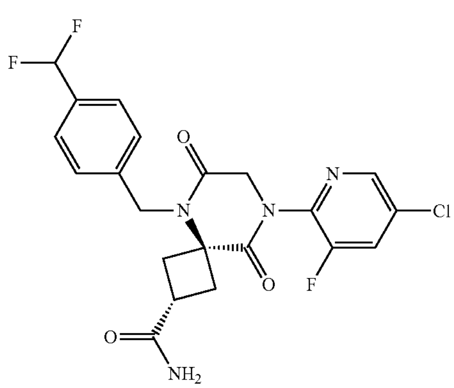 [SMILES: NC(=O)[C@H]1C[C@]2(C1)C(=O)N(c1ncc(Cl)cc1F)CC(=O)N2Cc1ccc(C(F)F)cc1] | (2r,4r)-8-(5-chloro-3-fluoropyridin-2-yl)-5-(4-(difluoromethyl)benzyl)-6,9-dioxo-5,8-diazaspiro[3.5]nonane-2-carboxamide |

TABLE 1-continued

| No. | Structure | Name |
|---|---|---|
| 753 | 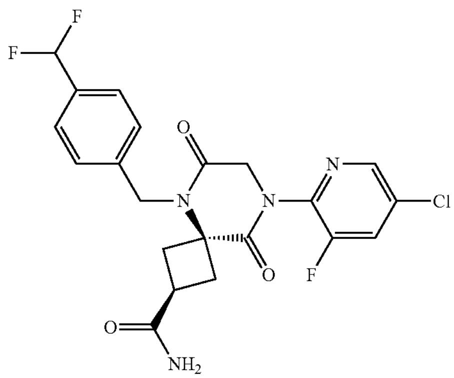 [SMILES: NC(=O)[C@H]1C[C@@]2(C1)C(=O)N(c1ncc(Cl)cc1F)CC(=O)N2Cc1ccc(C(F)F)cc1] | (2s,4s)-8-(5-chloro-3-fluoropyridin-2-yl)-5-(4-(difluoromethyl)benzyl)-6,9-dioxo-5,8-diazaspiro[3.5]nonane-2-carboxamide |
| 754 | 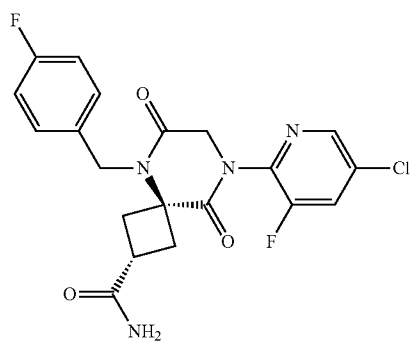 [SMILES: NC(=O)[C@H]1C[C@]2(C1)C(=O)N(c1ncc(Cl)cc1F)CC(=O)N2Cc1ccc(F)cc1] | (2r,4r)-8-(5-chloro-3-fluoropyridin-2-yl)-5-(4-fluorobenzyl)-6,9-dioxo-5,8-diazaspiro[3.5]nonane-2-carboxamide |
| 755 | 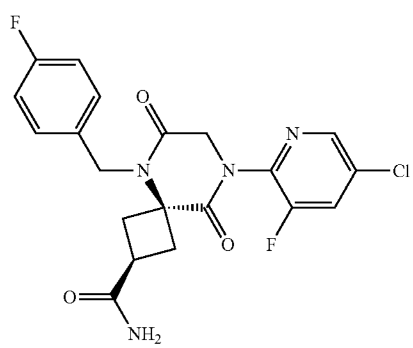 [SMILES: NC(=O)[C@H]1C[C@@]2(C1)C(=O)N(c1ncc(Cl)cc1F)CC(=O)N2Cc1ccc(F)cc1] | (2s,4s)-8-(5-chloro-3-fluoropyridin-2-yl)-5-(4-fluorobenzyl)-6,9-dioxo-5,8-diazaspiro[3.5]nonane-2-carboxamide |
| 756 | 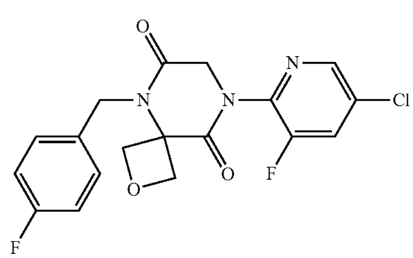 [SMILES: O=C1CN(c2ncc(Cl)cc2F)C(=O)C2(COC2)N1Cc1ccc(F)cc1] | 8-(5-chloro-3-fluoropyridin-2-yl)-5-(4-fluorobenzyl)-2-oxa-5,8-diazaspiro[3.5]-nonane-6,9-dione |
| 757 | 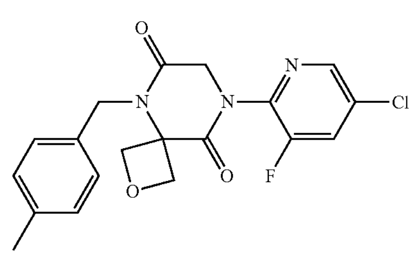 [SMILES: Cc1ccc(CN2C(=O)CN(c3ncc(Cl)cc3F)C(=O)C23COC3)cc1] | 8-(5-chloro-3-fluoropyridin-2-yl)-5-(4-methylbenzyl)-2-oxa-5,8-diazaspiro[3.5]-nonane-6,9-dione |

TABLE 1-continued

| No. | Structure | Name |
|---|---|---|
| 758 | 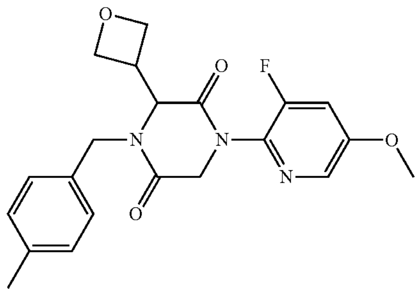 [SMILES: COc1cnc(N2CC(=O)N(Cc3ccc(C)cc3)C(C3COC3)C2=O)c(F)c1] | 1-(3-fluoro-5-methoxy-pyridin-2-yl)-4-(4-methyl-benzyl)-3-(oxetan-3-yl)-piperazine-2,5-dione |
| 759 | 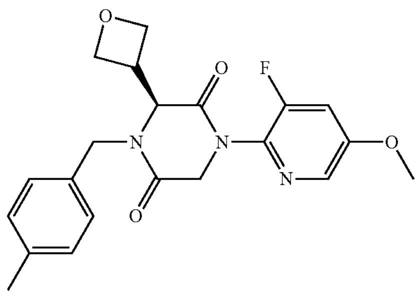 [SMILES: COc1cnc(N2CC(=O)N(Cc3ccc(C)cc3)[C@@H](C3COC3)C2=O)c(F)c1] | (S)-1-(3-fluoro-5-methoxy-pyridin-2-yl)-4-(4-methyl-benzyl)-3-(oxetan-3-yl)-piperazine-2,5-dione |
| 760 | 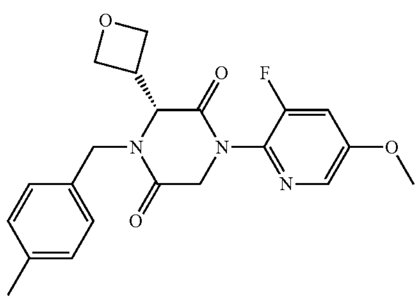 | (R)-1-(3-fluoro-5-methoxy-pyridin-2-yl)-4-(4-methyl-benzyl)-3-(oxetan-3-yl)-piperazine-2,5-dione |
| 761 | 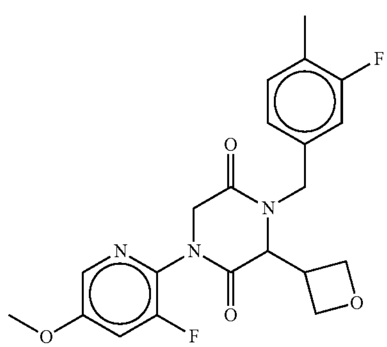 | 4-(3-fluoro-4-methyl-benzyl)-1-(3-fluoro-5-methoxypyridin-2-yl)-3-(oxetan-3-yl)piperazine-2,5-dione |
| 762 | 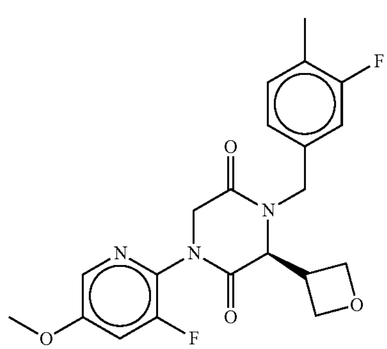 | (S)-4-(3-fluoro-4-methyl-benzyl)-1-(3-fluoro-5-methoxypyridin-2-yl)-3-(oxetan-3-yl)piperazine-2,5-dione |

TABLE 1-continued

| No. | Structure | Name |
| --- | --- | --- |
| 763 | 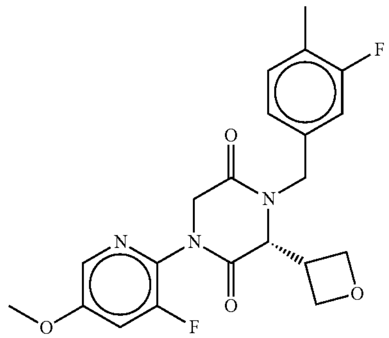 | (R)-4-(3-fluoro-4-methylbenzyl)-1-(3-fluoro-5-methoxypyridin-2-yl)-3-(oxetan-3-yl)piperazine-2,5-dione |
| 764 | 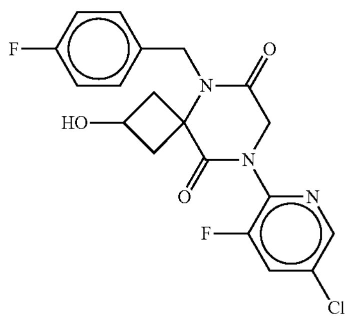 | 8-(5-chloro-3-fluoropyridin-2-yl)-5-(4-fluorobenzyl)-2-hydroxy-5,8-diazaspiro-[3.5]nonane-6,9-dione |
| 765 | 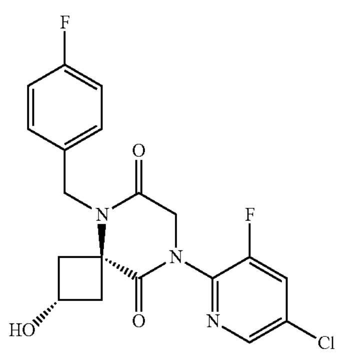 [SMILES: O=C1CN(c2ncc(Cl)cc2F)C(=O)[C@]2(C[C@@H](O)C2)N1Cc1ccc(F)cc1] | (2r,4r)-8-(5-chloro-3-fluoropyridin-2-yl)-5-(4-fluorobenzyl)-2-hydroxy-5,8-diazaspiro[3.5]nonane-6,9-dione |
| 766 | 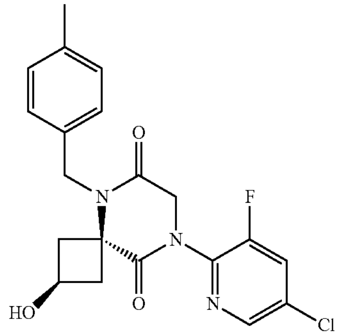 [SMILES: Cc1ccc(CN2C(=O)CN(c3ncc(Cl)cc3F)C(=O)[C@]23C[C@H](O)C3)cc1] | (2s,4s)-8-(5-chloro-3-fluoropyridin-2-yl)-2-hydroxy-5-(4-methyl-benzyl)-5,8-diazaspiro-[3.5]nonane-6,9-dione |

TABLE 1-continued

| No. | Structure | Name |
|---|---|---|
| 767 | 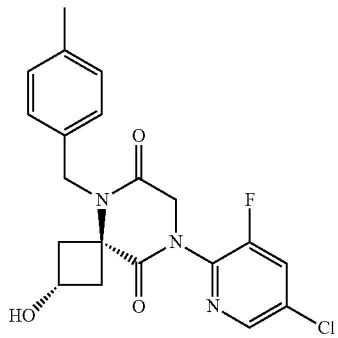 [SMILES: Cc1ccc(CN2C(=O)CN(c3ncc(Cl)cc3F)C(=O)[C@]23C[C@@H](O)C3)cc1] | (2r,4r)-8-(5-chloro-3-fluoropyridin-2-yl)-2-hydroxy-5-(4-methyl-benzyl)-5,8-diazaspiro-[3.5]nonane-6,9-dione |
| 768 | 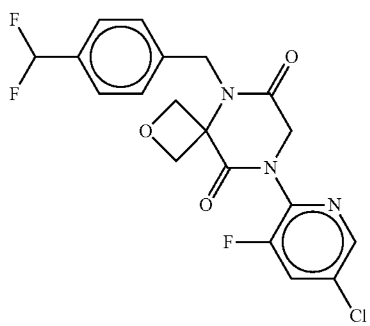 | 8-(5-chloro-3-fluoropyridin-2-yl)-5-(4-(difluoromethyl)-benzyl)-2-oxa-5,8-diazaspiro[3.5]nonane-6,9-dione |
| 769 | 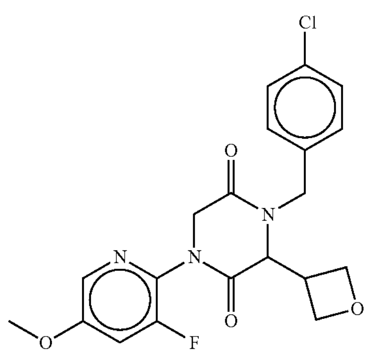 | 4-(4-chlorobenzyl)-1-(3-fluoro-5-methoxypyridin-2-yl)-3-(oxetan-3-yl)-piperazine-2,5-dione |
| 770 | 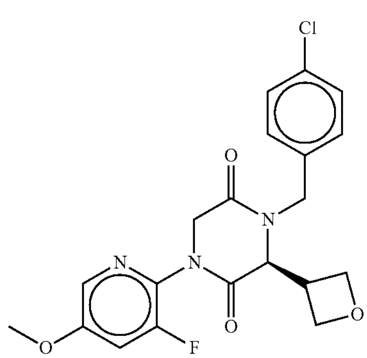 | (S)-4-(4-chlorobenzyl)-1-(3-fluoro-5-methoxy-pyridin-2-yl)-3-(oxetan-3-yl)piperazine-2,5-dione |

TABLE 1-continued
| No. | Structure | Name |
|---|---|---|
| 771 | 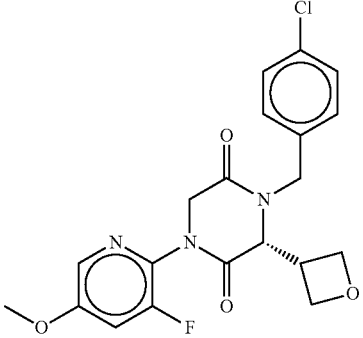 | (R)-4-(4-chlorobenzyl)-1-(3-fluoro-5-methoxy-pyridin-2-yl)-3-(oxetan-3-yl)piperazine-2,5-dione |
| 772 | 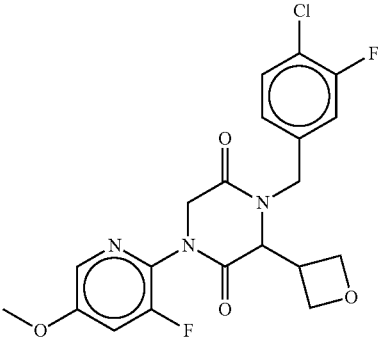 | 4-(4-chloro-3-fluoro-benzyl)-1-(3-fluoro-5-methoxypyridin-2-yl)-3-(oxetan-3-yl)piperazine-2,5-dione |
| 773 | 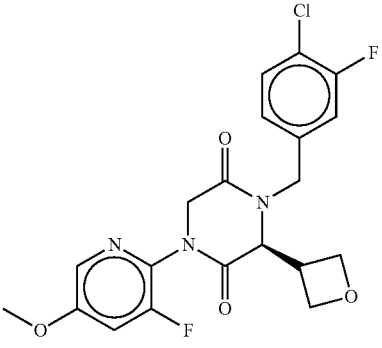 | (S)-4-(4-chloro-3-fluoro-benzyl)-1-(3-fluoro-5-methoxypyridin-2-yl)-3-(oxetan-3-yl)piperazine-2,5-dione |
| 774 | 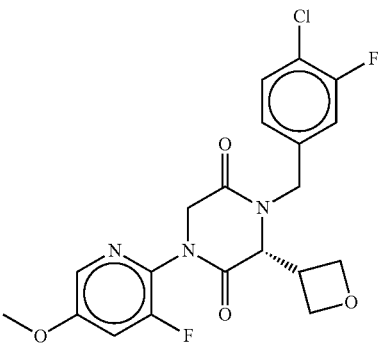 | (R)-4-(4-chloro-3-fluoro-benzyl)-1-(3-fluoro-5-methoxypyridin-2-yl)-3-(oxetan-3-yl)piperazine-2,5-dione |

TABLE 1-continued

| No. | Structure | Name |
|---|---|---|
| 775 | 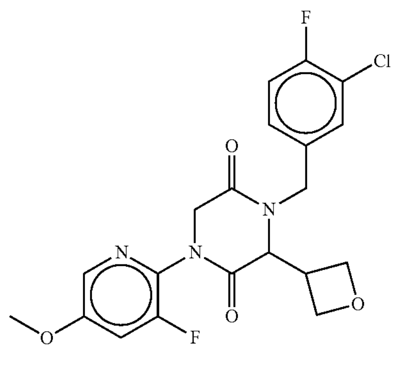 | 4-(3-chloro-4-fluoro-benzyl)-1-(3-fluoro-5-methoxypyridin-2-yl)-3-(oxetan-3-yl)piperazine-2,5-dione |
| 776 | 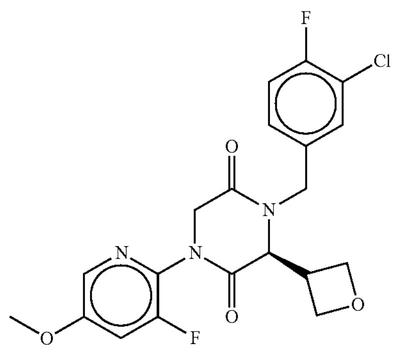 | (S)-4-(3-chloro-4-fluoro-benzyl)-1-(3-fluoro-5-methoxypyridin-2-yl)-3-(oxetan-3-yl)piperazine-2,5-dione |
| 777 | 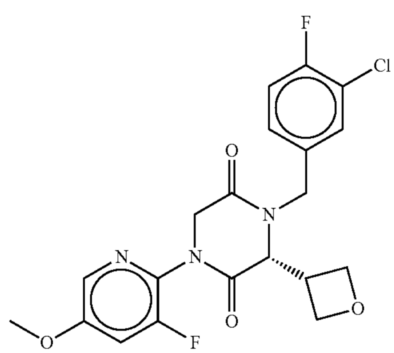 | (R)-4-(3-chloro-4-fluoro-benzyl)-1-(3-fluoro-5-methoxypyridin-2-yl)-3-(oxetan-3-yl)piperazine-2,5-dione |
| 778 | 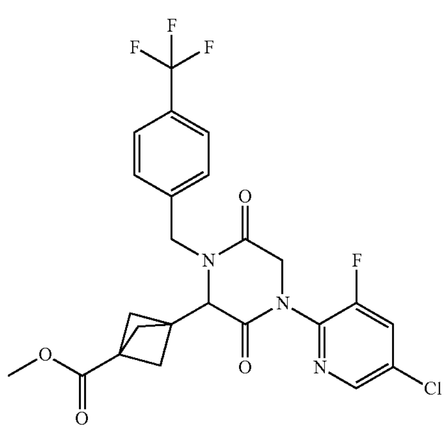 [SMILES: COC(=O)C12CC(C3C(=O)N(c4ncc(Cl)cc4F)CC(=O)N3Cc3ccc(C(F)(F)F)cc3)(C1)C2] | methyl 3-(4-(5-chloro-3-fluoropyridin-2-yl)-3,6-dioxo-1-(4-(trifluoromethyl)benzyl)piperazin-2-yl)bicydo[1.1.1]pentane-1-carboxylate |

TABLE 1-continued

| No. | Structure | Name |
|---|---|---|
| 779 | 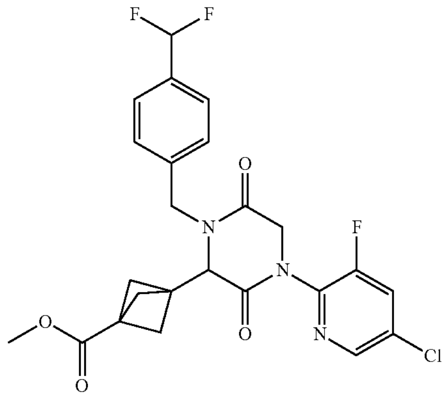 [SMILES: COC(=O)C12CC(C3C(=O)N(c4ncc(Cl)cc4F)CC(=O)N3Cc3ccc(C(F)F)cc3)(C1)C2] | methyl 3-(4-(5-chloro-3-fluoropyridin-2-yl)-1-(4-(difluoromethyl)benzyl)-3,6-dioxopiperazin-2-yl)bicyclo[1.1.1]pentane-1-carboxylate |
| 780 | 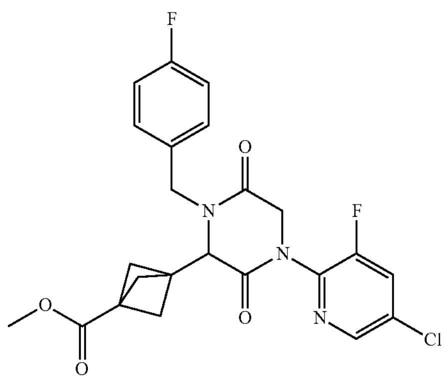 [SMILES: COC(=O)C12CC(C3C(=O)N(c4ncc(Cl)cc4F)CC(=O)N3Cc3ccc(F)cc3)(C1)C2] | methyl 3-(4-(5-chloro-3-fluoropyridin-2-yl)-1-(4-fluorobenzyl)-3,6-dioxopiperazin-2-yl)bicyclo[1.1.1]pentane-1-carboxylate |
| 781 | 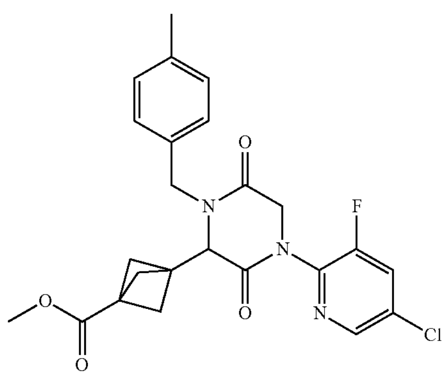 [SMILES: COC(=O)C12CC(C3C(=O)N(c4ncc(Cl)cc4F)CC(=O)N3Cc3ccc(C)cc3)(C1)C2] | methyl 3-(4-(5-chloro-3-fluoropyridin-2-yl)-1-(4-methylbenzyl)-3,6-dioxopiperazin-2-yl)bicyclo[1.1.1]pentane-1-carboxylate |
| 782 | 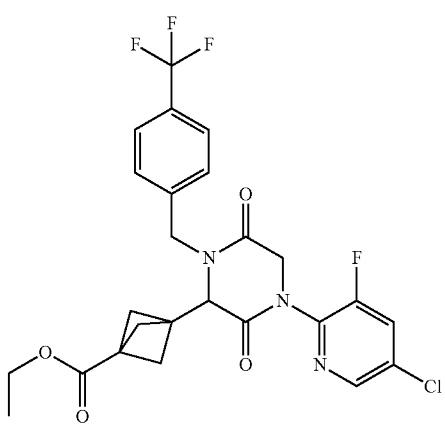 [SMILES: CCOC(=O)C12CC(C3C(=O)N(c4ncc(Cl)cc4F)CC(=O)N3Cc3ccc(C(F)(F)F)cc3)(C1)C2] | ethyl 3-(4-(5-chloro-3-fluoropyridin-2-yl)-3,6-dioxo-1-(4-(trifluoromethyl)benzyl)piperazin-2-yl)bicyclo[1.1.1]pentane-1-carboxylate |

TABLE 1-continued

| No. | Structure | Name |
|---|---|---|
| 783 | 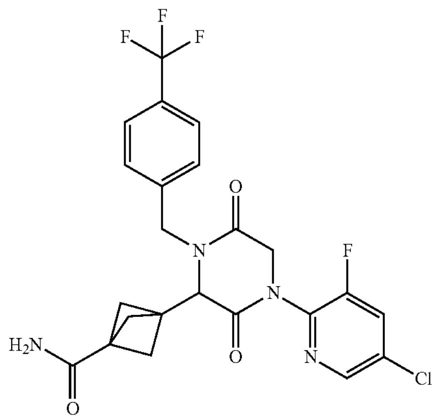 [SMILES: NC(=O)C12CC(C3C(=O)N(c4ncc(Cl)cc4F)CC(=O)N3Cc3ccc(C(F)(F)F)cc3)(C1)C2] | 3-(4-(5-chloro-3-fluoro-pyridin-2-yl)-3,6-dioxo-1-(4-(trifluoromethyl)-benzyl)piperazin-2-yl)bicyclo[1.1.1]pentane-1-carboxamide |
| 784 | 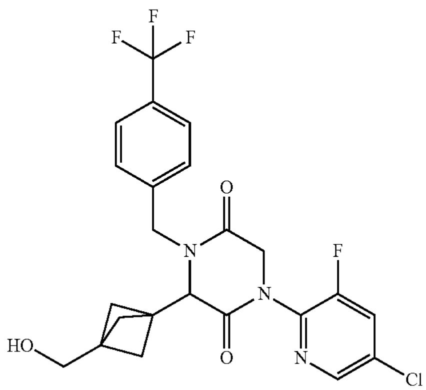 [SMILES: O=C1C(C23CC(CO)(C2)C3)N(Cc2ccc(C(F)(F)F)cc2)C(=O)CN1c1ncc(Cl)cc1F] | 1-(5-chloro-3-fluoropyridin-2-yl)-3-(3-(hydroxymethyl)-bicyclo[1.1.1]pentan-1-yl)-4-(4-(trifluoromethyl)-benzyl)piperazine-2,5-dione |
| 785 | 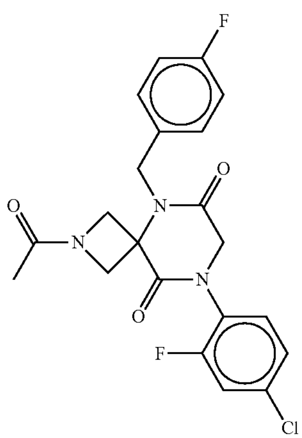 | 2-acetyl-8-(4-chloro-2-fluorophenyl)-5-(4-fluorobenzyl)-2,5,8-triazaspiro[3.5]nonane-6,9-dione |
| 786 | 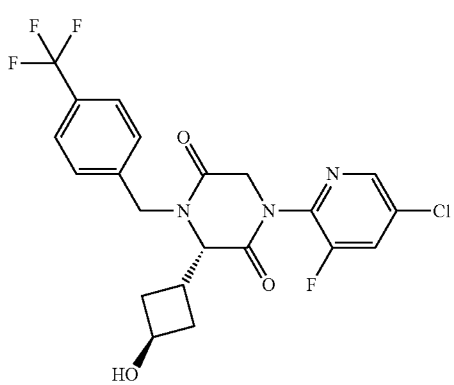 | (S)-1-(5-chloro-3-fluoro-pyridin-2-yl)-3-((1s,3R)-3-hydroxycyclobutyl)-4-(4-(trifluoromethyl)-benzyl)piperazine-2,5-dione |

TABLE 1-continued

| No. | Structure | Name |
|---|---|---|
| 787 | 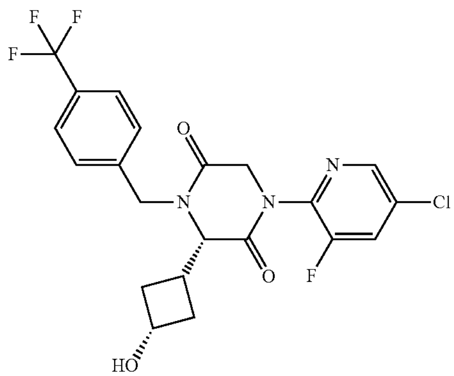 | (S)-1-(5-chloro-3-fluoro-pyridin-2-yl)-3-((1r,3S)-3-hydroxycyclobutyl)-4-(4-(trifluoromethyl)-benzyl)piperazine-2,5-dione |
| 788 | 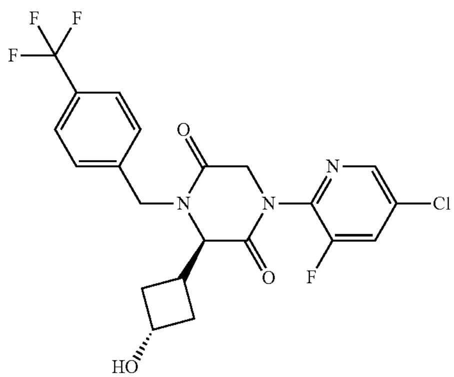 | (R)-1-(5-chloro-3-fluoro-pyridin-2-yl)-3-((1s,3S)-3-hydroxycyclobutyl)-4-(4-(trifluoromethyl)-benzyl)piperazine-2,5-dione |
| 789 | 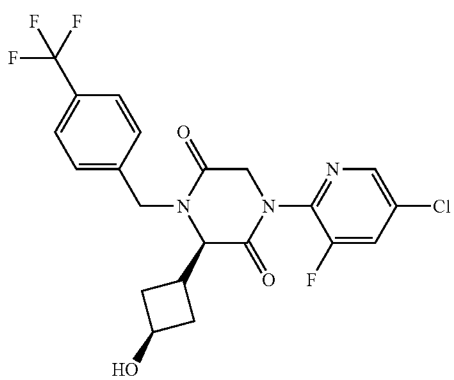 | (R)-1-(5-chloro-3-fluoro-pyridin-2-yl)-3-((1r,3R)-3-hydroxycyclobutyl)-4-(4-(trifluoromethyl)-benzyl)piperazine-2,5-dione |
| 790 | 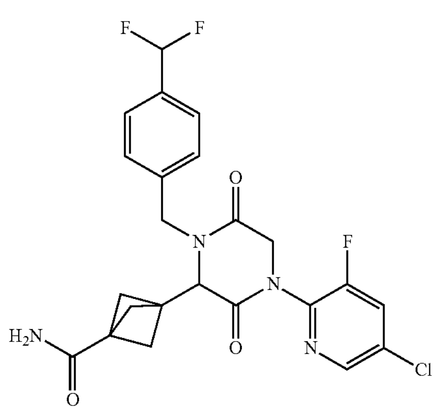 [SMILES: NC(=O)C12CC(C3C(=O)N(c4ncc(Cl)cc4F)CC(=O)N3Cc3ccc(C(F)F)cc3)(C1)C2] | 3-(4-(5-chloro-3-fluoro-pyridin-2-yl)-1-(4-(difluoromethyl)benzyl)-3,6-dioxopiperazin-2-yl)bicyclo[1.1.1]pentane-1-carboxamide |

TABLE 1-continued

| No. | Structure | Name |
| --- | --- | --- |
| 791 | 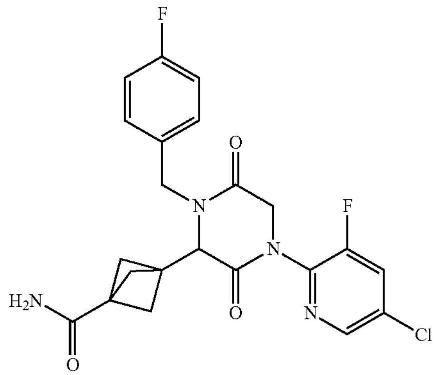 [SMILES: NC(=O)C12CC(C3C(=O)N(c4ncc(Cl)cc4F)CC(=O)N3Cc3ccc(F)cc3)(C1)C2] | 3-(4-(5-chloro-3-fluoro-pyridin-2-yl)-1-(4-fluoro-benzyl)-3,6-dioxopiperazin-2-yl)bicyclo[1.1.1]pentane-1-carboxamide |
| 792 | 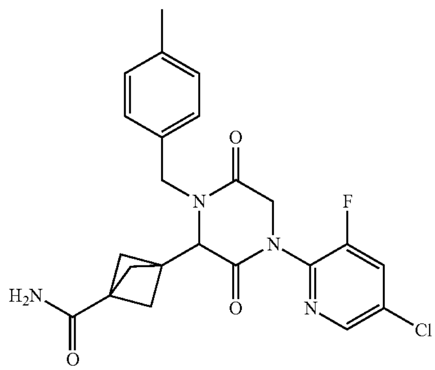 [SMILES: Cc1ccc(CN2C(=O)CN(c3ncc(Cl)cc3F)C(=O)C2C23CC(C(N)=O)(C2)C3)cc1] | 3-(4-(5-chloro-3-fluoro-pyridin-2-yl)-1-(4-methyl-benzyl)-3,6-dioxopiperazin-2-yl)bicyclo[1.1.1]pentane-1-carboxamide |
| 793 | 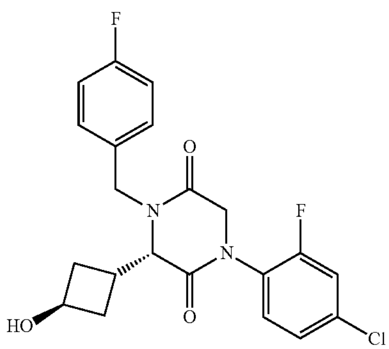 | (S)-1-(4-chloro-2-fluoro-phenyl)-4-(4-fluorobenzyl)-3-((1s,3R)-3-hydroxy-cyclobutyl)piperazine-2,5-dione |
| 794 | 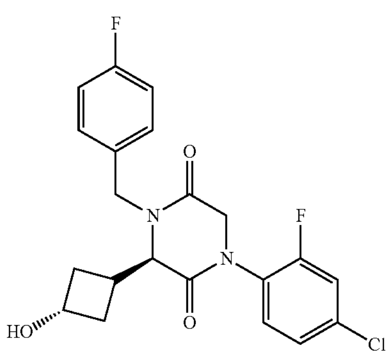 | (R)-1-(4-chloro-2-fluoro-phenyl)-4-(4-fluorobenzyl)-3-((1s,3S)-3-hydroxy-cyclobutyl)piperazine-2,5-dione |

TABLE 1-continued

| No. | Structure | Name |
| --- | --- | --- |
| 795 | 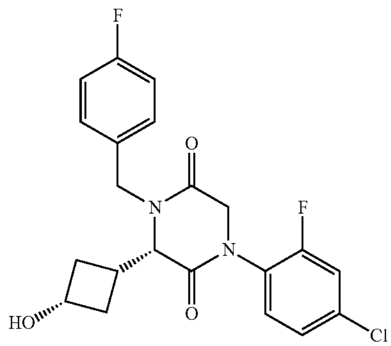 | (S)-1-(4-chloro-2-fluorophenyl)-4-(4-fluorobenzyl)-3-((1r,3S)-3-hydroxycyclobutyl)-piperazine-2,5-dione |
| 796 | 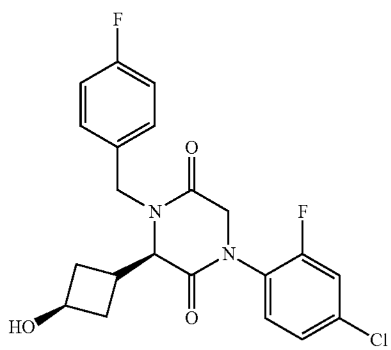 | (R)-1-(4-chloro-2-fluorophenyl)-4-(4-fluorobenzyl)-3-((1r,3R)-3-hydroxycyclobutyl)piperazine-2,5-dione |
| 797 | 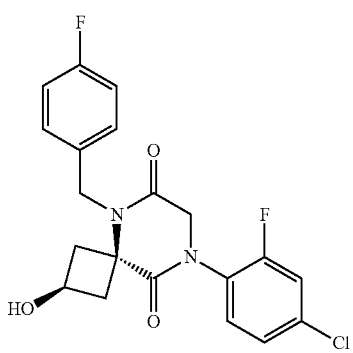 [SMILES: O=C1CN(c2ccc(Cl)cc2F)C(=O)[C@]2(C[C@H](O)C2)N1Cc1ccc(F)cc1] | (2s,4s)-8-(4-chloro-2-fluorophenyl)-5-(4-fluorobenzyl)-2-hydroxy-5,8-diazaspiro[3.5]nonane-6,9-dione |
| 798 | 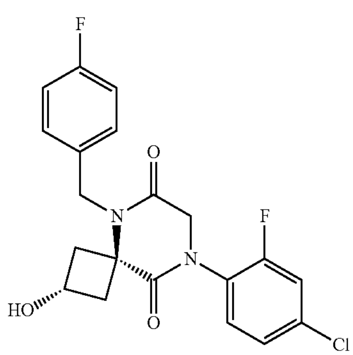 [SMILES: O=C1CN(c2ccc(Cl)cc2F)C(=O)[C@]2(C[C@@H](O)C2)N1Cc1ccc(F)cc1] | (2r,4r)-8-(4-chloro-2-fluorophenyl)-5-(4-fluorobenzyl)-2-hydroxy-5,8-diazaspiro[3.5]nonane-6,9-dione |

TABLE 1-continued

| No. | Structure | Name |
|---|---|---|
| 799 | 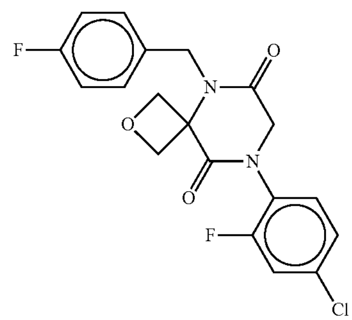 | 8-(4-chloro-2-fluoro-phenyl)-5-(4-fluorobenzyl)-2-oxa-5,8-diazaspiro-[3.5]nonane-6,9-dione |
| 800 | 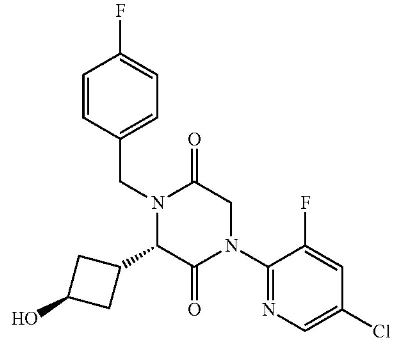 | (S)-1-(5-chloro-3-fluoropyridin-2-yl)-4-(4-fluorobenzyl)-3-((1s,3R)-3-hydroxycyclobutyl)-piperazine-2,5-dione |
| 801 | 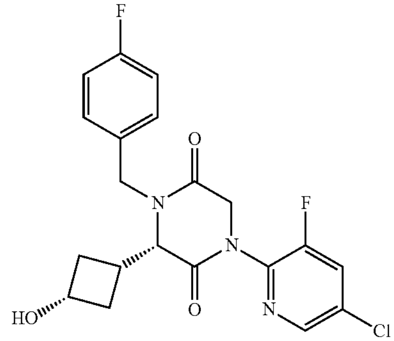 | (S)-1-(5-chloro-3-fluoro-pyridin-2-yl)-4-(4-fluoro-benzyl)-3-((1r,3S)-3-hydroxycyclobutyl)-piperazine-2,5-dione |
| 802 | 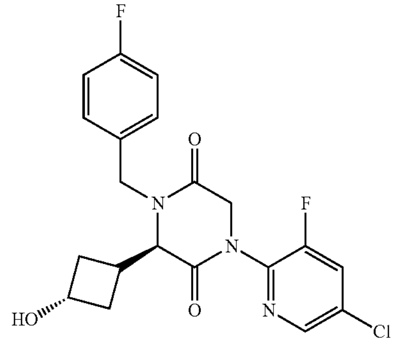 | (R)-1-(5-chloro-3-fluoro-pyridin-2-yl)-4-(4-fluoro-benzyl)-3-((1s,3S)-3-hydroxycyclobutyl)-piperazine-2,5-dione |

TABLE 1-continued

| No. | Structure | Name |
|---|---|---|
| 803 | 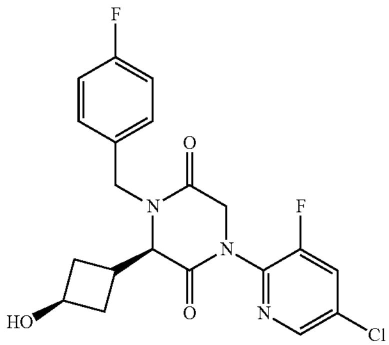 | (R)-1-(5-chloro-3-fluoro-pyridin-2-yl)-4-(4-fluoro-benzyl)-3-((1r,3R)-3-hydroxycyclobutyl)-piperazine-2,5-dione |
| 804 | 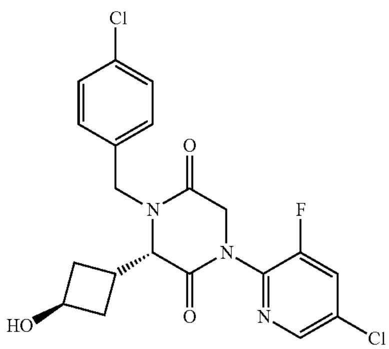 | (S)-1-(5-chloro-3-fluoro-pyridin-2-yl)-4-(4-chloro-benzyl)-3-((1s,3R)-3-hydroxycyclobutyl)-piperazine-2,5-dione |
| 805 | 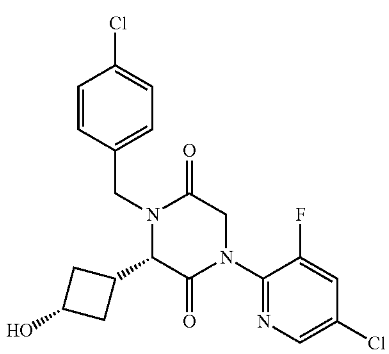 | (S)-1-(5-chloro-3-fluoro-pyridin-2-yl)-4-(4-chloro-benzyl)-3-((1r,3S)-3-hydroxycyclobutyl)-piperazine-2,5-dione |
| 806 | 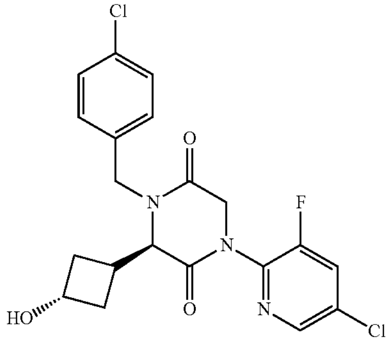 | (R)-1-(5-chloro-3-fluoro-pyridin-2-yl)-4-(4-chloro-benzyl)-3-((1s,3S)-3-hydroxycyclobutyl)-piperazine-2,5-dione |

TABLE 1-continued

| No. | Structure | Name |
|---|---|---|
| 807 | 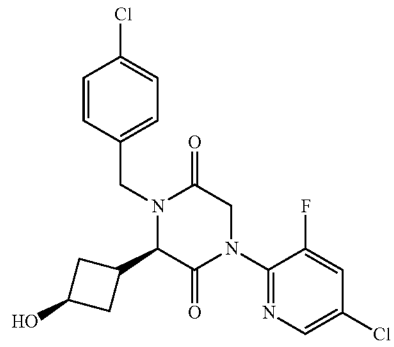 | (R)-1-(5-chloro-3-fluoro-pyridin-2-yl)-4-(4-chloro-benzyl)-3-((1r,3R)-3-hydroxycyclobutyl)-piperazine-2,5-dione |
| 808 | 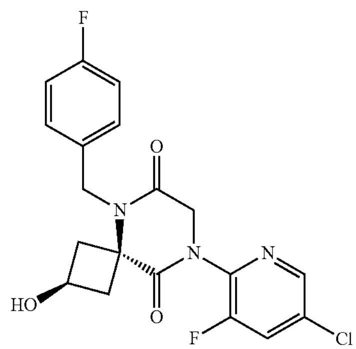 [SMILES: O=C1CN(c2ncc(Cl)cc2F)C(=O)[C@]2(C[C@H](O)C2)N1Cc1ccc(F)cc1] | (2s,4s)-8-(5-chloro-3-fluoropyridin-2-yl)-5-(4-fluorobenzyl)-2-hydroxy-5,8-diazaspiro[3.5]nonane-6,9-dione |
| 809 | 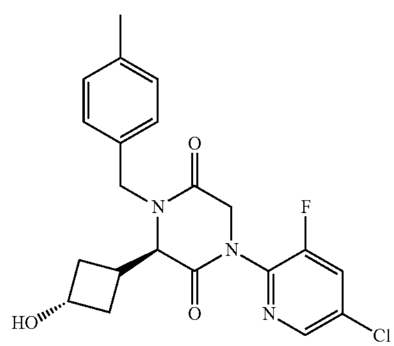 | (R)-1-(5-chloro-3-fluoro-pyridin-2-yl)-3-((1s,3S)-3-hydroxycyclobutyl)-4-(4-methylbenzyl)piperazine-2,5-dione |
| 810 | 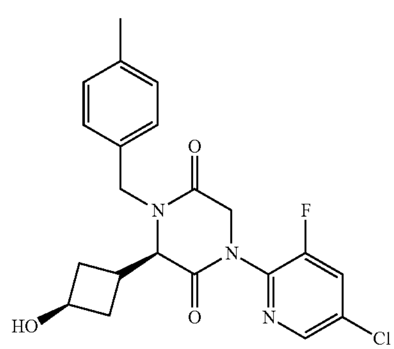 | (R)-1-(5-chloro-3-fluoro-pyridin-2-yl)-3-((1r,3R) 3-hydroxycyclobutyl)-4-(4-methylbenzyl)-piperazine-2,5-dione |

TABLE 1-continued

| No. | Structure | Name |
|---|---|---|
| 811 | 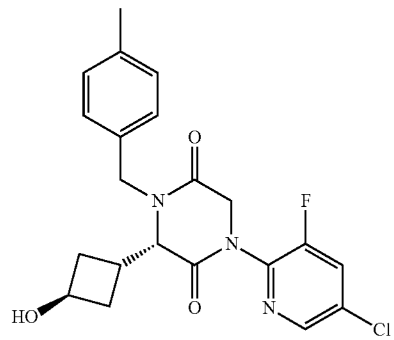 | (S)-1-(5-chloro-3-fluoro-pyridin-2-yl)-3-((1s,3R)-3-hydroxycyclobutyl)-4-(4-methylbenzyl)piperazine-2,5-dione |
| 812 | 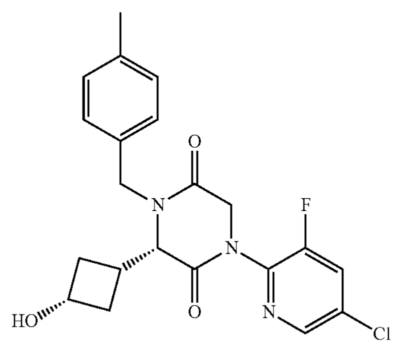 | (S)-1-(5-chloro-3-fluoro-pyridin-2-yl)-3-((1r,3S)-3-hydroxycyclobutyl)-4-(4-methylbenzyl)piperazine-2,5-dione |
| 813 | 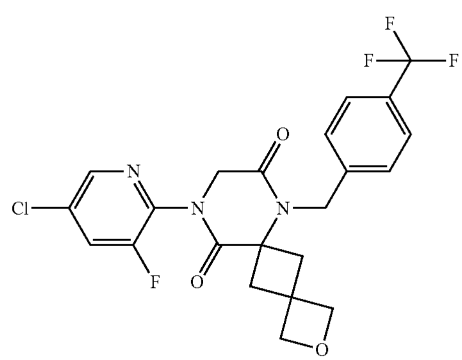 [SMILES: O=C1CN(c2ncc(Cl)cc2F)C(=O)C2(CC3(COC3)C2)N1Cc1ccc(C(F)(F)F)cc1] | 10-(5-chloro-3-fluoro-pyridin-2-yl)-7-(4-(trifluoromethyl)benzyl)-2-oxa-7,10-diazadispiro-[3.1.56.14]dodecane-8,11-dione |
| 814 | 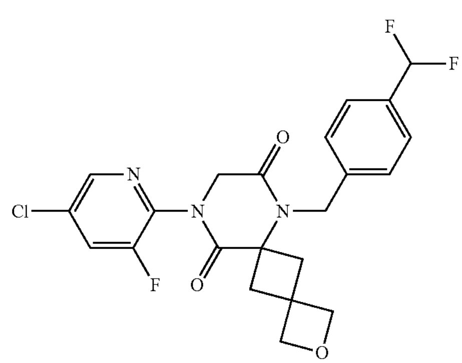 [SMILES: O=C1CN(c2ncc(Cl)cc2F)C(=O)C2(CC3(COC3)C2)N1Cc1ccc(C(F)F)cc1] | 10-(5-chloro-3-fluoro-pyridin-2-yl)-7-(4-(difluoromethyl)benzyl)-2-oxa-7,10-diazadispiro-[3.1.56.14]dodecane-8,11-dione |

TABLE 1-continued

| No. | Structure | Name |
|---|---|---|
| 815 | 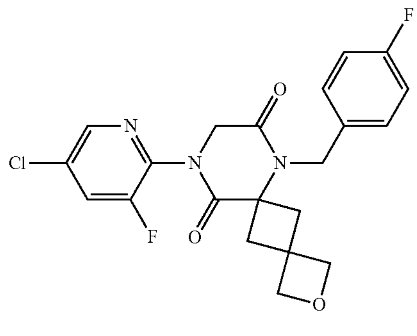 [SMILES: O=C1CN(c2ncc(Cl)cc2F)C(=O)C2(CC3(COC3)C2)N1Cc1ccc(F)cc1] | 10-(5-chloro-3-fluoro-pyridin-2-yl)-7-(4-Fluorobenzyl)-2-oxa-7,10-diazadispiro-[3.1.56.14]dodecane-8,11-dione |
| 816 | 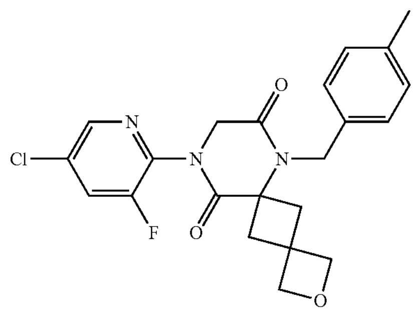 [SMILES: Cc1ccc(CN2C(=O)CN(c3ncc(Cl)cc3F)C(=O)C23CC2(COC2)C3)cc1] | 10-(5-chloro-3-fluoro-pyridin-2-yl)-7-(4-methyl-benzyl)-2-oxa-7,10-diazadispiro[3.1.56.14]-dodecane-8,11-dione |
| 817 | 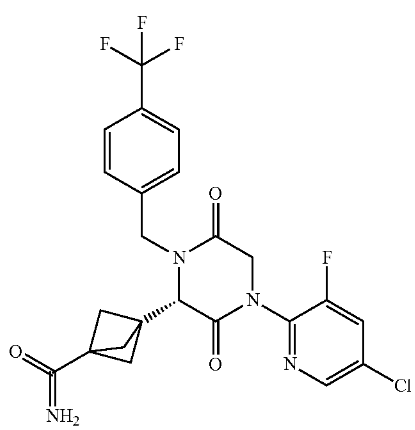 | (S)-3-(4-(5-chloro-3-fluoropyridin-2-yl)-3,6-dioxo-1-(4-(trifluoro-methyl)benzyl)piperazin-2-yl)bicyclo[1.1.1]pentane-1-carboxamide |
| 818 | 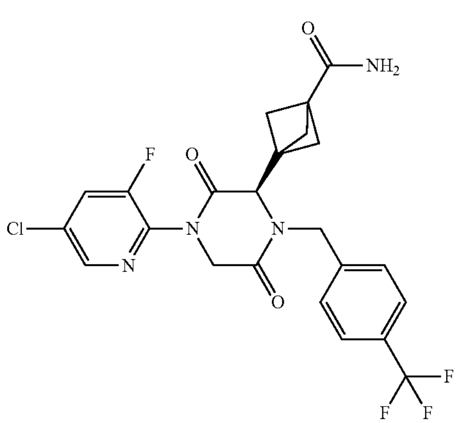 | (R)-3-(4-(5-chloro-3-fluoropyridin-2-yl)-3,6-dioxo-1-(4-(trifluoro-methyl)benzyl)piperazin-2-yl)bicyclo[1.1.1]pentane-1-carboxamide |

TABLE 1-continued

| No. | Structure | Name |
|---|---|---|
| 819 | 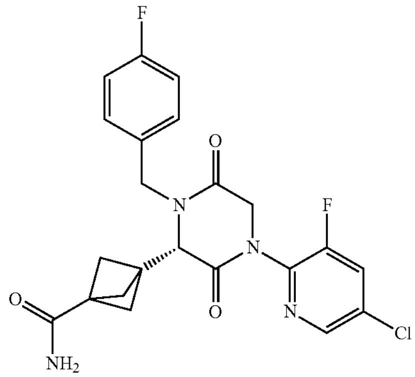 [SMILES: NC(=O)C12CC([C@H]3C(=O)N(c4ncc(Cl)cc4F)CC(=O)N3Cc3ccc(F)cc3)(C1)C2] | (S)-3-(4-(5-chloro-3-fluoropyridin-2-yl)-3,6-dioxo-1-(4-fluorobenzyl)-piperazin-2-yl)bicyclo[1.1.1]pentane-1-carboxamide |
| 820 | 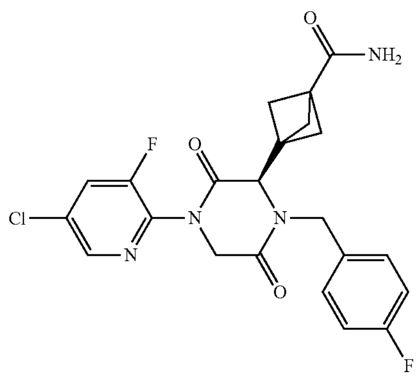 [SMILES: NC(=O)C12CC([C@@H]3C(=O)N(c4ncc(Cl)cc4F)CC(=O)N3Cc3ccc(F)cc3)(C1)C2] | (R)-3-(4-(5-chloro-3-fluoropyridin-2-yl)-3,6-dioxo-1-(4-fluorobenzyl)piperazin-2-yl)bicyclo[1.1.1]pentane-1-carboxamide |
| 821 | 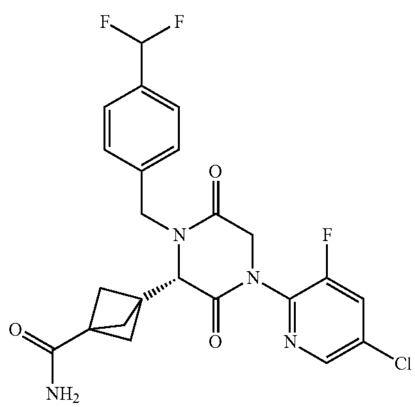 [SMILES: NC(=O)C12CC([C@H]3C(=O)N(c4ncc(Cl)cc4F)CC(=O)N3Cc3ccc(C(F)F)cc3)(C1)C2] | (S)-3-(4-(5-chloro-3-fluoropyridin-2-yl)-3,6-dioxo-1-(4-(difluoromethyl)benzyl)piperazin-2-yl)bicyclo[1.1.1]pentane-1-carboxamide |
| 822 | 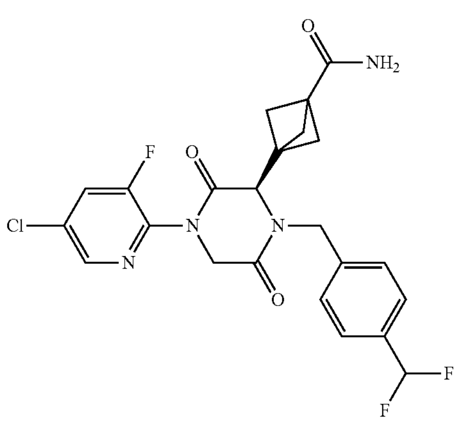 [SMILES: NC(=O)C12CC([C@@H]3C(=O)N(c4ncc(Cl)cc4F)CC(=O)N3Cc3ccc(C(F)F)cc3)(C1)C2] | (R)-3-(4-(5-chloro-3-fluoropyridin-2-yl)-3,6-dioxo-1-(4-(difluoromethyl)benzyl)piperazin-2-yl)bicyclo[1.1.1]pentane-1-carboxamide |

TABLE 1-continued

| No. | Structure | Name |
|---|---|---|
| 823 | 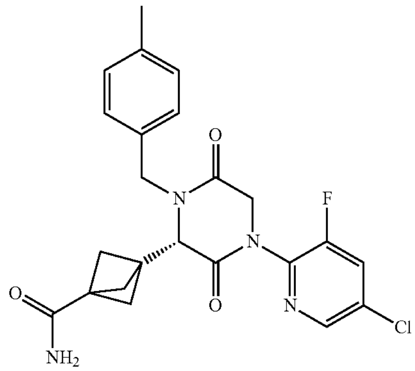 [SMILES: Cc1ccc(CN2C(=O)CN(c3ncc(Cl)cc3F)C(=O)[C@@H]2C23CC(C(N)=O)(C2)C3)cc1] | (S)-3-(4-(5-chloro-3-fluoropyridin-2-yl)-1-(4-methylbenzyl)-3,6-dioxopiperazin-2-yl)bicyclo[1.1.1]pentane-1-carboxamide |
| 824 | 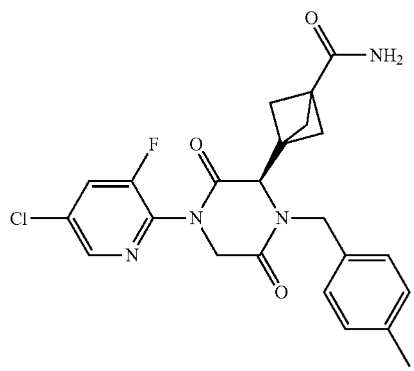 [SMILES: Cc1ccc(CN2C(=O)CN(c3ncc(Cl)cc3F)C(=O)[C@H]2C23CC(C(N)=O)(C2)C3)cc1] | (R)-3-(4-(5-chloro-3-fluoropyridin-2-yl)-1-(4-methylbenzyl)-3,6-dioxopiperazin-2-yl)-bicyclo[1.1.1]pentane-1-carboxamide |
| 825 | 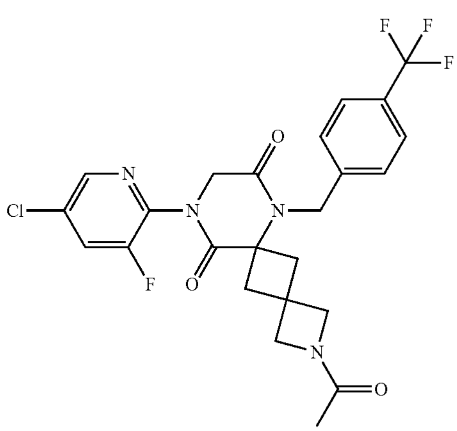 [SMILES: CC(=O)N1CC2(C1)CC1(C2)C(=O)N(c2ncc(Cl)cc2F)CC(=O)N1Cc1ccc(C(F)(F)F)cc1] | 2-acetyl-10-(5-chloro-3-fluoropyridin-2-yl)-7-(4-(trifluoromethyl)benzyl)-2,7,10-triazadispiro-[3.1.56.14]dodecane-8,11-dione |

TABLE 1-continued
| No. | Structure | Name |
|---|---|---|
| 826 | 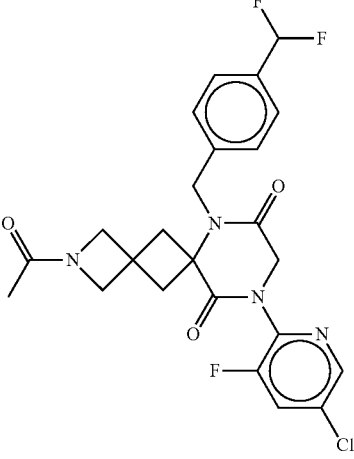 | 2-acetyl-10-(5-chloro-3-fluoropyridin-2-yl)-7-(4-(difluoromethyl)benzyl)-2,7,10-triazadispiro-[3.1.5⁶.1⁴]dodecane-8,11-dione |
| 827 | 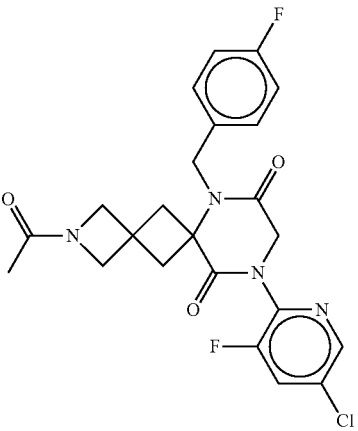 | 2-acetyl-10-(5-chloro-3-fluoropyridin-2-yl)-7-(4-fluorobenzyl)-2,7,10-triazadispiro[3.1.5⁶.1⁴]-dodecane-8,11-dione |
| 828 | 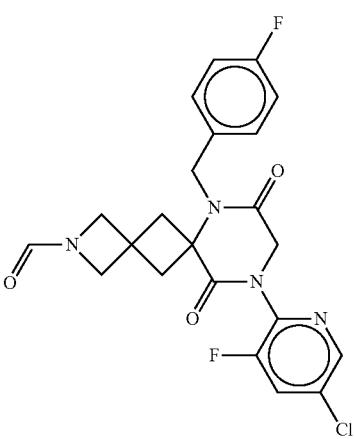 | 10-(5-chloro-3-fluoro-pyridin-2-yl)-7-(4-fluoro-benzyl)-8,11-dioxo-2,7,10-triazadispiro[3.1.5⁶.1⁴]-dodecane-2-carbaldehyde |

TABLE 1-continued

| No. | Structure | Name |
| --- | --- | --- |
| 829 | 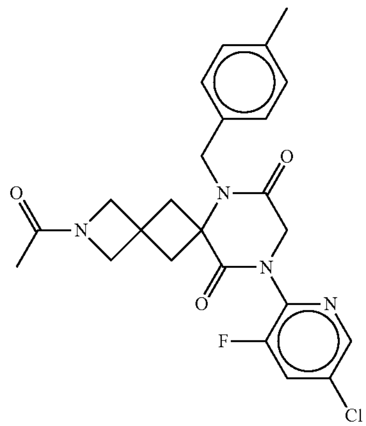 | 2-acetyl-10-(5-chloro-3-fluoropyridin-2-yl)-7-(4-methylbenzyl)-2,7,10-triazadispiro[3.1.56.14]-dodecane-8,11-dione |
| 830 | 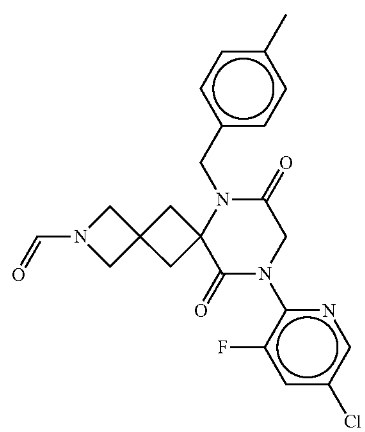 | 10-(5-chloro-3-fluoropyridin-2-yl)-7-(4-methylbenzyl)-8,11-dioxo-2,7,10-triazadispiro[3.1.56.14]-dodecane-2-carbaldehyde |
| 831 | 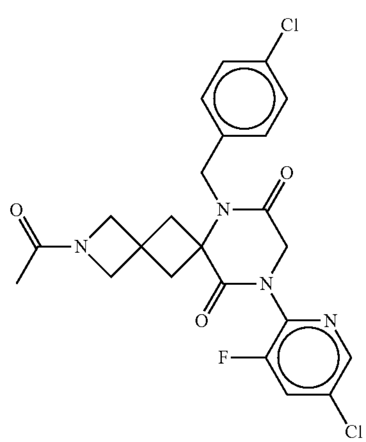 | 2-acetyl-10-(5-chloro-3-fluoropyridin-2-yl)-7-(4-chlorobenzyl)-2,7,10-triazadispiro[3.1.56.14]-dodecane-8,11-dione |

TABLE 1-continued
| No. | Structure | Name |
|---|---|---|
| 832 | 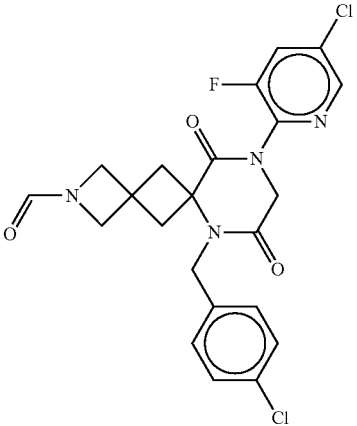 | 10-(5-chloro-3-fluoro-pyridin-2-yl)-7-(4-chloro-benzyl)-8,11-dioxo-2,7,10-triazadispiro[3.1.56.14]-dodecane-2-carbaldehyde |
| 833 | 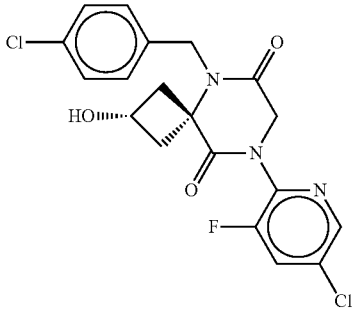 | (2s,4s)-8-(5-chloro-3-fluoropyridin-2-yl)-5-(4-chlorobenzyl)-2-hydroxy-5,8-diazaspiro[3.5]nonane-6,9-dione |
| 834 | 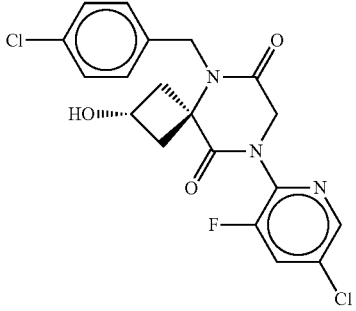 | (2r,4r)-8-(5-chloro-3-fluoropyridin-2-yl)-5-(4-chlorobenzyl)-2-hydroxy-5,8-diazaspiro[3.5]nonane-6,9-dione |
| 835 | 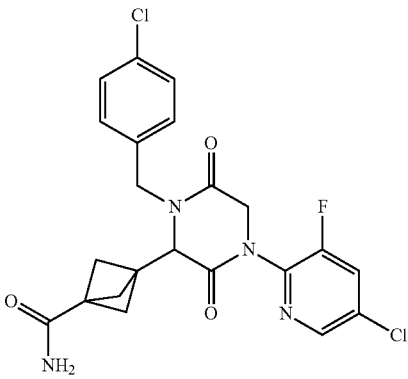 | 3-(4-(5-chloro-3-fluoro-pyridin-2-yl)-1-(4-chloro-benzyl)-3,6-dioxopiperazin-2-yl)bicydo[1.1.1]pentane-1-carboxamide |

TABLE 1-continued

| No. | Structure | Name |
|---|---|---|
| 836 | 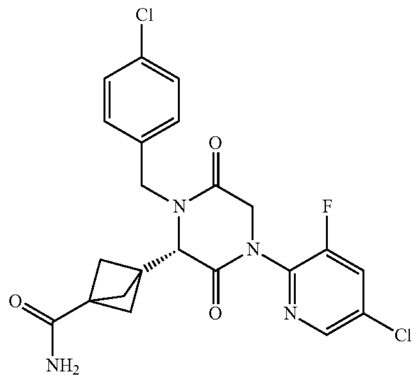 | (S)-3-(4-(5-chloro-3-fluoro-pyridin-2-yl)-1-(4-chloro-benzyl)-3,6-dioxo-piperazin-2-yl)bicyclo-[1.1.1]pentane-1-carboxamide |
| 837 | 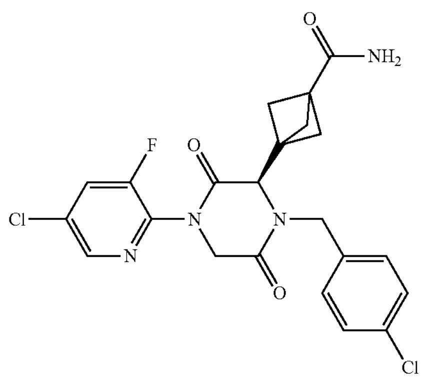 [SMILES: NC(=O)C12CC([C@@H]3C(=O)N(c4ncc(Cl)cc4F)CC(=O)N3Cc3ccc(Cl)cc3)(C1)C2] | (R)-3-(4-(5-chloro-3-fluoro-pyridin-2-yl)-1-(4-chloro-benzyl)-3,6-dioxo-piperazin-2-yl)bicyclo-[1.1.1]pentane-1-carboxamide |
| 838 | 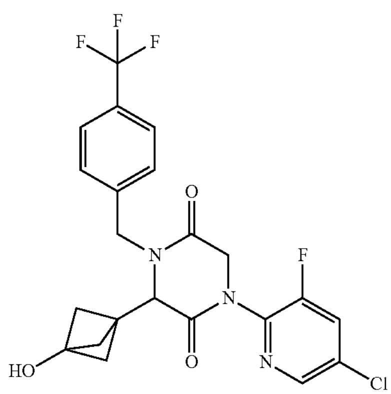 [SMILES: O=C1C(C23CC(O)(C2)C3)N(Cc2ccc(C(F)(F)F)cc2)C(=O)CN1c1ncc(Cl)cc1F] | 1-(5-chloro-3-fluoropyridin-2-yl)-3-(3-hydroxy-bicyclo[1.1.1]pentan-1-yl)-4-(4-(trifluoromethyl)-benzyl)piperazine-2,5-dione |
| 839 | 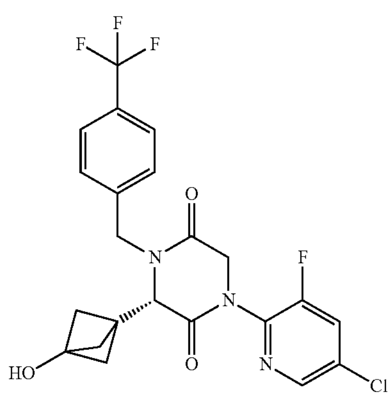 [SMILES: O=C1[C@H](C23CC(O)(C2)C3)N(Cc2ccc(C(F)(F)F)cc2)C(=O)CN1c1ncc(Cl)cc1F] | (S)-1-(5-chloro-3-fluoro-pyridin-2-yl)-3-(3-hydroxy-bicyclo[1.1.1]pentan-1-yl-4-(4-(trifluoromethyl)-benzyl)piperazine-2,5-dione |

TABLE 1-continued

| No. | Structure | Name |
|---|---|---|
| 840 | 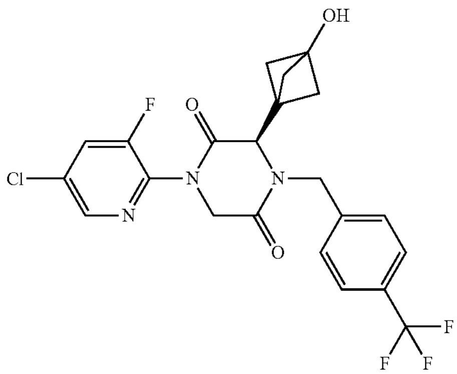 [SMILES: O=C1[C@@H](C23CC(O)(C2)C3)N(Cc2ccc(C(F)(F)F)cc2)C(=O)CN1c1ncc(Cl)cc1F] | (R)-1-(5-chloro-3-fluoro-pyridin-2-yl)-3-(3-hydroxy-bicyclo[1.1.1]pentan-1-yl)-4-(4-(trifluoromethyl)-benzyl)piperazine-2,5-dione |
| 841 | 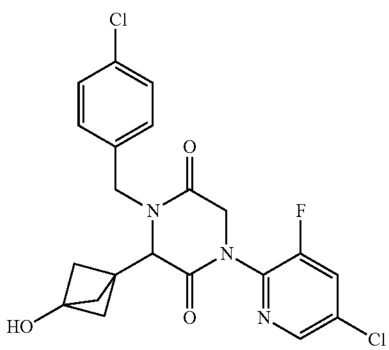 | 1-(5-chloro-3-fluoropyridin-2-yl)-4-(4-chlorobenzyl)-3-(3-hydroxybicyclo[1.1.1]-pentan-1-yl)piperazine-2,5-dione |
| 842 | 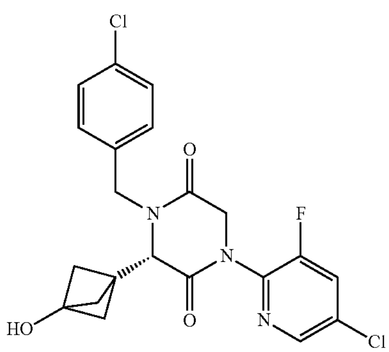 [SMILES: O=C1[C@H](C23CC(O)(C2)C3)N(Cc2ccc(Cl)cc2)C(=O)CN1c1ncc(Cl)cc1F] | (S)-1-(5-chloro-3-fluoro-pyridin-2-yl)-4-(4-chloro-benzyl)-3-(3-hydroxy-bicyclo[1.1.1]pentan-1-yl)piperazine-2,5-dione |
| 843 | 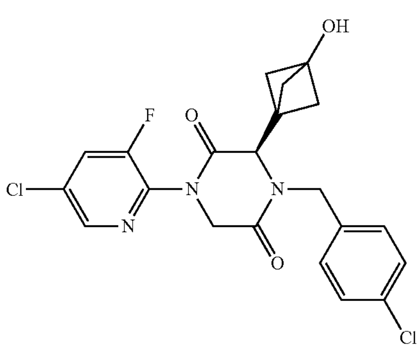 [SMILES: O=C1[C@@H](C23CC(O)(C2)C3)N(Cc2ccc(Cl)cc2)C(=O)CN1c1ncc(Cl)cc1F] | (R)-1-(5-chloro-3-fluoro-pyridin-2-yl)-4-(4-chloro-benzyl)-3-(3-hydroxy-bicyclo-[1.1.1]pentan-1-yl)piperazine-2,5-dione |

TABLE 1-continued

| No. | Structure | Name |
| --- | --- | --- |
| 844 | 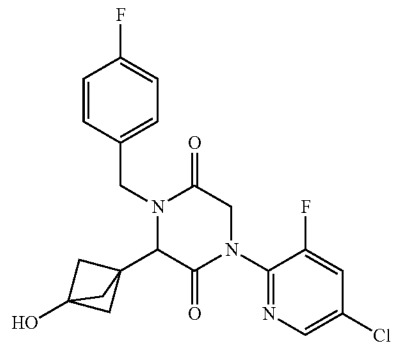 [SMILES: O=C1C(C23CC(O)(C2)C3)N(Cc2ccc(F)cc2)C(=O)CN1c1ncc(Cl)cc1F] | 1-(5-chloro-3-fluoropyridin-2-yl)-4-(4-fluorobenzyl)-3-(3-hydroxybicyclo[1.1.1]-pentan-1-yl)piperazine-2,5-dione |
| 845 | 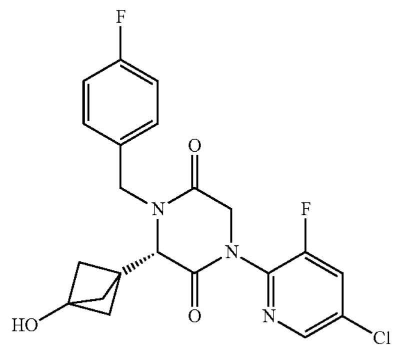 [SMILES: O=C1[C@H](C23CC(O)(C2)C3)N(Cc2ccc(F)cc2)C(=O)CN1c1ncc(Cl)cc1F] | (S)-1-(5-chloro-3-fluoro-pyridin-2-yl)-4-(4-fluoro-benzyl)-3-(3-hydroxy-bicyclo[1.1.1]pentan-1-yl)piperazine-2,5-dione |
| 846 | 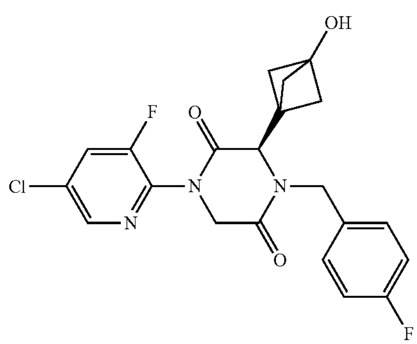 [SMILES: O=C1[C@@H](C23CC(O)(C2)C3)N(Cc2ccc(F)cc2)C(=O)CN1c1ncc(Cl)cc1F] | (R)-1-(5-chloro-3-fluoro-pyridin-2-yl)-4-(4-fluoro-benzyl)-3-(3-hydroxy-bicydo[1.1.1]pentan-1-yl)piperazine-2,5-dione |
| 847 | 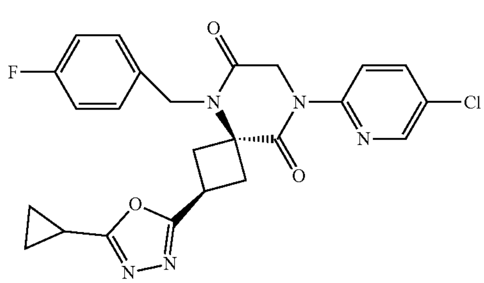 [SMILES: O=C1CN(c2ccc(Cl)cn2)C(=O)[C@]2(C[C@H](c3nnc(C4CC4)o3)C2)N1Cc1ccc(F)cc1] | (2s,4s)-8-(5-chloropyridin-2-yl)-2-(5-cyclopropyl-1,3,4-oxadiazol-2-yl)-5-(4-fluorobenzyl)-5,8-diazaspiro[3.5]nonane-6,9-dione |

TABLE 1-continued

| No. | Structure | Name |
|---|---|---|
| 848 | 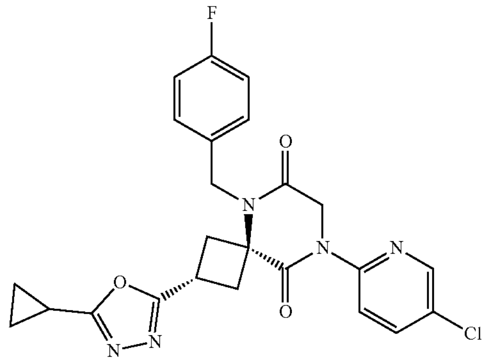 [SMILES: O=C1CN(c2ccc(Cl)cn2)C(=O)[C@]2(C[C@@H](c3nnc(C4CC4)o3)C2)N1Cc1ccc(F)cc1] | (2r,4r)-8-(5-chloropyridin-2-yl)-2-(5-cyclopropyl-1,3,4-oxadiazol-2-yl)-5-(4-fluorobenzyl)-5,8-diazaspiro[3.5]nonane-6,9-dione |
| 849 | 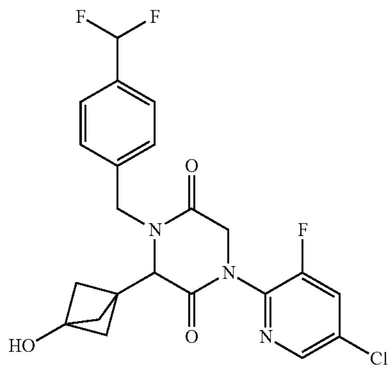 [SMILES: O=C1C(C23CC(O)(C2)C3)N(Cc2ccc(C(F)F)cc2)C(=O)CN1c1ncc(Cl)cc1F] | 1-(5-chloro-3-fluoropyridin-2-yl)-4-(4-(difluoromethyl)-benzyl)-3-(3-hydroxy-bicyclo[1.1.1]pentan-1-yl)piperazine-2,5-dione |
| 850 | 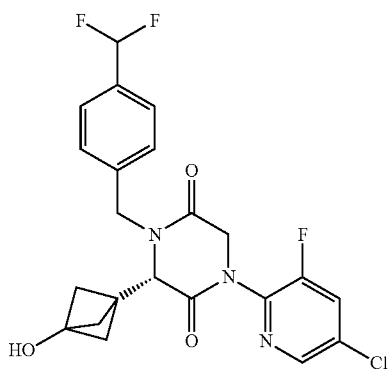 [SMILES: O=C1[C@H](C23CC(O)(C2)C3)N(Cc2ccc(C(F)F)cc2)C(=O)CN1c1ncc(Cl)cc1F] | (S)-1-(5-chloro-3-fluoro-pyridin-2-yl)-4-(4-(difluoromethyl)benzyl)-3-(3-hydroxybicyclo[1.1.1]-pentan-1-yl)piperazine-2,5-dione |
| 851 | 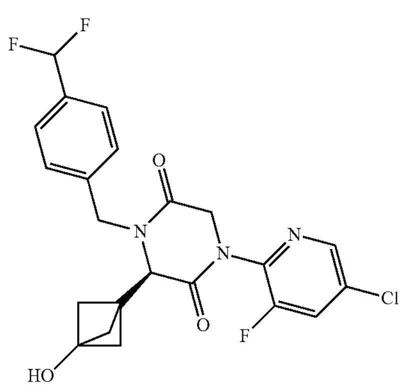 [SMILES: O=C1[C@@H](C23CC(O)(C2)C3)N(Cc2ccc(C(F)F)cc2)C(=O)CN1c1ncc(Cl)cc1F] | (R)-1-(5-chloro-3-fluoro-pyridin-2-yl)-4-(4-(difluoromethyl)benzyl)-3-(3-hydroxybicyclo[1.1.1]-pentan-1-yl)piperazine-2,5-dione |

TABLE 1-continued

| No. | Structure | Name |
|---|---|---|
| 852 | 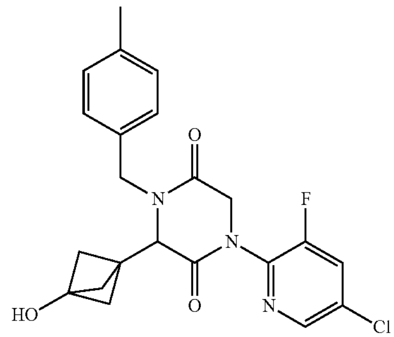 [SMILES: Cc1ccc(CN2C(=O)CN(c3ncc(Cl)cc3F)C(=O)C2C23CC(O)(C2)C3)cc1] | 1-(5-chloro-3-fluoropyridin-2-yl)-3-(3-hydroxybicyclo-[1.1.1]pentan-1-yl)-4-(4-methylbenzyl)piperazine-2,5-dione |
| 853 | 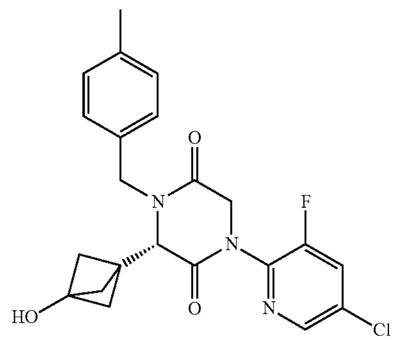 [SMILES: Cc1ccc(CN2C(=O)CN(c3ncc(Cl)cc3F)C(=O)[C@@H]2C23CC(O)(C2)C3)cc1] | (S)-1-(5-chloro-3-fluoro-pyridin-2-yl)-3-(3-hydroxybicydo[1.1.1]-pentan-1-yl)-4-(4-methyl-benzyl)piperazine-2,5-dione |
| 854 | 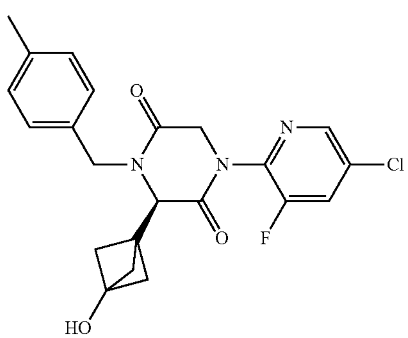 [SMILES: Cc1ccc(CN2C(=O)CN(c3ncc(Cl)cc3F)C(=O)[C@H]2C23CC(O)(C2)C3)cc1] | (R)-1-(5-chloro-3-fluoro-pyridin-2-yl)-3-(3-hydroxybicydo[1.1.1]-pentan-1-yl)-4-(4-methylbenzyl)piperazine-2,5-dione |
| 855 | 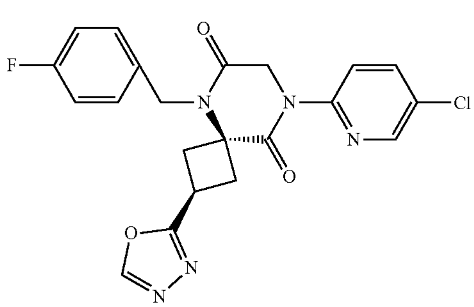 [SMILES: O=C1CN(c2ccc(Cl)cn2)C(=O)[C@]2(C[C@H](c3nnco3)C2)N1Cc1ccc(F)cc1] | (2s,4s)-8-(5-chloropyridin-2-yl)-5-(4-fluorobenzyl)-2-(1,3,4-oxadiazol-2-yl)-5,8-diazaspiro[3.5]nonane-6,9-dione |

TABLE 1-continued

| No. | Structure | Name |
|---|---|---|
| 856 | 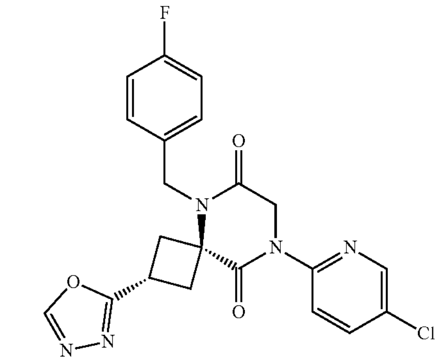 [SMILES: O=C1CN(c2ccc(Cl)cn2)C(=O)[C@]2(C[C@@H](c3nnco3)C2)N1Cc1ccc(F)cc1] | (2r,4r)-8-(5-chloropyridin-2-yl)-5-(4-fluorobenzyl)-2-(1,3,4-oxadiazol-2-yl)-5,8-diazaspiro[3.5]nonane-6,9-dione |
| 857 | 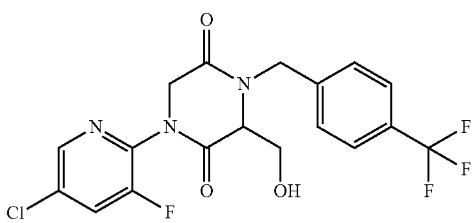 [SMILES: O=C1C(CO)N(Cc2ccc(C(F)(F)F)cc2)C(=O)CN1c1ncc(Cl)cc1F] | 1-(5-chloro-3-fluoropyridin-2-yl)-3-(hydroxymethyl)-4-(4-(trifluoromethyl)benzyl)-piperazine-2,5-dione |
| 858 | 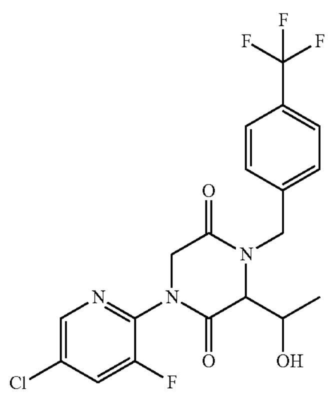 [SMILES: CC(O)C1C(=O)N(c2ncc(Cl)cc2F)CC(=O)N1Cc1ccc(C(F)(F)F)cc1] | 1-(5-chloro-3-fluoro-pyridin-2-yl)-3-(1-hydroxy-ethyl)-4-(4-(trifluoro-methyl)benzyl)piperazine-2,5-dione |
| 859 | 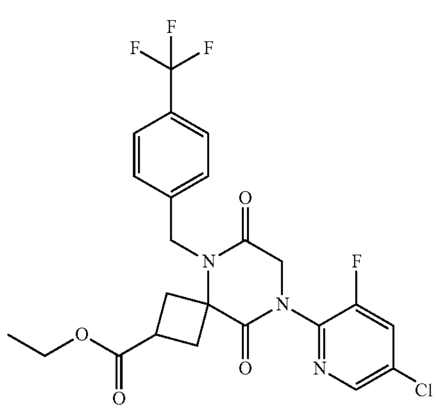 [SMILES: CCOC(=O)C1CC2(C1)C(=O)N(c1ncc(Cl)cc1F)CC(=O)N2Cc1ccc(C(F)(F)F)cc1] | ethyl 8-(5-chloro-3-fluoro-pyridin-2-yl)-6,9-dioxo-5-(4-(trifluoromethyl)benzyl)-5,8-diazaspiro[3.5]nonane-2-carboxylate |

TABLE 1-continued
| No. | Structure | Name |
|---|---|---|
| 860 | 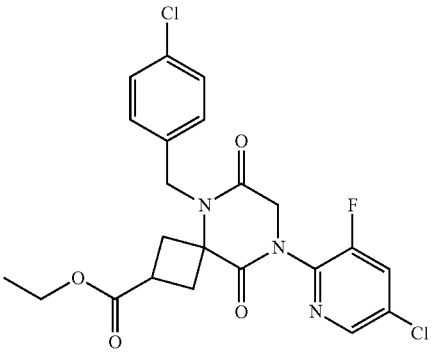 [SMILES: CCOC(=O)C1CC2(C1)C(=O)N(c1ncc(Cl)cc1F)CC(=O)N2Cc1ccc(Cl)cc1] | ethyl 8-(5-chloro-3-fluoro-pyridin-2-yl)-5-(4-chloro-benzyl)-6,9-dioxo-5,8-diazaspiro[3.5]nonane-2-carboxylate |
| 861 | 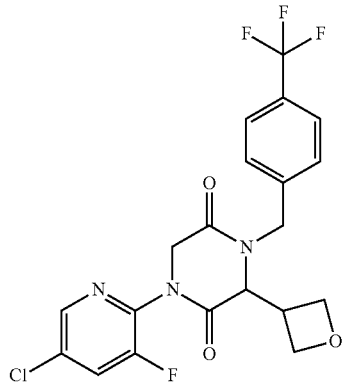 [SMILES: O=C1C(C2COC2)N(Cc2ccc(C(F)(F)F)cc2)C(=O)CN1c1ncc(Cl)cc1F] | 1-(5-chloro-3-fluoropyridin-2-yl)-3-(oxetan-3-yl)-4-(4-(trifluoromethyl)benzyl)-piperazine-2,5-dione |
| 862 | 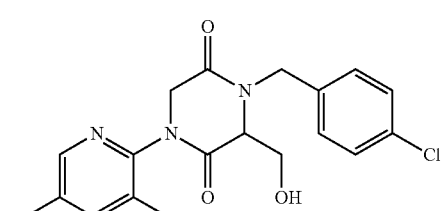 | 1-(5-chloro-3-fluoropyridin-2-yl)-4-(4-chlorobenzyl)-3-(hydroxymethyl)piperazine-2,5-dione |
| 863 | 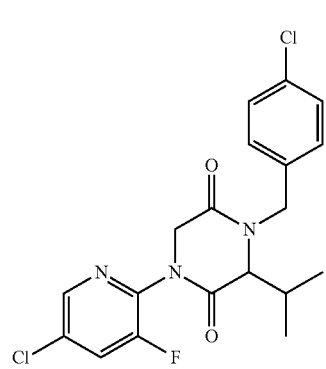 [SMILES: CC(C)C1C(=O)N(c2ncc(Cl)cc2F)CC(=O)N1Cc1ccc(Cl)cc1] | 1-(5-chloro-3-fluoropyridin-2-yl)-4-(4-chlorobenzyl)-3-isopropylpiperazine-2,5-dione |

TABLE 1-continued

| No. | Structure | Name |
|---|---|---|
| 864 | 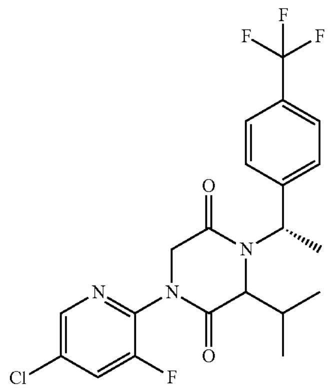 [SMILES: CC(C)C1C(=O)N(c2ncc(Cl)cc2F)CC(=O)N1[C@@H](C)c1ccc(C(F)(F)F)cc1] | 1-(5-chloro-3-fluoropyridin-2-yl)-3-isopropyl-4-((S)-1-(4-(trifluoromethyl)phenyl)-ethyl)piperazine-2,5-dione |
| 865 | 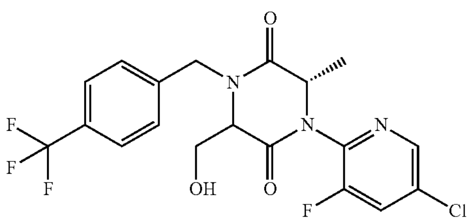 [SMILES: C[C@H]1C(=O)N(Cc2ccc(C(F)(F)F)cc2)C(CO)C(=O)N1c1ncc(Cl)cc1F] | (6S)-1-(5-chloro-3-fluoro-pyridin-2-yl)-3-(hydroxy-methyl)-6-methyl-4-(4-(trifluoromethyl)benzyl)-piperazine-2,5-dione |
| 866 | 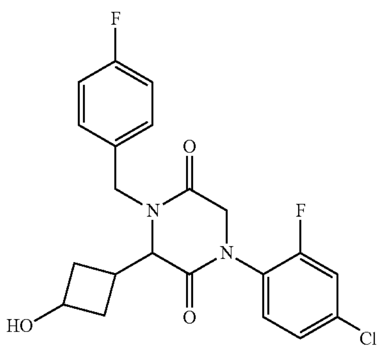 [SMILES: O=C1C(C2CC(O)C2)N(Cc2ccc(F)cc2)C(=O)CN1c1ccc(Cl)cc1F] | 1-(4-chloro-2-fluoro-phenyl)-4-(4-fluoro-benzyl)-3-(3-hydroxy-cyclobutyl)piperazine-2,5-dione |
| 867 | 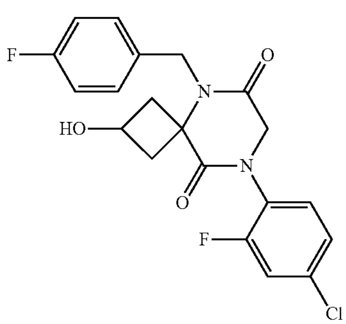 [SMILES: O=C1CN(c2ccc(Cl)cc2F)C(=O)C2(CC(O)C2)N1Cc1ccc(F)cc1] | 8-(4-chloro-2-fluoro-phenyl)-5-(4-fluorobenzyl)-2-hydroxy-5,8-diazaspiro-[3.5]nonane-6,9-dione |
| 868 | 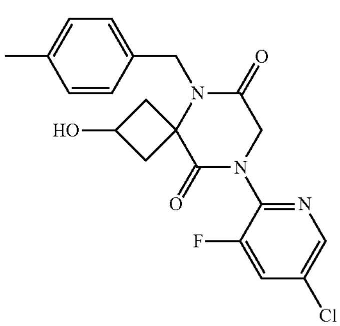 [SMILES: Cc1ccc(CN2C(=O)CN(c3ncc(Cl)cc3F)C(=O)C23CC(O)C3)cc1] | 8-(5-chloro-3-fluoropyridin-2-yl)-2-hydroxy-5-(4-methylbenzyl)-5,8-diazaspiro[3.5]nonane-6,9-dione |

TABLE 1-continued

| No. | Structure | Name |
|---|---|---|
| 869 | 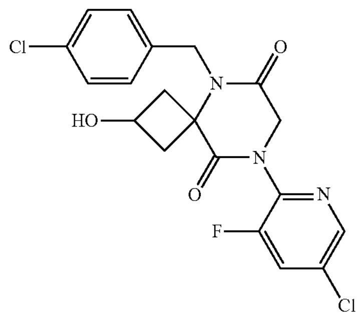 [SMILES: O=C1CN(c2ncc(Cl)cc2F)C(=O)C2(CC(O)C2)N1Cc1ccc(Cl)cc1] | 8-(5-chloro-3-fluoropyridin-2-yl)-5-(4-chlorobenzyl)-2-hydroxy-5,8-diazaspiro-[3.5]nonane-6,9-dione |
| 870 | 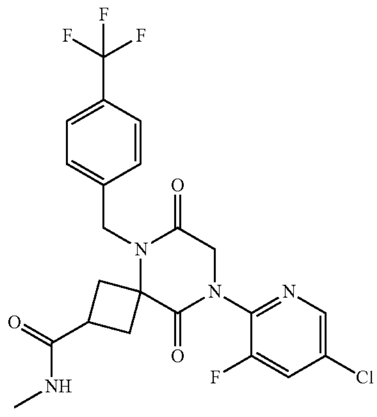 [SMILES: CNC(=O)C1CC2(C1)C(=O)N(c1ncc(Cl)cc1F)CC(=O)N2Cc1ccc(C(F)(F)F)cc1] | 8-(5-chloro-3-fluoropyridin-2-yl)-N-methyl-6,9-dioxo-5-(4-(trifluoromethyl)benzyl)-5,8-diazaspiro[3.5]nonane-2-carboxamide |
| 871 | 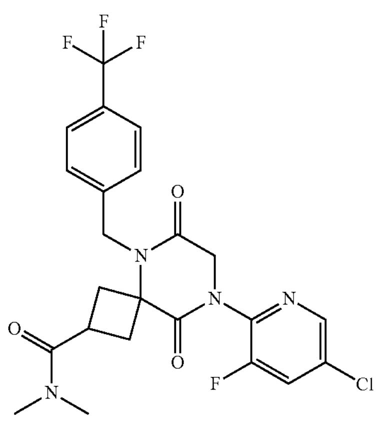 [SMILES: CN(C)C(=O)C1CC2(C1)C(=O)N(c1ncc(Cl)cc1F)CC(=O)N2Cc1ccc(C(F)(F)F)cc1] | 8-(5-chloro-3-fluoropyridin-2-yl)-N,N-dimethyl-6,9-dioxo-5-(4-(trifluoromethyl)benzyl)-5,8-diazaspiro[3.5]nonane-2-carboxamide |
| 872 | 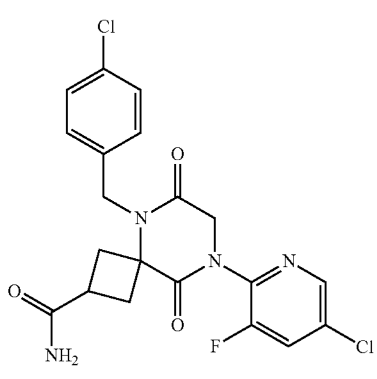 [SMILES: NC(=O)C1CC2(C1)C(=O)N(c1ncc(Cl)cc1F)CC(=O)N2Cc1ccc(Cl)cc1] | 8-(5-chloro-3-fluoropyridin-2-yl)-5-(4-chlorobenzyl)-6,9-dioxo-5,8-diazaspiro[3.5]nonane-2-carboxamide |

TABLE 1-continued

| No. | Structure | Name |
|---|---|---|
| 873 | 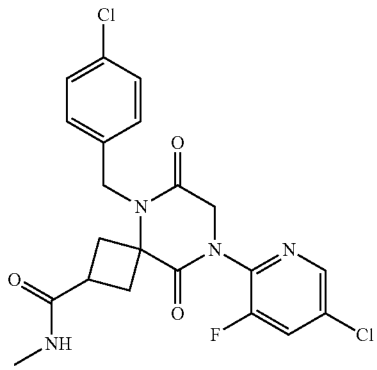 [SMILES: CNC(=O)C1CC2(C1)C(=O)N(c1ncc(Cl)cc1F)CC(=O)N2Cc1ccc(Cl)cc1] | 8-(5-chloro-3-fluoro-pyridin-2-yl)-5-(4-chloro-benzyl)-N-methyl-6,9-dioxo-5,8-diazaspiro-[3.5]nonane-2-carboxamide |
| 874 | 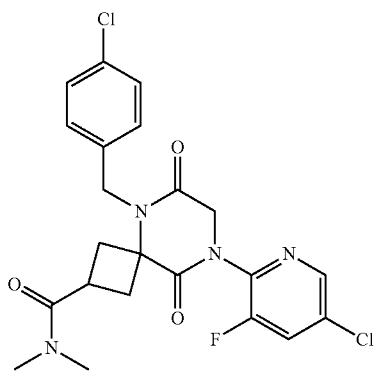 [SMILES: CN(C)C(=O)C1CC2(C1)C(=O)N(c1ncc(Cl)cc1F)CC(=O)N2Cc1ccc(Cl)cc1] | 8-(5-chloro-3-fluoropyridin-2-yl)-5-(4-chlorobenzyl)-N,N-dimethyl-6,9-dioxo-5,8-diazaspiro[3.5]nonane-2-carboxamide |
| 875 | 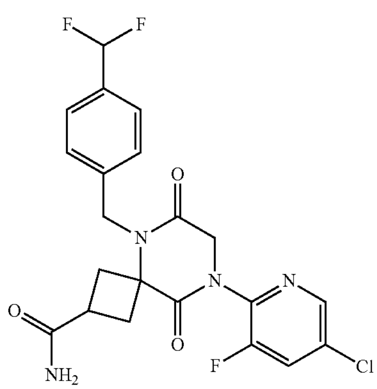 [SMILES: NC(=O)C1CC2(C1)C(=O)N(c1ncc(Cl)cc1F)CC(=O)N2Cc1ccc(C(F)F)cc1] | 8-(5-chloro-3-fluoropyridin-2-yl)-5-(4-(difluoro-methyl)benzyl)-6,9-dioxo-5,8-diazaspiro[3.5]nonane-2-carboxamide |
| 876 | 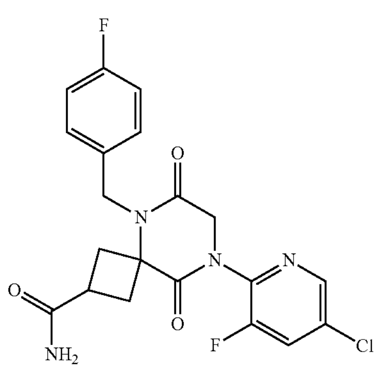 | 8-(5-chloro-3-fluoropyridin-2-yl)-5-(4-fluorobenzyl)-6,9-dioxo-5,8-diazaspiro-[3.5]nonane-2-carboxamide |

TABLE 1-continued

| No. | Structure | Name |
|---|---|---|
| 877 | 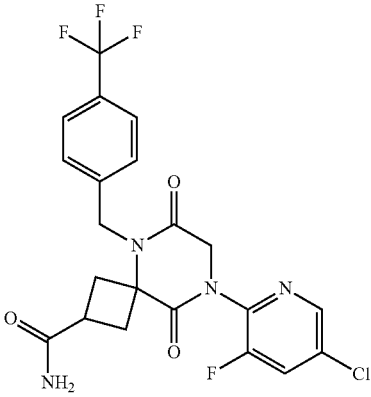 [SMILES: NC(=O)C1CC2(C1)C(=O)N(c1ncc(Cl)cc1F)CC(=O)N2Cc1ccc(C(F)(F)F)cc1] | 8-(5-chloro-3-fluoropyridin-2-yl)-6,9-dioxo-5-(4-(trifluoromethyl)benzyl)-5,8-diazaspiro[3.5]nonane-2-carboxamide |
| 878 | 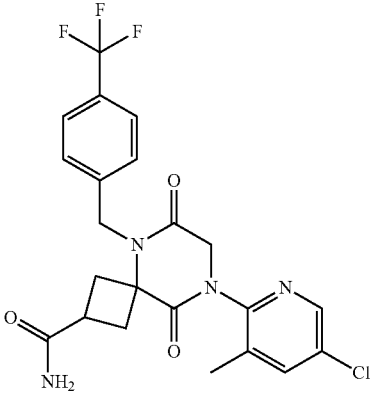 [SMILES: Cc1cc(Cl)cnc1N1CC(=O)N(Cc2ccc(C(F)(F)F)cc2)C2(CC(C(N)=O)C2)C1=O] | 8-(5-chloro-3-methyl-pyridin-2-yl)-6,9-dioxo-5-(4-(trifluoromethyl)benzyl)-5,8-diazaspiro[3.5]nonane-2-carboxamide |
| 879 | 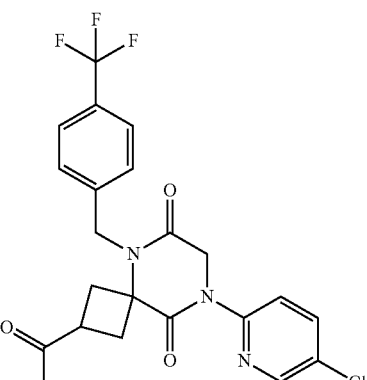 | 8-(5-chloropyridin-2-yl)-6,9-dioxo-5-(4-(trifluoromethyl)benzyl)-5,8-diazaspiro[3.5]nonane-2-carboxamide |
| 880 | 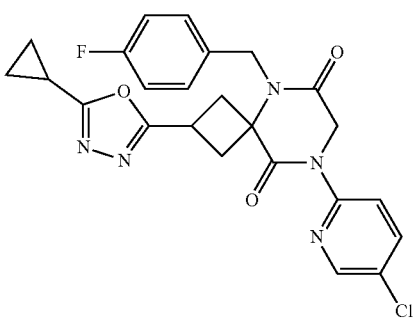 [SMILES: O=C1CN(c2ccc(Cl)cn2)C(=O)C2(CC(c3nnc(C4CC4)o3)C2)N1Cc1ccc(F)cc1] | 8-(5-chloropyridin-2-yl)-2-(5-cyclopropyl-1,3,4-oxadiazol-2-yl)-5-(4-fluorobenzyl)-5,8-diazaspiro[3.5]nonane-6,9-dione |

TABLE 1-continued

| No. | Structure | Name |
|---|---|---|
| 881 | 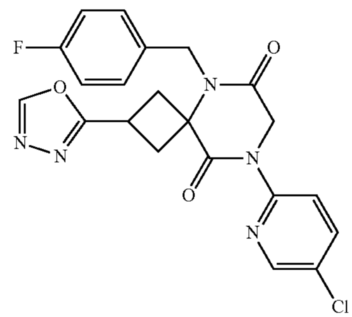 [SMILES: O=C1CN(c2ccc(Cl)cn2)C(=O)C2(CC(c3nnco3)C2)N1Cc1ccc(F)cc1] | 8-(5-chloropyridin-2-yl)-5-(4-fluorobenzyl)-2-(1,3,4-oxadiazol-2-yl)-5,8-diazaspiro[3.5]nonane-6,9-dione |
| 882 | 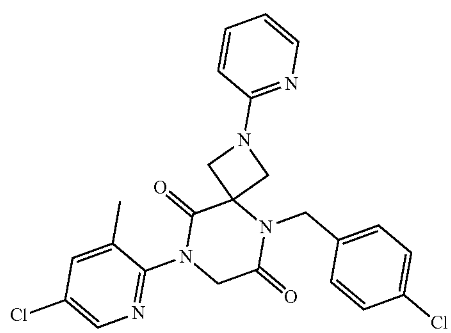 [SMILES: Cc1cc(Cl)cnc1N1CC(=O)N(Cc2ccc(Cl)cc2)C2(CN(c3ccccn3)C2)C1=O] | 8-(5-chloro-3-methyl-pyridin-2-yl)-5-(4-chloro-benzyl)-2-(pyridin-2-yl)-2,5,8-triazaspiro[3.5]-nonane-6,9-dione |
| 883 | 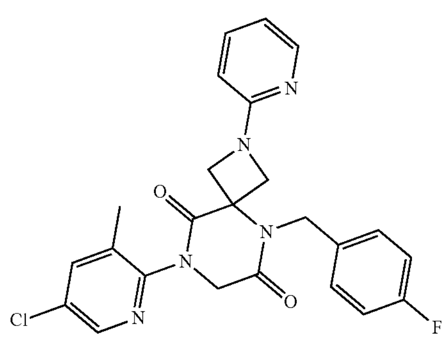 [SMILES: Cc1cc(Cl)cnc1N1CC(=O)N(Cc2ccc(F)cc2)C2(CN(c3ccccn3)C2)C1=O] | 8-(5-chloro-3-methyl-pyridin-2-yl)-5-(4-fluoro-benzyl)-2-(pyridin-2-yl)-2,5,8-triazaspiro[3.5]-nonane-6,9-dione |
| 884 | 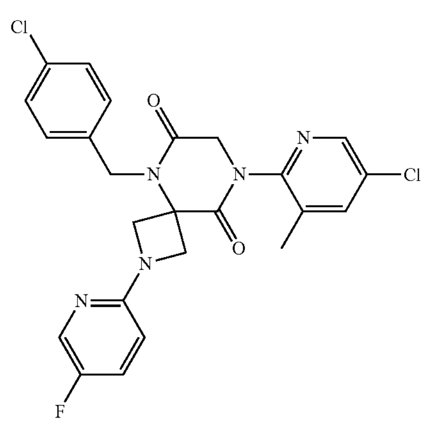 [SMILES: Cc1cc(Cl)cnc1N1CC(=O)N(Cc2ccc(Cl)cc2)C2(CN(c3ccc(F)cn3)C2)C1=O] | 8-(5-chloro-3-methyl-pyridin-2-yl)-5-(4-chloro-benzyl)-2-(5-fluoropyridin-2-yl)-2,5,8-triazaspiro[3.5]-nonane-6,9-dione |

TABLE 1-continued

| No. | Structure | Name |
|---|---|---|
| 885 | 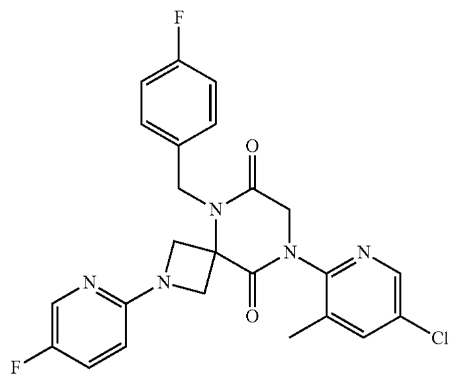 [SMILES: Cc1cc(Cl)cnc1N1CC(=O)N(Cc2ccc(F)cc2)C2(CN(c3ccc(F)cn3)C2)C1=O] | 8-(5-chloro-3-methyl-pyridin-2-yl)-5-(4-fluoro-benzyl)-2-(5-fluoropyridin-2-yl)-2,5,8-triazaspiro-[3.5]nonane-6,9-dione |
| 886 | 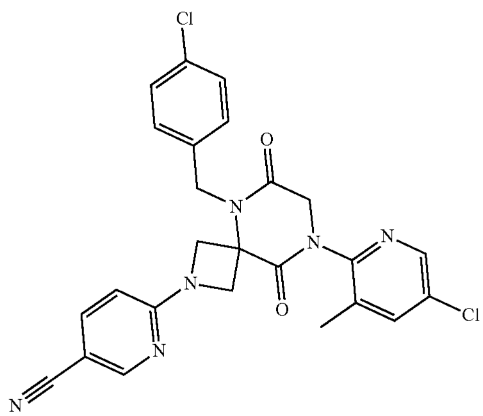 [SMILES: Cc1cc(Cl)cnc1N1CC(=O)N(Cc2ccc(Cl)cc2)C2(CN(c3ccc(C#N)cn3)C2)C1=O] | 6-(8-(5-chloro-3-methyl-pyridin-2-yl)-5-(4-chloro-benzyl)-6,9-dioxo-2,5,8-triazaspiro[3.5]nonan-2-yl)nicotinonitrile |
| 887 | 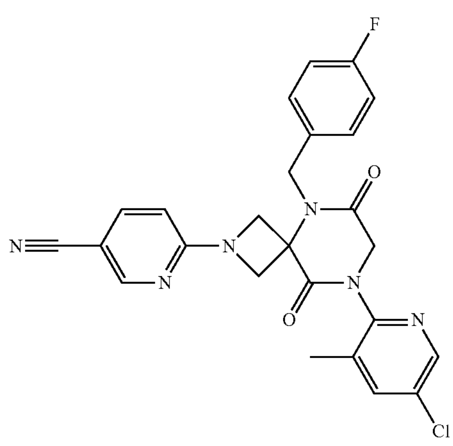 [SMILES: Cc1cc(Cl)cnc1N1CC(=O)N(Cc2ccc(F)cc2)C2(CN(c3ccc(C#N)cn3)C2)C1=O] | 6-(8-(5-chloro-3-methyl-pyridin-2-yl)-5-(4-fluoro-benzyl)-6,9-dioxo-2,5,8-triazaspiro[3.5]nonan-2-yl)nicotinonitrile |
| 888 | 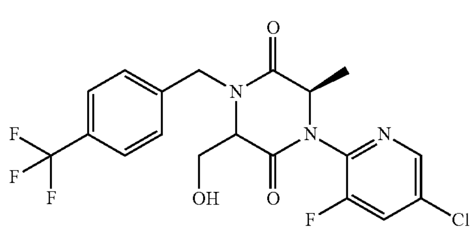 [SMILES: C[C@@H]1C(=O)N(Cc2ccc(C(F)(F)F)cc2)C(CO)C(=O)N1c1ncc(Cl)cc1F] | (6R)-1-(5-chloro-3-fluoro-pyridin-2-yl)-3-(hydroxy-methyl)-6-methyl-4-(4-(trifluoromethyl)benzyl)-piperazine-2,5-dione |

TABLE 1-continued

| No. | Structure | Name |
|---|---|---|
| 889 | 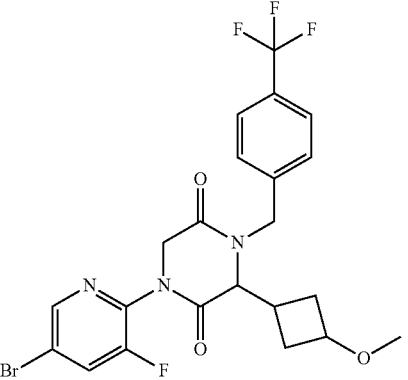 [SMILES: COC1CC(C2C(=O)N(c3ncc(Br)cc3F)CC(=O)N2Cc2ccc(C(F)(F)F)cc2)C1] | 1-(5-bromo-3-fluoro-pyridin-2-yl)-3-(3-methoxy-cyclobutyl)-4-(4-(trifluoro-methyl)benzyl)piperazine-2,5-dione |
| 890 | 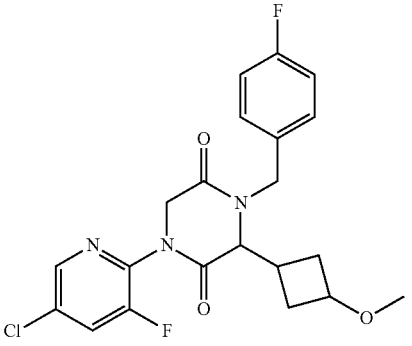 [SMILES: COC1CC(C2C(=O)N(c3ncc(Cl)cc3F)CC(=O)N2Cc2ccc(F)cc2)C1] | 1-(5-chloro-3-fluoropyridin-2-yl)-4-(4-fluorobenzyl)-3-(3-methoxycyclobutyl)-piperazine-2,5-dione |
| 891 | 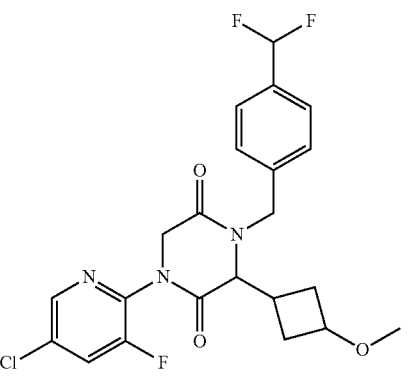 [SMILES: COC1CC(C2C(=O)N(c3ncc(Cl)cc3F)CC(=O)N2Cc2ccc(C(F)F)cc2)C1] | 1-(5-chloro-3-fluoropyridin-2-yl)-4-(4-(difluoromethyl)-benzyl)-3-(3-methoxycyclo-butyl)piperazine-2,5-dione |
| 892 | 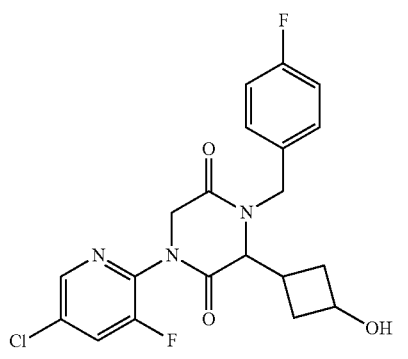 [SMILES: O=C1C(C2CC(O)C2)N(Cc2ccc(F)cc2)C(=O)CN1c1ncc(Cl)cc1F] | 1-(5-chloro-3-fluoropyridin-2-yl)-4-(4-fluorobenzyl)-3-(3-hydroxycyclobutyl)-piperazine-2,5-dione |

TABLE 1-continued

| No. | Structure | Name |
|---|---|---|
| 893 | 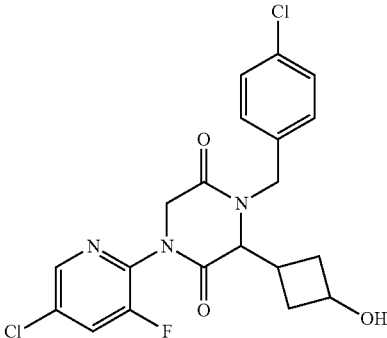 | 1-(5-chloro-3-fluoropyridin-2-yl)-4-(4-chlorobenzyl)-3-(3-hydroxycyclobutyl)-piperazine-2,5-dione |
| 894 | 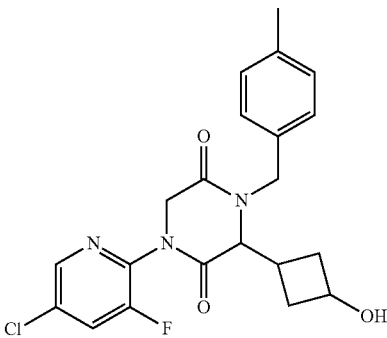 [SMILES: Cc1ccc(CN2C(=O)CN(c3ncc(Cl)cc3F)C(=O)C2C2CC(O)C2)cc1] | 1-(5-chloro-3-fluoropyridin-2-yl)-3-(3-hydroxycyclobutyl)-4-(4-methylbenzyl)-piperazine-2,5-dione |

In some variations, any of the compounds described herein, such as a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (Ia), (Ib), (Ic), (Id), (Ie), (If), (Ig), (Ih), (Ii), (Ij), (Ik-1), (Ik-2), (Il), (Im), (In-1), or (In-2), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $G^1$, $R^1$, $R^{2A}$, $R^{2B}$, $R^3$, $R^4$, and $R^5$ provided herein $R^{2A}$, $R^{2B}$, $R^3$, $R^4$, and can be combined with every other variation or embodiment of $G^1$, $R^1$, $R^5$, as if each combination had been individually and specifically described.

Any variation or embodiment of $G^1$, $R^1$, $R^{2A}$, $R^{2B}$, $R^3$, $R^4$, $R^5$, $R^{1a}$, $R^{2a}$, $R^{2b}$, $R^{3a}$, m, n, p, q, X, and Q provided herein can be combined with every other variation or embodiment of $G^1$, $R^1$, $R^{2A}$, $R^{2B}$, $R^3$, $R^4$, $R^5$, $R^{1a}$, $R^{2a}$, $R^{2b}$, $R^{1a}$ m, n, p, q, X, and Q, as if each combination had been individually and specifically described.

As used herein, when any variable occurs more than one time in a chemical formula, its definition on each occurrence is independent of its definition at every other occurrence.

Formula (I) includes all subformulae thereof. For example, Formula (I) includes compounds of Formula (Ia), (Ib), (Ic), (Id), (Ie), (If), (Ig), (Ih), (Ii), (Ij), (Ik-1), (Ik-2), (Il), (Im), (In-1), and (In-2).

Certain compound names provided herein, including in Table 1, are provided by ChemBioDraw Professional 15.0.0.106. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

The compounds and pharmaceutical compositions herein may be used to treat or prevent a disease or condition in an individual or subject.

When used in a prophylactic manner, the compounds disclosed and/or described herein may prevent a disease or disorder from developing or lessen the extent of a disease or disorder that may develop in an individual or subject at risk of developing the disease or disorder.

Without being bound by theory, the compounds and pharmaceutical compositions disclosed herein are believed to act by inhibiting myosin. This inhibition potentially decreases the number of independent myosin heads interacting with actin filaments reducing the amount of contraction. Reducing contraction of cardiac muscle can be important for the treatment of heart diseases in which overcontraction is an issue. In some embodiments, provided are methods of treating or preventing heart disease in an individual or subject, comprising administering to the individual or subject in need thereof a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. In some embodiments, provided are methods of treating or preventing heart disease in a subject in need thereof comprising administering to the subject a therapeutically effective amount of at least one chemical entity as described herein. In some embodiments, provided are methods of treating heart disease in a subject in need thereof comprising administering to the subject a therapeutically effective amount of at least one chemical entity as described herein. In some embodiments, provided are methods of treating an established or diagnosed heart disease in a subject in need thereof comprising administering to the subject a therapeutically effective amount of at least one chemical entity as described herein. In some embodiments, provided are methods of preventing heart disease in a subject in need thereof comprising administering to the subject a therapeutically effective amount of at least one chemical entity as described herein.

Also provided herein is the use of a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for treatment of a heart disease in a subject. In some aspects, provided is a compound or composition as described herein for use in a method of treatment of the human or animal body by therapy. In some embodiments, provided herein are compounds of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof, for use in a method of treatment of the human or animal body by therapy. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating or preventing heart disease. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating heart disease. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating an established or diagnosed heart disease. In other embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in preventing heart disease. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating a disease or condition associated with HCM. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating a disease or condition associated with secondary left ventricular wall thickening. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in ameliorating a symptom associated with heart disease. In other embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in reducing the risk of a symptom associated with heart disease. In other embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis. In certain embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating a disease or condition associated with small left ventricular cavity and cavity obliteration, hyperdynamic left ventricular contraction, myocardial ischemia, or cardiac fibrosis. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating muscular dystrophies. In some embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in treating a glycogen storage disease. In other embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in modulating the cardiac sarcomere, such as inhibiting the cardiac sarcomere. In yet other embodiments, provided herein are compounds of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, for use in potentiating cardiac myosin.

In some embodiments, the subject is a mammal. In some embodiments, the subject is a mouse, rat, dog, cat, pig, sheep, horse, cow, or human. In some embodiments, the subject is a human. In some embodiments, the subject has an established or diagnosed heart disease. In some embodiments, the subject has established or diagnosed hypertrophic cardiomyopathy (HCM). In some embodiments, the subject is at risk for developing heart disease. In some embodiments, the subject has a mutation that increases risk for heart disease. In some embodiments, the subject has a mutation that increases risk for hypertrophic cardiomyopathy (HCM). In some embodiments, the mutation is a sarcomeric mutation. In some embodiments, the mutation is a mutation in myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, muscle LIM protein (MLP), or protein kinase AMP-activated non-catalytic subunit gamma 2 (PRKAG2). In some embodiments, the mutation is a mutation in MHC-β. In some embodiments, the subject has established or diagnosed hypertrophic cardiomyopathy without a confirmed genetic etiology.

In some embodiments, the subject has a high risk of progressive symptoms. In some embodiments, the subject has a high risk of atrial fibrillation, ventricular tachyarrhythmias, stroke, and/or sudden death. In some embodiments, the subject has a reduced exercise capacity. In some embodiments, the reduced exercise capacity is as compared to an age-matched control population. In some embodiments, the subject is eligible for surgical intervention or percutaneous ablation to treat the heart disease.

In some embodiments, the heart disease is hypertrophic cardiomyopathy (HCM). In some embodiments, the heart disease is obstructive HCM. In some embodiments, the heart disease is nonobstructive HCM. In some embodiments, the HCM is associated with a sarcomeric mutation. In some embodiments, the HCM is associated with a non-sarcomeric mutation. In some embodiments, the heart disease is obstructive or nonobstructive HCM caused by sarcomeric and/or non-sarcomeric mutations. In some embodiments, the sarcomeric mutation is a mutation in a myosin heavy chain β (MHC-β), cardiac muscle troponin T (cTnT), tropomyosin alpha-1 chain (TPM1), myosin-binding protein C cardiactype (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, or muscle LIM protein (MLP). In some embodiments, the sarcomeric mutation is a mutation in MHC-β. In some embodiments, the non-sarcomeric mutation is a mutation in protein kinase AMP-activated noncatalytic subunit gamma 2 (PRKAG2).

In some embodiments, provided herein are methods of treating a disease or condition associated with HCM, comprising administering to the individual or subject in need thereof a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. In some embodiments, the disease or condition is Fabry's Disease, Danon Disease, mitochondrial cardiomyopathies, or Noonan Syndrome.

Also provided herein is the use of a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for treatment of a disease or condition associated with HCM.

In some embodiments, the heart disease is heart failure with preserved ejection fraction (HFpEF). In some embodiments, the heart disease is diastolic dysfunction. In some embodiments, the heart disease is cardiomyopathy. In some embodiments, the heart disease is primary or secondary restrictive cardiomyopathy. In some embodiments, the heart disease is condition or symptoms caused by coronary artery disease. In some embodiments, the heart disease is myocardial infarction or angina pectoris. In some embodiments, the heart disease is left ventricular outflow tract obstruction. In some embodiments, the heart disease is hypertensive heart disease. In some embodiments, the heart disease is congenital heart disease. In some embodiments, the heart disease is cardiac ischemia and/or coronary heart disease. In some embodiments, the heart disease is diabetic heart disease. In other embodiments, the heart disease is congestive heart failure. In some embodiments, the heart disease is right heart failure. In other embodiments, the heart disease is cardiorenal syndrome. In some embodiments, the heart disease is infiltrative cardiomyopathy. In some embodiments, the heart disease is a condition that is or is related to cardiac senescence or diastolic dysfunction due to aging. In some embodiments, the heart disease is a condition that is or is related to left ventricular hypertrophy and/or concentric left ventricular remodeling.

In some embodiments, the provided are methods of treating a disease or condition associated with secondary left ventricular wall thickening in an individual or subject, comprising administering to the individual or subject in need thereof a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. In some embodiments, the disease is hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, or Pompe disease.

Also provided herein is the use of a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for treatment of a disease or condition associated with secondary left ventricular wall thickening.

In some embodiments, provided are methods of ameliorating a symptom associated with heart disease in a subject, comprising administering to the individual or subject in need thereof a compound of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, wherein the symptom is one or more selected from poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of reducing the risk of a symptom associated with heart disease in a subject, comprising administering to the individual or subject in need thereof a compound of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof, wherein the symptom is one or more selected from sudden cardiac death, poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis in an individual or subject, comprising administering to the individual or subject in need thereof a compound of Formula (I), (Ia), (Ib), (Ic), (Id), (Ie), (If), (Ig), (Ih), (Ii), (Ij), (Ik-1), or (Ik-2), or a compound of Table 1, or a pharmaceutically acceptable salt thereof.

In some embodiments, provided are methods of treating a disease or condition associated with small left ventricular cavity and cavity obliteration, hyperdynamic left ventricular contraction, myocardial ischemia, or cardiac fibrosis in an individual or subject, comprising administering to the individual or subject in need thereof a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof.

Also provided herein is the use of a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for treatment of a disease or condition associated with small left ventricular cavity and cavity obliteration, hyperdynamic left ventricular contraction, myocardial ischemia, or cardiac fibrosis.

In some embodiments, the provided are methods of treating muscular dystrophies in an individual or subject (e.g., Duchenne muscular dystrophy), comprising administering to the individual or subject in need thereof a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. Also provided herein is the use of a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for treatment of muscular dystrophies (e.g., Duchenne muscular dystrophy).

In some embodiments, the provided are methods of treating a glycogen storage disease in an individual or subject, comprising administering to the individual or subject in need thereof a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. Also provided herein is the use of a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for treatment of a glycogen storage disease.

Also provided are methods for modulating the cardiac sarcomere in an individual or subject which method comprises administering to an individual or subject in need thereof a therapeutically effective amount of at least one chemical entity as described herein. In some embodiments, provided are methods of inhibiting the cardiac sarcomere, comprising contacting the cardiac sarcomere with at least one chemical entity as described herein, such as a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. Additionally provided herein is the use of at least one chemical entity as described herein, such as a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for inhibiting the cardiac sarcomere of an individual or subject.

Also provided are methods for potentiating cardiac myosin in an individual or subject which method comprises administering to an individual or subject in need thereof a therapeutically effective amount of at least one chemical entity as described herein such as a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof. Additionally provided herein is the use of at least one chemical entity as described herein, such as a compound of Formula (I), (Ia), (Ib), (Ic), (Id), (Ie), (If), (Ig), (Ih), (Ii), (Ij), (Ik-1), (Ik-2), (Il), (Im), (In-1), or (In-2), or a compound of Table 1, or a pharmaceutically acceptable salt thereof in the manufacture of a medicament for potentiating cardiac myosin in an individual or subject.

In some embodiments, the methods provided herein further comprise monitoring the effectiveness of the treatment. Examples of indicators include, but are not limited to improvement in one or more of the following: New York Heart Association (NYHA) Functional Classification, exercise capacity, cardiac elasticity, diastolic left ventricular relaxation, left atrial pressure, paroxysmal or permanent atrial fibrillation, left atrial and pulmonary capillary wedge pressures, left ventricular diastolic pressures, syncope, ventricular relaxation during diastole, ventricular fibrosis, left ventricular hypertrophy, left ventricular mass, left ventricular wall thickness, left ventricular mid-cavity obstruction systolic anterior motion of mitral valve, left ventricular outflow tract obstruction, chest pain, exertional dyspnea, pre-syncope, abnormal exercise capacity, and fatigue. These indicators can be monitored by techniques known in the art including self-reporting; ECG, including ambulatory ECG; echocardiography; cardiac MRI; CT; biopsy; cardiopulmonary exercise testing (CPET); and actigraphy.

In some embodiments, the compound reduces the contractility of a cardiomyocyte. In some embodiments, the compound reduces the contractility of a cardiomyocyte by greater than 40%, such as greater than 45%, 50%, 60%, 70%, 80%, or 90%. In some embodiments, the compound reduced the contractility of a cardiomyocyte 40%-90%, such as 40%-80%, 40-70%, 50%-90%, 50%-80% or 50%-70%. In some embodiments, the compound does not significantly alter calcium transients in the cardiomyocyte. In some embodiments, the compound decreases the ATPase activity in a cardiomyocyte. Methods of measuring contractility, ATPase activity, and calcium transients are known in the art, for example, by calcium labeling, electrophysiological recordings, and microscopic imaging. In some embodiments, the compound does not significantly inhibit or induce a cytochrome P450 (CYP) protein.

Without being bound by theory, it is believed that the stereoisomer of a compound of Formula (I) or any variation thereof in which the carbon bearing the $R^{2A}$ and $R^{2B}$ moieties is in the "S" stereochemical configuration is more active as measured by a myofibril assay (such as the assay described in Example B-1) than the corresponding stereoisomer in which the carbon bearing the $R^{2A}$ and $R^{2B}$ moieties is in the "R" stereochemical configuration. A crystal structure was obtained for a representative compound of Formula (I), demonstrating that, as between the "S" isomer and the "R" isomer, the more active stereoisomer, as measured by the myofibril assay described in Example B-1, is the stereoisomer in which the carbon bearing the $R^{2A}$ and $R^{2B}$ moieties is in the "S" stereochemical configuration.

In some embodiments, the subject has a left ventricular wall that is thicker than normal prior to treatment. In some embodiments, the subject has a left ventricular wall thickness that is greater than 15 mm, such as greater than 18 mm, 20 mm, 22 mm, 25 mm, or 30 mm prior to treatment. In some embodiments, the left ventricular wall thickness is reduced by greater than 5%, such as greater than 8%, 10%, 12%, 15%, 20%, or 30% following treatment. Left ventricular wall thickness can be measured by methods known in the art, such as by echocardiography, CT scan, or a cardiac MRI.

In some embodiments, the subject has abnormal cardiac fibrosis prior to treatment. In some embodiments, the abnormal cardiac fibrosis is reduced by greater than 5%, such as greater than 8%, 10%, 12%, 15%, 20%, or 30% following treatment. Cardiac fibrosis can be measured by methods known in the art, such as by biopsy or a cardiac MRI.

In some embodiments, the subject has reduced exercise capacity prior to treatment. In some embodiments, the exercise capacity of the subject is increased by greater than 5%, such as greater than 8%, 10%, 12%, 15%, 20% or 30% following treatment. In some embodiments, the exercise capacity is measured by cardiopulmonary exercise testing (CPET). CPET measures changes in oxygen consumption ($VO_2$ max). Methods of measuring CPET and $VO_2$ max are well known in the art (Malhotra et al., JACC: Heart Failure, 2016, 4(8): 607-616; Guazzi et al., J Amer College Cardiol, 2017, 70 (13): 1618-1636; Rowin et al., JACC: Cariovasc Imaging, 2017, 10(11):1374-1386). In some embodiments, $VO_2$ max is improved by more than 1 mL/kg/m², such as more than 1.2 mL/kg/m², 1.4 mL/kg/m², 1.5 mL/kg/m², 1.7 mL/kg/m², 2 mL/kg/m², 2.2 mL/kg/m², 2.5 mL/kg/m², 3 mL/kg/m², 3.2 mL/kg/m², or 3.5 mL/kg/m² following treatment.

In some embodiments, the subject has a New York Heart Association (NYHA) Functional Classification of II, III, or IV prior to treatment. In some embodiments, the subject has a New York Heart Association (NYHA) Functional Classification of III or IV prior to treatment. In some embodiments, the subject has a New York Heart Association (NYHA) Functional Classification of IV prior to treatment. In some embodiments, the subject remains in the same NYHA functional class or has a reduced NYHA functional class following treatment.

In some embodiments, $VO_2$ max is improved by more than 1 mL/kg/m², such as more than 1.2 mL/kg/m², 1.4 mL/kg/m², 1.5 mL/kg/m², 1.7 mL/kg/m², or 2 mL/kg/m² and the subject has a reduced NYHA functional class following treatment. In some embodiments, $VO_2$ max is improved by more than 2.5 mL/kg/m², 3 mL/kg/m², 3.2 mL/kg/m², or 3.5 mL/kg/m² and the subject remains in the same NYHA functional class or has a reduced NYHA functional class following treatment.

In some embodiments, daily function and/or activity level of the subject is improved following treatment. Improved daily function and/or activity level may be measured, for example, by journaling or actigraphy, such as a FitBit or FitBit-like monitors.

In some embodiments, the subject has one or more of decreased shortness of breath, decreased chest pain, decreased arrhythmia burden, such as atrial fibrillation and ventricular arrhythmias, decreased incidence of heart failure, and decreased ventricular outflow obstruction following treatment.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pa.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

The compounds and compositions described and/or disclosed herein may be combined with one or more other therapies to treat a heart disease, such as HCM or HFpEF. In some embodiments, the one or more therapies include therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors). In some embodiments, the one or more therapies include therapies that improve cardiac function by stimulating cardiac contractility (e.g., positive inotropic agents, such as the β-adrenergic agonist dobutamine or the phosphodiesterase inhibitor milrinone). In other embodiments, the one or more therapies include therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The compounds and compositions described and/or disclosed herein may be combined with one or more other therapies to treat HCM or HFpEF. In some embodiments, the compounds and/compositions may be combined with a β-blocker, verapamil, and/or disopyramide.

General Synthetic Methods

Compounds of Formula (I), (Ia), (Ib), (Ic), (Id), (Ie), (If), (Ig), (Ih), (Ii), (Ij), (Ik-1), (Ik-2), (Il), (Im), (In-1), and (In-2) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (Ia), (Ib), (Ic), (Id), (Ie), (If), (Ig), (Ih), (Ii), (Ij), (Ik-1), (Ik-2), (Il), (Im), (In-1), and (In-2).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (Ia), (Ib), (Ic), (Id), (Ie), (If), (Ig), (Ih), (Ii), (Ij), (Ik-1), (Ik-2), (Il), (Im), (In-1), and (In-2), or any variation thereof. Other compounds described herein may be prepared by similar methods.

In some embodiments, compounds provided herein may be synthesized according to Scheme 1.

Scheme 1

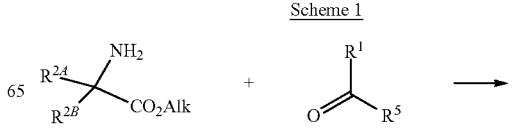

511

-continued

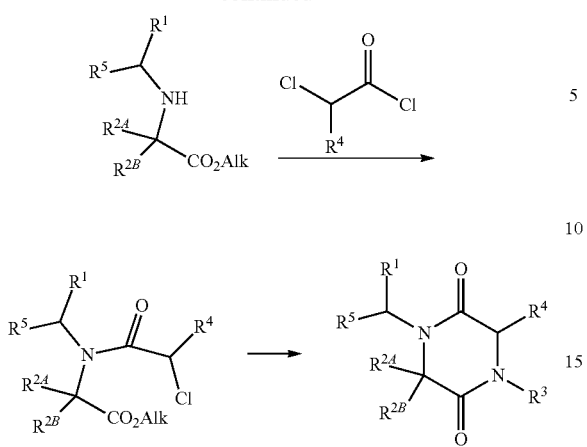

wherein $R^1$, $R^{2A}$, $R^{2B}$, $R^3$, $R^4$, and $R^5$ are as defined for formula (I), or any variation thereof detailed herein.

An exemplary embodiment of the preparative method in Scheme 1 is shown in Scheme 1a.

Scheme 1a

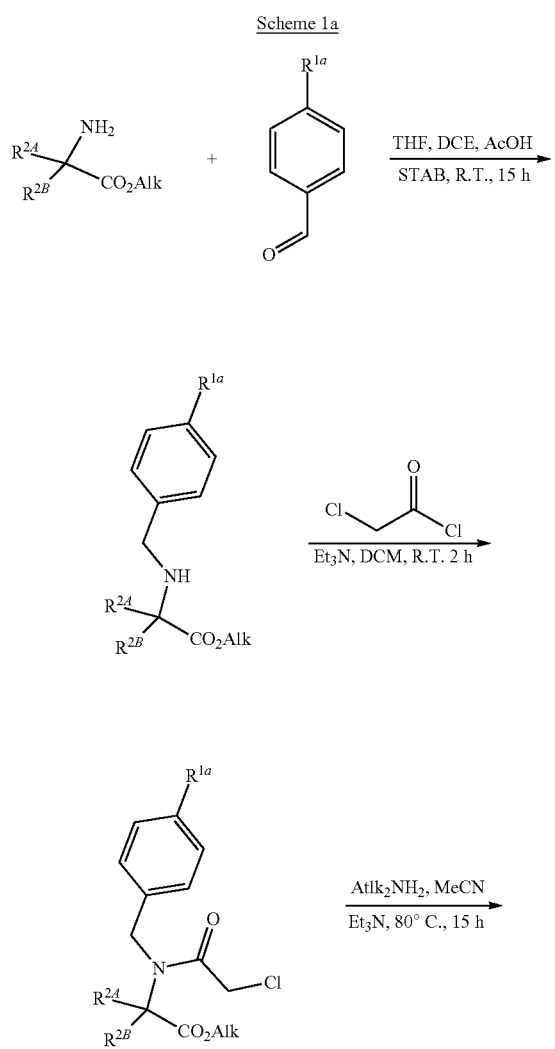

512

-continued

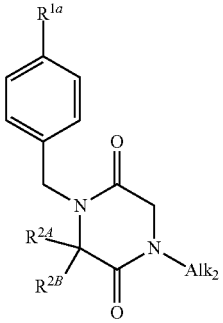

wherein $R^{2A}$ and $R^{2B}$ are as defined for formula (I), or any variation thereof detailed herein; and wherein $R^{1a}$ is as defined for formula (If), or any variation thereof detailed herein.

Another exemplary embodiment of the preparative method in Scheme 1 is shown in Scheme 1b.

Scheme 1b

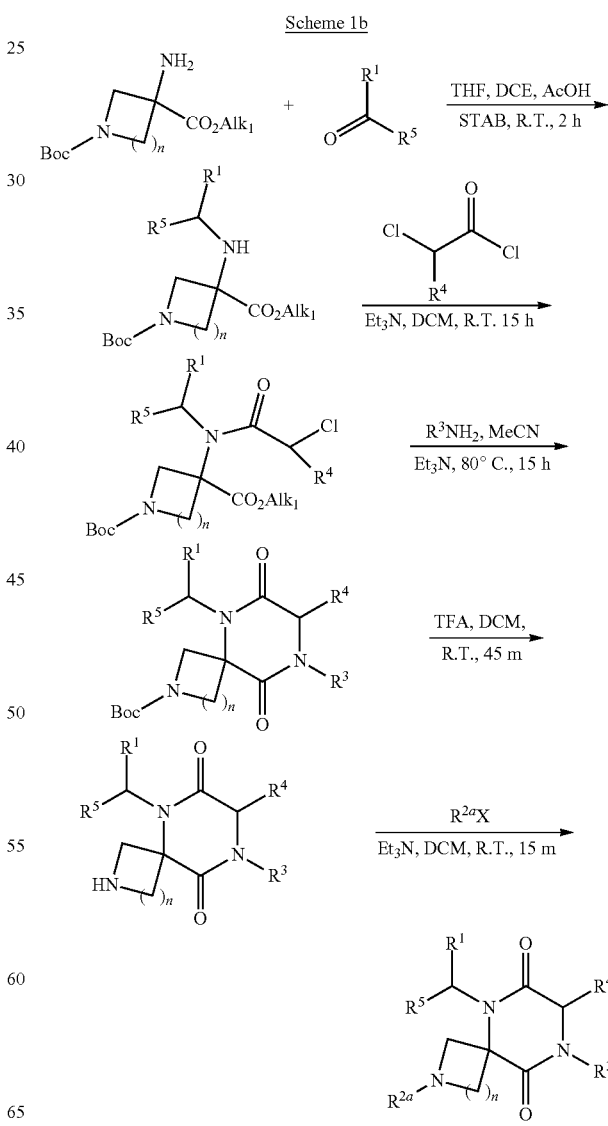

wherein $R^1$, $R^3$, $R^4$, and $R^5$ are as defined for formula (I), or any variation thereof detailed herein, and wherein $R^{2a}$ is as defined for formula (If), or any variation thereof detailed herein.

Another exemplary embodiment of the preparative method in Scheme 1 is shown in Scheme 1c.

Scheme 1c

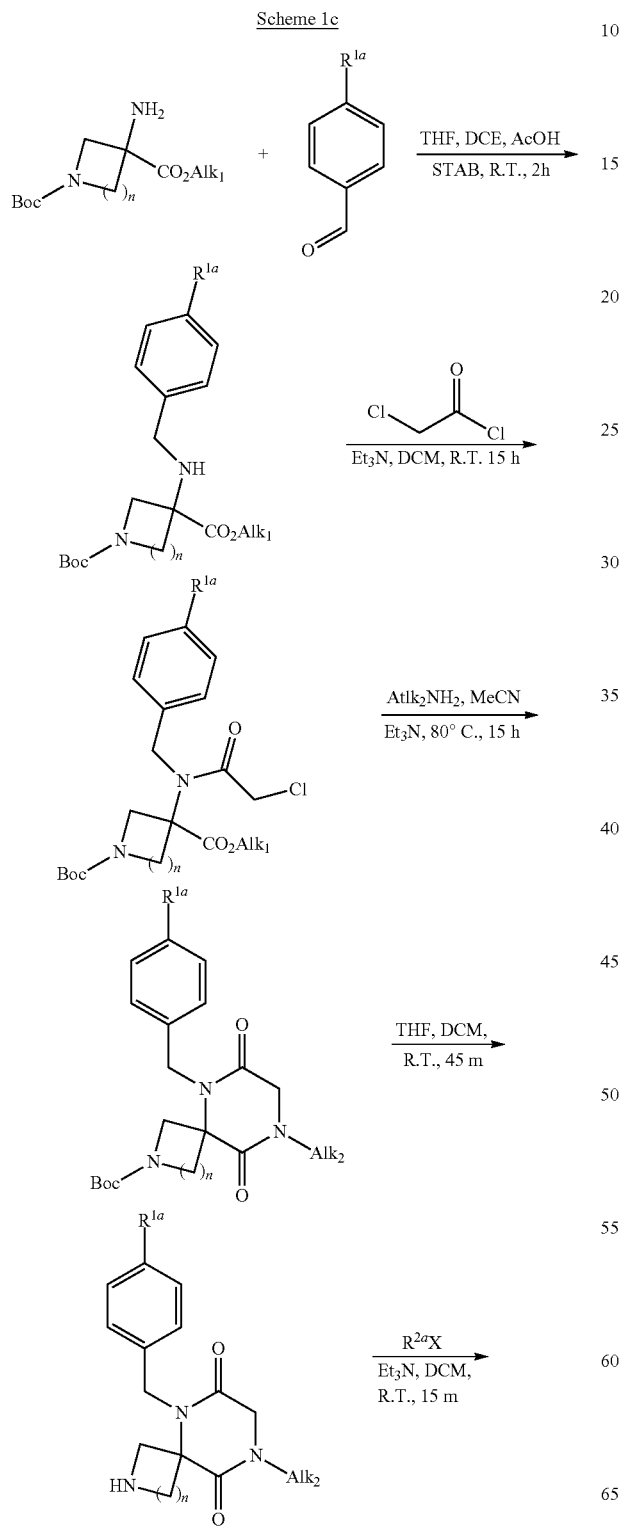

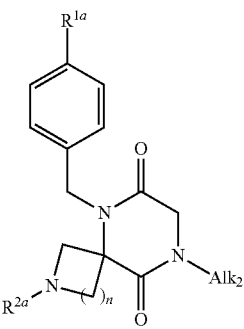

wherein $R^{1a}$ and $R^{2a}$ are as defined for formula (If), or any variation thereof detailed herein.

In some embodiments, compounds provided herein may be synthesized according to Scheme 2.

Scheme 2

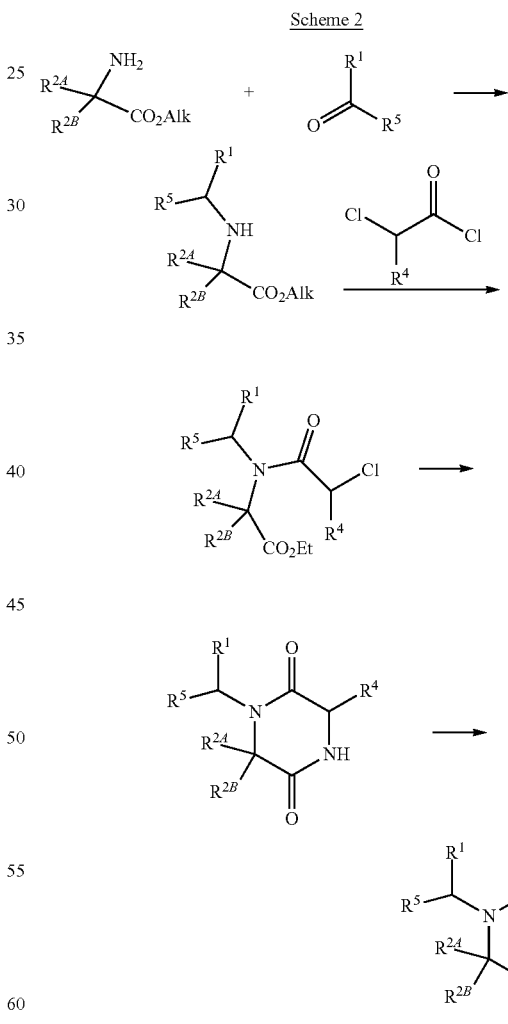

wherein $R^1$, $R^{2A}$, $R^{2B}$, $R^3$, $R^4$, and $R^5$ are as defined for formula (I), or any variation thereof detailed herein.

Another exemplary embodiment of the preparative method in Scheme 2 is shown in Scheme 2a.

Scheme 2a

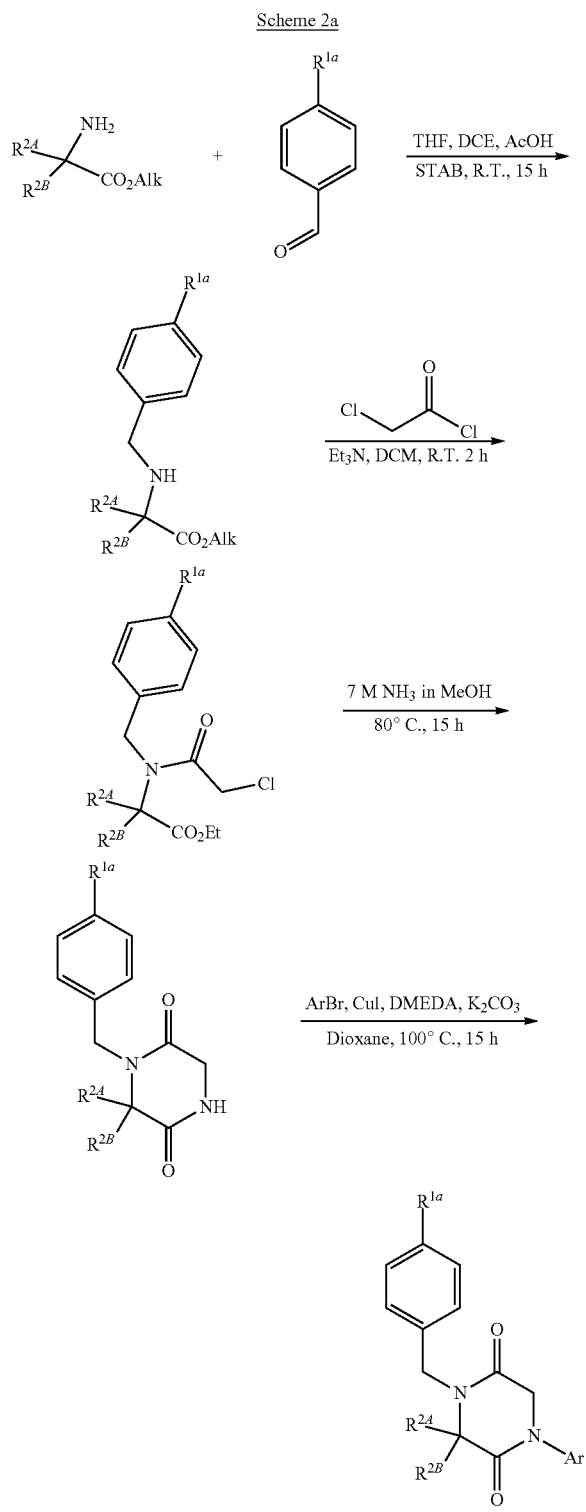

Scheme 2b

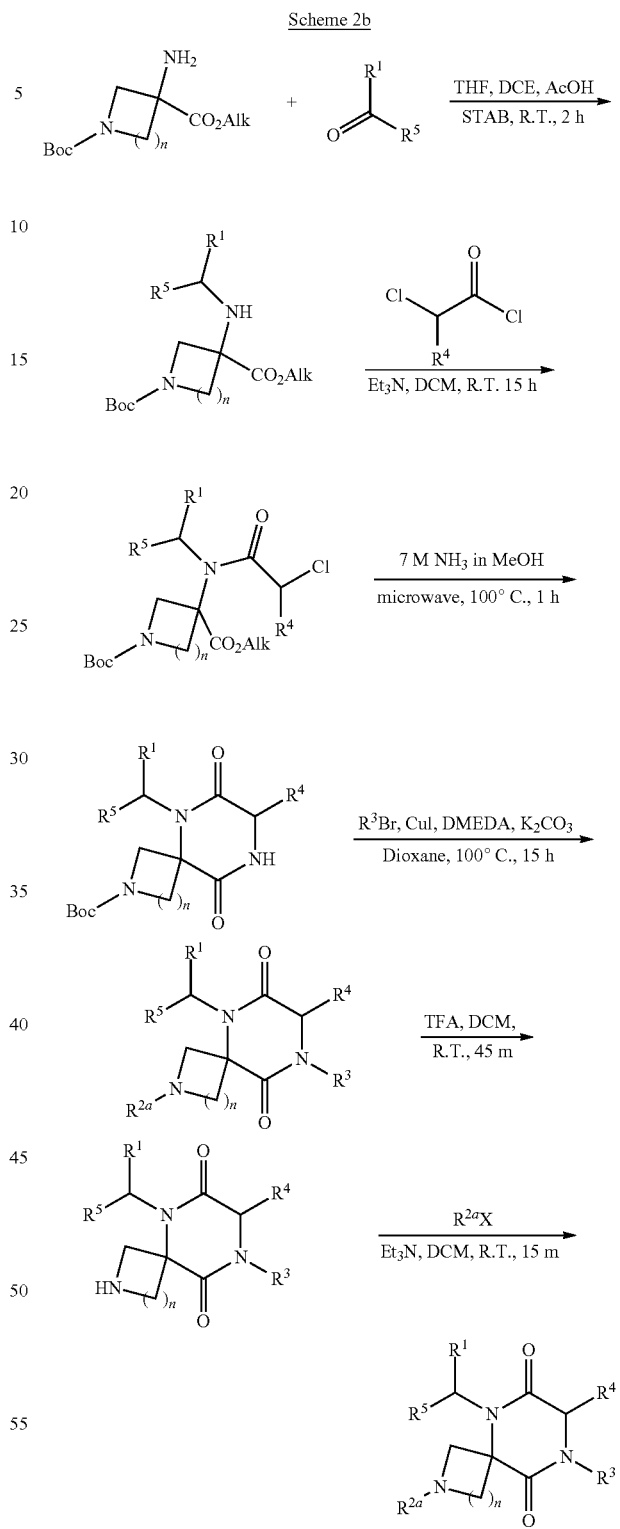

wherein $R^{2A}$ and $R^{2B}$ are as defined for formula (I), or any variation thereof detailed herein; and wherein $R^{1a}$ is as defined for formula (If), or any variation thereof detailed herein.

Another exemplary embodiment of the preparative method in Scheme 2 is shown in Scheme 2b.

wherein $R^1$, $R^3$, $R^4$, and $R^5$ are as defined for formula (I), or any variation thereof detailed herein, wherein $R^{2a}$ is as defined for formula (If), or any variation thereof detailed herein, and wherein X is halogen.

Another exemplary embodiment (e.g., of the preparative method in Scheme 2) is shown in Scheme 2c.

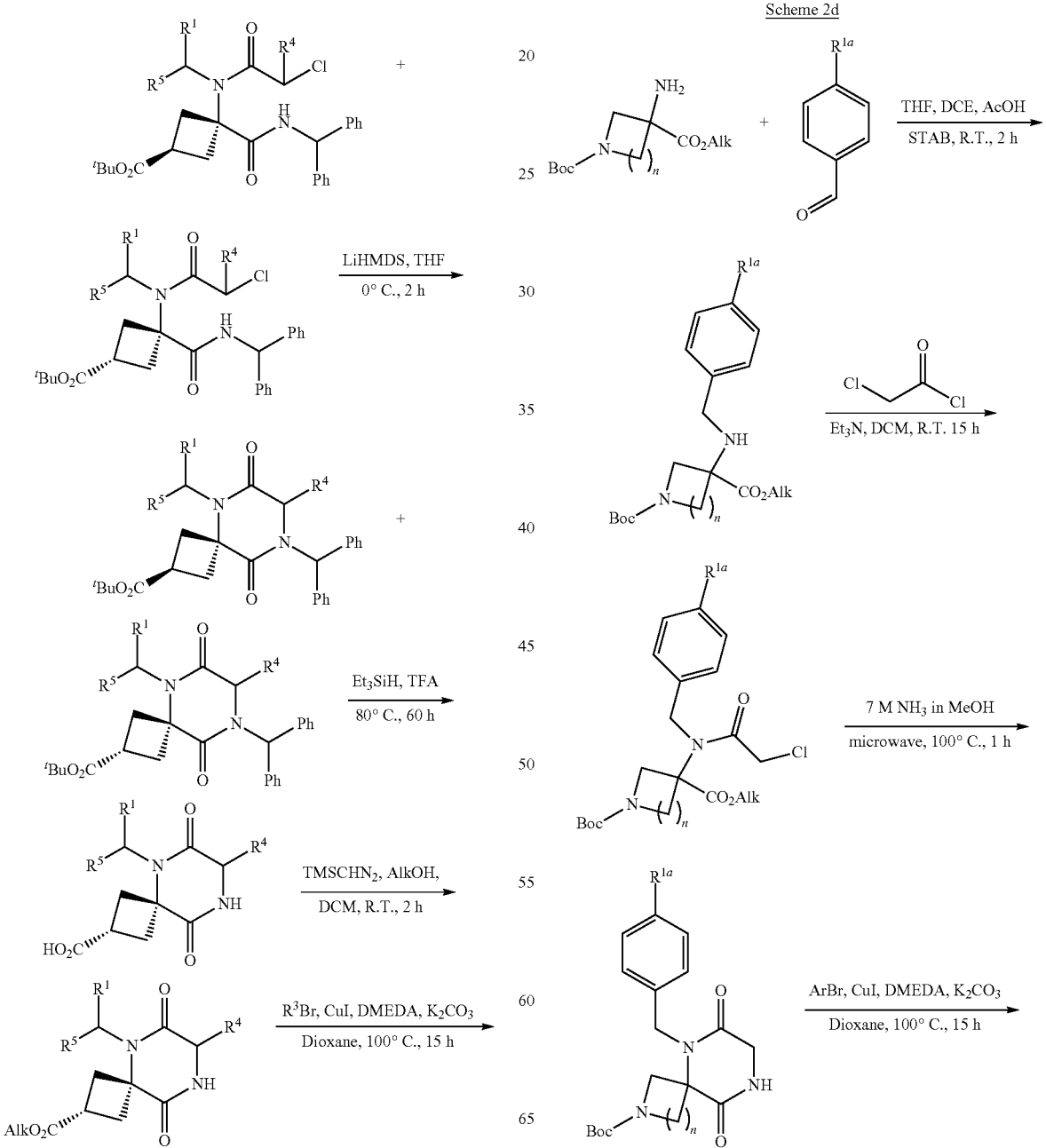
wherein $R^1$, $R^3$, $R^4$, and $R^5$ are as defined for formula (I), or any variation thereof detailed herein.
Another exemplary embodiment of the preparative method in Scheme 2 is shown in Scheme 2d.

519 -continued
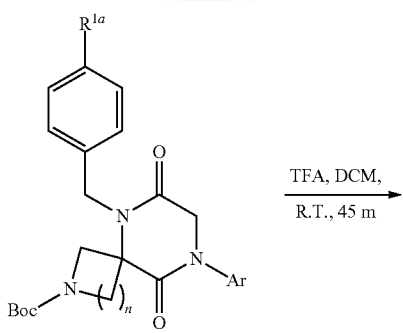
TFA, DCM,
R.T., 45 m
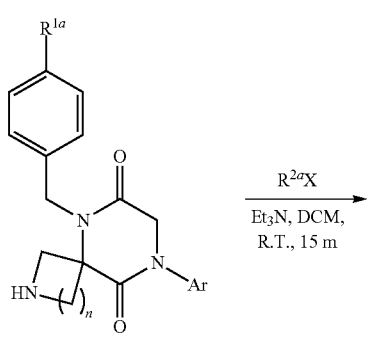
R²ᵃX
―――――→
Et₃N, DCM,
R.T., 15 m
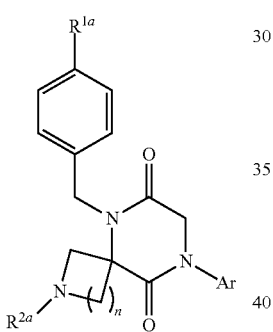
wherein R¹ᵃ and R²ᵃ are as defined for formula (If), or any variation thereof detailed herein.
Another exemplary embodiment (e.g., of the preparative method in Scheme 2) is shown in Scheme 2e.
520 -continued
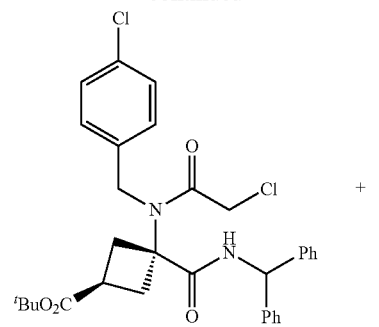
LiHMDS, THF
―――――→
0° C., 2 h
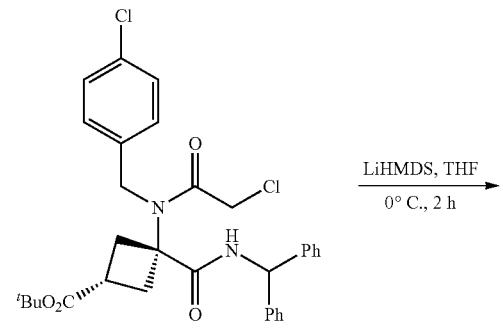
Et₃SiH, TFA
―――――→
80° C., 60 h
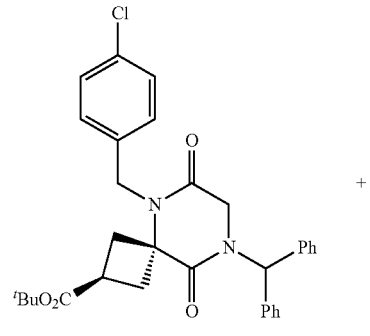
TMSCHN₂, MeOH
―――――→
DCM, R.T., 2 h
Scheme 2e
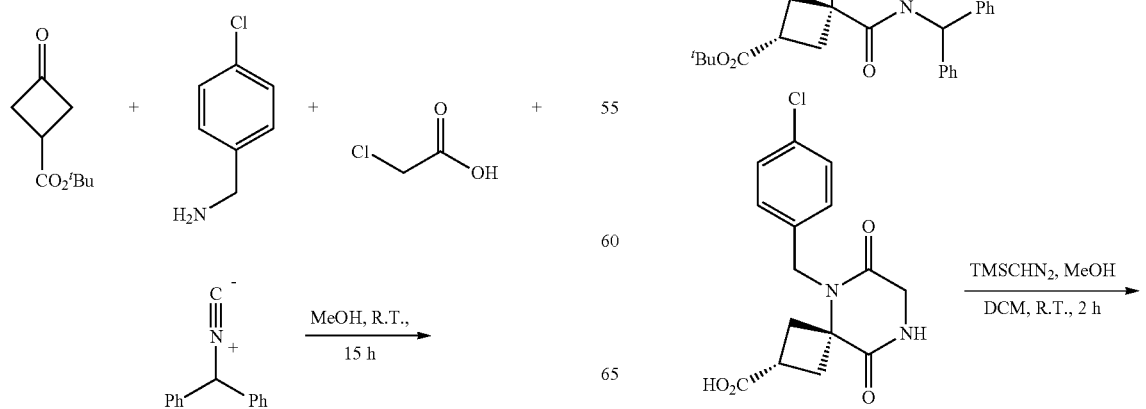
MeOH, R.T.,
15 h

521
-continued
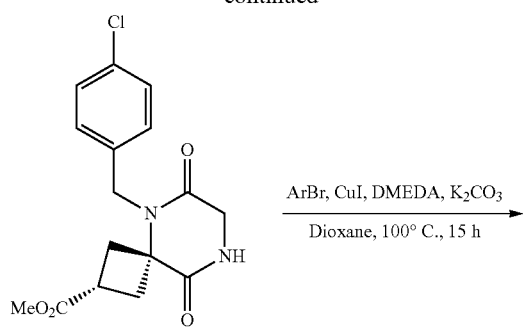
Another exemplary embodiment (e.g., of the preparative method in Scheme 2) is shown in Scheme 2f
Scheme 2f
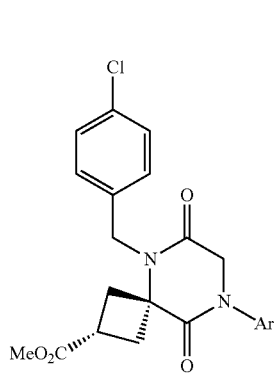
522
-continued
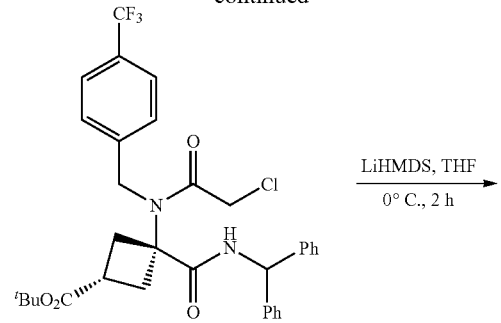
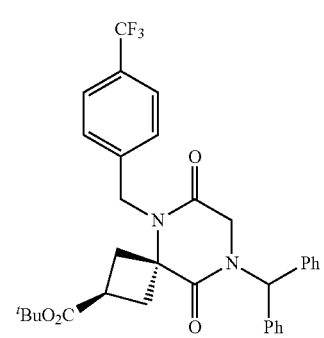
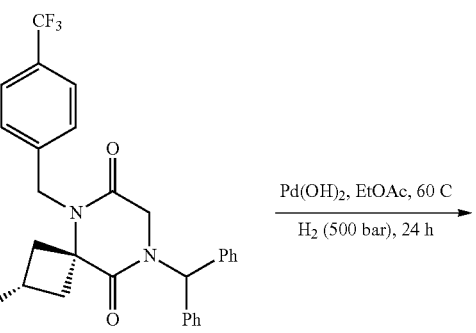
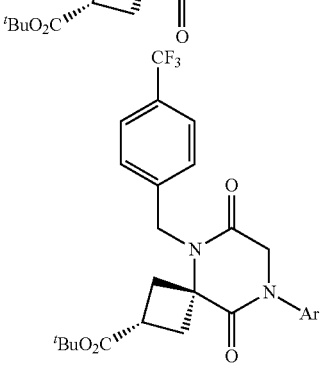

-continued

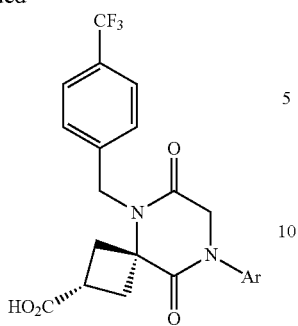

Another exemplary embodiment of the preparative method in Scheme 2 is shown in Scheme 2g.

Scheme 2g

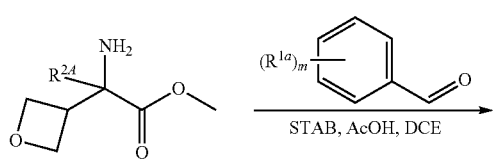

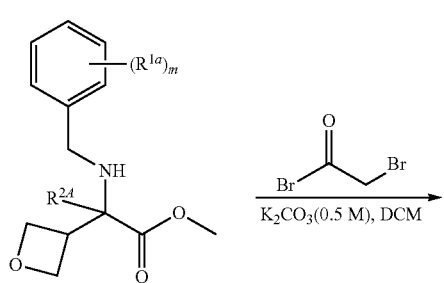

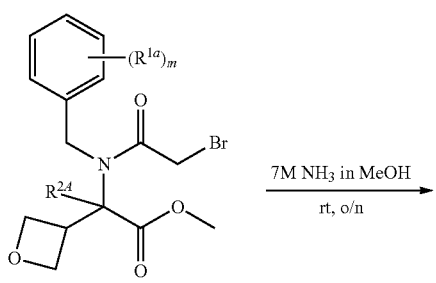

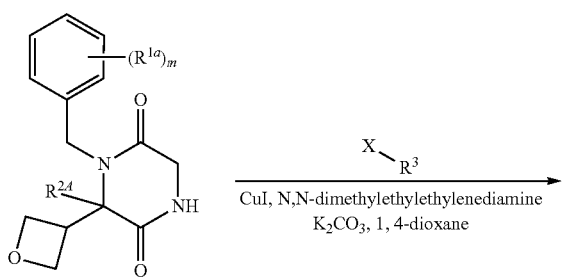

-continued

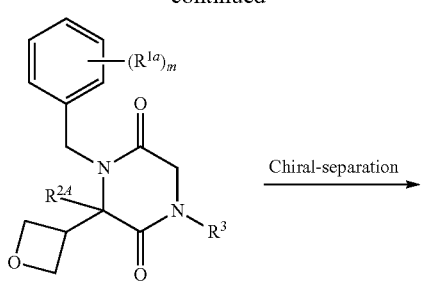

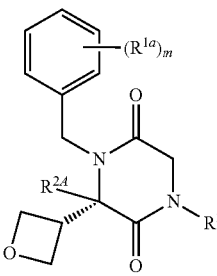

+

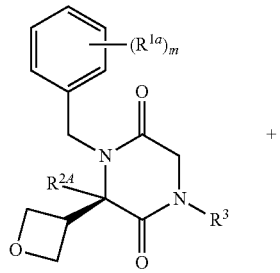

wherein X is halide; wherein $R^{2A}$ and $R^3$ are as defined for formula (I), or any variation thereof detailed herein; and wherein $R^{1a}$ and m are as defined for formula (Ik-1), or any variation thereof detailed herein.

In some embodiments, compounds provided herein may be synthesized according to Scheme 3.

Scheme 3

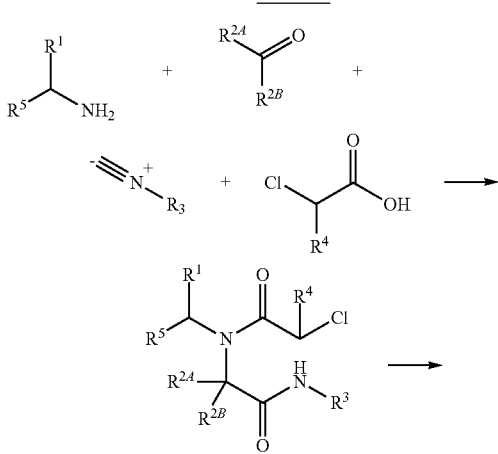

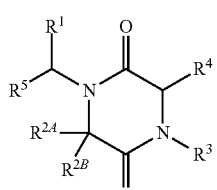
wherein $R^1$, $R^{2A}$, $R^{2B}$, $R^3$, $R^4$, and $R^5$ are as defined for formula (I), or any variation thereof detailed herein.
Another exemplary embodiment of the preparative method in Scheme 3 is shown in Scheme 3a.
Scheme 3a
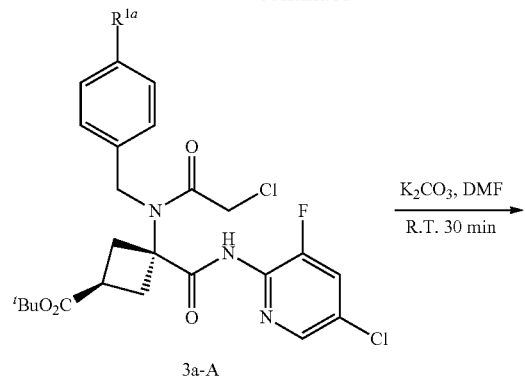
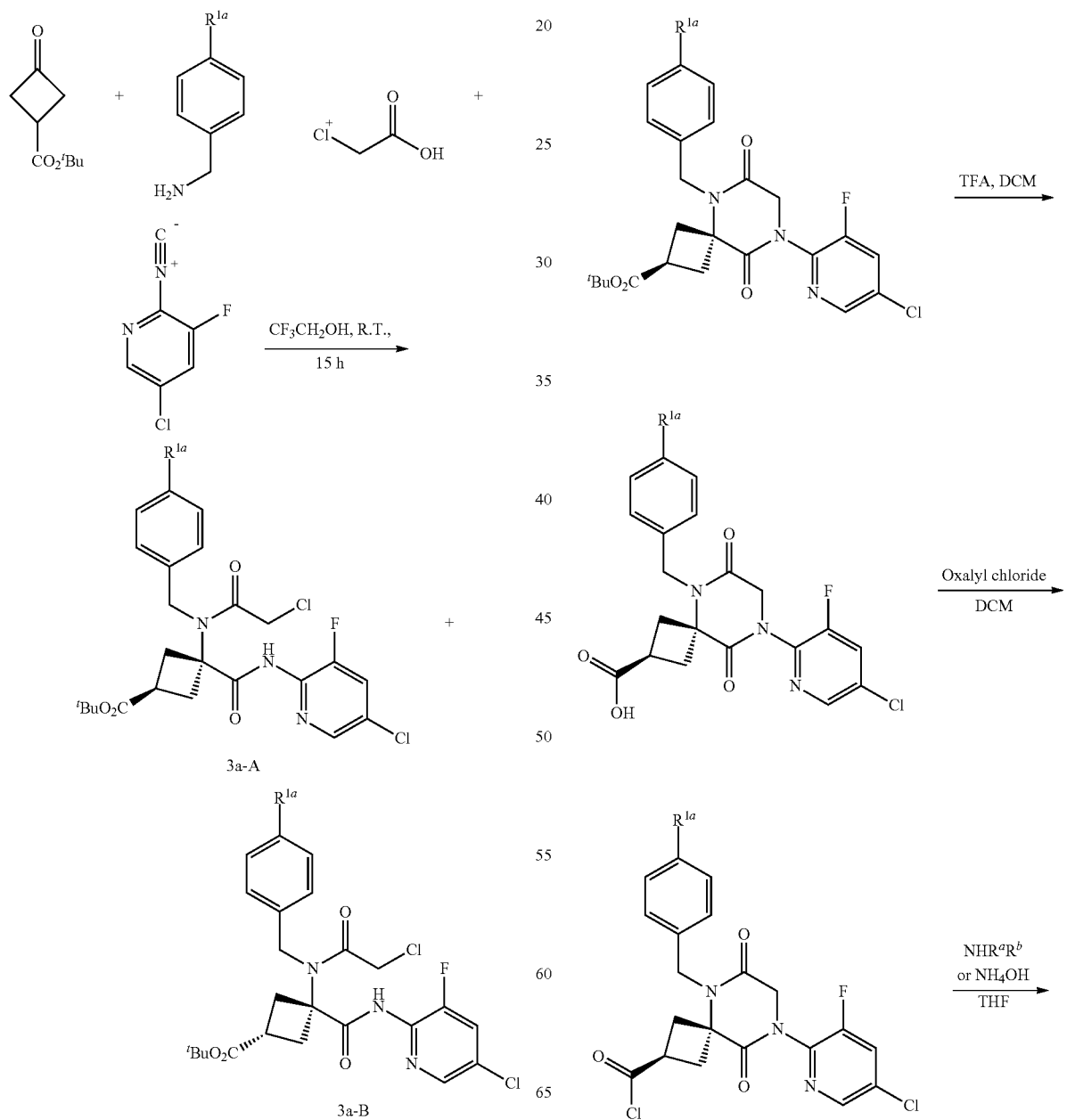

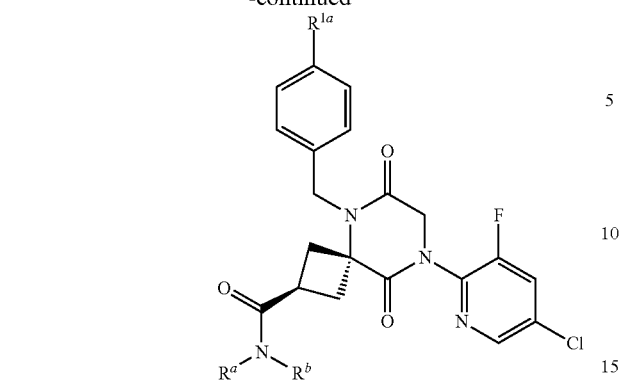
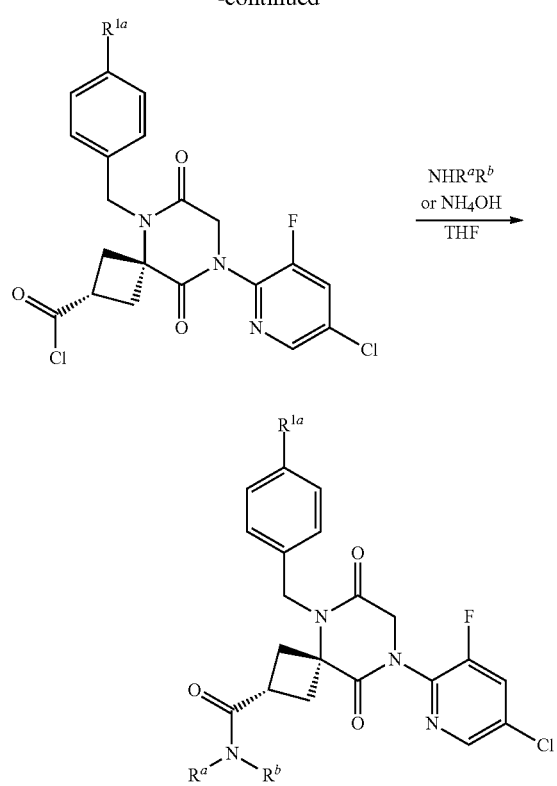
wherein $R^{1a}$ is as defined for formula (If), or any variation thereof detailed herein; and wherein $R^a$ and $R^b$ are independently H or $C_1$-$C_6$ alkyl.
Another exemplary embodiment of the preparative method in Scheme 3 is shown in Scheme 3b-1.
Scheme 3b-1
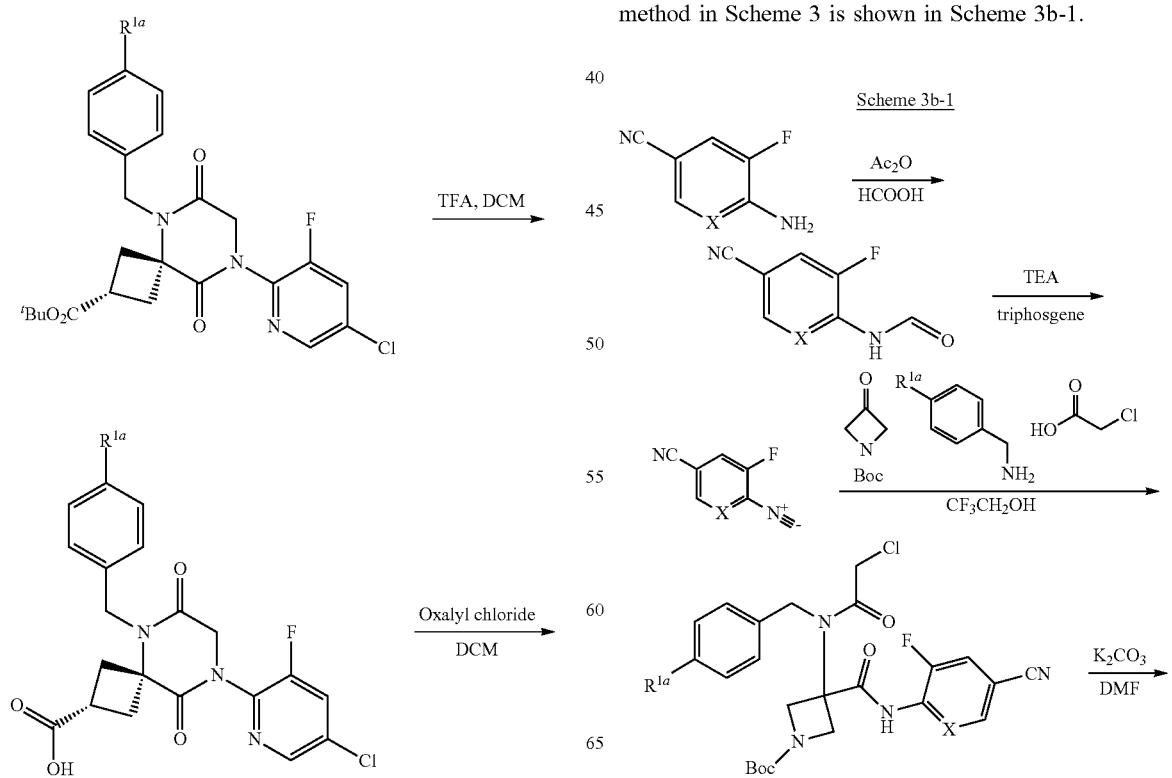

529
-continued

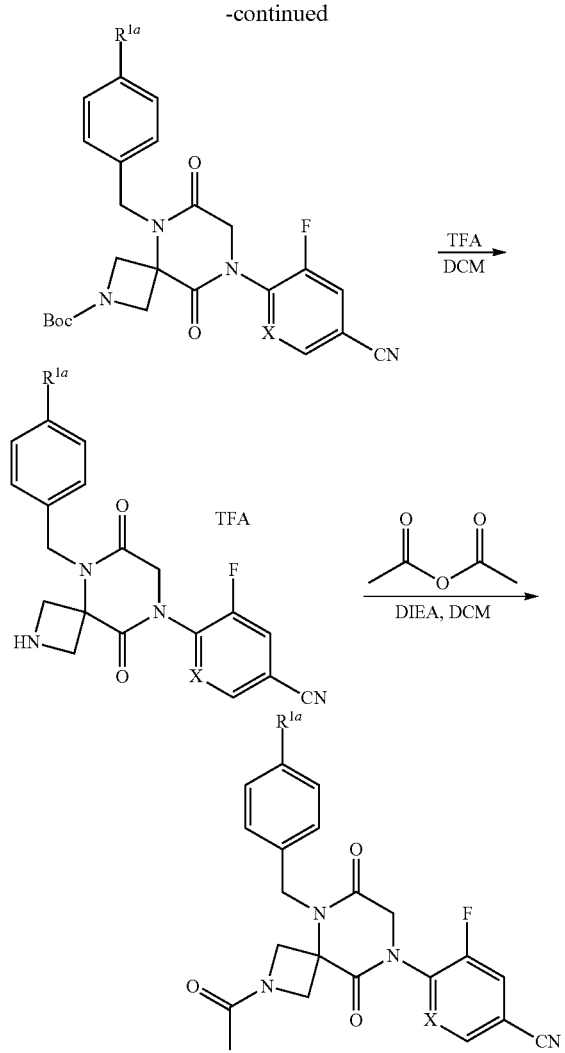

wherein X is CH or N; and wherein $R^{1a}$ is as defined for formula (If), or any variation thereof detailed herein.

Another exemplary embodiment of the preparative method in Scheme 3 is shown in Scheme 3b-2.

Scheme 3b-2

530
-continued

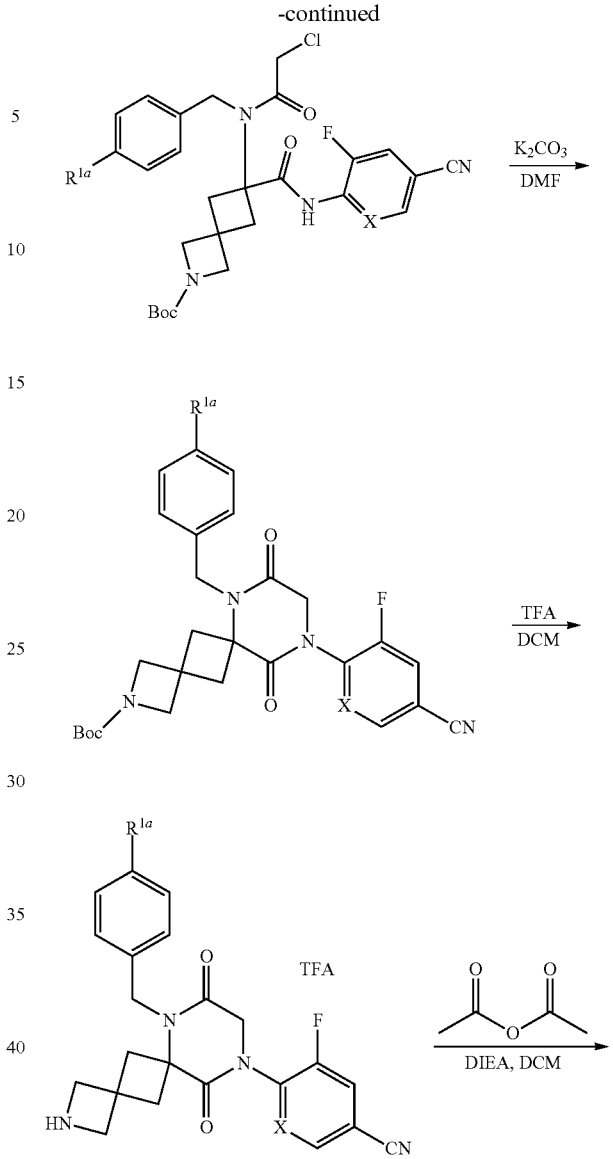

wherein X is CH or N; and wherein $R^{1a}$ is as defined for formula (If), or any variation thereof detailed herein.

Another exemplary embodiment of the preparative method in Scheme 3 is shown in Scheme 3c.

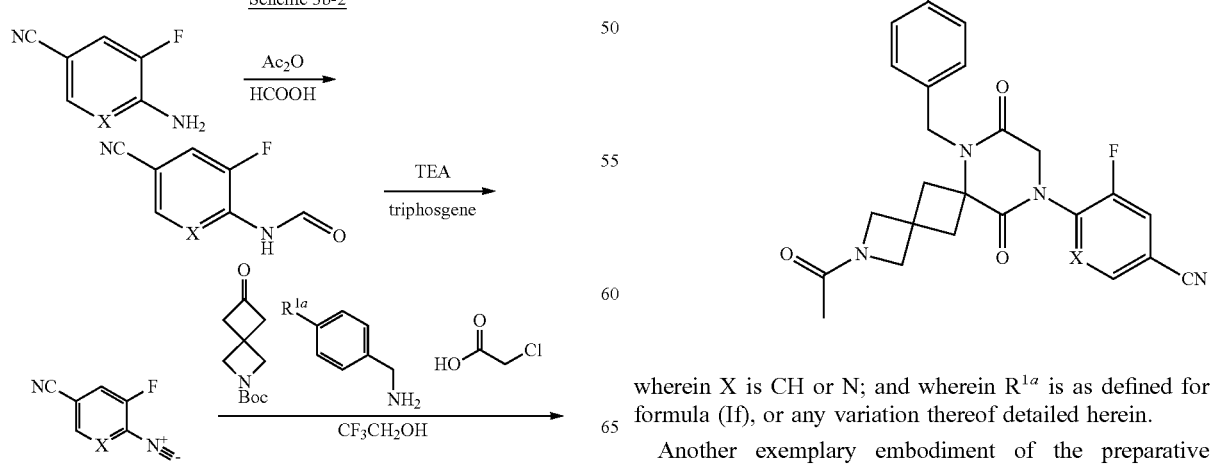

Scheme 3c

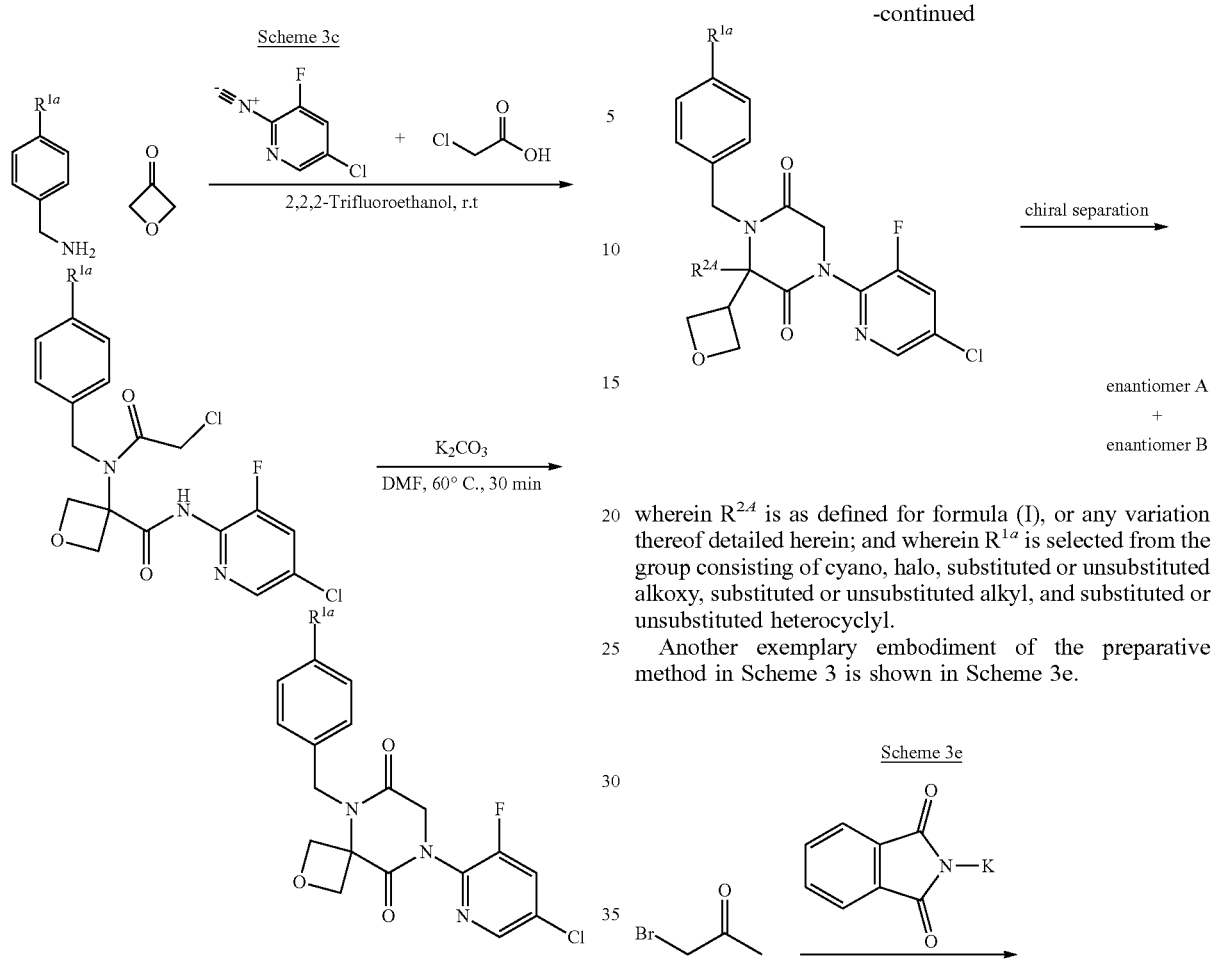

wherein $R^{1a}$ is as defined for formula (If), or any variation thereof detailed herein.

Another exemplary embodiment of the preparative method in Scheme 3 is shown in Scheme 3d.

wherein $R^{2A}$ is as defined for formula (I), or any variation thereof detailed herein; and wherein $R^{1a}$ is selected from the group consisting of cyano, halo, substituted or unsubstituted alkoxy, substituted or unsubstituted alkyl, and substituted or unsubstituted heterocyclyl.

Another exemplary embodiment of the preparative method in Scheme 3 is shown in Scheme 3e.

Scheme 3e

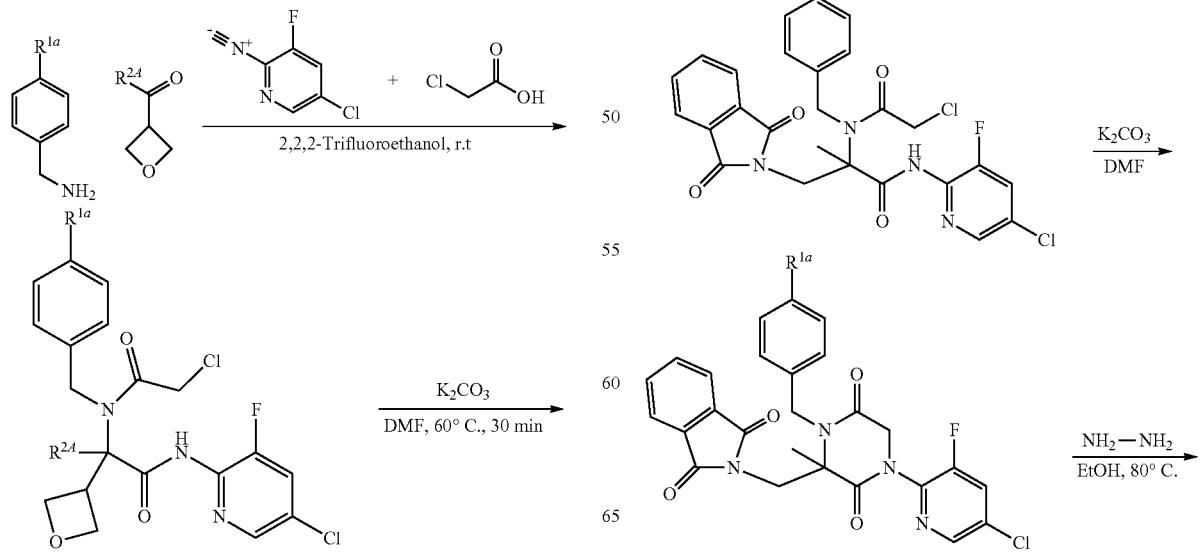

-continued
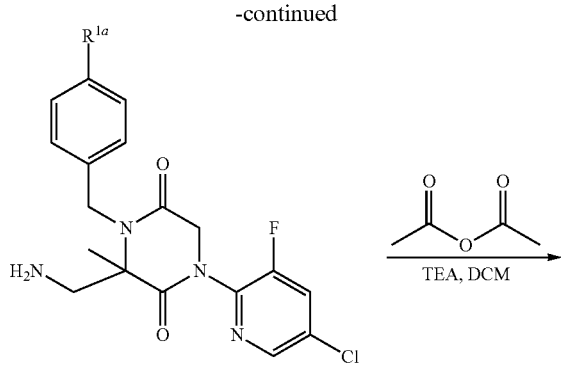
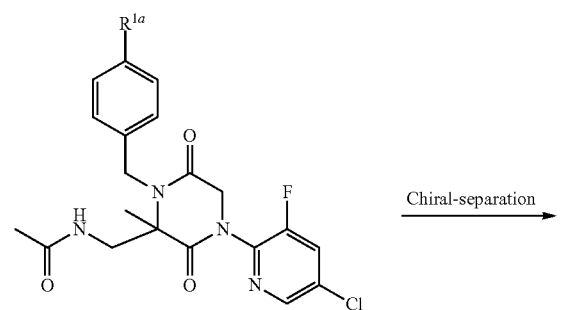
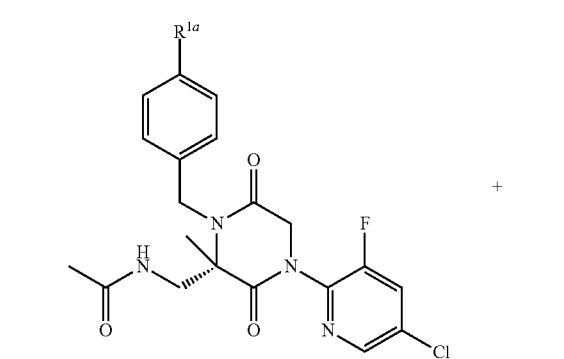
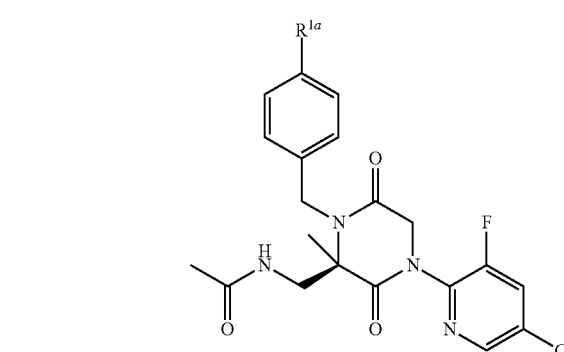
wherein $R^{1a}$ is selected from the group consisting of cyano, halo, substituted or unsubstituted alkoxy, substituted or unsubstituted alkyl, and substituted or unsubstituted heterocyclyl.
Another exemplary embodiment of the preparative method in Scheme 3 is shown in Scheme 3f
Scheme 3f
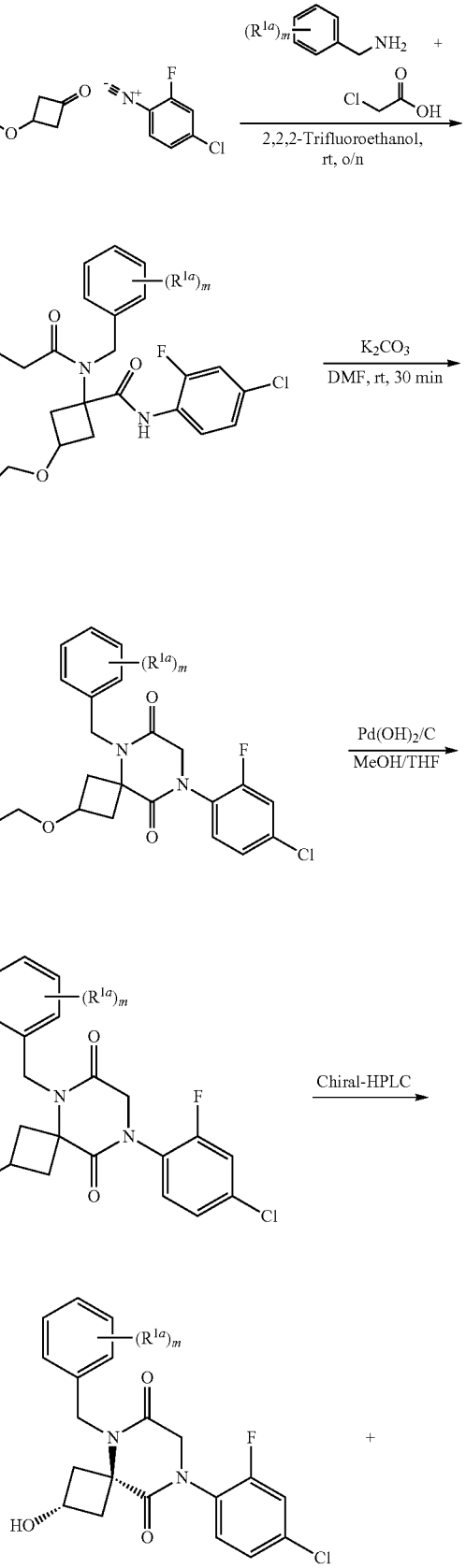

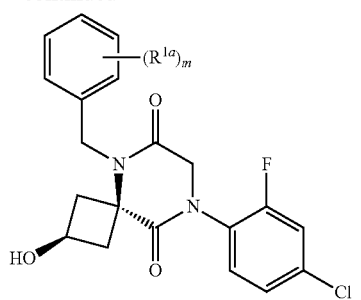
wherein $R^{1a}$ is selected from the group consisting of halo and substituted or unsubstituted alkyl; and wherein m is 0, 1, or 2.
Another exemplary embodiment of the preparative method in Scheme 3 is shown in Scheme 3g.
Scheme 3g
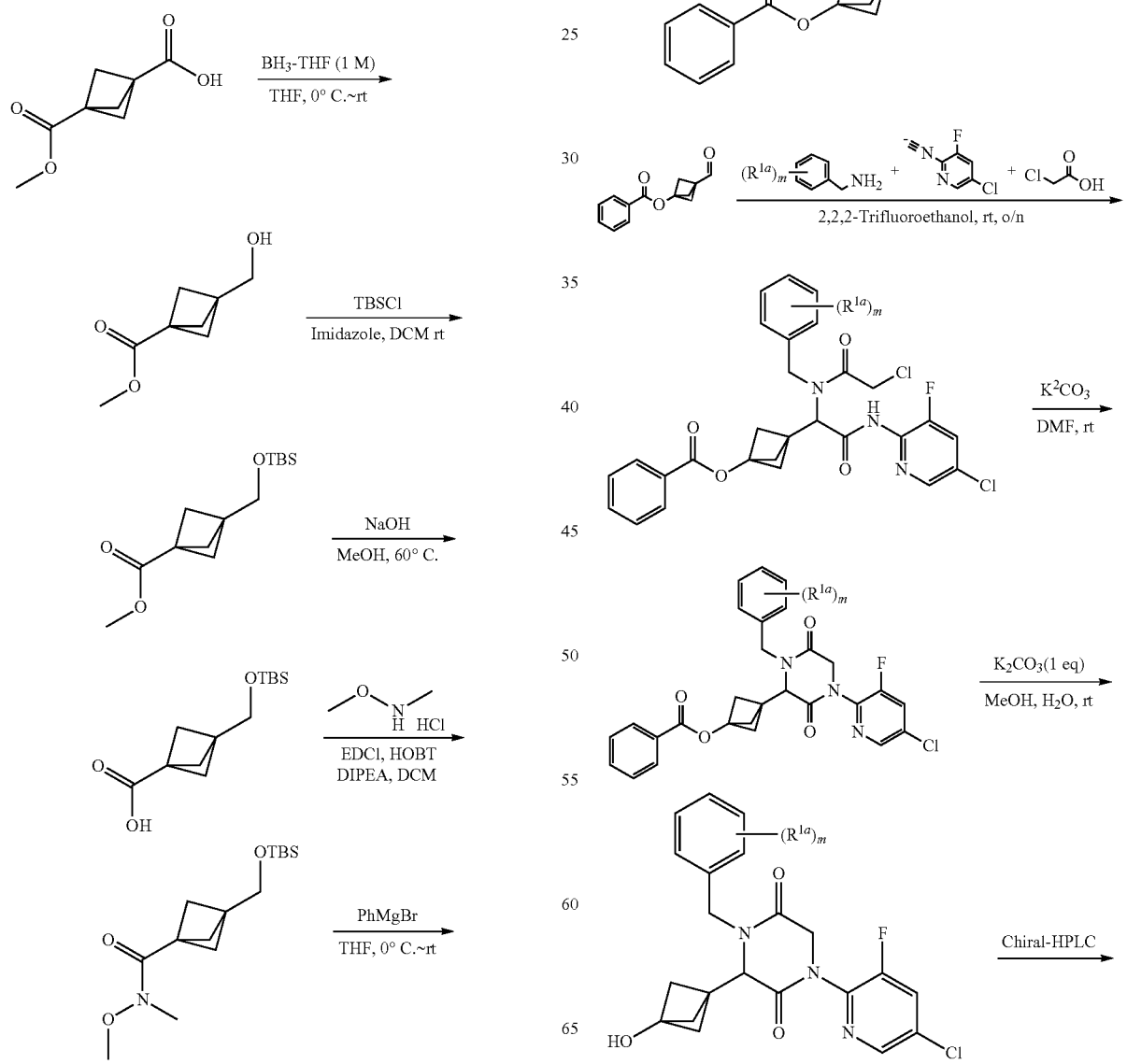
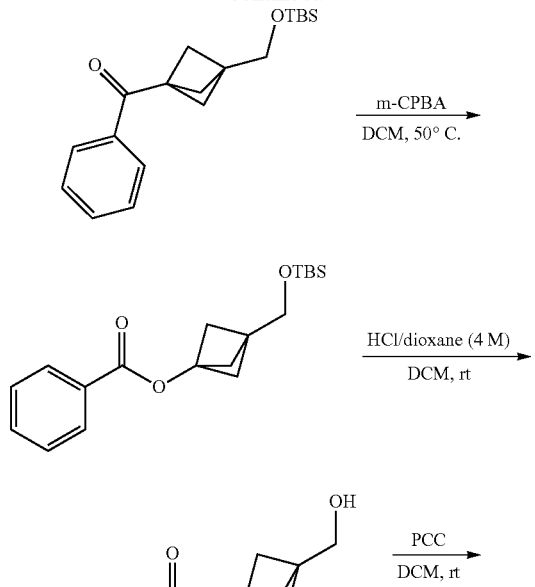

537
-continued

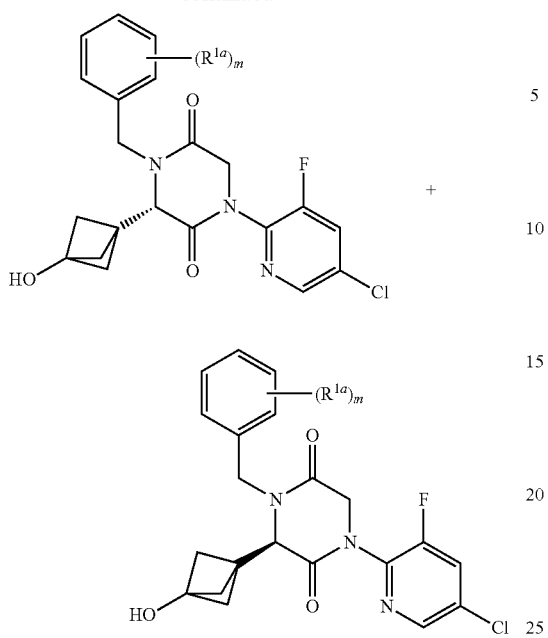

wherein R¹ᵃ and m are as defined for formula (Ik-1), or any variation thereof detailed herein.

Another exemplary preparative method is shown in Scheme 4.

538
-continued

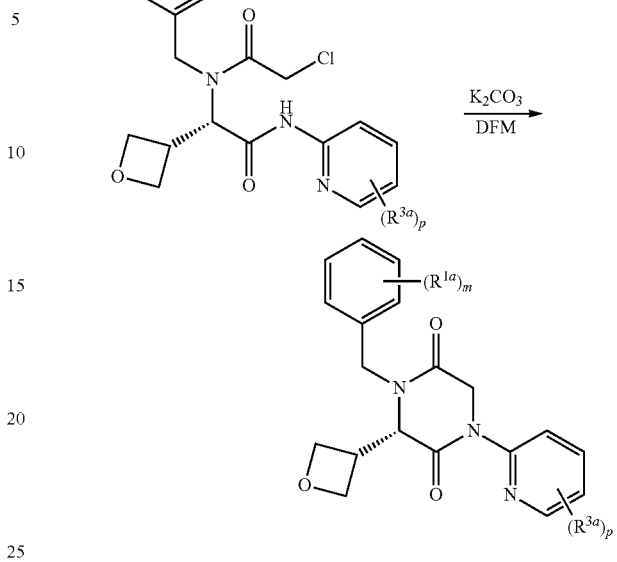

wherein R¹ᵃ, R³ᵃ, m, and p are as defined for formula (Ik-1), or any variation thereof detailed herein.

Particular non-limiting examples are provided in the Example section below.

EXAMPLES

The following examples are offered to illustrate but not to limit the compositions, uses, and methods provided herein. The compounds are prepared using the general methods described above. In the following examples, designation of a compound by use of a compound number followed by a particular letter indicates a stereoisomeric form or mixture of stereoisomers of such compound, as will be clear from the context of the particular example. Thus, it will be appreciated that if a compound such as Compound 288 may exist as two individual stereoisomeric forms, two letter designations, 288A and 288B, may be used herein to refer to the individual stereoisomeric forms. Similarly, individual diastereomers or mixtures thereof, as will be clear from the examples below, may be designated as 858A, 858B, 858C, and 858D. It is appreciated that the data tables presented herein, for example Table A, where applicable, will provide the data associated with a particular stereoisomer by using the designations indicated in these examples. By virtue of the terminology used herein, it is also appreciated that certain compounds referred to in a particular stereoisomeric form in these examples with the letter designation may find counterparts in Table 1 where such compounds are indicated by structure and name.

The following abbreviations are used throughout the Examples: TEA (trimethylamine), DCM (dichloromethane), (Boc)₂O (di-tert-butyl decarbonate), EA (Ethyl acetate), PE (Petroleum ether, DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-Hydroxy-7-azabenzotriazole), HOBt (Hydroxybenzotriazole), EDCI (1-Ethyl-3-(3-dimethylaminopropyl)carbodiimide), MeOH (methanol), EtOH (ethanol), IPA (iPrOH; propan-2-ol), NMP (1-methylpyrrolidin-2-one), STAB (sodium triacetoxyhyd-

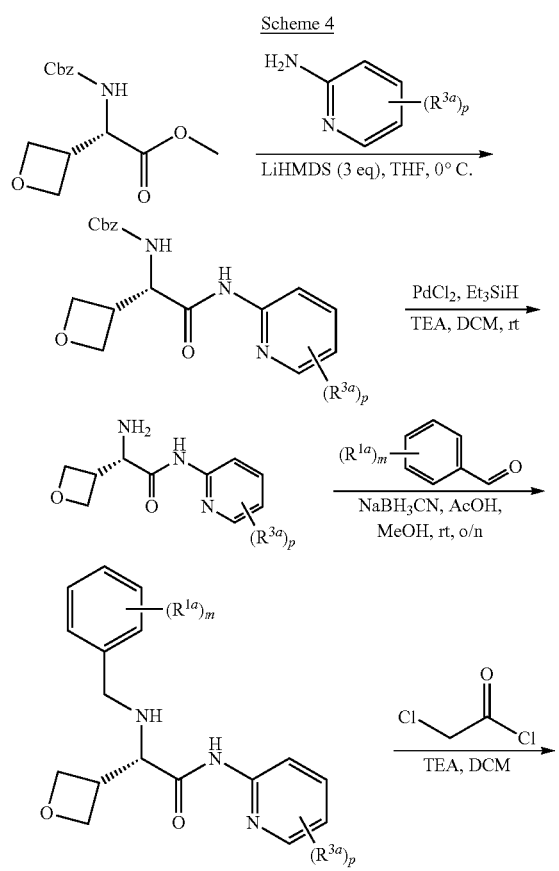

roborate), ACN (acetonitrile), TFA (trifluoroacetic acid), DPPA (Diphenylphosphoryl azide), DBU (1,8-Diazabicyclo (5.4.0)undec-7-ene), THF (tetrahydrofuran), PPh₃ (triphenylphosphane), SM (starting material), Hex (hexane), NCS (N-chlorosuccinimide), r.t. (room temperature), DCE (dichloroethane), FA (formic acid), CHCl₃ (Chloroform), BnBr (benzyl bromide), HCl (hydrogen chloride), equiv (equivalent), RT (retention time), SFC (supercritical fluid chromatography), and DSC (bis(2,5-dioxopyrrolidin-1-yl) carbonate).

Example 1: Synthesis of Compound 288

1. Synthesis of Intermediate 1-2

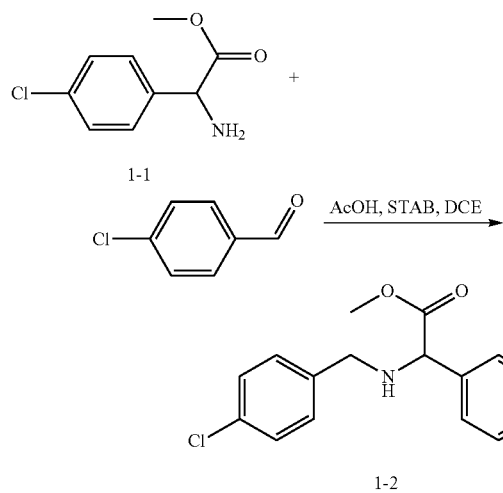

To a solution of methyl 2-amino-2-(4-chlorophenyl)acetate (1.5 g, 7.51 mmol, 1.0 equiv) in DCE (20 mL) at r.t were added 4-chlorobenzaldehyde (1.05 g, 7.47 mmol, 1.00 equiv), acetic acid (900 mg, 14.99 mmol, 2.00 equiv) and STAB (2.4 g, 11.32 mmol, 1.50 equiv). The mixture was stirred at r.t for 2 h, diluted with EA (100 mL), washed with brine (50 mL) twice, dried over anhydrous sodium sulfate and concentrated under reduced pressure to give 2.4 g (99%) of methyl 2-(4-chlorophenyl)-2-[[(4-chlorophenyl)methyl]amino]acetate as a brown oil.

2. Synthesis of Intermediate 1-3

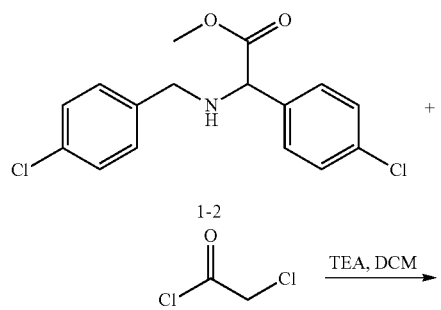

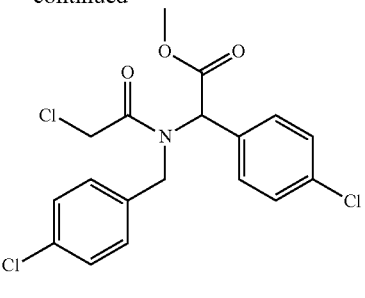

1-3

To a solution of methyl 2-(4-chlorophenyl)-2-[[(4-chlorophenyl)methyl]amino]acetate (2.4 g, 7.40 mmol, 1.00 equiv) in DCM (30 mL) at r.t were added TEA (1.5 g, 14.82 mmol, 2.00 equiv) and 2-chloroacetyl chloride (1 g, 8.85 mmol, 1.20 equiv) dropwise. The mixture was stirred at r.t for 2 h, diluted with DCM (50 mL), washed with brine (20 mL) twice, dried over anhydrous sodium sulfate, concentrated under reduced pressure, and purified by silica gel column with ACN and water (3:1) to give 2 g (67%) of methyl 2-[2-chloro-N-[(4-chlorophenyl)methyl]acetamido]-2-(4-chlorophenyl)acetate as a brown oil.

3. Synthesis of Compound 288

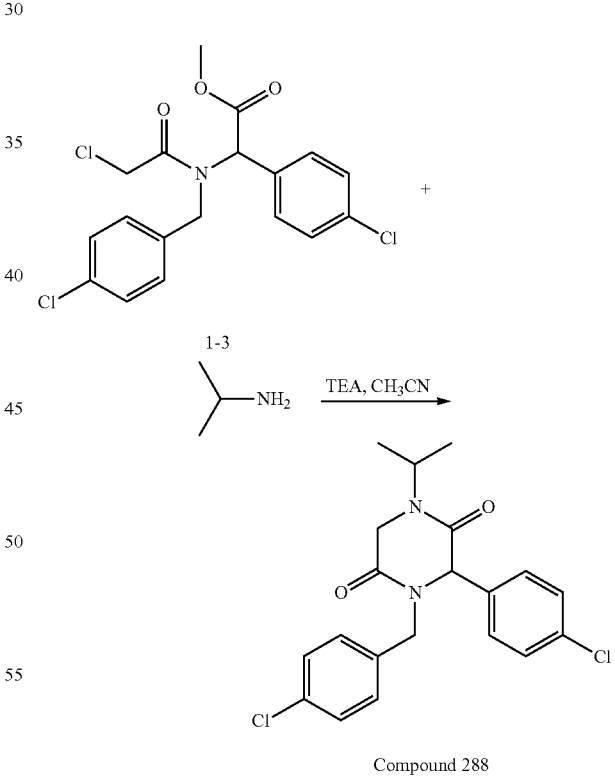

Compound 288

To a solution of methyl 2-[2-chloro-N-[(4-chlorophenyl)methyl]acetamido]-2-(4-chlorophenyl)acetate (150 mg, 0.37 mmol, 1.0 equiv) in ACN (10 mL) at r.t were added propan-2-amine (66.5 mg, 1.1 mmol, 3.0 equiv) and TEA (115 mg, 1.1 mmol, 3.0 equiv). The mixture was stirred at r.t for 1 h and at 80° C. for 2 h, concentrated under reduced pressure, and purified by Prep-HPLC with the following conditions (2 #-AnalyseHPLC-SHIMADZU (HPLC-10)): Column, XBridge Shield RP18 OBD column, 5 um, 19*150 mm; mobile phase, water (0.05% $NH_3H_2O$) and ACN (48.0% ACN up to 68.0% in 8 min); Detector, UV 220 nm) to give 100 mg of 3-(4-chlorophenyl)-4-[(4-chlorophenyl)methyl]-1-(propan-2-yl)piperazine-2,5-dione. LRMS (ES) m/z 391 (M+H). $^1$H NMR (DMSO-$d_6$, 300 MHz) δ 7.44-7.33 (m, 2H), 7.36-7.22 (m, 4H), 7.22-7.13 (m, 2H), 4.95 (s, 1H), 4.88 (d, J=15.1 Hz, 1H), 4.40 (h, J=6.9 Hz, 1H), 4.15 (d, J=17.7 Hz, 1H), 3.98 (d, J=17.8 Hz, 1H), 3.86 (d, J=15.1 Hz, 1H), 1.07 (d, J=6.8 Hz, 3H), 0.96 (d, J=6.8 Hz, 3H).

The following compounds were prepared by methods analogous to the method described for Compound 288:

| Compound No. | LRMS (ES) m/z |
| --- | --- |
| 293 | M + H = 392 |
| 294 | M + H = 357 |
| 297 | M + H = 392 |
| 298 | M + H = 391 |
| 299 | M + H = 375 |
| 300 | M + H = 371 |
| 301 | M + H = 382 |
| 302 | M + H = 391 |
| 303 | M + H = 375 |
| 304 | M + H = 371 |
| 305 | M + H = 371 |
| 306 | M + H = 382 |
| 307 | M + H = 382 |
| 308 | M + H = 425 |
| 309 | M + H = 425 |
| 310 | M + H = 391 |
| 311 | M + H = 375 |
| 312 | M + H = 391 |
| 313 | M + H = 387 |
| 314 | M + H = 425 |
| 315 | M + H = 426 |
| 316 | M + H = 405 |
| 317 | M + H = 383 |
| 318 | M + H = 397.2 |
| 319 | M + H = 417.1 |

4. Separation of Compound 288 Enantiomers: Enantiomers 288A and 288B

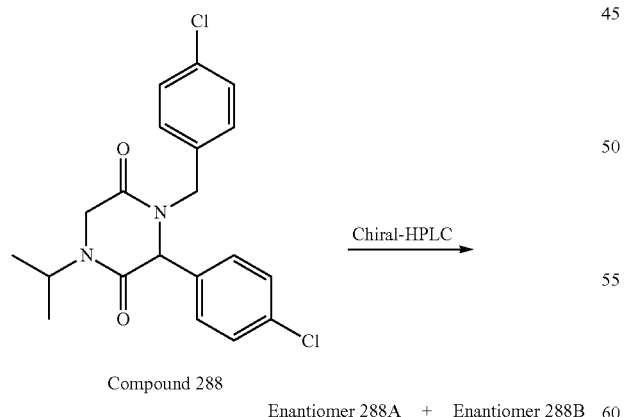

Compound 288 → Enantiomer 288A + Enantiomer 288B

The racemic compound 3-(4-chlorophenyl)-4-[(4-chlorophenyl)methyl]-1-cyclopentylpiperazine-2,5-dione (80 mg, 0.19 mmol, 1.0 equiv) was separated by Chiral-HPLC with the following conditions (Column: CHIRAL ART Cellulose-SB, 2*25 cm, 5 um; Mobile Phase A: Hex-HPLC, Mobile Phase B: EtOH-HPLC; Flow rate: 20 mL/min; Gradient: 30 B to 30 B in 10 min; 220/254 nm) to give 25.4 mg (first eluted peak) of Enantiomer 288A and 32 mg (second eluted peak) of Enantiomer 288B. The chiral analytical data (Column: CHIRAL Cellulose-SB; 0.46 cm×15 cm; 5 micron; Hex (0.2% IPAmine):EtOH=70:30 at 1 ml/min) shows that Enantiomer 288A is the first eluting peak (RT 3.3 min) and Enantiomer 288B is the second eluting peak (RT 4.0 min).

Enantiomer 288A: LRMS (ES) m/z 391 (M+H). $^1$H NMR (300 MHz, DMSO-$d_6$) δ 7.44-7.34 (m, 2H), 7.39-7.22 (m, 4H), 7.27-7.13 (m, 2H), 4.95 (s, 1H), 4.87 (d, J=15.1 Hz, 1H), 4.39 (h, J=6.8 Hz, 1H), 4.15 (d, J=17.7 Hz, 1H), 3.97 (d, J=17.8 Hz, 1H), 3.86 (d, J=15.1 Hz, 1H), 1.07 (d, J=6.8 Hz, 3H), 0.96 (d, J=6.9 Hz, 3H).

Enantiomer 288B: LRMS (ES) m/z 391 (M+H). $^1$H NMR (300 MHz, DMSO-$d_6$) δ 7.44-7.33 (m, 2H), 7.36-7.22 (m, 4H), 7.22-7.13 (m, 2H), 4.95 (s, 1H), 4.87 (d, J=15.1 Hz, 1H), 4.41 (p, J=6.8 Hz, 1H), 4.15 (d, J=17.7 Hz, 1H), 3.97 (d, J=17.8 Hz, 1H), 3.86 (d, J=15.1 Hz, 1H), 1.07 (d, J=6.8 Hz, 3H), 0.96 (d, J=6.9 Hz, 3H).

The following compounds were prepared by methods analogous to the method described for Enantiomers 288A and 288B:

| Enantiomer No. | HPLC RT (min) | LRMS (ES) m/z | HPLC separation conditions |
| --- | --- | --- | --- |
| 293A | 2.1 | M + H = 392 | CHIRALPAK IA-3; |
| 293B | 2.5 | M + H = 392 | 0.46 cm × 5 cm; 3 micro; |
| 297A | 1.7 | M + H = 392 | Hex(0.1% DEA):EtOH = 50:50 |
| 297B | 2.3 | M + H = 392 | at 1 mL/min |
| 629A | 1.48 | M + H = 473 | CHIRALPAK IE-3; |
|  |  |  | 0.46 cm × 5 cm; 3 micro; |
| 629B | 1.90 | M + H = 473 | Hex(0.1% DEA):EtOH = 50:50 |
|  |  |  | at 1 ml/min |

Example 2: Synthesis of Compound 20

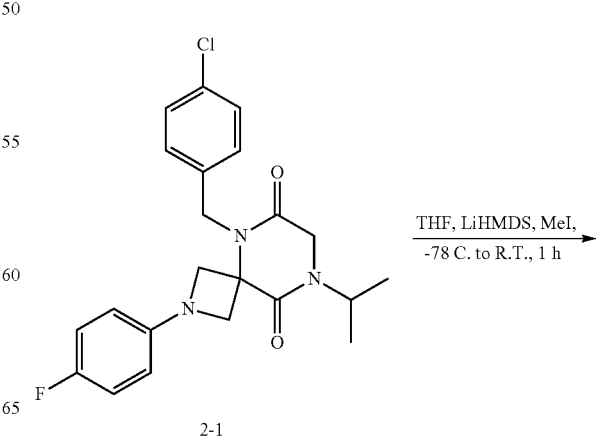

2-1

543
-continued

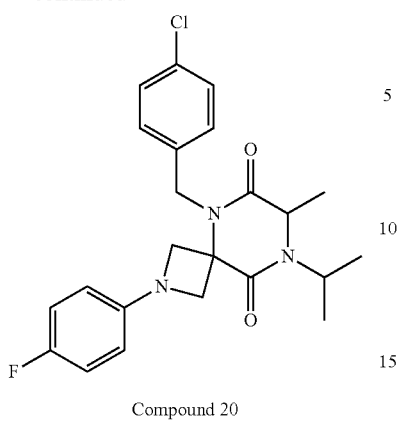

Compound 20

To a solution of 5-(4-chlorobenzyl)-2-(4-fluorophenyl)-8-isopropyl-2,5,8-triazaspiro[3.5]nonane-6,9-dione (20.5 mg, 0.049 mmol, 1.0 equiv) in dry THF (2 mL) at −78° C. was added LHMDS (1 M in THF, 54 µL, 0.054 mmol, 1.1 equiv). The mixture was stirred at −78° C. for 2 min, added MeI (2 M in ether, 30 µL, 0.059 mmol, 1.2 equiv) into the mixture, stirred at −78° C. for 5 min, slowly warmed to r.t., and diluted with water and EA. The organic layer was dried over $Na_2SO_4$, filtered, concentrated, and purified by silica gel chromatography (40 g column, 0-60% EtOAc in hexanes) to provide 9.9 mg (47%) of 5-(4-chlorobenzyl)-2-(4-fluorophenyl)-8-isopropyl-7-methyl-2,5,8-triazaspiro[3.5]nonane-6,9-dione as a white solid. LRMS (ES) m/z 430.1 (M+H). (Methylenechloride-$d_2$, 400 MHz, ppm) δ 7.40-7.28 (m, 2H), 7.24-7.13 (m, 2H), 7.06-6.91 (m, 2H), 6.46-6.37 (m, 2H), 5.29 (d, J=16.2 Hz, 1H), 4.87 (d, J=16.3 Hz, 1H), 4.72 (d, J=8.6 Hz, 1H), 4.44 (hept, J=6.8 Hz, 1H), 4.28-4.14 (m, 2H), 4.03 (dd, J=9.8, 8.2 Hz, 2H), 1.49 (d, J=7.0 Hz, 3H), 1.33 (dd, J=6.9, 5.0 Hz, 6H).

The following compound was prepared by methods analogous to the method described for Compound 20:

| Compound No. | LRMS (ES) m/z |
|---|---|
| 329 | M + H = 412.1 |

Example 3: Synthesis of Compound 65

1. Synthesis of Intermediate 3-2

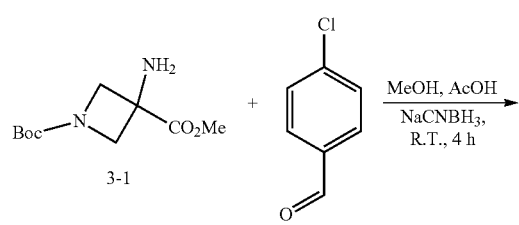

544
-continued

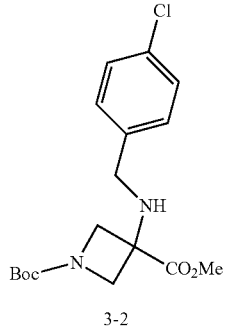

3-2

To a solution of 1-(tert-butyl) 3-methyl-3-aminoazetidine-1,3-dicarboxylate (5.0 g, 21.7 mmol, 1.0 equiv) in MeOH (50 mL) was added 4-chlorobenzaldehyde (4.5 g, 32.6 mmol, 1.5 equiv). The mixture was stirred for 1 h at r.t. To this mixture were added $NaCNBH_3$ (1.4 g, 21.7 mmol, 1.0 equiv) and AcOH (1 mL). This mixture was continued to be stirred for 4 h, concentrated under reduced pressure, and diluted with DCM (60 mL) and saturated aqueous sodium bicarbonate (60 mL). The aqueous layer was extracted with DCM (25 mL). The combined organic layers were dried over sodium sulfate, filtered through celite, concentrated under reduced pressure, and purified by silica gel chromatography (80 g column, 0-100% EtOAc in hexanes) to provide 6.0 g (78%) of 1-(tert-butyl) 3-methyl 3-((4-chlorobenzyl)amino)azetidine-1,3-dicarboxylate. LRMS (ES) m/z 355.2 (M+H). $^1$H-NMR (Methylenechloride-$d_2$, 400 MHz, ppm) δ 7.35 (s, 4H), 4.19 (d, J=8.8 Hz, 2H), 3.86 (d, J=8.8 Hz, 2H), 3.82 (s, 3H), 3.68 (s, 2H), 1.46 (s, 9H).

2. Synthesis of Intermediate 3-3

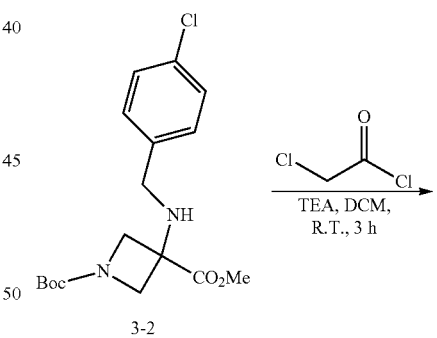

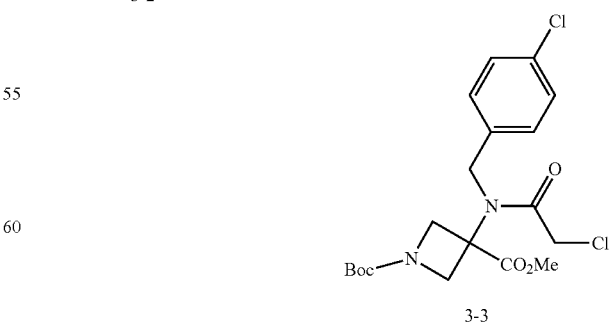

To a solution of 1-(tert-butyl) 3-methyl 3-((4-chlorobenzyl)amino)azetidine-1,3-dicarboxylate (6.0 g, 16.9 mmol, 1.0 equiv) in DCM (50 mL) cooled down to 0° C. were added TEA (7.1 mL, 50.7 mmol, 3.0 equiv) and chloroacetyl chloride (2.7 mL, 33.8 mmol, 2.0 equiv). The ice bath was removed and the mixture was stirred for 3 h at r.t. before pouring into saturated aqueous NH₄Cl (200 mL). The aqueous layer was extracted with DCM (100 mL) three times. The combined organic layers were dried over MgSO₄ and concentrated to give an intermediate product, 1-(tert-butyl) 3-methyl 3-(2-chloro-N-(4-chlorobenzyl)acetamido)azetidine-1,3-dicarboxylate. LRMS (ES) m/z 431.1 (M+H).

3. Synthesis of Intermediate 3-4

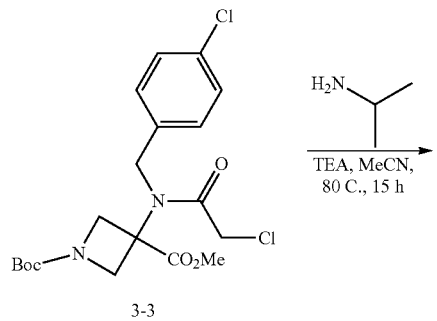

3-3

4. Synthesis of Intermediate 3-5

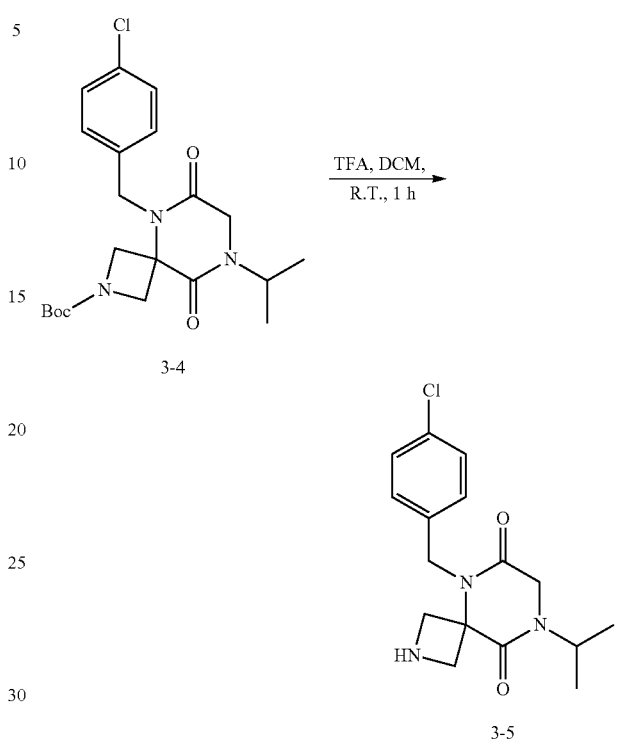

To a solution of tert-butyl 5-(4-chlorobenzyl)-8-isopropyl-6,9-dioxo-2,5,8-triazaspiro[3.5]nonane-2-carboxylate (6.5 g, 15.4 mmol, 1.0 equiv) in DCM (40 mL) was added TFA (12 mL). The mixture was stirred for 1 h at r.t, concentrated, diluted with saturated aqueous NaHCO₃ (200 mL), and extracted with DCM three times. The combined organic layers were dried over MgSO₄, concentrated, and purified by silica gel chromatography (40 g column, 0-50% MeOH in DCM) to provide 4.1 g (83%) of 5-(4-chlorobenzyl)-8-isopropyl-2,5,8-triazaspiro[3.5]nonane-6,9-dione as an off-white solid. LRMS (ES) m/z 322.1 (M+H). ¹H-NMR (Dichloromethane-d₂, 400 MHz, ppm) δ 7.36-7.32 (m, 2H), 7.28-7.24 (m, 2H), 5.16 (s, 2H), 4.85 (p, J=6.9 Hz, 1H), 4.30-4.19 (m, 4H), 4.00 (s, 2H), 1.24 (d, J=6.8 Hz, 6H).

5. Synthesis of Compound 65

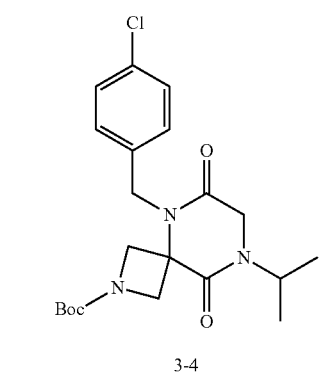

3-4

To a solution of 1-(tert-butyl) 3-methyl 3-(2-chloro-N-(4-chlorobenzyl)acetamido)azetidine-1,3-dicarboxylate (16.9 mmol, 1.0 equiv assuming 100% yield) in ACN (300 mL) were added isopropylamine (2.9 mL, 33.9 mmol, 2.0 equiv) and TEA (7.1 mL, 50.8 mmol, 3.0 equiv). The mixture was heated to 80° C. for 15 h, concentrated, and purified by silica gel chromatography (80 g, 0-100% EtOAc in hexanes) to provide 6.5 g (91%) of tert-butyl 5-(4-chlorobenzyl)-8-isopropyl-6,9-dioxo-2,5,8-triazaspiro[3.5]nonane-2-carboxylate as a colored solid. LRMS (ES) m/z 366.1 (M+H-ᵗBu).

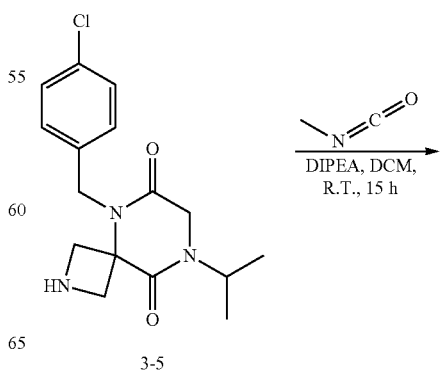

3-5

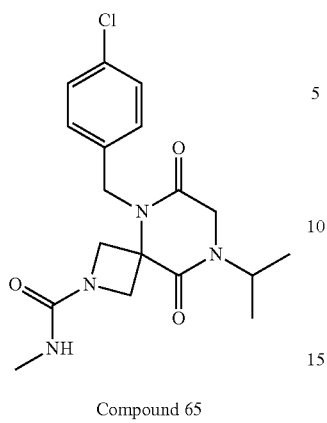

Compound 65

To a solution of 5-(4-chlorobenzyl)-8-isopropyl-2,5,8-triazaspiro[3.5]nonane-6,9-dione (20 mg, 0.062 mmol, 1.0 equiv) in DCM (0.2 mL) were added DIEA (22 µL, 0.12 mmol, 2.0 equiv) and methyl isocyanate (5.0 mg, 0.093 mmol, 1.5 equiv). The mixture was stirred for 15 h at r.t., concentrated, and purified by reverse phase HPLC (Phenomenex, gemini 5 micron C18 150×21.2 mm, 10-70% acetonitrile in water both with 0.1% formic acid gradient over 25 min) to provide 8.6 mg (37%) of 5-(4-chlorobenzyl)-8-isopropyl-N-methyl-6,9-dioxo-2,5,8-triazaspiro[3.5]nonane-2-carboxamide as a white foamy solid. LRMS (ES) m/z 379.1 (M+H). (Methanol-$d_4$, 400 MHz, ppm) δ 7.39-7.34 (m, 2H), 7.32-7.27 (m, 2H), 4.98 (s, 2H), 4.75 (hept, J=6.9 Hz, 1H), 4.41-4.37 (m, 2H), 4.08 (s, 2H), 4.07-4.04 (m, 2H), 2.69 (s, 3H), 1.24 (d, J=6.8 Hz, 6H).

The following compounds were prepared by methods analogous to the method described for Compound 65:

| Compound No. | LRMS (ES) m/z |
| --- | --- |
| 64 | M + H = 380.1 |
| 66 | M + H = 445.2 |
| 67 | M + H = 413.1 |
| 68 | M + H = 399.1 |
| 69 | M + H = 384.1 |
| 70 | M + H = 439.2 |

Example 4: Synthesis of Compound 373

1. Synthesis of Intermediate 4-2

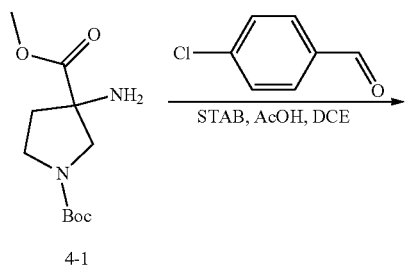

4-1

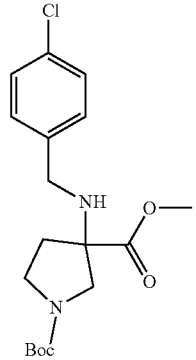

4-2

To a solution of 1-tert-butyl 3-methyl 3-aminopyrrolidine-1,3-dicarboxylate (1.9 g, 7.78 mmol, 1.0 equiv) in DCE (30 mL) at r.t were added 4-chlorobenzaldehyde (1.1 g, 7.83 mmol, 1.0 equiv) and acetic acid (934 mg, 15.55 mmol, 2.0 equiv). The mixture was stirred for 10 min at r.t. To this mixture was added STAB (2.5 g, 11.80 mmol, 1.50 equiv) in portions. The mixture was continued to stir for 1.5 h, quenched with water (20 mL), and extracted with DCM (20 mL) twice. The combined organic layers were washed with aqueous $NaHCO_3$ (20 mL) and brine (20 mL), dried over anhydrous sodium sulfate, concentrated under reduced pressure, and purified by reverse phase HPLC with the following conditions: (column, C18 silica gel; mobile phase, A: water (10 mmol/L $NH_4HCO_3$), B: ACN, 65% B to 75% B gradient in 20 min; detector, UV 210/254 nm) to give 2.2 g (77%) of 1-tert-butyl 3-methyl 3-[[(4-chlorophenyl)methyl]amino]pyrrolidine-1,3-dicarboxylate as a brown oil. LRMS (ES) m/z 313 (M+H-56).

2. Synthesis of Intermediate 4-3

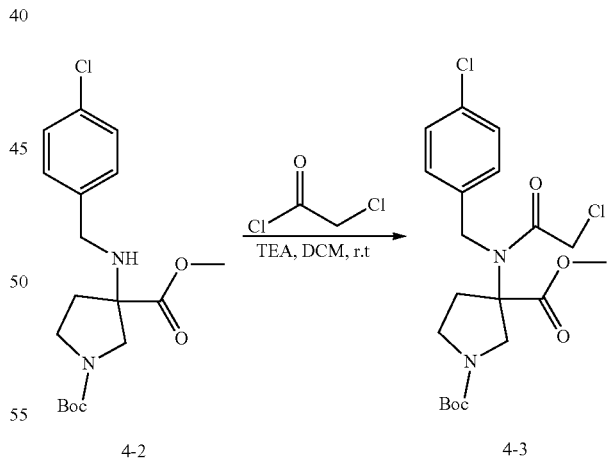

4-2 → 4-3

To a solution of 1-tert-butyl 3-methyl 3-[[(4-chlorophenyl)methyl]amino]pyrrolidine-1,3-dicarboxylate (2.28 g, 6.18 mmol, 1.0 equiv) in DCM (30 mL) cooled to 0° C. were added 2-chloroacetyl chloride (3.12 g, 27.62 mmol, 4.50 equiv) and TEA (5.63 g, 55.64 mmol, 9.00 equiv). The mixture was stirred overnight at r.t., quenched with water (20 mL), and extracted with DCM (20 mL) twice. The combined organic layers were washed with brine (20 mL) twice, dried over anhydrous sodium sulfate, and concentrated under reduced pressure to give 2.9 g of 1-tert-butyl 3-methyl 3-[2-chloro-N-[(4-chlorophenyl)methyl]acetamido]pyrrolidine-1,3-dicarboxylate as a brown oil. LRMS (ES) m/z 389 (M+H-56).

3. Synthesis of Intermediate 4-4

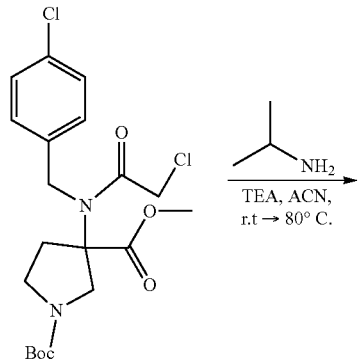

4-3

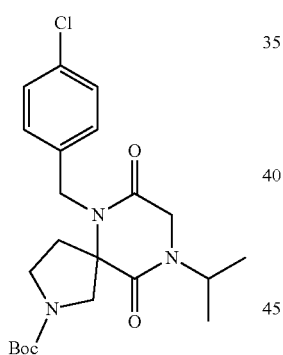

4-4

To a solution of 1-tert-butyl 3-methyl 3-[2-chloro-N-[(4-chlorophenyl)methyl]acetamido]pyrrolidine-1,3-dicarboxylate (2.9 g, 6.51 mmol, 1.0 equiv) in ACN (30 mL) at r.t were added propan-2-amine (1.9 g, 32.14 mmol, 5.00 equiv) and TEA (5.3 g, 8.00 equiv). The mixture was stirred for 1 h at r.t and then heated to 80° C. overnight. The following day the mixture was cooled to r.t, concentrated under reduced pressure, and purified by reverse phase HPLC with the following conditions: column, C18 silica gel; mobile phase, A: water (10 mmol/L NH$_4$HCO$_3$), B: ACN, 20% B to 25% B gradient in 20 min; detector, UV 210/254 nm to give 2.4 g (85%) of tert-butyl 6-[(4-chlorophenyl)methyl]-7,10-dioxo-9-(propan-2-yl)-2,6,9-triazaspiro[4.5]decane-2-carboxylate as a brown solid. LRMS (ES) m/z 380 (M+H-56).

4. Synthesis of Intermediate 4-5

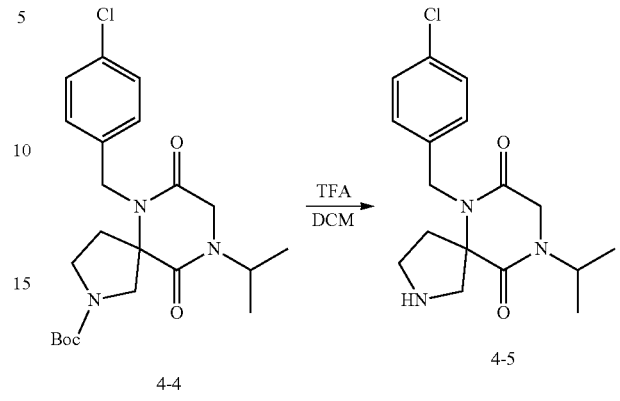

To a solution of tert-butyl 6-[(4-chlorophenyl)methyl]-7,10-dioxo-9-(propan-2-yl)-2,6,9-triazaspiro[4.5]decane-2-carboxylate (2.4 g, 5.51 mmol, 1.0 equiv) in DCM (30 mL) at r.t was added TFA (8 mL). The mixture was stirred for 1 h at r.t. The pH of the solution was adjusted to 9 with sodium hydroxide (6 N, ~3 mL). The mixture was diluted with water and extracted with DCM (20 mL) twice. The combined organic layers were washed with brine (20 mL) twice, dried over anhydrous sodium sulfate, and concentrated under reduced pressure to give 1.7 g (92%) of 6-[(4-chlorophenyl)methyl]-9-(propan-2-yl)-2,6,9-triazaspiro[4.5]decane-7,10-dione as a brown solid. LRMS (ES) m/z 336 (M+H).

5. Synthesis of Compound 373

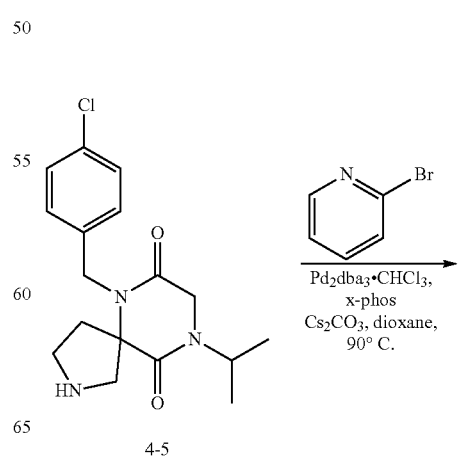

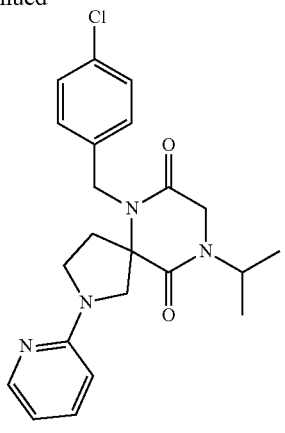

Compound 373

To a solution of 2-bromopyridine (200 mg, 1.27 mmol, 1.0 equiv) in dioxane (5 mL) were added 6-[(4-chlorophenyl)methyl]-9-(propan-2-yl)-2,6,9-triazaspiro[4.5]decane-7,10-dione (94 mg, 0.28 mmol, 1.0 equiv), Pd$_2$(dba)$_3$CHCl$_3$ (62 mg, 0.06 mmol, 0.10 equiv), Xphos (57 mg, 0.12 mmol 0.20 equiv), and Cs$_2$CO$_3$ (389 mg, 1.19 mmol, 2.0 equiv) under nitrogen. The mixture was stirred at 90° C. overnight, cooled to r.t, filtered to remove solids, and purified by Prep-HPLC with the following conditions (2 #-AnalyseHPLC-SHIMADZU (HPLC-10)): Column, XBridge Prep C18 OBD Column, 5 um, 19*150 mm; mobile phase, water (10 mmol/L NH$_4$HCO$_3$) and ACN (39.0% ACN up to 53.0% gradient over 8 min); Detector, UV 254 nm to give 15 mg (6%) of 6-[(4-chlorophenyl)methyl]-9-(propan-2-yl)-2-(pyridin-2-yl)-2,6,9-triazaspiro[4.5]decane-7,10-dione as a white solid. LRMS (ES) m/z 413 (M+H). $^1$H-NMR: (300 MHz, Methanol-d$_4$, ppm): δ 8.01-7.93 (m, 1H), 7.50 (ddd, J=8.9, 7.2, 1.9 Hz, 1H), 7.28-7.19 (m, 2H), 7.10 (d, J=8.4 Hz, 2H), 6.61 (dd, J=6.9, 5.2 Hz, 1H), 6.41 (d, J=8.6 Hz, 1H), 4.76-4.54 (m, 3H), 4.16 (s, 2H), 3.97 (d, J=11.9 Hz, 1H), 3.75 (d, J=11.8 Hz, 1H), 3.66-3.42 (m, 2H), 2.62-2.38 (m, 2H), 1.20 (dd, J=6.8, 1.4 Hz, 6H).

6. Separation of Compound 373 Enantiomers

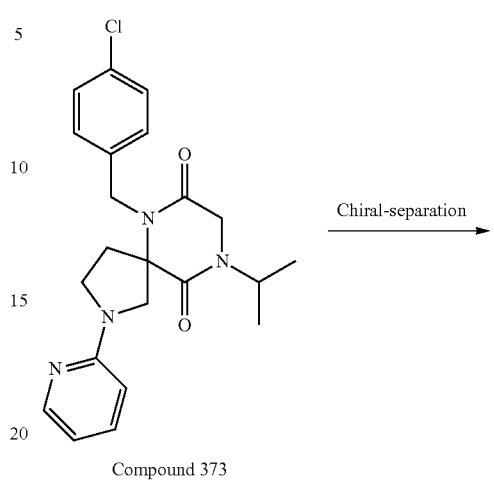

Compound 373 →(Chiral-separation) Enantiomer 373A + Enantiomer 373B

The racemic compound 6-[(4-chlorophenyl)methyl]-9-(propan-2-yl)-2-(pyridin-2-yl)-2,6,9-triazaspiro[4.5]decane-7,10-dione (80 mg, 0.19 mmol, 1.0 equiv) was separated by Chiral-HPLC with the following conditions (Prep-HPLC-009): Column: Chiralpak IC, 2*25 cm, 5 um; Mobile Phase A: Hex-HPLC, Mobile Phase B: EtOH-HPLC; Flow rate: 15 mL/min; isocratic elution for 21 min; 220/254 nm) to give 28.7 mg (36%, first eluted peak) of Enantiomer 373A and 29 mg (second eluted peak) of Enantiomer 373B as white solids. The chiral analytical data (CHIRALPAK IC-3; 0.46 cm×5 cm; 3 μm; Hex (0.1% DEA):EtOH=55:45 at 1 ml/min) shows that Enantiomer 373A is the first eluted peak (RT 2.2 min) and Enantiomer 373B is the second eluted peak (RT 3.2 min). Enantiomer 373A: LRMS (ES) m/z 413 (M+H). $^1$H-NMR: (300 MHz, Methanol-d$_4$, ppm) δ 7.97 (ddd, J=5.2, 1.9, 0.9 Hz, 1H), 7.50 (ddd, J=8.8, 7.1, 1.9 Hz, 1H), 7.28-7.18 (m, 2H), 7.10 (d, J=8.4 Hz, 2H), 6.61 (ddd, J=7.2, 5.1, 0.9 Hz, 1H), 6.41 (d, J=8.6 Hz, 1H), 4.86 (s, 1H), 4.76-4.54 (m, 2H), 4.15 (s, 2H), 3.97 (d, J=11.8 Hz, 1H), 3.75 (d, J=11.8 Hz, 1H), 3.66-3.42 (m, 2H), 2.62-2.38 (m, 2H), 1.20 (dd, J=6.8, 1.4 Hz, 6H).

Enantiomer 373B: LRMS (ES) m/z 413 (M+H). $^1$H NMR: (300 MHz, Methanol-d$_4$) δ 8.01-7.93 (m, 1H), 7.50 (ddd, J=8.8, 7.2, 1.9 Hz, 1H), 7.28-7.18 (m, 2H), 7.10 (d, J=8.3 Hz, 2H), 6.61 (dd, J=6.9, 5.4 Hz, 1H), 6.41 (d, J=8.5 Hz, 1H), 4.76-4.54 (m, 2H), 4.16 (s, 2H), 3.97 (d, J=11.8 Hz, 1H), 3.75 (d, J=11.8 Hz, 1H), 3.66-3.42 (m, 2H), 2.62-2.38 (m, 2H), 1.20 (dd, J=6.9, 1.4 Hz, 6H).

The following compounds were prepared by methods analogous to the method described for Compound 373:

| HPLC Separation Conditions | |
|---|---|
| Letter | HPLC Conditions |
| A | Repaired Chiral IA; 0.46 cm × 10 cm; 5 micro; Hex:EtOH = 50:50 at 1 ml/min |
| B | Repaired IA; 0.46 cm × 10 cm; 5 micro; (Hex:DCM = 3:1)(0.1% DEA):EtOH = 50:50 at 1 ml/min |
| C | CHIRALPAK IA-3; 0.46 cm × 5 cm; 3 micro; Hex(0.1% DEA):EtOH = 50:50 at 1 ml/min |
| D | CHIRALPAK IC-3; 0.46 cm × 5 cm; 3 micro; Hex(0.1% DEA):EtOH = 55:45 at 1 ml/min |
| E | CHIRALPAK IC-3; 0.46 cm × 5 cm; 3 micro; Hex(0.1% DEA):EtOH = 50:50 at 1 ml/min |
| F | CHIRALPAK IC-3; 0.46 cm × 5 cm; 3 micro; Hex(0.1% DEA):EtOH = 70:30 at 1 ml/min |
| G | CHIRALART Cellulose-SB; 0.46 cm × 10 cm; 3 micro; Hex(0.1% DEA):EtOH = 50:50 at 1 ml/min |

| | HPLC Separation Conditions |
|---|---|
| H | CHIRALPAK IE-3; 0.46 cm × 10 cm; 3 micro; (Hex:DCM = 3:1)(0.1% DEA):EtOH = 50:50 at 1 ml/min |

| Enantiomer No. | LRMS (ES) m/z | Retention Time (min) | HPLC Separation Conditions |
|---|---|---|---|
| 375A | M + H = 412 | 3.4 | A |
| 375B | M + H = 412 | 4.1 | |
| 377A | M + H = 427 | 2.9 | D |
| 377B | M + H = 427 | 3.7 | |
| 351A | M + H = 414 | 3.0 | C |
| 351B | M + H = 414 | 4.9 | |
| 353A | M + H = 414 | 3.8 | C |
| 353B | M + H = 414 | 5.0 | |
| 355A | M + H = 427 | 2.0 | E |
| 355B | M + H = 427 | 4.0 | |
| 357A | M + H = 431 | 1.7 | D |
| 357B | M + H = 431 | 2.3 | |
| 359A | M + H = 414 | 2.6 | C |
| 359B | M + H = 414 | 3.9 | |
| 361A | M + H = 443 | 3.8 | B |
| 361B | M + H = 443 | 5.5 | |
| 363A | M + H = 429 | 2.6 | C |
| 363B | M + H = 429 | 3.6 | |
| 365A | M + H = 416 | 2.4 | B |
| 365B | M + H = 416 | 3.8 | |
| 379A | M + H = 393 | 2.4 | E |
| 379B | M + H = 393 | 2.9 | |
| 381A | M + H = 407 | 2.1 | E |
| 381B | M + H = 407 | 2.5 | |
| 383A | M + H = 421 | 3.0 | F |
| 383B | M + H = 421 | 3.6 | |
| 369A | M + H = 419 | 2.7 | D |
| 369B | M + H = 419 | 3.4 | |
| 371A | M + H = 455 | 2.8 | G |
| 371B | M + H = 455 | 3.7 | |
| 385A | M + H = 456 | 1.6 | E |
| 385B | M + H = 456 | 3.1 | |
| 387A | M + H = 437 | 3.3 | H |
| 387B | M + H = 437 | 4.8 | |

Example 5: Synthesis of Compound 108

1. Synthesis of Intermediate 5-2

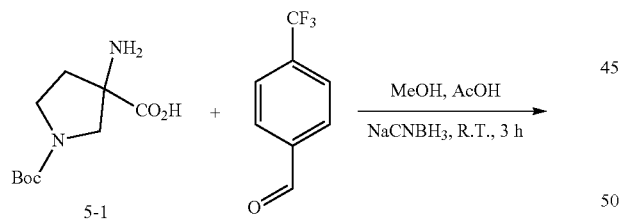

To a solution of 3-amino-1-(tert-butoxycarbonyl)pyrrolidine-3-carboxylic acid (7.0 g, 30.4 mmol, 1.0 equiv) in MeOH (80 mL) was added 4-(trifluoromethyl)benzaldehyde (5.6 g, 31.9 mmol, 1.05 equiv). The mixture was stirred for 1 h at r.t., added NaCNBH$_3$ (2.9 g, 45.6 mmol, 1.5 equiv) and AcOH (0.5 mL), and stirred for 2 h. The mixture containing 1-(tert-butoxycarbonyl)-3-((4-(trifluoromethyl)benzyl)amino)pyrrolidine-3-carboxylic acid was used directly in the next step. LRMS (ES) m/z 389.2 (M+H).

2. Synthesis of Intermediate 5-3

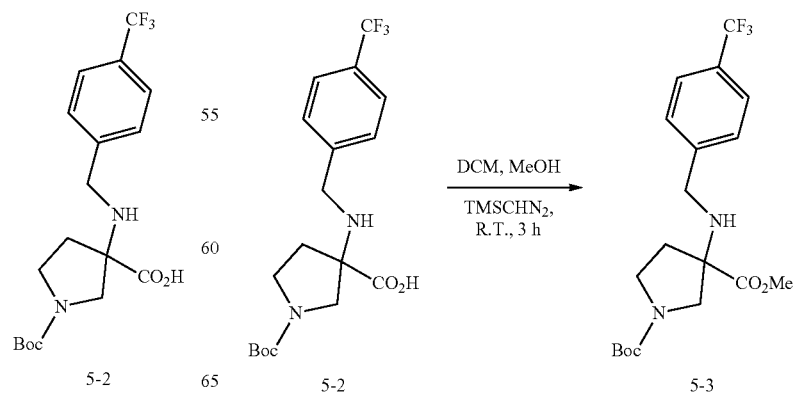

To the solution containing 1-(tert-butoxycarbonyl)-3-((4-(trifluoromethyl)benzyl) amino)pyrrolidine-3-carboxylic acid (30.4 mmol, 1.0 equiv) obtained from the previous reaction were added DCM (100 mL) and (trimethylsilyl) diazomethane (2 M in hexanes, 45.6 mL, 91.1 mmol, 3.0 equiv). The mixture was stirred for 3 h at r.t., added AcOH (5.0 g), concentrated onto silica (30 g), and purified by silica gel chromatography (120 g, 0-100% EtOAc in hexanes) to provide 7.4 g (61% over steps) of 1-(tert-butyl) 3-methyl 3-((4-(trifluoromethyl)benzyl)amino)pyrrolidine-1,3-dicarboxylate as a white solid. LRMS (ES) m/z 403.2 (M+H).

3. Synthesis of Intermediate 5-4

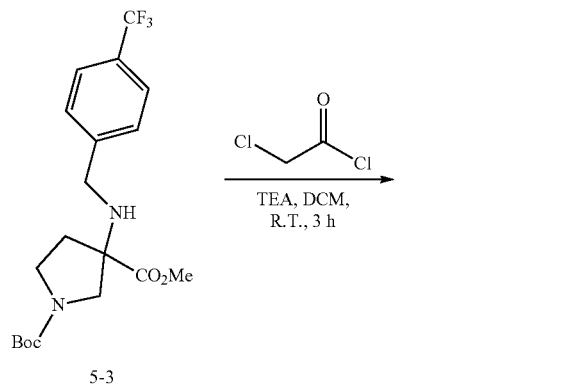

5-3

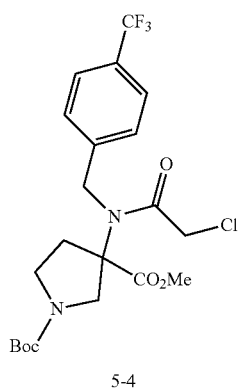

5-4

To a solution of 1-(tert-butyl) 3-methyl 3-((4-(trifluoromethyl)benzyl)amino) pyrrolidine-1,3-dicarboxylate (7.4 g, 18.4 mmol, 1.0 equiv) in DCM (50 mL) cooled to 0° C. were added TEA (7.7 mL, 84.9 mmol, 3.0 equiv) and chloroacetyl chloride (2.9 mL, 36.8 mmol, 2.0 equiv). The ice bath was removed and the mixture was stirred for 3 h at r.t before pouring into saturated aqueous NH$_4$Cl (200 mL). The aqueous layer was extracted with DCM (100 mL) three times. The combined organic layers were dried over MgSO$_4$ and concentrated to give an intermediate product, 1-(tert-butyl) 3-methyl 3-(2-chloro-N-(4-(trifluoromethyl)benzyl)acetamido) pyrrolidine-1,3-dicarboxylate. LRMS (ES) m/z 379.1 (M+H-Boc).

4. Synthesis of Intermediate 5-5

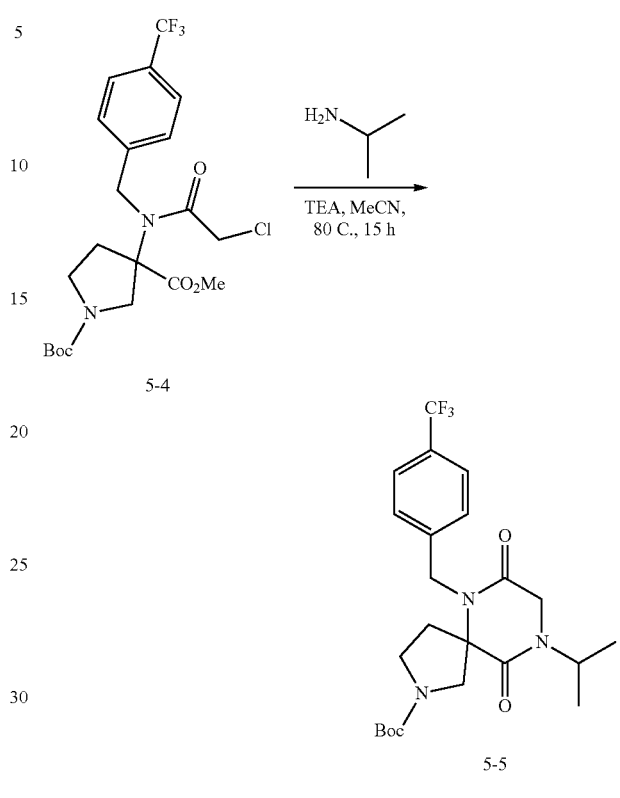

5-4

5-5

To a solution of 1-(tert-butyl) 3-methyl 3-(2-chloro-N-(4-(trifluoromethyl)benzyl)acetamido)pyrrolidine-1,3-dicarboxylate (18.4 mmol, 1.0 equiv assuming 100% yield) in ACN (300 mL) were added isopropylamine (4.7 mL, 55.1 mmol, 3.0 equiv) and TEA (7.7 mL, 55.1 mmol, 3.0 equiv). The mixture was heated at 80° C. for 15 h, concentrated, and purified by silica gel chromatography (80 g, 0-100% EtOAc in hexanes) to provide an intermediate mixture containing tert-butyl 9-isopropyl-7,10-dioxo-6-(4-(trifluoromethyl)benzyl)-2,6,9-triazaspiro[4.5]decane-2-carboxylate. LRMS (ES) m/z 414.2 (M+H-$^t$Bu).

5. Synthesis of Intermediate 5-6

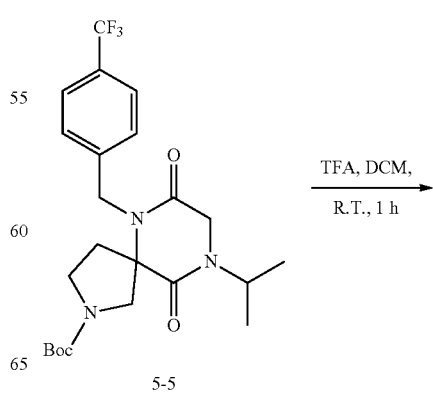

5-5

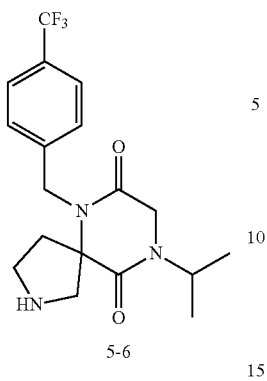

5-6

To a solution of tert-butyl 9-isopropyl-7,10-dioxo-6-(4-(trifluoromethyl)benzyl)-2,6,9-triazaspiro[4.5]decane-2-carboxylate (18.4 mmol, 1.0 equiv) in DCM (40 mL) was added TFA (20 mL). The mixture was stirred for 1 h at r.t, concentrated, diluted with saturated aqueous NaHCO₃ (200 mL), and extracted with DCM three times. The combined organic layers were dried over MgSO₄, filtered, concentrated, and purified by silica gel chromatography (40 g column, 0-50% MeOH in DCM with 1% TEA) to provide 2.8 g (41% over 3 steps) of 9-isopropyl-6-(4-(trifluoromethyl)benzyl)-2,6,9-triazaspiro[4.5]decane-7,10-dione as a solid. LRMS (ES) m/z 370.2 (M+H). ¹H-NMR (Dichloromethane-d₂, 400 MHz, ppm) δ 7.65-7.60 (m, 2H), 7.39-7.33 (m, 2H), 4.93-4.65 (m, 3H), 4.02 (s, 2H), 3.46-3.40 (m, 1H), 3.16 (ddd, J=11.3, 8.2, 5.3 Hz, 1H), 3.00 (ddd, J=11.3, 8.1, 6.7 Hz, 1H), 2.92 (d, J=12.1 Hz, 1H), 2.45 (ddd, J=13.6, 8.3, 6.7 Hz, 1H), 1.98 (ddd, J=13.5, 8.0, 5.2 Hz, 1H), 1.23 (d, J=6.8 Hz, 6H).

6. Synthesis of Compound 108

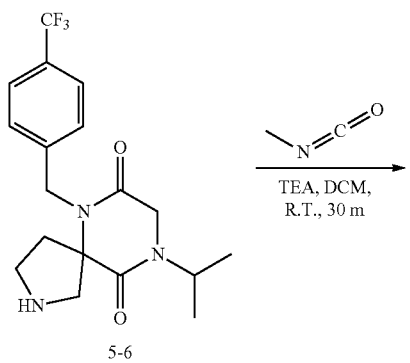

5-6

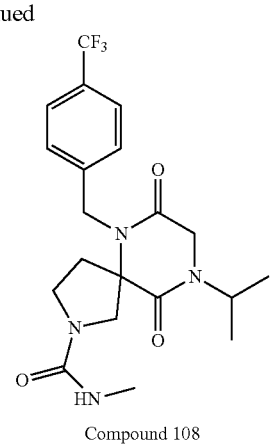

Compound 108

To a solution of 9-Isopropyl-6-(4-(trifluoromethyl)benzyl)-2,6,9-triazaspiro[4.5]decane-7,10-dione (50 mg, 0.14 mmol, 1.0 equiv) in DCM (2 mL) were added TEA (27 mg, 0.27 mmol, 2.0 equiv) and methyl isocyanate (15 mg, 0.27 mmol, 2.0 equiv). The mixture was stirred for 30 min at r.t., concentrated, and purified by reverse phase HPLC (Phenomenex, gemini 5 micron C18 150×21.2 mm, 10-100% acetonitrile in water both with 0.1% formic acid gradient over 40 min) to provide 49 mg (85%) of 9-isopropyl-N-methyl-7,10-dioxo-6-(4-(trifluoromethyenzyl)-2,6,9-triazaspiro[4.5]decane-2-carboxamide as a white foamy solid. LRMS (ES) m/z 327.2 (M+H). ¹H-NMR (Methanol-d₄, 400 MHz, ppm) δ 7.67-7.62 (m, 2H), 7.43-7.36 (m, 2H), 4.95 (d, J=17.0 Hz, 1H), 4.79-4.65 (m, 2H), 4.18 (d, J=2.1 Hz, 2H), 3.95 (d, J=11.7 Hz, 1H), 3.59 (d, J=11.7 Hz, 1H), 3.52-3.43 (m, 2H), 2.69 (s, 3H), 2.49-2.33 (m, 2H), 1.24 (dd, J=6.8, 1.3 Hz, 6H).

The following compounds were prepared by methods analogous to the method described for Compound 108:

| Compound No. | LRMS (ES) m/z |
| --- | --- |
| 107 | M + H = 413.2 |
| 109 | M + H = 489.2 |
| 1 | M + H = 467.2 |
| 110 | M + H = 428.2 |
| 111 | M + H = 490.2 |
| 112 | M + H = 469.2 |
| 113 | M + H = 490.2 |
| 114 | M + H = 493.2 |
| 115 | M + H = 507.2 |
| 116 | M + H = 441.2 |
| 117 | M + H = 455.2 |
| 118 | M + H = 453.2 |
| 119 | M + H = 407 |
| 120 | M + H = 379 |
| 121 | M + H = 393 |
| 122 | M + H = 419 |
| 123 | M + H = 455 |

Example 6: Synthesis of Compound 76

1. Synthesis of Intermediate 6-2

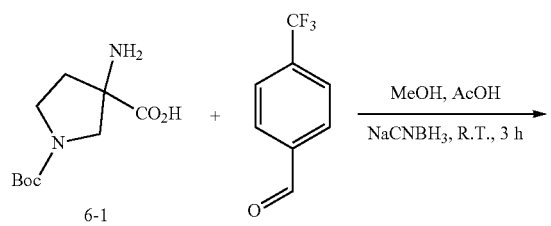

To a solution of 3-amino-1-(tert-butoxycarbonyl)pyrrolidine-3-carboxylic acid (7.0 g, 30.4 mmol, 1.0 equiv) in MeOH (80 mL) was added 4-(trifluoromethyl)benzaldehyde (5.6 g, 31.9 mmol, 1.05 equiv) and the mixture was stirred for 1 h at r.t. To this mixture were added NaCNBH$_3$ (2.9 g, 45.6 mmol, 1.5 equiv) and AcOH (0.5 mL). The mixture was stirred for 2 h at r.t. to give a solution containing 1-(tert-butoxycarbonyl)-3-((4-(trifluoromethyl)benzyl)amino)pyrrolidine-3-carboxylic acid, which was used for next reaction without working up. LRMS (ES) m/z 389.2 (M+H).

2. Synthesis of Intermediate 6-3

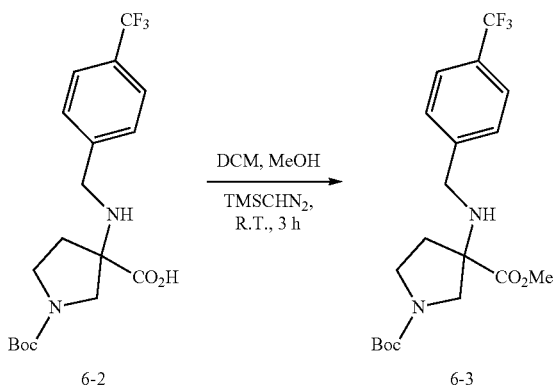 [SMILES: CC(C)(C)OC(=O)N1CCC(NCc2ccc(C(F)(F)F)cc2)(C(=O)O)C1 ; COC(=O)C1(NCc2ccc(C(F)(F)F)cc2)CCN(C(=O)OC(C)(C)C)C1]

To the solution containing 1-(tert-butoxycarbonyl)-3-((4-(trifluoromethyl)benzyl)amino)pyrrolidine-3-carboxylic acid (30.4 mmol, 1.0 equiv) from the previous step were added DCM (100 mL) and (trimethylsilyl)diazomethane (2 M in hexanes, 45.6 mL, 91.1 mmol, 3.0 equiv). The mixture was stirred for 3 h at r.t., quenched with AcOH (5 g), concentrated onto 30 g SiO$_2$, and purified by silica gel chromatography (120 g, 0-100% EtOAc in hexanes) to provide 7.4 g (61% over 2 steps) of 1-(tert-butyl) 3-methyl 3-((4-(trifluoromethyl)benzyl)amino)pyrrolidine-1,3-dicarboxylate as a white solid. LRMS (ES) m/z 403.15 (M+H).

3. Synthesis of Intermediate 6-4

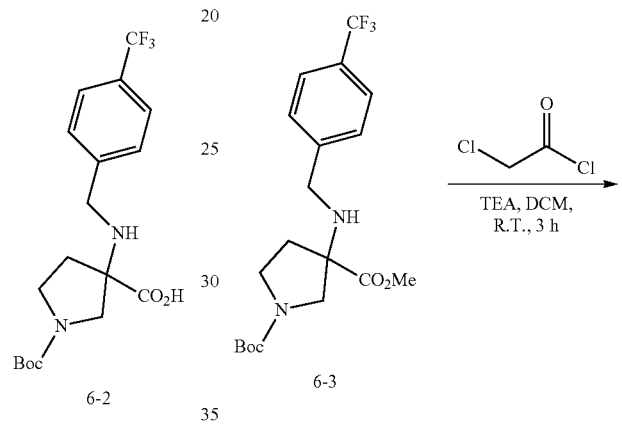

To a solution of 1-(tert-butyl) 3-methyl 3-((4-(trifluoromethyl)benzyl)amino) pyrrolidine-1,3-dicarboxylate (7.4 g, 18.4 mmol, 1.0 equiv) in DCM (50 mL) at 0° C. were added TEA (7.7 mL, 84.9 mmol, 3.0 equiv) and chloroacetyl chloride (2.9 mL, 36.8 mmol, 2.0 equiv). The ice bath was removed and the mixture was stirred for 3 h at r.t. The reaction was poured into saturated aqueous NH$_4$Cl (200 mL) solution and the layers were separated.

The aqueous layer was extracted with DCM (100 mL) three times. The combined organic layers were dried over MgSO$_4$ and concentrated to give an intermediate product, 1-(tert-butyl) 3-methyl 3-(2-chloro-N-(4-(trifluoromethyl)benzyl)acetamido)pyrrolidine-1,3-dicarboxylate. LRMS (ES) m/z 379.1 (M+H-Boc).

4. Synthesis of Intermediate 6-5

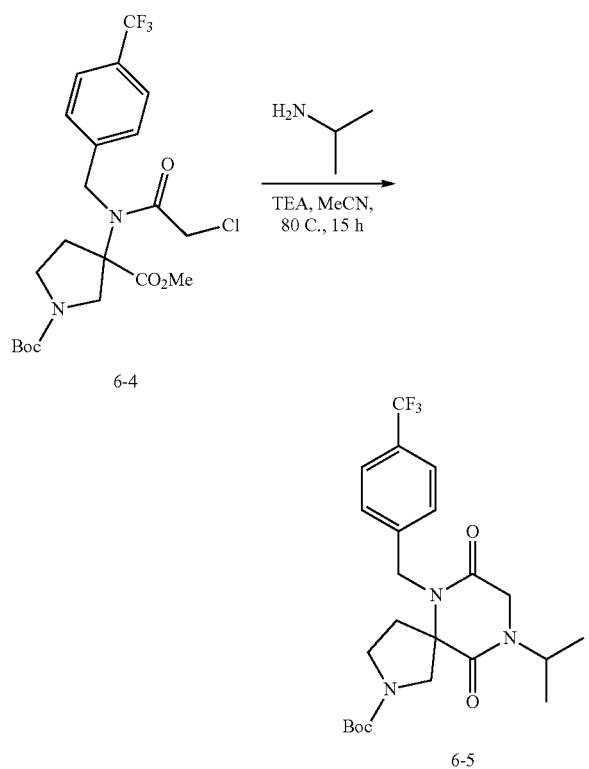

To a solution of 1-(tert-butyl) 3-methyl 3-(2-chloro-N-(4-(trifluoromethyl)benzyl)acetamido)pyrrolidine-1,3-dicarboxylate (18.4 mmol, 1.0 equiv assuming 100% yield) in ACN (300 mL) were added isopropylamine (4.7 mL, 55.1 mmol, 3.0 equiv) and TEA (7.7 mL, 55.1 mmol, 3.0 equiv). The mixture was heated at 80° C. for 15 h, concentrated, and purified by silica gel chromatography (80 g, 0-100% EtOAc in hexanes) to provide an intermediate product, tert-butyl 9-isopropyl-7,10-dioxo-6-(4-(trifluoromethyl)benzyl)-2,6,9-triazaspiro[4.5]decane-2-carboxylate as a colored solid. LRMS (ES) m/z 414.15 (M+H-$^t$Bu).

5. Synthesis of Intermediate 6-6

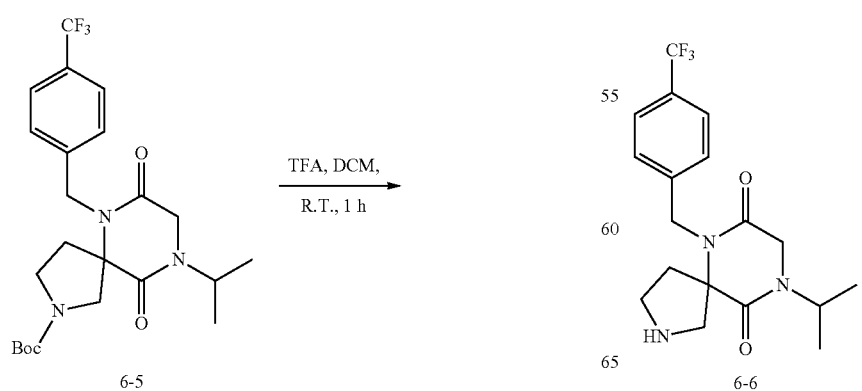

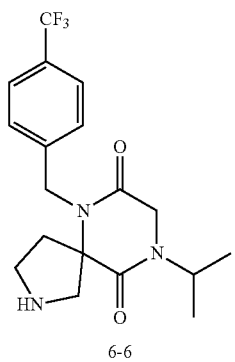

To a solution of tert-butyl 9-isopropyl-7,10-dioxo-6-(4-(trifluoromethyl)benzyl)-2,6,9-triazaspiro[4.5]decane-2-carboxylate (18.4 mmol, 1.0 equiv) from the previous step in DCM (40 mL) was added TFA (20 mL). The mixture was stirred for 1 h at r.t., concentrated, diluted with saturated NaHCO$_3$ (200 mL), and extracted with DCM three times. The combined organic layers were dried over MgSO$_4$, filtered, concentrated, and purified by silica gel chromatography (40 g column, 0-50% MeOH in DCM with 1% TEA) to provide 2.8 g (41% over 3 steps) of 9-isopropyl-6-(4-(trifluoromethyl)benzyl)-2,6,9-triazaspiro[4.5]decane-7,10-dione as a dark tacky solid. LRMS (ES) m/z 370.2 (M+H). (Dichloromethane-d$_2$, 400 MHz, ppm) δ 7.65-7.60 (m, 2H), 7.39-7.33 (m, 2H), 4.93-4.65 (m, 3H), 4.02 (s, 2H), 3.46-3.40 (m, 1H), 3.16 (ddd, J=11.3, 8.2, 5.3 Hz, 1H), 3.00 (ddd, J=11.3, 8.1, 6.7 Hz, 1H), 2.92 (d, J=12.1 Hz, 1H), 2.45 (ddd, J=13.6, 8.3, 6.7 Hz, 1H), 1.98 (ddd, J=13.5, 8.0, 5.2 Hz, 1H), 1.23 (d, J=6.8 Hz, 6H).

6. Synthesis of Compound 76

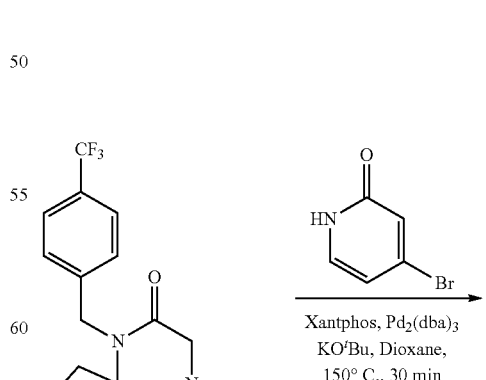

-continued

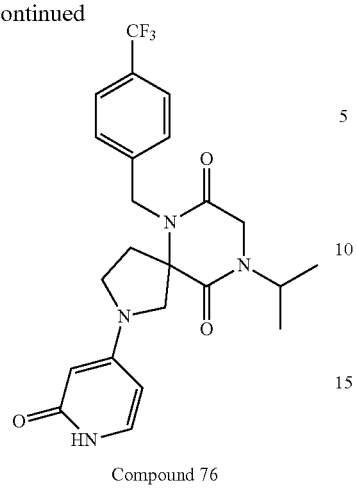

Compound 76

To a mixture of 9-isopropyl-6-(4-(trifluoromethyl)benzyl)-2,6,9-triazaspiro[4.5]decane-7,10-dione (50 mg, 0.14 mmol, 1.0 equiv), potassium tert-butoxide (61 mg, 0.54 mmol, 4.0 equiv), $Pd_2(dba)_3$ (12 mg, 0.014 mmol, 0.1 equiv), and xantphos (16 mg, 0.027 mmol, 0.2 equiv) combined in a 5 mL microwave vial (5 mL) were added 4-bromopyridin-2(1H)-one (47 mg, 0.27 mmol, 2.0 equiv) and dioxane (2 mL). The mixture was sealed and heated at 150° C. in the microwave reactor for 30 min, filtered, and purified by reverse phase HPLC (Phenomenex, gemini 5 μm C18 150×21.2 mm, 10-100% acetonitrile in water both with 0.1% formic acid gradient over 40 min) to afford 4.8 mg (8%) of 9-isopropyl-2-(2-oxo-1,2-dihydropyridin-4-yl)-6-(4-(trifluoromethyl)benzyl)-2,6,9-triazaspiro[4.5]decane-7,10-dione as a foamy solid. LRMS (ES) m/z 463.2 (M+H). (Methanol-$d_4$, 400 MHz, ppm) δ 8.18 (s, 1H), 7.62 (d, J=8.1 Hz, 2H), 7.41-7.36 (m, 2H), 7.20 (d, J=7.4 Hz, 1H), 5.88 (dd, J=7.4, 2.4 Hz, 1H), 5.30 (d, J=2.4 Hz, 1H), 4.99 (d, J=16.9 Hz, 1H), 4.79-4.68 (m, 2H), 4.23 (d, J=2.0 Hz, 2H), 3.88 (d, J=11.8 Hz, 1H), 3.66 (d, J=11.7 Hz, 1H), 3.57-3.49 (m, 2H), 2.67-2.46 (m, 2H), 1.26 (d, J=6.8 Hz, 6H).

The following compounds were prepared by methods analogous to the method described for Compound 76:

| Compound No. | LRMS (ES) m/z |
| --- | --- |
| 127 | M + H = 412 |
| 128 | M + H = 413 |
| 129 | M + H = 427 |
| 71 | M + H = 414 |
| 72 | M + H = 461.2 |
| 73 | M + H = 448.2 |
| 74 | M + H = 414 |
| 75 | M + H = 427 |
| 92 | M + H = 431 |
| 77 | M + H = 475.2 |
| 78 | M + H = 416 |
| 79 | M + H = 414 |
| 80 | M + H = 443 |
| 81 | M + H = 429 |
| 82 | M + H = 399.1 |
| 83 | M + H = 439.2 |
| 84 | M + H = 427.2 |
| 85 | M + H = 425.2 |
| 86 | M + H = 443.2 |
| 93 | M + H = 441.2 |
| 94 | M + H = 441.1 |
| 87 | M + H = 443.2 |
| 95 | M + H = 438.2 |
| 96 | M + H = 438.2 |

| Compound No. | LRMS (ES) m/z |
| --- | --- |
| 97 | M + H = 456.1 |
| 98 | M + H = 456.2 |
| 88 | M + H = 472.2 |
| 89 | M + H = 490.2 |
| 90 | M + H = 472.1 |
| 91 | M + H = 490.1 |

Example 7: Synthesis of Compound 49

1. Synthesis of Intermediate 7-2

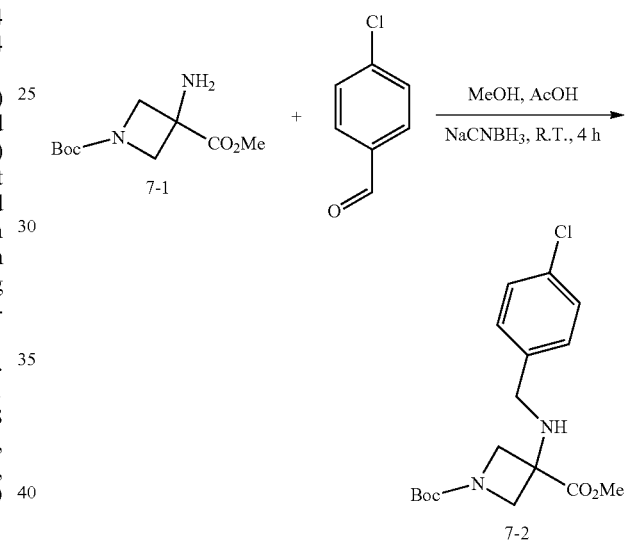

To a solution of 1-(tert-butyl) 3-methyl-3-aminoazetidine-1,3-dicarboxylate (5.0 g, 21.7 mmol, 1.0 equiv) in MeOH (50 mL) was added 4-chlorobenzaldehyde (4.5 g, 32.6 mmol, 1.5 equiv). The mixture was stirred for 1 h at r.t. To the mixture were added $NaCNBH_3$ (1.4 g, 21.7 mmol, 1.0 equiv) and AcOH (1 mL). The mixture was continued to stir for 4 h, concentrated under reduced pressure, and partitioned between DCM (60 mL) and saturated sodium bicarbonate (60 mL). The layers were separated, and the aqueous phase was extracted with DCM (25 mL). The combined organic layers were dried over sodium sulfate, filtered through celite, concentrated under reduced pressure, and purified by silica gel chromatography (80 g column, 0-100% EtOAc in hexanes) to provide 6.0 g (78%) of 1-(tert-butyl) 3-methyl 3-((4-chlorobenzyl)amino) azetidine-1,3-dicarboxylate. LRMS (ES) m/z 355.2 (M+H). $^1$H-NMR (Methylenechloride-$d_2$, 400 MHz, ppm) δ 7.35 (s, 4H), 4.19 (d, J=8.8 Hz, 2H), 3.86 (d, J=8.8 Hz, 2H), 3.82 (s, 3H), 3.68 (s, 2H), 1.46 (s, 9H).

2. Synthesis of Intermediate 7-3

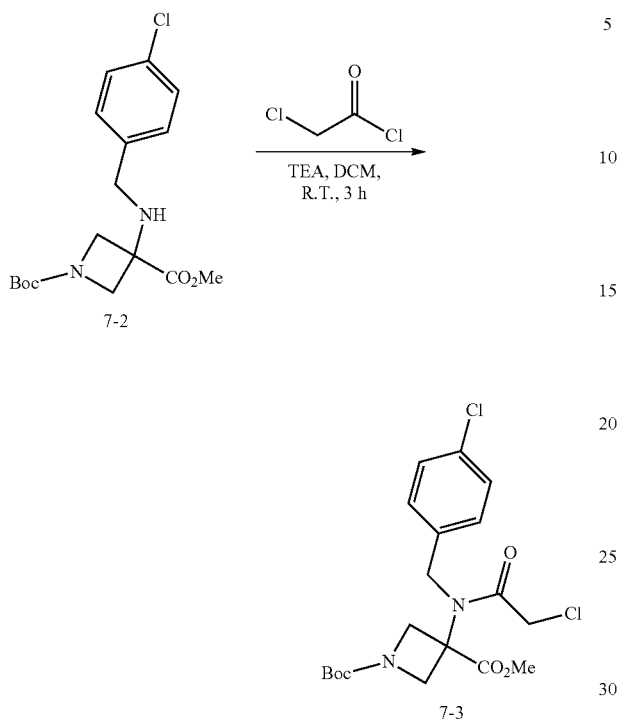

To a solution of 1-(tert-butyl) 3-methyl 3-((4-chlorobenzyl)amino)azetidine-1,3-dicarboxylate (6.0 g, 16.9 mmol, 1.0 equiv) in DCM (50 mL) cooled to 0° C. were added TEA (7.1 mL, 50.7 mmol, 3.0 equiv) and chloroacetyl chloride (2.7 mL, 33.8 mmol, 2.0 equiv). The mixture was stirred for 3 h at r.t and poured into saturated aqueous NH₄Cl (200 mL) solution. The aqueous layer was extracted with DCM (100 mL) three times. The combined organic layers were dried over MgSO₄ and concentrated to give an intermediate product, 1-(tert-butyl) 3-methyl 3-(2-chloro-N-(4-chlorobenzyl)acetamido)azetidine-1,3-dicarboxylate. LRMS (ES) m/z 431.1 (M+H).

3. Synthesis of Intermediate 7-4

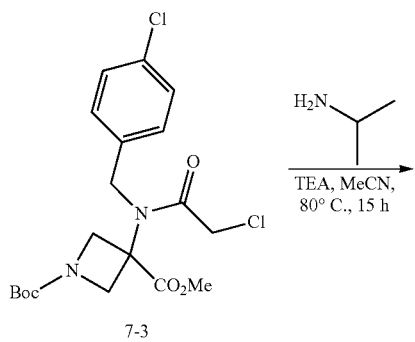

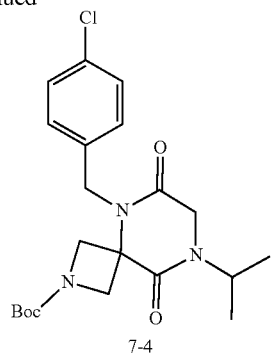

To a solution of 1-(tert-butyl) 3-methyl 3-(2-chloro-N-(4-chlorobenzyl)acetamido)azetidine-1,3-dicarboxylate (16.9 mmol, 1.0 equiv) in ACN (300 mL) were added isopropylamine (2.9 mL, 33.9 mmol, 2.0 equiv) and TEA (7.1 mL, 50.8 mmol, 3.0 equiv). The mixture was heated at 80° C. for 15 h, cooled to r.t., concentrated, and purified by silica gel chromatography (80 g, 0-100% EtOAc in hexanes) to provide 6.5 g (91%) of tert-butyl 5-(4-chlorobenzyl)-8-isopropyl-6,9-dioxo-2,5,8-triazaspiro[3.5]nonane-2-carboxylate as a colored solid. LRMS (ES) m/z 366.1 (M+H-ᵗBu).

4. Synthesis of Intermediate 7-5

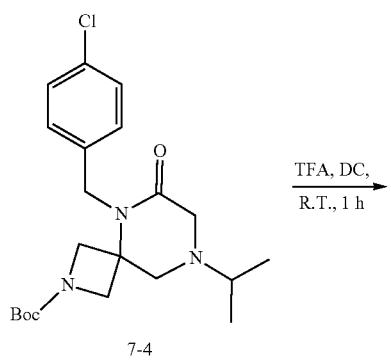

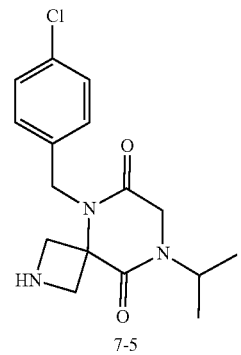

To a solution of tert-butyl 5-(4-chlorobenzyl)-8-isopropyl-6,9-dioxo-2,5,8-triazaspiro[3.5]nonane-2-carboxylate (6.5 g, 15.4 mmol, 1.0 equiv) in DCM (40 mL) was added TFA (12 mL). The mixture was stirred for 1 h at r.t., concentrated, diluted with saturated NaHCO₃ (200 mL), and extracted with DCM three times. The combined organic washes were dried over MgSO₄, filtered, concentrated, and purified by silica gel chromatography (40 g column, 0-50%

MeOH in DCM) to provide 4.1 g (83%) of 5-(4-chlorobenzyl)-8-isopropyl-2,5,8-triazaspiro[3.5]nonane-6,9-dione as an off-white solid. LRMS (ES) m/z 322.1 (M+H). $^1$H-NMR (Dichloromethane-$d_2$, 400 MHz, ppm) δ 7.36-7.32 (m, 2H), 7.28-7.24 (m, 2H), 5.16 (s, 2H), 4.85 (p, J=6.9 Hz, 1H), 4.30-4.19 (m, 4H), 4.00 (s, 2H), 1.24 (d, J=6.8 Hz, 6H).

5. Synthesis of Compound 49

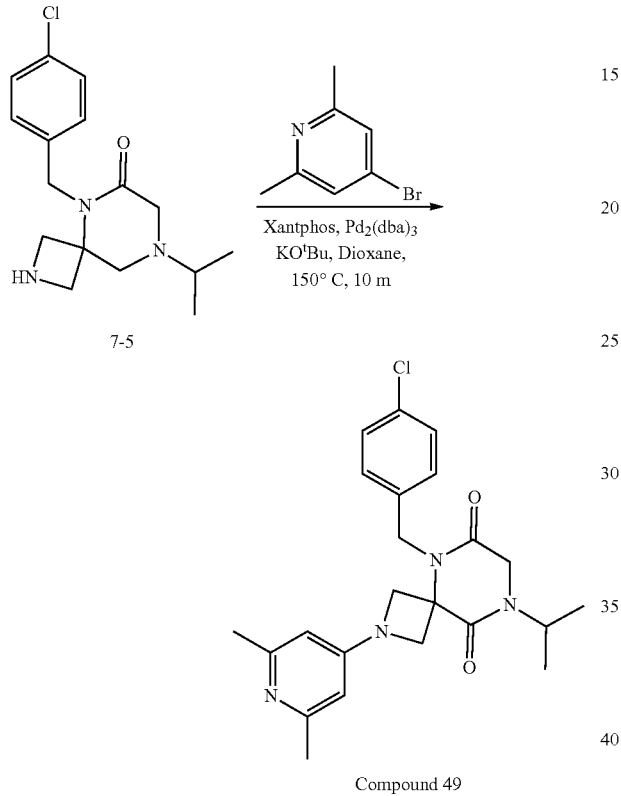

Compound 49

To a mixture of 5-(4-chlorobenzyl)-8-isopropyl-2,5,8-triazaspiro[3.5]nonane-6,9-dione (50 mg, 0.16 mmol, 1.0 equiv), potassium tert-butoxide (70 mg, 0.62 mmol, 4.0 equiv), Pd$_2$(dba)$_3$ (7 mg, 0.008 mmol, 0.05 equiv), and xantphos (9 mg, 0.016 mmol, 0.1 equiv) combined in a microwave vial (5 mL) were added 4-bromo-2,6-dimethylpyridine (58 mg, 0.31 mmol, 2.0 equiv) and dioxane (2 mL). The mixture was sealed, heated at 150° C. in the microwave reactor for 10 min, filtered, and purified by reverse phase HPLC (Phenomenex, gemini 5 μm C18 150× 21.2 mm, 10-100% acetonitrile in water both with 0.1% formic acid gradient over 40 min) to afford 7.1 mg (10%) of 5-(4-chlorobenzyl)-2-(2,6-dimethylpyridin-4-yl)-8-isopropyl-2,5,8-triazaspiro[3.5]nonane-6,9-dione as a white foamy solid. LRMS (ES) m/z 427.15 (M+H). (Methylenechloride-$d_2$, 400 MHz, ppm) δ 7.42-7.33 (m, 2H), 7.24-7.17 (m, 2H), 6.07 (s, 2H), 4.95 (s, 2H), 4.84 (p, J=6.9 Hz, 1H), 4.62 (dd, J=9.5, 1.1 Hz, 2H), 4.25 (dd, J=9.5, 1.1 Hz, 2H), 4.06 (s, 2H), 2.57 (s, 6H), 1.25 (d, J=6.8 Hz, 6H).

The following compounds were prepared by methods analogous to the method described for Compound 49:

| Compound No. | LRMS (ES) m/z |
|---|---|
| 2 | M + H = 398 |
| 3 | M + H = 416 |
| 4 | M + H = 432 |
| 5 | M + H = 432 |
| 6 | M + H = 399.1 |
| 7 | M + H = 399 |
| 8 | M + H = 399 |
| 9 | M + H = 413 |
| 10 | M + H = 413 |
| 11 | M + H = 400 |
| 12 | M + H = 400 |
| 13 | M + H = 413.1 |
| 14 | M + H = 413.1 |
| 15 | M + H = 413.1 |
| 16 | M + H = 413 |
| 17 | M + H = 417 |
| 18 | M + H = 417 |
| 19 | M + H = 400 |
| 21 | M + H = 402.2 |
| 22 | M + H = 405.1 |
| 23 | M + H = 400 |
| 24 | M + H = 400 |
| 25 | M + H = 400 |
| 26 | M + H = 402.2 |
| 27 | M + H = 424.1 |
| 28 | M + H = 415.1 |
| 29 | M + H = 449.1 |
| 30 | M + H = 393.2 |
| 31 | M + H = 447.2 |
| 32 | M + H = 405.1 |
| 33 | M + H = 405.1 |
| 34 | M + H = 439.1 |
| 35 | M + H = 457.2 |
| 36 | M + H = 443.1 |
| 37 | M + H = 442.1 |
| 38 | M + H = 456.2 |
| 39 | M + H = 473.1 |
| 40 | M + H = 448.1 |
| 41 | M + H = 388.1 |
| 42 | M + H = 429.3 |
| 43 | M + H = 419.1 |
| 44 | M + H = 419.1 |
| 45 | M + H = 404.1 |
| 46 | M + H = 433.2 |
| 47 | M + H = 461.1 |
| 48 | M + H = 449.1 |
| 50 | M + H = 434.1 |
| 51 | M + H = 430.2 |
| 52 | M + H = 416.1 |
| 53 | M + H = 468.1 |
| 54 | M + H = 443.1 |
| 55 | M + H = 414.2 |
| 56 | M + H = 434.1 |
| 57 | M + H = 444.1 |
| 58 | M + H = 484.2 |
| 59 | M + H = 472.2 |
| 60 | M + H = 434.1 |
| 61 | M + H = 434.1 |
| 62 | M + H = 498.2 |
| 63 | M + H = 424.2 |

Example 8: Synthesis of Compound 142

1. Synthesis of Intermediate 8-2

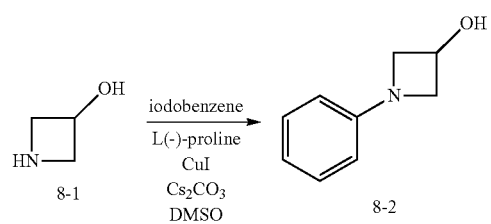 [SMILES: OC1CNC1 ; OC1CN(c2ccccc2)C1]

A mixture of azetin-3-ol hydrochloride (1.3 g, 11.9 mmol, 1.0 equiv), L(−)-proline (0.55 g, 4.8 mmol, 0.4 equiv), copper (I) iodide (0.45 g, 2.4 mmol, 0.2 equiv) and cesium carbonate (9.7 g, 29.7 mmol, 2.5 equiv) combined in a flask with a septum was vacuum-nitrogen purged 3 times. To this container were added iodobenzene (2.0 mL, 18 mmol, 1.5 equiv) and dry DMSO (30 mL). The mixture was heated at 90° C. for 15 h, diluted with water, and extracted with EA three times. The combined organic layers were dried over magnesium sulfate, filtered, evaporated, and purified by silica gel chromatography (40 g, 60 5 µm, 0-100% ethyl acetate in hexanes gradient over 14 min) to give 1.6 g (90%) of 1-phenylazetidin-3-ol as a clear colorless oil. LRMS (ES) m/z 150 (M+H). $^1$H NMR (400 MHz, Methylene Chloride-d$_2$) δ 7.27-7.20 (m, 2H), 6.81-6.74 (m, 1H), 6.55-6.49 (m, 2H), 4.80-4.72 (m, 1H), 4.23-4.16 (m, 2H), 3.71-3.65 (m, 2H).

2. Synthesis of Intermediate 8-3

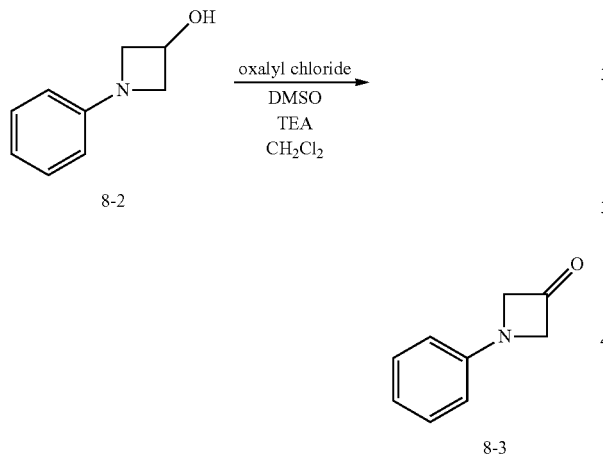

To a solution of oxalyl chloride (1.5 mL, 17 mmol, 1.7 equiv) in dry DCM (15 mL) was added DMSO (2.4 mL, 34 mmol, 3.3 equiv) dropwise at −78° C. The mixture was stirred for 10 min at −78° C., followed by addition of 1-phenylazetidin-3-ol (1.5 g, 10.3 mmol, 1.0 equiv) in dry DCM (15 mL) dropwise and stirred for 1 h. To this mixture at −78° C. was added TEA (10.0 mL, 71.9 mmol, 7.0 equiv). The mixture was continued to stir for 1 h at −78° C., diluted with saturated sodium bicarbonate, and extracted with DCM three times. The combined organic extractions were washed with brine, dried over magnesium sulfate, filtered, evaporated, and purified by silica gel chromatography (40 g, 60 um, 0-10% ethyl acetate in hexanes, gradient over 28 min) to give 0.96 g (63%) of 1-phenylazetidin-3-one as a clear yellow oil. LRMS (ES) m/z 148 (M+H). $^1$H NMR (400 MHz, Methylene Chloride-d$_2$) δ 7.36-7.29 (m, 2H), 6.92-6.87 (m, 1H), 6.69-6.63 (m, 2H), 4.70 (s, 4H).

3. Synthesis of Intermediate 8-4

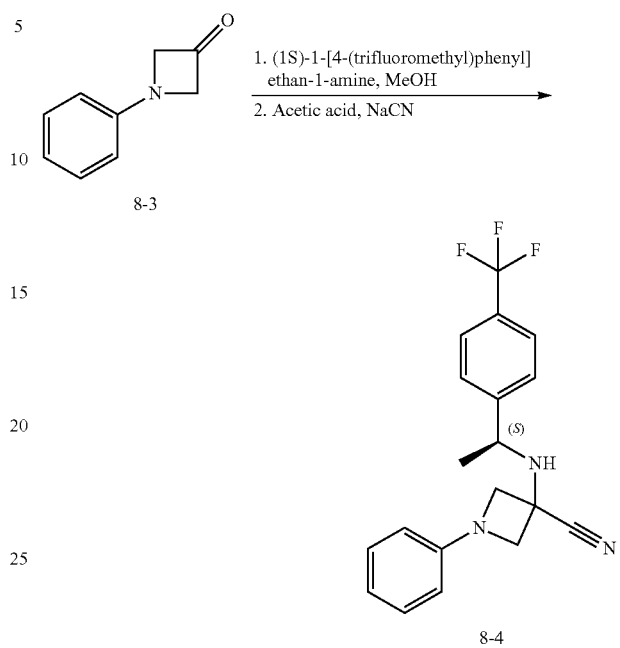

1-Phenylazetidin-3-one (0.31 g, 2.1 mmol, 1.0 equiv) and (1S)-1-[4-(trifluoromethyl)phenyl]ethan-1-amine (0.44 g, 2.3 mmol, 1.1 equiv) were combined in dry MeOH (3 mL) and the mixture was heated at 60° C. for 1 h. To this mixture cooled to 0° C. were added acetic acid (0.13 mL, 2.3 mmol, 1.1 equiv) and sodium cyanide (0.11 g, 2.3 mmol, 1.1 equiv) sequentially. The mixture was heated at 60° C. for 15 h, diluted with water, and extracted with EA three times. The combined organic washes were dried over magnesium sulfate, filtered, evaporated, and purified by silica gel chromatography (12 g, 60 um, 0-20% ethyl acetate in hexanes, gradient over 22 min) to give 0.46 g (62%) of (S)-1-phenyl-3-((1-(4-(trifluoromethyl)phenyl)ethyl)amino)azetidine-3-carbonitrile as a clear colorless oil. LRMS (ES) m/z 346 (M+H). $^1$H NMR (400 MHz, Methylene Chloride-d$_2$) δ 7.69-7.65 (m, 2H), 7.64-7.59 (m, 2H), 7.26-7.19 (m, 2H), 6.85-6.79 (m, 1H), 6.42-6.38 (m, 2H), 4.38-4.35 (m, 1H), 4.26 (q, J=6.6 Hz, 1H), 3.92-3.88 (m, 1H), 3.83-3.79 (m, 1H), 3.38-3.34 (m, 1H), 1.48 (d, J=6.6 Hz, 3H).

4. Synthesis of Intermediate 8-5

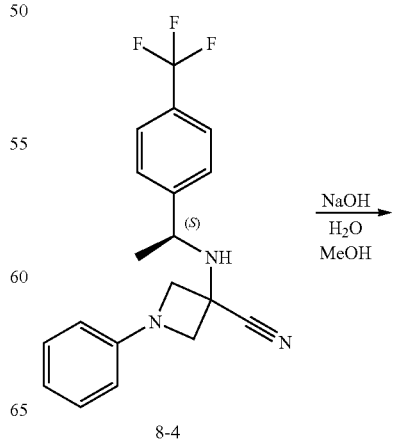

-continued

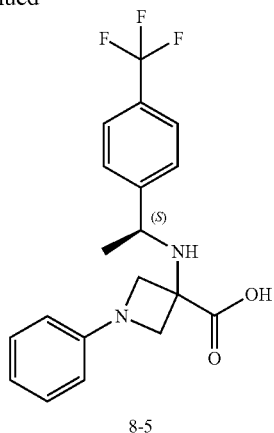

8-5

To a solution of (S)-1-phenyl-3-((1-(4-(trifluoromethyl)phenyl)ethyl)amino) azetidine-3-carbonitrile (0.20 g, 0.58 mmol, 1.0 equiv) in dry MeOH (2 mL) was added aqueous sodium hydroxide (1N, 1.2 mL, 1.2 mmol, 2.0 equiv). The mixture was heated at 100° C. for 15 h, cooled to r.t., neutralized with HCl (1M, 1.2 mL, 1.2 mmol, 2.0 equiv), and extracted with EA twice. The combined organic washes were dried over magnesium sulfate, filtered, and concentrated under reduced pressure to give 89 mg (42%) of (S)-1-phenyl-3-((1-(4-(trifluoromethyl)phenyl)ethyl) amino)azetidine-3-carboxylic acid as a pale yellow solid.

5. Synthesis of Intermediate 8-6

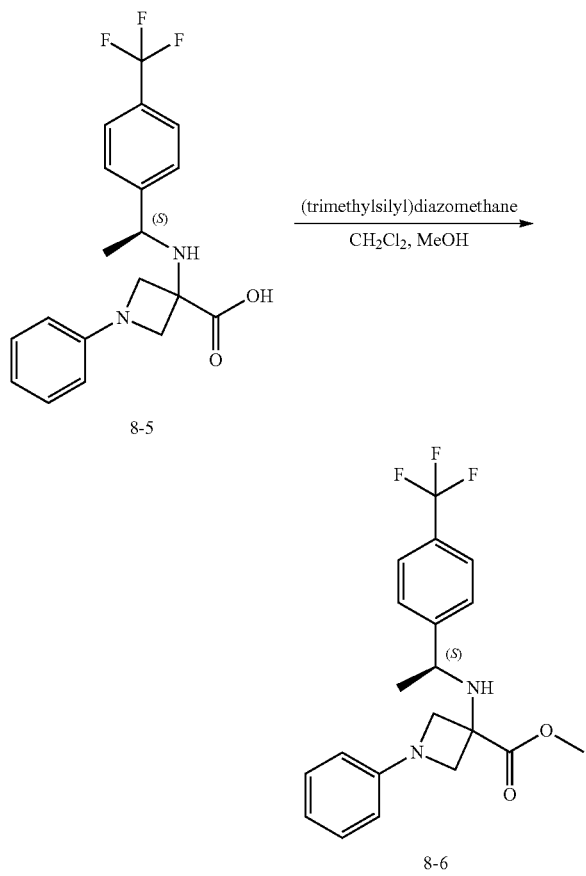

To a solution of (S)-1-Phenyl-3-((1-(4-(trifluoromethyl)phenyl)ethyl)amino) azetidine-3-carboxylic acid (89 mg, 0.24 mmol, 1.0 equiv) in a mixture of DCM (1 mL) and methanol (1 mL) was added (trimethylsilyl)diazomethane in hexanes (2 M, 0.37 mL, 0.74 mmol, 3.0 equiv) dropwise. The mixture was stirred at r.t. for 2 h, concentrated, and purified by silica gel chromatography (12 g, 60 micron, 0-30% ethyl acetate in hexanes, gradient over 22 min) to give 79 mg (86%) of methyl (S)-1-phenyl-3-((1-(4-(trifluoromethyl)phenyl)ethyl) amino)azetidine-3-carboxylate as a clear colorless oil. LRMS (ES) m/z 379 (M+H).

6. Synthesis of Intermediate 8-7

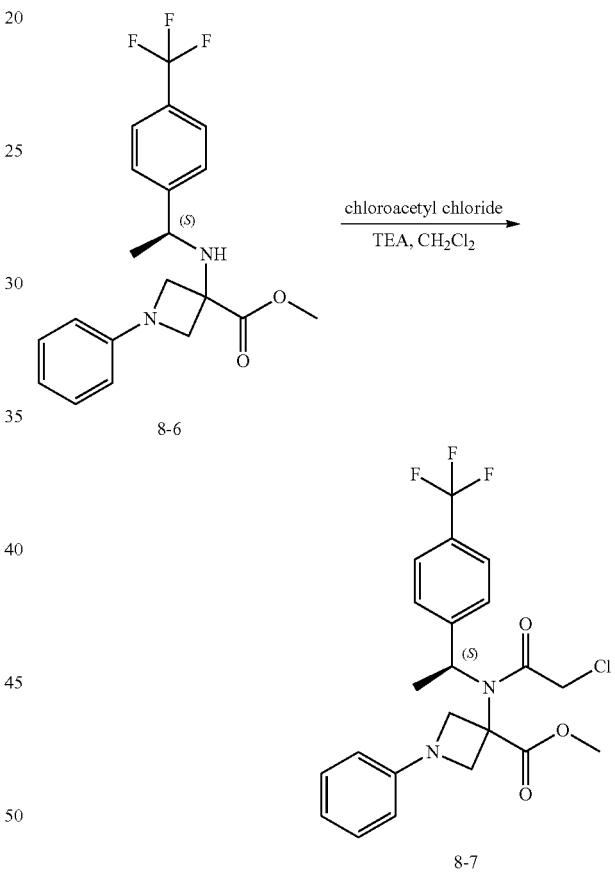

To a solution of methyl (S)-1-phenyl-3-((1-(4-(trifluoromethyl)phenyl)ethyl) amino)azetidine-3-carboxylate (79 mg, 0.21 mmol, 1.0 equiv) in DCM (1 mL) were added TEA (0.18 mL, 1.2 mmol, 6.0 equiv) and chloroacetyl chloride (0.067 mL, 0.84 mmol, 4.0 equiv) dropwise. The mixture was stirred for 30 min at r.t., diluted with saturated sodium bicarbonate, and extracted with DCM. The organic layer was dried over magnesium sulfate, filtered, and concentrated to give 140 mg of methyl (S)-3-(2-chloro-N-(1-(4-(trifluoromethyl)phenyl)ethyl)acetamido)-1-phenylazetidine-3-carboxylate as a red oil. LRMS (ES) m/z 455 (M+H).

7. Synthesis of Compound 142

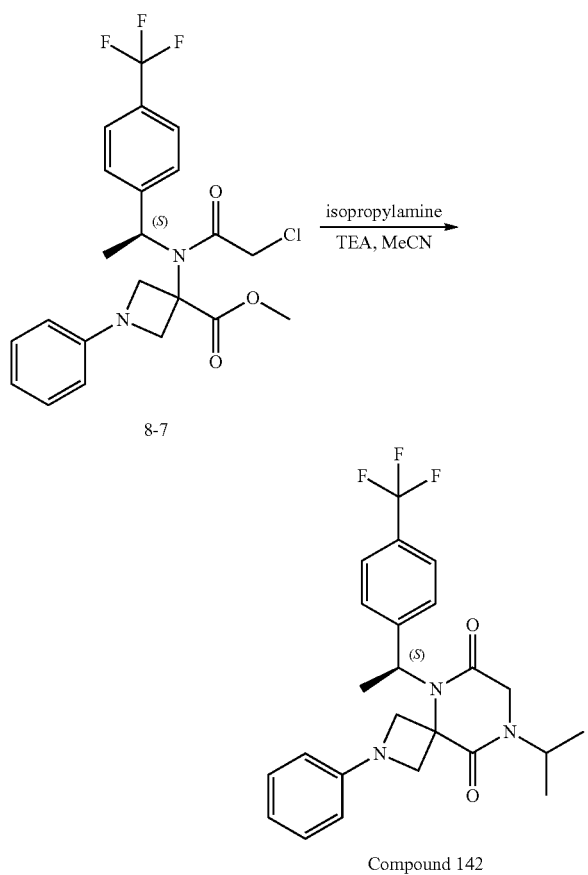

To a solution of methyl (S)-3-(2-chloro-N-(1-(4-(trifluoromethyl)phenyl)ethyl) acetamido)-1-phenylazetidine-3-carboxylate (0.21 mmol, 1.0 equiv) in dry ACN (7.5 mL) were added triethylamine (0.13 mL, 0.94 mmol, 4.5 equiv) and isopropylamine (0.053 mL, 0.62 mmol, 3.0 equiv). The mixture was heated at 80° C. for 15 h, concentrated, and purified by reverse phase HPLC (Phenomenex, gemini 5u C18 150×21.2 mm, 10-100% acetonitrile in water both with 0.1% formic acid gradient over 25 min) to give 19 mg (20% over 2 steps) of (S)-8-isopropyl-2-phenyl-5-(1-(4-(trifluoromethyl)phenyl)ethyl)-2,5,8-triazaspiro[3.5]nonane-6,9-dione. LRMS (ES) m/z 446 (M+H). $^1$H NMR (400 MHz, Methanol-d$_4$) δ 7.67-7.62 (m, 2H), 7.60-7.55 (m, 2H), 7.22-7.16 (m, 2H), 6.79-6.73 (m, 1H), 6.49-6.44 (m, 2H), 5.74-5.65 (m, 1H), 4.73 (hept, J=6.8 Hz, 1H), 4.46-4.41 (m, 1H), 4.37-4.32 (m, 1H), 4.27-4.21 (m, 1H), 4.13-4.09 (m, 1H), 4.07-3.96 (m, 2H), 2.01 (d, J=7.0 Hz, 3H), 1.23 (d, J=6.8 Hz, 6H).

The following compounds were prepared by methods analogous to the method described for Compound 142:

| Compound No. | LRMS (ES) m/z |
| --- | --- |
| 138 | M + H = 447.2 |
| 139 | M + H = 427.2 |
| 140 | M + H = 446.2 |
| 141 | M + H = 446.2 |

Example 9: Synthesis of Compound 327

1. Synthesis of Intermediate 9-2

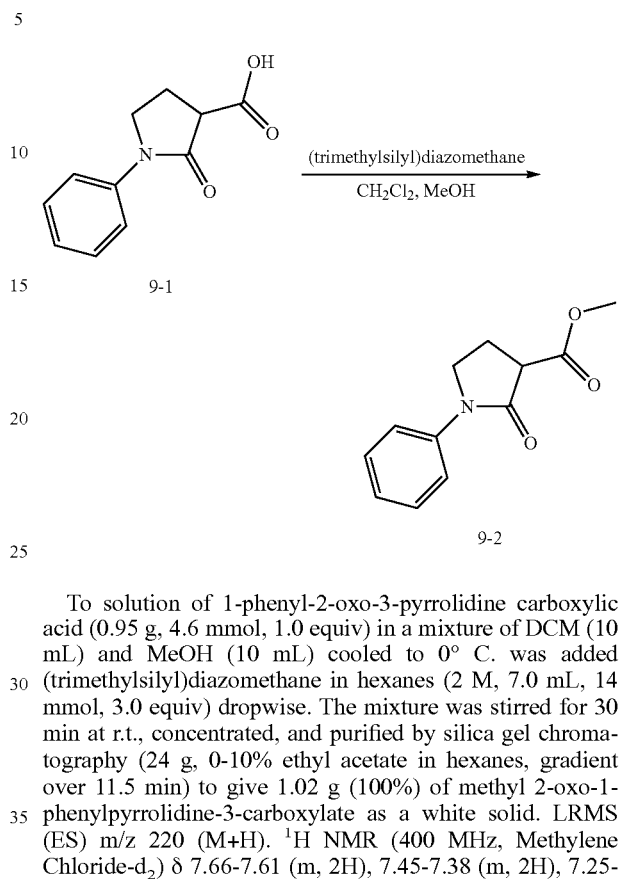

To solution of 1-phenyl-2-oxo-3-pyrrolidine carboxylic acid (0.95 g, 4.6 mmol, 1.0 equiv) in a mixture of DCM (10 mL) and MeOH (10 mL) cooled to 0° C. was added (trimethylsilyl)diazomethane in hexanes (2 M, 7.0 mL, 14 mmol, 3.0 equiv) dropwise. The mixture was stirred for 30 min at r.t., concentrated, and purified by silica gel chromatography (24 g, 0-10% ethyl acetate in hexanes, gradient over 11.5 min) to give 1.02 g (100%) of methyl 2-oxo-1-phenylpyrrolidine-3-carboxylate as a white solid. LRMS (ES) m/z 220 (M+H). $^1$H NMR (400 MHz, Methylene Chloride-d$_2$) δ 7.66-7.61 (m, 2H), 7.45-7.38 (m, 2H), 7.25-7.19 (m, 1H), 4.02-3.95 (m, 1H), 3.91-3.84 (m, 1H), 3.81 (s, 3H), 3.68-3.63 (m, 1H), 2.59-2.50 (m, 1H), 2.48-2.38 (m, 1H).

2. Synthesis of Intermediate 9-3

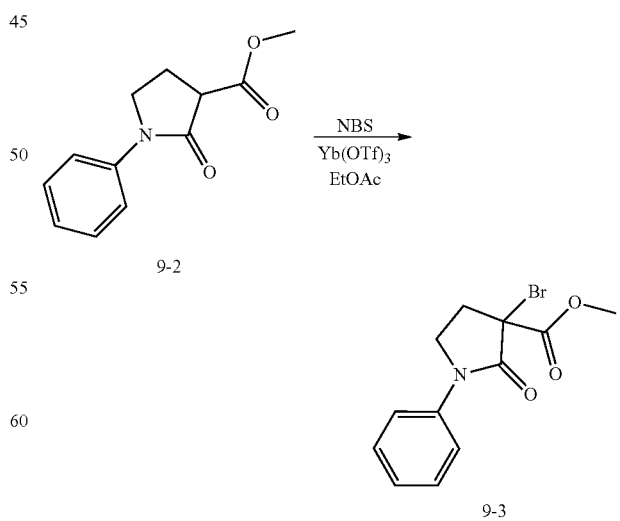

To a mixture of methyl 2-oxo-1-phenylpyrrolidine-3-carboxylate (0.30 g, 1.4 mmol, 1.0 equiv) and ytterbium (III)

trifluoromethane sulfonate (0.255 g, 0.41 mmol, 0.30 equiv) in EA (9 mL) was added NBS (0.244 g, 1.4 mmol, 1.0 equiv). The mixture was stirred for 30 min at r.t., concentrated, and purified by silica gel chromatography (24 g, 0-30% Ethyl acetate in hexanes, gradient over 11.5 min) to give 408 mg (100%) of 3-bromo-2-oxo-1-phenylpyrrolidine-3-carboxylate as a white solid. LRMS (ES) m/z 298 (M+H). $^1$H NMR (400 MHz, Methylene Chloride-$d_2$) δ 7.68-7.62 (m, 2H), 7.48-7.42 (m, 2H), 7.30-7.24 (m, 1H), 4.04-3.97 (m, 1H), 3.94-3.88 (m, 4H), 3.19-3.10 (m, 1H), 2.72-2.64 (m, 1H).

3. Synthesis of Intermediate 9-4

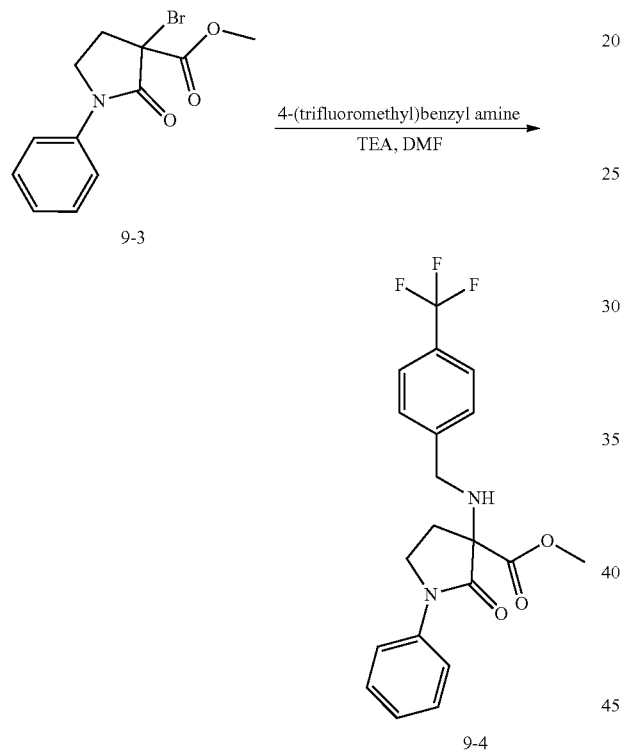

To a solution of 3-bromo-2-oxo-1-phenylpyrrolidine-3-carboxylate (0.113 g, 0.38 mmol, 1.0 equiv) in DMF (1 mL) were added TEA (0.21 mL, 1.5 mmol, 4.0 equiv) and 4-(trifluoromethyl)benzyl amine (0.11 mL, 0.76 mmol, 2.0 equiv). The mixture was stirred for 15 min at r.t., heated at 50° C. for 1 h, diluted with water, and extracted with EA three times. The combined organic extractions were washed once with brine, dried over magnesium sulfate, filtered, concentrated, purified by silica gel chromatography (12 g, 60 um, 0-40% ethyl acetate in hexanes, gradient over 22 min), and purified again by silica gel chromatography (12 g, 60 um, 0-30% ethyl acetate in hexanes, gradient over 22 min) to give 24 mg (16%) of methyl 2-oxo-1-phenyl-3-((4-(trifluoromethyl)benzyl)amino)pyrrolidine-3-carboxylate as a clear colorless oil. LRMS (ES) m/z 393 (M+H). $^1$H NMR (400 MHz, Methylene Chloride-$d_2$) δ 7.59-7.54 (m, 2H), 7.54-7.49 (m, 2H), 7.49-7.44 (m, 2H), 7.35-7.29 (m, 2H), 7.15-7.09 (m, 1H), 3.95-3.84 (m, 2H), 3.81-3.69 (m, 5H), 2.68-2.61 (m, 1H), 2.24-2.14 (m, 1H).

4. Synthesis of Intermediate 9-5

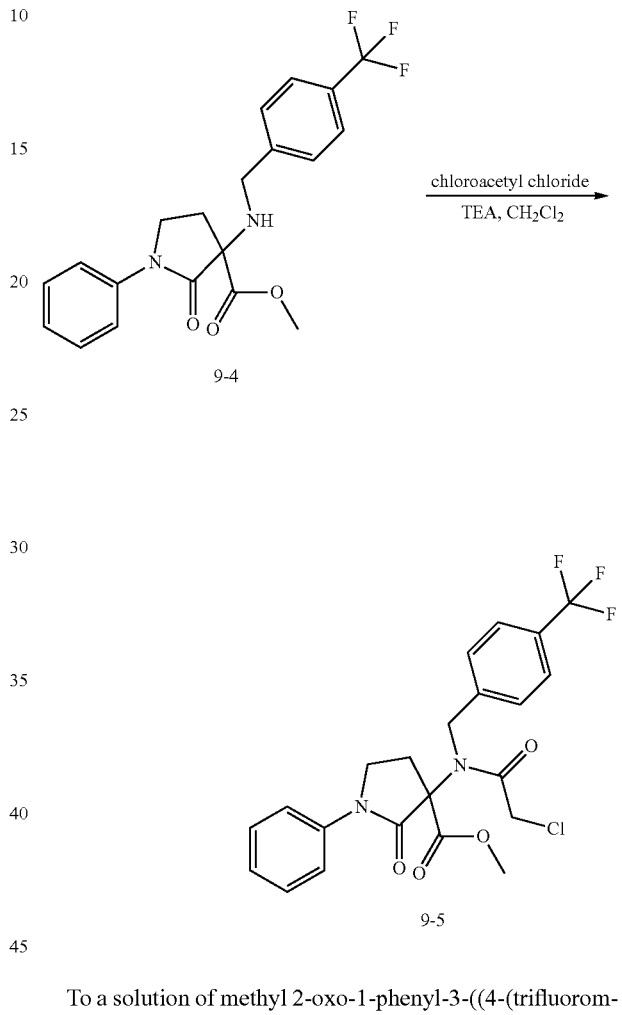

To a solution of methyl 2-oxo-1-phenyl-3-((4-(trifluoromethyl)benzyl)amino) pyrrolidine-3-carboxylate (0.024 g, 0.061 mmol, 1.0 equiv) in DCM (1 mL) were added TEA (0.051 mL, 0.36 mmol, 6.0 equiv) and chloroacetyl chloride (0.022 mL, 0.24 mmol, 4.0 equiv). The mixture was stirred for 15 minutes. To this mixture were added additional TEA (0.051 mL, 0.36 mmol, 6.0 equiv) and chloroacetyl chloride (0.022 mL, 0.24 mmol, 4.0 equiv) twice. The mixture was stirred for 15 minutes, diluted with dichloroethane (2 mL), heated at 83° C. overnight, cooled to r.t., diluted with saturated sodium bicarbonate, and extracted with DCM three times. The combined organic extractions were then washed once with brine, dried over magnesium sulfate, filtered, and concentrated to give 29 mg (quantitative) of methyl 3-(2-chloro-N-(4-(trifluoromethyl)benzyl)acetamido)-2-oxo-1-phenylpyrrolidine-3-carboxylate as a brown solid. LRMS (ES) m/z 469 (M+H).

5. Synthesis of Compound 327

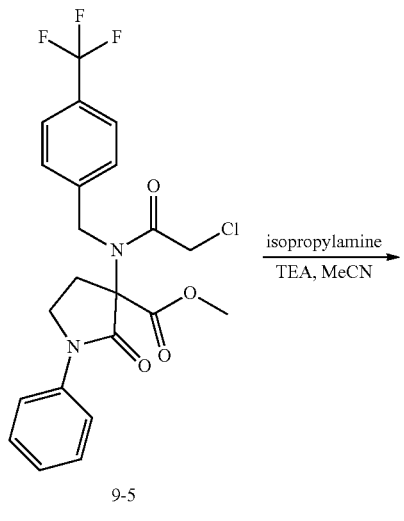

9-5 isopropylamine
TEA, MeCN
→

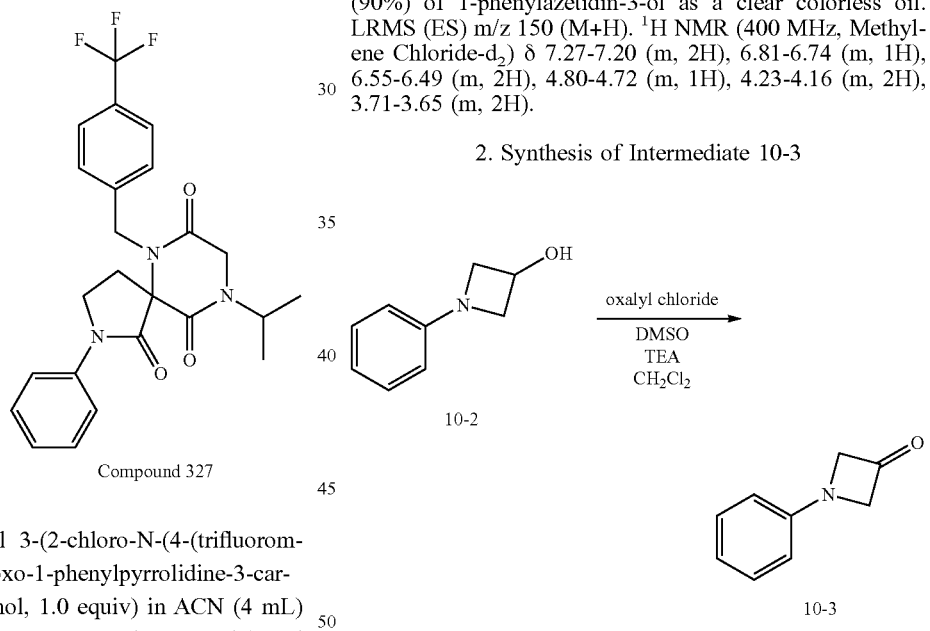

Compound 327

To a solution of methyl 3-(2-chloro-N-(4-(trifluoromethyl)benzyl)acetamido)-2-oxo-1-phenylpyrrolidine-3-carboxylate (29 mg, 0.079 mmol, 1.0 equiv) in ACN (4 mL) were added TEA (0.067 mL, 0.48 mmol, 7.8 equiv) and isopropylamine (0.027 mL, 0.32 mmol, 6.3 equiv). The mixture was heated at 80° C. for 1 h, concentrated, and purified by reverse phase HPLC (Phenomenex, gemini 5u C18 150×21.2 mm, 10-100% acetonitrile in water both with 0.1% formic acid gradient over 25 min) to give 15 mg (20%) of 9-isopropyl-2-phenyl-6-(4-(trifluoromethyl)benzyl)-2,6,9-triazaspiro[4.5]decane-1,7,10-trione as a clear colorless oil. LRMS (ES) m/z 460 (M+H). $^1$H NMR (400 MHz, Methanol-$d_4$) δ 7.64-7.59 (m, 2H), 7.57-7.53 (m, 2H), 7.53-7.49 (m, 2H), 7.42-7.36 (m, 2H), 7.27-7.21 (m, 1H), 4.99-4.92 (m, 1H), 4.76-4.67 (m, 2H), 4.33-4.16 (m, 2H), 4.16-4.08 (m, 1H), 3.87-3.78 (m, 1H), 2.86-2.77 (m, 1H), 2.59-2.48 (m, 1H), 1.28-1.20 (m, 6H).

Example 10: Synthesis of Compound 328

1. Synthesis of Intermediate 10-2

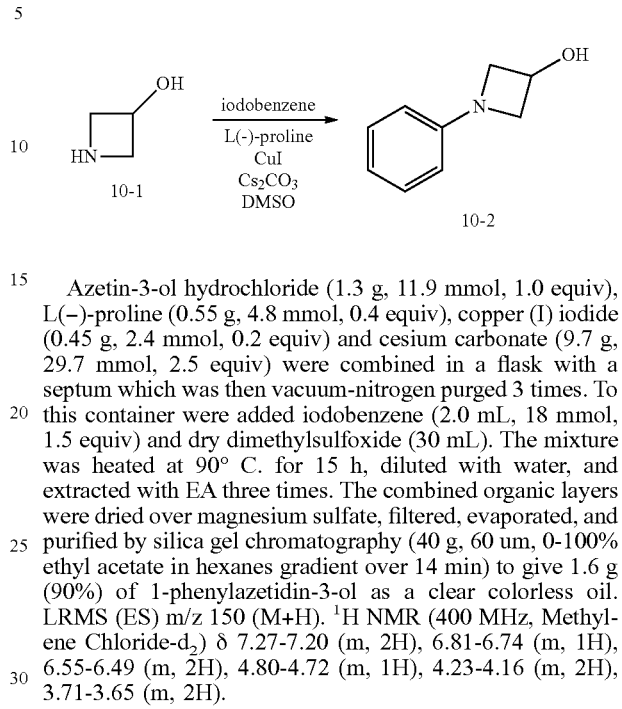

Azetin-3-ol hydrochloride (1.3 g, 11.9 mmol, 1.0 equiv), L(−)-proline (0.55 g, 4.8 mmol, 0.4 equiv), copper (I) iodide (0.45 g, 2.4 mmol, 0.2 equiv) and cesium carbonate (9.7 g, 29.7 mmol, 2.5 equiv) were combined in a flask with a septum which was then vacuum-nitrogen purged 3 times. To this container were added iodobenzene (2.0 mL, 18 mmol, 1.5 equiv) and dry dimethylsulfoxide (30 mL). The mixture was heated at 90° C. for 15 h, diluted with water, and extracted with EA three times. The combined organic layers were dried over magnesium sulfate, filtered, evaporated, and purified by silica gel chromatography (40 g, 60 um, 0-100% ethyl acetate in hexanes gradient over 14 min) to give 1.6 g (90%) of 1-phenylazetidin-3-ol as a clear colorless oil. LRMS (ES) m/z 150 (M+H). $^1$H NMR (400 MHz, Methylene Chloride-$d_2$) δ 7.27-7.20 (m, 2H), 6.81-6.74 (m, 1H), 6.55-6.49 (m, 2H), 4.80-4.72 (m, 1H), 4.23-4.16 (m, 2H), 3.71-3.65 (m, 2H).

2. Synthesis of Intermediate 10-3

To a solution of oxalyl chloride (1.5 mL, 17 mmol, 1.7 equiv) in dry DCM (15 mL) was added DMSO (2.4 mL, 34 mmol, 3.3 equiv) dropwise at −78° C. The mixture was stirred for 10 min at −78° C. and added 1-phenylazetidin-3-ol (1.5 g, 10.3 mmol, 1.0 equiv) in dry DCM (15 mL) dropwise, stirred for 1 h, added TEA (10.0 mL, 71.9 mmol, 7.0 equiv), continued to stir for 1 h at −78° C., diluted with saturated sodium bicarbonate, and extracted with DCM three times. The combined organic extractions were washed with brine, dried over magnesium sulfate, filtered, evaporated, and purified by silica gel chromatography (40 g, 60 um, 0-10% ethyl acetate in hexanes, gradient over 28 min) to give 0.96 g (63%) of 1-phenylazetidin-3-one as a clear yellow oil. LRMS (ES) m/z 148 (M+H). $^1$H NMR (400 MHz, Methylene Chloride-$d_2$) δ 7.36-7.29 (m, 2H), 6.92-6.87 (m, 1H), 6.69-6.63 (m, 2H), 4.70 (s, 4H).

3. Synthesis of Intermediate 10-4

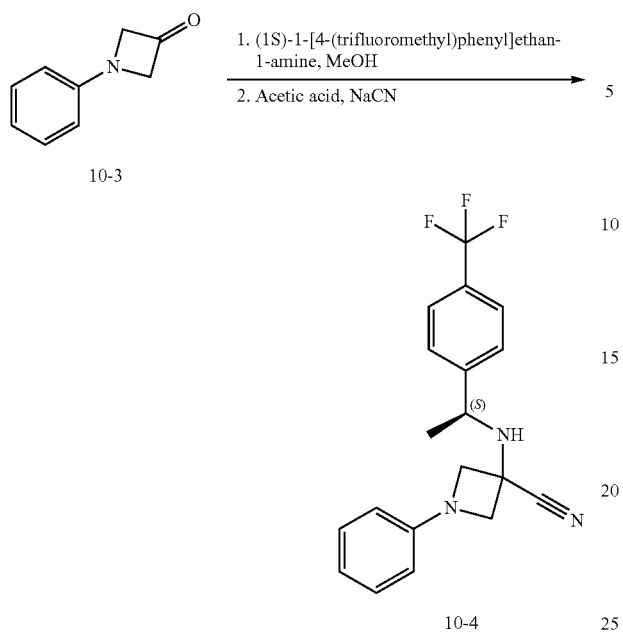

1-Phenylazetidin-3-one (0.31 g, 2.1 mmol, 1.0 equiv) and (1S)-1-[4-(trifluoromethyl)phenyl]ethan-1-amine (0.44 g, 2.3 mmol, 1.1 equiv) were combined in dry MeOH (3 mL) and the mixture was heated at 60° C. for 1 h. To this mixture cooled to 0° C. were added acetic acid (0.13 mL, 2.3 mmol, 1.1 equiv) and sodium cyanide (0.11 g, 2.3 mmol, 1.1 equiv) sequentially. The mixture was heated at 60° C. for 15 h, diluted with water, and extracted with EA three times. The combined organic washes were dried over magnesium sulfate, filtered, evaporated, and purified by silica gel chromatography (12 g, 60 um, 0-20% ethyl acetate in hexanes, gradient over 22 min) to give 0.46 g (62%) of (S)-1-phenyl-3-((1-(4-(trifluoromethyl)phenyl)ethyl)amino)azetidine-3-carbonitrile as a clear colorless oil. LRMS (ES) m/z 346 (M+H). $^1$H NMR (400 MHz, Methylene Chloride-d$_2$) δ 7.69-7.65 (m, 2H), 7.64-7.59 (m, 2H), 7.26-7.19 (m, 2H), 6.85-6.79 (m, 1H), 6.42-6.38 (m, 2H), 4.38-4.35 (m, 1H), 4.26 (q, J=6.6 Hz, 1H), 3.92-3.88 (m, 1H), 3.83-3.79 (m, 1H), 3.38-3.34 (m, 1H), 1.48 (d, J=6.6 Hz, 3H).

4. Synthesis of Intermediate 10-5

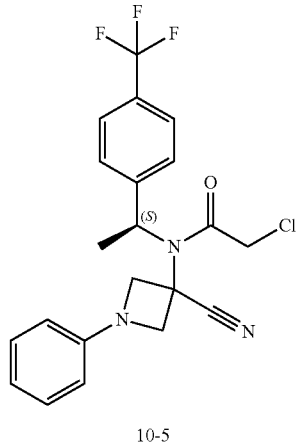

To a solution of (S)-1-phenyl-3-((1-(4-(trifluoromethyl)phenyl)ethyl)amino) azetidine-3-carbonitrile (0.272 g, 0.787 mmol, 1.0 equiv) in DCM (3 mL) were added TEA (0.33 mL, 2.4 mmol, 3.0 equiv) and chloroacetyl chloride (0.12 mL, 1.6 mmol, 2.0 equiv) dropwise. The mixture was stirred for 15 min. To this mixture were added TEA (0.33 mL, 2.4 mmol, 3.0 equiv) and chloroacetyl chloride (0.12 mL, 1.6 mmol, 2.0 equiv). The mixture was stirred for 30 min, diluted with saturated sodium bicarbonate, and extracted with DCM twice. The combined extractions were dried over magnesium sulfate, filtered, and concentrated to give 332 mg (100%) of (S)-2-chloro-N-(3-cyano-1-phenylazetidin-3-yl)-N-(1-(4-(trifluoromethyl)phenyl)ethyl)acetamide as a red oil. LRMS (ES) m/z 422 (M+H). $^1$H NMR (400 MHz, Methylene Chloride-d$_2$) δ 7.72-7.67 (m, 2H), 7.59-7.54 (m, 2H), 7.28-7.21 (m, 2H), 6.89-6.84 (m, 1H), 6.45-6.41 (m, 2H), 5.19-5.11 (m, 1H), 4.49-4.45 (m, 1H), 4.42-4.39 (m, 1H), 4.07-3.94 (m, 3H), 3.83-3.79 (m, 1H), 1.96 (d, J=7.1 Hz, 3H).

5. Synthesis of Intermediate 10-6

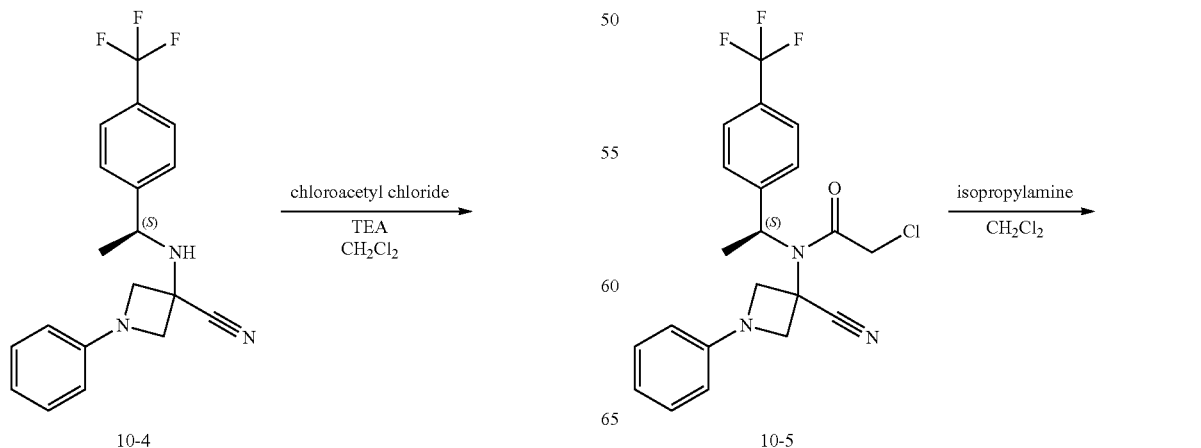

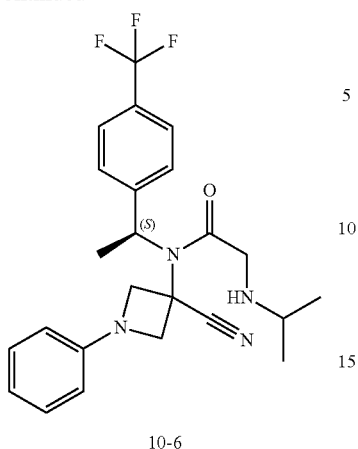

10-6

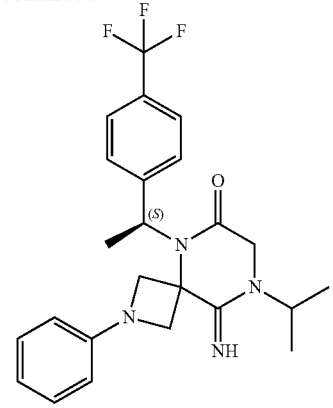

Compound 328

To a solution of (S)-2-chloro-N-(3-cyano-1-phenylazetidin-3-yl)-N-(1-(4-(trifluoromethyl)phenyl)ethyl)acetamide (0.332 g, 0.787 mmol, 1.0 equiv) in dry DCM (3 mL) was added isopropylamine (3.4 mL, 39 mmol, 50 equiv). The mixture was stirred for 3 days at r.t., concentrated, and purified by silica gel chromatography (12 g, 60 um, 0-10% methanol in dichloromethane, gradient over 22 min) to give 314 mg (90%) of (S)—N-(3-cyano-1-phenylazetidin-3-yl)-2-(isopropylamino)-N-(1-(4-(trifluoromethyl)phenyl)ethyl)acetamide as a clear slightly yellow oil. LRMS (ES) m/z 445 (M+H). $^1$H NMR (400 MHz, Methylene Chloride-$d_2$) δ 7.64-7.60 (m, 2H), 7.43-7.38 (m, 2H), 7.24-7.18 (m, 2H), 6.82-6.77 (m, 1H), 6.43-6.39 (m, 2H), 5.90-5.80 (m, 1H), 4.60-4.46 (m, 1H), 4.41-4.35 (m, 1H), 4.30-4.21 (m, 1H), 4.07-3.99 (m, 2H), 3.90-3.83 (m, 1H), 3.79-3.73 (m, 1H), 1.87 (d, J=7.2 Hz, 3H), 1.28-1.21 (m, 6H).

6. Synthesis of Compound 328

To a solution of (S)—N-(3-Cyano-1-phenylazetidin-3-yl)-2-(isopropylamino)-N-(1-(4-(trifluoromethyl)phenyl)ethyl)acetamide (54 mg, 0.12 mmol, 1.0 equiv) in dry toluene (0.5 mL) was heated to 150° C. in the microwave reactor for 30 min. The mixture was concentrated and purified by reverse phase HPLC (Phenomenex, gemini 5u C18 150×21.2 mm, 10-100% acetonitrile in water both with 0.1% formic acid gradient over 25 min) to give 28 mg (52%) of (S)-9-imino-8-isopropyl-2-phenyl-5-(1-(4-(trifluoromethyl)phenyl)ethyl)-2,5,8-triazaspiro[3.5]nonan-6-one as a clear colorless oil. LRMS (ES) m/z 445 (M+H). $^1$H NMR (400 MHz, Methanol-$d_4$) δ 8.38 (s, 1H), 7.69-7.63 (m, 2H), 7.56-7.50 (m, 2H), 7.25-7.19 (m, 2H), 6.89-6.82 (m, 1H), 6.56-6.48 (m, 2H), 5.73-5.61 (m, 1H), 4.54-4.45 (m, 2H), 4.32-4.14 (m, 5H), 1.86 (d, J=7.1 Hz, 3H), 1.46-1.39 (m, 6H).

Example 11: Synthesis of Compound 332

1. Synthesis of Intermediate 11-2

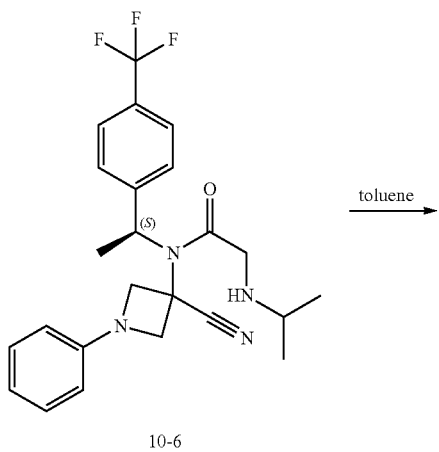

10-6

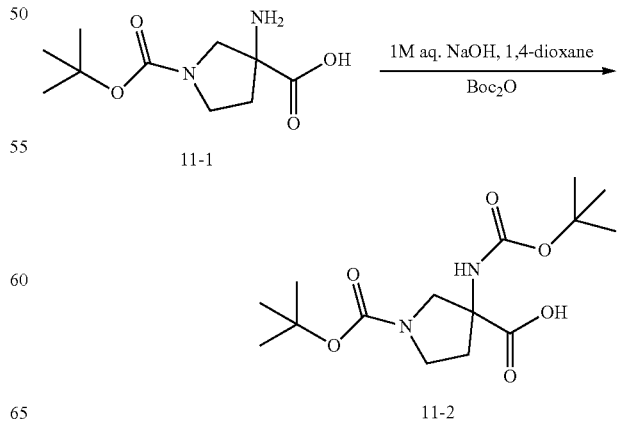

To a solution of racemic 3-amino-1-(tert-butoxycarbonyl)pyrrolidine-3-carboxylic acid (2.00 g, 8.69 mmol) in NaOH (1 M, 15 mL) was added di-tert-butyl dicarbonate (3.79 g, 17.37 mmol, 2.0 equiv.) in 1,4-dioxane (15 mL). The resulting mixture was stirred at r.t. for 18 h. The pH was adjusted to 3 using 3 M aqueous HCl, and the resulting mixture was extracted twice with EA (total volume=125 mL). The organic extracts were combined, washed with brine, dried over sodium sulfate, and concentrated under reduced pressure to provide 1-(tert-butoxycarbonyl)-3-((tert-butoxycarbonyl)amino)pyrrolidine-3-carboxylic acid (2.93 g, 7.98 mmol, 92% yield) as a sticky foam which was used in the following step without additional purification. LRMS (APCI) m/z 329.1 (M−H). $^1$H NMR (400 MHz, DMSO-$d_6$) δ 12.68 (s, 1H), 7.54 (s, 1H), 3.74-3.66 (m, 1H), 3.51 (dd, J=20.3, 11.4 Hz, 1H), 3.34-3.26 (m, 2H), 2.21-2.04 (m, 2H), 1.39 (s, 18H).

2. Synthesis of Intermediate 11-3

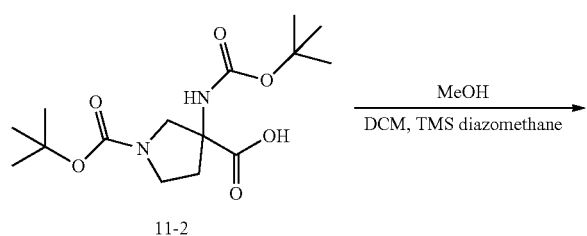

To a solution of 1-(tert-butoxycarbonyl)-3-((tert-butoxycarbonyl)amino)pyrrolidine-3-carboxylic acid (2.93 g, 7.98 mmol) in a mixture of DCM (40 mL) and MeOH (20 mL) was added (diazomethyl)trimethylsilane (11.97 mL of 2.0 M in hexanes, 23.95 mmol, 3.0 equiv.) portionwise. The resulting solution was stirred at r.t. for 30 minutes, quenched with glacial acetic acid (1 mL) until gas evolution ceased, and concentrated under reduced pressure. The remaining residue was dissolved in DCM (100 mL) and washed with 2 M aqueous $K_2CO_3$ (25 mL). The organic phase was dried over sodium sulfate, concentrated, and purified with silica gel using 30% EA/Hex to give the 2.12 g (77%) of 1-(tert-butyl) 3-methyl 3-((tert-butoxycarbonyl)amino)pyrrolidine-1,3-dicarboxylate as a colorless sticky solid. LRMS (APCI) m/z 245.2 (M+H) (Boc loss). $^1$H NMR (400 MHz, Methanol-$d_4$) δ 3.84-3.75 (m, 1H), 3.64 (s, 3H), 3.57-3.44 (m, 1H), 3.43-3.30 (m, 2H), 2.24-2.13 (m, 1H), 2.12-2.02 (m, 1H), 1.41-1.32 (m, 18H).

3. Synthesis of Intermediates 11-4A and 11-4B

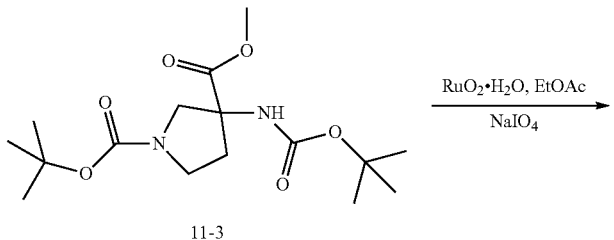

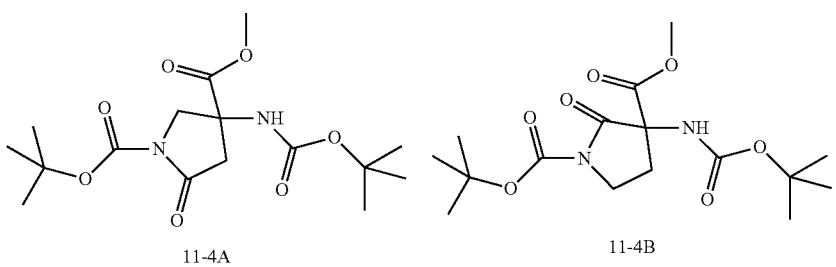

This step followed the published method in *Chem. Pharm. Bull.* 42(8) 1302-1306, 1995. To a mixture of ruthenium oxide hydrate (386 mg, 2.90 mmol, 0.5 equiv.) and sodium periodate (6.21 g, 29.04 mmol, 5.0 equiv.) in a round-bottom flask (250 mL) were added water (25 mL) and 1-(tert-butyl) 3-methyl 3-((tert-butoxycarbonyl)amino)pyrrolidine-1,3-dicarboxylate (2.00 g, 5.81 mmol, 1.0 equiv.) in EA (25 mL). The resulting biphasic mixture was stirred vigorously for 3 h, diluted with additional EA (50 mL), and filtered through celite. The layers were separated and the aqueous phase was extracted once with EA (50 mL). The organic phases were combined and diluted with MeOH (5 mL). The resulting black solution was stirred at r.t. for 30 minutes and filtered again through celite. The solvent was evaporated in vacuo and the remaining solid residue was purified with silica gel using 30% EA/Hex to provide 1.44 g (69%) of 1-(tert-butyl) 3-methyl 3-((tert-butoxycarbonyl)amino)-5-oxopyrrolidine-1,3-dicarboxylate (11-4A) and 437 mg (21%) of 1-(tert-butyl) 3-methyl 3-((tert-butoxycarbonyl)amino)-2-oxopyrrolidine-1,3-dicarboxylate (11-4B), both visualized on TLC with KMnO$_4$ stain.

Characterization for Intermediate 11-4A: LRMS (APCI) m/z 203.1 (M+H) (Boc loss and tert-butyl loss). $^1$H NMR (400 MHz, Methanol-d$_4$) δ 4.21 (d, J=11.5 Hz, 1H), 3.95 (d, J=11.5 Hz, 1H), 3.78 (s, 3H), 3.13 (d, J=17.5 Hz, 1H), 2.80 (dd, J=17.5, 0.8 Hz, 1H), 1.55 (s, 9H), 1.46 (s, 9H).

Characterization for Intermediate 11-4B: LRMS (APCI) m/z 203.1 (M+H) (Boc loss and tert-butyl loss). $^1$H NMR (400 MHz, Methanol-d$_4$) δ 3.94-3.74 (m, 5H), 2.63 (ddd, J=13.4, 7.9, 2.2 Hz, 1H), 2.42 (dt, J=13.5, 9.2 Hz, 1H), 1.56 (s, 9H), 1.46 (s, 9H).

4. Synthesis of Intermediate 11-5

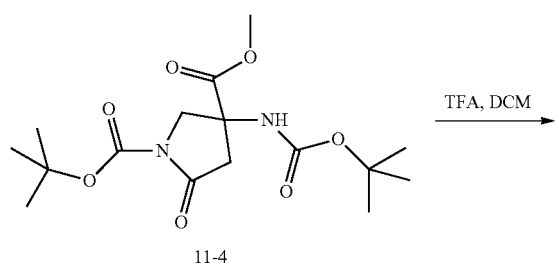

11-4

To a solution of 1-(tert-butyl) 3-methyl 3-((tert-butoxycarbonyl)amino)-5-oxopyrrolidine-1,3-dicarboxylate (916 mg, 2.56 mmol) in DCM (5 mL) was added TFA (5 mL). The resulting mixture was stirred at r.t. for 30 minutes. The solvents were removed under reduced pressure and dried under high vacuum to provide 692 mg (quantitative yield) of methyl 3-amino-5-oxopyrrolidine-3-carboxylate as TFA salt without further purification. LRMS (APCI) m/z 159.1 (M+H).

5. Synthesis of Intermediate 11-6

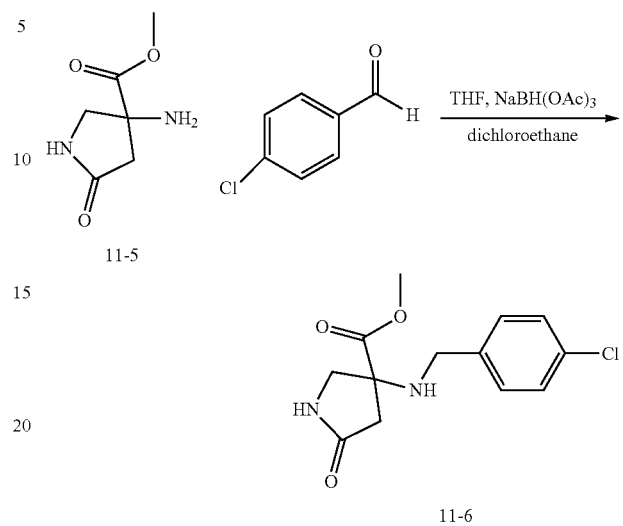

11-6

To a mixture of methyl 3-amino-5-oxopyrrolidine-3-carboxylate TFA salt (692 mg, 2.55 mmol) and p-chlorobenzaldehyde (1.07 g, 7.63 mmol, 3.0 equiv.) in a mixture of THF (30 mL) and dichloroethane (10 mL) stirred for 15 minutes was added NaBH(OAc)$_3$ (2.69 g, 12.71 mmol, 5.0 equiv.). The resulting mixture was stirred at r.t. for 1 h, during which time a homogeneous solution was observed. The solvents were evaporated under reduced pressure and the remaining residue was partitioned between DCM (60 mL) and saturated aqueous NaHCO$_3$ (60 mL). The aqueous phase was extracted with DCM (25 mL). The organic phases were combined, dried over sodium sulfate, filtered through celite, and concentrated under reduced pressure. The remaining residue was purified with silica gel using a gradient from 0%-100% EA/Hex as eluent to provide 548 mg (76%) of methyl 3-((4-chlorobenzyl)amino)-5-oxopyrrolidine-3-carboxylate. LRMS (APCI) m/z 159.1 (M+H).

6. Synthesis of Intermediate 11-7

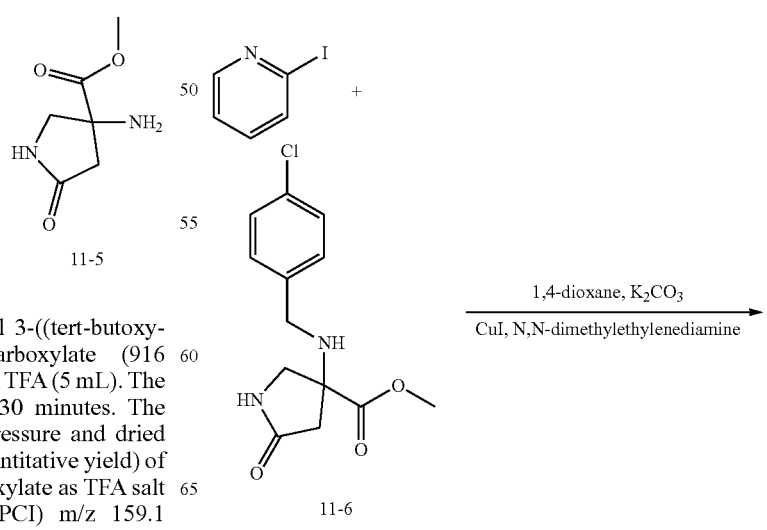

587
-continued

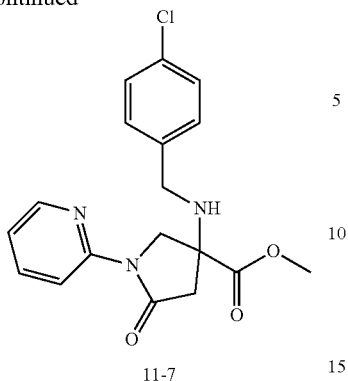

11-7

588
-continued

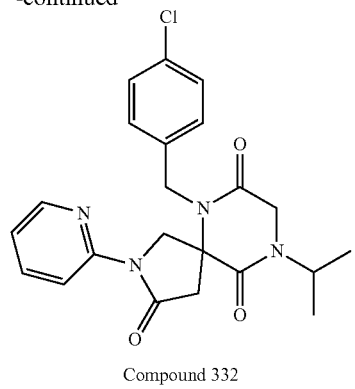

Compound 332

To a mixture of CuI (25 mg, 0.13 mmol, 0.5 equiv.) and K$_2$CO$_3$ (143 mg, 1.03 mmol, 4.0 equiv.) were added methyl 3-((4-chlorobenzyl)amino)-5-oxopyrrolidine-3-carboxylate (73 mg, 0.26 mmol, 1.0 equiv.) in anhydrous 1,4-dioxane (2 mL), 2-iodopyridine (41 μL, 0.39 mmol, 1.5 equiv.) and N,N-dimethylethylenediamine (13 μL, 0.13 mmol, 0.5 equiv.) sequentially. The resulting mixture was flushed with nitrogen, sealed and heated at 115° C. in an oil bath for 18 h. The reaction was filtered through a syringe filter, concentrated under reduced pressure, and purified with reverse phase HPLC using 10%-100% ACN/water (both with 0.1% formic acid; Phenomenex Gemini C18 5 micron column) to provide 59 mg (62%) of methyl 3-((4-chlorobenzyl)amino)-5-oxo-1-(pyridin-2-yl)pyrrolidine-3-carboxylate. LRMS (APCI) m/z 360.1 (M+H). $^1$H NMR (400 MHz, Methanol-d$_4$) δ 8.40-8.23 (m, 2H), 7.79 (ddd, J=8.3, 7.3, 2.1 Hz, 1H), 7.33 (d, 2H), 7.26 (d, 2H), 7.14 (ddd, J=7.3, 4.8, 1.1 Hz, 1H), 4.37 (d, J=11.8 Hz, 1H), 4.19 (dd, J=11.7, 0.7 Hz, 1H), 3.81 (s, 3H), 3.73 (d, J=2.1 Hz, 2H), 3.22 (d, J=17.1 Hz, 1H), 2.80 (dd, J=17.2, 0.7 Hz, 1H).

7. Synthesis of Compound 332

To a solution of methyl 3-((4-chlorobenzyl)amino)-5-oxo-1-(pyridin-2-yl)pyrrolidine-3-carboxylate (59 mg, 0.16 mmol) in DCM (3 mL) was added Et$_3$N (229 μL, 1.64 mmol, 10.0 equiv.). To the resulting solution cooled to 0° C. with an ice bath was added chloroacetyl chloride (131 μL, 1.64 mmol, 10.0 equiv.) dropwise. The ice bath was removed and the resulting mixture was stirred at r.t. for 30 min, diluted with DCM (20 mL), washed with saturated aqueous NaHCO$_3$ (15 mL), dried over sodium sulfate, and concentrated in vacuo. To the remaining residue was dissolved in ACN (3 mL) were added Et$_3$N (229 μL, 1.64 mmol, 10.0 equiv.) and isopropyl amine (140 μL, 1.64 mmol, 10.0 equiv.). The resulting solution was heated in a sealed tube at 100° C. in an oil bath for 45 minutes, cooled to r.t., concentrated under reduced pressure, and purified with reverse phase HPLC using 10%-100% ACN/water (both with 0.1% formic acid; Phenomenex Gemini C18 5 micron column) and by silica gel using 50% EA/Hex as eluent to provide 32 mg (46%) of 6-(4-chlorobenzyl)-9-isopropyl-2-(pyridin-2-yl)-2,6,9-triazaspiro[4.5]decane-3,7,10-trione as a white solid. LRMS (APCI) m/z 427.2 (M+H). $^1$H NMR (400 MHz, Methanol-d$_4$) δ 8.31-8.22 (m, 2H), 7.78 (ddd, J=8.5, 7.3, 2.0 Hz, 1H), 7.20 (s, 4H), 7.13 (ddd, J=7.3, 4.9, 1.0 Hz, 1H), 4.98-4.89 (m, 1H), 4.80-4.68 (m, 2H), 4.46 (d, J=12.4 Hz, 1H), 4.33-4.25 (m, 2H), 4.18 (d, J=17.8 Hz, 1H), 3.40 (d, J=17.8 Hz, 1H), 3.11 (d, J=17.8 Hz, 1H), 1.30-1.22 (m, 6H).

Example 12: Synthesis of Compound 331

Compound 331

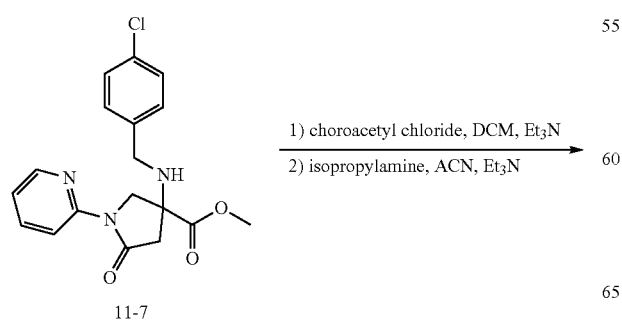

11-7

1) choroacetyl chloride, DCM, Et$_3$N
2) isopropylamine, ACN, Et$_3$N

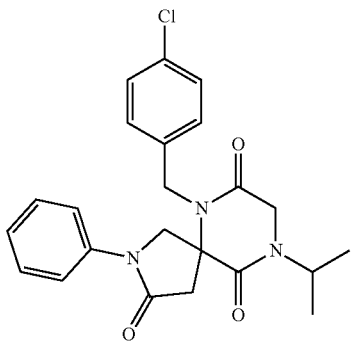

Method analogous to Example 11 was used with the exception that iodobenzene was used in step 6 instead of 2-iodopyridine.

Example 13: Synthesis of Compound 330

1. Synthesis of Intermediate 13-1

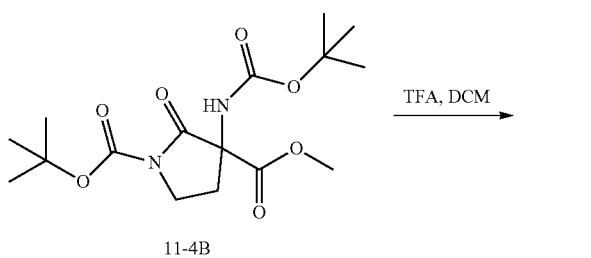

To a solution of 1-(tert-butyl) 3-methyl 3-((tert-butoxycarbonyl)amino)-2-oxopyrrolidine-1,3-dicarboxylate (437 mg, 1.22 mmol) in DCM (5 mL) was added TFA (5 mL). The resulting mixture was stirred at r.t. for 30 minutes, dried under reduced pressure and concentrated to provide 330 mg (quantitative yield) of methyl 3-amino-2-oxopyrrolidine-3-carboxylate as the TFA salt. LRMS (APCI) m/z 159.1 (M+H).

2. Synthesis of Intermediate 13-2

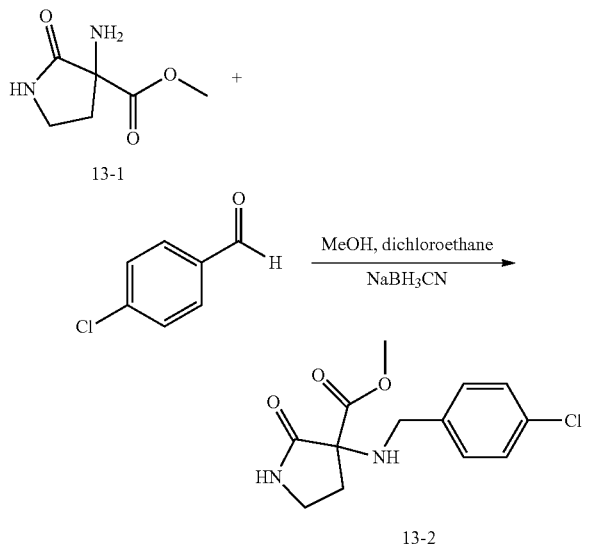

To a mixture of methyl 3-amino-2-oxopyrrolidine-3-carboxylate TFA salt (330 mg, 1.22 mmol) and p-chlorobenzaldehyde (513 mg, 3.65 mmol, 3.0 equiv.) in a mixture of dichloroethane (5 mL) and MeOH (5 mL) stirred at r.t. for 15 minutes was added NaBH$_3$CN (229 mg, 3.65 mmol, 3.0 equiv.). The resulting mixture was stirred at r.t. for 18 h. To the mixture was added additional p-chlorobenzaldehyde (513 mg, 3.65 mmol, 3.0 equiv.) and NaBH$_3$CN (229 mg, 3.65 mmol, 3.0 equiv.). The mixture was heated in an oil bath at 65° C. for 2 h, evaporated in vacuo, and partitioned between EA (40 mL) and saturated aqueous NaHCO$_3$ (40 mL). The layers were separated and the aqueous phase was extracted with additional EA (30 mL). The organic phases were combined, dried over sodium sulfate, concentrated under reduced pressure, and purified with silica gel chromatography using a EA/Hex (0-100%) to provide 258 mg (75%) of methyl 3-((4-chlorobenzyl)amino)-2-oxopyrrolidine-3-carboxylate. LRMS (APCI) m/z 283.1 (M+H). $^1$H NMR (400 MHz, Methanol-d$_4$) δ 7.37-7.15 (m, 4H), 3.74 (d, J=12.4 Hz, 1H), 3.59 (d, J=12.4 Hz, 1H), 3.47-3.33 (m, 2H), 2.59 (ddd, J=13.4, 7.3, 3.6 Hz, 1H), 2.23 (ddd, J=13.4, 8.7, 7.5 Hz, 1H).

3. Synthesis of Intermediate 13-3

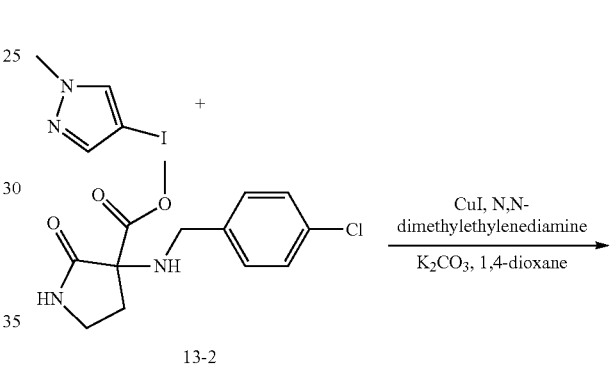

To a mixture of CuI (6 mg, 0.033 mmol, 0.2 equiv.), 4-iodo-1-methyl-1H-pyrazole (41 mg, 0.195 mmol, 1.2 equiv.) and K$_2$CO$_3$ (90 mg, 0.651 mmol, 4.0 equiv.) were added methyl 3-((4-chlorobenzyl)amino)-2-oxopyrrolidine-3-carboxylate (46 mg, 0.163 mmol, 1.0 equiv.) in anhydrous 1,4-dioxane (2 mL) and N,N-dimethylethylenediamine (4 μL, 0.033 mmol, 0.2 equiv.). The resulting mixture was flushed with nitrogen, sealed, heated in an oil bath at 115° C. for 18 h, cooled to room temperature, filtered through a syringe filter, and purified with reverse phase HPLC using 10%-100% ACN/water (both with 0.1% formic acid; Phenomenex Gemini C18 5 micron column) to provide 8 mg (14%) of methyl 3-((4-chlorobenzyl)amino)-1-(1-methyl-1H-pyrazol-4-yl)-2-oxopyrrolidine-3-carboxylate. LRMS (APCI) m/z 363.2 (M+H).

4. Synthesis of Compound 330

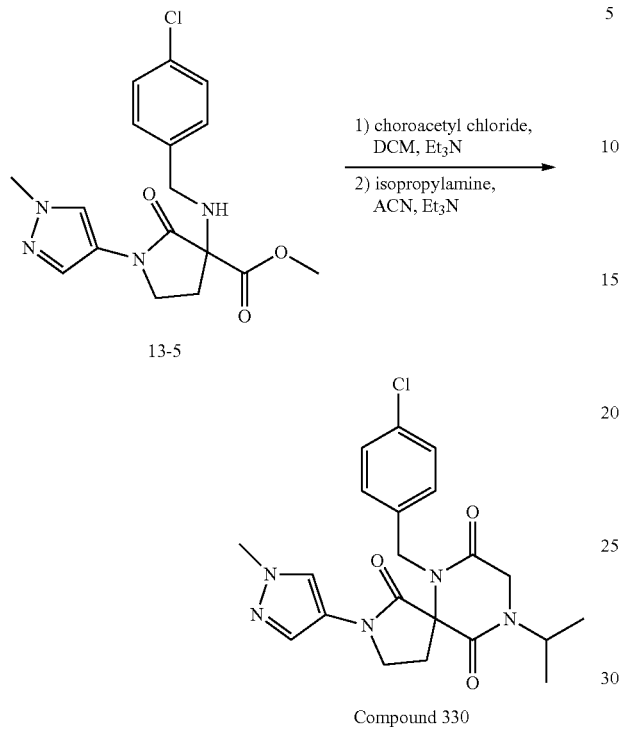

Compound 330

To a solution of methyl 3-((4-chlorobenzyl)amino)-1-(1-methyl-1H-pyrazol-4-yl)-2-oxopyrrolidine-3-carboxylate (8 mg, 0.022 mmol) in DCM (1 mL) was added Et$_3$N (31 µL, 0.22 mmol, 10.0 equiv.). To the resulting solution cooled to 0° C. with an ice bath was added chloroacetyl chloride (18 µL, 0.22 mmol, 10.0 equiv.) dropwise and the ice bath was removed upon the completion of addition. The resulting mixture was stirred at r.t. for 30 minutes, diluted with DCM (10 mL), washed once with saturated aqueous NaHCO$_3$ (10 mL), dried over sodium sulfate, and concentrated in vacuo. The remaining residue was dissolved in ACN (1 mL). To the mixture were added Et$_3$N (62 µL, 0.44 mmol, 20.0 equiv.) and isopropyl amine (38 µL, 0.44 mmol, 20.0 equiv.) sequentially. The resulting solution was heated in a sealed tube at 100° C. in an oil bath for 45 min, cooled to r.t., evaporated under reduced pressure, and purified with reverse phase HPLC using 10%-100% ACN/water (both with 0.1% formic acid; Phenomenex Gemini C18 5 micron column) to provide 5 mg (53%) of 6-(4-chlorobenzyl)-9-isopropyl-2-(1-methyl-1H-pyrazol-4-yl)-2,6,9-triazaspiro [4.5]decane-1,7,10-trione. LRMS (APCI) m/z 430.2 (M+H). $^1$H NMR (400 MHz, Methanol-d$_4$) δ 7.91 (s, 1H), 7.64 (s, 1H), 7.34-7.23 (m, 4H), 4.84 (d, J=16.1 Hz, 1H), 4.68 (p, J=6.9 Hz, 1H), 4.55 (d, J=16.1 Hz, 1H), 4.27 (d, J=17.7 Hz, 1H), 4.17 (d, J=17.7 Hz, 1H), 3.93-3.83 (m, 4H), 3.70 (td, J=9.4, 2.6 Hz, 1H), 2.82 (ddd, J=14.0, 8.4, 2.6 Hz, 1H), 2.57-2.45 (m, 1H), 1.23 (dd, J=10.0, 6.8 Hz, 6H).

Example 14: Synthesis of Compound 333

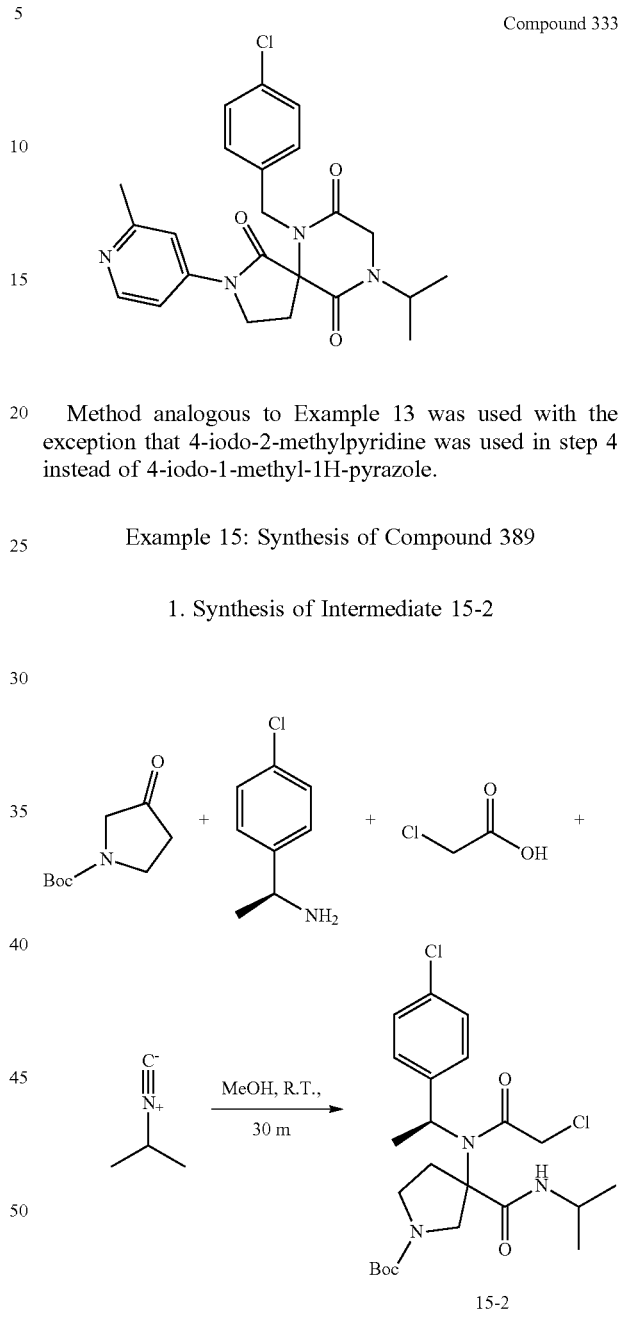

Method analogous to Example 13 was used with the exception that 4-iodo-2-methylpyridine was used in step 4 instead of 4-iodo-1-methyl-1H-pyrazole.

Example 15: Synthesis of Compound 389

1. Synthesis of Intermediate 15-2

To a solution of (S)-1-(4-chlorophenyl)ethan-1-amine (2.4 mL, 16.7 mmol, 1.0 equiv) and tert-butyl 3-oxopyrrolidine-1-carboxylate (3.1 g, 16.7 mmol, 1.0 equiv) in MeOH (16 mL) were added 2-isocyanopropane (1.6 mL, 16.7 mmol, 1.0 equiv) and chloroacetic acid (1.6 g, 16.7 mmol, 1.0 equiv). The mixture was stirred for 30 min, concentrated, and purified by silica gel chromatography to provide 3.2 g (39%) of tert-butyl 3-(2-chloro-N—((S)-1-(4-chlorophenyl)ethyl)acetamido)-3-(isopropylcarbamoyl)pyrrolidine-1-carboxylate as a mixture of diastereomers. LRMS (ES) m/z 486.2 (M+H).

2. Synthesis of Intermediate 15-3

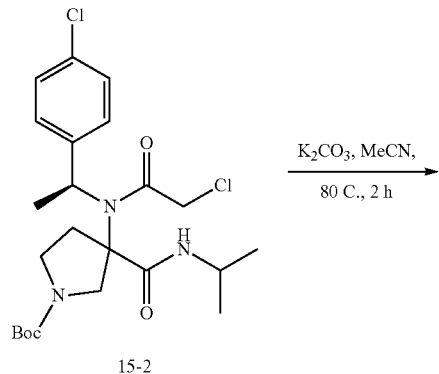

To a solution of tert-butyl 3-(2-chloro-N—((S)-1-(4-chlorophenyl)ethyl)acetamido)-3-(isopropylcarbamoyl)pyrrolidine-1-carboxylate (3.2 g, 6.6 mmol, 1.0 equiv) in ACN (20 mL) was added potassium carbonate (0.9 g, 6.6 mmol, 2.0 equiv). The mixture was heated to 80° C. for 2 h, filtered, concentrated, and purified by silica gel chromatography (80 g, 0-100% EtOAc in hexanes) to provide 1.0 g (34%) of tert-butyl 6-((S)-1-(4-chlorophenyl)ethyl)-9-isopropyl-7,10-dioxo-2,6,9-triazaspiro[4.5]decane-2-carboxylate as a mixture of diastereomers. LRMS (ES) m/z 394.15 (M+H-$^t$Bu).

3. Synthesis of Intermediate 15-4

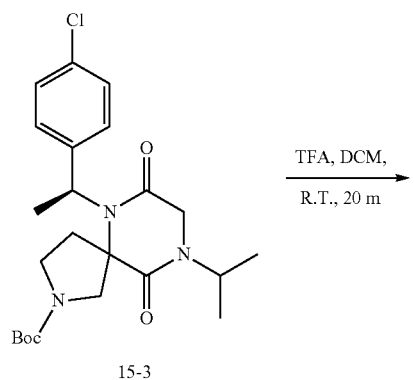

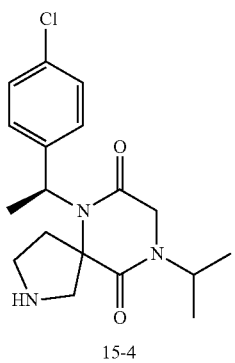

To a solution of tert-butyl 6-((S)-1-(4-chlorophenyl)ethyl)-9-isopropyl-7,10-dioxo-2,6,9-triazaspiro[4.5]decane-2-carboxylate (1.0 g, 2.2 mmol, 1.0 equiv) in DCM (5.0 mL) was added TFA (5 mL). The mixture was stirred for 20 min, concentrated, diluted with saturated aqueous NaHCO$_3$ (200 mL), and layers were separated. The aqueous layer was extracted with DCM three times. The combined organic washes were dried over MgSO$_4$, filtered, and concentrated, and purified by silica gel chromatography (24 g column, 0-40% MeOH in DCM) to provide 380 mg (49%) of 6-4S)-1-(4-chlorophenyl)ethyl)-9-isopropyl-2,6,9-triazaspiro[4.5]decane-7,10-dione as a mixture of diastereomers. LRMS (ES) m/z 350.2 (M+H).

4. Synthesis of Compound 389 (Diastereomers 389A and 389B

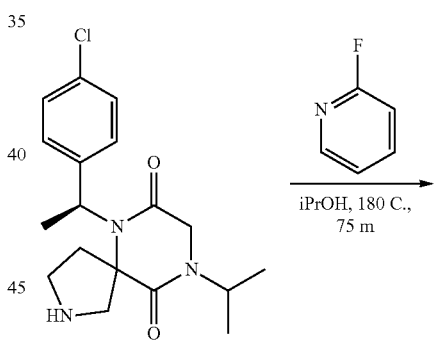

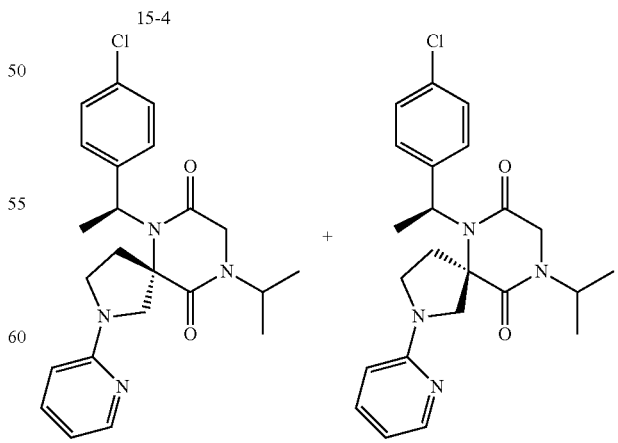

Compound 389, mixture of Diastereomers 389A and 389B

To a mixture of 6-4S)-1-(4-chlorophenyl)ethyl)-9-isopropyl-2,6,9-triazaspiro[4.5]decane-7,10-dione (190 mg, 0.54 mmol, 1.0 equiv) and 2-fluoropyridine (132 mg, 1.4 mmol, 2.5 equiv) in a microwave vial was added IPA (3 mL). The mixture was heated at 180° C. in the microwave reactor for 75 min, concentrated, and purified by reverse phase HPLC (Phenomenex, gemini 5 uM C18 150×21.2 mm, 10-100% acetonitrile in water both with 0.1% formic acid gradient over 40 min) to provide 16 mg (14%) of the first eluting peak as Diastereomer 389A and 15 mg of the second eluting peak as Diastereomer 389B. Diastereomer 389A characterization: LRMS (ES) m/z 427.1 (M+H). $^1$H-NMR (Methanol-$d_4$, 400 MHz, ppm) δ 8.01 (ddd, J=5.3, 1.9, 0.9 Hz, 1H), 7.59 (ddd, J=8.9, 7.1, 1.9 Hz, 1H), 7.29 (s, 4H), 6.69 (ddd, J=7.2, 5.2, 0.9 Hz, 1H), 6.57 (dt, J=8.7, 0.9 Hz, 1H), 4.70 (p, J=6.9 Hz, 1H), 4.19-4.00 (m, 3H), 3.83 (d, J=11.9 Hz, 2H), 3.60 (q, J=8.5 Hz, 1H), 2.73-2.52 (m, 2H), 1.89 (d, J=6.9 Hz, 3H), 1.23 (dd, J=6.8, 2.1 Hz, 6H). Diastereomer 389B characterization: LRMS (ES) m/z 427.1 (M+H). $^1$H-NMR: (Methanol-$d_4$, 400 MHz, ppm) δ 8.06 (ddd, J=5.2, 1.9, 0.8 Hz, 1H), 7.63 (ddd, J=8.8, 7.1, 1.9 Hz, 1H), 7.37-7.27 (m, 4H), 6.73 (ddd, J=7.1, 5.3, 0.9 Hz, 1H), 6.62 (d, J=8.6 Hz, 1H), 4.70 (p, J=6.9 Hz, 1H), 4.08 (d, J=2.6 Hz, 2H), 4.02 (d, J=11.3 Hz, 1H), 3.92 (d, J=11.8 Hz, 1H), 3.71 (td, J=9.2, 4.0 Hz, 1H), 3.60 (t, J=8.5 Hz, 1H), 2.77 (ddd, J=13.8, 8.2, 3.9 Hz, 1H), 2.52 (dt, J=13.8, 8.3 Hz, 1H), 1.87 (d, J=6.9 Hz, 3H), 1.23 (dd, J=6.8, 3.4 Hz, 6H).

The following compound was prepared by methods analogous to the method described for Compound 389:

| Enantiomer No. | LRMS (ES) m/z |
| --- | --- |
| 504A | M + H = 468.2 |

Example 16: Synthesis of Compound 367

1. Synthesis of Intermediate 16-2

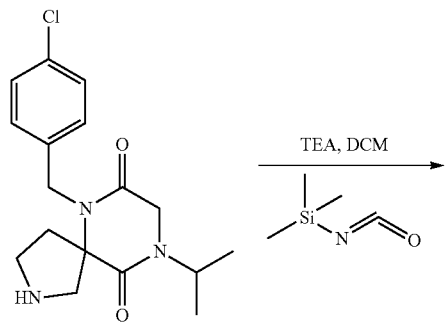

TEA, DCM

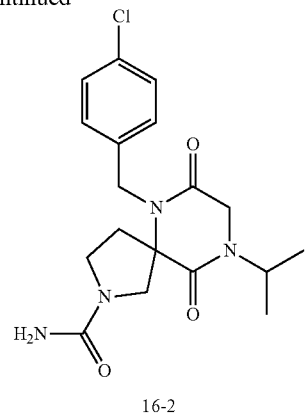

16-2

To a solution of 6-[(4-chlorophenyl)methyl]-9-(propan-2-yl)-2,6,9-triazaspiro[4.5]decane-7,10-dione (150 mg, 0.45 mmol, 1.00 equiv) in DCM (5 mL) at r.t were added isocyanatotrimethylsilane (103 mg, 0.89 mmol, 2.00 equiv) and TEA (90 mg, 0.89 mmol, 2.00 equiv). The mixture was stirred at r.t for 2 h, concentrated under reduced pressure, and purified by reverse phase-HPLC with the following conditions [(2 #-AnalyseHPLC-SHIMADZU): Column, XBridge Prep OBD C18 Column, 5 um, 30*150 mm; mobile phase, Water (10 mmol/L $NH_4HCO_3$) and ACN (22.0% ACN up to 35.0% in 8 min); Detector, UV 220 nm] to give 105 mg (62%) of 6-[(4-chlorophenyl)methyl]-7,10-dioxo-9-(propan-2-yl)-2,6,9-triazaspiro[4.5]decane-2-carboxamide as a white solid. LRMS (ES) m/z 379 (M+H). $^1$H NMR (300 MHz, DMSO-$d_6$) δ 7.40-7.28 (m, 2H), 7.16-7.07 (m, 2H), 5.77 (s, 2H), 4.69 (d, J=16.8 Hz, 1H), 4.62-4.45 (m, 2H), 4.04 (d, J=2.8 Hz, 2H), 3.77 (d, J=11.7 Hz, 1H), 3.34 (s, 1H), 3.27 (s, 2H), 2.20 (dt, J=8.8, 4.7 Hz, 2H), 1.09 (d, J=6.8 Hz, 6H).

2. Separation of Compound 367

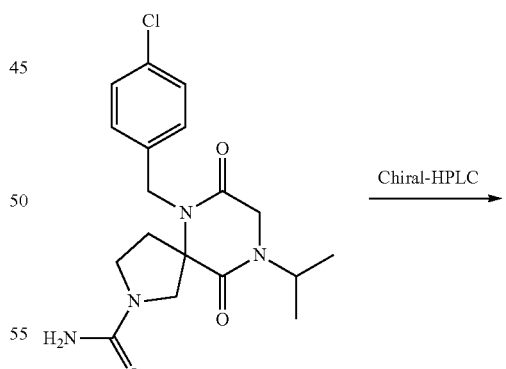

Compound 367

Enantiomer 367A + Enantiomer 367B

The racemic compound 6-[(4-chlorophenyl)methyl]-7,10-dioxo-9-(propan-2-yl)-2,6,9-triazaspiro[4.5]decane-2-carboxamide (80 mg, 0.21 mmol, 1.00 equiv) was separated by Chiral-HPLC with the following conditions (Column: CHIRALPAK IC, 2*25 cm, 5 um; Mobile Phase A: Hex-HPLC, Mobile Phase B: EtOH-HPLC; Flow rate: 16 mL/min; isocratic at 50% B for 28 min; 254/220 nm) to give 37.7 mg of the first eluted peak as Enantiomer 367A and 33.2 mg of second eluted peak as Enantiomer 367B. The chiral analytical data (CHIRALPAK IC-3; 0.46 cm×5 cm; 3 micron; Hex (0.1% DEA):EtOH=50:50 at 1 ml/min) shows that the first peak (RT: 3.75 min) is Enantiomer 367A and second peak (RT: 4.61 min) is Enantiomer 367B.

Enantiomer 367A: LRMS (ES) m/z 379 (M+H). $^1$HNMR (300 MHz, DMSO-$d_6$) δ 7.40-7.30 (m, 2H), 7.16-7.07 (m, 2H), 5.77 (s, 2H), 4.69 (d, J=16.8 Hz, 1H), 4.62-4.45 (m, 2H), 4.04 (d, J=2.8 Hz, 2H), 3.77 (d, J=11.7 Hz, 1H), 3.34 (s, 1H), 3.27 (s, 2H), 2.26-2.14 (m, 2H), 1.09 (d, J=6.8 Hz, 6H).

Enantiomer 367B: LRMS (ES) m/z 379 (M+H). $^1$HNMR (300 MHz, DMSO-$d_6$) δ 7.40-7.30 (m, 2H), 7.17-7.07 (m, 2H), 5.77 (s, 2H), 4.69 (d, J=16.7 Hz, 1H), 4.62-4.45 (m, 2H), 4.04 (d, J=2.8 Hz, 2H), 3.77 (d, J=11.7 Hz, 1H), 3.34 (s, 1H), 3.27 (s, 2H), 2.20 (dt, J=8.9, 4.7 Hz, 2H), 1.09 (d, J=6.8 Hz, 6H).

Example 17: Synthesis of Compound 347

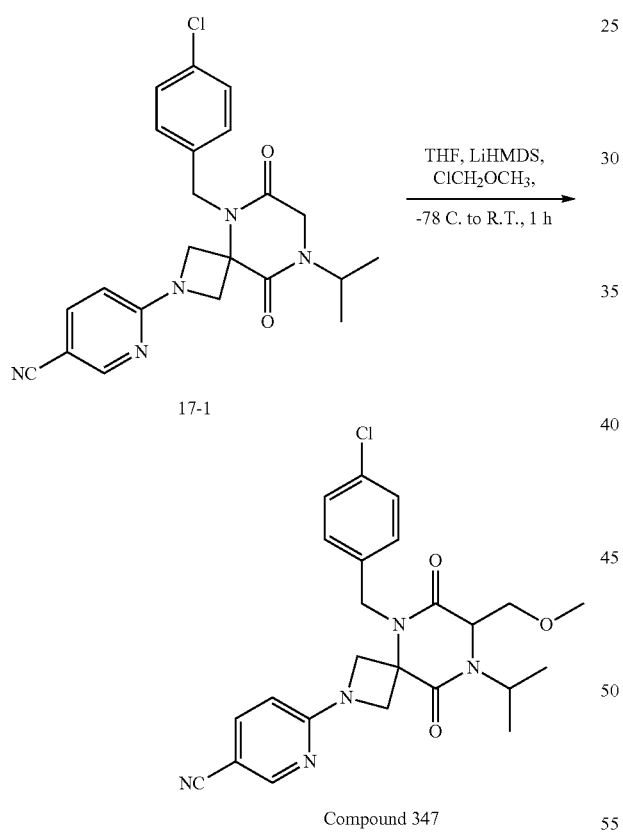

To a solution of 6-(5-(4-chlorobenzyl)-8-isopropyl-6,9-dioxo-2,5,8-triazaspiro[3.5]nonan-2-yl)nicotinonitrile (100 mg, 0.236 mmol, 1.0 equiv) in THF (4 mL) at −78° C. was added LHMDS (1 M in THF, 354 μL, 0.35 mmol, 1.5 equiv) and chloromethyl methyl ether (38 mg, 0.47 mmol, 2.0 equiv) sequentially. The mixture was stirred for 5 min at −78° C., warmed to r.t. over a period of 1 h, quenched with MeOH (0.5 mL), and purified by reverse phase HPLC (Phenomenex, gemini 5u C18 150×21.2 mm, 20-100% acetonitrile in water both with 0.1% formic acid gradient over 40 min) to provide 7.2 mg (7%) of 6-(5-(4-chlorobenzyl)-8-isopropyl-7-(methoxymethyl)-6,9-dioxo-2,5,8-triazaspiro[3.5]nonan-2-yl)nicotinonitrile as a white solid. LRMS (ES) m/z 468.2 (M+H). $^1$H-NMR (Methanol-$d_4$, 400 MHz, ppm) δ 8.38 (dd, J=2.2, 0.8 Hz, 1H), 7.77 (dd, J=8.8, 2.2 Hz, 1H), 7.35-7.30 (m, 2H), 7.25 (d, J=8.6 Hz, 2H), 6.48 (dd, J=8.8, 0.9 Hz, 1H), 5.12 (d, J=16.4 Hz, 1H), 4.75 (d, J=10.0 Hz, 1H), 4.40-4.31 (m, 2H), 4.26 (d, J=10.2 Hz, 1H), 4.18-4.04 (m, 2H), 3.81 (dd, J=9.8, 1.7 Hz, 1H), 3.74 (dd, J=9.8, 2.7 Hz, 1H), 3.40 (s, 3H), 1.40 (dd, J=6.8, 5.1 Hz, 6H).

Example 18: Synthesis of Compound 348

1. Synthesis of Intermediate 18-2

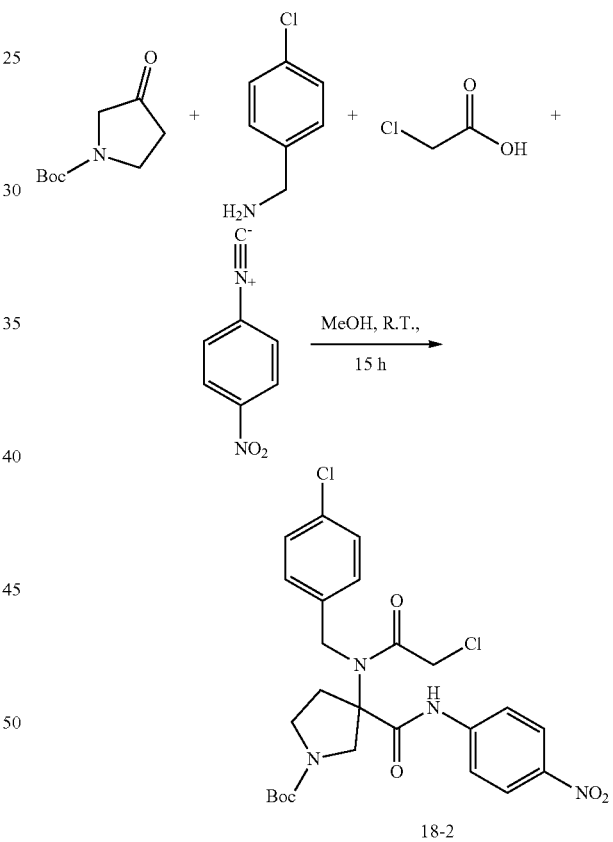

To a solution of (4-Chlorophenyl)methanamine (0.27 g, 1.9 mmol, 1.0 equiv) and tert-butyl 3-oxopyrrolidine-1-carboxylate (0.36 g, 1.9 mmol, 1.0 equiv) in MeOH (5 mL) were added 1-isocyano-4-nitrobenzene (0.30 g, 2.0 mmol, 1.05 equiv) and chloroacetic acid (0.18 g, 1.9 mmol, 1.0 equiv). The mixture was stirred for 15 h at r.t., concentrated, and purified by silica gel chromatography (0-100% EtOAc in hexanes) to provide 200 mg of tert-butyl 3-(2-chloro-N-(4-chlorobenzyl)acetamido)-3-((4-nitrophenyl)carbamoyl) pyrrolidine-1-carboxylate. LRMS (ES) m/z 495.1 (M+H-$^t$Bu).

2. Synthesis of Intermediate 18-3

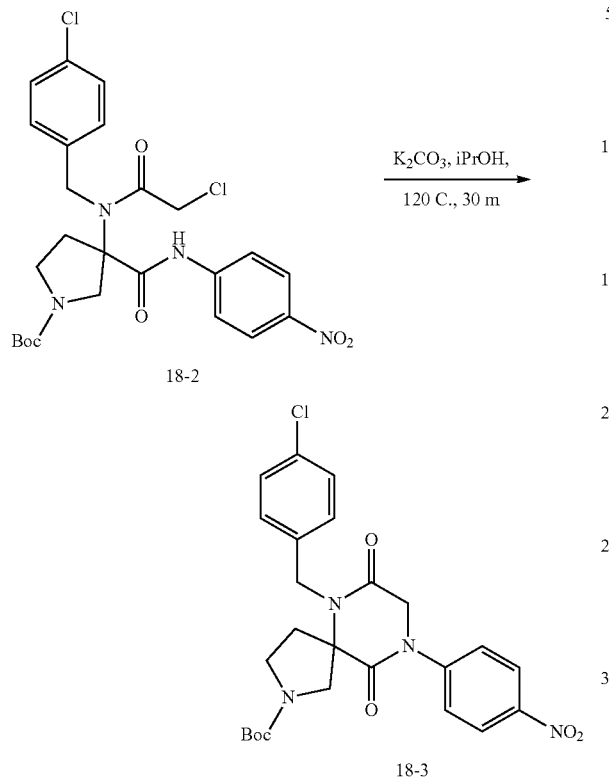

To a solution of tert-butyl 3-(2-chloro-N-(4-chlorobenzyl)acetamido)-3-((4-nitrophenyl)carbamoyl)pyrrolidine-1-carboxylate (200 mg, 0.36 mmol, 1.0 equiv) in IPA (5 mL) was added potassium carbonate (151 mg, 1.1 mmol, 3.0 equiv). The mixture was heated at 120° C. for 30 min, cooled to r.t., filtered, concentrated, and purified by silica gel chromatography (0-100% EtOAc in hexanes) to provide tert-butyl 6-(4-chlorobenzyl)-9-(4-nitrophenyl)-7,10-dioxo-2,6,9-triazaspiro[4.5]decane-2-carboxylate. LRMS (ES) m/z 459.1 (M+H-$^t$Bu).

3. Synthesis of Intermediate 18-4

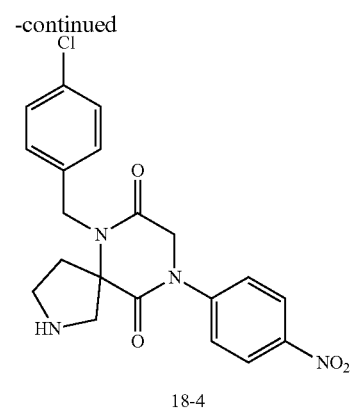

To a solution of tert-butyl 6-(4-chlorobenzyl)-9-(4-nitrophenyl)-7,10-dioxo-2,6,9-triazaspiro[4.5]decane-2-carboxylate (0.36 mmol, 1.0 equiv assuming 100% yield) in DCM (2 mL) was added TFA (2 mL). The mixture was stirred for 20 min, concentrated, diluted with saturated NaHCO$_3$ (200 mL), and extracted with DCM three times. The combined organic washes were dried over MgSO$_4$, filtered, and concentrated to provide 6-(4-chlorobenzyl)-9-(4-nitrophenyl)-2,6,9-triazaspiro[4.5]decane-7,10-dione. This material was split into two equal portions and used in the subsequent reaction. LRMS (ES) m/z 415.1 (M+H).

4. Synthesis of Compound 348

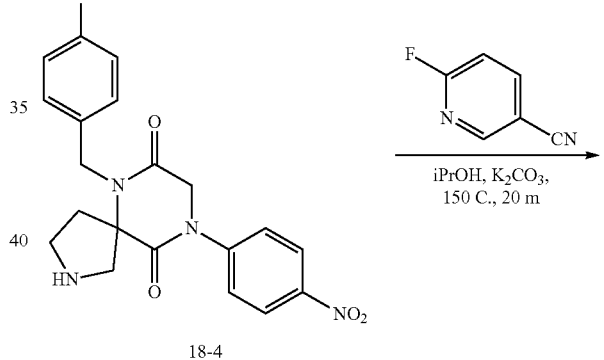

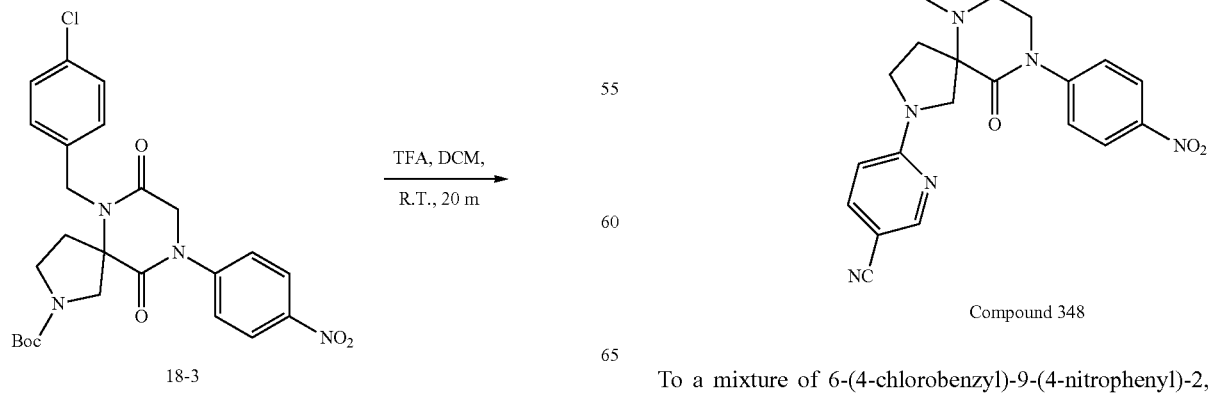

Compound 348

To a mixture of 6-(4-chlorobenzyl)-9-(4-nitrophenyl)-2,6,9-triazaspiro[4.5]decane-7,10-dione (0.18 mmol, 1.0 equiv), 5-cyano-2-fluoropyridine (33 mg, 0.27 mmol, 1.5 equiv), and potassium carbonate (50 mg, 0.36 mmol, 2.0 equiv) in a microwave tube was added IPA (3 mL). The mixture was sealed and heated at 150° C. in the microwave reactor for 20 min, concentrated, and purified by reverse phase HPLC (Phenomenex, gemini 5u C18 150×21.2 mm, 20-100% acetonitrile in water both with 0.1% formic acid gradient over 40 min) to provide 16 mg (17% over 3 steps) of 6-(6-(4-chlorobenzyl)-9-(4-nitrophenyl)-7,10-dioxo-2,6,9-triazaspiro[4.5]decan-2-yl)nicotinonitrile as a white foamy solid. LRMS (ES) m/z 517.0 (M+H). $^1$H-NMR: (Methanol-d$_4$, 400 MHz, ppm) δ 8.41-8.27 (m, 3H), 7.81-7.68 (m, 3H), 7.35-7.29 (m, 2H), 7.28-7.20 (m, 2H), 6.49 (d, J=8.9 Hz, 1H), 4.99 (d, J=16.6 Hz, 1H), 4.85-4.69 (m, 3H), 4.23 (d, J=12.6 Hz, 1H), 3.99 (d, J=12.6 Hz, 1H), 3.79-3.58 (m, 2H), 2.79 (ddd, J=13.1, 8.2, 4.7 Hz, 1H), 2.68 (dt, J=13.6, 8.1 Hz, 1H).

Example 19: Synthesis of Compound 349

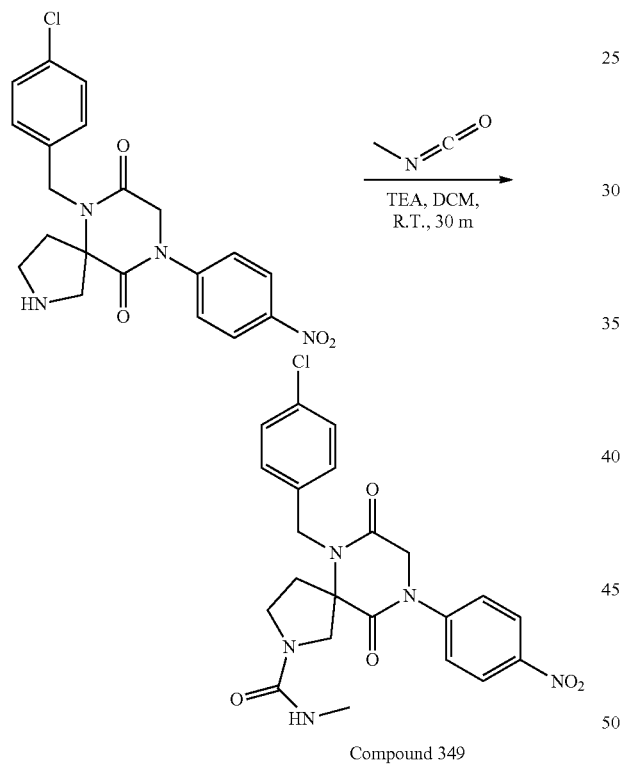

Compound 349

To a solution of 6-(4-chlorobenzyl)-9-(4-nitrophenyl)-2,6,9-triazaspiro[4.5]decane-7,10-dione (0.18 mmol, 1.0 equiv) in DCM (4 mL) were added TEA (55 mg, 0.54 mmol, 3.0 equiv) and methyl isocyanate (31 mg, 0.54 mmol, 3.0 equiv). The mixture was stirred for 30 min, concentrated, and purified by reverse phase HPLC (Phenomenex, gemini 5u C18 150×21.2 mm, 20-100% acetonitrile in water both with 0.1% formic acid gradient over 40 min) to provide 17 mg (20% over 3 steps) of 6-(4-chlorobenzyl)-N-methyl-9-(4-nitrophenyl)-7,10-dioxo-2,6,9-triazaspiro[4.5]decane-2-carboxamide as a white foamy solid. LRMS (ES) m/z 472.1 (M+H). (Methanol-d$_4$, 400 MHz, ppm) δ 8.37-8.30 (m, 2H), 7.77-7.69 (m, 2H), 7.40-7.34 (m, 2H), 7.32-7.28 (m, 2H), 4.92 (d, J=16.8 Hz, 1H), 4.81-4.63 (m, 3H), 4.09 (d, J=11.8 Hz, 1H), 3.72 (d, J=11.9 Hz, 1H), 3.47 (dd, J=8.1, 6.4 Hz, 2H), 2.70 (s, 3H), 2.64-2.46 (m, 2H).

The following compounds were prepared by methods analogous to the method described for Compound 349:

| Compound No. | LRMS (ES) m/z |
|---|---|
| 552 | M + H = 500 |
| 559 | M + H = 506 |
| 560 | M + H = 494 |
| 561 | M + H = 508.1 |
| 562 | M + H = 550.1 |
| 563 | M + H = 480 |
| 564 | M + H = 481 |
| 565 | M + H = 499 |
| 567 | M + H = 481 |
| 568 | M + H = 451 |
| 569 | M + H = 530.9 |
| 570 | M + H = 499.1 |
| 571 | M + H = 543 |
| 592 | M + H = 514 |
| 615 | M + H = 515 |

Example 20: Synthesis of Compound 350

1. Synthesis of Intermediate 20-2

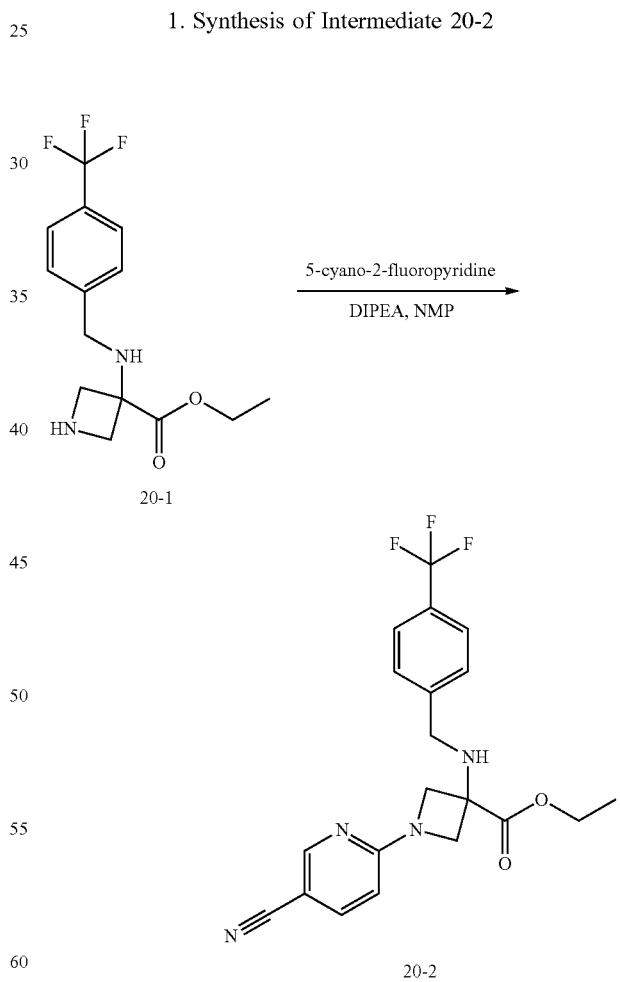

To a mixture of ethyl 3-((4-(trifluoromethyl)benzyl)amino)azetidine-3-carboxylate (1.53 g, 5.1 mmol, 1.0 equiv) and 5-cyano-2-fluoropyridine (1.86 g, 15.2 mmol, 3.0 equiv) in NMP (15 mL) was added diisopropylethylamine (4.4 mL, 25 mmol, 5.0 equiv). The mixture was heated at 130° C. for 15 min, diluted with water, and extracted with DCM three times. The combined extractions were dried over magnesium sulfate, filtered, concentrated, and purified by silica gel chromatography (0-50% ethyl acetate in hexanes, gradient over 26 min) to give 1.7 g (83%) of ethyl 1-(5-cyanopyridin-2-yl)-3-((4-(trifluoromethyl)benzyl)amino)azetidine-3-carboxylate as a clear yellow oil. LRMS (ES) m/z 405 (M+H). $^1$H NMR (400 MHz, Methylene Chloride-$d_2$) δ 8.43-8.41 (m, 1H), 7.69-7.61 (m, 3H), 7.59-7.53 (m, 2H), 6.35-6.31 (m, 1H), 4.44-4.40 (m, 2H), 4.30 (q, J=7.1 Hz, 2H), 4.13-4.07 (m, 2H), 3.87 (s, 2H), 1.34 (t, J=7.1 Hz, 3H).

2. Synthesis of Intermediate 20-3

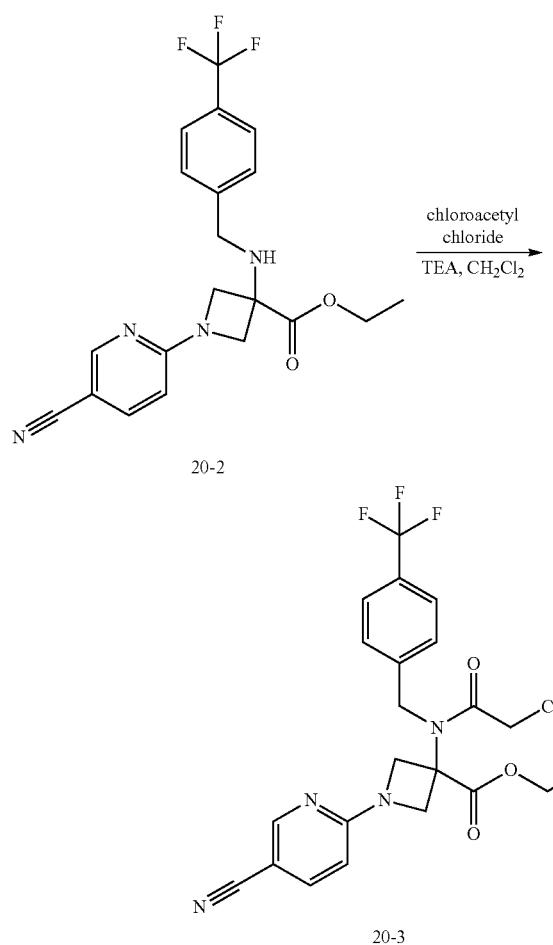

To a solution of ethyl 1-(5-cyanopyridin-2-yl)-3-((4-(trifluoromethyl)benzyl) amino)azetidine-3-carboxylate (1.7 g, 4.2 mmol, 1.0 equiv) in DCM (17 mL) cooled to 0° C. were added TEA (3.6 mL, 25 mmol, 6.0 equiv) and chloroacetyl chloride (1.4 mL, 17 mmol, 4.0 equiv) dropwise. The mixture was stirred at 0° C. for 30 min, diluted with saturated sodium bicarbonate, and extracted with DCM three times. The combined organic extracts were dried over magnesium sulfate, filtered, concentrated, and purified by silica gel chromatography (0-40% ethyl acetate in hexanes, gradient over 25 min) to give 2.1 g (100%) of ethyl 3-(2-chloro-N-(4-(trifluoromethyl)benzyl)acetamido)-1-(5-cyanopyridin-2-yl)azetidine-3-carboxylate as a clear yellow oil. LRMS (ES) m/z 481 (M+H). $^1$H NMR (400 MHz, Methylene Chloride-$d_2$) δ 8.38-8.35 (m, 1H), 7.70-7.66 (m, 3H), 7.53-7.48 (m, 2H), 6.36-6.32 (m, 1H), 4.83-4.81 (m, 2H), 4.61-4.56 (m, 2H), 4.31 (q, J=7.2 Hz, 2H), 4.27-4.21 (m, 2H), 4.01 (s, 2H), 1.31 (t, J=7.1 Hz, 3H).

3. Synthesis of Intermediate 20-4

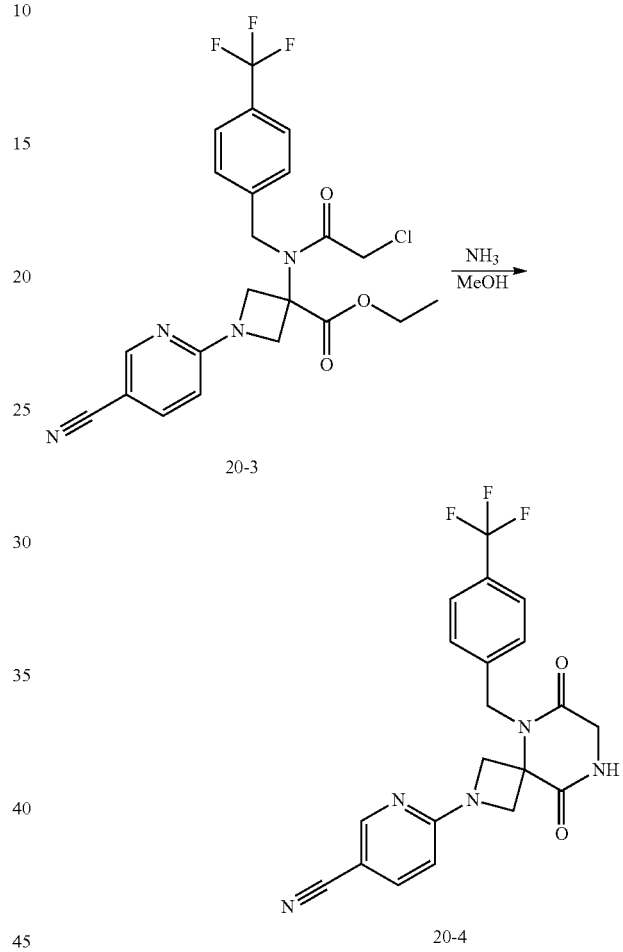

To a solution of ethyl 3-(2-chloro-N-(4-(trifluoromethyl)benzyl)acetamido)-1-(5-cyanopyridin-2-yl)azetidine-3-carboxylate (214 mg, 0.45 mmol, 1.0 equiv) in a round-bottom flask was added ammonia (7 N in MeOH, 1.3 mL, 8.9 mmol, 20 equiv). The mixture was sealed, heated at 80° C. for 2 h, cooled to r.t., diluted with water, and extracted with EA three times. The combined organic extracts were dried over magnesium sulfate, filtered, concentrated, and purified by silica gel chromatography (0-10% MeOH/DCM, gradient over 11 min) to give 185 mg (quantitative) of 6-(6,9-dioxo-5-(4-(trifluoromethyl)benzyl)-2,5,8-triazaspiro[3.5]nonan-2-yl) nicotinonitrile as a clear colorless oil. LRMS (ES) m/z 416 (M+H). $^1$H NMR (400 MHz, Methylene Chloride-$d_2$) δ 8.43 (dd, J=2.2, 0.8 Hz, 1H), 7.69 (dd, J=8.7, 2.2 Hz, 1H), 7.66-7.62 (m, 2H), 7.42-7.37 (m, 2H), 6.79 (s, 1H), 6.32 (dd, J=8.7, 0.9 Hz, 1H), 5.09 (s, 2H), 4.69-4.63 (m, 2H), 4.28-4.23 (m, 2H), 4.22-4.18 (m, 2H).

4. Synthesis of Compound 350

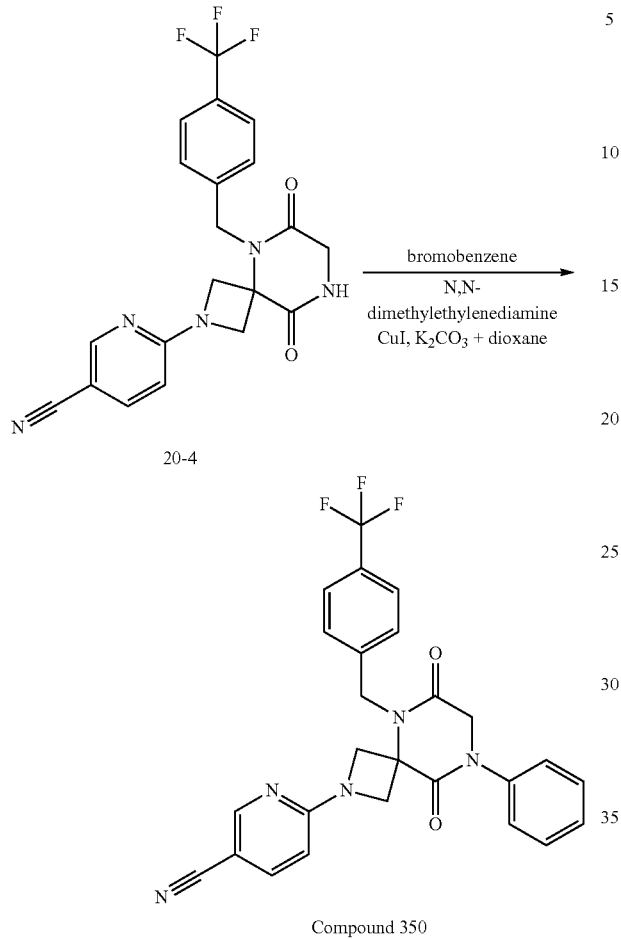

20-4

Compound 350

To a mixture of copper (I) iodide (10 mg, 0.06 mmol, 0.5 equiv) and potassium carbonate (61 mg, 0.44 mmol, 4.0 equiv) in a flask which was vacuum-nitrogen purged 3 times were added bromobenzene (0.017 mL, 0.16 mmol, 1.5 equiv), N,N'-dimethylethylenediamine (0.006 mL, 0.06 mmol, 0.5 equiv), 6-(6,9-dioxo-5-(4-(trifluoromethyl)benzyl)-2,5,8-triazaspiro[3.5]nonan-2-yl)nicotinonitrile (46 mg, 0.11 mmol, 1.0 equiv), and dioxane (1 mL). The mixture was then heated to 115° C. for 15 h, cooled to r.t, filtered, and purified by reverse phase HPLC (Phenomenex, gemini 5u C18 150×21.2 mm, 10-100% acetonitrile in water both with 0.1% formic acid gradient over 25 min) to give 12 mg (22%) of 6-(6,9-dioxo-8-phenyl-5-(4-(trifluoromethyl)benzyl)-2,5,8-triazaspiro[3.5]nonan-2-yl)nicotinonitrile as a white solid. LRMS (ES) m/z 492 (M+H). $^1$H NMR (400 MHz, Methanol-$d_4$) δ 8.38 (dd, J=2.2, 0.7 Hz, 1H), 7.77 (dd, J=8.8, 2.2 Hz, 1H), 7.69-7.64 (m, 2H), 7.61-7.56 (m, 2H), 7.53-7.44 (m, 4H), 7.42-7.37 (m, 1H), 6.49 (dd, J=8.8, 0.8 Hz, 1H), 5.19 (s, 2H), 4.71-4.66 (m, 2H), 4.58 (s, 2H), 4.44-4.38 (m, 2H).

The following compounds were prepared by methods analogous to the method described for Compound 350:

| Compound No. | LRMS (ES) m/z |
|---|---|
| 882 | M + H = 482.0 |
| 883 | M + H = 466.1 |
| 884 | M + H = 500.0 |
| 885 | M + H = 484.0 |
| 886 | M + H = 507.0 |
| 887 | M + H = 491.0 |

Example 21: Synthesis of Compound 334

1. Synthesis of Intermediate 21-2

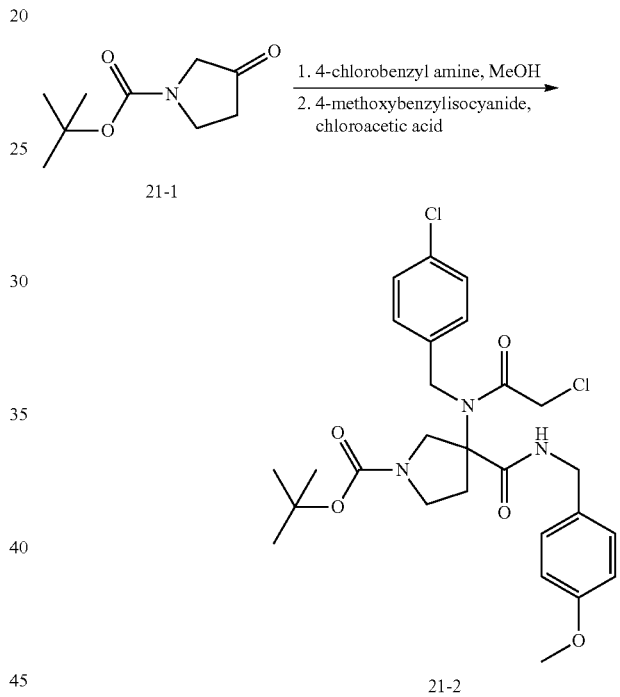

21-1

21-2

To a mixture of tert-butyl 3-oxopyrrolidine-1-carboxylate (1.26 g, 6.8 mmol, 1.0 equiv) and 4-chlorobenzyl amine (0.96 g, 6.8 mmol, 1.0 equiv) in MeOH (15 mL) were added 4-methoxybenzylisocyanide (1.0 g, 6.8 mmol, 1.0 equiv) and chloroacetic acid (0.64 g, 6.8 mmol, 1.0 equiv). The mixture was stirred for 2 h at r.t., diluted with EA, washed with saturated sodium bicarbonate and saturated ammonium chloride, dried over magnesium sulfate, filtered, concentrated, and purified by silica gel chromatography (0-30% ethyl acetate in hexanes, gradient over 25 min) to give 1.2 g (32%) of tert-butyl 3-(2-chloro-N-(4-chlorobenzyl)acetamido)-3-((4-methoxybenzyl)carbamoyl)pyrrolidine-1-carboxylate as a white foam. LRMS (ES) m/z 494 (M+H-tertbutyl). $^1$H NMR (400 MHz, Methylene Chloride-$d_2$) δ 7.41-7.37 (m, 2H), 7.25-7.18 (m, 4H), 6.92-6.87 (m, 2H), 4.82-4.64 (m, 2H), 4.55-4.47 (m, 1H), 4.41-4.36 (m, 2H), 4.08-4.02 (m, 1H), 4.01-3.96 (m, 1H), 3.82 (s, 3H), 3.54-3.48 (m, 1H), 3.45-3.34 (m, 1H), 3.33-3.24 (m, 1H), 2.69-2.52 (m, 1H), 2.19-2.08 (m, 1H), 1.44 (s, 9H).

2. Synthesis of Intermediate 21-3

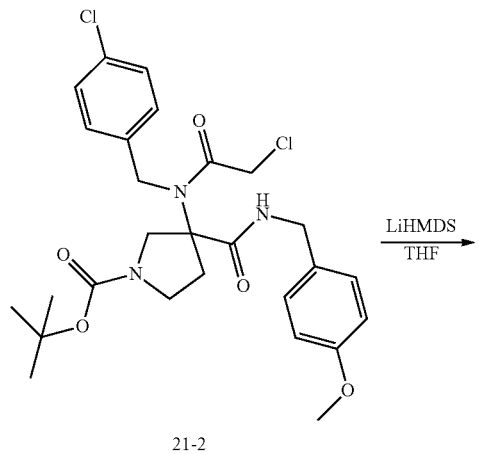

21-2

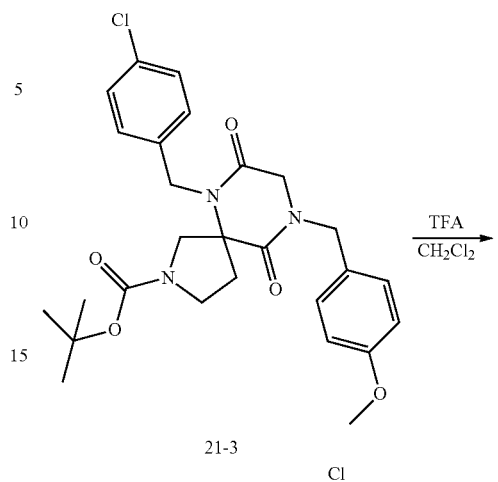

21-3

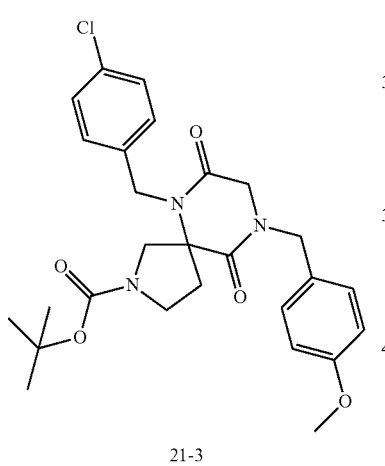

21-3

To a solution of tert-butyl 3-(2-chloro-N-(4-chlorobenzyl) acetamido)-3-((4-methoxybenzyl)carbamoyl)pyrrolidine-1-carboxylate (1.6 g, 2.9 mmol, 1.0 equiv) in THF (16 mL) cooled to 0° C. was added LHMDS (1.0 M in THF, 9.0 mL, 8.6 mmol, 3.0 equiv) dropwise. The mixture was stirred at 0° C. for 1 h, quenched with MeOH, concentrated, and purified by silica gel chromatography (0-100% ethyl acetate in hexanes, gradient over 14 min) to give 54 mg (4%) of tert-butyl 6-(4-chlorobenzyl)-9-(4-methoxybenzyl)-7,10-dioxo-2,6,9-triazaspiro[4.5]decane-2-carboxylate as a clear colorless oil. $^{1}$H NMR (400 MHz, Methylene Chloride-d$_{2}$) δ 7.23-6.68 (m, 8H), 5.11-4.62 (m, 2H), 4.53-4.13 (m, 3H), 3.91-3.79 (m, 1H), 3.69-3.57 (m, 3H), 3.51-3.22 (m, 3H), 2.43-1.95 (m, 2H), 1.39-1.20 (m, 9H).

3. Synthesis of Intermediate 21-4

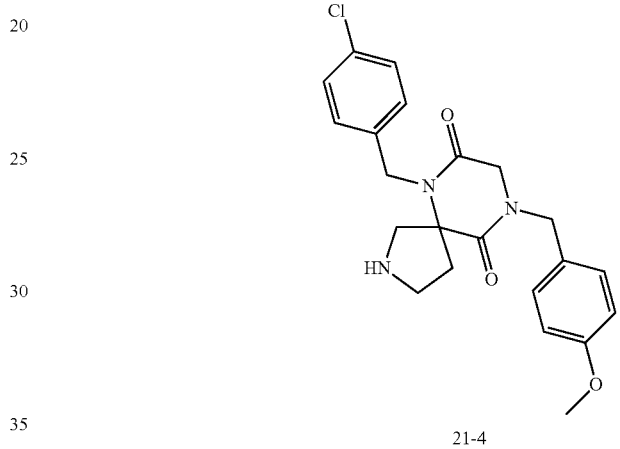

21-4

To a solution of tert-butyl 6-(4-chlorobenzyl)-9-(4-methoxybenzyl)-7,10-dioxo-2,6,9-triazaspiro[4.5]decane-2-carboxylate (0.055 g, 0.11 mmol, 1.0 equiv) in DCM (1 mL) was added TFA (0.080 mL, 1.0 mmol, 10 equiv). The mixture was heated at 40° C. for 1 h, concentrated, and vacuum pump dried for 2 h to give 56 mg (quantitative) of 6-(4-chlorobenzyl)-9-(4-methoxybenzyl)-2,6,9-triazaspiro [4.5]decane-7,10-dione as TFA salt. LRMS (ES) m/z 414 (M+H).

4. Synthesis of Compound 334

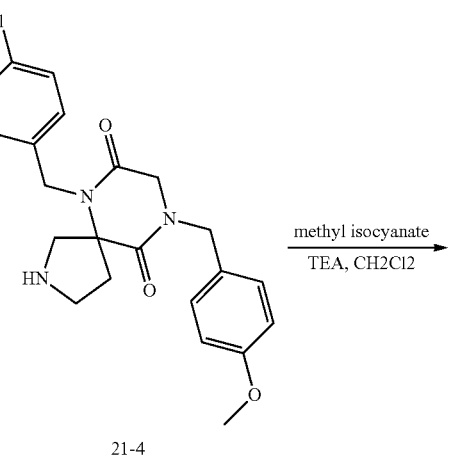

21-4

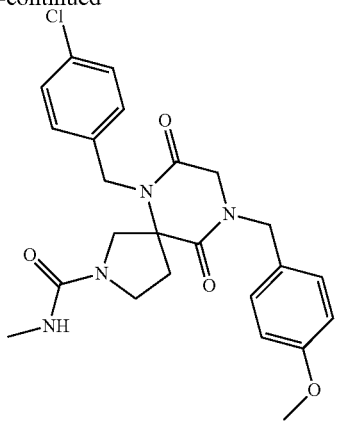

Compound 334

To a solution of 6-(4-chlorobenzyl)-9-(4-methoxybenzyl)-2,6,9-triazaspiro[4.5]decane-7,10-dione TFA salt (56 mg 0.11 mmol, 1.0 equiv) in DCM (1 mL) cooled to 0° C. were added TEA (0.06 mL, 0.4 mmol, 4 equiv) and methyl isocyanate (9 mg, 0.2 mmol, 1.5 equiv). The mixture was stirred at 0° C. for 30 min, concentrated, and purified by reverse phase HPLC (Phenomenex, gemini 5u C18 150× 21.2 mm, 10-70% acetonitrile in water both with 0.1% formic acid gradient over 25 min) to give 46 mg (90%) of 6-(4-chlorobenzyl)-9-(4-methoxybenzyl)-N-methyl-7,10-dioxo-2,6,9-triazaspiro[4.5]decane-2-carboxamide as a clear colorless oil. LRMS (ES) m/z 471 (M+H). $^1$H NMR (400 MHz, Methanol-$d_4$) δ 7.36-7.31 (m, 2H), 7.29-7.23 (m, 2H), 7.20-7.14 (m, 2H), 6.98-6.93 (m, 2H), 4.87-4.81 (m, 1H), 4.66-4.59 (m, 3H), 4.17-4.06 (m, 2H), 3.98-3.93 (m, 1H), 3.82 (s, 3H), 3.63-3.58 (m, 1H), 3.55-3.44 (m, 2H), 2.71 (s, 3H), 2.47-2.39 (m, 2H).

Example 22: Synthesis of Compound 202

1. Synthesis of Intermediate 22-2

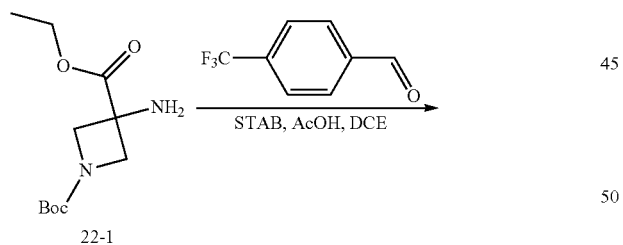

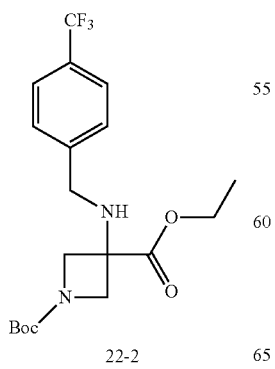

To a solution of 1-tert-butyl 3-ethyl 3-aminoazetidine-1,3-dicarboxylate (20 g, 81.9 mmol, 1.0 equiv) in DCE (200 mL) were added 4-(trifluoromethyl)benzaldehyde (15.7 g, 90.2 mmol, 1.10 equiv) and AcOH (9.8 g, 163.2 mmol, 2.0 equiv) at r.t. The mixture was stirred for 10 min. To this mixture was added STAB (26 g, 122.676 mmol, 1.50 equiv) in portions. The mixture was stirred for 4 h, quenched with water (200 mL), and extracted with DCM (200 mL) twice. The combined organic layers were washed with aqueous NaHCO$_3$ solution (200 mL) and brine (200 mL) twice, dried over anhydrous sodium sulfate, and concentrated under reduced pressure to give 33 g of 1-tert-butyl 3-ethyl 3-([[4-(trifluoromethyl)phenyl]methyl]amino)azetidine-1,3-dicarboxylate (crude) as a yellow oil. LRMS (ES) m/z 347 (M+H-56).

2. Synthesis of Intermediate 22-3

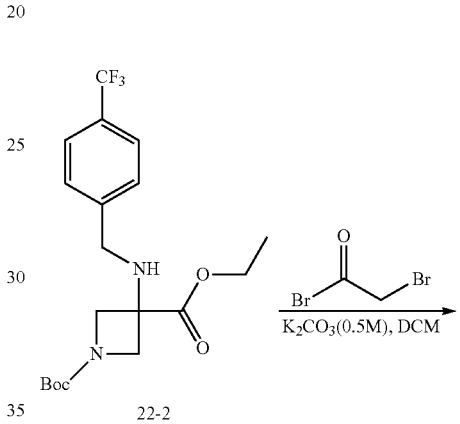

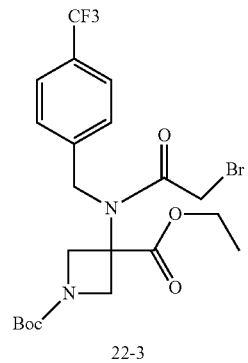

To a mixture of 1-tert-butyl 3-ethyl 3-([[4-(trifluoromethyl)phenyl]methyl]amino)azetidine-1,3-dicarboxylate (33 g, 82.005 mmol, 1 equiv) in DCM (300 mL) and K$_2$CO$_3$ (17 g, 123.0 mmol, 1.50 equiv, 0.5) in water (246 mL) cooled to 0° C. was added 2-bromoacetyl bromide (19.8 g, 98.1 mmol, 1.2 equiv) dropwise over a period of 15 min. The mixture was stirred at r.t. overnight and extracted with DCM (300 mL) twice. The combined organic layers were washed with brine (300 mL) twice, dried over anhydrous Na$_2$SO$_4$, and concentrated under reduced pressure to give 42 g (95%) of 1-tert-butyl 3-ethyl 3-(2-bromo-N-[[4-(trifluoromethyl)phenyl]methyl]acetamido)azetidine-1,3-dicarboxylate as a yellow oil. LRMS (ES) m/z 467 (M+H-56).

3. Synthesis of Intermediate 22-4

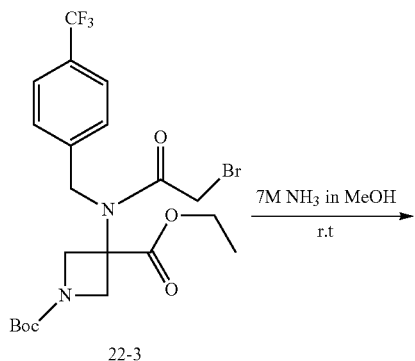

22-3

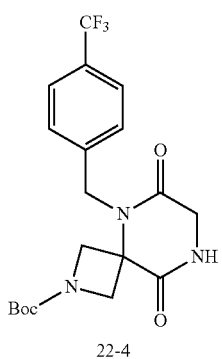

22-4

To 1-tert-butyl 3-ethyl 3-(2-bromo-N-[[4-(trifluoromethyl)phenyl]methyl]acetamido)azetidine-1,3-dicarboxylate (42 g, 80.3 mmol, 1 equiv) in a round-bottom flask was added NH$_3$ in MeOH (7 M, 300 mL). The mixture was stirred at r.t. overnight, concentrated under reduced pressure, and diluted with EtOAc (300 mL). The solid was collected and dried to afford 29 g (87%) of tert-butyl 6,9-dioxo-5-[[4-(trifluoromethyl)phenyl]methyl]-2,5,8-triazaspiro[3.5]nonane-2-carboxylate as a white solid. LRMS (ES) m/z 358 (M+H−56).

4. Synthesis of Intermediate 22-5

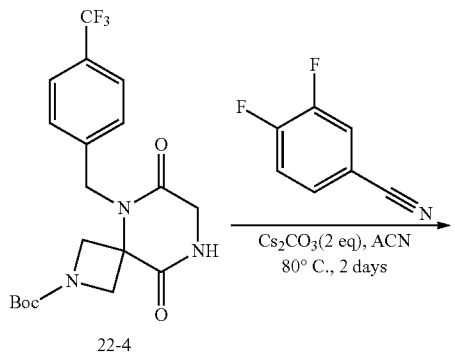

22-4

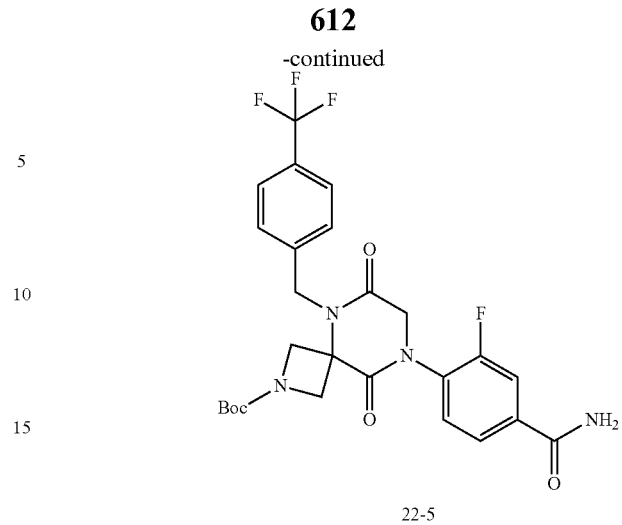

22-5

To a solution of tert-butyl 6,9-dioxo-5-[[4-(trifluoromethyl)phenyl]methyl]-2,5,8-triazaspiro[3.5]nonane-2-carboxylate (33 g, 79.8 mmol, 1 equiv) in ACN (330 mL) at r.t were added 3,4-difluorobenzonitrile (16.6 g, 119.3 mmol, 1.5 equiv) and Cs$_2$CO$_3$ (52 g, 159.6 mmol, 2.0 equiv). The mixture was stirred at 80° C. for 2 days, cooled to r.t., and filtered to remove solids. The filtrate was concentrated under reduced pressure and purified by silica gel column chromatography using EA/MeOH (7:3) as eluent and again with reverse phase chromatography using ACN/water (gradient from 35-45% over 20 min) give 20 g (45%) of tert-butyl 8-(4-carbamoyl-2-fluorophenyl)-6,9-dioxo-5-[[4-(trifluoromethyl)phenyl]methyl]-2,5,8-triazaspiro[3.5]nonane-2-carboxylate as an off-white solid. LRMS (ES) m/z 495 (M+H−56).

5. Synthesis of Intermediate 22-6

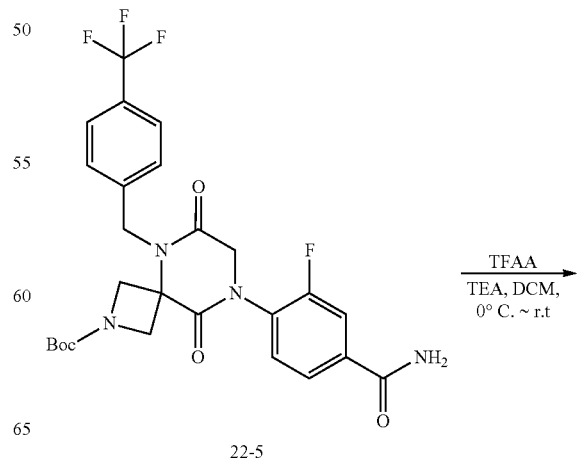

22-5

613

-continued

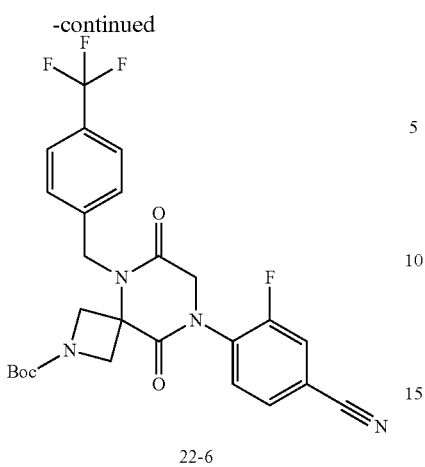

22-6

To a solution of tert-butyl 8-(4-carbamoyl-2-fluorophenyl)-6,9-dioxo-5-[[4-(trifluoromethyl)phenyl]methyl]-2,5,8-triazaspiro[3.5]nonane-2-carboxylate (20 g, 36.3 mmol, 1 equiv) in DCM (200 mL) cooled at 0° C. were added TEA (11 g, 108.7 mmol, 3.0 equiv) and TFAA (15 g, 71.4 mmol, 2.0 equiv). The mixture was stirred at r.t. overnight, quenched with water (200 mL), and extracted with DCM (200 mL) twice. The combined organic layers were washed with brine (300 mL) twice, dried over anhydrous Na₂SO₄, concentrated under reduced pressure, purified by silica gel chromatography using PE/EtOAc (1:2) as eluent to afford 13 g (68%) of tert-butyl 8-(4-cyano-2-fluorophenyl)-6,9-dioxo-5-[[4-(trifluoromethyl)phenyl]methyl]-2,5,8-triazaspiro[3.5]nonane-2-carboxylate as a yellow oil. LRMS (ES) m/z 477 (M+H−56).

6. Synthesis of Intermediate 22-7

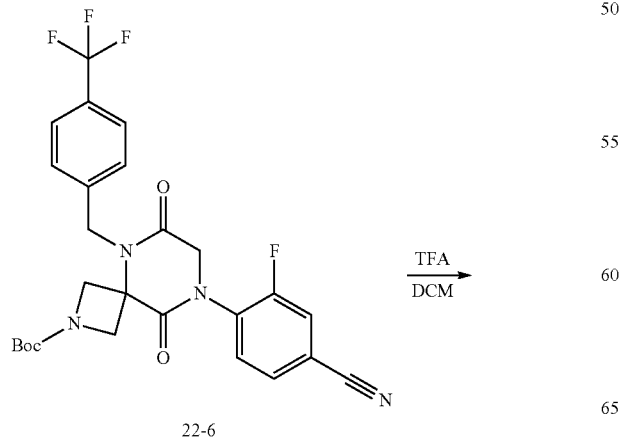

22-6

TFA / DCM →

614

-continued

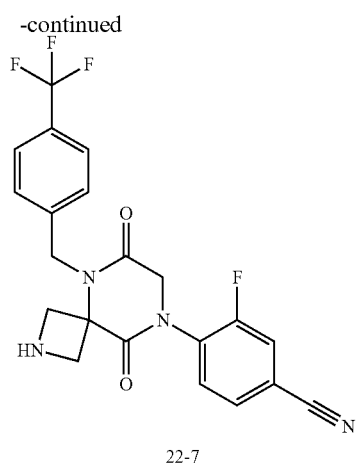

22-7

To a solution of tert-butyl 8-(4-cyano-2-fluorophenyl)-6,9-dioxo-5-[[4-(trifluoromethyl)phenyl]methyl]-2,5,8-triazaspiro[3.5]nonane-2-carboxylate (13 g, 24.4 mmol, 1 equiv) in DCM (120 mL) was added TFA (30 mL) at r.t. The mixture was stirred at r.t. for 4 h and concentrated under reduced pressure to give 10 g (98%) of 4-(6,9-dioxo-5-[[4-(trifluoromethyl)phenyl]methyl]-2,5,8-triazaspiro[3.5]nonan-8-yl)-3-fluorobenzonitrile as TFA salt. LRMS (ES) m/z 433 (M+H).

7. Synthesis of Compound 202

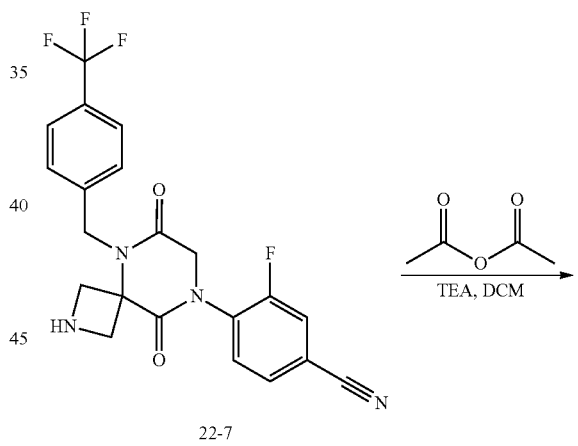

22-7

TEA, DCM →

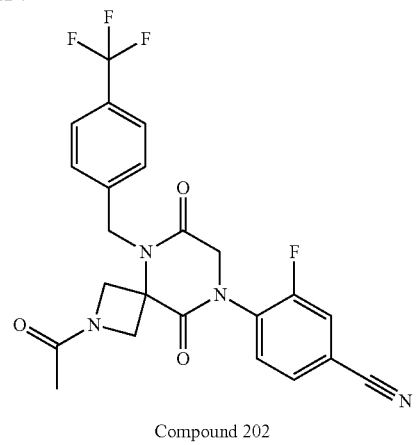

Compound 202

To a solution of 4-(6,9-dioxo-5-[[4-(trifluoromethyl)phenyl]methyl]-2,5,8-triazaspiro[3.5]nonan-8-yl)-3-fluorobenzonitrile (10 g, 23.1 mmol, 1 equiv) in DCM (100 mL) at r.t were added acetyl acetate (3.5 g, 34.3 mmol, 1.5 equiv) and TEA (7 g, 69.2 mmol, 3.0 equiv). The mixture was stirred at r.t. for 3 h, quenched with water (100 mL), and extracted with DCM (100 mL) twice. The combined organic layers were washed with brine (100 mL) twice, dried over anhydrous $Na_2SO_4$, concentrated under reduced pressure, and purified by reverse phase chromatography using ACN/water (10 M $NH_4HCO_3$, gradient from 35-45% over 20 min) to give 7.8 g (70%) of 4-(2-acetyl-6,9-dioxo-5-(4-(trifluoromethyl)benzyl)-2,5,8-triazaspiro[3.5]nonan-8-yl)-3-fluorobenzonitrile as an off-white solid. LRMS (ES) m/z 475 (M+H). $^1$H-NMR: (400 MHz, Methanol-$d_4$, ppm) δ 7.83-7.77 (m, 1H), 7.77-7.67 (m, 4H), 7.57 (d, J=8.1 Hz, 2H), 4.86 (s, 2H), 4.75-4.68 (m, 1H), 4.60-4.55 (m, 2H), 4.55-4.47 (m, 2H), 4.25 (d, J=11.0 Hz, 1H), 1.87 (s, 3H).

Example 23: Synthesis of Compound 169

1. Synthesis of Intermediate 23-2

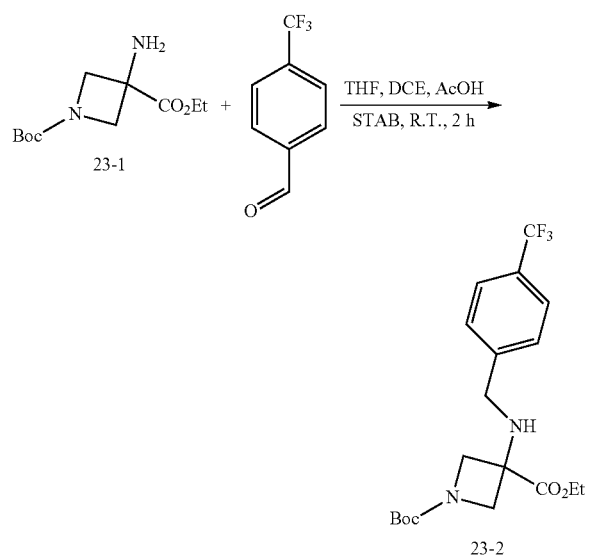

To a solution of 1-(tert-butyl) 3-ethyl-3-aminoazetidine-1,3-dicarboxylate (6.0 g, 24.6 mmol, 1.0 equiv) in a mixture of THF (30 mL) and DCE (10 mL) was added 4-trifluoromethylbenzaldehyde (6.4 g, 36.8 mmol, 1.5 equiv). The mixture was stirred for 15 min. To this mixture were added STAB (26.0 g, 123 mmol, 5.0 equiv) and AcOH (5 mL). The mixture was stirred for 2 h, evaporated under reduced pressure, and partitioned between DCM (60 mL) and saturated aqueous sodium bicarbonate (60 mL). The layers were separated and the aqueous phase was extracted with DCM (25 mL). The combined organic phases were dried over sodium sulfate, filtered through celite, concentrated under reduced pressure, and purified with silica gel chromatography using EtOAc/Hexanes (gradient from 0-100%), to provide 9.4 g (95%) of 1-(tert-butyl) 3-ethyl 3-((4-(trifluoromethyl)benzyl)amino)azetidine-1,3-dicarboxylate. LRMS (ES) m/z 347.1 (M+H-$^t$Bu).

2. Synthesis of Intermediate 23-3

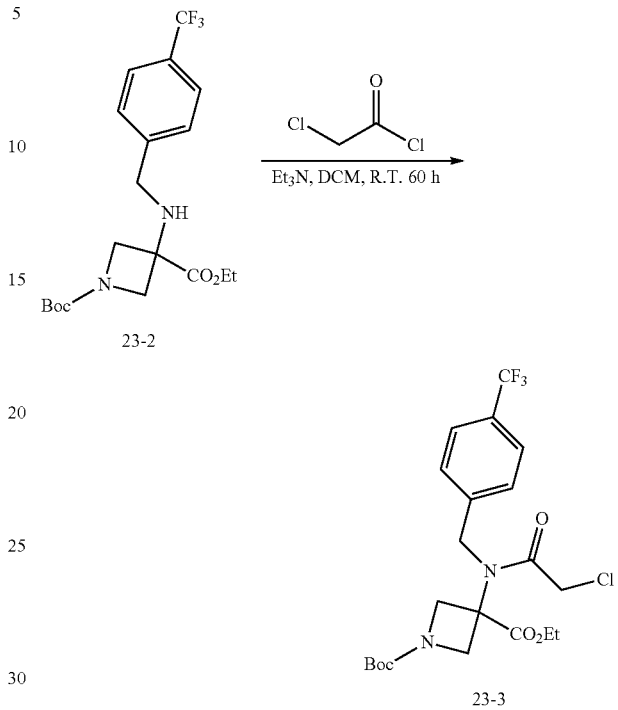

To a solution of 1-(tert-butyl) 3-ethyl 3-((4-(trifluoromethyl)benzyl)amino) azetidine-1,3-dicarboxylate (5.0 g, 12.4 mmol, 1.0 equiv) in DCM (50 mL) at 0° C. were added TEA (8.7 mL, 62.1 mmol, 5.0 equiv) and chloroacetyl chloride (4.0 mL, 49.7 mmol, 4.0 equiv). The ice bath was removed and the mixture was stirred at R.T. for 60 h before pouring into of saturated aqueous $NH_4Cl$ (200 mL). The layers were separated and the aqueous layer was extracted with DCM three times. The combined organic layers were dried over $MgSO_4$ and concentrated under reduced pressure to give 1-(tert-butyl) 3-ethyl 3-(2-chloro-N-(4-(trifluoromethyl)benzyl)acetamido)azetidine-1,3-dicarboxylate. The product was used directly in the next reaction without further purification.

3. Synthesis of Intermediate 23-4

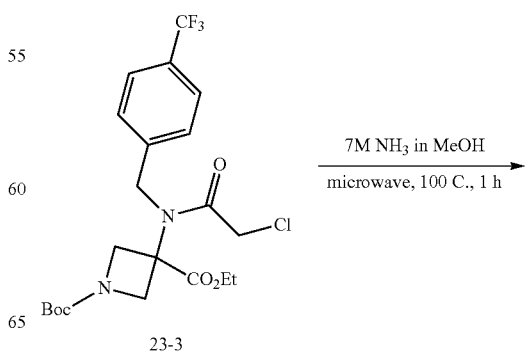

617
-continued

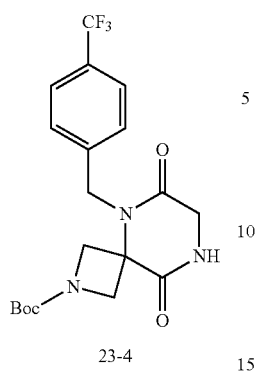

23-4

To a solution of 1-(tert-butyl) 3-ethyl 3-(2-chloro-N-(4-(trifluoromethyl)benzyl)acetamido) azetidine-1,3-dicarboxylate (5.75 g, 12.4 mmol) in a microwave vial was added 7 M NH₃ in MeOH (7 N, 30 mL). The mixture was sealed, heated at 100° C. in the microwave reactor for 1 h, concentrated under reduced pressure, and purified by silica gel chromatography using EtOAc/hexanes 9 gradient from 0-100%) and MeOH/DCM (isocratic at 20%) as eluent to provide 3.6 g (70% over 2 steps) of tert-butyl 6,9-dioxo-5-(4-(trifluoromethyl)benzyl)-2,5,8-triazaspiro[3.5]nonane-2-carboxylate as a white solid. LRMS (ES) m/z 358.1 (M+H-$^t$Bu). $^1$H-NMR: (Methanol-d₄, 400 MHz, ppm) δ 7.68 (d, J=7.7 Hz, 2H), 7.50 (d, J=7.9 Hz, 2H), 5.06 (s, 2H), 4.41 (d, J=9.7 Hz, 2H), 4.19-3.93 (m, 4H), 1.44 (s, 9H).

Intermediate 23-4 has the same structure as Intermediate 22-4. In some embodiments, Intermediate 23-4 is prepared by following steps 1-3 in Example 22. In some embodiments, Intermediate 22-4 is prepared by following steps 1-3 in Example 23.

4. Synthesis of Intermediate 23-5

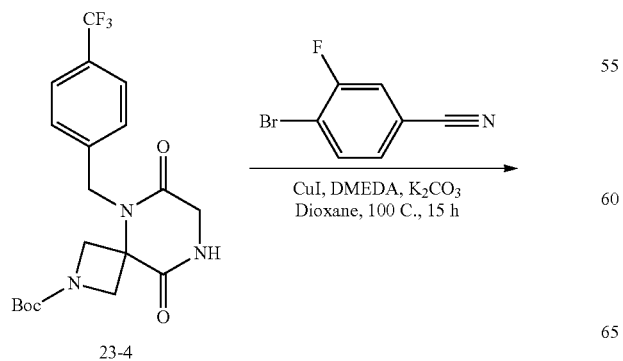

23-4

618
-continued

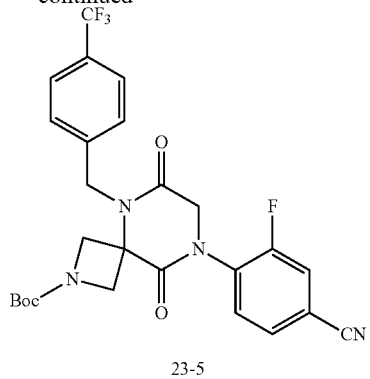

23-5

To a mixture of copper iodide (12 mg, 0.06 mmol, 0.5 equiv), potassium carbonate (67 mg, 0.48 mmol, 4 equiv), 4-bromo-3-fluorobenzonitrile (36 mg, 0.18 mmol, 1.5 equiv), and tert-butyl 6,9-dioxo-5-(4-(trifluoromethyl)benzyl)-2,5,8-triazaspiro[3.5]nonane-2-carboxylate (50 mg, 0.12 mmol, 1.0 equiv) in a vial (3.0 mL) was added dioxane (1 mL) and N,N'-dimethylethylene diamine (7 µL, 0.06 mmol, 0.5 equiv). The mixture was sealed in the vial, heated at 100° C. for 15 h, cooled to r.t., filtered, and concentrated under reduced pressure to give tert-butyl 8-(4-cyano-2-fluorophenyl)-6,9-dioxo-5-(4-(trifluoromethyl)benzyl)-2,5,8-triazaspiro[3.5]nonane-2-carboxylate which was used in the next step without purification.

5. Synthesis of Intermediate 23-6

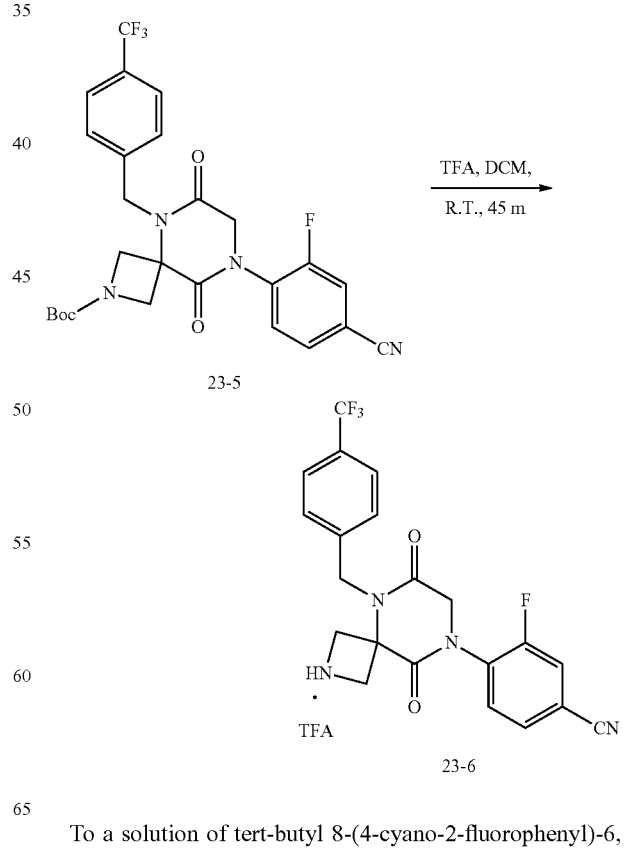

To a solution of tert-butyl 8-(4-cyano-2-fluorophenyl)-6,9-dioxo-5-(4-(trifluoromethyl)benzyl)-2,5,8-triazaspiro

[3.5]nonane-2-carboxylate (64 mg, 0.12 mmol) in DCM (2 mL) was added TFA (2 mL). The mixture was stirred at r.t. for 45 m and then concentrated to provide 4-(6,9-dioxo-5-(4-(trifluoromethyl)benzyl)-2,5,8-triazaspiro[3.5]nonan-8-yl)-3-fluorobenzonitrile as a glassy solid. The product was used in the next reaction without further purification.

6. Synthesis of Compound 169

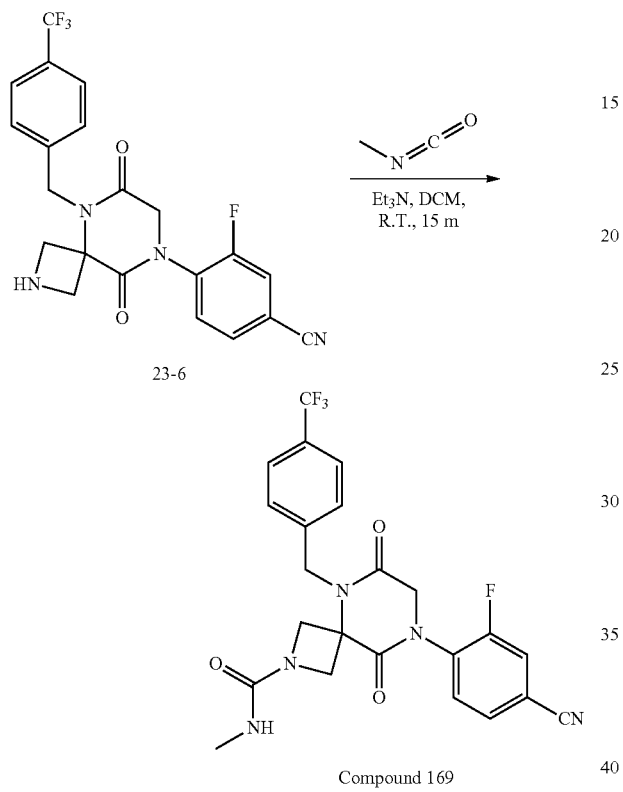

Compound 169

To a solution of 4-(6,9-dioxo-5-(4-(trifluoromethyl)benzyl)-2,5,8-triazaspiro[3.5]nonan-8-yl)-3-fluorobenzonitrile (52 mg, 0.12 mmol) in DCM (2 mL) were added TEA (0.5 mL) and methyl isocyanate (15 mg, 0.26 mmol, 2.2 equiv) sequentially. The mixture was stirred for 15 min, concentrated under reduced pressure, and purified with reverse phase HPLC (Phenomenex, gemini 5u C18 150×21.2 mm, 10-100% acetonitrile in water with 0.1% formic acid gradient over 40 min) to provide 15.6 mg (27% yield over 3 steps) of 8-(4-cyano-2-fluorophenyl)-N-methyl-6,9-dioxo-5-(4-(trifluoromethyl)benzyl)-2,5,8-triazaspiro[3.5]nonane-2-carboxamide as a white foamy solid. LRMS (ES) m/z 490.2 (M+H). $^1$H-NMR: (Methanol-$d_4$, 400 MHz, ppm) δ 7.82-7.77 (m, 1H), 7.75-7.67 (m, 4H), 7.57 (d, J=8.6 Hz, 2H), 5.15 (s, 2H), 4.56 (s, 2H), 4.48 (d, J=9.5 Hz, 2H), 4.17 (d, J=9.5 Hz, 2H), 2.68 (s, 3H).

The following compounds were prepared by methods analogous to the method described for Compound 169:

| Compound No. | LRMS (ES) m/z |
|---|---|
| 145 | M + H = 477.2 |
| 146 | M + H = 472.1 |
| 147 | M + H = 473.1 |

-continued

| Compound No. | LRMS (ES) m/z |
|---|---|
| 148 | M + H = 505.1 |
| 149 | M + H = 465.2 |
| 150 | M + H = 481.1 |
| 151 | M + H = 515.1 |
| 152 | M + H = 483.2 |
| 153 | M + H = 461.1 |
| 154 | M + H = 478.2 |
| 155 | M + H = 499.1 |
| 156 | M + H = 482.1 |
| 157 | M + H = 497.1 |
| 158 | M + H = 487.2 |
| 159 | M + H = 513.1 |
| 160 | M + H = 531.1 |
| 161 | M + H = 487.2 |
| 162 | M + H = 490.1 |
| 163 | M + H = 481.1 |
| 164 | M + H = 438.1 |
| 165 | M + H = 565.2 |
| 186 | M + H = 457.1 |
| 187 | M + H = 471.2 |
| 188 | M + H = 473.1 |
| 189 | M + H = 488.1 |
| 190 | M + H = 443.1 |
| 191 | M + H = 479.2 |
| 193 | M + H = 497.2 |
| 194 | M − H = 459.2 |
| 195 | M + H = 506.1 |
| 196 | No mass signal |
| 197 | M + H = 475.1 |
| 198 | M + H = 476.1 |
| 199 | M + H = 516.2 |
| 200 | No mass product |
| 201 | M + H = 504.2 |
| 166 | M + H = 495.1 |
| 167 | M + H = 486.2 |
| 168 | M + H = 499.1 |
| 170 | M + H = 495.1 |
| 171 | M + H = 531.1 |
| 203 | M + H = 501.1 |
| 204 | M + H = 476.1 |
| 172 | M + H = 551.2 |
| 173 | M + H = 530.2 |
| 174 | M + H = 503.1 |
| 175 | M + H = 441.1 |
| 176 | M + H = 425.1 |
| 177 | M + H = 515.1 |
| 178 | M + H = 529.2 |
| 179 | M + H = 461.1 |
| 180 | M + H = 515.1 |
| 181 | M + H = 555.1 |
| 182 | M + H = 451.1 |
| 566 | M + H = 487 |
| 593 | M + H = 521 |

Example 24: Synthesis of Compound 335

1. Synthesis of Intermediate 24-1

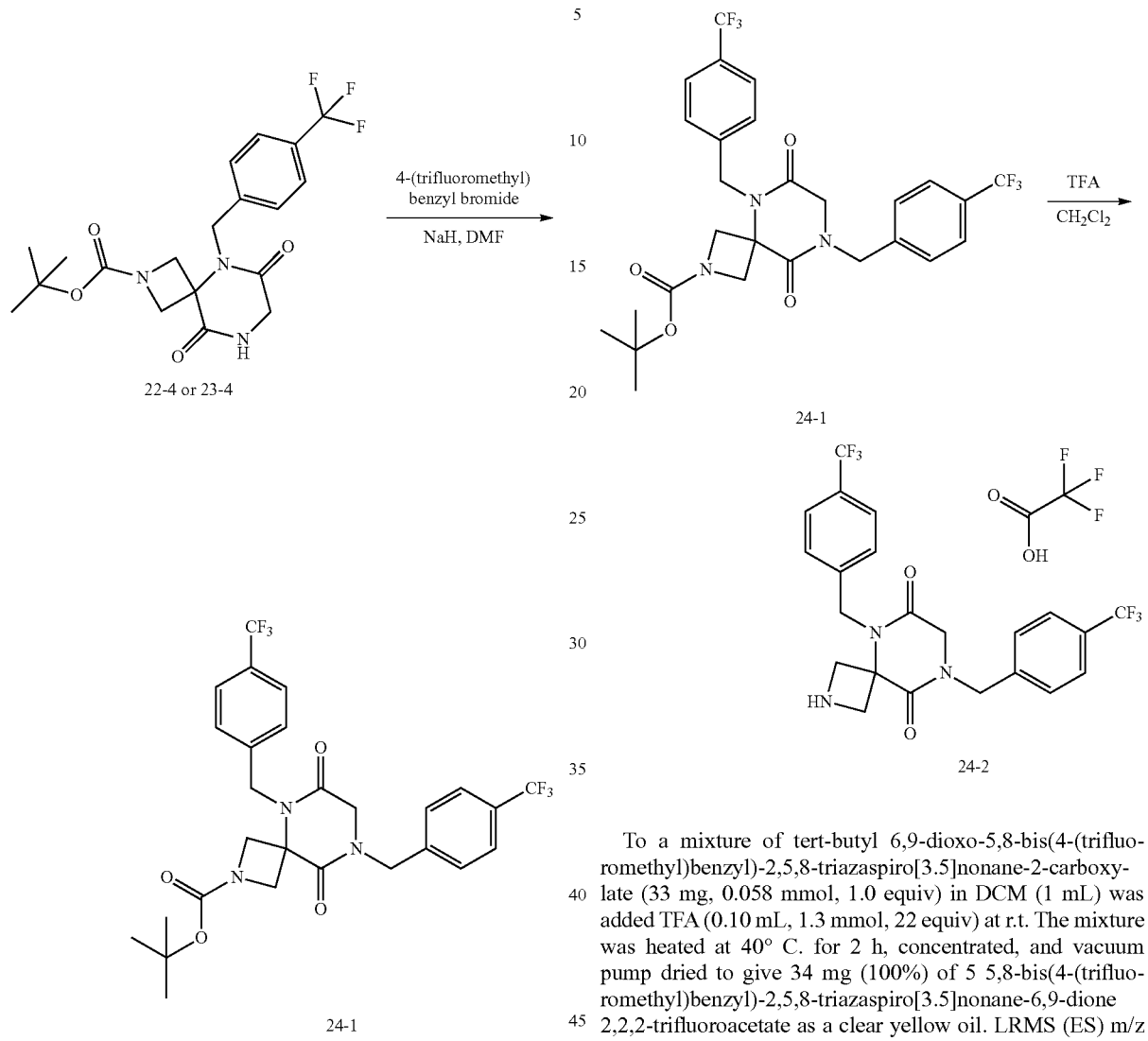

To a mixture of tert-butyl 6,9-dioxo-5-(4-(trifluoromethyl)benzyl)-2,5,8-triazaspiro[3.5]nonane-2-carboxylate (50 mg, 0.12 mmol, 1.0 equiv) and 4-(trifluoromethyl)benzyl bromide (32 mg, 0.13 mmol, 1.1 equiv) in DMF (1 mL) was added NaH (60% in mineral oil, 5 mg, 0.13 mmol, 1.1 equiv) at 0° C. The mixture was stirred at 0° C. for 30 min, quenched with water, and extracted with EA three times. The combined organic washes were dried over magnesium sulfate, filtered, concentrated, and purified by silica gel chromatography (0-100% ethyl acetate in hexanes, gradient over 11 min) to give 33 mg (48%) of tert-butyl 6,9-dioxo-5,8-bis(4-(trifluoromethyl)benzyl)-2,5,8-triazaspiro[3.5]nonane-2-carboxylate as a clear colorless oil. LRMS (ES) m/z 516 (M+H-tert-butyl).

2. Synthesis of Intermediate 24-2

To a mixture of tert-butyl 6,9-dioxo-5,8-bis(4-(trifluoromethyl)benzyl)-2,5,8-triazaspiro[3.5]nonane-2-carboxylate (33 mg, 0.058 mmol, 1.0 equiv) in DCM (1 mL) was added TFA (0.10 mL, 1.3 mmol, 22 equiv) at r.t. The mixture was heated at 40° C. for 2 h, concentrated, and vacuum pump dried to give 34 mg (100%) of 5 5,8-bis(4-(trifluoromethyl)benzyl)-2,5,8-triazaspiro[3.5]nonane-6,9-dione 2,2,2-trifluoroacetate as a clear yellow oil. LRMS (ES) m/z 472 (M+H).

3. Synthesis of Compound 335

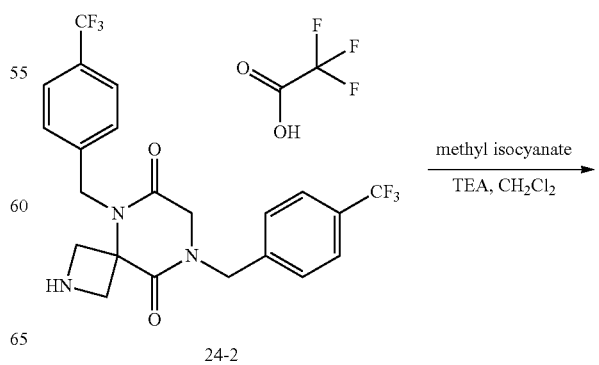

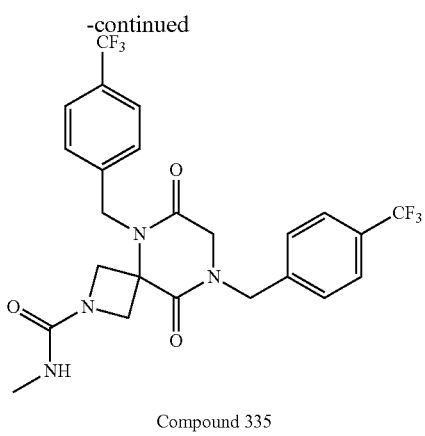

Compound 335

To a solution of 5,8-bis(4-(trifluoromethyl)benzyl)-2,5,8-triazaspiro[3.5]nonane-6,9-dione 2,2,2-trifluoroacetate (34 mg, 0.06 mmol, 1.0 equiv) in DCM (1 mL) cooled to 0° C. were added TEA (32 µL, 0.23 mmol, 4.0 equiv) and methyl isocyanate (5 mg, 0.087 mmol, 1.5 equiv). The mixture was stirred at 0° C. for 30 min, concentrated, and purified by reverse phase HPLC (Phenomenex, gemini 5u C18 150× 21.2 mm, 10-100% acetonitrile in water both with 0.1% formic acid gradient over 25 min) to give 21 mg (69%) of N-methyl-6,9-dioxo-5,8-bis(4-(trifluoromethyl)benzyl)-2,5,8-triazaspiro[3.5]nonane-2-carboxamide as a white solid. LRMS (ES) m/z 529 (M+H). $^1$H NMR (400 MHz, Methanol-d$_4$) δ 7.73-7.69 (m, 2H), 7.69-7.64 (m, 2H), 7.60-7.56 (m, 2H), 7.52-7.47 (m, 2H), 5.08 (s, 2H), 4.79 (s, 2H), 4.48-4.43 (m, 2H), 4.14 (s, 2H), 4.12-4.05 (m, 2H), 2.70 (s, 3H).

Example 25

Synthesis of Compound 192

1. Synthesis of Intermediate 25-1

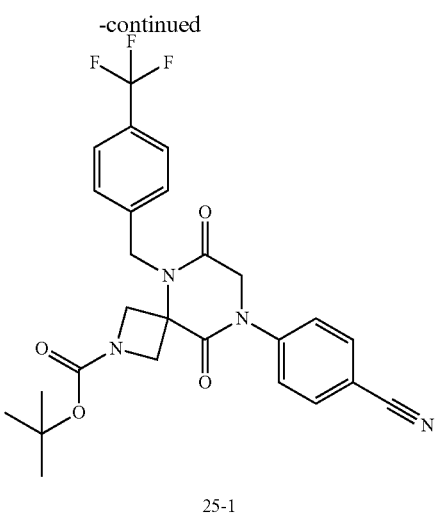

25-1

To a mixture of tert-butyl 6,9-dioxo-5-(4-(trifluoromethyl)benzyl)-2,5,8-triazaspiro[3.5]nonane-2-carboxylate (0.871 g, 2.11 mmol, 1.0 equiv), 4-bromobenzonitrile (0.575 g, 3.16 mmol, 1.5 equiv), copper (I) iodide (0.201 g, 1.05 mmol, 0.50 equiv), and potassium carbonate (0.873 g, 6.32 mmol, 3.0 equiv) suspended in anhydrous 1,4-dioxane was added N,N-dimethylethylenediamine (0.11 mL, 1.0 mmol, 0.50 equiv). The mixture was flushed with nitrogen, sealed, and heated at 100° C. for 15 h, cooled to r.t., filtered through celite, concentrated, and purified by silica gel chromatography using EtOAc/Hexanes (gradient from 0-100%) to give 0.968 g (89%) of tert-butyl 8-(4-cyanophenyl)-6,9-dioxo-5-(4-(trifluoromethyl)benzyl)-2,5,8-triazaspiro[3.5]nonane-2-carboxylate as a white foam. LRMS (ES) m/z 459 (M+H-tert-butyl).

2. Synthesis of Intermediate 25-2

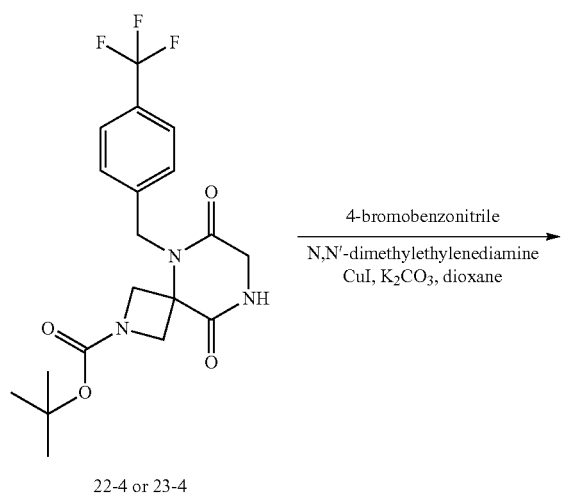

22-4 or 23-4

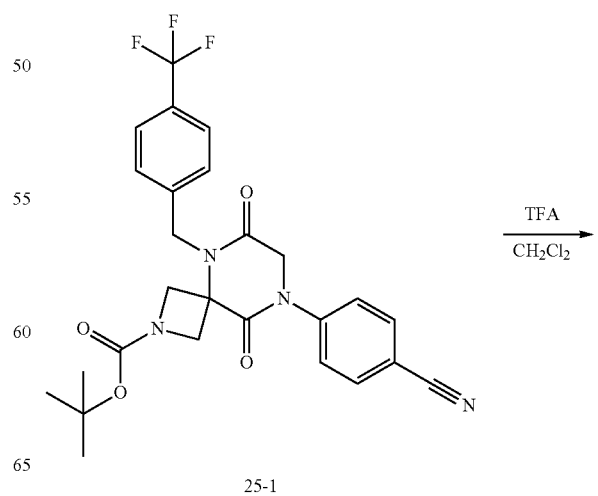

25-1

625

-continued

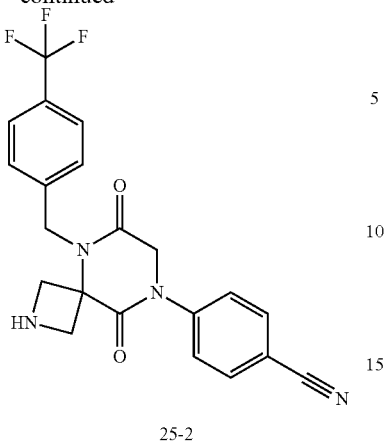

25-2

To a solution of tert-butyl 8-(4-cyanophenyl)-6,9-dioxo-5-(4-(trifluoromethyl)benzyl)-2,5,8-triazaspiro[3.5]nonane-2-carboxylate (0.968 g, 1.88 mmol, 1.0 equiv) in DCM (14 mL) was added TFA (1.4 mL, 19 mmol, 10 equiv). The mixture was heated at 40° C. for 3 h, concentrated, diluted with saturated aqueous sodium bicarbonate, and extracted with ethyl acetate three times. The combined organic layers were washed with brine, dried over magnesium sulfate, and concentrated to give 0.751 g (96%) of 4-(6,9-dioxo-5-(4-(trifluoromethyl)benzyl)-2,5,8-triazaspiro[3.5]nonan-8-yl)benzonitrile as a white foam. LRMS (ES) m/z 415 (M+H). $^1$H NMR (400 MHz, Methylene Chloride-d$_2$) δ 7.70-7.66 (m, 2H), 7.57-7.53 (m, 2H), 7.46-7.42 (m, 2H), 7.38-7.34 (m, 2H), 5.19 (s, 2H), 4.34 (s, 2H), 4.31-4.24 (m, 2H), 3.74-3.66 (m, 2H).

3. Synthesis of Compound 192

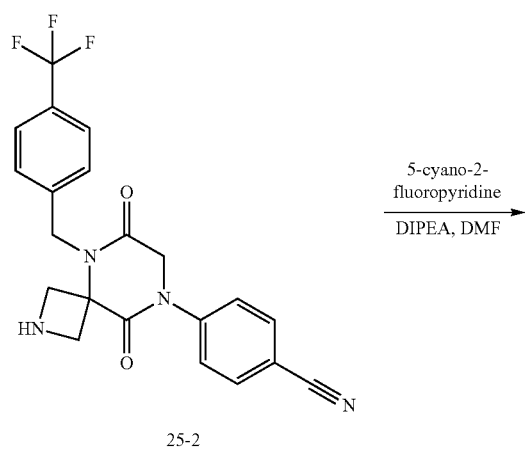

25-2

626

-continued

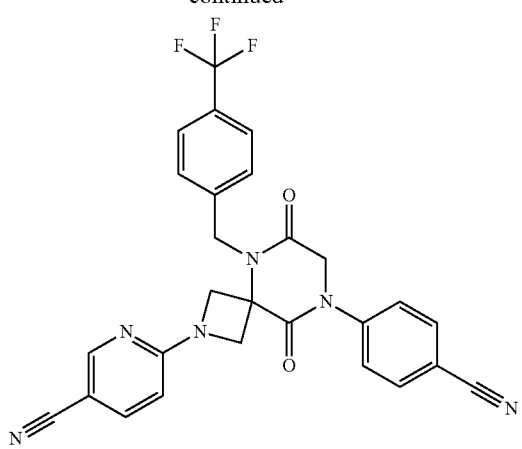

Compound 192

To a mixture of 4-(6,9-Dioxo-5-(4-(trifluoromethyl)benzyl)-2,5,8-triazaspiro[3.5]nonan-8-yl)benzonitrile (67 mg, 0.16 mmol, 1.0 equiv) and 5-cyano-2-fluoropyridine (0.024 g, 0.19 mmol, 1.2 equiv) in DMF (1 mL) was added DIEA (0.042 mL, 0.24 mmol, 1.5 equiv). The mixture was heated at 100° C. for 15 h, cooled to r.t., and purified with reverse phase HPLC (Phenomenex, gemini 5u C18 150×21.2 mm, 10-100% acetonitrile in water both with 0.1% formic acid gradient over 25 min) to give 40 mg (48%) of 6-(8-(4-cyanophenyl)-6,9-dioxo-5-(4-(trifluoromethyl)benzyl)-2,5,8-triazaspiro[3.5]nonan-2-yl)nicotinonitrile as a clear colorless oil. LRMS (ES) m/z 517 (M+H). $^1$H NMR (400 MHz, Methanol-d$_4$) δ 8.38 (dd, J=2.2, 0.8 Hz, 1H), 7.89-7.83 (m, 2H), 7.77 (dd, J=8.8, 2.2 Hz, 1H), 7.72-7.68 (m, 2H), 7.68-7.63 (m, 2H), 7.60-7.55 (m, 2H), 6.49 (dd, J=8.8, 0.8 Hz, 1H), 5.18 (s, 2H), 4.71-4.66 (m, 2H), 4.64 (s, 2H), 4.43-4.38 (m, 2H).

Example 26: Synthesis of Compound 336

1. Synthesis of Intermediate 26-1

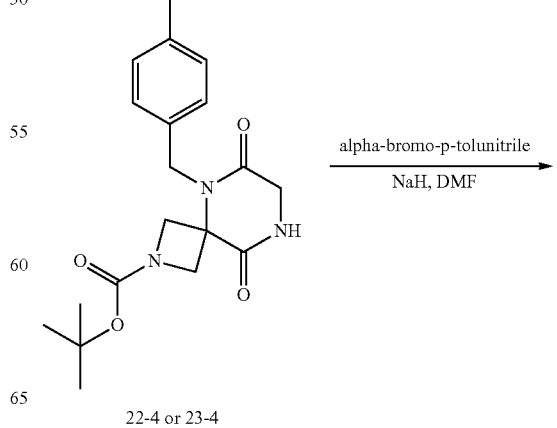

22-4 or 23-4

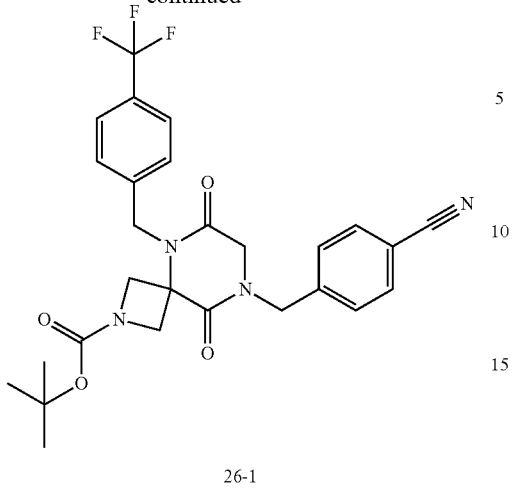

26-1

To a mixture of tert-butyl 6,9-dioxo-5-(4-(trifluoromethyl)benzyl)-2,5,8-triazaspiro[3.5]nonane-2-carboxylate (0.050 g, 0.12 mmol, 1.0 equiv) and 4-(bromomethyl)benzonitrile (25 mg, 0.13 mmol, 1.1 equiv) in DMF (1 mL) at 0° C. was added NaH (60% in mineral oil, 5 mg, 0.13 mmol, 1.1 equiv) at 0° C. and then added 60% sodium hydride in mineral oil (0.005 g, 0.13 mmol, 1.1 equiv). The mixture was stirred at 0° C. for 30 min, quenched with water, and extracted with EA three times. The combined organic washes were dried over magnesium sulfate, filtered, concentrated, and purified by silica gel chromatography (0-100% ethyl acetate in hexanes, gradient over 11 min) to give 55 mg (87%) of tert-butyl 8-(4-cyanobenzyl)-6,9-dioxo-5-(4-(trifluoromethyl)benzyl)-2,5,8-triazaspiro[3.5]nonane-2-carboxylate as a clear colorless oil. LRMS (ES) m/z 473 (M+H-tert-butyl).

2. Synthesis of Intermediate 26-2

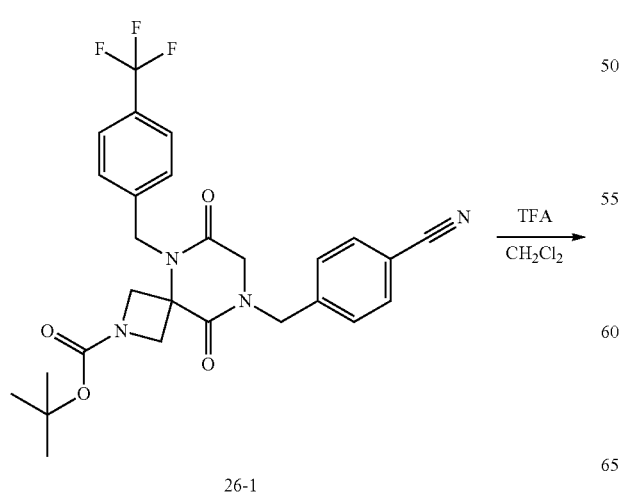

26-1

→ TFA, CH₂Cl₂

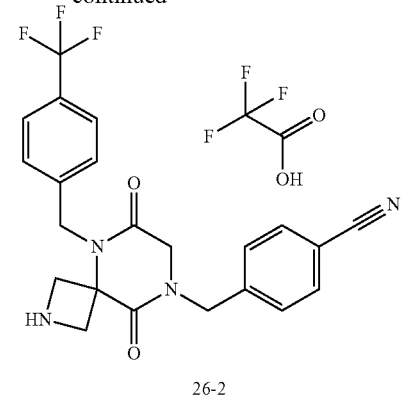

26-2

To a mixture of tert-butyl 8-(4-cyanobenzyl)-6,9-dioxo-5-(4-(trifluoromethyl)benzyl)-2,5,8-triazaspiro[3.5]nonane-2-carboxylate (55 mg, 0.10 mmol, 1.0 equiv) in DCM (1 mL) was added TFA (0.10 mL, 1.3 mmol, 12 equiv) at r.t. The mixture was heated at 40° C. for 2 h, concentrated, and vacuum pump dried to give 57 mg (100%) of 4-((6,9-dioxo-5-(4-(trifluoromethyl)benzyl)-2,5,8-triazaspiro[3.5]nonan-8-yl)methyl)benzonitrile 2,2,2-trifluoroacetate as a clear yellow oil. LRMS (ES) m/z 429 (M+H).

3. Synthesis of Compound 336

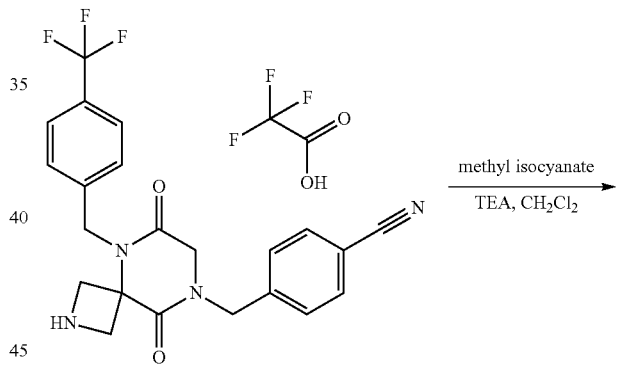

26-2 methyl isocyanate
TEA, CH₂Cl₂
→

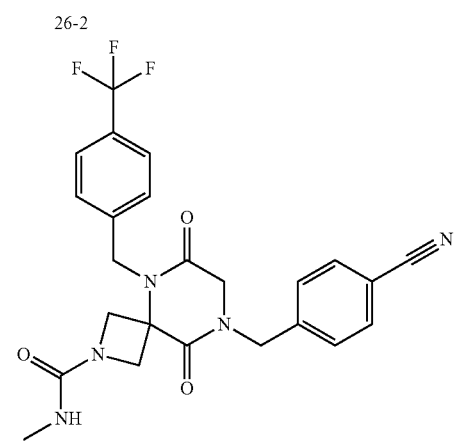

Compound 336

To a solution of 4-((6,9-dioxo-5-(4-(trifluoromethyl)benzyl)-2,5,8-triazaspiro[3.5]nonan-8-yl)methyl)benzonitrile 2,2,2-trifluoroacetate (57 mg, 0.10 mmol, 1.0 equiv) in DCM (1 mL) cooled to 0° C. were added TEA (59 μL, 0.42 mmol, 4.0 equiv) and methyl isocyanate (9 mg, 0.087 mmol, 1.5 equiv). The mixture was stirred at 0° C. for 30 min, concentrated, and purified by reverse phase HPLC (Phenomenex, gemini 5u C18 150×21.2 mm, 10-80% acetonitrile in water both with 0.1% formic acid in 25 min) to give 32 mg (62%) of 8-(4-cyanobenzyl)-N-methyl-6,9-dioxo-5-(4-(trifluoromethyl)benzyl)-2,5,8-triazaspiro[3.5]nonane-2-carboxamide as a white solid. LRMS (ES) m/z 486 (M+H). ¹H NMR (400 MHz, DMSO-d$_6$) δ 7.89-7.84 (m, 2H), 7.74-7.69 (m, 2H), 7.57-7.47 (m, 4H), 6.43-6.38 (m, 1H), 4.94 (s, 2H), 4.69 (s, 2H), 4.28-4.20 (m, 2H), 4.08 (s, 2H), 3.91-3.83 (m, 2H), 2.54-2.47 (m, 3H).

Example 27: Synthesis of Compound 338

1. Synthesis of Intermediate 27-1

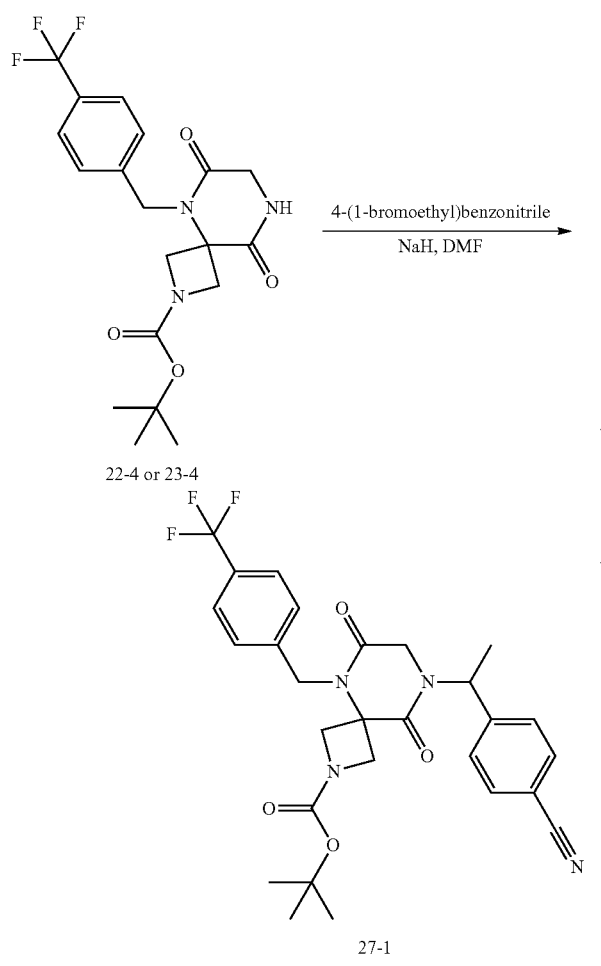

To a solution of tert-butyl 6,9-dioxo-5-(4-(trifluoromethyl)benzyl)-2,5,8-triazaspiro[3.5]nonane-2-carboxylate and 4-(1-bromoethyl)benzonitrile (50 mg, 0.12 mmol, 1.0 equiv) in DMF (1 mL) at 0° C. was added NaH (5 mg of 60% dispersion in mineral oil, 0.13 mmol, 1.1 equiv.). The resulting mixture was stirred at 0° C. for 1 h, quenched with addition of water (1 mL) dropwise, and extracted with EA three times. The combined organic layers were washed with saturated brine, dried over magnesium sulfate, concentrated under reduced pressure, and purified with silica gel using a gradient from 0-100% EtOAc/hexanes to give 58 mg (88%) of tert-butyl 8-(1-(4-cyanophenyl)ethyl)-6,9-dioxo-5-(4-(trifluoromethyl)benzyl)-2,5,8-triazaspiro[3.5]nonane-2-carboxylate as a clear colorless oil. LRMS (ES) m/z 487 (M+H-tertbutyl).

2. Synthesis of Intermediate 27-2

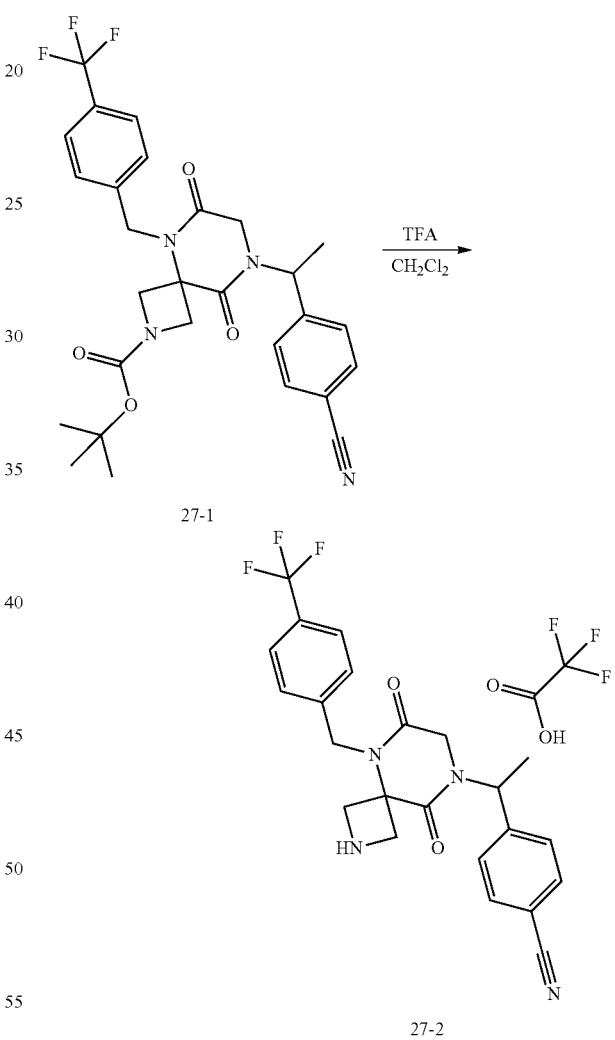

To a solution of tert-butyl 8-(1-(4-cyanophenyl)ethyl)-6,9-dioxo-5-(4-(trifluoromethyl)benzyl)-2,5,8-triazaspiro[3.5]nonane-2-carboxylate (58 mg, 0.11 mmol, 1.0 equiv) in DCM (1 mL) was added trifluoroacetic acid (0.082 mL, 1.1 mmol, 10 equiv). The mixture was heated at 40° C. for 1 h and then concentrated under reduced pressure to give 59 mg (100%) of 4-(1-(6,9-dioxo-5-(4-(trifluoromethyl)benzyl)-2,5,8-triazaspiro[3.5]nonan-8-yl)ethyl)benzonitrile 2,2,2-trifluoroacetate as a yellow oil. LRMS (ES) m/z 443 (M+H).

3. Synthesis of Compound 338

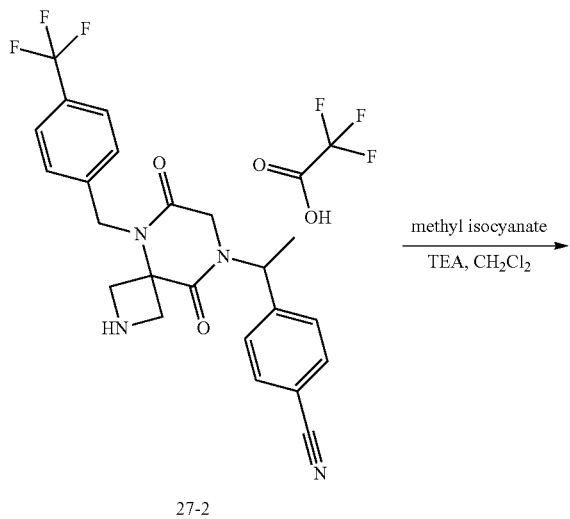

27-2

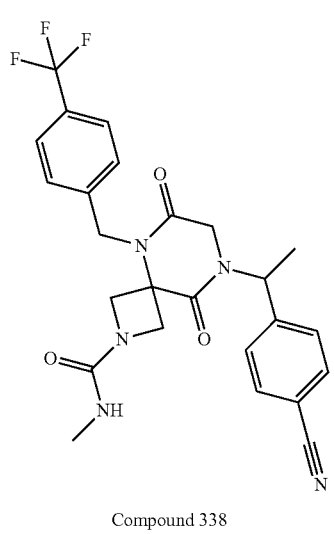

Compound 338

To a solution of 4-(1-(6,9-dioxo-5-(4-(trifluoromethyl)benzyl)-2,5,8-triazaspiro[3.5]nonan-8-yl)ethyl)benzonitrile 2,2,2-trifluoroacetate (59 mg, 0.11 mmol, 1.0 equiv) in dry DCM (1 mL) at 0° C. were added TEA (59 μL, 0.42 mmol, 4.0 equiv) and methyl isocyanate (9 mg, 0.16 mmol, 1.5 equiv). The mixture was stirred at 0° C. for 30 min, concentrated, and purified with reverse phase HPLC (Phenomenex, gemini 5u C18 150×21.2 mm, 10-80% acetonitrile in water both with 0.1% formic acid gradient over 25 min) to give 34 mg (63%) of 8-(1-(4-cyanophenyl)ethyl)-N-methyl-6,9-dioxo-5-(4-(trifluoromethyl)benzyl)-2,5,8-triazaspiro[3.5]nonane-2-carboxamide as a clear red oil. LRMS (ES) m/z 500 (M+H). $^1$H NMR (400 MHz, Methanol-$d_4$) δ 7.81-7.76 (m, 2H), 7.69-7.64 (m, 2H), 7.63-7.58 (m, 2H), 7.50-7.45 (m, 2H), 5.95 (q, J=7.1 Hz, 1H), 5.06 (s, 2H), 4.46-4.40 (m, 2H), 4.21-4.13 (m, 1H), 4.11-4.03 (m, 2H), 3.74-3.65 (m, 1H), 2.69 (s, 3H), 1.67 (d, J=7.2 Hz, 3H).

Example 28: Synthesis of Compound 216

1. Synthesis of Intermediate 28-2

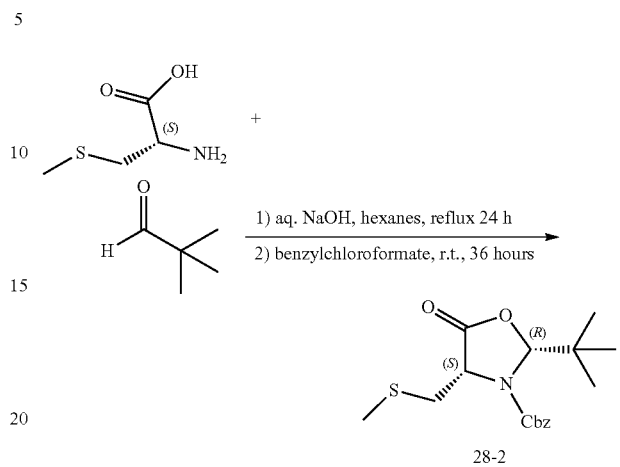

28-2

This step followed the published method in *Aust. J. Chem.*, 1993, 46, 73-93 and *Org. Biomol. Chem.*, 2010, 8, 5120-5125. (S)—S-methylcysteine (5.61 g, 41.5 mmol) was treated with a solution of NaOH (1.7 g, 41.5 mmol, 1 equiv.) in water (25 mL) and after 5 minutes the resulting homogeneous solution was evaporated to dryness under reduced pressure to provide a white solid. To this mixture was added a solution of pivaldehyde (5.35 g, 62.2 mmol, 1.5 equiv.) in hexanes (75 mL). The resulting suspension was heated to reflux with stirring for 24 h with a Dean-Stark trap to remove water. Refluxing was periodically interrupted to scrape solid material from the walls of the flask to facilitate stirring. After refluxing for 24 h, the reaction was evaporated to dryness providing a white solid. To the white solid suspended in DCM (75 mL) cooled to 0° C. with an ice bath was added benzyl chloroformate (8.88 mL, 62.2 mmol, 1.5 equiv.). The resulting mixture was stirred at r.t. for 36 h, quenched with saturated aqueous NaHCO$_3$ (50 mL), stirred for 3 h, and the layers were separated. The aqueous phase was extracted with DCM (50 mL). The combined organic phases were dried over sodium sulfate, concentrated under reduced pressure, and purified with silica gel chromatography using EA/HE (1/9) as eluents to provide 3.0 g (21%) of benzyl (2R,4S)-2-(tert-butyl)-4-((methylthio)methyl)-5-oxooxazolidine-3-carboxylate (visualized with iodine) as a viscous colorless oil. LRMS (APCI) m/z 338.2 (M+H). $^1$H NMR (400 MHz, Chloroform-d) δ 7.35-7.28 (m, 5H), 5.48 (s, 1H), 5.12 (d, J=1.7 Hz, 2H), 4.43 (dd, J=7.9, 5.7 Hz, 1H), 2.93 (dd, J=14.0, 8.0 Hz, 1H), 2.79 (dd, J=14.0, 5.7 Hz, 1H), 2.03 (s, 3H), 0.89 (s, 9H).

2. Synthesis of Intermediate 28-3

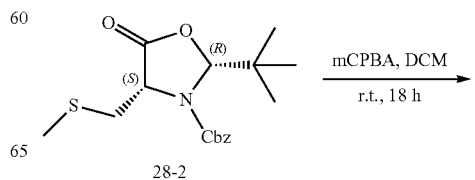

28-2

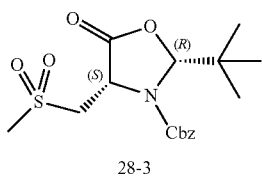

28-3

To a solution of benzyl (2R,4S)-2-(tert-butyl)-4-((methylthio)methyl)-5-oxooxazolidine-3-carboxylate (2.95 g, 8.7 mmol) in DCM (100 mL) was added mCPBA (3.77 g, 21.8 mmol, 2.5 equiv.). The resulting solution was stirred at r.t. for 18 h and quenched with saturated aqueous NaHCO$_3$ (150 mL). The aqueous phase was extracted with DCM (50 mL). The combined organic phases were combined, dried over sodium sulfate, concentrated under reduced pressure, and purified by silica gel chromatography using EA/Hex (1/3) as eluent to provide 3.1 g (95%) of benzyl (2R,4S)-2-(tert-butyl)-4-((methylsulfonyl)methyl)-5-oxooxazolidine-3-carboxylate. LRMS (APCI) m/z 370.1 (M+H). $^1$H NMR (400 MHz, Chloroform-d) δ 7.46-7.37 (m, 5H), 5.65 (s, 1H), 5.34-5.20 (m, 2H), 5.01 (dd, J=8.0, 3.7 Hz, 1H), 3.60 (dd, J=15.1, 8.0 Hz, 1H), 3.49-3.36 (m, 1H), 3.14 (s, 3H), 0.97 (s, 9H).

3. Synthesis of Intermediate 28-4

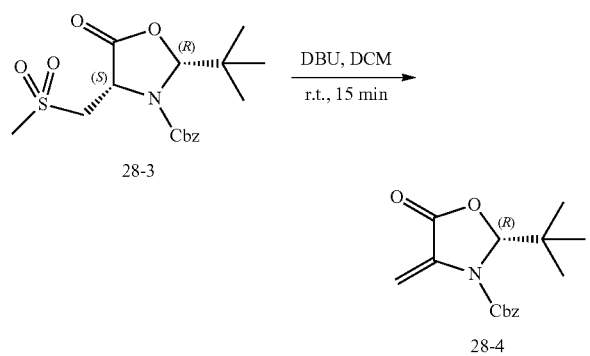

This step was followed using the published method in Org. Biomol. Chem., 2010, 8, 5120-5125. To a solution of benzyl (2R,4S)-2-(tert-butyl)-4-((methylsulfonyl)methyl)-5-oxooxazolidine-3-carboxylate (3.05 g, 8.3 mmol) in DCM (50 mL) cooled to 0° C. with an ice bath was added DBU (1.36 mL, 9.1 mmol, 1.1 equiv.) dropwise. The resulting solution was stirred at 0° C. for 30 min, diluted with water (50 mL), and the layers were separated. The organic phase was washed with additional water (50 mL) twice, dried over sodium sulfate, concentrated under reduced pressure, and purified through a short plug of silica gel using EA/Hex (1/2) as eluents to provide 2.3 g (94%) of benzyl (R)-2-(tert-butyl)-4-methylene-5-oxooxazolidine-3-carboxylate as a colorless oil. LRMS (APCI) m/z 290.0 (M+H). $^1$H NMR (400 MHz, Chloroform-d) δ 7.46-7.37 (m, 5H), 5.79-5.58 (m, 3H), 5.28 (d, J=1.5 Hz, 2H), 0.96 (s, 9H).

4. Synthesis of Intermediate 28-5

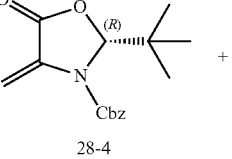

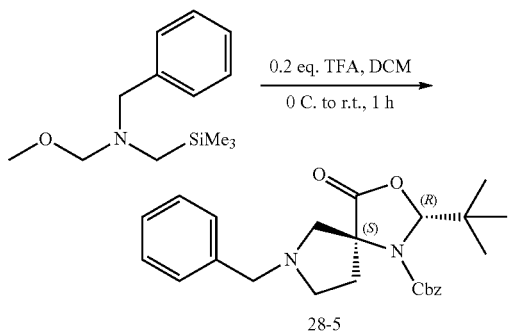

This step followed the published method in Tetrahedron Letters, Vol. 33, No. 45, pp. 6755-6758, 1992 and Synthetic Communications, 25(9), 1295-1302 (1995). To a solution of benzyl (R)-2-(tert-butyl)-4-methylene-5-oxooxazolidine-3-carboxylate (1.49 g, 5.1 mmol) in DCM (25 mL) was added N-(methoxymethyl)-N-(trimethylsilylmethyl) benzylamine (3.95 mL, 15.4 mmol, 3 equiv.). To the resulting solution cooled to 0° C. with an ice bath was added TFA (0.079 mL, 0.2 equivalents) dropwise. The mixture was stirred at 0° C. for 5 min and the ice bath was removed. The mixture was stirred at r.t. for 1 h, diluted with DCM (40 mL), washed with saturated aqueous NaHCO$_3$ (50 mL), dried over sodium sulfate, concentrated under reduced pressure, and purified by silica gel chromatography using EA/HE (1/4) as eluents to provide 2.2 g (96%) of benzyl (2R,5S)-7-benzyl-2-(tert-butyl)-4-oxo-3-oxa-1,7-diazaspiro[4.4]nonane-1-carboxylate (2.20 g, 4.9 mmol, 96% yield) as a colorless, viscous oil. LRMS (APCI) m/z 423.3 (M+H). $^1$H NMR (400 MHz, DMSO-d$_6$) δ 7.45-7.32 (m, 5H), 7.28-7.17 (m, 5H), 5.58 (s, 1H), 5.16 (d, J=12.1 Hz, 1H), 5.09 (d, J=12.2 Hz, 1H), 3.46 (s, 2H), 3.01-2.58 (m, 4H), 2.22 (t, J=6.5 Hz, 2H), 0.83 (s, 9H).

5. Synthesis of Intermediate 28-6

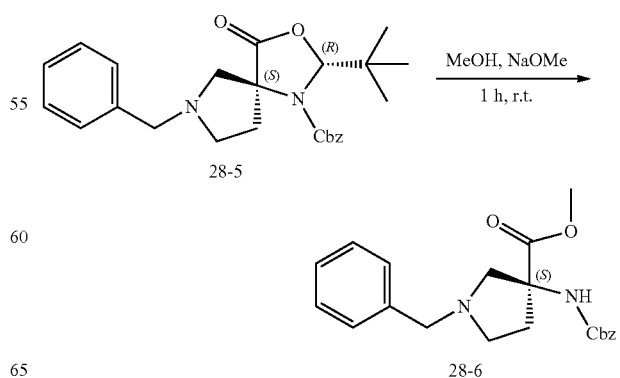

To a solution of benzyl (2R,5S)-7-benzyl-2-(tert-butyl)-4-oxo-3-oxa-1,7-diazaspiro[4.4]nonane-1-carboxylate (2.18 g, 5.2 mmol) in MeOH (30 mL) was added NaOMe (2.8 mL of 25% in MeOH) dropwise at r.t. The resulting mixture was stirred at r.t. for 30 min and diluted with EtOAc (200 mL), saturated NH$_4$Cl (100 mL) and water (100 mL). The layers were separated and the aqueous phase was extracted with EtOAc (100 mL). The combined organic phases were washed with brine, dried over sodium sulfate, concentration under reduced pressure, and purified by silica gel chromatography using EA/HE (1/1) as eluents to provide 1.8 g (94%) of methyl (S)-1-benzyl-3-(((benzyloxy)carbonyl)amino)pyrrolidine-3-carboxylate as a colorless, sticky solid. LRMS (APCI) m/z 369.2 (M+H). $^1$H NMR (400 MHz, Methanol-d$_4$) δ 7.37-7.18 (m, 10H), 5.04 (s, 2H), 3.73-3.43 (m, 5H), 3.12 (d, J=10.7 Hz, 1H), 2.89 (d, J=10.7 Hz, 1H), 2.84-2.74 (m, 1H), 2.61 (dt, J=9.3, 7.1 Hz, 1H), 2.40 (ddd, J=13.2, 7.4, 5.6 Hz, 1H), 2.05 (dt, J=13.6, 7.0 Hz, 1H).

6. Synthesis of Intermediate 28-7

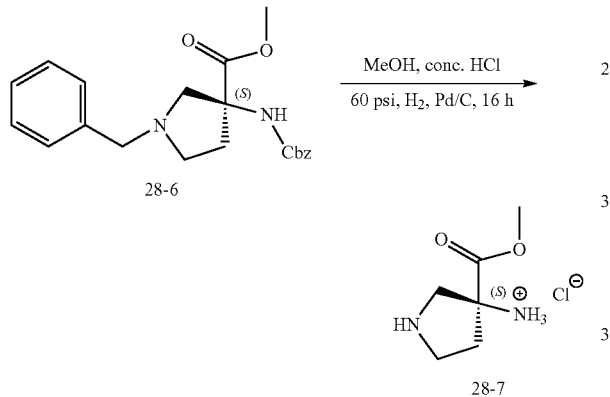

To a solution of methyl (S)-1-benzyl-3-(((benzyloxy)carbonyl)amino)pyrrolidine-3-carboxylate (1.78 g, 4.8 mmol) in MeOH (25 mL) were added concentrated HCl (0.150 mL) and palladium (5% on carbon, 300 mg). The resulting mixture was sparged with hydrogen for 30 minutes and then stirred at r.t. under hydrogen (1 atm) for 18 h. The reaction mixture was filtered through celite and the filtrate was concentrated under reduced pressure to provide 691 mg (61%) of methyl (S)-3-aminopyrrolidine-3-carboxylate dihydrogen chloride as a sticky salt. LRMS (APCI) m/z 145.1 (M+H). $^1$H NMR (400 MHz, Methanol-d$_4$) δ 3.73 (s, 3H), 3.42-3.31 (m, 2H), 3.28-3.20 (m, 1H), 3.03 (d, J=11.9 Hz, 1H), 2.29 (dt, J=13.3, 8.5 Hz, 1H), 1.92 (td, J=8.0, 3.9 Hz, 1H).

7. Synthesis of Intermediate 28-8

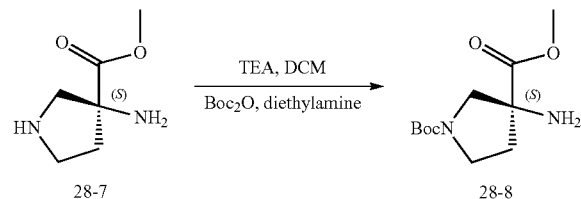

To a solution of methyl (S)-3-aminopyrrolidine-3-carboxylate dihydrogen chloride (631 mg, 2.9 mmol) in DCM (20 mL) were added TEA (3.1 mL, 22.0 mmol, 7.6 equiv.) and (Boc)$_2$O (960 mg, 4.4 mmol, 1.5 equiv.) in DCM (5 mL). The resulting solution was stirred at r.t. for 15 min, quenched with diethylamine (0.453 mL, 4.4 mmol, 1.5 equiv.), stirred at r.t. for 15 min, washed with saturated aqueous NaHCO$_3$ (25 mL), dried over sodium sulfate, concentrated, and purified by silica gel chromatography using EA/HE (gradient from 0-100%) to provide 656 mg (61%) of 1-(tert-butyl) 3-methyl (S)-3-aminopyrrolidine-1,3-dicarboxylate. LRMS (APCI) m/z 189.1 (M+H)–C$_4$H$_9$). $^1$H NMR (400 MHz, Methanol-d$_4$) δ 3.77 (s, 3H), 3.72 (dd, J=11.2, 4.4 Hz, 1H), 3.53 (dq, J=8.4, 4.6, 3.7 Hz, 2H), 3.32-3.31 (m, 1H), 2.33 (dq, J=12.8, 8.2 Hz, 1H), 2.00-1.88 (m, 1H), 1.48 (s, 9H).

8. Synthesis of Intermediate 28-9

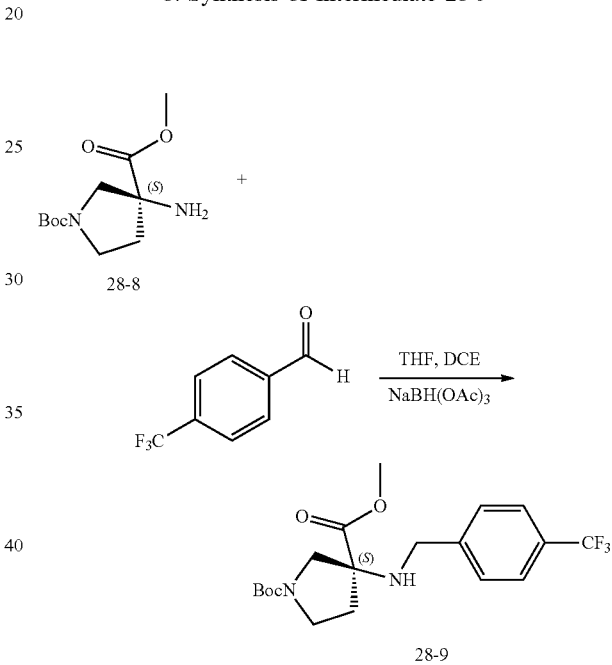

To a mixture of 1-(tert-butyl) 3-methyl (S)-3-aminopyrrolidine-1,3-dicarboxylate (1.20 g, 4.91 mmol) and p-trifluoromethylbenzaldehyde (1.71 g, 9.8 mmol, 2.0 equiv.) in a mixture of THF (30 mL) and DCE (10 mL) was added HOAc (1 mL). To the resulting mixture stirred at r.t. for 5 min was added STAB (5.21 g, 24.56 mmol, 5.0 equiv.). The mixture was continued to stir at r.t. for 48 h, evaporated under reduced pressure, and partitioned between DCM (150 mL) and saturated NaHCO$_3$ (60 mL). The aqueous phase was extracted with DCM (25 mL). The combined organic phases were dried over sodium sulfate, and concentrated under reduced pressure, and purified by silica gel chromatography using EA/Hex (1/4) as eluents to provide 1.2 g (62%) of 1-(tert-butyl) 3-methyl (S)-3-((4-(trifluoromethyl)benzyl)amino)pyrrolidine-1,3-dicarboxylate. LRMS (APCI) m/z 403.1 (M+H). $^1$H NMR (400 MHz, Methanol-d$_4$) δ 7.61 (d, J=8.1 Hz, 2H), 7.55 (d, J=8.1 Hz, 2H), 3.90-3.79 (m, 1H), 3.79-3.65 (m, 5H), 3.55 (qd, J=8.3, 7.9, 4.2 Hz, 1H), 3.50-3.40 (m, 2H), 2.37-2.26 (m, 1H), 2.09 (ddt, J=12.0, 7.5, 3.7 Hz, 1H), 1.46 (d, J=20.4 Hz, 9H).

9. Synthesis of Intermediate 28-10

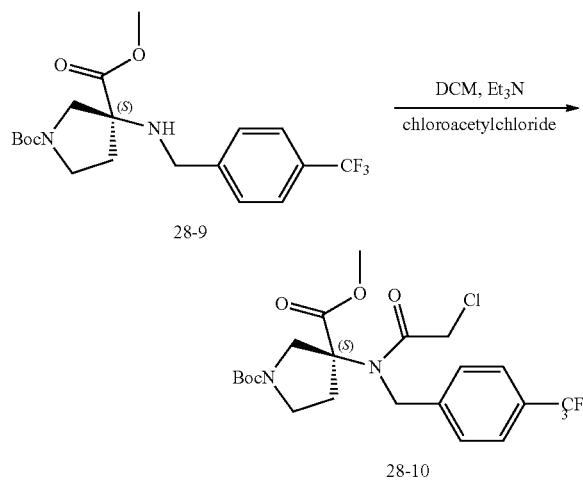

To a mixture of 1-(tert-butyl) 3-methyl (S)-3-((4-(trifluoromethyl)benzyl)amino) pyrrolidine-1,3-dicarboxylate (1.20 g, 2.98 mmol) and TEA (6.24 mL, 44.73 mmol, 15.0 equiv.) in DCM (50 mL) cooled to 0° C. was added chloroacetylchloride (3.37 g, 29.82 mmol, 10.0 equiv.) dropwise using a syringe. Upon completion of the addition, the ice bath was removed. The resulting brown suspension was stirred at r.t. for 1.5 h, diluted with DCM (75 mL), and washed with saturated aqueous NaHCO₃ (75 mL). The organic phase was dried over sodium sulfate, concentrated, and purified by silica gel chromatography using EA/Hex (4/6) as eluents to provide 0.92 g (64%) of 1-(tert-butyl) 3-methyl (S)-3-(2-chloro-N-(4-(trifluoromethyl)benzyl)acetamido)pyrrolidine-1,3-dicarboxylateas. LRMS (APCI) m/z 379.2 (M+H with Boc loss). $^1$H NMR (400 MHz, Methanol-$d_4$) δ 7.75 (d, J=8.1 Hz, 2H), 7.63 (d, J=6.9 Hz, 2H), 5.02 (d, J=19.3 Hz, 1H), 4.85 (d, 1H), 4.34-4.16 (m, 3H), 3.78 (s, 3H), 3.53-3.42 (m, 1H), 3.40-3.33 (m, 2H), 2.46-2.21 (m, 2H), 1.46 (d, J=4.3 Hz, 9H).

10. Synthesis of Intermediate 28-11

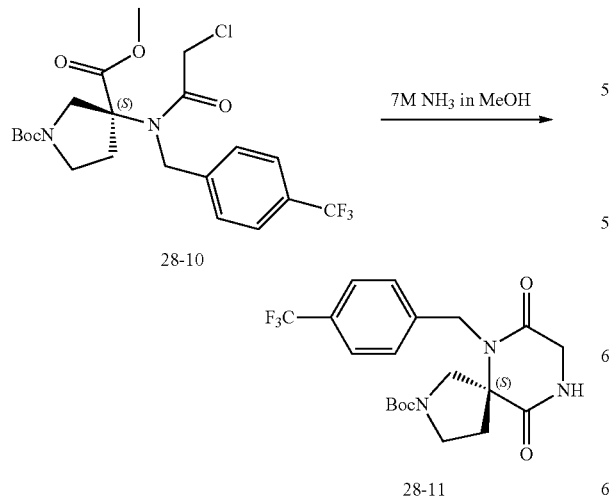

To 1-(tert-butyl) 3-methyl (S)-3-(2-chloro-N-(4-(trifluoromethyl)benzyl) acetamido)pyrrolidine-1,3-dicarboxylate (0.90 g. 1.88 mmol) was added NH₃ in MeOH (7 M, 25 mL). The mixture was sealed, heated at 80° C. for 1.5 h, cooled down to r.t., evaporated under reduced pressure, and partitioned between DCM (100 mL) and water (50 mL). The aqueous phase was extracted with DCM (25 mL). The combined organic phases were dried over sodium sulfate, concentrated, and purified by silica gel chromatography using EA/Hex (gradient from 0-100% and 100%) as eluents to provide 0.72 g (89%) of tert-butyl (S)-7,10-dioxo-6-(4-(trifluoromethyl)benzyl)-2,6,9-triazaspiro[4.5]decane-2-carboxylate. LRMS (APCI) m/z 372.1 (M+H) (—C₄H₉). $^1$H NMR (400 MHz, Methanol-$d_4$) δ 7.66 (d, J=7.9 Hz, 2H), 7.43 (d, J=8.0 Hz, 2H), 5.01 (dd, J=33.8, 17.0 Hz, 1H), 4.69 (dd, J=37.6, 17.1 Hz, 1H), 4.18 (d, J=4.5 Hz, 2H), 3.95-3.84 (m, 1H), 3.61-3.46 (m, 3H), 2.49-2.33 (m, 2H), 1.42 (d, J=24.0 Hz, 9H).

11. Synthesis of Intermediate 28-12

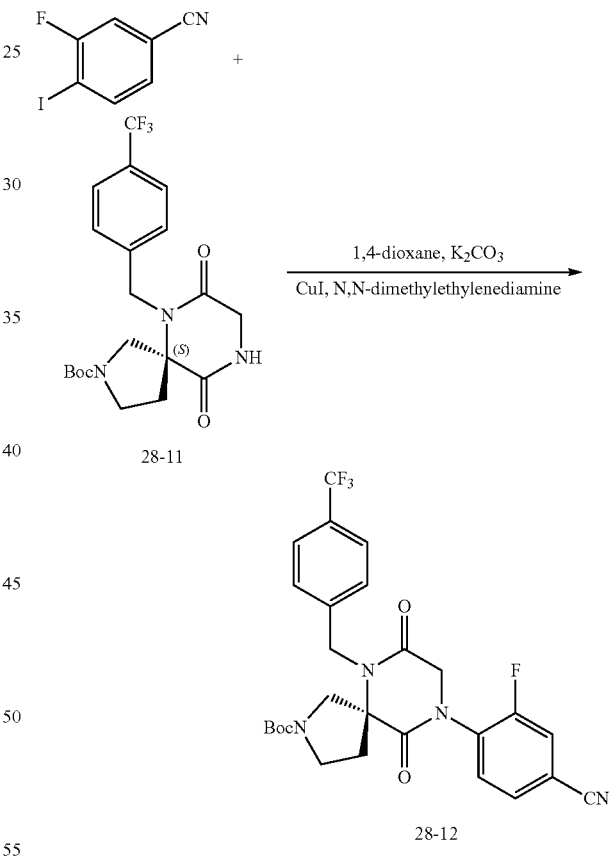

To a mixture of tert-butyl (S)-7,10-dioxo-6-(4-(trifluoromethyl)benzyl)-2,6,9-triazaspiro[4.5]decane-2-carboxylate (280 mg, 0.63 mmol), CuI (60 mg, 0.32 mmol, 0.5 equiv.), K₂CO₃ (349 mg, 2.53 mmol, 4.0 equiv.) and aryl iodide (234 mg, 0.95 mmol, 1.5 equiv.) in 1,4-dioxane (6 mL) was added N,N-dimethylethylenediamine (0.034 mL, 0.32 mmol, 0.5 equiv.). The resulting mixture was heated at 115° C. under N₂ for 18 h in a sealed tube, cooled to r.t., filtered through celite, washed with additional dioxane (15 mL) and DCM (30 mL), concentrated under reduced pressure, and purified by silica gel chromatography using EA/Hex (1/1) as eluents to provide 187 mg (54%) of tert-butyl (S)-9-(4-cyano-2-fluorophenyl)-7,10-dioxo-6-(4-(trifluoromethyl)benzyl)-2,6,9-triazaspiro[4.5]decane-2-carboxylate. LRMS (APCI) m/z 491.1 (M+H) (—$C_4H_9$). $^1$H NMR (400 MHz, Methanol-$d_4$) δ 7.82-7.64 (m, 5H), 7.50 (d, J=8.0 Hz, 2H), 5.15-5.02 (m, 1H), 4.81-4.57 (m, 3H), 4.00 (d, J=12.1 Hz, 1H), 3.66 (d, J=12.3 Hz, 1H), 3.62-3.47 (m, 2H), 2.59-2.48 (m, 2H), 1.43 (d, J=15.3 Hz, 9H).

12. Synthesis of Intermediate 28-13

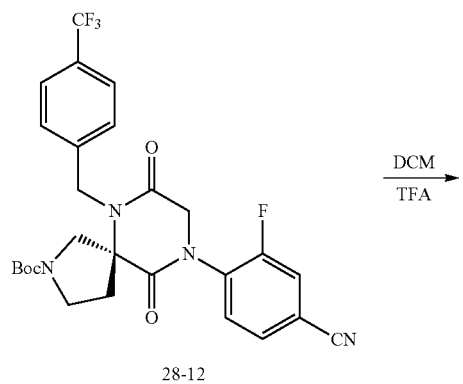

28-12

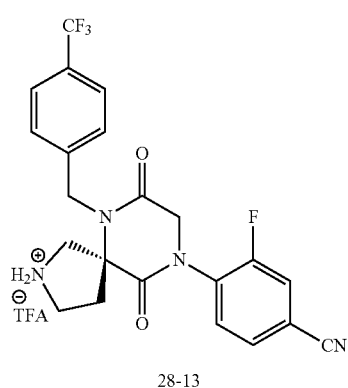

28-13

To a solution of tert-butyl (S)-9-(4-cyano-2-fluorophenyl)-7,10-dioxo-6-(4-(trifluoromethyl)benzyl)-2,6,9-triazaspiro[4.5]decane-2-carboxylate (186 mg, 0.34 mmol) in DCM (3 mL) was added TFA (3 mL). The resulting mixture was stirred at r.t. for 30 min and concentrated under reduced pressure to provide 189 mg (99%) of (S)-4-(7,10-dioxo-6-(4-(trifluoromethyl)benzyl)-2,6,9-triazaspiro[4.5]decan-9-yl)-3-fluorobenzonitrile as a TFA salt. LRMS (APCI) m/z 447.1 (M+H).

13. Synthesis of Compound 216

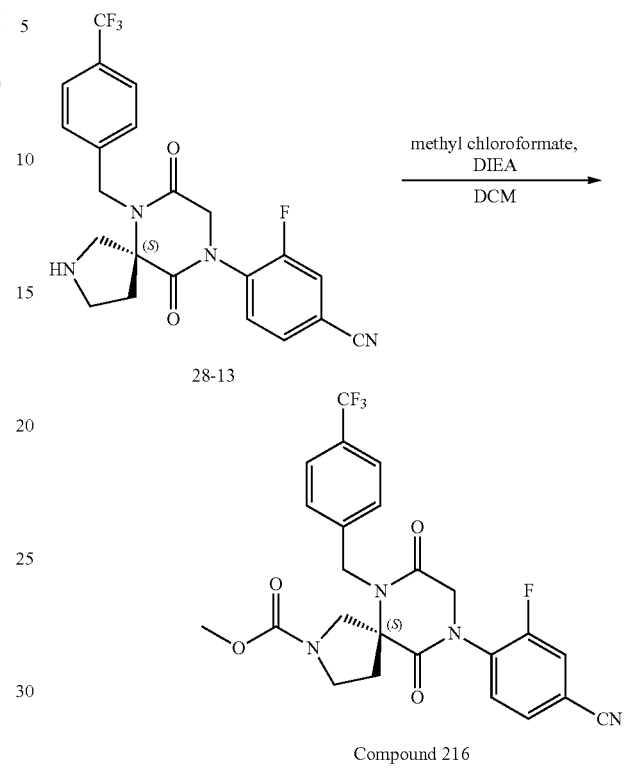

Compound 216

To a mixture of (S)-4-(7,10-dioxo-6-(4-(trifluoromethyl)benzyl)-2,6,9-triazaspiro[4.5]decan-9-yl)-3-fluorobenzonitrile (30 mg TFA salt, 0.054 mmol) and DIEA (0.047 mL, 0.27 mmol, 5.0 equiv.) in DCM (1.0 mL) was added methyl chloroformate (0.012 mL, 0.16 mmol, 3.0 equiv.). The mixture was stirred at r.t. for 5 min, evaporated under reduced pressure, and purified with reverse phase HPLC using 10-100% ACN/water (both with 0.1% formic acid; Phenomenex Gemini C18 5 micron column) to provide 21 mg (78%) of methyl (S)-9-(4-cyano-2-fluorophenyl)-7,10-dioxo-6-(4-(trifluoromethyl)benzyl)-2,6,9-triazaspiro[4.5]decane-2-carboxylate (21 mg, 0.042 mmol, 78% yield, Compound 216) as a white amorphous solid. LRMS (APCI) m/z 505 (M+H). $^1$H NMR (400 MHz, Methanol-$d_4$) δ 7.84-7.65 (m, 5H), 7.49 (d, J=8.0 Hz, 2H), 5.05 (dt, J=9.5, 5.2 Hz, 1H), 4.87-4.73 (m, 1H), 4.73-4.56 (m, 2H), 4.05 (d, J=12.2 Hz, 1H), 3.76-3.48 (m, 6H), 2.64-2.45 (m, 2H).

The following compounds were prepared by methods analogous to the method described for Compound 216:

| Compound No. | LRMS (ES) m/z |
| --- | --- |
| 183 | M + H = 486.1 |
| 184 | M + H = 487.2 |
| 185 | M + H = 452.1 |
| 205 | M + H = 455.1 |
| 206 | M + H = 455.1 |
| 207 | M + H − Boc = 413.1 |
| 208 | M + H − Boc = 447.1 |
| 209 | M + H = 489.2 |
| 210 | M + H = 497.2 |
| 211 | M + H = 471.1 |
| 212 | M + H = 495.2 |

-continued

| Compound No. | LRMS (ES) m/z |
|---|---|
| 213 | M + H = 481.2 |
| 214 | M + H = 469.1 |
| 215 | M + H = 531.2 |
| 217 | M + H = 529.2 |
| 218 | M + H = 503.2 |
| 219 | M + H = 515.2 |
| 220 | M + H = 441.1 |
| 221 | M + H = 483.2 |
| 222 | M + H = 475.1 |
| 223 | M + H = 517.2 |
| 224 | M + H = 478.1 |
| 225 | M + H = 443.2 |

Example 29: Synthesis of Compound 211

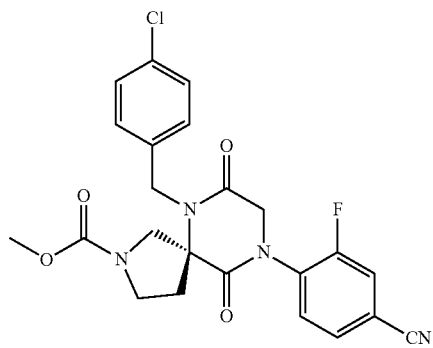

Compound 211

Method analogous to Example 28 was used with the only exception that p-chlorobenzaldehyde was used in step 8 instead of p-CF$_3$ benzaldehyde.

Example 30: Synthesis of Compound 320

1. Synthesis of Intermediate 30-2

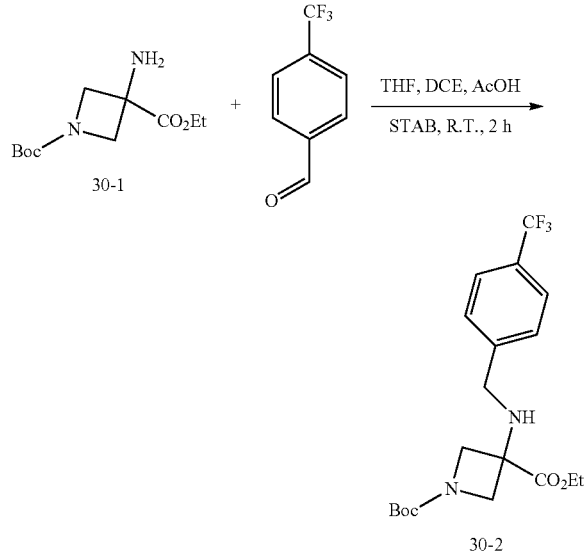

To a solution of 1-(tert-butyl) 3-ethyl-3-aminoazetidine-1,3-dicarboxylate (5.0 g, 20.5 mmol, 1.0 equiv) in a mixture of THF (50 mL) and DCE (10 mL) was added 4-trifluoromethylbenzaldehyde (5.3 g, 30.7 mmol, 1.5 equiv). To the mixture was stirred for 15 min were added STAB (13.0 g, 61.4 mmol, 3.0 equiv) and AcOH (5 mL). The mixture was stirred at r.t. for 2 h, evaporated under reduced pressure, and partitioned between DCM (60 mL) and saturated aqueous sodium bicarbonate (60 mL). The layers were separated and the aqueous phase was extracted with DCM (25 mL). The combined organic phases were dried over sodium sulfate, filtered through celite, concentrated under reduced pressure, and purified by silica gel chromatography (gradient from 0-100% EtOAc/Hexanes) to provide 1-(tert-butyl) 3-ethyl 3-((4-(trifluoromethyl)benzyl)amino)azetidine-1,3-dicarboxylate. LRMS (ES) m/z 347.15 (M+H-$^t$Bu).

2. Synthesis of Intermediate 30-3

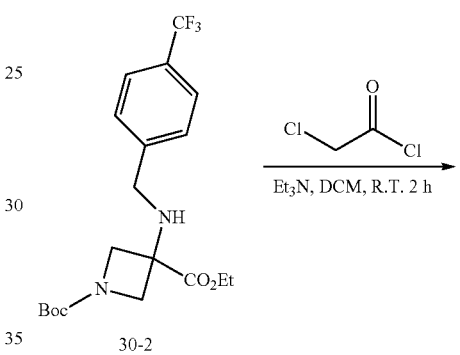

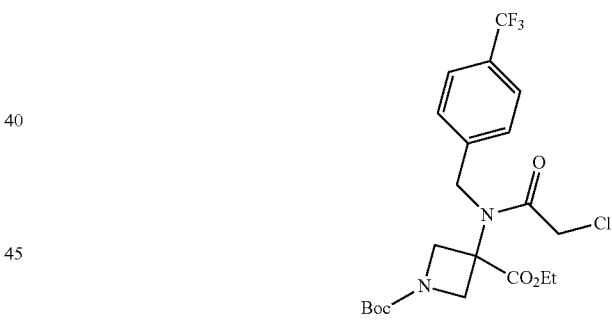

To a solution of 1-(tert-butyl) 3-ethyl 3-((4-(trifluoromethyl)benzyl)amino) azetidine-1,3-dicarboxylate (20.5 mmol, 1.0 equiv) in DCM (50 mL) at 0° C. were added TEA (14.3 mL, 102 mmol, 5.0 equiv) and chloroacetyl chloride (3.3 mL, 40.9 mmol, 2.0 equiv). The ice bath was removed and the mixture was stirred at r.t. for 2 h before pouring into saturated aqueous NH$_4$Cl (200 mL). The layers were separated and the aqueous layer was extracted with DCM (100 mL) three times. The combined organic layers were dried over MgSO$_4$, concentrated, and purified by silica gel chromatography (gradient from 0-100% EtOAc/Hexanes) to give 8.2 g (84% over 2 steps) of 1-(tert-butyl) 3-ethyl 3-(2-chloro-N-(4-(trifluoromethyl)benzyl)acetamido)azetidine-1,3-dicarboxylate as an off-white solid. LRMS (ES) m/z 479.15 (M+H).

3. Synthesis of Intermediate 30-4

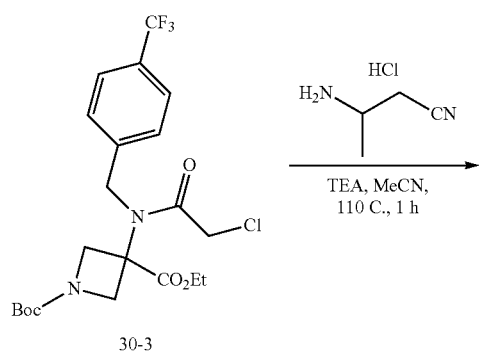

30-3

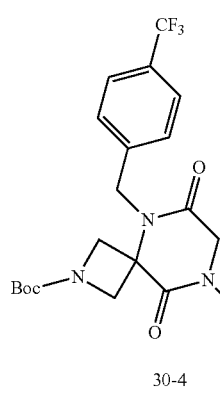

30-4

To a solution of 1-(tert-butyl) 3-ethyl 3-(2-chloro-N-(4-(trifluoromethyl)benzyl) acetamido)azetidine-1,3-dicarboxylate (0.20 g, 0.42 mmol, 1.0 equiv) in ACN (2 mL) in a microwave vial were added 3-aminobutanenitrile hydrochloride (76 mg, 0.63 mmol, 1.5 equiv) and TEA (175 μL, 1.3 mmol, 3.0 equiv). The mixture was heated at 110° C. in the microwave reactor for 1 h. The mixture containing tert-butyl 8-(1-cyanopropan-2-yl)-6,9-dioxo-5-(4-(trifluoromethyl)benzyl)-2,5,8-triazaspiro[3.5]nonane-2-carboxylate was used directly in the next step. LRMS (ES) m/z 481.1 (M+H).

4. Synthesis of Intermediate 30-5

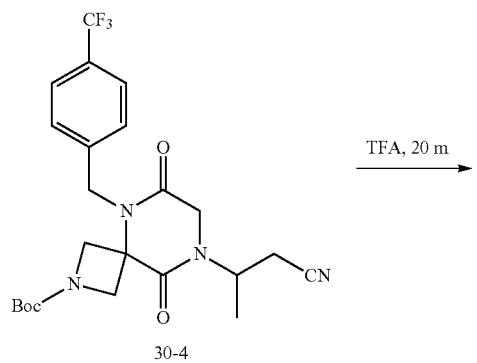

30-4

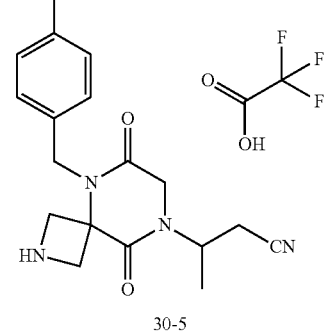

30-5

To the mixture containing tert-butyl 8-(1-cyanopropan-2-yl)-6,9-dioxo-5-(4-(trifluoromethyl)benzyl)-2,5,8-triazaspiro[3.5]nonane-2-carboxylate (202 mg, 0.42 mmol) in DCM was added TFA (2 mL). The mixture was stirred at r.t. for 20 minutes and concentrated to provide 3-(6,9-dioxo-5-(4-(trifluoromethyl)benzyl)-2,5,8-triazaspiro[3.5]nonan-8-yl)butanenitrile 2,2,2-trifluoroacetate. LRMS (ES) m/z 381.1 (M+H).

5. Synthesis of Compound 320

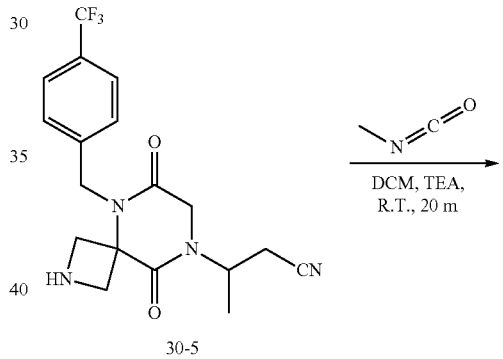

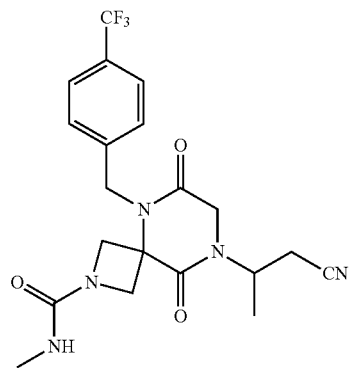

Compound 320

To a solution of 3-(6,9-dioxo-5-(4-(trifluoromethyl)benzyl)-2,5,8-triazaspiro[3.5]nonan-8-yl)butanenitrile 2,2,2-trifluoroacetate (160 mg, 0.42 mmol) in DCM (3 mL) were added TEA (0.5 mL) and methyl isocyanate (200 mg, 3.5 mmol, 8.3 equiv). The mixture was stirred at r.t. for 20 min, evaporated under reduced pressure, and purified with reverse phase HPLC (Phenomenex, gemini 5u C18 150× 21.2 mm, 10-70% acetonitrile in water both with 0.1% formic acid gradient over 40 min) to provide 6.8 mg (4% over 3 steps) of 8-(1-cyanopropan-2-yl)-N-methyl-6,9-dioxo-5-(4-(trifluoromethyl)benzyl)-2,5,8-triazaspiro[3.5]nonane-2-carboxamide. LRMS (ES) m/z 438.1 (M+H). $^1$H-NMR: (Methanol-d$_4$, 400 MHz, ppm) δ 7.66 (d, J=8.0 Hz, 2H), 7.50 (d, J=8.6 Hz, 2H), 5.22-5.01 (m, 2H), 4.87-4.75 (m, 1H), 4.44 (dd, J=17.3, 9.3 Hz, 2H), 4.18 (d, J=1.6 Hz, 2H), 4.07 (dd, J=9.3, 0.6 Hz, 2H), 2.98 (dd, J=17.1, 8.6 Hz, 1H), 2.86 (dd, J=17.1, 6.1 Hz, 1H), 2.68 (s, 3H), 1.40 (d, J=6.9 Hz, 3H).

The following compounds were prepared by methods analogous to the method described for Compound 320:

| Compound No. | LRMS (ES) m/z |
| --- | --- |
| 518A | M + H = 464.2 |
| 516A | M + H = 452.2 |
| 323 | M + H = 466.2 |
| 324 | M + H = 488.2 |
| 520A | M + H = 463.2 |
| 326 | M + H = 452.2 |

Example 31: Synthesis of Compound 429B

1. Synthesis of Intermediate 31-1

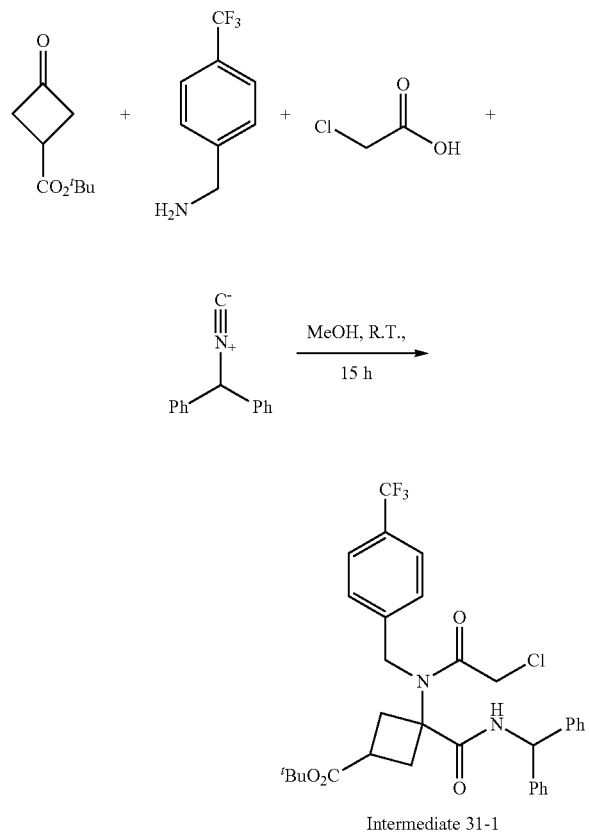

To a mixture of 4-trifluoromethylbenzyl amine (1.8 g, 10.4 mmol, 1.0 equiv) and tert-butyl 3-oxocyclobutane-1-carboxylate (1.8 g, 10.4 mmol, 1.0 equiv) in MeOH (30 mL) were added (isocyanomethylene)dibenzene (2.1 g, 10.9 mmol, 1.05 equiv) and chloroacetic acid (1.0 g, 10.4 mmol, 1.05 equiv). The mixture was stirred at r.t. for 15 h, concentrated under reduced pressure, and purified by silica gel chromatography EA/HE (gradient from 0-100%) to provide 4.5 g (70%) of tert-butyl 3-(benzhydrylcarbamoyl)-3-(2-chloro-N-(4-(trifluoromethyl)benzyl)acetamido)cyclobutane-1-carboxylate (Intermediate 1-1). LRMS (ES) m/z 615.2 (M+H).

2. Synthesis of Diastereomer 31-2A and Diastereomer 31-2B

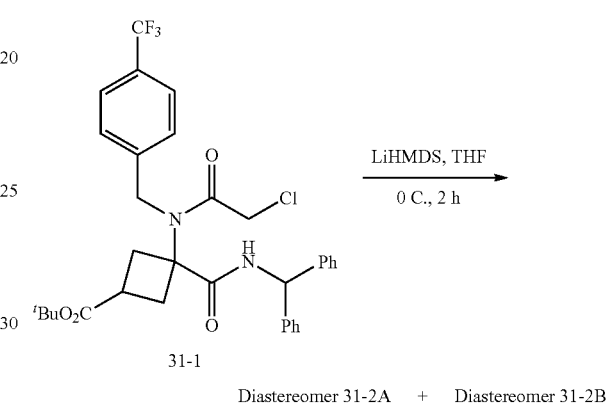

To a solution of tert-butyl 3-(benzhydrylcarbamoyl)-3-(2-chloro-N-(4-(trifluoromethyl)benzyl)acetamido)cyclobutane-1-carboxylate (Intermediate 31-1) (4.5 g, 7.3 mmol, 1.0 equiv) in THF (20 mL) cooled to 0° C. with an ice bath was added LiHMDS (1 M in THF, 8.8 mmol, 1.2 equiv) dropwise over 10 min. The mixture was stirred at 0° C. for 2 h, quenched with MeOH (5 mL), concentrated onto SiO$_2$ (20 g), and purified by silica gel chromatography using EA/HE (gradient from 0-100%) to provide the corresponding diastereomers. Diastereomer 31-2A (1.8 g, 42%), diastereomer 31-2B (1.8 g, 42%).

Characterization of Diastereomer 31-2A: LRMS (ES) m/z 579.2 (M+H). $^1$H-NMR (Methanol-d$_4$, 400 MHz, ppm) δ 7.60-7.48 (m, 2H), 7.35-7.24 (m, 8H), 7.17-7.06 (m, 4H), 6.89 (s, 1H), 4.76 (s, 2H), 3.76 (s, 2H), 2.88-2.76 (m, 1H), 2.68-2.46 (m, 4H), 1.29 (s, 9H).

Characterization of Diastereomer 31-2B: LRMS (ES) m/z 579.2 (M+H). $^1$H-NMR (Methanol-d$_4$, 400 MHz, ppm) δ 7.49 (d, J=7.9 Hz, 2H), 7.34-7.25 (m, 6H), 7.21 (d, J=7.9 Hz, 2H), 7.13-7.07 (m, 4H), 6.88 (s, 1H), 4.86 (s, 2H), 3.68 (s, 2H), 3.01-2.79 (m, 3H), 2.59-2.40 (m, 2H), 1.32 (s, 9H).

Diastereomer 31-2B was used in the subsequent examples. The final compounds derived from Diastereomer 31-2A were isolated using Diastereomer 31-2A as the starting material in an analogous sequence.

3. Synthesis of Intermediate 31-3B

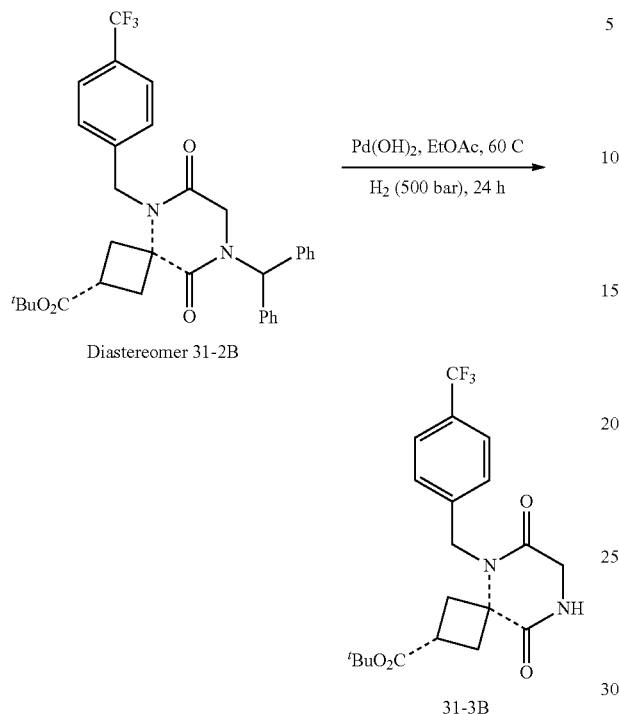

Diastereomer 31-2B 31-3B

To a solution of Diastereomer 31-2B (1.8 g, 3.1 mmol, 1.0 equiv) in EtOAc (20 mL) was added Pd(OH)$_2$ (20% on carbon, 2 g). The mixture was sparged with hydrogen for 10 min, heated at 60° C. under hydrogen (initially at 700 psi) for 24 h, cooled to r.t., filtered through celite, concentrated under reduced pressure, and purified by silica gel chromatography using MeOH/DCM (gradient from 0-20%) to give 1.0 g (78%) of Intermediate 31-3B. LRMS (ES) m/z 357.1 (M+H-$^t$Bu). $^1$H-NMR: (Methanol-d$_4$, 400 MHz, ppm) δ 7.67 (d, J=8.0 Hz, 2H), 7.44 (d, J=7.9 Hz, 2H), 5.04 (s, 2H), 4.04 (s, 2H), 3.16-3.02 (m, 1H), 3.02-2.86 (m, 2H), 2.73-2.59 (m, 2H), 1.46 (s, 9H). As used in this example, the dashed bond --- indicates that the stereochemical configuration of the starting material is retained in the product compound.

4. Synthesis of 429B

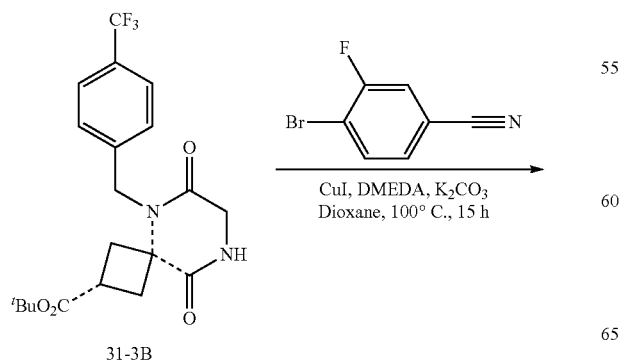

31-3B

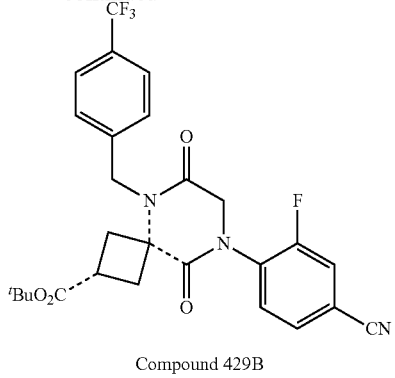

Compound 429B

To a mixture of copper iodide (109 mg, 0.57 mmol, 0.5 equiv), potassium carbonate (0.32 g, 2.3 mmol, 2.0 equiv), 4-bromo-3-fluorobenzonitrile (0.27 g, 1.4 mmol, 1.2 equiv), and Intermediate 1-3B (0.47 g, 1.1 mmol, 1.0 equiv) in a vial were added 1,4-dioxane (5 mL) and N,N'-dimethylethylene diamine (61 µl, 0.57 mmol, 0.5 equiv). The mixture was sealed and heated at 100° C. for 4 h, cooled to r.t., filtered through celite, and purified by silica gel chromatography using EA/HE (gradient from 0-100%) to provide 0.40 g (66%) of Compounds 429B. LRMS (ES) m/z 476.1 (M+H-$^t$Bu). $^1$H-NMR (Methanol-d$_4$, 400 MHz, ppm) δ 7.80-7.74 (m, 1H), 7.71-7.66 (m, 4H), 7.53-7.46 (m, 2H), 5.10 (s, 2H), 4.50 (s, 2H), 3.15-2.99 (m, 3H), 2.85-2.71 (m, 2H), 1.42 (s, 9H).

Example 32: Synthesis of Compound 486B

1. Synthesis of Intermediate 32-1B

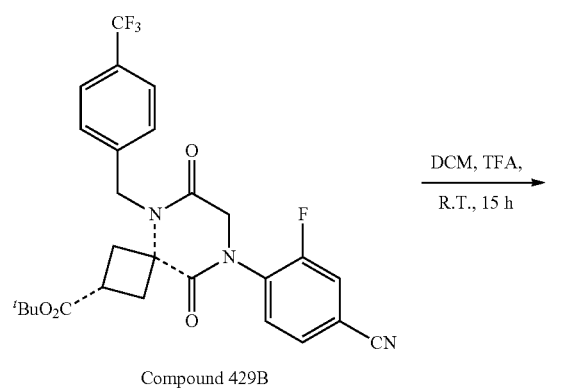

Compound 429B

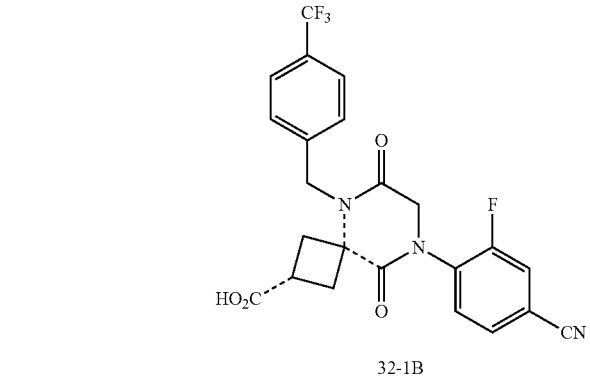

32-1B

To a flask containing Compound 429B (0.36 g, 0.68 mmol, 1.0 equiv) was added TFA (5 mL). The mixture was stirred at r.t. for 15 h and concentrated to provide Intermediate 32-1B. LRMS (ES) m/z 474.1 (M–H). As used in this example, the dashed bond --- indicates that the stereochemical configuration of the starting material is retained in the product compound.

2. Synthesis of Intermediate 32-2B

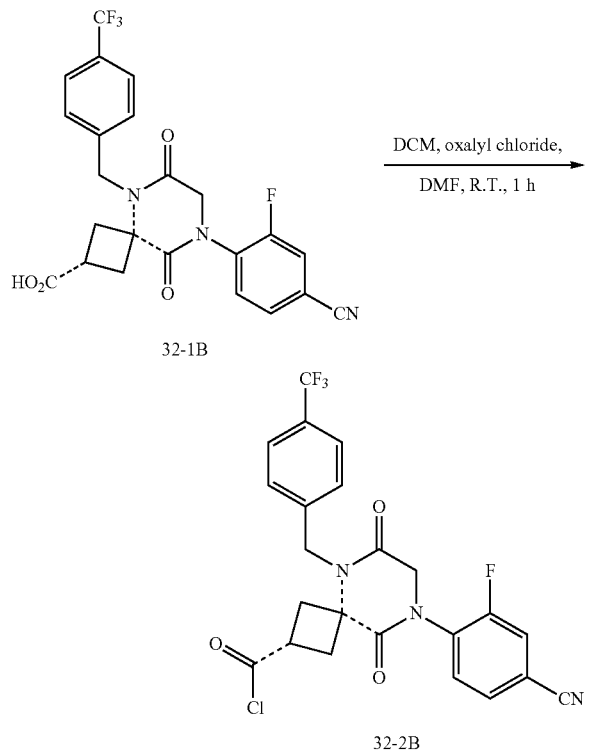

3. Synthesis of Compound 486B

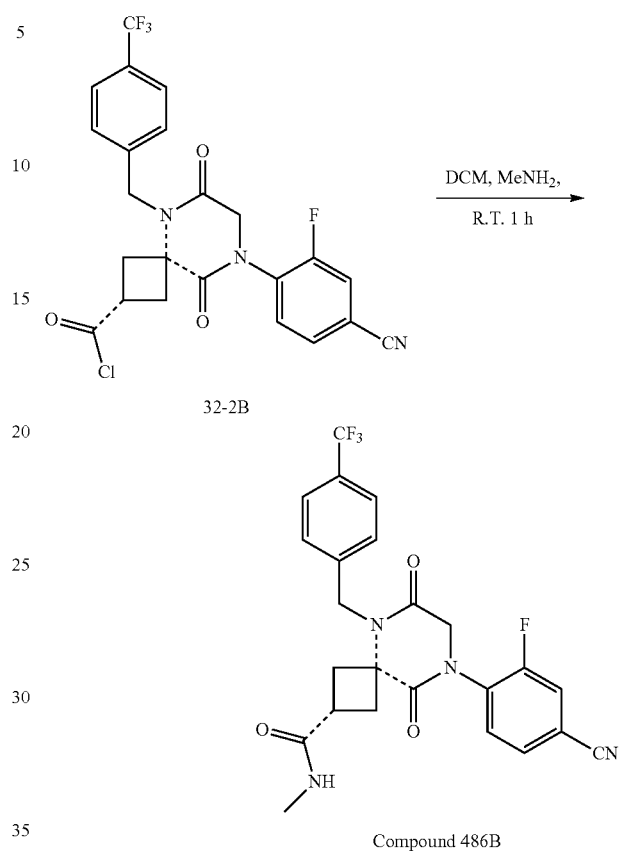

To Intermediate 32-1B (0.32 g, 0.68 mmol, 1.0 equiv) dissolved in DCM (5 mL) were added oxalyl chloride (0.17 g, 1.36 mmol, 2.0 equiv) and a drop of DMF (~50 mg). The mixture was stirred at r.t. for 1 h and concentrated to provide Intermediate 32-2B which was used directly without characterization.

To Intermediate 32-2B (50 mg, 0.10 mmol, 1.0 equiv) dissolved in DCM (3 mL) was added methylamine (2 M in THF, 2 mL). The mixture was stirred at r.t. for 1 h and concentrated. This material was dissolved in DMF (2.0 mL), filtered, and purified with reverse phase HPLC (Phenomenex, gemini 5u C18 150×21.2 mm, 20-100% acetonitrile in water both with 0.1% formic acid gradient over 25 min) to give 31.4 mg (64%) of Compound 486B. LRMS (ES) m/z 489.1 (M+H). $^1$H NMR (400 MHz, Methanol-$d_4$) δ 7.78-7.74 (m, 1H), 7.72-7.65 (m, 4H), 7.50-7.45 (m, 2H), 5.12 (s, 2H), 4.49 (s, 2H), 3.18-3.07 (m, 3H), 2.78-2.67 (m, 5H).

The following compounds were prepared by methods analogous to the method described for Compound 486B:

| Diastereomer No. | LRMS (ES) m/z | $^1$H NMR |
|---|---|---|
| 429B | M + H-$^t$Bu = 476.1 | (400 MHz, Methanol-$d_4$) δ 7.78-7.64 (m, 5H), 7.53-7.47 (m, 2H), 5.06 (s, 2H), 4.50 (s, 2H), 2.99-2.89 (m, 1H), 2.87-2.79 (m, 2H), 2.75-2.67 (m, 2H), 1.40 (s, 9H) |
| 429A | M + H = 532.2 | (400 MHz, Methanol-$d_4$) δ 7.77-7.72 (m, 1H), 7.70-7.64 (m, 4H), 7.50-7.45 (m, 2H), 5.09 (s, 2H), 4.48 (s, 2H), 3.12-3.01 (m, 3H), 2.81-2.71 (m, 2H), 1.40 (s, 9H) |
| 485A | M + H = 475.1 | (400 MHz, Methanol-$d_4$) δ 7.81-7.76 (m, 1H), 7.75-7.69 (m, 2H), 7.68-7.63 (m, 2H), 7.51-7.45 (m, 2H), 5.15 (s, 2H), 4.51 (s, 2H), 3.10-2.99 (m, 1H), 2.82-2.76 (m, 4H) |
| 485B | M + H = 475.1 | (400 MHz, Methanol-$d_4$) δ 7.78-7.73 (m, 1H), 7.71-7.64 (m, 4H), 7.51-7.46 (m, 2H), 5.12 (s, 2H), 4.49 (s, 2H), 3.22-3.08 (m, 3H), 2.79-2.68 (m, 2H) |

-continued

| Diastereomer No. | LRMS (ES) m/z | $^1$H NMR |
|---|---|---|
| 486B | M + H = 489.1 | (400 MHz, Methanol-$d_4$) δ 7.78-7.74 (m, 1H), 7.72-7.65 (m, 4H), 7.50-7.45 (m, 2H), 5.12 (s, 2H), 4.49 (s, 2H), 3.18-3.07 (m, 3H), 2.78-2.67 (m, 5H) |
| 487A | M + H = 503.2 | (400 MHz, Methanol-$d_4$) δ 7.80-7.76 (m, 1H), 7.76-7.69 (m, 2H), 7.68-7.63 (m, 2H), 7.50-7.45 (m, 2H), 5.07 (s, 2H), 4.52 (s, 2H), 3.38-3.27 (m, 1H), 2.94 (s, 3H), 2.92 (s, 3H), 2.88-2.76 (m, 4H) |
| 486A | M + H = 489.2 | (400 MHz, Methanol-$d_4$) δ 7.80-7.75 (m, 1H), 7.74-7.68 (m, 2H), 7.68-7.64 (m, 2H), 7.51-7.46 (m, 2H), 5.18 (s, 2H), 4.51 (s, 2H), 3.04-2.93 (m, 1H), 2.84-2.68 (m, 7H) |
| 487B | M + H = 503.2 | (400 MHz, Methanol-$d_4$) δ 7.78-7.73 (m, 1H), 7.72-7.64 (m, 4H), 7.54-7.48 (m, 2H), 5.15 (s, 2H), 4.50 (s, 2H), 3.29-3.09 (m, 3H), 2.87 (s, 3H), 2.83 (s, 3H), 2.78-2.69 (m, 2H) |
| 877A | M + H = 485 | (400 MHz, DMSO-d6) δ 8.52 (d, J = 2.1 Hz, 1H), 8.29 (dd, J = 9.5, 2.2 Hz, 1H), 7.72 (d, J = 8.1 Hz, 2H), 7.46 (d, J = 8.0 Hz, 2H), 7.38 (s, 1H), 6.89 (s, 1H), 5.04 (s, 2H), 4.57 (s, 2H), 2.95-2.82 (m, 1H), 2.67-2.56 (m, 4H). |

Example 33: Synthesis of Compound 444B

1. Synthesis of Intermediate 33-1

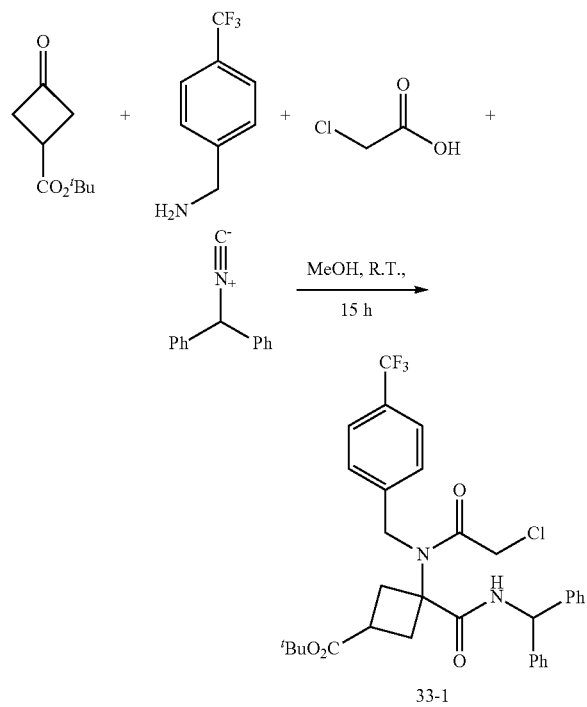

To a mixture of 4-trifluoromethylbenzyl amine (3.2 g, 18.4 mmol, 1.0 equiv) and tert-butyl 3-oxocyclobutane-1-carboxylate (3.1 g, 18.4 mmol, 1.0 equiv) in MeOH (30 mL) were added (isocyanomethylene)dibenzene (3.7 g, 19.3 mmol, 1.05 equiv) and chloroacetic acid (1.8 g, 19.3 mmol, 1.05 equiv). The mixture was stirred at r.t. for 15 h, concentrated under reduced pressure, and purified by silica gel chromatography EA/HE (gradient from 0-100%) to provide 10.5 g (93%) of ten-butyl 3-(benzhydrylcarbamoyl)-3-(2-chloro-N-(4-(trifluoromethyl)benzyl)acetamido)cyclobutane-1-carboxylate (Intermediate 33-1). LRMS (ES) m/z 615.25 (M+H).

2. Synthesis of Diastereomer 33-2B

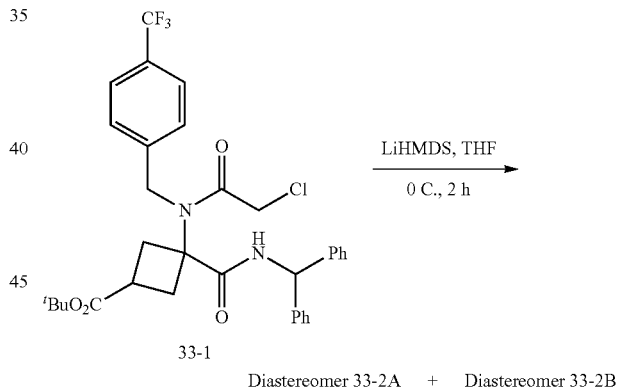

Diastereomer 33-2A + Diastereomer 33-2B

To a solution of ten-butyl 3-(benzhydrylcarbamoyl)-3-(2-chloro-N-(4-(trifluoromethyl)benzyl)acetamido)cyclobutane-1-carboxylate (Intermediate 33-1) (10.5 g, 17.1 mmol, 1.0 equiv) in THF (200 mL) cooled to 0° C. with an ice bath was added LHMDS (1 M in THF, 20.5 mmol, 1.2 equiv) dropwise over 10 min. The mixture was stirred at 0° C. for 2 h, and MeOH was added (5 mL), concentrated onto Sift (20 g), and purified by silica gel chromatography using EA/HE (gradient from 0-100%) to provide the corresponding diastereomers. Diastereomer 33-2A ((discarded), diastereomer 33-2B (3.0 g, 30%).

Characterization of Diastereomer 33-2B: LRMS (ES) m/z 579.2 (M+H). $^1$H-NMR (Methanol-$d_4$, 400 MHz, ppm) δ 7.49 (d, J=7.9 Hz, 2H), 7.34-7.25 (m, 6H), 7.21 (d, J=7.9 Hz, 2H), 7.13-7.07 (m, 4H), 6.88 (s, 1H), 4.86 (s, 2H), 3.68 (s, 2H), 3.01-2.79 (m, 3H), 2.59-2.40 (m, 2H), 1.32 (s, 9H).

3. Synthesis of Intermediate 33-3B

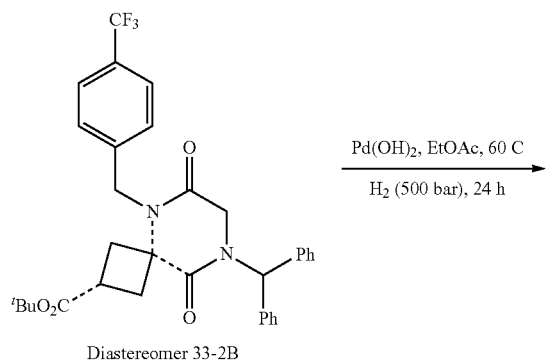

To a solution of Diastereomer 33-2B (3.0 g, 5.2 mmol, 1.0 equiv) in EtOAc (80 mL) was added Pd(OH)$_2$ (20% on carbon, 6 g). The mixture was sparged with hydrogen for 10 min, heated at 60° C. under hydrogen (initially at 500 psi) for 24 h, cooled to r.t., filtered through celite, concentrated under reduced pressure, and purified by silica gel chromatography using MeOH/DCM (gradient from 0-20%) to give 1.75 g (82%) of Intermediate 33-3B. LRMS (ES) m/z 357.1 (M+H-$^t$Bu). $^1$H-NMR: (Methanol-d$_4$, 400 MHz, ppm) δ 7.67 (d, J=8.0 Hz, 2H), 7.44 (d, J=7.9 Hz, 2H), 5.04 (s, 2H), 4.04 (s, 2H), 3.16-3.02 (m, 1H), 3.02-2.86 (m, 2H), 2.73-2.59 (m, 2H), 1.46 (s, 9H). As used in this example, the dashed bond --- indicates that the stereochemical configuration of the starting material is retained in the product compound.

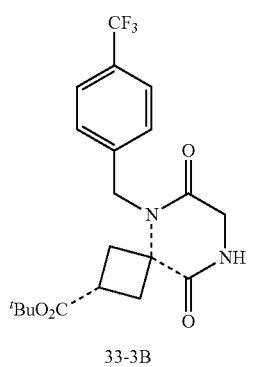

4. Synthesis of Intermediate 33-4B

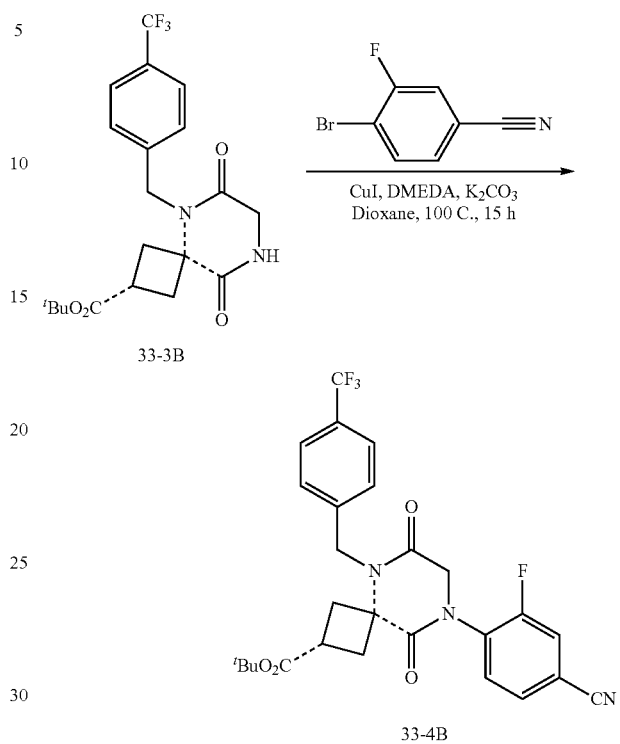

To a mixture of copper iodide (369 mg, 1.9 mmol, 0.5 equiv), potassium carbonate (1.6 g, 11.6 mmol, 3.0 equiv), 4-bromo-3-fluorobenzonitrile (1.4 g, 7.0 mmol, 1.8 equiv), and Intermediate 33-3B (1.6 g, 3.9 mmol, 1.0 equiv) in vial were added 1,4-dioxane (16 mL) and N,N'-dimethylethylene diamine (209 μL, 1.9 mmol, 0.5 equiv). The mixture was sealed and heat at 100° C. for 15 h, cooled to r.t., filtered through celite, and purified by silica gel chromatography using EA/HE (gradient from 0-100%) to provide 1.7 g (84%) of Intermediate 33-4B. LRMS (ES) m/z 476.1 (M+H-$^t$Bu). (CD$_2$Cl$_2$, 400 MHz, ppm) δ 7.70-7.65 (m, 2H), 7.63-7.60 (m, 1H), 7.60-7.56 (m, 1H), 7.56-7.51 (m, 1H), 7.44-7.39 (m, 2H), 5.02 (s, 2H), 4.40-4.38 (m, 2H), 3.19-3.11 (m, 2H), 3.03-2.94 (m, 1H), 2.70-2.62 (m, 2H), 1.42 (s, 9H).

5. Synthesis of Intermediate 33-5B

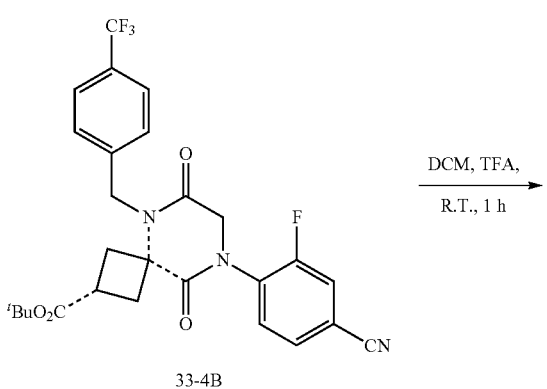

-continued

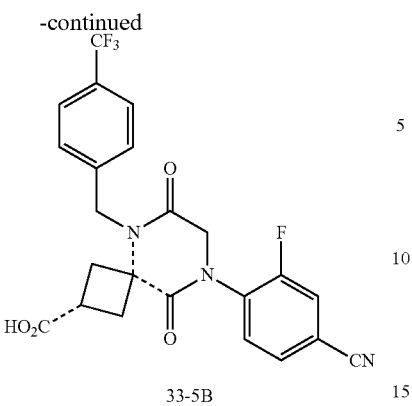

33-5B

To a solution of Intermediate 1-4B (1.7 g, 3.3 mmol, 1.0 equiv) in DCM (18 mL) was added TFA (18 mL). The mixture was stirred at r.t. for 1 h and concentrated to provide Intermediate 33-5B. LRMS (ES) m/z 474.0 (M−H).

6. Synthesis of Compound 444B

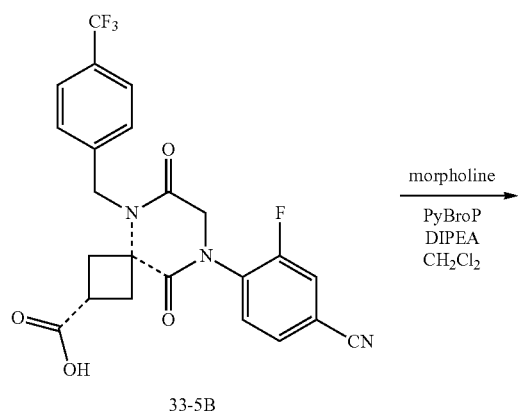

33-5B morpholine
PyBroP
DIPEA
CH$_2$Cl$_2$

-continued

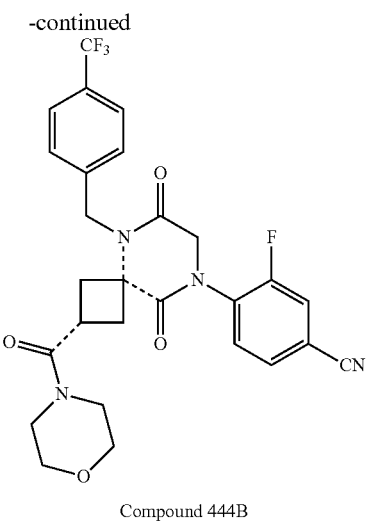

Compound 444B

To a mixture of morpholine (9.0 mg, 0.10 mmol, 1.0 equiv), PyBroP (49 mg, 0.10 mmol, 1.0 equiv), and Intermediate 33-5B (50 mg, 0.10 mmol, 1.0 equiv) in DCM (1 mL) cooled to 0° C. with an ice bath was added DIEA (0.073 mL, 0.42 mmol, 4.0 equiv) dropwise. The mixture was warmed to r.t., stirred for 30 min, concentrated under reduce pressure, and purified with reverse phase HPLC (Phenomenex, gemini 5u C18 150×21.2 mm, 10-80% acetonitrile in water both with 0.1% formic acid gradient over 25 min) to give a mixture, which was purified again by silica gel chromatography using MeOH/DCM (1/9) to give 26.4 mg (46%) of Compound 444B. LRMS (ES) m/z 545 (M+H). $^1$H NMR (400 MHz, Methanol-d$_4$) δ 7.81-7.75 (m, 1H), 7.74-7.66 (m, 4H), 7.55-7.49 (m, 2H), 5.15 (s, 2H), 4.52 (s, 2H), 3.65-3.57 (m, 4H), 3.55-3.49 (m, 2H), 3.31-3.14 (m, 5H), 2.81-2.72 (m, 2H).

The following compounds were prepared by methods analogous to the method described for Compound 444B:

| Diastereomer No. | LRMS (ES) m/z | $^1$H NMR |
| --- | --- | --- |
| 446B | M + H = 515.2 | (400 MHz, Methanol-d$_4$) δ 7.80-7.76 (m, 1H), 7.73-7.66 (m, 4H), 7.56-7.50 (m, 2H), 5.15 (s, 2H), 4.51 (s, 2H), 4.06-3.94 (m, 4H), 3.19-3.11 (m, 2H), 3.06-2.95 (m, 1H), 2.73-2.64 (m, 2H), 2.33-2.23 (m, 2H) |
| 448B | M + H = 529.2 | (400 MHz, Methanol-d$_4$) δ 7.80-7.76 (m, 1H), 7.75-7.67 (m, 4H), 7.60-7.49 (m, 2H), 5.20-5.13 (m, 2H), 4.54-4.50 (m, 2H), 3.52-3.41 (m, 1H), 3.29-3.20 (m, 2H), 2.88-2.79 (m, 3H), 2.79-2.71 (m, 2H), 2.61-2.53 (m, 1H), 0.80-0.69 (m, 2H), 0.69-0.58 (m, 2H) |
| 450B | M + H = 559.2 | (400 MHz, Methanol-d$_4$) δ 7.80-7.75 (m, 1H), 7.74-7.67 (m, 4H), 7.56-7.50 (m, 2H), 5.23-5.09 (m, 2H), 4.57-4.46 (m, 2H), 4.04-3.95 (m, 1H), 3.86-3.77 (m, 1H), 3.51-3.42 (m, 1H), 3.30-3.01 (m, 5H), 2.81-2.71 (m, 2H), 1.85-1.77 (m, 2H), 1.45-1.34 (m, 2H) |
| 452B | M + H = 531.1 | (400 MHz, Methanol-d$_4$) δ 7.81-7.75 (m, 1H), 7.73-7.66 (m, 4H), 7.53-7.48 (m, 2H), 5.14 (s, 2H), 4.95-4.80 (m, 3H), 4.55-4.49 (m, 4H), 3.21-3.09 (m, 3H), 2.84-2.72 (m, 2H) |
| 458B | M + H = 515.10 | (400 MHz, Methanol-d$_4$) δ 7.80-7.75 (m, 1H), 7.73-7.66 (m, 4H), 7.51-7.45 (m, 2H), 5.12 (s, 2H), 4.50 (s, 2H), 3.16-3.04 (m, 3H), 2.77-2.66 (m, 2H), 2.64-2.56 (m, 1H), 0.71-0.64 (m, 2H), 0.48-0.42 (m, 2H) |

-continued

| Diastereomer No. | LRMS (ES) m/z | $^1$H NMR |
|---|---|---|
| 462B | M + H = 545.1 | (400 MHz, Methanol-$d_4$) δ 7.80-7.75 (m, 1H), 7.74-7.66 (m, 4H), 7.52-7.46 (m, 2H), 5.14 (s, 2H), 4.51 (s, 2H), 4.39-4.31 (m, 1H), 4.30-4.21 (m, 1H), 3.19-3.07 (m, 3H), 2.80-2.67 (m, 2H), 2.28-2.16 (m, 4H) |
| 469B | M + H = 519.2 | (400 MHz, Methanol-$d_4$) δ 7.80-7.75 (m, 1H), 7.73-7.67 (m, 4H), 7.52-7.47 (m, 2H), 5.14 (s, 2H), 4.51 (s, 2H), 3.57 (t, J = 5.8 Hz, 2H), 3.28 (t, J = 5.8 Hz, 2H), 3.23-3.09 (m, 3H), 2.82-2.70 (m, 2H) |
| 473B | M + H = 565.1 | (400 MHz, Methanol-$d_4$) δ 7.80-7.75 (m, 1H), 7.73-7.67 (m, 4H), 7.52-7.47 (m, 2H), 5.14 (s, 2H), 4.51 (s, 2H), 4.13-4.02 (m, 1H), 3.19-3.07 (m, 3H), 2.94-2.81 (m, 2H), 2.81-2.70 (m, 2H), 2.59-2.43 (m, 2H) |
| 477B | M + H = 545.2 | (400 MHz, Methanol-$d_4$) δ 7.80-7.75 (m, 1H), 7.74-7.66 (m, 4H), 7.56-7.50 (m, 2H), 5.24-4.67 (m, 7H), 4.54-4.49 (m, 2H), 3.36-2.91 (m, 6H), 2.84-2.73 (m, 2H) |
| 462A | M + H = 545 | (400 MHz, Methanol-$d_4$) δ 7.81-7.75 (m, 1H), 7.73-7.66 (m, 4H), 7.52-7.46 (m, 2H), 5.14 (s, 2H), 4.51 (s, 2H), 3.98-3.89 (m, 1H), 3.82-3.70 (m, 1H), 3.20-3.06 (m, 3H), 2.78-2.67 (m, 2H), 2.67-2.58 (m, 2H), 1.84-1.74 (m, 2H). |
| 249B | M + H = 529 | (400 MHz, Methanol-$d_4$) δ 7.80-7.75 (m, 1H), 7.72-7.66 (m, 4H), 7.51-7.47 (m, 2H), 5.14 (s, 2H), 4.50 (s, 2H), 4.30-4.19 (m, 1H), 3.20-3.06 (m, 3H), 2.77-2.65 (m, 2H), 2.29-2.18 (m, 2H), 1.99-1.85 (m, 2H), 1.76-1.61 (m, 2H). |
| 878B | M + H = 481.0 | (400 MHz, Methanol-$d_4$) δ 8.41 (s, 1H), 7.90 (s, 1H), 7.67 (d, J = 8.0 Hz, 2H), 7.50 (d, J = 8.0 Hz, 2H), 5.18 (s, 2H), 4.65 (br, 1H), 4.39 (br, 1H), 3.08 (p, J = 8.7 Hz, 1H), 2.82 (s, 4H), 2.30 (s, 3H). |
| 879B | M + H = 467 | (400 MHz, Methanol-$d_4$) δ 8.49 (d, J = 2.5 Hz, 1H), 8.11 (d, J = 8.9 Hz, 1H), 7.91 (dd, J = 8.9, 2.5 Hz, 1H), 7.66 (d, J = 8.0 Hz, 2H), 7.48 (d, J = 8.0 Hz, 2H), 5.14 (s, 2H), 4.80 (s, 2H), 3.05 (p, J = 8.7 Hz, 1H), 2.80 (p, J = 11.4 Hz, 4H). |

Example 34: Synthesis of Compound 463B

1. Synthesis of Intermediate 34-1B

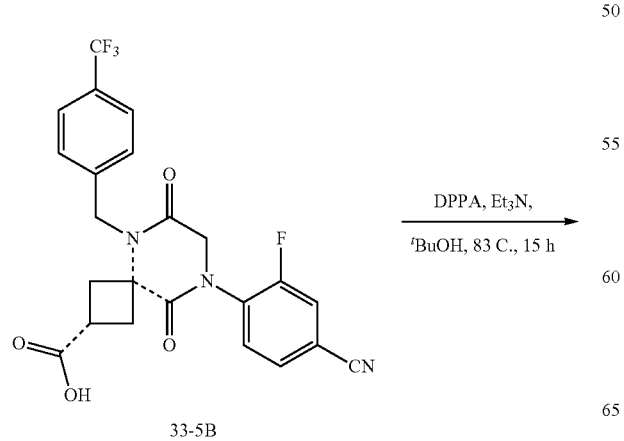

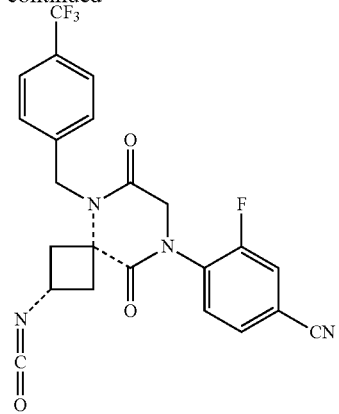

To a mixture of triethylamine (0.070 mL, 0.51 mmol, 1.2 equiv) and diphenyl phosphoryl azide (0.10 mL, 0.46 mmol, 1.1 equiv) in tert-butyl alcohol (1.3 mL) was added Intermediate 33-5B (0.20 g, 0.42 mmol, 1.0 equiv). The mixture was warmed to 83° C. and stirred for 15 hours overnight. The reaction was diluted with water and extracted three times with DCM. The DCM extracts were combined, dried over MgSO₄, filtered, evaporated, and purified by silica gel chromatography using EA in hexanes (0-100% gradient) to give 94 mg (48%) of Intermediate 34-1B. ¹H NMR (400 MHz, Methylene Chloride-d₂) δ 7.71-7.66 (m, 2H), 7.66-7.63 (m, 1H), 7.63-7.59 (m, 1H), 7.57-7.50 (m, 1H), 7.46-7.39 (m, 2H), 4.99 (s, 2H), 4.49-4.37 (m, 3H), 3.05-2.88 (m, 2H), 2.79-2.70 (m, 2H). As used in this example, the dashed bond --- indicates that the stereochemical configuration of the starting material is retained in the product compound.

2. Synthesis of Compound 463B

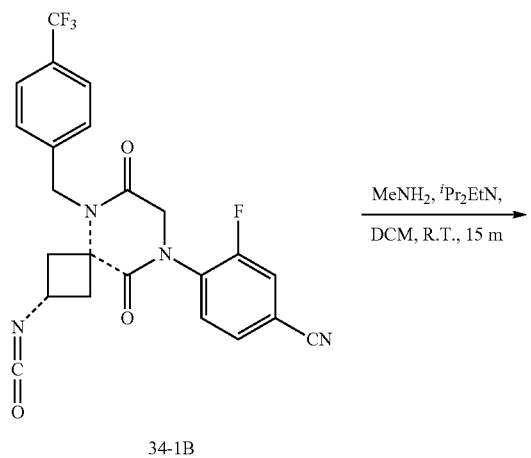

34-1B

MeNH₂, ⁱPr₂EtN,
DCM, R.T., 15 m

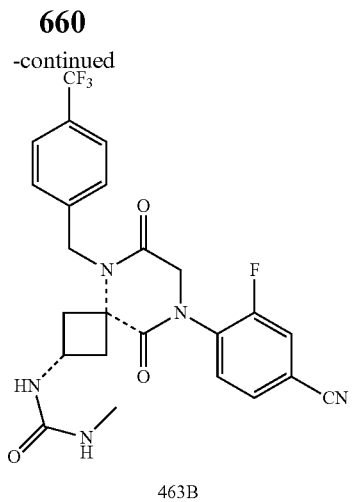

463B

To Intermediate 34-1B (32 mg, 0.067, 1.0 equiv) in dry dichloromethane (1 mL) were added diisopropylethylamine (0.035 mL, 0.20 mmol, 3.0 equiv) followed by methylamine (2.0 M/THF, 0.10 mL, 0.20 mmol, 3.0 equiv). The mixture was stirred for 15 minutes at r.t., evaporated, and purified by reverse phase HPLC (Phenomenex, gemini 5u C18 150× 21.2 mm, 10-80% acetonitrile in water with 0.1% formic acid in 25 min) to give 15 mg (45%) of compound 463B. LRMS (ES) m/z 504.1 (M+H). ¹H NMR (400 MHz, Methanol-d₄) δ 7.81-7.77 (m, 1H), 7.74-7.66 (m, 4H), 7.52-7.46 (m, 2H), 5.12 (s, 2H), 4.51 (s, 2H), 4.41-4.31 (m, 1H), 2.97-2.89 (m, 2H), 2.79-2.71 (m, 2H), 2.66 (s, 3H).

The following compounds were prepared by methods analogous to the method described for Compound 463B:

| Diastereomer No. | LRMS (ES) m/z | ¹H NMR |
|---|---|---|
| 463B | M + H = 504.1 | (400 MHz, Methanol-d₄) δ 7.81-7.77 (m, 1H), 7.74-7.66 (m, 4H), 7.52-7.46 (m, 2H), 5.12 (s, 2H), 4.51 (s, 2H), 4.41-4.31 (m, 1H), 2.97-2.89 (m, 2H), 2.79-2.71 (m, 2H), 2.66 (s, 3H) |
| 465B | M + H = 530.1 | (400 MHz, Methanol-d₄) δ 7.82-7.77 (m, 1H), 7.75-7.66 (m, 4H), 7.53-7.47 (m, 2H), 5.12 (s, 2H), 4.52 (s, 2H), 4.44-4.34 (m, 1H), 3.02-2.92 (m, 2H), 2.78-2.70 (m, 2H), 2.45-2.38 (m, 1H), 0.70-0.64 (m, 2H), 0.46-0.40 (m, 2H) |
| 467B | M + H = 546.1 | (400 MHz, Methanol-d₄) δ 7.82-7.77 (m, 1H), 7.75-7.66 (m, 4H), 7.52-7.46 (m, 2H), 5.11 (s, 2H), 4.85-4.75 (m, 3H), 4.52 (s, 2H), 4.51-4.45 (m, 2H), 4.39-4.30 (m, 1H), 2.99-2.89 (m, 2H), 2.78-2.70 (m, 2H) |

Example 35: Synthesis of Compound 454B

1. Synthesis of Intermediate 35-1B

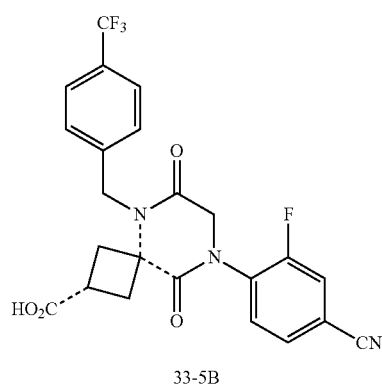

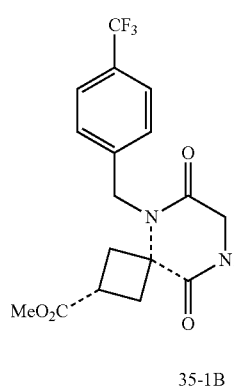

To a solution of Intermediate 33-5B (0.25 g, 0.53 mmol, 1.0 equiv) in a mixture of DCM (10 mL) and MeOH (10 mL) was added TMSCHN₂ (2 M in hexanes, 0.79 mL, 3.0 equiv). The mixture was stirred at r.t. for 2 h and concentrated to provide Intermediate 35-1B. LRMS (ES) m/z 490.1 (M+H). As used in this example, the dashed bond --- indicates that the stereochemical configuration of the starting material is retained in the product compound.

2. Synthesis of Intermediate 35-2B

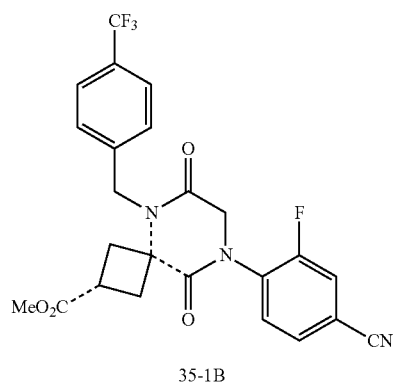

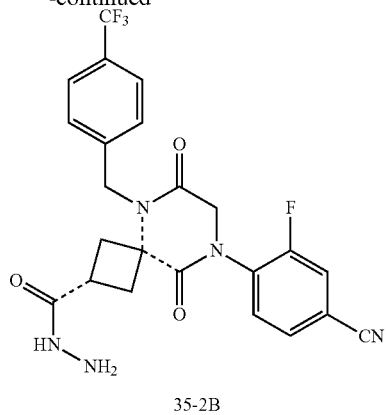

To a solution of Intermediate 35-1B (259 mg, 0.53 mmol, 1.0 equiv) in MeOH (5 mL) was added NH₂NH₂ (35% in water, 1 mL). The mixture was heated at 70° C. for 2 h, cooled to r.t., concentrated under reduced pressure, and purified by silica gel chromatography using MeOH/DCM (1/4) to provide 75 mg (29% over 2 steps) of Intermediate 35-2B. LRMS (ES) m/z 490.2 (M+H). ¹H-NMR: (Methanol-d₄, 400 MHz, ppm) δ 7.76-7.71 (m, 1H), 7.67-7.61 (m, 4H), 7.44 (d, J=8.1 Hz, 2H), 5.09 (s, 2H), 4.46 (s, 2H), 3.17-3.02 (m, 3H), 2.78-2.62 (m, 2H), 1.87 (s, 2H).

3. Synthesis of Compound 454B

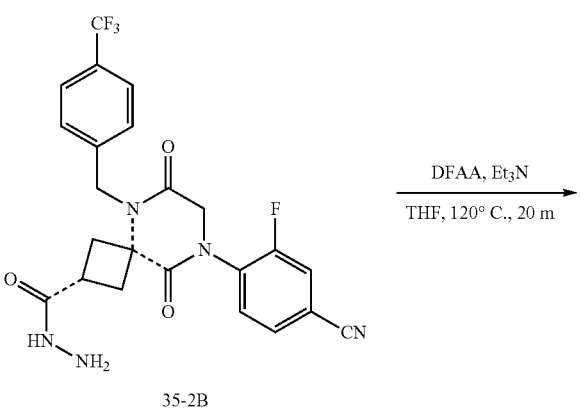

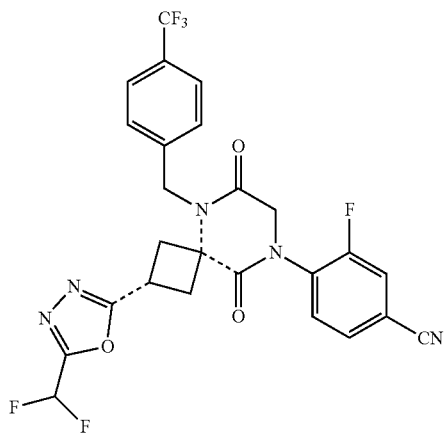

Compound 454B

To a solution of Intermediate 35-2B (25 mg, 0.051 mmol, 1.0 equiv) in THF (1 mL) were added TEA (0.2 mL) and difluoro acetic anhydride (13 mg, 0.077 mmol, 1.5 equiv).

The resulting mixture was heated at 120° C. in a microwave for 20 minutes and purified with reverse phase HPLC (Phenomenex, gemini 5u C18 150×21.2 mm, 10-80% acetonitrile in water both with 0.1% formic acid gradient over 40 min) to provided 10.2 mg (36%) of Compound 454B. LRMS (ES) m/z 550.1 (M+H). $^1$H-NMR: (Methanol-$d_4$, 400 MHz, ppm) δ 7.80-7.74 (m, 1H), 7.74-7.66 (m, 4H), 7.54 (d, J=8.1 Hz, 2H), 7.09 (t, J=51.7 Hz, 1H), 5.20 (s, 2H), 4.55 (s, 2H), 3.92 (dq, J=10.8, 6.0, 5.4 Hz, 1H), 3.39-3.28 (m, 2H), 3.16 (dd, J=14.1, 10.5 Hz, 2H).

The following compounds were prepared by methods analogous to the method described for Compound 454B:

| Diastereomer No. | LRMS (ES) m/z | $^1$H NMR |
|---|---|---|
| 430B | M + H = 500.1 | (400 MHz, Methanol-$d_4$) δ 8.82 (s, 1H), 7.77-7.72 (m, 1H), 7.71-7.66 (m, 4H), 7.54-7.49 (m, 2H), 5.19 (s, 2H), 4.52 (s, 2H), 3.92-3.81 (m, 1H), 3.38-3.26 (m, 2H), 3.15-3.06 (m, 2H) |
| 440B | M + H = 514.2 | (400 MHz, Methanol-$d_4$) δ 7.80-7.75 (m, 1H), 7.73-7.66 (m, 4H), 7.55-7.51 (m, 2H), 5.20 (s, 2H), 4.54 (s, 2H), 3.86-3.75 (m, 1H), 3.31-3.25 (m, 2H), 3.13-3.04 (m, 2H), 2.48 (s, 3H) |

To a solution of Intermediate 33-5B (100 mg, 0.21 mmol, 1.0 equiv) in DMF (2 mL) were added HATU (88 mg, 0.23 mmol, 1.1 equiv), acetamidine hydrochloride (30 mg, 0.32 mmol, 1.5 equiv), and TEA (106 mg, 1.1 mmol, 5.0 equiv). The mixture was stirred at r.t. for 15 h to provide intermediate 36-1B, which was used directly in the next step. LRMS (ES) m/z 516.1 (M+H). As used in this example, the dashed bond --- indicates that the stereochemical configuration of the starting material is retained in the product compound.

Example 36: Synthesis of Compound 432B

1. Synthesis of Intermediate 36-1B

2. Synthesis of Compound 432B

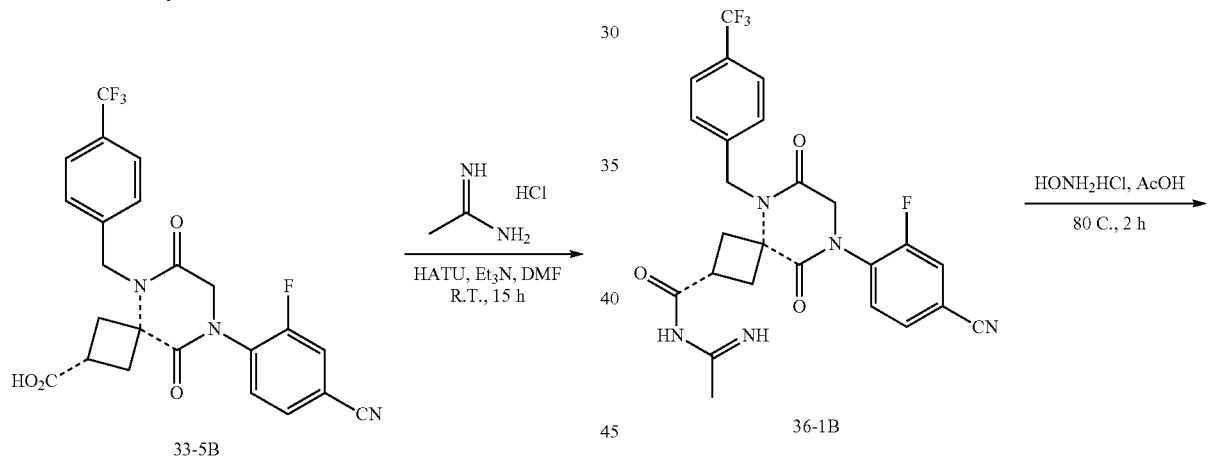

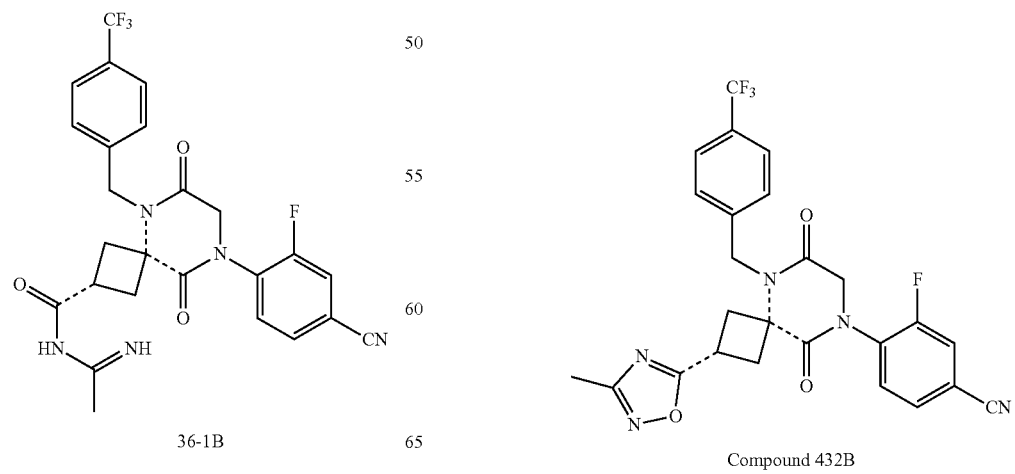

Compound 432B

To the DMF solution containing 36-1B were added hydroxylamine hydrochloride (100 mg, 1.44 mmol, 6.9 equiv) and AcOH (2 mL). The resulting mixture was heated at 80° C. for 2 h, concentrated under reduced pressure, and purified with reverse phase HPLC (Phenomenex, gemini 5u C18 150×21.2 mm, 20-100% acetonitrile in water both with 0.1% formic acid gradient over 40 min) to provide 15.3 mg (14% over 2 steps) of compound 432B. LRMS (ES) m/z 514.1 (M+H). (Methanol-$d_4$, 400 MHz, ppm) δ 7.77-7.73 (m, 1H), 7.72-7.64 (m, 4H), 7.54-7.49 (m, 2H), 5.18 (s, 2H), 4.52 (s, 2H), 3.87-3.77 (m, 1H), 3.34-3.24 (m, 2H), 3.14-3.05 (m, 2H), 2.30 (s, 3H).

The following compounds were prepared by methods analogous to the method described for Compound 432B:

| Diastereomer No. | LRMS (ES) m/z | $^1$H NMR |
| --- | --- | --- |
| 432B | M + H = 514.1 | (400 MHz, Methanol-$d_4$) δ 7.77-7.73 (m, 1H), 7.72-7.64 (m, 4H), 7.54-7.49 (m, 2H), 5.18 (s, 2H), 4.52 (s, 2H), 3.87-3.77 (m, 1H), 3.34-3.24 (m, 2H), 3.14-3.05 (m, 2H), 2.30 (s, 3H) |
| 434B | M + H = 544.1 | (400 MHz, Methanol-$d_4$) δ 7.79-7.74 (m, 1H), 7.74-7.66 (m, 4H), 7.56-7.51 (m, 2H), 5.20 (s, 2H), 4.94-4.83 (m, 1H), 4.54 (s, 2H), 3.91-3.81 (m, 1H), 3.40-3.29 (m, 2H), 3.17-3.09 (m, 2H), 1.49 (d, J = 6.7 Hz, 3H) |
| 438B | M + H = 540.10 | (400 MHz, DMSO-$d_6$) δ 8.06-8.00 (m, 1H), 7.86-7.82 (m, 1H), 7.79-7.72 (m, 3H), 7.53-7.47 (m, 2H), 5.11 (s, 2H), 4.51 (s, 2H), 3.93-3.82 (m, 1H), 3.13-3.05 (m, 2H), 3.03-2.93 (m, 2H), 2.09-2.01 (m, 1H), 1.05-0.98 (m, 2H), 0.83-0.78 (m, 2H) |
| 456B | M + H = 550.1 | (400 MHz, Methanol-$d_4$) δ 7.78-7.74 (m, 1H), 7.73-7.65 (m, 4H), 7.57-7.51 (m, 2H), 6.95 (t, J = 52.3 Hz, 1H), 5.20 (s, 2H), 4.54 (s, 2H), 3.99-3.89 (m, 1H), 3.39-3.30 (m, 2H), 3.23-3.14 (m, 2H) |
| 880B | M + H = 482 | (300 MHz, DMSO-d6) δ 8.53 (d, J = 2.5 Hz, 1H), 8.06-7.90 (m, 2H), 7.32 (dd, J = 8.4, 5.6 Hz, 2H), 7.18 (t, J = 8.7 Hz, 2H), 4.96 (s, 2H), 4.71 (s, 2H), 3.65 (t, J = 7.9 Hz, 1H), 3.12 (dd, J = 13.4, 6.9 Hz, 2H), 2.92 (t, J = 11.7 Hz, 2H), 2.15 (tt, J = 8.5, 4.8 Hz, 1H), 1.12-1.01 (m, 2H), 0.97-0.88 (m, 2H) |
| 880A | M + H = 482 | (300 MHz, DMSO-d6) δ 8.56 (d, J = 2.4 Hz, 1H), 8.14-7.99 (m, 2H), 7.31 (dd, J = 8.5, 5.5 Hz, 2H), 7.16 (t, J = 8.8 Hz, 2H), 4.84 (s, 2H), 4.72 (s, 2H), 3.45 (q, J = 9.2 Hz, 1H), 3.03 (t, J = 10.7 Hz, 2H), 2.78 (t, J = 10.9 Hz, 2H), 2.15 (tt, J = 8.8, 4.9 Hz, 1H), 1.17-1.04 (m, 2H), 0.98-0.87 (m, 2H) |
| 881B | M + H = 442 | (300 MHz, DMSO-d6) δ 9.11 (s, 1H), 8.53 (d, J = 2.5 Hz, 1H), 8.05-7.89 (m, 2H), 7.39-7.28 (m, 2H), 7.18 (t, J = 8.8 Hz, 2H), 4.98 (s, 2H), 4.72 (s, 2H), 3.76 (t, J = 9.4 Hz, 1H), 3.15 (dd, J = 13.5, 6.8 Hz, 2H), 3.05-2.91 (m, 2H). |
| 881A | M + H = 442 | (300 MHz, DMSO-d6) δ 9.12 (s, 1H), 8.56 (d, J = 2.5 Hz, 1H), 8.15-8.00 (m, 2H), 7.30 (dd, J = 8.6, 5.6 Hz, 2H), 7.15 (t, J = 8.7 Hz, 2H), 4.86 (s, 2H), 4.73 (s, 2H), 3.65-3.48 (m, 1H), 3.07 (t, J = 10.5 Hz, 2H), 2.83 (t, J = 10.7 Hz, 2H). |

Example 37: Synthesis of Compound 442B

1. Synthesis of Intermediate 37-1B

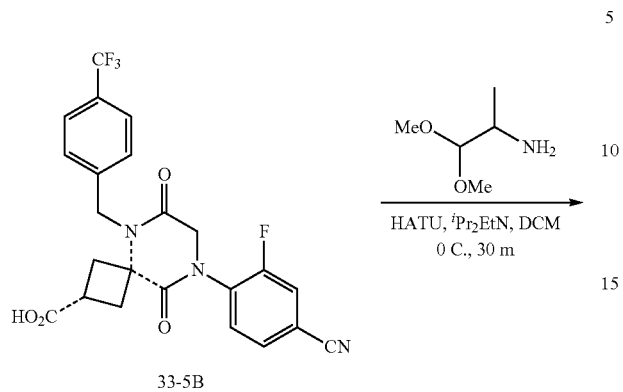

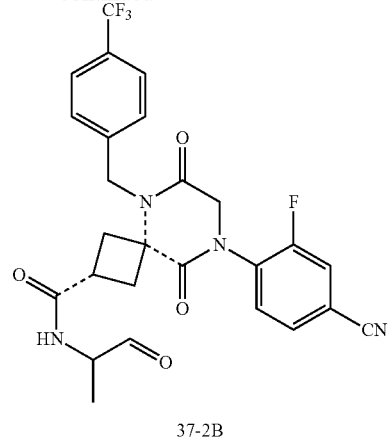

To a solution of Intermediate 33-5B (200 mg, 0.42 mmol, 1.0 equiv) in DCM (2 mL) at 0° C. were added HATU (192 mg, 0.51 mmol, 1.2 equiv), 1,1-dimethoxypropan-2-amine (55 mg, 0.46 mmol, 1.1 equiv), and DIEA (106 mg, 1.1 mmol, 5.0 equiv). The mixture was stirred at 0° C. for 30 min, concentrated under reduced pressure, and purified by silica gel chromatography (12 g, 60 um, 0-10% MeOH in DCM gradient) to provide intermediate 37-1B. LRMS (ES) m/z 577.2 (M+H).

2. Synthesis of Intermediate 37-2B

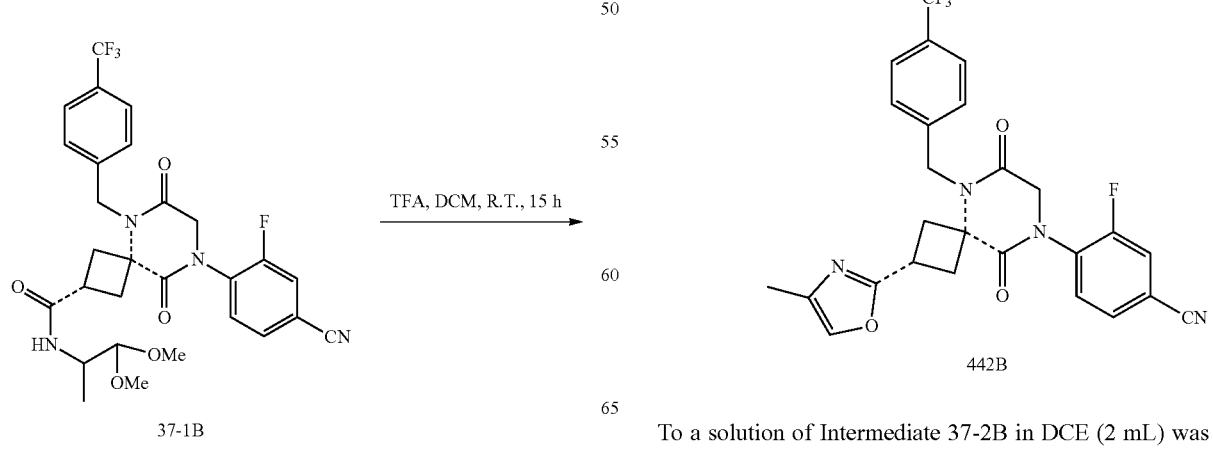

To a solution of Intermediate 37-1B in DCM (3 mL) was added TFA (0.3 mL). The mixture was stirred at r.t. for 15 h, concentrated under reduced pressure, and purified by silica gel chromatography (4 g, 60 um, 0-10% MeOH in DCM gradient) to provide Intermediate 37-2B. LRMS (ES) m/z 531.2 (M+H). As used in this example, the dashed bond --- indicates that the stereochemical configuration of the starting material is retained in the product compound.

3. Synthesis of Compound 442B

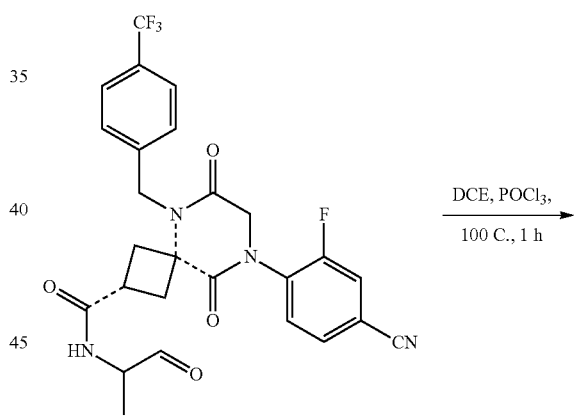

To a solution of Intermediate 37-2B in DCE (2 mL) was added POCl$_3$ (1 mL) and the mixture was stirred at 100 0°

C. for 1 h. The mixture was concentrated, diluted with DCM, and poured into NaOH (1 N) solution. The aqueous layer was extracted with DCM (3×). The combined DCM layers were washed with brine, dried over MgSO$_4$, filtered, concentrated, and purified with reverse phase HPLC (Phenomenex, gemini 5u C18 150×21.2 mm, 10-100% acetonitrile in water both with 0.1% formic acid gradient over 40 min) to provide 33.9 mg (33% over 3 steps) of Compound 442B. LRMS (ES) m/z 513.1 (M+H). $^1$H-NMR: (Methanol-d$_4$, 400 MHz, ppm) δ 7.79-7.74 (m, 1H), 7.73-7.66 (m, 4H), 7.56-7.51 (m, 2H), 7.49 (q, J=1.3 Hz, 1H), 5.20 (s, 2H), 4.53 (s, 2H), 3.75-3.65 (m, 1H), 3.35-3.25 (m, 2H), 3.03-2.95 (m, 2H), 2.10 (d, J=1.3 Hz, 3H).

Example 38: Synthesis of Compound 475B

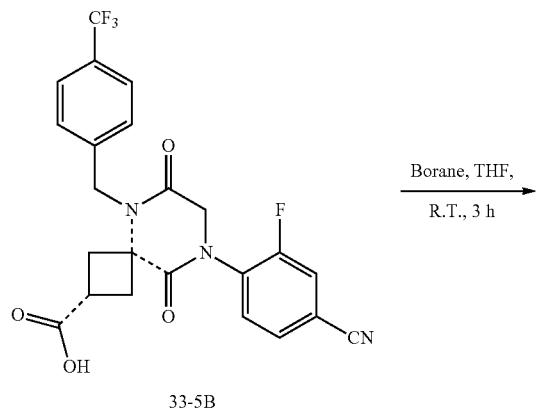

To a mixture of Intermediate 33-5B (50 mg, 0.10 mmol, 1.0 equiv) in THF (5 mL) was added borane in THF (1.0 M, 0.21 mL, 0.21 mmol, 2.0 equiv). The mixture was stirred at r.t. for 3 h, quenched with MeOH, and concentrated under reduce pressure. This material was dissolved in 2 mL of DMF and purified with reverse phase HPLC (Phenomenex, gemini 5u C18 150×21.2 mm, 10-70% acetonitrile in water both with 0.1% formic acid gradient over 25 min) to give a mixture, which was purified again with the same conditions to give 4.3 mg (9%) of Compound 475B. LRMS (ES) m/z 462.1 (M+H). $^1$H NMR (400 MHz, Methanol-d$_4$) δ 7.79-7.74 (m, 1H), 7.72-7.65 (m, 4H), 7.52-7.47 (m, 2H), 5.12 (s, 2H), 4.48 (s, 2H), 3.57-3.54 (m, 2H), 2.72-2.63 (m, 2H), 2.63-2.44 (m, 3H).

Example 39: Synthesis of Compound 479B

1. Synthesis of Intermediate 39-1

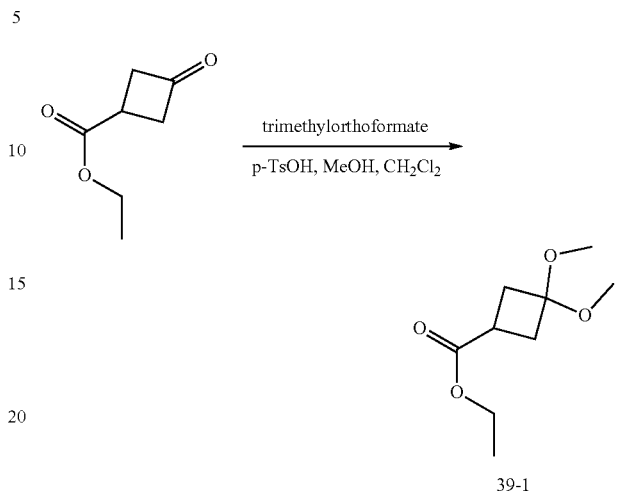

To solution of ethyl 3-oxocyclobutanecarboxylate (5.0 g, 35 mmol, 1.0 equiv) in a mixture of dry dichloromethane (50 mL) and dry methanol (50 mL) were added trimethylorthoformate (38 mL, 350 mmol, 10 equiv) and p-toluenesulfonic acid monohydrate (0.67 g, 3.5 mmol, 0.10 equiv) sequentially. The mixture was stirred overnight, concentrated, diluted with ethyl acetate, washed saturated sodium bicarbonate twice and brine, dried over magnesium sulfate, filtered, concentrated, and purified by silica gel chromatography (80 g, 0-20% ethyl acetate in hexanes gradient over 25 minute) to give 4.6 g (70%) of ethyl 3,3-dimethoxycyclobutane-1-carboxylate as a colorless oil (Intermediate 39-1). $^1$H NMR (400 MHz, Methylene Chloride-d$_2$) δ 4.26-4.11 (m, 2H), 3.17 (s, 3H), 3.15 (s, 3H), 2.91-2.81 (m, 1H), 2.49-2.30 (m, 4H), 1.33-1.25 (m, 3H).

2. Synthesis of Intermediate 39-2

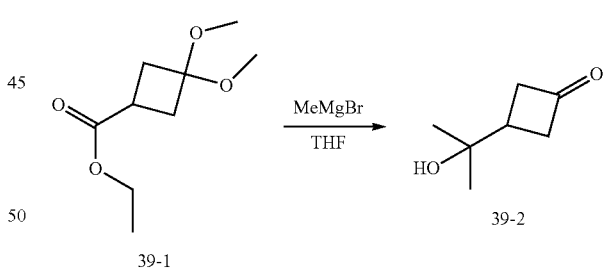

To a solution of ethyl 3,3-dimethoxycyclobutane-1-carboxylate (1.0 g, 5.3 mmol, 1.0 equiv) in dry THF (100 mL) at 0° C. was added methyl magnesium bromide in diethyl ether (3.0 M, 18 mL, 53 mmol, 10 equiv) dropwise. The mixture was heated at 85° C. for 2 h, cooled to 0° C., quenched with HCl (4 M), stirred for 1 hour, and extracted with ethyl acetate three times. The combined organic layers were dried over magnesium sulfate, filtered, concentrated, and purified by silica gel chromatography (12 g, 0-100% ethyl acetate in hexanes gradient over 11 minute) to give 0.78 g (quantitative) of 3-(2-hydroxypropan-2-yl)cyclobutan-1-one (Intermediate 39-2) as a clear yellow oil. $^1$H NMR (400 MHz, Methylene Chloride-d$_2$) δ 3.13-3.02 (m, 2H), 2.99-2.88 (m, 2H), 2.50-2.40 (m, 1H), 1.28 (s, 6H).

3. Synthesis of Intermediate 39-3

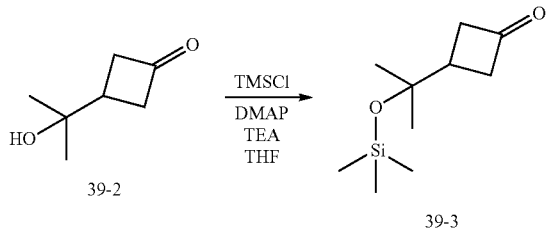

To a mixture of 3-(2-hydroxypropan-2-yl)cyclobutan-1-one (0.78 g, 6.0 mmol, 1.0 equiv) and 4-(dimethylamino)pyridine (37 mg, 0.30 mmol, 0.05 equiv) in dry tetrahydrofuran (30 mL), cooled to 0° C., were added triethylamine (1.6 mL, 12 mmol, 1.9 equiv) and followed by chlorotrimethylsilane (1.2 mL, 9.1 mmol, 1.5 equiv) dropwise. The mixture was warmed to room temperature, stirred for 3 days, diluted with water, and extracted with ethyl acetate twice. The combined organic layers were washed with brine, dried over magnesium sulfate, filtered, concentrated, and purified by silica gel chromatography (12 g, 0-20% ethyl acetate in hexanes gradient over 11 minute) to give 1.1 g (92%) of 3-(2-((trimethylsilyloxy)propan-2-yl)cyclobutan-1-one (Intermediate 39-3) as a colorless oil. $^1$H NMR (400 MHz, Methylene Chloride-d$_2$) δ 3.07-2.98 (m, 2H), 2.86-2.76 (m, 2H), 2.32-2.23 (m, 1H), 1.25 (s, 6H), 0.12 (s, 9H).

4. Synthesis of Intermediate 39-4

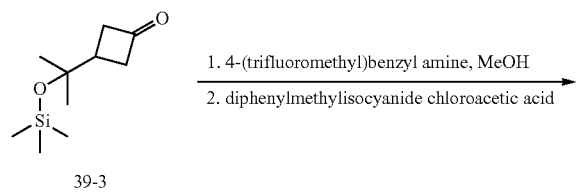

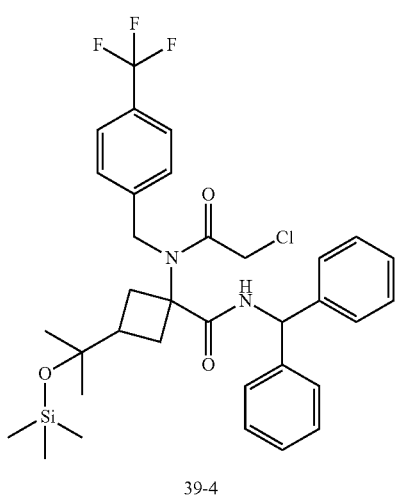

To a solution of 3-(2-((trimethylsilyl)oxy)propan-2-yl)cyclobutan-1-one (0.5 g, 2.5 mmol, 1.0 equiv) in dry methanol (7.5 mL) was added 4-(trifluoromethyl)benzyl amine (0.36 g, 2.5 mmol, 1.0 equiv). The mixture was stirred for 5 min. To this mixture were added diphenylmethyl isocyanide (0.48 g, 2.5 mmol, 1.0 equiv) and chloroacetic acid (0.24 g, 2.5 mmol, 1.0 equiv). The mixture was stirred for 1 h, concentrated, and purified by silica gel chromatography (40 g, 0-20% ethyl acetate in hexanes gradient over 14 minute) to give 0.86 g (53%) of N-benzhydryl-1-(2-chloro-N-(4-(trifluoromethyl)benzyl)acetamido)-3-(2-((trimethylsilyl)oxy)propan-2-yl)cyclobutane-1-carboxamide (Intermediate 39-4, mixture of stereoisomers) as a white solid. LRMS (ES) 573 (M+H-TMS). $^1$H NMR (400 MHz, Methylene Chloride-d$_2$) δ 7.68-7.23 (m, 14H), 6.14-6.06 (m, 1H), 4.67-4.52 (m, 2H), 3.94-3.80 (m, 2H), 2.69-2.59 (m, 2H), 2.26-2.16 (m, 2H), 1.94-1.82 (m, 1H), 1.10-1.02 (m, 6H), 0.44--0.00 (m, 9H).

5. Synthesis of Diastereomer 39-5B

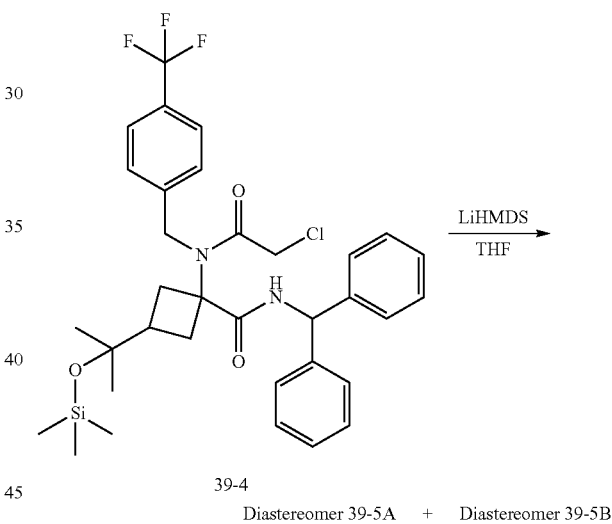

To a solution of N-benzhydryl-1-(2-chloro-N-(4-(trifluoromethyl)benzyl)acetamido)-3-(2-((trimethylsilyl)oxy)propan-2-yl)cyclobutane-1-carboxamide (0.86 g, 1.3 mmol, 1.0 equiv) in dry THF (9 mL) at 0° C. was added LHMDS (1.0 M, 1.6 mL, 1.6 mmol, 1.2 equiv) in dry THF (9 mL) dropwise. The mixture was stirred at 0° C. for 2 h, slowly quenched with MeOH, concentrated, and purified by silica gel chromatography (40 g, 0-20% ethyl acetate in hexanes gradient over 28 minute) to give Diastereomer 39-5A which was discarded and 0.4 g (49%) of Diastereomer 39-5B as a colorless oil. LRMS (ES) 537 (M+H-TMS). $^1$H NMR (400 MHz, Methylene Chloride-d$_2$) δ 7.60-7.56 (m, 2H), 7.42-7.34 (m, 6H), 7.30-7.25 (m, 2H), 7.21-7.17 (m, 4H), 6.99 (s, 1H), 4.97 (s, 2H), 3.71 (s, 2H), 2.98-2.88 (m, 2H), 2.17-2.04 (m, 3H), 1.06 (s, 6H), 0.12 (s, 9H).

6. Synthesis of Intermediate 39-6B

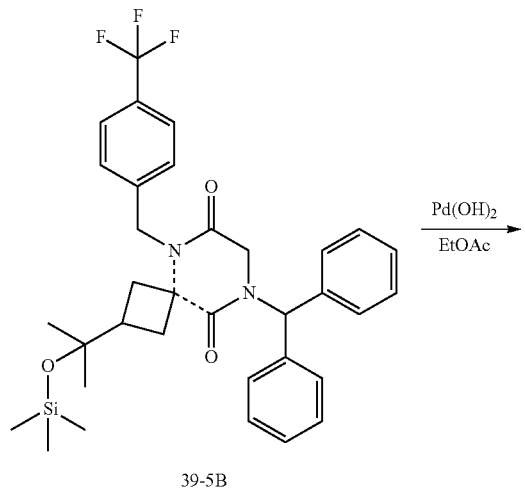

7. Synthesis of Compound 479B

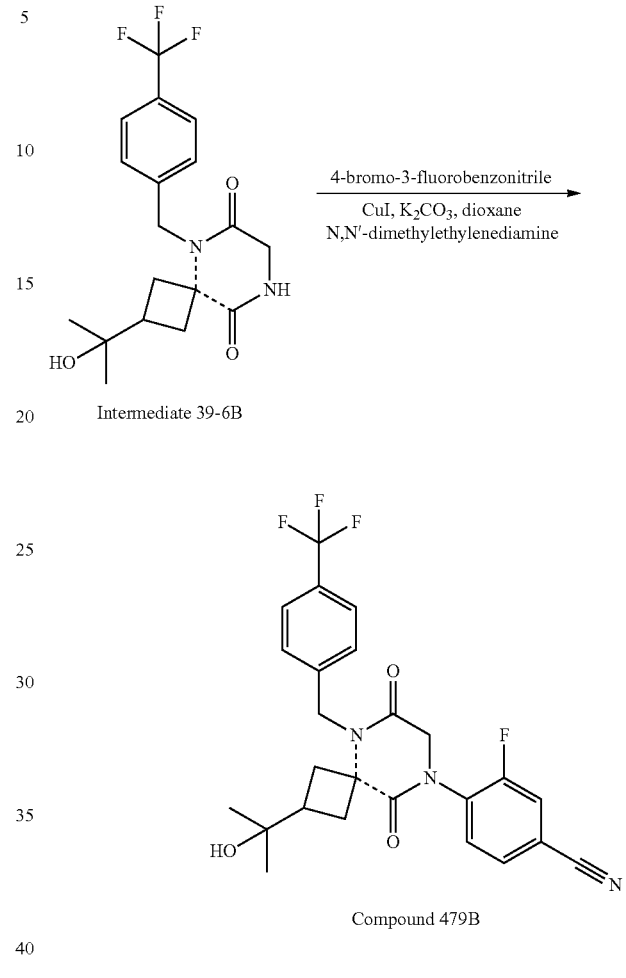

To a solution of Diastereomer 39-5B (0.40 g, 0.65 mmol, 1.0 equiv) in ethyl acetate (25 mL) was added 20% palladium hydroxide on carbon (1.5 g, 2.1 mmol, 3.3 equiv), and the resulting mixture is sparged with hydrogen for 5 min, followed by stirring under 500 psi in a Parr pressure reactor at 50° C. for 18 h. The reaction mixture was then cooled, filtered through a pad of celite, concentrated, and purified by chromatography (12 g, 60 um, 0-10% methanol in dichloromethane gradient over 22 minute) to give 0.13 g (57%) of intermediate 39-6B as a white solid. LRMS (ES) 371 (M+H). $^1$H NMR (400 MHz, Methylene Chloride-d$_2$) δ 7.64-7.56 (m, 2H), 7.38-7.30 (m, 2H), 6.80-6.55 (m, 1H), 5.01-4.93 (m, 2H), 4.05-4.02 (m, 2H), 2.98-2.85 (m, 2H), 2.48-2.24 (m, 3H), 1.06-1.02 (m, 6H). As used in this example, the dashed bond --- indicates that the stereochemical configuration of the starting material is retained in the product compound.

4-Bromo-3-fluorobenzonitrile (65 mg, 0.33 mmol, 1.8 equiv), copper (I) iodide (17 mg, 0.090 mmol, 0.50 equiv), and potassium carbonate (75 mg, 0.54 mmol, 3.0 equiv) were combined in a flask which was vacuum-nitrogen purged 3 times. To this mixture were added N,N-dimethylethylenediamine (0.010 mL, 0.090 mmol, 0.50 equiv), intermediate 6-6B (67 mg, 0.18 mmol, 1.0 equiv), and dry dioxane (1 mL). The reaction vessel was then heated at 100° C. with stirring overnight, cooled to r.t., filtered, and purified by reverse phase HPLC (Phenomenex, gemini 5u C18 150×21.2 mm, 10-90% acetonitrile in water with 0.1% formic acid in 25 minutes The combined fractions was purified again by silica gel chromatography (4 g, 60 um, 0-100% ethyl acetate in hexanes gradient over 11 min) to give 34 mg (38%) of Compound 479B. LRMS (ES) 490 (M+H). $^1$H NMR (400 MHz, Methanol-d$_4$) δ 7.78-7.73 (m, 1H), 7.70-7.63 (m, 4H), 7.49-7.44 (m, 2H), 5.14 (s, 2H), 4.48 (s, 2H), 3.00-2.87 (m, 2H), 2.47-2.32 (m, 3H), 1.05 (s, 6H).

The following compounds were prepared by methods analogous to the method described for Compound 479B:

| Diastereomer No. | LRMS (ES) m/z | $^1$H NMR |
|---|---|---|
| 479B | M + H = 490.2 | (400 MHz, Methanol-$d_4$) δ 7.78-7.73 (m, 1H), 7.70-7.63 (m, 4H), 7.49-7.44 (m, 2H), 5.14 (s, 2H), 4.48 (s, 2H), 3.00-2.87 (m, 2H), 2.47-2.32 (m, 3H), 1.05 (s, 6H) |
| 481B | M + H = 499.1 | (400 MHz, Methanol-$d_4$) δ 7.70-7.66 (m, 2H), 7.51-7.44 (m, 3H), 7.43-7.40 (m, 1H), 7.35-7.32 (m, 1H), 5.15 (s, 2H), 4.44 (s, 2H), 3.02-2.91 (m, 2H), 2.49-2.33 (m, 3H), 1.07 (s, 6H) |

Example 40: Synthesis of Compound 436B

1. Synthesis of Intermediate 40-2

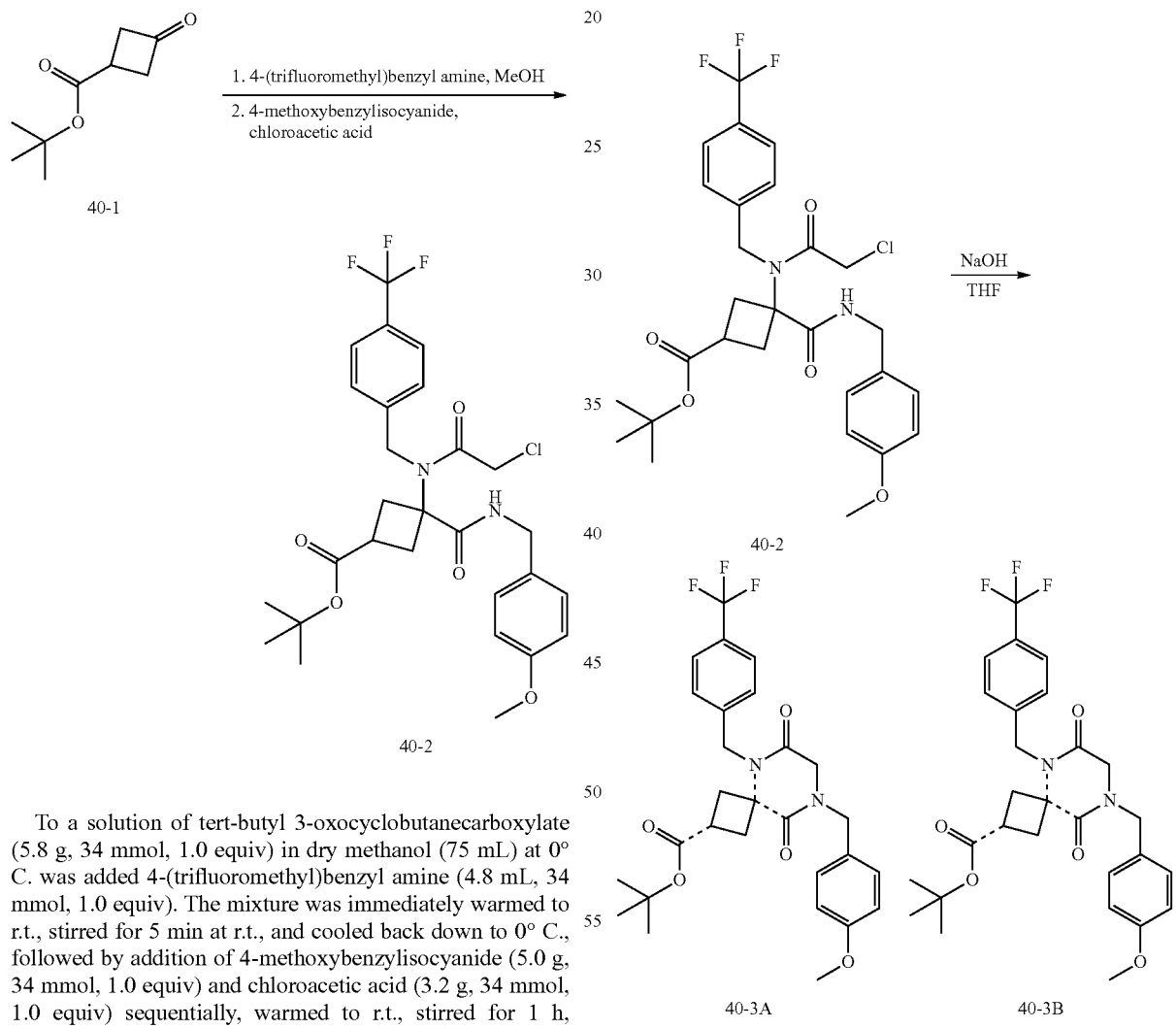

To a solution of tert-butyl 3-oxocyclobutanecarboxylate (5.8 g, 34 mmol, 1.0 equiv) in dry methanol (75 mL) at 0° C. was added 4-(trifluoromethyl)benzyl amine (4.8 mL, 34 mmol, 1.0 equiv). The mixture was immediately warmed to r.t., stirred for 5 min at r.t., and cooled back down to 0° C., followed by addition of 4-methoxybenzylisocyanide (5.0 g, 34 mmol, 1.0 equiv) and chloroacetic acid (3.2 g, 34 mmol, 1.0 equiv) sequentially, warmed to r.t., stirred for 1 h, concentrated, and purified by silica chromatography using EA/HE (gradient from 0-100% and 100%) and then MeOH/DCM (1/9) as eluents to give 11.4 g (79%) of 3-(2-chloro-N-(4-(trifluoromethyl)benzyl)acetamido)-3-((4-methoxy-benzyl)carbamoyl)cyclobutane-1-carboxylate as a mixture of isomers. LRMS (ES) m/z 569 (M+H). $^1$H NMR (400 MHz, Methylene Chloride-$d_2$) δ 7.71-7.61 (m, 2H), 7.46-7.37 (m, 2H), 7.28-7.19 (m, 2H), 6.93-6.87 (m, 2H), 4.69-4.62 (m, 2H), 4.42-4.36 (m, 2H), 3.93-3.88 (m, 2H), 3.84-3.81 (m, 3H), 3.03-2.75 (m, 3H), 2.73-2.61 (m, 1H), 2.55-2.45 (m, 1H), 1.43 (s, 9H).

2. Synthesis of Intermediate 40-3B

To a solution of 3-(2-Chloro-N-(4-(trifluoromethyl)benzyl)acetamido)-3-((4-methoxybenzyl)carbamoyl)cyclobutane-1-carboxylate (11.4 g, 20 mmol, 1.0 equiv) in THF (60 mL) cooled to 0° C. was added sodium hydroxide (1 N, 60.0 mL, 60.1 mmol, 3.0 equiv) in water dropwise. The mixture was allowed to warm to r.t., stirred for 3 h, concentrated partially, and extracted with ethyl acetate three times. The combined organic washes were dried over magnesium sulfate, filtered, concentrated, and purified by silica chromatography using EA/HE (gradient from 0-50%, isocratic at 50%, gradient from 50-100%) to give the first eluted diastereomer 40-3A which was discarded and 2.1 g (20%) of the second eluted diastereomer 40-3B. LRMS (ES) m/z 533 (M+H). $^1$H NMR (400 MHz, Methylene Chloride-d$_2$) δ 7.66-7.61 (m, 2H), 7.36-7.31 (m, 2H), 7.28-7.23 (m, 2H), 6.96-6.90 (m, 2H), 4.93 (s, 2H), 4.61 (s, 2H), 3.89 (s, 2H), 3.83 (s, 3H), 3.11-3.04 (m, 2H), 3.02-2.93 (m, 1H), 2.58-2.51 (m, 2H), 1.48 (s, 9H). As used in this example, the dashed bond --- indicates that the stereochemical configuration of the starting material is retained in the product compound.

3. Synthesis of Intermediate 40-4B

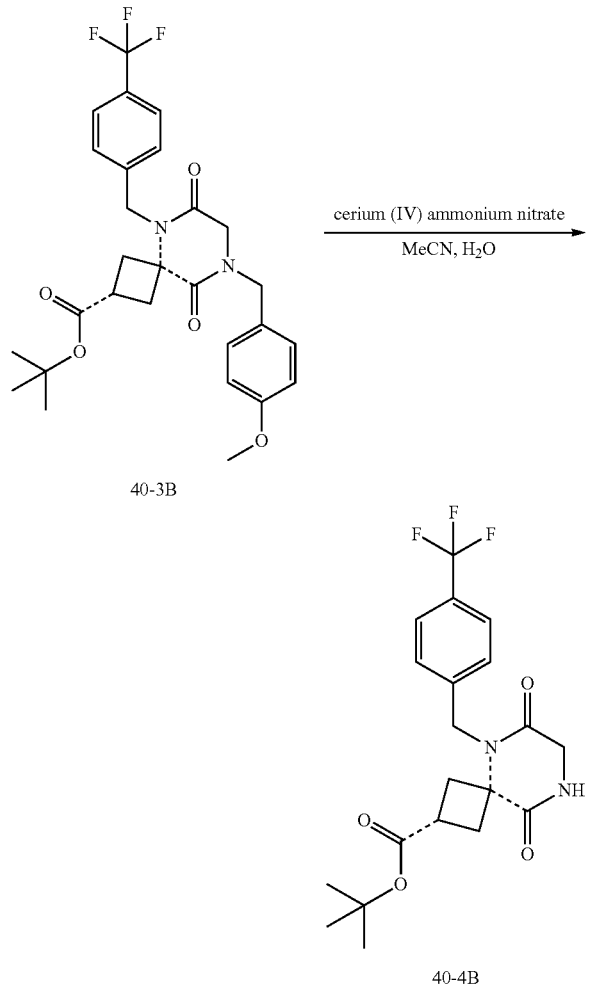

again by silica gel chromatography using EA/HE (gradient from 0-100%) as eluent to give 0.44 g (28%) of 40-4B. LRMS (ES) m/z 357 (M+H-tertbutyl). $^1$H NMR (400 MHz, Methylene Chloride-d$_2$) δ 7.68-7.60 (m, 2H), 7.42-7.34 (m, 2H), 4.96 (s, 2H), 4.07-4.04 (m, 2H), 3.09-2.92 (m, 3H), 2.62-2.54 (m, 2H), 1.46 (s, 9H).

4. Synthesis of Intermediate 40-5B

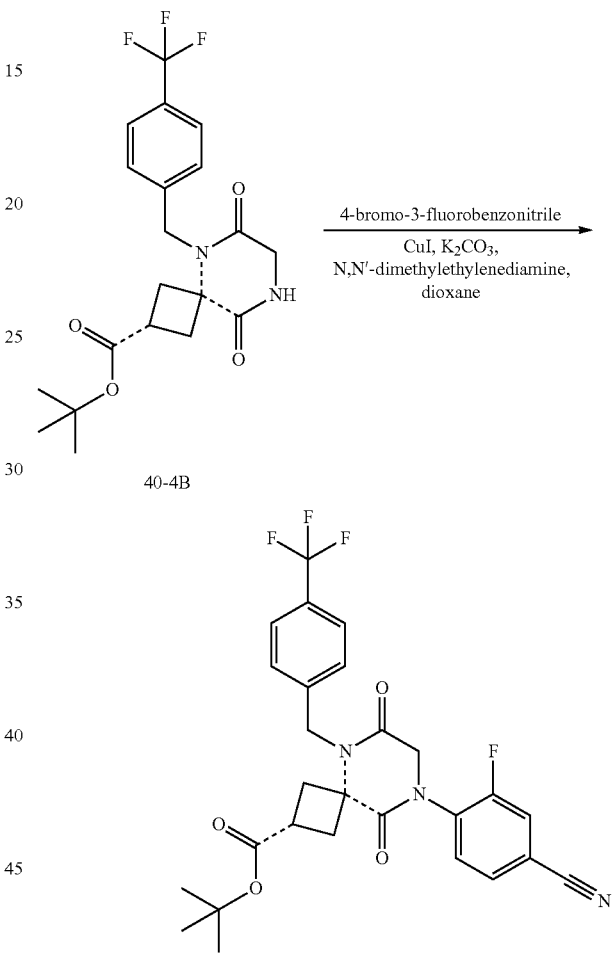

To a solution of 40-3B (2.1 g, 3.9 mmol, 1.0 equiv) in acetonitrile (32 mL) cooled at 0° C. was added cerium (IV) ammonium nitrate (6.4 g, 11.7 mmol, 3.0 equiv) in water (16 mL) dropwise. The mixture was sonicated for 10 min, stirred for 1 h at r.t., concentrated, and extracted with ethyl acetate three times. The combined organic washes were dried over magnesium sulfate, filtered, concentrated, and purified by silica chromatography using MeOH/DCM (gradient from 0-10%) as eluents. The fractions were collected and purified To a mixture of 40-4B (0.37 g, 0.90 mmol, 1.0 equiv), 4-bromo-3-fluorobenzonitrile (0.33 g, 1.6 mmol, 1.8 equiv), copper (I) iodide (0.086 g, 0.45 mmol, 0.5 equiv), and potassium carbonate (0.38 g, 2.7 mmol, 3.0 equiv) in a vacuum-nitrogen purged flask were added N,N-dimethylethylenediamine (0.049 mL, 0.45 mmol, 0.5 equiv) and dry dioxane (4 mL). The mixture was heated at 100° C. for 15 h, filtered through celite, concentrated, and purified by silica chromatography using EA/HE (gradient from 0-100%) as eluent to give 0.29 g (61%) of 40-5B. LRMS (APCI) m/z 476.1 (M+H-C$_4$H$_9$ $^1$H NMR (400 MHz, Methylene Chloride-d$_2$) δ 7.70-7.66 (m, 2H), 7.63-7.60 (m, 1H), 7.60-7.56 (m, 1H), 7.56-7.51 (m, 1H), 7.44-7.40 (m, 2H), 5.02 (s, 2H), 4.40-4.38 (m, 2H), 3.18-3.11 (m, 2H), 3.03-2.94 (m, 1H), 2.70-2.62 (m, 2H), 1.42 (s, 9H).

5. Synthesis of Intermediate 40-6B

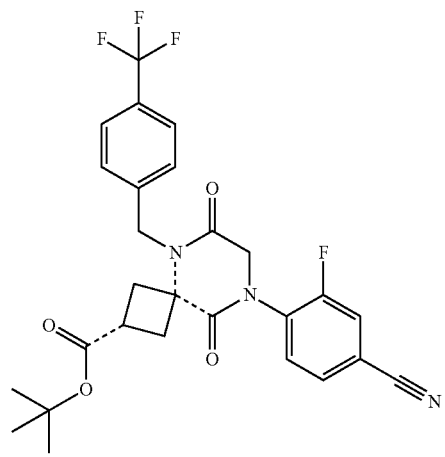

40-5B

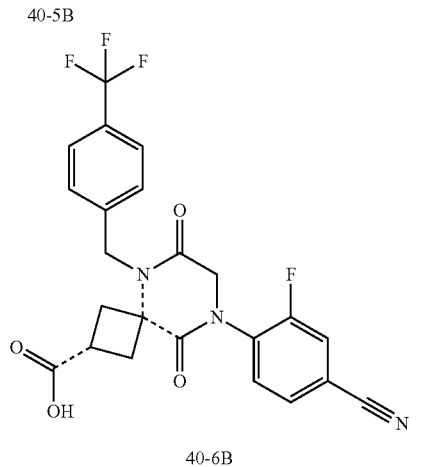

40-6B 40-5B (0.29 g, 0.55 mmol, 1.0 equiv) and TFA (3.0 mL, 39 mmol, 71 equiv) were combined, stirred for 30 min, concentrated, and dried under vacuum to give 40-6B. LRMS (ES) m/z 476 (M+H).

6. Synthesis of Intermediate 40-7B 40-6B

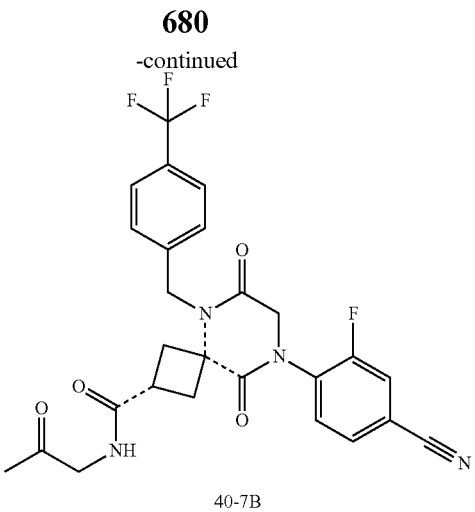

40-7B

To a mixture of 1-aminopropan-2-one HCl (10 mg, 0.092 mmol, 0.92 equiv), PyBop (52 mg, 0.10 mmol, 1.0 equiv), and 40-6B (49 mg, 0.10 mmol, 1.0 equiv) in dry DCM (1 mL) was added DIEA (0.073 mL, 0.42 mmol, 4.2 equiv). The mixture was stirred for 30 min at r.t., concentrated, and purified by silica chromatography using MeOH/DCM (gradient from 0-10%) to give 45 mg (92%) of 40-7B. LRMS (ES) m/z 531 (M+H).

7. Synthesis of Compound 436B 40-7B

Compound 436B

To a solution of 40-7B (45 mg, 0.085 mmol, 1.0 equiv) in DCE (1 mL) was added phosphorus (V) oxychloride (0.39 mL, 4.2 mmol, 50 equiv) dropwise. The mixture was heated at 100° C. for 1 h, cooled to 0° C., basified to pH greater than 14 with NaOH (1 N) dropwise, warmed to r.t., and stirred overnight. The mixture was extracted with DCM three times. The combined organic layers were dried over magnesium sulfate, filtered, concentrated, and purified by RP-HPLC (Phenomenex, gemini 5u C18 150×21.2 mm, 10-100% acetonitrile in water both with 0.1% formic acid gradient over 25 min) to give 14.9 mg (35%) of Compound 436B. LRMS (ES) m/z 513 (M+H). ¹H NMR (400 MHz, Methanol-d₄) δ 7.80-7.75 (m, 1H), 7.73-7.66 (m, 4H), 7.56-7.51 (m, 2H), 6.66 (q, J=1.2 Hz, 1H), 5.20 (s, 2H), 4.54 (s, 2H), 3.74-3.63 (m, 1H), 3.31-3.24 (m, 2H), 3.02-2.94 (m, 2H), 2.27 (d, J=1.2 Hz, 3H).

Example 41: Synthesis of Compound 496

1. Synthesis of Intermediate 41-2

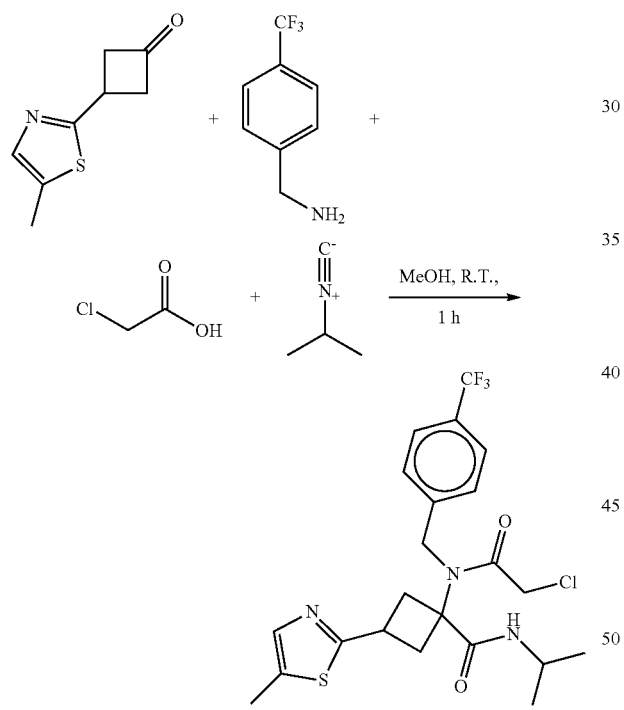

41-2

To a mixture of (4-(trifluoromethyl)phenyl)methanamine (143 mg, 0.82 mmol, 1.05 equiv) and 3-(5-methylthiazol-2-yl)cyclobutan-1-one (130 mg, 0.78 mmol, 1.0 equiv) in MeOH (10 mL) were added 2-isocyanopropane (56 mg, 0.82 mmol, 1.05 equiv) and chloroacetic acid (77 mg, 0.82 mmol, 1.05 equiv). The mixture was stirred at r.t. for 1 h, concentrated under reduced pressure, and purified by silica gel chromatography using EtOAc/Hexanes (7/3) as eluents to provide 380 mg of Intermediate 41-2 as a mixture of isomers which were used in the subsequent step without further purification LRMS (ES) m/z 488.1 (M+H).

2. Synthesis of Compound 496B

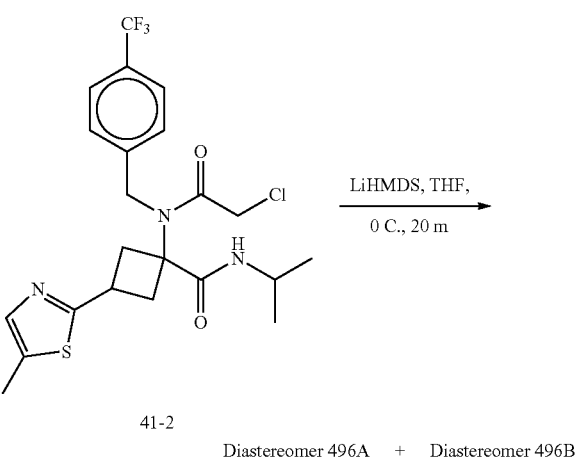

41-2

Diastereomer 496A + Diastereomer 496B

To a mixture of Intermediate 41-2 (380 mg, 0.78 mmol, 1.0 equiv.) in THF (5 mL) cooled to 0° C. with an ice bath was added LHMDS (1 M in THF, 0.78 mL, 0.78 mmol, 1.0 equiv) dropwise. The mixture was stirred at 0° C. for 2 h, added MeOH, concentrated under reduced pressure, and purified with reverse phase HPLC (Phenomenex, gemini 5u C18 150×21.2 mm, 10-80% acetonitrile in water both with 0.1% formic acid gradient over 40 min) to provide 3.6 mg (2% over 2 steps) of the first eluted eluent peak as Diastereomer 496B and 8.1 mg (5% over 2 steps) of the second eluted peak as Diastereomer 496A.

Characterization for Diastereomer 496B: LRMS (ES) m/z 452.1 (M+H). NMR (Methanol-d₄, 400 MHz, ppm) δ 7.68 (d, J=8.1 Hz, 2H), 7.46 (d, J=8.0 Hz, 2H), 7.31 (q, J=1.2 Hz, 1H), 5.14 (s, 2H), 4.70 (p, J=6.8 Hz, 1H), 4.06 (s, 2H), 3.93-3.77 (m, 1H), 3.20-3.08 (m, 2H), 2.98-2.86 (m, 2H), 2.45 (d, J=1.2 Hz, 3H), 1.22 (d, J=6.8 Hz, 6H).

Characterization for Diastereomer 496A: LRMS (ES) m/z 452.1 (M+H). ¹H NMR (400 MHz, Methanol-d₄) δ 7.65 (d, J=8.1 Hz, 2H), 7.44 (d, J=8.0 Hz, 2H), 7.36 (q, J=1.2 Hz, 1H), 5.07 (s, 2H), 4.86-4.74 (m, 1H), 4.08 (s, 2H), 3.69 (p, J=8.9 Hz, 1H), 2.99 (ddd, J=10.0, 8.4, 2.7 Hz, 2H), 2.76 (td, J=9.5, 2.8 Hz, 2H), 2.43 (d, J=1.2 Hz, 3H), 1.26 (d, J=6.8 Hz, 6H).

Example 42: Synthesis of Compound 498B

1. Synthesis of Intermediate 42-1

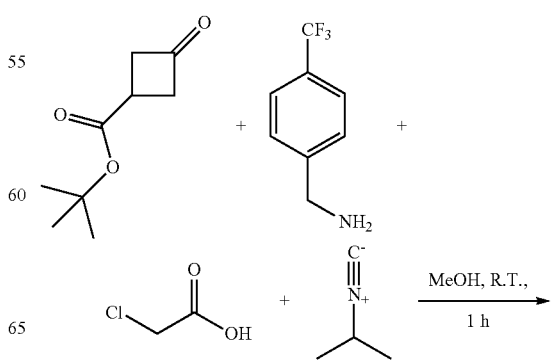

1. (continued)

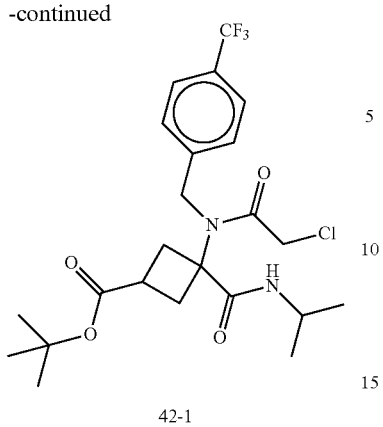

42-1

To a mixture of (4-(trifluoromethyl)phenyl)methanamine (6.7 g, 38.0 mmol, 1.05 equiv) and tert-butyl 3-oxocyclobutane-1-carboxylate (6.2 g, 36.2 mmol, 1.0 equiv) in MeOH (100 mL) were added 2-isocyanopropane (3.0 g, 43.4 mmol, 1.2 equiv) and chloroacetic acid (3.6 mg, 38.0 mmol, 1.05 equiv). The mixture was stirred at r.t. for 1 h, concentrated under reduced pressure, and purified with silica gel chromatography using EtOAc/Hexanes (7/3) as eluents to provide intermediate 42-1 as a mixture of diastereomers which was used in the subsequent step without further purification. LRMS (ES) m/z 491.2 (M+H)

2. Synthesis of Diastereomer 42-2B

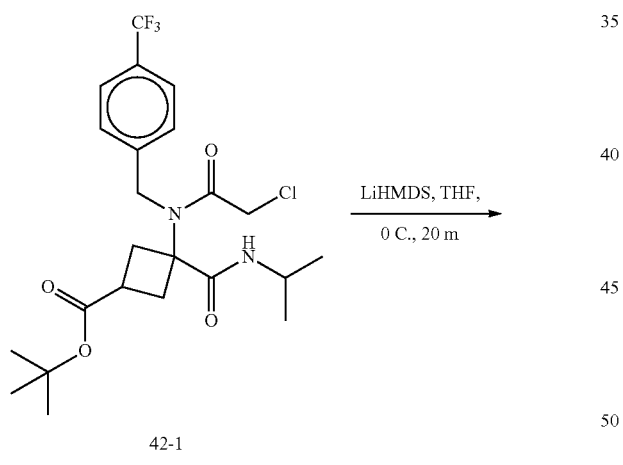

To a solution of intermediate 42-1 (16.5 g, 33.6 mmol, 1.0 equiv.) in THF (200 mL) cooled to 0° C. with an ice bath was added LHMDS (1 M in THF, 40.3 mL, 40.3 mmol, 1.2 equiv) dropwise. The mixture was stirred at 0° C. for 2 h, added MeOH, concentrated under reduced pressure, and purified with silica gel chromatography (220 g, 0-50% EtOAc in hexanes gradient) to provide impure product. This material was purified again by silica gel chromatography (120 g, 0-50% EtOAc in hexanes gradient) to provide the first eluting Diastereomer 42-2A which was discarded and 2.5 g (16%) of the second eluting Diastereomer 42-2B.

Characterization for Diastereomer 42-2B: LRMS (ES) m/z 455.25 (M+H). $^1$H NMR (400 MHz, Methanol-$d_4$) δ 7.72-7.63 (m, 2H), 7.45-7.36 (m, 2H), 5.03 (s, 2H), 4.72 (p, J=6.9 Hz, 1H), 4.02 (s, 2H), 3.11-2.89 (m, 3H), 2.71-2.56 (m, 2H), 1.46 (s, 9H), 1.23 (d, J=6.8 Hz, 6H).

3. Synthesis of Intermediate 42-3B

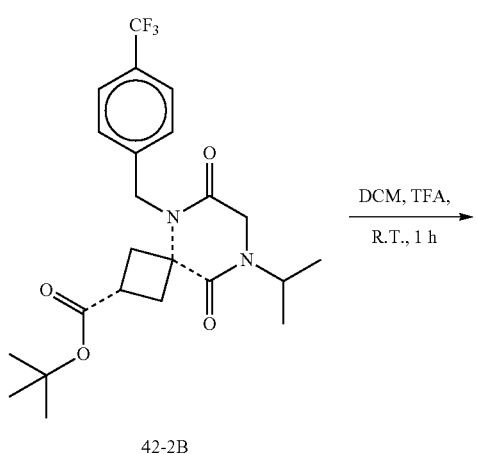

42-2B

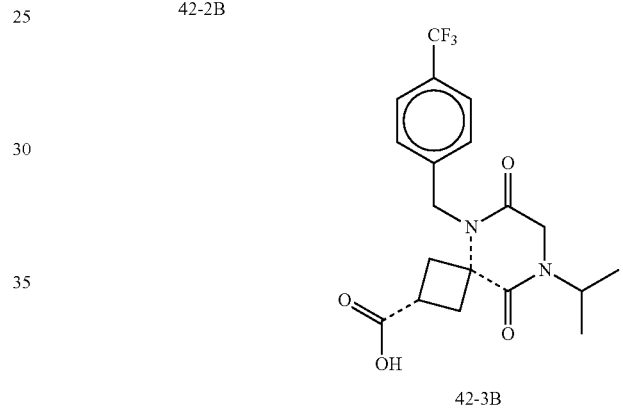

42-3B

To a solution of Diastereomer 42-2B (2.5 g, 5.5 mmol, 1.0 equiv.) in DCM (10 mL) was added TFA (10 mL). The mixture was stirred at r.t. for 1 h and concentrated to give 2.2 g (99% yield) of intermediate 42-3B. LRMS (ES) m/z 399.2 (M+H).

4. Synthesis of Compound 498B

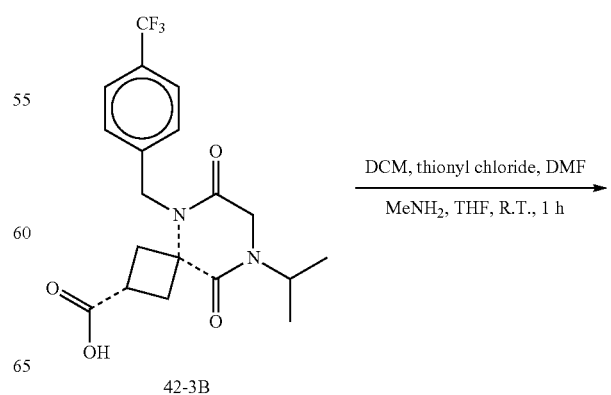

42-3B

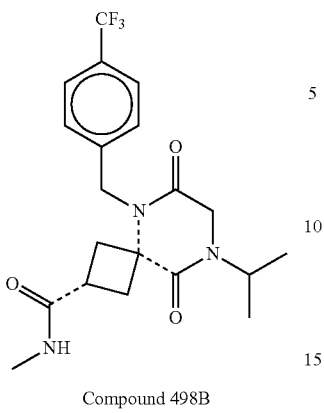

Compound 498B

To a solution of 42-3B (0.20 g, 0.50 mmol, 1.0 equiv) in DCM (3 mL) were added thionyl chloride (0.2 mL, 2.7 mmol, 5.5 equiv) and a drop of DMF (~50 mg). The mixture was stirred at r.t. for 1 min, followed by addition of MeNH$_2$ (2 M in THF, 6 mL, 12 mmol, 24 equiv), stirred at r.t. for 1 h, poured into water, and extracted with DCM. The organic layer was concentrated and purified by reverse phase HPLC (Phenomenex, gemini 5u C18 150×21.2 mm, 10-700% acetonitrile in water both with 0.1% formic acid gradient over 25 min) to give 8.6 mg (4%) of Compound 498B. LRMS (ES) m/z 412.2 (M+H). $^1$H NMR (400 MHz, Methanol-d$_4$) δ 7.81-7.72 (m, 1H), 7.67-7.62 (m, 2H), 7.42-7.36 (m, 2H), 5.04 (s, 2H), 4.70 (hept, J=6.8 Hz, 1H), 4.01 (s, 2H), 3.14-2.96 (m, 3H), 2.74-2.69 (m, 3H), 2.66-2.56 (m, 2H), 1.20 (d, J=6.8 Hz, 6H).

Example 43: Synthesis of Compound 500B

1. Synthesis of Intermediate 43-1B

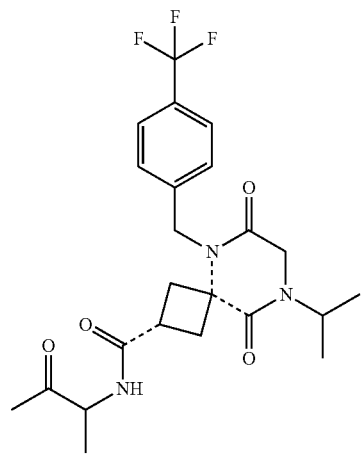

43-1B

To a mixture of 3-aminobutan-2-one (68 mg, 0.55 mmol, 1.1 equiv), HATU (229 mg, 0.60 mmol, 1.2 equiv), and 42-3B (200 mg, 0.50 mmol, 1.0 equiv) in dry DCM (2 mL) was added DIEA (0.35 mL, 2.0 mmol, 4.0 equiv). The mixture was stirred for 1 h at r.t., concentrated, and purified by silica chromatography using MeOH/DCM (gradient from 0-10%) to give 239 mg of 43-1B. LRMS (ES) m/z 468.2 (M+H). As used in this example, the dashed bond --- indicates that the stereochemical configuration of the starting material is retained in the product compound.

2. Synthesis of Compound 500B

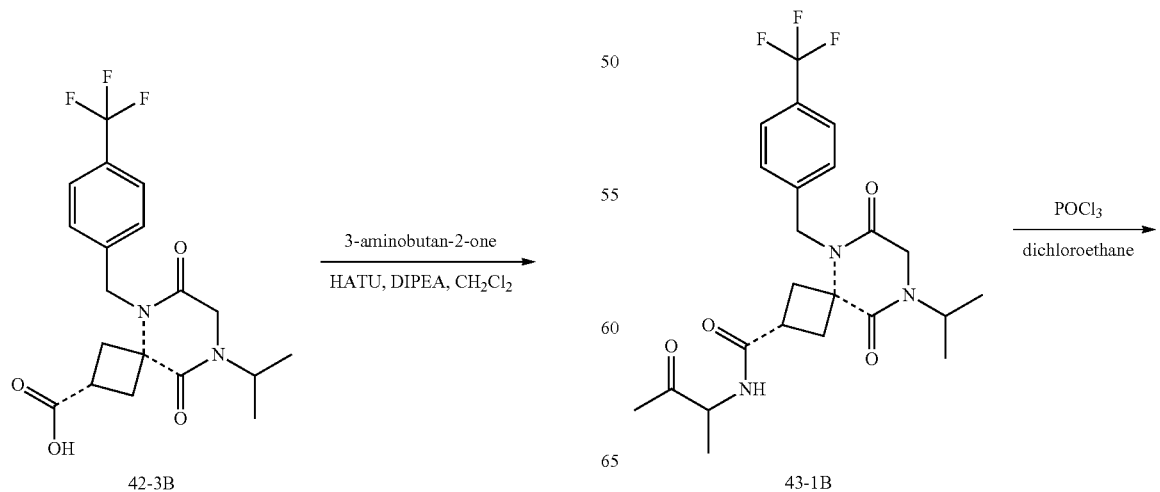

687
-continued

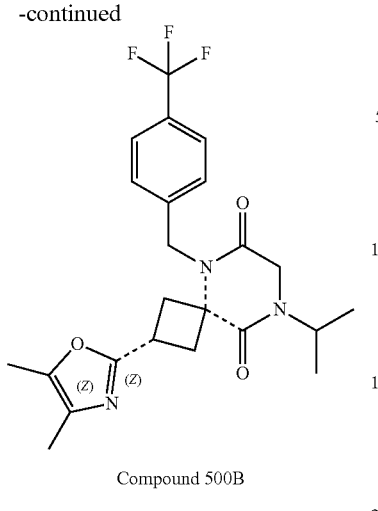

Compound 500B

To a solution of 43-1B (239 mg, 0.50 mmol, 1.0 equiv) in DCE (3 mL) was added phosphorus (V) oxychloride (2.4 mL, 25.5 mmol, 50 equiv) dropwise. The mixture was heated at 100° C. for 1 h, cooled to 0° C., basified to pH greater than 14 with NaOH (1 N) dropwise, warmed to r.t., and stirred overnight. The mixture was extracted with DCM three times. The combined organic layers were dried over magnesium sulfate, filtered, concentrated, and purified by reverse phase HPLC (Phenomenex, gemini 5u C18 150× 21.2 mm, 10-100% acetonitrile in water both with 0.1% formic acid gradient over 25 min) to give 103 mg (45%) of compound 500B. LRMS (ES) m/z 450.2 (M+H). $^1$H NMR (400 MHz, Methanol-$d_4$) δ 7.70-7.65 (m, 2H), 7.47-7.42 (m, 2H), 5.11 (s, 2H), 4.68 (hept, J=6.8 Hz, 1H), 4.05 (s, 2H), 3.63-3.51 (m, 1H), 3.21-3.13 (m, 2H), 2.87-2.77 (m, 2H), 2.23-2.21 (m, 3H), 2.04-2.02 (m, 3H), 1.22 (d, J=6.8 Hz, 6H).

The following compounds were prepared by methods analogous to the method described for Compound 500B:

688

Example 44: Synthesis of Compounds 488B and 490B

1. Synthesis of Intermediate 44-2

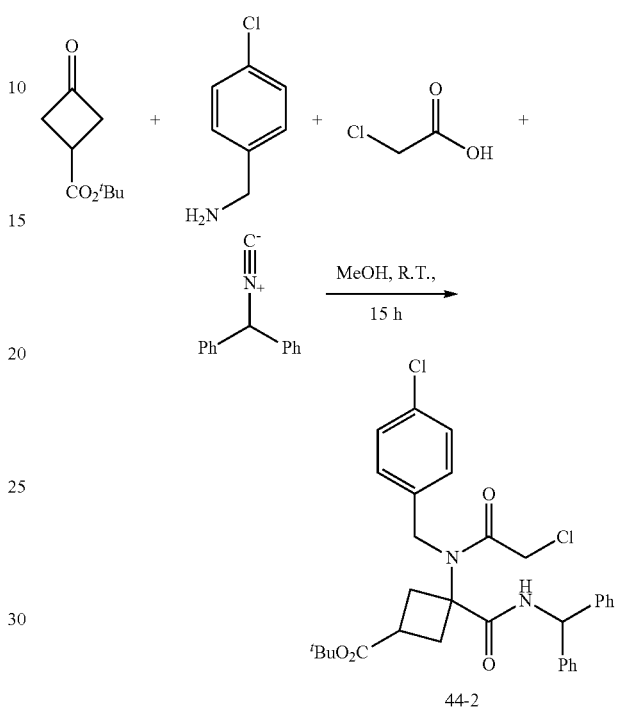

To a mixture of 4-chlorobenzyl amine (2.9 g, 20.2 mmol, 1.0 equiv) and tert-butyl 3-oxocyclobutane-1-carboxylate (3.4 g, 20.2 mmol, 1.0 equiv) in MeOH (30 mL) were added (isocyanomethylene)dibenzene (4.1 g, 21.2 mmol, 1.05 equiv) and chloroacetic acid (2.0 g, 21.2 mmol, 1.05 equiv). The mixture was stirred at r.t. for 15 h, concentrated under reduced pressure, and purified by silica gel chromatography using EA/HE (gradient from 0-100%) to provide 9.0 g (77%) of tert-butyl 3-(benzhydrylcarbamoyl)-3-(2-chloro-N-(4-chlorobenzyl)acetamido) cyclobutane-1-carboxylate) as a mixture of diastereomers. LRMS (ES) m/z 581.2 (M+H).

| Diastereomer No. | LRMS (ES) m/z | $^1$H NMR |
|---|---|---|
| 500B | M + H = 450.2 | (400 MHz, Methanol-$d_4$) δ 7.70-7.65 (m, 2H), 7.47-7.42 (m, 2H), 5.11 (s, 2H), 4.68 (hept, J = 6.8 Hz, 1H), 4.05 (s, 2H), 3.63-3.51 (m, 1H), 3.21-3.13 (m, 2H), 2.87-2.77 (m, 2H), 2.23-2.21 (m, 3H), 2.04-2.02 (m, 3H), 1.22 (d, J = 6.8 Hz, 6H) |
| 502B | M + H = 436.2 | (400 MHz, Methanol-$d_4$) δ 7.70-7.65 (m, 2H), 7.51 (q, J = 1.3 Hz, 1H), 7.47-7.42 (m, 2H), 5.12 (s, 2H), 4.67 (hept, J = 6.8 Hz, 1H), 4.05 (s, 2H), 3.68-3.58 (m, 1H), 3.23-3.16 (m, 2H), 2.90-2.81 (m, 2H), 2.12 (d, J = 1.3 Hz, 3H), 1.22 (d, J = 6.8 Hz, 6H) |

2. Synthesis of Diastereomer 44-2B

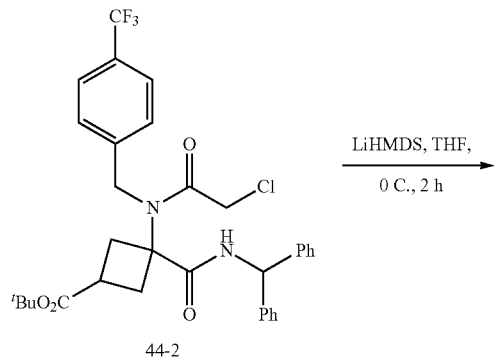

44-2

Diastereomer 44-2A + Diastereomer 44-2B

To a solution of tert-butyl 3-(benzhydrylcarbamoyl)-3-(2-chloro-N-4-(chlorobenzyl)acetamido)cyclobutane-1-carboxylate) (9.0 g, 15.5 mmol, 1.0 equiv) in THF (200 mL) cooled to 0° C. with an ice bath was added LHMDS (1 M in THF, 18.6 mmol, 1.2 equiv) dropwise over 10 minutes. The mixture was stirred at 0° C. for 2 h, quenched with MeOH (5 mL), concentrated onto SiO$_2$ (20 g), and purified by silica gel chromatography using EA/HE (gradient from 0-100%) to provide two separate diastereomers. The first eluted peak (Diastereomer 44-2A) was discarded and the second eluted peak (Diastereomer 44-2B) was collected (3.0 g, 36%). Characterization of Diastereomer 44-2B: LRMS (ES) m/z 545.3 (M+H). $^1$H-NMR (Methanol-d$_4$, 400 MHz, ppm) δ 7.45-7.30 (m, 8H), 7.24-7.12 (m, 6H), 6.99 (s, 1H), 4.88 (s, 2H), 3.77 (s, 2H), 3.08-2.86 (m, 3H), 2.69-2.51 (m, 2H), 1.44 (s, 9H).

3. Synthesis of Intermediate 44-4B

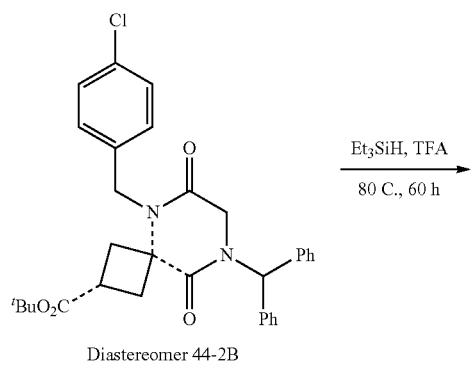

Diastereomer 44-2B

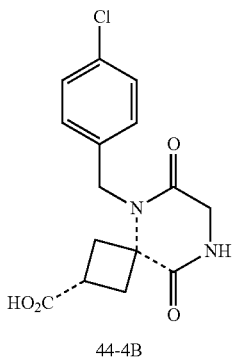

44-4B

To a solution of diastereomer 44-2B (0.6 g, 1.1 mmol, 1.0 equiv) in TFA (20 mL) was added Et$_3$SiH (20 mL). The mixture was stirred at 80° C. for 60 h, concentrated under reduced pressure, and purified by silica gel chromatography using MeOH/DCM (0-30%) to provide 0.3 g (84%) of Intermediate 44-4B. LRMS (ES) m/z 323.1 (M+H). As used in this example, the dashed bond --- indicates that the stereochemical configuration of the starting material is retained in the product compound.

4. Synthesis of Intermediate 44-5B

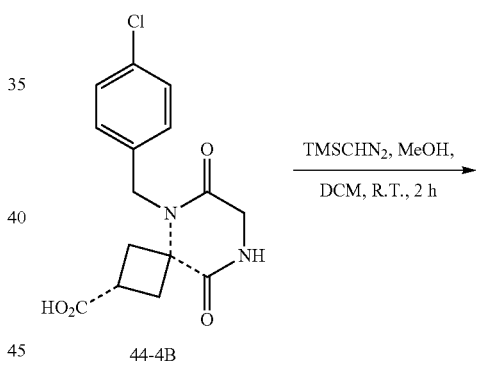

44-4B

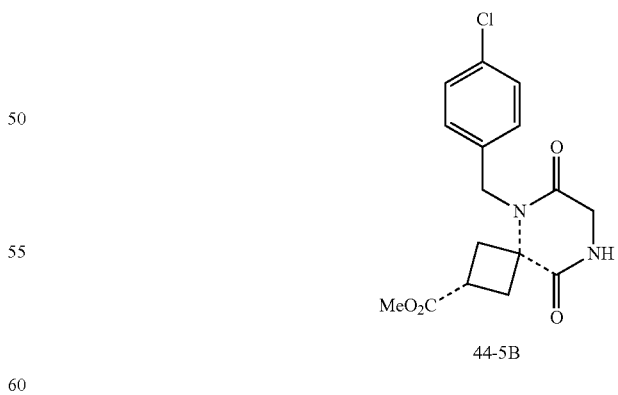

44-5B

To a solution of Intermediate 44-4B (354 mg, 1.1 mmol) in a mixture of DCM (5 mL) and MeOH (5 mL) was added TMSCHN$_2$ (2 M in hexanes, 2.8 mL, 5.1 equiv). The mixture was stirred at r.t. for 2 h and concentrated under reduced pressure to provide Intermediate 44-5B. LRMS (ES) m/z 337.1 (M+H).

5. Synthesis of Compound 488B

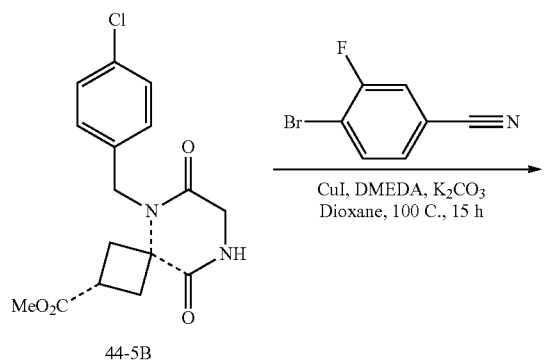

44-5B

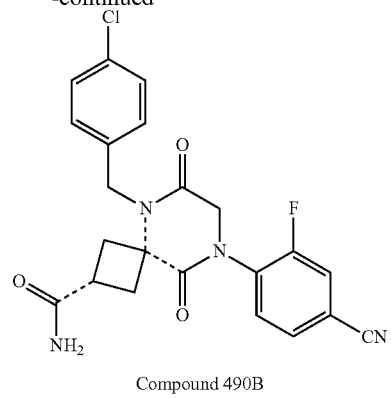

Compound 490B

To a mixture of copper iodide (113 mg, 0.59 mmol, 0.5 equiv), potassium carbonate (492 mg, 3.6 mmol, 3.0 equiv), 4-bromo-3-fluorobenzonitrile (428 mg, 2.1 mmol, 1.8 equiv), and intermediate 44-5B (370 mg, 1.1 mmol, 1.0 equiv.) in a vial were added 1,4-dioxane (16 mL) and N,N'-dimethylethylene diamine (64 μL, 0.59 mmol, 0.5 equiv). The mixture was sealed and heated at 100° C. for 15 h, cooled to r.t., filtered through celite, and purified by silica gel chromatography using EA/HE (gradient from 0-100%) to provide 100 mg (19% over 3 steps) of Compound 488B. LRMS (ES) m/z 456.1 (M+H). $^1$H-NMR: (400 MHz, Methanol-$d_4$) δ 7.78-7.73 (m, 1H), 7.71-7.63 (m, 2H), 7.40-7.35 (m, 2H), 7.31-7.26 (m, 2H), 4.99 (s, 2H), 4.47 (s, 2H), 3.64 (s, 3H), 3.18-3.02 (m, 3H), 2.87-2.78 (m, 2H).

6. Synthesis of Compound 490B

To a solution of Compound 488B (70 mg, 0.15 mmol, 1.0 equiv) in MeOH (2 mL) was added NH$_4$OH (2 mL). The resulting mixture was stirred at r.t. for 5 h, concentrated in vacuo, and purified by reverse phase HPLC (Phenomenex, gemini 5u C18 150×21.2 mm, 10-100% acetonitrile in water both with 0.1% formic acid gradient over 40 min) to provide 2.4 mg (4%) of Isomer B of Compound 490 (490B). LRMS (ES) m/z 441.1 (M+H). $^1$H-NMR: (Methanol-$d_4$, 400 MHz, ppm) δ 7.80-7.75 (m, 1H), 7.73-7.65 (m, 2H), 7.43-7.36 (m, 2H), 7.34-7.28 (m, 2H), 5.04 (s, 2H), 4.49 (s, 2H), 3.21-3.06 (m, 3H), 2.84-2.68 (m, 2H).

Example 45: Synthesis of Compounds 492B

1. Synthesis of Intermediate 45-1B

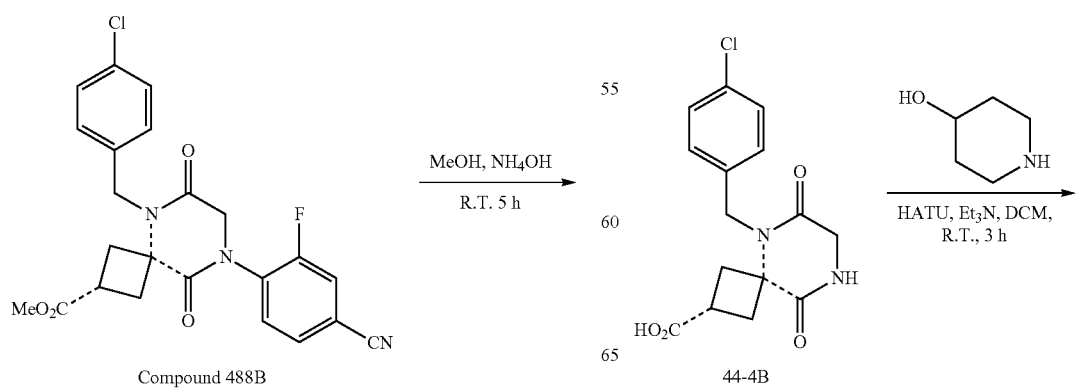

-continued

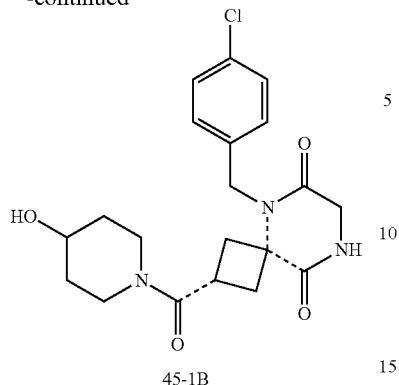

45-1B

To a mixture of piperidin-4-ol (269 mg, 2.7 mmol, 1.1 equiv), HATU (1.1 g, 2.9 mmol, 1.2 equiv), and 44-4B (0.78 g, 2.4 mmol, 1.0 equiv) in dry DCM (10 mL) was added TEA (1.0 mL, 7.3 mmol, 3.0 equiv). The mixture was stirred for 3 h at r.t., concentrated, and purified by silica chromatography using MeOH/DCM (gradient from 0-30%) to give 150 mg (15%) of 45-1B. LRMS (ES) m/z 406.2 (M+H).

2. Synthesis of Compound 492B

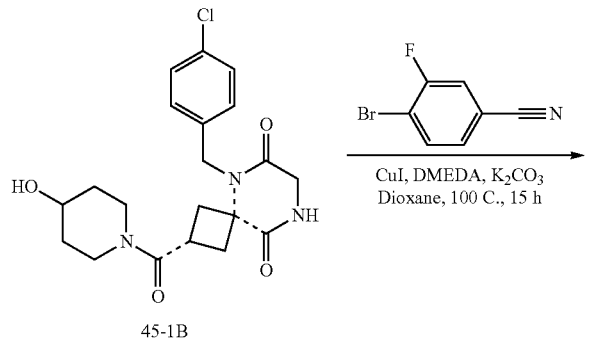

-continued

492B

To a mixture of copper iodide (12 mg, 0.062 mmol, 0.5 equiv), potassium carbonate (51 mg, 0.37 mmol, 3.0 equiv), 4-bromo-3-fluorobenzonitrile (44 mg, 0.22 mmol, 1.8 equiv), and intermediate 45-1B (50 mg, 0.12 mmol, 1.0 equiv) in vial were added 1,4-dioxane (3 mL) and N,N'-dimethylethylene diamine (7 μL, 0.062 mmol, 0.5 equiv). The mixture was sealed and heated at 100° C. for 15 h, cooled to r.t., filtered through celite, and purified by reverse phase HPLC (Phenomenex, gemini 5u C18 150×21.2 mm, 10-80% acetonitrile in water both with 0.1% formic acid gradient over 40 min) to provide 13.1 mg (20%) of compound 492B. LRMS (ES) m/z 525.2 (M+H). $^1$H-NMR: (400 MHz, Methanol-$d_4$) δ 7.79-7.75 (m, 1H), 7.72-7.66 (m, 2H), 7.43-7.39 (m, 2H), 7.37-7.32 (m, 2H), 5.10-5.00 (m, 2H), 4.55-4.45 (m, 2H), 4.04-3.95 (m, 1H), 3.86-3.78 (m, 1H), 3.51-3.42 (m, 1H), 3.22-3.01 (m, 5H), 2.81-2.70 (m, 2H), 1.87-1.77 (m, 2H), 1.45-1.34 (m, 2H).

The following compounds were prepared by methods analogous to the method described for Compound 492B:

| Compound No. | LRMS (ES) m/z | $^1$H NMR |
| --- | --- | --- |
| 492B | M + H = 525.2 | (400 MHz, Methanol-$d_4$) δ 7.79-7.75 (m, 1H), 7.72-7.66 (m, 2H), 7.43-7.39 (m, 2H), 7.37-7.32 (m, 2H), 5.10-5.00 (m, 2H), 4.55-4.45 (m, 2H), 4.04-3.95 (m, 1H), 3.86-3.78 (m, 1H), 3.51-3.42 (m, 1H), 3.22-3.01 (m, 5H), 2.81-2.70 (m, 2H), 1.87-1.77 (m, 2H), 1.45-1.34 (m, 2H) |
| 494B | M + H = 534.1 | (400 MHz, Methanol-$d_4$) δ 7.48-7.43 (m, 1H), 7.42-7.36 (m, 3H), 7.35-7.29 (m, 3H), 5.09-4.98 (m, 2H), 4.47-4.37 (m, 2H), 4.02-3.93 (m, 1H), 3.84-3.76 (m, 1H), 3.49-3.40 (m, 1H), 3.20-2.99 (m, 5H), 2.78-2.68 (m, 2H), 1.85-1.75 (m, 2H), 1.43-1.32 (m, 2H) |

Example 46: Synthesis of Compound 483B

1. Synthesis of Diastereomers 46-1A and 46-1B

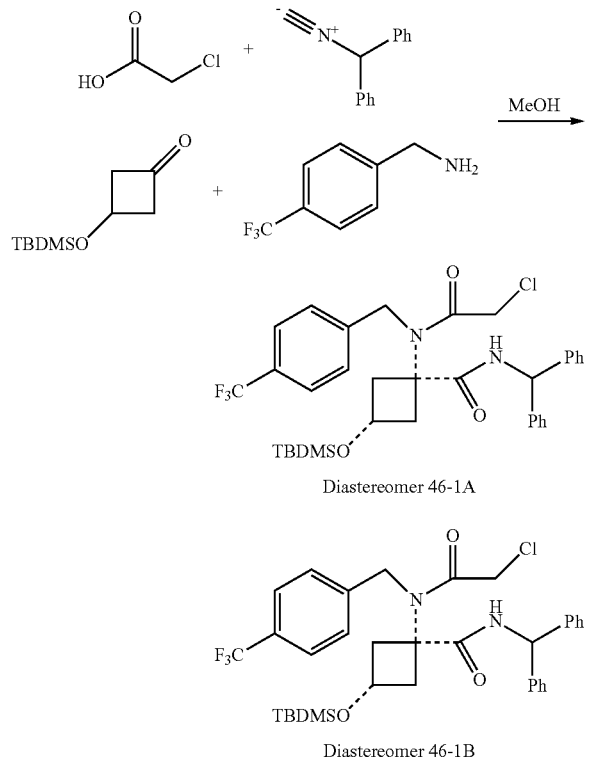

Diastereomer 46-1A

Diastereomer 46-1B

To a mixture of 3-((tert-butyldimethylsilyl)oxy)cyclobutan-1-one (1.0 g, 5.0 mmol) and (4-(trifluoromethyl)phenyl)methanamine (874 mg, 5.0 mmol) in a RB flask was added MeOH (10 mL). The mixture was stirred at r.t. for 5 min. To this mixture were added (isocyanomethylene)dibenzene (965 mg, 5.0 mmol) and 2-chloroacetic acid (472 mg, 5.0 mmol) sequentially. The resulting mixture was stirred at r.t. for 5 h, diluted with EtOAc (150 mL), washed with saturated aqueous NaHCO$_3$ (50 mL), saturated aqueous NH$_4$Cl (50 mL), and brine, dried over sodium sulfate, concentration under reduced pressure, and purified by silica chromatography using 20% EA/Hex to provide 1.2 g (1.8 mmol, 36% yield) of the first eluting Diastereomer 46-1A and 698 mg (1.08 mmol, 21% yield) of the second eluting Diastereomer 46-1B.

Characterization of Diastereomer 46-1A: LRMS (APCI) m/z 645.3 (M+H). $^1$H NMR (400 MHz, Methanol-d$_4$) δ 7.57 (d, J=8.0 Hz, 2H), 7.46 (d, J=8.1 Hz, 2H), 7.41-7.10 (m, 10H), 6.13 (s, 1H), 4.82 (s, 2H), 4.24 (s, 2H), 4.18 (t, J=7.0 Hz, 1H), 3.07 (ddd, J=9.8, 6.8, 3.0 Hz, 2H), 2.26 (t, J=9.9 Hz, 2H), 0.84 (s, 9H), 0.00 (s, 6H).

Characterization of Diastereomer 46-1B: LRMS (APCI) m/z 645.3 (M+H). $^1$H NMR (400 MHz, Methanol-d$_4$) δ 7.66 (d, J=8.1 Hz, 2H), 7.51 (d, J=8.1 Hz, 2H), 7.37-7.25 (m, 10H), 6.18 (s, 1H), 4.75 (s, 2H), 4.28-4.22 (m, 1H), 4.18 (s, 2H), 2.85-2.74 (m, 2H), 2.66-2.53 (m, 2H), 0.74 (s, 9H), −0.12 (s, 6H).

2. Synthesis of Intermediate 46-2B

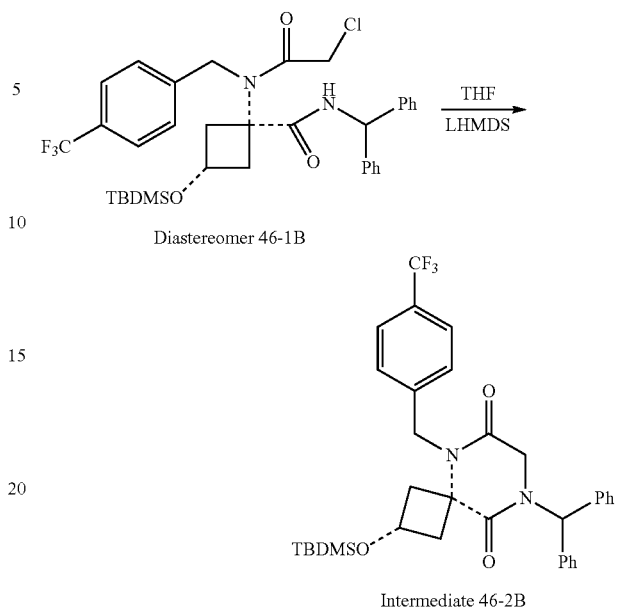

Diastereomer 46-1B

Intermediate 46-2B

To a solution of Diastereomer 46-1B (698 mg, 1.08 mmol) in THF (5 mL) cooled to 0° C. with an ice bath was added LHMDS (1.3 mL, 1.3 mmol, 1.2 equiv) was dropwise over 5 min. The mixture was stirred at 0° C. for 1 h, quenched with saturated aqueous NH$_4$Cl (30 mL), and diluted with EtOAc (75 mL). The organic phase was washed with brine, dried over sodium sulfate, concentrated under reduced pressure, and purified by silica gel chromatography using 10% EtOAc/Hex as eluent to provide 600 mg (92%) of Intermediate 46-2B. LRMS (APCI) m/z 609.3 (M+H).

3. Synthesis of Intermediate 46-3B

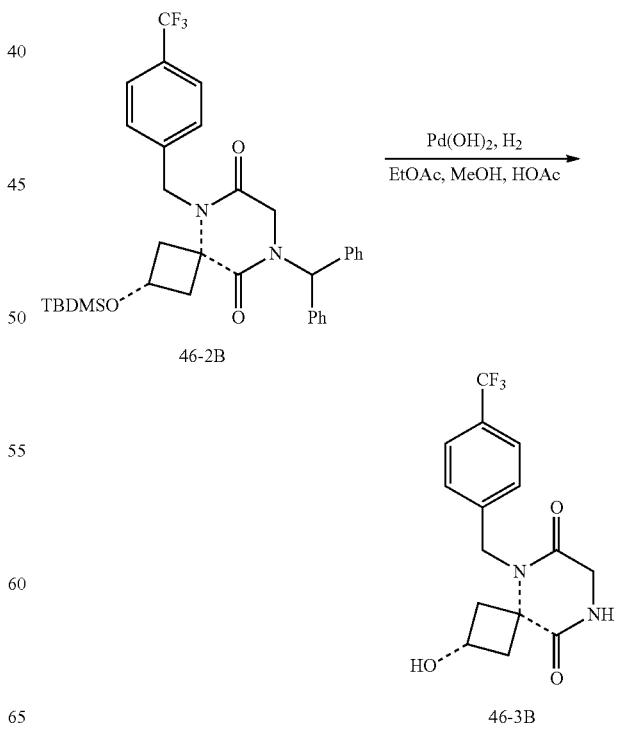

46-2B 46-3B

To a solution of intermediate 46-2B (600 mg, 0.99 mmol) in a mixture of MeOH (25 mL), EtOAc (25 mL) and Acetic acid (0.5 mL) was added Pd(OH)$_2$. The mixture was sparged with hydrogen for 5 min, stirred under 400 psi hydrogen for 20 h, filtered through celite, concentrated in vacuo, and dissolved in EtOAc (75 mL). The organic phase was washed with saturated aqueous NaHCO$_3$ (50 mL) and brine, dried over sodium sulfate, concentrated under reduced pressure, and purified by silica gel chromatography using 50% EtOAc/Hex and 5% MeOH/DCM as eluent to provide 256 mg (79%) of Intermediate 46-3B. LRMS (APCI) m/z 329.1 (M+H). $^1$H NMR (400 MHz, Methanol-d$_4$) δ 7.72 (d, J=8.1 Hz, 2H), 7.48 (d, J=8.1 Hz, 2H), 5.03 (s, 2H), 4.35 (p, J=7.2 Hz, 1H), 4.10 (s, 2H), 2.79 (d, J=7.2 Hz, 4H).

4. Synthesis of Compound 483B

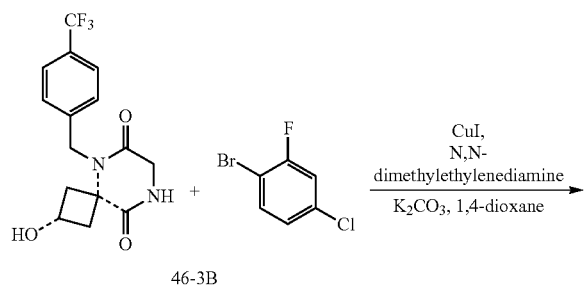

To a mixture of intermediate 46-3B (100 mg, 0.31 mmol), K$_2$CO$_3$ (126 mg, 0.91 mmol, 3.0 equiv), CuI (29 mg, 0.15 mmol, 0.5 equiv) and 1-bromo-4-chloro-2-fluorobenzene (57 μL, 0.46 mmol, 1.5 equiv) were added anhydrous 1,4-dioxane (3 mL) and N,N-dimethylethylenediamine (16 μL, 0.15 mmol, 0.5 equiv). The resulting suspension was heated in a sealed tube under nitrogen at 115° C. for 18 h, cooled to room temperature, filtered through celite, washed with additional 1,4-dioxane (20 mL), evaporated in vacuo, and purified with reverse phase HPLC using 10-100% ACN/water (both with 0.1% formic acid; Phenomenex Gemini 5 micron C18 column) and silica gel chromatography using 75% EA/Hex as eluent to provide 19 mg (14%) of Compound 483B. LRMS (APCI) m/z 457.1 (M+H). $^1$H NMR (400 MHz, Methanol-d$_4$) δ 7.69-7.64 (m, 2H), 7.49-7.39 (m, 4H), 7.35-7.31 (m, 1H), 5.03 (s, 2H), 4.43 (s, 2H), 4.33-4.24 (m, 1H), 2.86-2.76 (m, 4H).

The following compounds were prepared by methods analogous to the method described for Compound 483B:

The final compounds derived from diastereomer 46-1A were isolated using Diastereomer 46-1A as the starting material in an analogous sequence.

| Compound No. | LRMS (ES) m/z | $^1$H NMR |
| --- | --- | --- |
| 483B | M + H = 457.1 | (400 MHz, Methanol-d$_4$) δ 7.69-7.64 (m, 2H), 7.49-7.39 (m, 4H), 7.35-7.31 (m, 1H), 5.03 (s, 2H), 4.43 (s, 2H), 4.33-4.24 (m, 1H), 2.86-2.76 (m, 4H) |
| 484B | M + H = 448.1 | (400 MHz, Methanol-d$_4$) δ 7.79-7.74 (m, 1H), 7.71-7.64 (m, 4H), 7.49-7.43 (m, 2H), 5.03 (s, 2H), 4.49 (s, 2H), 4.33-4.23 (m, 1H), 2.88-2.76 (m, 4H) |
| 483A | M + H = 457.1 | (400 MHz, Methanol-d$_4$) δ 7.70-7.62 (m, 2H), 7.51-7.37 (m, 4H), 7.36-7.29 (m, 1H), 5.07 (s, 2H), 4.44 (s, 2H), 4.21-4.11 (m, 1H), 3.00-2.89 (m, 2H), 2.47-2.36 (m, 2H) |
| 484A | M + H = 448.1 | (400 MHz, Methanol-d$_4$) δ 7.78-7.73 (m, 1H), 7.72-7.64 (m, 4H), 7.49-7.43 (m, 2H), 5.07 (s, 2H), 4.50 (s, 2H), 4.20-4.12 (m, 1H), 3.00-2.91 (m, 2H), 2.47-2.37 (m, 2H) |

-continued

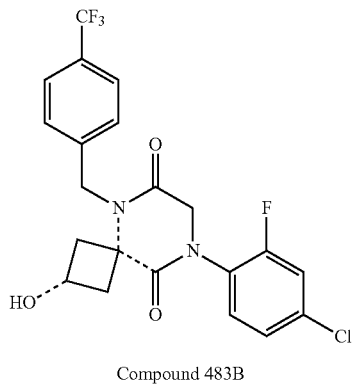

Compound 483B

Example 47: Synthesis of Compound 339

1. Synthesis of Intermediate 47-2

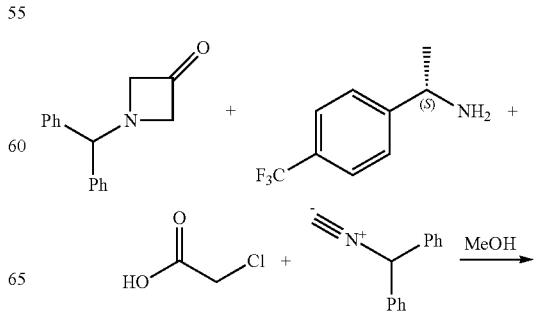

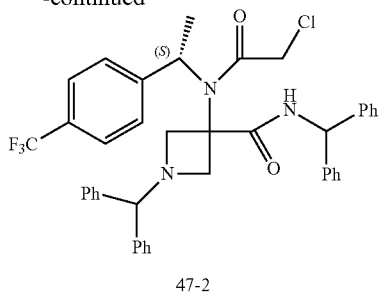

47-2

This step followed the published method in Synlett 2007, No. 2, pp. 0227-0230. Briefly, to a solution of 1-benzhydrylazetidin-3-one (1.84 g, 7.76 mmol) and (S)-1-(4-(trifluoromethyl)phenyl)ethan-1-amine (1.47 g, 7.76 mmol, 1.0 equiv.) in MeOH (10 mL) were added diphenylmethyl isocyanide (1.50 g, 7.76 mmol, 1.0 equiv.) and 2-chloroacetic acid (733 mg, 7.76 mmol, 1.0 equiv.) sequentially. The resulting mixture was stirred at r.t. for 5 h, diluted with EA (150 mL), washed with saturated aqueous NaHCO$_3$ (100 mL), saturated aqueous NH$_4$Cl (100 mL) and brine, dried over sodium sulfate, concentrated under reduced pressure, and purified by silica gel chromatography using EA/Hex (1/4) to provide 2.0 g (36%) of (S)—N,1-dibenzhydryl-3-(2-chloro-N-(1-(4-(trifluoromethyl)phenyl) ethyl)acetamido)azetidine-3-carboxamide. LRMS (APCI) m/z 696.3 (M+H).

2. Synthesis of Intermediate 47-3

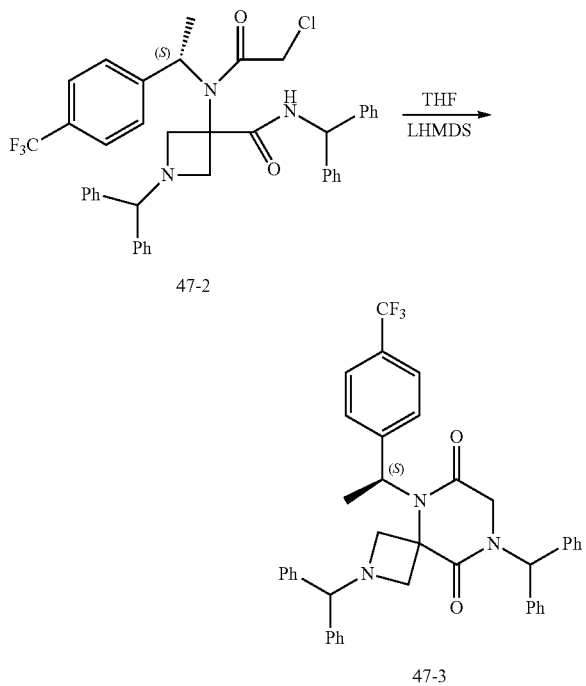

To a solution of (S)—N,1-dibenzhydryl-3-(2-chloro-N-(1-(4-(trifluoromethyl)phenyl)ethyl)acetamido)azetidine-3-carboxamide (1.97 g, 2.83 mmol) in THF (25 mL) cooled to 0° C. with an ice bath was added LHMDS (3.39 mL of 1.0 M in THF, 3.39 mmol, 1.2 equiv.) dropwise over 5 minutes. The resulting mixture was stirred at 0° C. for 1 h, quenched with saturated aqueous NH$_4$Cl (30 mL), and diluted with EA (75 mL). The organic phase was washed with brine, dried over sodium sulfate, concentrated, and purified by silica gel chromatography using EA/HE (15/85) to provide 1.1 g (59%) of (S)-2,8-dibenzhydryl-5-(1-(4-(trifluoromethyl)phenyl)ethyl)-2,5,8-triazaspiro[3.5]nonane-6,9-dione. LRMS (APCI) m/z 660.4 (M+H). $^1$H NMR (400 MHz, Methanol-d$_4$) δ 7.61 (d, J=8.2 Hz, 2H), 7.49 (d, J=8.2 Hz, 2H), 7.34-7.03 (m, 20H), 6.85 (s, 1H), 5.84 (t, J=7.0 Hz, 1H), 4.12 (s, 1H), 3.76 (d, J=8.9 Hz, 1H), 3.71-3.59 (m, 2H), 3.49 (d, J=8.8 Hz, 1H), 3.39 (t, J=9.1 Hz, 2H), 1.79 (d, J=7.1 Hz, 3H).

3. Synthesis of Intermediate 47-4

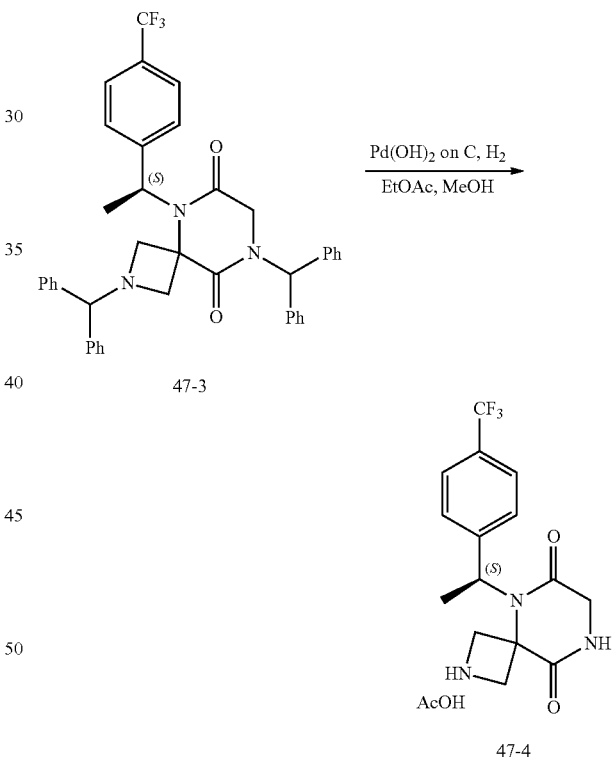

To a solution of (S)-2,8-dibenzhydryl-5-(1-(4-(trifluoromethyl)phenyl)ethyl)-2,5,8-triazaspiro[3.5]nonane-6,9-dione (1.10 g, 1.66 mmol) in a mixture of MeOH (100 mL) and EA (100 mL) were added Pd(OH)$_2$ (20% on carbon, 1.3 g) and acetic acid (0.5 mL). The resulting mixture was sparged with hydrogen for 5 minutes, heated at 50° C. under hydrogen (initially at 500 psi) for 20 h, filtered through celite, and concentrated under reduced pressure to provide 640 mg of (S)-5-(1-(4-(trifluoromethyl)phenyl)ethyl)-2,5,8-triazaspiro[3.5]nonane-6,9-dione acetate. LRMS (APCI) m/z 328.1 (M+H).

4. Synthesis of Intermediate 47-5

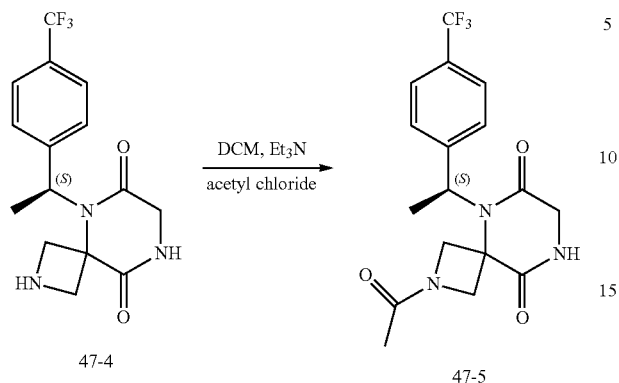

47-4 → 47-5

To a mixture of (S)-5-(1-(4-(trifluoromethyl)phenyl)ethyl)-2,5,8-triazaspiro[3.5]nonane-6,9-dione acetate (320 mg, 0.83 mmol) in DCM (10 mL) cooled to 0° C. with an ice bath was added TEA (346 μL, 3.0 equiv.) and acetyl chloride (1.66 mL of 1.0 M solution in DCM, 1.66 mmol, 2.0 equiv.) sequentially. The ice bath was removed upon the completion of addition. The mixture was stirred at r.t. for 30 min, diluted with DCM (20 mL), and washed with saturated aqueous $NaHCO_3$ (15 mL). The aqueous phase was extracted with DCM (20 mL). The combined organic phases were dried over sodium sulfate and concentrated. The mixture was suspended in $Et_2O$ (10 mL), sonicated, filtered, and dried to provide 188 mg (61%) of (S)-2-acetyl-5-(1-(4-(trifluoromethyl)phenyl)ethyl)-2,5,8-triazaspiro[3.5]nonane-6,9-dione. LRMS (APCI) m/z 370.1 (M+H). $^1$H NMR (400 MHz, DMSO-$d_6$) δ 8.52 (s, 1H), 7.67 (d, J=8.1 Hz, 2H), 7.55 (d, J=8.1 Hz, 2H), 5.1-5.30 (bs, 1H), 4.51 (dd, J=36.1, 9.5 Hz, 1H), 4.40-4.24 (m, 1H), 4.18 (t, J=9.5 Hz, 1H), 4.06-3.82 (m, 3H), 1.87 (dd, J=6.9, 3.5 Hz, 3H), 1.74 (d, J=23.2 Hz, 3H).

5. Synthesis of Compound 339

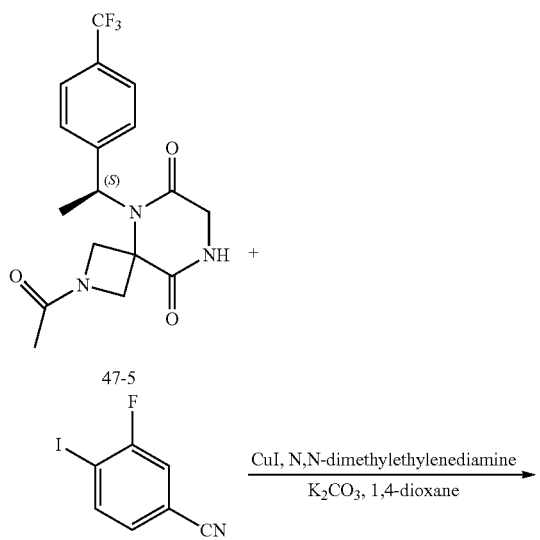

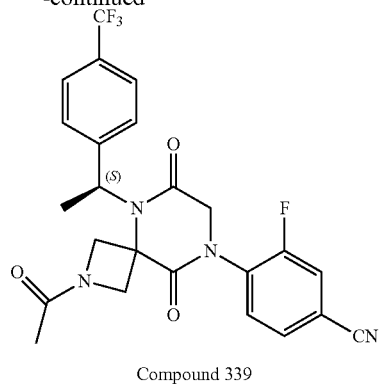

Compound 339

To a mixture of (S)-2-acetyl-5-(1-(4-(trifluoromethyl)phenyl)ethyl)-2,5,8-triazaspiro[3.5]nonane-6,9-dione (102 mg, 0.28 mmol), CuI (26 mg, 0.14 mmol, 0.5 equiv.), $K_2CO_3$ (115 mg, 0.83 mmol, 3.0 equiv.) and 3-fluoro-4-iodobenzonitrile (136 mg, 0.55 mmol, 2.0 equiv.) in a tube were added 1,4-dioxane (1.5 mL) and N,N-dimethylethylenediamine (15 μL, 0.14 mmol, 0.5 equiv.). The mixture was purged with $N_2$, sealed, heated at 115° C. for 18 h, cooled to r.t., and filtered through celite. The solid was washed with 1,4-dioxane (20 mL). The filtrate was evaporated in vacuo and purified with reverse phase HPLC using ACN/water (both with 0.1% formic acid with a gradient from 10 to 100%; Phenomenex Gemini 5 micron C18 column). The collected fractions provided a mixture which was purified again by silica gel chromatography using EA/Hex (3/7) and MeOH/DCM (1/9) as eluents to provide 24 mg (18%) of (S)-4-(2-acetyl-6,9-dioxo-5-(1-(4-(trifluoromethyl) phenyl)ethyl)-2,5,8-triazaspiro[3.5]nonan-8-yl)-3-fluorobenzonitrile. LRMS (APCI) m/z 489.2 (M+H). $^1$H NMR (400 MHz, Methanol-$d_4$) δ 7.83-7.61 (m, 7H), 5.4-5.6 (bs, 1H), 4.82-4.43 (m, 5H), 4.37 (d, J=11.0 Hz, 1H), 2.03 (t, J=6.8 Hz, 3H), 1.88 (d, J=23.1 Hz, 3H).

Example 48: Synthesis of Compound 340

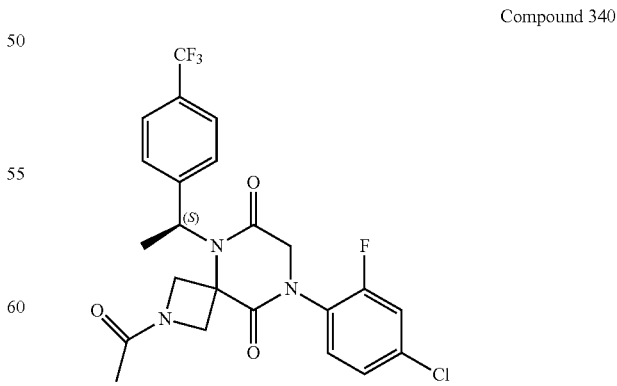

Compound 340

Method analogous to Example 47 was used with the only exception that 1-bromo-4-chloro-2-fluorobenzene was used in step 5 instead of 3-fluoro-4-iodobenzonitrile.

Example 49: Synthesis of Compound 341

1. Synthesis of Intermediate 49-2

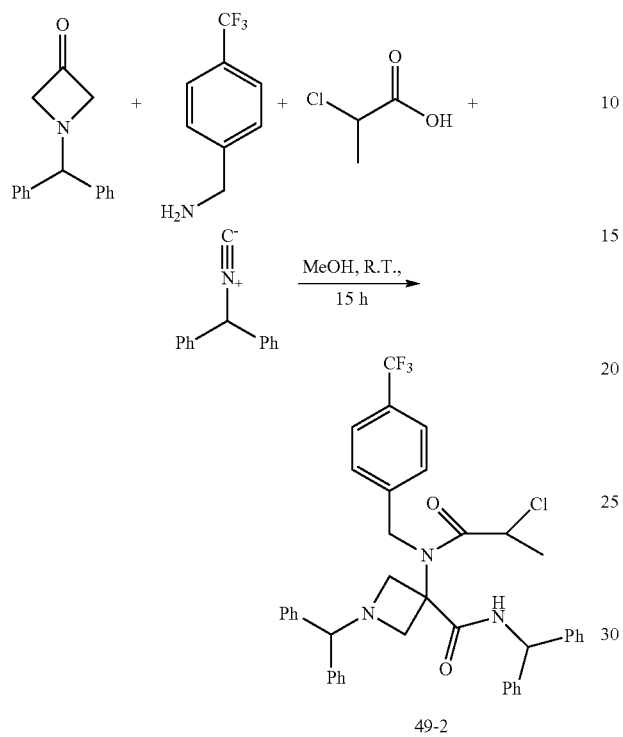

To a mixture of 4-trifluoromethylbenzyl amine (1.2 g, 7.0 mmol, 1.1 equiv) and 1-benzhydrylazetidin-3-one (1.5 g, 6.3 mmol, 1.0 equiv) in MeOH (30 mL) were added (isocyanomethylene)dibenzene (1.3 g, 7.0 mmol, 1.1 equiv) and 2-chloropropionic acid (0.76 g, 7.0 mmol, 1.1 equiv). The resulting mixture was stirred at r.t. for 15 h, concentrated under reduced pressure, and purified by silica gel chromatography using EA/HE (1/3) as eluents to provide 1.8 g (41%) of N,1-dibenzhydryl-3-(2-chloro-N-(4-(trifluoromethyl)benzyl)propanamido)azetidine-3-carboxamide. LRMS (ES) m/z 696.3 (M+H).

2. Synthesis of Intermediate 49-3

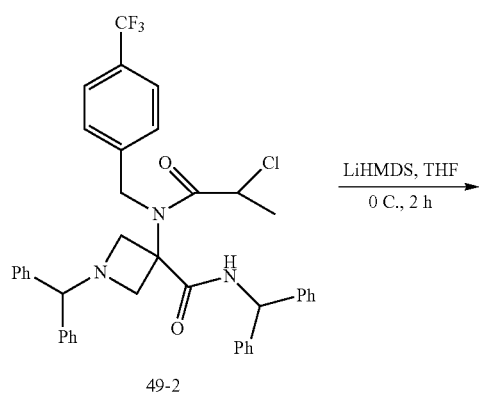

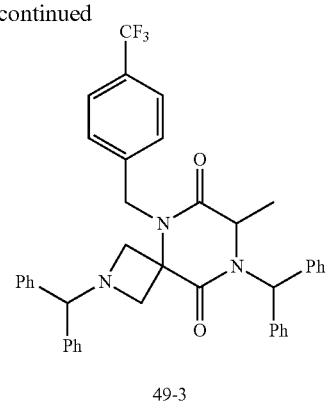

To a solution of N,1-dibenzhydryl-3-(2-chloro-N-(4-(trifluoromethyl)benzyl) propanamido)azetidine-3-carboxamide (1.8 g, 2.6 mmol, 1.0 equiv) in THF (200 mL) cooled to 0° C. with an ice bath was added LHMDS (1 M in THF, 3.1 mL, 3.1 mmol, 1.2 equiv) dropwise over 10 min. The resulting mixture was stirred at 0° C. for 2 h, quenched with MeOH (5 mL), and concentrated onto SiO$_2$ (20 g). The mixture was purified by silica gel chromatography using EA/HE (gradient from 0-100%) to provide 1.2 g (70%) of 2,8-dibenzhydryl-7-methyl-5-(4-(trifluoromethyl)benzyl)-2,5,8-triazaspiro[3.5]nonane-6,9-dione. LRMS (ES) m/z 660.3 (M+H).

3. Synthesis of Intermediate 49-4

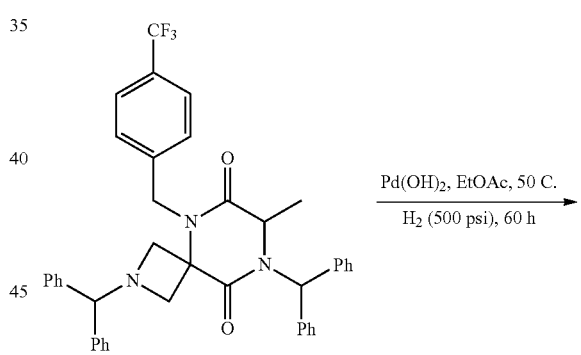

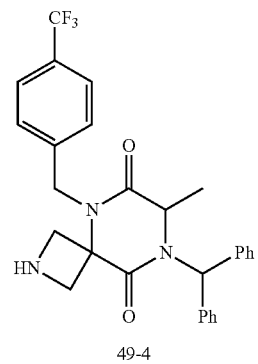

To a solution of 2,8-dibenzhydryl-7-methyl-5-(4-(trifluoromethyl)benzyl)-2,5,8-triazaspiro[3.5]nonane-6,9-dione (1.2 g, 1.8 mmol, 1.0 equiv) in EtOAc (100 mL) was added Pd(OH)$_2$ (20% on carbon, 6 g). The resulting mixture was sparged with hydrogen for 10 min, heated at 50° C. under hydrogen (initially at 500 psi) for 60 h, cooled to r.t., filtered through celite, and concentrated under reduced pressure to provide 887 mg of 8-benzhydryl-7-methyl-5-(4-(trifluoromethyl)benzyl)-2,5,8-triazaspiro[3.5]nonane-6,9-dione as a mixture. LRMS (ES) m/z 494.2 (M+H).

4. Synthesis of Intermediate 49-5

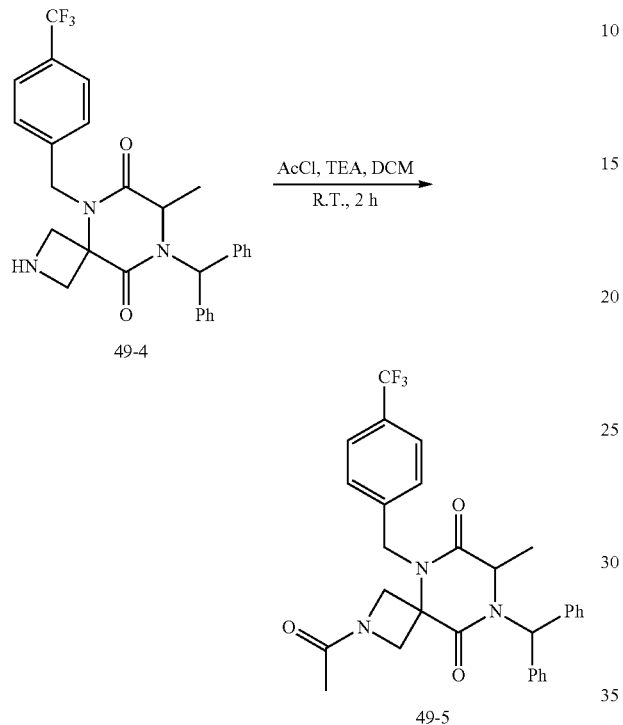

To a solution of 8-benzhydryl-7-methyl-5-(4-(trifluoromethyl)benzyl)-2,5,8-triazaspiro[3.5]nonane-6,9-dione (887 mg, 1.8 mmol, 1.0 equiv.) in DCM (20 mL) were added TEA (1 mL) and acetyl chloride (1 M in DCM, 5 mL, 5.0 mmol, 2.8 equiv). The resulting mixture was stirred at r.t. for 2 h, concentrated under reduced pressure, and purified by silica gel chromatography using EtOAc (100%) and MeOH/DCM (1/4) as eluents to provide 963 mg of 2-acetyl-8-benzhydryl-7-methyl-5-(4-(trifluoromethyl)benzyl)-2,5,8-triazaspiro[3.5]nonane-6,9-dione as a mixture. LRMS (ES) m/z 536.2 (M+H).

5. Synthesis of Intermediate 49-6

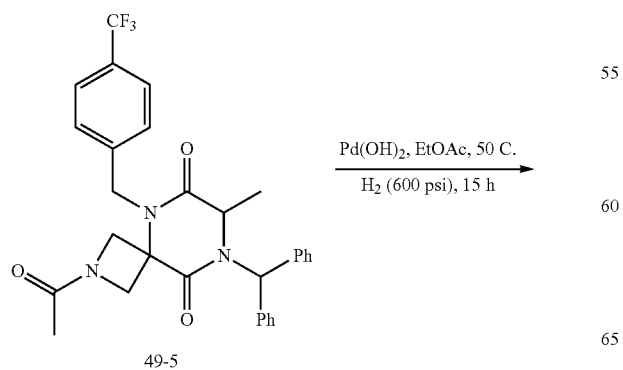

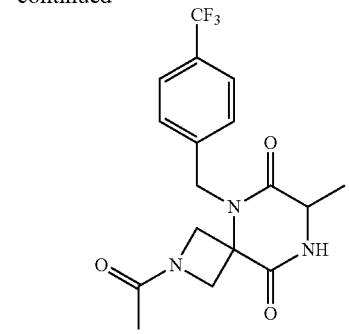

To a solution of 2-Acetyl-8-benzhydryl-7-methyl-5-(4-(trifluoromethyl)benzyl)-2,5,8-triazaspiro[3.5]nonane-6,9-dione (963 mg, 1.8 mmol, 1.0 equiv) in EtOAc (100 mL) was added Pd(OH)$_2$ (20% on carbon, 6 g). The resulting mixture was sparged with hydrogen for 10 min, heated at 50° C. under hydrogen (initially at 600 psi) for 15 h, cooled to r.t., filtered through celite, concentrated under reduced pressure, and purified by silica gel chromatography using EtOAc (100%) and MeOH/DCM (1/4) as eluents to provide 200 mg of 2-acetyl-7-methyl-5-(4-(trifluoromethyl)benzyl)-2,5,8-triazaspiro[3.5]nonane-6,9-dione. LRMS (ES) m/z 370.2 (M+H).

6. Synthesis of Compound 341

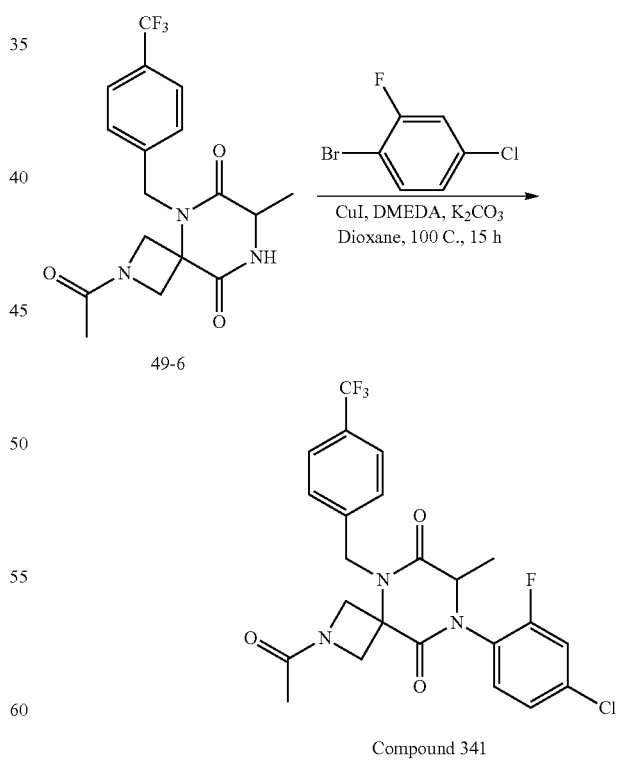

To a mixture of copper iodide (26 mg, 0.14 mmol, 0.5 equiv), potassium carbonate (112 mg, 0.81 mmol, 3.0 equiv), 1-bromo-4-chloro-2-fluorobenzene (102 mg, 0.49 mmol, 1.8 equiv), and 2-acetyl-7-methyl-5-(4-(trifluoromethyl)benzyl)-2,5,8-triazaspiro[3.5]nonane-6,9-dione (200 mg, 0.27 mmol, 1.0 equiv) in a vial were added 1.4-dioxane (3 mL) and N,N'-dimethylethylene diamine (15 µL, 0.14 mmol, 0.5 equiv). The vial was sealed and the mixture was heated at 100° C. for 15 h. The mixture was cooled to r.t., filtered through celite, concentrated under reduced pressure, and purified with reverse phase HPLC (Phenomenex, gemini 5u C18 150×21.2 mm, 10-70% acetonitrile in water both with 0.1% formic acid gradient over 40 min) to provide 1.4 mg (1%) of 2-acetyl-8-(4-chloro-2-fluorophenyl)-7-methyl-5-(4-(trifluoromethyl)benzyl)-2,5,8-triazaspiro[3.5]nonane-6,9-dione. LRMS (ES) m/z 498.1 (M+H). $^1$H-NMR (Methanol-d$_4$, 400 MHz, ppm) δ 7.71 (d, J=8.1 Hz, 2H), 7.55 (dd, J=8.1, 4.8 Hz, 3H), 7.50-7.44 (m, 1H), 7.40 (dt, J=8.5, 1.6 Hz, 1H), 5.22 (d, J=16.8 Hz, 1H), 5.11-5.01 (m, 1H), 4.68-4.41 (m, 4H), 4.26 (t, J=11.5 Hz, 1H), 1.88 (d, J=6.1 Hz, 3H), 1.45 (d, J=7.0 Hz, 3H).

Example 50: Synthesis of Compound 278

1. Synthesis of Intermediate 50-2

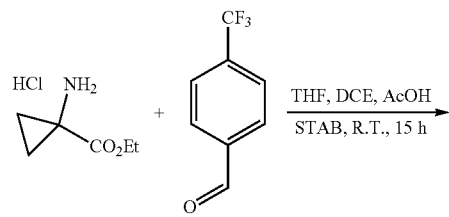

To a solution of ethyl 1-aminocyclopropane-1-carboxylate hydrochloride (0.5 g, 3.0 mmol, 1.0 equiv) in a mixture of THF (50 mL) and DCE (10 mL) was added 4-trifluoromethylbenzaldehyde (0.79 g, 4.5 mmol, 1.5 equiv). To the mixture stirred at r.t. for 15 min were added STAB (1.9 g, 9.1 mmol, 3.0 equiv) and AcOH (5 mL). The mixture was stirred at r.t. for 15 h, evaporated under reduced pressure, and partitioned between DCM (60 mL) and saturated aqueous sodium bicarbonate (60 mL). The layers were separated and the aqueous phase was extracted with DCM (25 mL). The combined organic phases were dried over sodium sulfate, filtered through celite, and concentrated under reduced pressure to provide ethyl 1-((4-(trifluoromethyl)benzyl)amino) cyclopropane-1-carboxylate as a viscous oil.

2. Synthesis of Intermediate 50-3

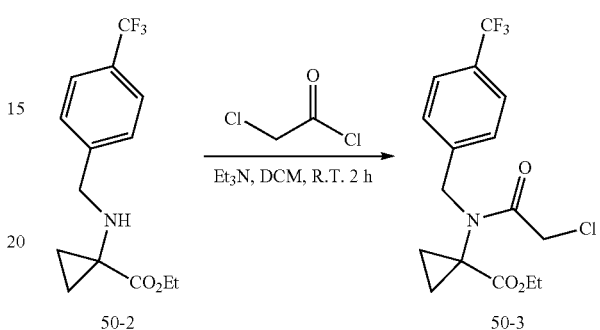

To a solution of ethyl 1-((4-(trifluoromethyl)benzyl) amino)cyclopropane-1-carboxylate (861 mg, 3.0 mmol, 1.0 equiv) in DCM (50 mL) were added TEA (1.5 g, 15.1 mmol, 5.0 equiv) and chloroacetyl chloride (0.68 g, 6.0 mmol, 2.0 equiv). The mixture was stirred at r.t. for 2 h before pouring into water (50 mL). The organic phase was separated, dried over MgSO$_4$, and concentrated under reduced pressure to give ethyl 1-(2-chloro-N-(4-(trifluoromethyl)benzyl)acetamido)cyclopropane-1-carboxylate.

3. Synthesis of Intermediate 50-4

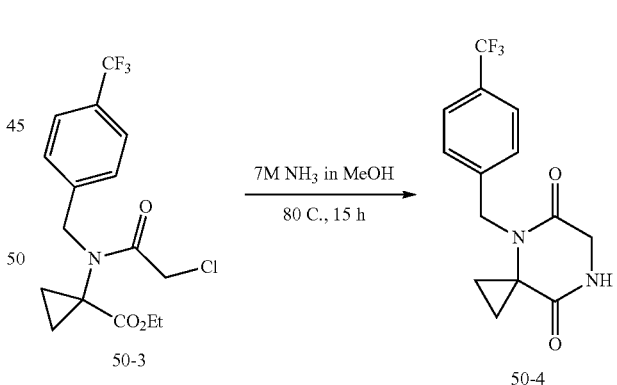

To a solution of ethyl 1-(2-chloro-N-(4-(trifluoromethyl) benzyl)acetamido) cyclopropane-1-carboxylate (1.1 g, 3.0 mmol) in MeOH (5 mL) was added NH$_3$ in MeOH (7 N, 5 mL). The resulting mixture was heated at 80° C. in a sealed tube for 15 h, cooled to r.t., concentrated under reduced pressure, and purified by silica gel chromatography using EA/HE (gradient from 0-100%) and MeOH/DCM (3/7) to provide 4-(4-(trifluoromethyl) benzyl)-4,7-diazaspiro[2.5] octane-5,8-dione. LRMS (ES) m/z 299.1 (M+H).

4. Synthesis of Compound 278

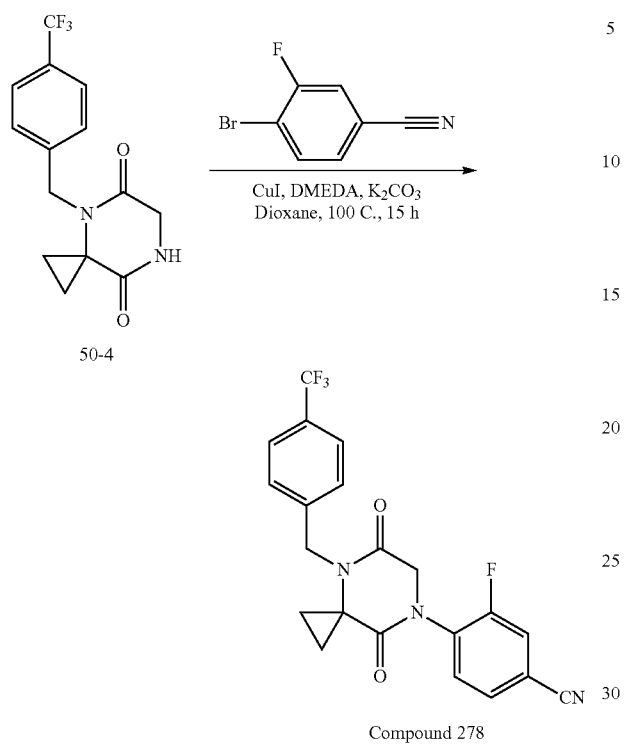

Compound 278

To a mixture of copper iodide (33 mg, 0.18 mmol, 0.5 equiv), potassium carbonate (146 mg, 1.1 mmol, 3.0 equiv), 4-bromo-3-fluorobenzonitrile (126 mg, 0.63 mmol, 1.8 equiv), and 4-(4-(trifluoromethyl)benzyl)-4,7-diazaspiro[2.5]octane-5,8-dione (200 mg, 0.35 mmol, 1.0 equiv) in a vial were added 1,4-dioxane (16 mL) and N,N'-dimethylethylene diamine (19 μL, 0.18 mmol, 0.5 equiv). The vial was sealed and the mixture was heated at 100° C. for 15 h. The mixture was cooled to r.t., filtered through celite, concentrated under reduced pressure, and purified with reverse phase HPLC (Phenomenex, gemini 5u C18 150× 21.2 mm, 10-100% acetonitrile in water both with 0.1% formic acid gradient over 40 min) to provide 40 mg (27%) of 4-(5,8-dioxo-4-(4-(trifluoromethyl)benzyl)-4,7-diazaspiro[2.5]octan-7-yl)-3-fluorobenzonitrile. LRMS (ES) m/z 418.1 (M+H). $^1$H-NMR (Methanol-$d_4$, 400 MHz, ppm) δ 7.76 (dd, J=10.2, 1.6 Hz, 1H), 7.71-7.62 (m, 4H), 7.48 (d, J=8.0 Hz, 2H), 4.74 (s, 2H), 4.66 (s, 2H), 1.55-1.30 (m, 4H).

The following compounds were prepared by methods analogous to the method described for Compound 278:

| Compound No. | LRMS (ES) m/z |
|---|---|
| 269 | M + H = 436.1 |
| 270 | M + H = 445.1 |
| 271 | M + H = 427.1 |
| 272 | M + H = 441.1 |
| 273 | M + H = 429.1 |
| 274 | M + H = 443.1 |
| 277 | M + H = 401.0 |
| 279 | M + H = 420.1 |
| 280 | M + H = 434.1 |
| 281 | M + H = 457.1 |
| 282 | M + H = 448.1 |
| 286 | M + H = 448.0 |

5. Separation of Enantiomers

The racemic compound was separated by Chiral-HPLC with the following conditions (Column: CHIRAL ART Cellulose-SB, 2*25 cm, 5 um; Mobile Phase A: Hex-HPLC, Mobile Phase B: EtOH-HPLC; Flow rate: 20 mL/min; Gradient: 30 B to 30 B in 10 min; 220/254 nm) to give a first eluting peak and a second eluting peak.

The following compounds were separated by the method described above:

| Compound No. | LRMS (ES) m/z |
|---|---|
| 275 | M + H = 415.1 |
| 276 | M + H = 415.1 |
| 283 | M + H = 434.0 |
| 285 | M + H = 478.1 |
| 287 | M + H = 422.1 |

Example 51: Synthesis of Compound 284

1. Synthesis of Intermediate 51-2

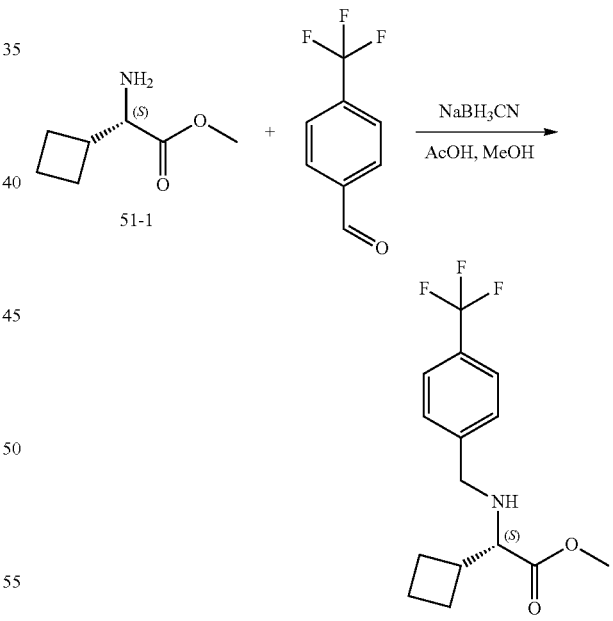

To a solution of (S)-methyl-2-amino-cyclobutylacetate HCl (0.50 g, 2.8 mmol, 1.0 equiv) in dry MeOH (16 mL) were added 4-(trifluoromethyl)benzaldehyde (0.42 mL, 3.1 mmol, 1.1 equiv) and acetic acid (0.32 mL, 5.6 mmol, 2.0 equiv). To the mixture stirred for 1 h was added sodium cyanoborohydride (0.306 g, 4.87 mmol, 1.8 equiv). The mixture was continued to stir overnight, diluted with water, and extracted with DCM three times. The combined organic layers were dried over magnesium sulfate, filtered, evaporated, and purified by silica gel chromatography through silica gel using EA/HE (gradient from 0-20%) as eluents to give 138 mg (16%) of methyl (S)-2-cyclobutyl-2-((4-(trifluoromethyl)benzyl)amino)acetate as a clear colorless oil. LRMS (ES) m/z 302 (M+H).

2. Synthesis of Intermediate 51-3

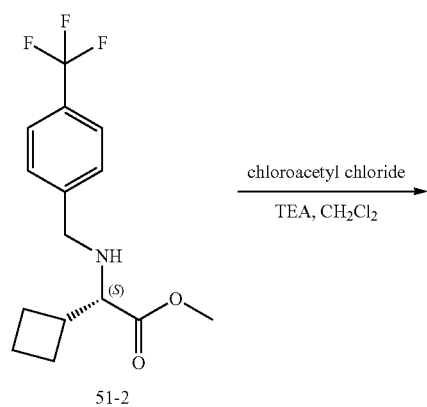

To a solution of methyl (S)-2-cyclobutyl-2-((4-(trifluoromethyl)benzyl)amino) acetate (138 mg, 0.46 mmol, 1.0 equiv) in DCM (2 mL) cooled to 0° C. were added TEA (0.38 mL, 2.8 mmol, 6.0 equiv) and chloroacetyl chloride (0.15 mL, 1.8 mmol, 4.0 equiv) dropwise. The mixture was stirred at 0° C. for 1 h, diluted with saturated sodium bicarbonate, extracted DCM twice. The combined organic layers were dried over magnesium sulfate, filtered, evaporated, and purified by silica gel chromatography through silica gel using EA/HE (gradient from 0-30%) as eluents to give 0.162 g (93%) of methyl (S)-2-(2-chloro-N-(4-(trifluoromethyl)benzyl)acetamido)-2-cyclobutylacetate as a clear yellow oil. LRMS (ES) m/z 378 (M+H).

3. Synthesis of Intermediate 51-4

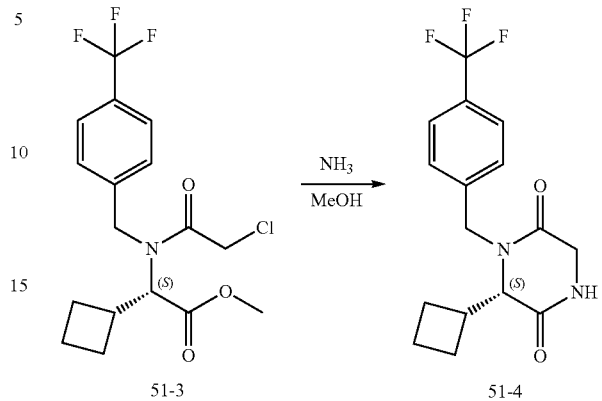

To a solution of methyl (S)-2-(2-chloro-N-(4-(trifluoromethyl)benzyl)acetamido)-2-cyclobutylacetate (162 mg, 0.43 mmol, 1.0 equiv) in dry methanol (1.2 mL) was added 7 M ammonia in methanol (1.2 mL, 8.6 mmol, 20 equiv). The mixture was sealed, heated at 80° C. overnight, diluted with water, and extracted twice with EA. The combined organic layers were dried over magnesium sulfate, filtered, evaporated, and purified by silica gel chromatography through silica gel using MeOH/DCM (gradient from 0-10%) as eluents to give 123 mg (88%) of (S)-6-cyclobutyl-1-(4-(trifluoromethyl)benzyl)piperazine-2,5-dione as a clear colorless oil. LRMS (ES) m/z 327 (M+H). $^1$H NMR (400 MHz, Methylene Chloride-d$_2$) δ 7.70-7.61 (m, 2H), 7.45-7.37 (m, 2H), 6.63-6.46 (m, 1H), 5.38-5.34 (m, 1H), 4.17-4.04 (m, 2H), 4.00-3.90 (m, 1H), 3.72-3.65 (m, 1H), 2.85-2.71 (m, 1H), 2.12-1.66 (m, 6H).

4. Synthesis of Compound 284

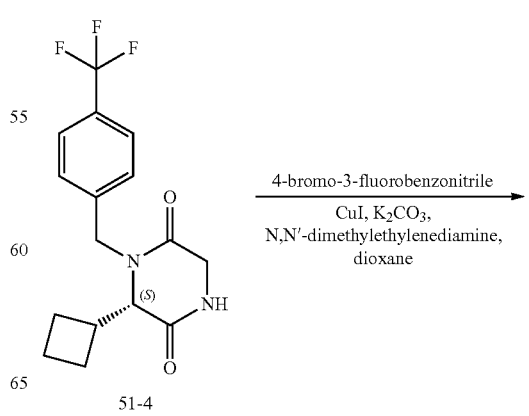

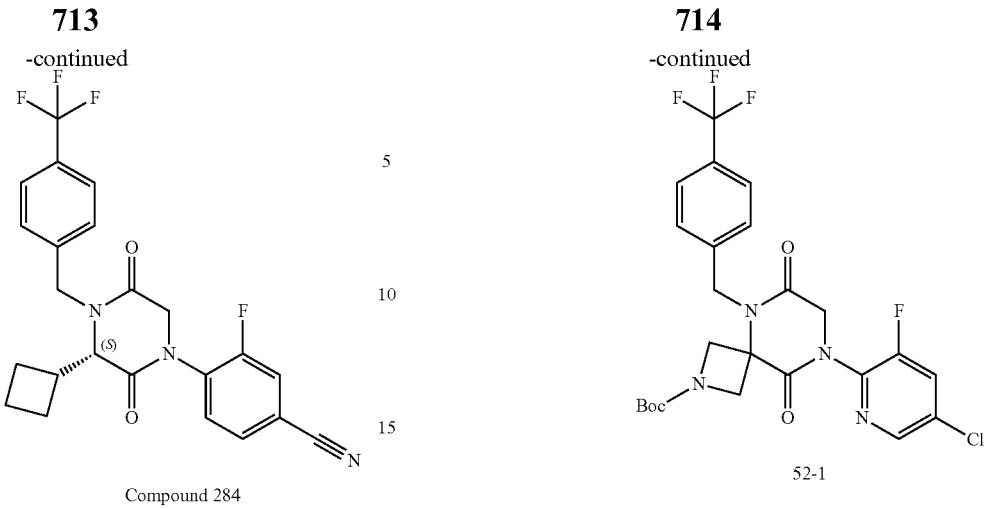

Compound 284

To a mixture of 4-bromo-3-fluorobenzonitrile (68 mg, 0.34 mmol, 1.8 equiv), copper (I) iodide (1.8 mg, 0.09 mmol, 0.50 equiv), and potassium carbonate (78 mg, 0.56 mmol, 3.0 equiv) in vacuum-nitrogen purged vial were added N,N'-dimethylethylenediamine (0.010 mL, 0.094 mmol, 0.50 equiv) and (S)-6-cyclobutyl-1-(4-(trifluoromethyl)benzyl) piperazine-2,5-dione (61 mg, 0.19 mmol, 1.0 equiv) in dry dioxane (1 mL). The vial was sealed and the mixture was heated at 100° C. overnight. The mixture was cooled to r.t., filtered, and purified by reverse phase HPLC (Phenomenex, gemini 5u C18 150×21.2 mm, 10-90% acetonitrile in water both with 0.1% formic acid gradient over 25 min) to give 39 mg (47%) of (S)-4-(3-cyclobutyl-2,5-dioxo-4-(4-(trifluoromethyl)benzyl)piperazin-1-yl)-3-fluorobenzonitrile as a clear colorless oil. LRMS (ES) m/z 446 (M+H). $^1$H NMR (400 MHz, Methanol-$d_4$) δ 7.77-7.72 (m, 1H), 7.71-7.62 (m, 4H), 7.55-7.50 (m, 2H), 5.26-5.18 (m, 1H), 4.83-4.76 (m, 1H), 4.43-4.36 (m, 1H), 4.25-4.17 (m, 1H), 4.02-3.97 (m, 1H), 3.04-2.91 (m, 1H), 2.16-1.75 (m, 6H).

Example 52: Synthesis of Compound 528

1. Synthesis of Intermediate 52-1

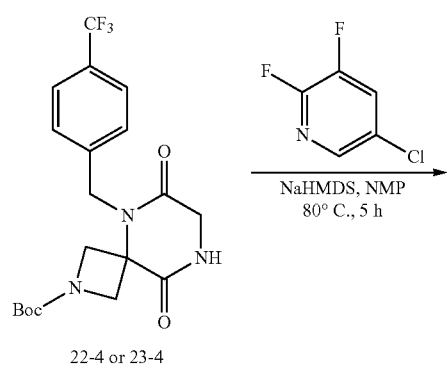

22-4 or 23-4

To a solution of tert-butyl 6,9-dioxo-5-[[4-(trifluoromethyl)phenyl]methyl]-2,5,8-triazaspiro[3.5]nonane-2-carboxylate (450 mg, 1.1 mmol, 1 equiv) in NMP (5 mL) was added NaHMDS (0.82 mL, 1.6 mmol, 1.5 equiv, 2 M in THF) dropwise at 0° C. After stirring at r.t. for 30 min, to the mixture was added 5-chloro-2,3-difluoropyridine (243 mg, 1.6 mmol, 1.5 equiv). The resulting mixture was stirred at 80° C. for 5 h and cooled to 0° C. The reaction was quenched with water (10 mL) at 0° C. and extracted with EtOAc (20 mL). The organic layer was washed twice with brine (20 mL), dried over anhydrous $Na_2SO_4$, concentrated under reduced pressure, and purified by silica gel column chromatography using with PE/EA (5/1) as eluent to afford 350 mg of tert-butyl 8-(5-chloro-3-fluoropyridin-2-yl)-6,9-dioxo-5-[[4-(trifluoromethyl)phenyl]methyl]-2,5,8-triazaspiro[3.5]nonane-2-carboxylate (Intermediate 52-1) as a yellow oil. LRMS (ES) m/z 487 (M+H-56).

2. Synthesis of Intermediate 52-2

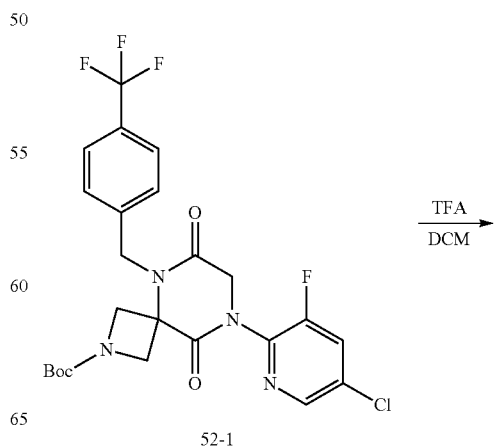

52-1

-continued

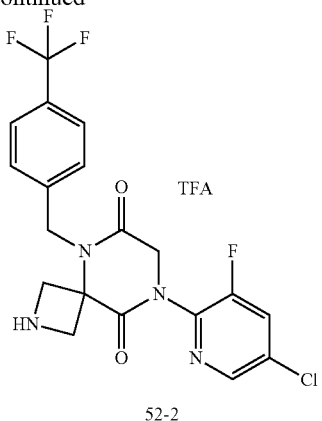

52-2

To a solution of tert-butyl 8-(5-chloro-3-fluoropyridin-2-yl)-6,9-dioxo-5-[[4-(trifluoromethyl)phenyl]methyl]-2,5,8-triazaspiro[3.5]nonane-2-carboxylate (350 mg, 0.6 mmol, 1 equiv) in DCM (3 mL) was added 2,2,2-trifluoroacetic acid (1 mL). The resulting mixture was stirred at r.t. for 3 h and concentrated under reduced pressure to give 300 mg of 8-(5-chloro-3-fluoropyridin-2-yl)-5-[[4-(trifluoromethyl)phenyl]methyl]-2,5,8-triazaspiro[3.5]nonane-6,9-dione trifluoroacetate (Intermediate 52-2) as a yellow oil. LRMS (ES) m/z 443 (M+H).

3. Synthesis of Compound 528

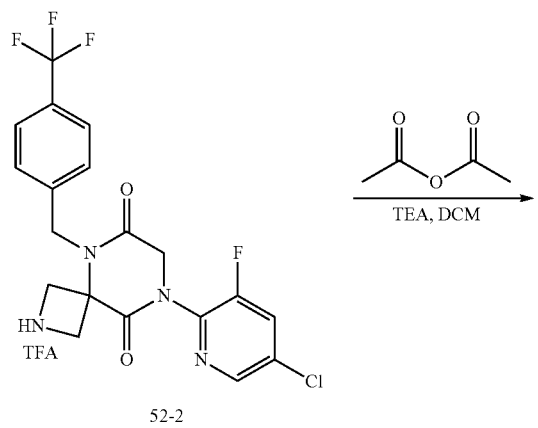

Compound 528

To a solution of 8-(5-chloro-3-fluoropyridin-2-yl)-5-[[4-(trifluoromethyl)phenyl]methyl]-2,5,8-triazaspiro[3.5]nonane-6,9-dione trifluoroacetate (300 mg, 0.6 mmol, 1 equiv) in DCM (5 mL) were added acetyl acetate (85 mg, 0.8 mmol, 1.5 equiv) and TEA (168 mg, 1.67 mmol, 3.0 equiv). The resulting mixture was stirred at r.t. for 2 h, concentrated under vacuum, and purified by Prep-HPLC with the following conditions (SHIMADZU (HPLC-01)): Column, XBridge Prep OBD C18 Column, 30*150 mm 5 um; mobile phase, Water (10 mM, NH$_4$HCO$_3$) and ACN (31% gradient up to 49% in 8 min); Detector, UV254 nm) to afford 90 mg of 2-acetyl-8-(5-chloro-3-fluoropyridin-2-yl)-5-(4-(trifluoromethyl)benzyl)-2,5,8-triazaspiro[3.5]nonane-6,9-dione (Compound 528) as a white solid. LRMS (ES) m/z 485 (M+H). $^1$H NMR (400 MHz, Methanol-d$_4$) δ 8.43 (d, J=1.9 Hz, 1H), 7.98 (dt, J=9.3, 2.0 Hz, 1H), 7.77-7.67 (m, 2H), 7.56 (d, J=8.0 Hz, 2H), 5.13 (s, 2H), 4.71 (d, J=10.1 Hz, 3H), 4.50 (d, J=10.2 Hz, 2H), 4.25 (d, J=10.9 Hz, 1H), 1.87 (s, 3H).

The following compounds were prepared by methods analogous to the method described for Compound 528:

| Compound No. | LRMS (ES) m/z |
| --- | --- |
| 529 | M + H = 472 |
| 530 | M + H = 476 |
| 556 | M + H = 465 |
| 619 | M + H = 479 |
| 620 | M + H = 485 |

Example 53: Synthesis of Compound 531

1. Synthesis of Compound 531

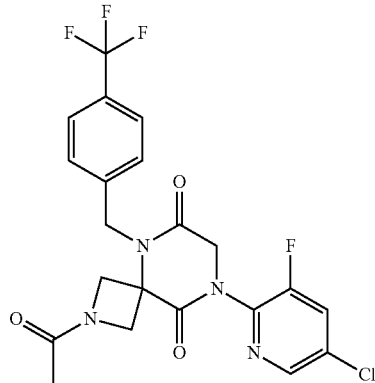

25-2

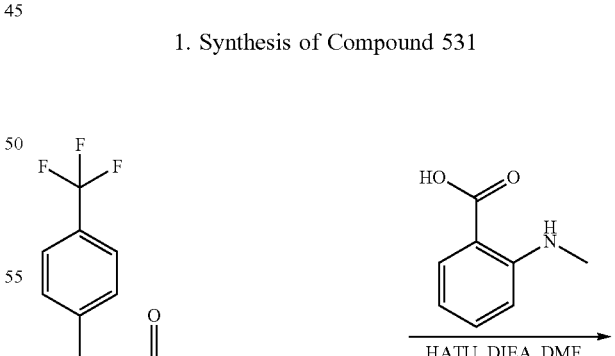

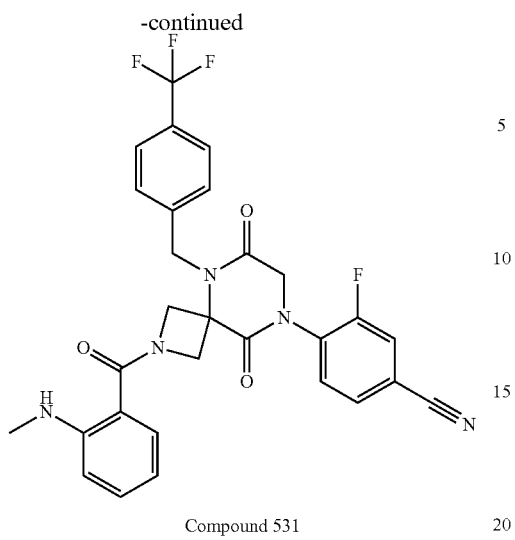

Compound 531

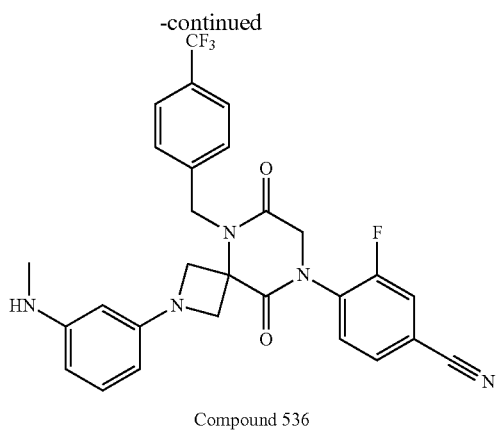

Compound 536

To a solution of 4-(6,9-dioxo-5-[[4-(trifluoromethyl)phenyl]methyl]-2,5,8-triazaspiro[3.5]nonan-8-yl)-3-fluorobenzonitrile (35.0 mg, 0.08 mmol, 1.0 equiv) in DMF (1.0 mL) were added 2-(methylamino)benzoic acid (12.0 mg, 0.08 mmol, 1.0 equiv), HATU (37.0 mg, 0.1 mmol, 1.2 equiv) and DIEA (21.0 mg, 0.2 mmol, 2.0 equiv). The resulting mixture was stirred at r.t. for 2 h. The solution was purified by Prep-HPLC with the following conditions (SHIMADZU (HPLC-01)): Column, XBridge Shield RP18 OBD Column, 5 um, 19*150 mm; mobile phase, Water (10 mM, $NH_4HCO_3$) and ACN (30% gradient up to 50% in 8 min); Detector, uv254/220 nm) to afford 20 mg of 3-fluoro-4-(2-(2-(methylamino)benzoyl)-6,9-dioxo-5-(4-(trifluoromethyl)benzyl)-2,5,8-triazaspiro[3.5]nonan-8-yl)benzonitrile (Compound 531) as a white solid. LRMS (ES) m/z 566 (M+H). $^1$H NMR (400 MHz, Methanol-$d_4$) δ 7.79 (d, J=9.8 Hz, 1H), 7.76-7.65 (m, 4H), 7.58 (d, J=8.1 Hz, 2H), 7.31 (t, J=8.0 Hz, 1H), 7.15 (dd, J=7.7, 1.5 Hz, 1H), 6.72 (d, J=8.4 Hz, 1H), 6.57 (t, J=7.4 Hz, 1H), 5.17 (s, 2H), 4.68 (d, J=10.6 Hz, 2H), 4.57 (s, 2H), 4.46 (d, J=10.6 Hz, 2H), 2.83 (s, 3H).

Example 54: Synthesis of Compound 536

1. Synthesis of Compound 536

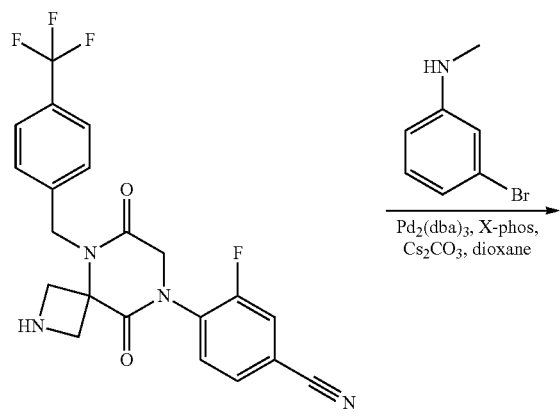

To a solution of 4-(6,9-dioxo-5-[[4-(trifluoromethyl)phenyl]methyl]-2,5,8-triazaspiro[3.5]nonan-8-yl)-3-fluorobenzonitrile (100.0 mg, 0.23 mmol, 1.0 equiv) in dioxane (2.0 mL) were added 3-bromo-N-methylaniline (50.0 mg, 0.27 mmol, 1.2 equiv), $Pd_2(dba)_3$ (24.0 mg, 0.03 mmol, 0.11 equiv), X-phos (22.0 mg, 0.05 mmol, 0.2 equiv) and $Cs_2CO_3$ (151.0 mg, 0.5 mmol, 2.0 equiv). The resulting mixture was stirred at 80° C. for 3 h under nitrogen atmosphere, cooled to rt, and purified by Prep-TLC (PE/EtOAc 1/1) to afford a mixture, which was purified by Prep-HPLC with the following conditions (SHIMADZU (HPLC-01)): Column, Xselect CSH OBD Column 30*150 mm 5 um; mobile phase, Water (10 mM, $NH_4HCO_3$) and ACN (45% gradient up to 80% in 9 min); Detector, UV254/220 nm) to afford 43 mg of 3-fluoro-4-[2-[3-(methylamino)phenyl]-6,9-dioxo-5-[[4-(trifluoromethyl)phenyl]methyl]-2,5,8-triazaspiro[3.5]nonan-8-yl]benzonitrile (Compound 536) as an off-white solid. LRMS (ES) m/z 538 (M+H). $^1$H NMR (300 MHz, Chloroform-d) δ 7.69-7.38 (m, 7H), 7.07 (t, J=7.9 Hz, 1H), 6.17 (d, J=8.0 Hz, 1H), 5.87 (d, J=7.9 Hz, 1H), 5.70 (s, 1H), 5.28 (s, 2H), 4.53 (d, J=8.3 Hz, 2H), 4.45 (s, 2H), 4.12 (d, J=8.3 Hz, 2H), 2.83 (s, 3H).

The following compounds were prepared by methods analogous to the method described for Compound 536:

| Compound No. | LRMS (ES) m/z |
|---|---|
| 535 | M + H = 538 |
| 538 | M + H = 538 |

Example 55: Synthesis of Compound 539

1. Synthesis of Intermediate 55-1

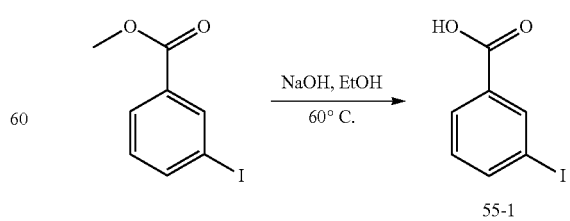

To a solution of methyl 3-iodobenoate (250.0 mg, 1.0 mmol, 1.0 equiv) in a mixture of EtOH (4.0 mL) and water (1.0 mL) was added NaOH (115 mg, 3.0 mmol, 3.0 equiv). The mixture was stirred at 60° C. for 2 h, cooled to rt, acidified to pH 3, and extracted with EA (20 mL). The organic layer was washed with brine twice, dried over Na₂SO₄, and concentrated under reduced pressure to afford 200 mg of 3-iodobenzoic acid (Intermediate 55-1) as an off-white solid. LRMS (ES) m/z 249 (M+H).

2. Synthesis of Intermediate 55-2

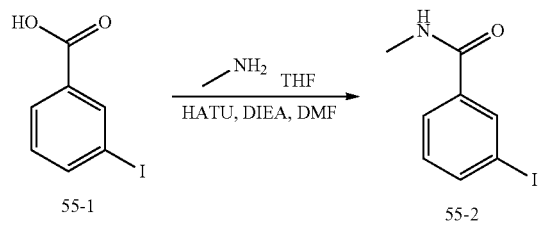

To a solution of methyl 3-iodobenoic acid (250.0 mg, 0.81 mmol, 1.0 equiv) in DMF (3.0 mL) were added methylamine (0.6 mL, 1.2 mmol, 1.5 equiv, 2M/THF), HATU (368 mg, 1.0 mmol, 1.2 equiv.), and DIEA (208 mg, 1.6 mmol, 2.0 equiv.). The mixture was stirred at rt overnight, diluted with water, and extracted with EA (20 mL). The organic layer was washed with brine twice, dried over Na₂SO₄, concentrated under reduced pressure, and purified by silica gel column chromatography using PE/EA (4/1) as eluent to afford 200 mg of 3-iodo-N-methylbenzamide (Intermediate 55-2) as an off-white solid. LRMS (ES) m/z 262 (M+H).

3. Synthesis of Compound 539

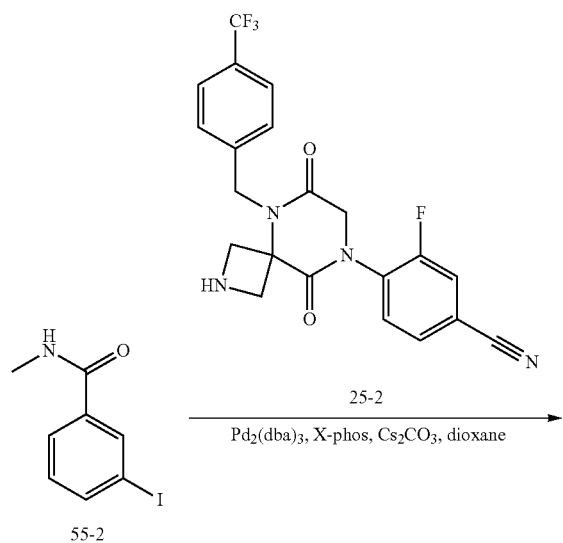

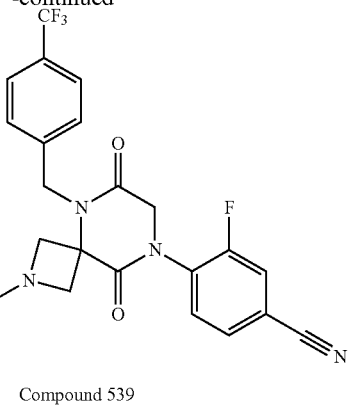

Compound 539

To a solution of 4-(6,9-dioxo-5-[[4-(trifluoromethyl)phenyl]methyl]-2,5,8-triazaspiro[3.5]nonan-8-yl)-3-fluorobenzonitrile (100.0 mg, 0.23 mmol, 1.0 equiv) in dioxane (2.0 mL) were added 3-iodo-N-methylbenzamide (90.0 mg, 0.35 mmol, 1.5 equiv), Pd₂(dba)₃ (24.0 mg, 0.03 mmol, 0.11 equiv), X-phos (22.0 mg, 0.05 mmol, 0.2 equiv) and Cs₂CO₃ (151.0 mg, 0.5 mmol, 2.0 equiv). The resulting mixture was stirred at 90° C. for 2 h under nitrogen atmosphere, cooled to rt, filtered, and purified by Prep-TLC (PE/EtOAc 1/8) to afford a mixture, which was further purified by Prep-HPLC with the following conditions (SHIMADZU (HPLC-01)): Column, Xselect CSHOBD Column 30*150 mm 5 um, mobile phase, Water (10 mM, NH₄HCO₃) and ACN (35% gradient up to 58% in 10 min); Detector, UV254/220 nm) to afford 45 mg of 3-(8-(4-cyano-2-fluorophenyl)-6,9-dioxo-5-(4-(trifluoromethyl)benzyl)-2,5,8-triazaspiro[3.5]nonan-2-yl)-N-methylbenzamide (Compound 539) as a white solid. LRMS (ES) m/z 566 (M+H). 1H NMR (400 MHz, Methanol-d₄) δ 7.82-7.75 (m, 1H), 7.78-7.68 (m, 2H), 7.68 (d, J=8.1 Hz, 2H), 7.57 (d, J=8.1 Hz, 2H), 7.30 (t, J=7.8 Hz, 1H), 7.21 (dt, J=7.8, 1.3 Hz, 1H), 6.92 (t, J=2.0 Hz, 1H), 6.68-6.61 (m, 1H), 5.29 (s, 2H), 4.60 (s, 2H), 4.48 (d, J=8.7 Hz, 2H), 4.27 (d, J=8.7 Hz, 2H), 2.90 (s, 3H).

The following compounds were prepared by methods analogous to the method described for Compound 539:

| Compound No. | LRMS (ES) m/z |
| --- | --- |
| 532 | M + H = 567 |
| 533 | M + H = 567 |
| 534 | M + H = 567 |
| 537 | M + H = 566 |
| 540 | M + H = 566 |

Example 56: Synthesis of Compound 541

1. Synthesis of Intermediate 56-1

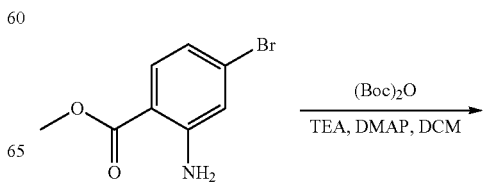

-continued

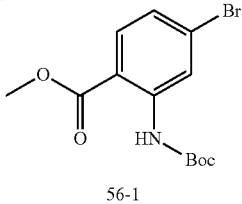

56-1

To a solution of methyl 2-amino-4-bromobenzoate (1.5 g, 6.5 mmol, 1.0 equiv.) in DCM (15.0 mL) were added TEA (2.0 g, 19.8 mmol, 3.0 equiv.), DMAP (797 mg, 6.5 mmol, 1.0 equiv.), and (Boc)₂O (1.7 g, 7.8 mmol, 1.2 equiv.) at 0° C. The mixture was stirred at rt overnight, diluted with DCM (50 mL), washed with brine (50 mL) twice, dried over Na₂SO₄, concentrated under reduced pressure, and purified by silica gel chromatography using PE/EA as eluent to afford 1.1 g of methyl 4-bromo-2-[[(tert-butoxy)carbonyl]amino]benzoate (Intermediate 56-1) as a white solid. LRMS (ES) m/z 274 (M+H-56).

2. Synthesis of Intermediate 56-2

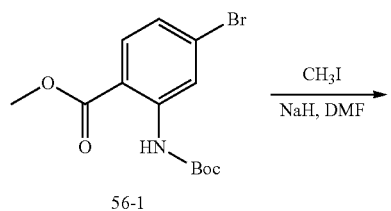

To a solution of methyl 4-bromo-2-[[(tert-butoxy)carbonyl]amino]benzoate (1.1 g, 3.3 mmol, 1.0 equiv.) in DMF (15.0 mL) was added NaH (60% in mineral oil, 160 mg, 4.0 mmol, 1.2 equiv.) at 0° C. After stirring for 30 min at 0° C., to this mixture was added iodomethane (521 mg, 3.7 mmol, 1.1 equiv.). The mixture was then stirred at rt overnight, quenched with water, and extracted with EA (100 mL). The organic layer was washed with saturated sodium bicarbonate solution (20 mL) once and brine (20 mL) twice, dried over Na₂SO₄, concentrated under reduced pressure, and purified by silica gel chromatography using PE/EA (50/1) as eluent to afford 800 mg of methyl 4-bromo-2-[[(tert-butoxy)carbonyl](methyl)amino]benzoate (Intermediate 56-2) as a yellow oil. LRMS (ES) 288 m/z (M+H-56).

3. Synthesis of Intermediate 56-3

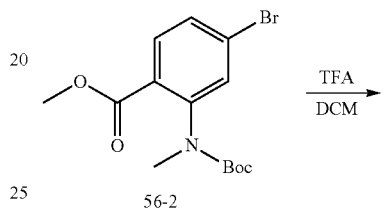

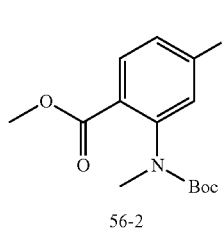

56-3

To a solution of methyl 4-bromo-2-[[(tert-butoxy)carbonyl](methyl)amino]benzoate (400 mg, 3.3 mmol, 1.0 equiv.) in DCM (4.0 mL) was added TFA (1.0 mL). The mixture was stirred at rt for 2 h, adjusted pH to 9 with sat sodium bicarbonate, and extracted with EA (20 mL). The organic layer was washed with brine (20 mL) twice, dried over Na₂SO₄, and concentrated under reduced pressure to afford methyl 4-bromo-2-(methylamino)benzoate (Intermediate 56-3) as a yellow oil. LRMS (ES) 244 m/z (M+H).

4. Synthesis of Compound 541

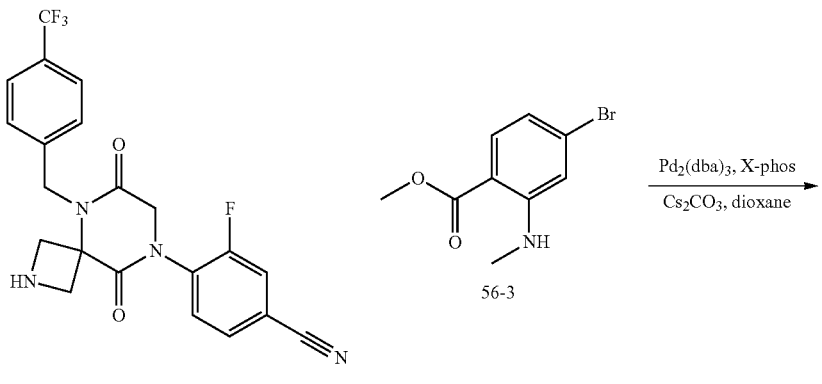

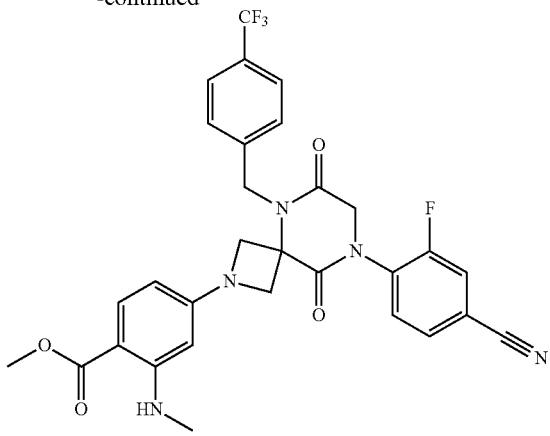

Compound 541

To a solution of 4-(6,9-dioxo-5-[[4-(trifluoromethyl)phenyl]methyl]-2,5,8-triazaspiro[3.5]nonan-8-yl)-3-fluorobenzonitrile (100.0 mg, 0.2 mmol, 1.0 equiv) in dioxane (2.0 mL) were added methyl 4-bromo-2-(methylamino)benzoate (80.0 mg, 0.3 mmol, 1.4 equiv), $Pd_2(dba)_3CHCl_3$ (24.0 mg, 0.023 mmol, 0.10 equiv), X-phos (22.0 mg, 0.05 mmol, 0.2 equiv), and $Cs_2CO_3$ (151.0 mg, 0.5 mmol, 2.0 equiv). The resulting mixture was stirred at 80° C. for 2 h under nitrogen atmosphere, cooled to r.t., and purified by Prep-TLC (PE/EtOAc 1:1) to afford a mixture, which was purified by Prep-HPLC with the following conditions (SHIMADZU (HPLC-01)): Column, XBridge Prep OBD C18 Column, 30*150 mm 5 um; mobile phase, Water (10 mM $NH_4HCO_3$) and ACN (50% gradient up to 80% in 8 min); Detector uv 254 nm) to afford 80 mg of methyl 4-(8-(4-cyano-2-fluorophenyl)-6,9-dioxo-5-(4-(trifluoromethyl)benzyl)-2,5,8-triazaspiro[3.5]nonan-2-yl)-2-(methylamino)benzoate (Compound 541) as a white solid. LRMS (ES) m/z 596 (M+H). $^1$H-NMR: (300 MHz, Methanol-$d_4$) δ 7.83-7.62 (m, 6H), 7.56 (d, J=8.1 Hz, 2H), 5.73 (dd, J=8.6, 2.2 Hz, 1H), 5.54 (d, J=2.2 Hz, 1H), 5.22 (s, 2H), 4.59 (s, 2H), 4.52 (d, J=9.1 Hz, 2H), 4.27 (d, J=9.0 Hz, 2H), 3.77 (s, 3H), 2.84 (s, 3H).

The following compounds were prepared by methods analogous to the method described for Compound 541:

| Compound No. | LRMS (ES) m/z |
|---|---|
| 542 | M + H = 595 |
| 543 | M + H = 596 |
| 544 | M + H = 596 |
| 545 | M + H = 595 |
| 546 | M + H = 596 |
| 547 | M + H = 595 |

Example 57: Synthesis of Compound 550

1. Synthesis of Intermediate 57-1

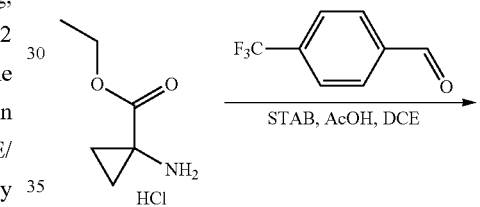

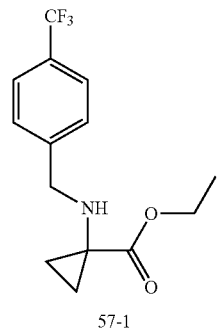

57-1

To a stirred solution of ethyl 1-aminocyclopropane-1-carboxylate hydrochloride (1.14 g, 7 mmol, 1.2 equiv) and 4-(trifluoromethyl)benzaldehyde (1.0 g, 6 mmol, 1.0 equiv) in DCE (20 mL) was added acetic acid (0.69 g, 11 mmol, 2.0 equiv). After stirring at rt for 5 min, to the mixture was added STAB (1.83 g, 9 mmol, 1.5 equiv). The resulting mixture was stirred for overnight at rt, diluted with DCM (20 m L), and washed with brine (20 mL), dried over anhydrous $Na_2SO_4$, and concentrated under reduced pressure to afford 1.48 g (73%) of ethyl 1-((4-(trifluoromethyl)benzyl)amino)cyclopropane-1-carboxylate (Intermediate 57-1) as a yellow oil. LRMS (ES) m/z 274 (M+H).

2. Synthesis of Intermediate 57-2

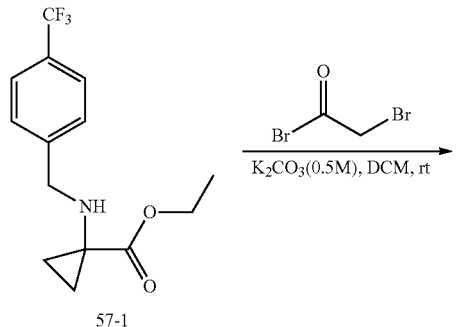

To a stirred solution of ethyl 1-((4-(trifluoromethyl)benzyl)amino)cyclopropane-1-carboxylate (1.48 g, 5.4 mmol, 1.0 equiv) in DCM (90 mL) cooled to 0° C. were added K$_2$CO$_3$ (16.2 mL, 0.5 M in water, 1.5 equiv) and 2-bromoacetyl bromide (1.31 g, 6 mmol, 1.2 equiv) dropwise. The resulting mixture was stirred for additional 3 h at rt, washed with brine (80 mL), dried over anhydrous Na$_2$SO$_4$, concentrated under reduced pressure to afford 1.8 g (82%) of ethyl 1-(2-bromo-N-(4-(trifluoromethyl)benzyl)acetamido)cyclopropane-1-carboxylate (Intermediate 57-2) as a yellow oil. LRMS (ES) m/z 394 (M+H).

3. Synthesis of Intermediate 57-3

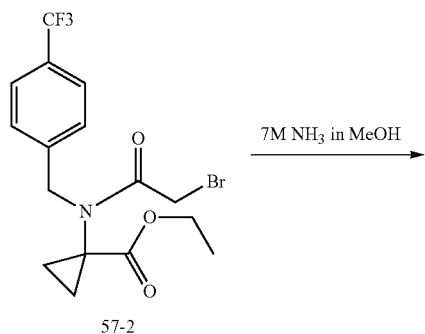

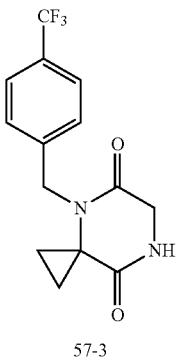

To a stirred solution of ethyl 1-(2-bromo-N-(4-(trifluoromethyl)benzyl)acetamido)cyclopropane-1-carboxylate (1.79 g, 4.4 mmol, 1.0 equiv) in MeOH (5 mL) was added ammonia (25.0 mL, 7M in MeOH). The resulting mixture was stirred for additional 1.5 h at room temperature, concentrated under reduced pressure, and triturated with EA (10 mL) to afford 1.0 g (76%) of 4-(4-(trifluoromethyl)benzyl)-4,7-diazaspiro[2.5]octane-5,8-dione (Intermediate 57-3) as a yellow solid. LRMS (ES) m/z 299 (M+H).

4. Synthesis of Compound 550

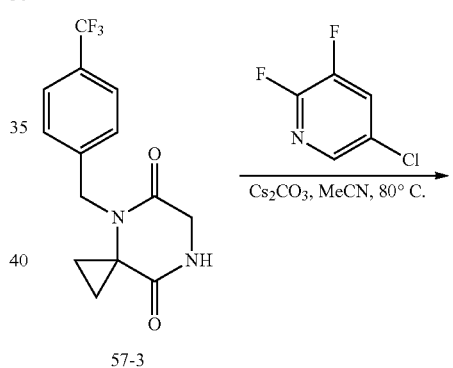

To a stirred solution of 4-(4-(trifluoromethyl)benzyl)-4,7-diazaspiro[2.5]octane-5,8-dione (300.0 mg, 1.0 mmol, 1.0 equiv) in ACN (3 mL) was added Cs$_2$CO$_3$ (651.0 mg, 2.0 mmol, 2.0 equiv). After stirring for 5 min at rt, to the mixture was added 5-chloro-2,3-difluoropyridine (179.3 mg, 1.2 mmol, 1.2 equiv). The resulting mixture was stirred for 2 days at 80° C., cooled to r.t, filtered to remove Cs$_2$CO$_3$, concentrated under reduced pressure, and purified by Prep-HPLC with the following conditions: (SHIMADZU (HPLC-01)): Column, XBridge Shield RP18 OBD Column, 5 um, 19*150 mm; mobile phase, Water (10 mM $NH_4HCO_{3+0.1}$% $NH_3.H_2O$) and ACN (41% gradient up to 71% in 8 min); Detector, UV 254 nm) to afford 6.7 mg (2%) of 7-(5-chloro-3-fluoropyridin-2-yl)-4-(4-(trifluoromethyl)benzyl)-4,7-diazaspiro[2.5]octane-5,8-dione (Compound 550) as a white solid. LRMS (ES) m/z 428 (M+H). $^1$H NMR (300 MHz, DMSO-$d_6$) δ 8.48 (d, J=2.1 Hz, 1H), 8.25 (dd, J=9.6, 2.1 Hz, 1H), 7.73 (d, J=8.0 Hz, 2H), 7.46 (d, J=8.0 Hz, 2H), 4.67 (s, 4H), 1.34 (d, J=4.4 Hz, 4H).

The following compounds were prepared by methods analogous to the method described for Compound 550:

| Compound No. | LRMS (ES) m/z |
|---|---|
| 548 | M + H = 442 |
| 554 | M + H = 444 |
| 555 | M + H = 456 |
| 577 | M + H = 394 |
| 616 | M + H = 408 |
| 629 | M + H = 473 |
| 632 | M + H = 439 |
| 660 | M + H = 406 |

Example 58: Synthesis of Compound 574

1. Synthesis of Intermediate 58-1

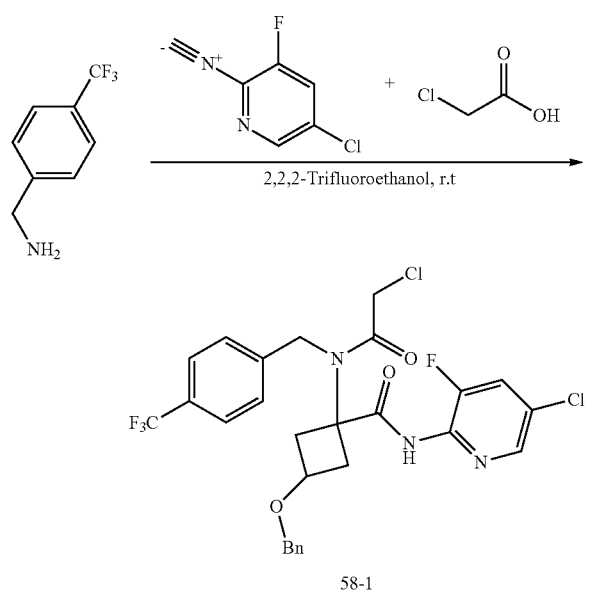

To a solution of 3-(benzyloxy)cyclobutan-1-one (1.80 g, 10.215 mmol, 1.07 equiv) in 2,2,2-trifluoroethanol (15 mL) was added 1-(4-trifluoromethyl)phenyl)methanamine (1.9 g, 10.8 g, 1.1 equiv.). After stirring at r.t. for 5 min, to this resulting mixture were added 5-chloro-3-fluoro-2-isocyanopyridine (1.5 g, 9.6 mmol, 1.0 equiv) and chloroacetic acid (994.0 mg, 10.5 mmol, 1.1 equiv). The resulting mixture was stirred at r.t. overnight, concentrated under reduced pressure, and purified by C18 column, eluted with water (0.5% $NH_4HCO_3$)/ACN (1:1) to afford 1.5 g of 3-(benzyloxy)-N-(5-chloro-3-fluoropyridin-2-yl)-1-(2-chloro-N-(4-(trifluoromethyl)benzyl)acetamido)cyclobutane-1-carboxamide (Intermediate 58-1) as a yellow oil. LRMS (ES) m/z 584 (M+H).

2. Synthesis of Intermediate 58-2

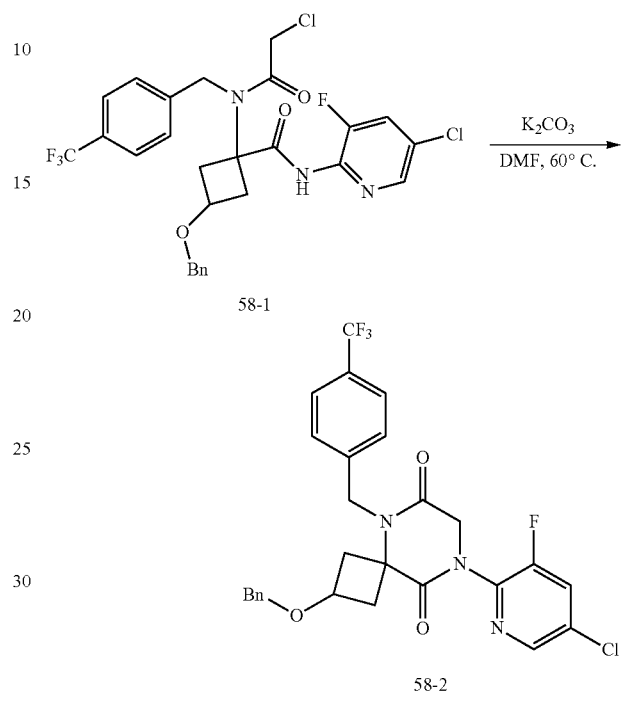

To a solution of 3-(benzyloxy)-N-(5-chloro-3-fluoropyridin-2-yl)-1-(2-chloro-N-(4-(trifluoromethyl)benzyl)acetamido)cyclobutane-1-carboxamide (1.4 g, 2.4 mmol, 1.0 equiv) in DMF (15.0 mL) at r.t was added $K_2CO_3$ (994 mg, 7.1 mmol, 3.0 equiv). The mixture was stirred at 60° C. for 30 min, cooled to rt, and diluted with water (30 mL). The precipitate was collected, washed with water, and dried to afford 1.2 g of 2-(benzyloxy)-8-(5-chloro-3-fluoropyridin-2-yl)-5-(4-(trifluoromethyl)benzyl)-5,8-diazaspiro[3.5]nonane-6,9-dione (Intermediate 58-2). LRMS (ES) m/z 548 (M+H).

3. Synthesis of Intermediate 58-3

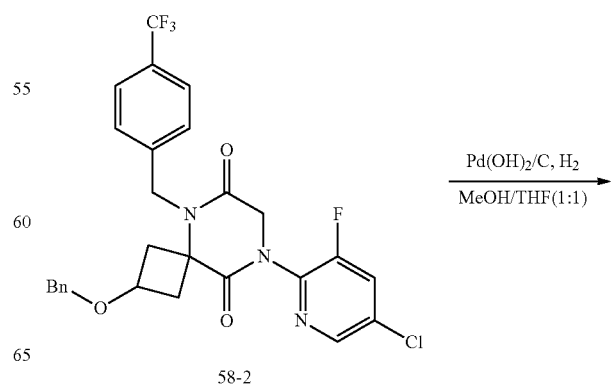

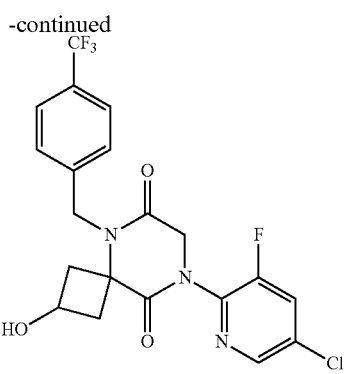

58-3

To a solution of 2-(benzyloxy)-8-(5-chloro-3-fluoropyridin-2-yl)-5-(4-(trifluoromethyl)benzyl)-5,8-diazaspiro[3.5]nonane-6,9-dione (500 mg, 0.9 mmol, 1.0 equiv.) in MeOH (5.0 mL) and THF (5.0 mL) was added Pd(OH)$_2$/C (20% wt., 250 mg). The mixture was stirred at rt for 1 h under hydrogen (1 atm, hydrogen balloon), filtered through a celite plug, and concentrated under reduced pressure to afford 400 mg of 8-(5-chloro-3-fluoropyridin-2-yl)-2-hydroxy-5-(4-(trifluoromethyl)benzyl)-5,8-diazaspiro[3.5]nonane-6,9-dione (Intermediate 58-3) as a yellow oil. LRMS (ES) 458 m/z (M+H).

4. Synthesis of Compound 574

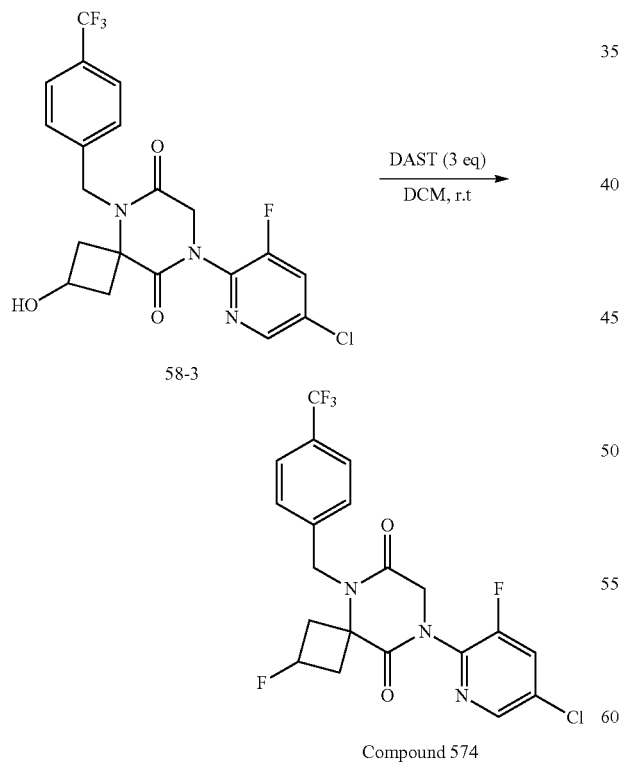

Compound 574

To a solution of 8-(5-chloro-3-fluoropyridin-2-yl)-2-hydroxy-5-(4-(trifluoromethyl)benzyl)-5,8-diazaspiro[3.5]nonane-6,9-dione (200.0 mg, 0.4 mmol, 1.0 equiv) in DCM (3.0 mL) was added DAST (211 mg, 1.3 mmol, 3.0 equiv.).

The mixture was stirred at rt for 1 h, concentrated under reduced pressure, and purified by Prep-HPLC with the following conditions (SHIMADZU (HPLC-01)): Column, Xselect CSH OBD C18 Column, 30*150 mm 5 um; mobile phase, Water (0.1% FA) and ACN (10% gradient up to 50% in 9 min); Detector uv 254 nm) to afford 70 mg of 8-(5-chloro-3-fluoropyridin-2-yl)-2-fluoro-5-(4-(trifluoromethyl)benzyl)-5,8-diazaspiro[3.5]nonane-6,9-dione (Compound 574) as a white solid. LRMS (ES) m/z 460 (M+H). $^1$HNMR: (DMSO-d$_6$) δ 8.52 (d, J=2.1 Hz, 1H), 8.29 (dd, J=9.5, 2.1 Hz, 1H), 7.75 (d, J=8.1 Hz, 2H), 7.51 (d, J=8.0 Hz, 2H), 5.12-4.80 (m, 3H), 4.61 (s, 2H), 2.99 (s, 2H), 2.71 (d, J=21.3 Hz, 2H).

Example 59: Synthesis of Compound 575

1. Synthesis of Intermediate 59-1

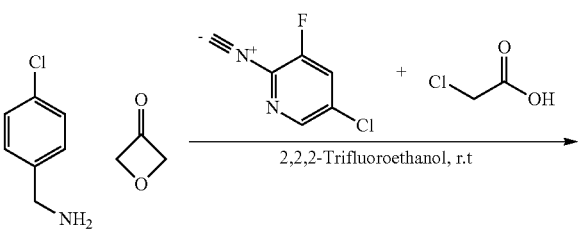

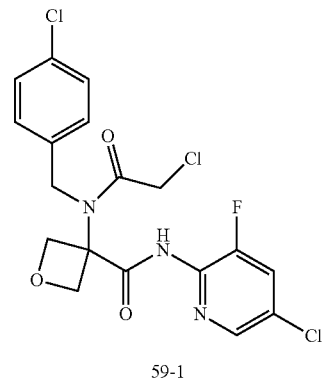

59-1

To a solution of 1-(4-chlorophenyl)methanamine (497.0 mg, 3.5 mmol, 1.1 equiv) in 2,2,2-trifluoroethanol (10.0 mL) was added 3-oxetanone (254.0 mg, 3.5 mmol, 1.1 equiv). After stirring at r.t. for 10 min, to the resulting mixture were added 5-chloro-3-fluoro-2-isocyanopyridine (500.0 mg, 3.2 mmol, 1.0 equiv) and chloroacetic acid (331.0 mg, 3.5 mmol, 1.1 equiv). The resulting mixture was stirred at r.t. overnight, concentrated under reduced pressure, and purified by C18 column, eluted with water (0.05% NH$_4$HCO$_3$)/ACN (1:1) to afford 260 mg of N-(5-chloro-3-fluoropyridin-2-yl)-3-[2-chloro-N-[(4-chlorophenyl)methyl]acetamido]oxetane-3-carboxamide (Intermediate 59-1) as a yellow solid. LRMS (ES) m/z 596 (M+H).

2. Synthesis of Compound 575

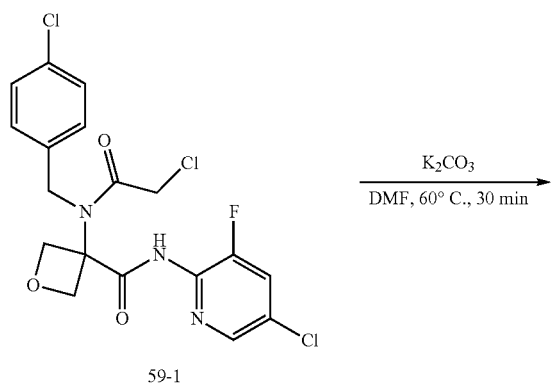

Compound 575

To a solution of N-(5-chloro-3-fluoropyridin-2-yl)-3-[2-chloro-N-[(4-chlorophenyl)methyl]acetamido]oxetane-3-carboxamide (260.0 mg, 0.58 mmol, 1.0 equiv) in DMF (5.0 mL) was added potassium carbonate (242.0 mg, 1.7 mmol, 3.0 equiv). The resulting mixture was stirred at 60° C. for 30 min and diluted with water (5 mL). The precipitates were collected by filtration, washed twice with water (5 mL), and purified by Prep-HPLC: Column: Xselect CSH OBD Column 30*150 mm 5 um; Mobile Phase A: Water (10 mM, $NH_4HCO_3$), Mobile Phase B: ACN; Flow rate: 60 mL/min; Gradient: 35% to 65% in 9 min; UV254 nm) to afford 60 mg of 8-(5-chloro-3-fluoropyridin-2-yl)-5-(4-chlorobenzyl)-2-oxa-5,8-diazaspiro[3.5]nonane-6,9-dione (Compound 575) as a white solid. LRMS (ES) m/z 410 (M+H). $^1$H NMR (300 MHz, DMSO-$d_6$) δ 8.52 (d, J=2.1 Hz, 1H), 8.29 (dd, J=9.6, 2.2 Hz, 1H), 7.47-7.32 (m, 4H), 5.08 (s, 2H), 4.93 (d, J=7.4 Hz, 2H), 4.75 (d, J=7.3 Hz, 2H), 4.54 (s, 2H).

The following compounds were prepared by methods analogous to the method described for Compound 575:

| Compound No. | LRMS (ES) m/z |
| --- | --- |
| 549 | M + H = 430 |
| 551 | M + H = 444.0 |
| 553 | M + H = 458 |
| 558 | M − H = 422 |
| 572 | M + H = 513.1 |
| 573 | M + H = 446 |
| 576 | M + H = 396 |
| 610 | M + H = 476 |
| 623 | M + H = 472.0 |
| 624 | M + H = 438 |
| 652 | M + H = 468 |

-continued

| Compound No. | LRMS (ES) m/z |
| --- | --- |
| 663 | M + H = 434 |
| 665 | M + H = 418.0 |
| 687 | M + H = 502.0 |
| 688 | M + H = 486.0 |
| 689 | M + H = 534 |
| 756 | M + H = 494.0 |
| 757 | M + H = 390.0 |
| 768 | M + H = 428.0 |
| 799 | M − H = 391 |
| 813 | M + H = 484.0 |
| 814 | M + H = 466.0 |
| 815 | M + H = 434.1 |
| 816 | M + H = 430.1 |

Example 60: Synthesis of Compound 857

1. Synthesis of Intermediate 60-1

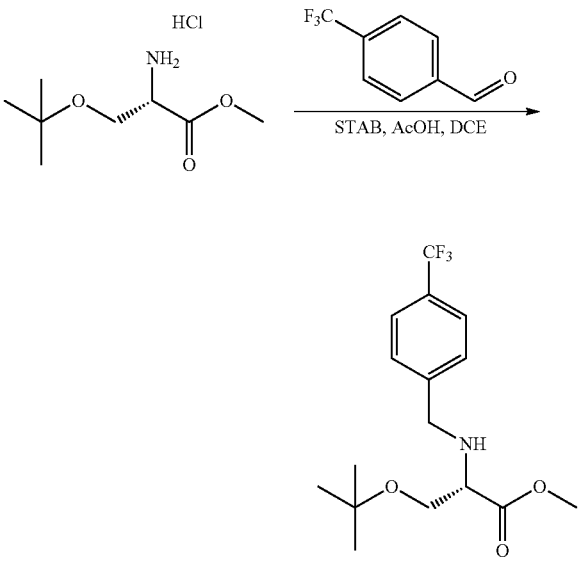

60-1

To a stirred solution of methyl O-(tert-butyl)-L-serinate hydrochloride (1.0 g, 4.7 mmol, 1.0 equiv, 1.0 equiv) and 4-(trifluoromethyl)benzaldehyde (818 mg, 4.7 mmol, 1.1 equiv) in DCE (10.0 mL) at r.t were added AcOH (564 mg, 9.4 mmol, 2. equiv) and STAB (1.50 g, 7.3 mmol, 1.5 equiv). The resulting mixture was stirred at room temperature for 2 h, neutralized to pH 7 with ammonium hydroxide, and diluted with $CH_2Cl_2$ (50 mL). The organic layer was washed twice with brine (50 mL), dried over anhydrous $Na_2SO_4$, and concentrated under reduced pressure to give 1.2 g of methyl O-(tert-butyl)-N-(4-(trifluoromethyl)benzyl)-L-serinate (Intermediate 60-1) as a light-yellow oil.

2. Synthesis of Intermediate 60-2

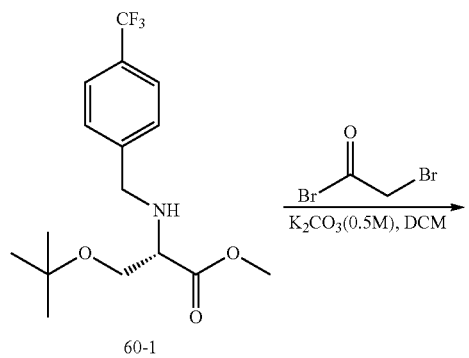

60-1

To a stirred solution of methyl O-(tert-butyl)-N-(4-(trifluoromethyl)benzyl)-L-serinate (1.2 g, 3.6 mmol, 1.0 equiv) and K$_2$CO$_3$ (0.5 M, 11 mL, 5.4 mmol, 1.5 equiv) in DCM (30 mL) at 0° C. was added bromoacetyl bromide (869 mg, 4.3 mmol, 1.2 equiv) dropwise. The resulting mixture was stirred at room temperature overnight, diluted with CH$_2$Cl$_2$ (50 mL). The organic layer was washed with brine (50 mL), dried over anhydrous Na$_2$SO$_4$, and concentrated under reduced pressure to give 1.3 g of methyl N-(2-bromoacetyl)-O-(tert-butyl)-N-(4-(trifluoromethyl)benzyl)-L-serinate (Intermediate 60-2) as a light-yellow oil.

3. Synthesis of Intermediate 60-3

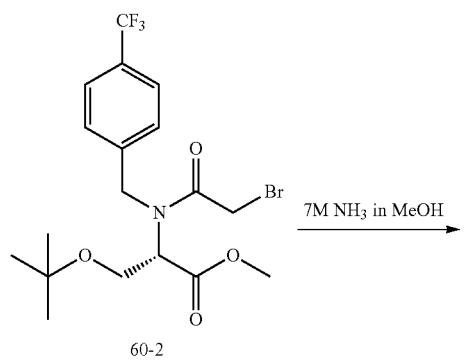

60-2

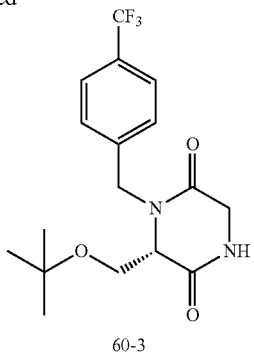

60-3

To a solution of ammonia (7 N in MeOH, 15.0 mL) was added methyl N-(2-bromoacetyl)-O-(tert-butyl)-N-(4-(trifluoromethyl)benzyl)-L-serinate (1.3 g, 2.9 mmol, 1.0 equiv). The mixture was stirred at room temperature for 5 h, concentrated under reduced pressure, and trituration with ethyl acetate (10 mL) to afford 500 mg of (S)-6-(tert-butoxymethyl)-1-(4-(trifluoromethyl)benzyl)piperazine-2,5-dione (Intermediate 60-3) as a white solid.

4. Synthesis of Intermediate 60-4

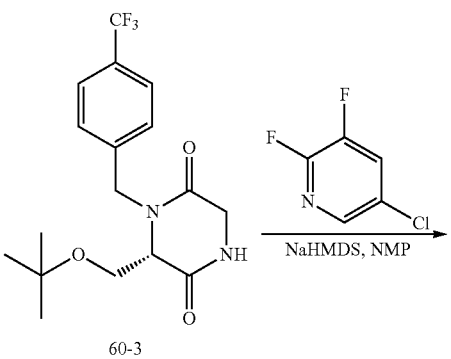

60-4

To a stirred solution of (S)-6-(tert-butoxymethyl)-1-(4-(trifluoromethyl)benzyl)piperazine-2,5-dione (500.0 mg, 1.4 mmol, 1.0 equiv) in NMP (6 mL) at 0° C. was added NaHMDS (2 mL, 1 M in THF, 1.5 equiv) dropwise. After stirring at room temperature for 15 min, to the mixture was added 5-chloro-2,3-difluoropyridine (314 mg, 2.1 mmol, 1.5 equiv). The mixture was stirred at rt for 2 h and purified by reverse phase flash chromatography with the following conditions water (0.05% NH$_4$HCO$_3$):ACN=1:1 to afford 300 mg (44%) of 3-(tert-butoxymethyl)-1-(5-chloro-3-fluoropyridin-2-yl)-4-(4-(trifluoromethyl)benzyl)piperazine-2,5-dione (Intermediate 60-4).

5. Synthesis of Compound 857

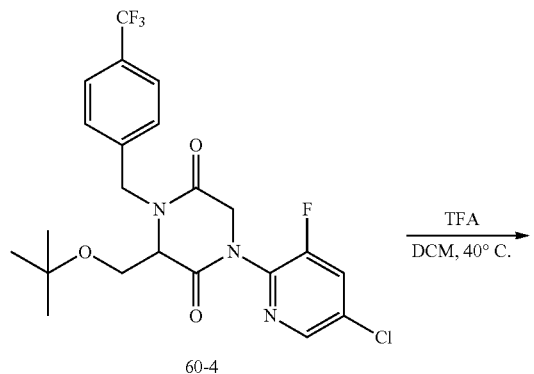

To a stirred solution of 3-(tert-butoxymethyl)-1-(5-chloro-3-fluoropyridin-2-yl)-4-(4-(trifluoromethyl)benzyl) piperazine-2,5-dione (300.0 mg, 0.6 mmol, 1.0 equiv) in DCM (24.0 mL) at room temperature was added TFA (6.0 mL). The resulting mixture was stirred at 40° C. for 2 h, concentrated under reduced pressure, and purified by Prep-HPLC with the following conditions (SHIMADZU (HPLC-01)): Column, X Bridge Prep OBD C18 Column, 30×150 mm 5 um; mobile phase A: Water (10 mM NH$_4$HCO$_3$+0.1% NH$_3$.H$_2$O) and mobile phase B: ACN (30% gradient up to 60% in 8 min); Detector UV 254/220 nm to afford 150 mg of 1-(5-chloro-3-fluoropyridin-2-yl)-3-(hydroxymethyl)-4-(4-(trifluoromethyl)benzyl)piperazine-2,5-dione (Compound 857).

6. Separation of Compound 857 Enantiomers: Enantiomers 857A and 857B

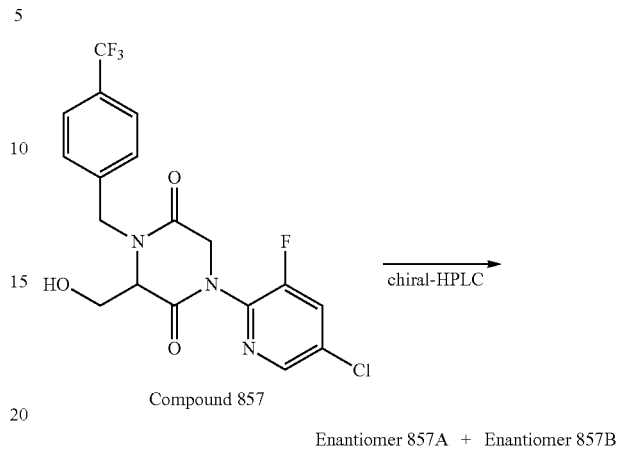

The racemic mixture of 1-(5-chloro-3-fluoropyridin-2-yl)-3-(hydroxymethyl)-4-(4-(trifluoromethyl)benzyl)piperazine-2,5-dione (320 mg) was separated by Chiral HPLC with the following condition: Column, CHIRALPAK IG, 2 cm*25 cm L (5 um); mobile phase A: Hex (8 mM NH$_3$.MeOH) and mobile phase B: EtOH; Flow rate: 18 mL/min; (50% B/A for 18 min); Detector, UV254/220 nm to afford 98 mg (first eluted peak) of Enantiomer 857A and 91 mg (second eluted peak) of Enantiomer 857B.

Enantiomer 857A: LCMS (ES) m/z 432 (M+H). $^1$H NMR (300 MHz, DMSO-d$_6$) δ 8.48 (t, J=2.2 Hz, 1H), 8.24 (dt, J=9.5, 2.3 Hz, 1H), 7.79-7.70 (m, 2H), 7.58 (d, J=7.8 Hz, 2H), 5.64-5.54 (m, 1H), 5.06 (d, J=15.6 Hz, 1H), 4.79 (dd, J=16.1, 2.0 Hz, 1H), 4.44 (d, J=15.6 Hz, 1H), 4.28-4.15 (m, 2H), 3.88-3.80 (m, 2H). Analytical chiral HPLC RT: 1.72 min (CHIRALPAK IG-3; 0.46 cm×5 cm; 3 micro; Hex (0.1% DEA):EtOH=50:50 at 1 ml/min).

Enantiomer 857B: LCMS (ES) m/z 432 (M+H). $^1$H NMR (300 MHz, DMSO-d$_6$) δ 8.48 (d, J=2.1 Hz, 1H), 8.24 (dd, J=9.5, 2.2 Hz, 1H), 7.75 (d, J=8.1 Hz, 2H), 7.58 (d, J=8.0 Hz, 2H), 5.59 (t, J=4.8 Hz, 1H), 5.06 (d, J=15.6 Hz, 1H), 4.79 (d, J=16.2 Hz, 1H), 4.44 (d, J=15.6 Hz, 1H), 4.27-4.15 (m, 2H), 3.83 (dd, J=5.0, 2.4 Hz, 2H. Analytical chiral HPLC RT: 2.61 min (CHIRALPAK IG-3; 0.46 cm×5 cm; 3 micro; Hex (0.1% DEA):EtOH=50:50 at 1 ml/min).

The following compounds were prepared by methods analogous to the method described for Enantiomers 857A and 857B:

| Enantiomer No. | LRMS (ES) m/z | Retention Time (min) | HPLC Separation Conditions |
|---|---|---|---|
| 862A | M + H = 398 | 1.34 | CHIRALPAK ID-3; 0.46 cm × 5 cm; 3 micro; Hex(0.1% DEA):EtOH = 50:50 at 1 ml/min |
| 862B | M + H = 398 | 1.83 | |

Example 61: Synthesis of Compound 859

1. Synthesis of Intermediate 61-1

2. Synthesis of Compound 859 (mixture of Diastereomers 859A and 859B)

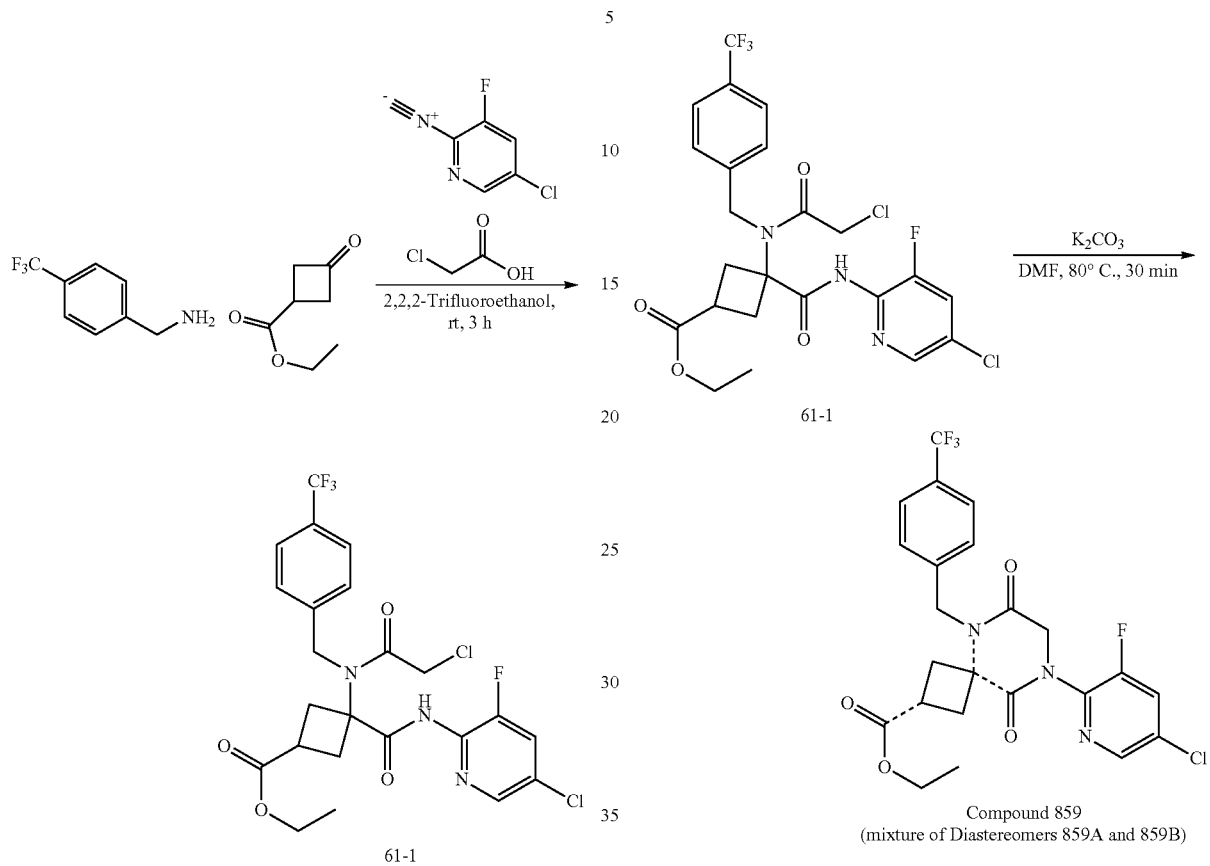

To a solution of (4-(trifluoromethyl)phenyl)methanamine (2.76 g, 15.73 mmol, 1.1 equiv) in 2,2,2-trifluoroethanol (10.0 mL) was added ethyl 3-oxocyclobutane-1-carboxylate (2.03 g, 14.30 mmol, 1.0 equiv). After stirring at r.t. for 10 min, to this resulting mixture were added 5-chloro-3-fluoro-2-isocyanopyridine (2.53 g, 14.30 mmol, 1.0 equiv) and chloroacetic acid (1.49 g, 15.73 mmol, 1.1 equiv). The resulting mixture was stirred at r.t. for 3 h, concentrated under reduced pressure, and purified silica gel chromatography, eluted with EA/HE to afford 1.6 g (20%) of ethyl 3-((5-chloro-3-fluoropyridin-2-yl)carbamoyl)-3-(2-chloro-N-(4-(trifluoromethyl)benzyl)acetamido)cyclobutane-1-carboxylate (Intermediate 61-1) as a foam. LRMS (ES) m/z 550 (M+H). $^1$H NMR (400 MHz, Methylene Chloride-$d_2$) δ 9.55 (s, OH), 9.36 (s, 1H), 8.15 (dd, J=4.5, 2.1 Hz, 1H), 7.57 (dd, J=17.6, 8.1 Hz, 2H), 7.46 (dd, J=9.2, 2.1 Hz, 1H), 7.34 (t, J=6.6 Hz, 2H), 4.57 (s, 2H), 4.09-3.97 (m, 2H), 3.90 (d, J=10.6 Hz, 2H), 3.07-2.97 (m, 3H), 2.83 (p, J=8.9 Hz, 1H), 2.74-2.61 (m, 1H), 2.52 (dd, J=12.3, 9.6 Hz, 1H), 1.12 (q, J=6.9 Hz, 3H).

To a solution of ethyl 3-((5-chloro-3-fluoropyridin-2-yl)carbamoyl)-3-(2-chloro-N-(4-(trifluoromethyl)benzyl)acetamido)cyclobutane-1-carboxylate (1.5 g, 2.73 mmol, 1.0 equiv) in DMF (10.0 mL) at r.t was added K$_2$CO$_3$ (1.14 g, 8.18 mmol, 3.0 equiv). The mixture was stirred at 80° C. for 1 h, diluted with EA (20 mL), filtered, and concentrated. The residue was purified on silica gel column with EA/HE as eluent to afford the corresponding Diastereomers 859A (680 mg, 49%) and 859B (610 mg, 44%) of ethyl 8-(5-chloro-3-fluoropyridin-2-yl)-6,9-dioxo-5-(4-(trifluoromethyl)benzyl)-5,8-diazaspiro[3.5]nonane-2-carboxylate (i.e., the (2r, 4r) and (2s,4s) diastereomers).

Characterization of Diastereomer 859A: LRMS (ES) m/z 514 (M+H). $^1$H NMR (400 MHz, Methylene Chloride-$d_2$) δ 8.23 (d, J=2.1 Hz, 1H), 7.58-7.50 (m, 3H), 7.30 (d, J=8.0 Hz, 2H), 4.95 (s, 2H), 4.43 (s, 2H), 4.01 (q, J=7.1 Hz, 2H), 3.01 (p, J=8.8 Hz, 1H), 2.83-2.72 (m, 2H), 2.63 (dd, J=12.9, 9.4 Hz, 2H), 1.12 (t, J=7.1 Hz, 3H).

Characterization of Diastereomer 859B: LRMS (ES) m/z 514 (M+H). $^1$H NMR (400 MHz, Methylene Chloride-$d_2$) δ 8.22 (s, 1H), 7.58-7.49 (m, 3H), 7.29 (d, J=8.0 Hz, 2H), 4.91 (s, 2H), 4.41 (s, 2H), 4.00 (q, J=7.1 Hz, 2H), 3.11-3.01 (m, 2H), 3.01-2.87 (m, 1H), 2.64-2.53 (m, 2H), 1.10 (t, J=7.1 Hz, 3H).

The following compounds were prepared by methods analogous to the method described for Compound 859:

| Compound No. | LRMS (ES) m/z | ¹H NMR |
|---|---|---|
| 860A | M + H = 480 | (400 MHz, Methylene Chloride-d₂) δ 8.23 (d, J = 2.1 Hz, 1H), 7.54 (dd, J = 8.9, 2.1 Hz, 1H), 7.28-7.18 (m, 2H), 7.12 (d, J = 8.3 Hz, 2H), 4.85 (s, 2H), 4.41 (s, 2H), 4.02 (q, J = 7.1 Hz, 2H), 3.07-2.93 (m, 1H), 2.81-2.71 (m, 2H), 2.69-2.59 (m, 2H), 1.13 (t, J = 7.1 Hz, 3H) |
| 860B | M + H = 480 | (400 MHz, Methylene Chloride-d2) δ 8.34 (d, J = 2.1 Hz, 1H), 7.65 (dd, J = 8.9, 2.1 Hz, 1H), 7.38 (d, J-8.2 Hz, 2H), 7.25 (d, J = 8.2 Hz, 2H), 4.94 (s, 2H), 4.52 (s, 2H), 4.13 (q, J = 7.1 Hz, 2H), 3.22-3.12 (m, 2H), 3.10-2.96 (m, 1H), 2.77-2.66 (m, 2H), 1.24 (t, J = 7.1 Hz, 3H) |

Example 62: Synthesis of Compound 861

1. Synthesis of Intermediate 62-1

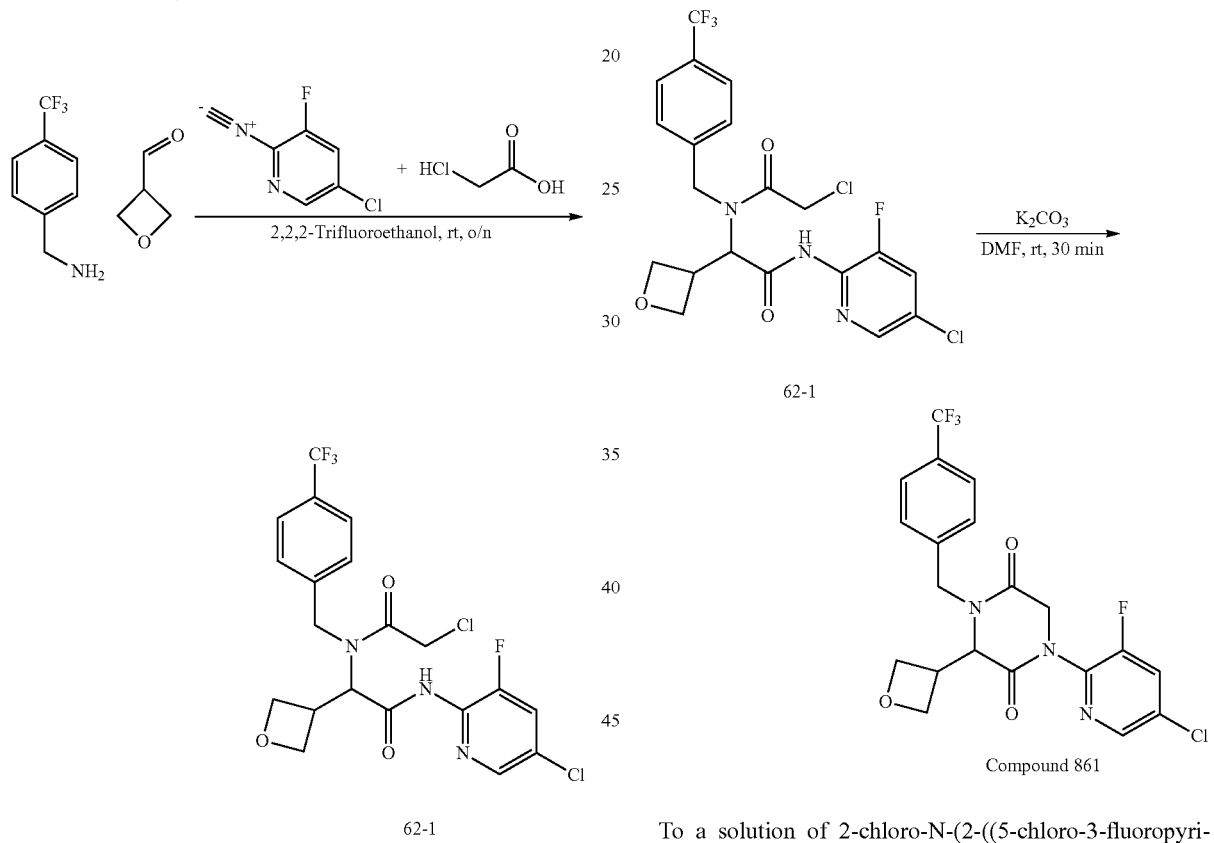

62-1

To a solution of 1-[4-(trifluoromethyl)phenyl]methanamine (15.3 g, 87.1 mmol, 1.1 equiv) in trifluoroethanol (40.0 mL) was added oxetane-3-carbaldehyde (7.5 g, 87.1 mmol, 1.1 equiv). After stirring at r.t. for 10 min, to the mixture was added 5-chloro-3-fluoro-2-isocyanopyridine (12.4 g, 79.2 mmol, 1.0 equiv) and chloroacetic acid (8.2 g, 87.1 mmol, 1.1 equiv). The resulting mixture was stirred at r.t. for overnight, concentrated under reduced pressure, and purified by silica gel column chromatography, eluted with PE/EtOAc (2/1) to afford 33.5 g of 2-chloro-N-(2-((5-chloro-3-fluoropyridin-2-yl)amino)-1-(oxetan-3-yl)-2-oxoethyl)-N-(4-(trifluoromethyl)benzyl)acetamide (Intermediate 62-1) as a yellow oil. LRMS (ES) m/z 494 (M+H).

2. Synthesis of Compound 861

To a solution of 2-chloro-N-(2-((5-chloro-3-fluoropyridin-2-yl)amino)-1-(oxetan-3-yl)-2-oxoethyl)-N-(4-(trifluoromethyl)benzyl)acetamide (33.5 g, 67.8 mmol, 1.0 equiv) in DMF (350.0 mL) was added potassium carbonate (18.9 g, 135.6 mmol, 2.0 equiv). To the resulting mixture stirred at r.t. for 30 min was added water (800 mL). The precipitates were collected by filtration, washed with water (400 mL) twice, and dried under high vacuum to afford 26 g of 1-(5-chloro-3-fluoropyridin-2-yl)-3-(oxetan-3-yl)-4-(4-(trifluoromethyl)benzyl)piperazine-2,5-dione (Compound 861) as an off-white solid. LRMS (ES) m/z 458 (M+H).

The following compounds were prepared by methods analogous to the method described for Compound 861:

| Compound No. | LRMS (ES) m/z |
|---|---|
| 612 | M + H = 508 |
| 633 | M + H = 424 |

-continued

| Compound No. | LRMS (ES) m/z |
|---|---|
| 636 | M + H = 432 |
| 639 | M + H = 472 |
| 640 | M + H = 438 |
| 645 | M + H = 454.0 |
| 646 | M + H = 408 |
| 647 | M + H = 426 |
| 648 | M + H = 442 |
| 649 | M + H = 476 |
| 650 | M + H = 440 |
| 651 | M + H = 468 |
| 654 | M + H = 420 |
| 655 | M + H = 434 |
| 656 | M + H = 487 |
| 657 | M + H = 466 |
| 661 | M + H = 513 |
| 662 | M + H = 479 |
| 664 | M + H = 422.0 |
| 666 | M + H = 404.0 |
| 667 | M + H = 422.0 |
| 668 | M + H = 442.0 |
| 700 | M + H = 451 |
| 706 | M + H = 398.0 |
| 707 | M + H = 452.0 |
| 708 | M + H = 468.0 |
| 714 | M + H = 404 |
| 717 | M + H = 438 |
| 720 | M + H = 422 |
| 724 | M + H = 418 |
| 727 | M + H = 418 |
| 730 | M + H = 438 |
| 733 | M + H = 400 |

3. Separation of Compound 861 Enantiomers: Enantiomers 861A and 861B

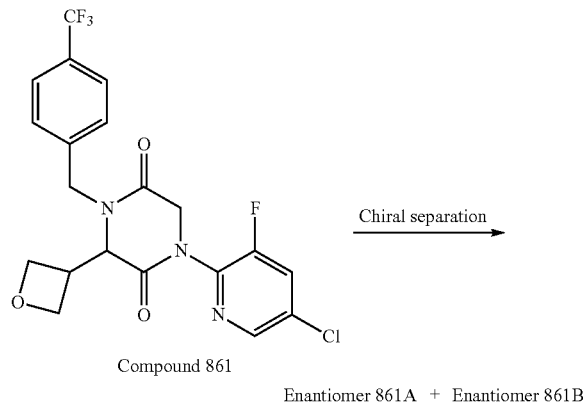

Compound 861

Enantiomer 861A + Enantiomer 861B

The racemic compound of 1-(5-chloro-3-fluoropyridin-2-yl)-3-(oxetan-3-yl)-4-(4-(trifluoromethyl)benzyl)piperazine-2,5-dione (26 g, 57 mmol, 1.0 equiv) was separated by Prep-SFC with the following conditions (Prep SFC80-1): Column, CHIRALPAK IC, 3*25 cm, 5 um; mobile phase, $CO_2$ (65%) and EtOH-(35%); Detector, UV254 nm) to afford 11.4 g (first eluted peak) of Enantiomer 861A and 11.2 g (second eluted peak) of Enantiomers 861B as white solids.

Characterization of Enantiomer 861A. LCMS (ES) m/z 458 (M+H). $^1$H NMR (300 MHz, DMSO-$d_6$) δ 8.48 (d, J=2.1 Hz, 1H), 8.24 (dd, J=9.5, 2.1 Hz, 1H), 7.72 (d, J=8.1 Hz, 2H), 7.49 (d, J=8.0 Hz, 2H), 4.84 (dd, J=16.4, 11.0 Hz, 2H), 4.71-4.51 (m, 3H), 4.54-4.38 (m, 2H), 4.37 (d, J=16.9 Hz, 1H), 4.25 (dd, J=7.9, 6.0 Hz, 1H), 3.76 (h, J=7.7 Hz, 1H). Analytical chiral HPLC RT: 0.51 min (CHIRALPAK IC-U; 0.3 cm×5 cm; 1.6 micro; MtBE (0.1% DEA): EtOH=60:40 at 0.7 ml/min).

Characterization of Enantiomer 861B. LCMS (ES) m/z 458 (M+H). $^1$H NMR (300 MHz, DMSO-$d_6$) δ 8.48 (d, J=2.1 Hz, 1H), 8.24 (dd, J=9.4, 2.2 Hz, 1H), 7.72 (d, J=8.1 Hz, 2H), 7.49 (d, J=8.0 Hz, 2H), 4.84 (dd, J=16.4, 11.1 Hz, 2H), 4.71-4.51 (m, 3H), 4.54-4.38 (m, 2H), 4.38 (d, J=16.9 Hz, 1H), 4.25 (dd, J=7.9, 6.0 Hz, 1H), 3.76 (h, J=7.8 Hz, 1H). Analytical chiral HPLC RT: 0.64 min (CHIRALPAK IC-U; 0.3 cm×5 cm; 1.6 micro; MtBE (0.1% DEA): EtOH=60:40 at 0.7 ml/min).

The following compounds were prepared by methods analogous to the method described for Enantiomers 861A and 861B:

| HPLC Separation Conditions | |
|---|---|
| Letter | HPLC Conditions |
| I | CHIRALPAK IE-3; 0.46 cm × 5 cm; 3 micro; Hex(0.1% DEA):EtOH = 50:50 at 1 ml/min |
| J | CHIRALPAK ID-3; 0.46 cm × 5 cm; 3 micro; Hex(0.1% DEA):EtOH = 50:50 at 1 ml/min |
| K | CHIRALPAK IA-U; 0.3 cm × 5 cm; 1.6 micro; MtBE(0.1% DEA):EtOH = 50:50 at 0.7 ml/min |
| L | CHIRALPAK IE-3; 0.46 cm × 5 cm; 3 micro; MtBE(0.1% DEA):MeOH = 50:50 at 1 ml/min |
| M | CHIRALPAK IG-3; 0.46 cm × 5 cm; 3 micro; MtBE(0.1% DEA):EtOH = 50:50 at 1 ml/min |
| N | CHIRALPAK IC-3; 0.46 cm × 5 cm; 3 micro; (Hex:DCM = 3:1)(0.1% DEA):EtOH = 50:50 at 1 ml/min |
| O | CHIRALPAK IC-3; 0.46 cm × 5 cm; 3 micro; (Hex:DCM = 3:1)(0.1% DEA):EtOH = 50:50 at 2 ml/min |
| P | CHIRALPAK IC-3; 0.46 cm × 5 cm; 3 micro; (Hex:DCM = 1:1)(0.1% DEA):EtOH = 50:50 at 1 ml/min |
| Q | CHIRALPAK IE-3; 0.46 cm × 5 cm; 3 micro; MtBE(0.1% DEA):EtOH = 50:50 at 1 ml/min |
| R | CHIRALPAK ID-3; 0.46 cm × 5 cm; 3 micro; MtBE(0.1% DEA):MeOH = 50:50 at 1 ml/min |
| S | CHIRAL Cellulose-SB; 0.46 cm × 10 cm; 3 micro; MtBE(0.1% DEA):EtOH = 70:30 at 1 ml/min |
| T | CHIRALPAK IE-3; 0.46 cm × 5 cm; 3 micro; (Hex:DCM = 3:1)(0.1% DEA):EtOH = 50:50 at 1 ml/min |
| X | CHIRALPAK ID-3; 0.46 cm × 5 cm; 3 micro; MtBE(0.1% DEA):EtOH = 50:50 at 1 ml/min |

| Compound No. | LRMS (ES) m/z | Retention Time (min) | HPLC Separation Conditions |
|---|---|---|---|
| 863A | M + H = 410 | 1.982 | I |
| 863B | M + H = 410 | 2.875 | I |
| 573A | M + H = 446 | 1.196 | J |
| 573B | M + H = 446 | 1.640 | J |
| 864A | M + H = 458 | 1.111 | J |
| 864B | M + H = 458 | 2.081 | J |
| 612A | M + H = 508 | 0.899 | K |
| 612B | M + H = 508 | 1.179 | K |
| 633A | M + H = 424 | 1.038 | L |
| 633B | M + H = 424 | 1.94 | L |
| 636A | M + H = 432 | 0.97 | M |
| 636B | M + H = 432 | 1.33 | M |
| 657A | M + H = 466 | 1.29 | I |
| 657B | M + H = 466 | 2.30 | I |
| 650A | M + H = 440 | 2.17 | N |
| 650B | M + H = 440 | 3.16 | N |
| 654A | M + H = 420 | 2.18 | N |
| 654B | M + H = 420 | 2.90 | N |
| 639A | M + H = 472 | 1.77 | N |
| 639B | M + H = 472 | 3.10 | N |
| 640A | M + H = 438 | 1.34 | O |
| 640B | M + H = 438 | 2.02 | O |
| 643A | M + H = 499 | 1.38 | O |
| 644A | M + H = 465 | 2.28 | P |
| 649A | M + H = 476 | 1.55 | N |

| | HPLC Separation Conditions | | | |
|---|---|---|---|---|
| 649B | M + H = 476 | 2.86 | N | |
| 647A | M + H = 426 | 1.47 | P | |
| 647B | M + H = 426 | 2.55 | P | |
| 646A | M + H = 408 | 2.24 | N | |
| 646B | M + H = 408 | 3.46 | N | |
| 648A | M + H = 442 | 1.52 | P | |
| 648B | M + H = 442 | 2.64 | P | |
| 645A | M + H = 454 | 1.01 | Q | |
| 664A | M + H = 422 | 2.61 | N | |
| 664B | M + H = 422 | 3.91 | N | |
| 667A | M + H = 422 | 2.21 | N | |
| 667B | M + H = 422 | 2.93 | N | |
| 668A | M + H = 442 | 2.07 | N | |
| 668B | M + H = 442 | 3.30 | N | |
| 714A | M + H = 404 | 1.10 | R | |
| 714B | M + H = 404 | 3.07 | R | |
| 717A | M + H = 438 | 2.87 | S | |
| 717B | M + H = 438 | 3.27 | S | |
| 720A | M + H = 422 | 1.02 | R | |
| 720B | M + H = 422 | 2.76 | R | |
| 724A | M + H = 418 | 1.46 | X | |
| 724B | M + H = 418 | 3.89 | X | |
| 727B | M + H = 418 | 1.78 | T | |
| 727A | M + H = 418 | 2.58 | T | |
| 730A | M + H = 438 | 1.14 | Q | |
| 730B | M + H = 438 | 2.15 | Q | |
| 730A | M + H = 400 | 1.31 | Q | |
| 730B | M + H = 400 | 2.54 | Q | |

| Compound No. | LRMS (ES) m/z | Retention Time (min) | SFC Conditions |
|---|---|---|---|
| 666A | M + H = 404 | 1.39 | CHIRALPAK AS-3; 0.3 cm × 10 cm; 3 micro; Gradient A: CO2; Gradient (B %): MeOH(0.1% DEA); Gradient (B %): 5% to 20% in 2 min, hold 1 min at 20%; at 2 ml/min |
| 666B | M + H = 404 | 1.83 | |

| Compound No. | LRMS (ES) m/z | ¹H NMR |
|---|---|---|
| 865A | M + H = 446 | (300 MHz, DMSO-$d_6$) δ 8.50 (d, J = 2.1 Hz 1H), 8.26 (dd, J = 9.0, 2.4 Hz, 1H), 7.73 (d, J = 8.2 Hz, 2H), 7.54 (d, J = 8.2 Hz, 2H), 5.52 (t, J = 4.6, Hz, 1H), 5.04 (d, J = 15.6 Hz, 1H), 4.64 (q, J = 6.9 Hz, 1H), 4.41 (d,J = 15.9 Hz, 1H), 4.11 (s, 1H), 3.90-3.75 (m, 2 H), 1.53 (d, J = 6.9 Hz, 3H) |
| 888A | M + H = 446 | (300 MHz, DMSO-$d_6$) δ 8.52 (s, 1H), 8.50 (d, J = 2.1 Hz 1H), 8.25 (dd, J = 9.3, 2.1 Hz, 1H), 7.72 (d, J = 8.1 Hz, 2H), 7.56 (d, J = 8.1 Hz, 2H), 5.52 (br, 1H), 5.13 (d, J = 15.9 Hz, 1H), 4.85 (q, J = 7 Hz, 1H), 4.42 (d,J = 15.9 Hz, 1H), 4.21 (s, 1H), 3.92-3.73 (m, 2 H), 1.18 (d, J = 7 Hz, 3H) |

The following compounds were prepared by methods analogous to the method described for Enantiomers 861A and 861B and using racemic 2-((tert-butyldimethylsilyl)oxy)propanal instead of oxetane-3-carbaldehyde:

| Compound No. | LRMS (ES) m/z | ¹H NMR |
|---|---|---|
| 858A | M + H = 446 | (400 MHz, Methylene Chloride-$d_2$) δ 8.21 (d, J = 2.1 Hz, 1H), 7.58-7.47 (m, 3H), 7.33 (d, J = 8.0 Hz, 2H), 5.37 (d, J = 15.5 Hz, 1H), 4.72 (dd, J = 16.7, 4.1 Hz, 1H), 4.29-4.19 (m, 2H), 4.16 (d, J = 15.5 Hz, 1H), 3.91 (d, J = 4.1 Hz, 1H), 2.57 (s, 1H), 1.27 (dd, J = 6.5, 4.1 Hz, 3H) |
| 858B | M + H = 446 | (400 MHz, Methylene Chloride-$d_2$) δ 8.19 (d, J = 2.1 Hz, 1H), 7.57-7.46 (m, 3H), 7.35 (d, J = 8.0 Hz, 2H), 5.19 (s, 1H), 4.72 (d, J = 16.6 Hz, 1H), 4.28-4.13 (m, 3H), 3.79 (d, J = 2.4 Hz, 1H), 3.00 (s, 1H), 1.24 (d, J = 6.6 Hz, 3H) |

The following compounds were prepared by methods analogous to the method described for Enantiomers 861A and 861B and using (S)-2-((tert-butyldimethylsilyl)oxy)propanal instead of oxetane-3-carbaldehyde:

| Compound No. | LRMS (ES) m/z | $^1$H NMR |
|---|---|---|
| 858C | M + H = 446 | (400 MHz, Methylene Chloride-d$_2$) δ 8.21 (d, J = 2.1 Hz, 1H), 7.58-7.47 (m, 3H), 7.35 (dd, J = 13.0, 8.0 Hz, 2H), 5.18 (d, J = 15.5 Hz, 1H), 4.72 (dd, J = 16.7, 3.2 Hz, 1H), 4.24 (dd, J = 16.0, 6.2 Hz, 2H), 4.22-4.12 (m, 1H), 3.81 (d, J = 2.4 Hz, 1H), 2.28 (s, 1H), 1.27 (d, J = 6.5 Hz, 3H). |
| 858D | M + H = 446 | (400 MHz, Methylene Chloride-d$_2$) δ 8.21 (d, J = 2.0 Hz, 1H), 7.58-7.48 (m, 3H), 7.33 (d,J = 8.0 Hz, 2H), 5.37 (d, J = 15.5 Hz, 1H), 4.71 (d, J = 16.8 Hz, 1H), 4.28-4.16 (m, 2H), 4.15 (d,J = 15.5 Hz, 1H), 3.90 (d, J = 4.1 Hz, 1H), 2.76 (s, 1H), 1.27 (d, J = 6.5 Hz, 3H). |

Example 63: Synthesis of tert-butyl 3-((5-chloro-3-fluoropyridin-2-yl)carbamoyl)-3-(2-chloro-N-(4-(difluoromethyl)benzyl)acetamido)cyclobutane-1-carboxylate (mixture of Intermediate Diastereomers 71-1A and 71-1B

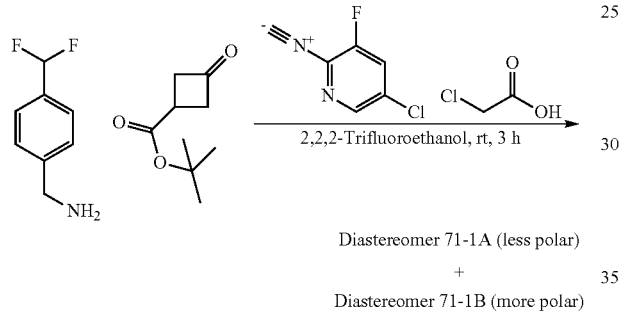

Diastereomer 71-1A (less polar)
+
Diastereomer 71-1B (more polar)

To a solution of (4-(difluoromethyl)phenyl)methanamine (1.0 g, 6.3 mmol, 1.0 equiv) in 2,2,2-trifluoroethanol (5.0 mL) was added tert-butyl 3-oxocyclobutane-1-carboxylate (1.1 g, 6.3 mmol, 1.0 equiv). After stirring at r.t. for 10 min, to this resulting mixture were added 5-chloro-3-fluoro-2-isocyanopyridine (1.0 g, 6.3 mmol, 1.0 equiv) and chloroacetic acid (0.66 g, 7.0 mmol, 1.1 equiv). The resulting mixture was stirred at r.t. overnight, concentrated under reduced pressure, and purified silica gel chromatography, eluted with EA/HE to afford 800 mg (22%) of Intermediate Diastereomer 71-1A (first peak, less polar) and 1.0 g (28%) of Intermediate Diastereomer 71-1B (second peak, more polar). LRMS (ES) m/z 560 (M+H) for both isomers.

Example 64: Synthesis of Compound 630

1. Synthesis of Intermediate 64-1

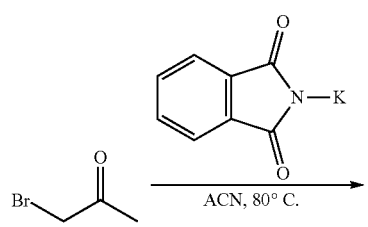

-continued

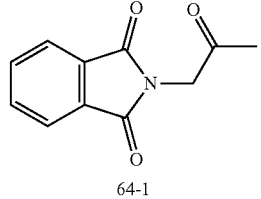

64-1

To a solution of 1-bromopropan-2-one (5 g, 36.5 mmol, 1.0 equiv) in ACN (50 mL) was added potassium 1,3-dioxoisoindolin-2-ide (7.5 g, 40.5 mmol, 1.11 equiv.). The mixture was stirred at 80° C. for 2 h, cooled to rt, and quenched with water (50 mL), and extracted with DCM (50 mL) twice. The combined organic layer was washed with brine (100 mL), dried over Na$_2$SO$_4$, concentrated under reduced pressure, and purified by silica gel column chromatography using PE/EA (1/2) as eluent to afford 6.6 g of 2-(2-oxopropyl)isoindoline-1,3-dione (Intermediate 64-1) as a yellow solid. LRMS (ES) m/z 204 (M+H).

2. Synthesis of Intermediate 64-2

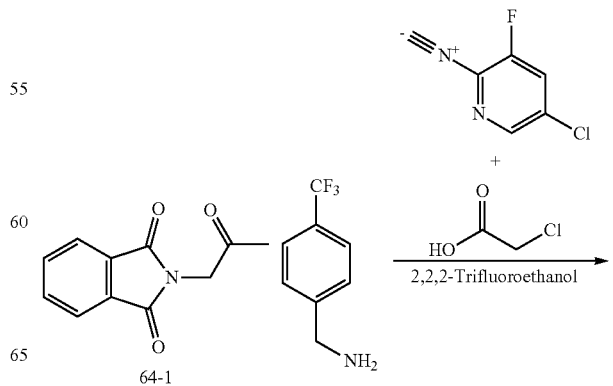

-continued

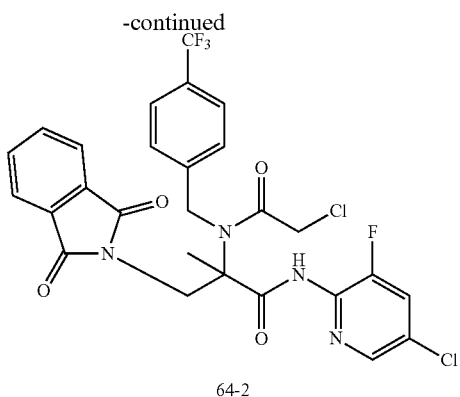

64-2

To a solution of 1-[4-(trifluoromethyl)phenyl]methanamine (1.7 g, 9.7 mmol, 1.5 equiv) in trifluoroethanol (10.0 mL) was added 2-(2-oxopropyl)isoindoline-1,3-dione (2.0 g, 9.6 mmol, 1.5 equiv). After stirring at r.t. for 10 min, to the mixture was added 5-chloro-3-fluoro-2-isocyanopyridine (1.0 g, 6.4 mmol, 1.0 equiv) and chloroacetic acid (899.4 mg, 9.5 mmol, 1.5 equiv). The resulting mixture was stirred at 60° C. overnight, concentrated under vacuum, and purified by C18 column, eluted with water (0.5% NH₄HCO₃)/ACN (1/5) to afford 750 mg of N-(5-chloro-3-fluoropyridin-2-yl)-2-(2-chloro-N-[[4-(trifluoromethyl)phenyl]methyl]acetamido)-3-(1,3-dioxoisoindol-2-yl)-2-methylpropanamide (Intermediate 64-2) as a yellow oil. LRMS (ES) m/z 611 (M+H).

3. Synthesis of Intermediate 64-3

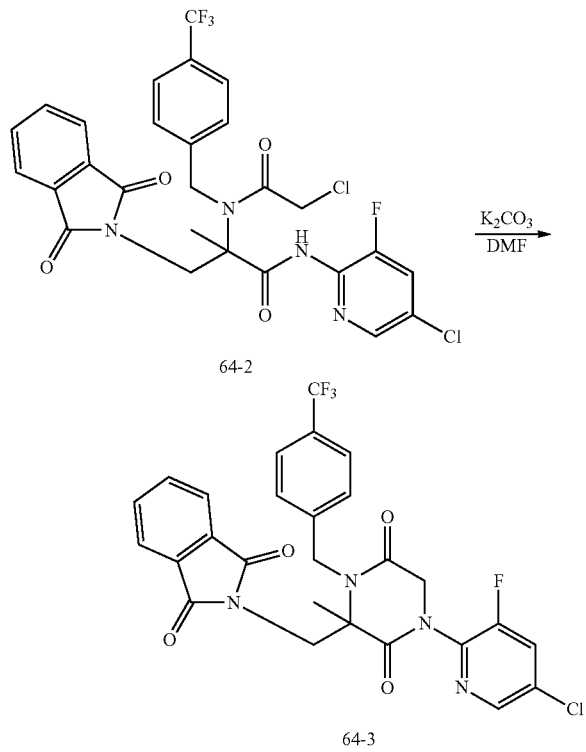

To a solution of N-(5-chloro-3-fluoropyridin-2-yl)-2-(2-chloro-N-[[4-(trifluoromethyl)phenyl]methyl]acetamido)-3-(1,3-dioxoisoindol-2-yl)-2-methylpropanamide (700.0 mg, 1.1 mmol, 1.0 equiv) in dimethylformamide (7.0 mL) was added potassium carbonate (317.0 mg, 2.3 mmol, 2.0 equiv). The resulting mixture was stirred at 60° C. for 30 min, cooled to r.t., and diluted with water (15 mL). The precipitates were collected by filtration, washed with water (10 mL) twice, dried, and purified by silica gel column chromatography, eluted with PE/EtOAc (4:/) to afford 400 mg of 2-((4-(5-chloro-3-fluoropyridin-2-yl)-2-methyl-3,6-dioxo-1-(4-(trifluoromethyl)benzyl)piperazin-2-yl)methyl)isoindoline-1,3-dione (Intermediate 64-3) as an off-white solid. LRMS (ES) m/z 575 (M+H).

4. Synthesis of Intermediate 64-4

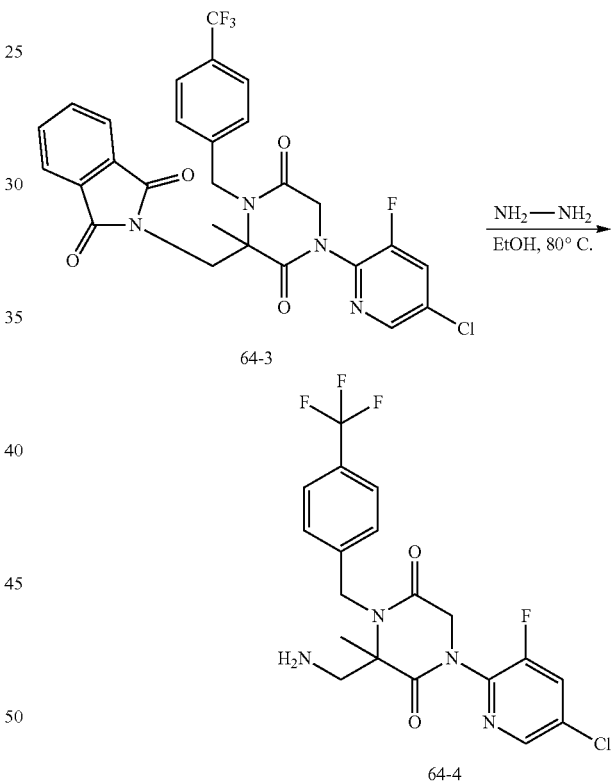

To a solution of 2-((4-(5-chloro-3-fluoropyridin-2-yl)-2-methyl-3,6-dioxo-1-(4-(trifluoromethyl)benzyl)piperazin-2-yl)methyl)isoindoline-1,3-dione (320.0 mg, 0.56 mmol, 1.0 equiv) in EtOH (5.0 mL) was added NH₂NH₂.H₂O (83.0 mg, 1.7 mmol, 3.0 equiv). The resulting mixture was stirred at 80° C. for 2 h, cooled to r.t, filtered to remove solids, and concentrated under reduced pressure to afford 200 mg of 3-(aminomethyl)-1-(5-chloro-3-fluoropyridin-2-yl)-3-methyl-4-(4-(trifluoromethyl)benzyl)piperazine-2,5-dione (Intermediate 64-4) as a yellow oil. LRMS (ES) m/z 445 (M+H).

5. Synthesis of Compound 630

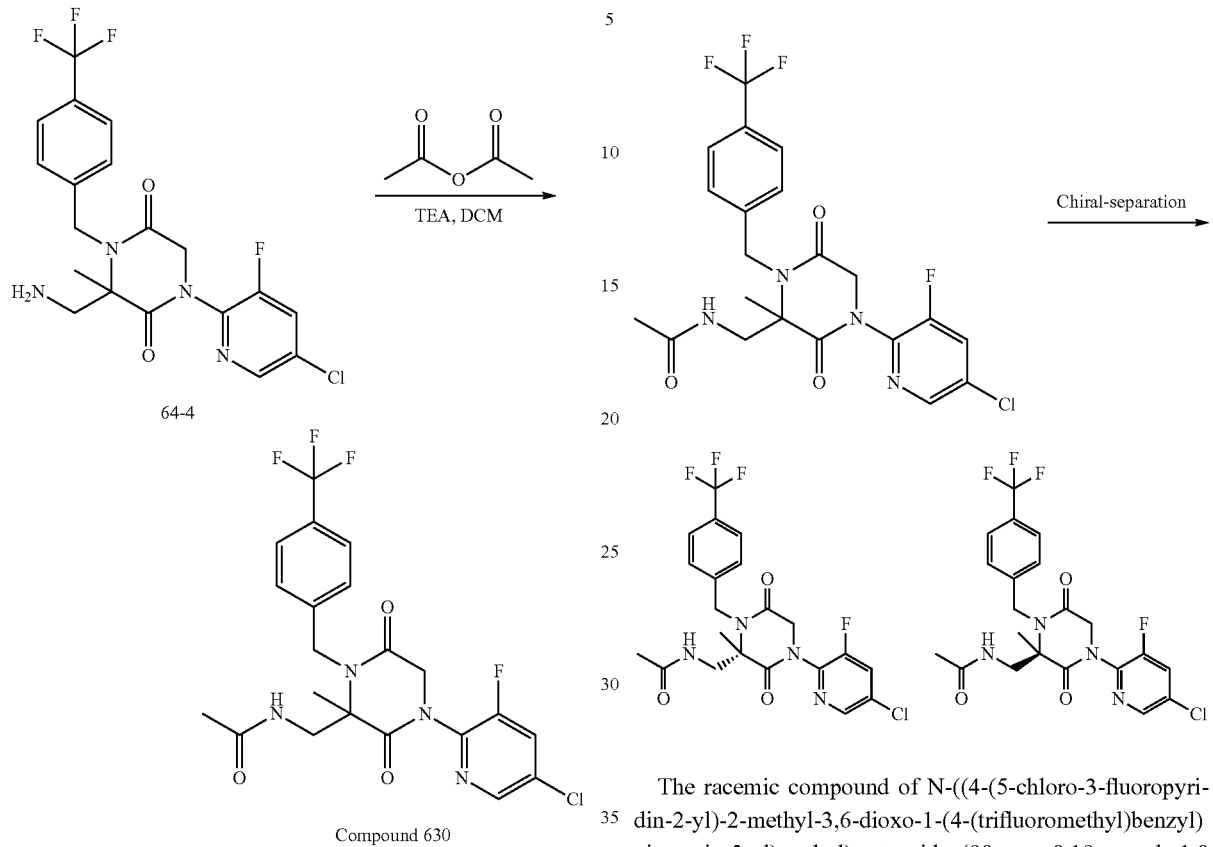

Compound 630

To a solution of 3-(aminomethyl)-1-(5-chloro-3-fluoropyridin-2-yl)-3-methyl-4-(4-(trifluoromethyl)benzyl)piperazine-2,5-dione (200 mg, 0.45 mmol, 1.0 equiv) in DCM (2 mL) were added acetic anhydride (55 mg, 0.54 mmol, 1.2 equiv.) and TEA (91 mg, 0.9 mmol, 2.0 equiv.). The mixture was stirred at rt for 2 h, concentrated under reduced pressure, and purified Prep-HPLC with the following conditions: (SHIMADZU (HPLC-01)): Column, XBridge Prep OBD C18 Column, 30*150 mm 5 um; mobile phase, Water (10 mM $NH_4HCO_3$+0.1% $NH_3·H_2O$) and ACN (38% gradient up to 60% in 9 min); Detector UV 254 nm) to afford 140 mg of N-((4-(5-chloro-3-fluoropyridin-2-yl)-2-methyl-3,6-dioxo-1-(4-(trifluoromethyl)benzyl)piperazin-2-yl)methyl)acetamide (Compound 630) as a white solid. LCMS (ES) m/z 487 (M+H). $^1$H NMR (300 MHz, Methanol-$d_4$) δ 8.42 (d, J=1.9 Hz, 1H), 7.94 (d, J=9.1 Hz, 1H), 7.66 (d, J=8.1 Hz, 2H), 7.53 (d, J=8.1 Hz, 2H), 5.29 (d, J=16.7 Hz, 1H), 4.83-4.75 (m, 1H), 4.58-4.44 (m, 2H), 3.96 (d, J=14.0 Hz, 1H), 3.53 (d, J=14.4 Hz, 1H), 1.96 (d, J=1.5 Hz, 3H), 1.58-1.51 (m, 3H).

The following compound was prepared by methods analogous to the method described for Compound 861:

| Compound No. | LRMS (ES) m/z |
|---|---|
| 631 | M + H = 453 |

6. Separation of Compound 630 Enantiomers: Enantiomers 630A and 630B

The racemic compound of N-((4-(5-chloro-3-fluoropyridin-2-yl)-2-methyl-3,6-dioxo-1-(4-(trifluoromethyl)benzyl)piperazin-2-yl)methyl)acetamide (90 mg, 0.19 mmol, 1.0 equiv) was purified by Chiral-Prep-HPLC with the following conditions ((Prep-HPLC-009): Column, CHIRALPAK IE, 2*25 cm, 5 um; mobile phase, 30% EtOH in Hex (8 mM $NH_3·MeOH$) for 15 min; Detector, UV254 nm) to afford 37 mg of (first eluted peak) Enantiomer 630A and 39 mg of (second eluted peak) Enantiomer 630B as white solids.

Characterization of Enantiomer 630A. LCMS (ES) m/z 487 (M+H). $^1$H NMR (300 MHz, DMSO-$d_6$) δ 8.51 (d, J=2.1 Hz, 1H), 8.29-8.20 (m, 2H), 7.70 (d, J=8.1 Hz, 2H), 7.52 (d, J=8.0 Hz, 2H), 5.07 (d, J=16.9 Hz, 1H), 4.64 (d, J=17.0 Hz, 1H), 4.46 (t, J=17.5 Hz, 2H), 3.81 (dd, J=14.1, 7.1 Hz, 1H), 3.37 (dd, J=14.1, 5.4 Hz, 1H), 1.82 (s, 3H), 1.43 (s, 3H). Analytical chiral HPLC RT: 2.33 min (CHIRALPAK IE-3; 0.46 cm×5 cm; 3 micro; Hex (0.1% DEA):EtOH=70:30 at 1 ml/min).

Characterization of Enantiomer 630B. LCMS (ES) m/z 487 (M+H). $^1$H NMR (300 MHz, DMSO-$d_6$) δ 8.51 (d, J=2.1 Hz, 1H), 8.30-8.20 (m, 2H), 7.70 (d, J=8.1 Hz, 2H), 7.52 (d, J=8.0 Hz, 2H), 5.07 (d, J=16.9 Hz, 1H), 4.64 (d, J=17.0 Hz, 1H), 4.46 (t, J=17.5 Hz, 2H), 3.81 (dd, J=14.1, 7.1 Hz, 1H), 3.44-3.33 (m, 1H), 1.82 (s, 3H), 1.43 (s, 3H). Analytical chiral HPLC RT: 2.71 min (CHIRALPAK IE-3; 0.46 cm×5 cm; 3 micro; Hex (0.1% DEA):EtOH=70:30 at 1 ml/min).

Example 65: Synthesis of Compound 691

1. Synthesis of Intermediate 65-1

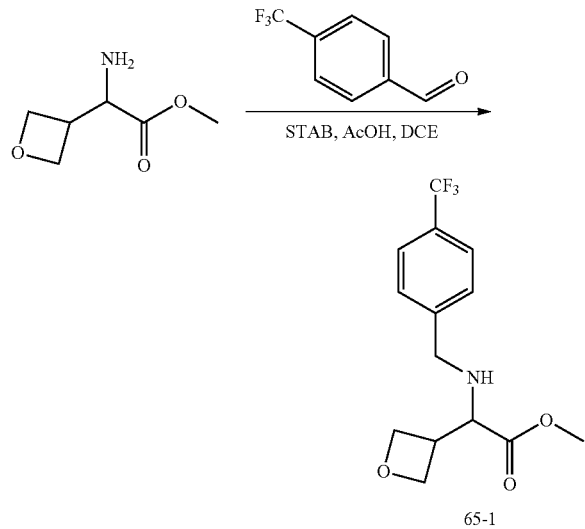

To a solution of methyl 2-amino-2-(oxetan-3-yl)acetate (3.0 g, 20.7 mmol, 1.0 equiv) in DCE (60.0 mL) was added 4-(trifluoromethyl)benzaldehyde (3.6 g, 21 mmol, 1.0 equiv). After stirring at r.t. for 30 min, to the mixture was added AcOH (2.50 g, 41.631 mmol, 2.01 equiv) and STAB (8.80 g, 41.521 mmol, 2.01 equiv) at room temperature. The resulting mixture was stirred at r.t. overnight, adjust the pH to 8 with ammonium hydroxide (200 mL), and extracted with DCM (300 mL) twice. The combined organic layers were washed with brine (200 mL) twice, dried over anhydrous Na$_2$SO$_4$, concentrated under reduced pressure, and purified by C18 column, eluted with water (0.5% NH$_4$HCO$_3$)/ACN (1:1) to afford 5.2 g of methyl 2-(oxetan-3-yl)-2-((4-(trifluoromethyl)benzyl)amino)acetate (Intermediate 65-1) as a yellow solid. LRMS (ES) m/z 304 (M+H).

2. Synthesis of Intermediate 65-2

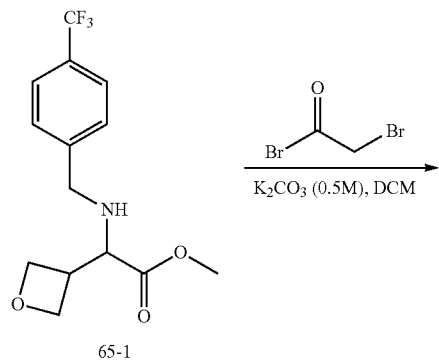

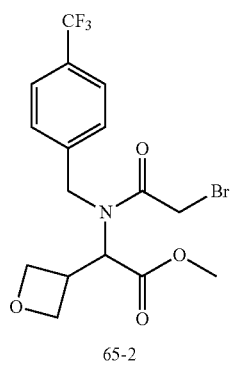

To a solution of methyl 2-(oxetan-3-yl)-2-((4-(trifluoromethyl)benzyl)amino)acetate (5.0 g, 16.5 mmol, 1.0 equiv) in DCM (100 mL) at 0° C. were added K$_2$CO$_3$ (0.5 M, 49 mL, 24.6 mmol, 1.5 equiv) and bromoacetyl bromide (4.0 g, 19.8 mmol, 1.2 equiv). The resulting mixture was stirred at r.t. for 2 h and extracted with DCM (50 mL) twice. The combined organic layers were washed with brine (100 mL) twice, dried over anhydrous Na$_2$SO$_4$, and concentrated under reduced pressure to afford 7.1 g of methyl 2-(2-bromo-N-[[4-(trifluoromethyl)phenyl]methyl]acetamido)-2-(oxetan-3-yl)acetate (Intermediate 65-2) as a yellow oil. LRMS (ES) m/z 424 (M+H).

3. Synthesis of Intermediate 65-3

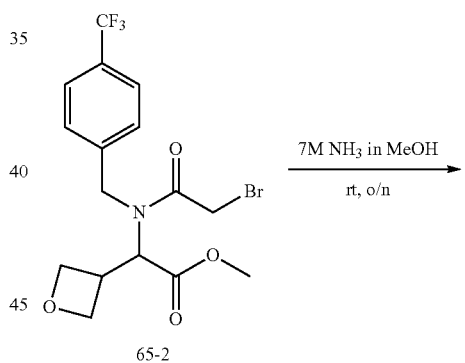

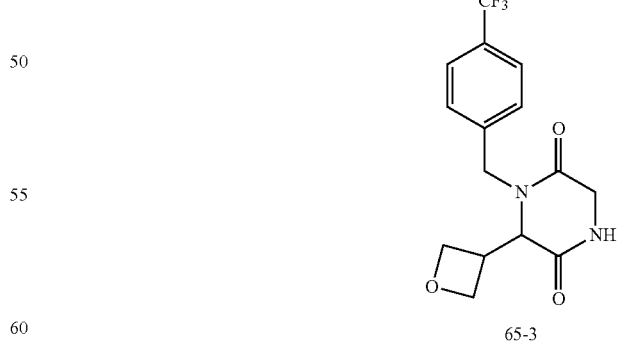

To methyl 2-(2-bromo-N-[[4-(trifluoromethyl)phenyl]methyl]acetamido)-2-(oxetan-3-yl)acetate (7.0 g, 16.5 mmol, 1.0 equiv) in RB flask was added NH$_3$ in MeOH (70.0 mL, 7M). The mixture was stirred at r.t. overnight, concentrated under vacuum, and triturated with ethyl acetate (100 mL) to afford 5.7 g of 6-(oxetan-3-yl)-1-(4-(trifluoromethyl)benzyl)piperazine-2,5-dione (Intermediate 65-3) as an off-white solid. LRMS (ES) m/z 329 (M+H).

4. Synthesis of Compound 691

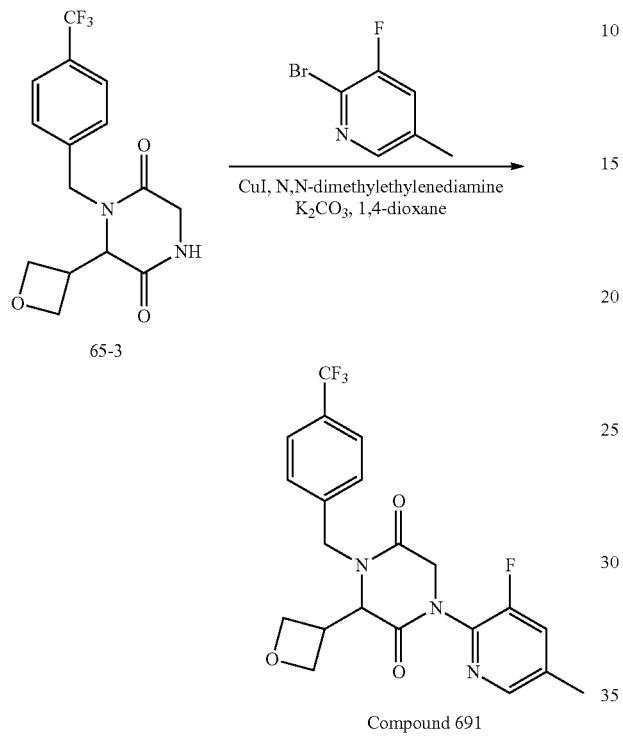

To a solution of 6-(oxetan-3-yl)-1-(4-(trifluoromethyl)benzyl)piperazine-2,5-dione (120.0 mg, 0.37 mmol, 1.0 equiv) in dioxane (4 mL) at r.t. were added (2-aminoethyl)dimethylamine (18.0 mg, 0.21 mmol, 0.56 equiv), 2-bromo-3-fluoro-5-methylpyridine (102.1 mg, 0.54 mmol, 1.5 equiv), CuI (36.2 mg, 0.19 mmol, 0.5 equiv), and $K_2CO_3$ (150.0 mg, 1.1 mmol, 3.0 equiv.). The resulting mixture was stirred at 115° C. for 2 h under nitrogen, cooled to r.t., diluted with water (10 mL), and extracted with EtOAc (10 mL) twice. The combined organic layers were washed with brine (10 mL) twice, dried over anhydrous $Na_2SO_4$, concentrated under reduced pressure, and purified by Prep-HPLC with the following conditions (SHIMADZU (HPLC-01)): Column, XBridge Shield RP18 OBD Column, 5 um, 19*150 mm; mobile phase, Water (0.05% TFA) and ACN (43% gradient up to 45% in 9 min); Detector, UV254 nm) to afford 100 mg of 1-(3-fluoro-5-methylpyridin-2-yl)-3-(oxetan-3-yl)-4-(4-(trifluoromethyl)benzyl)piperazine-2,5-dione (Compound 691) as a yellow oil. LRMS (ES) m/z 438 (M+H). 1H NMR (300 MHz, Methanol-$d_4$) δ 8.21 (s, 1H), 7.69 (d, J=8.1 Hz, 2H), 7.60 (d, J=10.5 Hz, 1H), 7.52 (d, J=8.1 Hz, 2H), 5.00 (d, J=16.1 Hz, 1H), 4.842-4.897 (m, 1H), 4.76 (d, J=17.4 Hz, 1H), 4.68-4.55 (m, 3H), 4.55-4.39 (m, 3H), 3.78 (dt, J=17.4, 8.4 Hz, 1H), 2.42 (d, J=0.8 Hz, 3H).

5. Separation of Compound 691 Enantiomers: Enantiomers 691A and 691B

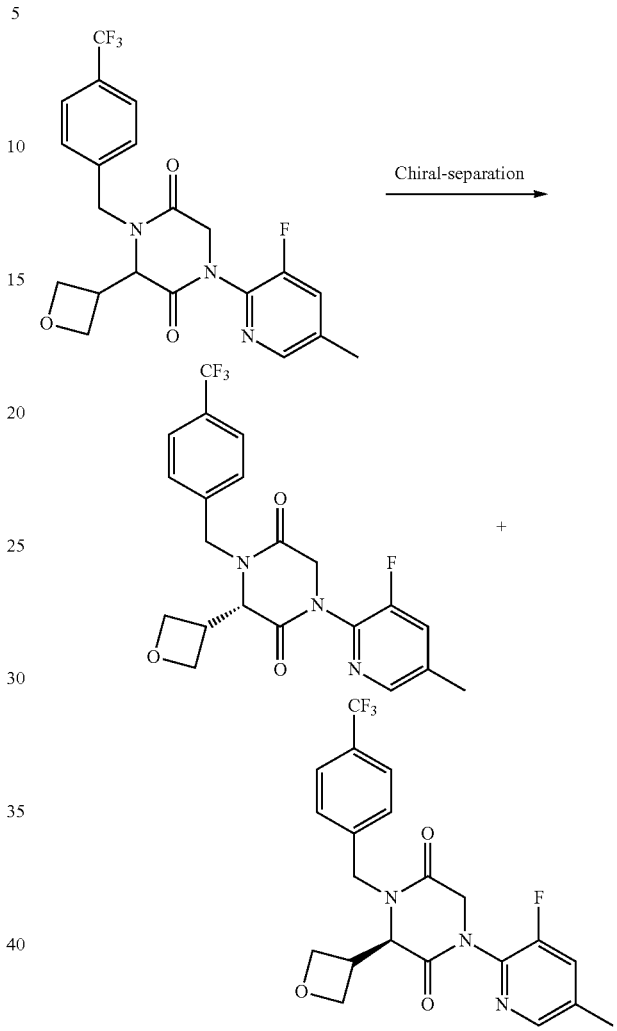

The racemic compound of 1-(3-fluoro-5-methylpyridin-2-yl)-3-(oxetan-3-yl)-4-(4-(trifluoromethyl)benzyl)piperazine-2,5-dione (80 mg, 0.18 mmol, 1.0 equiv) was purified by Chiral-Prep-HPLC with the following conditions ((Prep-HPLC-009): Column, CHIRALPAK IE, 2*25 cm, 5 um; mobile phase, 40% EtOH in MTBE (8 mM $NH_3$.MeOH) for 19 min; Detector, UV 254 nm) to afford 25 mg of (first eluted peak) Enantiomer 691A and 17 mg of (second eluted peak) Enantiomer 691B as white solids.

Characterization of Enantiomer 691A. LCMS (ES) m/z 438 (M+H). $^1$H NMR (300 MHz, Methanol-$d_4$) δ 8.21 (s, 1H), 7.69 (d, J=8.1 Hz, 2H), 7.60 (d, J=10.4 Hz, 1H), 7.52 (d, J=8.1 Hz, 2H), 5.00 (d, J=15.9 Hz, 1H), 4.84-4.89 (m, 1H), 4.76 (d, J=17.4 Hz, 1H), 4.68-4.56 (m, 3H), 4.56-4.40 (m, 3H), 3.86-3.72 (m, 1H), 2.42 (s, 3H). Analytical chiral HPLC RT: 1.16 min (CHIRALPAK IE-3; 0.46 cm×5 cm; 3 micro; MtBE (0.1% DEA):EtOH=50:50 at 1 ml/min).

Characterization of Enantiomer 691B. LCMS (ES) m/z 438 (M+H). $^1$H NMR (300 MHz, Methanol-$d_4$) δ 8.21 (s, 1H), 7.69 (d, J=8.1 Hz, 2H), 7.60 (d, J=10.4 Hz, 1H), 7.52 (d, J=8.0 Hz, 2H), 5.00 (d, J=15.9 Hz, 1H), 4.84-4.89 (m, 1H), 4.76 (d, J=17.4 Hz, 1H), 4.68-4.55 (m, 3H), 4.55-4.40

(m, 3H), 3.86-3.72 (m, 1H), 2.42 (s, 3H). Analytical chiral HPLC RT: 2.76 min (CHIRALPAK IE-3; 0.46 cm×5 cm; 3 micro; MtBE (0.1% DEA):EtOH=50:50 at 1 ml/min).

Example 66: Synthesis of Compound 701

1. Synthesis of Intermediate 66-1

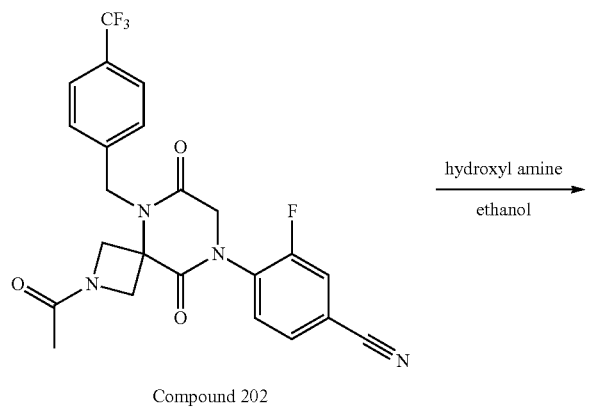

Compound 202

2. Synthesis of Compound 701

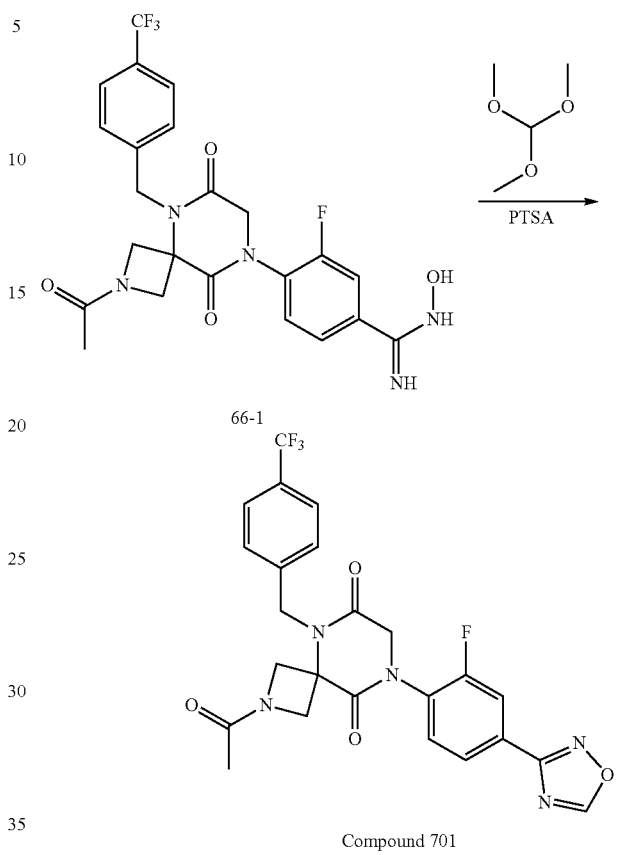

66-1

Compound 701

To a suspension of compound 202 (3.0 g, 6.3 mmol, 1.0 equiv) in ethanol (20.0 mL) was added hydroxyl amine (2.0 mL, 50% wt in water). After stirring at r.t. overnight, the precipitate was collected by filtration, washed with additional water, and dried to give 1.6 g (50%) of 4-(2-acetyl-6,9-dioxo-5-(4-(trifluoromethyl)benzyl)-2,5,8-triazaspiro[3.5]nonan-8-yl)-3-fluoro-N-hydroxybenzimidamide (Intermediate 66-1) as a white solid. LRMS (ES) m/z 508 (M+H). $^1$H NMR (400 MHz, DMSO-$d_6$) δ 9.87 (d, J=1.6 Hz, 1H), 7.78-7.71 (m, 2H), 7.60 (dt, J=19.1, 8.2 Hz, 5H), 5.97 (s, 2H), 5.03 (s, 2H), 4.56 (d, J=9.9 Hz, 1H), 4.49 (s, 2H), 4.38 (d, J=9.7 Hz, 1H), 4.28 (d, J=10.5 Hz, 1H), 4.04 (d, J=10.5 Hz, 1H), 1.75 (s, 3H).

To a solution of 4-(2-acetyl-6,9-dioxo-5-(4-(trifluoromethyl)benzyl)-2,5,8-triazaspiro[3.5]nonan-8-yl)-3-fluoro-N-hydroxybenzimidamide (100 mg, 0.2 mmol, 1.0 equiv) in trimethoxymethane (1.0 mL) at r.t was added PTSA (3.39 mg, 0.02 mmol, 0.1 equiv). The mixture was stirred at reflux overnight, cooled to r.t., concentrated to dryness, and triturated with ACN (5.0 mL). The solid was collected and dried to afford 81 mg (79%) of 2-acetyl-8-(2-fluoro-4-(1,2,4-oxadiazol-3-yl)phenyl)-5-(4-(trifluoromethyl)benzyl)-2,5,8-triazaspiro[3.5]nonane-6,9-dione (Compound 701). LRMS (ES) m/z 518.1 (M+H). $^1$H NMR (400 MHz, Methylene Chloride-$d_2$) δ 8.90 (d, J=1.7 Hz, 1H), 8.07 (dd, J=16.1, 9.6 Hz, 2H), 7.71 (d, J=7.9 Hz, 2H), 7.60-7.51 (m, 1H), 7.47 (d, J=8.0 Hz, 2H), 5.21 (d, J=16.5 Hz, 1H), 5.00 (d, J=16.4 Hz, 1H), 4.77 (d, J=9.3 Hz, 1H), 4.61 (d, J=10.6 Hz, 1H), 4.51 (s, 2H), 4.27 (dd, J=20.0, 9.9 Hz, 2H), 1.86 (d, J=1.7 Hz, 3H).

The following compound was prepared by methods analogous to the method described for Compound 701:

| Compound No. | LRMS (ES) m/z |
|---|---|
| 702 | M + H = 532.0 |

Example 67: Synthesis of Compound 703

1. Synthesis of Intermediate 67-1

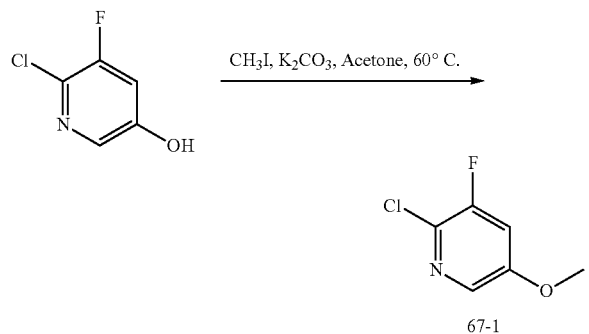

To a solution of 6-chloro-5-fluoropyridin-3-ol (500.0 mg, 3.4 mmol, 1.0 equiv) in acetone (5.0 mL) at r.t. were added K₂CO₃ (697.9 mg, 5.1 mmol, 1.5 equiv) and iodomethane (524.4 mg, 3.7 mmol, 1.1 equiv). The resulting mixture was stirred at 60° C. for 2 h, cooled to r.t., diluted with water (20 mL), and extracted with EtOAc (30 mL) twice. The combined organic layers were washed with brine (30 mL) twice, dried over anhydrous Na₂SO₄, and concentrated under reduced pressure to afford 500 mg of 2-chloro-3-fluoro-5-methoxypyridine (Intermediate 67-1) as a yellow oil. LRMS (ES) m/z 162 (M+H).

2. Synthesis of Compound 703

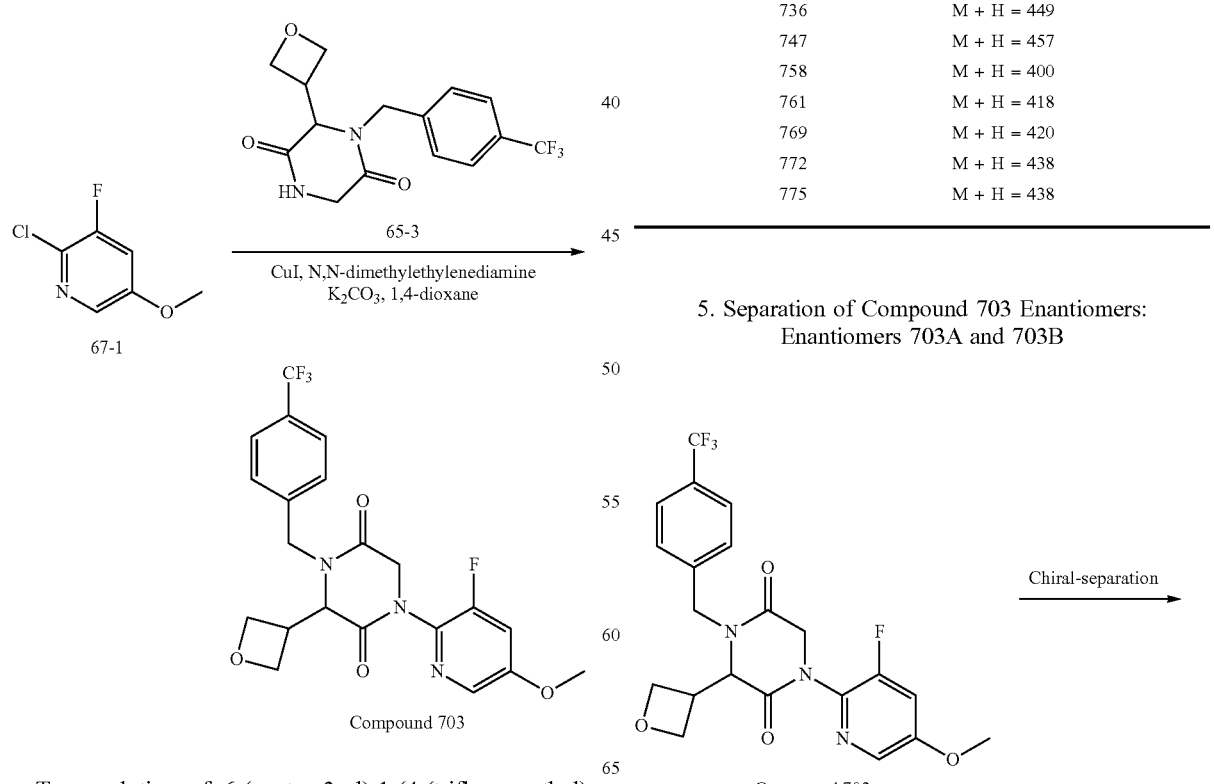

To a solution of 6-(oxetan-3-yl)-1-(4-(trifluoromethyl)benzyl)piperazine-2,5-dione (150.0 mg, 0.46 mmol, 1.0 equiv) in dioxane (1.0 mL) at r.t. were added copper(I) iodide (45.3 mg, 0.24 mmol, 0.5 equiv), 2-chloro-3-fluoro-5-methoxypyridine (112.2 mg, 0.7 mmol, 1.5 equiv), (2-aminoethyl)dimethylamine (22.6 mg, 0.26 mmol, 0.56 equiv), and K₂CO₃ (187.6 mg, 1.36 mmol, 3.0 equiv). The resulting mixture was stirred at 110° C. for 2 h, cooled to r.t., filtered off the solids, diluted with water (10 mL), and extracted with EA (10 ml) twice. The combined organic layers were washed with brine (10 mL) twice, dried over anhydrous Na₂SO₄, concentrated under reduced pressure, and purified by Prep-HPLC with the following conditions ((SHIMADZU (HPLC-01)): Column, XBridge Prep OBD C18 Column, 30*150 mm 5 um; mobile phase, Water (0.05% TFA) and ACN (40% gradient up to 48% in 9 min); Detector, UV254 nm) to afford 100 mg of 1-(3-fluoro-5-methoxypyridin-2-yl)-3-(oxetan-3-yl)-4-(4-(trifluoromethyl)benzyl)piperazine-2,5-dione (Compound 703) as a white solid. LRMS (ES) m/z 454 (M+H). 1H NMR (300 MHz, Methanol-d₄) δ 8.08 (d, J=2.6 Hz, 1H), 7.69 (d, J=8.1 Hz, 2H), 7.52 (d, J=8.1 Hz, 2H), 7.42 (dd, J=10.9, 2.6 Hz, 1H), 5.00 (d, J=15.8 Hz, 1H), 4.83-4.69 (m, 2H), 4.69-4.35 (m, 6H), 3.93 (s, 3H), 3.86-3.69 (m, 1H).

The following compounds were prepared by methods analogous to the method described for Compound 703:

| Compound No. | LRMS (ES) m/z |
| --- | --- |
| 691 | M + H = 438 |
| 711 | M + H = 490 |
| 723 | M + H = 416.1 |
| 736 | M + H = 449 |
| 747 | M + H = 457 |
| 758 | M + H = 400 |
| 761 | M + H = 418 |
| 769 | M + H = 420 |
| 772 | M + H = 438 |
| 775 | M + H = 438 |

5. Separation of Compound 703 Enantiomers: Enantiomers 703A and 703B

-continued

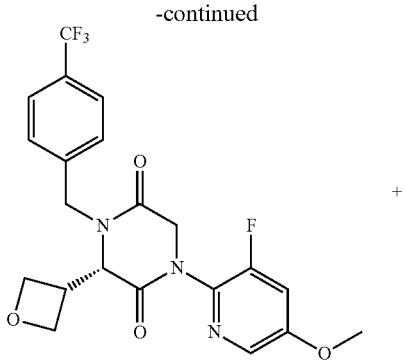

+

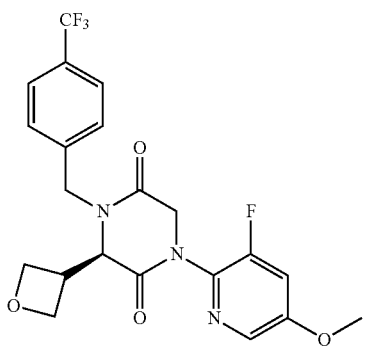

The racemic compound of 1-(3-fluoro-5-methoxypyridin-2-yl)-3-(oxetan-3-yl)-4-(4-(trifluoromethyl)benzyl)piperazine-2,5-dione (80 mg, 0.18 mmol, 1.0 equiv) was purified by Chiral-Prep-HPLC with the following conditions (Agela High-pressure Flash): Column, CHIRALPAK IC, 2*25 cm, 5 um; mobile phase, Hex:DCM=3:1 and EtOH (1/1 for 19 min); Detector, UV254 nm) to afford 28 mg of (first eluted peak) Enantiomer 703A and 28 mg of (second eluted peak) Enantiomer 703B as white solids.

Characterization of Enantiomer 703A. LCMS (ES) m/z 454 (M+H). $^1$H NMR (300 MHz, Methanol-$d_4$) δ 8.08 (d, J=2.5 Hz, 1H), 7.70 (d, J=8.1 Hz, 2H), 7.52 (d, J=8.0 Hz, 2H), 7.42 (dd, J=11.0, 2.6 Hz, 1H), 5.00 (d, J=15.9 Hz, 1H), 4.82 (t, J=7.0 Hz, 1H), 4.75 (d, J=17.3 Hz, 1H), 4.68-4.55 (m, 3H), 4.49 (dd, J=12.6, 8.6 Hz, 2H), 4.47-4.36 (m, 1H), 3.93 (s, 3H), 3.79 (dq, J=16.2, 7.8 Hz, 1H). Analytical chiral HPLC RT: 1.99 min (CHIRALPAK IC-3; 0.46 cm×5 cm; 3 micro; (Hex:DCM=3:1)(0.1% DEA):EtOH=50:50 at 1 ml/min).

Characterization of Enantiomer 703B. LCMS (ES) m/z 454 (M+H). $^1$H NMR (300 MHz, Methanol-$d_4$) δ 8.08 (d, J=2.5 Hz, 1H), 7.70 (d, J=8.1 Hz, 2H), 7.52 (d, J=8.0 Hz, 2H), 7.42 (dd, J=11.0, 2.6 Hz, 1H), 5.00 (d, J=15.9 Hz, 1H), 4.85-4.68 (m, 2H), 4.68-4.55 (m, 3H), 4.54-4.32 (m, 3H), 3.93 (s, 3H), 3.79 (dq, J=16.2, 7.8 Hz, 1H). Analytical chiral HPLC RT: 2.63 min (CHIRALPAK IC-3; 0.46 cm×5 cm; 3 micro; (Hex:DCM=3:1)(0.1% DEA):EtOH=50:50 at 1 ml/min).

The following compounds were prepared by methods analogous to the method described for Enantiomers 703A and 703B:

| HPLC Separation Conditions | |
|---|---|
| Letter | HPLC Conditions |
| Q | CHIRALPAK IE-3; 0.46 cm × 5 cm; 3 micro; MtBE(0.1% DEA):EtOH = 50:50 at 1 ml/min |
| U | CHIRALPAK IE-3; 0.46 cm × 5 cm; 3 micro; MtBE(0.1% DEA):EtOH = 65:35 at 1 ml/min |

| Enantiomer No. | LRMS (ES) m/z | Retention Time (min) | HPLC |
|---|---|---|---|
| 691A | M + H = 438 | 1.16 | Q |
| 691B | M + H = 438 | 2.76 | Q |
| 711A | M + H = 490 | 2.30 | S |
| 711B | M + H = 490 | 2.92 | S |
| 281A | M + H = 457 | 1.20 | T |
| 281B | M + H = 457 | 1.63 | T |
| 747A | M + H = 457 | 0.79 | U |
| 747B | M + H = 457 | 1.66 | U |
| 758A | M + H = 400 | 2.43 | T |
| 758B | M + H = 400 | 4.44 | T |
| 761A | M + H = 418 | 1.41 | U |
| 761B | M + H = 418 | 3.37 | U |
| 769A | M + H = 420 | 1.56 | Q |
| 769B | M + H = 420 | 4.19 | Q |
| 772A | M + H = 438 | 1.23 | L |
| 772B | M + H = 438 | 3.21 | L |
| 775A | M + H = 438 | 1.32 | Q |
| 775B | M + H = 438 | 3.32 | Q |

Example 68: Synthesis of Compound 739

1. Synthesis of Intermediate 68-1

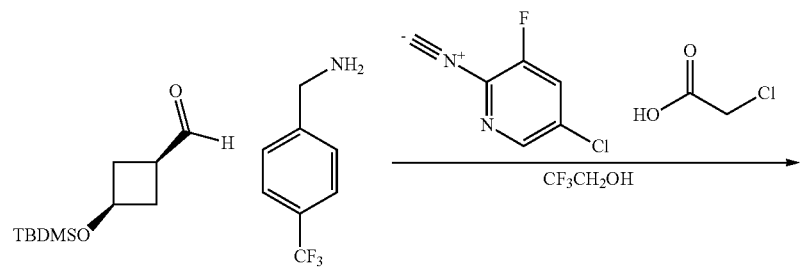

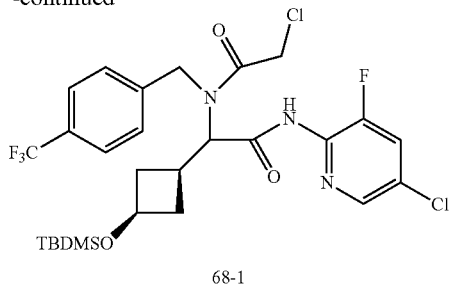

68-1

The mixture of (1s,3s)-3-((tert-butyldimethylsilyl)oxy)cyclobutane-1-(680 mg, 3.17 mmol, 1.0 equiv) and (4-(trifluoromethyl)phenyl)methanamine (556 mg, 3.17 mmol, 1.0 equiv) in 2,2,2-trifluoroethanol (8.0 mL) was stirred at r.t. for 10 min. To this mixture were added 5-chloro-3-fluoro-2-isocyanopyridine (500 mg, 3.17 mmol, 1.0 equiv) and 2-chloroacetic acid (300 mg, 3.17 mmol, 1.0 equiv). The mixture was stirred at r.t. for 3 h, evaporated, purified with 20% EA/Hex to afford 933 mg (47%) of 2-((1s,3s)-3-((tert-butyldimethylsilyl)oxy)cyclobutyl)-N-(5-chloro-3-fluoropyridin-2-yl)-2-(2-chloro-N-(4-(trifluoromethyl)benzyl)acetamido)acetamide (Intermediate 68-1). LRMS (APCI) m/z 623.1 (M+H).

2. Synthesis of Intermediate 68-2

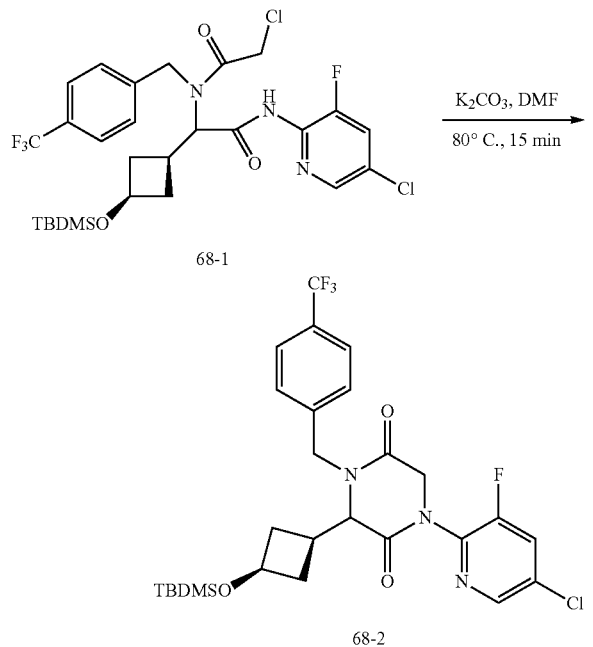

To a solution of 2-((1s,3s)-3-((tert-butyldimethylsilyl)oxy)cyclobutyl)-N-(5-chloro-3-fluoropyridin-2-yl)-2-(2-chloro-N-(4-(trifluoromethyl)benzyl)acetamido)acetamide (933 mg, 1.5 mmol, 1.0 equiv) in DMF (10 mL) was added K₂CO₃ (626 mg, 4.5 mmol, 3.0 equiv). The resulting mixture was stirred at 80° C. for 15 min, cooled to r.t., diluted with EA (100 mL), washed with water (50 mL) three times and brine (50 mL) once, dried over sodium sulfate, and concentrated under reduced pressure to afford 760 mg (87%) of 3-((1s,3s)-3-((tert-butyldimethylsilyl)oxy)cyclobutyl)-1-(5-chloro-3-fluoropyridin-2-O-4-(4-(trifluoromethyl)benzyl)piperazine-2,5-dione (Intermediate 68-2) as a white foam. LRMS (APCI) m/z 586.1 (M+H).

3. Synthesis of Compound 739

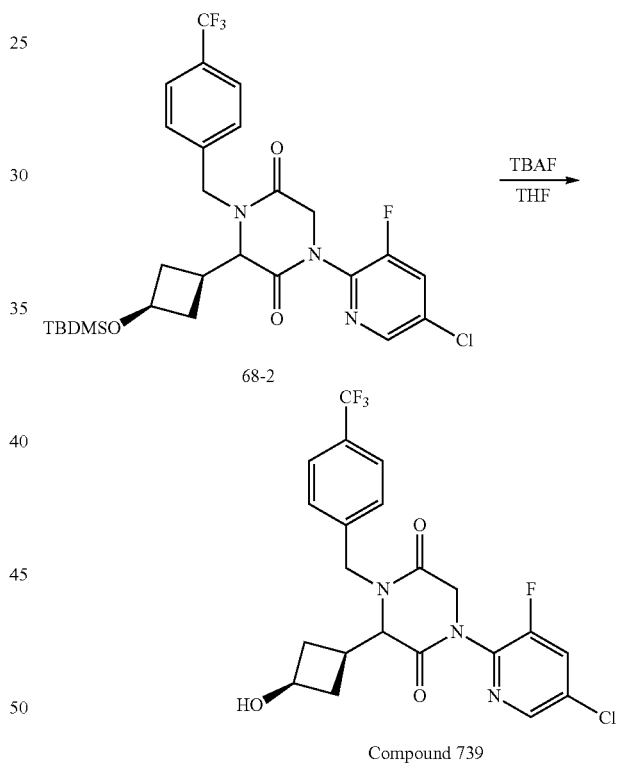

Compound 739

To a solution of 3-((1s,3s)-3-((tert-butyldimethylsilyl)oxy)cyclobutyl)-1-(5-chloro-3-fluoropyridin-2-yl)-4-(4-(trifluoromethyl)benzyl)piperazine-2,5-dione (760 mg, 1.30 mmol, 1.0 equiv) in THF (10 mL) was added TBAF (2.59 mL of 1.0 M in THF, 2.59 mmol, 2.0 equiv). The resulting mixture was stirred at r.t. for 30 min, quenched with saturated aqueous sodium bicarbonate (30 mL), and diluted with DCM (125 mL). The organic phase was washed with brine (75 mL), dried over sodium sulfate, concentrated in vacuo, and purified with silica gel using a gradient from 0-100% EA/Hex to afford 420 mg (69%) of 1-(5-chloro-3-fluoropyridin-2-yl)-3-((1s,3s)-3-hydroxycyclobutyl)-4-(4-(trifluoromethyl)benzyl)piperazine-2,5-dione (Compound 739)

as a white foam. (LRMS (APCI) m/z 472.0 (M+H). $^1$H NMR (400 MHz, DMSO-d$_6$) δ 8.49 (d, J=2.1 Hz, 1H), 8.26 (dd, J=9.4, 2.1 Hz, 1H), 7.75 (d, J=8.1 Hz, 2H), 7.52 (d, J=8.1 Hz, 2H), 5.10-5.01 (m, 2H), 4.75 (d, J=17.0 Hz, 1H), 4.37 (dd, J=17.0, 13.5 Hz, 2H), 4.05 (d, J=8.0 Hz, 1H), 3.92-3.81 (m, 1H), 2.35-2.14 (m, 3H), 1.76 (m, 2H).

Example 69: Synthesis of Compound 740

1. Synthesis of Intermediate 69-1

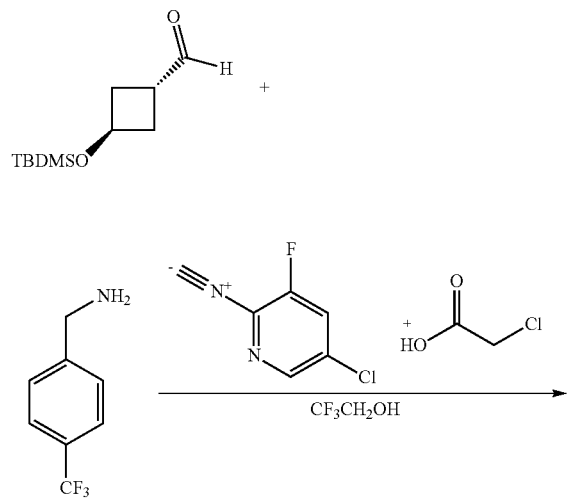

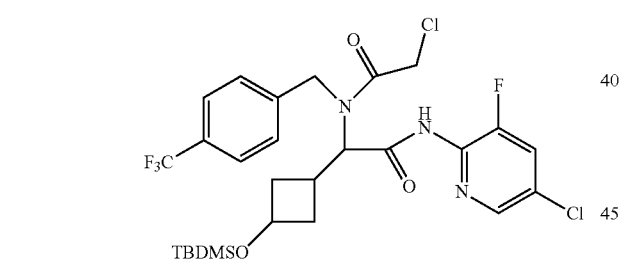

The mixture of (1r,3r)-3-((tert-butyldimethylsilyl)oxy)cyclobutane-1-carbaldehyde (680 mg, 3.17 mmol, 1.0 equiv) and (4-(trifluoromethyl)phenyl)methanamine (556 mg, 3.17 mmol, 1.0 equiv) in 2,2,2-trifluoroethanol (8.0 mL) was stirred at r.t. for 10 min. To this mixture were added 5-chloro-3-fluoro-2-isocyanopyridine (500 mg, 3.17 mmol, 1.0 equiv) and 2-chloroacetic acid (300 mg, 3.17 mmol, 1.0 equiv). The mixture was stirred at r.t. for 3 h, evaporated, purified with 20% EA/Hex to afford 1.2 g (59%) of 2-(3-((tert-butyldimethylsilyl)oxy)cyclobutyl)-N-(5-chloro-3-fluoropyridin-2-yl)-2-(2-chloro-N-(4-(trifluoromethyl)benzyl)acetamido)acetamide (Intermediate 69-1; racemic mixture of cis and trans isomer) as a white foam. LRMS (APCI) m/z 623.1 (M+H).

2. Synthesis of Intermediate 69-2

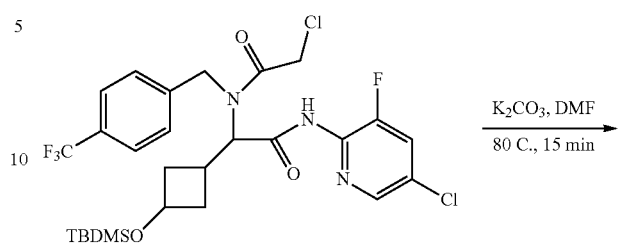

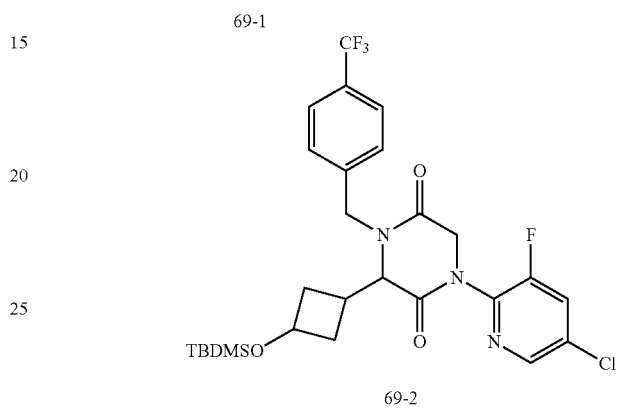

To a solution of 2-(3-(((tert-butyldimethylsilyl)oxy)cyclobutyl)-N-(5-chloro-3-fluoropyridin-2-yl)-2-(2-chloro-N-(4-(trifluoromethyl)benzyl)acetamido)acetamide (1.2 g, 2.0 mmol, 1.0 equiv) in DMF (10 mL) was added K$_2$CO$_3$ (781 mg, 5.6 mmol, 3.0 equiv). The resulting mixture was stirred at 80° C. for 15 min, cooled to r.t., diluted with EA (100 mL), washed with water (50 mL) three times and brine (50 mL) once, dried over sodium sulfate, and concentrated under reduced pressure to afford 988 mg (90%) of 3-(3-((tert-butyldimethylsilyl)oxy)cyclobutyl)-1-(5-chloro-3-fluoropyridin-2-yl)-4-(4-(trifluoromethyl)benzyl)piperazine-2,5-dione (Intermediate 69-2; racemic mixture of cis and trans-isomers) as a white foam. LRMS (APCI) m/z 586.1 (M+H).

3. Synthesis of Compound 740

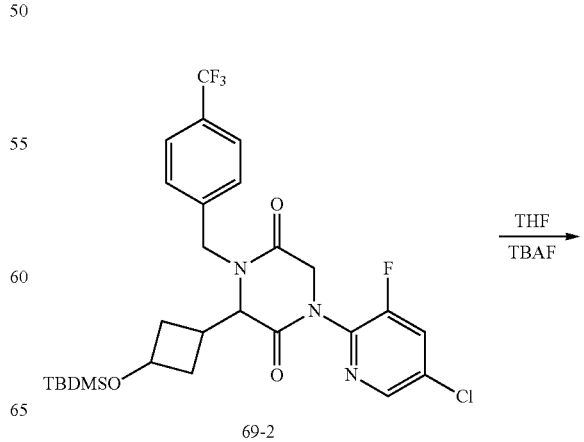

765

-continued

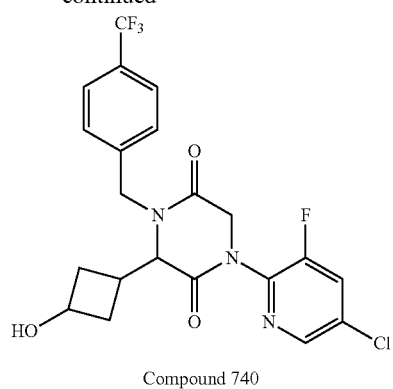

Compound 740

766

To a solution of 3-(3-((tert-butyldimethylsilyl)oxy)cyclobutyl)-1-(5-chloro-3-fluoropyridin-2-yl)-4-(4-(trifluoromethyl)benzyl)piperazine-2,5-dione (988 mg, 1.69 mmol, 1.0 equiv) in THF (10 mL) was added TBAF (3.37 mL of 1.0 M in THF, 3.37 mmol, 2.0 equiv). The resulting mixture was stirred at r.t. for 30 min, quenched with saturated aqueous sodium bicarbonate (30 mL), and diluted with DCM (125 mL). The organic phase was washed with brine (75 mL), dried over sodium sulfate, concentrated in vacuo, and purified with silica gel using a gradient from 0% EA/Hex to 100% EA/Hex to afford 530 mg (66%) of 1-(5-chloro-3-fluoropyridin-2-yl)-3-(3-hydroxycyclobutyl)-4-(4-(trifluoromethyl)benzyl)piperazine-2,5-dione (Compound 740; 1:1 mixture of cis and trans-isomers) as a white foam. LRMS (APCI) m/z 472.0 (M+H).

4. Separation of Compound 740 Stereoisomers: Stereoisomers 740A, 740B, 740C, and 740D

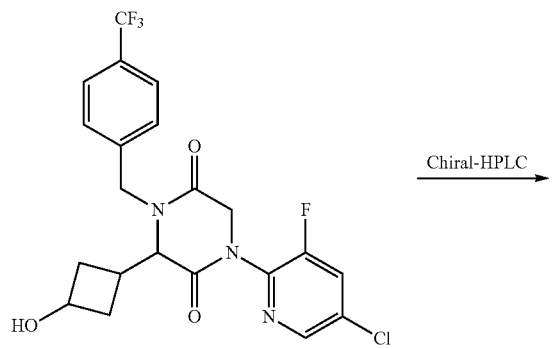

Chiral-HPLC →

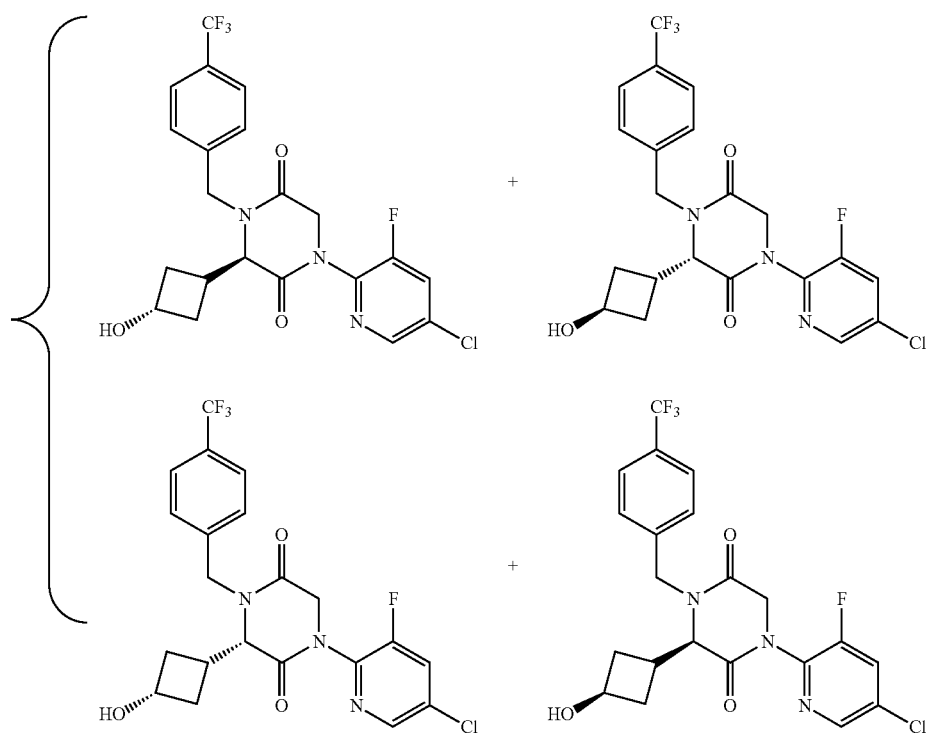

The stereoisomers of 1-(4-chloro-2-fluorophenyl)-3-(3-hydroxycyclobutyl)-4-(4-(trifluoromethyl)benzyl)piperazine-2,5-dione (796 mg) was purified by Chiral-Prep-HPLC with the following conditions: Column, CHIRALPAK IG, 2*25 cm, 5 um; mobile phase, hexane (8 mM NH₃/MeOH) and EtOH (hold 35% EtOH for 18 min); Detector, UV 254 nm/220 nm) to afford 150 mg of Stereoisomer 740C, 96 mg of Stereoisomer 740D, and 250 mg mixture of Stereoisomer 740A and Stereoisomer 740B, which was further purified by Chiral HPLC with the following condition; Column CHIRALPAK IG 20*25 cm, 5 um; mobile phase, hexane (8 mM NH₃/MeOH) and EtOH (hold 35% EtOH for 18 min); Detector, UV 254 nm/220 nm)) to afford 63 mg of Stereoisomer 740B and 118 mg of Stereoisomer 740A as white solids.

Characterization of Stereoisomer 740A. LCMS (ES) m/z 472 (M+H). ¹H NMR (300 MHz, DMSO-d₆) δ 8.47 (d, J=2.1 Hz, 1H), 8.24 (dd, J=9.4, 2.2 Hz, 1H), 7.73 (d, J=8.0 Hz, 2H), 7.51 (d, J=8.0 Hz, 2H), 5.12-5.00 (m, 2H), 4.74 (d, J=17.0 Hz, 1H), 4.36 (dd, J=16.3, 9.8 Hz, 2H), 4.04 (d, J=7.7 Hz, 1H), 3.86 (q, J=6.6 Hz, 1H), 2.22 (dp, J=17.1, 6.6 Hz, 3H), 1.73 (q, J=9.4 Hz, 2H). Analytical chiral HPLC RT: 0.85 min (CHIRALPAK IG-3; 0.46 cm×5 cm; 3 micro; MtBE (0.1% DEA):EtOH=60:40 at 1 ml/min).

Characterization of Stereoisomer 740B. LCMS (ES) m/z 472 (M+H). ¹H NMR (300 MHz, DMSO-d₆) δ 8.47 (d, J=2.1 Hz, 1H), 8.25 (dd, J=9.4, 2.2 Hz, 1H), 7.72 (d, J=8.0 Hz, 2H), 7.49 (d, J=8.0 Hz, 2H), 5.09-4.97 (m, 2H), 4.78 (d, J=17.1 Hz, 1H), 4.49 (d, J=15.7 Hz, 1H), 4.35 (d, J=17.1 Hz, 1H), 4.18 (t, J=8.7 Hz, 2H), 2.95 (s, 1H), 2.23 (s, 2H), 1.87 (td, J=8.8, 4.4 Hz, 2). Analytical chiral HPLC RT: 0.82 min (CHIRALPAK IG-3; 0.46 cm×5 cm; 3 micro; MtBE (0.1% DEA):EtOH=60:40 at 1 ml/min).

Characterization of Stereoisomer 740C. LCMS (ES) m/z 472 (M+H). ¹H NMR (300 MHz, DMSO-d₆) δ 8.47 (d, J=2.1 Hz, 1H), 8.24 (dd, J=9.4, 2.1 Hz, 1H), 7.73 (d, J=8.1 Hz, 2H), 7.51 (d, J=8.0 Hz, 2H), 5.11-5.00 (m, 2H), 4.74 (d, J=16.9 Hz, 1H), 4.36 (dd, J=16.3, 10.0 Hz, 2H), 4.04 (d, J=7.7 Hz, 1H), 3.87 (p, J=7.1 Hz, 1H), 2.35-2.12 (m, 2H), 2.20 (s, 1H), 1.73 (q, J=9.4 Hz, 2H). Analytical chiral HPLC RT: 1.56 min (CHIRALPAK IG-3; 0.46 cm×5 cm; 3 micro; MtBE (0.1% DEA):EtOH=60:40 at 1 ml/min).

Characterization of Stereoisomer 740D. LCMS (ES) m/z 472 (M+H). ¹H NMR (300 MHz, DMSO-d₆) δ 8.47 (t, J=1.9 Hz, 1H), 8.25 (dt, J=9.4, 1.8 Hz, 1H), 7.72 (d, J=7.9 Hz, 2H), 7.49 (d, J=7.9 Hz, 2H), 5.09-4.97 (m, 2H), 4.78 (d, J=17.1 Hz, 1H), 4.49 (d, J=15.7 Hz, 1H), 4.35 (d, J=17.1 Hz, 1H), 4.24-4.12 (m, 2H), 2.95 (d, J=9.3 Hz, 1H), 2.28-2.17 (m, 2H), 1.94-1.80 (m, 2H). Analytical chiral HPLC RT: 2.98 min (CHIRALPAK IG-3; 0.46 cm×5 cm; 3 micro; MtBE (0.1% DEA):EtOH=60:40 at 1 ml/min).

Example 70: Synthesis of Compound 750

1. Synthesis of Intermediate 70-1

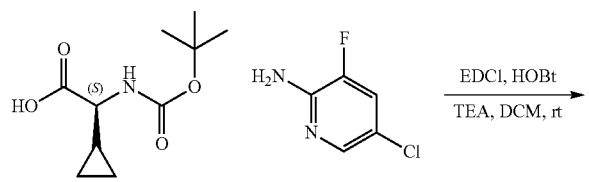

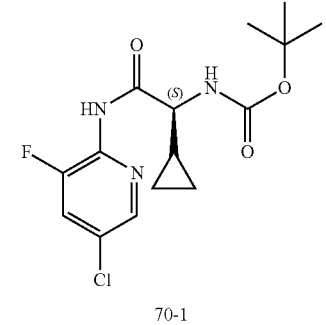

70-1

To a solution of (S)-2-((tert-butoxycarbonyl)amino)-2-cyclopropylacetic acid (1.0 g, 4.6 mmol, 1.0 equiv) in DCM (50.0 mL) were added EDCI (1.8 g, 9.3 mmol, 2.0 equiv.), HOBt (0.63 g, 4.6 mmol, 1.0 equiv.), and TEA (1.3 mL, 9.3 mmol, 2.0 equiv.). After stirring at r.t. for 5 min, to this mixture was added 5-chloro-3-fluoropyridin-2-amine (0.8 g, 5.6 mmol, 1.2 equiv.). The mixture continued to stir for overnight, concentrated to dryness, diluted with EA, washed with water and brine, dried over Na₂SO₄, concentrated under reduced pressure, and purified by silica gel using EA/HE as eluent to afford 730 mg (46%) of tert-butyl (S)-(2-((5-chloro-3-fluoropyridin-2-yl)amino)-1-cyclopropyl-2-oxoethyl)carbamate (Intermediate 70-1) as a white solid. LRMS (ES) m/z 344.1 (M+H).

2. Synthesis of Intermediate 70-2

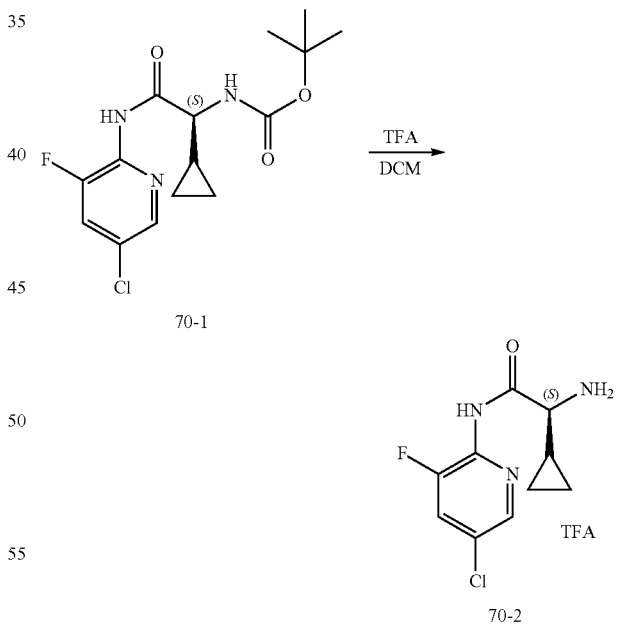

To a solution of tert-butyl (S)-(2-((5-chloro-3-fluoropyridin-2-yl)amino)-1-cyclopropyl-2-oxoethyl)carbamate (560 mg, 1.6 mmol, 1.0 equiv) in DCM (10.0 mL) at r.t was added TFA (2.0 mL). The mixture was stirred at rt for 1 h and concentrated to dryness to afford 550 mg (98%) of (S)-2-amino-N-(5-chloro-3-fluoropyridin-2-yl)-2-cyclopropylacetamide 2,2,2-trifluoroacetate (Intermediate 70-2). LRMS (ES) m/z 244.0 (M+H).

3. Synthesis of Intermediate 70-3

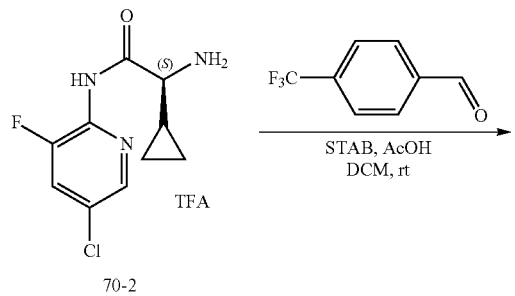

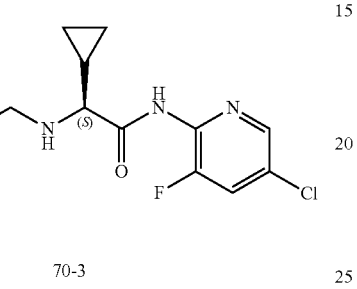

To a solution of (S)-2-amino-N-(5-chloro-3-fluoropyridin-2-yl)-2-cyclopropylacetamide 2,2,2-trifluoroacetate (280 mg, 0.8 mmol, 1.0 equiv) in DCM (5.0 mL) at r.t was added 4-(trifluoromethyl)benzaldehyde (177 mg, 1.0 mmol, 1.3 equiv). After stirring at rt for 5 min, to this mixture was added STAB (497 mg, 2.3 mmol, 3.0 equiv.). The mixture was for 4 h at rt, quenched with addition of HCl (1N) until Ph reached to 1-2, stirred for 10 min, basified to pH 9-10 with sat. sodium bicarbonate solution, and extracted with DCM five times. The combined organic extracts were dried over MgSO₄, concentrated, and purified by silica gel using a gradient of 20-100% EA/HE as eluent to afford 300 mg (95%) of (S)—N-(5-chloro-3-fluoropyridin-2-yl)-2-cyclopropyl-2-((4-(trifluoromethyl)benzyl)amino)acetamide (Intermediate 70-3). LRMS (ES) m/z 402 (M+H).

4. Synthesis of Intermediate 70-4

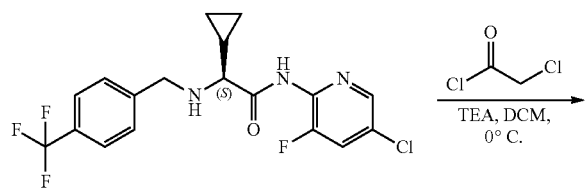

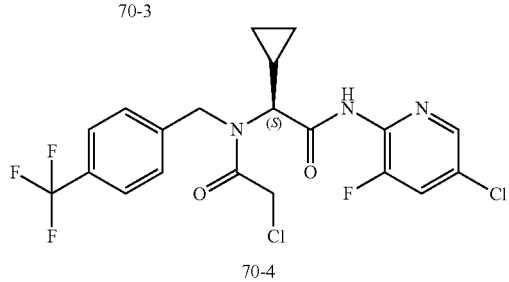

To a solution of (S)—N-(5-chloro-3-fluoropyridin-2-yl)-2-cyclopropyl-2-((4-(trifluoromethyl)benzyl)amino)acetamide (300 mg, 0.7 mmol, 1.0 equiv) in DCM (10.0 mL) cooled to 0° C. were added 2-chloroacetyl chloride (110 mg, 1.0 mmol, 1.3 equiv) and TEA (0.2 mL, 1.5 mmol, 2.0 equiv.). The mixture was stirred at 0° C. for 30 min, quenched with sat. NH₄Cl solution, and extracted with DCM twice. The combined organic extracts were dried over MgSO₄ and concentrated to afford 350 mg of (S)-2-chloro-N-(2-((5-chloro-3-fluoropyridin-2-yl)amino)-1-cyclopropyl-2-oxoethyl)-N-(4-(trifluoromethyl)benzyl)acetamide (Intermediate 70-4). LRMS (ES) m/z 478 (M+H).

5. Synthesis of Compound 750

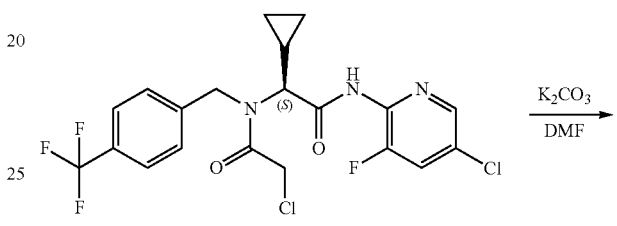

To a solution of (S)-2-chloro-N-(2-((5-chloro-3-fluoropyridin-2-yl)amino)-1-cyclopropyl-2-oxoethyl)-N-(4-(trifluoromethyl)benzyl)acetamide (350 mg, 0.7 mmol, 1.0 equiv) in DMF (5.0 mL) at r.t was added K₂CO₃ (204 mg, 1.5 mmol, 2.0 equiv). The mixture was stirred at 80° C. for 1 h, cooled, diluted with EA, filtered through celite, concentrated, and purified by reverse phase HPLC (Phenomenex, gemini 5u C18 150×21.2 mm, gradient over 10-100% acetonitrile in water both with 0.1% formic acid gradient in 30 min) to afford 34 mg (10% over two steps) of (S)-1-(5-chloro-3-fluoropyridin-2-yl)-3-cyclopropyl-4-(4-(trifluoromethyl)benzyl)piperazine-2,5-dione (Compound 750). LRMS (ES) m/z 442 (M+H). $^1$H NMR (400 MHz, Methylene Chloride-d₂) δ 8.22 (d, J=2.1 Hz, 1H), 7.58-7.47 (m, 3H), 7.34 (d, J=8.0 Hz, 2H), 5.18 (d, J=15.6 Hz, 1H), 4.59 (d, J=17.0 Hz, 1H), 4.45-4.29 (m, 2H), 3.25 (d, J=8.7 Hz, 1H), 1.15-1.02 (m, 1H), 0.67-0.45 (m, 3H), 0.38-0.27 (m, 1H).

The following compound was prepared by methods analogous to the method described for Compound 750:

| Compound No. | LRMS (ES) m/z |
|---|---|
| 751 | M + H = 392.0 |

Example 71: Synthesis of Diastereomer 875A

1. Synthesis of Intermediate Diastereomer 71-2A

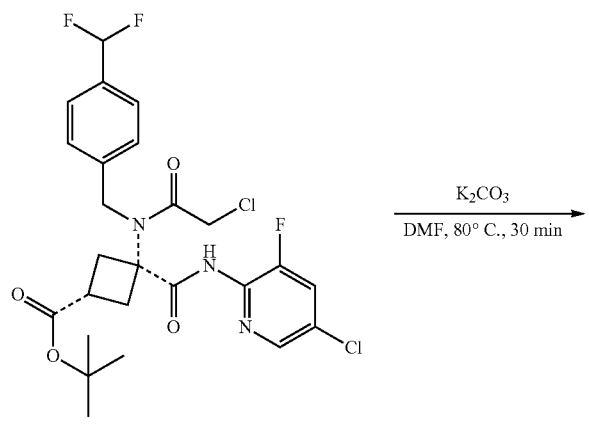

71-1A (less polar)

To a solution of Intermediate Diastereomer 71-1A (800 mg, 1.4 mmol, 1.0 equiv) in DMF (3.0 mL) at r.t was added K₂CO₃ (397 mg, 2.9 mmol, 2.0 equiv). The mixture was stirred at 80° C. for 30 min, cooled to rt, filtered, and purified by reverse phase HPLC (Phenomenex, gemini 5u C18 150×21.2 mm, 40-100% acetonitrile in water both with 0.1% formic acid gradient over 25 min) to afford 510 mg, 68% of a diastereomer of tert-butyl 8-(5-chloro-3-fluoropyridin-2-yl)-5-(4-(difluoromethyl)benzyl)-6,9-dioxo-5,8-diazaspiro [3.5]nonane-2-carboxylate (Intermediate Diastereomer 71-2A). LRMS (ES) m/z 468 (M+H-ᵗBu). As used in this example, the dashed bond --- indicates that the stereochemical configuration of the starting material is retained in the product compound.

2. Synthesis Intermediate Diastereomer 71-3A

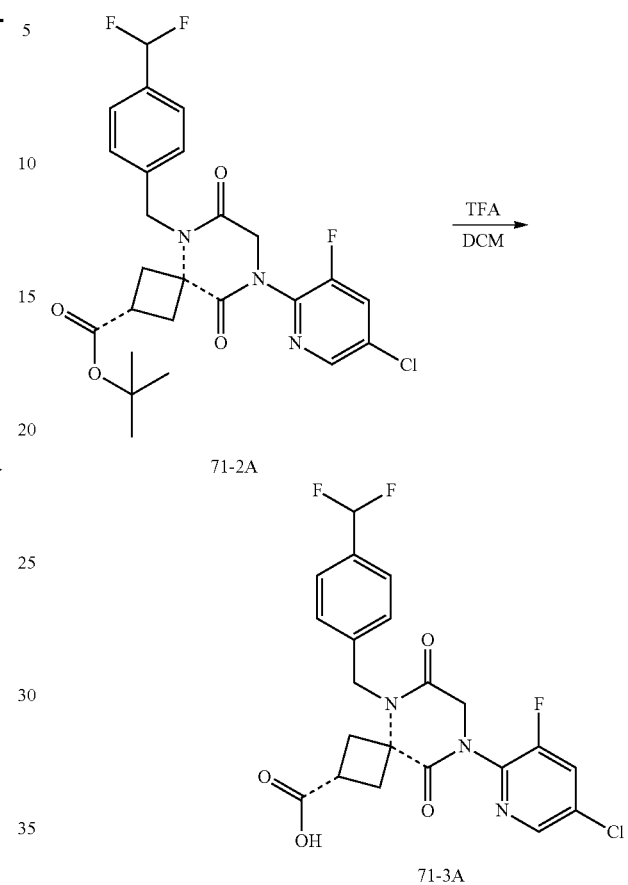

To a solution of Intermediate Diastereomer 71-2A (510 mg, 1.0 mmol, 1.0 equiv) in DCM (5.0 mL) at r.t was added TFA (1.0 mL). The mixture was stirred at rt for 30 min and concentrated to obtain the corresponding acid as a diastereomer of 8-(5-chloro-3-fluoropyridin-2-yl)-5-(4-(difluoromethyl)benzyl)-6,9-dioxo-5,8-diazaspiro[3.5]nonane-2-carboxylic acid (Intermediate Diastereomer 71-3A), which was used for next step without further purification.

3. Synthesis of Intermediate Diastereomer 71-4A

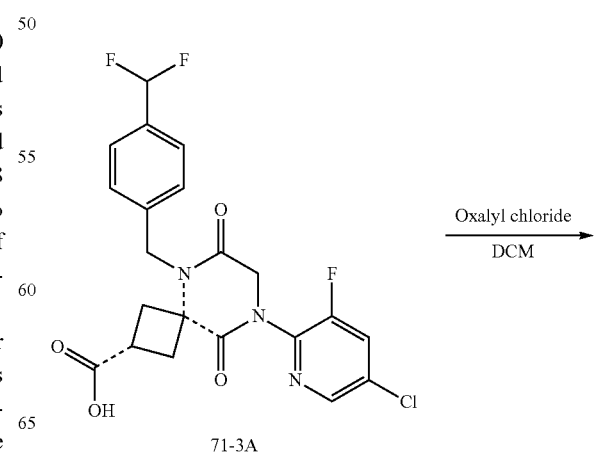

-continued

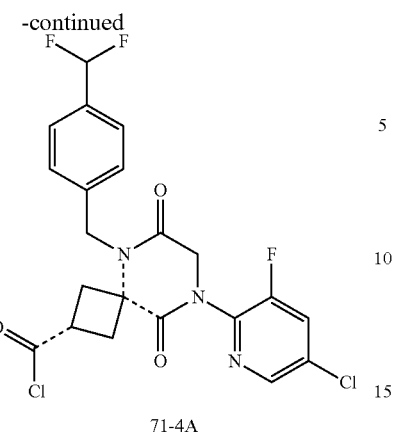

71-4A

To a solution of Intermediate Diastereomer 71-3A (455 mg, 1.0 mmol, 1.0 equiv) in DCM (5.0 mL) at r.t were added oxalyl chloride (1.0 mL) and one drop of DMF. The mixture was stirred at rt for 30 min and concentrated to obtain a diastereomer of 8-(5-chloro-3-fluoropyridin-2-yl)-5-(4-(difluoromethyl)benzyl)-6,9-dioxo-5,8-diazaspiro[3.5]nonane-2-carbonyl chloride (Intermediate Diastereomer 71-4A), which was used for next step without further purification.

4. Synthesis of Diastereomer 875A

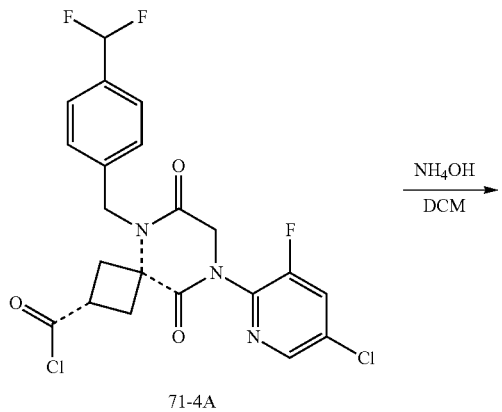

71-4A

-continued

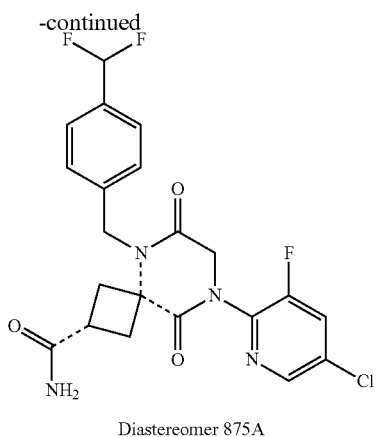

Diastereomer 875A

To a solution of Intermediate Diastereomer 71-4A (472 mg, 1.0 mmol, 1.0 equiv) in DCM (10.0 mL) at r.t was added ammonium hydroxide (1.0 mL, 30% wt). The mixture was stirred at rt for 30 min, concentrated, and purified by reverse phase HPLC (Phenomenex, gemini 5u C18 150×21.2 mm, 10-100% acetonitrile in water both with 0.1% formic acid gradient over 25 min) to afford 121 mg (27% over three steps) of a diastereomer of 8-(5-chloro-3-fluoropyridin-2-yl)-5-(4-(difluoromethyl)benzyl)-6,9-dioxo-5,8-diazaspiro[3.5]nonane-2-carboxamide (Diastereomer 875A). LRMS (ES) m/z 467 (M+H). $^1$H NMR (400 MHz, Methylene Chloride-d$_2$) δ 8.36 (s, 1H), 7.71-7.63 (d, J=8.0 Hz, 1H), 7.53 (d, J=7.9 Hz, 2H), 7.39 (d, J=7.9 Hz, 2H), 6.70 (t, J=56.4 Hz, 1H), 5.58 (s, 1H), 5.51 (s, 1H), 5.13 (s, 2H), 4.55 (s, 2H), 3.04 (p, J=8.5 Hz, 1H), 2.90-2.76 (m, 4H), 2.01 (s, 3H).

The following compounds were prepared by methods analogous to the method described for Diastereomer 875A:

| Diastereomer No. | LRMS (ES) m/z | $^1$H NMR |
|---|---|---|
| 870A | M + H = 499 | (400 MHz, Methylene Chloride-d2) δ 8.36 (d, J = 2.0 Hz, 1H), 7.71-7.59 (m, 3H), 7.45 (d, J = 8.0 Hz, 2H), 5.47 (br, 1H), 5.20 (s, 2H), 4.55 (s, 2H), 3.05-2.69 (m, 8H). |
| 871A | M + H = 513 | (400 MHz, Methylene Chloride-d2) δ 8.37 (d, J = 2.0 Hz, 1H), 7.71-7.61 (m, 3H), 7.43 (d, J = 8.0 Hz, 2H), 5.10 (s, 2H), 4.56 (s, 2H), 3.41-3.27 (m, 1H), 2.92 (d, J = 5.6 Hz, 6H), 2.84 (d, J = 8.9 Hz, 4H). |
| 872A | M + H = 451 | (400 MHz, Methylene Chloride-d2) δ 8.36 (d, J = 2.0 Hz, 1H), 7.67 (dd, J = 9.0, 2.0 Hz, 1H), 7.36 (d, J = 8.3 Hz, 2H), 7.26 (d, J = 8.2 Hz, 2H), 5.43 (s, 1H), 5.32 (s, 1H), 5.05 (s, 2H), 4.54 (s, 2H), 3.03 (p, J = 8.5 Hz, 1H), 2.83 (t, J = 7.3 Hz, 4H). |
| 873A | M + H = 465 | (400 MHz, Methylene Chloride-d$_2$) δ 8.23 (s, 1H), 7.57-7.50 (d, J = 8.0 Hz, 1H), 7.22 (d, J = 8.0 Hz, 2H), 7.14 (d, J = 8.2 Hz, 2H), 5.43 (s, 1H), 4.96 (s, 2H), 4.40 (s, 2H), 2.84-2.68 (m, 3H), 2.71-2.59 (m, 5H). |

| Diastereomer No. | LRMS (ES) m/z | ¹H NMR |
|---|---|---|
| 874A | M + H = 479 | (400 MHz, Methylene Chloride-$d_2$) δ 8.23 (d, J = 2.0 Hz, 1H), 7.54 (dd, J = 8.9, 2.0 Hz, 1H), 7.22 (d, J = 8.0 Hz, 2H), 7.12 (d, J = 8.2 Hz, 2H), 4.86 (s, 2H), 4.40 (s, 2H), 3.19 (p, J = 8.7 Hz, 1H), 2.81 (s, 3H), 2.78 (d, J = 0.9 Hz, 3H), 2.70 (d, J = 8.8 Hz, 4H). |
| 876A | M + H = 435.0 | (400 MHz, Methylene Chloride-$d_2$) δ 8.23 (s, 1H), 7.53 (d, J = 8.9 Hz, 1H), 7.21-7.13 (m, 2H), 6.94 (t, J = 8.5 Hz, 2H), 5.30 (s, 1H), 5.19 (s, 1H), 4.91 (s, 2H), 4.40 (s, 2H), 2.97-2.84 (m, 1H), 2.79-2.63 (m, 4H). |

Example 72: Synthesis of Diastereomer 875B

1. Synthesis of Intermediate Diastereomer 71-2B

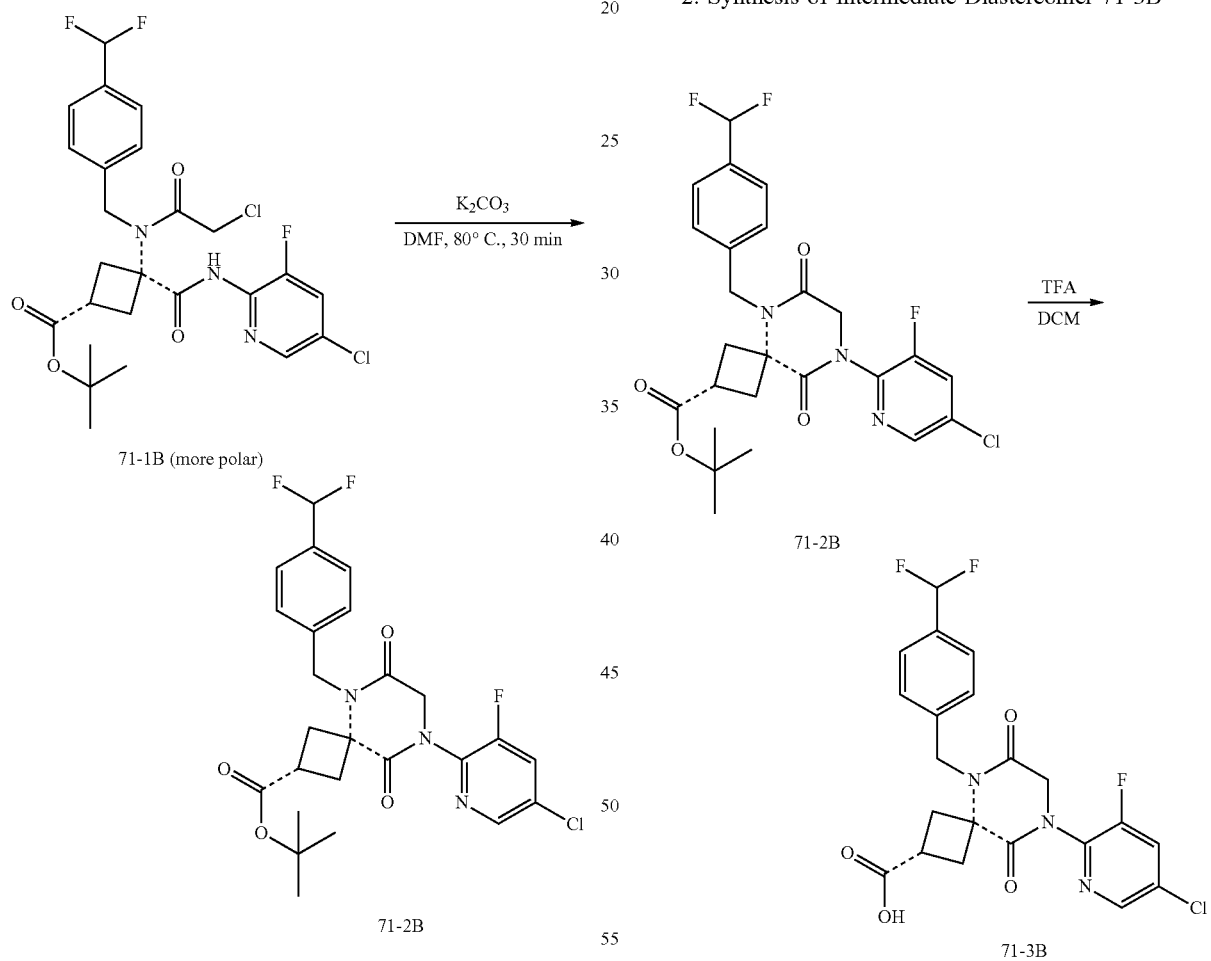

To a solution of Intermediate Diastereomer 71-2B (1000 mg, 1.8 mmol, 1.0 equiv) in DMF (3.0 mL) at r.t was added $K_2CO_3$ (497 mg, 3.6 mmol, 2.0 equiv). The mixture was stirred at 80° C. for 30 min, cooled to rt, filtered, and purified by reverse phase HPLC (Phenomenex, gemini 5u C18 150×21.2 mm, 40-100% acetonitrile in water both with 0.1% formic acid gradient over 25 min) to afford 680 mg, 72% of a diastereomer of tert-butyl 8-(5-chloro-3-fluoropyridin-2-yl)-5-(4-(difluoromethyl)benzyl)-6,9-dioxo-5,8-diazaspiro[3.5]nonane-2-carboxylate (Intermediate Diastereomer 71-2B). LRMS (ES) m/z 524 (M+H). As used in this example, the dashed bond --- indicates that the stereochemical configuration of the starting material is retained in the product compound.

2. Synthesis of Intermediate Diastereomer 71-3B

To a solution of Intermediate Diastereomer 71-2B (680 mg, 1.3 mmol, 1.0 equiv) in DCM (5.0 mL) at r.t was added TFA (1.0 mL). The mixture was stirred at rt for 30 min and concentrated to obtain the corresponding acid as a diastereomer of 8-(5-chloro-3-fluoropyridin-2-yl)-5-(4-(difluoromethyl)benzyl)-6,9-dioxo-5,8-diazaspiro[3.5]nonane-2-carboxylic acid (Intermediate Diastereomer 71-3B), which was used for next step without further purification.

3. Synthesis of Intermediate Diastereomer 71-4B

4. Synthesis of Diastereomer 875B

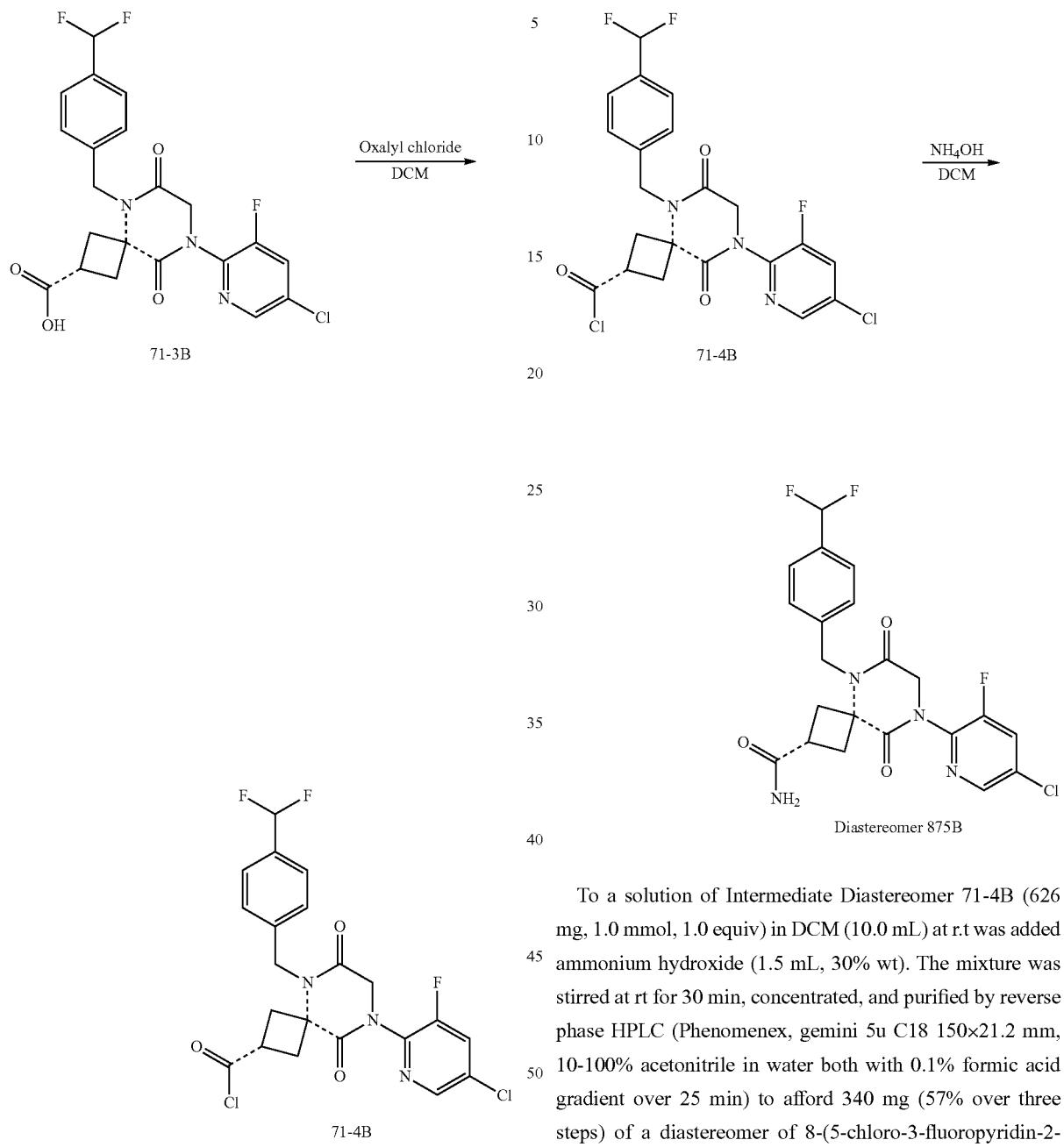

To a solution of Intermediate Diastereomer 71-3B (606 mg, 1.0 mmol, 1.0 equiv) in DCM (5.0 mL) at r.t were added oxalyl chloride (1.0 mL) and one drop of DMF. The mixture was stirred at rt for 30 min and concentrated to obtain the corresponding acid chloride as a diastereomer of 8-(5-chloro-3-fluoropyridin-2-yl)-5-(4-(difluoromethyl)benzyl)-6,9-dioxo-5,8-diazaspiro[3.5]nonane-2-carbonyl chloride (Intermediate Diastereomer 71-4B), which was used for next step without further purification.

To a solution of Intermediate Diastereomer 71-4B (626 mg, 1.0 mmol, 1.0 equiv) in DCM (10.0 mL) at r.t was added ammonium hydroxide (1.5 mL, 30% wt). The mixture was stirred at rt for 30 min, concentrated, and purified by reverse phase HPLC (Phenomenex, gemini 5u C18 150×21.2 mm, 10-100% acetonitrile in water both with 0.1% formic acid gradient over 25 min) to afford 340 mg (57% over three steps) of a diastereomer of 8-(5-chloro-3-fluoropyridin-2-yl)-5-(4-(difluoromethyl)benzyl)-6,9-dioxo-5,8-diazaspiro[3.5]nonane-2-carboxamide (Diastereomer 875B). LRMS (ES) m/z 467 (M+H). $^1$H NMR (400 MHz, Methylene Chloride-d$_2$) δ 8.36 (d, J=1.8 Hz, 1H), 7.67 (dd, J=9.0, 2.1 Hz, 1H), 7.56 (d, J=7.9 Hz, 2H), 7.41 (d, J=7.9 Hz, 2H), 6.71 (t, J=56.4 Hz, 1H), 6.32 (s, 1H), 5.52 (s, 1H), 5.03 (s, 2H), 4.56 (s, 2H), 3.22-3.11 (m, 2H), 3.10-2.96 (m, 1H), 2.82-2.71 (m, 2H).

The following compounds were prepared by methods analogous to the method described for Diastereomer 875B:

| Diastereomer No. | LRMS (ES) m/z | ¹H NMR |
|---|---|---|
| 870B | M + H = 499 | (400 MHz, Methylene Chloride-$d_2$) δ 8.36 (d, J = 2.0 Hz, 1H), 7.71-7.63 (m, 3H), 7.43 (d, J = 8.0 Hz, 2H), 6.25 (s, 1H), 5.04 (s, 2H), 4.55 (s, 2H), 3.21-3.11 (m, 2H), 3.09-2.96 (m, 1H), 2.79-2.65 (m, 5H). |
| 871B | M + H = 513 | (400 MHz, Methylene Chloride-$d_2$) δ 8.34 (d, J = 2.0 Hz, 1H), 7.72-7.61 (m, 3H), 7.46 (d, J = 8.0 Hz, 2H), 5.08 (s, 2H), 4.55 (s, 2H), 3.28 (dd, J = 13.8, 8.0 Hz, 2H), 3.00 (p, J = 8.9 Hz, 1H), 2.83 (br, 6H), 2.65-2.54 (m, 2H). |
| 872B | M + H = 451 | (400 MHz, Methylene Chloride-$d_2$) δ 8.23 (d, J = 2.0 Hz, 1H), 7.54 (dt, J = 9.0, 1.6 Hz, 1H), 7.26 (d, J = 8.1 Hz, 2H), 7.14 (d, J = 8.2 Hz, 2H), 6.17 (s, 1H), 5.23 (s, 1H), 4.82 (s, 2H), 4.41 (d, J = 1.1 Hz, 2H), 3.08-2.98 (m, 2H), 2.95-2.82 (m, 1H), 2.70-2.59 (m, 2H). |
| 873B | M + H = 465 | (400 MHz, Methylene Chloride-$d_2$) δ 8.35 (d, J = 1.9 Hz, 1H), 7.67 (dd, J = 9.0, 2.0 Hz, 1H), 7.38 (d, J = 8.1 Hz, 2H), 7.26 (d, J = 8.1 Hz, 2H), 6.20 (s, 1H), 4.95 (s, 2H), 4.53 (s, 2H), 3.18-3.08 (m, 2H), 3.04-2.90 (m, 1H), 2.79-2.66 (m, 5H). |
| 874B | M + H = 479 | (400 MHz, Methylene Chloride-$d_2$) δ 8.20 (d, J = 2.0 Hz, 1H), 7.51 (dd, J = 8.9, 2.1 Hz, 1H), 7.26 (d, J = 8.4 Hz, 2H), 7.16 (d, J = 8.3 Hz, 2H), 4.85 (s, 2H), 4.40 (s, 2H), 3.18-3.07 (m, 2H), 2.90-2.76 (m, 1H), 2.76 (s, 3H), 2.64 (s, 3H), 2.53-2.42 (m, 2H). |
| 876B | M + H = 435.0 | (400 MHz, Methylene Chloride-$d_2$) δ 8.35 (d, J = 1.8 Hz, 1H), 7.66 (dd, J = 8.8, 2.2 Hz, 1H), 7.31 (dd, J = 8.2, 5.3 Hz, 2H), 7.10 (t, J = 8.5 Hz, 2H), 6.33 (s, 1H), 5.56 (s, 1H), 5.36 (s, 0H), 4.95 (s, 2H), 4.54 (s, 2H), 3.20-3.10 (m, 2H), 3.07-2.93 (m, 1H), 2.83-2.72 (m, 2H). |
| 877B | M + H = 485 | (400 MHz, Methylene Chloride-d2) δ 8.36 (d, J = 2.0 Hz, 1H), 7.71-7.63 (m, 3H), 7.44 (d, J = 8.0 Hz, 2H), 6.30 (s, 1H), 5.44 (s, 1H), 5.04 (s, 2H), 4.56 (s, 2H), 3.23-3.13 (m, 2H), 3.05 (qd, J = 10.3, 6.8 Hz, 1H), 2.81-2.70 (m, 2H). |

Example 73: Synthesis of Compound 784

1. Synthesis of Intermediate 73-1

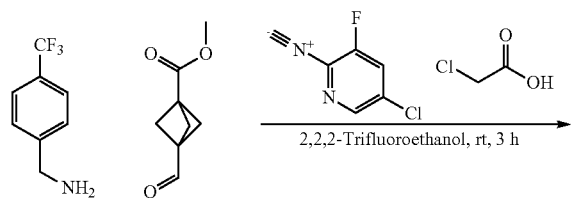

To a solution of (4-(trifluoromethyl)phenyl)methanamine (568 mg, 3.2 mmol, 1.0 equiv) in 2,2,2-trifluoroethanol (5.0 mL) was added methyl 3-formylbicyclo[1.1.1]pentane-1-carboxylate (500 mg, 3.2 mmol, 1.0 equiv). After stirring at r.t. for 10 min, to this resulting mixture were added 5-chloro-3-fluoro-2-isocyanopyridine (511 mg, 3.2 mmol, 1.0 equiv) and chloroacetic acid (337 mg, 3.6 mmol, 1.1 equiv). The resulting mixture was stirred at r.t. overnight, concentrated under reduced pressure, and purified silica gel chromatography, eluted with EA/HE to afford 1.8 g (99%) of methyl 3-(2-((5-chloro-3-fluoropyridin-2-yl)amino)-1-(2-chloro-N-(4-(trifluoromethyl)benzyl)acetamido)-2-oxoethyl)bicyclo[1.1.1]pentane-1-carboxylate (Intermediate 73-1) as a foam. LRMS (ES) m/z 562 (M+H).

2. Synthesis of Intermediate 73-2

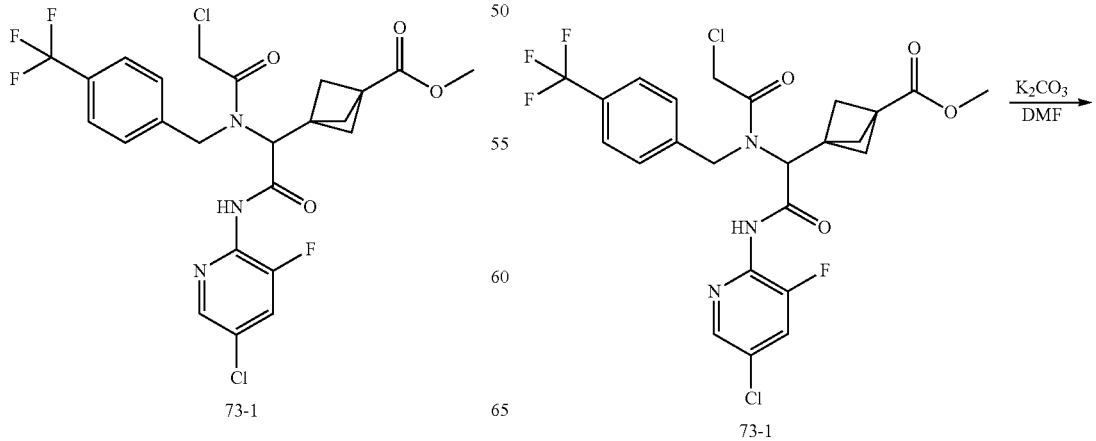

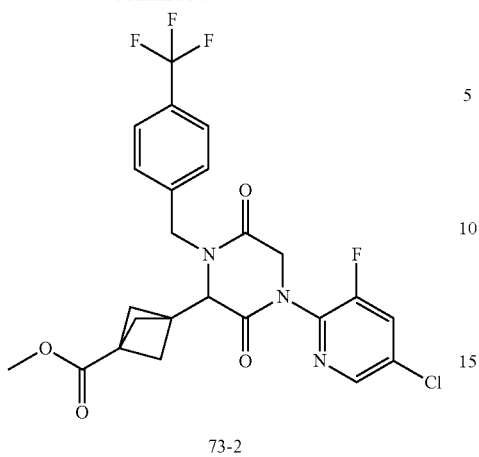

To a solution of methyl 3-(2-((5-chloro-3-fluoropyridin-2-yl)amino)-1-(2-chloro-N-(4-(trifluoromethyl)benzyl)acetamido)-2-oxoethyl)bicyclo[1.1.1]pentane-1-carboxylate (1.8 g, 3.2 mmol, 1.0 equiv) in DMF (5.0 mL) at r.t was added K$_2$CO$_3$ (0.9 g, 6.4 mmol, 2.0 equiv). The mixture was stirred at 80° C. for 30 min, diluted with EA (20 mL), filtered, and concentrated. The residue was triturated with ACN to afford 1.2 g (71%) of methyl 3-(4-(5-chloro-3-fluoropyridin-2-yl)-3,6-dioxo-1-(4-(trifluoromethyl)benzyl)piperazin-2-yl)bicyclo[1.1.1]pentane-1-carboxylate (Intermediate 73-2). LRMS (ES) m/z 526.1 (M+H). $^1$H NMR (400 MHz, Methylene Chloride-d$_2$) δ 8.31 (d, J=2.0 Hz, 1H), 7.68-7.57 (m, 3H), 7.43 (d, J=8.0 Hz, 2H), 5.45 (d, J=15.3 Hz, 1H), 4.50 (s, 2H), 4.04 (s, 1H), 4.01 (d, J=15.3 Hz, 1H), 3.66 (s, 3H), 2.16 (s, 6H).

To a solution of methyl 3-(4-(5-chloro-3-fluoropyridin-2-yl)-3,6-dioxo-1-(4-(trifluoromethyl)benzyl)piperazin-2-yl)bicyclo[1.1.1]pentane-1-carboxylate (1.2 g, 2.3 mmol, 1.0 equiv) in dioxane (2.0 mL) at r.t was added LiOH (2.3 mL, 2 N, 4.6 mmol, 2.0 equiv.). The mixture was stirred at rt for 30 min, acidified to pH 1-3, and extracted with EA three times. The combined extracts were washed with brine, dried over MgSO$_4$, and concentrated to afford 1.16 g (99%) of 3-(4-(5-chloro-3-fluoropyridin-2-yl)-3,6-dioxo-1-(4-(trifluoromethyl)benzyl)piperazin-2-yl)bicyclo[1.1.1]pentane-1-carboxylic acid (Intermediate 73-3). LRMS (ES) m/z 512 (M+H). $^1$H NMR (400 MHz, Chloroform-d) δ 8.23 (d, J=2.1 Hz, 1H), 7.59-7.48 (m, 3H), 7.31 (d, J=8.0 Hz, 2H), 5.43 (d, J=15.2 Hz, 1H), 4.44 (s, 2H), 3.97 (s, 1H), 3.89 (d, J=15.2 Hz, 1H), 2.14 (s, 6H).

3. Synthesis of Intermediate 73-3

4. Synthesis of Intermediate 73-4

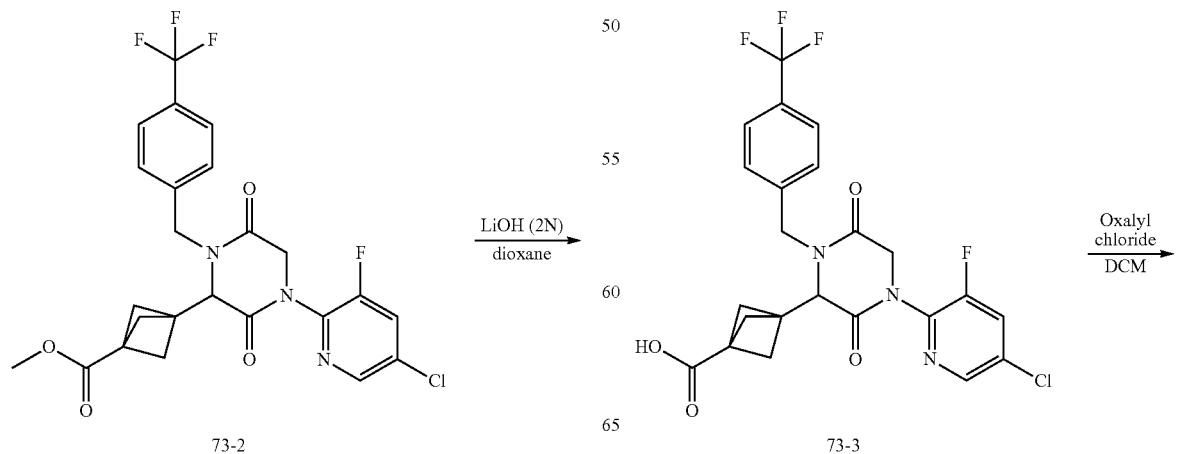

783
-continued

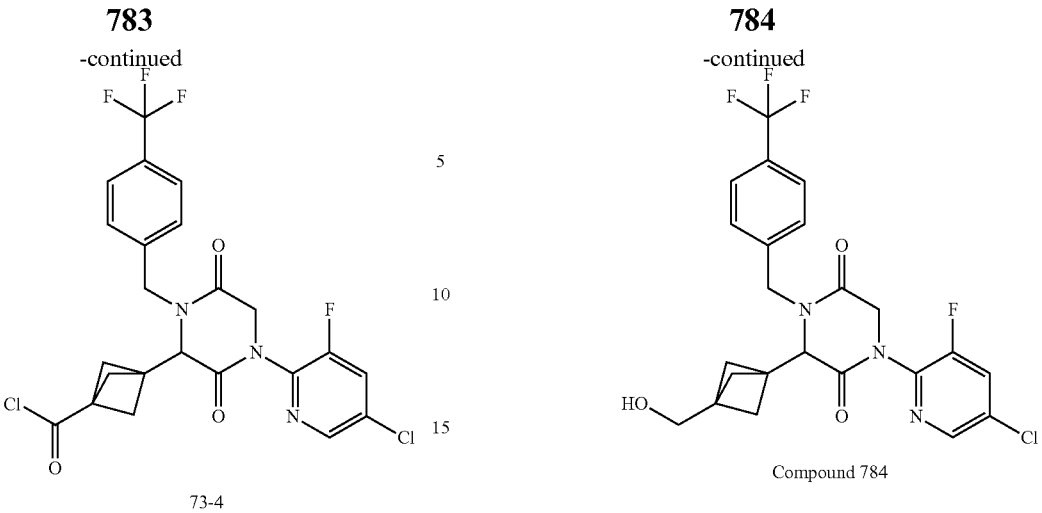

73-4

To a solution of 3-(4-(5-chloro-3-fluoropyridin-2-yl)-3,6-dioxo-1-(4-(trifluoromethyl)benzyl)piperazin-2-yl)bicyclo[1.1.1]pentane-1-carboxylic acid (80 mg, 0.16 mmol, 1.0 equiv) in DCM (6.0 mL) at r.t were added oxalyl chloride (0.5 mL) and one drop of DMF. The mixture was stirred at rt for 30 min and concentrated to obtain 3-(4-(5-chloro-3-fluoropyridin-2-yl)-3,6-dioxo-1-(4-(trifluoromethyl)benzyl)piperazin-2-yl)bicyclo[1.1.1]pentane-1-carbonyl chloride (Intermediate 73-4), which was used for next step without further purification.

5. Synthesis of Compound 784

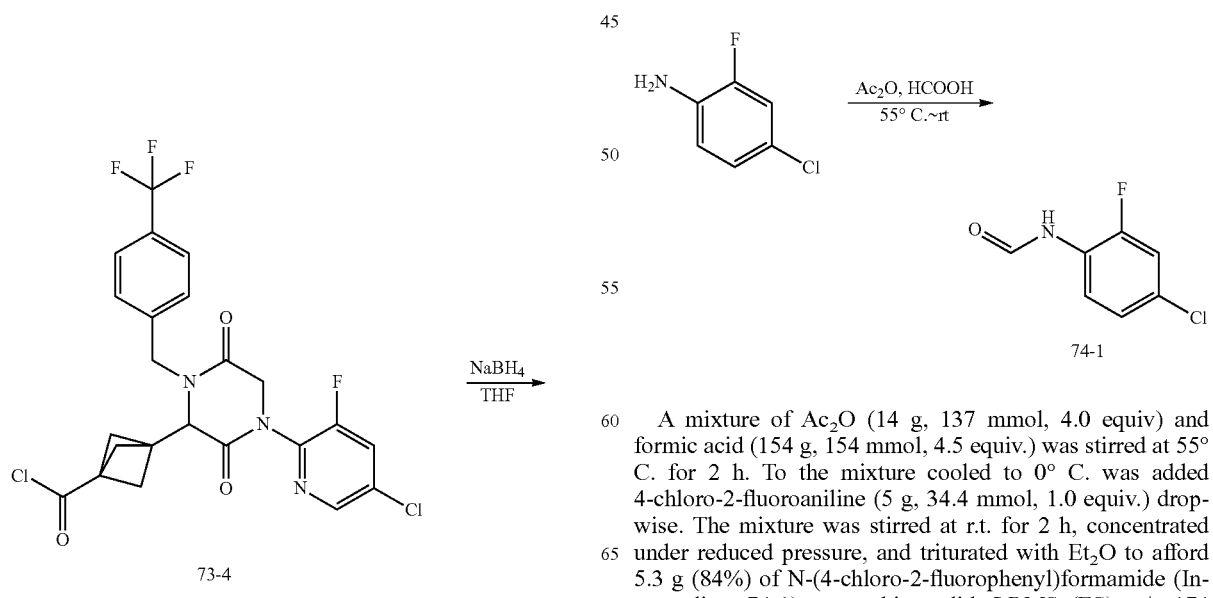

73-4

784
-continued

Compound 784

To a solution of 3-(4-(5-chloro-3-fluoropyridin-2-yl)-3,6-dioxo-1-(4-(trifluoromethyl)benzyl)piperazin-2-yl)bicyclo[1.1.1]pentane-1-carbonyl chloride (0.16 mmol, 1.0 equiv) in THF (6.0 mL) cooled to 0° C. was added sodium borohydride (12 mg, 0.31 mmol, 2.0 equiv.). The mixture was stirred at 0° C. for 30 min, acidified to pH 1-3 with HCl (1 N), and extracted with EA three times. The combined extracts were washed with brine, dried over $MgSO_4$, concentrated, and purified by reverse phase HPLC (Phenomenex, gemini 5u C18 150×21.2 mm, gradient over 10-100% acetonitrile in water both with 0.1% formic acid in 25 min) to afford 14 mg (18% over two steps) of 1-(5-chloro-3-fluoropyridin-2-yl)-3-(3-(hydroxymethyl)bicyclo[1.1.1]pentan-1-yl)-4-(4-(trifluoromethyl)benzyl)piperazine-2,5-dione (Compound 784). LRMS (ES) m/z 498.1 (M+H). $^1$H NMR (400 MHz, Chloroform-d) δ 8.22 (d, J=2.1 Hz, 1H), 7.58-7.46 (m, 3H), 7.31 (d, J=8.0 Hz, 2H), 5.45 (d, J=15.2 Hz, 1H), 4.42 (q, J=15.1 Hz, 2H), 3.95 (s, 1H), 3.89 (d, J=15.1 Hz, 1H), 3.57 (d, J=4.1 Hz, 2H), 1.78 (s, 6H).

Example 74: Synthesis of Compound 866

1. Synthesis of Intermediate 74-1

74-1

A mixture of $Ac_2O$ (14 g, 137 mmol, 4.0 equiv) and formic acid (154 g, 154 mmol, 4.5 equiv.) was stirred at 55° C. for 2 h. To the mixture cooled to 0° C. was added 4-chloro-2-fluoroaniline (5 g, 34.4 mmol, 1.0 equiv.) dropwise. The mixture was stirred at r.t. for 2 h, concentrated under reduced pressure, and triturated with $Et_2O$ to afford 5.3 g (84%) of N-(4-chloro-2-fluorophenyl)formamide (Intermediate 74-1) as a white solid. LRMS (ES) m/z 174

(M+H). $^1$H NMR (NMR (300 MHz, DMSO-d$_6$) δ 10.23 (s, 1H), 8.31 (s, 1H), 8.13 (t, J=8.7 Hz, 1H), 7.56-7.36 (m, 1H), 7.25 (ddd, J=8.8, 2.4, 1.3 Hz, 1H).

2. Synthesis of Intermediate 74-2

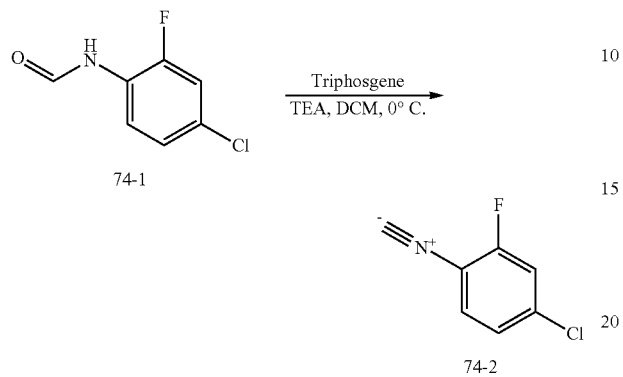

To a stirred solution of N-(4-chloro-2-fluorophenyl)formamide (5.1 g, 29.4 mmol, 1.0 equiv.) and TEA (9.0 g, 87.9 mmol, 6 equiv.) in DCM (100 mL) cooled to 0° C. was added triphosgene (3.8 g, 12.6 mmol, 0.43 equiv.) in DCM (20 mL) dropwise over a period of 10 min. The mixture was stirred at r.t. overnight, cooled to 0° C., quenched with MeOH, concentrated under reduced pressure, and purified by silica gel using PE/EA (10/1) as eluent to afford 13 g (27% pure) of 4-chloro-2-fluoro-1-isocyanobenzene (Intermediate 74-2) as a yellow solid. LRMS (ES) m/z 156 (M+H).

3. Synthesis of Intermediate 74-3

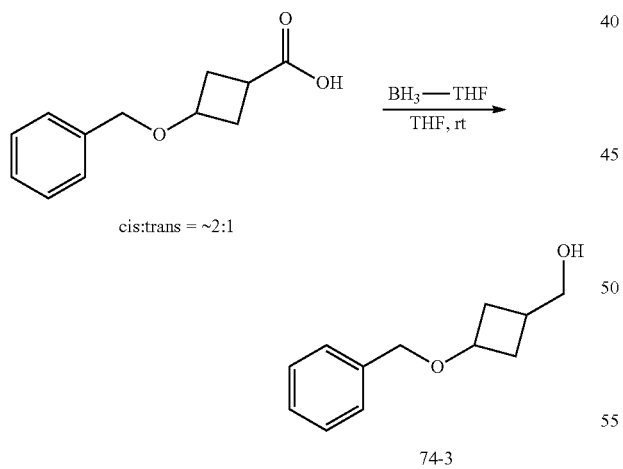

To a stirred solution of 3-(benzyloxy)cyclobutane-1-carboxylic acid (6.5 g, 31.5 mmol, 1.0 equiv.) in THF (50 mL) cooled to 0° C. was added BH$_3$-THF (1 M in THF, 157.6 mL, 157.6 mmol, 5.0 equiv.) dropwise over a period of 1 h. The mixture was stirred at rt overnight, cooled to 0° C., quenched with MeOH, and concentrated under reduced pressure to afford 6.9 g of (3-(benzyloxy)cyclobutyl)methanol (Intermediate 74-3) as a yellow solid. LRMS (ES) m/z 193 (M+H).

4. Synthesis of Intermediate 74-4

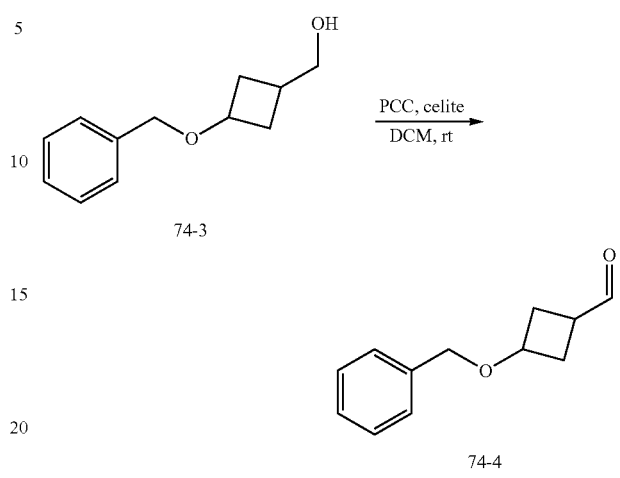

To a solution of PCC (11.4 g, 53.1 mmol, 1.5 equiv.) in DCM (70 mL) was added celite (13 g, 216.3 mmol, 6.1 equiv.). After stirring at rt for 30 min, to this mixture was added (3-(benzyloxy)cyclobutyl)methanol (6.8 g, 35.3 mmol, 1.0 equiv.). The mixture was stirred at rt for 2 h, diluted with Et$_2$O (140 mL), filtered off solid, and concentrated under reduced pressure to afford 6 g of 3-(benzyloxy)cyclobutane-1-carbaldehyde (Intermediate 74-4) as a yellow solid. LRMS (ES) m/z 191 (M+H).

5. Synthesis of Intermediate 74-5

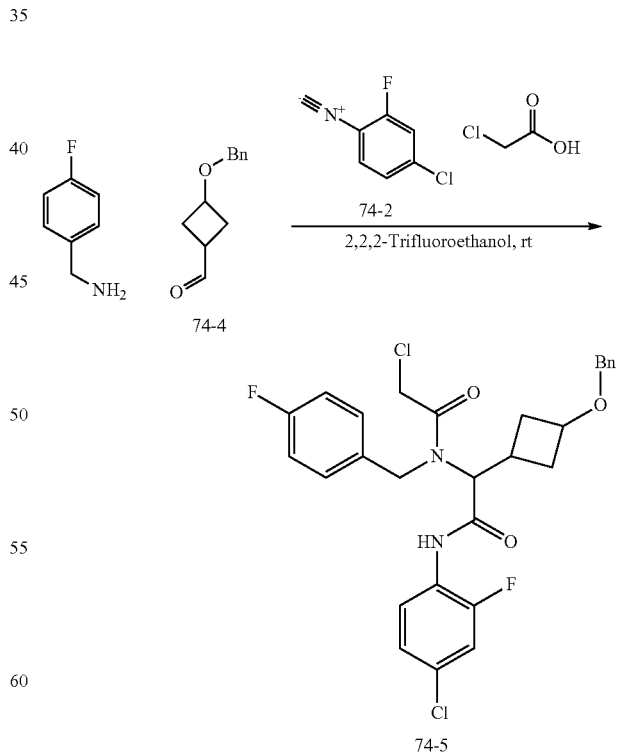

To a solution of 4-fluorophenylmethanamine (441 mg, 3.5 mmol, 1.0 equiv) in 2,2,2-trifluoroethanol (10.0 mL) was added 3-(benzyloxy)cyclobutane-1-carbaldehyde (673 mg, 3.5 mmol, 1.0 equiv). After stirring at r.t. for 10 min, to this resulting mixture were added 4-chloro-2-fluoro-1-isocyanobenzene (1.85 g, 27% pure, 3.2 mmol, 1.0 equiv) and chloroacetic acid (331 mg, 3.5 mmol, 1.0 equiv). The resulting mixture was stirred at r.t. overnight, concentrated under reduced pressure, and purified silica gel chromatography, eluted with EA/PE (1/6) to afford 1.1 g of 2-(3-(benzyloxy)cyclobutyl)-N-(4-chloro-2-fluorophenyl)-2-(2-chloro-N-(4-fluorobenzyl)acetamido)acetamide (Intermediate 74-5) as a yellow oil. LRMS (ES) m/z 562 (M+H).

6. Synthesis of Intermediate 74-6

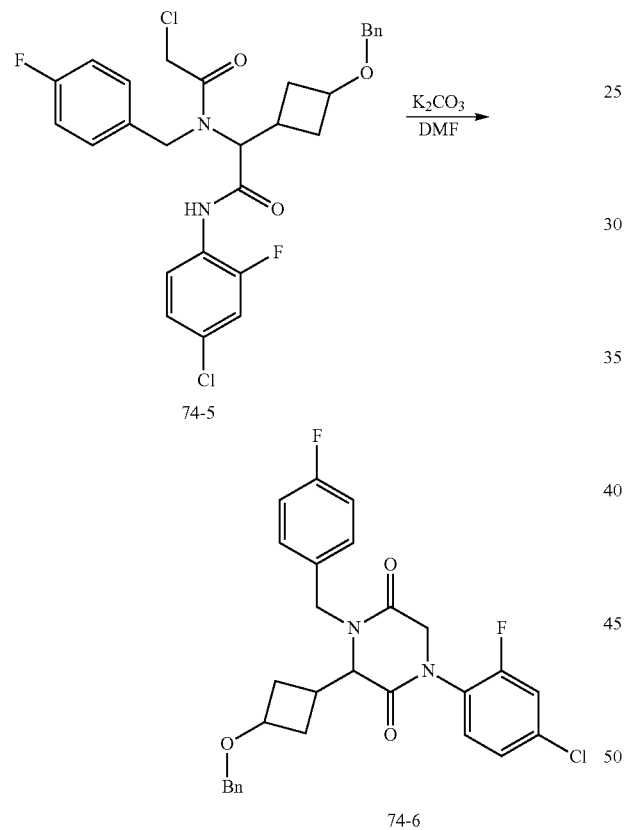

74-5

74-6

To a solution of 2-(3-(benzyloxy)cyclobutyl)-N-(4-chloro-2-fluorophenyl)-2-(2-chloro-N-(4-fluorobenzyl)acetamido)acetamide (1.1 g, 2.0 mmol, 1.0 equiv) in DMF (15.0 mL) at r.t was added K$_2$CO$_3$ (555 mg, 4.0 mmol, 2.0 equiv). The mixture was stirred at rt for 30 min, diluted water (30 mL), and extracted with EA (30 mL) twice. The combined organic layers were washed with brine (30 mL) twice, dried over Na$_2$SO$_4$, and concentrated under reduced pressure to afford 1 g of 3-(3-(benzyloxy)cyclobutyl)-1-(4-chloro-2-fluorophenyl)-4-(4-fluorobenzyl)piperazine-2,5-dione (Intermediate 74-6). LRMS (ES) m/z 511 (M+H).

7. Synthesis of Compound 866

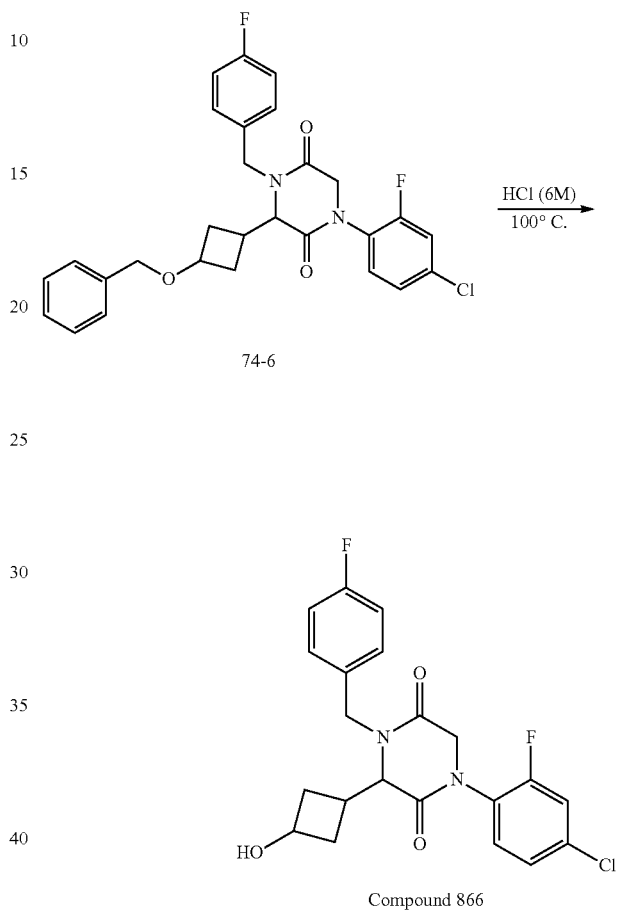

74-6

Compound 866

A solution of 3-(3-(benzyloxy)cyclobutyl)-1-(4-chloro-2-fluorophenyl)-4-(4-fluorobenzyl)piperazine-2,5-dione (700 mg, 1.4 mmol, 1.0 equiv) in HCl (6 N, 15 mL) was stirred at 100° C. overnight, cooled to r.t., concentrated under reduced pressure, diluted with water, adjusted the pH to 9 with sodium bicarbonate, and extracted with EA (20 mL) twice. The combined organic layer was washed with brine (20 mL), dried over Na$_2$SO$_4$, concentrated under reduced pressure, and purified by Prep-HPLC with the following conditions: (SHIMADZU (HPLC-01)): Column, XBridge Prep C18 OBD Column, 5 um, 19*150 mm; mobile phase, Water (10 mM NH$_4$HCO$_3$) and ACN (25% gradient to 50% in 8 min); Detector UV 254 nm) to afford 230 mg of 1-(4-chloro-2-fluorophenyl)-4-(4-fluorobenzyl)-3-(3-hydroxycyclobutyl)piperazine-2,5-dione (Compound 866). LRMS (ES) m/z 421 (M+H).

8. Separation of Compound 866 Stereoisomers: Stereoisomers 866A, 866B, 866C, and 866D

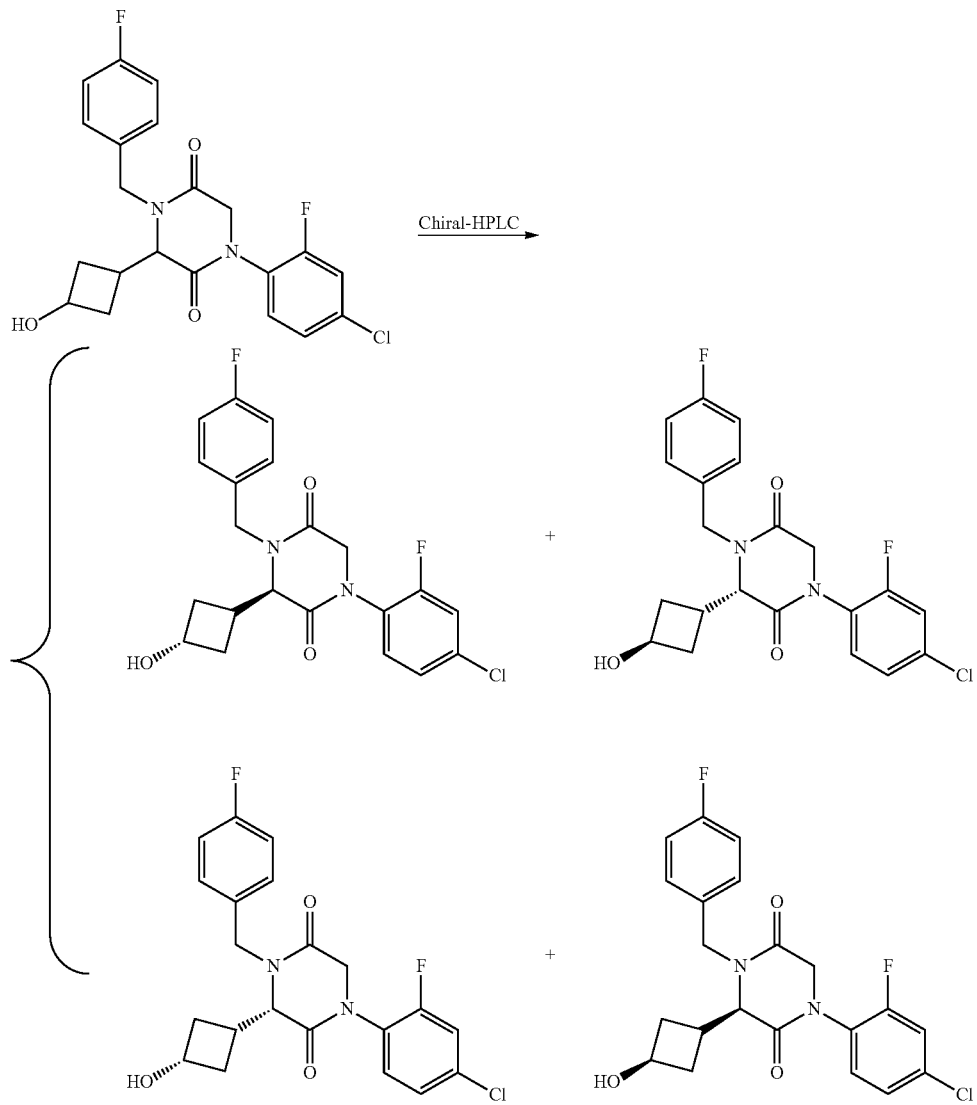

The stereoisomers of 1-(4-chloro-2-fluorophenyl)-4-(4-fluorobenzyl)-3-(3-hydroxycyclobutyl)piperazine-2,5-dione (230 mg, 0.55 mmol, 1.0 equiv) was purified by Chiral-Prep-HPLC with the following conditions: Column, CHIRALPAK IF, 2*25 cm, 5 um; mobile phase, MTBE (10 mM NH$_3$/MeOH) and EtOH (hold 5% EtOH for 13 min); Detector, UV 254 nm/220 nm) to afford 86 mg of Stereoisomer 866A, 23 mg of Stereoisomer 866D, and 100 mg mixture of Stereoisomer 866B and Stereoisomer 866C, which was further purified by Chiral HPLC with the following condition; Column CHIRALPAK IG 20*25 cm, 5 um; mobile phase, MTBE (10 mM NH$_3$/MeOH) and EtOH (hold 30% EtOH for 10 min); Detector, UV 254 nm/220 nm) to afford 68 mg of Stereoisomer 866B and 18 mg of Stereoisomer 866C as white solids.

Characterization of Stereoisomer 866A. LCMS (ES) m/z 421 (M+H). $^1$H NMR (300 MHz, DMSO-d$_6$) δ 7.65-7.50 (m, 2H), 7.44-7.32 (m, 3H), 7.22 (t, J=8.8 Hz, 2H), 5.13-4.98 (m, 2H), 4.72 (d, J=17.0 Hz, 1H), 4.21 (d, J=15.2 Hz, 1H), 4.09 (d, J=17.0 Hz, 1H), 3.89 (d, J=7.1 Hz, 2H), 2.23 (s, 3H), 1.75 (s, 2H). Analytical chiral HPLC RT: 0.90 min (CHIRALPAK IG-3; 0.46 cm×5 cm; 3 micro; MtBE (0.1% DEA):EtOH=70:30 at 1 ml/min).

Characterization of Stereoisomer 866B. LCMS (ES) m/z 421 (M+H). $^1$H NMR (300 MHz, DMSO-d$_6$) δ 7.66-7.50 (m, 2H), 7.44-7.32 (m, 3H), 7.22 (t, J=8.8 Hz, 2H), 5.09 (d, J=6.5 Hz, 1H), 5.03 (d, J=15.2 Hz, 1H), 4.73 (d, J=17.1 Hz, 1H), 4.21 (d, J=15.1 Hz, 1H), 4.09 (d, J=17.1 Hz, 1H), 3.89 (d, J=7.0 Hz, 2H), 2.27-2.17 (m, 3H), 1.74 (s, 2H). Analytical chiral HPLC RT: 1.5 min (CHIRALPAK IG-3; 0.46 cm×5 cm; 3 micro; MtBE (0.1% DEA):EtOH=70:30 at 1 ml/min).

Characterization of Stereoisomer 866C. LCMS (ES) m/z 421 (M+H). $^1$H NMR (300 MHz, DMSO-d$_6$) δ 7.65-7.49 (m, 2H), 7.44-7.29 (m, 3H), 7.27-7.13 (m, 2H), 5.06-4.94 (m, 2H), 4.77 (d, J=17.1 Hz, 1H), 4.32 (d, J=15.2 Hz, 1H), 4.19 (s, 1H), 4.08 (d, J=17.1 Hz, 1H), 4.00 (d, J=8.9 Hz, 1H), 2.94 (dq, J=9.2, 4.7, 2.8 Hz, 1H), 2.23 (qd, J=8.0, 6.6, 4.7 Hz, 2H), 1.88 (td, J=8.8, 4.5 Hz, 2H). Analytical chiral HPLC RT: 0.89 min (CHIRALPAK IG-3; 0.46 cm×5 cm; 3 micro; MtBE (0.1% DEA):EtOH=70:30 at 1 ml/min).

Characterization of Stereoisomer 866D. LCMS (ES) m/z 421 (M+H). $^1$H NMR (300 MHz, DMSO-$d_6$) δ 7.65-7.50 (m, 2H), 7.44-7.29 (m, 3H), 7.27-7.14 (m, 2H), 5.07-4.94 (m, 2H), 4.77 (d, J=17.1 Hz, 1H), 4.32 (d, J=15.2 Hz, 1H), 4.18 (d, J=4.8 Hz, 1H), 4.08 (d, J=17.1 Hz, 1H), 4.00 (d, J=8.9 Hz, 1H), 2.95 (q, J=7.2 Hz, 1H), 2.23 (qd, J=8.2, 6.6, 4.5 Hz, 2H), 1.87 (ddd, J=13.0, 8.9, 4.2 Hz, 2H). Analytical chiral HPLC RT: 1.86 min (CHIRALPAK IG-3; 0.46 cm×5 cm; 3 micro; MtBE (0.1% DEA):EtOH=70:30 at 1 ml/min).

The following compounds were prepared by methods analogous to the method described for Stereoisomers 866A, 866B, 866C, and 866D:

| Number | HPLC Conditions |
|---|---|
| Q | CHIRALPAK IE-3; 0.46 cm × 5 cm; 3 micro; MtBE(0.1% DEA):EtOH = 50:50 at 1 ml/min |
| V | CHIRALPAK IG-3; 0.46 cm × 5 cm; 3 micro; MtBE(0.1% DEA):EtOH = 70:30 at 1 ml/min |
| W | CHIRALPAK IG-3; 0.46 cm × 5 cm; 3 micro; MtBE(0.1% DEA):EtOH = 60:40 at 1 ml/min |

| Compound No. | LRMS (ES) m/z | $^1$H NMR |
|---|---|---|
| 889A | M + H = 530.0 | (400 MHz, Methylene Chloride-$d_2$) δ 8.44 (s, 1H), 7.78 (d, J = 8.5 Hz, 1H), 7.68 (d, J = 7.6 Hz, 2H), 7.46 (d, J = 7.9 Hz, 2H), 5.37 (d, J = 15.5 Hz, 1H), 4.74-4.39 (m, 2H), 4.21 (d, J = 15.5 Hz, 1H), 3.94 (dd, J = 7.7, 1.6 Hz, 1H), 3.74 (p, J = 7.2 Hz, 1H), 3.24-3.19 (m, 3H), 2.56-2.23 (m, 3H), 1.91 (q, J = 10.2 Hz, 2H). |
| 889B | M + H = 530.0 | (400 MHz, Methylene Chloride-$d_2$) δ 8.44 (d, J = 2.0 Hz, 1H), 7.78 (d, J = 8.5 Hz, 1H), 7.68 (d, J = 8.0 Hz, 2H), 7.45 (d, J = 7.9 Hz, 2H), 5.36 (d, J = 15.6 Hz, 1H), 4.69-4.45 (m, 2H), 4.25 (d, J = 15.7 Hz, 1H), 3.99-3.89 (m, 2H), 3.23 (s, 3H), 3.05 (h, J = 8.4 Hz, 1H), 2.38-2.09 (m, 4H). |
| 890A | M + H = 436.1 | (400 MHz, Methylene Chloride-$d_2$) δ 8.34 (d, J = 2.1 Hz, 1H), 7.63 (dd, J = 8.9, 2.1 Hz, 1H), 7.36-7.25 (m, 2H), 7.16-7.05 (m, 2H), 5.28 (d, J = 15.2 Hz, 1H), 4.69-4.42 (m, 2H), 4.13 (d, J = 15.2 Hz, 1H), 3.97-3.84 (m, 2H), 3.23 (s, 3H), 3.11-2.95 (m, 1H), 2.36-2.23 (m, 2H), 2.23-2.07 (m, 2H). |
| 890B | M + H = 436.0 | (400 MHz, Methylene Chloride-$d_2$) δ 8.33 (d, J = 2.1 Hz, 1H), 7.63 (dd, J = 8.9, 2.1 Hz, 1H), 7.36-7.27 (m, 2H), 7.10 (t, J = 8.7 Hz, 2H), 5.28 (d, J = 15.1 Hz, 1H), 4.65-4.43 (m, 2H), 4.12 (d, J = 15.1 Hz, 1H), 3.93 (d, J = 7.7 Hz, 1H), 3.73 (tt, J = 7.9, 6.4 Hz, 1H), 3.21 (s, 3H), 2.51-2.33 (m, 2H), 2.36-2.23 (m, 1H), 1.96-1.82 (m, 2H). |
| 891A | M + H = 468.1 | (400 MHz, Methylene Chloride-$d_2$) δ 8.34 (d, J = 2.1 Hz, 1H), 7.64 (dd, J = 8.9, 2.1 Hz, 1H), 7.56 (d, J = 7.9 Hz, 2H), 7.41 (d, J = 8.4 Hz, 2H), 6.71 (t, J = 56.4 Hz, 1H), 5.36 (d, J = 15.5 Hz, 1H), 4.66-4.46 (m, 2H), 4.22 (d, J = 15.4 Hz, 1H), 3.98-3.85 (m, 2H), 3.23 (s, 3H), 3.12-2.92 (m, 1H), 2.54-2.07 (m, 4H). |
| 891B | M + H = 468.1 | (400 MHz, Methylene Chloride-$d_2$) δ 8.34 (d, J = 2.1 Hz, 1H), 7.64 (dd, J = 8.9, 2.1 Hz, 1H), 7.56 (d, J = 7.9 Hz, 2H), 7.41 (d, J = 8.4 Hz, 2H), 6.71 (t, J = 56.4 Hz, 1H), 5.36 (d, J = 15.5 Hz, 1H), 4.66-4.46 (m, 2H), 4.22 (d, J = 15.4 Hz, 1H), 3.98-3.85 (m, 2H), 3.23 (s, 3H), 3.12-2.92 (m, 1H), 2.54-2.07 (m, 4H). |
| 740A | M + H = 472 | (300 MHz, DMSO-$d_6$) δ 8.47 (d, J = 2.1 Hz, 1H), 8.24 (dd, J = 9.4, 2.2 Hz, 1H), 7.73 (d, J = 8.0 Hz, 2H), 7.51 (d, J = 8.0 Hz, 2H), 5.12-5.00 (m, 2H), 4.74 (d, J = 17.0 Hz, 1H), 4.36 (dd, J = 16.3, 9.8 Hz, 2H), 4.04 (d, J = 7.7 Hz, 1H), 3.86 (q, J = 6.6 Hz, 1H), 2.43-2.12 (m, 3H), 1.73 (q, J = 9.4 Hz, 2H). |
| 740B | M + H = 472 | (300 MHz, DMSO-d6) δ 8.47 (d, J = 2.1 Hz, 1H), 8.25 (dd, J = 9.4, 2.2 Hz, 1H), 7.72 (d, J = 8.0 Hz, 2H), 7.49 (d, J = 8.0 Hz, 2H), 5.09-4.97 (m, 2H), 4.78 (d, J = 17.1 Hz, 1H), 4.49 (d, J = 15.7 Hz, 1H), 4.35 (d, J = 17.1 Hz, 1H), 4.18 (t, J = 8.7 Hz, 2H), 2.97-2.94 (, m 1H), 2.26-2.28 (m, 2H), 1.87 (td, J = 8.8, 4.4 Hz, 2H). |
| 740C | M + H = 472 | (300 MHz, DMSO-$d_6$) δ 8.47 (d, J = 2.1 Hz, 1H), 8.24 (dd, J = 9.4, 2.1 Hz, 1H), 7.73 (d, J = 8.1 Hz, 2H), 7.51 (d, J = 8.0 Hz, 2H), 5.11-5.00 (m, 2H), 4.74 (d, J = 16.9 Hz, 1H), 4.36 (dd, J = 16.3, 10.0 Hz, 2H), 4.04 (d, J = 7.7 Hz, 1H), 3.87 (p, J = 7.1 Hz, 1H), 2.37-2.04 (m, 3H), 1.73 (q, J = 9.4 Hz, 2H). |
| 740D | M + H = 472 | (300 MHz, DMSO-$d_6$) δ 8.47 (t, J = 1.9 Hz, 1H), 8.25 (dt, J = 9.4, 1.8 Hz, 1H), 7.72 (d, J = 7.9 Hz, 2H), 7.49 (d, J = 7.9 Hz, 2H), 5.09-4.97 (m, 2H), 4.78 (d, J = 17.1 Hz, 1H), 4.49 (d, J = 15.7 Hz, 1H), 4.35 (d, J = 17.1 Hz, 1H), 4.24-4.12 (m, 2H), 2.95 (d, J = 9.3 Hz, 1H), 2.28-2.17 (m, 2H), 1.94-1.80 (m, 2H). |

| | | |
|---|---|---|
| 892A | M + H = 422 | (300 MHz, Methanol-d$_4$) δ 8.39 (d, J = 2.1 Hz, 1H), 7.93 (dd, J = 9.1, 2.2 Hz, 1H), 7.42-7.30 (m, 2H), 7.17-7.04 (m, 2H), 5.20 (d, J = 15.2 Hz, 1H), 4.73 (d, J = 17.2 Hz, 1H), 4.46 (d, J = 17.2 Hz, 1H), 4.25 (d, J = 15.1 Hz, 1H), 4.01 (dd, J = 26.0, 6.9 Hz, 2H), 2.50-2.26 (m, J = 6.5 Hz, 3H), 1.87 (t, J = 7.2 Hz, 2H). |
| 892B | M + H = 422 | (300 MHz, Methanol-d$_4$) δ 8.40 (d, J = 2.1 Hz, 1H), 7.94 (dd, J = 9.2, 2.1 Hz, 1H), 7.42-7.31 (m, 2H), 7.18-7.04 (m, 2H), 5.16 (d, J = 15.3 Hz, 1H), 4.73 (d, J = 17.3 Hz, 1H), 4.49 (d, J = 17.3 Hz, 1H), 4.39-4.24 (m, 2H), 4.03 (d, J = 8.7 Hz, 1H), 3.19-3.00 (m, 1H), 2.38 (dtt, J = 13.3, 6.6, 3.1 Hz, 2H), 2.15-1.96 (m, 2H). |
| 892C | M + H = 422 | (300 MHz, Methanol-d$_4$) δ 8.39 (d, J = 2.1 Hz, 1H), 7.94 (dd, J = 9.1, 2.1 Hz, 1H), 7.37 (dd, J = 8.7, 5.3 Hz, 2H), 7.12 (t, J = 8.8 Hz, 1H), 5.20 (d, J = 15.2 Hz, 1H), 4.74 (d, J = 17.2 Hz, 1H), 4.47 (d, J = 17.2 Hz, 1H), 4.25 (d, J = 15.1 Hz, 1H), 4.09-3.92 (m, 2H), 2.39 (dh, J = 14.1, 7.4, 6.9 Hz, 3H), 1.94-1.80 (m, 2H). |
| 892D | M + H = 422 | (300 MHz, Methanol-d$_4$) δ 8.40 (d, J = 2.1 Hz, 1H), 7.94 (dd, J = 9.2, 2.1 Hz, 1H), 7.42-7.31 (m, 2H), 7.18-7.05 (m, 2H), 5.16 (d, J = 15.2 Hz, 1H), 4.73 (d, J = 17.3 Hz, 1H), 4.49 (d, J = 17.3 Hz, 1H), 4.39-4.24 (m, 2H), 4.03 (d, J = 8.7 Hz, 1H), 3.08 (dq, J = 15.5, 8.3, 7.7 Hz, 1H), 2.39 (dtt, J = 12.3, 6.0, 3.3 Hz, 2H), 2.05 (dtt, J = 13.1, 8.9, 4.1 Hz, 2H). |
| 893A | M + H = 438 | (300 MHz, DMSO-d$_6$) δ 8.48 (d, J = 2.1 Hz, 1H), 8.26 (dd, J = 9.4, 2.1 Hz, 1H), 7.44 (d, J = 8.4 Hz, 2H), 7.33 (d, J = 8.4 Hz, 2H), 5.09 (d, J = 6.4 Hz, 1H), 4.99 (d, J = 15.2 Hz, 1H), 4.73 (d, J = 17.0 Hz, 1H), 4.29 (dd, J = 23.0, 16.1 Hz, 2H), 3.98 (d, J = 7.6 Hz, 1H), 3.86 (d, J = 6.7 Hz, 1H), 2.21 (dd, J = 15.7, 9.6 Hz, 3H), 1.79-1.67 (m, 2H). |
| 893B | M + H = 438 | (300 MHz, DMSO-d$_6$) δ 8.48 (d, J = 2.1 Hz, 1H), 8.26 (dd, J = 9.4, 2.1 Hz, 1H), 7.48-7.38 (m, 2H), 7.36-7.27 (m, 2H), 5.07-4.90 (m, 2H), 4.77 (d, J = 17.1 Hz, 1H), 4.35 (dd, J = 16.3, 8.1 Hz, 2H), 4.19 (q, J = 5.9 Hz, 1H), 4.10 (d, J = 9.3 Hz, 1H), 3.06-2.81 (m, 1H), 2.22 (dt, J = 12.3, 6.6 Hz, 2H), 1.94-1.77 (m, 2H). |
| 893C | M + H = 438 | (300 MHz, DMSO-d$_6$) δ 8.48 (d, J = 2.1 Hz, 1H), 8.25 (dd, J = 9.4, 2.2 Hz, 1H), 7.49-7.39 (m, 2H), 7.33 (d, J = 8.4 Hz, 2H), 5.09 (d, J = 6.4 Hz, 1H), 4.99 (d, J = 15.3 Hz, 1H), 4.73 (d, J = 17.0 Hz, 1H), 4.33 (d, J = 17.0 Hz, 1H), 4.26 (d, J = 15.3 Hz, 1H), 3.98 (d, J = 7.6 Hz, 1H), 3.86 (q, J = 7.0 Hz, 1H), 2.32-2.12 (m, 3H), 1.72 (q, J = 9.0 Hz, 2H). |
| 893D | M + H = 438 | (300 MHz, DMSO-d$_6$) δ 8.48 (d, J = 2.1 Hz, 1H), 8.26 (dd, J = 9.4, 2.2 Hz, 1H), 7.47-7.38 (m, 2H), 7.36-7.27 (m, 2H), 5.03 (d, J = 5.1 Hz, 1H), 4.96 (d, J = 15.4 Hz, 1H), 4.77 (d, J = 17.0 Hz, 1H), 4.35 (dd, J = 16.3, 8.1 Hz, 2H), 4.23-4.15 (m, 1H), 4.10 (d, J = 9.3 Hz, 1H), 2.96 (d, J = 22.1 Hz, 1H), 2.22 (dt, J = 12.3, 6.5 Hz, 2H), 1.86 (td, J = 11.9, 11.2, 4.2 Hz, 2H). |
| 894A | M + H = 418 | (300 MHz, Methanol-d$_4$) δ 8.39 (d, J = 2.1 Hz, 1H), 7.92 (dd, J = 9.1, 2.1 Hz, 1H), 7.20 (s, 4H), 5.25 (d, J = 15.1 Hz, 1H), 4.73 (d, J = 17.2 Hz, 1H), 4.46 (d, J = 17.2 Hz, 1H), 4.16 (d, J = 15.0 Hz, 1H), 4.10-3.95 (m, 1H), 3.91 (d, J = 7.3 Hz, 1H), 2.50-2.35 (m, 3H), 2.34 (s, 3H), 1.88 (t, J = 8.7 Hz, 2H). |
| 894B | M + H = 418 | (300 MHz, Methanol-d$_4$) δ 8.39 (d, J = 2.1 Hz, 1H), 7.93 (dd, J = 9.2, 2.1 Hz, 1H), 7.20 (s, 4H), 5.22 (d, J = 15.1 Hz, 1H), 4.72 (d, J = 17.3 Hz, 1H), 4.49 (d, J = 17.3 Hz, 1H), 4.36-4.18 (m, 2H), 3.97 (d, J = 8.8 Hz, 1H), 3.09 (q, J = 7.9 Hz, 1H), 2.43-2.35 (m, 2H), 2.34 (s, 3H), 2.16-1.95 (m, 2H). |
| 894C | M + H = 418 | (300 MHz, Methanol-d$_4$) δ 8.39 (d, J = 2.1 Hz, 1H), 7.92 (dd, J = 9.1, 2.1 Hz, 1H), 7.20 (s, 4H), 5.25 (d, J = 15.0 Hz, 1H), 4.73 (d, J = 17.2 Hz, 1H), 4.46 (d, J = 17.2 Hz, 1H), 4.16 (d, J = 15.0 Hz, 1H), 4.03 (t, J = 7.3 Hz, 1H), 3.91 (d, J = 7.3 Hz, 1H), 2.49-2.29 (m, 6H), 1.86 (d, J = 8.6 Hz, 2H). |
| 894D | M + H = 418 | (300 MHz, Methanol-d$_4$) δ 8.39 (d, J = 2.1 Hz, 1H), 7.93 (dd, J = 9.1, 2.1 Hz, 1H), 7.20 (s, 4H), 5.22 (d, J = 15.1 Hz, 1H), 4.72 (d, J = 17.2 Hz, 1H), 4.48 (d, J = 17.3 Hz, 1H), 4.36-4.18 (m, 2H), 3.97 (d, J = 8.7 Hz, 1H), 3.09 (h, J = 8.3 Hz, 1H), 2.37 (dt, J = 13.5, 6.8 Hz, 5H), 2.16-1.93 (m, 2H). |

| Compound No. | Retention Time (min) | HPLC Condition |
|---|---|---|
| 740A | 0.85 | W |
| 740B | 0.82 | W |
| 740C | 1.56 | W |
| 740D | 2.98 | W |
| 892A | 0.95 | Q |
| 892B | 0.98 | Q |
| 892C | 1.49 | Q |

-continued

| | | |
|---|---|---|
| 892D | 1.88 | Q |
| 893A | 1.37 | T |
| 893B | 1.40 | T |
| 893C | 2.00 | T |
| 893D | 2.80 | T |
| 894A | 2.73 | V |
| 894B | 3.86 | V |
| 894C | 1.16 | V |
| 894D | 1.17 | V |

Example 75: Synthesis of Compound 867

1. Synthesis of Intermediate 75-1

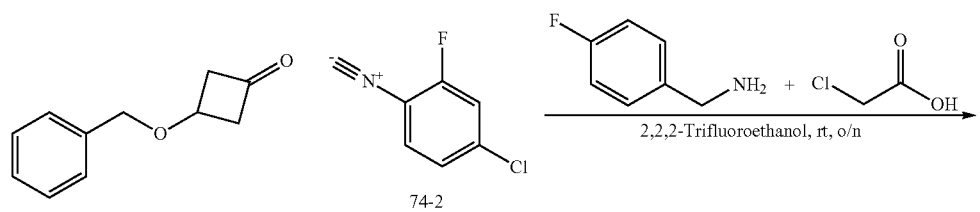

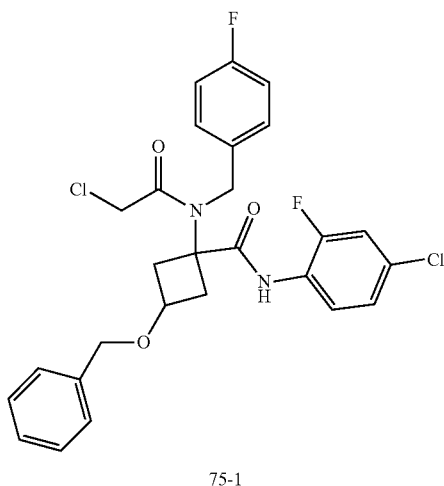

75-1

To a solution of 4-fluorophenylmethanamine (355 mg, 2.8 mmol, 1.0 equiv) in 2,2,2-trifluoroethanol (10.0 mL) was added 3-(benzyloxy)cyclobutan-1-one (500 mg, 2.8 mmol, 1.0 equiv). After stirring at r.t. for 10 min, to this resulting mixture were added 4-chloro-2-fluoro-1-isocyanobenzene (1.5 g, unpurified mixture) and chloroacetic acid (266 mg, 2.8 mmol, 1.0 equiv). The resulting mixture was stirred at r.t. overnight, concentrated under reduced pressure, and purified silica gel chromatography, eluted with EA/PE (1/5) to afford 1.1 g (21%) of 3-(benzyloxy)-N-(4-chloro-2-fluorophenyl)-1-(2-chloro-N-(4-fluorobenzyl)acetamido)cyclobutane-1-carboxamide (Intermediate 75-1) as a yellow oil. LRMS (ES) m/z 533 (M+H).

2. Synthesis of Intermediate 75-2

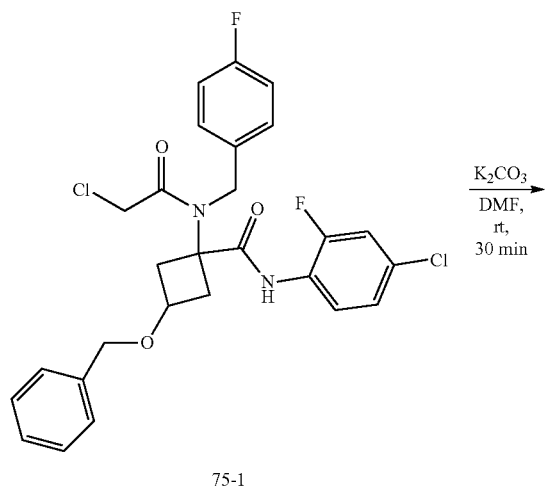

75-1

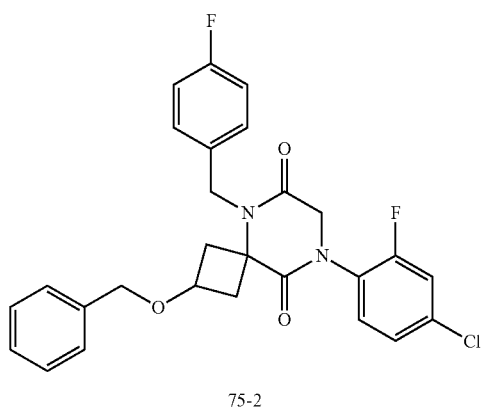

75-2

To a solution of 3-(benzyloxy)-N-(4-chloro-2-fluorophenyl)-1-(2-chloro-N-(4-fluorobenzyl)acetamido)cyclobutane-1-carboxamide (546 mg, 1.0 mmol, 1.0 equiv) in DMF (8.0 mL) was added $K_2CO_3$ (285 mg, 2.0 mmol, 2.0 equiv). The mixture was stirred at rt for 1 h, diluted water (20 mL), and extracted with EA (60 mL) three times. The combined organic layers were washed with brine (30 mL) twice, dried over $Na_2SO_4$, and concentrated under reduced pressure to afford 550 mg of 2-(benzyloxy)-8-(4-chloro-2-fluorophenyl)-5-(4-fluorobenzyl)-5,8-diazaspiro[3.5]nonane-6,9-dione (Intermediate 75-2). LRMS (ES) m/z 497 (M+H).

3. Synthesis of Compound 867

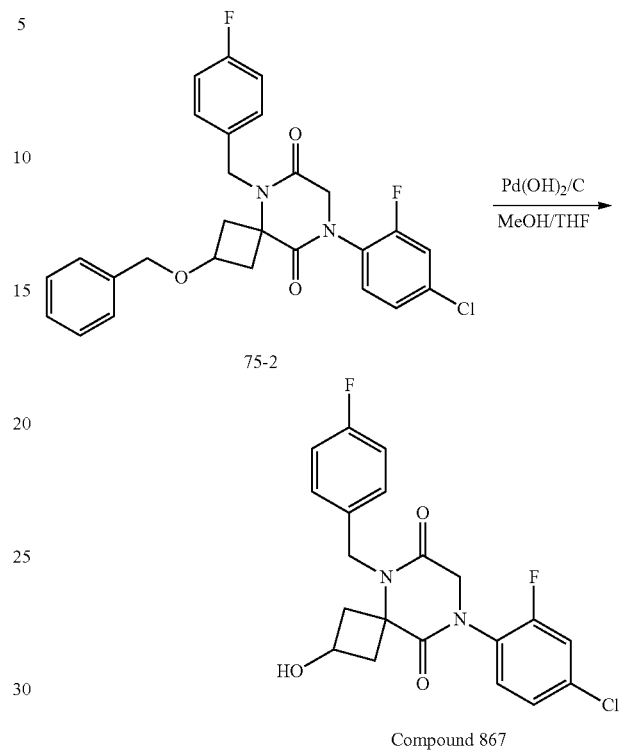

Compound 867

To a stirred solution of 2-(benzyloxy)-8-(4-chloro-2-fluorophenyl)-5-(4-fluorobenzyl)-5,8-diazaspiro[3.5]nonane-6,9-dione (660 mg, 1.3 mmol, 1.0 equiv) in MeOH (7 mL) and THF (7 mL) was added $Pd(OH)_2$/C (132 mg) in portions. The mixture was stirred at r.t. for 3 h under hydrogen (balloon), filtered off the solid, concentrated, and purified by Prep-HPLC with the following conditions: (SHIMADZU) Column, XBridge Prep C18 OBD Column, 5 um, 30*150 mm; mobile phase, Water (10 mM $NH_4HCO_3$) and ACN (25% gradient up to 50% in 8 min); Detector UV 254 nm) to afford 150 mg (27%) of 8-(4-chloro-2-fluorophenyl)-5-(4-fluorobenzyl)-2-hydroxy-5,8-diazaspiro[3.5]nonane-6,9-dione (Compound 867). LRMS (ES) m/z 407 (M+H).

4. Separation of Compound 867 Diastereomers: Diastereomers 867A and 867B

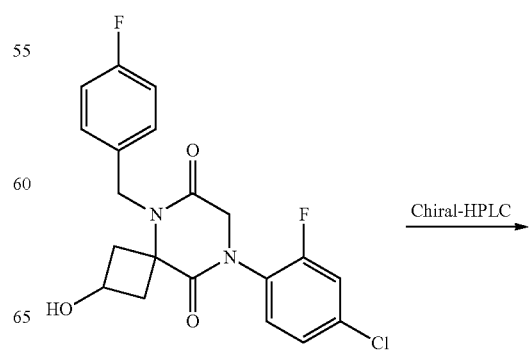

-continued

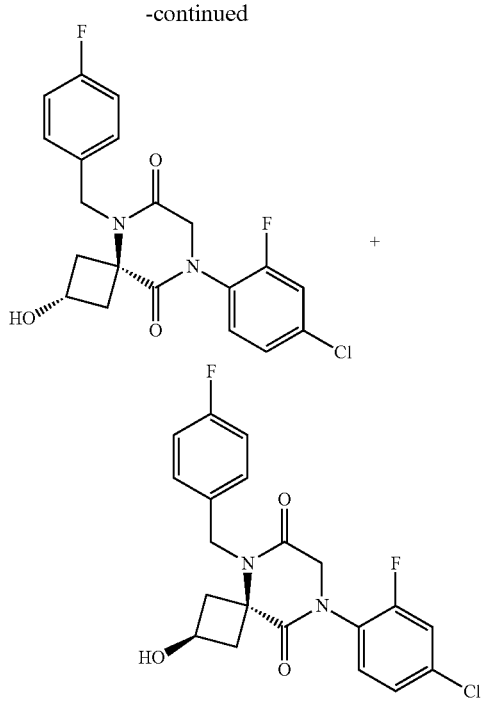

The racemic compound of 8-(4-chloro-2-fluorophenyl)-5-(4-fluorobenzyl)-2-hydroxy-5,8-diazaspiro[3.5]nonane-6,9-dione (150 mg, 0.37 mmol, 1.0 equiv) was purified by Chiral-Prep-HPLC with the following conditions: Column, CHIRALPAK IF-3, 2*25 mm, 5 um; mobile phase, Hex (8 mM, $NH_3$ in MeOH) and EtOH (60/40); Detector, UV254 nm) to afford 89 mg of first eluted peak (Diastereomer 867A) and 31 mg of second eluted peak (Diastereomer 867B) as white solids Characterization of Diastereomer 867A. LCMS (ES) m/z 407 (M+H). $^1$H NMR (NMR (300 MHz, DMSO-$d_6$) δ 7.67-7.50 (m, 2H), 7.40 (ddd, J=8.6, 2.3, 1.0 Hz, 1H), 7.29 (dd, J=8.6, 5.5 Hz, 2H), 7.19 (t, J=8.9 Hz, 2H), 5.30 (d, J=6.2 Hz, 1H), 4.83 (s, 2H), 4.38 (s, 2H), 4.09 (q, J=7.3 Hz, 1H), 2.65 (s, 3H), 2.75-2.55 (m, 1H). Analytical chiral HPLC RT: 1.79 min (CHIRALPAK IF-3; 0.46 cm×5 cm; 3 micro; HEX (0.1% DEA):EtOH=60:40 at 1 ml/min).

Characterization of Diastereomer 867B. LCMS (ES) m/z 407 (M+H). $^1$H NMR (300 MHz, DMSO-$d_6$) δ 7.66-7.54 (m, 2H), 7.46-7.37 (m, 1H), 7.31-7.13 (m, 4H), 5.32 (d, J=7.0 Hz, 1H), 4.89 (s, 2H), 4.40 (s, 2H), 3.93 (q, J=6.8 Hz, 1H), 2.79 (s, 2H), 2.31 (d, J=9.7 Hz, 2H). Analytical chiral HPLC RT: 2.66 min (CHIRALPAK IF-3; 0.46 cm×5 cm; 3 micro; HEX (0.1% DEA):EtOH=60:40 at 1 ml/min).

The following compounds were prepared by methods analogous to the method described for Diastereomers 867A and 867B:

| Compound No. | LRMS (ES) m/Z | $^1$H NMR |
|---|---|---|
| 764 | M + H = 408.0 | $^1$H NMR (400 MHz, Methylene Chloride-$d_2$) δ 8.28-8.20 (m, 1H), 7.60-7.50 (m, 1H), 7.20-7.11 (m, 2H), 7.03-6.93 (m, 2H), 4.83 (s, 1H), 4.75 (s, 1H), 4.42 (d, J = 9.1 Hz, 2H), 4.29-4.04 (m, 1.5H), 3.22 (s, 0.3H), 2.91 (ddd, J = 10.1, 7.0, 3.0 Hz, 1H), 2.86-2.72 (m, 1H), 2.60 (dd, J = 14.9, 3.8 Hz, 1H), 2.31 (ddd, J = 10.0, 6.8, 3.0 Hz, 1H), 0.83 (s, 0H). |
| 764A | M + H = 408.0 | $^1$H NMR (400 MHz, DMSO-$d_6$) δ 8.53 (d, J = 2.1 Hz, 1H), 8.30 (dd, J = 9.5, 2.1 Hz, 1H), 7.33-7.24 (m, 2H), 7.22 (t, J = 8.8 Hz, 2H), 5.38 (d, J = 6.9 Hz, 1H), 4.93 (s, 2H), 4.56 (s, 2H), 4.04-3.91 (m, 1H), 2.88-2.78 (m, 2H), 2.40-2.31 (m, 2H). |
| 764B | M + H = 408.0 | $^1$H NMR (400 MHz, DMSO-$d_6$) δ 8.53 (d, J = 2.1 Hz, 1H), 8.30 (dd, J = 9.4, 2.1 Hz, 1H), 7.31 (dd, J = 8.5, 5.5 Hz, 2H), 7.22 (t, J = 8.8 Hz, 2H), 4.87 (s, 2H), 4.54 (s, 2H), 4.18-4.06 (m, 1H), 3.61 (s, 1H), 2.81-2.70 (m, 2H), 2.69-2.58 (m, 2H). |
| 868A | M + H = 404.0 | $^1$H NMR (400 MHz, Methylene Chloride-$d_2$) δ 8.21 (d, J = 2.1 Hz, 1H), 7.52 (dd, J = 9.0, 2.1 Hz, 1H), 7.05 (q, J = 8.1 Hz, 4H), 4.79 (s, 2H), 4.38 (s, 2H), 4.23-4.11 (m, 1H), 2.92-2.82 (m, 2H), 2.36-2.25 (m, 2H), 2.24 (s, 3H), 1.91 (s, 1H). |
| 868B | M + H = 404.0 | $^1$H NMR (400 MHz, Methylene Chloride-$d_2$) δ 8.23 (d, J = 2.0 Hz, 1H), 7.54 (dd, J = 8.9, 2.1 Hz, 1H), 7.11-6.98 (m, 4H), 4.72 (s, 2H), 4.40 (s, 2H), 4.10 (s, 1H), 3.21 (d, J = 9.7 Hz, 1H), 2.84-2.73 (m, 2H), 2.56 (dd, J = 14.8, 3.8 Hz, 2H), 2.24 (s, 3H). |
| 869A | M − H = 422 | $^1$H NMR (300 MHz, DMSO-$d_6$) δ 8.49 (d, J = 2.1 Hz, 1H), 8.27 (dd, J = 9.5, 2.1 Hz, 1H), 7.47-7.37 (m, 2H), 7.32-7.22 (m, 2H), 5.35 (d, J = 6.2 Hz, 1H), 4.85 (s, 2H), 4.52 (s, 2H), 4.08 (p, J = 7.4 Hz, 1H), 2.78-2.65 (m, 2H), 2.65-2.53 (m, 2H). |
| 869B | M + H = 424 | $^1$H NMR (300 MHz, DMSO-$d_6$) δ 8.50 (d, J = 2.1 Hz, 1H), 8.27 (dd, J = 9.5, 2.2 Hz, 1H), 7.47-7.38 (m, 2H), 7.24 (d, J = 8.4 Hz, 2H), 5.36 (d, J = 7.1 Hz, 1H), 4.90 (s, 2H), 4.53 (s, 2H), 3.94 (q, J = 6.9 Hz, 1H), 2.79 (t, J = 9.7 Hz, 2H), 2.31 (dd, J = 11.3, 8.1 Hz, 2H). |

Example 76: Synthesis of Compound 838

1. Synthesis of Intermediate 76-1

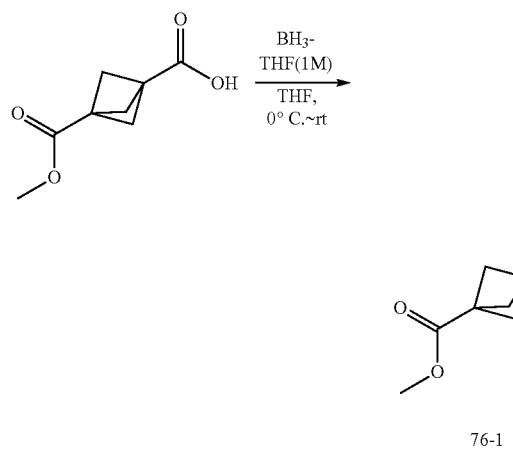

To a solution of methyl 3-(methoxycarbonyl)bicyclo[1.1.1]pentane-1-carboxylic acid (23.0 g, 135.2 mmol, 1.0 equiv) in THF (400.0 mL) at 0° C. was added BH$_3$-THF (1 M/THF, 162 mL, 162 mmol, 1.2 equiv.) dropwise over a period of 1 h. The mixture was stirred at rt overnight, cooled to 0° C., quenched with MeOH, and concentrated under reduced pressure to afford 21 g (99%) of methyl 3-(hydroxymethyl)bicyclo[1.1.1]pentane-1-carboxylate (Intermediate 76-1) as a yellow oil. LRMS (ES) m/z 157 (M+H).

2. Synthesis of Intermediate 76-2

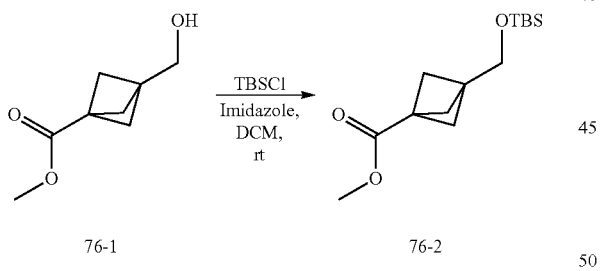

To a stirred solution of methyl 3-(hydroxymethyl)bicyclo[1.1.1]pentane-1-carboxylate (15.0 g, 96.0 mmol, 1.0 equiv) and imidazole (18.0 g, 264.4 mmol, 2.75 equiv.) in DCM (300.0 mL) cooled to 0° C. was added TBSCl (19.0 g, 126.1 mmol, 1.3 equiv.). The mixture was stirred at rt for 1 h, and filtered through celite plug. The filtrate was concentrated under reduced pressure, re-dissolved in EA (300 mL), and added water (300 mL) into the mixture. The aqueous layer was extract with EA (300 mL). The combined organic layers were washed with brine (300 mL) twice, dried over Na$_2$SO$_4$, concentrated under reduced pressure, and purified by silica gel column chromatography using PE/EA (20/1) as eluent to afford 28 g (86%) of methyl 3-(((tert-butyldimethylsilyl)oxy)methyl)bicyclo[1.1.1]pentane-1-carboxylate (Intermediate 76-2) as a yellow oil. LRMS (ES) m/z 271 (M+H).

3. Synthesis of Intermediate 76-3

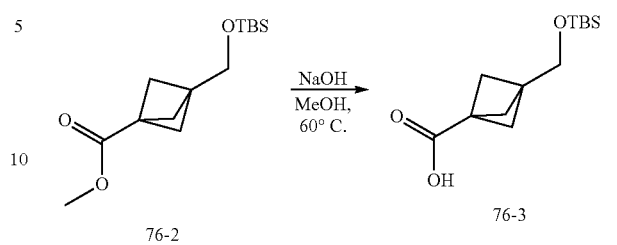

To a solution of methyl 3-(((tert-butyldimethylsilyl)oxy)methyl)bicyclo[1.1.1]pentane-1-carboxylate (28.0 g, 103.5 mmol, 1.0 equiv) in MeOH (250.0 mL) was added NaOH (4.6 g, 115.0 mmol, 1.1 equiv.). The mixture was stirred at 60° C. for 1 h, cooled to rt, acidified to pH 4 with HCl (4 N/water), concentrated under reduced pressure, added water (300 mL) to the mixture, and extracted with EA (300 mL) twice. The combined organic layer was washed with brine (300 mL) twice, dried over Na$_2$SO$_4$, and concentrated under reduced pressure to afford 24 g (90%) of 3-(((tert-butyldimethylsilyl)oxy)methyl)bicyclo[1.1.1]pentane-1-carboxylic acid (Intermediate 76-3) as a yellow oil. LRMS (ES) m/z 257 (M+H).

4. Synthesis of Intermediate 76-4

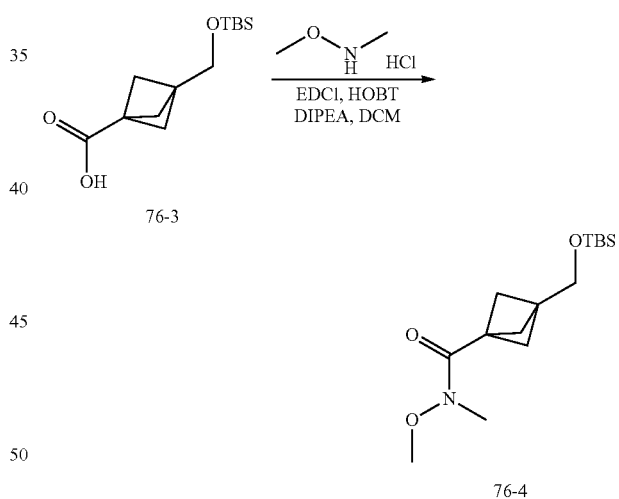

To a solution of 3-(((tert-butyldimethylsilyl)oxy)methyl)bicyclo[1.1.1]pentane-1-carboxylic acid (24.0 g, 93.6 mmol, 1.0 equiv) in DCM (400.0 mL) was EDCI (23.3 g, 121.7 mmol, 1.3 equiv.). After stirring at rt for 10 min, to the mixture were added HOBt (2.4 g, 17.8 mmol, 0.19 equiv.), DIEA (38.7 g, 299.5 mmol, 3.2 equiv.), and N,O-dimethylhydroxylamine hydrochloride (18.0 g, 184.4 mmol, 2.0 equiv.). The mixture was stirred at rt for 2 h, washed with saturated solution of sodium carbonate (300 mL) once and brine (300 mL) twice, dried over Na$_2$SO$_4$, and concentrated under reduced pressure to afford 28 g (90% purity) of 3-(((tert-butyldimethylsilyl)oxy)methyl)-N-methoxy-N-methylbicyclo[1.1.1]pentane-1-carboxamide (Intermediate 76-4) as a yellow oil. LRMS (ES) m/z 300 (M+H).

5. Synthesis of Intermediate 76-5

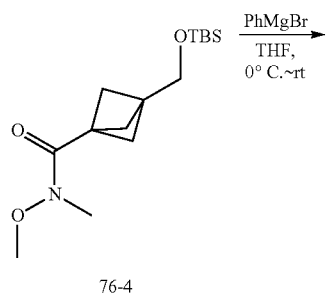

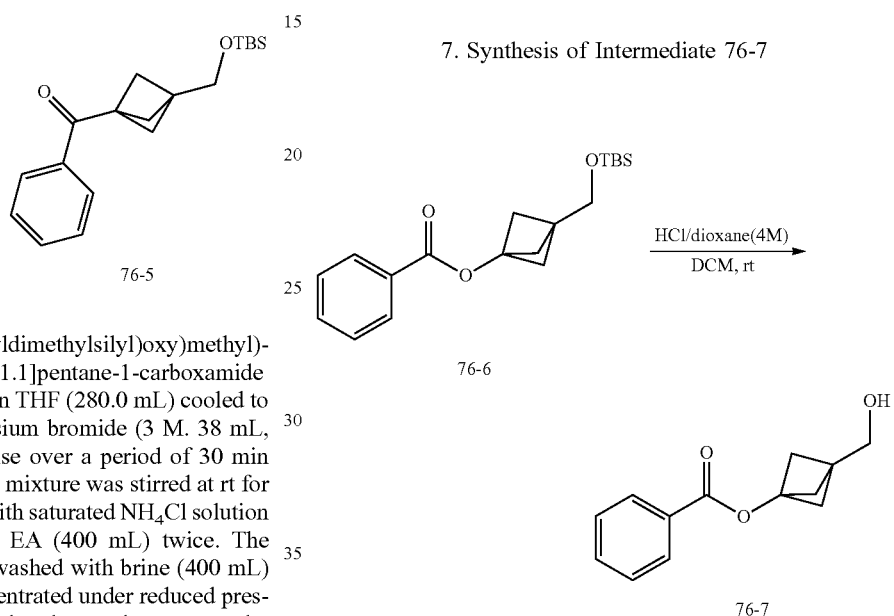

To a solution of 3-(((tert-butyldimethylsilyl)oxy)methyl)-N-methoxy-N-methylbicyclo[1.1.1]pentane-1-carboxamide (28.0 g, 93.5 mmol, 1.0 equiv) in THF (280.0 mL) cooled to 0° C. was added phenylmagnesium bromide (3 M, 38 mL, 114 mmol, 1.22 equiv.) dropwise over a period of 30 min under nitrogen atmosphere. The mixture was stirred at rt for 2 h, cooled to 0° C., quenched with saturated NH$_4$Cl solution (300 mL), and extracted with EA (400 mL) twice. The combined organic layers were washed with brine (400 mL) twice, dried over Na$_2$SO$_4$, concentrated under reduced pressure, and purified by silica gel column chromatography eluting with PE/EA (10/1) to afford 17 g (57%) of (3-(((tert-butyldimethylsilyl)oxy)methyl)bicyclo[1.1.1]pentan-1-yl)(phenyl)methanone (Intermediate 76-5) as a yellow oil. LRMS (ES) m/z 317 (M+H).

6. Synthesis of Intermediate 76-6

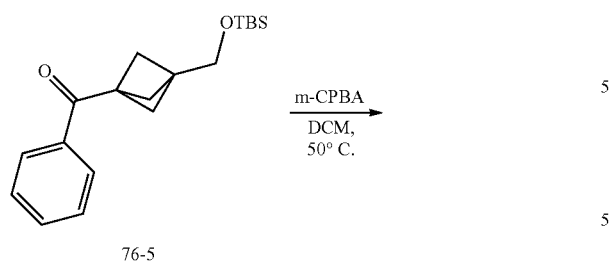

To a solution of (3-(((tert-butyldimethylsilyl)oxy)methyl)bicyclo[1.1.1]pentan-1-yl)(phenyl)methanone (17.0 g, 53.7 mmol, 1.0 equiv.) in DCM (340.0 mL) was added mCPBA (24.0 g, 118.2 mmol, 2.2 equiv., 85% purity). The mixture was stirred at 50° C. for 2 days, cooled to 0° C., quenched with saturated NaHSO$_3$ solution (200 mL), and extracted with EA (200 mL) twice. The combined organic layers were washed with saturated sodium carbonate solution (200 mL) once and brine (200 mL) twice, dried over Na$_2$SO$_4$, and concentrated under reduced pressure to afford 18 g (90% purity, 90%) of 3-(((tert-butyldimethylsilyl)oxy)methyl)bicyclo[1.1.1]pentan-1-yl benzoate (Intermediate 76-6) as a yellow oil. LRMS (ES) m/z 333 (M+H).

7. Synthesis of Intermediate 76-7

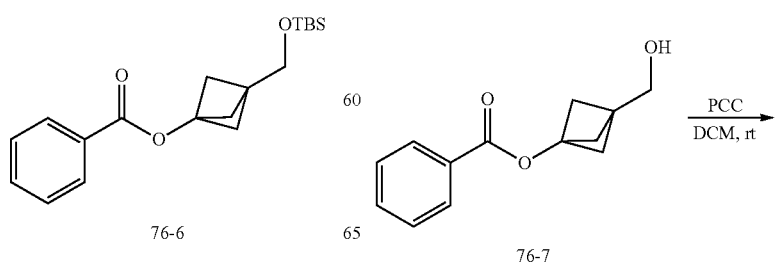

To a solution of 3-(((tert-butyldimethylsilyl)oxy)methyl) bicyclo[1.1.1]pentan-1-yl benzoate (18.0 g, 54.1 mmol, 1.0 equiv.) in DCM (180.0 mL) was added HCl (4 N/dioxane, 45 mL, 180 mmol). The mixture was stirred was stirred at rt for 2 h, concentrated under reduced pressure, diluted with water (200 mL), and extracted with EA (200 mL) twice. The combined organic layers were washed with brine (200 mL) twice, dried over Na$_2$SO$_4$, concentrated under reduced pressure, and purified by silica gel column chromatography eluting with PE/EA (3/1) to afford 6.2 g (52%) of 3-(hydroxymethyl)bicyclo[1.1.1]pentan-1-yl benzoate (Intermediate 76-7) as a yellow oil. LRMS (ES) m/z 219 (M+H).

8. Synthesis of Intermediate 76-8

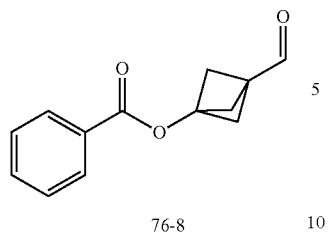

76-8

To a solution of 3-(hydroxymethyl)bicyclo[1.1.1]pentan-1-yl benzoate (6.2 g, 28.4 mmol, 1.0 equiv) in DCM (60.0 mL) at r.t. was added PCC (7.35 g, 34.1 mmol, 1.2 equiv) in portions. The mixture was stirred at rt for 2 h, diluted with ether (120 mL), stirred for 20 min, filtered off the solid, concentrated under reduced pressure, and purified by silica gel column chromatography eluting with PE/EA (10/1) to afford 2.7 g (65% purity) of 3-formylbicyclo[1.1.1]pentan-1-yl benzoate (Intermediate 76-8) as a yellow solid. LRMS (ES) m/z 217 (M+H).

9. Synthesis of Intermediate 76-9

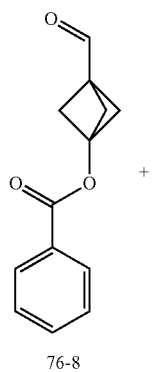

76-8

+

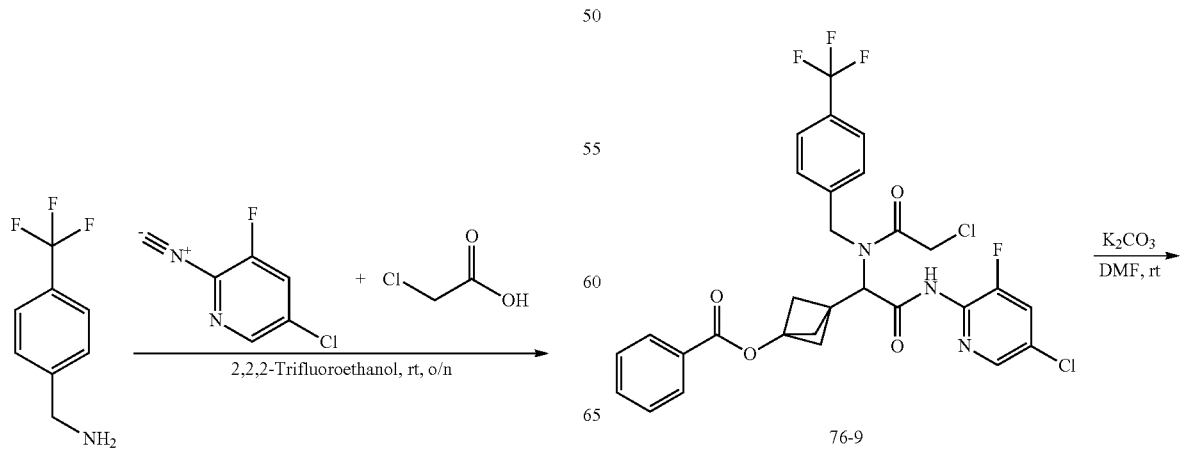

76-9

To a solution of (4-(trifluoromethyl)phenyl)methanamine (221.5 mg, 1.3 mmol, 1.1 equiv) in trifluoroethanol (5.0 mL) was added 3-formylbicyclo[1.1.1]pentan-1-yl benzoate (420 mg, 1.3 mmol, 1.1 equiv, ~65% purity). After stirring at r.t. for 10 min, to the mixture were added 5-chloro-3-fluoro-2-isocyanopyridine (180 mg, 1.15 mmol, 1.0 equiv) and chloroacetic acid (119.5 mg, 1.3 mmol, 1.1 equiv). The resulting mixture was stirred at r.t. overnight, concentrated under reduced pressure, and purified by silica gel column chromatography, eluted with PE/EtOAc (5:1) to afford 640 mg (89%) of 3-(2-((5-chloro-3-fluoropyridin-2-yl)amino)-1-(2-chloro-N-(4-(trifluoromethyl)benzyl)acetamido)-2-oxoethyl)bicyclo[1.1.1]pentan-1-yl benzoate (Intermediate 76-9) as a yellow oil. LRMS (ES) m/z 624 (M+H).

10. Synthesis of Intermediate 76-10

807

-continued

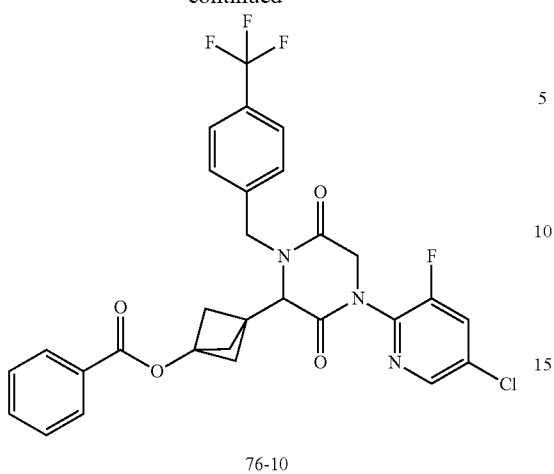

76-10

To a solution of 3-(2-((5-chloro-3-fluoropyridin-2-yl)amino)-1-(2-chloro-N-(4-(trifluoromethyl)benzyl)acetamido)-2-oxoethyl)bicyclo[1.1.1]pentan-1-yl benzoate (640 mg, 1.0 mmol, 1.0 equiv) in DMF (10.0 mL) was added potassium carbonate (283 mg, 2.0 mmol, 2.0 equiv). The resulting mixture was stirred at r.t. for 30 min, diluted with water (20 mL), and extracted with EA (20 mL) twice. The combined organic layers were washed with brine (20 mL), dried over Na₂SO₄, and concentrated under reduced pressure to afford 600 mg (99%) of 3-(4-(5-chloro-3-fluoropyridin-2-yl)-3,6-dioxo-1-(4-(trifluoromethyl)benzyl)piperazin-2-yl)bicyclo[1.1.1]pentan-1-yl benzoate (Intermediate 76-10) as a brown oil. LRMS (ES) m/z 588 (M+H).

11. Synthesis of Compound 838

808

-continued

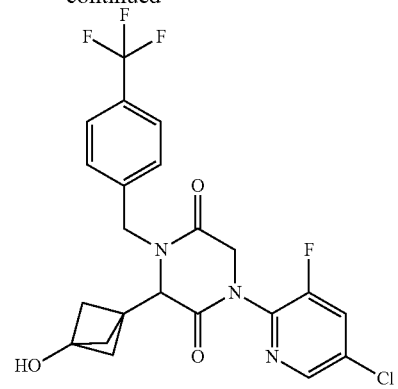

Compound 838

To a solution of 3-(4-(5-chloro-3-fluoropyridin-2-yl)-3,6-dioxo-1-(4-(trifluoromethyl)benzyl)piperazin-2-yl)bicyclo[1.1.1]pentan-1-yl benzoate (450 mg, 0.77 mmol, 1.0 equiv) in a mixture of MeOH and water (5/1, 12 mL) was added potassium carbonate (105.8 mg, 0.77 mmol, 1.0 equiv). The mixture was stirred at r.t. for 1 h, concentrated under reduced pressure, and purified by RP-HPLC using the following condition: Column XBridge Prep OBD C18 3*15 cm, 5 um; mobile phase acetonitrile in water (10 mM NH₄HCO₃) gradient from 45 to 75% in 8 min; detector, UV254 nm to afford 190 mg of 1-(5-chloro-3-fluoropyridin-2-yl)-3-(3-hydroxybicyclo[1.1.1]pentan-1-yl)-4-(4-(trifluoromethyl)benzyl)piperazine-2,5-dione (Compound 838) as a white oil. LRMS (ES) m/z 484 (M+H). ¹H NMR (300 MHz, DMSO-d₆) δ 8.49 (d, J=2.1 Hz, 1H), 8.27 (dd, J=9.5, 2.1 Hz, 1H), 7.74 (d, J=8.1 Hz, 2H), 7.52 (d, J=8.0 Hz, 2H), 5.12 (d, J=15.9 Hz, 1H), 4.73 (d, J=17.5 Hz, 1H), 4.67 (s, 1H), 4.50 (dd, J=16.8, 8.9 Hz, 2H), 3.58 (d, J=16.6 Hz, 1H), 3.43 (s, 1H), 2.51 (s, 1H), 2.48 (s, 1H), 1.36 (s, 3H).

12. Separation of Compound 838 Enantiomers: Enantiomers 838A and 838B

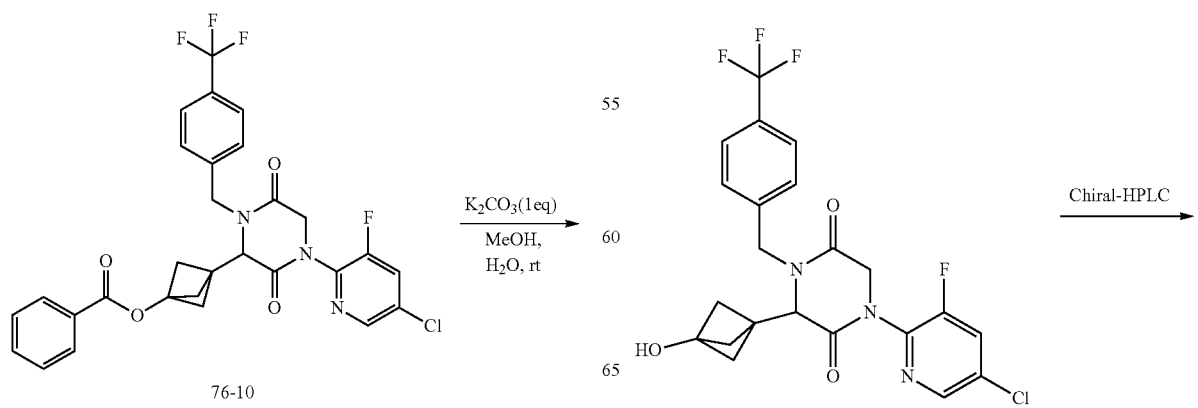

76-10

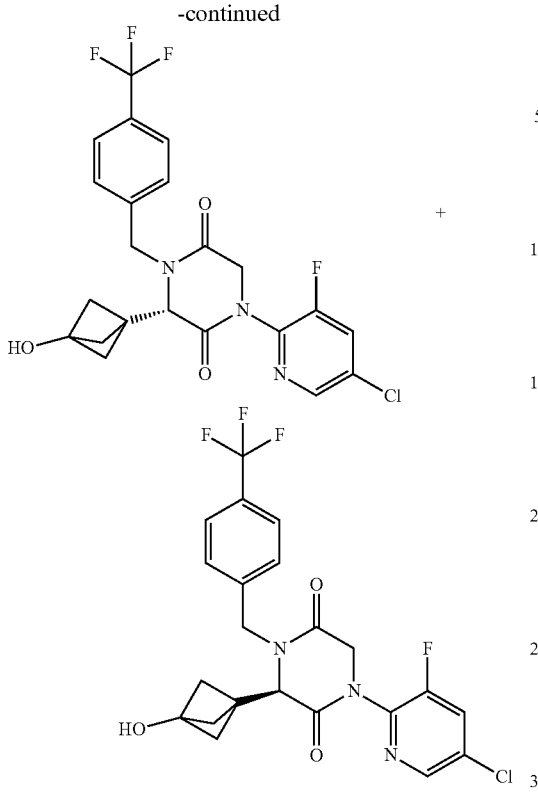

The racemic compound 1-(5-chloro-3-fluoropyridin-2-yl)-3-(3-hydroxybicyclo[1.1.1]pentan-1-yl)-4-(4-(trifluoromethyl)benzyl)piperazine-2,5-dione (140 mg) was separated by Chiral HPLC with the following conditions (Column, CHIRALPAK ID-2, 2*25 cm, 5 um; mobile phase, 50% MTBE (10 mM NH₃ in MeOH) in EtOH; flow rate: 13 mL/min; detector, UV 220/254 nm) to afford 60 mg (first eluted peak) of Enantiomer 838A and 60 mg (second eluted peak) of Enantiomer 838B as white solids.

Characterization of Enantiomer 838A. LCMS (ES) m/z 484 (M+H). $^1$H NMR (300 MHz, DMSO-$d_6$) δ 8.49 (d, J=2.1 Hz, 1H), 8.27 (dd, J=9.4, 2.2 Hz, 1H), 7.74 (d, J=8.1 Hz, 2H), 7.52 (d, J=8.0 Hz, 2H), 5.12 (d, J=16.0 Hz, 1H), 4.73 (d, J=17.6 Hz, 1H), 4.67 (s, 1H), 4.50 (dd, J=16.8, 9.0 Hz, 2H), 3.58 (d, J=16.8 Hz, 1H), 3.41 (d, J=16.2 Hz, 1H), 2.63-2.54 (m, 1H), 2.45 (d, J=7.7 Hz, 1H), 1.36 (s, 3H). Analytical chiral HPLC RT: 0.89 min (CHIRALPAK ID-3; 0.46 cm×5 cm; 3 micro; MtBE (0.1% DEA):EtOH=50:50 at 1 ml/min).

Characterization of Enantiomer 838B. LCMS (ES) m/z 484 (M+H). $^1$H NMR (300 MHz, DMSO-$d_6$) δ 8.49 (d, J=2.1 Hz, 1H), 8.27 (dd, J=9.4, 2.2 Hz, 1H), 7.74 (d, J=8.1 Hz, 2H), 7.52 (d, J=8.0 Hz, 2H), 5.12 (d, J=16.0 Hz, 1H), 4.73 (d, J=17.6 Hz, 1H), 4.67 (s, 1H), 4.50 (dd, J=16.8, 9.0 Hz, 2H), 3.58 (d, J=16.8 Hz, 1H), 3.41 (d, J=16.2 Hz, 1H), 2.63-2.54 (m, 1H), 2.45 (d, J=7.7 Hz, 1H), 1.36 (s, 3H). Analytical chiral HPLC RT: 1.75 min (CHIRALPAK ID-3; 0.46 cm×5 cm; 3 micro; MtBE (0.1% DEA):EtOH=50:50 at 1 ml/min).

The following compounds were prepared by methods analogous to the method described for Compound 838:

| Compound No. | LRMS (ES) m/z |
|---|---|
| 841 | M + H = 450 |
| 844 | M + H = 434 |
| 849 | M + H = 466 |
| 852 | M + H = 430 |

The following compounds were prepared by methods analogous to the method described for Enantiomers 838A and 838B:

HPLC Separation Conditions

| Number | HPLC Conditions |
|---|---|
| X | CHIRALPAK ID-3; 0.46 cm × 5 cm; 3 micro; MtBE(0.1% DEA):EtOH = 50:50 at 1 ml/min |
| Y | CHIRALPAK IA-3; 0.46 cm × 5 cm; 3 micro; MtBE(0.1% DEA):EtOH = 50:50 at 1 |
| Z | CHIRALPAK IE-3; 0.46 cm × 5 cm; 3 micro; (Hex:DCM = 3:1)(0.1% DEA):EtOH = 50:50 at 1 ml/min |

| Enantiomer No. | LRMS (ES) m/z | Retention Time (min) | HPLC Separation Conditions |
|---|---|---|---|
| 841A | M + H = 450 | 1.06 | X |
| 841B | M + H = 450 | 2.38 | X |
| 844A | M + H = 434 | 1.46 | Y |
| 844B | M + H = 434 | 2.27 | Y |
| 849A | M + H = 466 | 1.60 | Z |
| 849B | M + H = 466 | 2.32 | Z |
| 852A | M + H = 430 | 1.58 | Y |
| 852B | M + H = 430 | 2.11 | Y |

Example 77: Synthesis of Intermediate 77-2 (5-chloro-3-fluoro-2-isocyanopyridine 1. Synthesis of Intermediate 77-1

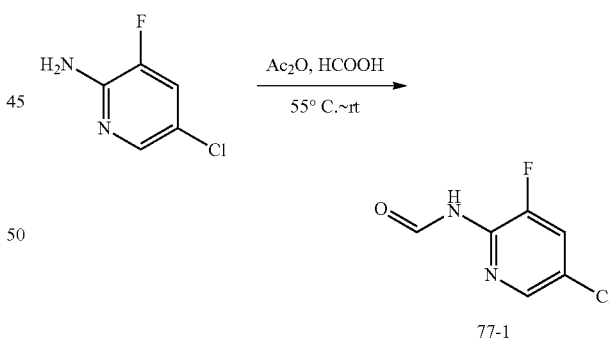

A mixture of Ac₂O (280 g, 2.74 mol, 4.0 equiv) and formic acid (140 g, 3.43 mol, 4.5 equiv.) was stirred at 55° C. for 2 h. To the mixture cooled to 0° C. was added 5-chloro-3-fluoropyridin-2-amine (100 g, 682 mmol, 1.0 equiv.) dropwise. The mixture was stirred for 2 h at rt, concentrated under reduced pressure, and triturated with Et₂O to afford 100 g (84%) of N-(5-chloro-3-fluoropyridin-2-yl)formamide (Intermediate 77-1) as a white solid. LRMS (ES) m/z 175 (M+H). $^1$H NMR (400 MHz, DMSO-$d_6$) δ 10.90 (s, 1H), 9.16 (s, 1H), 8.24 (s, 1H), 8.11 (dd, J=10.1, 2.1 Hz, 1H).

2. Synthesis of Intermediate 77-2

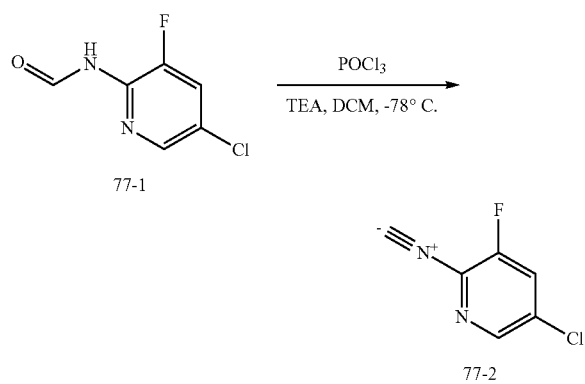

To a stirred solution of N-(5-chloro-3-fluoropyridin-2-yl)formamide (40 g) and TEA (140.1 g, 1.38 mol, 6 equiv.) in DCM (400 mL) cooled to −78° C. was added POCl₃ (40.4 g, 263.5 mmol, 1.15 equiv.) in DCM (100 mL) dropwise. The mixture was stirred at rt overnight, cooled to 0° C., quenched with MeOH (32 mL), concentrated under reduced pressure, and purified by silica gel using PE/EA (10/1) as eluent to afford 11 g (31%) of 5-chloro-3-fluoro-2-isocyanopyridine (Intermediate 77-2) as a yellow solid. LRMS (ES) m/z 156 (M+H).

Example 78: Synthesis of Compound 202

1. Synthesis of Intermediate 78-1

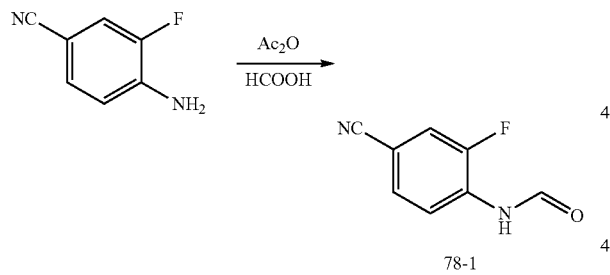

A mixture of Ac₂O (500 mL) and FA (200 mL) was stirred at 60° C. for 2 h and cooled to rt. To the mixture was added 4-amino-3-fluorobenzonitrile (120.0 g, 0.88 mol, 1.0 equiv). The mixture was stirred for 2 h at room temperature and concentrated under reduced pressure. The solid was triturated with Et₂O (2 L) to give 124 g of N-(4-cyano-2-fluorophenyl)formamide (Intermediate 78-1) as a white solid.

2. Synthesis of Intermediate 78-2

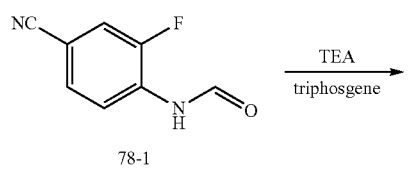

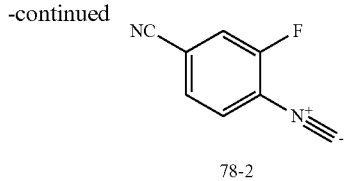

To a solution of N-(4-cyano-2-fluorophenyl)formamide (70.0 g, 426.5 mmol, 1.0 equiv) in DCM (800 mL) cooled to 0° C. were added TEA (135 g, 1334.8 mmol, 3.1 equiv) and a solution of triphosgene (54.4 g, 183.4 mmol, 0.43 equiv) in DCM (300 mL) dropwise over a period of 30 min. The mixture was stirred at room temperature overnight, cooled to 0° C., quenched with MeOH (200 mL), concentrated under reduced pressure, and purified by silica gel column chromatography, eluted with PE/DCM (5/1) to afford 54 g (87%) of 3-fluoro-4-isocyanobenzonitrile (Intermediate 78-2) as a yellow solid.

3. Synthesis of Intermediate 78-3

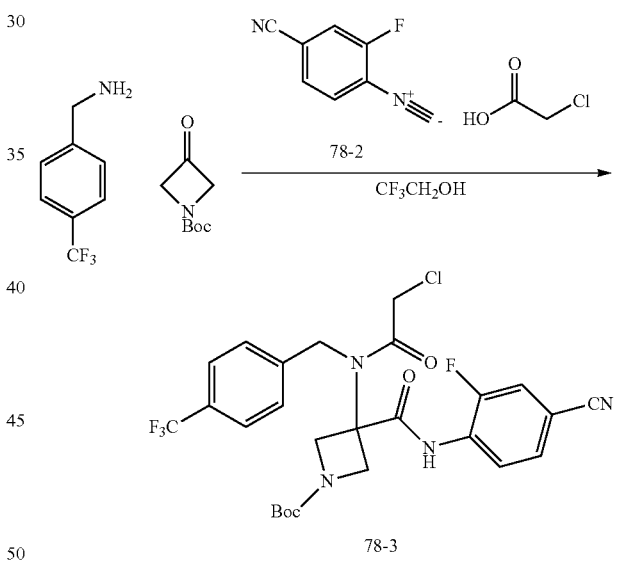

To a solution of 1-[4-(trifluoromethyl)phenyl]methanamine (71.2 g, 406.5 mmol, 1.1 equiv) in trifluoroethanol (1 L) was added tert-butyl 3-oxoazetidine-1-carboxylate (69.6 g, 406.5 mmol, 1.1 equiv)). After stirring at r.t. for 10 min, to the mixture was added 3-fluoro-4-isocyanobenzonitrile (54 g, 369.5 mmol, 1.0 equiv) and chloroacetic acid (38.4 g, 406.5 mmol, 1.1 equiv). The resulting mixture was stirred at r.t. overnight, concentrated under reduced pressure, and triturated with MeOH (500 mL) to afford 113 g (54%) of tert-butyl 3-(2-chloro-N-(4-(trifluoromethyl)benzyl)acetamido)-3-((4-cyano-2-fluorophenyl)carbamoyl)azetidine-1-carboxylate (Intermediate 78-3) as a yellow solid.

4. Synthesis of Intermediate 78-4

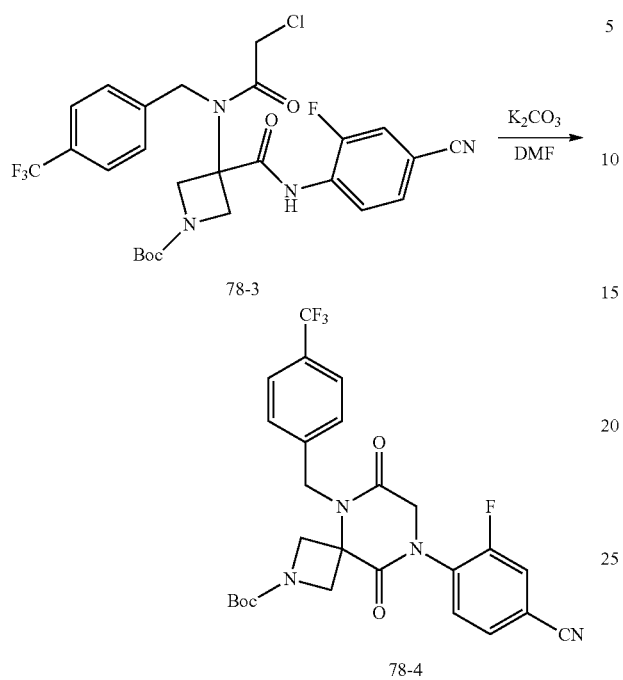

To a solution of tert-butyl 3-(2-chloro-N-(4-(trifluoromethyl)benzyl)acetamido)-3-((4-cyano-2-fluorophenyl)carbamoyl)azetidine-1-carboxylate (113 g, 210 mmol, 1.0 equiv) in DMF (550 mL) was added K₂CO₃ (88 g, 630 mmol, 3.0 equiv). The resulting mixture was stirred for 30 min at 60° C. under argon atmosphere, cooled to room temperature, and diluted with water (1000 mL). The precipitates were collected by filtration and dried by oven below 45° C. to afford 106 g (95%) of tert-butyl 8-(4-cyano-2-fluorophenyl)-6,9-dioxo-5-[[4-(trifluoromethyl)phenyl]methyl]-2,5,8-triazaspiro[3.5]nonane-2-carboxylate (Intermediate 78-4) as a white solid.

5. Synthesis of Intermediate 78-5

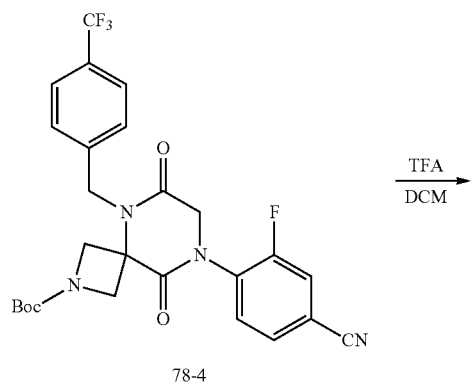

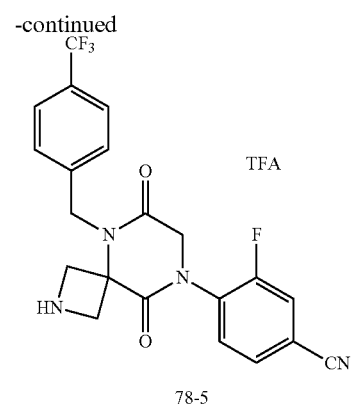

To a solution of tert-butyl 8-(4-cyano-2-fluorophenyl)-6,9-dioxo-5-[[4-(trifluoromethyl)phenyl]methyl]-2,5,8-triazaspiro[3.5]nonane-2-carboxylate (106 g, 200 mmol, 1.0 equiv) in DCM (1000 mL) was added 2,2,2-trifluoroacetic acid (200 mL) at room temperature. The mixture was stirred for 2 h at room temperature and concentrated under reduced pressure to afford 106 g (95%) of 4-(6,9-dioxo-5-(4-(trifluoromethyl)benzyl)-2,5,8-triazaspiro[3.5]nonan-8-yl)-3-fluorobenzonitrile 2,2,2-trifluoroacetate (Intermediate 78-5) as a brown oil.

5. Synthesis of Compound 202

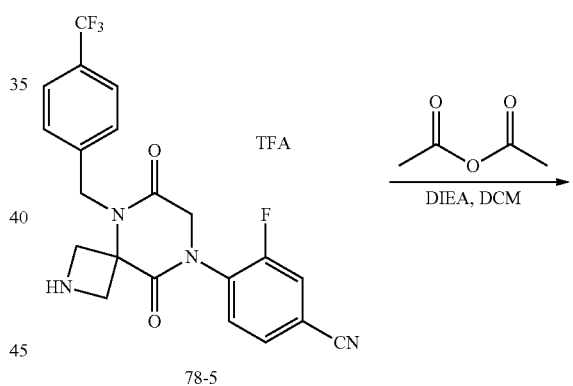

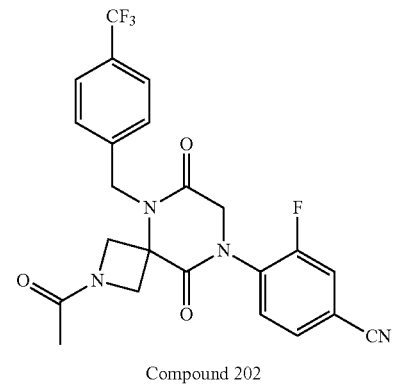

Compound 202

To a solution of 4-(6,9-dioxo-5-[[4-(trifluoromethyl)phenyl]methyl]-2,5,8-triazaspiro[3.5]nonan-8-yl)-3-fluorobenzonitrile (150 g product described above) in DCM (1000 mL) were added TEA (7 g, 69.2 mmol, 3.0 equiv) and acetyl acetate (3.5 g, 34.3 mmol, 1.5 equiv) at 0° C. The mixture was stirred for 4 h at room temperature, washed with brine (200 mL), dried over anhydrous $Na_2SO_4$, concentrated under reduced pressure, and purified by reverse phase flash chromatography with the following conditions: column, $C_{18}$ silica gel; mobile phase, A: water (10 mM $NH_4HCO_3$), B: ACN gradient from 35% to 45% (B/A) in 20 min; detector, UV 210/254 nm to afford 75 g (71%) of 4-(2-acetyl-6,9-dioxo-5-[[4-(trifluoromethyl)phenyl]methyl]-2,5,8-triazaspiro[3.5]nonan-8-yl)-3-fluorobenzonitrile (Compound 202) as a white solid. LRMS (ES) m/z 475 (M+H). $^1$H NMR (400 MHz, Methanol-$d_4$, ppm) δ 7.83-7.77 (m, 1H), 7.77-7.67 (m, 4H), 7.57 (d, J=8.1 Hz, 2H), 4.86 (s, 2H), 4.75-4.68 (m, 1H), 4.60-4.55 (m, 2H), 4.55-4.47 (m, 2H), 4.25 (d, J=11.0 Hz, 1H), 1.87 (s, 3H).

The following compounds were prepared by methods analogous to the method described for Compound 202 as described in Example 78:

| Compound No. | LRMS (ES) m/z |
| --- | --- |
| 641 | M + H = 514.1 |
| 642 | M + H = 480 |
| 643 | M + H = 499 |
| 644 | M + H = 465 |
| 653 | M + H = 495.1 |
| 785 | M + H = 434 |
| 825 | M + H = 525.0 |
| 826 | M + H = 507.1 |
| 827 | M + H = 475.1 |
| 828 | M + H = 461.0 |
| 829 | M + H = 371.1 |
| 830 | M + H = 457.1 |
| 831 | M + H = 493.0 |
| 832 | M + H = 379.0 |

Example 79: Synthesis of Compound 835

1. Synthesis of Intermediate 79-1

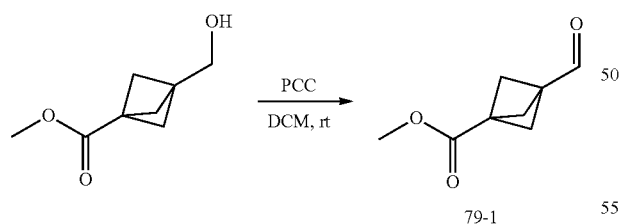

To a solution of methyl 3-(hydroxymethyl)bicyclo[1.1.1]pentane-1-carboxylate (2.0 g, 12.81 mmol, 1.0 equiv) in DCM (68.0 mL) at r.t. were added PCC (4.1 g, 19.21 mmol, 1.5 equiv) in portions. The mixture was stirred at rt for 2 h, diluted with ether (180 mL), stirred for 20 min, filtered off the solid, concentrated under reduced pressure to afford 1.9 g (96%) of methyl 3-formylbicyclo[1.1.1]pentane-1-carboxylate (Intermediate 79-1) as a brown solid.

2. Synthesis of Intermediate 79-2

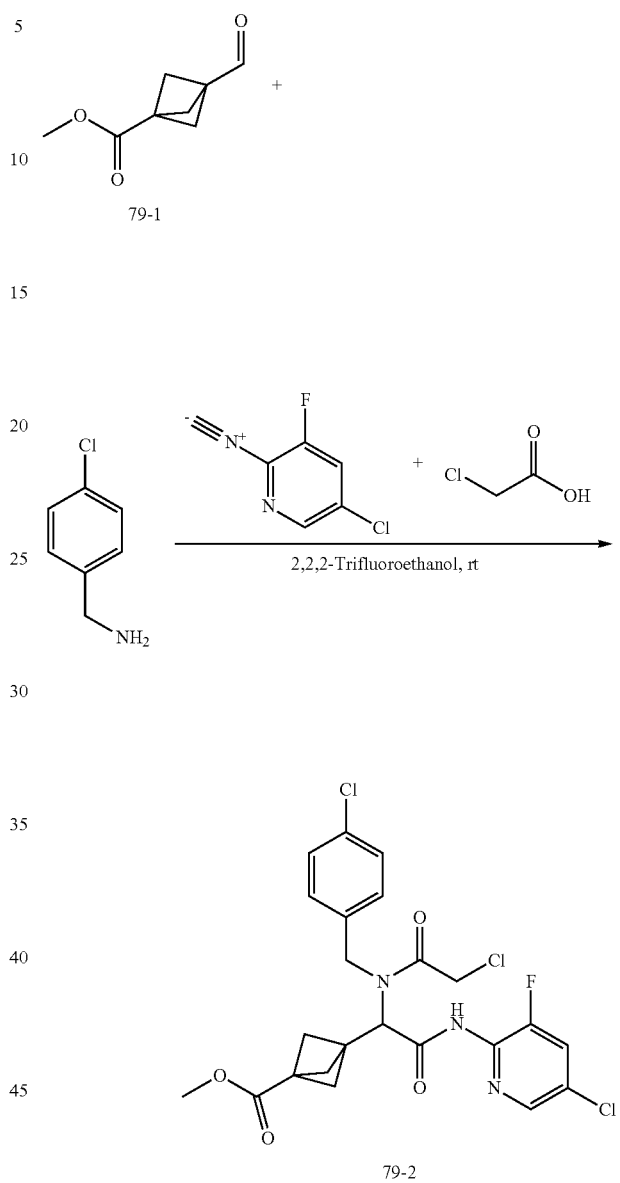

To a solution of (4-chlorophenyl)methanamine (498 mg, 3.5 mmol, 1.1 equiv) in trifluoroethanol (5.0 mL) was added methyl 3-formylbicyclo[1.1.1]pentane-1-carboxylate (541 mg, 3.5 mmol, 1.1 equiv). After stirring at r.t. for 10 min, to the mixture was added 5-chloro-3-fluoro-2-isocyanopyridine (500 mg, 1.0 equiv) and chloroacetic acid (332 mg, 3.5 mmol, 1.1 equiv). The resulting mixture was stirred at rt overnight, concentrated under reduced pressure, and purified by silica gel column chromatography, eluted with PE/EtOAc (3:1) to afford 600 mg (36%) of methyl 3-(2-((5-chloro-3-fluoropyridin-2-yl)amino)-1-(2-chloro-N-(4-chlorobenzyl)acetamido)-2-oxoethyl)bicyclo[1.1.1]pentane-1-carboxylate (Intermediate 79-2) as a yellow oil. LRMS (ES) m/z 528 (M+H).

3. Synthesis of Intermediate 79-3

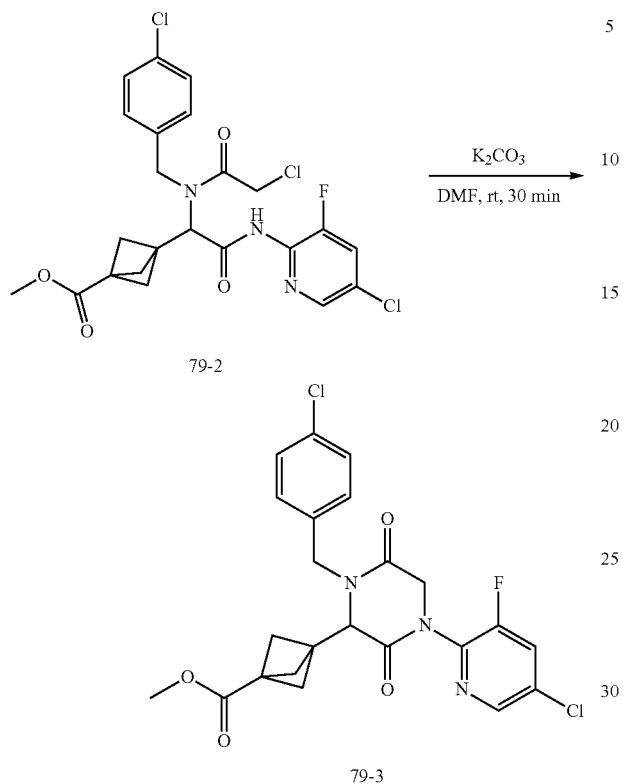

To a solution of methyl 3-(2-((5-chloro-3-fluoropyridin-2-yl)amino)-1-(2-chloro-N-(4-chlorobenzyl)acetamido)-2-oxoethyl)bicyclo[1.1.1]pentane-1-carboxylate (580 mg, 1.1 mmol, 1.0 equiv) in DMF (6.0 mL) was added potassium carbonate (305 mg, 2.2 mmol, 2.0 equiv). The resulting mixture was stirred at r.t. for 1 h and filtered. The filtrate was concentrated under reduced pressure, re-dissolved in EA (20 mL), washed with brine (10 mL) twice, dried over Na$_2$SO$_4$, and concentrated under reduced pressure to afford 500 mg (93%) of methyl 3-(4-(5-chloro-3-fluoropyridin-2-yl)-1-(4-chlorobenzyl)-3,6-dioxopiperazin-2-yl)bicyclo[1.1.1]pentane-1-carboxylate (Intermediate 79-3) as a brown oil. LRMS (ES) m/z 492 (M+H).

4. Synthesis of Compound 835

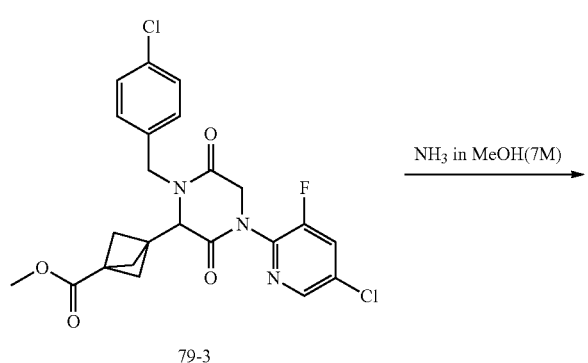

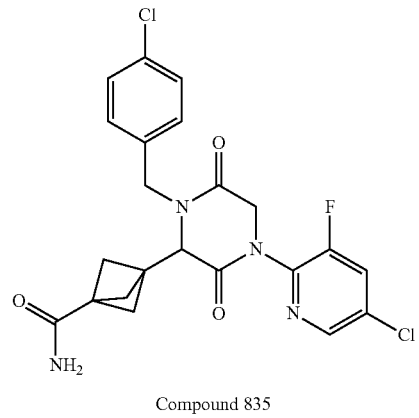

Compound 835

A solution of methyl 3-(4-(5-chloro-3-fluoropyridin-2-yl)-1-(4-chlorobenzyl)-3,6-dioxopiperazin-2-yl)bicyclo[1.1.1]pentane-1-carboxylate (490 mg, 1.0 mmol, 1.0 equiv) in NH$_3$ solution (7 N in MeOH) was stirred at r.t. for 3, concentrated under reduced pressure, and purified by RP-HPLC using the following condition: C$_{18}$ silica gel; mobile phase acetonitrile in water (both with 0.5% NH$_4$HCO$_3$) gradient from 40 to 50% in 10 min; detector, UV254 nm to afford 350 mg (74%) of 3-(4-(5-chloro-3-fluoropyridin-2-yl)-1-(4-chlorobenzyl)-3,6-dioxopiperazin-2-yl)bicyclo[1.1.1]pentane-1-carboxamide (Compound 835) as a brown oil. LRMS (ES) m/z 477 (M+H). $^1$H NMR (400 MHz, DMSO-d$_6$) δ 8.50 (d, J=2.1 Hz, 1H), 8.29 (dd, J=9.4, 2.1 Hz, 1H), 7.49-7.41 (m, 2H), 7.37 (d, J=8.4 Hz, 2H), 7.31 (s, 1H), 7.00 (s, 1H), 5.05 (d, J=15.1 Hz, 1H), 4.58 (d, J=17.3 Hz, 1H), 4.39 (d, J=17.3 Hz, 1H), 4.26 (s, 1H), 4.12 (d, J=15.0 Hz, 1H), 1.94 (qd, J=9.5, 1.6 Hz, 6H).

The following compounds were prepared by methods analogous to the method described for Compound 835:

| Compound No. | LRMS (ES) m/z |
| --- | --- |
| 778 | M + H = 528.1 |
| 779 | M + H = 508.0 |
| 780 | M + H = 476.0 |
| 781 | M + H = 472.1 |
| 782 | M + H = 540.0 |
| 783 | M + H = 511.0 |
| 790 | M + H = 493.0 |
| 791 | M + H = 461.1 |
| 792 | M + H = 457.0 |

5. Separation of Compound 835 Enantiomers: Enantiomers 835A and 835B

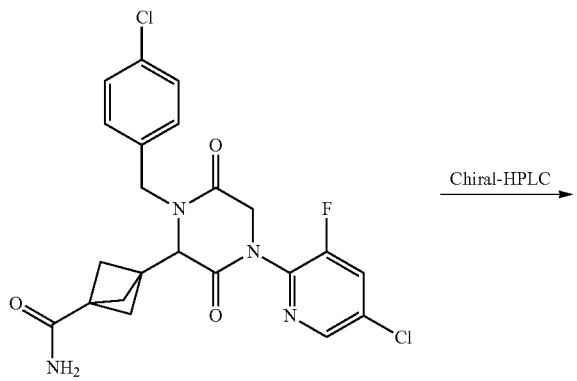

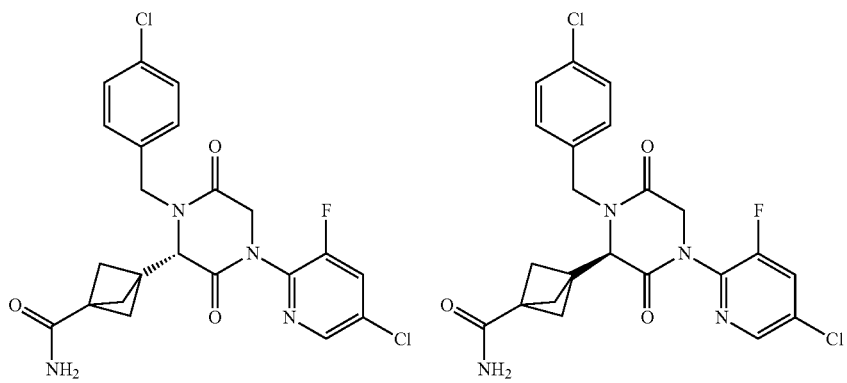

The racemic compound of 3-(4-(5-chloro-3-fluoropyridin-2-yl)-1-(4-chlorobenzyl)-3,6-dioxopiperazin-2-yl)bicyclo[1.1.1]pentane-1-carboxamide (270 mg) was separated by Chiral HPLC with the following conditions (Column, CHIRALPAK IF, 2*25 cm, 5 um; mobile phase, 50% MTBE (10 mM $NH_3$ in MeOH) in EtOH; flow rate: 13 mL/min; detector, UV 220/254 nm) to afford 123 mg (first eluted peak) of Enantiomer 835A and 123 mg (second eluted peak) of Enantiomer 835B as white solids.

Characterization of Enantiomer 835A. LCMS (ES) m/z 477 (M+H). $^1$H NMR (300 MHz, DMSO-$d_6$) δ 8.48 (d, J=2.1 Hz, 1H), 8.27 (dd, J=9.4, 2.2 Hz, 1H), 7.44 (d, J=8.4 Hz, 2H), 7.35 (d, J=8.4 Hz, 2H), 7.28 (s, 1H), 6.97 (s, 1H), 5.04 (d, J=15.1 Hz, 1H), 4.56 (d, J=17.3 Hz, 1H), 4.37 (d, J=17.4 Hz, 1H), 4.25 (s, 1H), 4.11 (d, J=15.0 Hz, 1H), 1.99-1.85 (m, 6H). Analytical chiral HPLC RT: 1.09 min (CHIRALPAK IF-3; 0.46 cm×5 cm; 3 micro; MtBE (0.1% DEA):EtOH=50:50 at 1 ml/min).

Characterization of Enantiomer 835B. LCMS (ES) m/z 477 (M+H). $^1$H NMR (300 MHz, DMSO-$d_6$) δ 8.48 (d, J=2.1 Hz, 1H), 8.27 (dd, J=9.4, 2.1 Hz, 1H), 7.43 (d, J=8.5 Hz, 2H), 7.35 (d, J=8.4 Hz, 2H), 7.28 (s, 1H), 6.97 (s, 1H), 5.04 (d, J=15.1 Hz, 1H), 4.56 (d, J=17.2 Hz, 1H), 4.37 (d, J=17.3 Hz, 1H), 4.24 (s, 1H), 4.10 (d, J=15.1 Hz, 1H), 1.99-1.85 (m, 6H). Analytical chiral HPLC RT: 1.82 min (CHIRALPAK IF-3; 0.46 cm×5 cm; 3 micro; MtBE (0.1% DEA):EtOH=50:50 at 1 ml/min).

The following compounds were prepared by methods analogous to the method described for Enantiomers 835A and 835B:

| Number | HPLC Conditions |
|---|---|
| J | CHIRALPAK ID-3; 0.46 cm × 5 cm; 3 micro; Hex(0.1% DEA):EtOH = 50:50 at 1 ml/min |
| AA | CHIRALPAK IE-3; 0.46 cm × 5 cm; 3 micro; MtBE(0.1% DEA):EtOH = 60:40 at 1 ml/min |
| BB | CHIRALPAK IE-3; 0.46 cm × 5 cm; 3 micro; (Hex:DCM = 3:1)(0.1% DEA):EtOH = 70:30 at 1 ml/min |

| Enantiomer No. | LRMS (ES) m/z | Retention Time (min) | HPLC Separation Conditions |
|---|---|---|---|
| 783A | M + H = 511 | 1.01 | AA |
| 783B | M + H = 511 | 1.37 | AA |
| 791A | M + H = 461 | 2.15 | J |
| 791B | M + H = 461 | 3.13 | J |
| 790A | M + H = 493 | 2.03 | BB |
| 790B | M + H = 493 | 2.53 | BB |
| 792A | M + H = 457 | 1.19 | AA |
| 792B | M + H = 457 | 1.64 | AA |

Biological Example B-1: Myofibril Assay

To evaluate the effect of compounds on the ATPase activity of full-length cardiac myosin in the context of the native sarcomere, skinned myofibril assays were performed. Bovine cardiac myofibrils were obtained by homogenizing bovine cardiac left ventricular tissue in the presence of a detergent such as triton X-100. Such treatment removes membranes and a majority of the soluble cytoplasmic proteins but leaves intact the cardiac sarcomeric acto-myosin apparatus. Myofibril preparations retain the ability to hydrolyze ATP in a $Ca^{2+}$ regulated manner. ATPase activities of such myofibril preparations in the presence and absence of compounds were assayed at $Ca^{2+}$ concentrations activating to a defined fraction of the maximal rate (i.e., 25%, 75%). Small molecule agents were assessed for their ability to inhibit the steady-state ATPase activity of bovine cardiac myofibrils using pyruvate kinase and lactate dehydrogenase (PK/LDH)-coupled enzyme system. This assay regenerates myosin-produced ADP into ATP by oxidizing NADH, producing an absorbance change at 340 nm. Prior to testing small molecule agents, the bovine cardiac myofibrils were assessed for their calcium responsiveness and the calcium concentration that achieves either a 50% ($pCa_{50}$) or 75% ($pCa_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM 12 buffer). Final assay conditions were 1 mg/mL of bovine cardiac myofibrils, 4 U/mL pyruvate kinase, 6 U/mL lactate dehydrogenase, 50 μM ATP, 0.1 mg/mL BSA (bovine serum albumin), 10 ppm antifoam, 1 mM DTT, 0.5 mM NADH, 1.5 mM PEP, 0.6 mM EGTA, and an amount of $CaCl_2$ sufficient to achieve either 50% or 75% activation of the myofibril ATPase activity. Results for compounds tested are provided in Table A. Compounds tested were prepared in accordance with the synthetic procedures described herein.

TABLE A

| Cmpd No. | CDMF75 $IC_{15}$ (μM) |
| --- | --- |
| 1 | 9.5 |
| 2 | 1.8 |
| 3 | 1.7 |
| 4 | 2.5 |
| 5 | 1.9 |
| 6 | 0.9 |
| 7 | 1.9 |
| 8 | 3.3 |
| 9 | 2.4 |
| 10 | 5.2 |
| 11 | 17.4 |
| 12 | 6.6 |
| 13 | 7.1 |
| 14 | 6.0 |
| 15 | 2.7 |
| 16 | 2.7 |
| 17 | 1.7 |
| 18 | 3.1 |
| 19 | 5.7 |
| 20 | 7.5 |
| 21 | 2.6 |
| 22 | 4.1 |
| 23 | 2.2 |
| 24 | 5.7 |
| 25 | 8.8 |
| 26 | 3.0 |
| 27 | 8.6 |
| 28 | 3.1 |
| 29 | 5.6 |
| 30 | 21.1 |
| 31 | 2.7 |
| 32 | 9.6 |
| 33 | 5.4 |
| 34 | 10.4 |
| 35 | 14.6 |
| 36 | 24.5 |
| 37 | 6.0 |
| 38 | 12.4 |
| 39 | 3.9 |
| 40 | 7.2 |
| 41 | 7.0 |
| 42 | 5.4 |
| 43 | 3.3 |
| 44 | 2.4 |
| 45 | 12.8 |
| 46 | 0.9 |
| 47 | 3.7 |
| 48 | 1.6 |
| 49 | 9.3 |
| 50 | 5.8 |
| 51 | 5.7 |
| 52 | 17.8 |
| 53 | 14.7 |
| 54 | 7.8 |
| 55 | 6.7 |
| 56 | 18.3 |
| 57 | 33.3 |
| 58 | 4.1 |
| 59 | 23.4 |
| 60 | 14.3 |
| 61 | 22.9 |
| 62 | 1.8 |
| 63 | 5.1 |
| 64 | 23.6 |
| 65 | 9.8 |
| 66 | 17.6 |
| 67 | 6.0 |
| 68 | 9.2 |
| 69 | 15.4 |
| 70 | 9.5 |
| 71 | 4.8 |
| 72 | 9.0 |
| 73 | 5.7 |
| 74 | 4.2 |
| 75 | 1.1 |
| 76 | 2.2 |
| 77 | 13.0 |
| 78 | 4.1 |
| 79 | 3.8 |
| 80 | 1.7 |
| 81 | 1.4 |
| 82 | 8.1 |
| 83 | 1.3 |
| 84 | 4.0 |
| 85 | 14.3 |
| 86 | 8.6 |
| 87 | 1.9 |
| 88 | 4.0 |
| 89 | 3.3 |
| 90 | 1.7 |
| 91 | 1.1 |
| 92 | 1.0 |
| 93 | 19.7 |
| 94 | 36.1 |
| 95 | 5.0 |
| 96 | 4.5 |
| 97 | 3.1 |
| 98 | 2.4 |
| 107 | 12.7 |
| 108 | 9.4 |
| 109 | 8.3 |
| 110 | 34.4 |
| 111 | 19.8 |
| 112 | 33.0 |

TABLE A-continued

| Cmpd No. | CDMF75 IC$_{15}$ (μM) |
|---|---|
| 113 | 18.5 |
| 114 | 7.9 |
| 115 | 10.2 |
| 116 | 7.2 |
| 117 | 16.6 |
| 118 | 14.0 |
| 119 | 10.8 |
| 120 | 18.3 |
| 121 | 9.9 |
| 122 | 20.5 |
| 123 | 11.2 |
| 127 | 0.8 |
| 128 | 0.8 |
| 129 | 4.6 |
| 138 | 7.0 |
| 139 | 14.8 |
| 140 | 4.4 |
| 141 | 10.7 |
| 142 | 0.8 |
| 145 | 3.8 |
| 146 | 1.2 |
| 147 | 8.1 |
| 148 | 2.3 |
| 149 | 8.9 |
| 150 | 1.1 |
| 151 | 12.2 |
| 152 | 2.8 |
| 153 | 6.4 |
| 154 | 19.8 |
| 155 | 0.6 |
| 156 | 7.1 |
| 157 | 5.5 |
| 158 | 9.7 |
| 159 | 3.2 |
| 160 | 7.1 |
| 161 | 4.7 |
| 162 | 0.4 |
| 163 | 7.3 |
| 164 | 1.6 |
| 165 | 1.4 |
| 166 | 2.4 |
| 167 | 1.3 |
| 168 | 0.3 |
| 169 | 0.2 |
| 170 | 2.9 |
| 171 | 2.0 |
| 172 | 18.5 |
| 173 | 0.6 |
| 174 | 8.0 |
| 175 | 1.2 |
| 176 | 8.5 |
| 177 | 1.8 |
| 178 | 0.8 |
| 179 | 0.3 |
| 180 | 1.6 |
| 181 | 6.2 |
| 182 | 2.9 |
| 183 | 4.6 |
| 184 | 25.5 |
| 185 | 3.2 |
| 186 | 15.8 |
| 187 | 15.9 |
| 188 | 2.6 |
| 189 | 1.4 |
| 190 | 4.0 |
| 191 | 14.3 |
| 192 | 0.6 |
| 193 | 1.7 |
| 194 | 0.4 |
| 195 | 0.4 |
| 196 | 0.4 |
| 197 | 2.7 |
| 198 | 0.5 |
| 199 | 2.3 |
| 200 | 0.9 |
| 201 | 5.1 |
| 202 | 0.8 |
| 203 | 0.6 |
| 204 | 0.2 |
| 205 | 0.7 |
| 206 | 0.5 |
| 207 | 4.8 |
| 208 | 3.6 |
| 209 | 0.5 |
| 210 | 1.7 |
| 211 | 0.4 |
| 212 | 0.9 |
| 213 | 0.4 |
| 214 | 0.5 |
| 215 | 1.3 |
| 216 | 0.3 |
| 217 | 0.9 |
| 218 | 0.4 |
| 219 | 0.4 |
| 220 | 0.8 |
| 221 | 4.1 |
| 222 | 0.7 |
| 223 | 2.3 |
| 224 | 12.1 |
| 225 | 29.6 |
| 249B | 0.2 |
| 266 | 0.7 |
| 269 | 1.2 |
| 270 | 1.9 |
| 271 | 0.6 |
| 272 | 0.5 |
| 273 | 1.8 |
| 274 | 1.0 |
| 275 | 6.0 |
| 276 | 3.0 |
| 277 | 32.7 |
| 278 | 0.5 |
| 279 | 1.2 |
| 280 | 0.9 |
| 281 | 4.3 |
| 281A | 1.7 |
| 281B | 11.8 |
| 282 | 3.8 |
| 283 | 0.6 |
| 284 | 0.5 |
| 285 | 8.3 |
| 286 | 0.7 |
| 287 | 3.2 |
| 288 | 1.8 |
| 288A | 0.8 |
| 288B | >39 |
| 293 | 36.0 |
| 293A | >39 |
| 293B | 15.4 |
| 294 | 33.3 |
| 297 | 11.6 |
| 297A | 6.5 |
| 297B | >39 |
| 298 | 5.4 |
| 299 | 7.0 |
| 300 | 28.3 |
| 301 | 18.6 |
| 302 | 15.2 |
| 303 | 3.7 |
| 304 | 16.4 |
| 305 | 6.0 |
| 306 | 27.0 |
| 307 | 36.7 |
| 308 | 22.7 |
| 309 | 2.8 |
| 310 | 13.1 |
| 311 | 5.9 |
| 312 | 4.9 |
| 313 | 3.9 |
| 314 | 8.4 |
| 315 | 28.9 |
| 316 | 14.3 |
| 317 | 2.3 |
| 318 | 7.3 |

TABLE A-continued

| Cmpd No. | CDMF75 IC$_{15}$ (μM) |
|---|---|
| 319 | 24.0 |
| 320 | 17.8 |
| 321 | 22.1 |
| 322 | 10.8 |
| 323 | 6.4 |
| 324 | 11.5 |
| 325 | 22.8 |
| 326 | 23.7 |
| 327 | 9.8 |
| 328 | 19.3 |
| 329 | 9.3 |
| 330 | 10.7 |
| 331 | 30.9 |
| 332 | 16.6 |
| 333 | 16.6 |
| 334 | 8.0 |
| 335 | 12.2 |
| 336 | 1.1 |
| 337 | 1.63 |
| 338 | 1.51 |
| 339 | 0.5 |
| 340 | 0.7 |
| 341 | 5.4 |
| 347 | 26.4 |
| 348 | 0.7 |
| 349 | 0.9 |
| 350 | 5.5 |
| 351A | >39 |
| 351B | 2.3 |
| 353A | >39 |
| 353B | 2.0 |
| 355A | 0.5 |
| 355B | >39 |
| 357A | 0.6 |
| 357B | >39 |
| 359A | >39 |
| 359B | 1.7 |
| 361A | >39 |
| 361B | 2.1 |
| 363A | >39 |
| 363B | 0.8 |
| 365A | >39 |
| 365B | 2.1 |
| 367A | 8.8 |
| 367B | >39 |
| 369A | 8.5 |
| 369B | >39 |
| 371A | 8.2 |
| 371B | >39 |
| 373A | 0.4 |
| 373B | >39 |
| 375A | >39 |
| 375B | 0.4 |
| 377A | >39 |
| 377B | 2.8 |
| 379A | 4.8 |
| 379B | >39 |
| 381A | 6.7 |
| 381B | >39 |
| 383 | >39 |
| 383A | 18.0 |
| 383B | >39 |
| 385 | >39 |
| 385A | 20.1 |
| 385B | >39 |
| 387 | >39 |
| 387A | 24.2 |
| 387B | >39 |
| 389A | 3.1 |
| 389B | 22.3 |
| 429A | 33.1 |
| 429B | 0.2 |
| 430B | 0.4 |
| 432B | 0.5 |
| 434B | 0.4 |
| 436B | 0.3 |
| 438B | 0.4 |

TABLE A-continued

| Cmpd No. | CDMF75 IC$_{15}$ (μM) |
|---|---|
| 440B | 0.2 |
| 442B | 0.4 |
| 444B | 0.2 |
| 446B | 0.9 |
| 448B | 0.8 |
| 450B | 0.3 |
| 452B | 0.3 |
| 454B | 0.1 |
| 456B | 0.3 |
| 548 | 0.6 |
| 458B | 0.4 |
| 459 | 4.5 |
| 462A | 0.2 |
| 462B | 0.4 |
| 463B | 0.4 |
| 465B | 0.3 |
| 467B | 0.8 |
| 469B | 0.6 |
| 473B | 0.2 |
| 475B | 0.6 |
| 477B | 0.4 |
| 479B | 2.8 |
| 481B | 3.7 |
| 483A | 0.4 |
| 483B | 0.7 |
| 484A | 0.5 |
| 484B | 0.6 |
| 485A | 2.1 |
| 485B | 0.7 |
| 486A | 12.7 |
| 486B | 0.7 |
| 487A | 3.2 |
| 487B | 0.61 |
| 488B | 0.2 |
| 492B | 0.4 |
| 494B | 0.4 |
| 496A | >39 |
| 496B | 17.7 |
| 498B | 29.8 |
| 500B | 35.5 |
| 502B | 15.2 |
| 504A | 21.9 |
| 528 | 2.9 |
| 529 | 5.5 |
| 530 | 4.7 |
| 531 | 5.0 |
| 532 | 0.2 |
| 533 | 0.3 |
| 534 | 0.2 |
| 535 | 0.3 |
| 536 | 0.2 |
| 537 | 0.3 |
| 538 | 0.2 |
| 539 | 0.2 |
| 540 | 0.2 |
| 541 | 0.2 |
| 542 | 0.2 |
| 543 | 0.3 |
| 544 | 0.3 |
| 545 | 0.2 |
| 546 | 1.0 |
| 547 | 0.4 |
| 550 | 0.8 |
| 551 | 2.48 |
| 552 | 0.5 |
| 553 | 1.4 |
| 554 | 0.4 |
| 555 | 0.9 |
| 556 | 2.7 |
| 558 | 7.04 |
| 559 | 25.1 |
| 560 | 8.6 |
| 561 | 19.8 |
| 562 | 29.0 |
| 563 | 2.2 |
| 564 | 13.0 |
| 565 | 17.8 |

TABLE A-continued

| Cmpd No. | CDMF75 IC$_{15}$ (μM) |
|---|---|
| 566 | 4.0 |
| 567 | 1.2 |
| 568 | 1.2 |
| 569 | 2.6 |
| 570 | 2.2 |
| 571 | 2.0 |
| 572 | 7.4 |
| 573 | 6.5 |
| 573A | 2.5 |
| 573B | >39 |
| 574 | 0.3 |
| 575 | 1.5 |
| 576 | 2.2 |
| 577 | 0.9 |
| 592 | 1.3 |
| 593 | 2.3 |
| 610 | 1.7 |
| 612 | 13.6 |
| 612A | 6.27 |
| 612B | >39 |
| 615 | 1.3 |
| 616 | 11.85 |
| 619 | 14.7 |
| 620 | 1.8 |
| 623 | 3.0 |
| 624 | 2.0 |
| 625 | 14.5 |
| 626 | >39 |
| 629 | 32.4 |
| 630 | 18.7 |
| 630A | 9.7 |
| 630B | >39 |
| 631 | 17.3 |
| 632 | 31.7 |
| 633 | 1.3 |
| 633A | 0.7 |
| 633B | 5.0 |
| 636 | 1.3 |
| 636A | 0.6 |
| 636B | >39 |
| 639 | 1.4 |
| 639A | 1.0 |
| 639B | >39 |
| 640 | 1.6 |
| 640A | 0.9 |
| 640B | >39 |
| 641 | 12.2 |
| 642 | 10.9 |
| 643 | 5.8 |
| 643A | 3.2 |
| 644 | 6.8 |
| 644A | 3.2 |
| 645 | 5.8 |
| 645A | 3.3 |
| 646 | 3.3 |
| 646A | 1.4 |
| 646B | >39 |
| 647 | 2.1 |
| 647A | 1.2 |
| 647B | 28.0 |
| 648 | 2.0 |
| 648A | 0.8 |
| 648B | 8.1 |
| 649 | 2.9 |
| 649A | 1.5 |
| 649B | 7.3 |
| 650 | 2.5 |
| 650A | 1.7 |
| 650B | 10.1 |
| 651 | 7.3 |
| 652 | 9.0 |
| 653 | 19.9 |
| 654 | 5.3 |
| 654A | 2.9 |
| 654B | 38.8 |
| 655 | 7.0 |
| 656 | 9.9 |

TABLE A-continued

| Cmpd No. | CDMF75 IC$_{15}$ (μM) |
|---|---|
| 657 | 1.4 |
| 657A | 0.7 |
| 657B | >39 |
| 660 | 0.84 |
| 661 | 17.0 |
| 662 | 16.4 |
| 663 | 7.3 |
| 664 | 2.9 |
| 664A | 1.7 |
| 664B | 23.7 |
| 665 | 7.3 |
| 666 | 2.3 |
| 666A | 26.9 |
| 666B | 1.3 |
| 667 | 1.1 |
| 667A | 0.9 |
| 667B | 8.7 |
| 668 | 1.4 |
| 668A | 0.7 |
| 668B | 8.4 |
| 687 | 6.2 |
| 688 | 3.7 |
| 689 | 27.9 |
| 691 | 27.6 |
| 691A | 12.06 |
| 691B | >39 |
| 700 | 3.4 |
| 701 | 3.9 |
| 702 | 25.5 |
| 703 | 10.1 |
| 703A | 4.0 |
| 703B | 37.2 |
| 706 | 4.5 |
| 707 | 2.9 |
| 708 | 1.4 |
| 711 | 24.6 |
| 711A | 10.1 |
| 711B | >39 |
| 714 | 12.4 |
| 714A | 6.8 |
| 714B | >39 |
| 717 | 7.3 |
| 717A | 4.0 |
| 717B | 33.2 |
| 720 | 9.2 |
| 720A | 5.4 |
| 720B | >39 |
| 723 | 7.1 |
| 724 | 13.8 |
| 724A | 8.7 |
| 724B | >39 |
| 727 | 3.2 |
| 727A | 1.5 |
| 727B | 24.3 |
| 730 | 3.4 |
| 730A | 1.6 |
| 730B | 19.1 |
| 733 | 11.8 |
| 733A | 7.2 |
| 733B | >39 |
| 736 | 2.0 |
| 739 | 2.2 |
| 740 | 2.3 |
| 740A | 1.1 |
| 740B | 0.97 |
| 740C | >39 |
| 740D | >39 |
| 747 | 3.7 |
| 747A | 1.6 |
| 747B | 10.8 |
| 750 | 1.0 |
| 751 | 1.3 |
| 756 | 5.0 |
| 757 | 7.2 |
| 758 | 19.4 |
| 758A | 8.3 |
| 758B | >39 |

TABLE A-continued

| Cmpd No. | CDMF75 IC$_{15}$ (μM) |
|---|---|
| 761 | 16.3 |
| 761A | 8.4 |
| 761B | >39 |
| 764 | 1.6 |
| 764A | 1.4 |
| 764B | 2.5 |
| 768 | 4.3 |
| 769 | 7.9 |
| 769A | 4.1 |
| 769B | >39 |
| 772 | 7.7 |
| 772A | 4.2 |
| 772B | >39 |
| 775 | 8.0 |
| 775A | 3.7 |
| 775B | >39 |
| 778 | 2.4 |
| 779 | 2.9 |
| 780 | 3.6 |
| 781 | 4.0 |
| 782 | 3.6 |
| 783 | 3.08 |
| 783A | 2.35 |
| 783B | >39 |
| 784 | 6.8 |
| 785 | 5.0 |
| 790 | 4.9 |
| 791 | 2.7 |
| 791A | 1.8 |
| 791B | >39 |
| 792 | 3.8 |
| 799 | 3.9 |
| 813 | 0.4 |
| 814 | 0.8 |
| 815 | 0.7 |
| 816 | 0.9 |
| 821 | 2.1 |
| 822 | >39 |
| 823 | 2.3 |
| 824 | >39 |
| 825 | 0.7 |
| 826 | 1.26 |
| 827 | 2.68 |
| 828 | 1.37 |
| 829 | 2.19 |
| 830 | 1.75 |
| 831 | 0.53 |
| 832 | 0.48 |
| 835 | 1.64 |
| 836 | 1.42 |
| 837 | >39 |
| 838 | 3.8 |
| 838A | 2.3 |
| 838B | >39 |
| 841 | 2.7 |
| 841A | 1.5 |
| 842B | >39 |
| 844 | 8.6 |
| 844A | 4.3 |
| 844B | >39 |
| 849 | 5.7 |
| 849B | 1.8 |
| 849A | >39 |
| 852 | 6.5 |
| 852A | 3.1 |
| 852B | >39 |
| 857A | 5.3 |
| 857B | >39 |
| 858A | 7.79 |
| 858B | 3.7 |
| 858C | 2.9 |
| 858D | 5.2 |
| 859A | 0.6 |
| 859B | 0.3 |
| 860A | 0.7 |
| 860B | 0.2 |
| 861A | 1.0 |
| 861B | 5.8 |
| 862A | 3.2 |
| 862B | >39 |
| 863A | 0.3 |
| 863B | >39 |
| 864A | 6.2 |
| 864B | >39 |
| 865A | 10.2 |
| 866A | 4.4 |
| 866B | >39 |
| 866C | 2.3 |
| 866D | >39 |
| 867A | 2.1 |
| 867B | 1.7 |
| 868A | 1.6 |
| 868B | 3.8 |
| 869A | 1.04 |
| 869B | 0.59 |
| 870A | 12.7 |
| 870B | 0.6 |
| 871A | 4.2 |
| 871B | 1.4 |
| 872A | 0.99 |
| 872B | 1.3 |
| 873A | 15.3 |
| 873B | 0.7 |
| 874A | 4.0 |
| 874B | 1.1 |
| 875A | 2.2 |
| 875B | 3.2 |
| 876A | 2.7 |
| 876B | 2.7 |
| 877A | 1.1 |
| 877B | 1.1 |
| 878B | 3.4 |
| 879B | 9.3 |
| 880A | >39 |
| 880B | 1.9 |
| 881B | 9.3 |
| 881A | >39 |
| 882 | 0.3 |
| 883 | 0.4 |
| 884 | 0.5 |
| 885 | 0.5 |
| 886 | 0.7 |
| 887 | 0.9 |
| 888A | >39 |
| 889A | 5.9 |
| 889B | 1.9 |
| 890A | 18.7 |
| 890B | 5.4 |
| 891A | 14.6 |
| 891B | 5.7 |
| 892A | 3.6 |
| 892B | 2.9 |
| 892C | >39 |
| 892D | >39 |
| 893A | 1.2 |
| 893B | 1.0 |
| 893C | >39 |
| 893D | >39 |
| 894A | >39 |
| 894B | >39 |
| 894C | 3.3 |
| 894D | 3.0 |

Biological Example B-2: Myocyte Assays (i) Preparation of Adult Cardiac Ventricular Rat Myocytes Adult male Sprague-Dawley rats were anesthetized and the hearts were quickly excised, rinsed and the ascending aorta was cannulated. Continuous retrograde perfusion was initiated on the hearts at a perfusion pressure of 60 cm $H_2O$. Hearts were first perfused with a nominally $Ca^{2+}$-free modified Krebs solution of the following composition: 113 mM NaCl, 4.7 mM KCl, 0.6 mM $KH_2PO_4$, 0.6 mM $Na_2HPO_4$, 1.2 mM $MgSO_4$, 12 mM $NaHCO_3$, 10 mM $KHCO_3$, 30 mM taurine, 5.5 mM glucose and 10 mM Hepes (all Sigma). This medium was not recirculated and was continually aerated with a 95% $O_2$/5% $CO_2$ mixture. After approximately 3 minutes, the heart was perfused with a modified Krebs buffer supplemented with collagenase (Worthington) and 12.5 µM final calcium concentration. The heart was removed from the cannulae after the heart appeared blanched and soft in appearance. The atria and vessels were removed and the ventricles were gently dissected into smaller pieces with forceps. The tissue was homogenized by repeated pipette trituration and the collagenase reaction was stopped by 10% bovine calf serum (BCS), sedimentation and resuspension in perfusion buffer containing 5% BCS and 12.5 uM $CaCl_2$. Myocytes were made calcium tolerant by stepwise addition of a $CaCl_2$ solution to a final concentration of 1.2 mM. Cells were then washed and resuspended in Tyrode's buffer (137 mM NaCl, 3.7 mM KCl, 0.5 mM MgCl, 11 mM glucose, 4 mM Hepes, and 1.2 mM $CaCl_2$, pH 7.4). Cells were kept for 60 min at 37° C. prior to initiating experiments and used within 5 hrs of isolation. Preparations of cells were used only if cells first passed QC criteria by demonstrating a contractile response to standard (>150% of basal) and isoproterenol (ISO; >250% of basal) treatment. Additionally, only cells whose basal contractility was between 3 and 8% were used in subsequent experiments with compounds.

(ii) Adult Ventricular Myocyte Contractility Experiments

Aliquots of myocytes in Tyrode's buffer were placed in perfusion chambers (series 20 RC-27NE; Warner Instruments) complete with heating platforms. Myocytes were allowed to attach, the chambers were heated to 37° C., and the cells were perfused with 37° C. Tyrode's buffer. Myocytes were field stimulated at 1 Hz in with platinum electrodes (20% above threshold). Only cells that had clear striations and were quiescent prior to pacing were used for contractility experiments. To determine basal contractility, myocytes were imaged through a 40× objective. Using a variable frame rate (60-240 Hz) charge-coupled device camera, the images were digitized and displayed on a computer screen at a sampling speed of 240 Hz (IonOptix Milton, Mass.). Once cell contraction was stable over time, test compounds (0.01-15 µM) were perfused into the chambers on the myocytes for 5 minutes. Contractility of the myocytes and contraction and relaxation velocities were then recorded using edge detection.

(iii) Contractility Analysis

Five or more individual myocytes were tested per compound from two or more different myocyte preparations. For each cell, twenty or more contractility transients at basal (defined as 1 min prior to compound infusion) and after compound addition (defined as 5 min after starting compound perfusion), were averaged and compared. These average transients were analyzed using the IonWizard software (IonOptix) to determine changes in diastolic length and fractional shortening. Fractional shortening was calculated as: ((resting length−length at peak contraction) divided by the resting length). The percent change in fractional shortening from baseline was calculated as: ((post-dose fractional shortening/basal fractional shortening)*100). The percent reduction in fractional shortening from baseline was calculated as: (100−percent change in fractional shortening from baseline). Maximum contraction and relaxation velocities (um/sec) was also determined. Results from individual cells were averaged and the SEM was calculated.

The effect of the compounds on the fractional shortening (FS) of the myocytes is shown in Table B.

TABLE B

| Compound No | Concentration (µM) | % FS (% reduction from baseline) ± SEM | # of cells tested |
|---|---|---|---|
| 206 | 10 | 95.1 ± 1.6 | 6 |
| 202 | 5 | 68.4 ± 9.5 | 7 |
| 373A | 10 | 76.6 ± 8.8 | 5 |
| 288A | 5 | 64.4 ± 9.7 | 6 |
| 861A | 5 | 88.0 ± 3.31 | 5 |
| 633A | 1 | 77.5 ± 5.26 | 6 |

% FS reduction = 100 − (average of each cell (post dose FS/pre dose FS) × 100)

Biological Example B-3: Echocardiography Assessment of Acute Pharmacodynamic Effect in Rat Cardiac Contractility Assessment of in vivo cardiac function by echocardiography was performed in male Sprague Dawley rats under isoflurane (1-3%) anesthesia. 2-D M-mode images of the left ventricle were acquired in the parasternal long-axis view before, during, and after administration of compounds by continuous IV infusion or oral gavage. In vivo fractional shortening was determined by M-mode image analysis with the following calculation: ((End diastolic diameter−end systolic diameter)/end diastolic diameter×100). For continuous IV infusion experiments, three pre-dose baseline M-mode images were taken at 1 minute intervals prior to infusion of compound. Compounds were formulated in 50% Propylene Glycol (PG): 16% Captisol: 10% dimethylacetamide (DMA) and delivered via a jugular vein catheter at the rate of 1 mL/kg/h. During infusion, M-mode images were taken at 5 minute intervals. The infusion was stopped when fractional shortening reached up to a 60% reduction from baseline. Blood samples were taken to determine the plasma concentration of the compounds. Data were reported as an estimated $IC_{50}$ value, which is the concentration at which fractional shortening is 50% of the pre-dose baseline contractility. The $IC_{50}$ results are summarized in Table C.

TABLE C

| Compound No. | IC50 (mean ± SD, µM) |
|---|---|
| 150 | 5.44 ± 0.12 |
| 202 | 3.24 ± 0.07 |

For oral dosing studies, three pre-dose baseline M-Mode images were taken at 1 minute intervals prior to compound administration. Compounds were formulated in a 0.5% hydroxypropyl methylcellulose 2910 (HPMC 2910): 0.1% Tween 80 suspension and delivered as a single dose (5 mL/kg) by oral gavage. At one and four hours post-dose, rats were lightly anesthetized for M-mode echocardiography measurement. The compound effect on cardiac fractional shortening are presented as a percent reduction of baseline fractional shortening (=100%) in Table D.

TABLE D

| Compound No. | Dose (mg/kg) | FS (% reduction from baseline) at 1 h (Mean ± SEM) | FS (% reduction from baseline) at 4 h (Mean ± SEM) |
|---|---|---|---|
| 202 | 3 | 21.88 ± 2.66 | 11.25 ± 5.54 |
|  | 15 | 51.08 ± 1.93 | 20.18 ± 3.59 |
| 278 | 3.0 | 15.8 ± 2.0 | 10.6 ± 5.6 |
|  | 6.0 | 34.4 ± 3.3 | 12.2 ± 4.2 |
| 484A | 2.5 | 21.4 ± 2.4 | 6.1 ± 3.0 |
|  | 5.0 | 49.7 ± 3.7 | 14.3 ± 5.3 |
| 339 | 2.5 | 21.8 ± 2.8 | 5.8 ± 4.4 |
|  | 5.0 | 66.2 ± 2.9 | 19.9 ± 2.0 |
| 179 | 3.0 | 33.8 ± 2.6 | 4.5 ± 4.2 |
|  | 6.0 | 51.9 ± 4.0 | 15.0 ± 5.4 |
| 877A | 9.0 | 12.0 ± 1.9 | 7.5 ± 1.5 |
|  | 30.0 | 49.6 ± 4.6 | 43.3 ± 5.5 |
| 861A | 10 | 13.4 ± 1.6 | 2.0 ± 3.1 |
|  | 100 | 50.0 ± 4.0 | 48.8 ± 5.0 |
| 650A | 10.0 | 7.0 ± 2.1 | −3.2 ± 1.1 |
|  | 70.0 | 59.7 ± 3.8 | 51.8 ± 2.3 |
| 633A | 20.0 | 25.2 ± 2.1 | 1.1 ± 3.5 |
|  | 50.0 | 54.8 ± 1.8 | 33.0 ± 3.0 |
| 646A | 37.5 | 28.4 ± 4.2 | 6.9 ± 6.0 |
|  | 100 | 57.5 ± 2.0 | 35.4 ± 6.4 |
| 666B | 25 | 10.4 ± 1.3 | 0.6 ± 3.1 |
|  | 100 | 53.2 ± 1.1 | 29.8 ± 3.7 |

Concurrent with echocardiography measurements, blood samples are taken to determine the corresponding compound plasma concentration, which may be represented as $IC_{50}$ and $IC_{10}$ values, which is the concentration at which fractional shortening is 50% and 10% of the pre-dose baseline contractility, respectively.

Biological Example B-4: Longitudinal Echocardiography Assessment of Mouse Model of HCM Assessment over time of in vivo cardiac function by echocardiography is performed using a previously reported mouse model of familial hypertrophic cardiomyopathy, which is generated by an arginine to glutamine mutation at residue 403 (R403Q) of the alpha cardiac myosin heavy chain (MHC) gene (Geisterfer-Lowrance et al., Science. 1996 May 3; 272(5262):731-4). Cardiac dysfunction, fibrosis, and measures of cardiac hypertrophy (including ventricular wall thickness) increase with age in this mouse model (Geisterfer-Lowrance, supra; Jiang et al., Science. 2013, 342(6154):111-4).

R403q mice receive vehicle or test compound formulated in chow for 24 weeks. Longitudinal echocardiography measurements are performed every 4 weeks. Echocardiography measurements are taken with mice under isoflurane (1-3%) anesthesia. 2-D M-mode images of the left ventricle are acquired in short-axis view. In vivo fractional shortening is determined by M-Mode image analysis with the following calculation: ((End diastolic diameter−end systolic diameter)/end diastolic diameter×100).

Biological Example B-5: Fibrosis Reduction in a Rat Model of Cardiac Hypertrophy Assessment of fibrosis reduction is performed using Dahl Salt Sensitive (DSS) rats, a previously reported hypertension-induced rat model of heart failure with preserved ejection fraction (Fillmore et al., Mol Med. 2018, 24(1):3; Dahl et al., J Exp Med. 1962, 115:1173-90). DSS rats fed a high salt diet demonstrate progressive cardiovascular dysfunction, including increased systolic blood pressure, diastolic dysfunction, cardiac hypertrophy, and cardiac fibrosis (Fillmore, supra; Dahl, supra, Sakata et al., J Am Coll Cardiol. 2001 January; 37(1):293-9; Kim-Mitsuyama et al., Hypertens Res. 2004 October; 27(10):771-9).

DSS rats receive vehicle or test compound formulated in low or high salt chow for 6 weeks. Perivascular and interstitial cardiac tissue samples are imaged and assayed for % cardiac fibrosis.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:

1. A compound of formula (I):

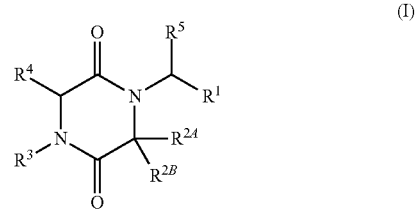

or a pharmaceutically acceptable salt thereof, wherein:
$R^1$ is selected from the group consisting of substituted or unsubstituted phenyl and substituted or unsubstituted pyridyl;
$R^{2A}$, $R^{2B}$, $R^3$, and $R^4$ are defined by any one of (i)-(iii):
(i) $R^{2A}$ is H or substituted or unsubstituted alkyl;
$R^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl;
$R^3$ is phenyl substituted with two or more substituents, or substituted or unsubstituted pyridyl; and
$R^4$ is H or substituted or unsubstituted alkyl;
or
(ii) $R^{2A}$ is H or substituted or unsubstituted alkyl;
$R^{2B}$ is substituted or unsubstituted phenyl or substituted or unsubstituted pyridyl;
$R^3$ is unsubstituted $C_2$-$C_4$ alkyl; and
$R^4$ is H or substituted or unsubstituted alkyl;
or
(iii) $R^{2A}$ and $R^{2B}$ are taken together with the carbon atom to which they are attached to form $G^1$, wherein $G^1$ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring;

R³ is selected from the group consisting of unsubstituted C$_2$-C$_6$ alkyl, alkyl substituted with alkoxy, cyano, or halo, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and R⁴ is H or unsubstituted alkyl; and R⁵ is H or substituted or unsubstituted alkyl;

wherein, when one or more of provisions (a)-(b) apply, then R¹ is substituted or unsubstituted pyridyl or phenyl substituted with at least one substituent other than methyl or methoxy:

(a) R$^{2A}$ and R$^{2B}$ are as defined by (i) and R³ is phenyl substituted with two or more substituents;

(b) R$^{2A}$ and R³ are as defined by (ii) and R$^{2B}$ is 4-methoxyphenyl.

2. The compound of claim 1, or a pharmaceutically acceptable salt thereof, wherein R$^{2A}$ is H or substituted or unsubstituted alkyl;

R$^{2B}$ is selected from the group consisting of H, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and R³ is phenyl substituted with two or more substituents, or substituted or unsubstituted pyridyl.

3. The compound of claim 2, or a pharmaceutically acceptable salt thereof, wherein R³ is phenyl substituted with two or more substituents.

4. The compound of claim 2, or a pharmaceutically acceptable salt thereof, wherein R³ is substituted or unsubstituted pyridyl.

5. The compound of claim 2, or a pharmaceutically acceptable salt thereof, wherein R³ is phenyl substituted with two or more halo substituents selected from the group consisting of F and Cl.

6. The compound of claim 5, or a pharmaceutically acceptable salt thereof, wherein R³ is further substituted with one, two, or three —CN substituents.

7. The compound of claim 2, or a pharmaceutically acceptable salt thereof, wherein R$^{2A}$ is substituted or unsubstituted alkyl.

8. The compound of claim 2, or a pharmaceutically acceptable salt thereof, wherein R$^{2A}$ is H.

9. The compound of claim 2, or a pharmaceutically acceptable salt thereof, wherein R$^{2B}$ is substituted or unsubstituted alkyl.

10. The compound of claim 2, or a pharmaceutically acceptable salt thereof, wherein R$^{2B}$ is selected from the group consisting of methyl, hydroxymethyl, and isopropyl.

11. The compound of claim 2, or a pharmaceutically acceptable salt thereof, wherein R$^{2B}$ is alkyl substituted with substituted or unsubstituted alkoxy.

12. The compound of claim 2, or a pharmaceutically acceptable salt thereof, wherein R$^{2B}$ is alkyl substituted with substituted or unsubstituted oxetanyl.

13. The compound of claim 12, or a pharmaceutically acceptable salt thereof, wherein R$^{2B}$ is methyl substituted with unsubstituted 3-oxetanyl.

14. The compound of claim 2, or a pharmaceutically acceptable salt thereof, wherein R$^{2B}$ is substituted or unsubstituted cycloalkyl.

15. The compound of claim 14, or a pharmaceutically acceptable salt thereof, wherein R$^{2B}$ is cyclobutanyl.

16. The compound of claim 2, or a pharmaceutically acceptable salt thereof, wherein R$^{2B}$ is substituted or unsubstituted heterocyclyl.

17. The compound of claim 16, or a pharmaceutically acceptable salt thereof, wherein R$^{2B}$ is oxetanyl.

18. The compound of claim 17, or a pharmaceutically acceptable salt thereof, wherein R$^{2B}$ is 3-oxetanyl.

19. The compound of claim 1, or a pharmaceutically acceptable salt thereof, wherein R$^{2A}$ is H or substituted or unsubstituted alkyl;

R$^{2B}$ is substituted or unsubstituted phenyl or substituted or unsubstituted pyridyl; and R³ is unsubstituted C$_2$-C$_4$ alkyl.

20. The compound of claim 19, or a pharmaceutically acceptable salt thereof, wherein R$^{2A}$ is unsubstituted alkyl.

21. The compound of claim 19, or a pharmaceutically acceptable salt thereof, wherein R$^{2A}$ is H.

22. The compound of claim 19, or a pharmaceutically acceptable salt thereof, wherein R$^{2B}$ is substituted phenyl or substituted pyridyl.

23. The compound of claim 19, or a pharmaceutically acceptable salt thereof, wherein R$^{2B}$ is phenyl or pyridyl, each of which is substituted with one or more substituents independently selected from the group consisting of halo, alkoxy, and substituted alkyl.

24. The compound of claim 19, or a pharmaceutically acceptable salt thereof, wherein R$^{2B}$ is phenyl or pyridyl, each of which is substituted with —CF$_3$.

25. The compound of claim 19, or a pharmaceutically acceptable salt thereof, wherein the R$^{2B}$ is phenyl or pyridyl, each of which is substituted with methoxy.

26. The compound of claim 19, or a pharmaceutically acceptable salt thereof, wherein R³ is isopropyl.

27. The compound of claim 1, or a pharmaceutically acceptable salt thereof, wherein R$^{2A}$ and R$^{2B}$ are taken together with the carbon atom to which they are attached to form G¹, wherein G¹ is a substituted or unsubstituted cycloalkyl, substituted or unsubstituted cycloalkenyl, substituted or unsubstituted cycloalkynyl, or substituted or unsubstituted heterocyclyl ring, each of which is optionally fused to a phenyl ring; and R³ is selected from the group consisting of unsubstituted C$_2$-C$_6$ alkyl, alkyl substituted with alkoxy, cyano, or halo, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl.

28. The compound of claim 27 or a pharmaceutically acceptable salt thereof, wherein G¹ is selected from the group consisting of substituted or unsubstituted cycloalkyl, substituted or unsubstituted heterocyclyl, and substituted or unsubstituted 2,3-dihydro-1H-indene.

29. The compound of claim 27, or a pharmaceutically acceptable salt thereof, wherein G¹ is a substituted or unsubstituted cycloalkyl or heterocyclyl selected from the group consisting of:

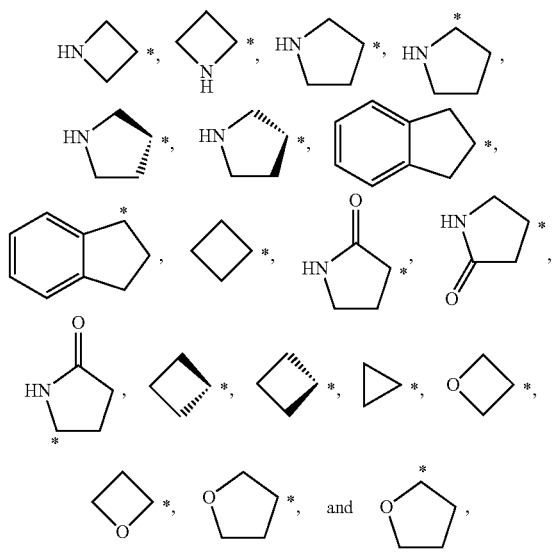

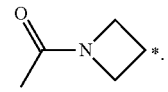

wherein * indicates the point of attachment to the parent structure.

30. The compound of claim 27, or a pharmaceutically acceptable salt thereof, wherein G¹ is substituted or unsubstituted

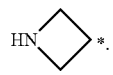

31. The compound of claim 27, or a pharmaceutically acceptable salt thereof, wherein G¹ is substituted with one, two, or three substituents selected from the group consisting of substituted or unsubstituted aryl, substituted or unsubstituted heteroaryl, substituted or unsubstituted alkoxycarbonyl, substituted or unsubstituted aminoacyl, substituted or unsubstituted acyl, substituted or unsubstituted aminosulfonyl, substituted or unsubstituted aminocarbonylamino, and substituted or unsubstituted alkyl.

32. The compound of claim 27, or a pharmaceutically acceptable salt thereof, wherein G¹ is 33. The compound of claim 27, or a pharmaceutically acceptable salt thereof, wherein R³ is selected from the group consisting of unsubstituted $C_2$-$C_6$ alkyl, alkyl substituted with alkoxy, cyano, or halo, substituted or unsubstituted cycloalkyl, substituted or unsubstituted heterocyclyl, and substituted or unsubstituted aryl.

34. The compound of claim 27, or a pharmaceutically acceptable salt thereof, wherein R³ is phenyl substituted with one or more substituents selected from the group consisting of nitro, alkoxy, halo, cycloalkyl, cyano, alkenyl, alkoxycarbonyl, phenylcarbonyl, and alkyl.

35. The compound of claim 27, or a pharmaceutically acceptable salt thereof, wherein R³ is phenyl substituted with F and CN.

36. The compound of claim 27, or a pharmaceutically acceptable salt thereof, wherein R³ is cycloalkyl substituted with one or more substituents selected from the group consisting of alkyl, cyano, and halo.

37. The compound of claim 27, or a pharmaceutically acceptable salt thereof, wherein R³ is alkyl substituted with one or more substituents selected from the group consisting of alkoxy, cyano, and halo.

38. The compound of claim 1 or a pharmaceutically acceptable salt thereof, wherein R⁴ is H.

39. The compound of claim 1 or a pharmaceutically acceptable salt thereof, wherein R⁴ is alkyl substituted with substituted or unsubstituted alkoxy.

40. The compound of claim 1 or a pharmaceutically acceptable salt thereof, wherein R⁵ is H.

41. The compound of claim 1 or a pharmaceutically acceptable salt thereof, wherein R¹ is phenyl or pyridinyl, each of which is substituted with one or more substituents independently selected from the group consisting of cyano, halo, substituted or unsubstituted alkoxy, substituted or unsubstituted alkyl, and substituted or unsubstituted heterocyclyl.

42. The compound of claim 1 or a pharmaceutically acceptable salt thereof, wherein R¹ is phenyl substituted with trifluoromethyl.

43. A compound selected from the group consisting of:

| No. | Structure |
|---|---|
| 1 | 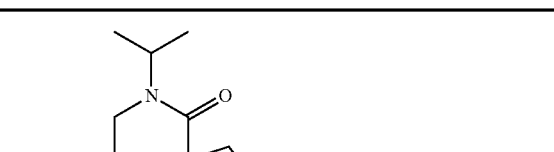 |

| No. | Structure |
|---|---|
| 2 | 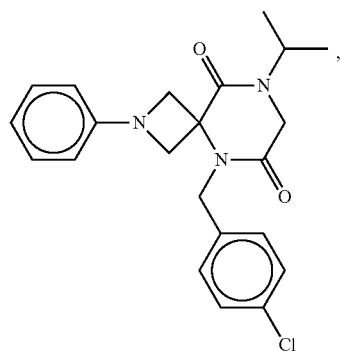 |
| 3 | 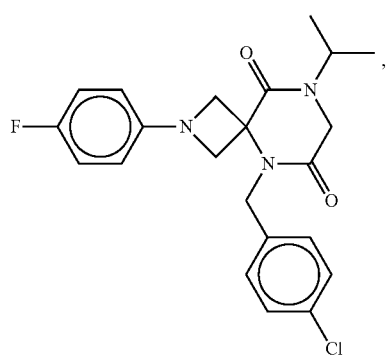 |
| 4 | 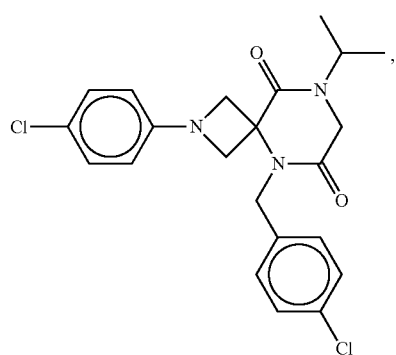 |
| 5 | 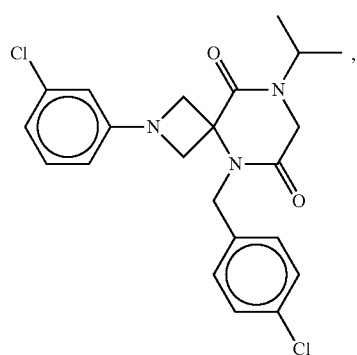 |

| No. | Structure |
|---|---|
| 6 | 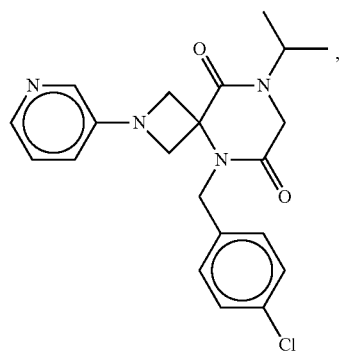 |
| 7 | 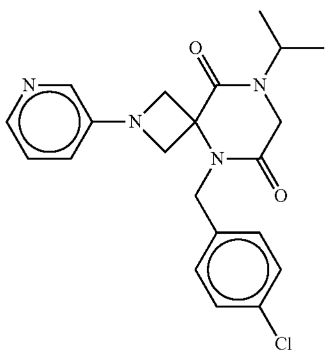 |
| 8 | 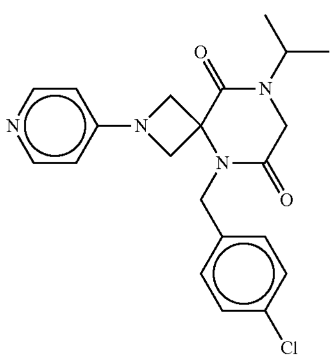 |
| 9 | 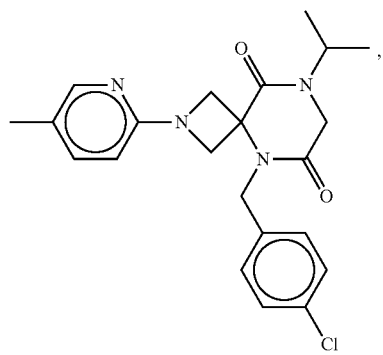 |

| No. | Structure |
|---|---|
| 10 | 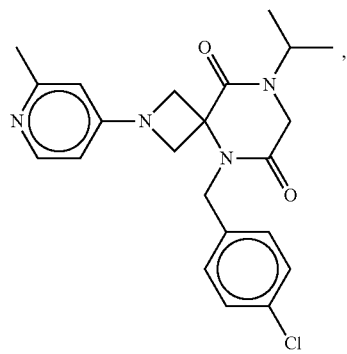 |
| 11 | 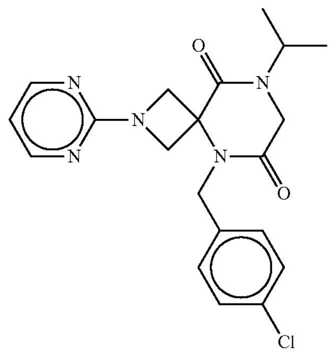 |
| 12 | 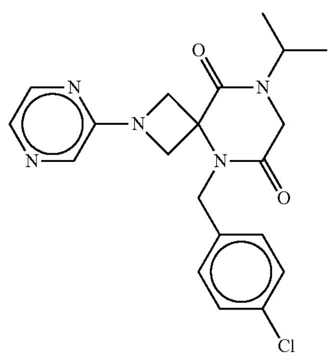 |
| 13 | 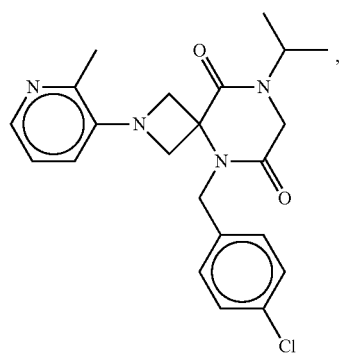 |

| No. | Structure |
|---|---|
| 14 | 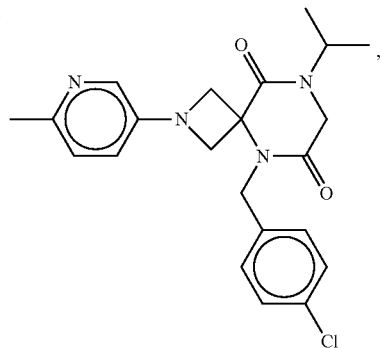 |
| 15 | 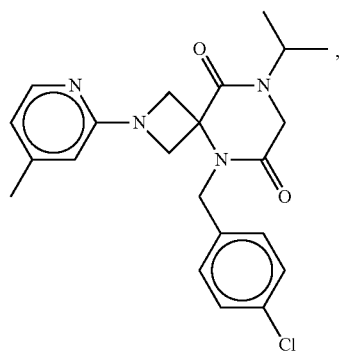 |
| 16 | 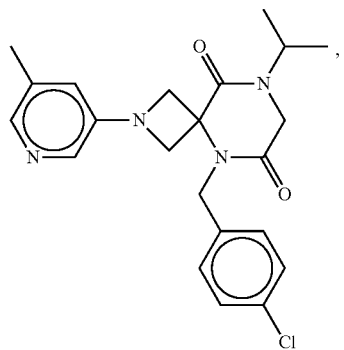 |
| 17 | 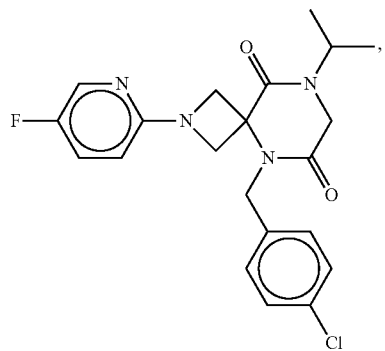 |

| No. | Structure |
|---|---|
| 18 | 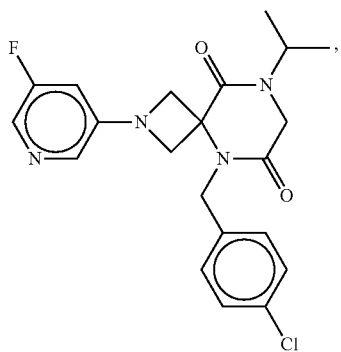 |
| 19 | 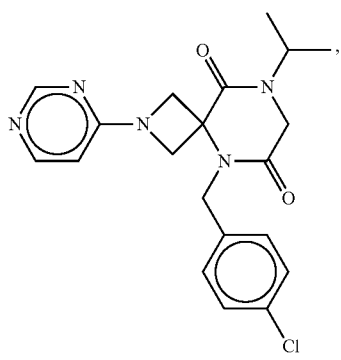 |
| 20 | 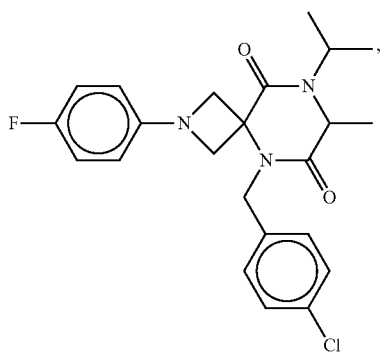 |
| 21 | 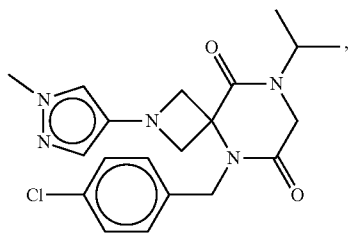 |
| 22 | 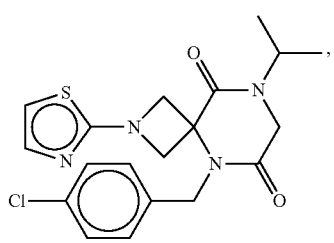 |

| No. | Structure |
|---|---|
| 23 | 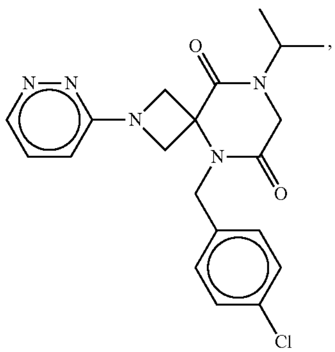 |
| 24 | 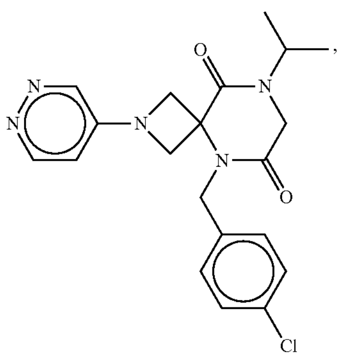 |
| 25 | 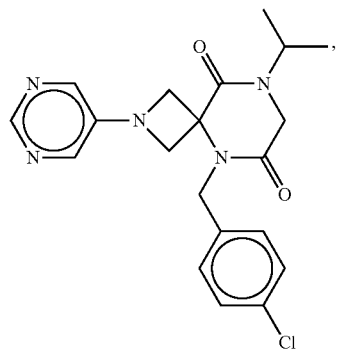 |
| 26 | 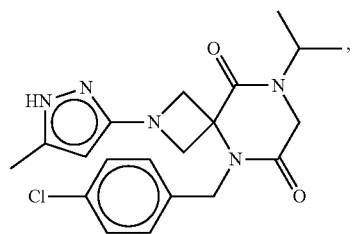 |

| No. | Structure |
|---|---|
| 27 | 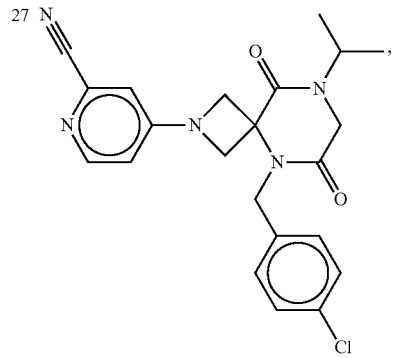 |
| 28 | 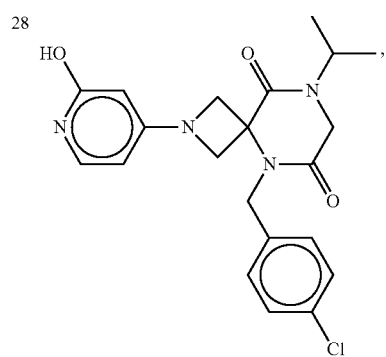 |
| 29 | 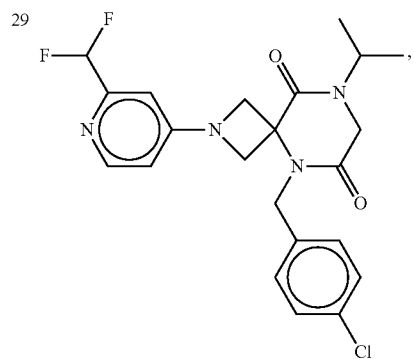 |
| 30 | 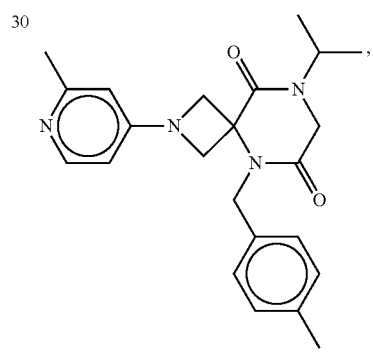 |

| No. | Structure |
|---|---|
| 31 | 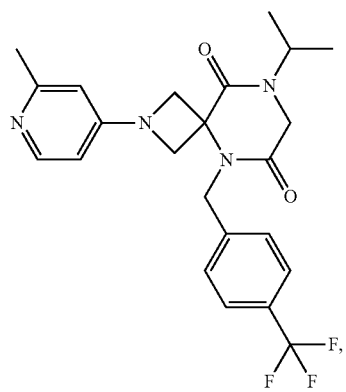 [SMILES: Cc1cc(N2CC3(C2)C(=O)N(C(C)C)CC(=O)N3Cc2ccc(C(F)(F)F)cc2)ccn1] |
| 32 | 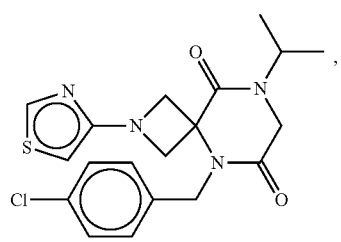 |
| 33 | 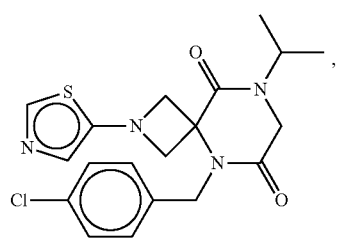 |
| 34 | 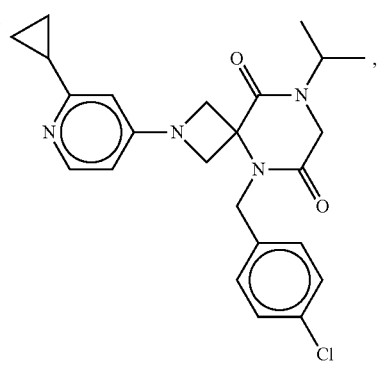 |
| 35 | 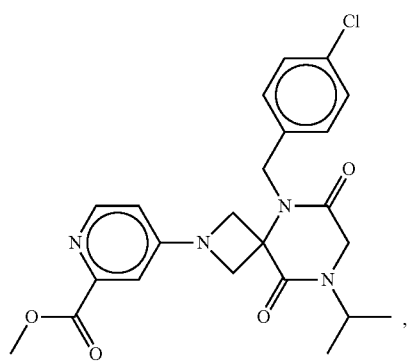 |

| No. | Structure |
|---|---|
| 36 | 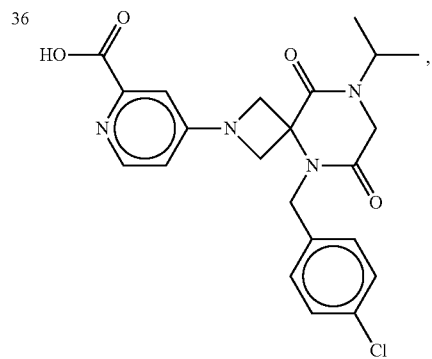 |
| 37 | 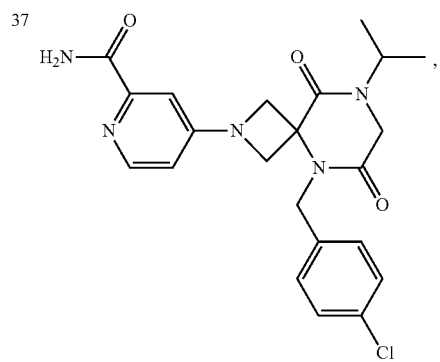 |
| 38 | 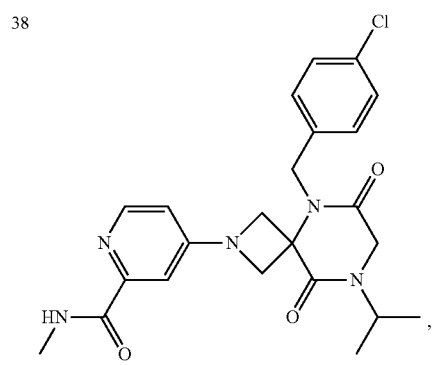 |
| 39 | 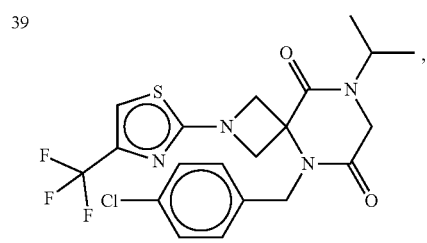 |
| 40 | 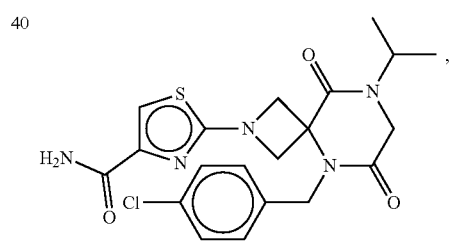 |

| No. | Structure |
|---|---|
| 41 | 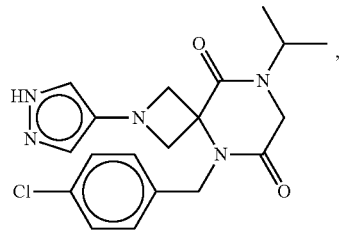 |
| 42 | 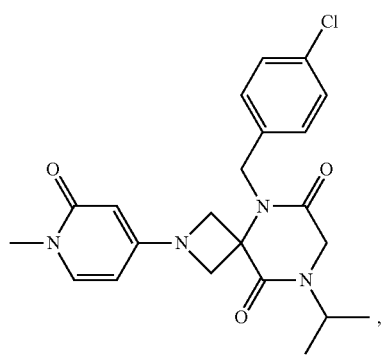 [SMILES: CC(C)N1CC(=O)N(Cc2ccc(Cl)cc2)C2(CN(c3ccn(C)c(=O)c3)C2)C1=O] |
| 43 | 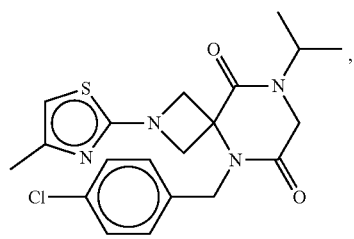 |
| 44 | 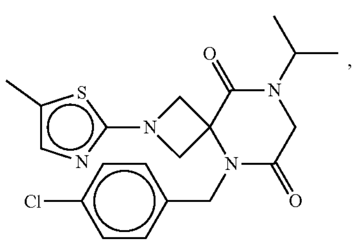 |
| 45 | 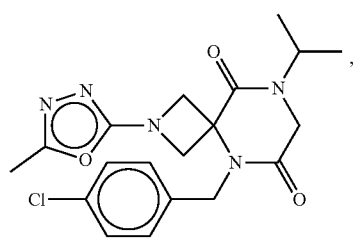 |

| No. | Structure |
|---|---|
| 46 | 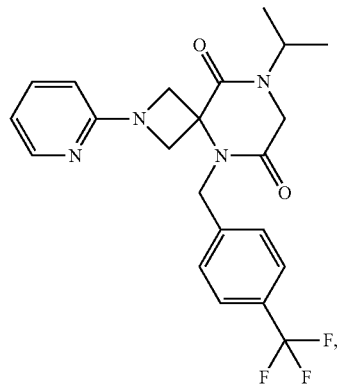 [SMILES: CC(C)N1CC(=O)N(Cc2ccc(C(F)(F)F)cc2)C2(CN(c3ccccn3)C2)C1=O] |
| 47 | 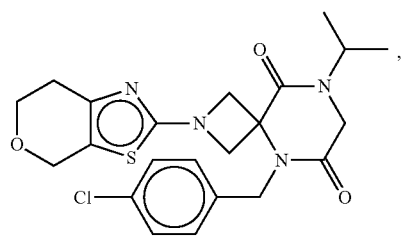 |
| 48 | 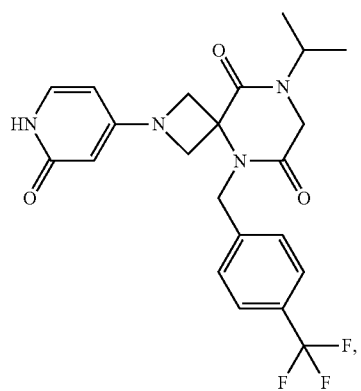 [SMILES: CC(C)N1CC(=O)N(Cc2ccc(C(F)(F)F)cc2)C2(CN(c3cc[nH]c(=O)c3)C2)C1=O] |
| 49 | 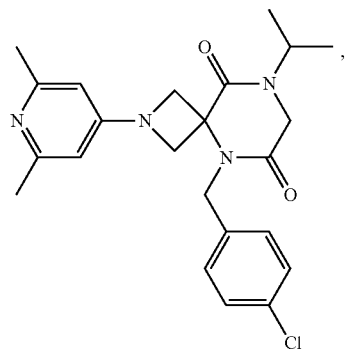 [SMILES: Cc1cc(N2CC3(C2)C(=O)N(C(C)C)CC(=O)N3Cc2ccc(Cl)cc2)cc(C)n1] |

| No. | Structure |
|---|---|
| 50 | 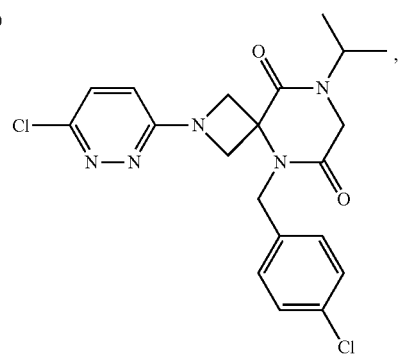 |
| 51 | 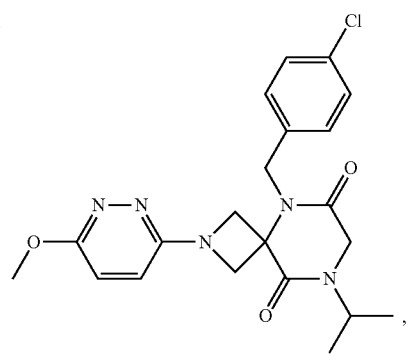 [SMILES: COc1ccc(N2CC3(C2)C(=O)N(C(C)C)CC(=O)N3Cc2ccc(Cl)cc2)nn1] |
| 52 | 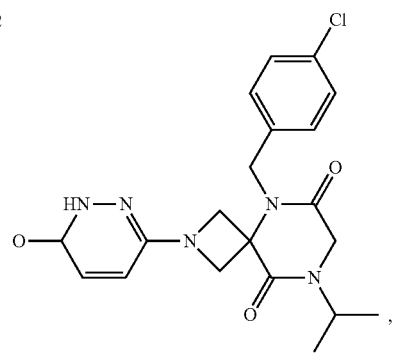 |
| 53 | 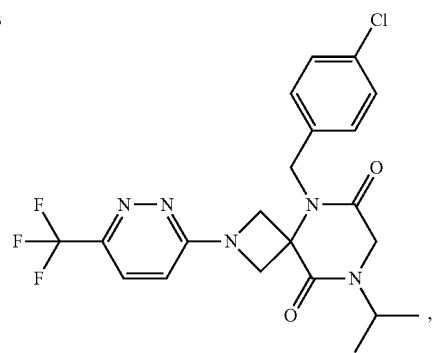 |

| No. | Structure |
|---|---|
| 54 | 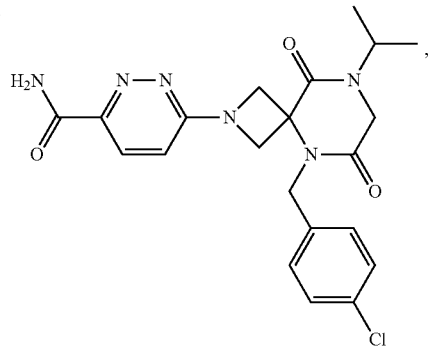 [SMILES: CC(C)N1CC(=O)N(Cc2ccc(Cl)cc2)C2(CN(c3ccc(C(N)=O)nn3)C2)C1=O] |
| 55 | 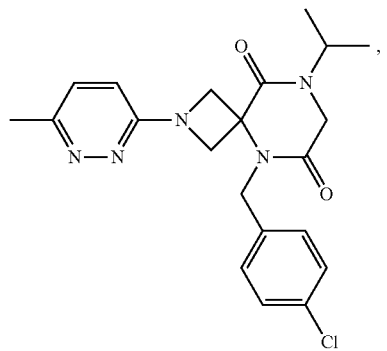 [SMILES: Cc1ccc(N2CC3(C2)C(=O)N(C(C)C)CC(=O)N3Cc2ccc(Cl)cc2)nn1] |
| 56 | 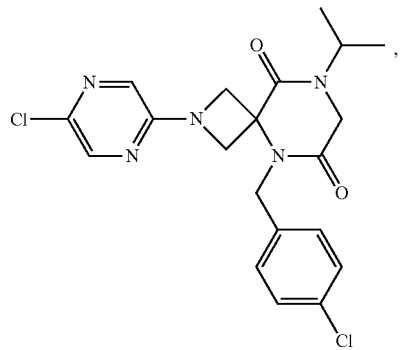 [SMILES: CC(C)N1CC(=O)N(Cc2ccc(Cl)cc2)C2(CN(c3cnc(Cl)cn3)C2)C1=O] |
| 57 | 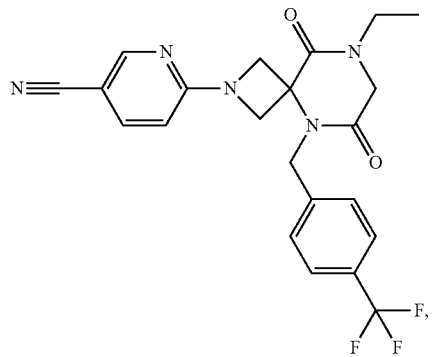 [SMILES: CCN1CC(=O)N(Cc2ccc(C(F)(F)F)cc2)C2(CN(c3ccc(C#N)cn3)C2)C1=O] |

| No. | Structure |
|---|---|
| 58 | 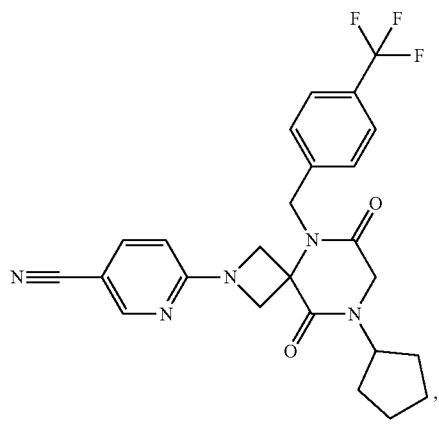 [SMILES: N#Cc1ccc(N2CC3(C2)C(=O)N(C2CCCC2)CC(=O)N3Cc2ccc(C(F)(F)F)cc2)nc1] |
| 59 | 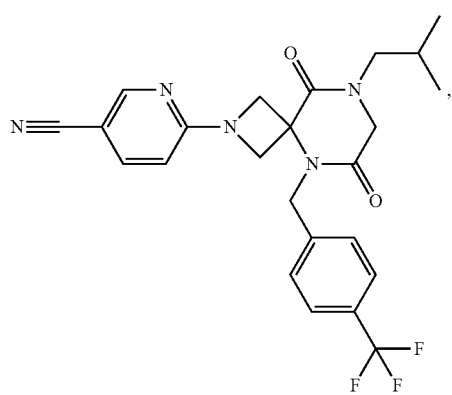 [SMILES: CC(C)CN1CC(=O)N(Cc2ccc(C(F)(F)F)cc2)C2(CN(c3ccc(C#N)cn3)C2)C1=O] |
| 60 | 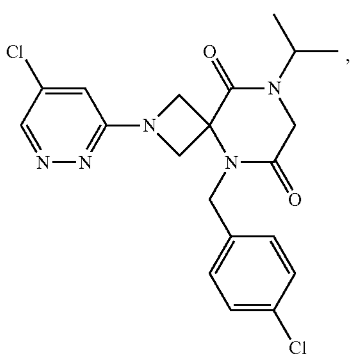 [SMILES: CC(C)N1CC(=O)N(Cc2ccc(Cl)cc2)C2(CN(c3cc(Cl)cnn3)C2)C1=O] |
| 61 | 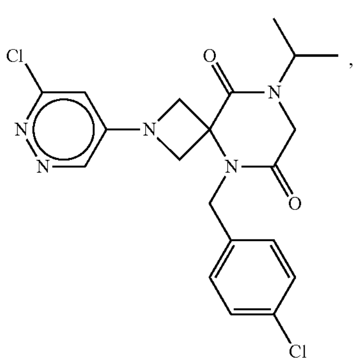 |

| No. | Structure |
|---|---|
| 62 | 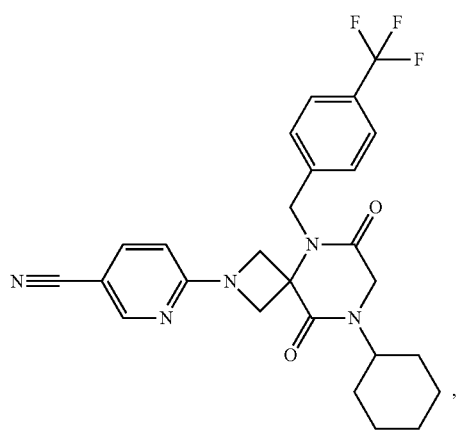 [SMILES: N#Cc1ccc(N2CC3(C2)C(=O)N(C2CCCCC2)CC(=O)N3Cc2ccc(C(F)(F)F)cc2)nc1] |
| 63 | 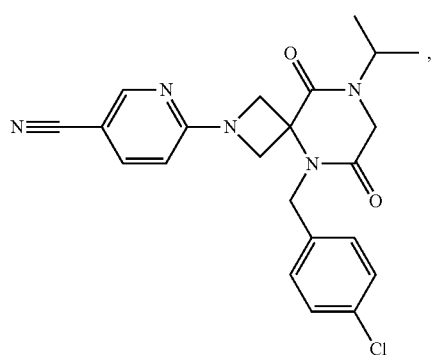 [SMILES: CC(C)N1CC(=O)N(Cc2ccc(Cl)cc2)C2(CN(c3ccc(C#N)cn3)C2)C1=O] |
| 64 | 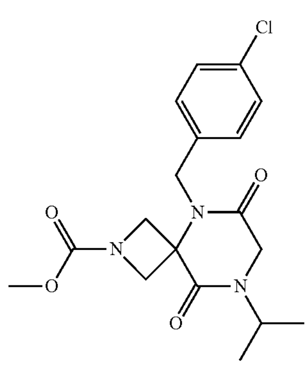 |
| 65 | 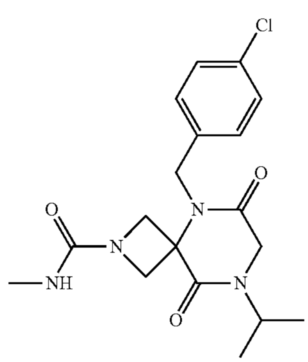 |

| No. | Structure |
|---|---|
| 66 | 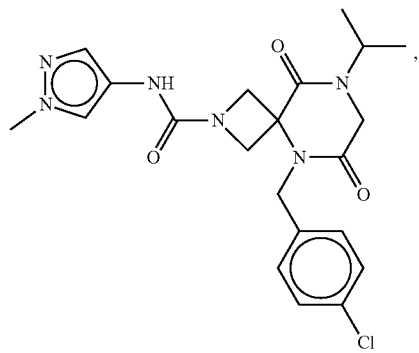 |
| 67 | 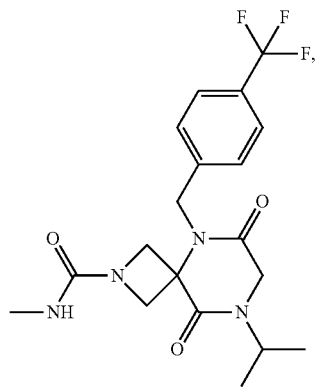 |
| 68 | 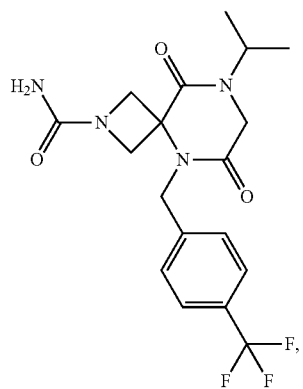 [SMILES: CC(C)N1CC(=O)N(Cc2ccc(C(F)(F)F)cc2)C2(CN(C(N)=O)C2)C1=O] |
| 69 | 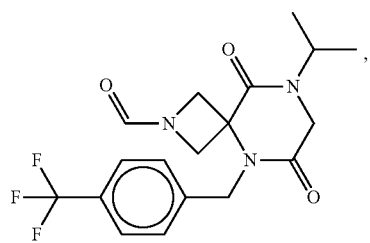 |

-continued
| No. | Structure |
|---|---|
| 70 | 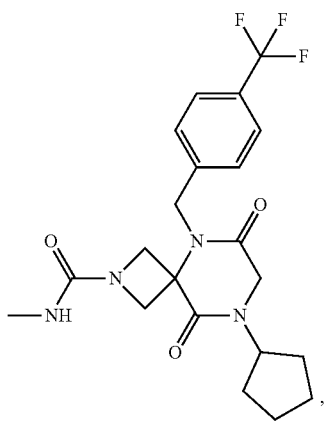 [SMILES: CNC(=O)N1CC2(C1)C(=O)N(C1CCCC1)CC(=O)N2Cc1ccc(C(F)(F)F)cc1] |
| 71 | 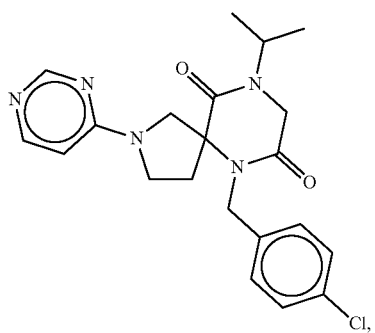 |
| 72 | 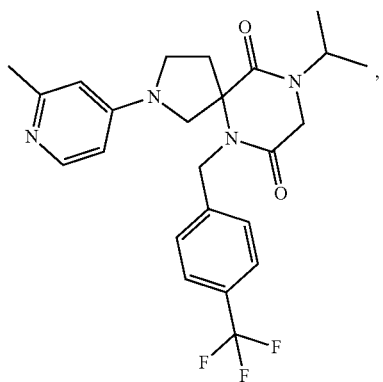 [SMILES: Cc1cc(N2CCC3(C2)C(=O)N(C(C)C)CC(=O)N3Cc2ccc(C(F)(F)F)cc2)ccn1] |
| 73 | 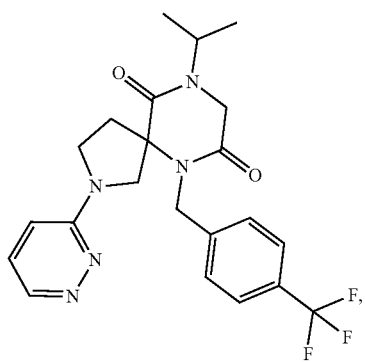 [SMILES: CC(C)N1CC(=O)N(Cc2ccc(C(F)(F)F)cc2)C2(CCN(c3cccnn3)C2)C1=O] |

| No. | Structure |
|---|---|
| 74 | 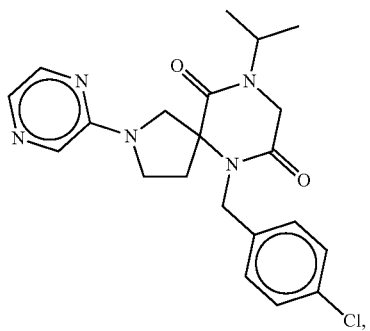 |
| 75 | 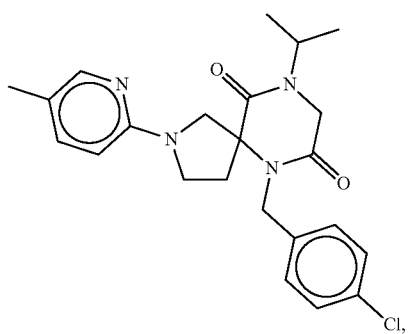 |
| 76 | 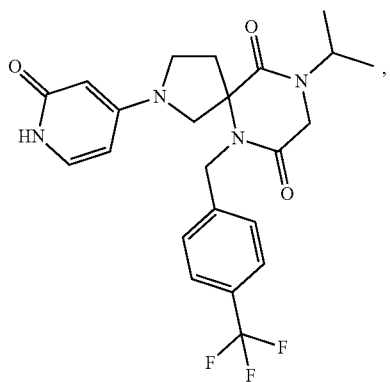 [SMILES: CC(C)N1CC(=O)N(Cc2ccc(C(F)(F)F)cc2)C2(CCN(c3cc[nH]c(=O)c3)C2)C1=O] |
| 77 | 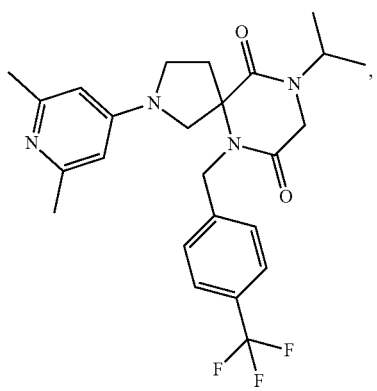 [SMILES: Cc1cc(N2CCC3(C2)C(=O)N(C(C)C)CC(=O)N3Cc2ccc(C(F)(F)F)cc2)cc(C)n1] |

| No. | Structure |
|---|---|
| 78 | 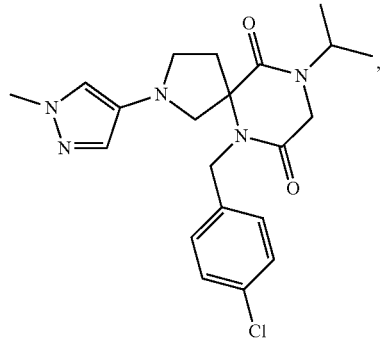 [SMILES: CC(C)N1CC(=O)N(Cc2ccc(Cl)cc2)C2(CCN(c3cnn(C)c3)C2)C1=O] |
| 79 | 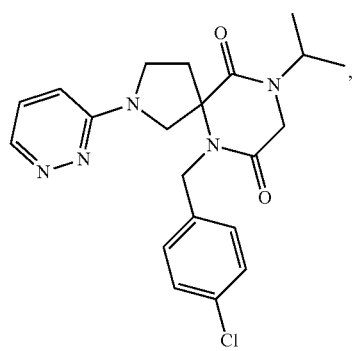 [SMILES: CC(C)N1CC(=O)N(Cc2ccc(Cl)cc2)C2(CCN(c3cccnn3)C2)C1=O] |
| 80 | 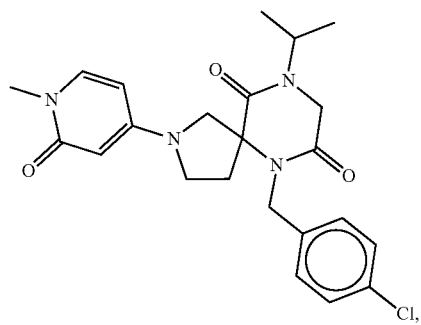 |
| 81 | 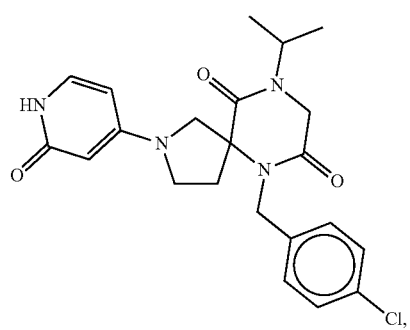 |

| No. | Structure |
|---|---|
| 82 | 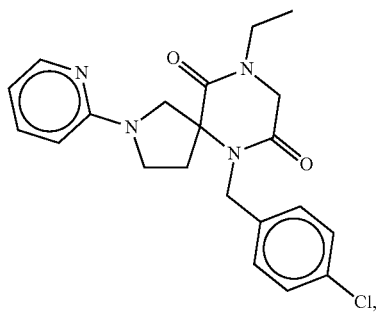 |
| 83 | 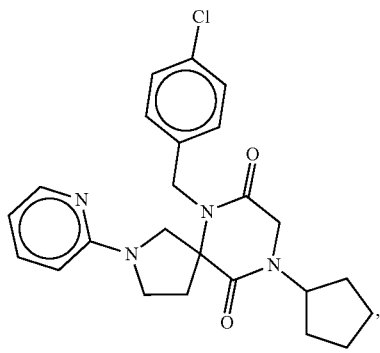 |
| 84 | 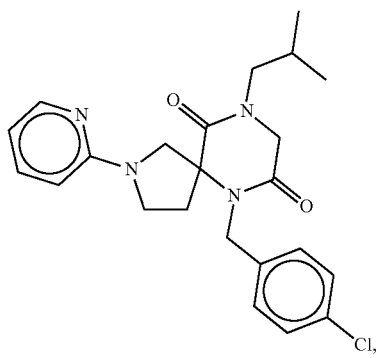 |
| 85 | 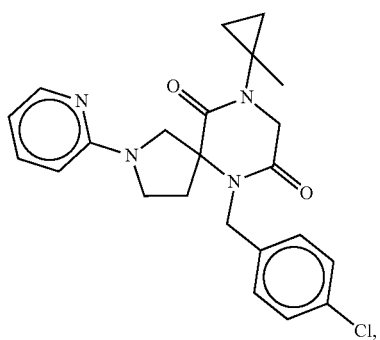 |

| No. | Structure |
|---|---|
| 86 | 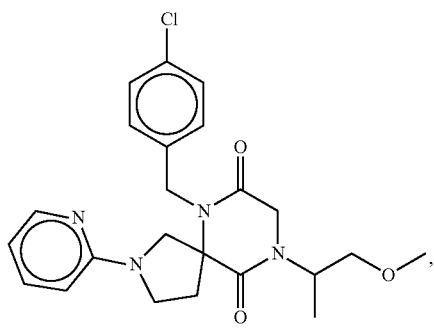 |
| 87 | 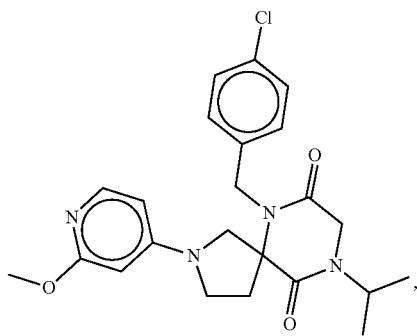 |
| 88 | 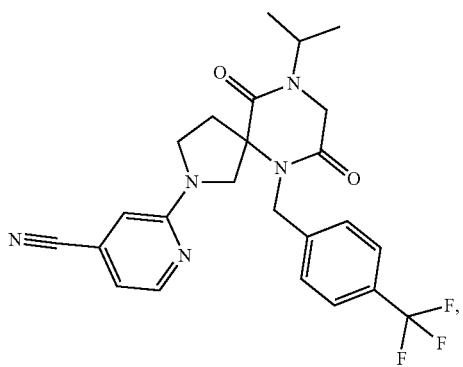 [SMILES: CC(C)N1CC(=O)N(Cc2ccc(C(F)(F)F)cc2)C2(CCN(c3cc(C#N)ccn3)C2)C1=O] |
| 89 | 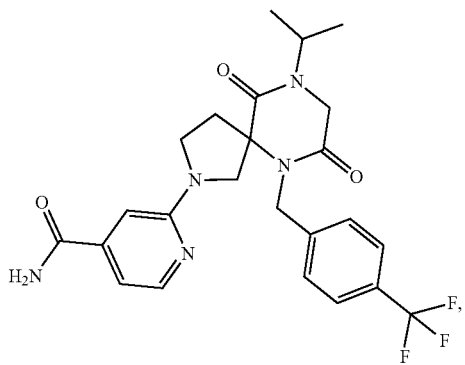 [SMILES: CC(C)N1CC(=O)N(Cc2ccc(C(F)(F)F)cc2)C2(CCN(c3cc(C(N)=O)ccn3)C2)C1=O] |

| No. | Structure |
|---|---|
| 90 | 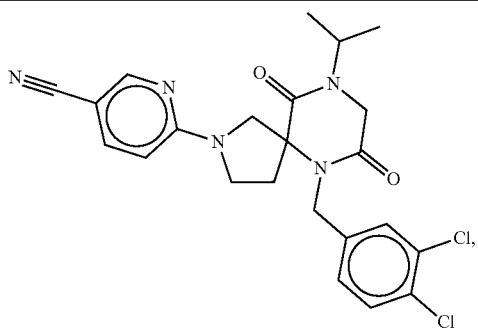 |
| 91 | 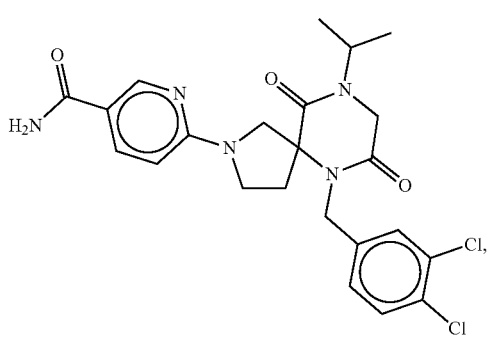 |
| 92 | 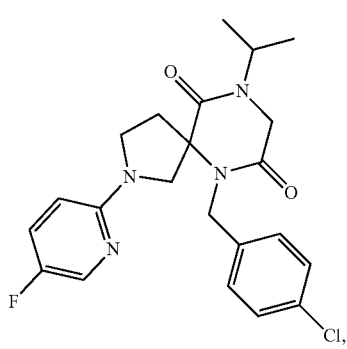 [SMILES: CC(C)N1CC(=O)N(Cc2ccc(Cl)cc2)C2(CCN(c3ccc(F)cn3)C2)C1=O] |
| 93 | 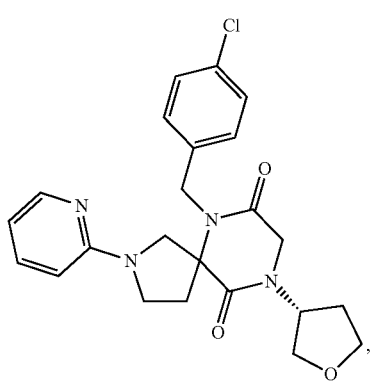 [SMILES: O=C1CN([C@@H]2CCOC2)C(=O)C2(CCN(c3ccccn3)C2)N1Cc1ccc(Cl)cc1] |

| No. | Structure |
|---|---|
| 94 | 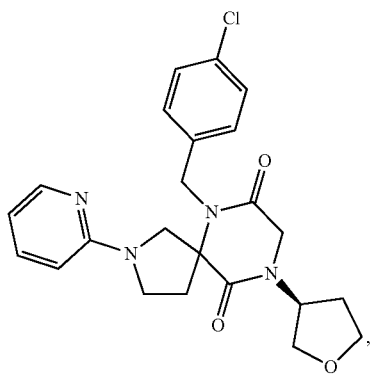 [SMILES: O=C1CN([C@H]2CCOC2)C(=O)C2(CCN(c3ccccn3)C2)N1Cc1ccc(Cl)cc1] |
| 95 | 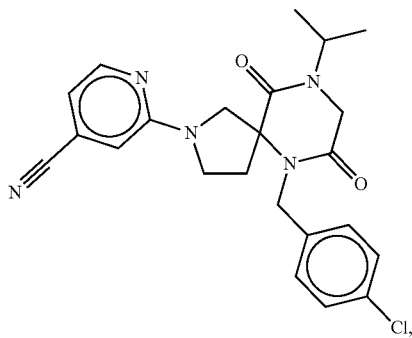 |
| 96 | 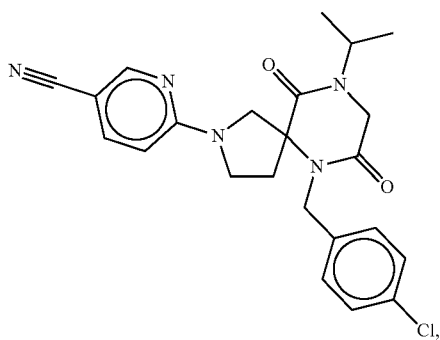 |
| 97 | 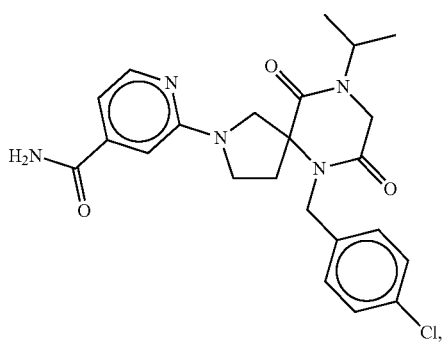 |

| No. | Structure |
|---|---|
| 98 | 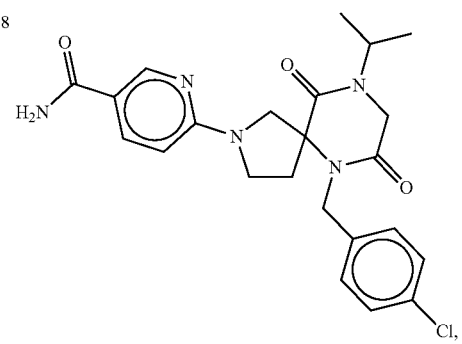 |
| 99 | 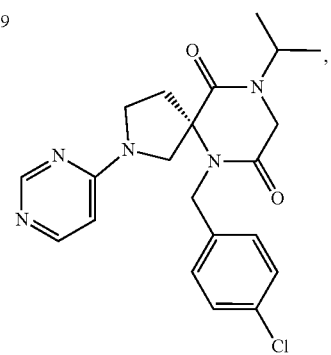 |
| 100 | 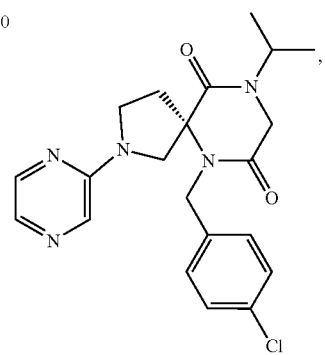 |
| 101 | 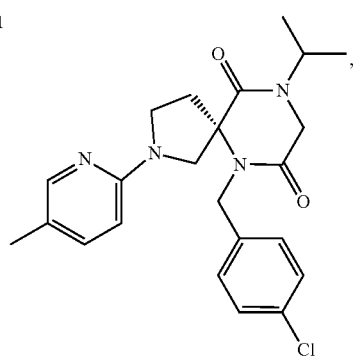 [SMILES: CC(C)N1CC(=O)N(Cc2ccc(Cl)cc2)[C@]2(CCN(c3ccc(F)cn3)C2)C1=O] |

-continued
| No. | Structure |
|---|---|
| 102 | 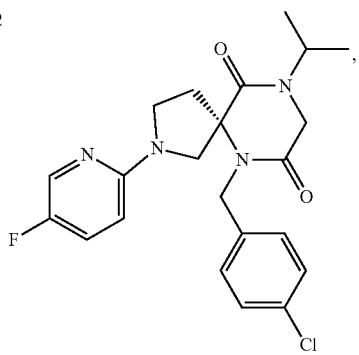 |
| 103 | 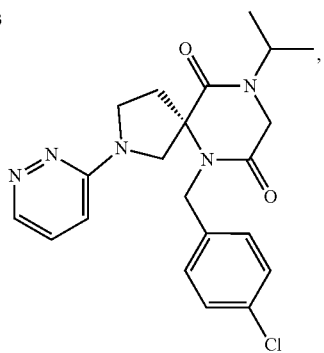 |
| 104 | 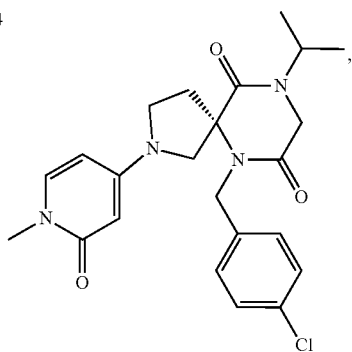 |
| 105 | 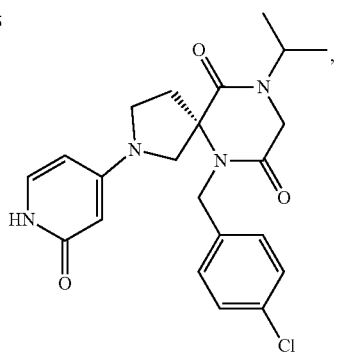 |

| No. | Structure |
|---|---|
| 106 | 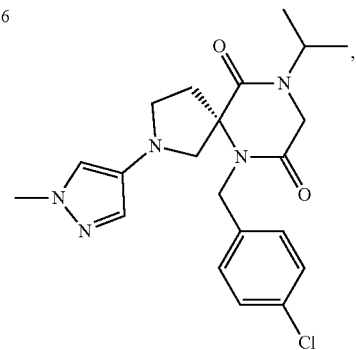 |
| 107 | 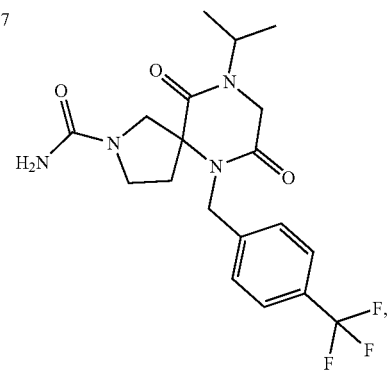 |
| 108 | 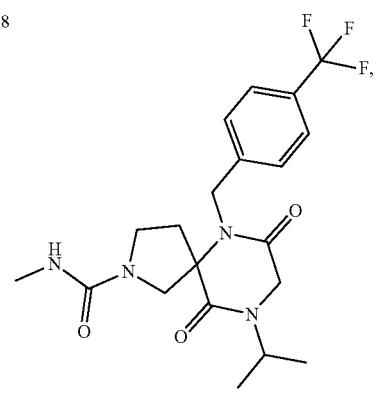 |
| 109 | 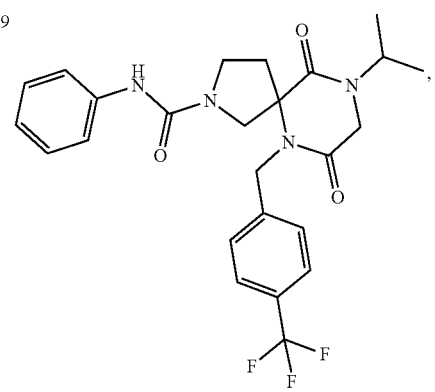 |

| No. | Structure |
|---|---|
| 110 | 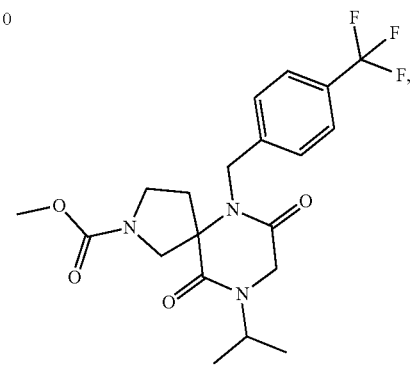 |
| 111 | 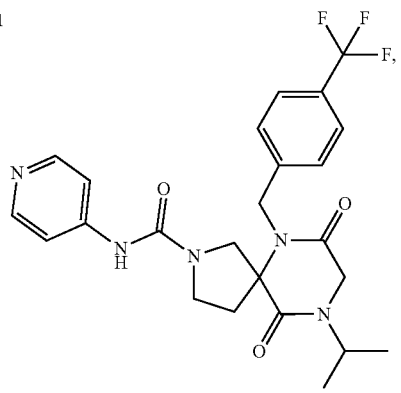 |
| 112 | 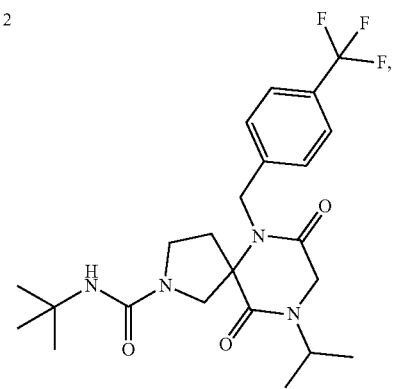 |
| 113 | 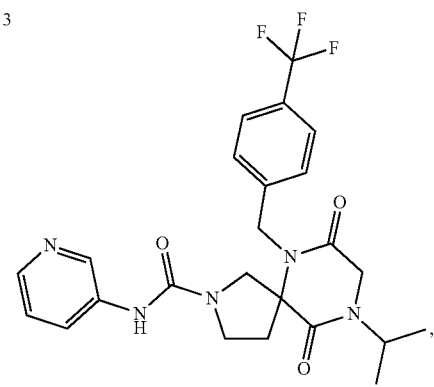 |

| No. | Structure |
|---|---|
| 114 | 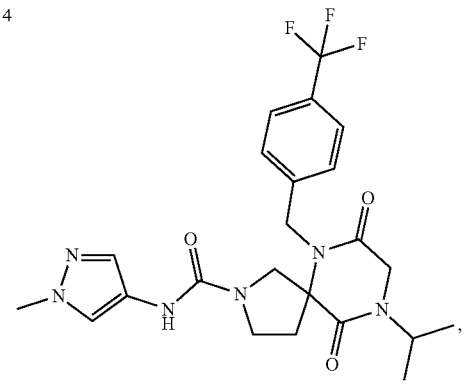 |
| 115 | 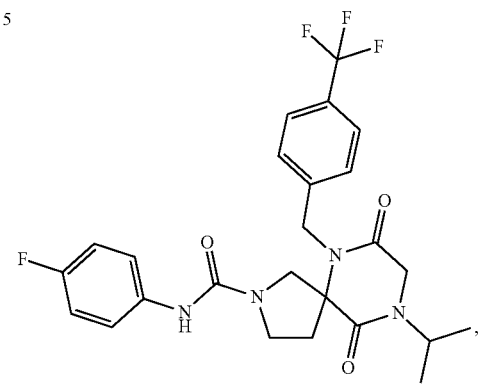 |
| 116 | 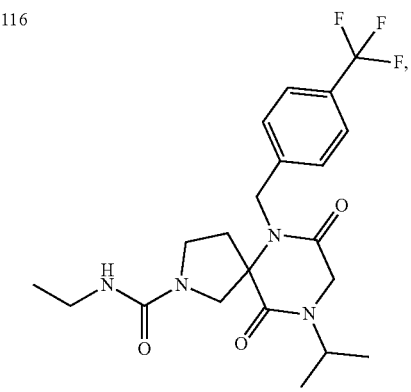 |
| 117 | 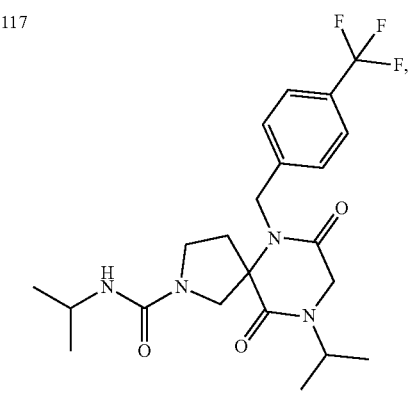 |

| No. | Structure |
|---|---|
| 118 | 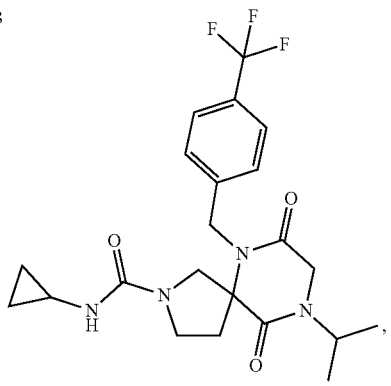 |
| 119 | 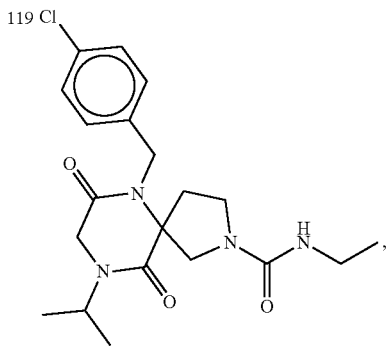 |
| 120 | 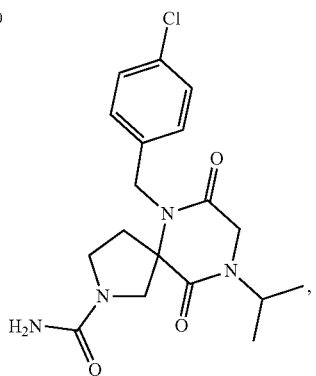 |
| 121 | 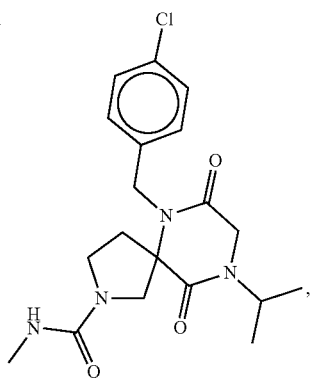 |

| No. | Structure |
|---|---|
| 122 | 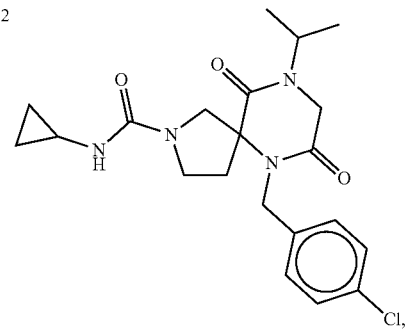 |
| 123 | 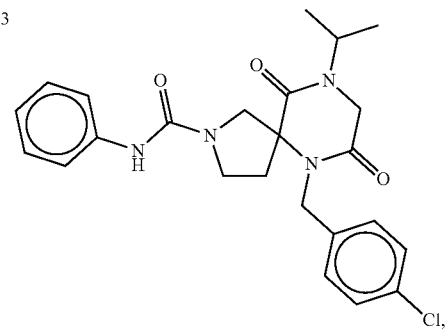 |
| 124 | 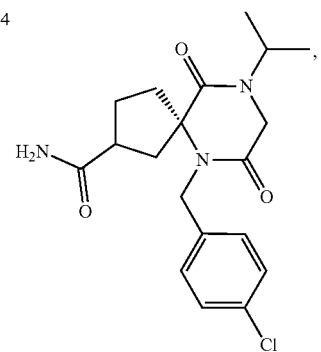 |
| 125 | 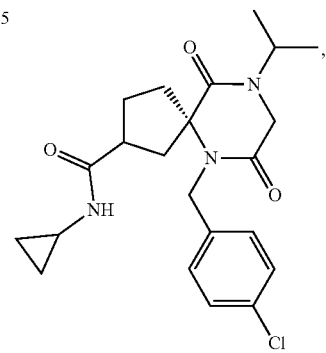 |

US 11,414,424 B2
-continued
| No. | Structure |
|---|---|
| 126 | 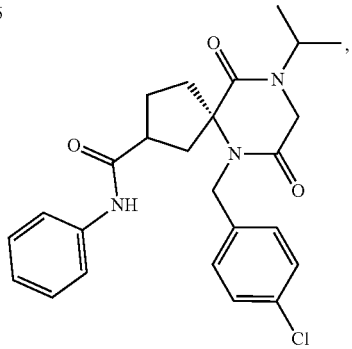 |
| 127 | 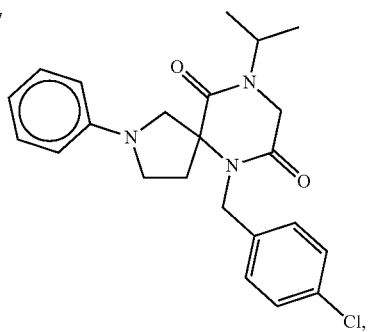 |
| 128 | 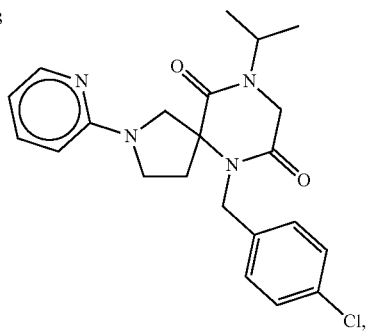 |
| 129 | 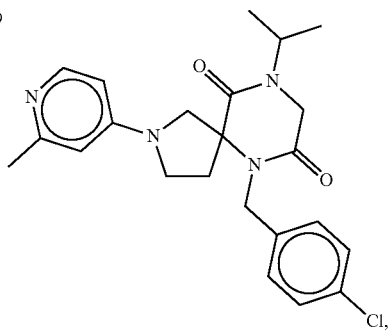 |

| No. | Structure |
|---|---|
| 130 | 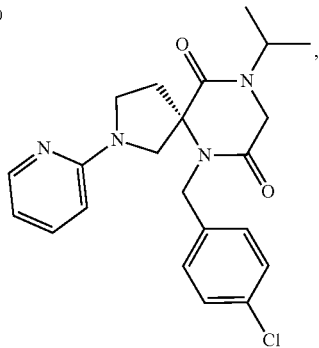 |
| 131 | 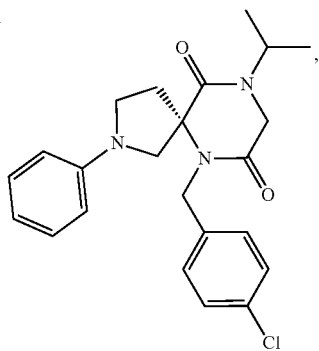 [SMILES: CC(C)N1CC(=O)N(Cc2ccc(Cl)cc2)[C@]2(CCN(c3ccccc3)C2)C1=O] |
| 132 | 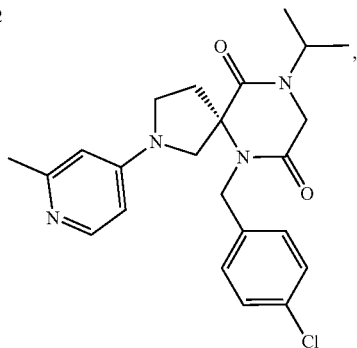 |
| 133 | 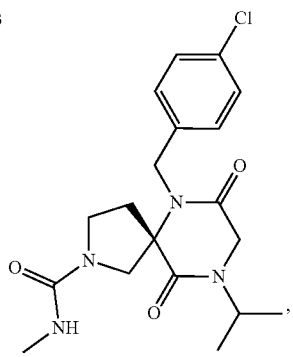 |

| No. | Structure |
|---|---|
| 134 | 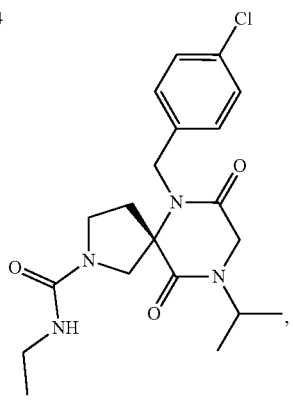 |
| 135 | 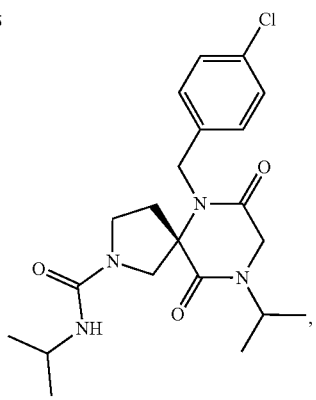 |
| 136 | 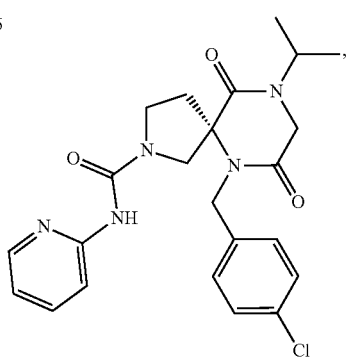 |
| 137 | 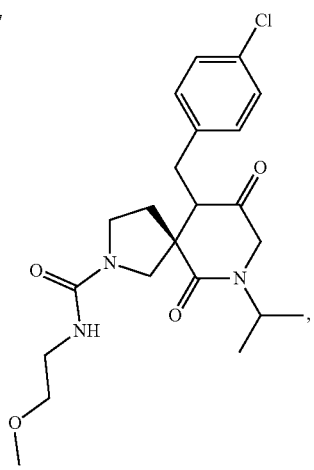 |

-continued
| No. | Structure |
|---|---|
| 138 | 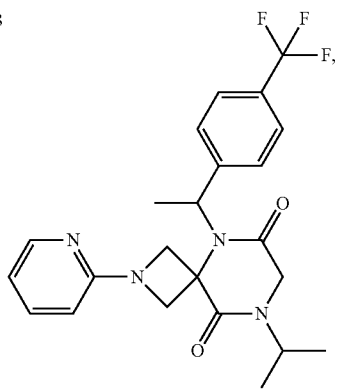 |
| 139 | 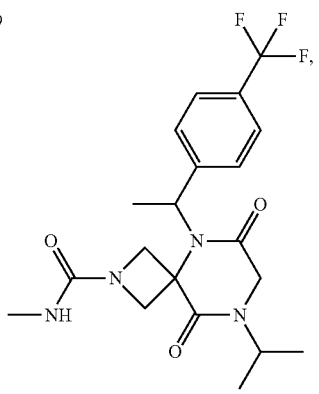 |
| 140 | 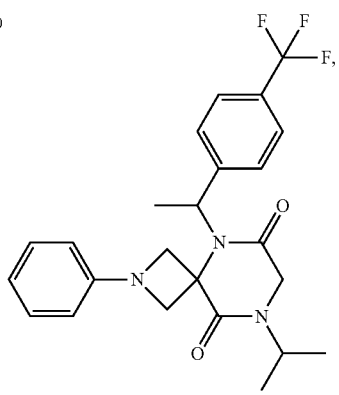 |
| 141 | 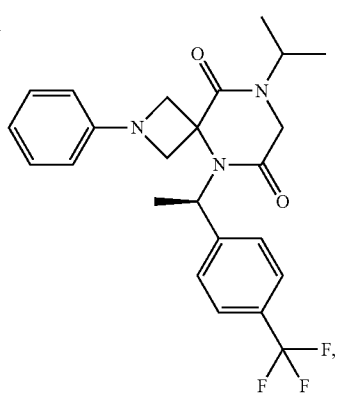 [SMILES: CC(C)N1CC(=O)N([C@H](C)c2ccc(C(F)(F)F)cc2)C2(CN(c3ccccc3)C2)C1=O] |

-continued
| No. | Structure |
|---|---|
| 142 | 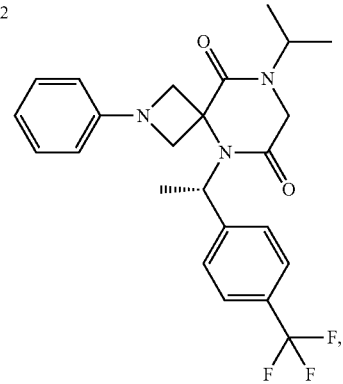 |
| 143 | 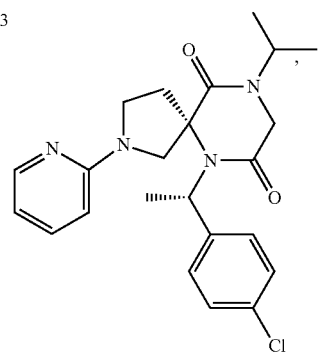 |
| 144 | 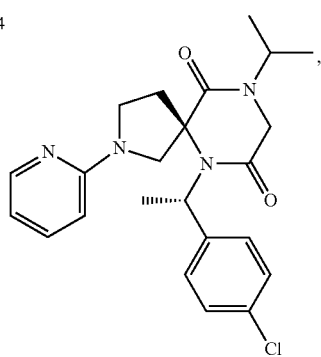 |
| 145 | 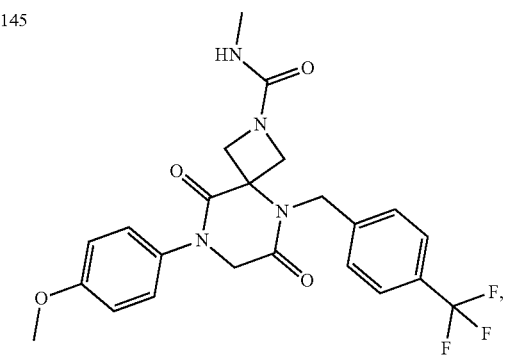 |

| No. | Structure |
|---|---|
| 146 | 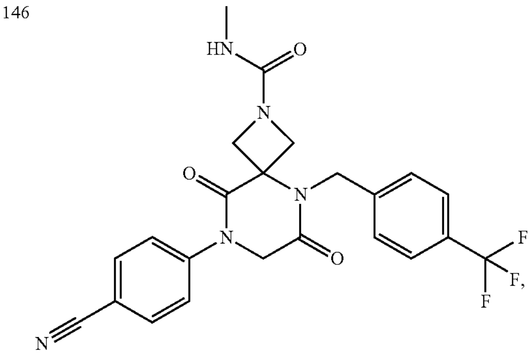 |
| 147 | 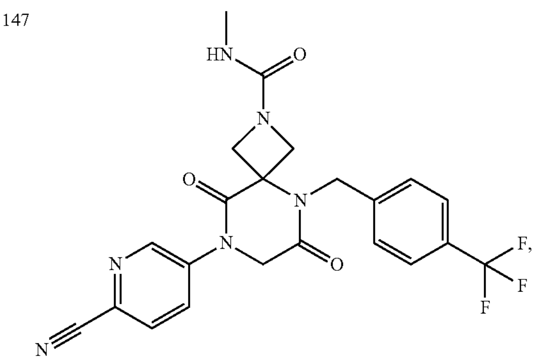 |
| 148 | 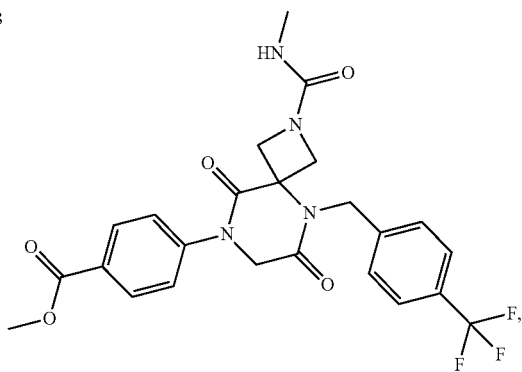 |
| 149 | 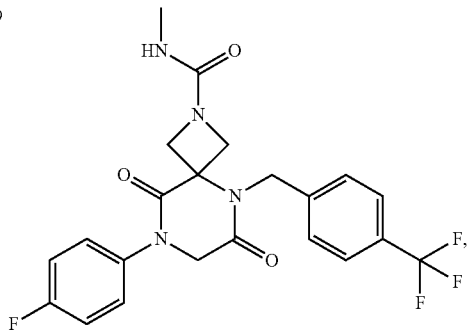 |

| No. | Structure |
|---|---|
| 150 | 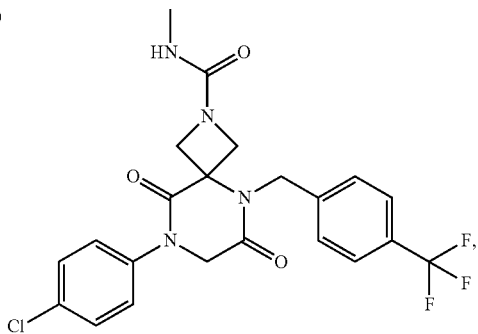 |
| 151 | 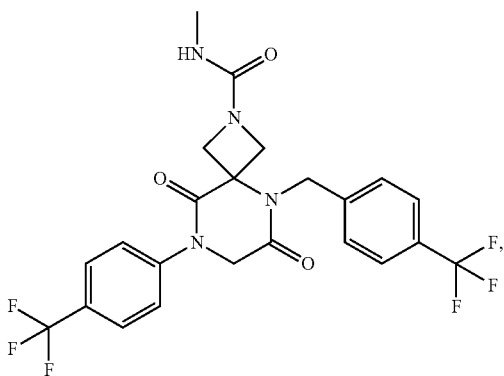 [SMILES: CNC(=O)N1CC2(C1)C(=O)N(c1ccc(C(F)(F)F)cc1)CC(=O)N2Cc1ccc(C(F)(F)F)cc1] |
| 152 | 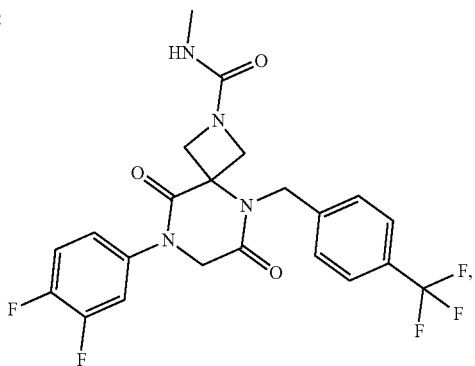 |
| 153 | 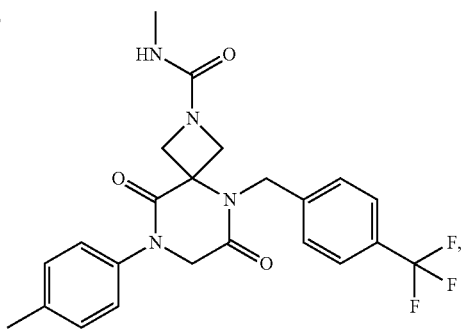 [SMILES: CNC(=O)N1CC2(C1)C(=O)N(c1ccc(C)cc1)CC(=O)N2Cc1ccc(C(F)(F)F)cc1] |

US 11,414,424 B2
913                                914
-continued
| No. | Structure |
|-----|-----------|
| 154 | 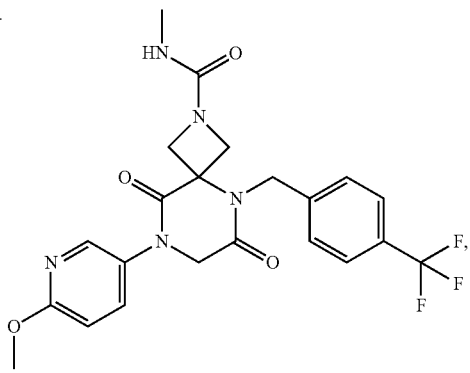 |
| 155 | 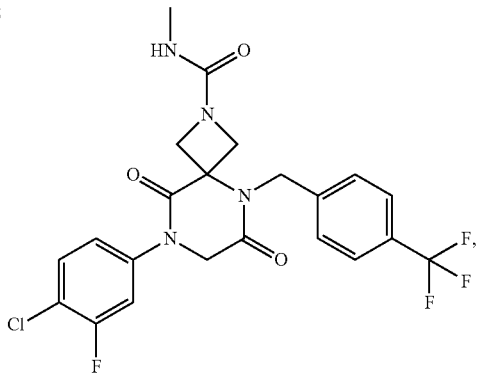 [SMILES: CNC(=O)N1CC2(C1)C(=O)N(c1ccc(Cl)c(F)c1)CC(=O)N2Cc1ccc(C(F)(F)F)cc1] |
| 156 | 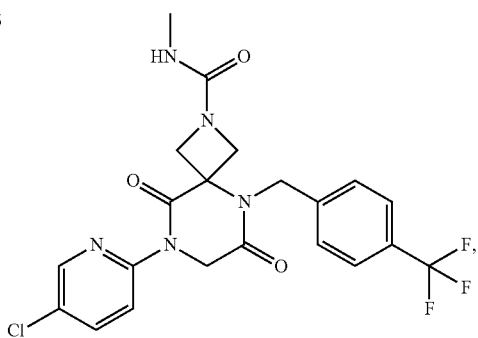 |
| 157 | 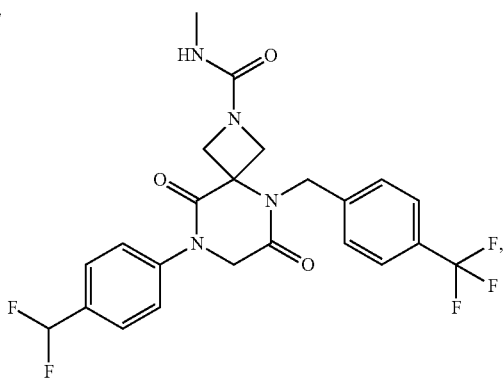 |

-continued
| No. | Structure |
|---|---|
| 158 | 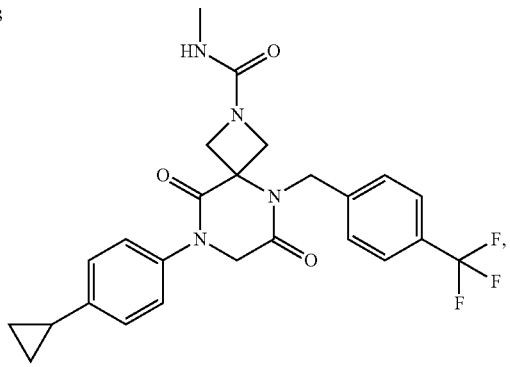 |
| 159 | 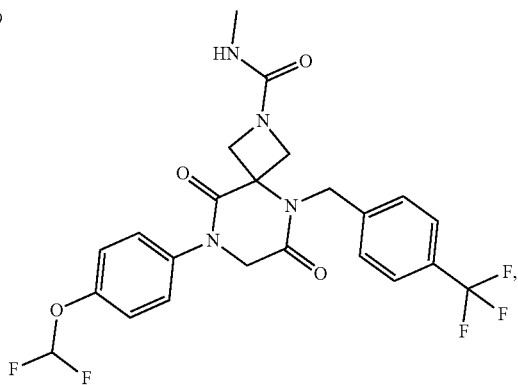 |
| 160 | 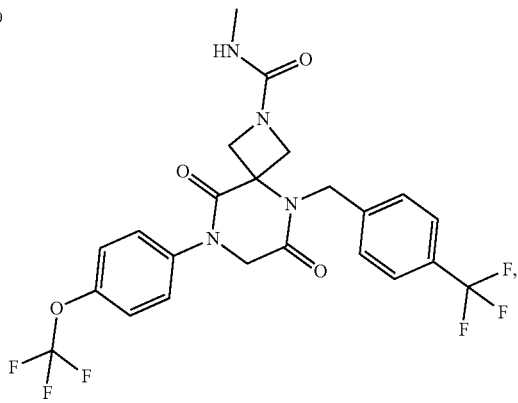 |
| 161 | 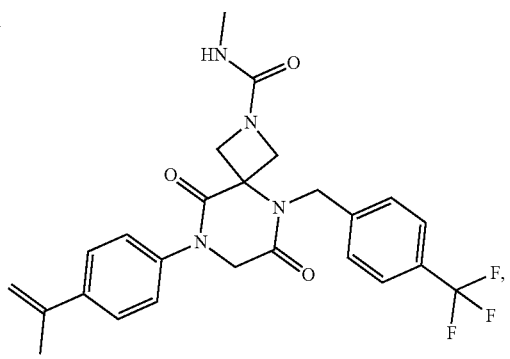 [SMILES: C=C(C)c1ccc(N2CC(=O)N(Cc3ccc(C(F)(F)F)cc3)C3(CN(C(=O)NC)C3)C2=O)cc1] |

| No. | Structure |
|---|---|
| 162 | 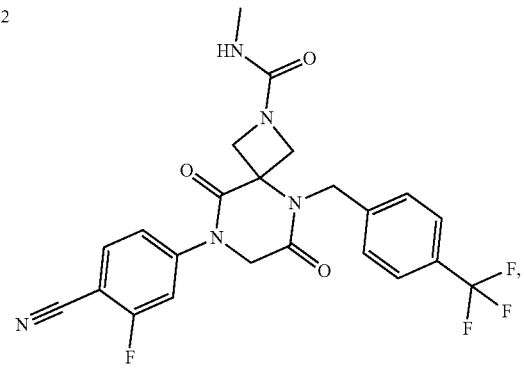 |
| 163 | 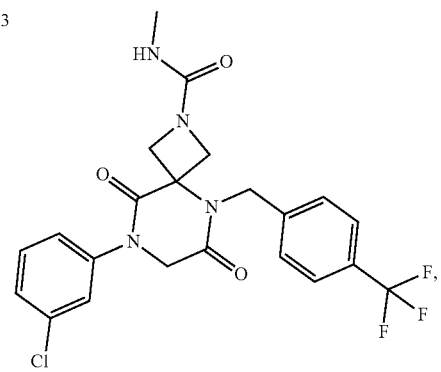 |
| 164 | 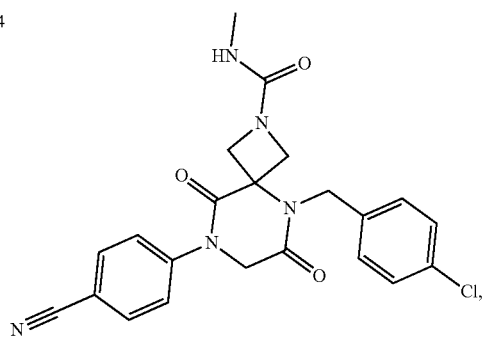 |
| 165 | 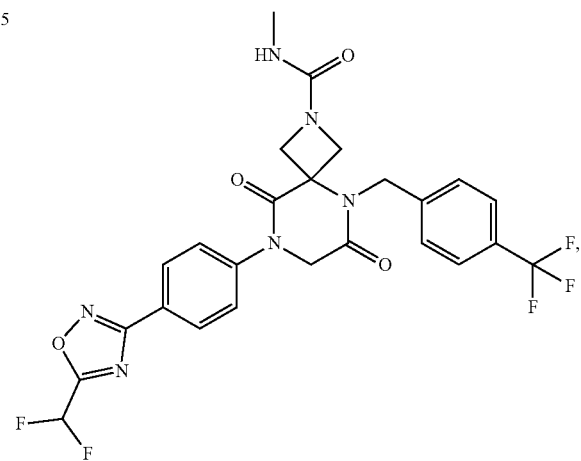 |

-continued
| No. | Structure |
|---|---|
| 166 | 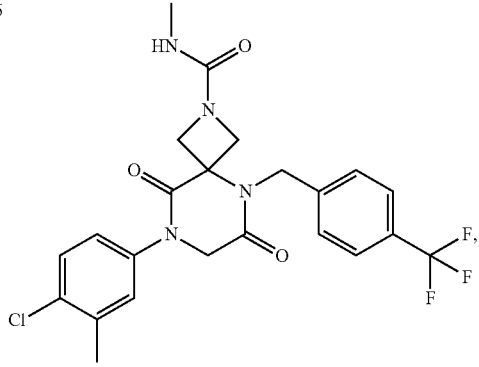 |
| 167 | 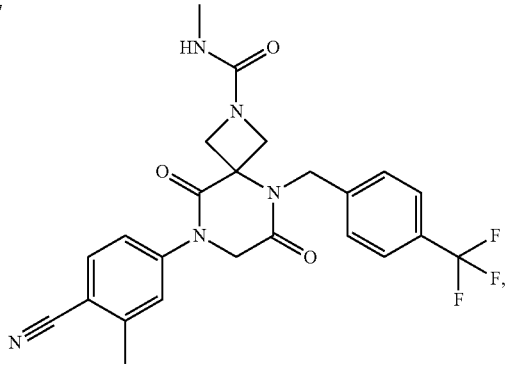 |
| 168 | 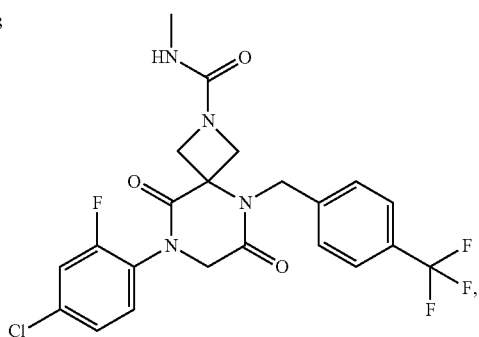 |
| 169 | 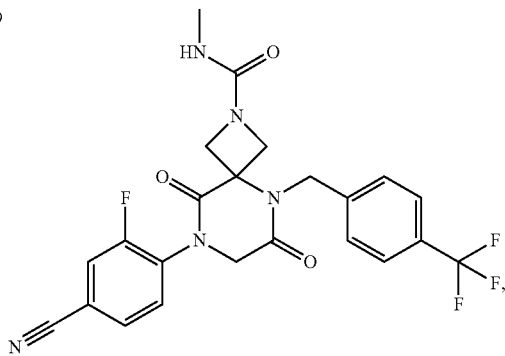 |

921
-continued
| No. | Structure |
|---|---|
| 170 | 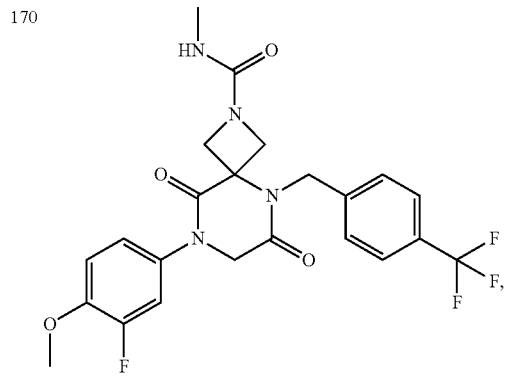 |
| 171 | 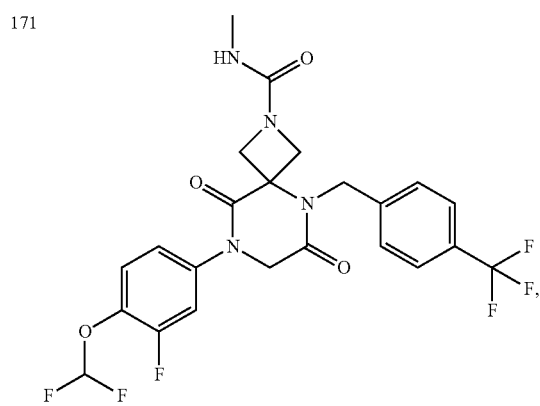 |
| 172 | 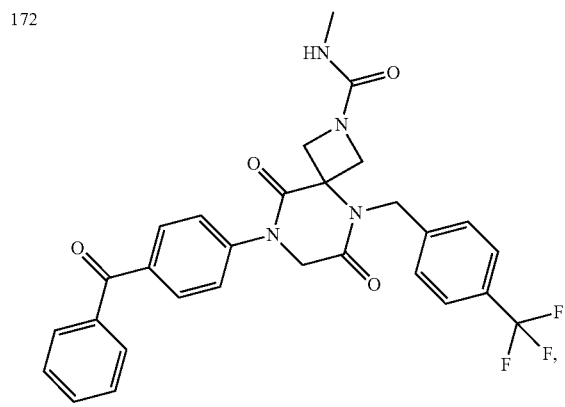 |
| 173 | 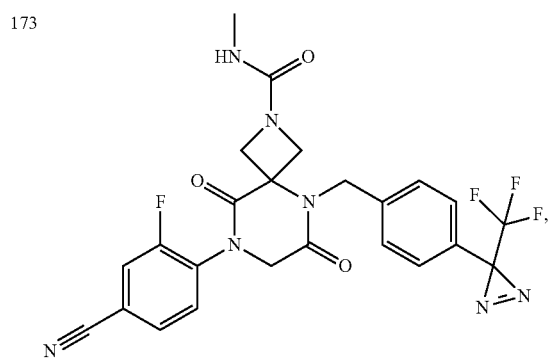 |
922

| No. | Structure |
|---|---|
| 174 | 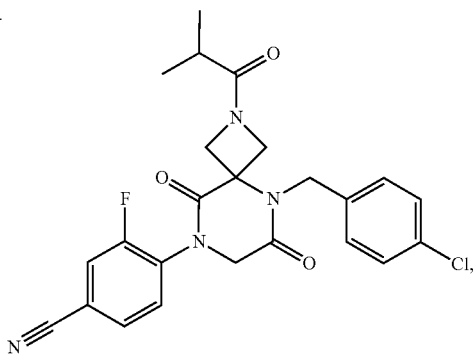 |
| 175 | 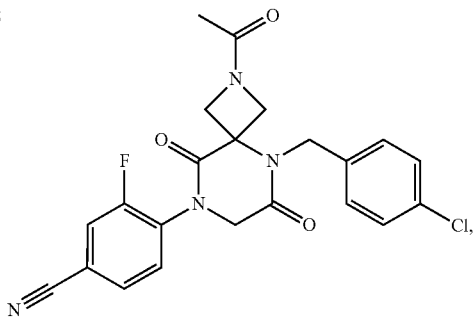 [SMILES: CC(=O)N1CC2(C1)C(=O)N(c1ccc(C#N)cc1F)CC(=O)N2Cc1ccc(Cl)cc1] |
| 176 | 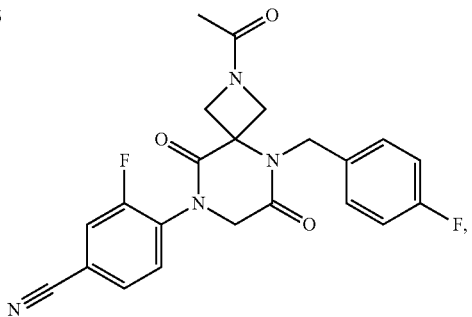 |
| 177 | 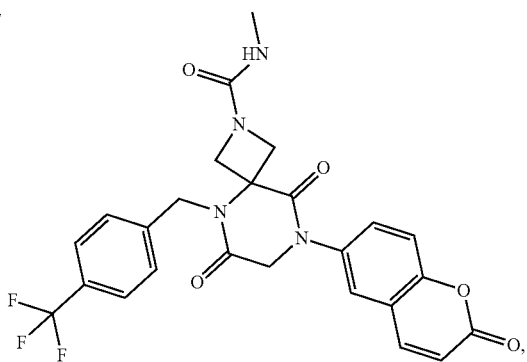 |

| No. | Structure |
|---|---|
| 178 | 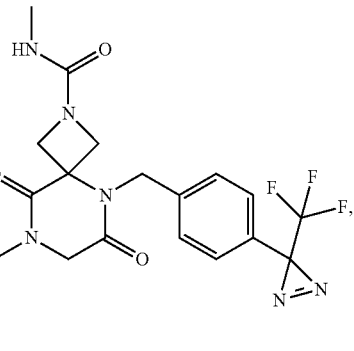 |
| 179 | 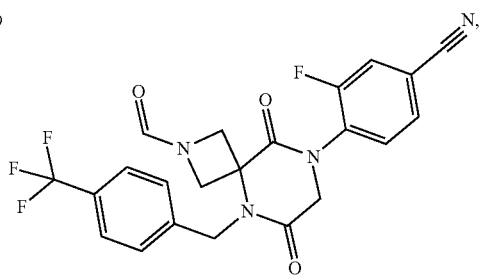 |
| 180 | 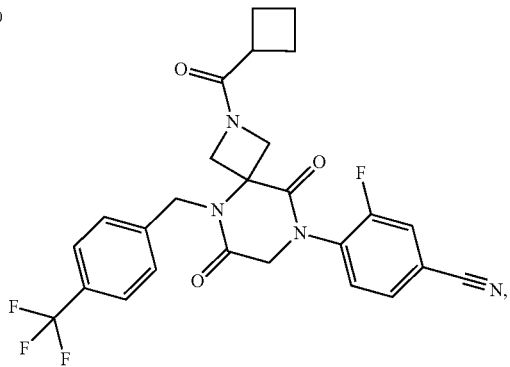 |
| 181 | 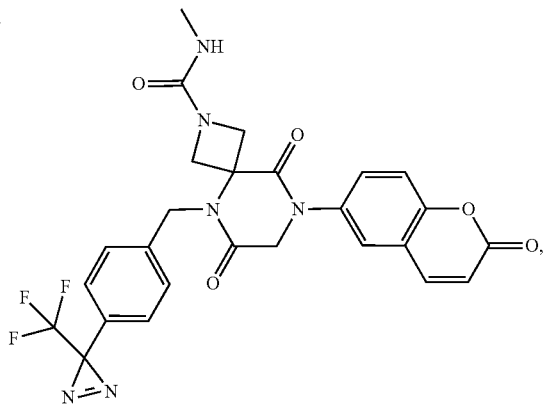 [SMILES: CNC(=O)N1CC2(C1)C(=O)N(c1ccc3oc(=O)ccc3c1)CC(=O)N2Cc1ccc(C2(C(F)(F)F)N=N2)cc1] |

| No. | Structure |
|---|---|
| 182 | 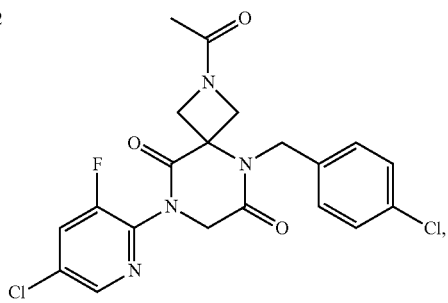 |
| 183 | 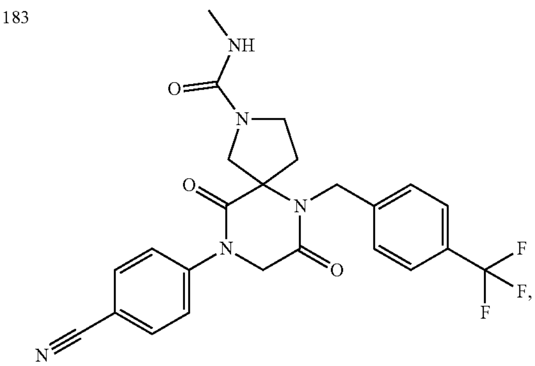 |
| 184 | 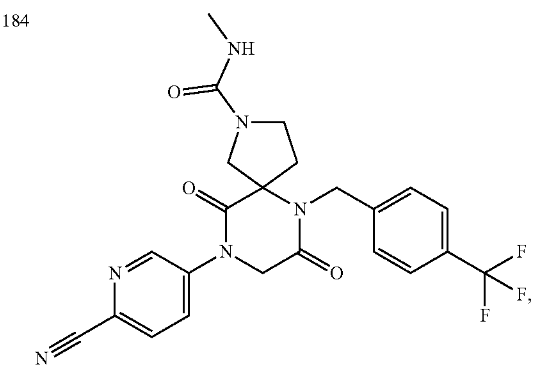 |
| 185 | 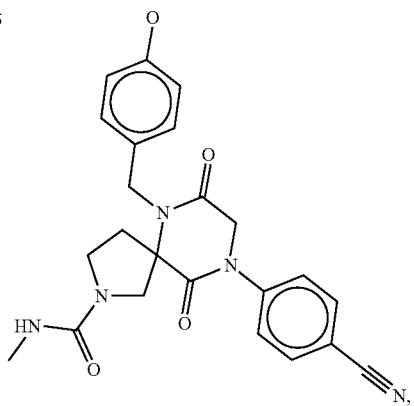 |

| No. | Structure |
|---|---|
| 186 | 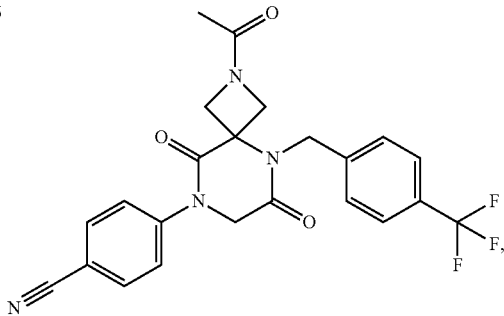 |
| 187 | 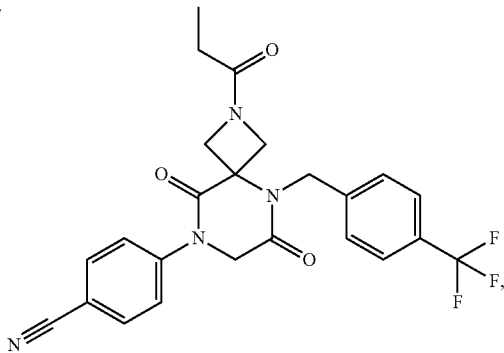 |
| 188 | 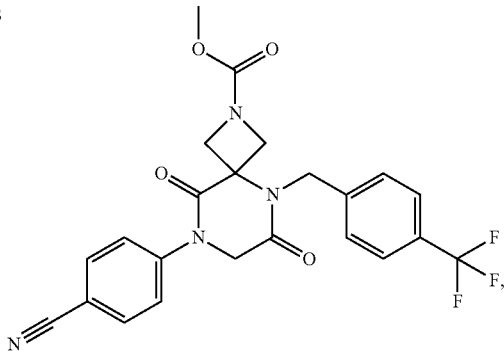 |
| 189 | 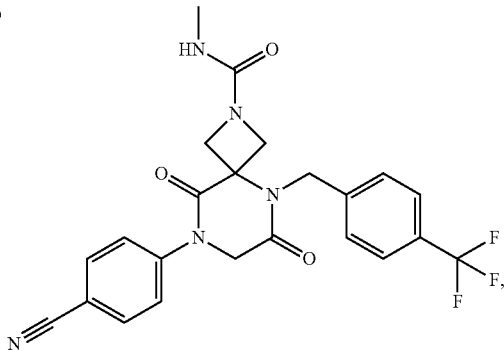 |

| No. | Structure |
|-----|-----------|
| 190 | 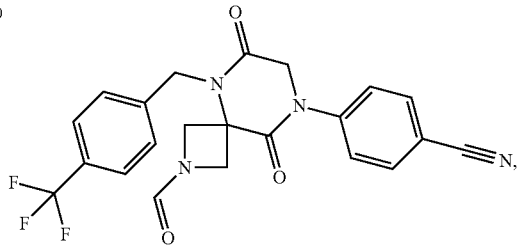 |
| 191 | 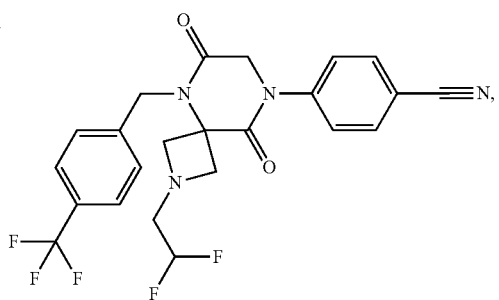 |
| 192 | 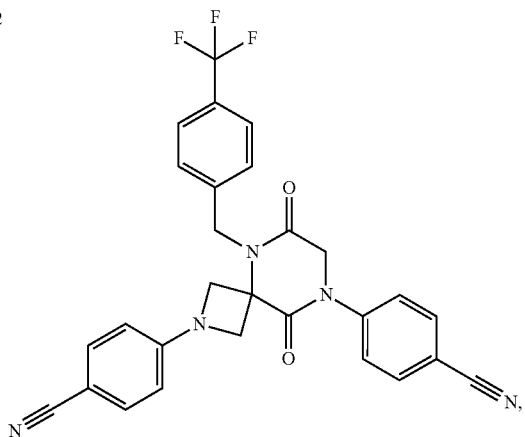 |
| 193 | 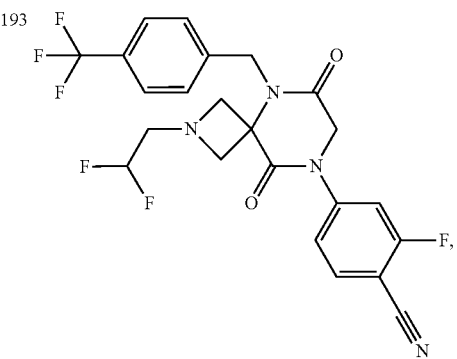 |

| No. | Structure |
|---|---|
| 194 | 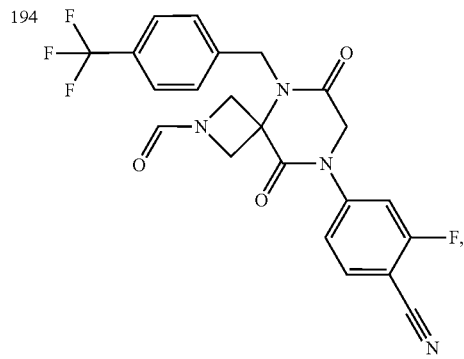 |
| 195 | 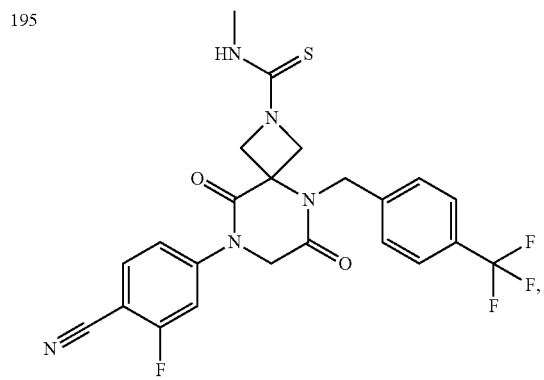 |
| 196 | 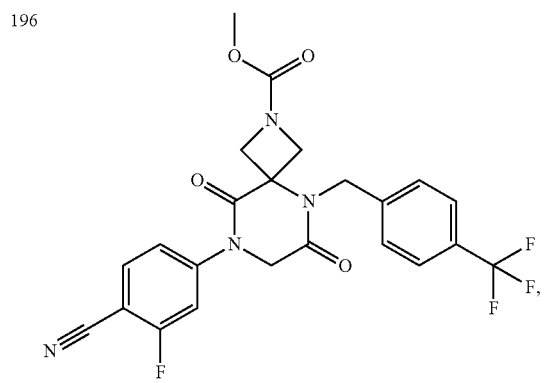 |
| 197 | 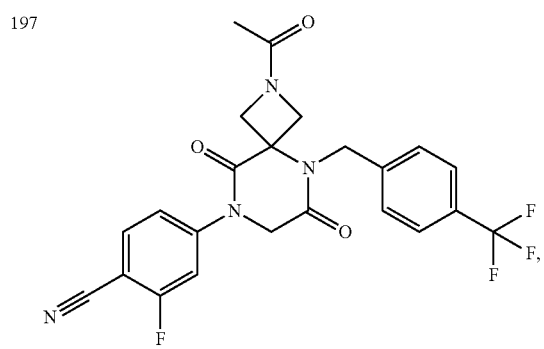 |

-continued
| No. | Structure |
|-----|-----------|
| 198 | 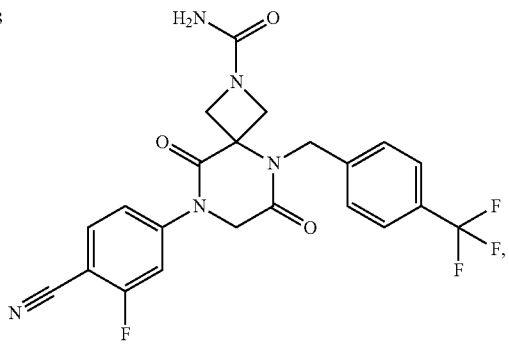 |
| 199 | 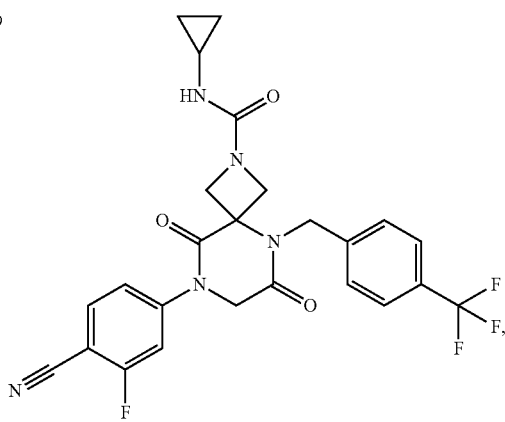 |
| 200 | 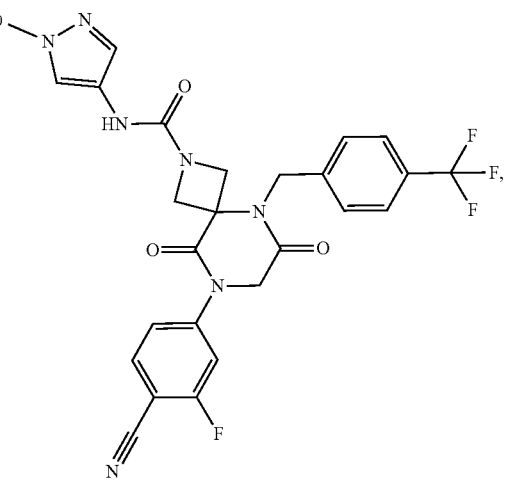 |
| 201 | 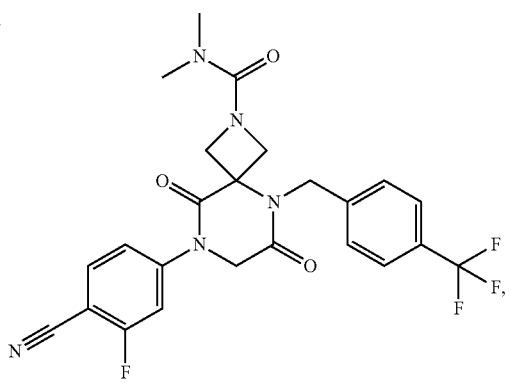 [SMILES: CN(C)C(=O)N1CC2(C1)C(=O)N(c1ccc(C#N)c(F)c1)CC(=O)N2Cc1ccc(C(F)(F)F)cc1] |

| No. | Structure |
|---|---|
| 202 | 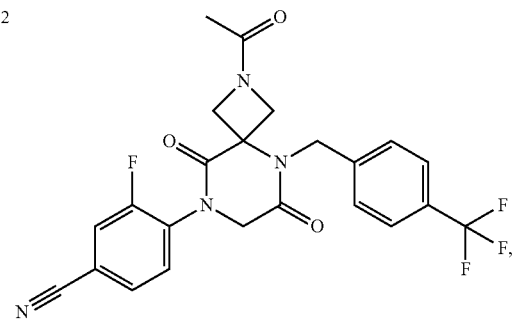 |
| 203 | 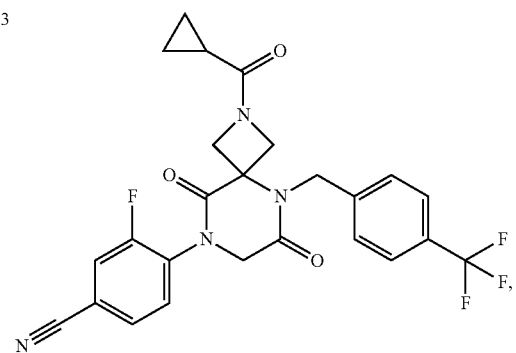 |
| 204 | 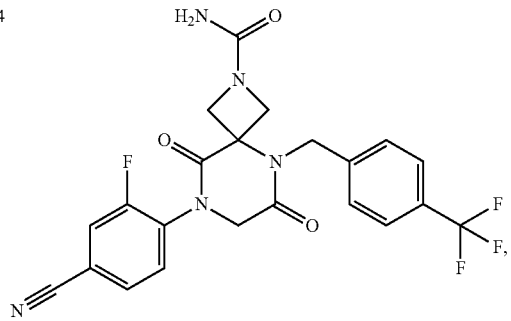 |
| 205 | 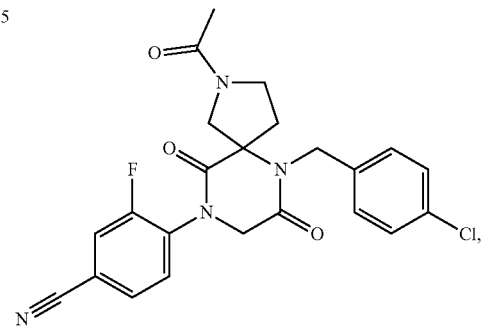 |

-continued
| No. | Structure |
|---|---|
| 206 | 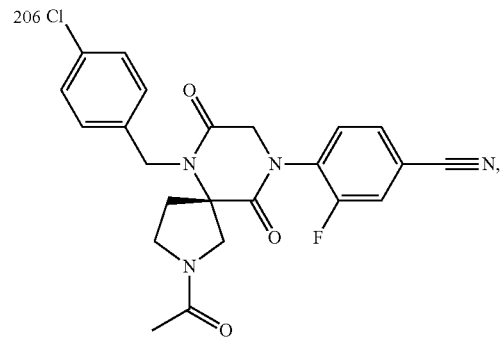 |
| 207 | 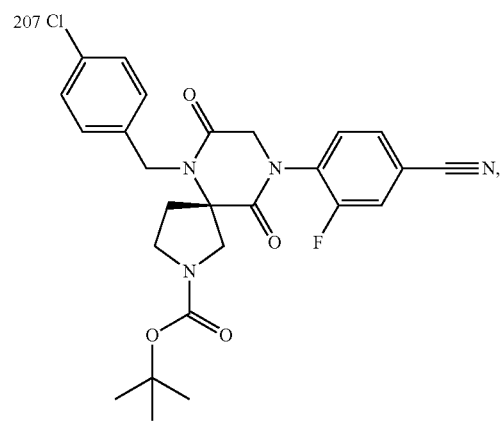 |
| 208 | 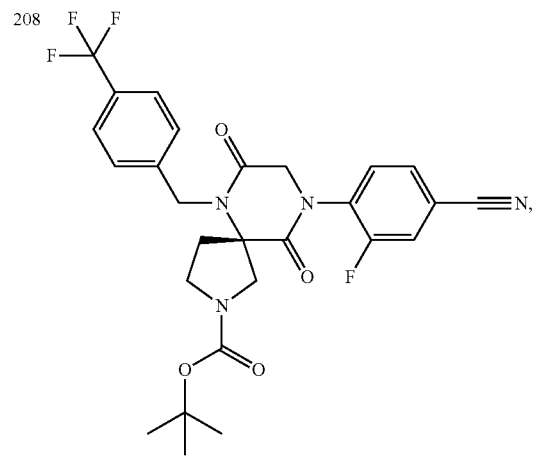 |
| 209 | 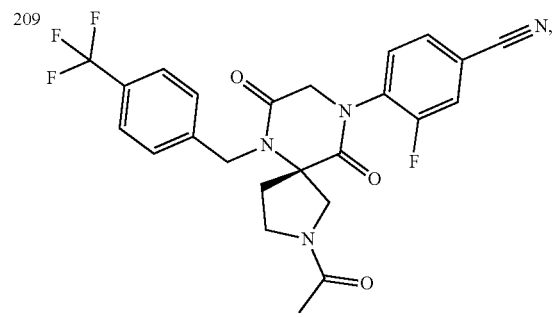 |

| No. | Structure |
|---|---|
| 210 | 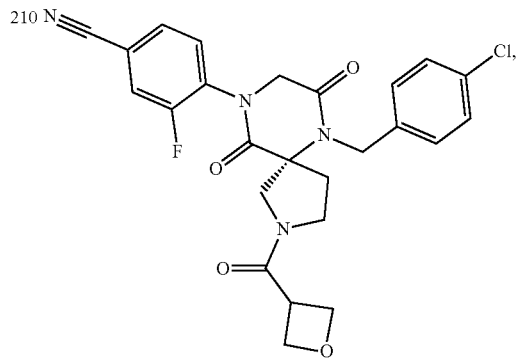 |
| 211 | 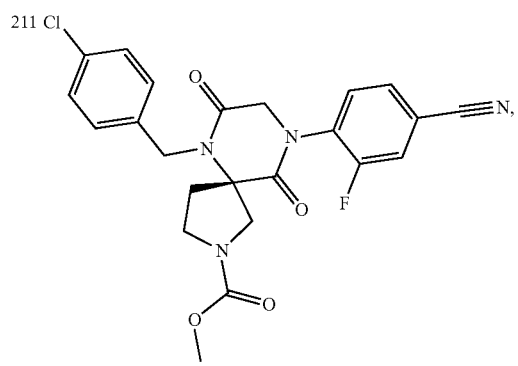 |
| 212 | 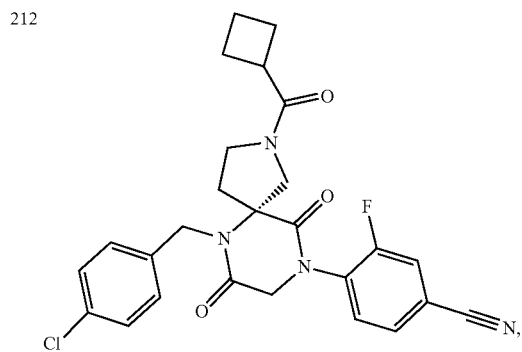 |
| 213 | 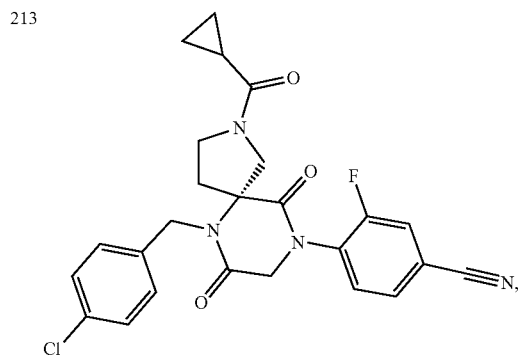 |

| No. | Structure |
|---|---|
| 214 | 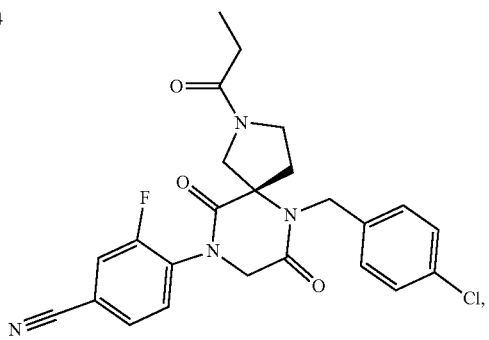 |
| 215 | 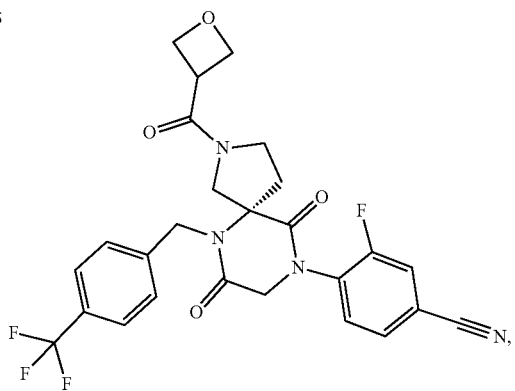 |
| 216 | 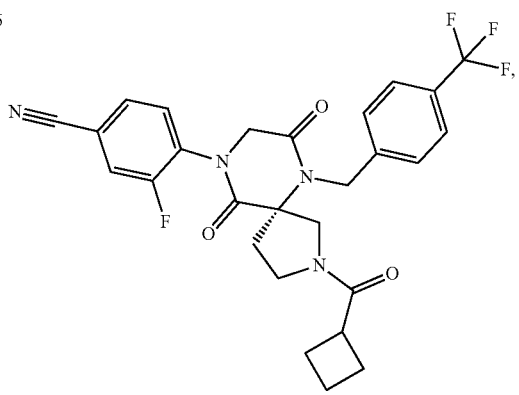 |
| 217 | 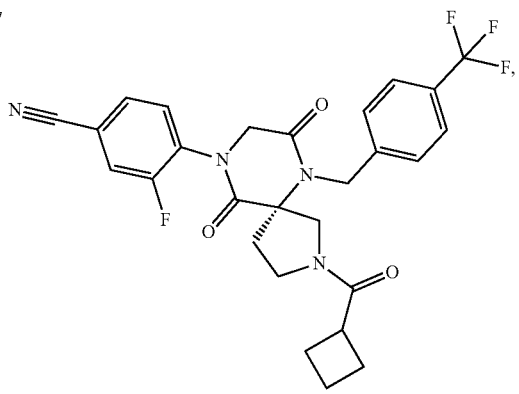 |

| No. | Structure |
|---|---|
| 218 | 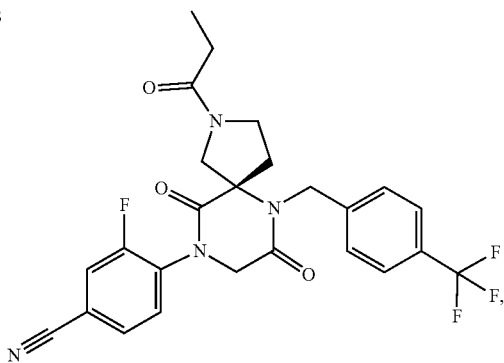 |
| 219 | 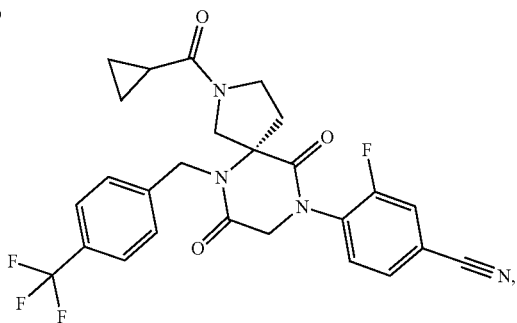 |
| 220 | 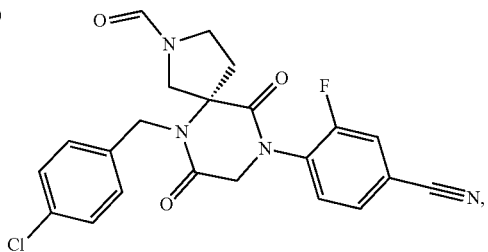 |
| 221 | 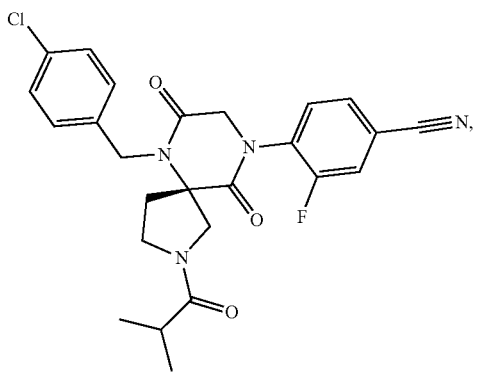 [SMILES: CC(C)C(=O)N1CC[C@]2(C1)C(=O)N(c1ccc(C#N)cc1F)CC(=O)N2Cc1ccc(Cl)cc1] |

| No. | Structure |
|---|---|
| 222 | 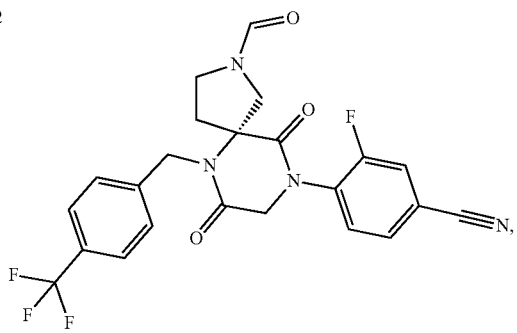 |
| 223 | 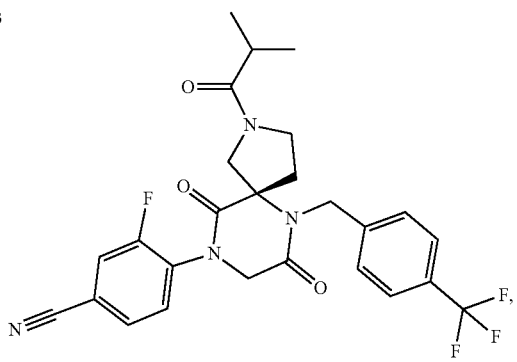 |
| 224 | 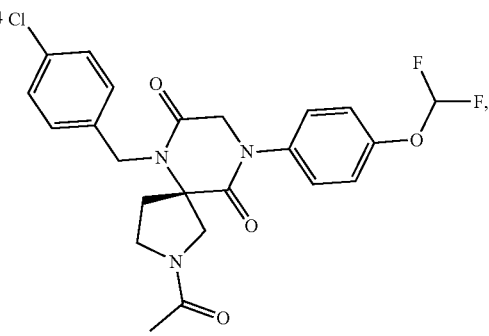 |
| 225 | 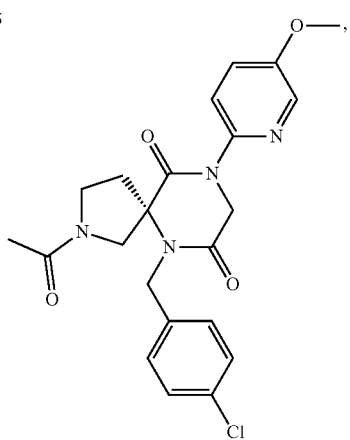 |

| No. | Structure |
|---|---|
| 226 | 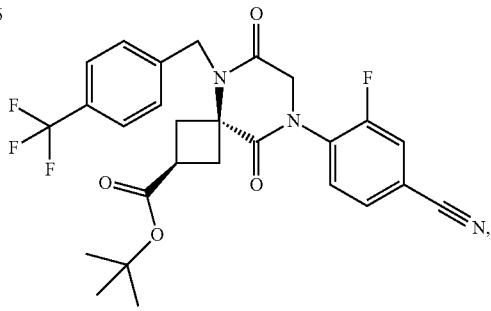 |
| 227 | 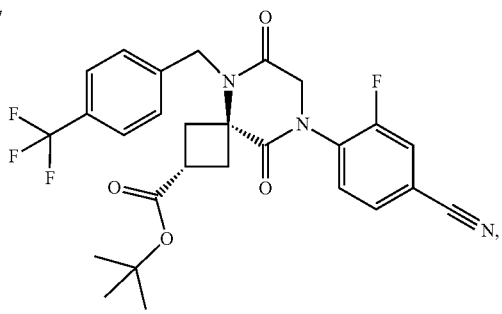 |
| 228 | 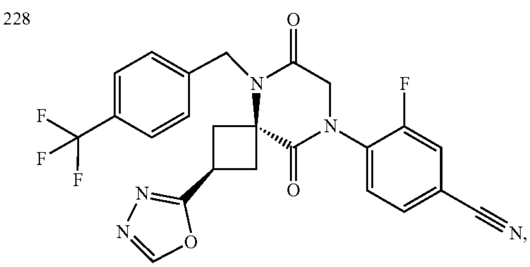 |
| 229 | 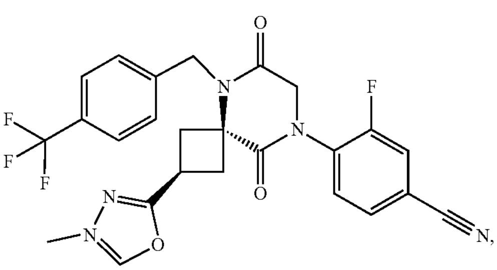 |
| 230 | 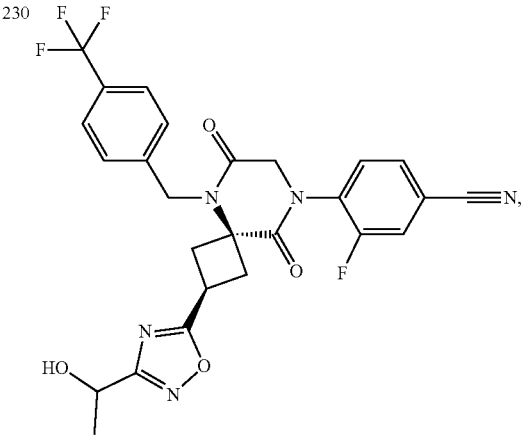 |

| No. | Structure |
|---|---|
| 231 | 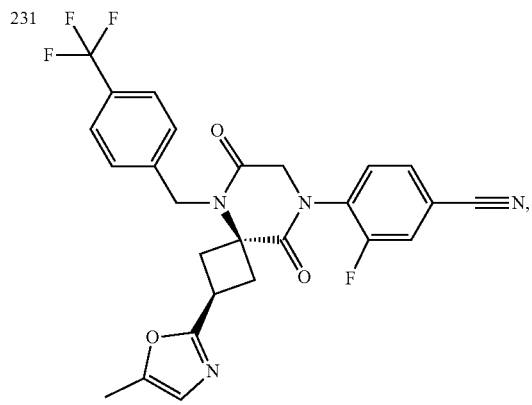 |
| 232 | 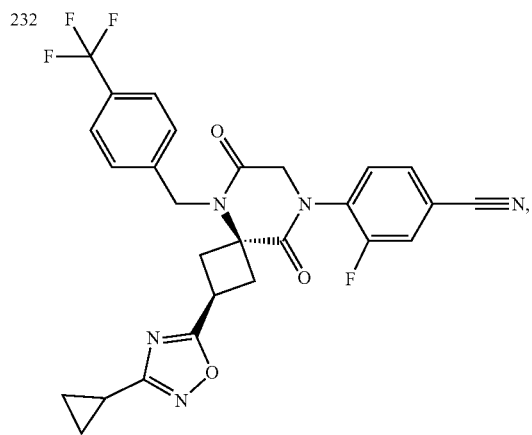 |
| 233 | 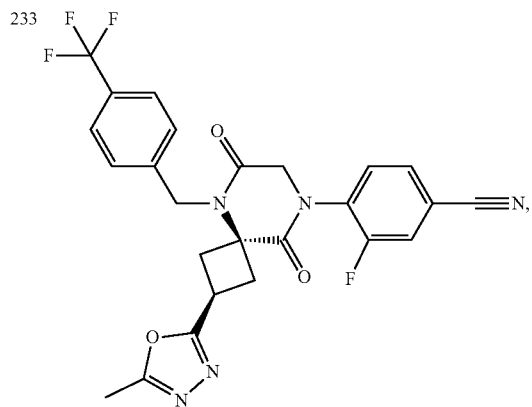 |
| 234 | 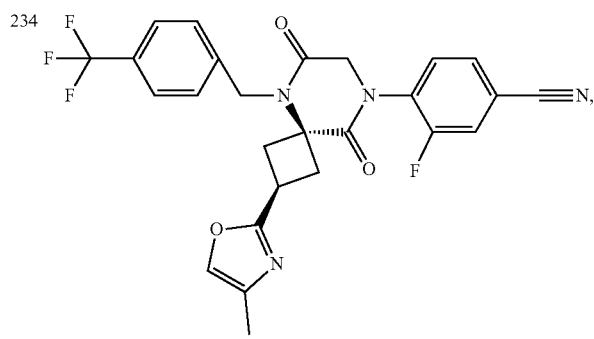 |

| No. | Structure |
|---|---|
| 235 | 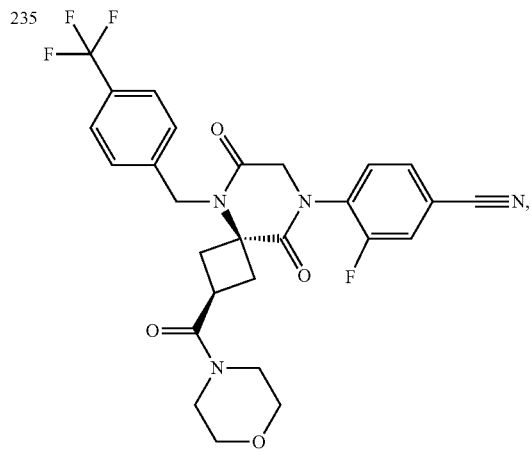 |
| 236 | 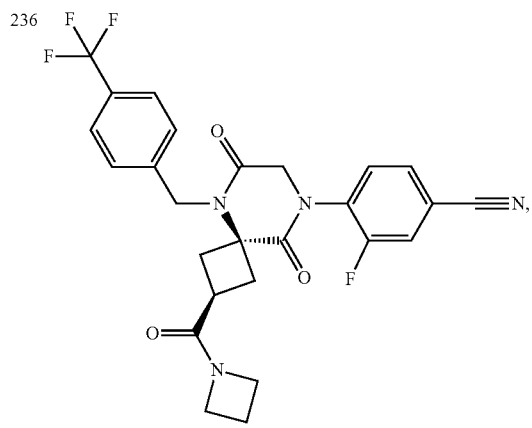 |
| 237 | 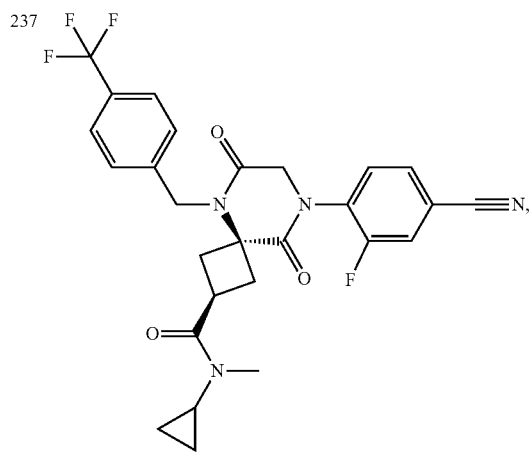 |

| No. | Structure |
|---|---|
| 238 | 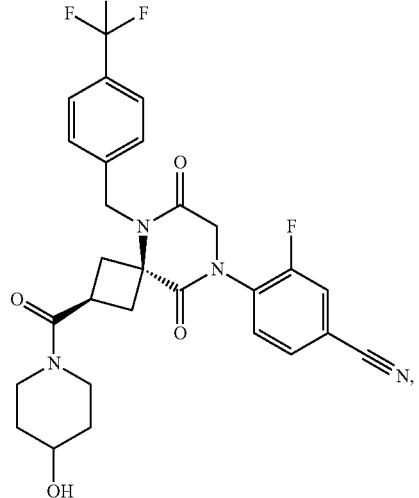 |
| 239 | 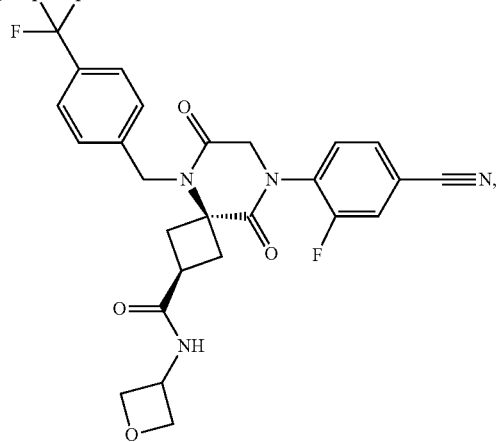 |
| 240 | 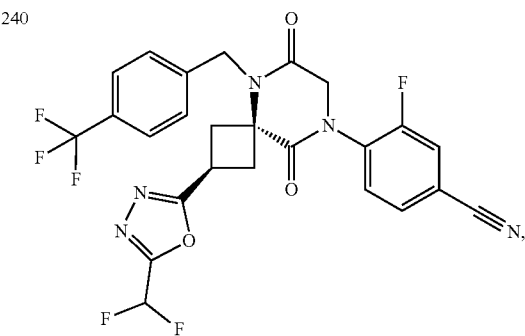 |

| No. | Structure |
|---|---|
| 241 | 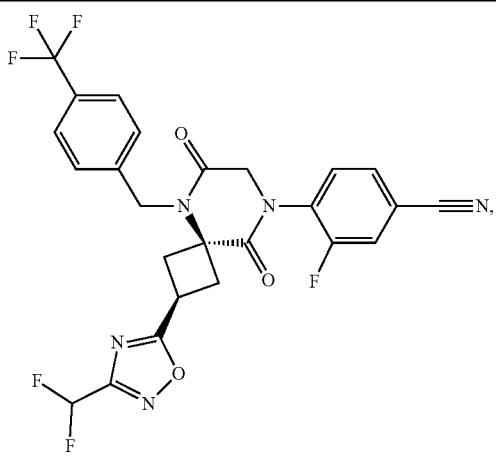 |
| 242 | 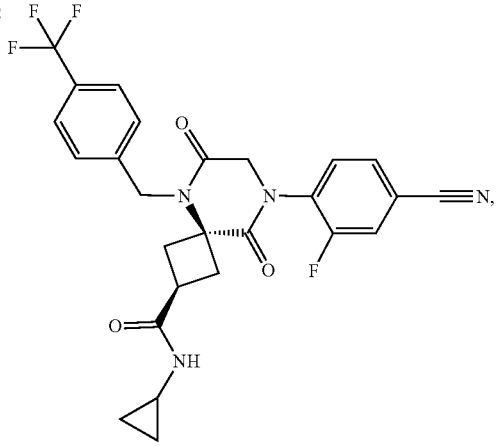 [SMILES: N#Cc1ccc(N2CC(=O)N(Cc3ccc(C(F)(F)F)cc3)[C@]3(C[C@@H](C(=O)NC4CC4)C3)C2=O)c(F)c1] |
| 243 | 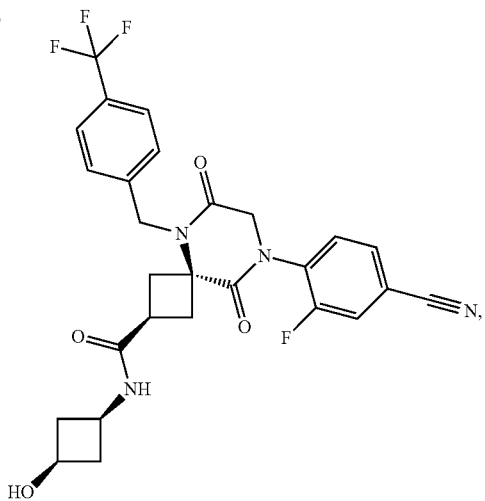 [SMILES: N#Cc1ccc(N2CC(=O)N(Cc3ccc(C(F)(F)F)cc3)[C@]3(C[C@@H](C(=O)N[C@H]4C[C@@H](O)C4)C3)C2=O)c(F)c1] |

| No. | Structure |
|---|---|
| 244 | 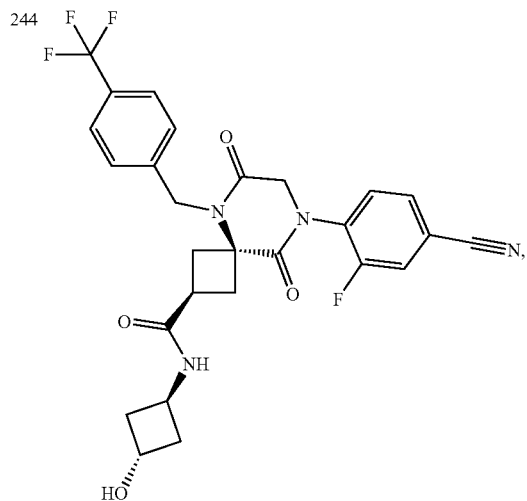 |
| 245 | 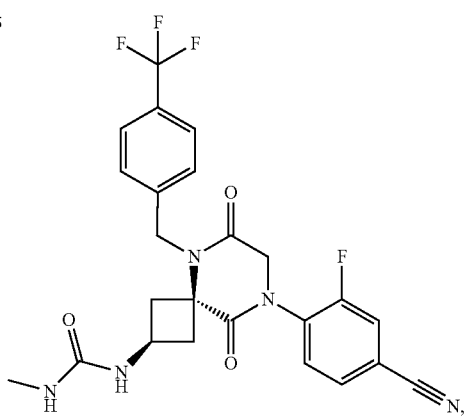 |
| 246 | 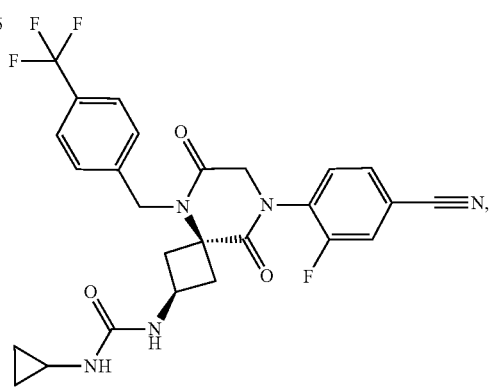 |

| No. | Structure |
|-----|-----------|
| 247 | 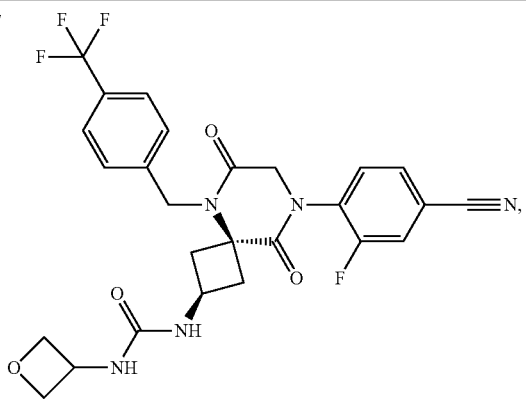 |
| 248 | 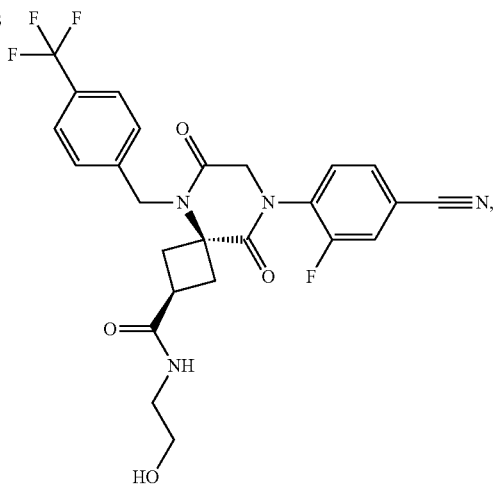 |
| 249 | 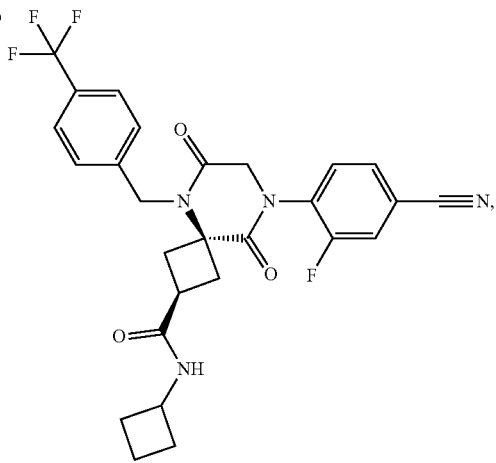 |

-continued
| No. | Structure |
|---|---|
| 250 | 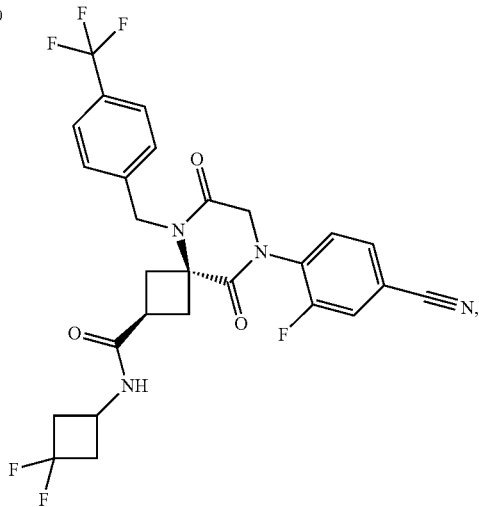 |
| 251 | 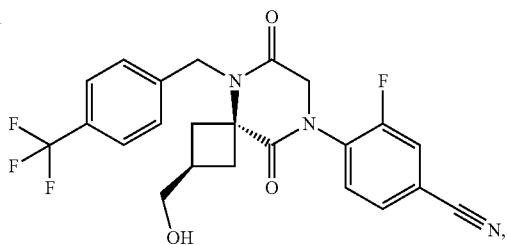 [SMILES: N#Cc1ccc(N2CC(=O)N(Cc3ccc(C(F)(F)F)cc3)[C@]3(C[C@@H](CO)C3)C2=O)c(F)c1] |
| 252 | 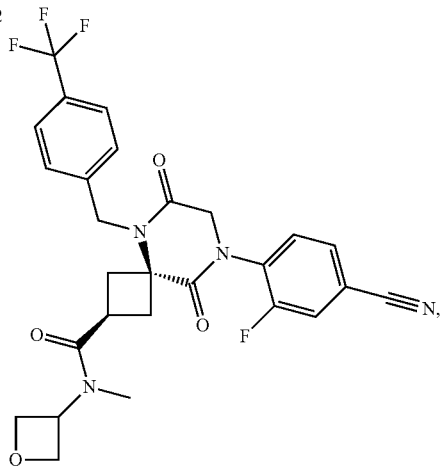 |

| No. | Structure |
|-----|-----------|
| 253 | 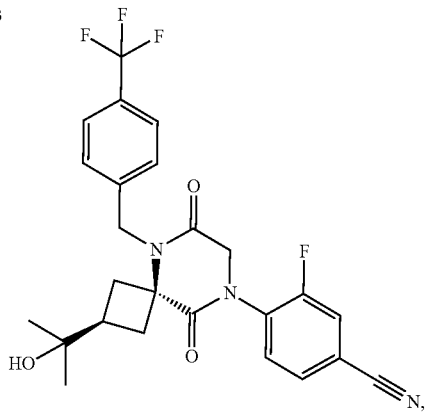 |
| 254 | 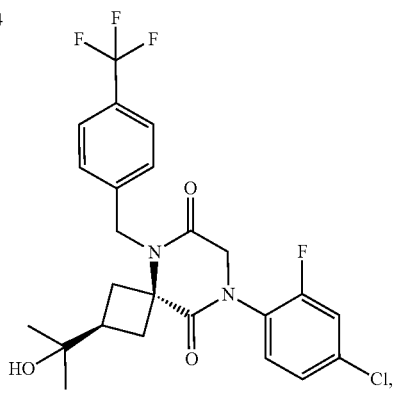 |
| 255 | 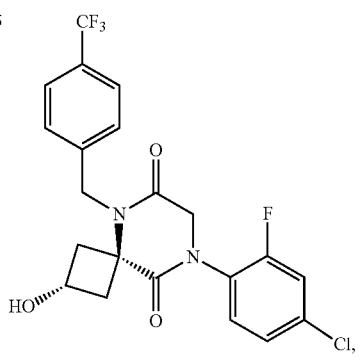 |
| 256 | 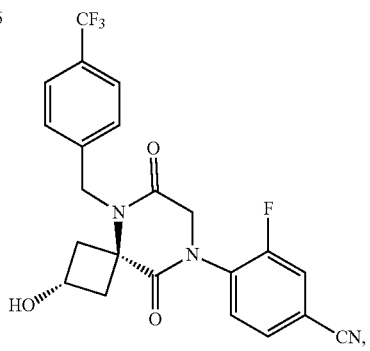 |

| No. | Structure |
|---|---|
| 257 | 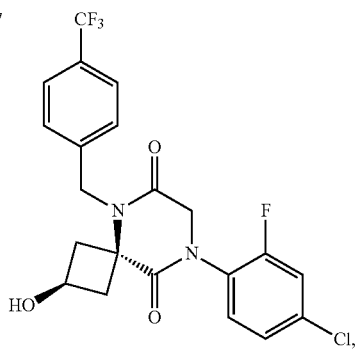 |
| 258 | 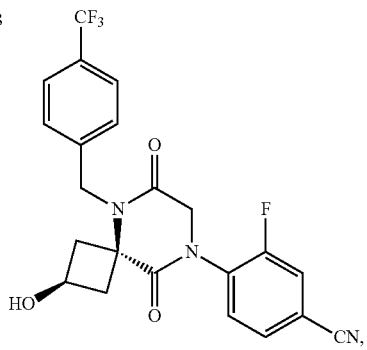 |
| 259 | 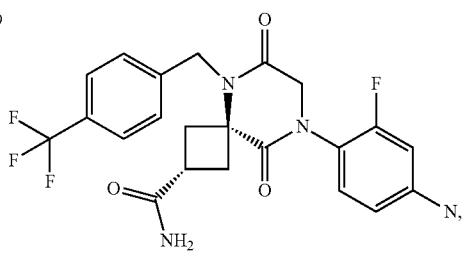 |
| 260 | 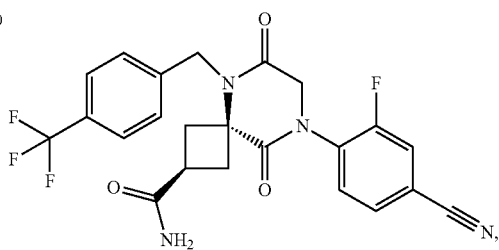 |
| 261 | 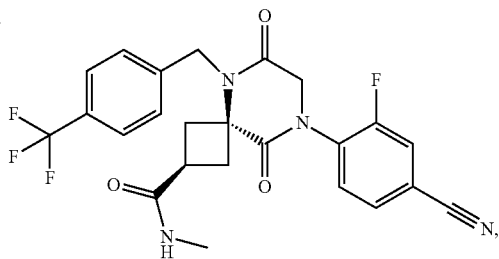 |

| No. | Structure |
|---|---|
| 262 | 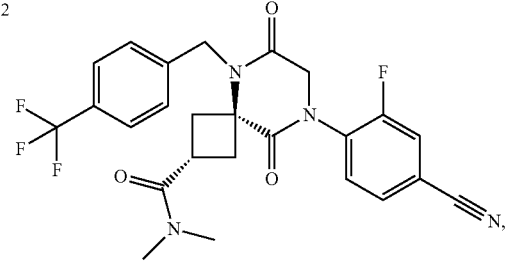 |
| 263 | 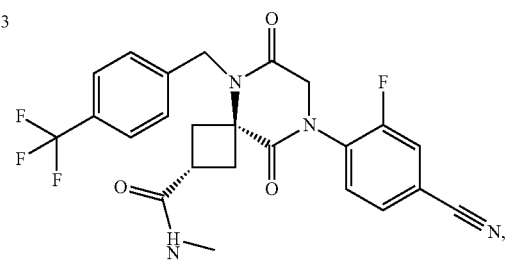 |
| 264 | 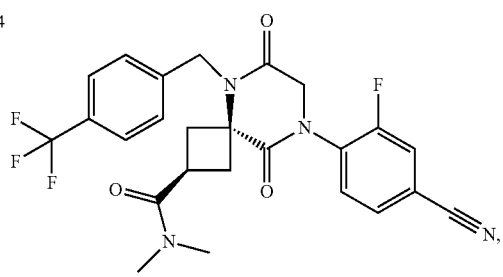 |
| 265 | 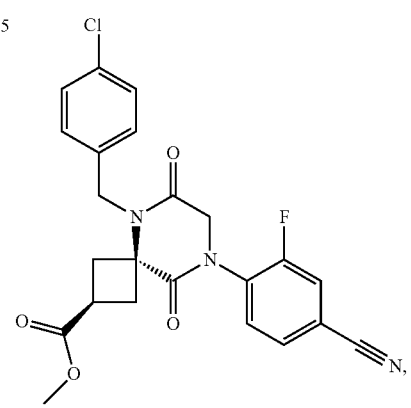 |
| 266 | 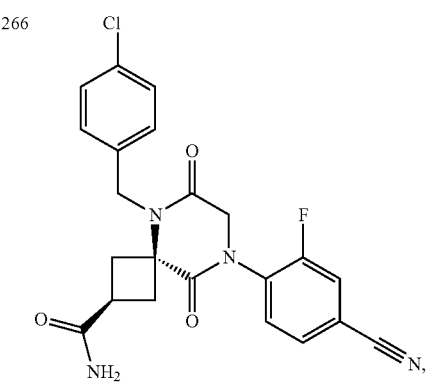 |

US 11,414,424 B2
971
972
-continued
| No. | Structure |
|---|---|
| 267 | 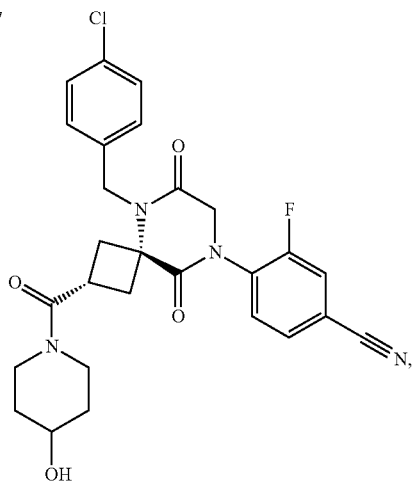 |
| 268 | 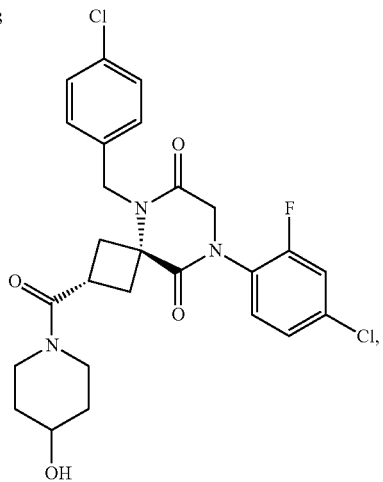 |
| 269 | 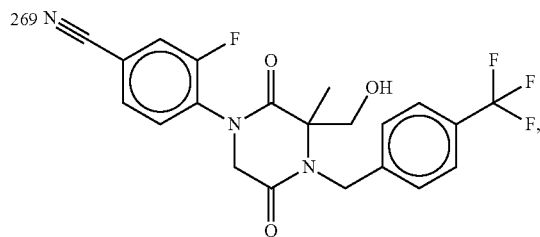 |
| 270 | 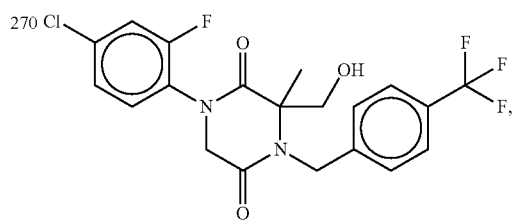 |

| No. | Structure |
|---|---|
| 271 | 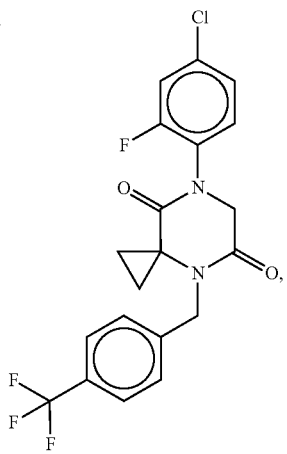 |
| 272 | 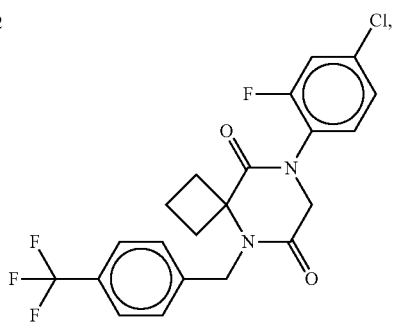 |
| 273 | 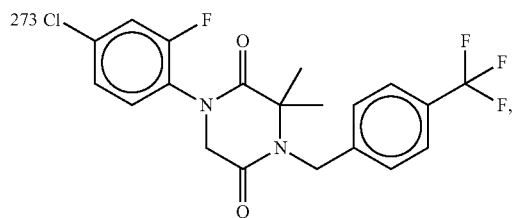 |
| 274 | 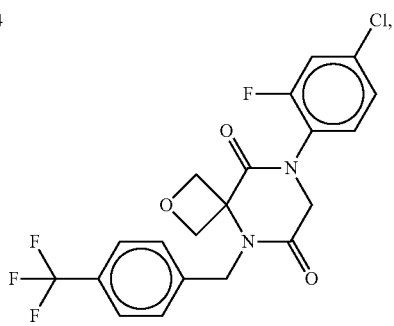 |
| 275 | 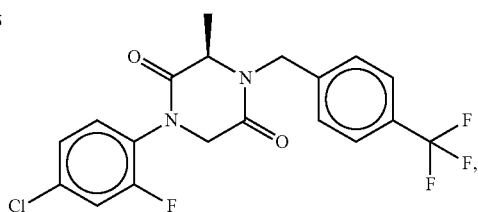 |

| No. | Structure |
|---|---|
| 276 | 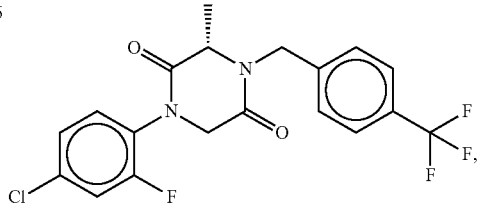 |
| 277 | 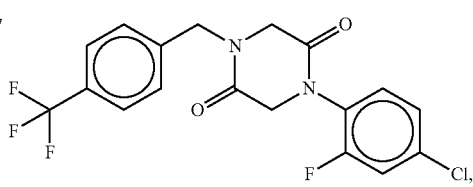 |
| 278 | 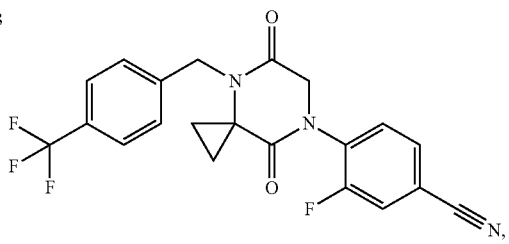 |
| 279 | 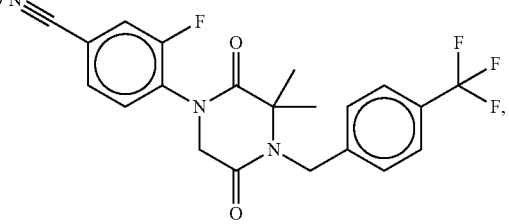 |
| 280 | 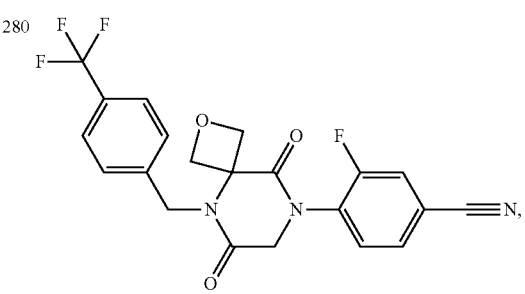 |
| 281 | 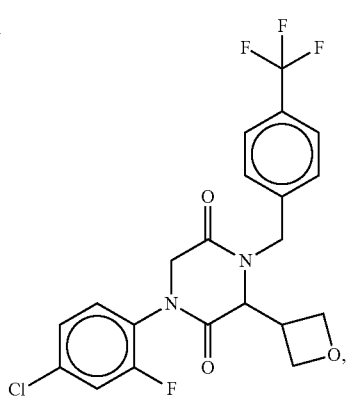 |

| No. | Structure |
|---|---|
| 282 | 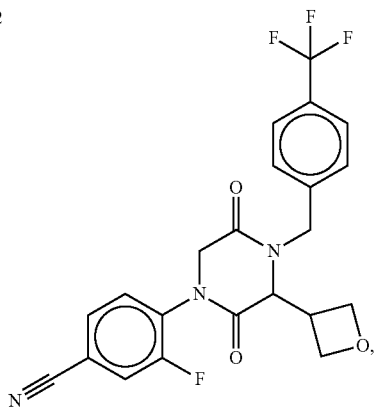 |
| 283 | 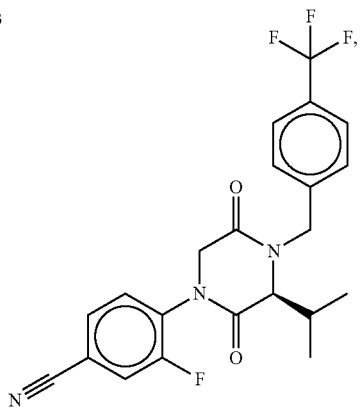 |
| 284 | 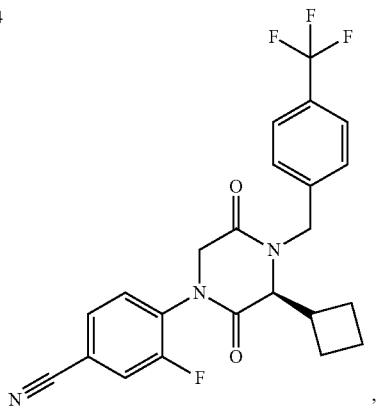 |
| 285 | 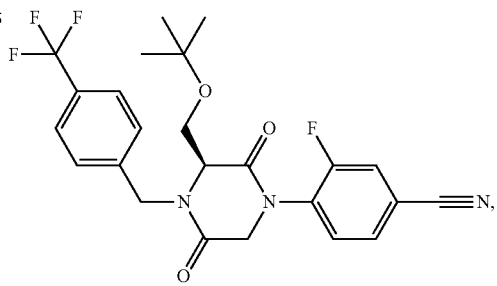 |

-continued
| No. | Structure |
|---|---|
| 286 | 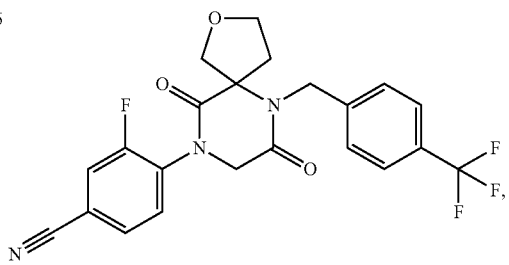 |
| 287 | 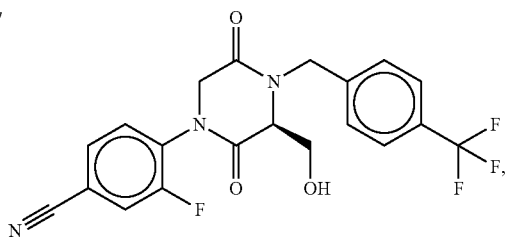 |
| 288 | 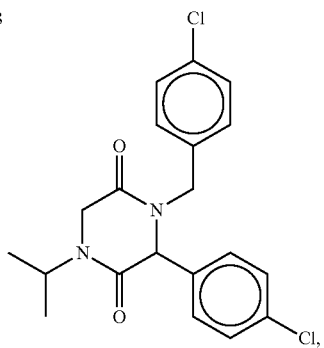 |
| 289 | 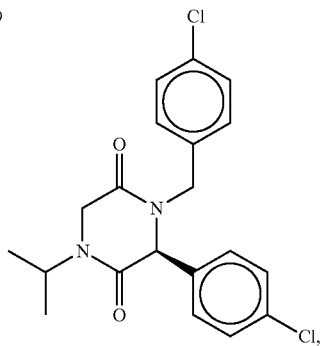 |
| 290 | 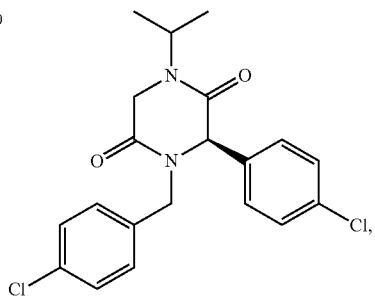 |

-continued
| No. | Structure |
|-----|-----------|
| 291 | 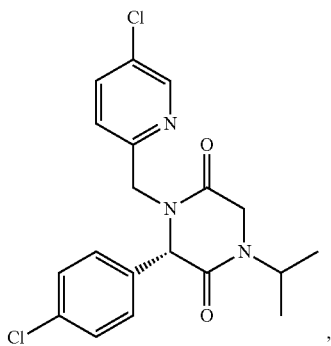 [SMILES: CC(C)N1CC(=O)N(Cc2ccc(Cl)cn2)[C@@H](c2ccc(Cl)cc2)C1=O] |
| 292 | 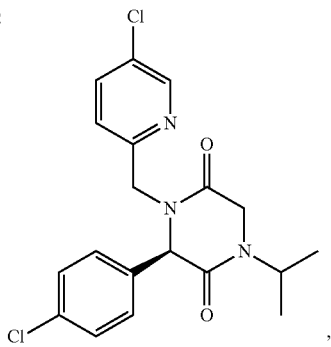 |
| 293 | 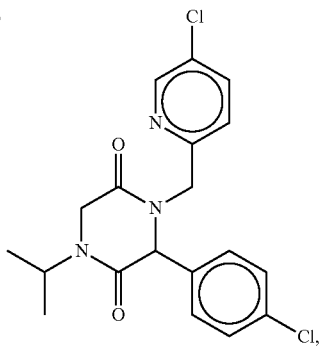 |
| 294 | 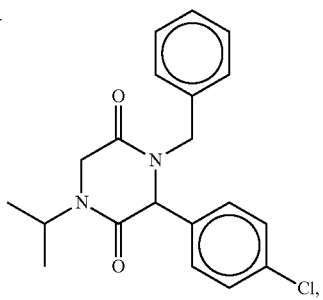 |

| No. | Structure |
|---|---|
| 295 | 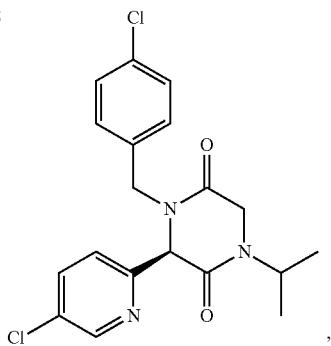 [SMILES: CC(C)N1CC(=O)N(Cc2ccc(Cl)cc2)[C@H](c2ccc(Cl)cn2)C1=O] |
| 296 | 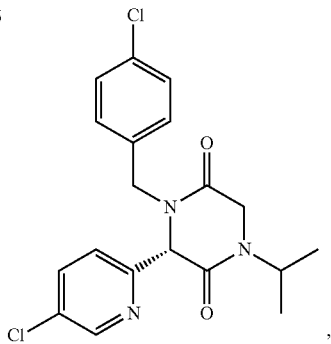 |
| 297 | 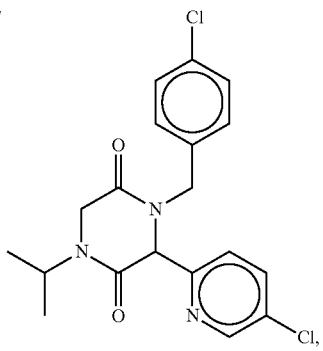 |
| 298 | 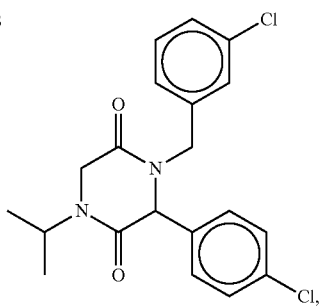 |

| No. | Structure |
|---|---|
| 299 | 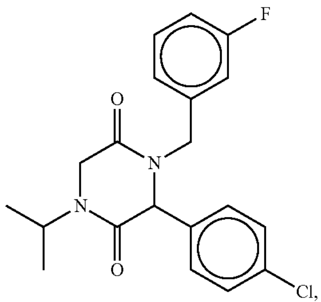 |
| 300 | 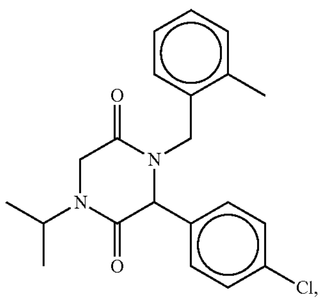 |
| 301 | 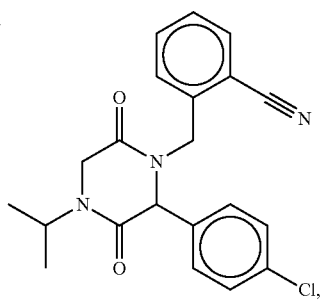 |
| 302 | 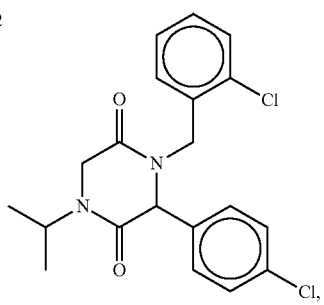 |
| 303 | 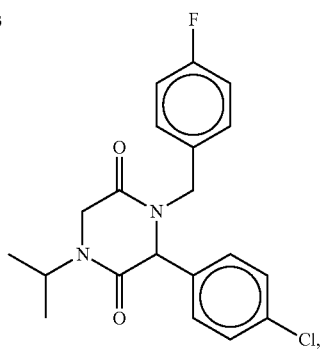 |

| No. | Structure |
|---|---|
| 304 | 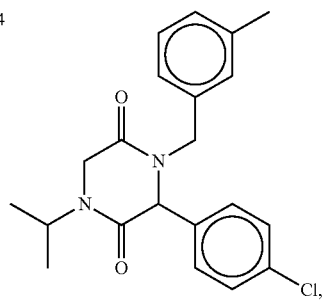 |
| 305 | 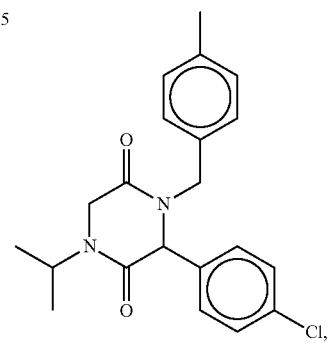 |
| 306 | 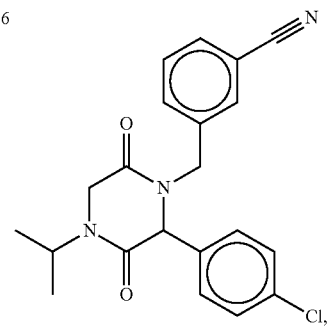 |
| 307 | 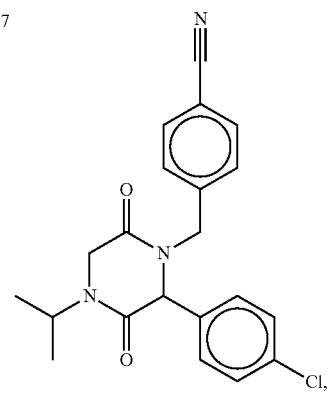 |

| No. | Structure |
|---|---|
| 308 | 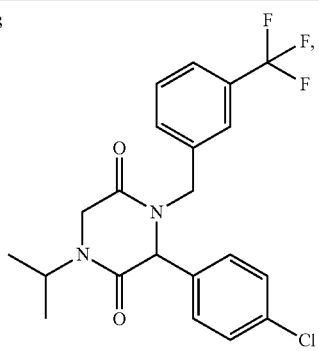 |
| 309 | 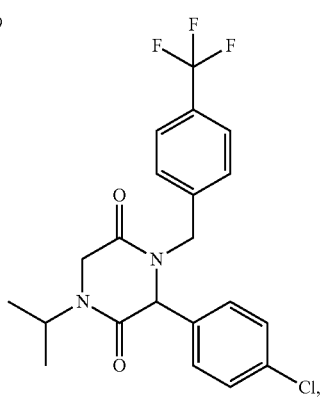 |
| 310 | 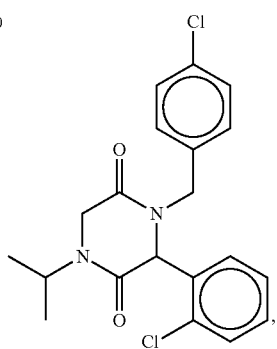 |
| 311 | 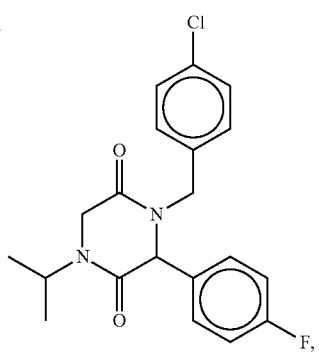 |

| No. | Structure |
|---|---|
| 312 | 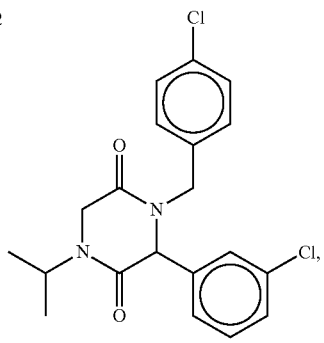 |
| 313 | 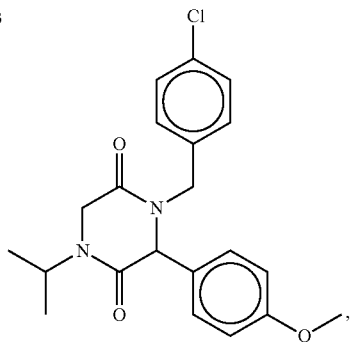 |
| 314 | 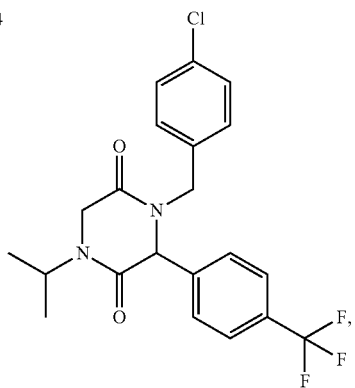 |
| 315 | 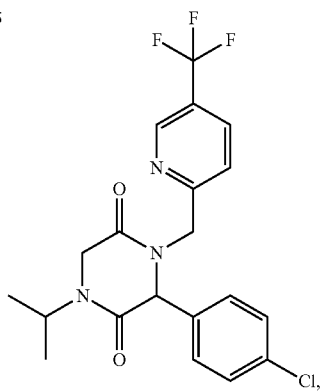 |

| No. | Structure |
|---|---|
| 316 | 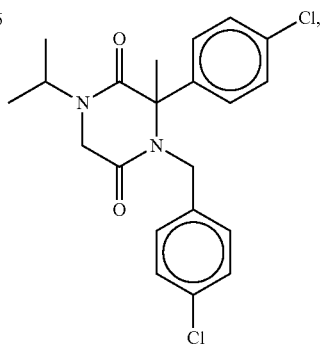 |
| 317 | 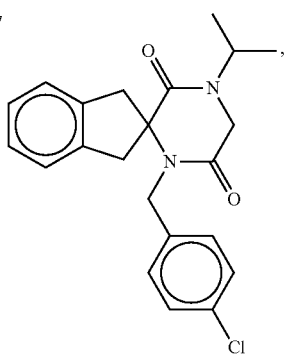 |
| 318 | 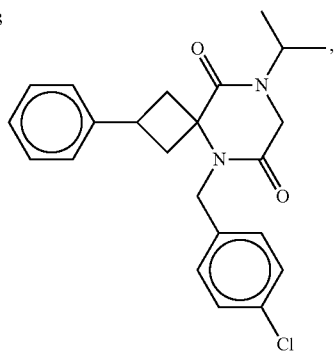 |
| 319 | 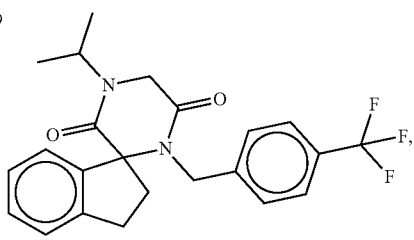 |

| No. | Structure |
|---|---|
| 320 | 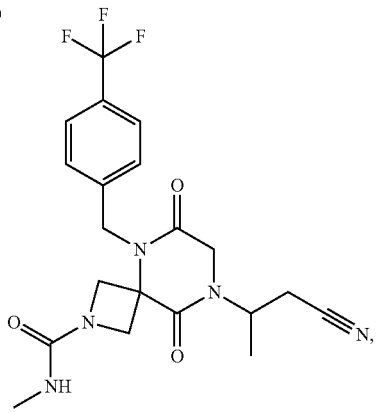 |
| 321 | 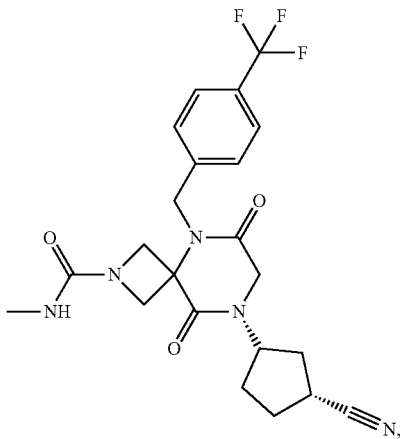 |
| 322 | 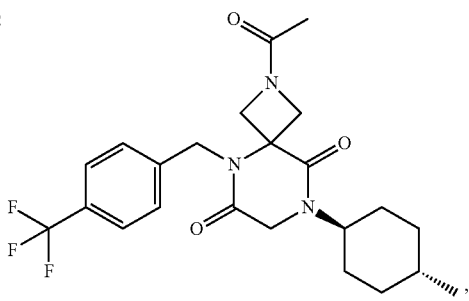 |
| 323 | 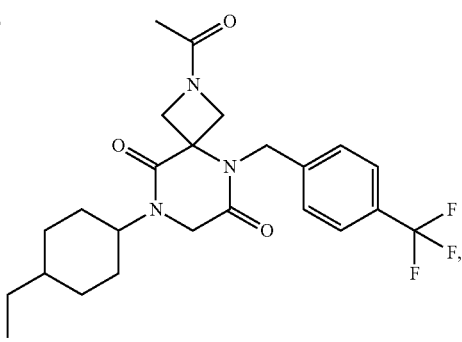 [SMILES: CCC1CCC(N2CC(=O)N(Cc3ccc(C(F)(F)F)cc3)C3(CN(C(C)=O)C3)C2=O)CC1] |

| No. | Structure |
|---|---|
| 324 | 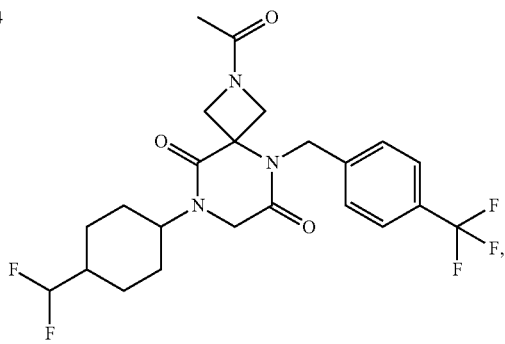 |
| 325 | 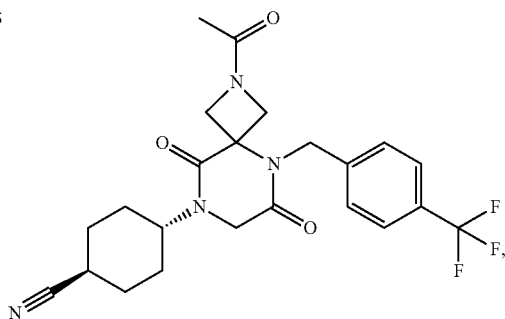 |
| 326 | 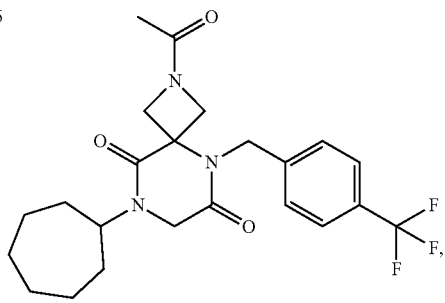 |
| 327 | 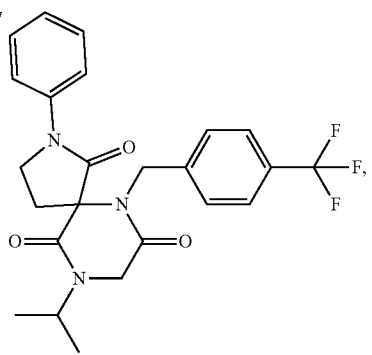 |

| No. | Structure |
|---|---|
| 328 | 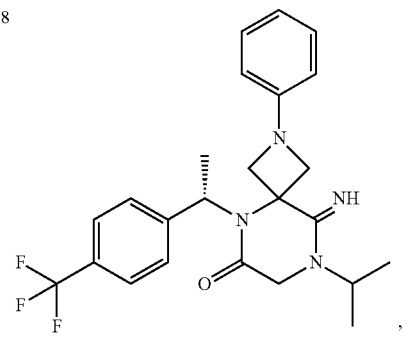 |
| 329 | 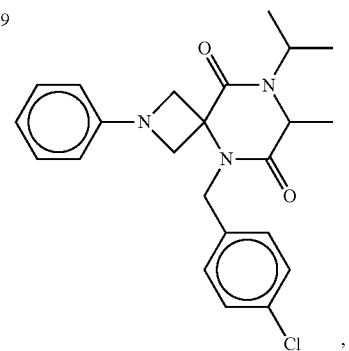 |
| 330 | 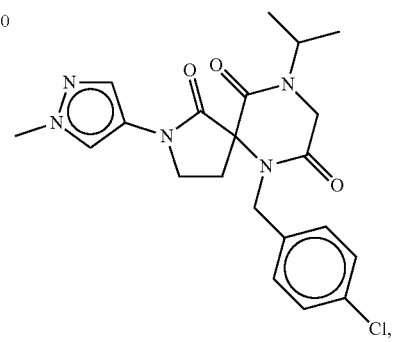 |
| 331 | 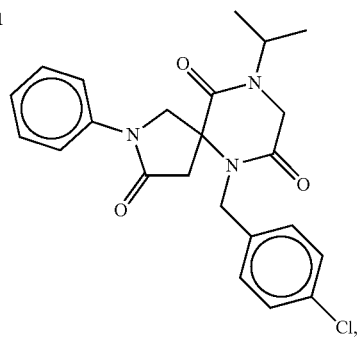 |

-continued
| No. | Structure |
|---|---|
| 332 | 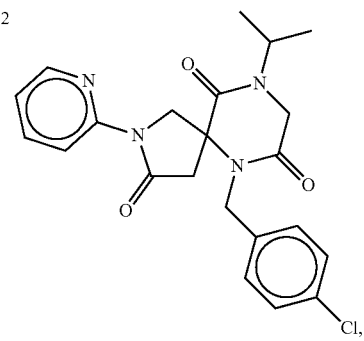 |
| 333 | 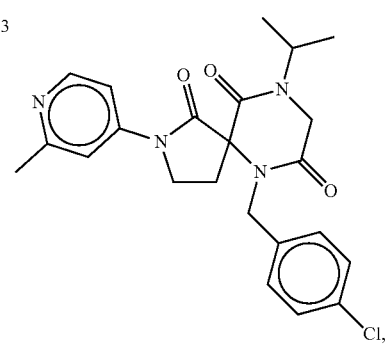 |
| 339 | 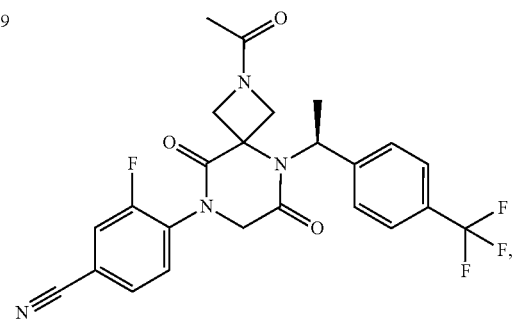 |
| 340 | 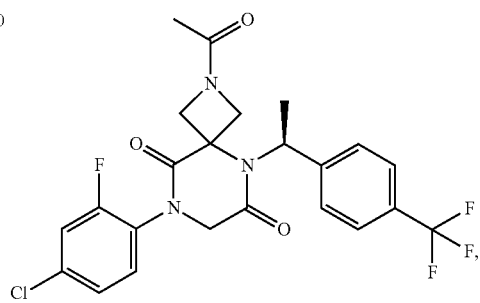 |
| 341 | 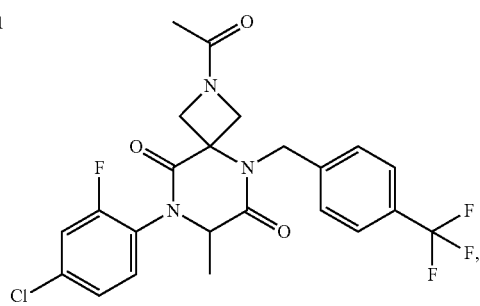 |

US 11,414,424 B2
-continued
| No. | Structure |
|---|---|
| 342 | 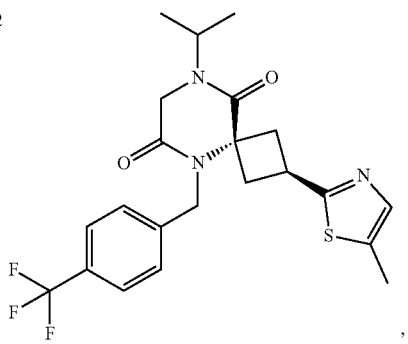 |
| 343 | 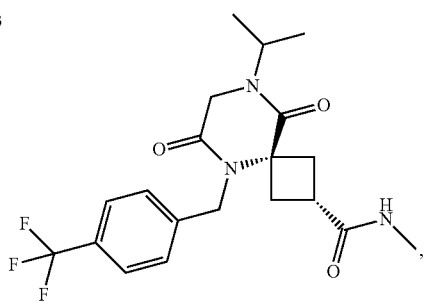 |
| 344 | 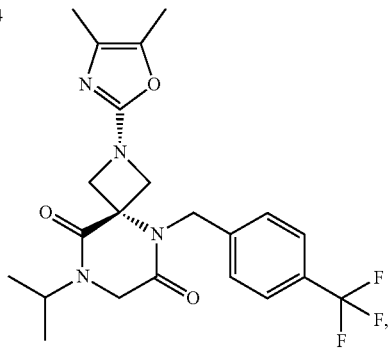 |
| 345 | 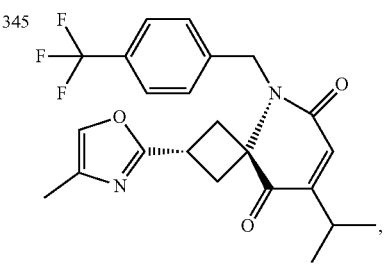 |

-continued
| No. | Structure |
|---|---|
| 346 | 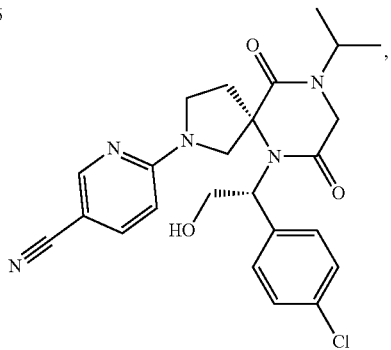 |
| 348 | 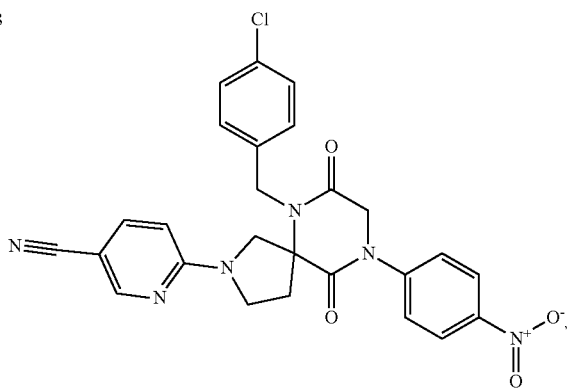 |
| 349 | 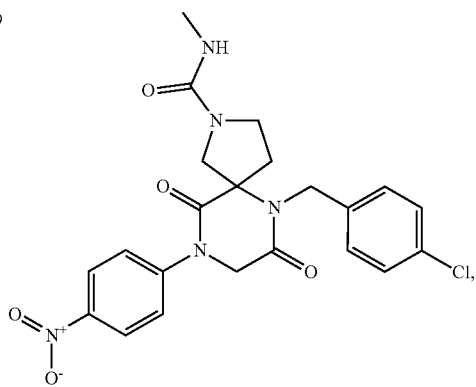 |
| 350 | 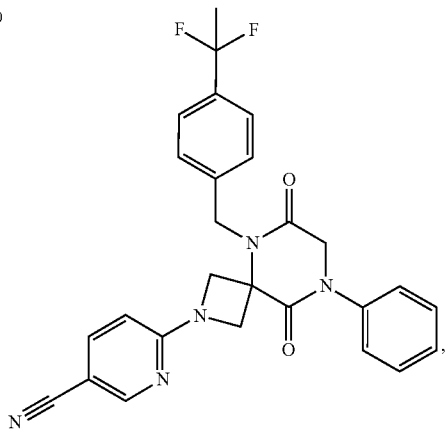 |

-continued
| No. | Structure |
|---|---|
| 351 | 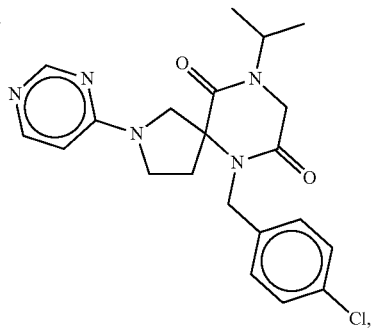 |
| 352 | 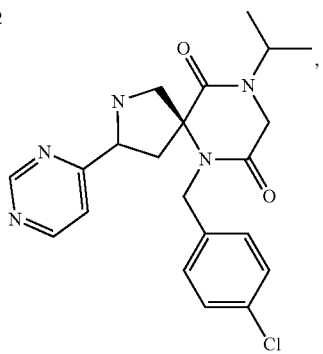 |
| 353 | 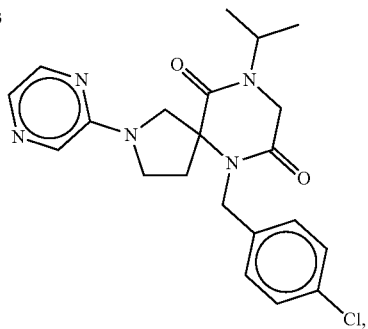 |
| 354 | 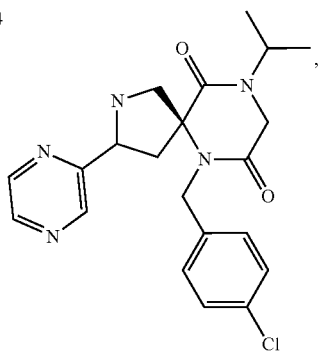 |

| No. | Structure |
|---|---|
| 355 | 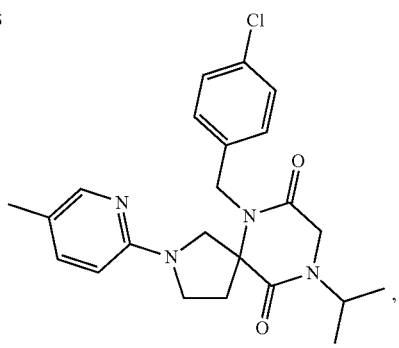 |
| 356 | 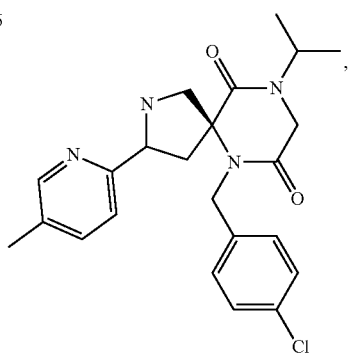 |
| 357 | 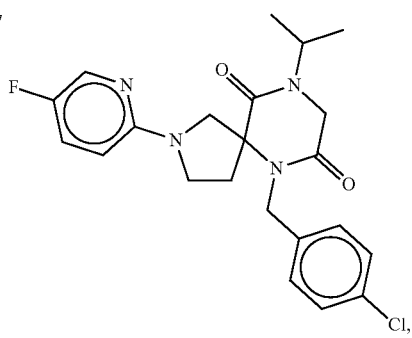 |
| 358 | 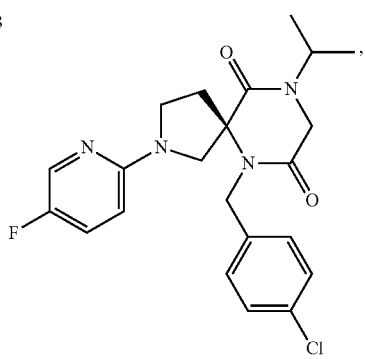 |

-continued
| No. | Structure |
|---|---|
| 359 | 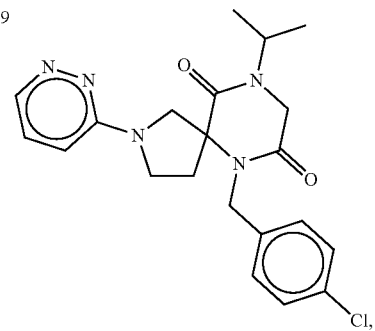 |
| 360 | 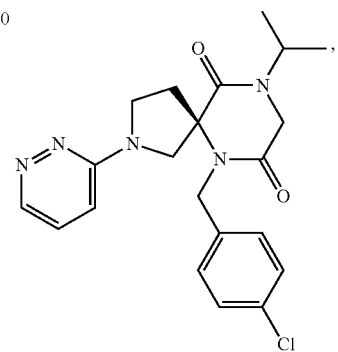 [SMILES: CC(C)N1CC(=O)N(Cc2ccc(Cl)cc2)[C@@]2(CCN(c3cc[nH]c(=O)c3)C2)C1=O] |
| 361 | 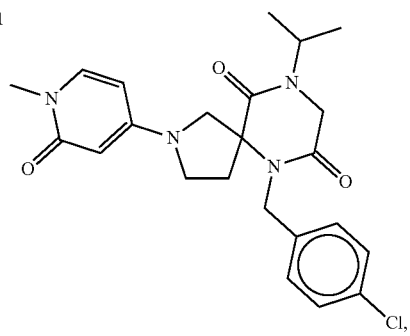 |
| 362 | 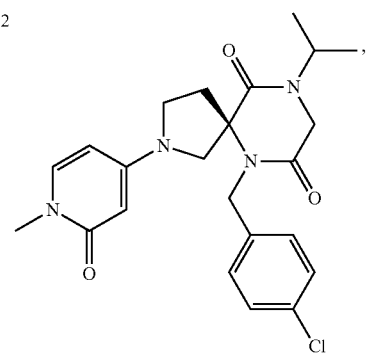 |

| No. | Structure |
|---|---|
| 363 | 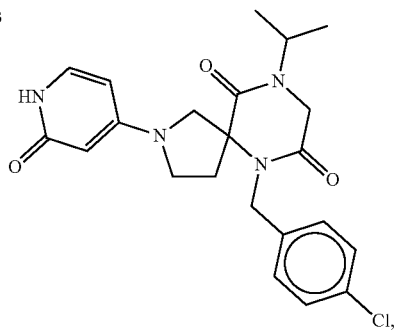 |
| 364 | 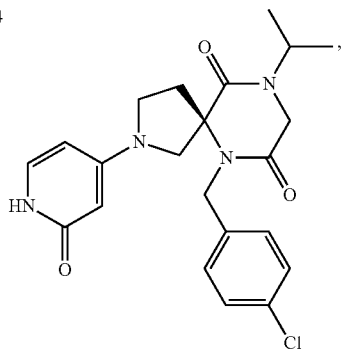 |
| 365 | 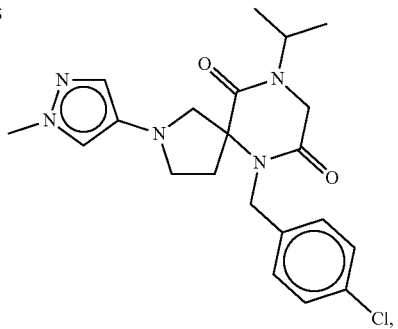 |
| 366 | 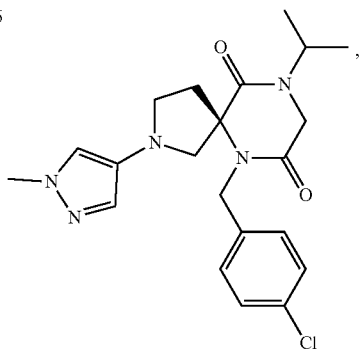 |

-continued
| No. | Structure |
|---|---|
| 367 | 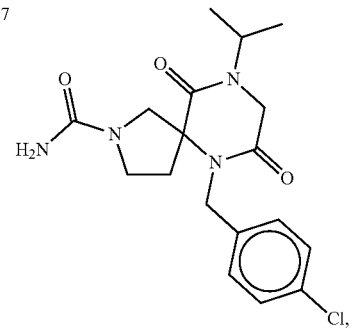 |
| 368 | 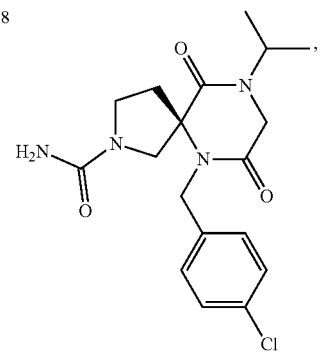 |
| 369 | 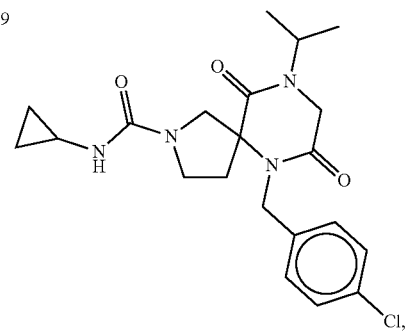 |
| 370 | 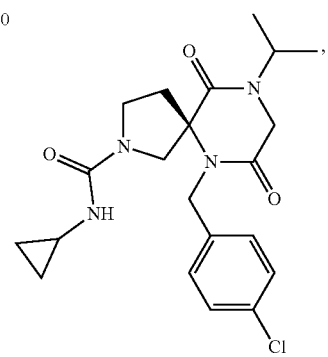 |

| No. | Structure |
|---|---|
| 371 | 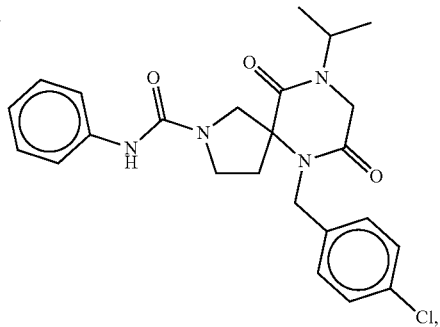 |
| 372 | 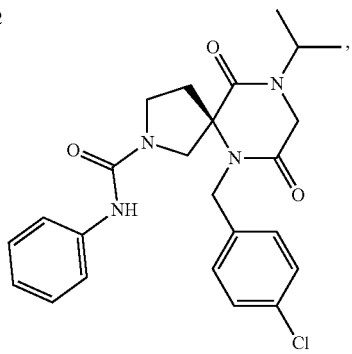 |
| 373 | 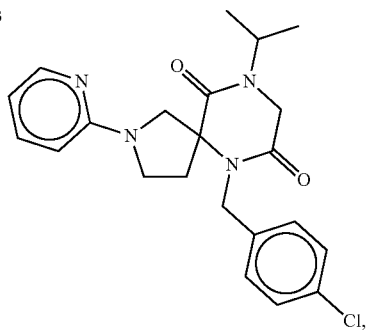 |
| 374 | 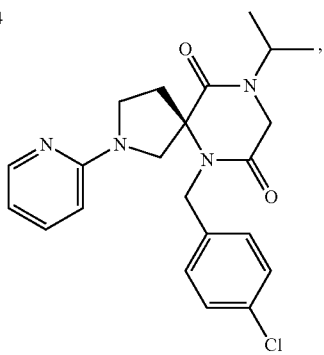 |

| No. | Structure |
|---|---|
| 375 | 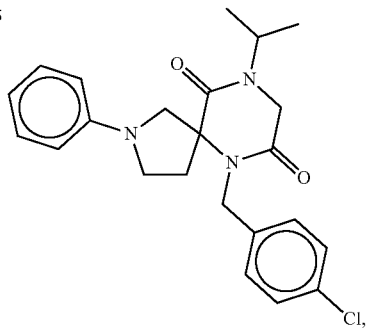 |
| 376 | 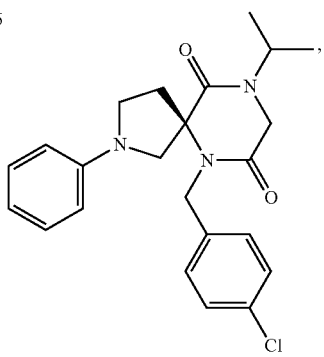 |
| 377 | 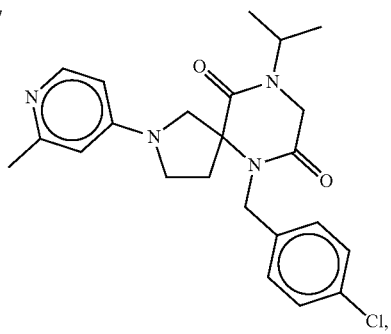 |
| 378 | 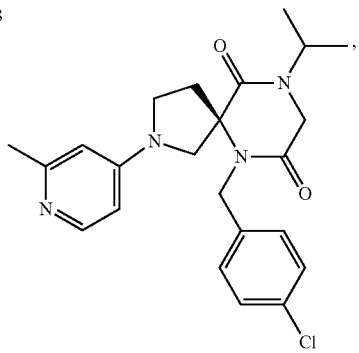 |

| No. | Structure |
|---|---|
| 379 | 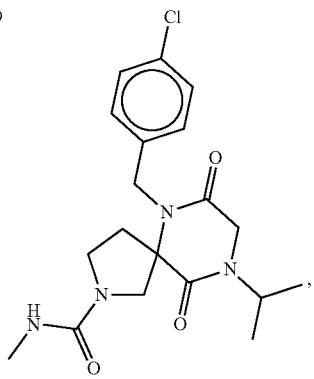 |
| 380 | 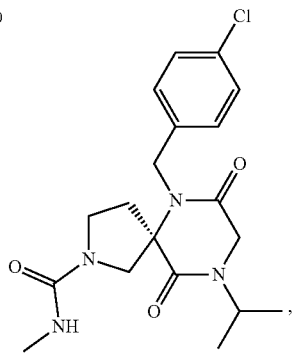 |
| 381 | 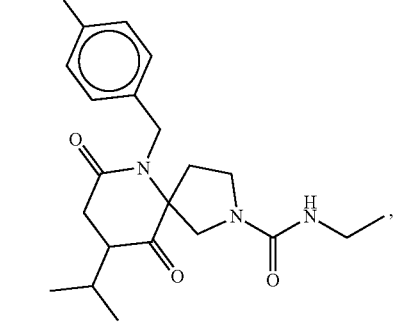 |
| 382 | 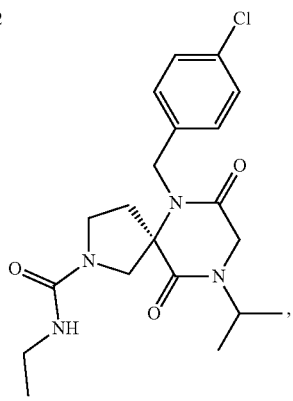 |

| No. | Structure |
|---|---|
| 383 | 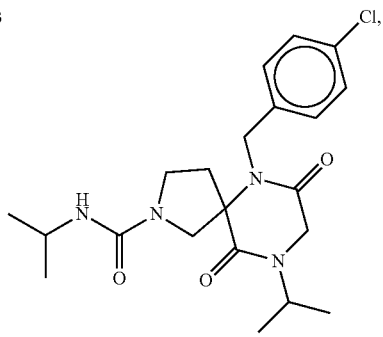 |
| 384 | 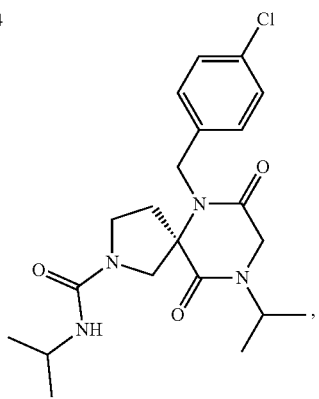 |
| 385 | 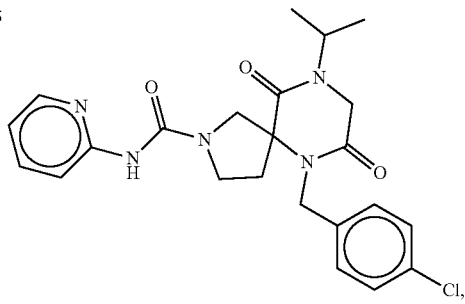 |
| 386 | 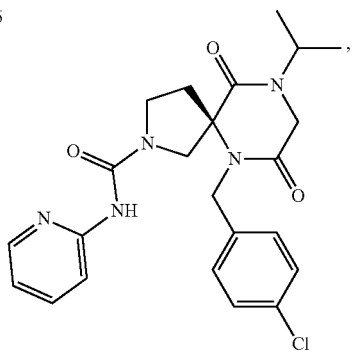 |

| No. | Structure |
|---|---|
| 387 | 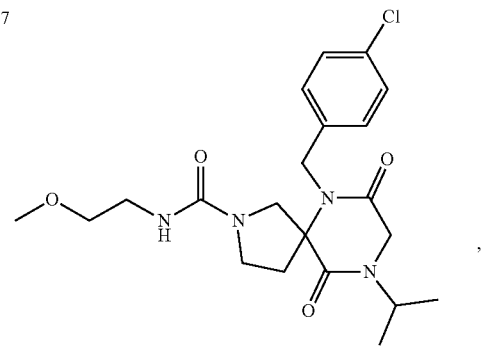 |
| 388 | 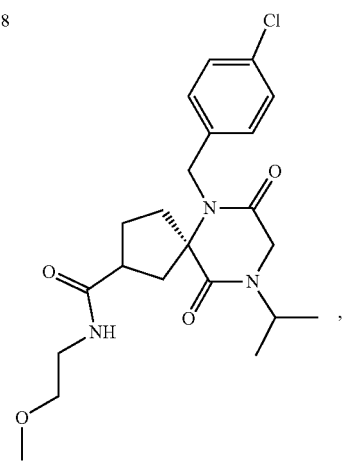 |
| 389 | 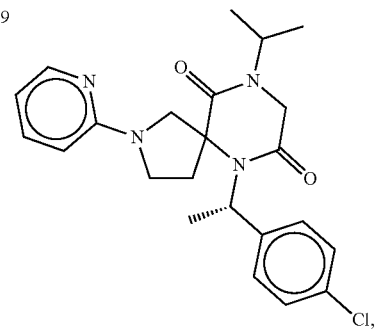 |
| 390 | 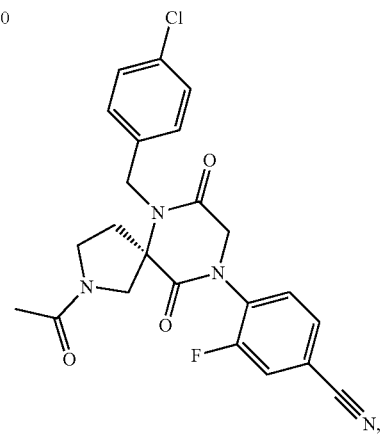 |

| No. | Structure |
|---|---|
| 391 | 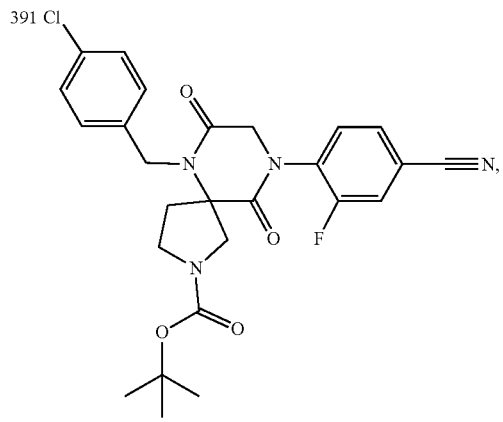 |
| 392 | 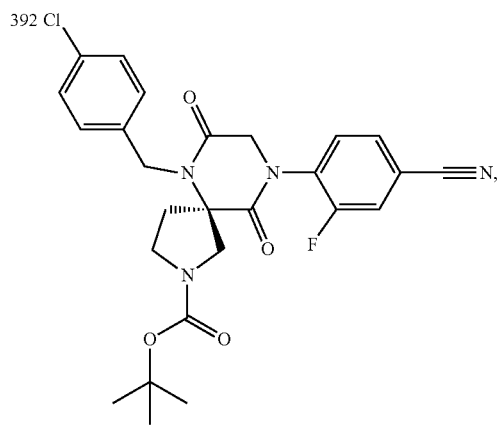 |
| 393 | 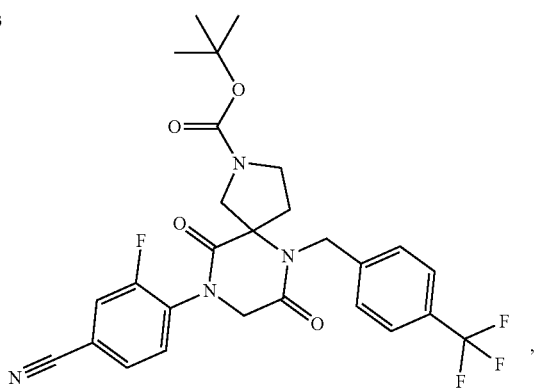 |

| No. | Structure |
|---|---|
| 394 | 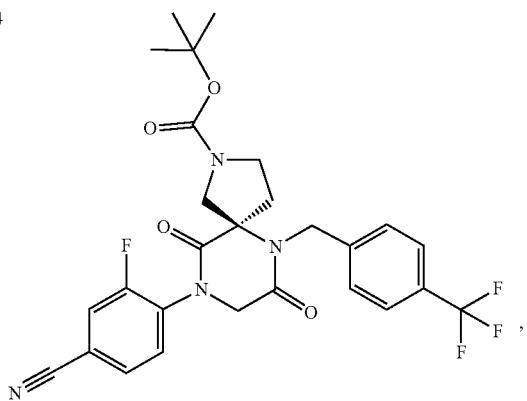 |
| 395 | 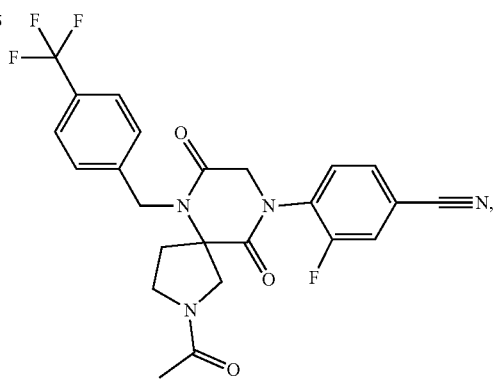 |
| 396 | 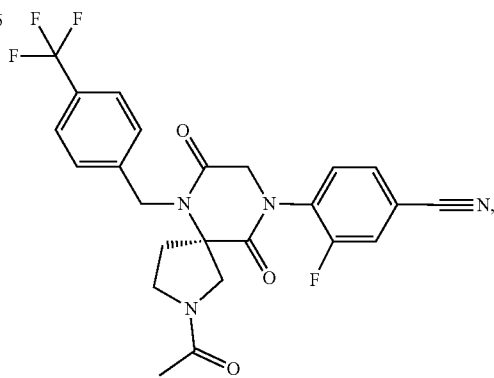 |
| 397 | 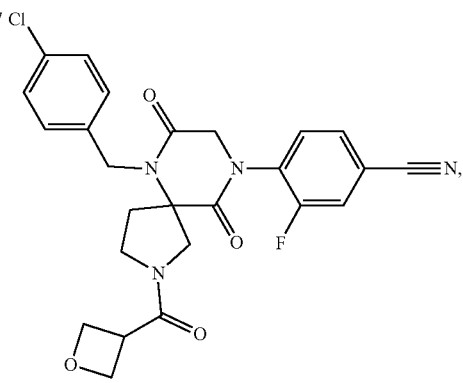 |

-continued
| No. | Structure |
|---|---|
| 398 | 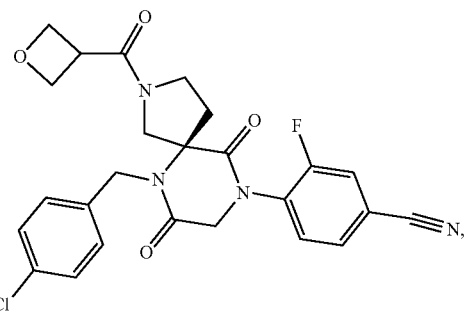 |
| 399 | 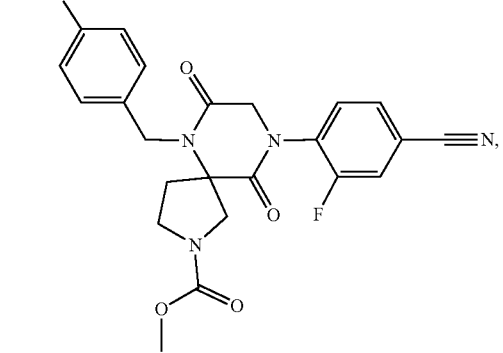 |
| 400 | 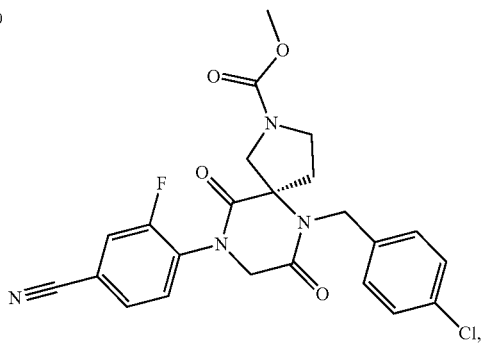 |
| 401 | 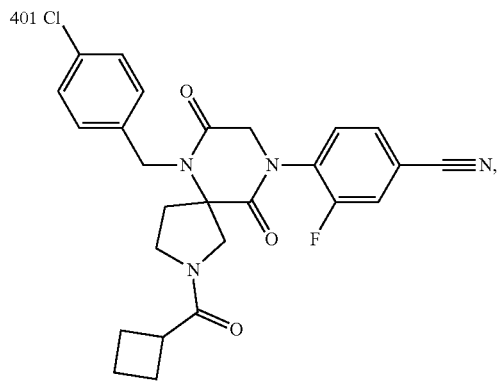 |

| No. | Structure |
|---|---|
| 402 | 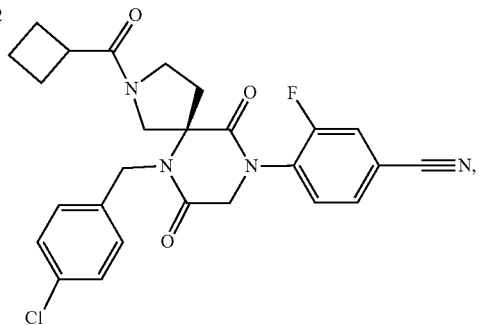 |
| 403 | 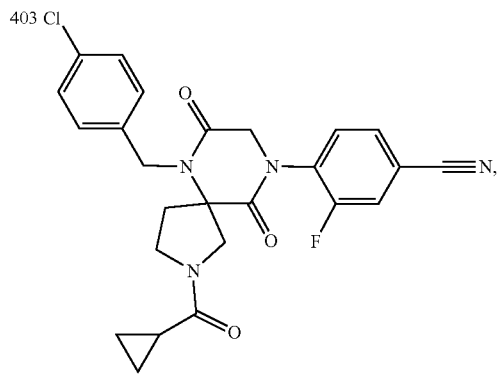 |
| 404 | 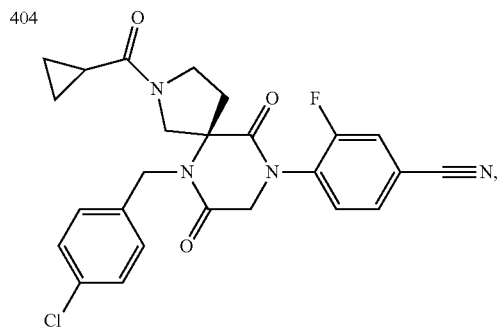 |
| 405 | 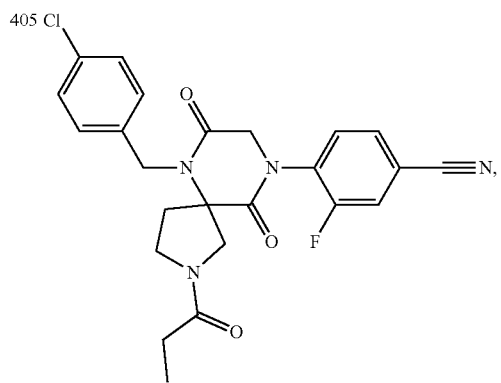 |

-continued
| No. | Structure |
|---|---|
| 406 | 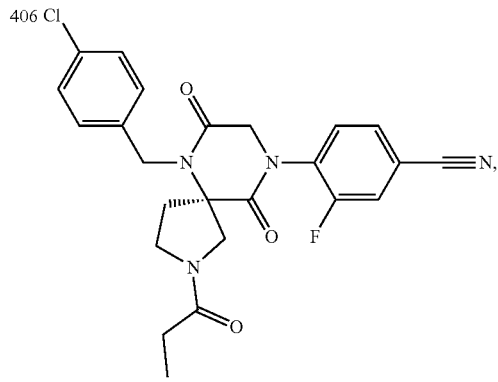 |
| 407 | 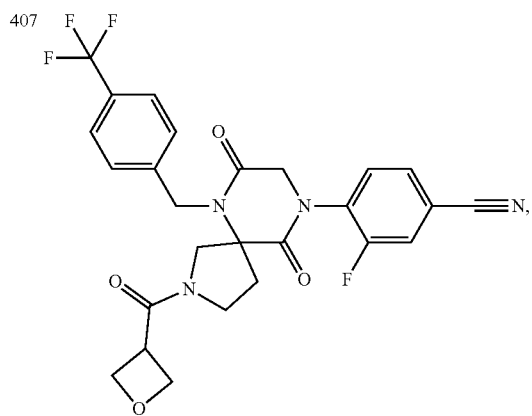 |
| 408 | 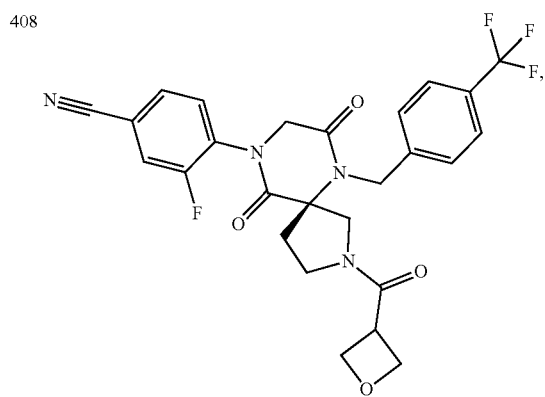 |
| 409 | 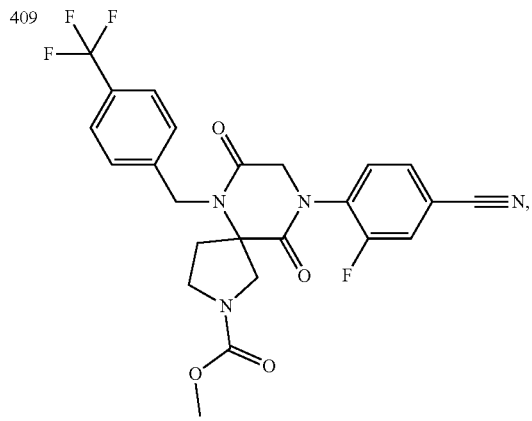 |

| No. | Structure |
|---|---|
| 410 | 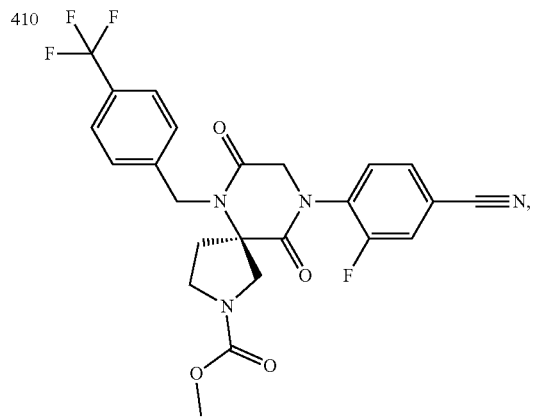 |
| 411 | 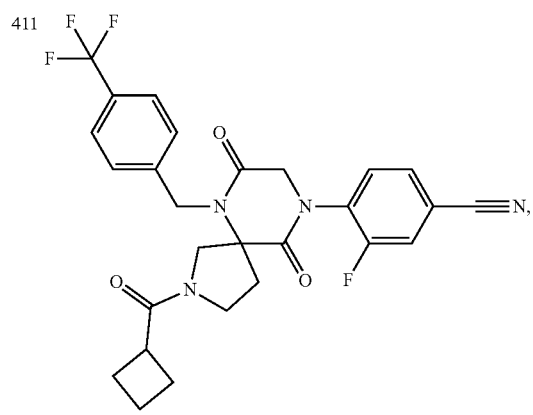 |
| 412 | 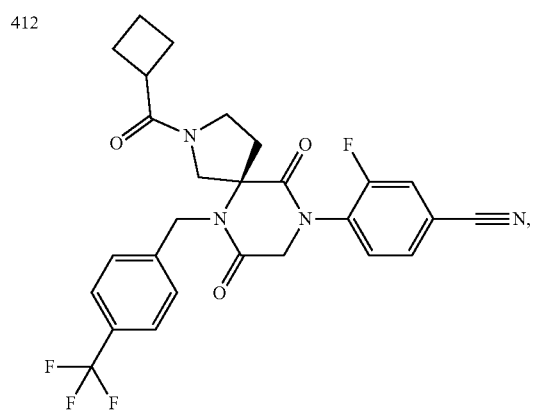 |

| No. | Structure |
|---|---|
| 413 | 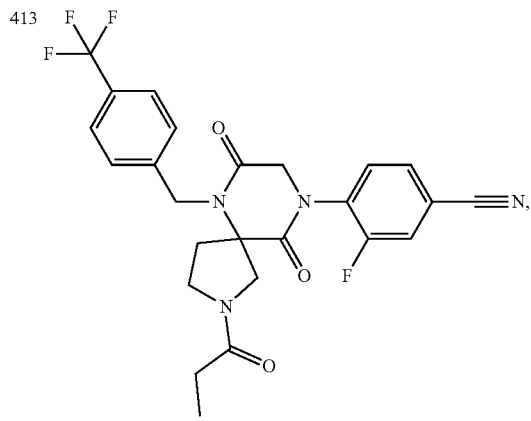 |
| 414 | 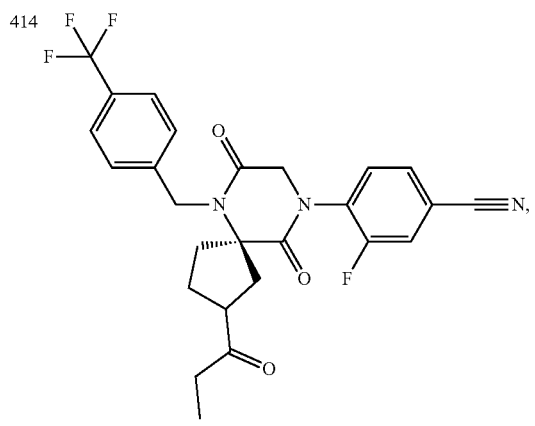 |
| 415 | 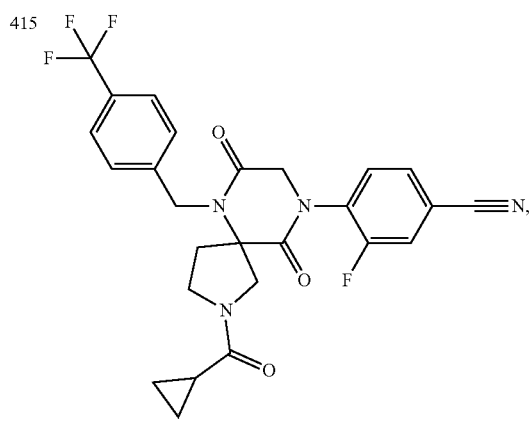 |
| 416 | 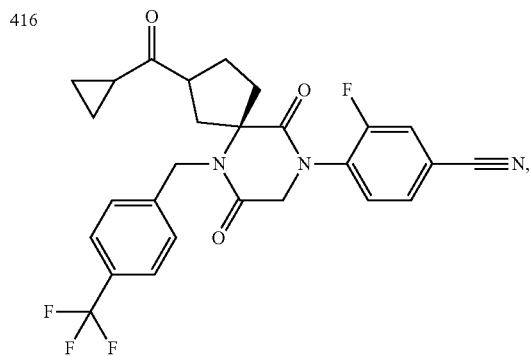 |

| No. | Structure |
|-----|-----------|
| 417 | 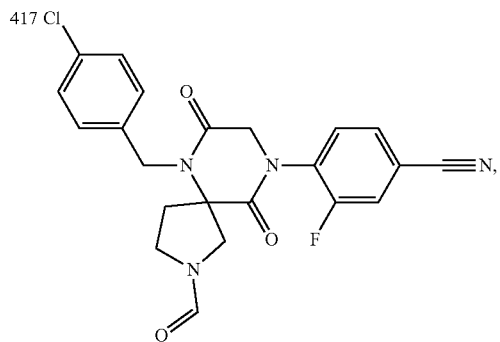 |
| 418 | 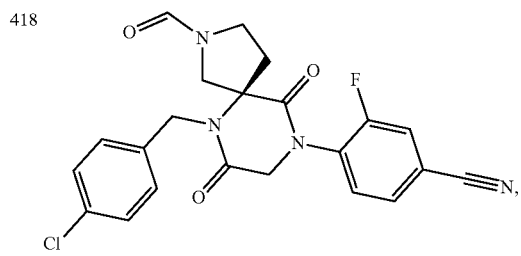 |
| 419 | 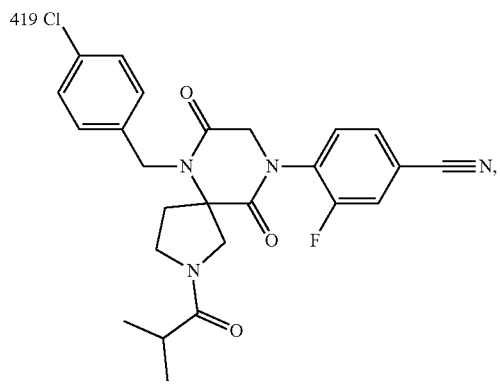 |
| 420 | 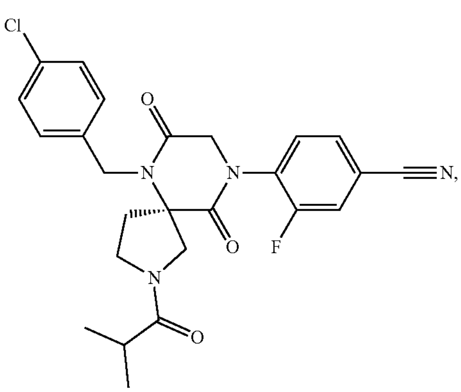 [SMILES: CC(C)C(=O)N1CC[C@@]2(C1)C(=O)N(c1ccc(C#N)cc1F)CC(=O)N2Cc1ccc(Cl)cc1] |

| No. | Structure |
|---|---|
| 421 | 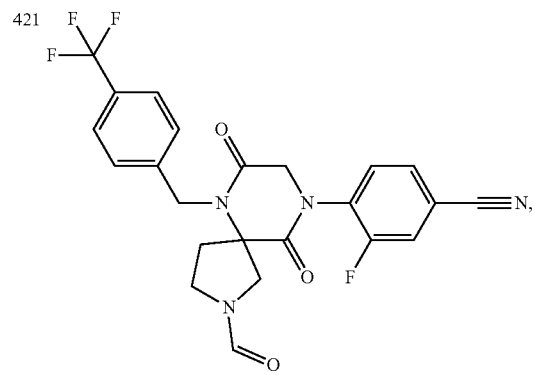 |
| 422 | 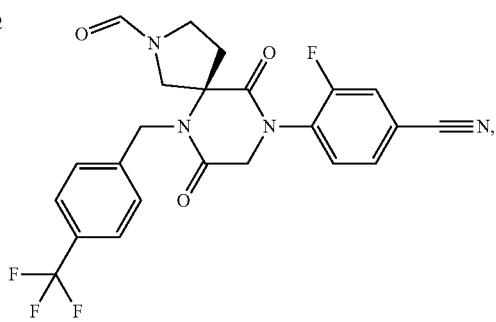 |
| 423 | 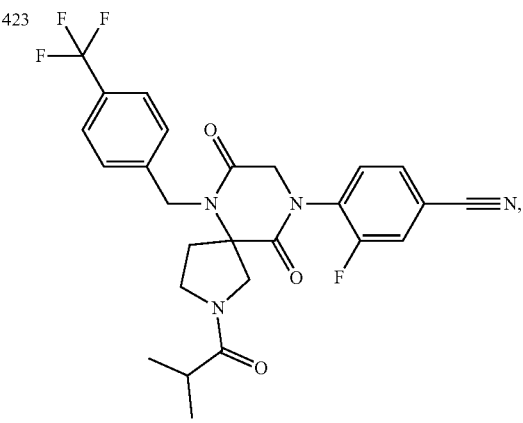 |
| 424 | 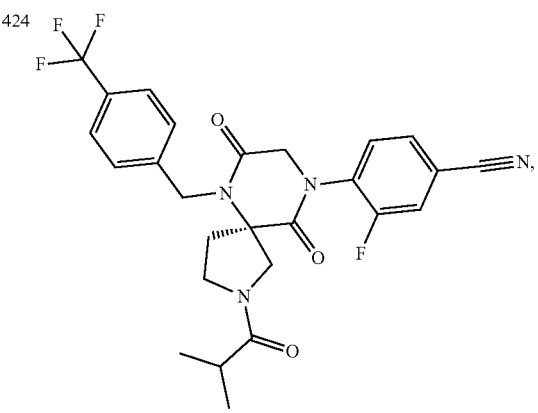 |

| No. | Structure |
|-----|-----------|
| 425 | 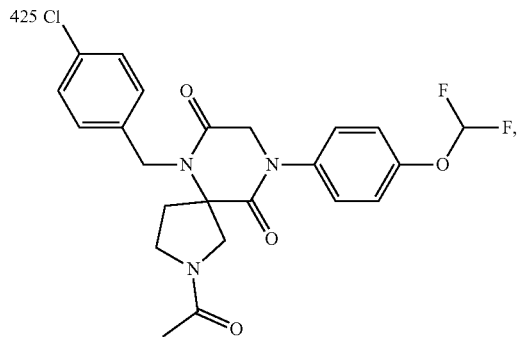 |
| 426 | 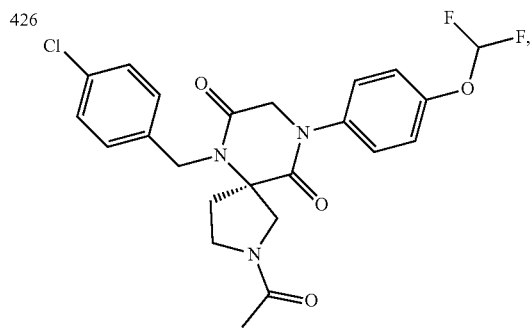 |
| 427 | 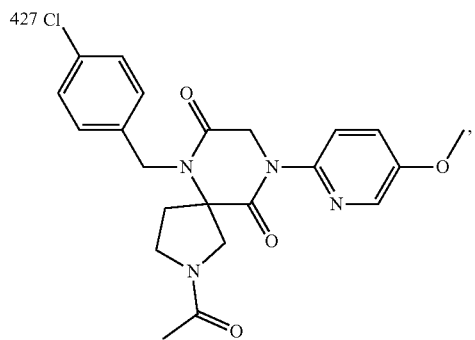 |
| 428 | 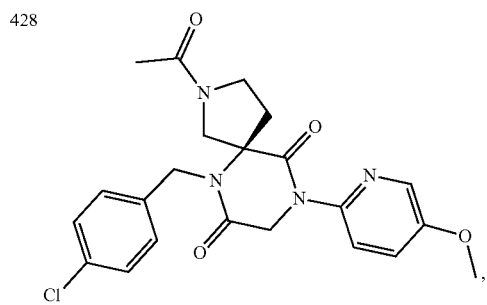 |

| No. | Structure |
|---|---|
| 429 | 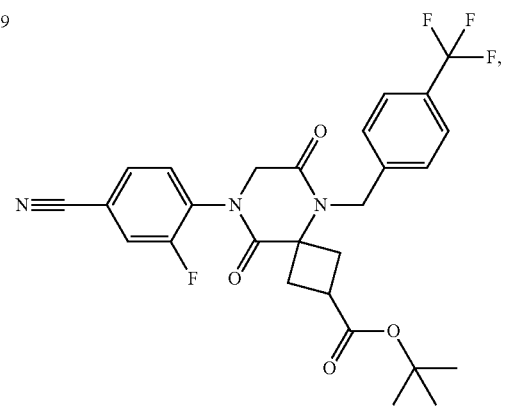 |
| 430 | 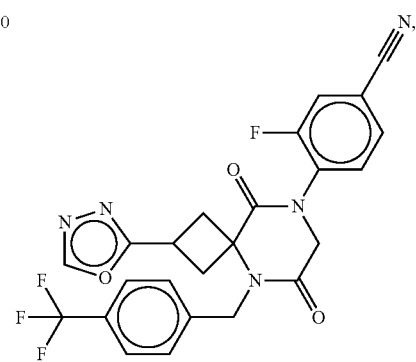 |
| 431 | 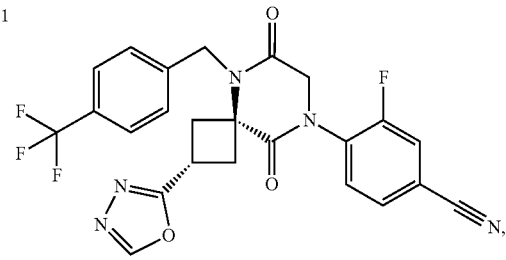 |
| 432 | 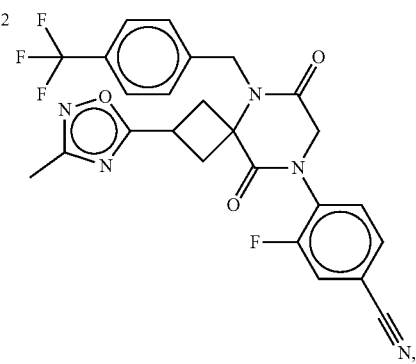 |

| No. | Structure |
|---|---|
| 433 | 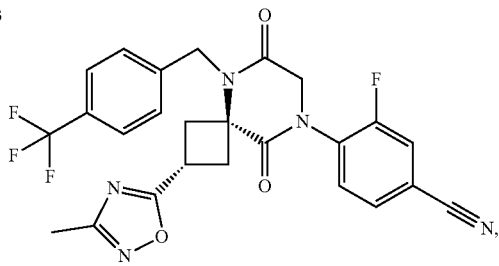 |
| 434 | 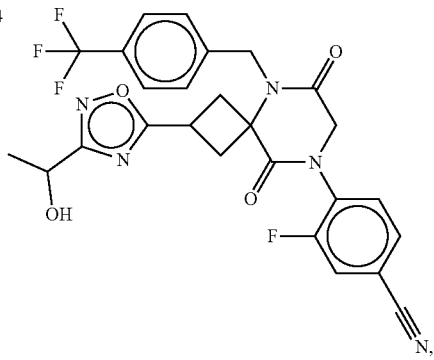 |
| 435 | 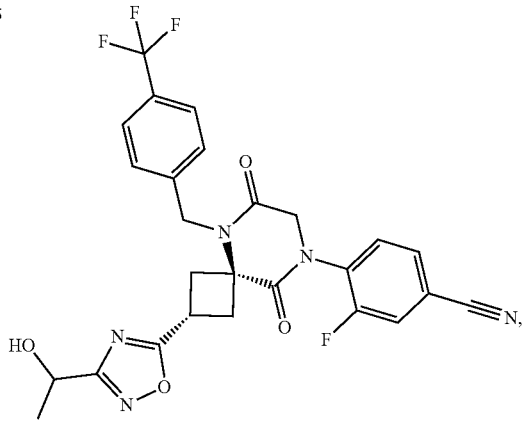 |
| 436 | 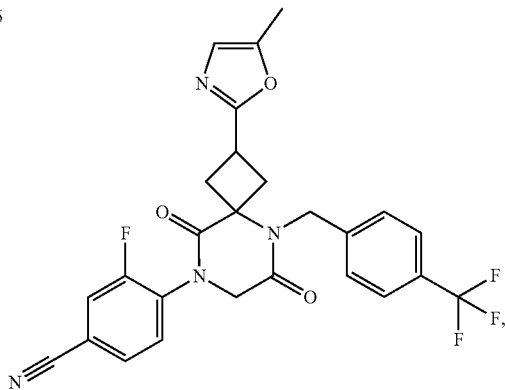 |

| No. | Structure |
|---|---|
| 437 | 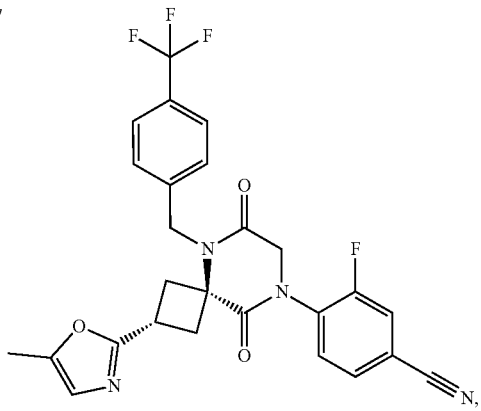 |
| 438 | 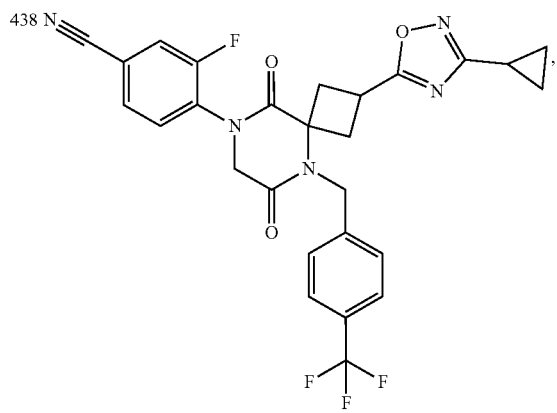 |
| 439 | 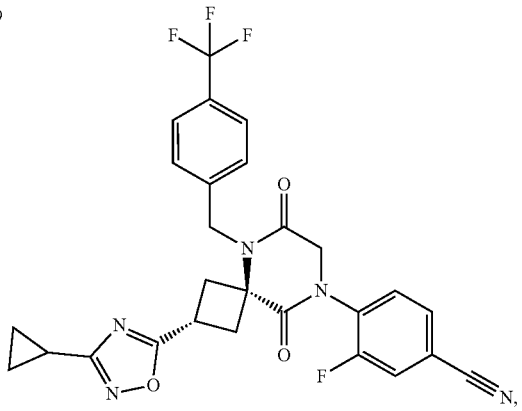 |

| No. | Structure |
|---|---|
| 440 | 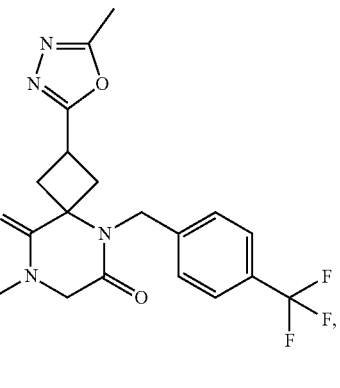 |
| 441 | 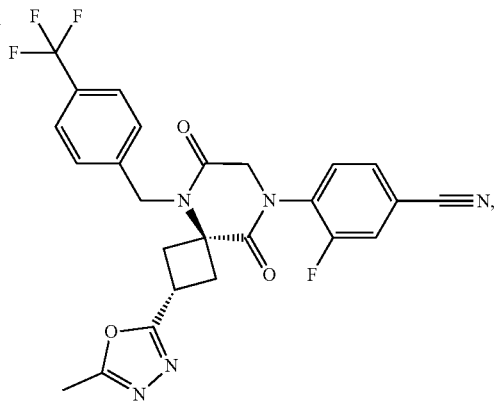 [SMILES: Cc1nnc([C@H]2C[C@]3(C2)C(=O)N(c2ccc(C#N)cc2F)CC(=O)N3Cc2ccc(C(F)(F)F)cc2)o1] |
| 442 | 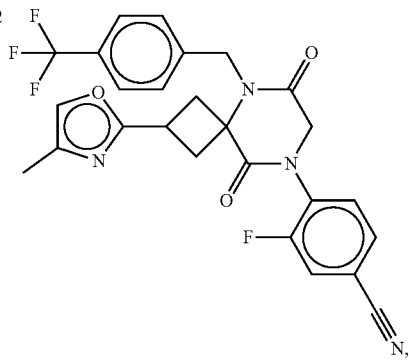 |
| 443 | 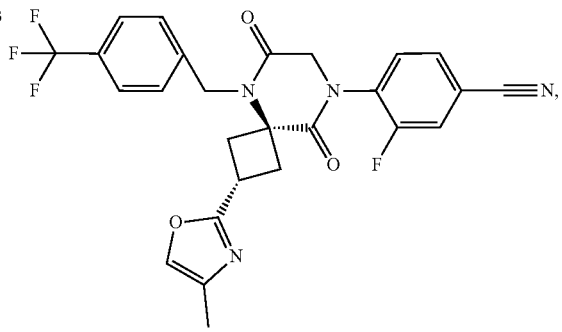 |

| No. | Structure |
|---|---|
| 444 | 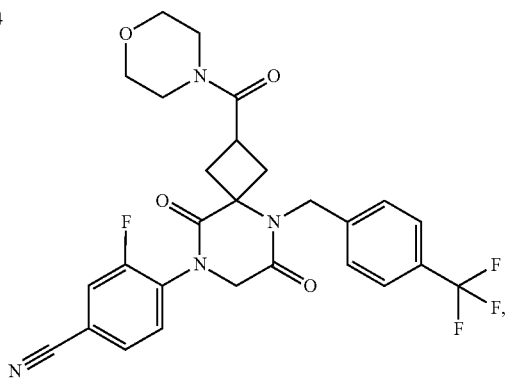 |
| 445 | 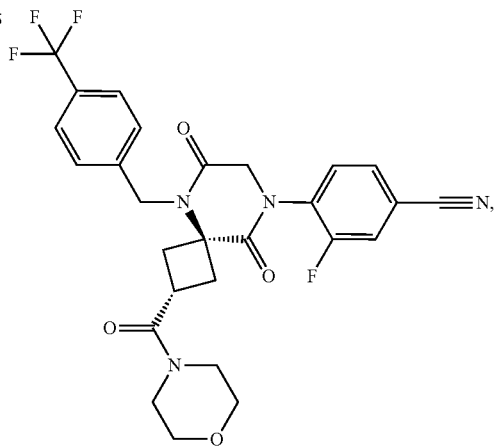 |
| 446 | 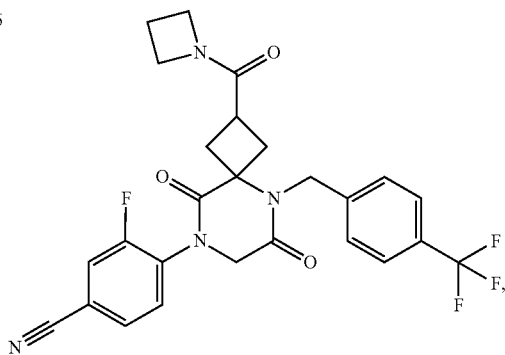 |
| 447 | 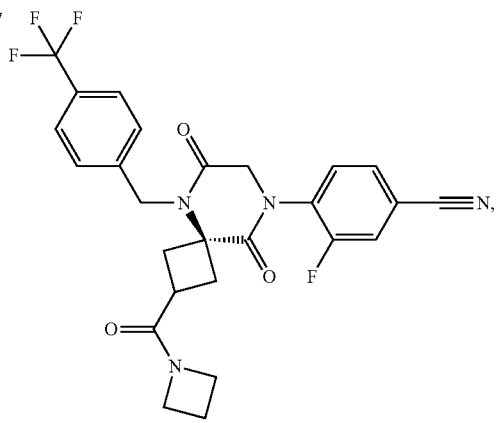 |

| No. | Structure |
|---|---|
| 448 | 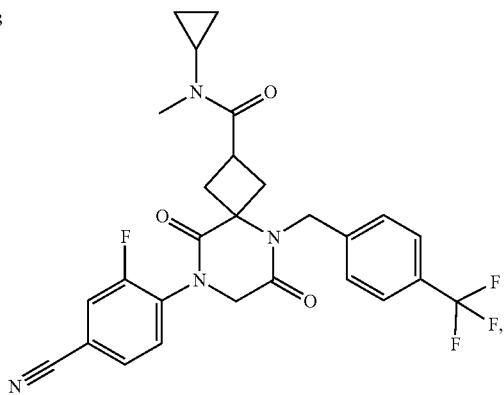 |
| 449 | 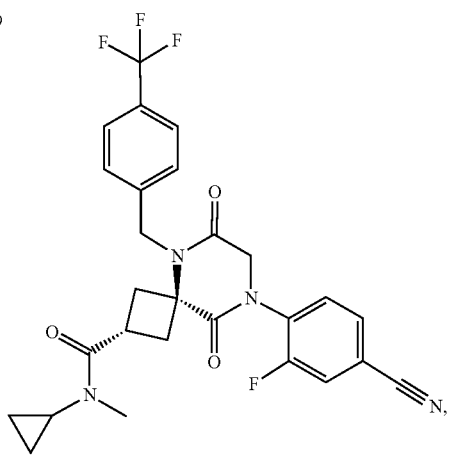 |
| 450 | 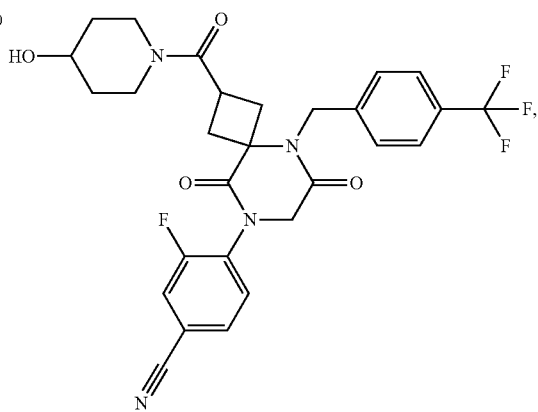 |

US 11,414,424 B2
-continued
| No. | Structure |
|---|---|
| 451 | 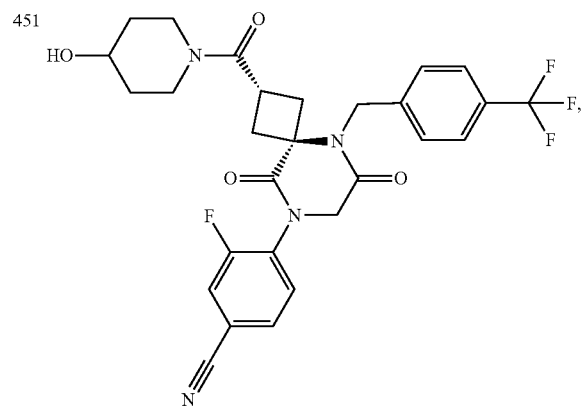 |
| 452 | 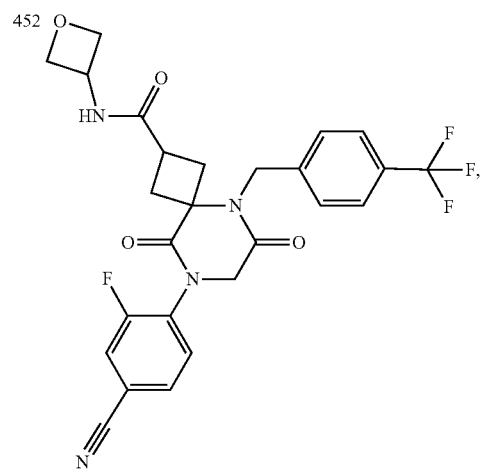 |
| 453 | 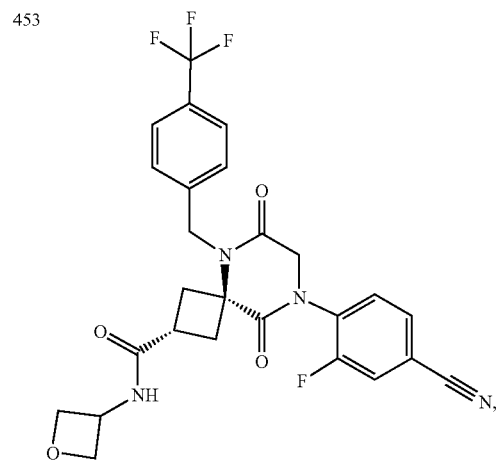 |

| No. | Structure |
|---|---|
| 454 | 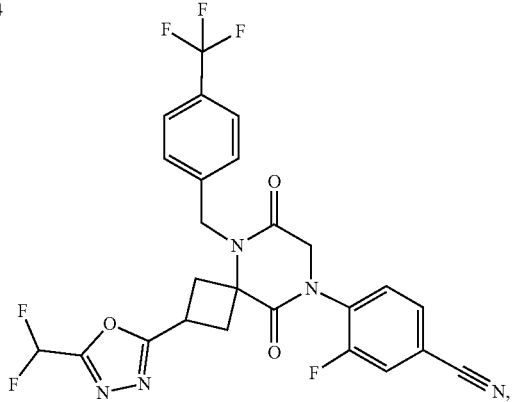 |
| 455 | 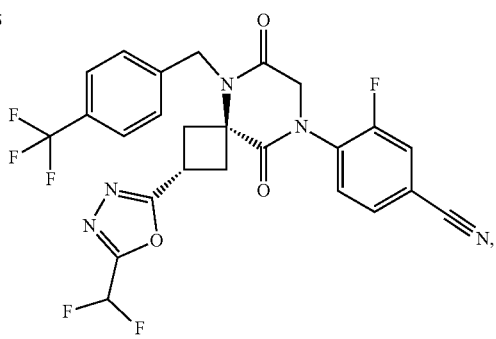 |
| 456 | 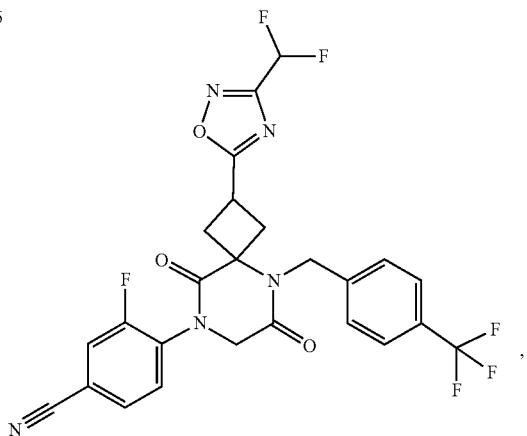 |

| No. | Structure |
|---|---|
| 457 | 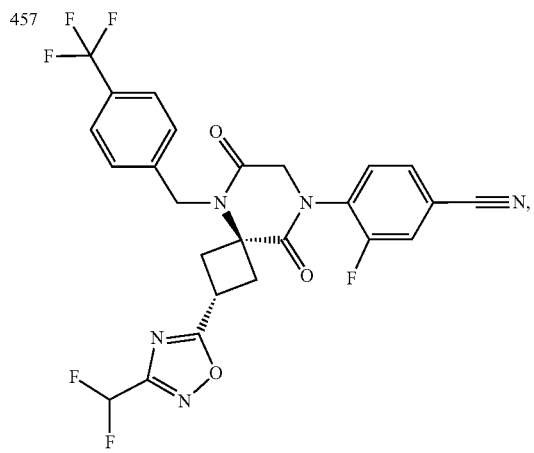 |
| 458 | 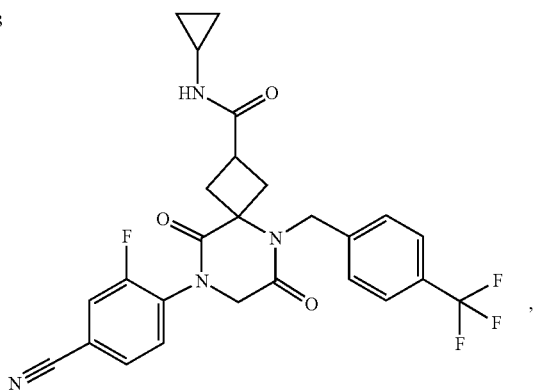 |
| 459 | 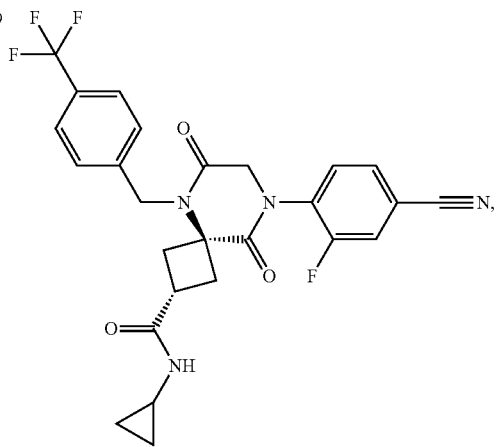 |

| No. | Structure |
|---|---|
| 460 | 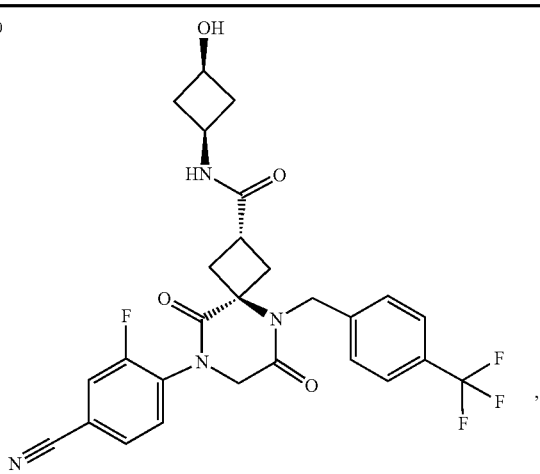 |
| 461 | 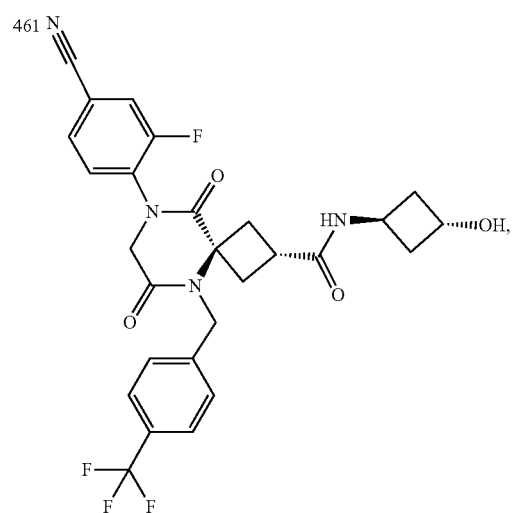 |
| 462 | 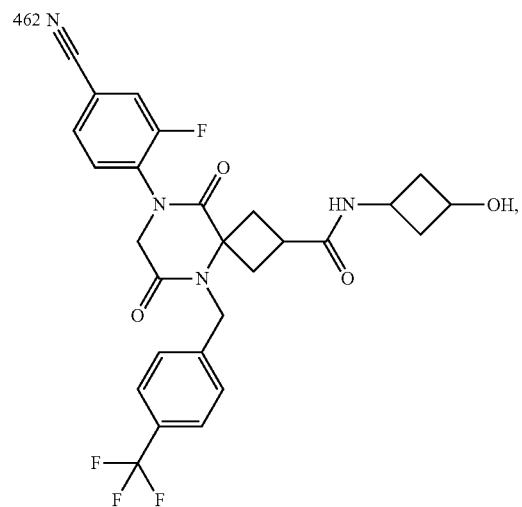 |

| No. | Structure |
|---|---|
| 463 | 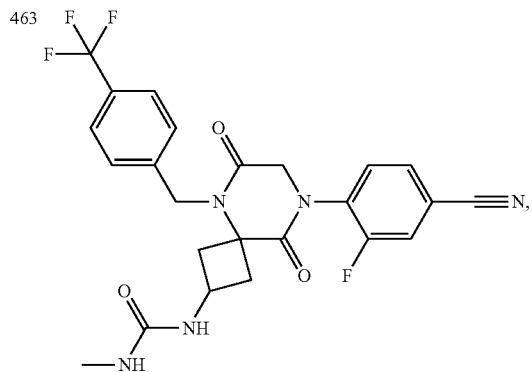 |
| 464 | 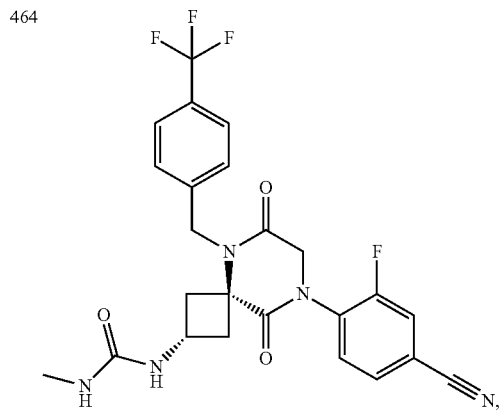 |
| 465 | 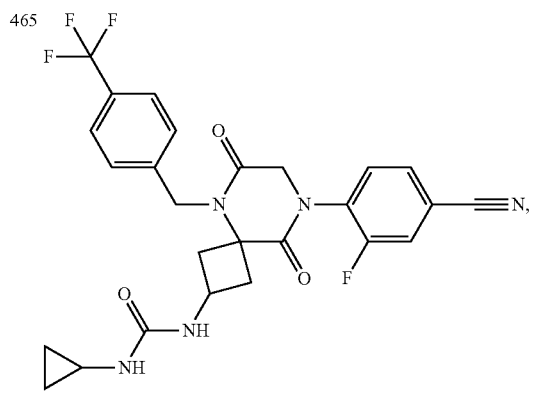 |
| 466 | 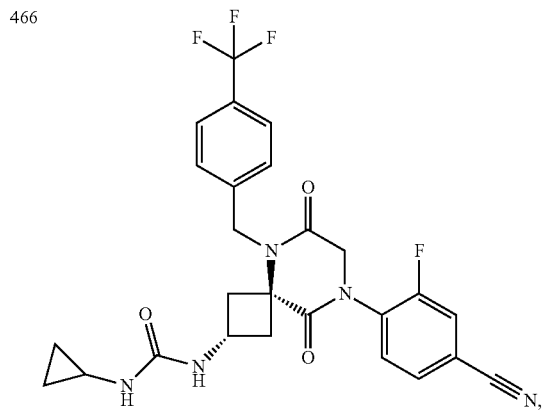 |

| No. | Structure |
|---|---|
| 467 | 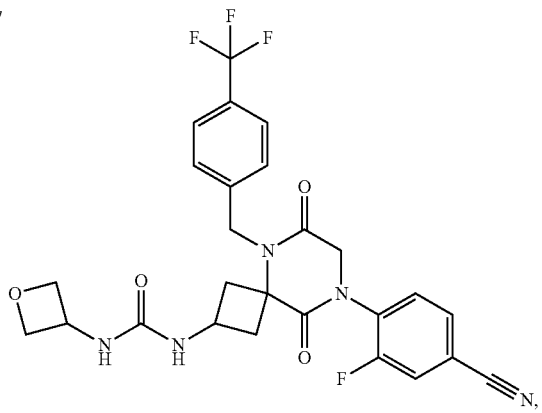 |
| 468 | 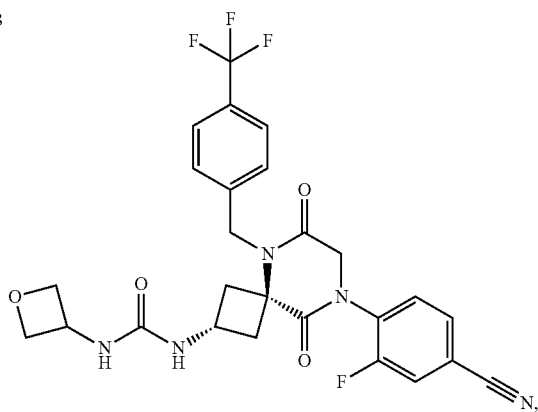 |
| 469 | 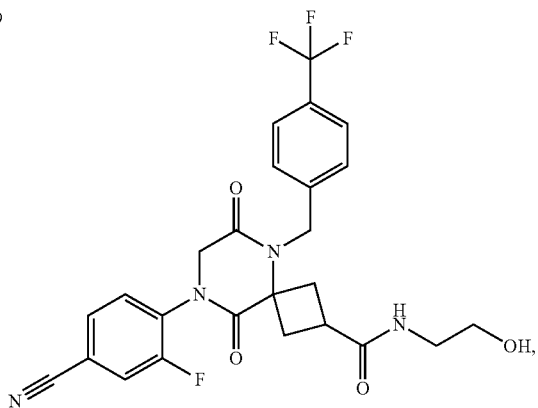 |

| No. | Structure |
|---|---|
| 470 | 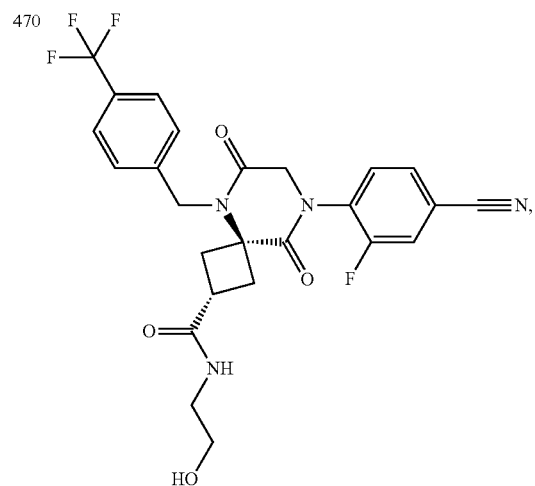 |
| 471 | 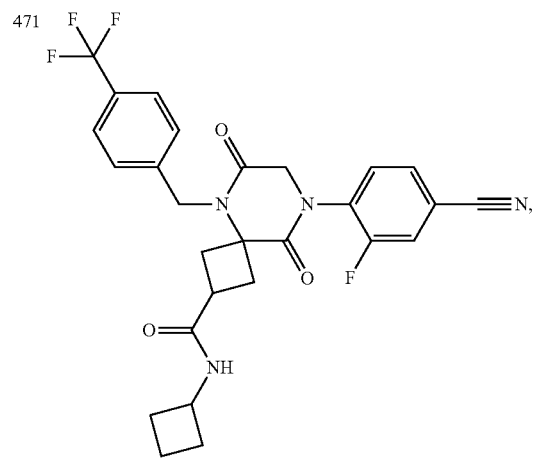 |
| 472 | 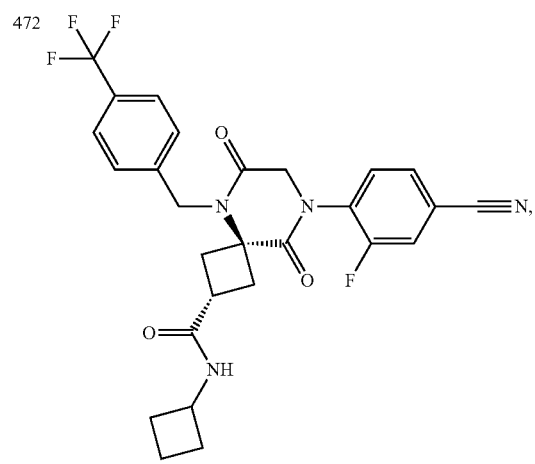 |

| No. | Structure |
|---|---|
| 473 | 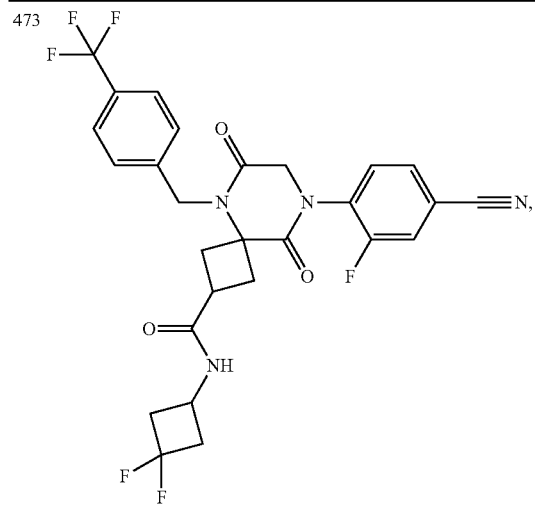 |
| 474 | 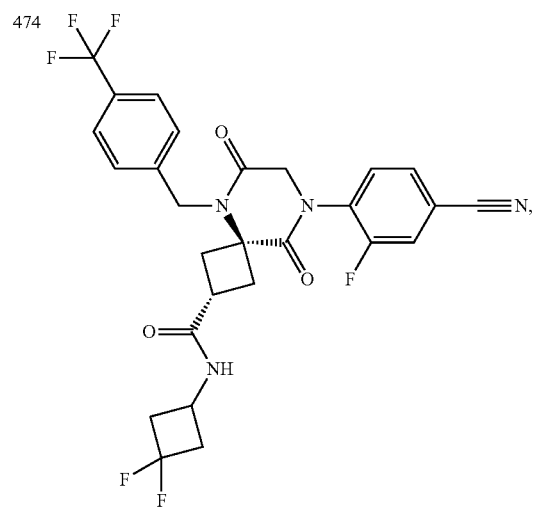 |
| 475 | 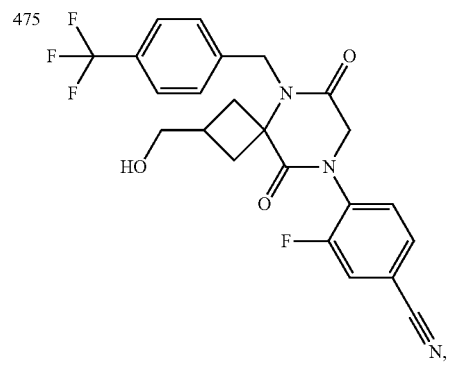 |
| 476 | 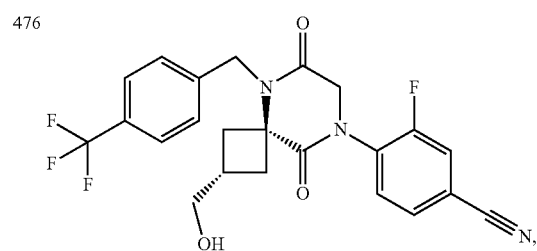 |

| No. | Structure |
|---|---|
| 477 | 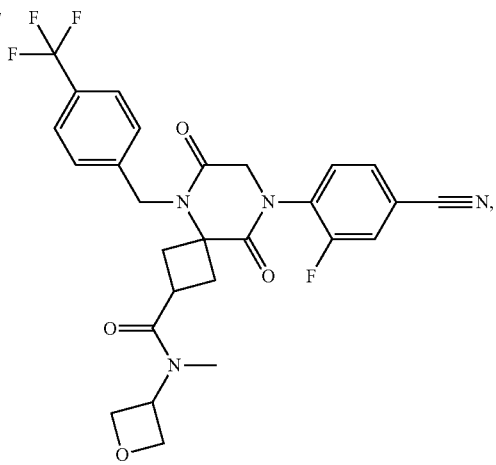 |
| 478 | 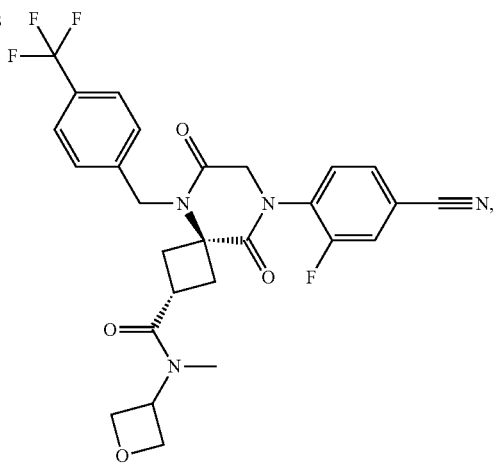 |
| 479 | 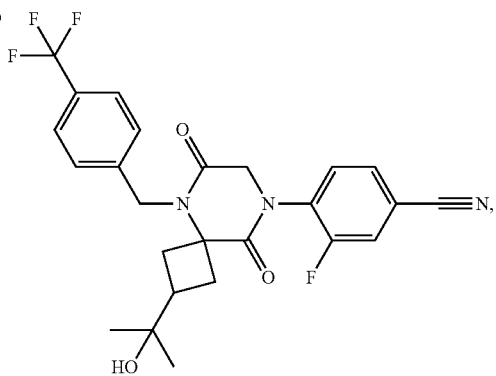 |

| No. | Structure |
|---|---|
| 480 | 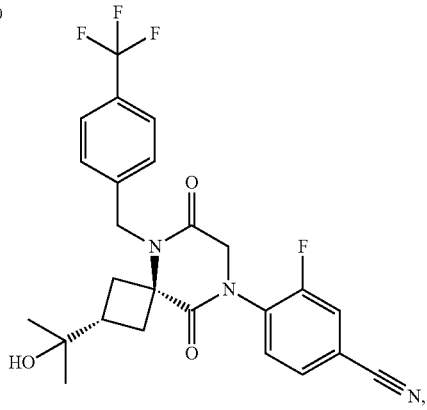 |
| 481 | 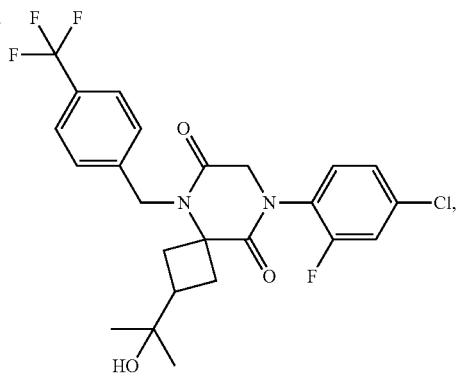 [SMILES: CC(C)(O)C1CC2(C1)C(=O)N(c1ccc(Cl)cc1F)CC(=O)N2Cc1ccc(C(F)(F)F)cc1] |
| 482 | 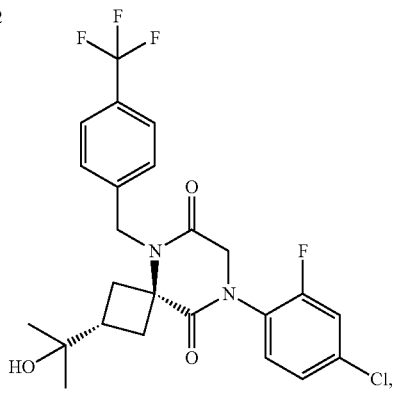 |
| 483 | 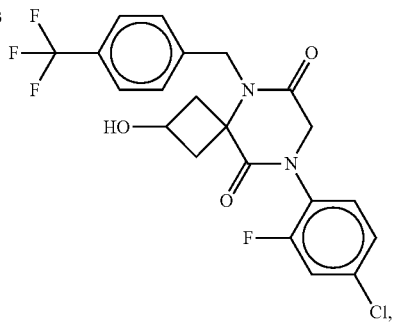 |

| No. | Structure |
|---|---|
| 484 | 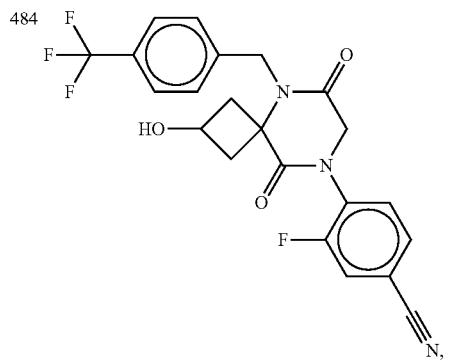 |
| 485 | 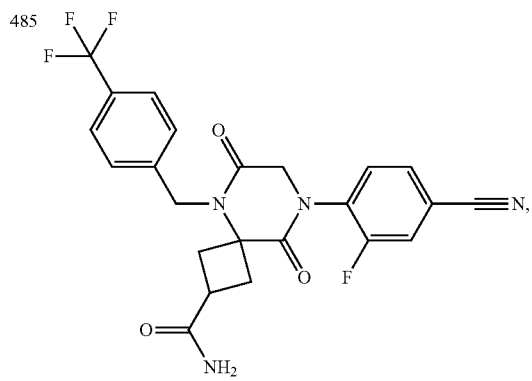 |
| 486 | 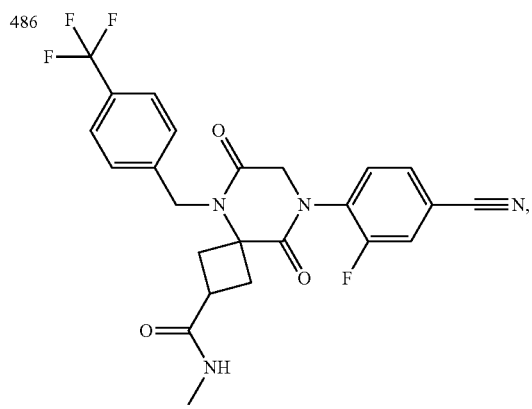 |
| 487 | 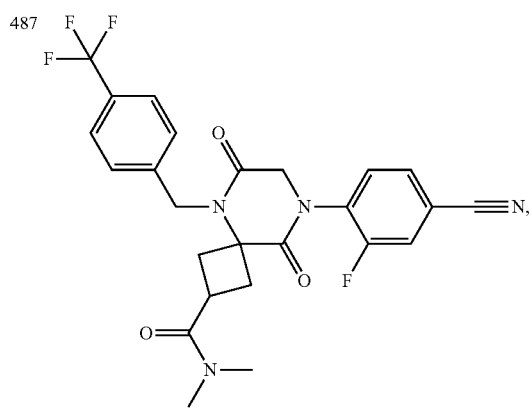 |

| No. | Structure |
|---|---|
| 488 | 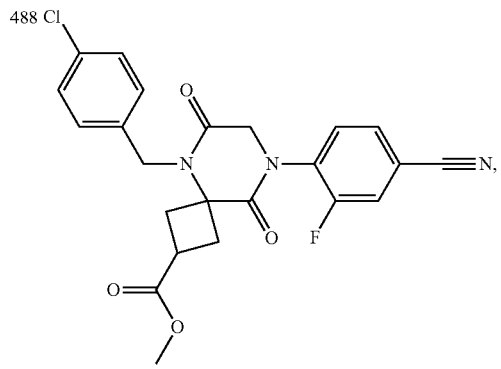 |
| 489 | 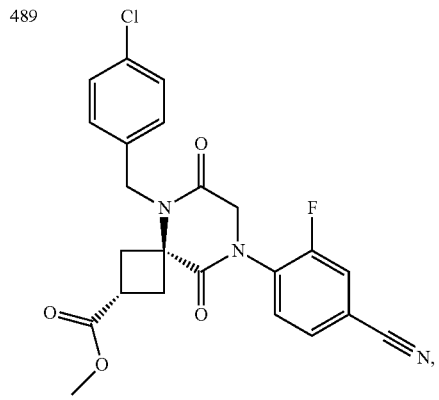 |
| 490 | 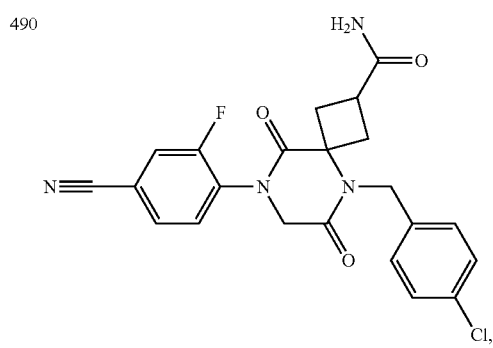 |
| 491 | 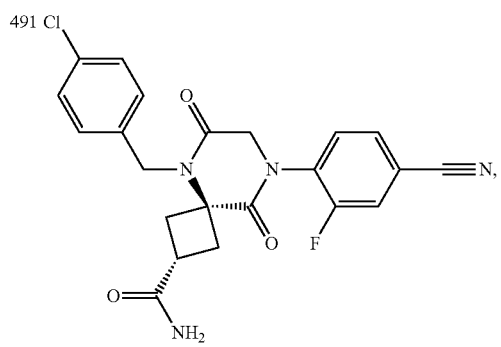 |

| No. | Structure |
|---|---|
| 492 | 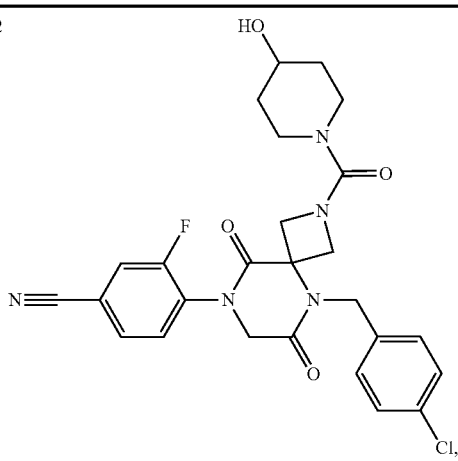 |
| 493 | 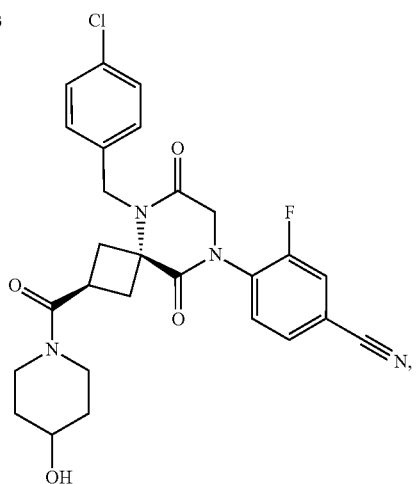 |
| 494 | 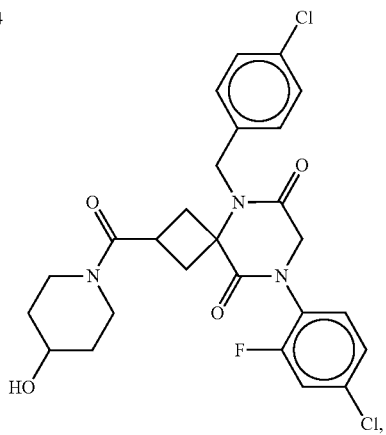 |

| No. | Structure |
|---|---|
| 495 | 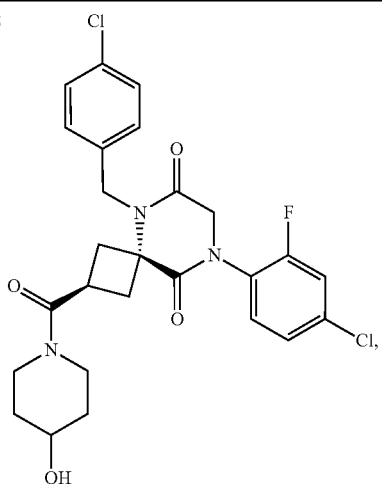 |
| 496 | 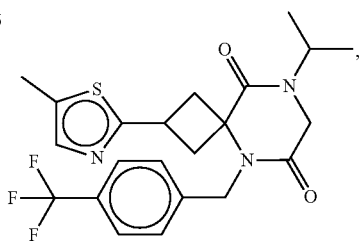 |
| 497 | 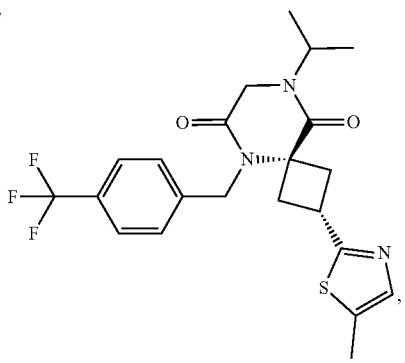 |
| 498 | 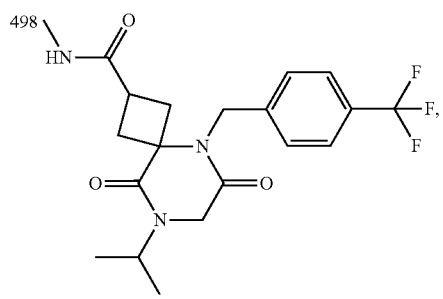 |

| No. | Structure |
|---|---|
| 499 | 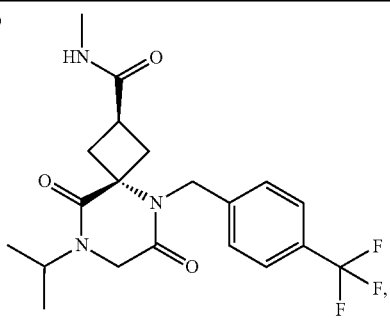 |
| 500 | 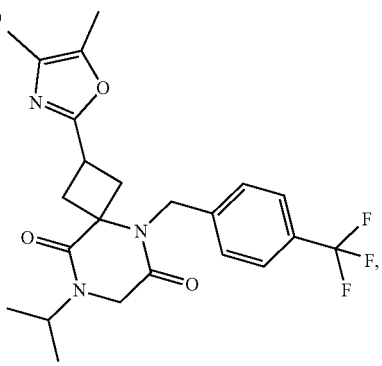 |
| 501 | 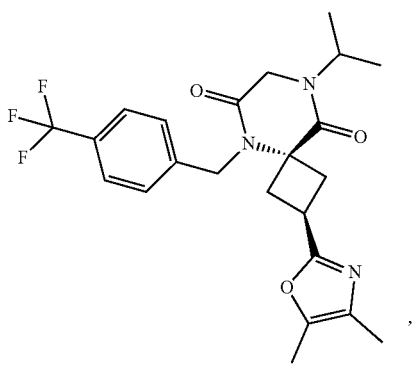 [SMILES: Cc1nc([C@H]2C[C@]3(C2)C(=O)N(C(C)C)CC(=O)N3Cc2ccc(C(F)(F)F)cc2)oc1C] |
| 502 | 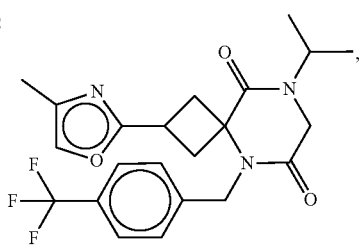 |
| 503 | 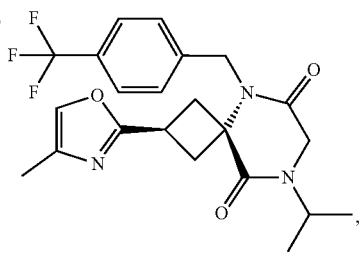 |

| No. | Structure |
|---|---|
| 504 | 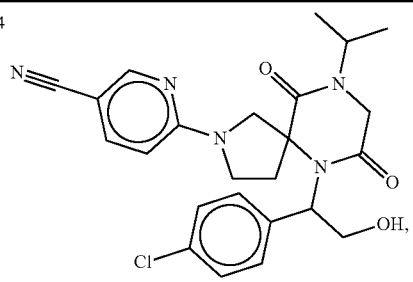 |
| 505 | 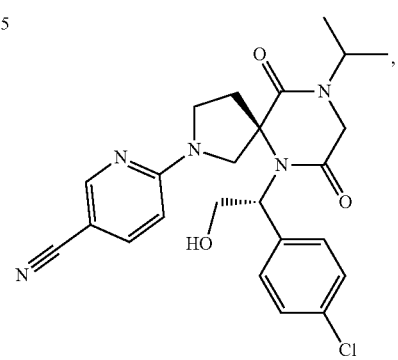 |
| 506 | 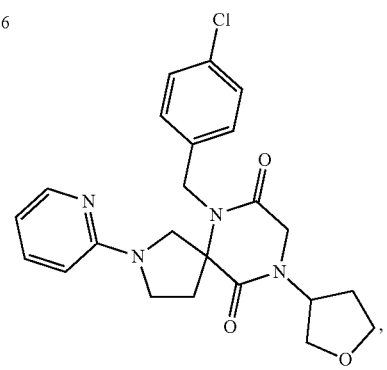 |
| 507 | 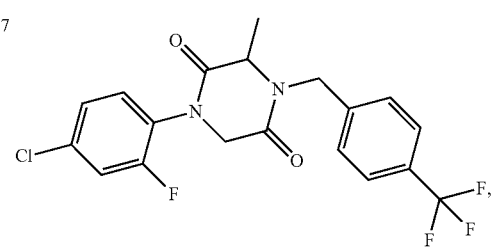 |
| 508 | 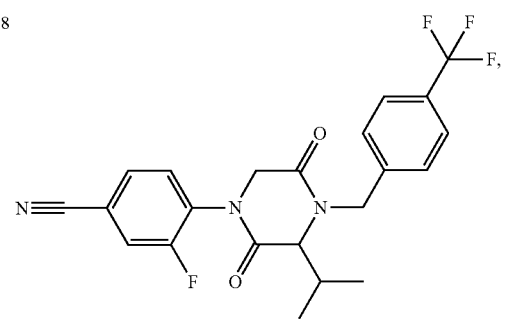 |

-continued
| No. | Structure |
|---|---|
| 509 | 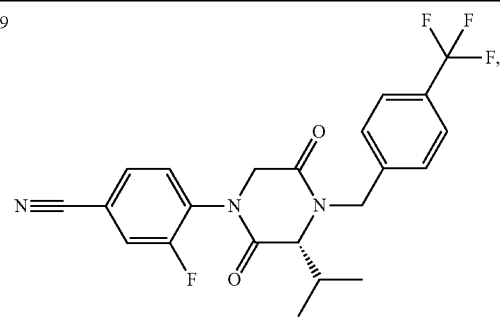 |
| 510 | 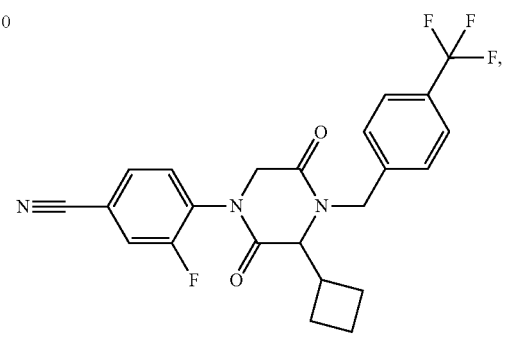 |
| 511 | 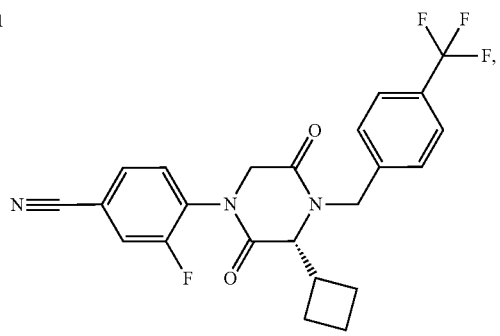 |
| 512 | 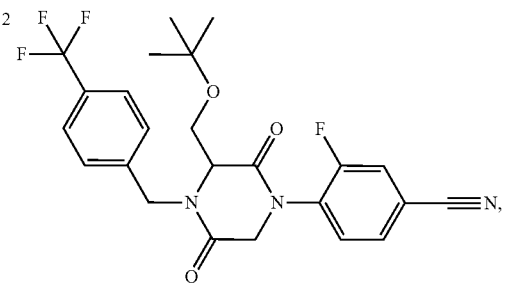 |
| 513 | 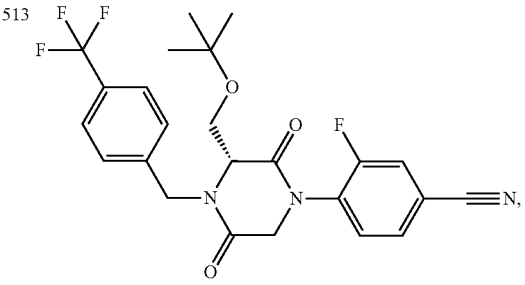 |

| No. | Structure |
|---|---|
| 514 | 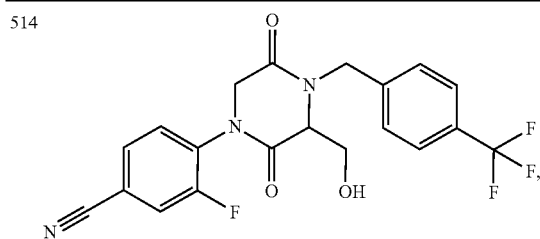 |
| 515 | 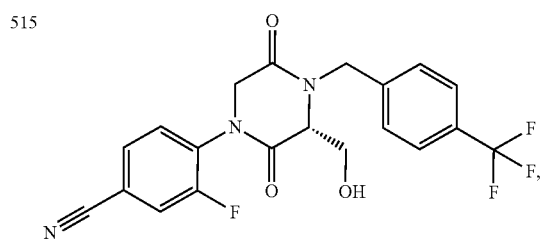 |
| 516 | 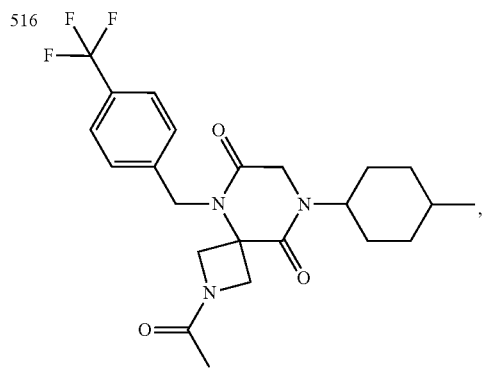 |
| 517 | 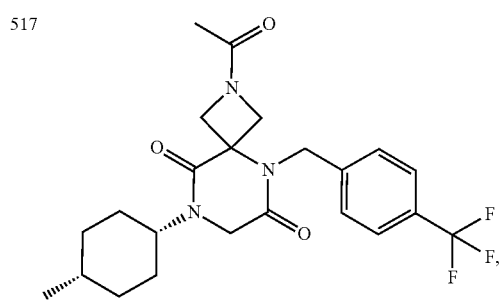 |
| 518 | 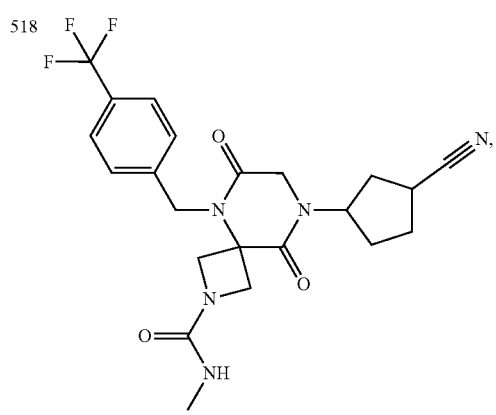 |

| No. | Structure |
|---|---|
| 519 | 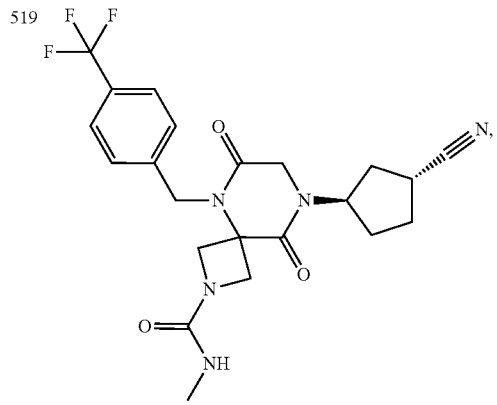 |
| 520 | 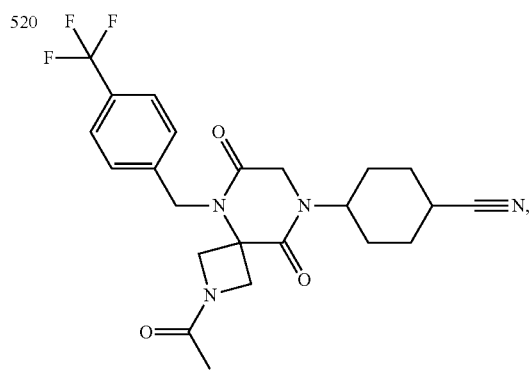 |
| 521 | 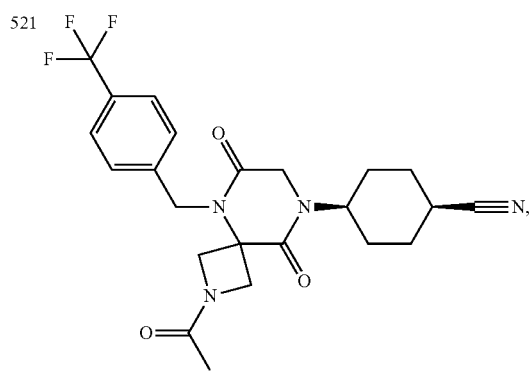 |
| 522 | 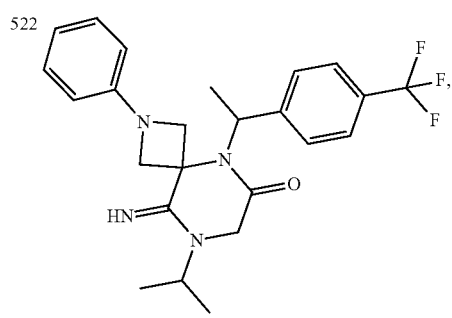 |

| No. | Structure |
|---|---|
| 523 | 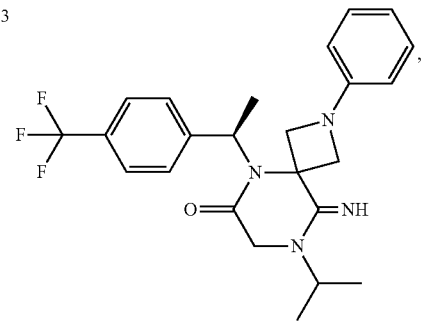 |
| 524 | 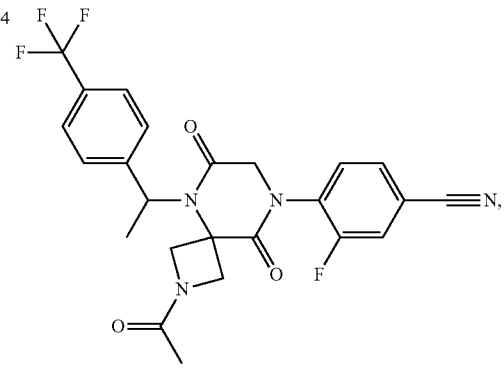 |
| 525 | 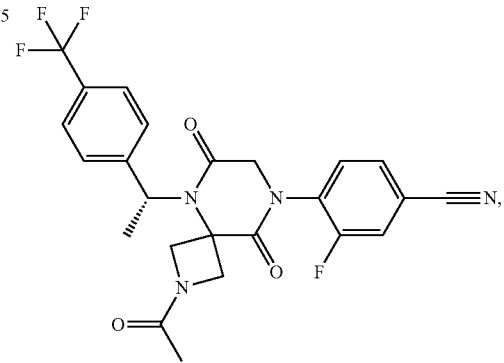 |
| 526 | 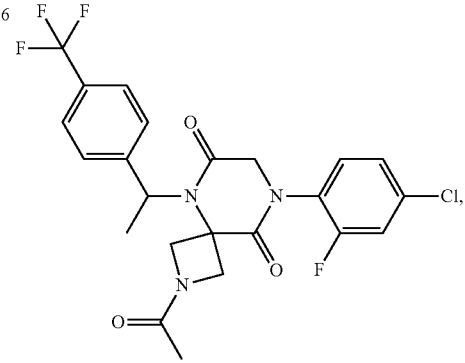 |

| No. | Structure |
|-----|-----------|
| 527 | 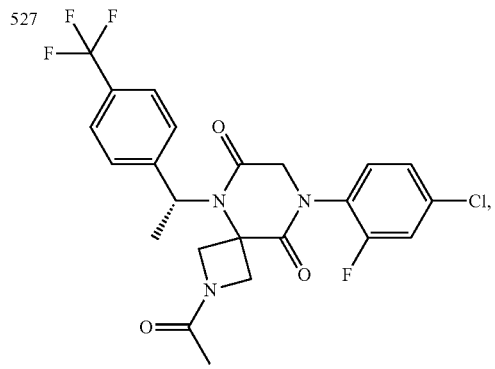 |
| 528 | 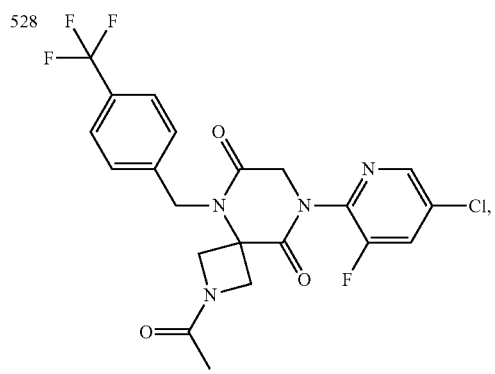 |
| 529 | 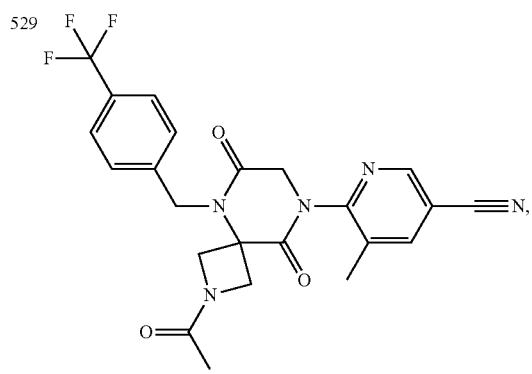 |
| 530 | 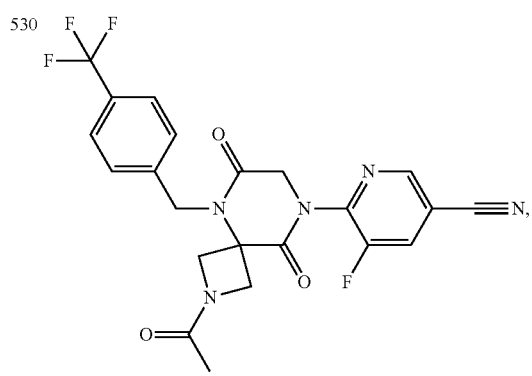 |

US 11,414,424 B2
| No. | Structure |
|---|---|
| 531 | 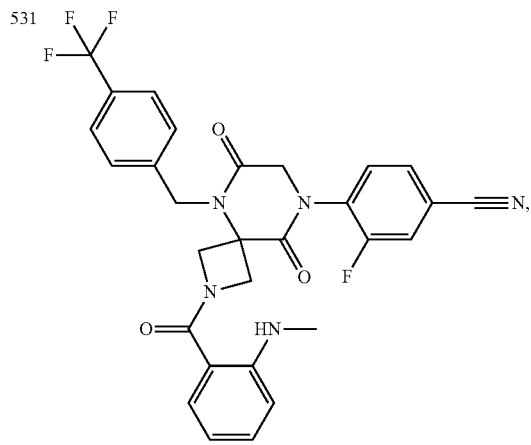 |
| 532 | 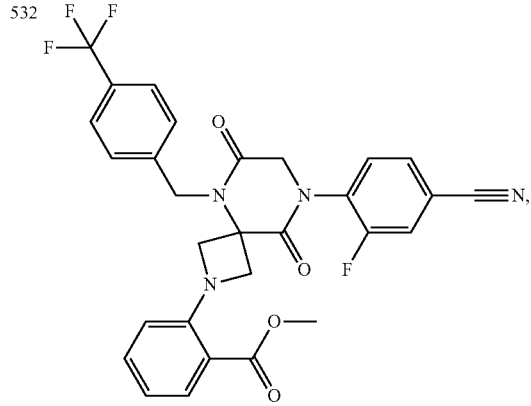 |
| 533 | 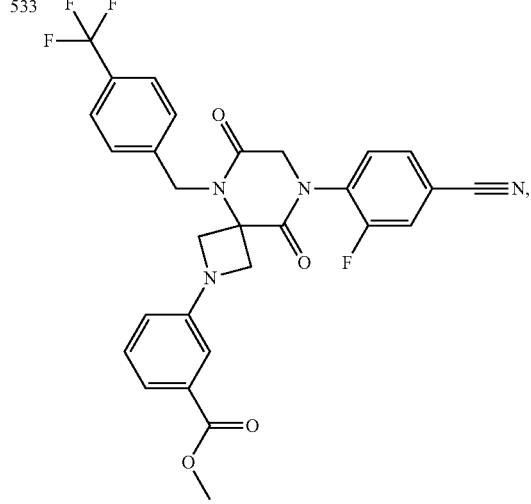 |

| No. | Structure |
|---|---|
| 534 | 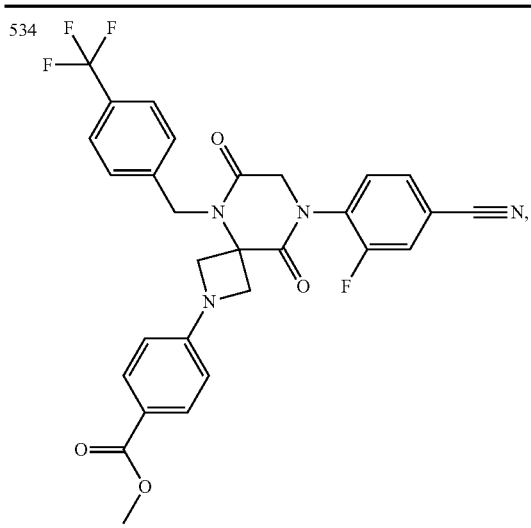 |
| 535 | 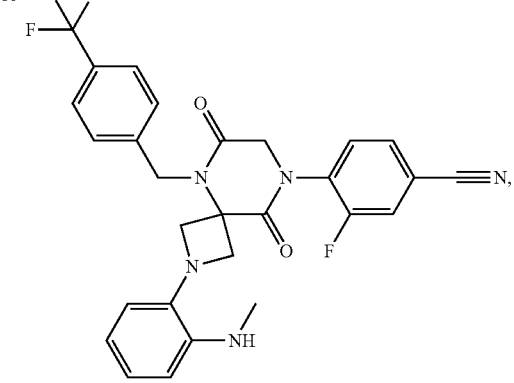 |
| 536 | 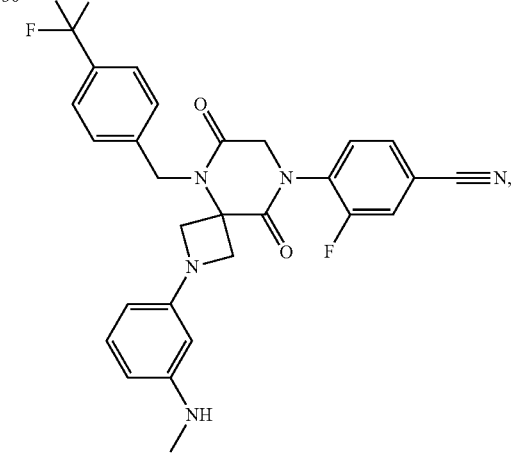 |

| No. | Structure |
|---|---|
| 537 | 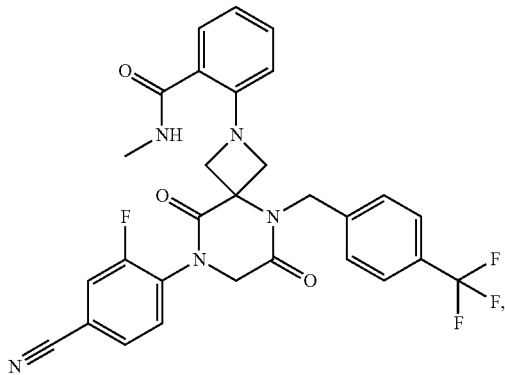 |
| 538 | 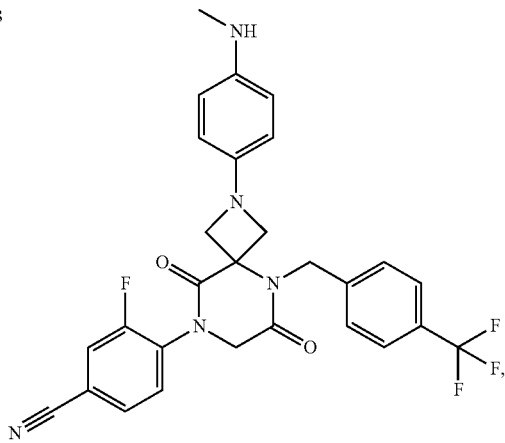 |
| 539 | 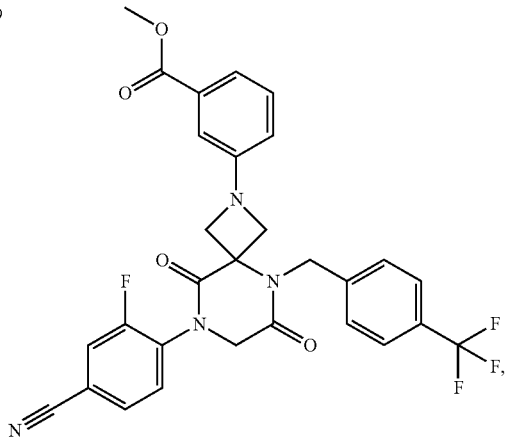 |

-continued
| No. | Structure |
|---|---|
| 540 | 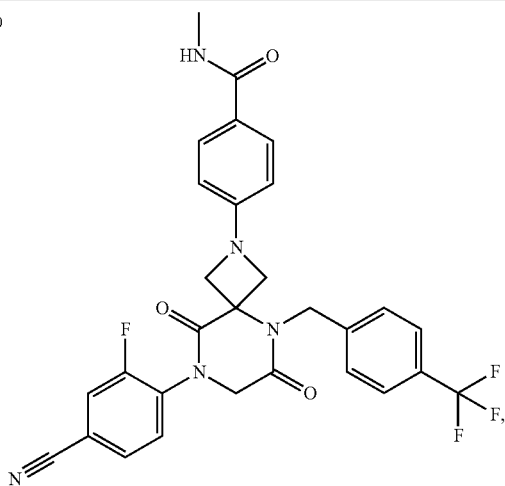 |
| 541 | 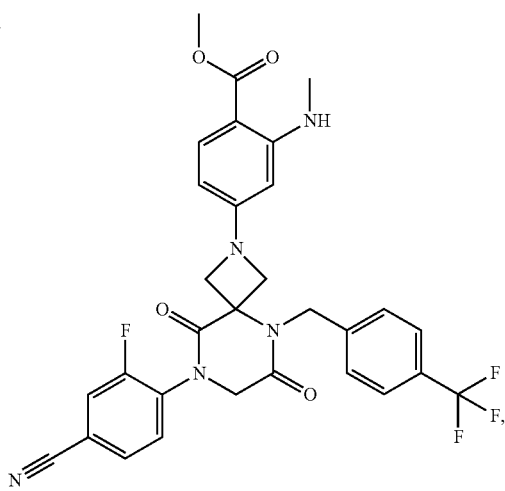 [SMILES: CNc1cc(N2CC3(C2)C(=O)N(c2ccc(C#N)cc2F)CC(=O)N3Cc2ccc(C(F)(F)F)cc2)ccc1C(=O)OC] |
| 542 | 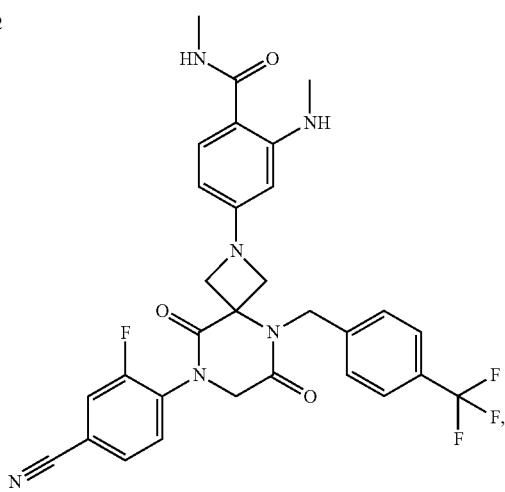 |

| No. | Structure |
|---|---|
| 543 | 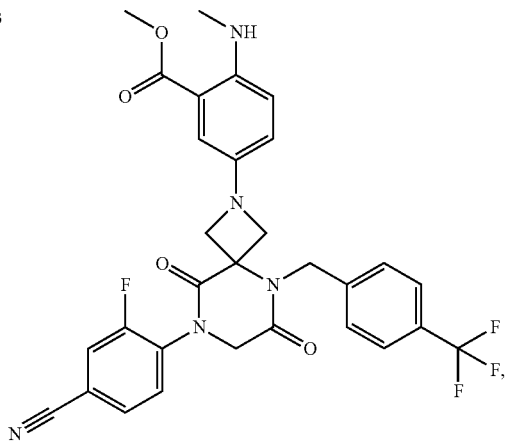 |
| 544 | 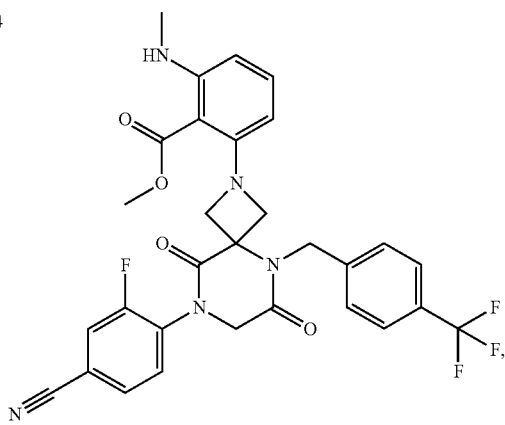 |
| 545 | 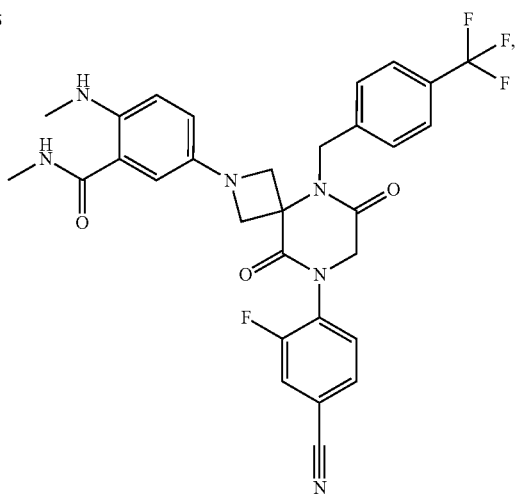 |

-continued
| No. | Structure |
|---|---|
| 546 | 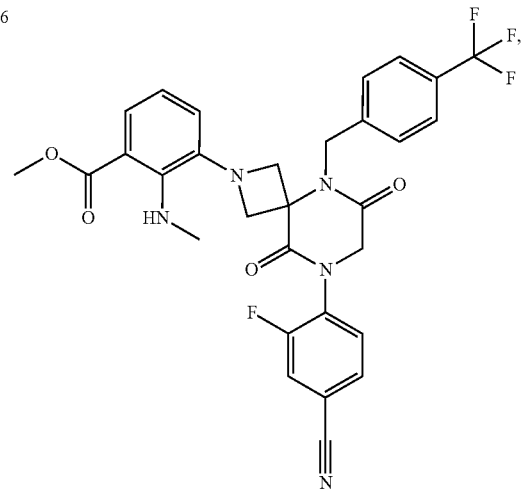 |
| 547 | 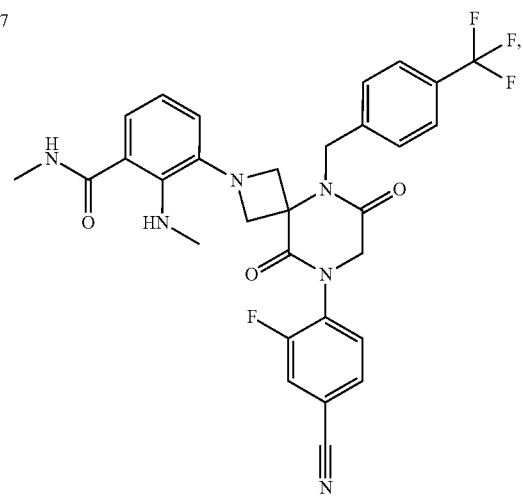 |
| 548 | 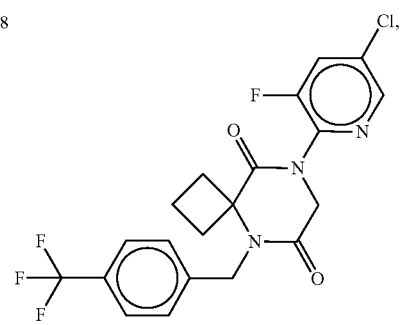 |
| 549 | 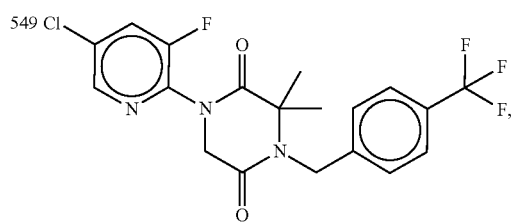 |

| No. | Structure |
|---|---|
| 550 | 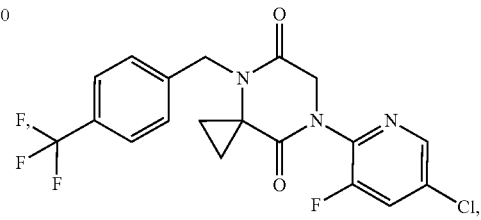 |
| 551 | 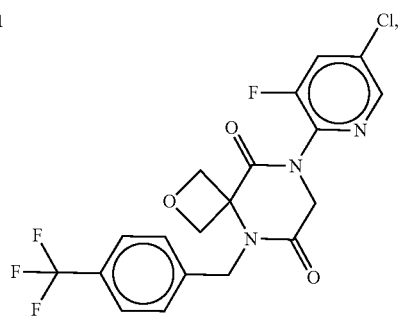 |
| 552 | 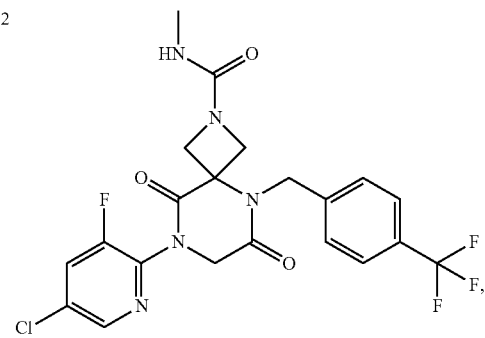 |
| 553 | 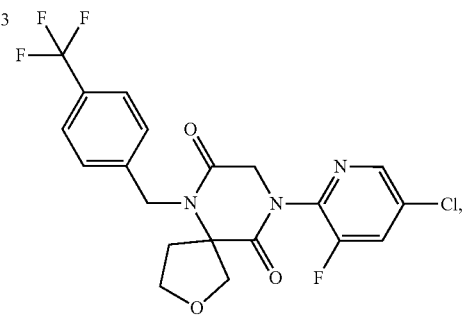 |
| 554 | 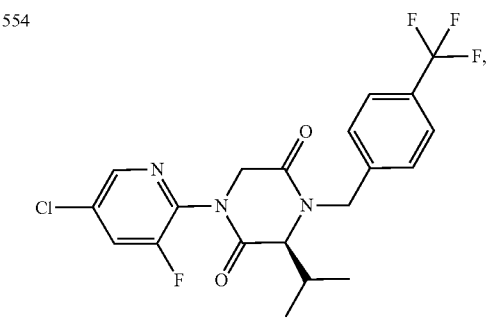 |

| No. | Structure |
|---|---|
| 555 | 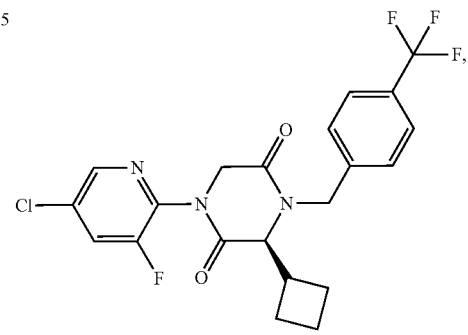 |
| 556 | 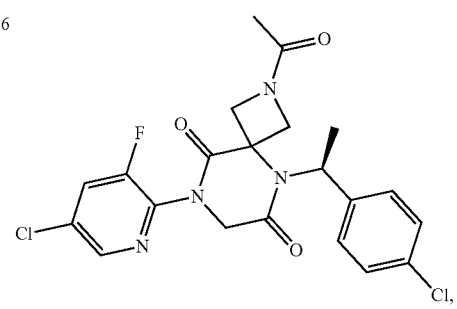 |
| 557 | 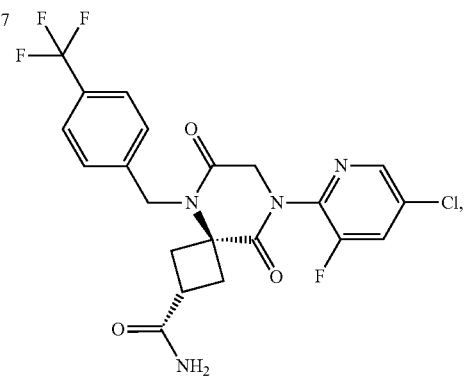 |
| 558 | 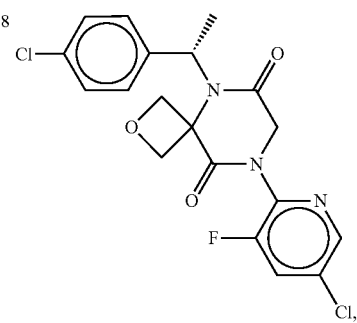 |

| No. | Structure |
|---|---|
| 559 | 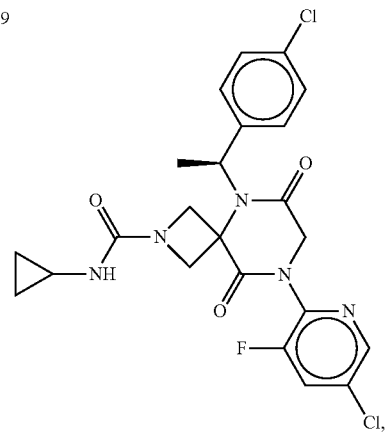 |
| 560 | 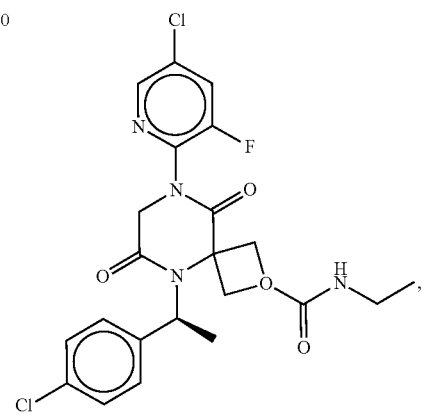 |
| 561 | 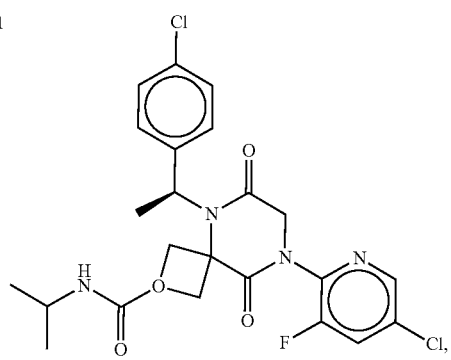 |
| 562 | 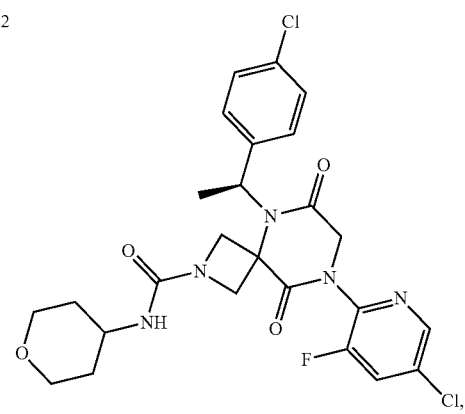 |

| No. | Structure |
|---|---|
| 563 | 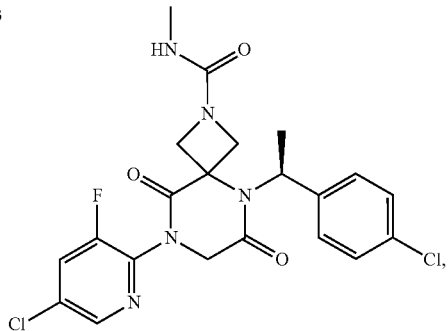 |
| 564 | 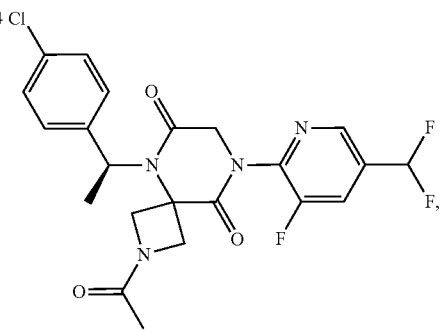 |
| 565 | 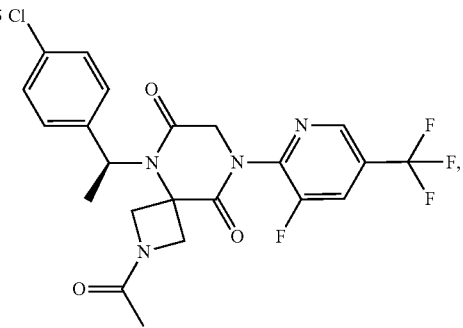 |
| 566 | 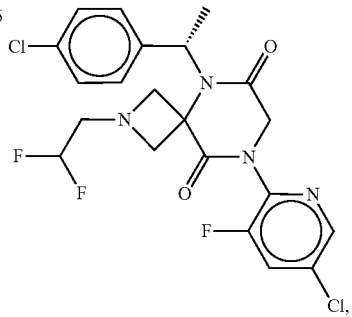 |

-continued
| No. | Structure |
|---|---|
| 567 | 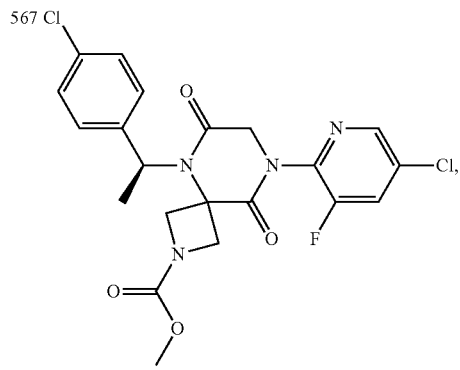 |
| 568 | 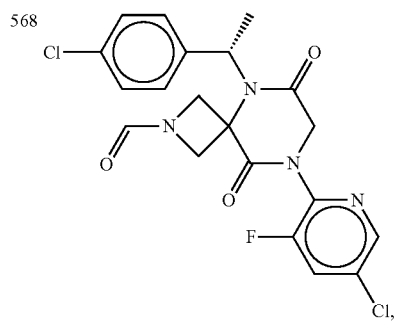 |
| 569 | 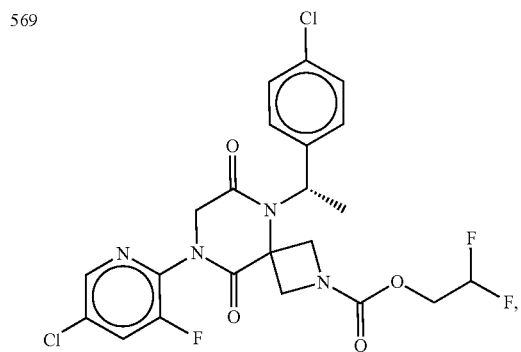 |
| 570 | 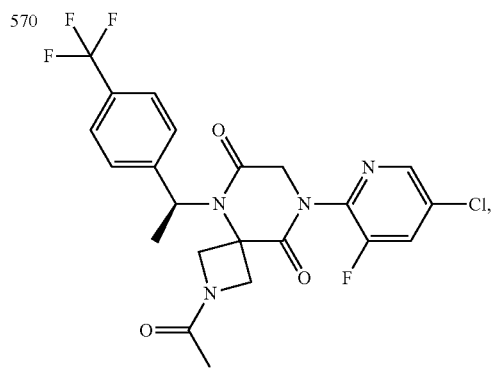 |

| No. | Structure |
|---|---|
| 571 | 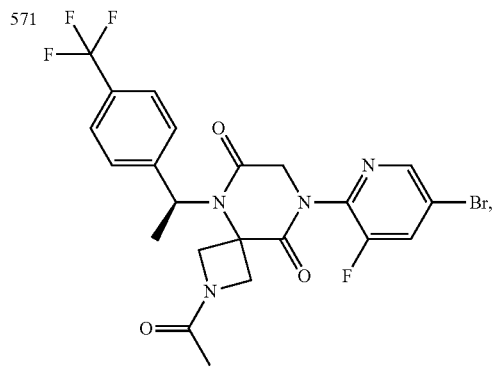 |
| 572 | 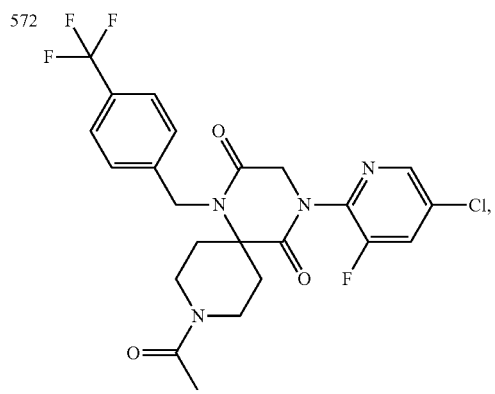 |
| 573 | 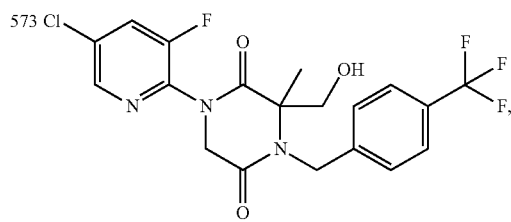 |
| 574 | 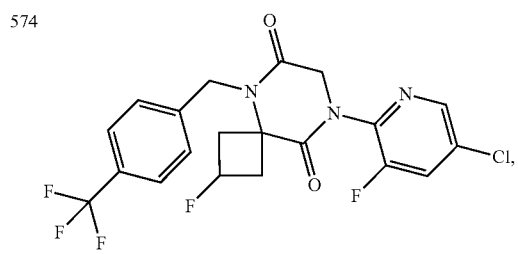 |
| 575 | 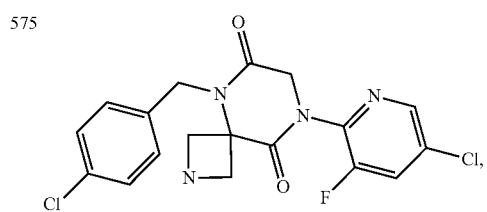 |

| No. | Structure |
|---|---|
| 576 | 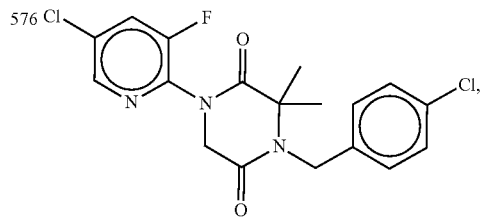 |
| 577 | 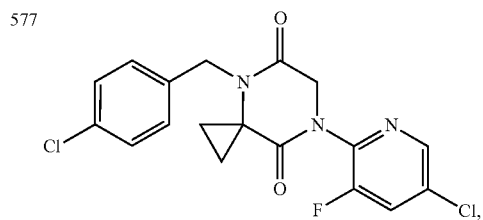 |
| 578 | 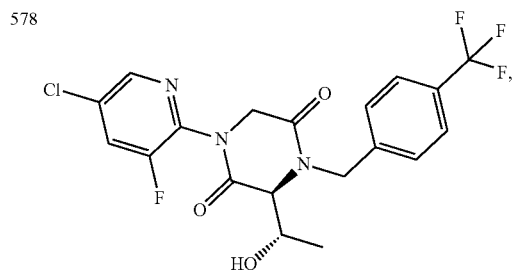 |
| 579 | 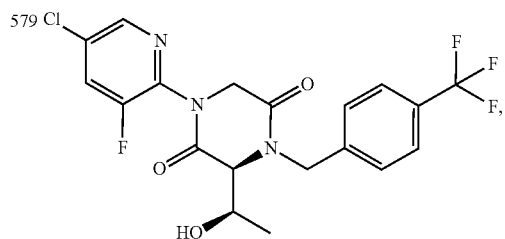 |
| 580 | 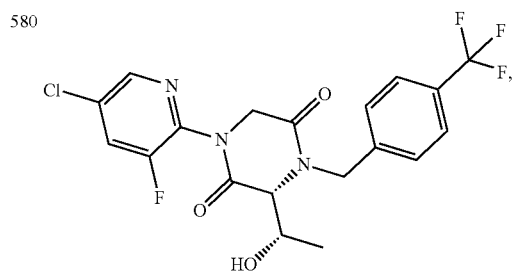 |
| 581 | 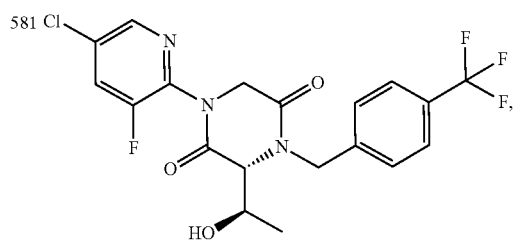 |

| No. | Structure |
|---|---|
| 582 | 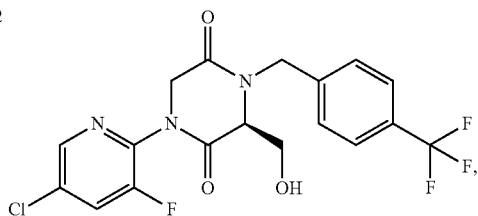 |
| 583 | 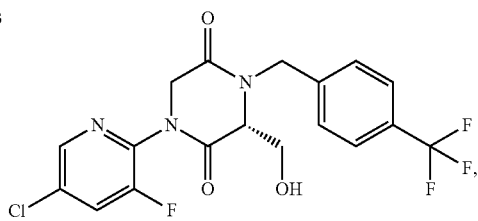 |
| 584 | 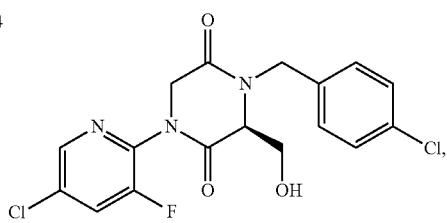 |
| 585 | 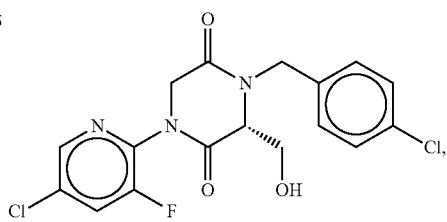 |
| 586 | 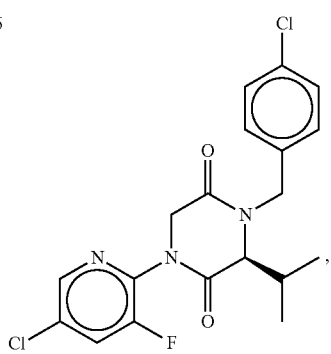 |
| 587 | 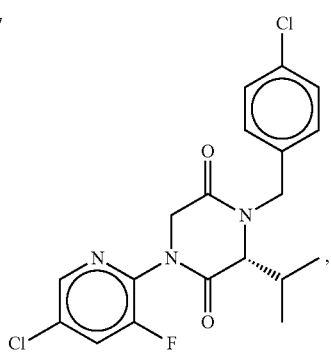 |

| No. | Structure |
|---|---|
| 588 | 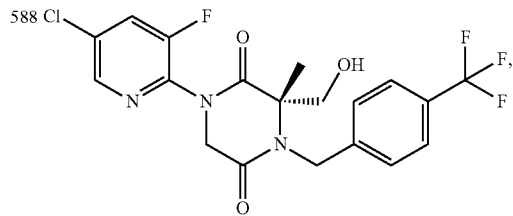 |
| 589 | 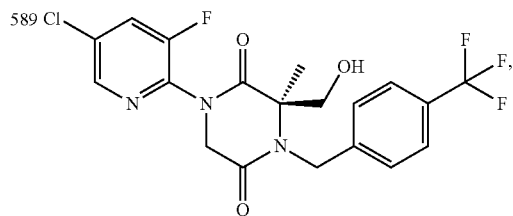 |
| 590 | 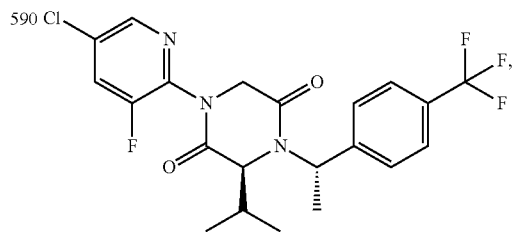 |
| 591 | 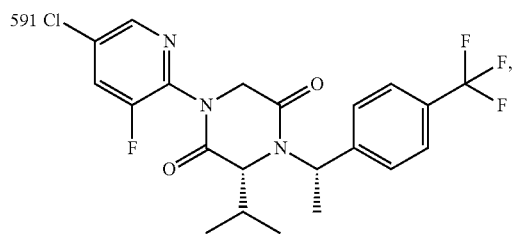 |
| 592 | 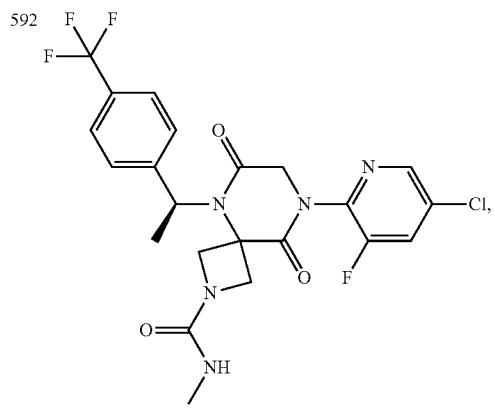 |

| No. | Structure |
|---|---|
| 593 | 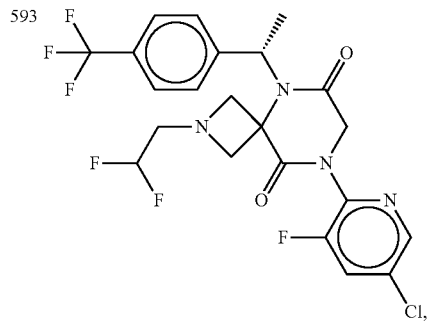 |
| 594 | 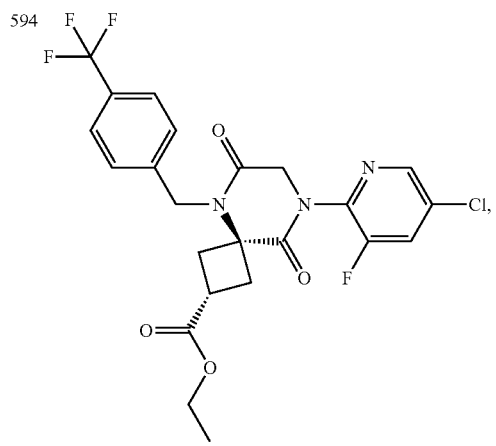 |
| 595 | 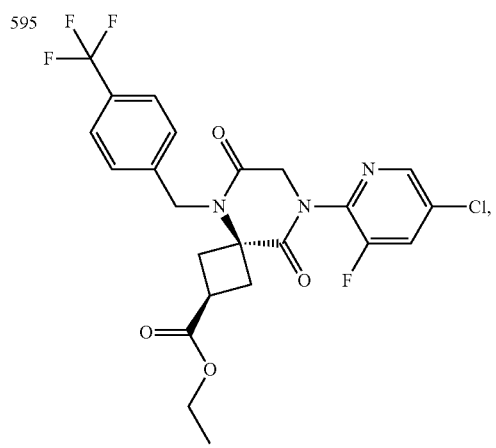 |
| 596 | 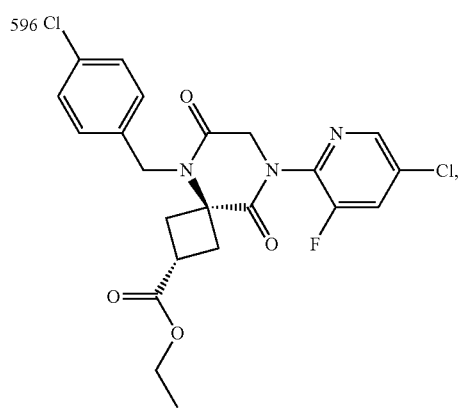 |

| No. | Structure |
|---|---|
| 597 | 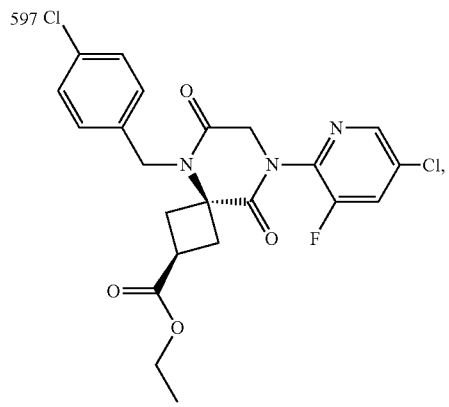 |
| 598 | 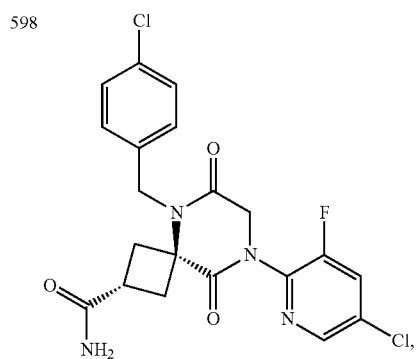 |
| 599 | 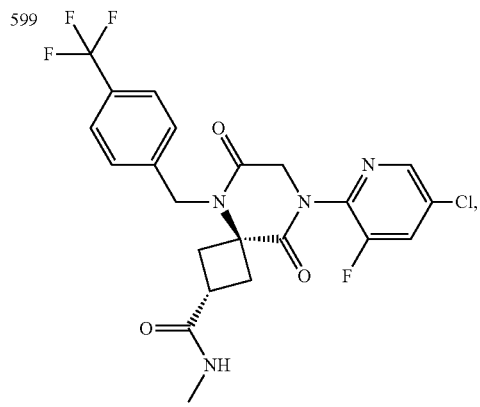 |
| 600 | 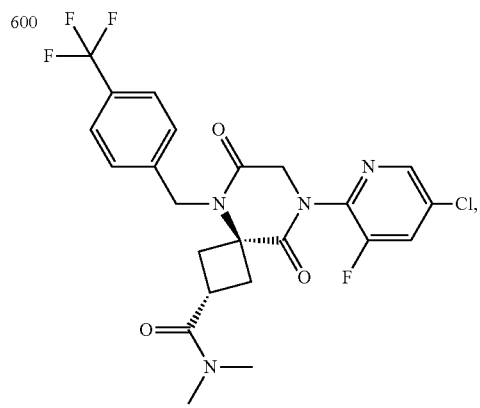 |

| No. | Structure |
|---|---|
| 601 | 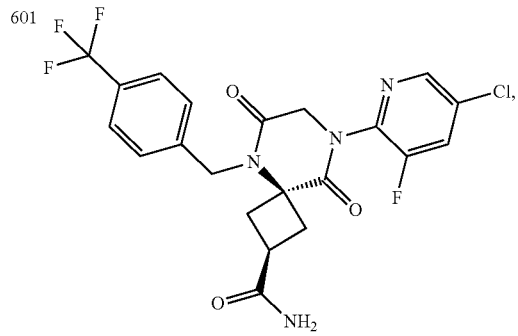 |
| 602 | 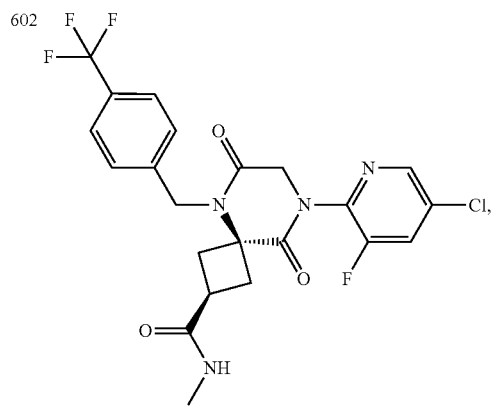 |
| 603 | 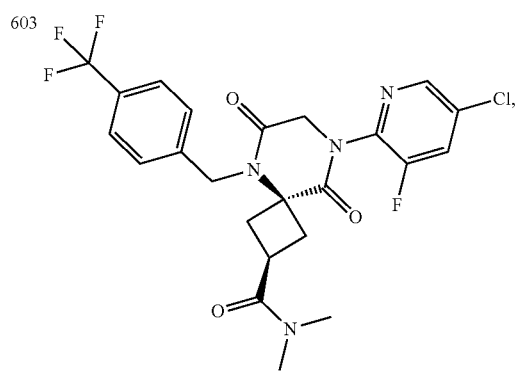 |
| 604 | 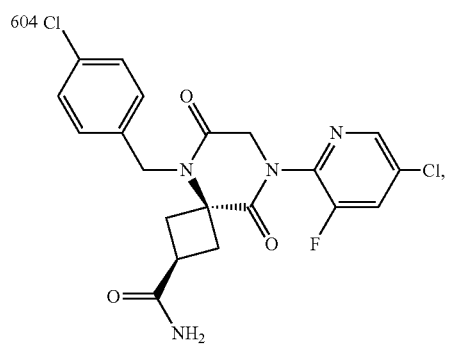 |

| No. | Structure |
|---|---|
| 605 | 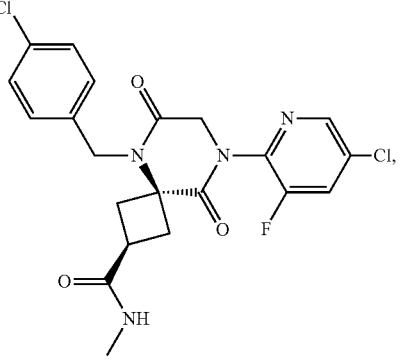 |
| 606 | 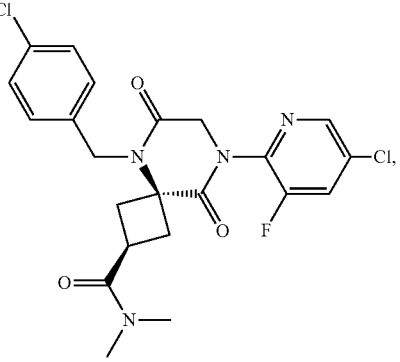 |
| 607 | 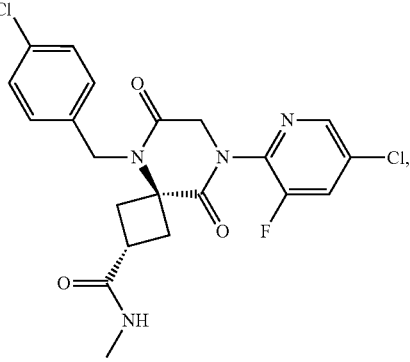 |
| 608 | 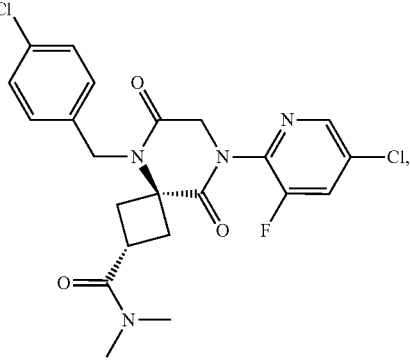 |

| No. | Structure |
|---|---|
| 609 | 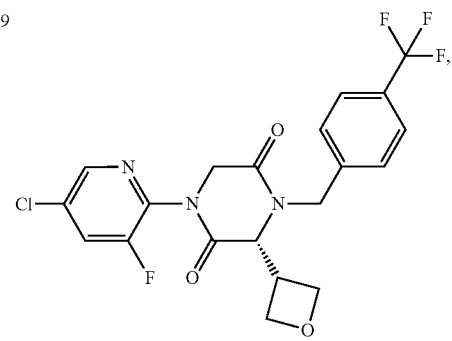 |
| 610 | 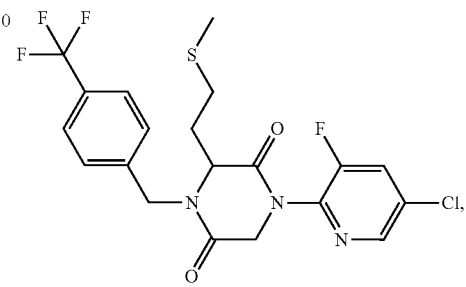 |
| 611 | 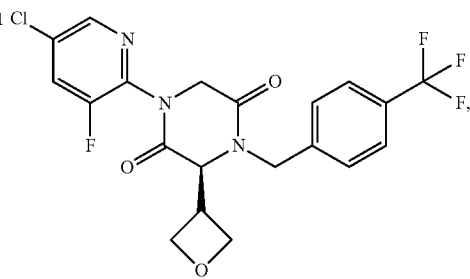 |
| 612 | 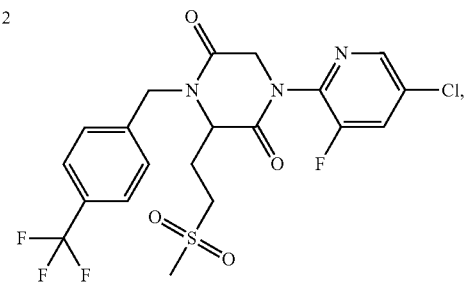 |
| 613 | 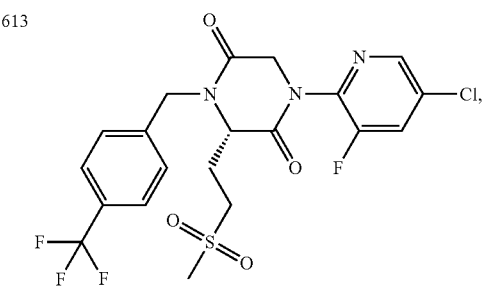 |

| No. | Structure |
|---|---|
| 614 | 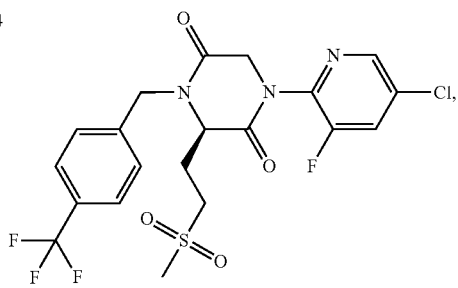 |
| 615 | 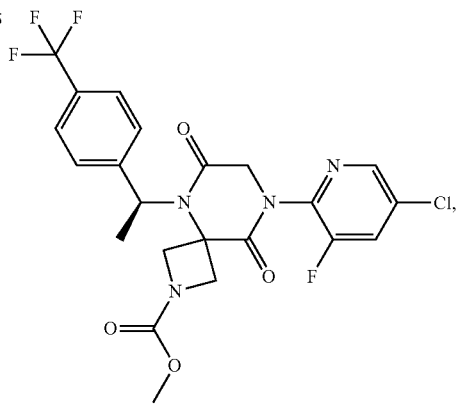 |
| 616 | 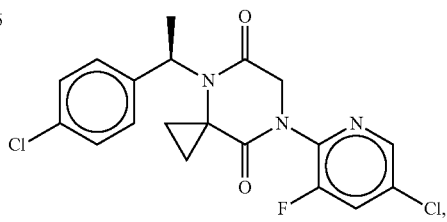 |
| 617 | 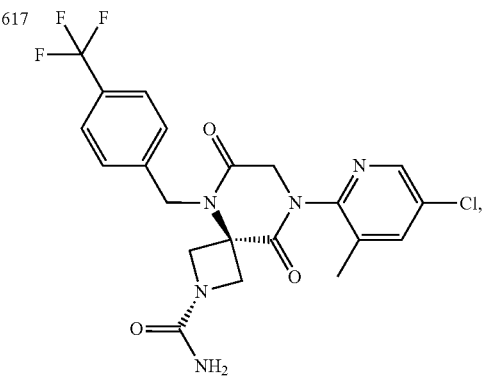 |

| No. | Structure |
|---|---|
| 618 | 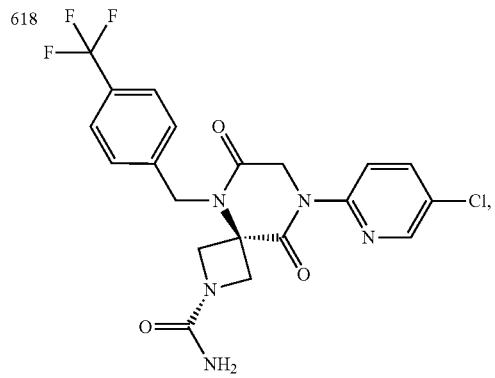 |
| 619 | 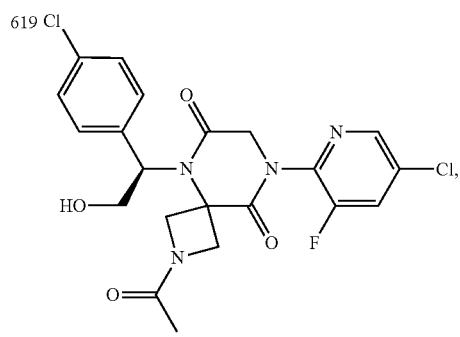 |
| 620 | 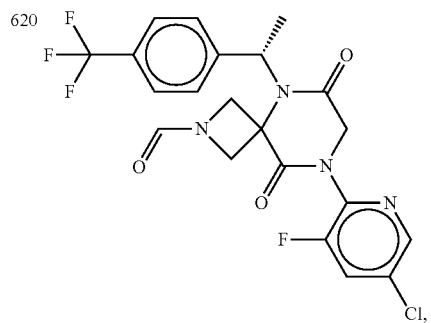 |
| 621 | 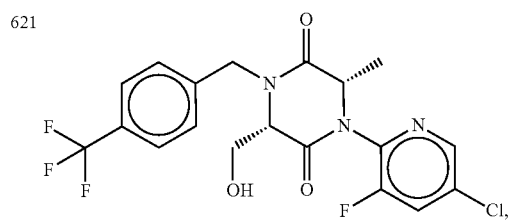 |
| 622 | 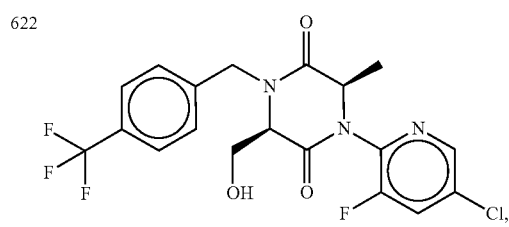 |

| No. | Structure |
|---|---|
| 623 | 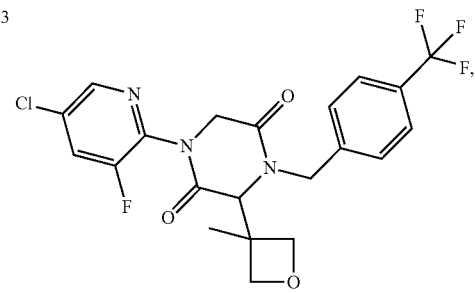 |
| 624 | 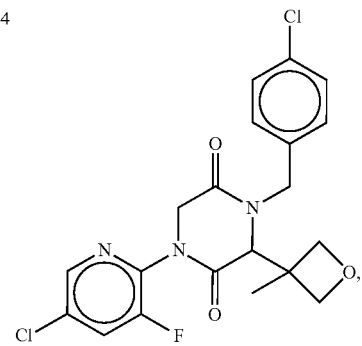 |
| 625 | 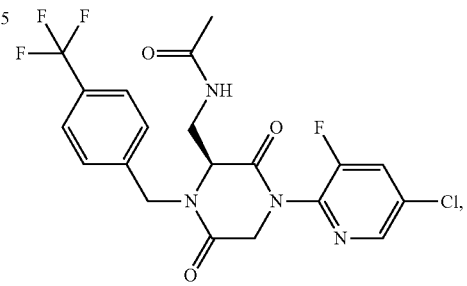 |
| 626 | 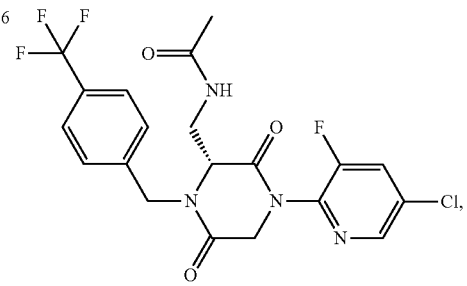 |
| 627 | 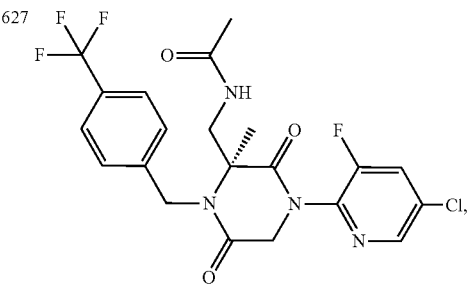 |

| No. | Structure |
|---|---|
| 628 | 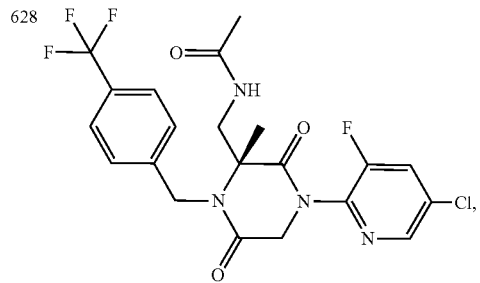 |
| 629 | 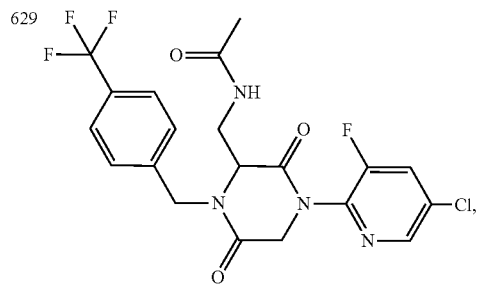 |
| 630 | 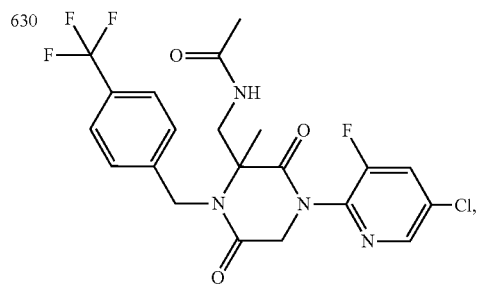 |
| 631 | 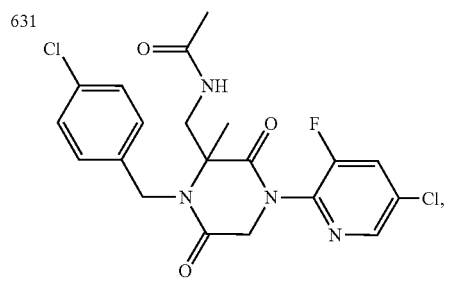 |
| 632 | 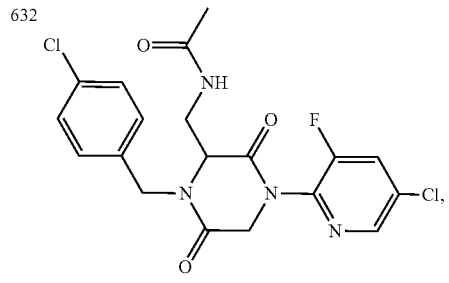 |

| No. | Structure |
|---|---|
| 633 | 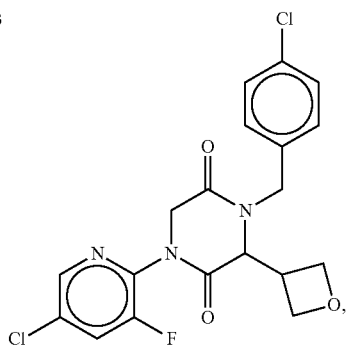 |
| 634 | 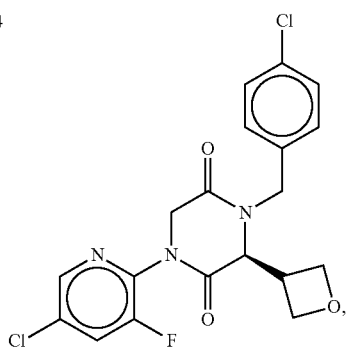 |
| 635 | 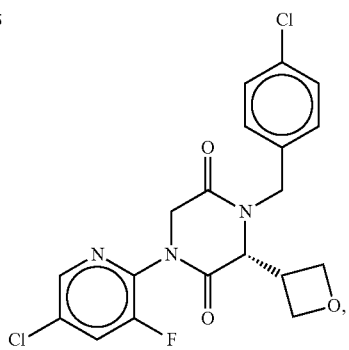 |
| 636 | 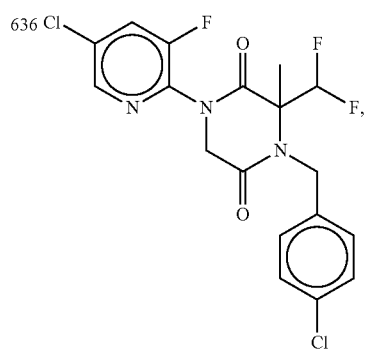 |

-continued
| No. | Structure |
|---|---|
| 637 | 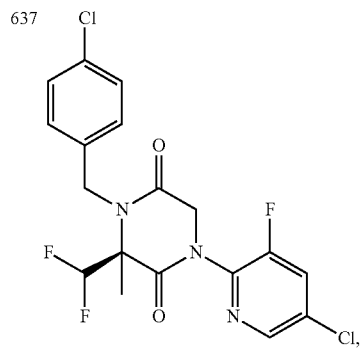 |
| 638 | 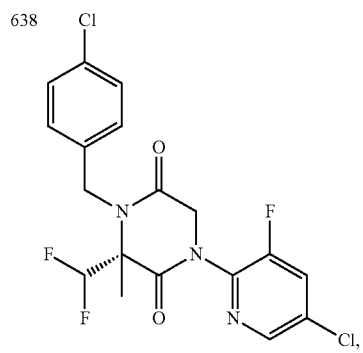 |
| 639 | 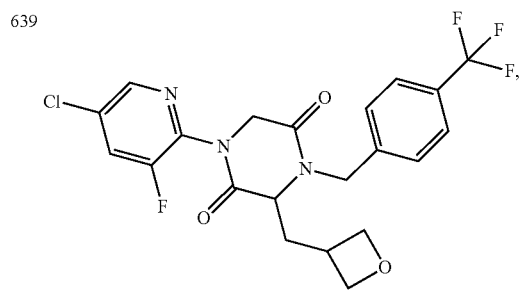 |
| 640 | 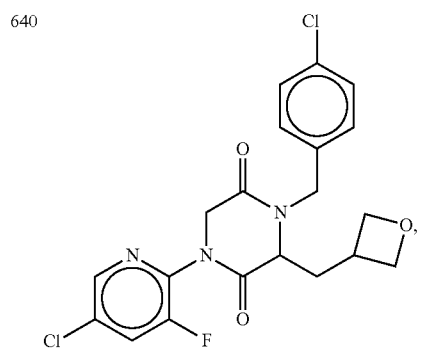 |

-continued
| No. | Structure |
|---|---|
| 641 | 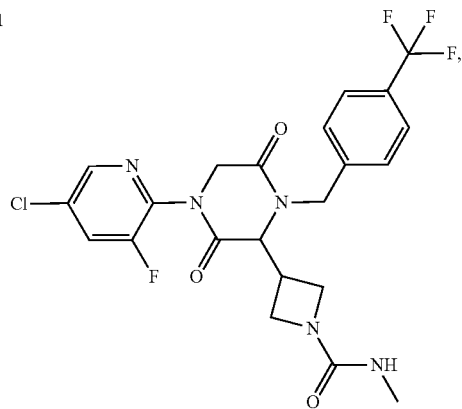 |
| 642 | 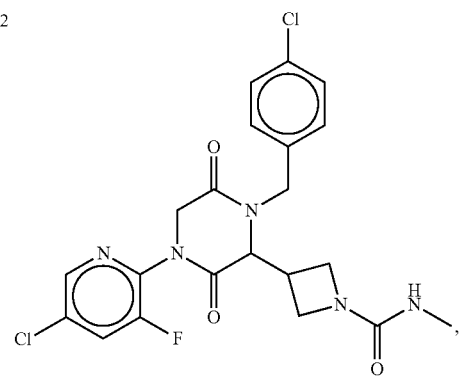 |
| 643 | 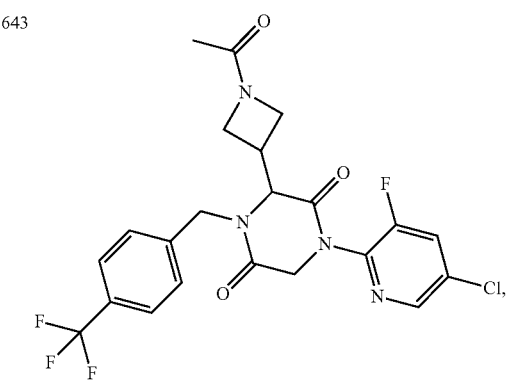 |
| 644 | 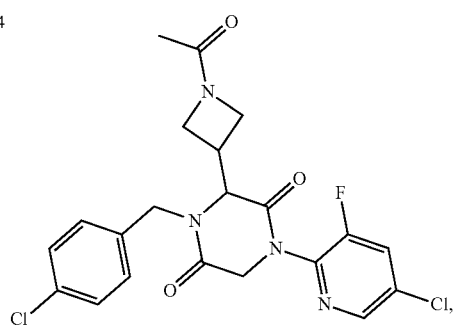 |

-continued
| No. | Structure |
|---|---|
| 645 | 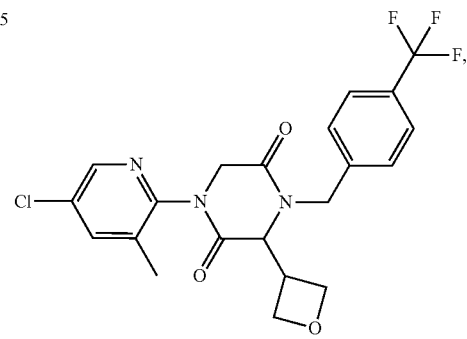 |
| 646 | 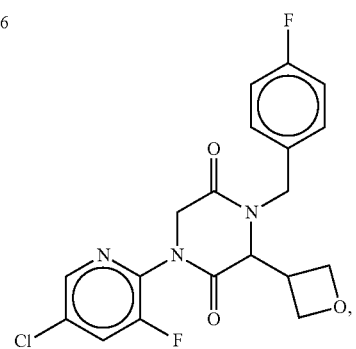 |
| 647 | 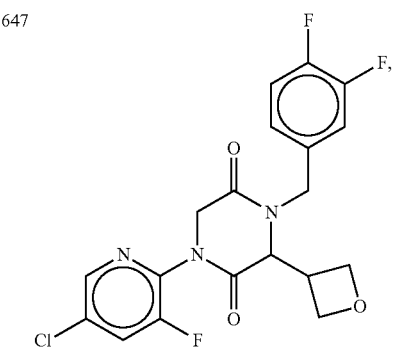 |
| 648 | 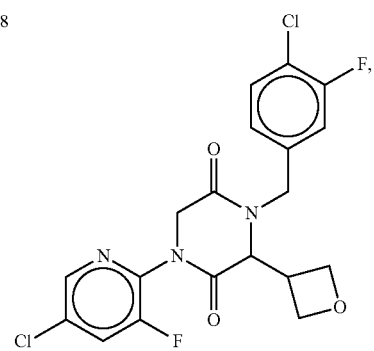 |

| No. | Structure |
|---|---|
| 649 | 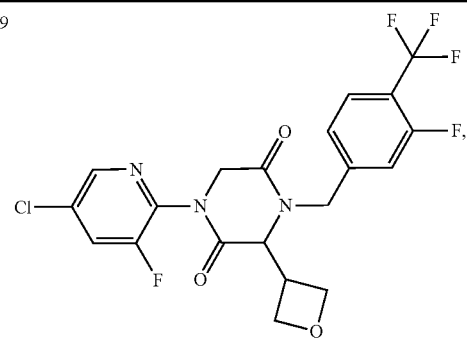 |
| 650 | 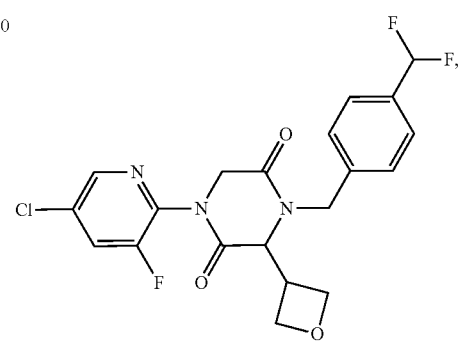 |
| 651 | 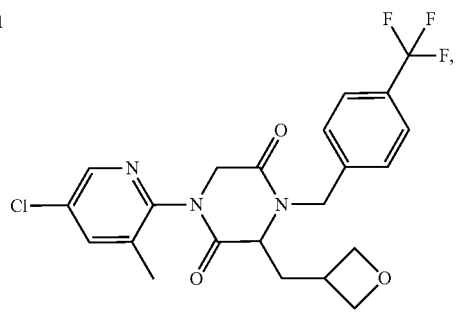 |
| 652 | 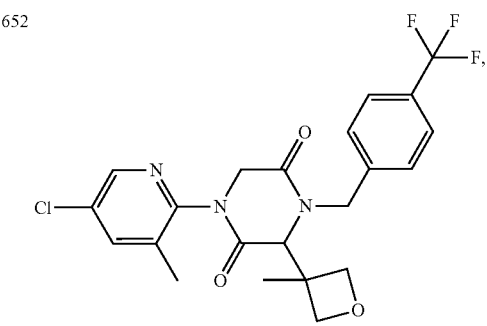 |

| No. | Structure |
|---|---|
| 653 | 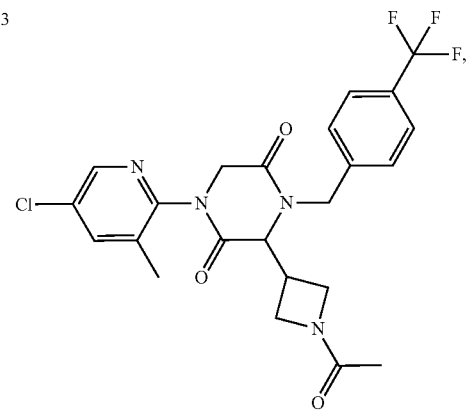 |
| 654 | 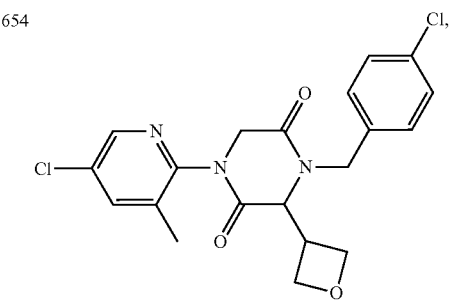 |
| 655 | 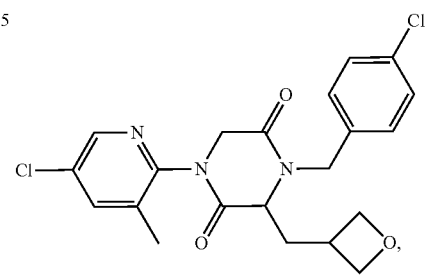 |
| 656 | 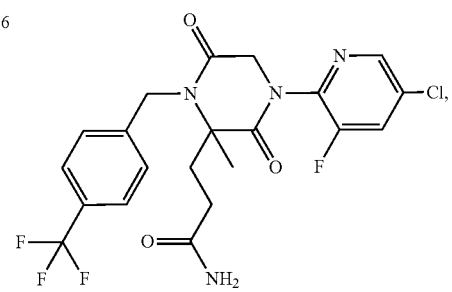 |
| 657 | 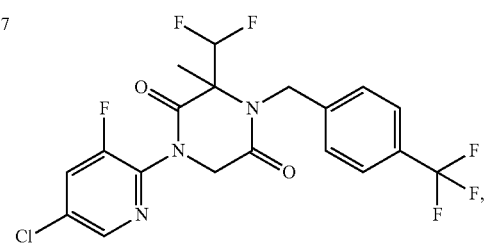 |

-continued
| No. | Structure |
|-----|-----------|
| 658 | 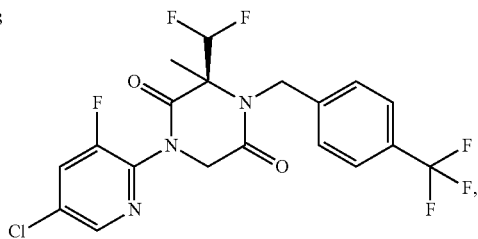 |
| 659 | 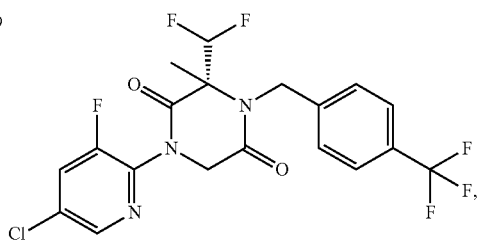 |
| 660 | 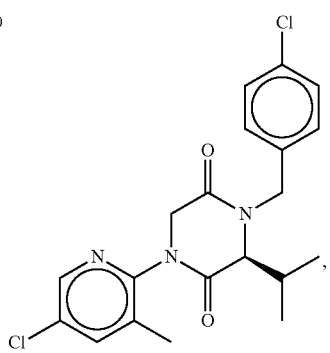 |
| 661 | 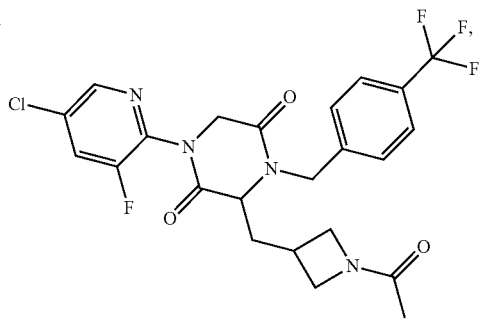 |
| 662 | 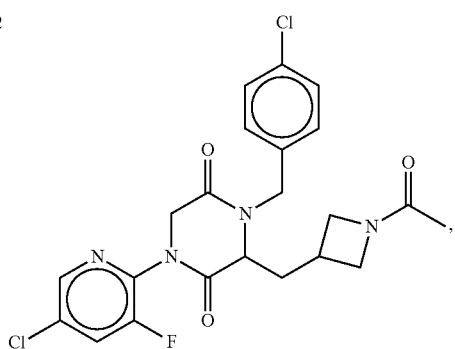 |

| No. | Structure |
|---|---|
| 663 | 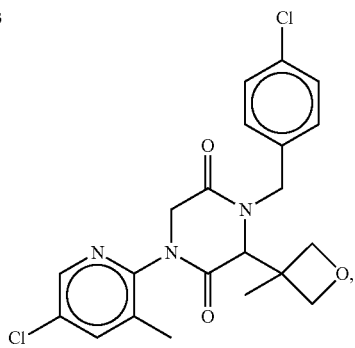 |
| 664 | 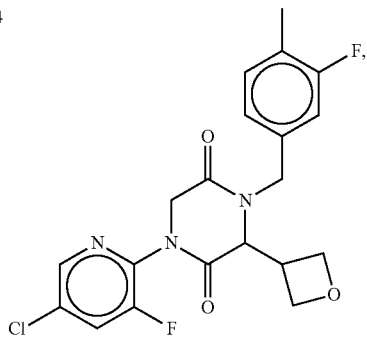 |
| 665 | 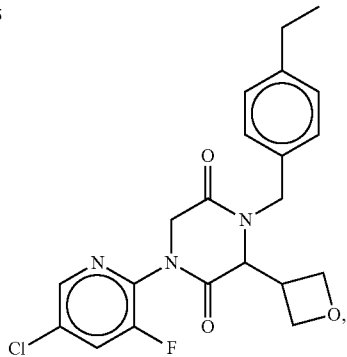 |
| 666 | 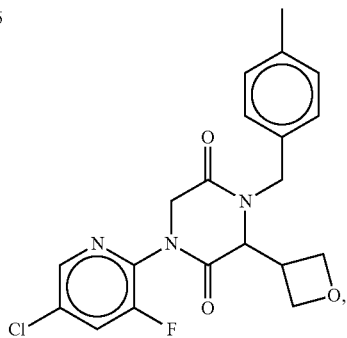 |

| No. | Structure |
|---|---|
| 667 | 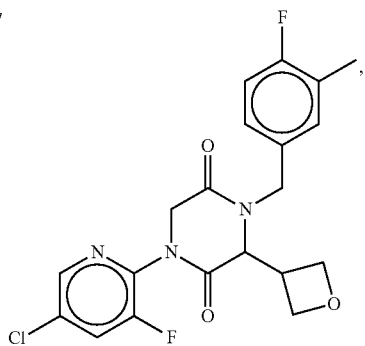 |
| 668 | 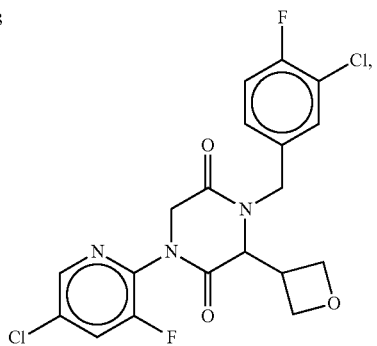 |
| 669 | 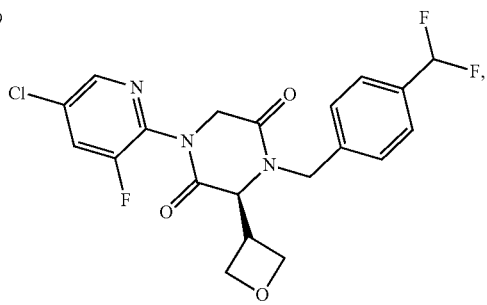 |
| 670 | 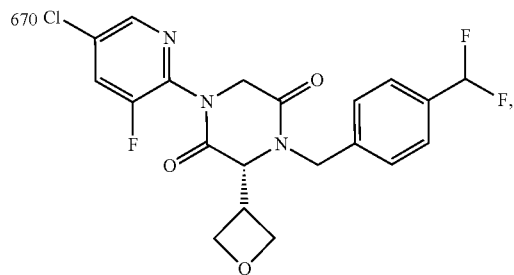 |

| No. | Structure |
|---|---|
| 671 | 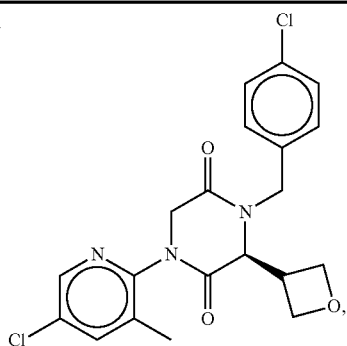 |
| 672 | 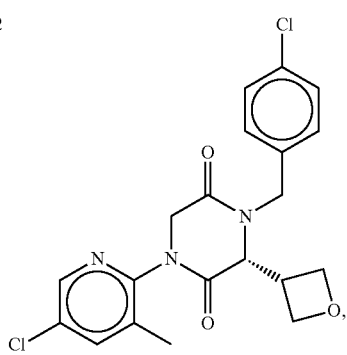 |
| 673 | 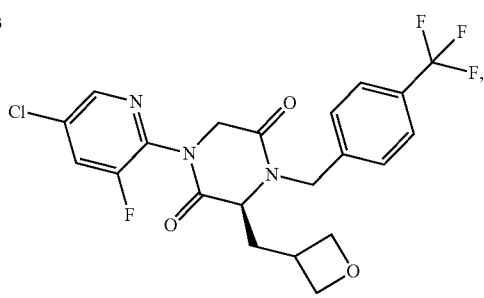 |
| 674 | 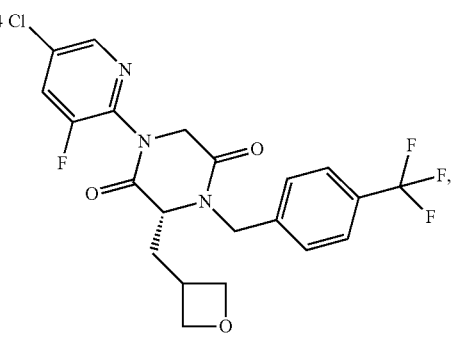 |
| 675 | 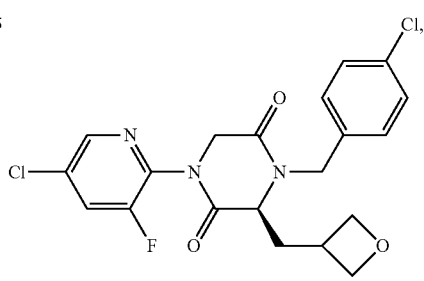 |

| No. | Structure |
|-----|-----------|
| 676 | 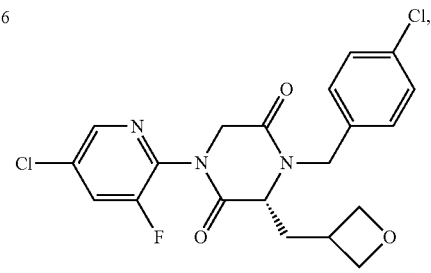 |
| 677 | 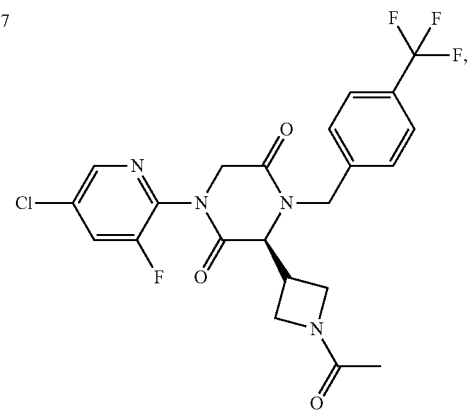 |
| 678 | 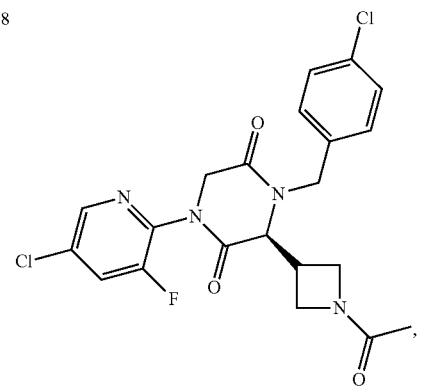 |
| 679 | 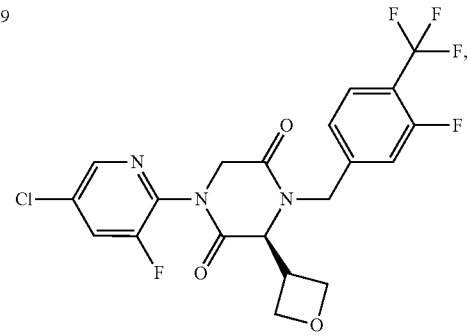 |

| No. | Structure |
|---|---|
| 680 | 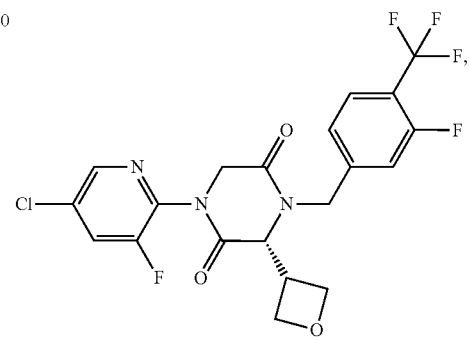 |
| 681 | 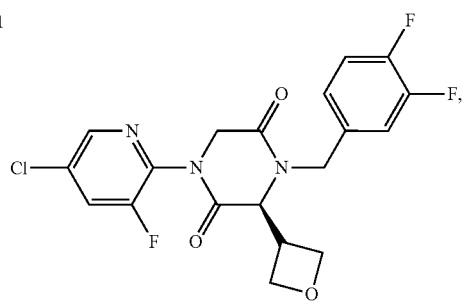 |
| 682 | 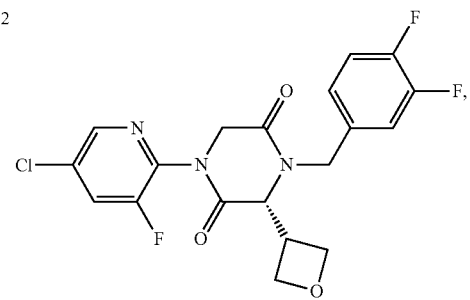 |
| 683 | 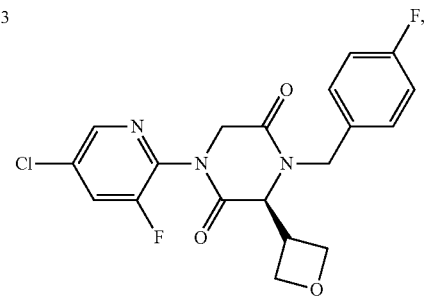 |
| 684 | 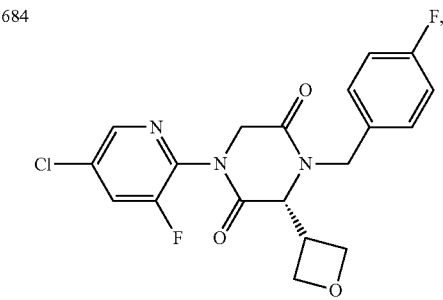 |

| No. | Structure |
|---|---|
| 685 | 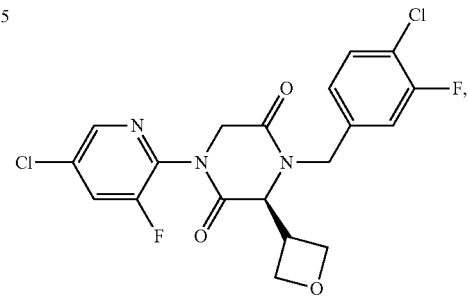 |
| 686 | 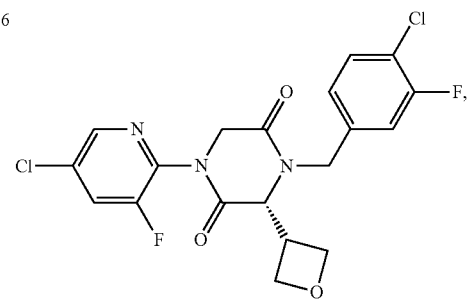 |
| 687 | 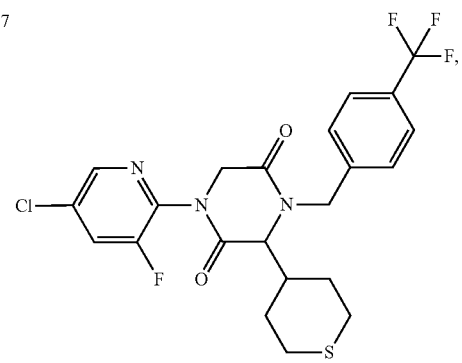 |
| 688 | 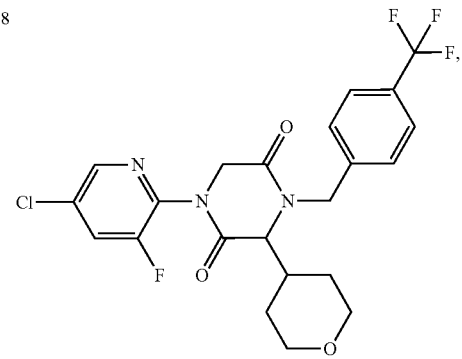 |

| No. | Structure |
|---|---|
| 689 | 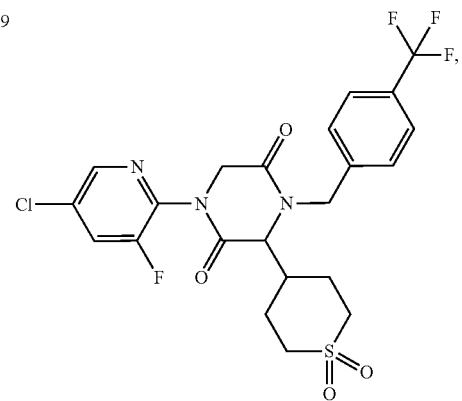 |
| 690 | 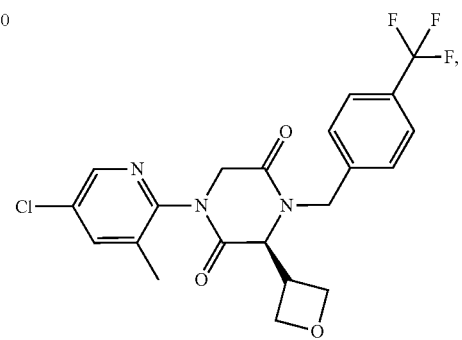 |
| 691 | 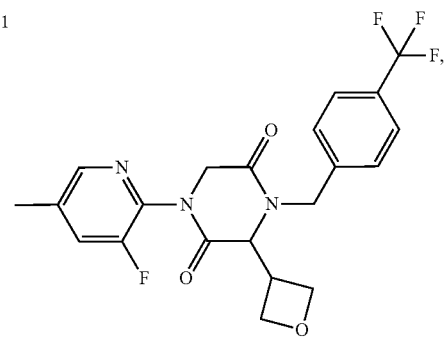 |
| 692 | 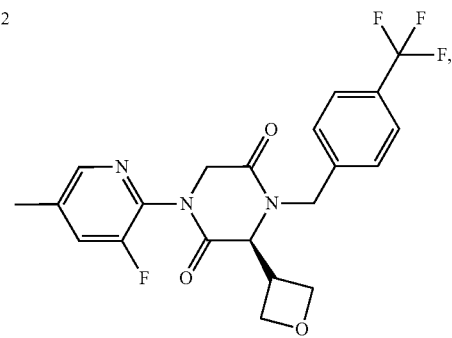 [SMILES: O=C1C(C2COC2)N(Cc2ccc(C(F)(F)F)c(F)c2)C(=O)CN1c1ncc(Cl)cc1F] |

| No. | Structure |
|---|---|
| 693 | 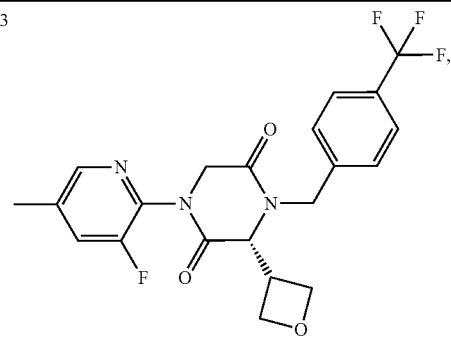 |
| 694 | 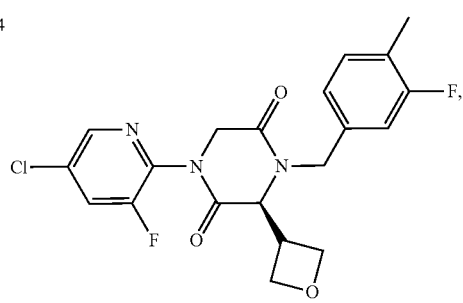 |
| 695 | 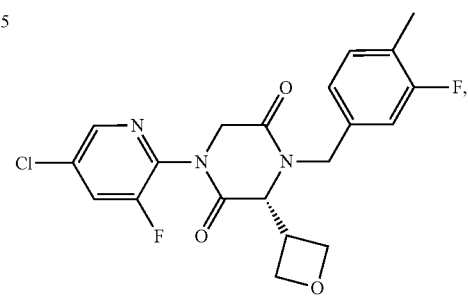 |
| 696 | 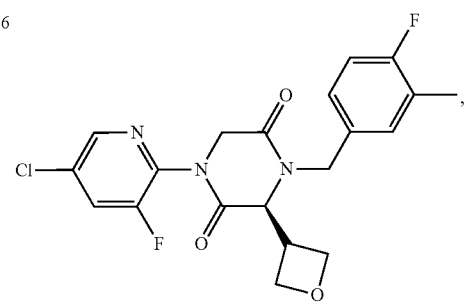 |
| 697 | 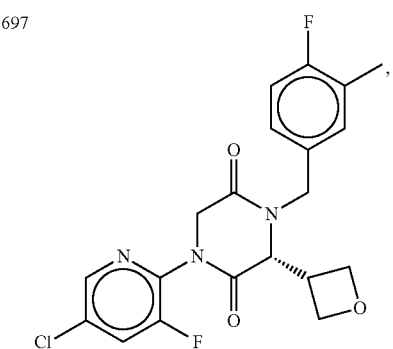 |

| No. | Structure |
|---|---|
| 698 | 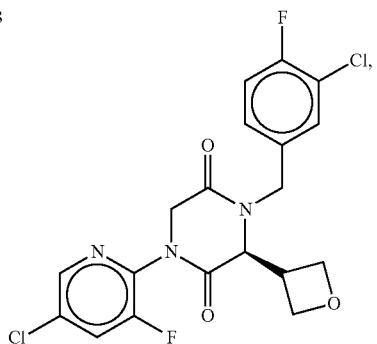 |
| 699 | 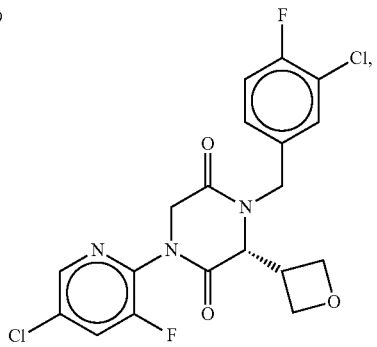 |
| 700 | 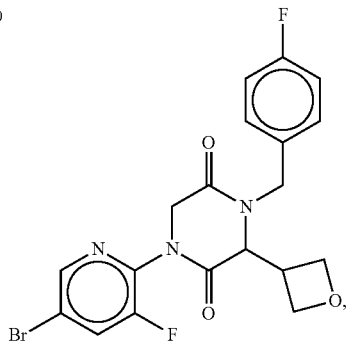 |
| 701 | 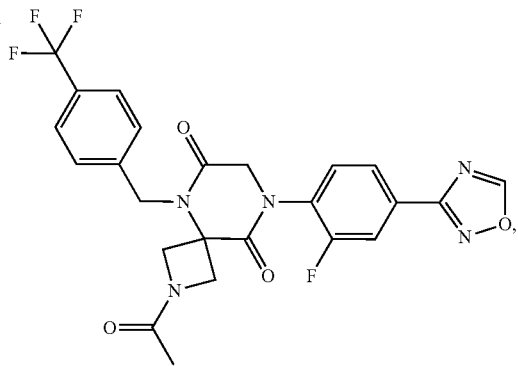 [SMILES: CC(=O)N1CC2(C1)C(=O)N(c1ccc(-c3ncon3)cc1F)CC(=O)N2Cc1ccc(C(F)(F)F)cc1] |

| No. | Structure |
|---|---|
| 702 | 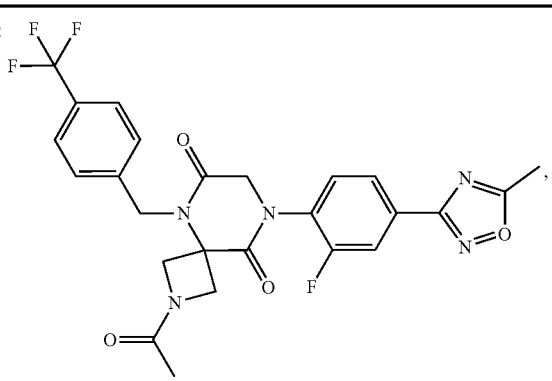 |
| 703 | 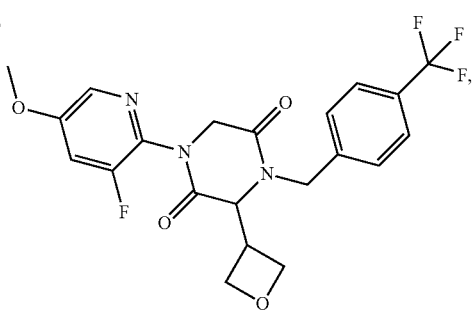 [SMILES: COc1cnc(N2CC(=O)N(Cc3ccc(C(F)(F)F)cc3)C(C3COC3)C2=O)c(F)c1] |
| 704 | 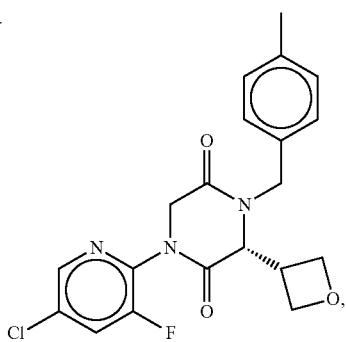 |
| 705 | 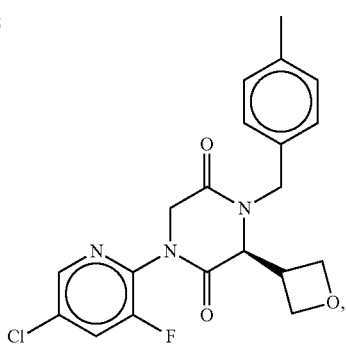 |

| No. | Structure |
|---|---|
| 706 | 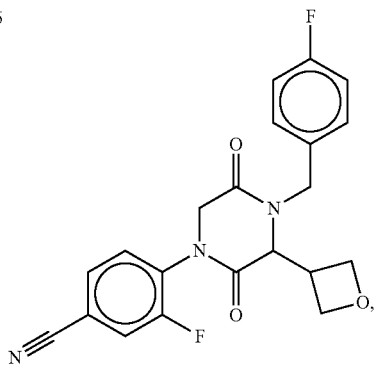 |
| 707 | 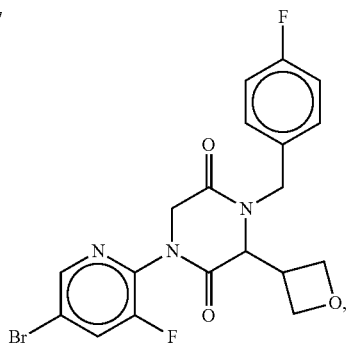 |
| 708 | 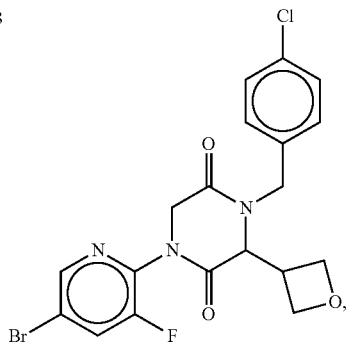 |
| 709 | 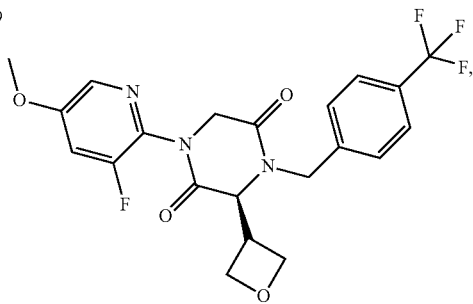 |

| No. | Structure |
|---|---|
| 710 | 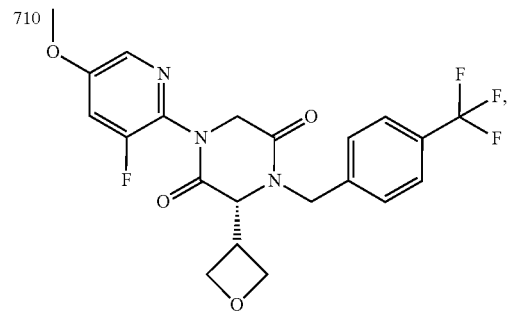 |
| 711 | 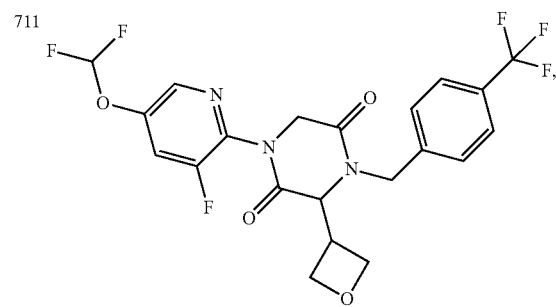 |
| 712 | 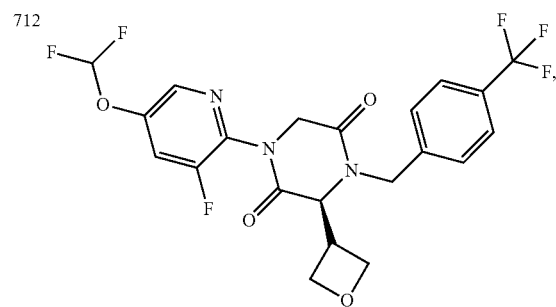 |
| 713 | 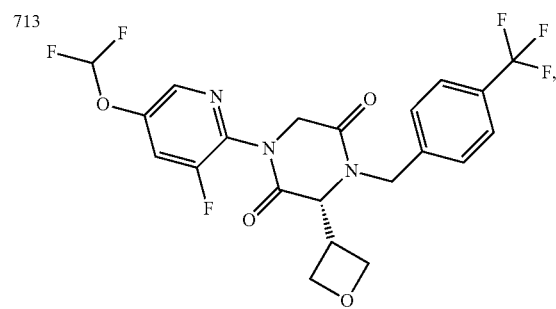 |
| 714 | 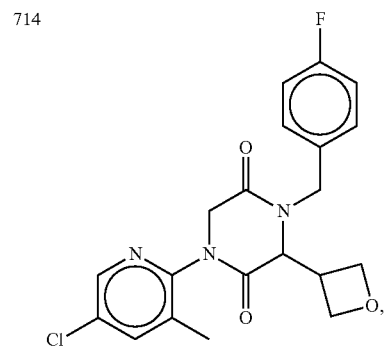 |

-continued
| No. | Structure |
|---|---|
| 715 | 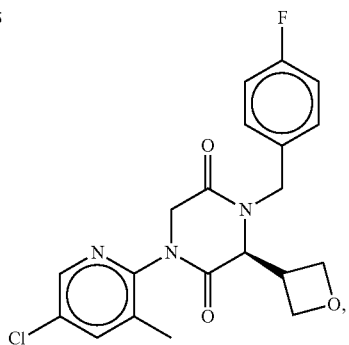 |
| 716 | 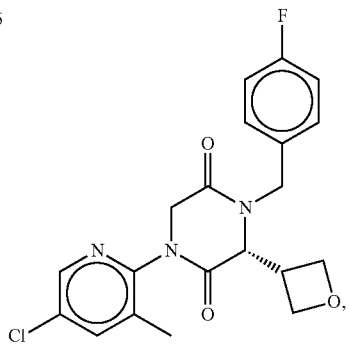 |
| 717 | 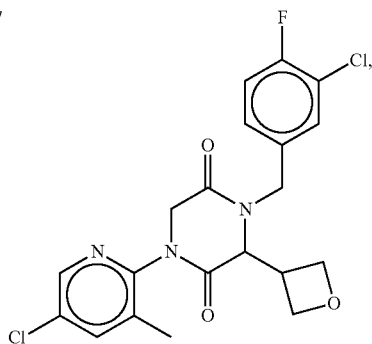 |
| 718 | 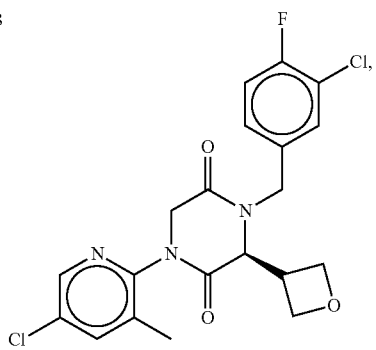 |

| No. | Structure |
|---|---|
| 719 | 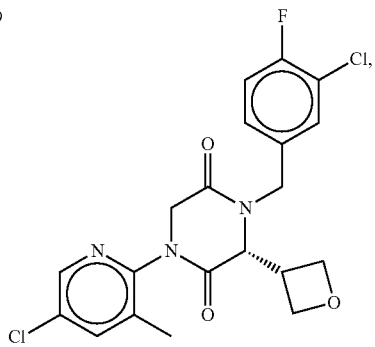 |
| 720 | 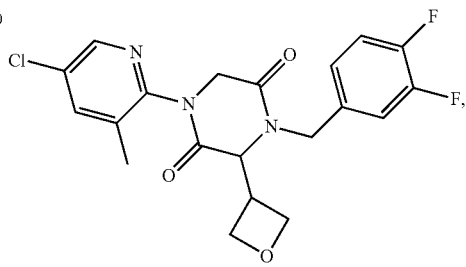 |
| 721 | 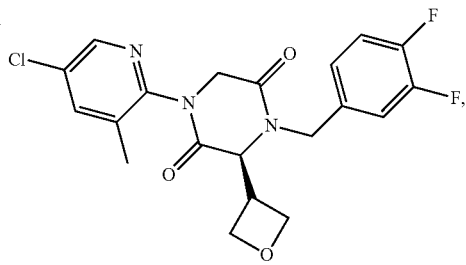 [SMILES: Cc1cc(Cl)cnc1N1CC(=O)N(Cc2ccc(F)c(F)c2)[C@@H](C2COC2)C1=O] |
| 722 | 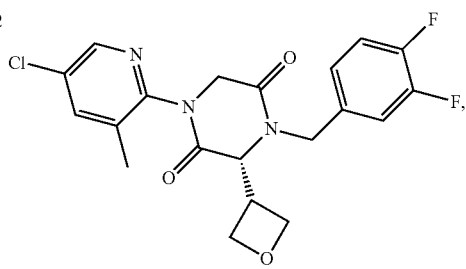 |
| 723 | 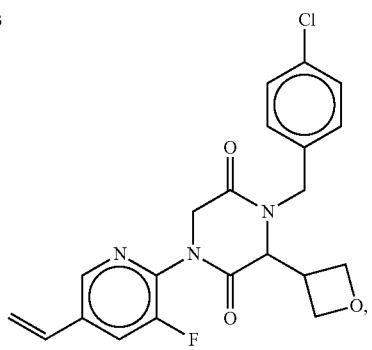 |

| No. | Structure |
|---|---|
| 724 | 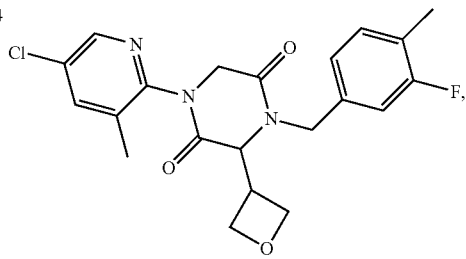 |
| 725 | 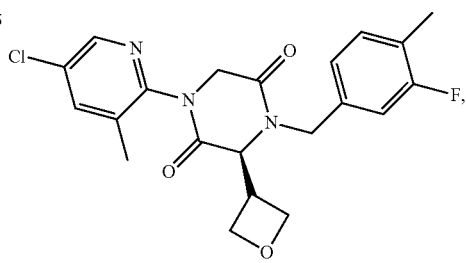 |
| 726 | 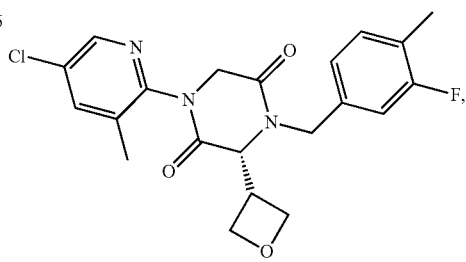 |
| 727 | 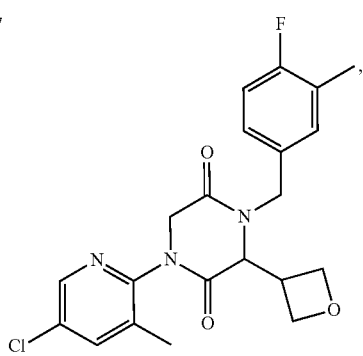 |
| 728 | 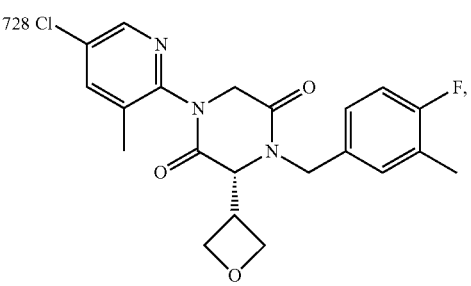 |

| No. | Structure |
|---|---|
| 729 | 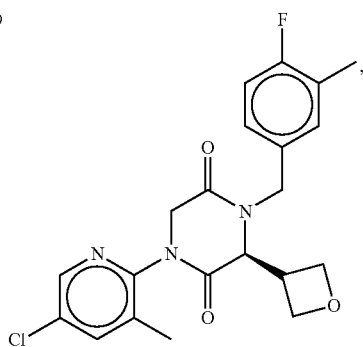 |
| 730 | 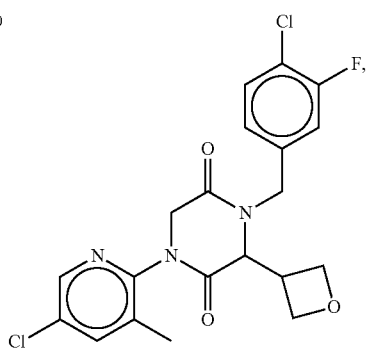 |
| 731 | 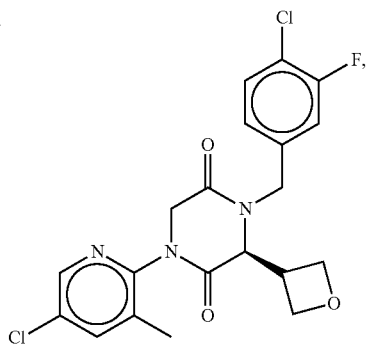 |
| 732 | 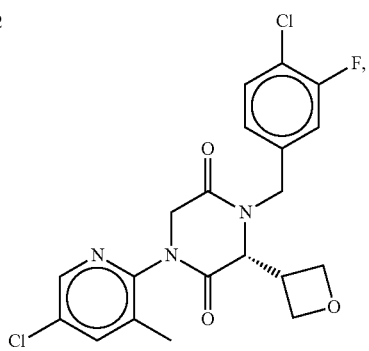 |

| No. | Structure |
|-----|-----------|
| 733 | 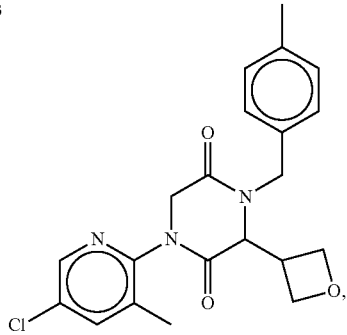 |
| 734 | 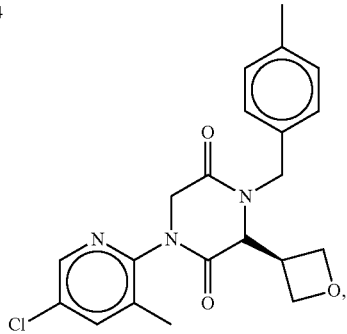 |
| 735 | 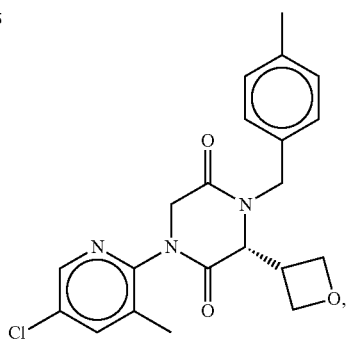 |
| 736 | 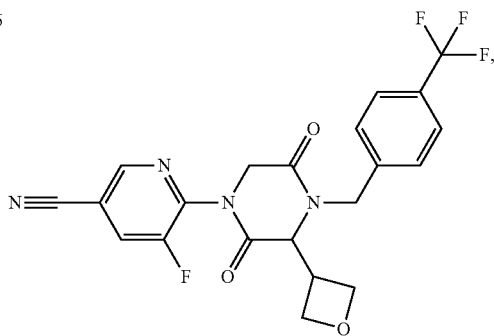 |

| No. | Structure |
|---|---|
| 737 | 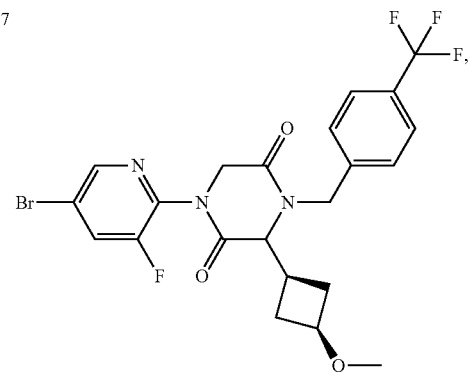 |
| 738 | 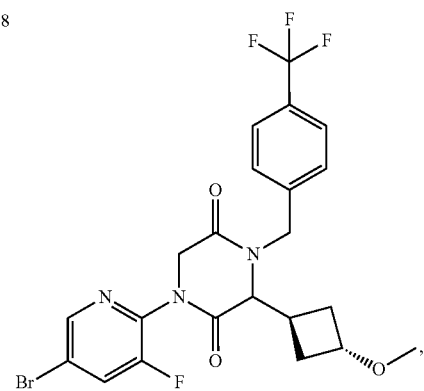 |
| 739 | 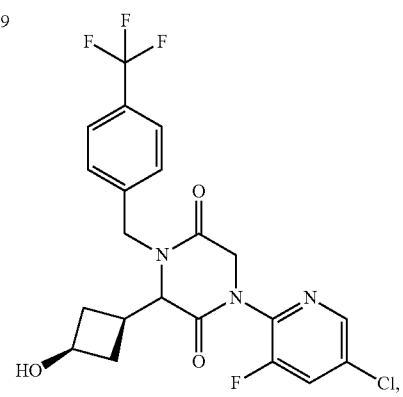 |
| 740 | 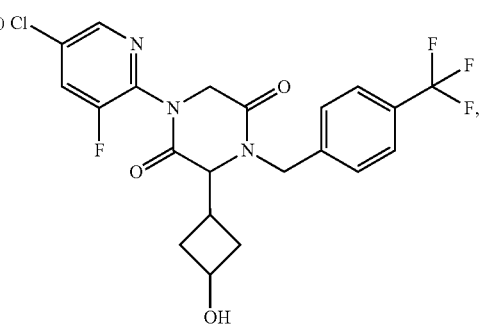 |

| No. | Structure |
|---|---|
| 741 | 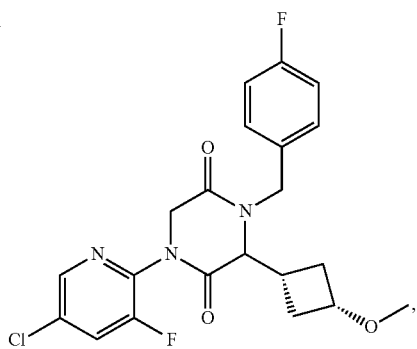 [SMILES: CO[C@H]1C[C@@H](C2C(=O)N(c3ncc(Cl)cc3F)CC(=O)N2Cc2ccc(F)cc2)C1] |
| 742 | 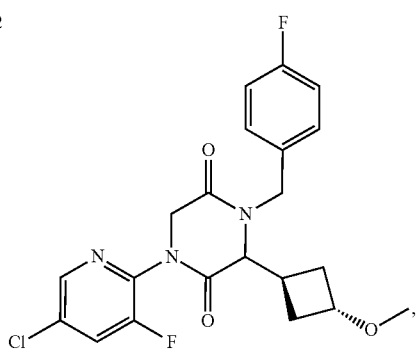 |
| 743 | 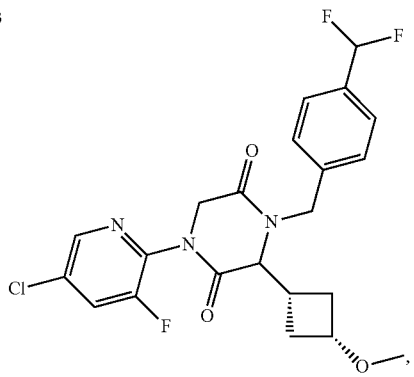 |
| 744 | 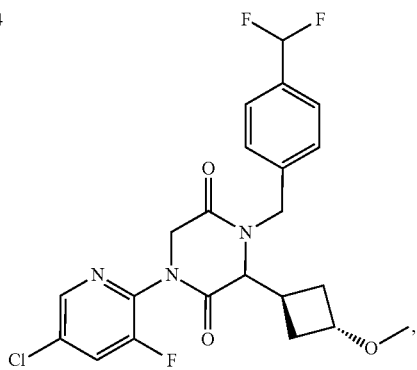 |

-continued
| No. | Structure |
|---|---|
| 745 | 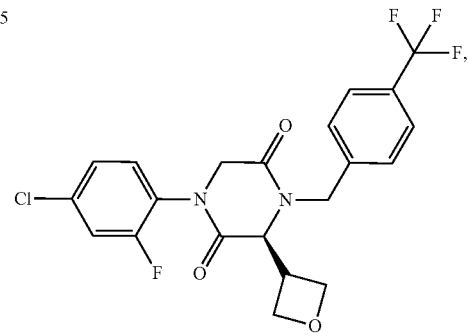 |
| 746 | 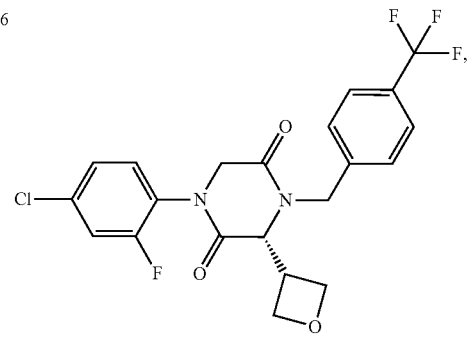 |
| 747 | 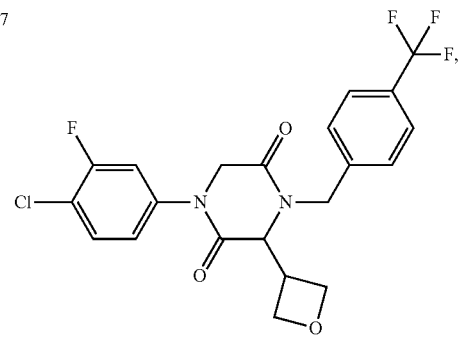 |
| 748 | 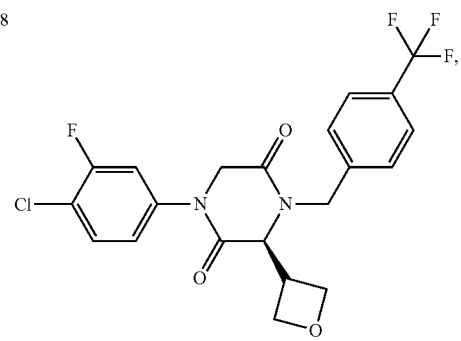 |

-continued
| No. | Structure |
|---|---|
| 749 | 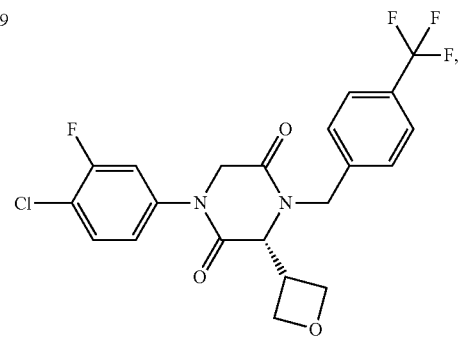 |
| 750 | 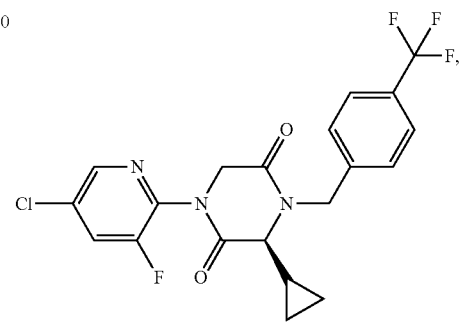 |
| 751 | 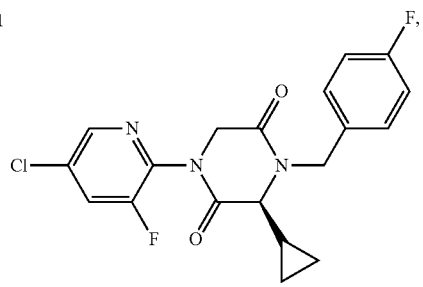 |
| 752 | 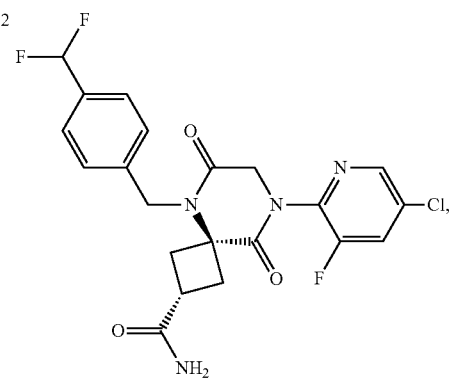 |

| No. | Structure |
|---|---|
| 753 | 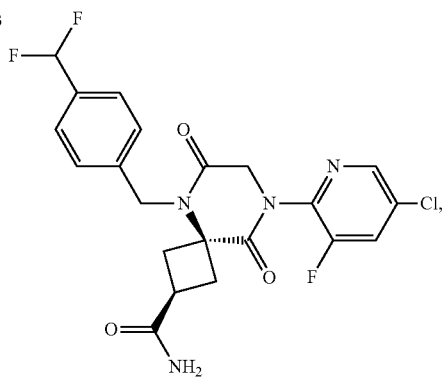 |
| 754 | 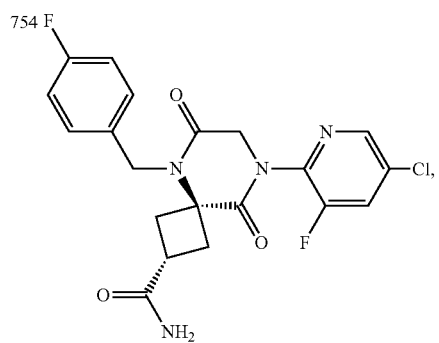 |
| 755 | 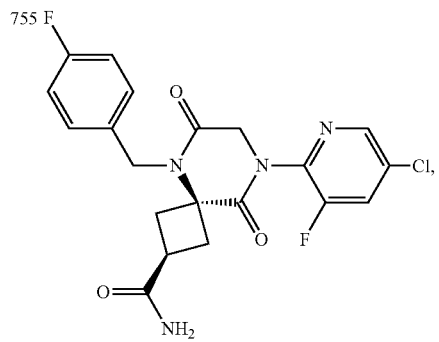 |
| 756 | 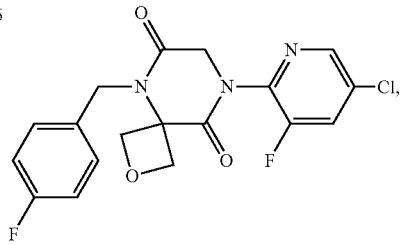 |
| 757 | 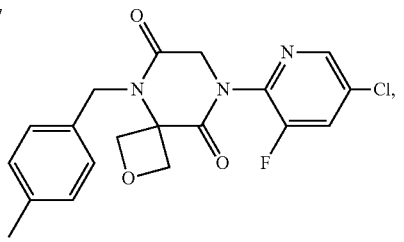 |

| No. | Structure |
|---|---|
| 758 | 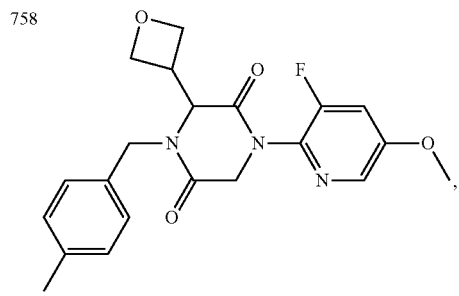 |
| 759 | 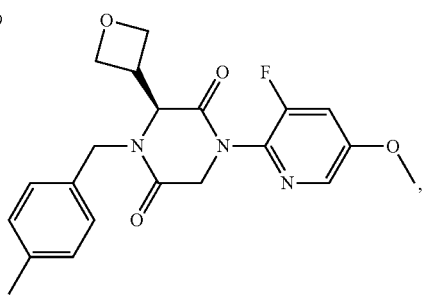 |
| 760 | 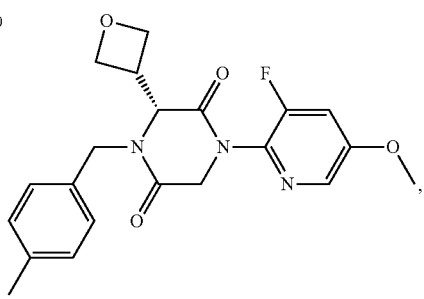 |
| 761 | 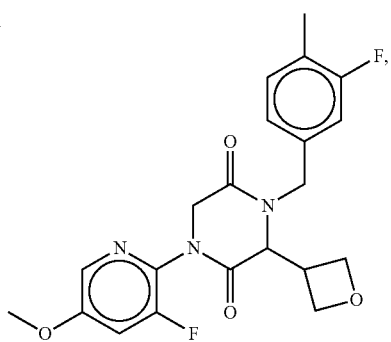 |
| 762 | 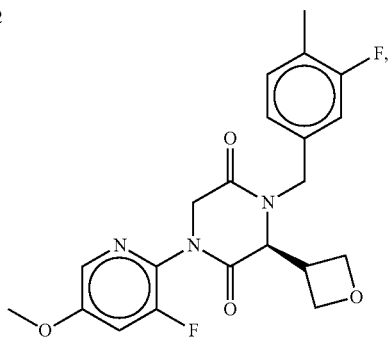 |

| No. | Structure |
|---|---|
| 763 | 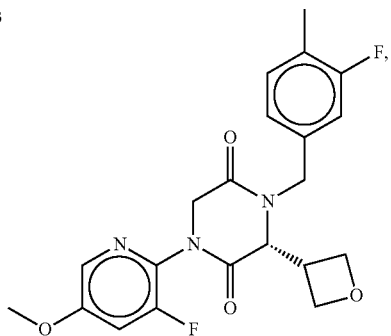 |
| 764 | 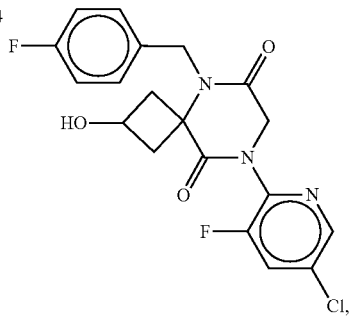 |
| 765 | 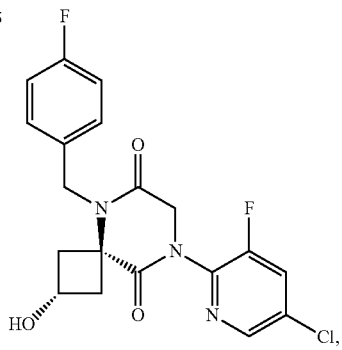 |
| 766 | 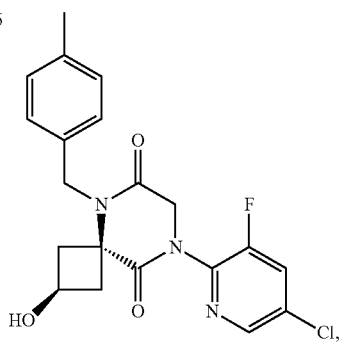 |

-continued
| No. | Structure |
|---|---|
| 767 | 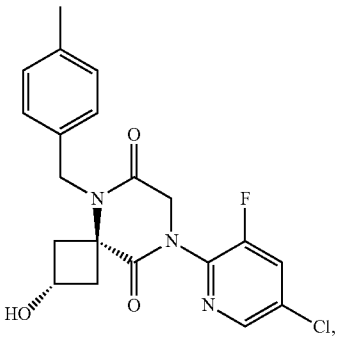 |
| 768 | 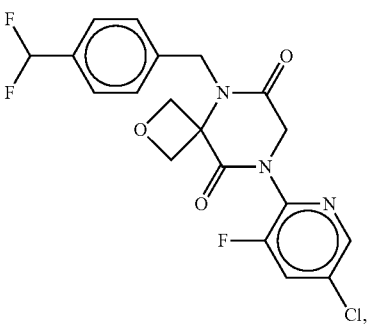 |
| 769 | 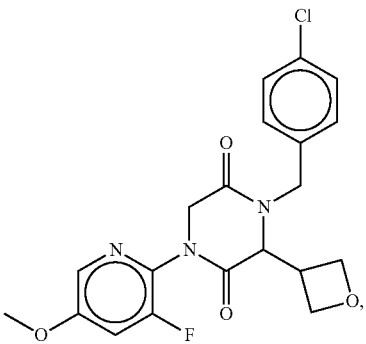 |
| 770 | 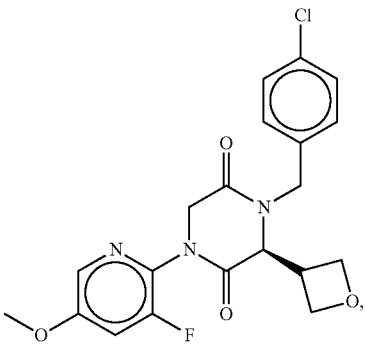 |

| No. | Structure |
|---|---|
| 771 | 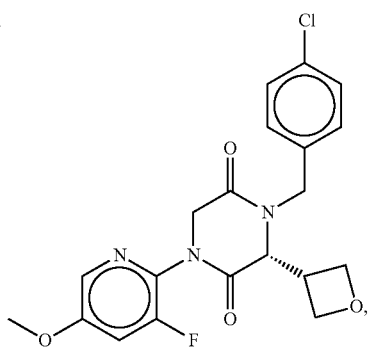 |
| 772 | 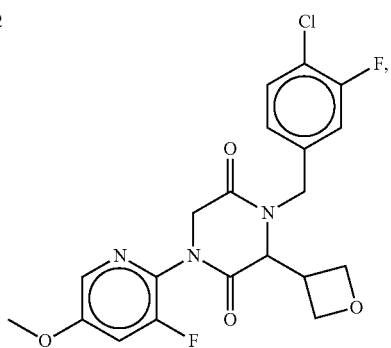 |
| 773 | 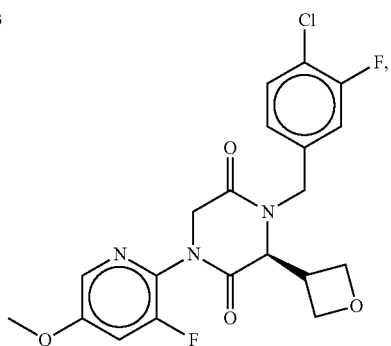 |
| 774 | 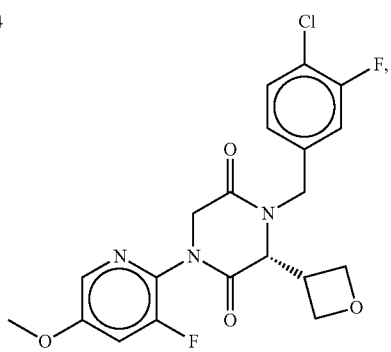 |

| No. | Structure |
|---|---|
| 775 | 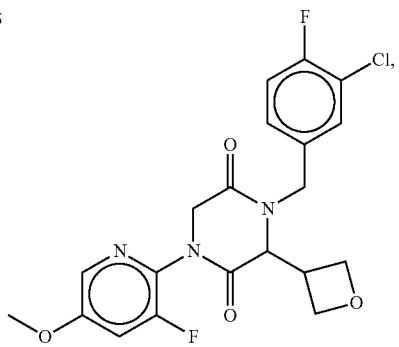 |
| 776 | 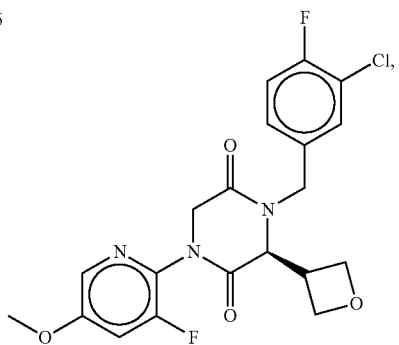 |
| 777 | 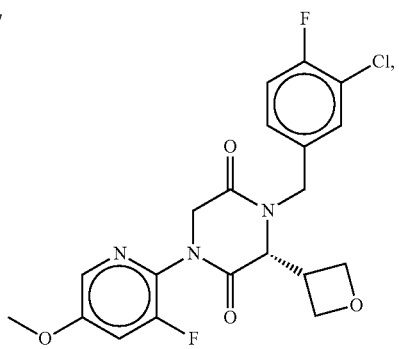 |
| 778 | 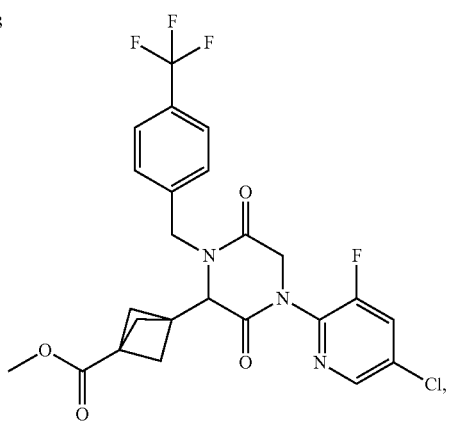 |

| No. | Structure |
|---|---|
| 779 | 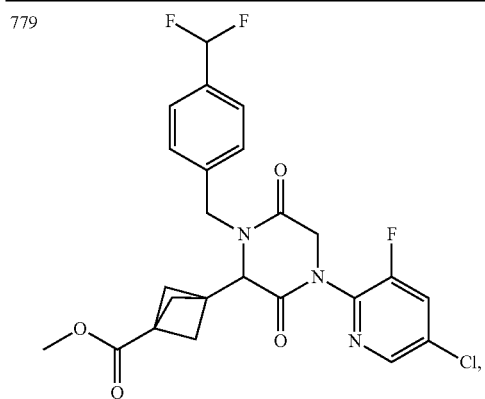 |
| 780 | 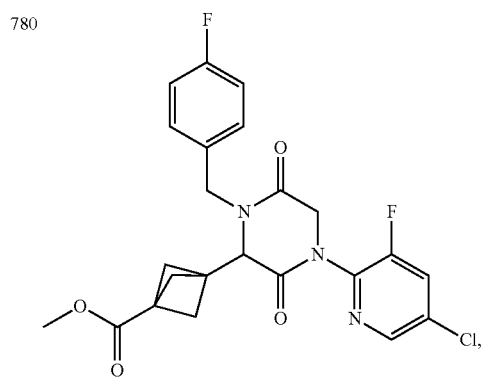 |
| 781 | 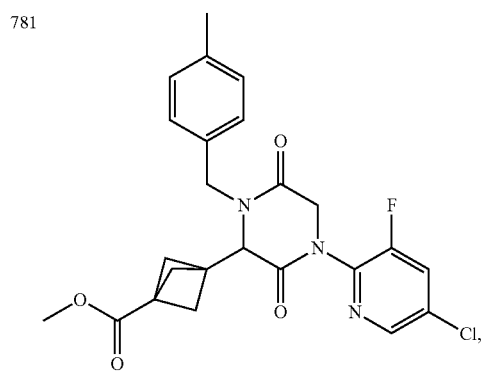 |
| 782 | 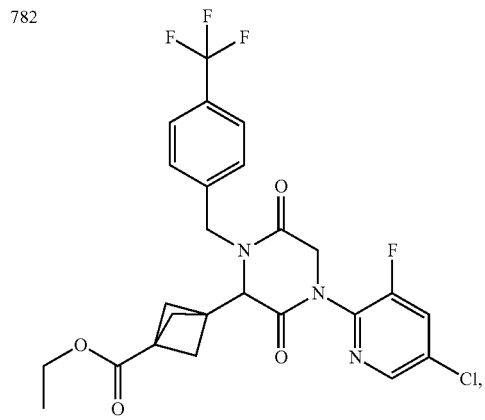 |

| No. | Structure |
|---|---|
| 783 | 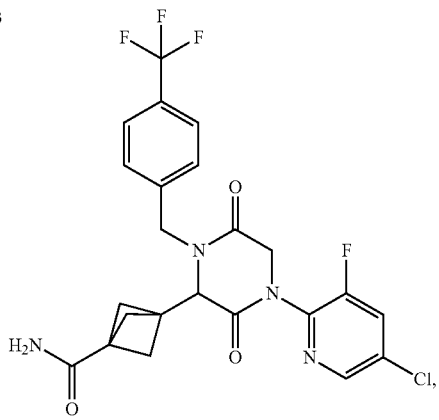 |
| 784 | 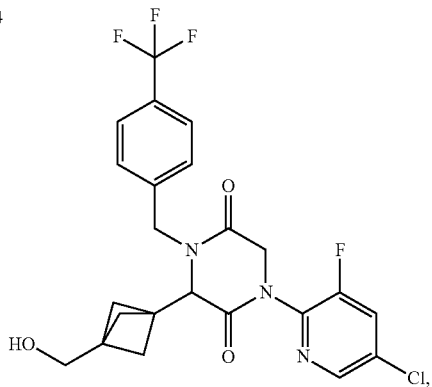 |
| 785 | 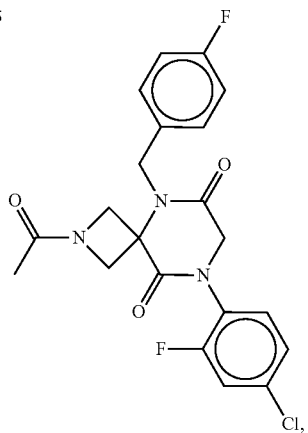 |

| No. | Structure |
|---|---|
| 786 | 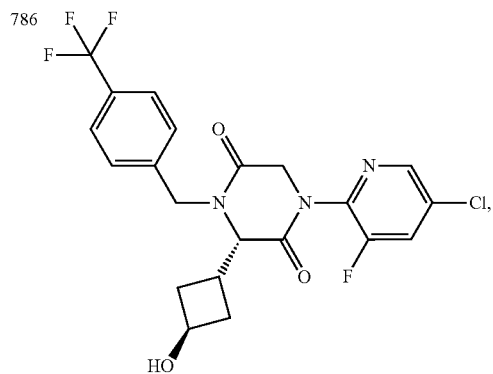 |
| 787 | 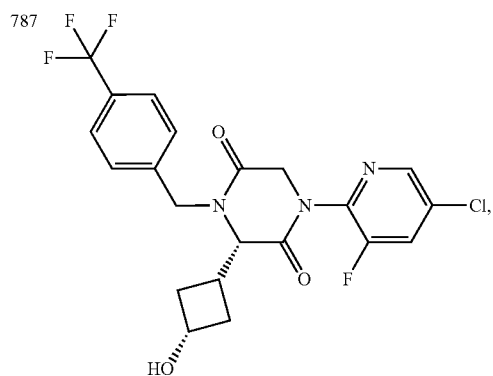 |
| 788 | 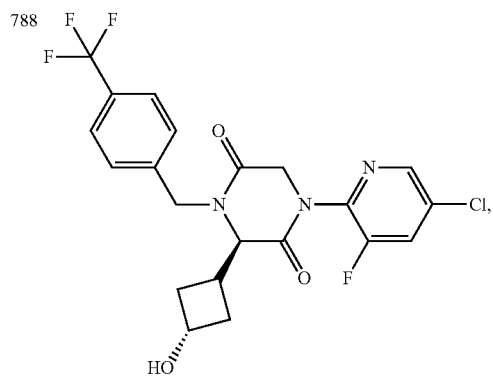 |
| 789 | 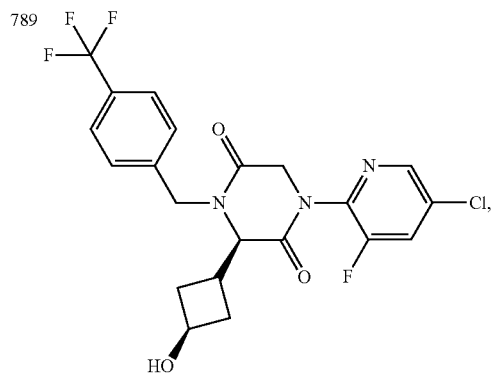 |

| No. | Structure |
|-----|-----------|
| 790 | 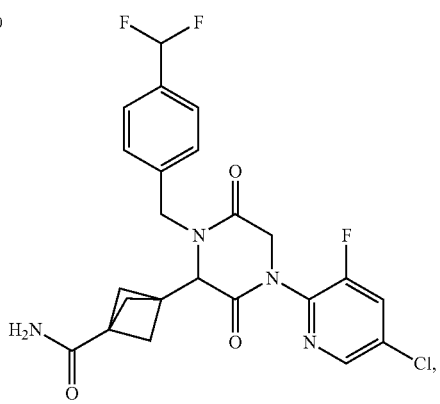 [SMILES: COC(=O)C12CC(C3C(=O)N(c4ncc(Cl)cc4F)CC(=O)N3Cc3ccc(C(F)F)cc3)(C1)C2] |
| 791 | 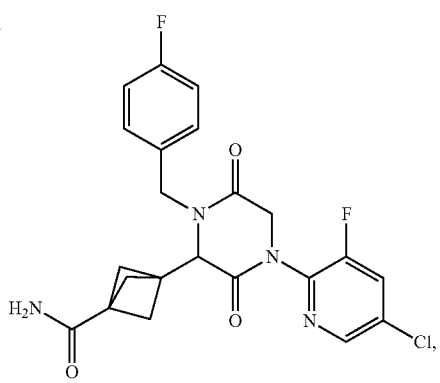 |
| 792 | 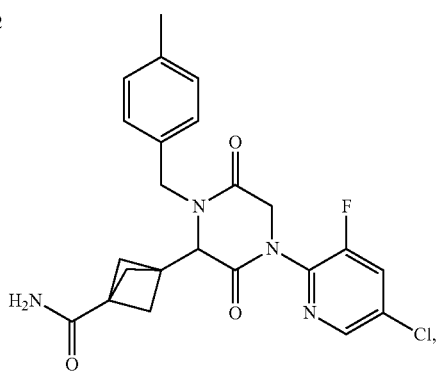 [SMILES: COC(=O)C12CC(C3C(=O)N(c4ncc(Cl)cc4F)CC(=O)N3Cc3ccc(C)cc3)(C1)C2] |
| 793 | 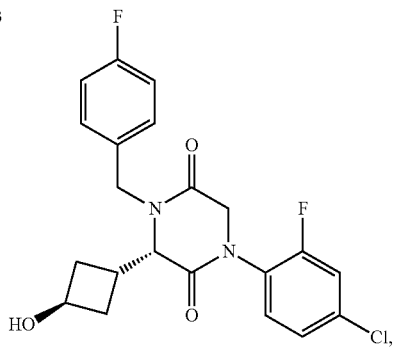 |

-continued
| No. | Structure |
|---|---|
| 794 | 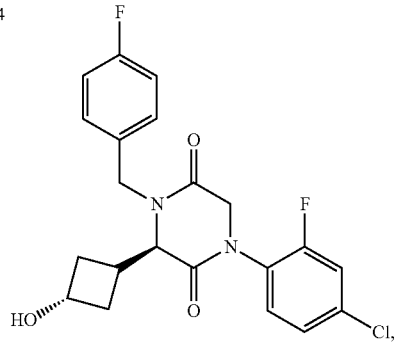 |
| 795 | 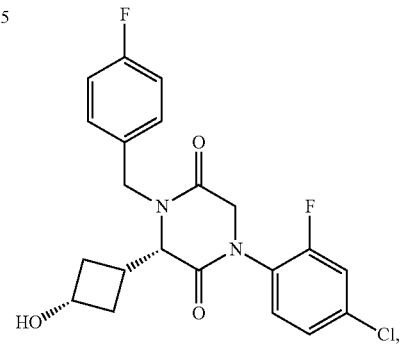 |
| 796 | 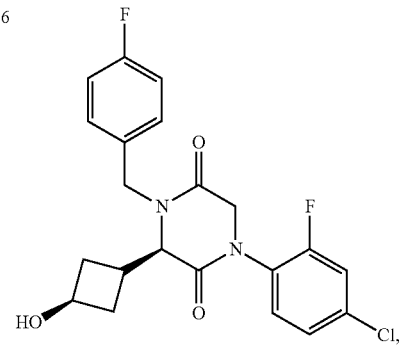 |
| 797 | 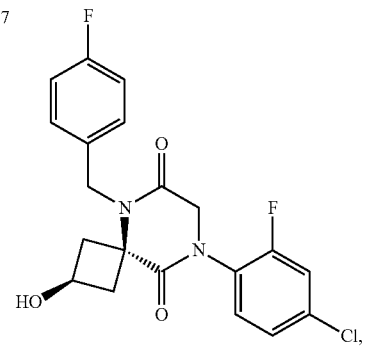 |

| No. | Structure |
|-----|-----------|
| 798 | 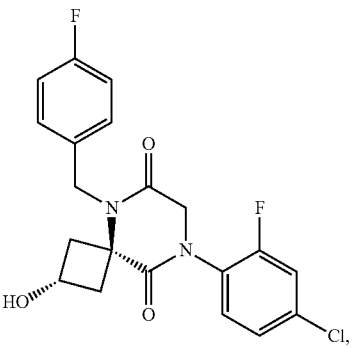 [SMILES: O=C1CN(c2ccc(Cl)cc2F)C(=O)[C@]2(C[C@@H](O)C2)N1Cc1ccc(F)cc1] |
| 799 | 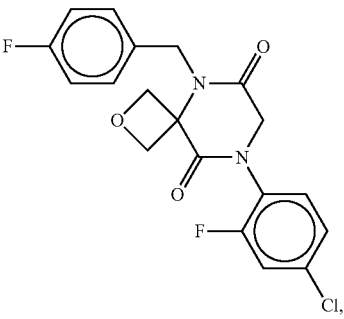 |
| 800 | 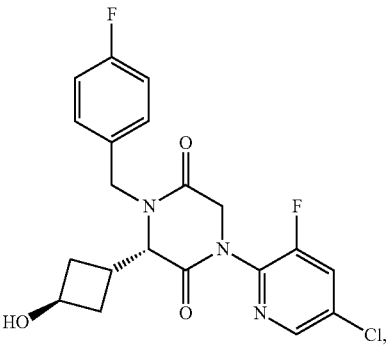 |
| 801 | 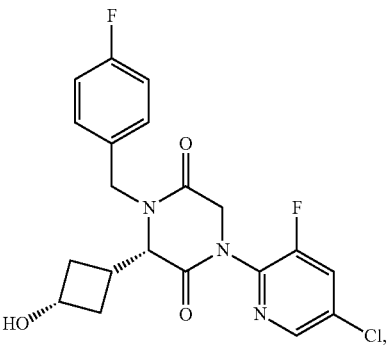 |

-continued
| No. | Structure |
|-----|-----------|
| 802 | 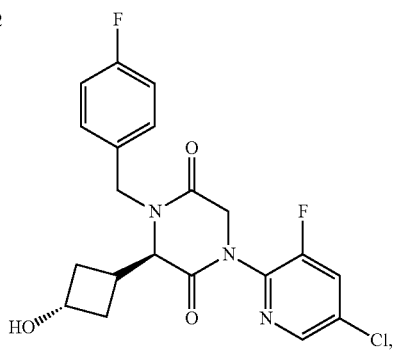 |
| 803 | 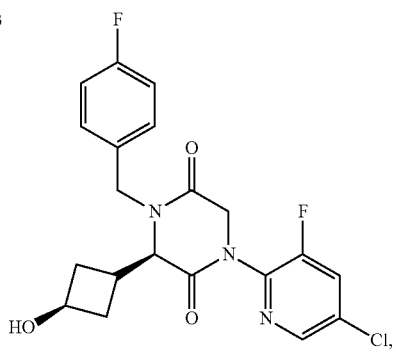 |
| 804 | 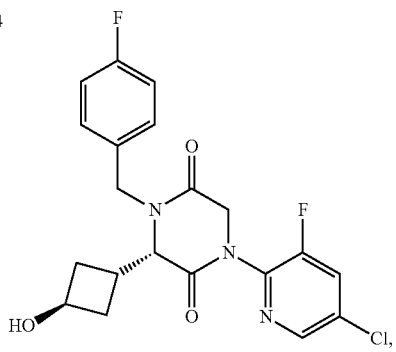 |
| 805 | 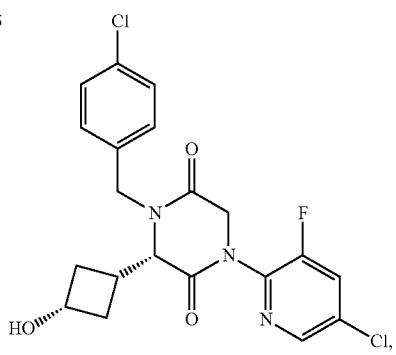 |

| No. | Structure |
|---|---|
| 806 | 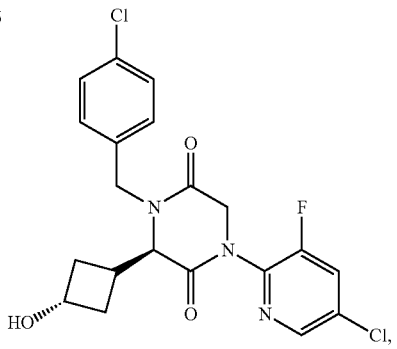 |
| 807 | 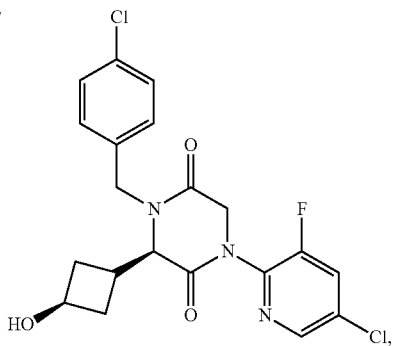 |
| 808 | 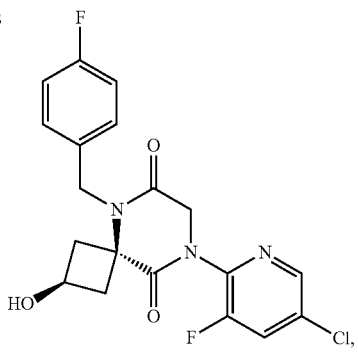 |
| 809 | 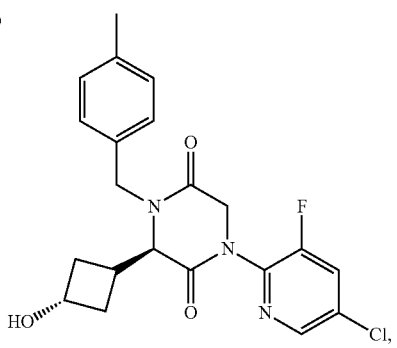 |

| No. | Structure |
|---|---|
| 810 | 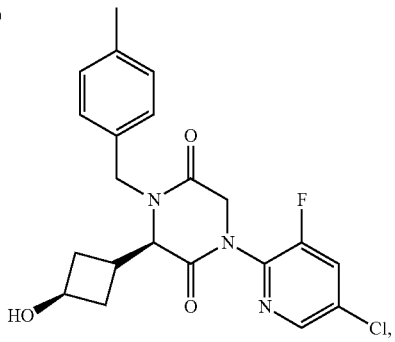 |
| 811 | 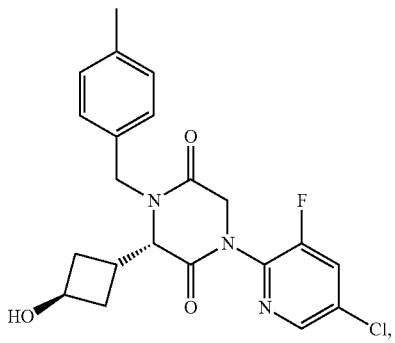 |
| 812 | 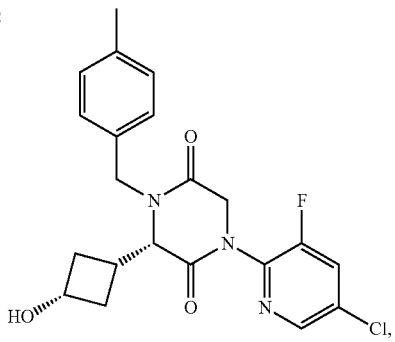 |
| 813 | 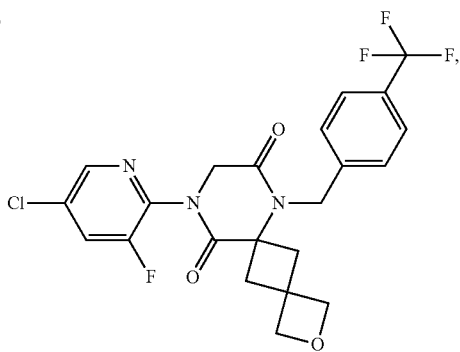 [SMILES: O=C1CN(c2ncc(Cl)cc2F)C(=O)C2(CC3(COC3)C2)N1Cc1ccc(C(F)(F)F)cc1] |

| No. | Structure |
|---|---|
| 814 | 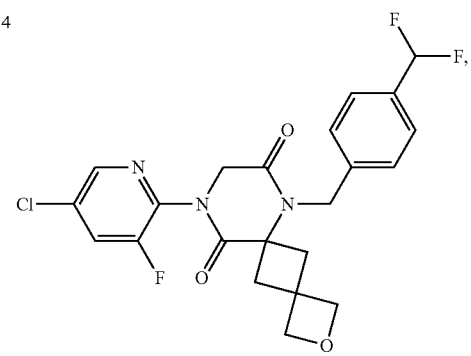 |
| 815 | 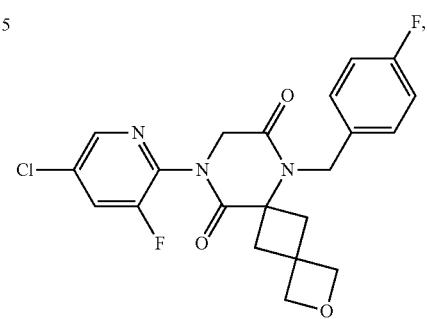 |
| 816 | 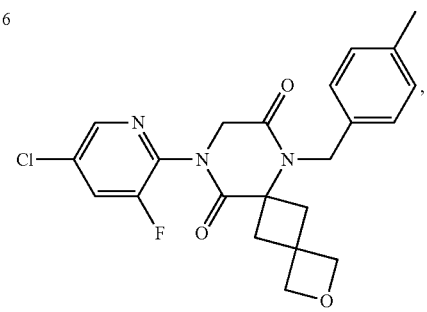 |
| 817 | 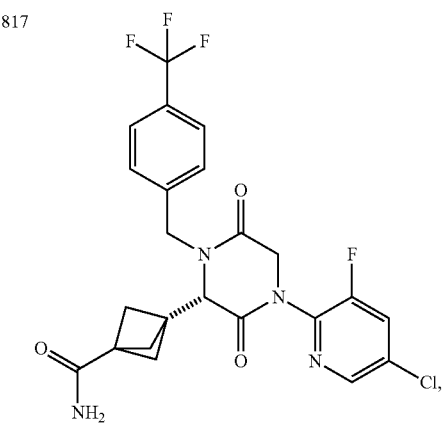 |

-continued
| No. | Structure |
|---|---|
| 818 | 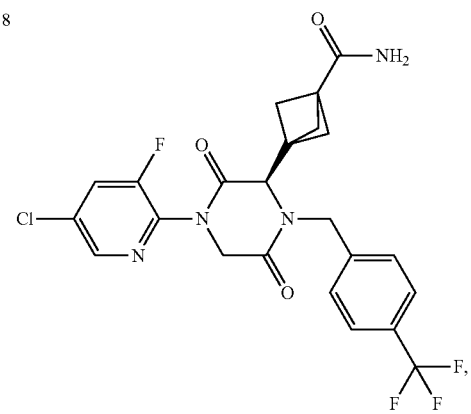 |
| 819 | 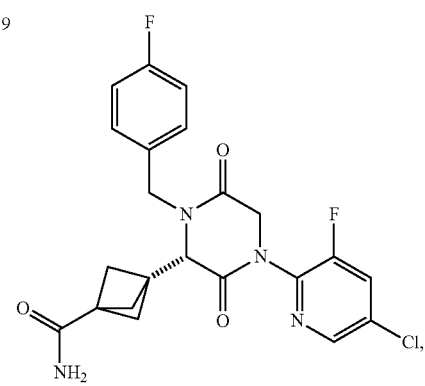 |
| 820 | 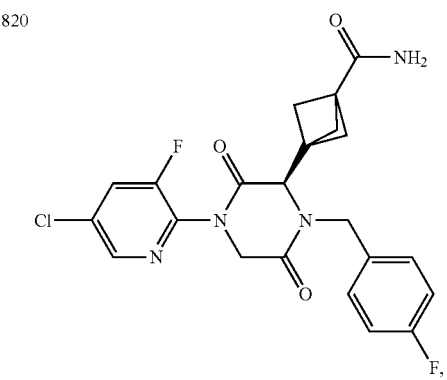 |
| 821 | 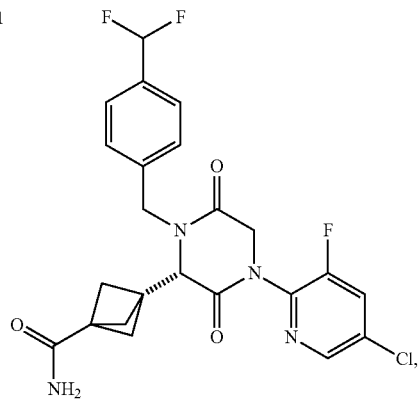 |

| No. | Structure |
|---|---|
| 822 | 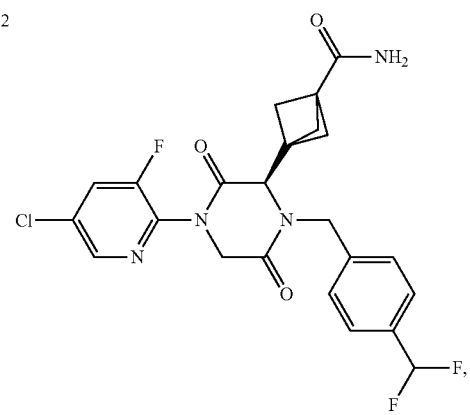 |
| 823 | 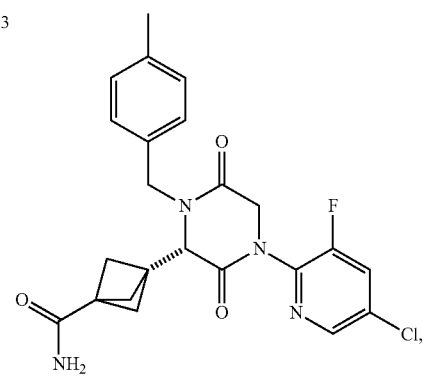 |
| 824 | 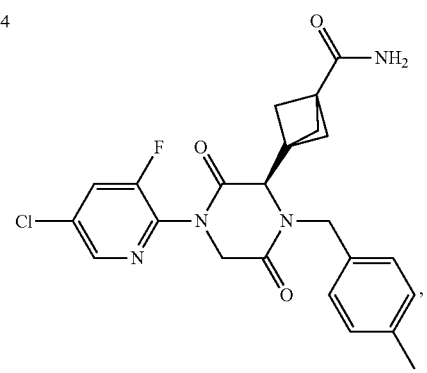 |
| 825 | 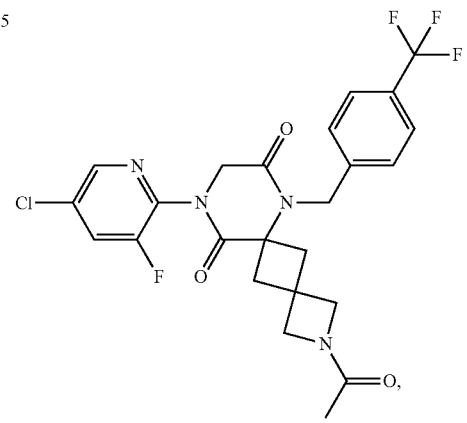 |

| No. | Structure |
|---|---|
| 826 | 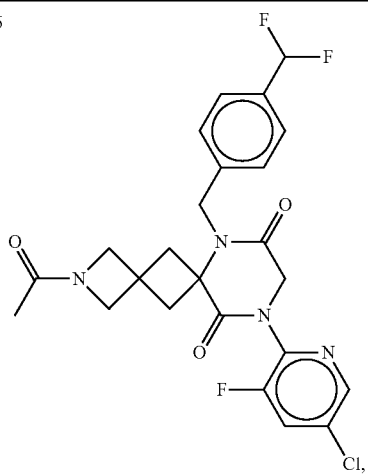 |
| 827 | 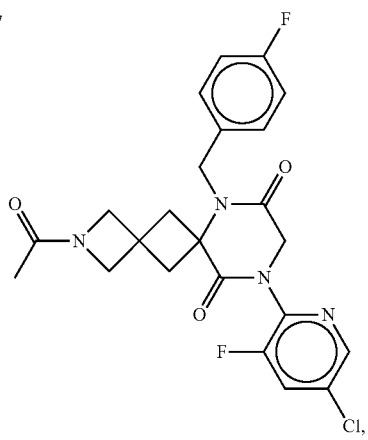 |
| 828 | 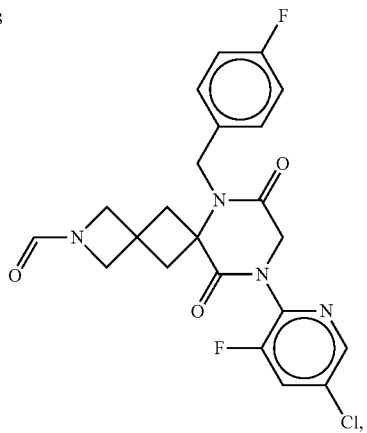 |

| No. | Structure |
|---|---|
| 829 | 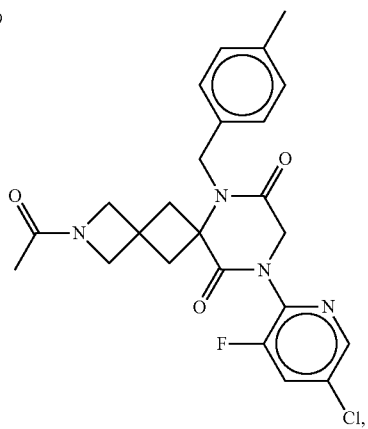 |
| 830 | 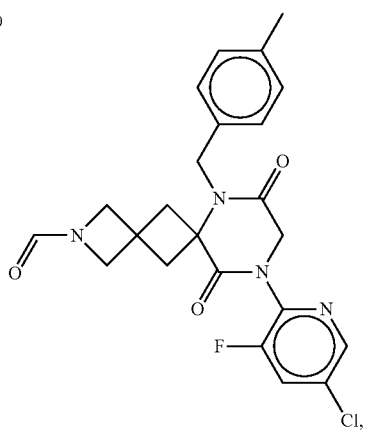 |
| 831 | 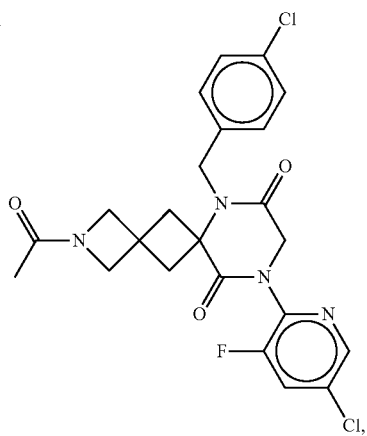 |

| No. | Structure |
|---|---|
| 832 | 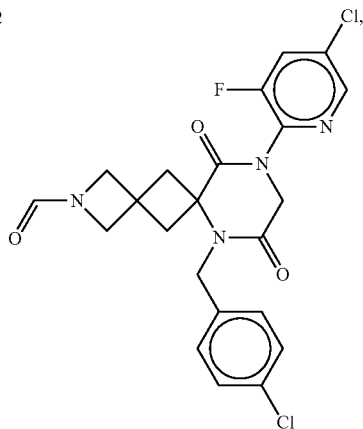 |
| 833 | 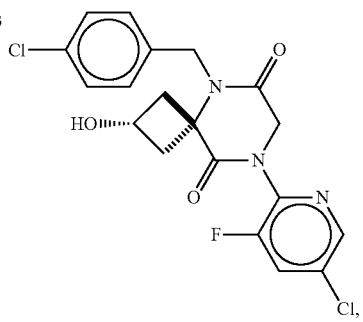 |
| 834 | 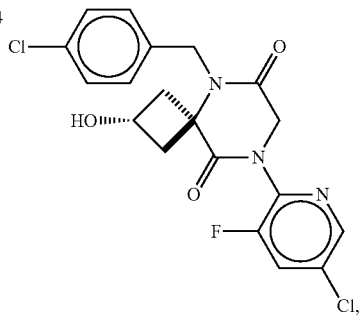 |
| 835 | 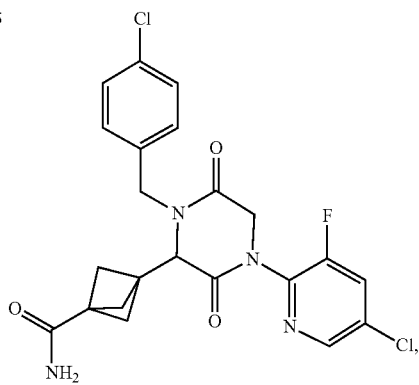 |

| No. | Structure |
|---|---|
| 836 | 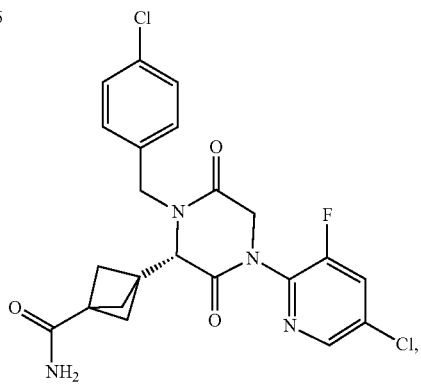 |
| 837 | 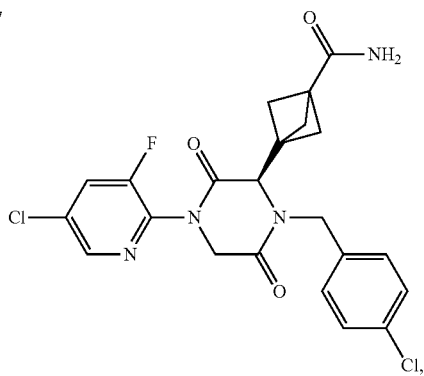 |
| 838 | 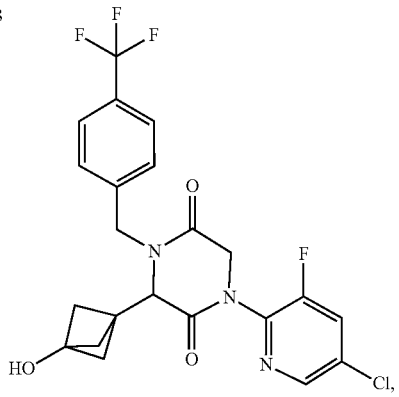 |
| 839 | 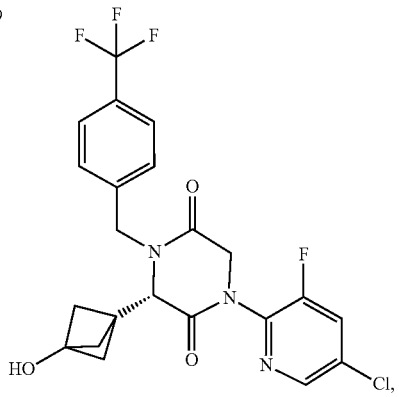 |

| No. | Structure |
|---|---|
| 840 | 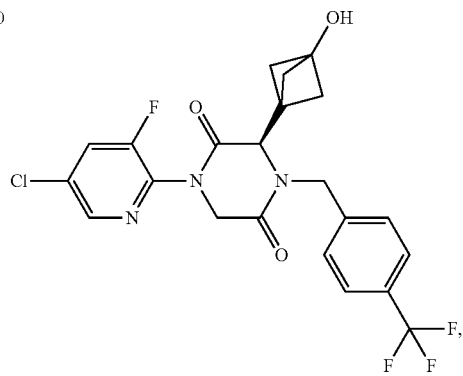 |
| 841 | 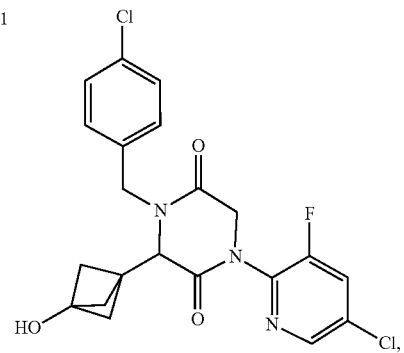 |
| 842 | 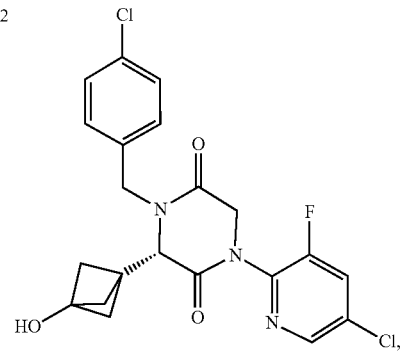 |
| 843 | 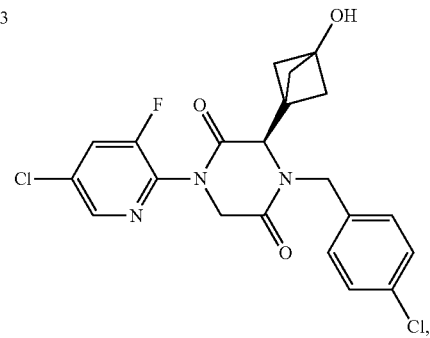 |

-continued
| No. | Structure |
|---|---|
| 844 | 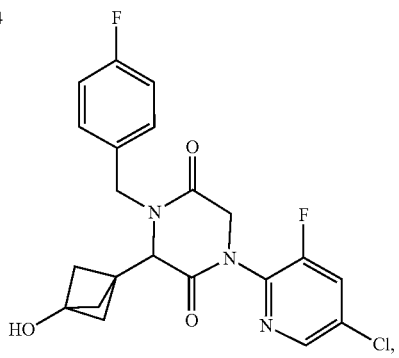 |
| 845 | 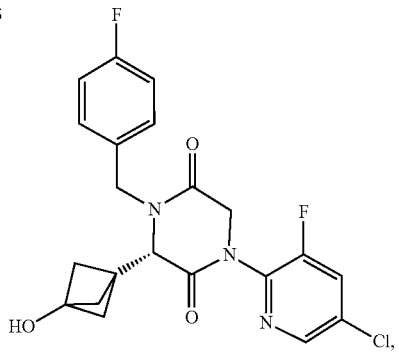 |
| 846 | 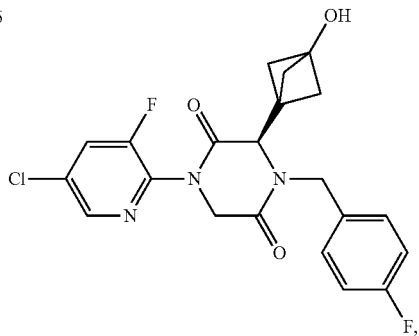 |
| 847 | 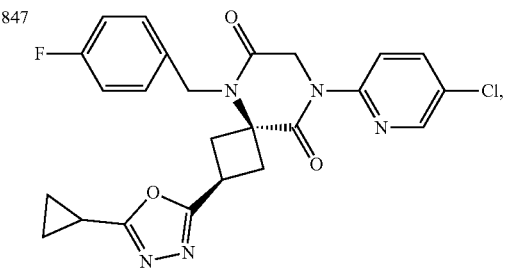 |

| No. | Structure |
|---|---|
| 848 | 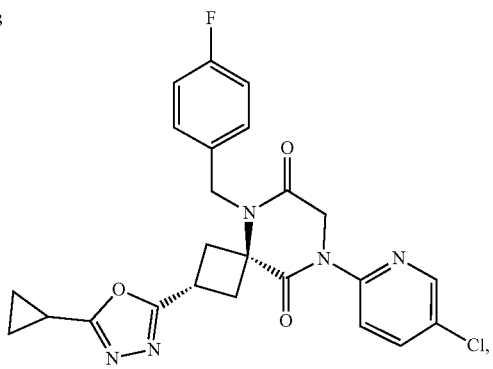 |
| 849 | 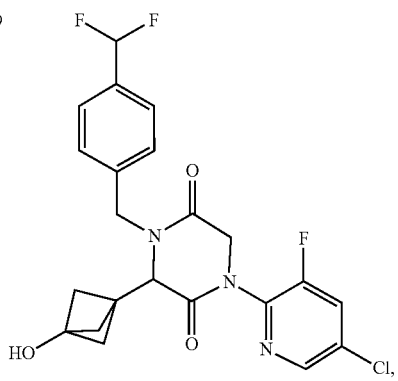 |
| 850 | 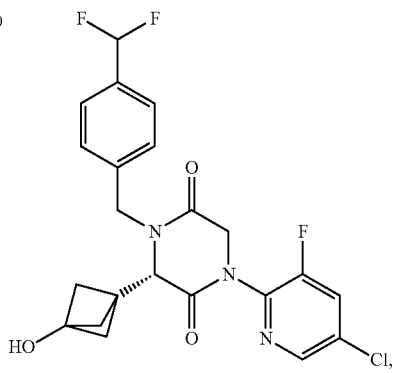 |
| 851 | 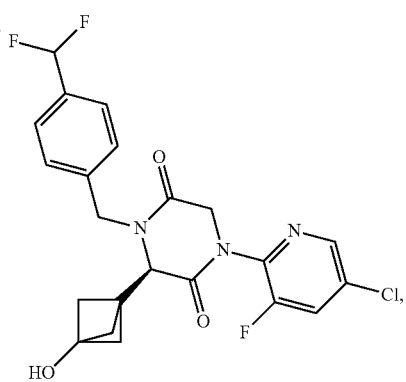 [SMILES: O=C1[C@@H](C23CC(O)(C2)C3)N(Cc2ccc(C(F)F)cc2)C(=O)CN1c1ncc(Cl)cc1F] |

| No. | Structure |
|---|---|
| 852 | 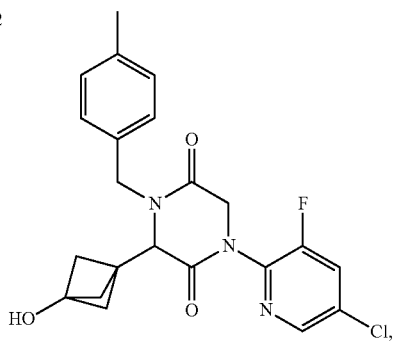 |
| 853 | 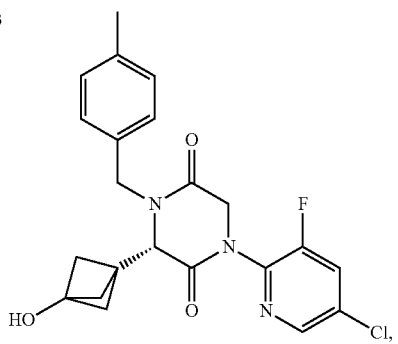 |
| 854 | 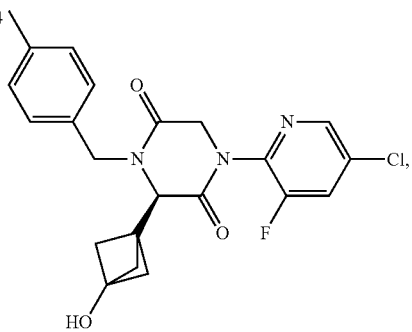 |
| 855 | 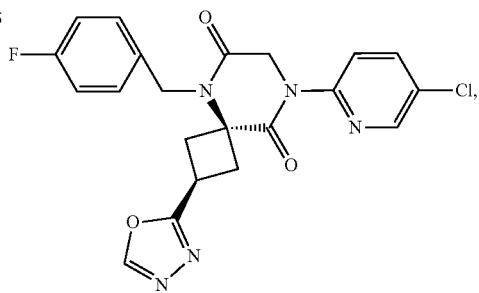 |

| No. | Structure |
|---|---|
| 856 | 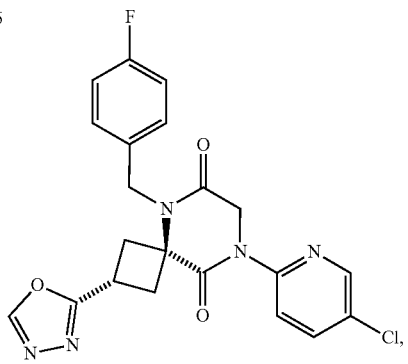 |
| 857 | 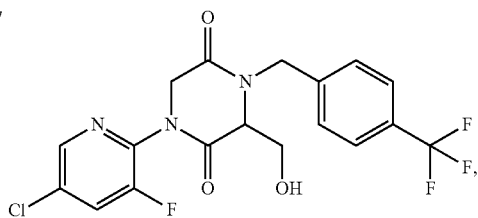 |
| 858 | 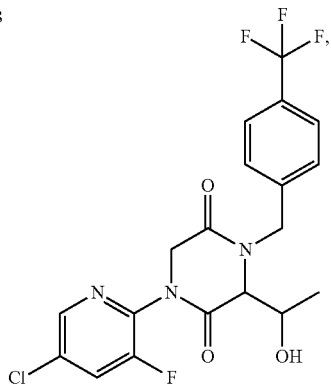 |
| 859 | 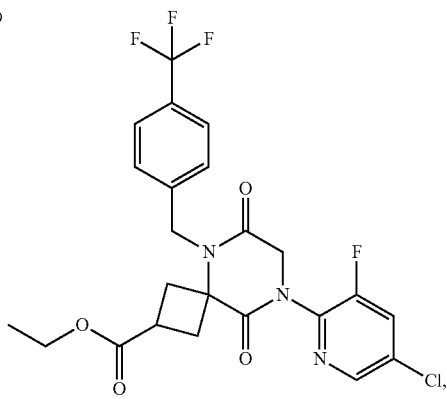 |

| No. | Structure |
|---|---|
| 860 | 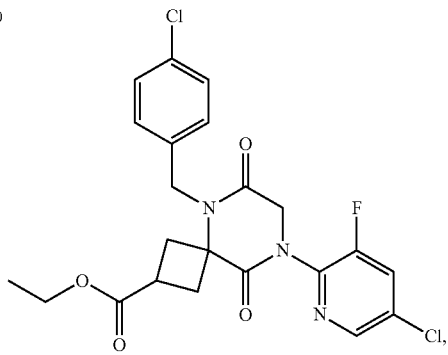 |
| 861 | 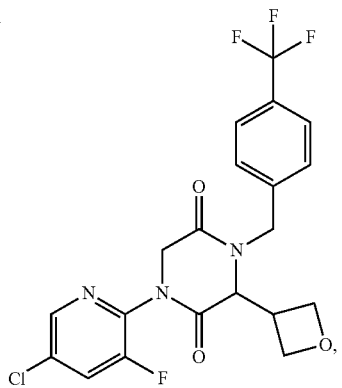 [SMILES: O=C1C(C2COC2)N(Cc2ccc(C(F)(F)F)cc2)C(=O)CN1c1ncc(Cl)cc1F] |
| 862 | 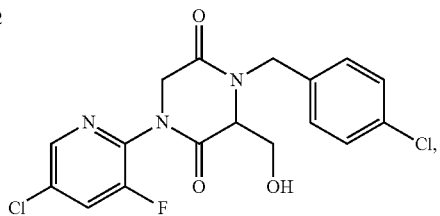 |
| 863 | 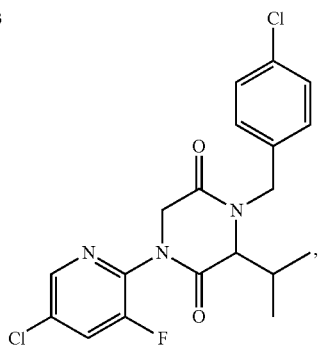 |

-continued
| No. | Structure |
|---|---|
| 864 | 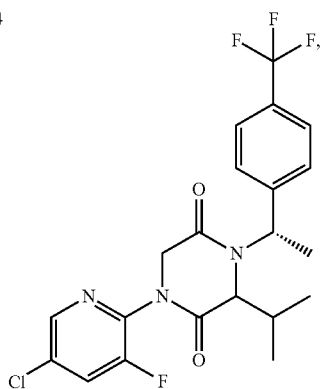 |
| 865 | 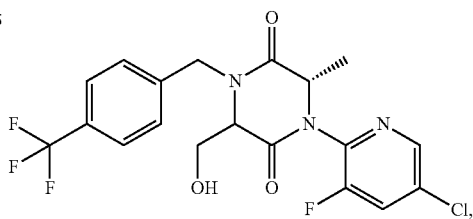 |
| 866 | 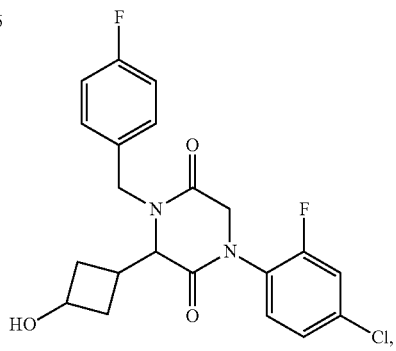 |
| 867 | 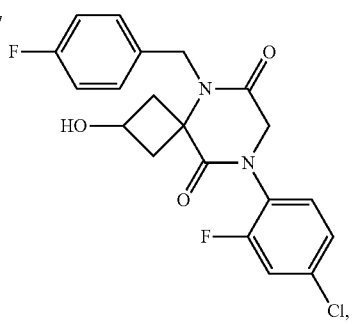 |
| 868 | 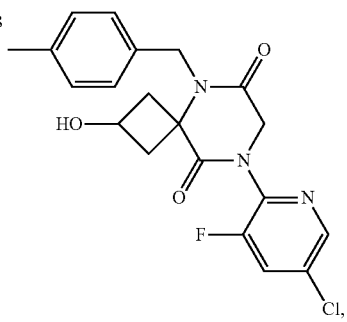 [SMILES: O=C1CN(c2ccc(Cl)cc2F)C(=O)C2(CC(O)C2)N1Cc1ccc(F)cc1] |

| No. | Structure |
|---|---|
| 869 | 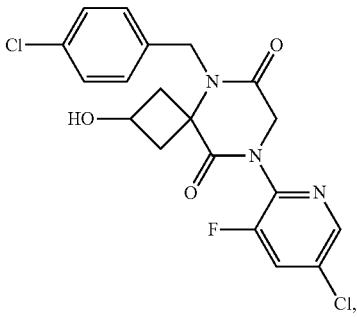 [SMILES: O=C1CN(c2ncc(Cl)cc2F)C(=O)C2(CC(O)C2)N1Cc1ccc(Cl)cc1] |
| 870 | 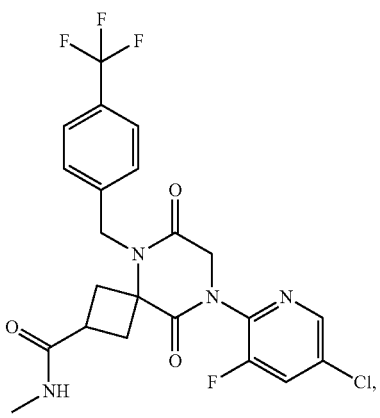 [SMILES: CNC(=O)C1CC2(C1)C(=O)N(c1ncc(Cl)cc1F)CC(=O)N2Cc1ccc(C(F)(F)F)cc1] |
| 871 | 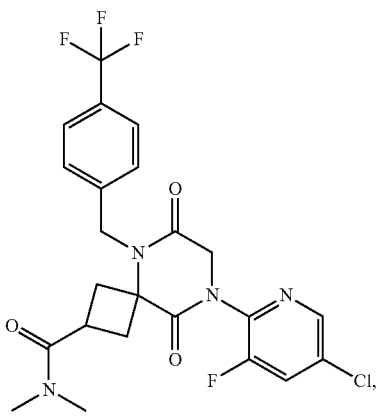 [SMILES: CN(C)C(=O)C1CC2(C1)C(=O)N(c1ncc(Cl)cc1F)CC(=O)N2Cc1ccc(C(F)(F)F)cc1] |
| 872 | 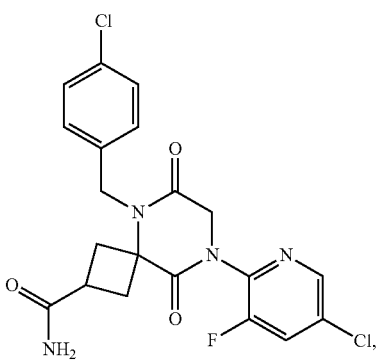 [SMILES: NC(=O)C1CC2(C1)C(=O)N(c1ncc(Cl)cc1F)CC(=O)N2Cc1ccc(Cl)cc1] |

-continued
| No. | Structure |
|---|---|
| 873 | 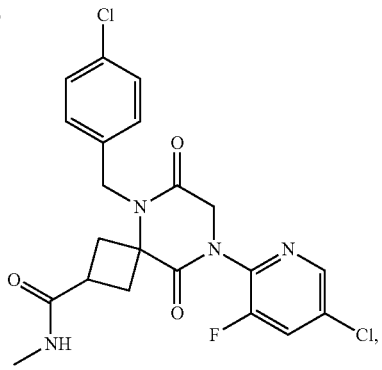 [SMILES: CNC(=O)C1CC2(C1)C(=O)N(c1ncc(Cl)cc1F)CC(=O)N2Cc1ccc(Cl)cc1] |
| 874 | 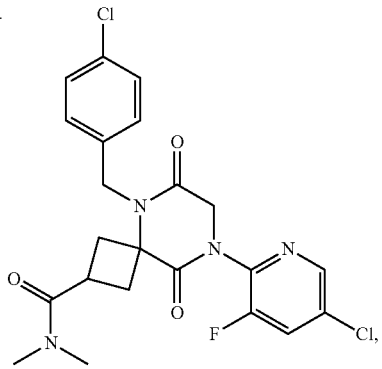 |
| 875 | 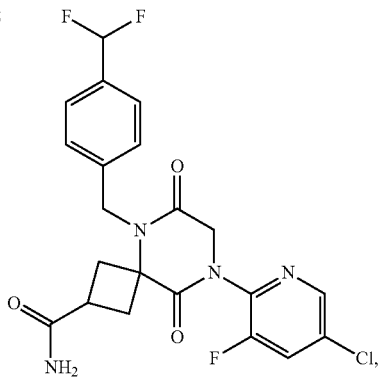 [SMILES: NC(=O)C1CC2(C1)C(=O)N(c1ncc(Cl)cc1F)CC(=O)N2Cc1ccc(C(F)F)cc1] |
| 876 | 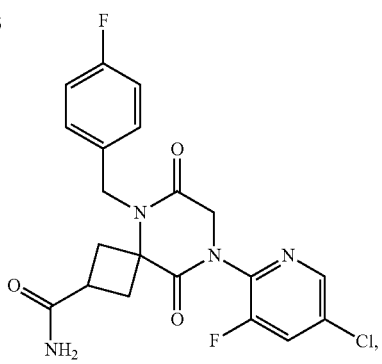 |

| No. | Structure |
|---|---|
| 877 | 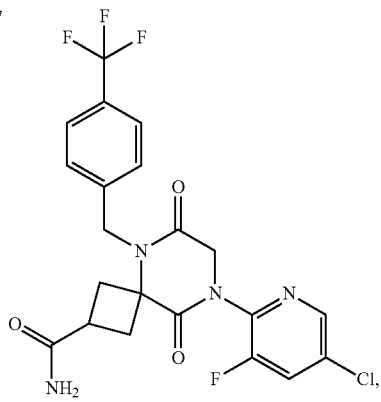 |
| 878 | 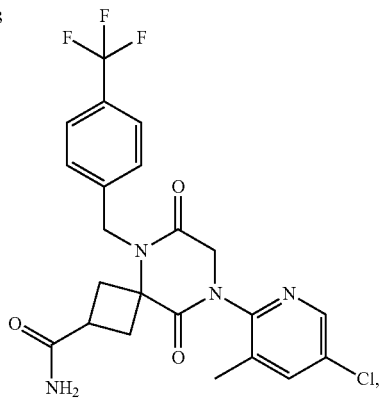 |
| 879 | 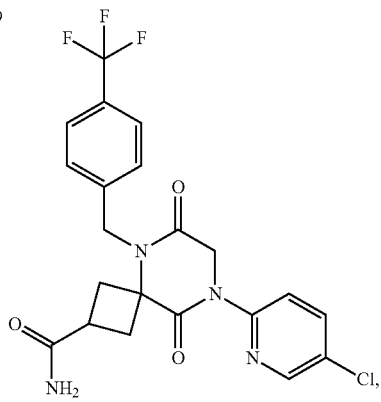 |
| 880 | 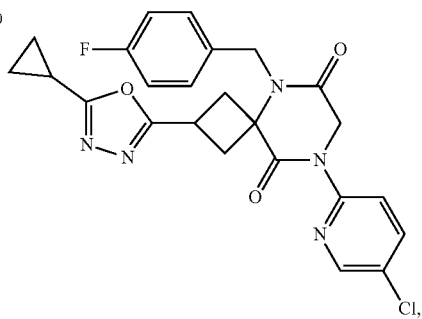 |

-continued
| No. | Structure |
|---|---|
| 881 | 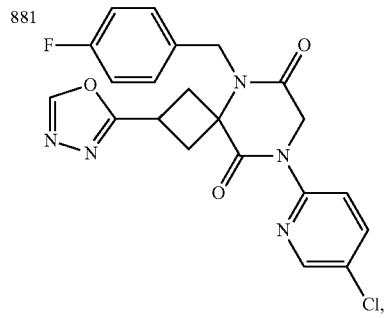 |
| 882 | 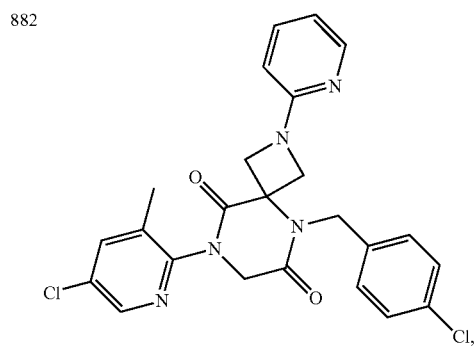 |
| 883 | 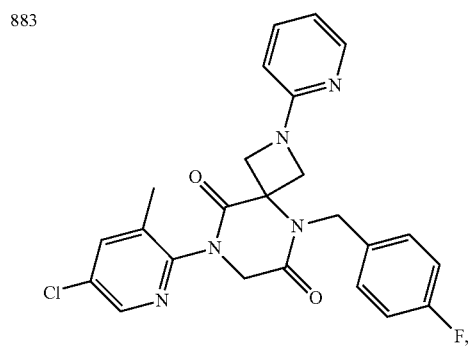 |
| 884 | 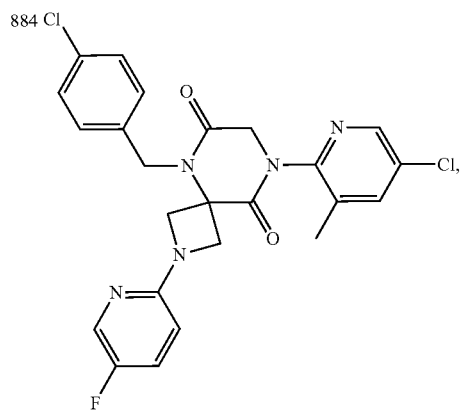 |

-continued
| No. | Structure |
|---|---|
| 885 | 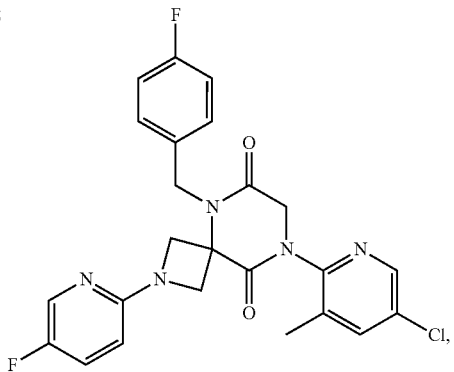 [SMILES: Cc1cc(Cl)cnc1N1CC(=O)N(Cc2ccc(F)cc2)C2(CN(c3ccc(F)cn3)C2)C1=O] |
| 886 | 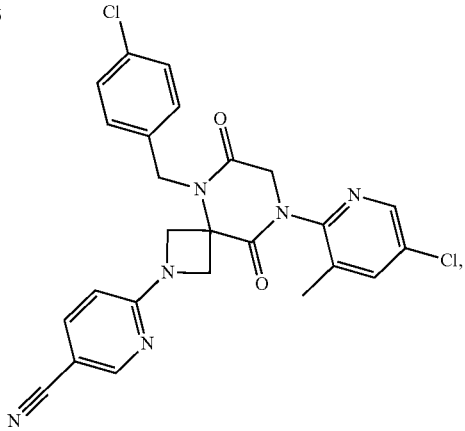 |
| 887 | 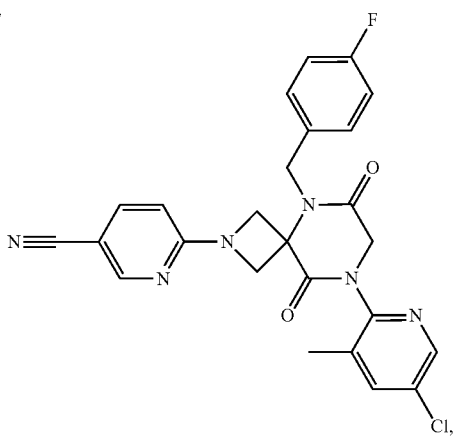 [SMILES: Cc1cc(Cl)cnc1N1CC(=O)N(Cc2ccc(F)cc2)C2(CN(c3ccc(C#N)cn3)C2)C1=O] |
| 888 | 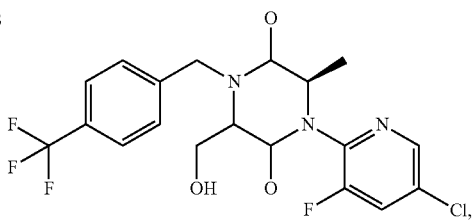 |

| No. | Structure |
|---|---|
| 889 | 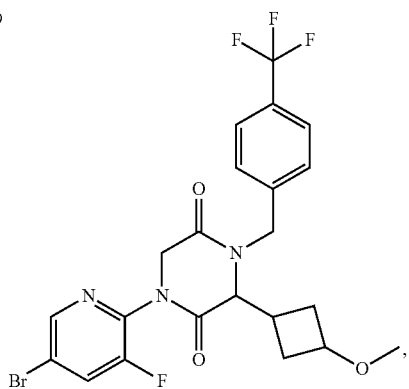 |
| 890 | 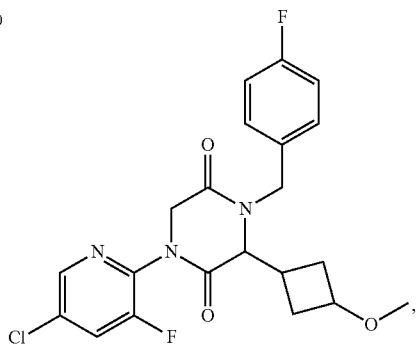 |
| 891 | 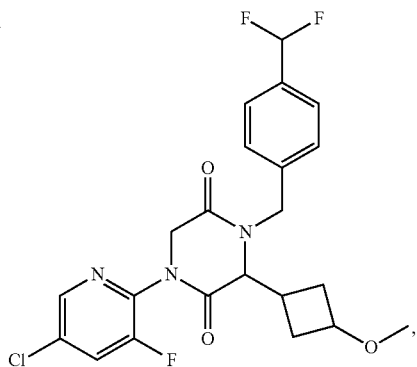 [SMILES: COC1CC(C2C(=O)N(c3ncc(Cl)cc3F)CC(=O)N2Cc2ccc(C(F)F)cc2)C1] |
| 892 | 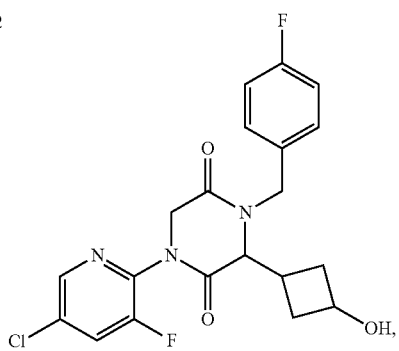 |

| No. | Structure |
|---|---|
| 983 | 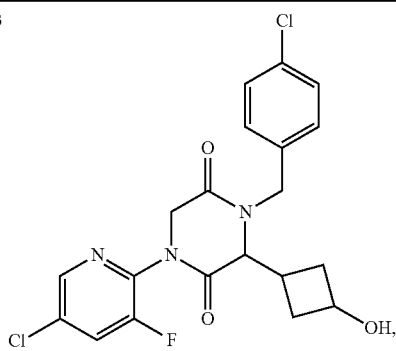 |
| 894 | and 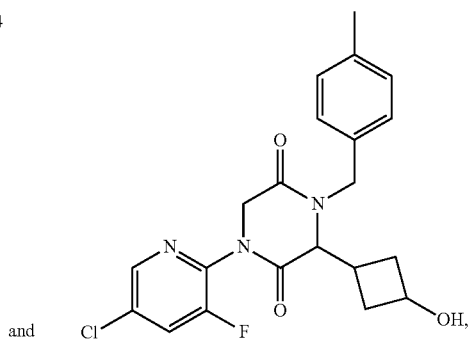 | or a pharmaceutically acceptable salt thereof.

44. A pharmaceutical composition comprising a compound according to claim 1, or a pharmaceutically acceptable salt thereof, and a pharmaceutically acceptable excipient.

45. A method of treating heart disease in a subject in need thereof, comprising administering to the subject a compound of claim 1, or a pharmaceutically acceptable salt thereof.

46. The method of claim 45, wherein the heart disease is hypertrophic cardiomyopathy.

47. The method of claim 46, wherein the hypertrophic cardiomyopathy is obstructive or nonobstructive or is caused by sarcomeric and/or non-sarcomeric mutations.

48. The method of claim 45, wherein the heart disease is heart failure with preserved ejection fraction.

49. The method of claim 45, wherein the heart disease is selected from the group consisting of diastolic dysfunction, primary or secondary restrictive cardiomyopathy, myocardial infarction and angina pectoris, left ventricular outflow tract obstruction, hypertensive heart disease, congenital heart disease, cardiac ischemia, coronary heart disease, diabetic heart disease, congestive heart failure, right heart failure, cardiorenal syndrome, and infiltrative cardiomyopathy.

50. The method of claim 45, wherein the heart disease is or is related to one or more conditions selected from the group consisting of cardiac senescence, diastolic dysfunction due to aging, left ventricular hypertrophy and concentric left ventricular remodeling.

51. A method of treating a disease or condition associated with hypertrophic cardiomyopathy in a subject in need thereof, comprising administering to the subject a compound of claim 1, or a pharmaceutically acceptable salt thereof.

52. The method of claim 51, wherein the disease or condition is selected from the group consisting of Fabry's Disease, Danon Disease, mitochondrial cardiomyopathies, and Noonan Syndrome.

53. A method of treating a disease or condition that is associated with secondary left ventricular wall thickening in a subject in need thereof, comprising administering to the subject a compound of claim 1, or a pharmaceutically acceptable salt thereof.

54. The method of claim 53, wherein the disease or condition is selected from the group consisting of hypertension, valvular heart diseases, aortic stenosis, Mitral valve regurgitation, metabolic syndromes, diabetes, obesity, end stage renal disease, scleroderma, sleep apnea, amyloidosis, Fabry's disease, Friedreich Ataxia, Danon disease, Noonan syndrome, and Pompe disease.

55. A method of treating a disease or condition that is associated with small left ventricular cavity and cavity obliteration, hyperdynamic left ventricular contraction, myocardial ischemia, or cardiac fibrosis in a subject in need thereof, comprising administering to the subject a compound of claim 1, or a pharmaceutically acceptable salt thereof.

56. A method of treating a disease or condition selected from muscular dystrophies and glycogen storage diseases in a subject in need thereof, comprising administering to the subject a compound of claim 1, or a pharmaceutically acceptable salt thereof.

57. A method of inhibiting the cardiac sarcomere, comprising contacting the cardiac sarcomere with a compound of claim 1, or a pharmaceutically acceptable salt thereof.

* * * * *